(12) United States Patent
Blanco-Pillado et al.

(10) Patent No.: US 11,970,514 B2
(45) Date of Patent: *Apr. 30, 2024

(54) NEUROACTIVE STEROIDS AND THEIR METHODS OF USE

(71) Applicant: SAGE THERAPEUTICS, INC., Cambridge, MA (US)

(72) Inventors: Maria Jesus Blanco-Pillado, Arlington, MA (US); Francesco G. Salituro, Marlborough, MA (US); Marshall Lee Morningstar, Framingham, MA (US)

(73) Assignee: Sage Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/334,124

(22) Filed: Jun. 13, 2023

(65) Prior Publication Data

US 2023/0322847 A1 Oct. 12, 2023

Related U.S. Application Data

(63) Continuation of application No. 17/311,056, filed as application No. PCT/US2019/064692 on Dec. 5, 2019.

(60) Provisional application No. 62/775,470, filed on Dec. 5, 2018.

(51) Int. Cl.
*C07J 43/00* (2006.01)
*C07J 41/00* (2006.01)

(52) U.S. Cl.
CPC ......... *C07J 43/003* (2013.01); *C07J 41/0044* (2013.01); *C07J 41/0094* (2013.01)

(58) Field of Classification Search
CPC .... C07J 41/003; C07J 41/0094; C07J 43/003; C07J 41/0044; A61K 31/573; A61K 31/58
See application file for complete search history.

(56) References Cited

U.S. PATENT DOCUMENTS

| | | | |
|---|---|---|---|
| 5,939,545 | A | 8/1999 | Upasani et al. |
| 8,569,275 | B2 | 10/2013 | Frincke |
| 9,512,165 | B2 | 12/2016 | Martinez Botella et al. |

(Continued)

FOREIGN PATENT DOCUMENTS

| | | |
|---|---|---|
| CN | 108727453 | 11/2018 |
| FR | 2969 M | 7/1904 |

(Continued)

OTHER PUBLICATIONS

U.S. Appl. No. 17/969,105, filed Oct. 19, 2022, Ravindra B. Upasani et al. Pending.
Chisari et al., "The Influence of Neuroactive Steroid Lipophilicity on GABAA Receptor Modulation: Evidence for a Low-Affinity Interaction", Journal of Neurophysiology, vol. 102, No. 2, Jun. 24, 2009, pp. 1254-1264.
Dansey et al., "Synthesis and GABA receptor activity of A-homo analogues of neuroactive steroids", European Journal of Medicinal Chemistry, vol. 45, n. 7, Mar. 26, 2021, pp. 3063-3069.
G. Akk et al. "Neurosteroid Access to the GABAA Receptor", The Journal of Neuroscience, vol. 25, No. 50, Dec. 14, 2005, pp. 11605-11613.
Phillipps G.H. et al., "Water-Soluble Steroidal Anasthetics", Journal of Steroid Biochemisty, vol. 11, No. 1, Jul. 1, 1979, pp. 79-86.
Search Report and Written Opinion for PCT/US2019/064692.
Search Report and Written Opinion for PCT/US2020/0401164.
H.J. Shu et al., "Photodynamic Effects of Steroid-Conjugated Fluorophores on GABAA Receptors", Molecular Pharmacology, vol. 76, No. 4, Oct. 1, 2009, pp. 754-765.

(Continued)

*Primary Examiner* — Barbara P Badio
(74) *Attorney, Agent, or Firm* — Honigman LLP; Andrew N. Weber; Jonathan P. O'Brien

(57) ABSTRACT

Provided herein is a compound of Formula (I) or a pharmaceutically acceptable salt thereof, wherein $R^{19}$, $R^5$, $R^{3a}$, $R^{1a}$, $R^{1b}$, $R^{2a}$, $R^{2b}$, $R^{4a}$, $R^{4b}$, $R^{6a}$, $R^{6b}$, $R^{7a}$, $R^{7b}$, $R^{11a}$, $R^{11b}$, $R^{12a}$, $R^{12b}$, $R^{18}$, $R^D$, and q are defined herein. L is selected from the group consisting of: wherein A indicates the point of attachment at C17 and wherein X is selected from the group consisting of $-C(O)N(R^{55a})(R^{55b})$, $-N(R^{55a})(R^{55b})$, $-N(R^{55b})C(O)(R^{55a})$, and $R^{55c}$ wherein $R^{55c}$ is carbon-bound substituted or unsubstituted heteroaryl or substituted or unsubstituted aryl. Also provided herein are pharmaceutical compositions comprising a compound of Formula (I) and methods of using the compounds, e.g., in the treatment of CNS-related disorders.

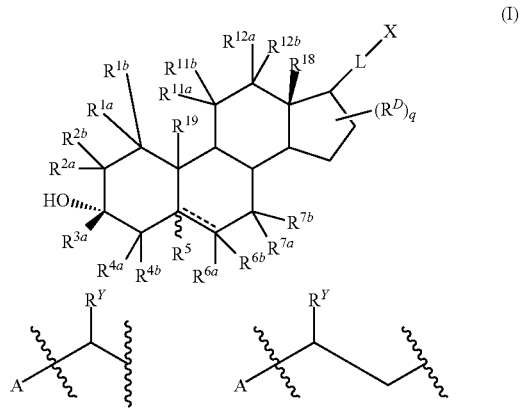

20 Claims, No Drawings

(56) References Cited

U.S. PATENT DOCUMENTS

| | | | |
|---|---|---|---|
| 11,236,121 | B2 | 2/2022 | Watson et al. |
| 11,643,434 | B2 | 5/2023 | Salituro et al. |
| 2020/0384003 | A1 | 12/2020 | Zheng et al. |
| 2021/0139530 | A1 | 5/2021 | Su et al. |
| 2022/0226350 | A1 | 7/2022 | Macconell et al. |
| 2022/0396597 | A1 | 12/2022 | Covey et al. |

FOREIGN PATENT DOCUMENTS

| | | |
|---|---|---|
| GB | 1494097 | 12/1977 |
| GB | 1521235 | 8/1978 |
| GB | 1538869 | 1/1979 |
| GB | 1570394 | 7/1980 |
| GB | 1581234 | 12/1980 |
| WO | 96/16076 A1 | 5/1996 |
| WO | 98/05337 A1 | 2/1998 |
| WO | 2016/061527 A1 | 4/2016 |
| WO | 2017/049044 A1 | 3/2017 |
| WO | 2017/187343 A2 | 11/2017 |
| WO | 2019/126761 A1 | 6/2019 |
| WO | 2020/061332 A1 | 3/2020 |
| WO | 2020210116 A1 | 10/2020 |
| WO | 2020210117 A1 | 10/2020 |
| WO | 2020/264512 A1 | 12/2020 |

OTHER PUBLICATIONS

Sunol, Cristina et al., "Activity of B-Nor analogues of Neurosteroids on the GABAA receptor in Primary Neuronal Cultures", Journal of Medicinal Chemistry, vol. 49, No. 11, Jun. 1, 2006 pp. 3225-3234.
U.S. Appl. No. 15/649,583, filed Jul. 13, 2017, U.S. Pat. No. 10,322,139, Issued.
U.S. Appl. No. 16/396,065, filed Apr. 26, 2019, U.S. Pat. No. 11,426,417, Issued.
U.S. Appl. No. 17/869,145, filed Jul. 20, 2022, Published.
U.S. Appl. No. 17/592,244, filed Feb. 3, 2022, Published.
U.S. Appl. No. 15/681,983, filed Aug. 21, 2017, U.S. Pat. No. 10,435,431, Issued.
U.S. Appl. No. 17/077,025, filed Oct. 22, 2020, Abandoned.
U.S. Appl. No. 15/698,151, filed Sep. 7, 2017, U.S. Pat. No. 10,323,059, Issued.
U.S. Appl. No. 16/393,396, filed Apr. 24, 2019, U.S. Pat. No. 11,046,728, Issued.
U.S. Appl. No. 15/143,312, filed Apr. 29, 2016, U.S. Pat. No. 10,377,790, Issued.
U.S. Appl. No. 16/440,527, filed Jun. 13, 2019, U.S. Pat. No. 11,261,211, Issued.
U.S. Appl. No. 14/785,192, Filed Oct. 16, 2015, U.S. Pat. No. 9,365,611, Issued.
U.S. Appl. No. 15/273,125, filed Sep. 22, 2016, U.S. Pat. No. 10,023,606, Issued.
U.S. Appl. No. 16/007,556, filed Jun. 13, 2018, U.S. Pat. No. 10,822,370, Issued.
U.S. Appl. No. 17/067,093, filed Oct. 9, 2020, Published.
U.S. Appl. No. 14/785,171, filed Oct. 16, 2015, U.S. Pat. No. 9,512,165, Issued.
U.S. Appl. No. 15/297,845, filed Oct. 19, 2016, U.S. Pat. No. 10,172,871, Issued.
U.S. Appl. No. 16/020,641, filed Jun. 27, 2018, U.S. Pat. No. 10,342,810, Issued.
U.S. Appl. No. 16/428,386, filed May 31, 2019, U.S. Pat. No. 11,241,446, Issued.
U.S. Appl. No. 17/560,732, filed Dec. 23, 2021, Published.
U.S. Appl. No. 15/639,702, filed Jun. 30, 2017, U.S. Pat. No. 10,391,106, Issued.
U.S. Appl. No. 16/507,214, filed Jul. 10, 2019, U.S. Pat. No. 11,344,563, Issued.
U.S. Appl. No. 14/785,175, filed Oct. 16, 2015, U.S. Pat. No. 9,725,481, Issued.
U.S. Appl. No. 16/843,822, filed Apr. 8, 2020, U.S. Pat. No. 11,498,940, Issued.
U.S. Appl. No. 14/132,386, filed Dec. 18, 2013, U.S. Pat. No. 9,630,986, Issued.
U.S. Appl. No. 15/459,492, filed Mar. 15, 2017, U.S. Pat. No. 10,342,809, Issued.
U.S. Appl. No. 16/419,255, filed May 55, 2019, Abandoned.
U.S. Appl. No. 14/652,717, filed Jun. 16, 2015, U.S. Pat. No. 9,676,812, Issued.
U.S. Appl. No. 17/304,433, filed Jun. 21, 2021, Published.
U.S. Appl. No. 17/094,783, filed Nov 10, 2020, Abandoned.
U.S. Appl. No. 15/314,565, filed Nov. 29, 2016, Published.
U.S. Appl. No. 15/531,313, filed May 26, 2017, U.S. Pat. No. 10,774,108, Issued.
U.S. Appl. No. 16/800,053, filed Feb. 25, 2020, Abandoned.
U.S. Appl. No. 15/319,503, filed Dec. 16, 2016, U.S. Pat. No. 10,246,482, Issued.
U.S. Appl. No. 16/269,779, filed Feb. 7, 2019, U.S. Pat. No. 10,745,436, Issued
U.S. Appl. No. 16/924,814, filed Jul. 9, 2020, U.S. Pat. No. 11,149,057, Issued.
U.S. Appl. No. 17/472,744, filed Sep. 13, 2021, Allowed.
U.S. Appl. No. 16/786,160, filed Feb. 10, 2020, Published.
U.S. Appl. No. 16/748,117, filed Jan. 21, 2020, U.S. Pat. No. 11,530,237, Issued.
U.S. Appl. No. 17/694,896, filed Mar. 15, 2022, Abandoned.
U.S. Appl. No. 17/695,033, filed Mar. 15, 2022, U.S. Pat. No. 11,542,297, Issued.
U.S. Appl. No. 15/519,480, filed Apr. 14, 2017, U.S. Pat. No. 10,577,390, Issued.
U.S. Appl. No. 16/365,123, filed Mar. 26, 2019, U.S. Pat. No. 10,870,677, Issued.
U.S. Appl. No. 17/112,125, filed Dec. 4, 2020, Abandoned.
U.S. Appl. No. 15/660,114, filed Jul. 26, 2017, U.S. Pat. No. 10,426,837, Issued.
U.S. Appl. No. 16/545,727, filed Aug. 20, 2019, U.S. Pat. No. 11,147,877, Issued.
U.S. Appl. No. 16/399,529, filed Apr. 30, 2019, U.S. Pat. No. 11,124,538, Issued.
U.S. Appl. No. 17/144,302, filed Jan. 8, 2021, Published.
U.S. Appl. No. 15/552,201, filed Aug. 18, 2017, U.S. Pat. No. 10,329,320.
U.S. Appl. No. 17/134,929, filed Dec. 28, 2020, Published.
U.S. Appl. No. 16/423,976, filed May 28, 2019, Abandoned.
U.S. Appl. No. 15/649,460, filed Jul. 13, 2017, U.S. Pat. No. 10,426,786, Issued.
U.S. Appl. No. 16/544,480, filed Aug. 19, 2019, U.S. Pat. No. 11,510,929, Issued.
U.S. Appl. No. 17/064,517, filed Oct. 6, 2020, Published.
U.S. Appl. No. 15/917,245, filed Mar. 9, 2018, U.S. Pat. No. 10,251,894, Issued.
U.S. Appl. No. 17/401,787, Aug. 13, 2021, Published.
U.S. Appl. No. 16/718,430, filed Dec. 18, 2019, U.S. Pat. No. 10,940,156, Issued.
U.S. Appl. No. 17/195,129, filed Mar. 8, 2021, U.S. Pat. No. 11,554,125, Issued.
U.S. Appl. No. 17/242,913, filed Apr. 28, 2021, Published.
U.S. Appl. No. 17/837,426, filed Jun. 10, 2022, Published.
U.S. Appl. No. 16/316,853, filed Jan. 10, 2019, U.S. Pat. No. 11,396,525, Issued.
U.S. Appl. No. 17/396,464, filed Aug. 6, 2021, Published.
U.S. Appl. No. 16/326,977, filed Feb. 21, 2019, U.S. Pat. No. 11,236,121, Issued.
U.S. Appl. No. 16/955,736, filed Jun. 18, 2020, Published.
U.S. Appl. No. 16/644,680, filed Mar. 5, 2020, Abandoned.
U.S. Appl. No. 17/251,475, Filed Dec. 11, 2020, Published.
U.S. Appl. No. 16/647,203, filed Mar. 13, 2020, Abandoned.
U.S. Appl. No. 16/645,975, filed Mar. 10, 2020, Published.
U.S. Appl. No. 17/545,290, filed Dec. 8, 2021, U.S. Pat. 11,667,688, Issued.
U.S. Appl. No. 16/961,097, filed Jul. 9, 2020, Allowed.
U.S. Appl. No. 16/955,714, filed Jun. 18, 2020, Published.
U.S. Appl. No. 17/286,524, filed Apr. 19, 2021, Published.

(56) References Cited

OTHER PUBLICATIONS

U.S. Appl. No. 17/284,206, Apr. 9, 2021, U.S. Pat. No. 11,634,453, Issued.
U.S. Appl. No. 17/311,056, filed Jun. 24, 2021, Published.
U.S. Appl. No. 17/416,367, filed Jun. 18, 2021, Published.
U.S. Appl. No. 63/322,725, filed Mar. 23, 2022, Expired.
U.S. Appl. No. 16/887,887, filed May 29, 2020, U.S. Pat. No. 11,643,434, Issued.
U.S. Appl. No. 17/902,159, filed Sep. 2, 2022, Pending.
U.S. Appl. No. 17/579,541, filed Jan. 19, 2022, Published.
U.S. Appl. No. 17/620,226, filed Dec. 17, 2021, Published.
U.S. Appl. No. 17/620,275, filed Dec. 17, 2021, Pending.
U.S. Appl. No. 17/782,362, filed Jun. 3, 2022, Published.
U.S. Appl. No. 17/843,031, filed Jun. 17, 2022, Published.
U.S. Appl. No. 17/620,303, filed Dec. 17, 2021, Published.
U.S. Appl. No. 63/289,296, filed Dec. 14, 2021, Published.
U.S. Appl. No. 63/284,592, filed Nov. 30, 2021, Expired.
U.S. Appl. No. 63/181,743, filed Apr. 29, 2021, Expired.
U.S. Appl. No. 63/197,025, filed Jun. 4, 2021, Expired.
U.S. Appl. No. 63/289,506, filed Dec. 14, 2021, Expired.
U.S. Appl. No. 63/181,807, filed Apr. 29, 2021, Expired.
U.S. Appl. No. 63/210,810, filed Jun. 15, 2021, Expired.
U.S. Appl. No. 63/239,096, filed Aug. 31, 2021, Expired.
U.S. Appl. No. 63/285,812, filed Dec. 3, 2021, Expired.
U.S. Appl. No. 63/289,520, filed Dec. 14, 2021, Expired.
U.S. Appl. No. 63/298,601, filed Jan. 11, 2022, Expired.
U.S. Appl. No. 63/392,579, filed Jul. 27, 2022, Pending.
U.S. Appl. No. 63/310,581, filed Feb. 16, 2022, Expired.
U.S. Appl. No. 63/337,828, filed May 3, 2022, Expired.
U.S. Appl. No. 63/310,583, filed Feb. 16, 2022, Expired.
U.S. Appl. No. 63/310,585, filed Feb. 16, 2022, Expired.
U.S. Appl. No. 63/442,059, filed Jan. 30, 2023, Pending.
U.S. Appl. No. 63/315,006, filed Feb. 28, 2022, Expired.
U.S. Appl. No. 63/482,207, filed Jan. 30, 2023, Pending.
U.S. Appl. No. 63/315,015, filed Feb. 28, 2022, Expired.
U.S. Appl. No. 63/442,056, filed Jan. 30, 2023, Pending.
U.S. Appl. No. 63/315,026, filed Feb. 28, 2022, Expired.
U.S. Appl. No. 63/442,005, filed Jan. 30, 2023, Pending.
U.S. Appl. No. 63/315,038, filed Feb. 28, 2022, Expired.
U.S. Appl. No. 63/442,027, filed Jan. 30, 2023, Pending.
U.S. Appl. No. 63/406,951, filed Sep. 15, 2022, Pending.
U.S. Appl. No. 17/969,105, filed Oct. 19, 2022, Pending.
U.S. Appl. No. 17/993,020, filed Nov. 23, 2022, Pending.
U.S. Appl. No. 18/087,870, filed Dec. 23, 2022, Published.
U.S. Appl. No. 18/169,964, filed Feb. 16, 2023, Pending.
U.S. Appl. No. 18/162,025, filed Jan. 31, 2023, Pending.
U.S. Appl. No. 18/107,965, filed Feb. 9, 2023, Pending.
U.S. Appl. No. 18/473,702, filed Sep. 25, 2023, Maria Jesus Blanco-Pillado et al., Pending.

NEUROACTIVE STEROIDS AND THEIR METHODS OF USE

CROSS-REFERENCE TO RELATED APPLICATIONS

This application is a continuation of U.S. application Ser. No. 17/311,056, filed Jun. 4, 2021, which is a national stage application under U.S.C. § 371 of International Application No. PCT/US2019/064692, filed Dec. 5, 2019, which claims the benefit of U.S. Provisional Patent Application No. 62/775,470, filed Dec. 5, 2018, the entire contents of which are incorporated by reference herein.

BACKGROUND OF THE INVENTION

Brain excitability is defined as the level of arousal of an animal, a continuum that ranges from coma to convulsions, and is regulated by various neurotransmitters. In general, neurotransmitters are responsible for regulating the conductance of ions across neuronal membranes. At rest, the neuronal membrane possesses a potential (or membrane voltage) of approximately −70 mV, the cell interior being negative with respect to the cell exterior. The potential (voltage) is the result of ion ($K^+$, $Na^+$, $Cl^-$, organic anions) balance across the neuronal semipermeable membrane. Neurotransmitters are stored in presynaptic vesicles and are released under the influence of neuronal action potentials. When released into the synaptic cleft, an excitatory chemical transmitter such as acetylcholine will cause membrane depolarization (a change of potential occurs from −70 mV to −50 mV). This effect is mediated by postsynaptic nicotinic receptors which are stimulated by acetylcholine to increase membrane permeability to $Na^+$ ions. The reduced membrane potential stimulates neuronal excitability in the form of a postsynaptic action potential.

In the case of the GABA receptor complex (GRC), the effect on brain excitability is mediated by γ-aminobutyric acid (GABA), a neurotransmitter. GABA has a profound influence on overall brain excitability because up to 40% of the neurons in the brain utilize GABA as a neurotransmitter. GABA regulates the excitability of individual neurons by regulating the conductance of chloride ions across the neuronal membrane. GABA interacts with its recognition site on the GRC to facilitate the flow of chloride ions down an electrochemical gradient of the GRC into the cell. An intracellular increase in the levels of this anion causes hyperpolarization of the transmembrane potential, rendering the neuron less susceptible to excitatory inputs, i.e., reduced neuron excitability. In other words, the higher the chloride ion concentration in the neuron, the lower the brain excitability and level of arousal.

It is well-documented that the GRC is responsible for the mediation of anxiety, seizure activity, and sedation. Thus, GABA and drugs that act like GABA or facilitate the effects of GABA (e.g., the therapeutically useful barbiturates and benzodiazepines (BZs), such as diazepam (VALIUM®)) produce their therapeutically useful effects by interacting with specific regulatory sites on the GRC. Accumulated evidence has now indicated that in addition to the benzodiazepine and barbiturate binding site, the GRC contains a distinct site for neuroactive steroids. See, e.g., Lan, N. C. et al., *Neurochem. Res.* (1991) 16:347-356.

Neuroactive steroids can occur endogenously. The most potent endogenous neuroactive steroids are 3α-hydroxy-5-reduced pregnan-20-one and 3α-21-dihydroxy-5-reduced pregnan-20-one, metabolites of hormonal steroids progesterone and deoxycorticosterone, respectively. The ability of these steroid metabolites to alter brain excitability was recognized in 1986 (Majewska, M. D. et al., *Science* 232: 1004-1007 (1986); Harrison, N. L. et al., *J Pharmacol. Exp. Ther.* 241:346-353 (1987)).

New and improved compounds are needed that act as modulating agents for brain excitability, as well as agents for the prevention and treatment of CNS-related diseases. The compounds, compositions, and methods described herein are directed toward this end.

SUMMARY OF THE INVENTION

Provided herein are compounds designed to act as GABA receptor modulators. In some embodiments, such compounds are envisioned to be useful as therapeutic agents for treating a CNS-related disorder.

In an aspect, provided herein is a compound of Formula (I):

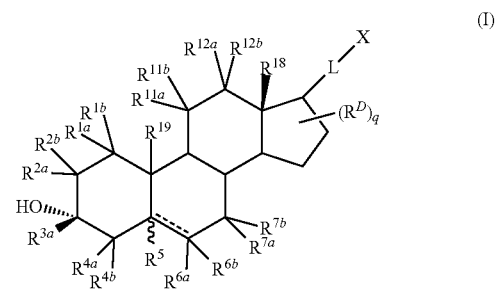

or a pharmaceutically acceptable salt thereof;
wherein:
 ----- represents a single or double bond, provided if a double bond is present, then one of $R^{6a}$ or $R^{6b}$ is absent and $R^5$ is absent;
L is selected from the group consisting of:

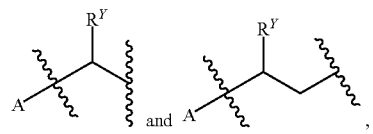

wherein A indicates the point of attachment at C17;
X is selected from the group consisting of —C(O)N($R^{55a}$)($R^{55b}$), —N($R^{55a}$)($R^{55b}$), —N($R^{55b}$)C(O)($R^{55a}$), and $R^{55c}$—;
$R^Y$ is each independently hydrogen, cyano, haloalkyl, or unsubstituted alkyl;
$R^{55c}$ is carbon-bound substituted or unsubstituted heteroaryl or substituted or unsubstituted aryl;
$R^{55a}$ and $R^{55b}$ is each independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{41}$, —N($R^{41}$)$_2$, —$SR^{41}$, —C(=O)$R^{41}$, —C(=O)$OR^{41}$, —C(=O)$SR^{41}$, —C(=O)N($R^{41}$)$_2$, —OC(=O)$R^{41}$, —OC(=O)$OR^{41}$, —OC(=O)N($R^{41}$)$_2$, —OC(=O)$SR^{41}$, —OS(=O)$_2R^{41}$, —OS(=O)$_2OR^{41}$, —OS(=O)$_2$N($R^{41}$)$_2$, —N($R^{41}$)C(=O)$R^{41}$, —N($R^{41}$)C (=NR^{A1})R^{A1}, —N(R^{A1})C(=O)OR^{A1}, —N(R^{A1})C(=O)N(R^{A1})$_2$, —N(R^{A1})C(=NR^{A1}) N(R^{A1})$_2$, —N(R^{A1})S(=O)$_2$R^{A1}, —N(R^{A1})S(=O)$_2$OR^{A1}, —N(R^{A1})S(=O)$_2$N(R^{A1})$_2$, —SC(=O)R^{A1}, —SC(=O)OR^{A1}, —SC(=O)SR^{A1}, —SC(=O)N(R^{A1})$_2$, —S(=O)$_2$R^{A1}, —S(=O)$_2$OR^{A1}, or —S(=O)$_2$N(R^{A1})$_2$, wherein each instance of R$^{A1}$ is independently selected from hydrogen, substituted or unsubstituted alkyl, substituted or unsubstituted alkenyl, substituted or unsubstituted alkynyl, substituted or unsubstituted carbocyclyl, or substituted or unsubstituted heterocyclyl, substituted or unsubstituted aryl, substituted or unsubstituted heteroaryl, an oxygen protecting group when attached to oxygen, a nitrogen protecting group when attached to nitrogen, a sulfur protecting group when attached to sulfur, or two R$^{A1}$ groups are taken with the intervening atoms to form a substituted or unsubstituted heterocyclic ring;

or R$^{55a}$ and R$^{55b}$ may join together with the intervening atoms to form a substituted or unsubstituted heterocyclyl or a substituted or unsubstituted heteroaryl;

each of R$_{1a}$, R$^{1b}$, R$^{2a}$, R$^{2b}$, R$^{4a}$, R$^{4b}$, R$^{7a}$, R$^{7b}$, R$^{11a}$, R$^{11b}$, R$^{12a}$, and R$^{12b}$ is independently hydrogen, halogen, cyano, —NO$_2$, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{A1}$, —N(R$^{A1}$)$_2$, —SR$^{A1}$, —C(=O)R$^{A1}$, —C(=O)OR$^{A1}$, —C(=O)SR$^{A1}$, —C(=O)N(R$^{A1}$)$_2$, —OC(=O)R$^{A1}$, —OC(=O)OR$^{A1}$, —OC(=O)N(R$^{A1}$)$_2$, —OC(=O)SR$^{A1}$, —OS(=O)$_2$R$^{A1}$, —OS(=O)$_2$OR$^{A1}$, —OS(=O)$_2$N(R$^{A1}$)$_2$, —N(R$^{A1}$)C(=O)R$^{A1}$, —N(R$^{A1}$)C(=NR$^{A1}$)R$^{A1}$, —N(R$^{A1}$)C(=O)OR$^{A1}$, —N(R$^{A1}$)C(=O)N(R$^{A1}$)$_2$, —N(R$^{A1}$)C(=NR$^{A1}$) N(R$^{A1}$)$_2$, —N(R$^{A1}$)S(=O)$_2$R$^{A1}$, —N(R$^{A1}$)S(=O)$_2$OR$^{A1}$, —N(R$^{A1}$)S(=O)$_2$N(R$^{A1}$)$_2$, —SC(=O)R$^{A1}$, —SC(=O)OR$^{A1}$, —SC(=O)SR$^{A1}$, —SC(=O)N(R$^{A1}$)$_2$, —S(=O)$_2$R$^{A1}$, —S(=O)$_2$OR$^{A1}$, or —S(=O)$_2$N(R$^{A1}$)$_2$, wherein each instance of R$^{A1}$ is independently selected from hydrogen, substituted or unsubstituted alkyl, substituted or unsubstituted alkenyl, substituted or unsubstituted alkynyl, substituted or unsubstituted carbocyclyl, or substituted or unsubstituted heterocyclyl, substituted or unsubstituted aryl, substituted or unsubstituted heteroaryl, an oxygen protecting group when attached to oxygen, a nitrogen protecting group when attached to nitrogen, or a sulfur protecting group when attached to sulfur; or R$^{11a}$ and R$^{11b}$ are joined to form an oxo (=O) group;

R$^{3a}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

R$^5$ is hydrogen or substituted or unsubstituted alkyl;

each of R$^{6a}$ and R$^{6b}$ is hydrogen, halogen, cyano, —NO$_2$, —OH, substituted or unsubstituted alkyl, substituted or unsubstituted alkenyl, or substituted or unsubstituted alkynyl; or R$^{6a}$ and R$^{6b}$ are joined to form an oxo (=O) group;

R$^D$ is independently hydrogen, halogen, —CN, —NO$_2$, oxo, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{C3}$, —N(R$^{C3}$)$_2$, —SR$^{C3}$, —C(=O)R$^{C3}$, —C(=O)OR$^{C3}$, —C(=O)SR$^{C3}$, —C(=O)N(R$^{C3}$)$_2$, —OC(=O)R$^{C3}$, —OC(=O)OR$^{C3}$, —OC(=O)N(R$^{C3}$)$_2$, —OC(=O)SR$^{C3}$, —OS(=O)$_2$R$^{C3}$, —OS(=O)$_2$OR$^{C3}$, —OS(=O)$_2$N(R$^{C3}$)$_2$, —N(R$^{C3}$)C(=O)R$^{C3}$, —N(R$^{C3}$)C(=NR$^{C3}$)R$^{C3}$, —N(R$^{C3}$)C(=O)OR$^{C3}$, —N(R$^{C3}$)C(=O)N(R$^{C3}$)$_2$, —N(R$^{C3}$)C(=NR$^{C3}$) N(R$^{C3}$)$_2$, —N(R$^{C3}$)S(=O)$_2$R$^{C3}$, —N(R$^{C3}$)S(=O)$_2$OR$^{C3}$, —N(R$^{C3}$)S(=O)$_2$N(R$^{C3}$)$_2$, —SC(=O)R$^{C3}$, —SC(=O)OR$^{C3}$, —SC(=O)SR$^{C3}$, —SC(=O)N(R$^{C3}$)$_2$, —S(=O)$_2$R$^{C3}$, —S(=O)$_2$OR$^{C3}$, or —S(=O)$_2$N(R$^{C3}$)$_2$, wherein each instance of R$^{C3}$ is independently selected from hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted carbocyclyl, or substituted or unsubstituted heterocyclyl, an oxygen protecting group when attached to oxygen, a nitrogen protecting group when attached to nitrogen, or a sulfur protecting group when attached to sulfur;

R$^{18}$ is substituted or unsubstituted alkyl;

R$^{19}$ is hydrogen, substituted or unsubstituted alkyl, substituted or unsubstituted alkenyl, or substituted or unsubstituted alkynyl; and q is an integer from 0 to 5;

provided that the compound is not:

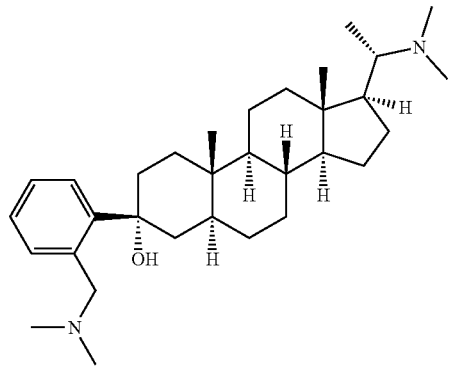

or a pharmaceutically acceptable salt thereof.

In some embodiments, the compound is a compound of Formula (I-I):

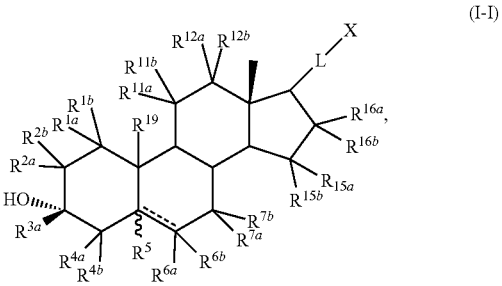

(I-I)

or a pharmaceutically acceptable salt thereof, wherein
each of R$^{15a}$, R$^{15b}$, R$^{16a}$, and R$^{16b}$ is independently hydrogen, halogen, —CN, —NO$_2$, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{C3}$, —N(R$^{C3}$)$_2$, —SR$^{C3}$, —C(=O)R$^{C3}$, —C(=O)OR$^{C3}$, —C(=O)SR$^{C3}$, —C(=O)N(R$^{C3}$)$_2$, —OC(=O)R$^{C3}$, —OC(=O)OR$^{C3}$, —OC(=O)N(R$^{C3}$)$_2$, —OC(=O)SR$^{C3}$, —OS(=O)$_2$R$^{C3}$, —OS(=O)$_2$OR$^{C3}$, —OS(=O)$_2$N(R$^{C3}$)$_2$, —N(R$^{C3}$)C(=O)R$^{C3}$, —N(R$^{C3}$)C(=NR$^{C3}$)R$^{C3}$, —N(R$^{C3}$)C(=O)OR$^{C3}$, —N(R$^{C3}$)C(=O)N(R$^{C3}$)$_2$, —N(R$^{C3}$)C(=NR$^{C3}$)N(R$^{C3}$)$_2$, —N(R$^{C3}$)S(=O)$_2$R$^{C3}$, —N(R$^{C3}$)S(=O)$_2$OR$^{C3}$, —N(R$^{C3}$)S(=O)$_2$N(R$^{C3}$)$_2$, —SC(=O)R$^{C3}$, —SC(=O)OR$^{C3}$, —SC(=O)SR$^{C3}$, —SC(=O)N(R$^{C3}$)$_2$, —S(=O)$_2$R$^{C3}$, —S(=O)$_2$OR$^{C3}$, or —S(=O)$_2$N(R$^{C3}$)$_2$, wherein each instance of R$^{C3}$ is independently selected from hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted carbocyclyl, or substituted or unsubstituted heterocyclyl, an oxygen protecting group when attached to oxygen, a nitrogen protecting group when attached to nitrogen, a sulfur protecting group when attached to sulfur; or R$^{15a}$ and R$^{15b}$ are joined to form an oxo (=O) group; or R$^{16a}$ and R$^{16b}$ are joined to form an oxo (=O) group.

In some embodiments, the compound is a compound of Formula (I-a):

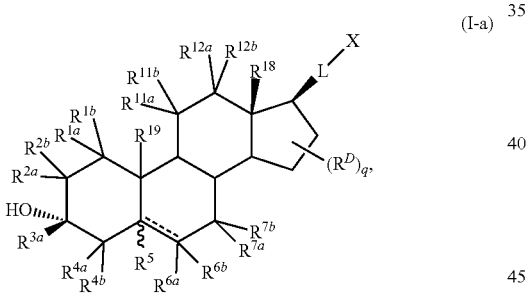

(I-a)

or a pharmaceutically acceptable salt thereof.

In some embodiments, the compound is a compound of Formula (I-Ia):

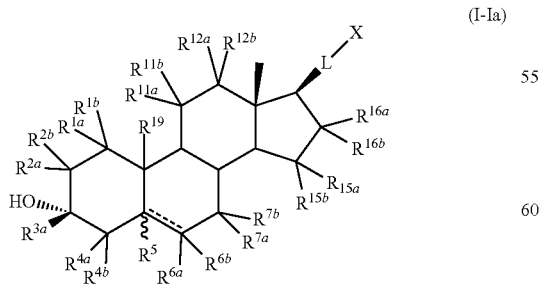

(I-Ia)

or a pharmaceutically acceptable salt thereof.

In some embodiments, the compound is a compound of Formula (I-b), (I-c), (I-d), (I-e), (I-l), (I-m), (I-n), or (I-p):

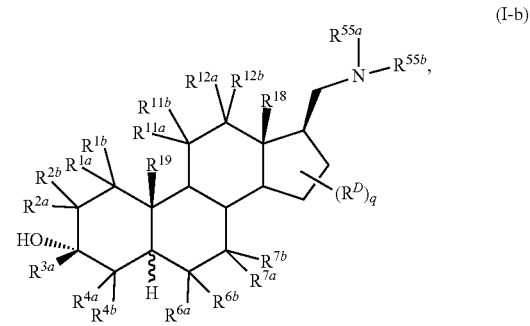

(I-b)

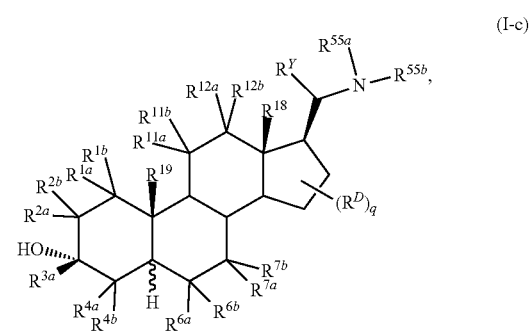

(I-c)

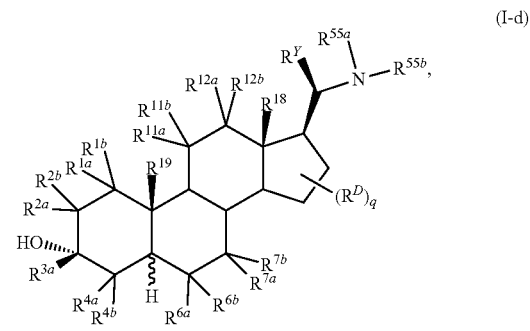

(I-d)

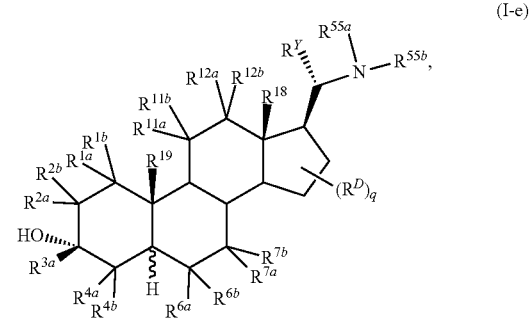

(I-e)

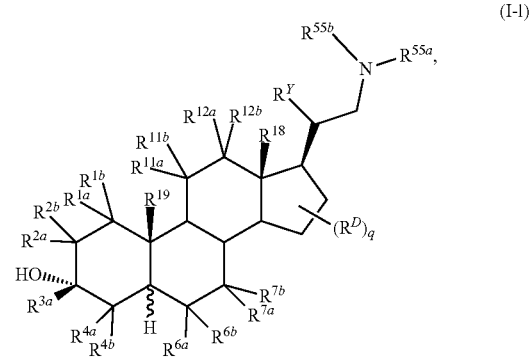

(I-l)

(I-m)
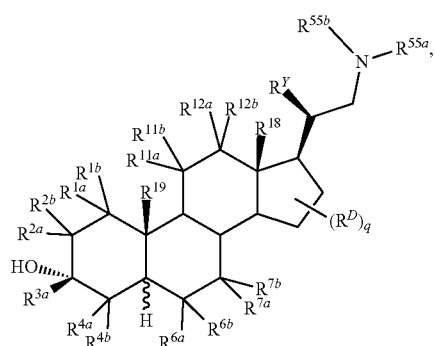
(I-n)
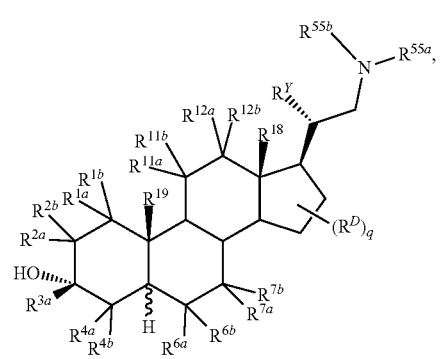
(I-p)
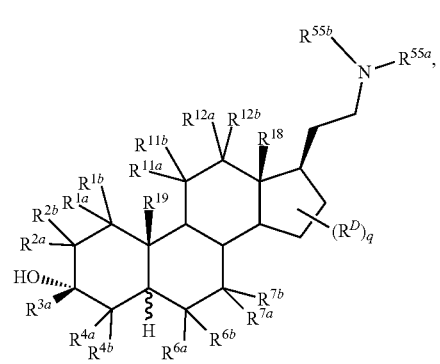
or a pharmaceutically acceptable salt thereof.
In some embodiments, the compound is a compound of Formula (I-f), (I-g), or (I-h):
(I-f)
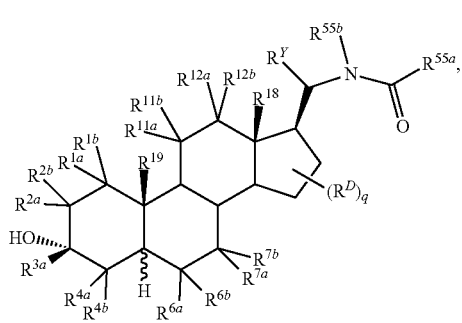
(I-g)
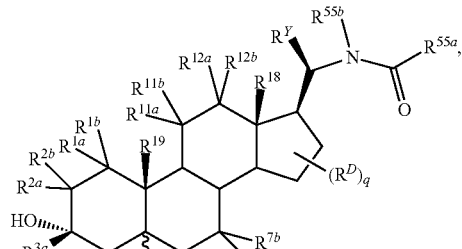
(I-h)
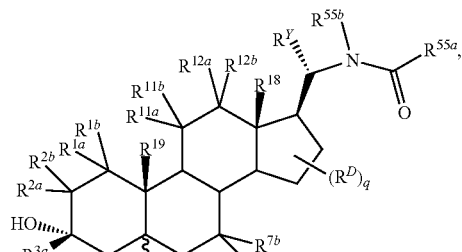
or a pharmaceutically acceptable salt thereof.
In some embodiments, the compound is a compound of Formula (I-i), (I-j), or (I-k):
(I-i)
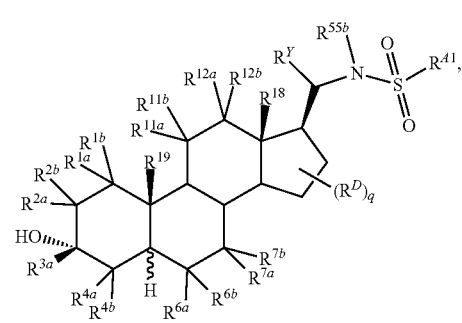
(I-j)
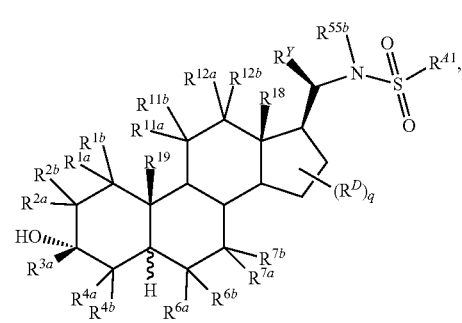

-continued (I-k)
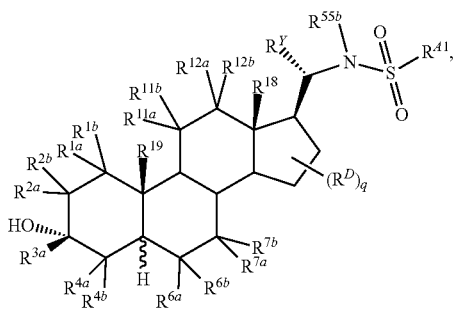

or a pharmaceutically acceptable salt thereof.

In some embodiments, the compound is a compound of Formula (I-o):

(I-o)
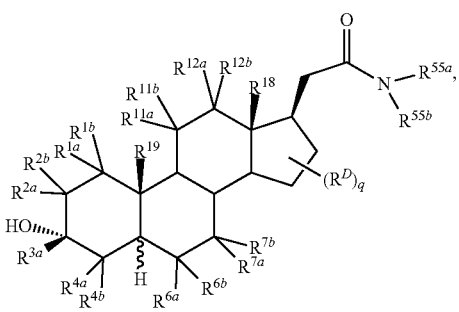

or a pharmaceutically acceptable salt thereof.

In some embodiments, the compound is a compound of Formula (I-qq), (I-q), (I-s), (I-t), or (I-u):

(I-qq)
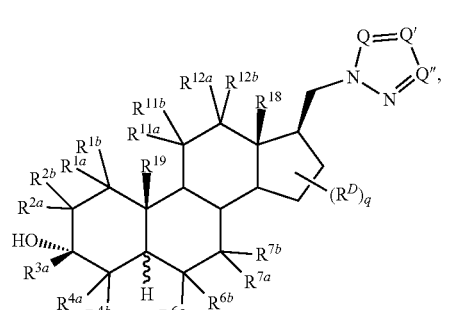

(I-q)
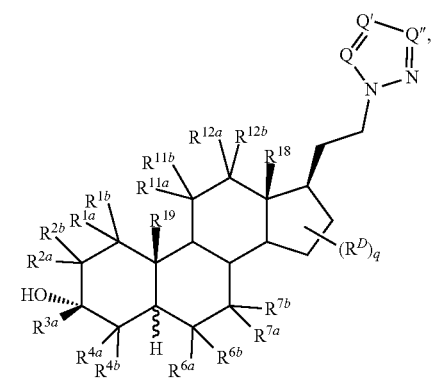

(I-s)
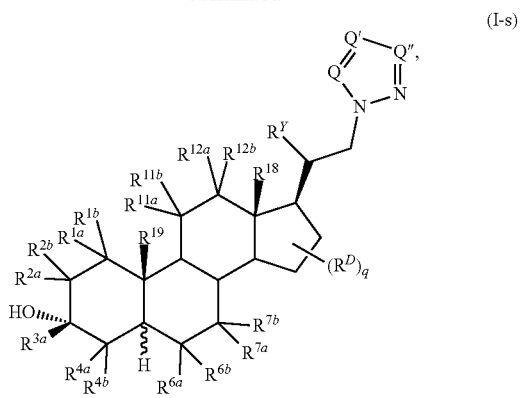

(I-t)
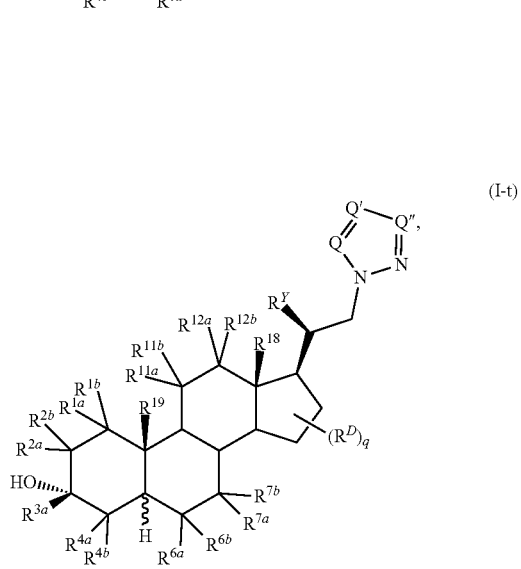

(I-u)
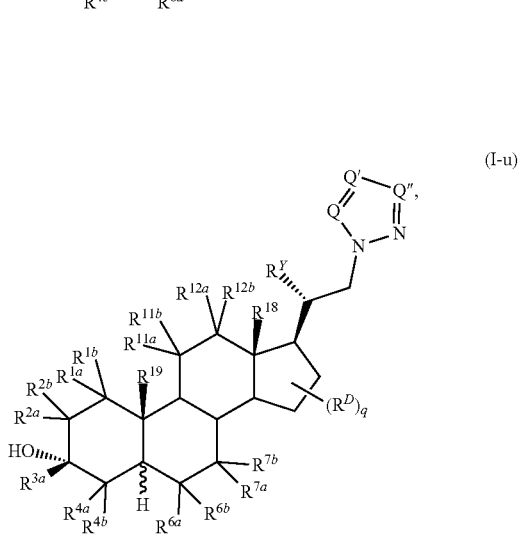

or a pharmaceutically acceptable salt thereof, wherein
Q, Q', and Q" are each independently $CR^w$ or N;
$R^w$ is hydrogen, cyano, —$NH_2$, or substituted or unsubstituted alkyl; and
at least one of Q, Q', and Q" is $CR^w$.

In some embodiments, the compound is a compound of Formula (I-r):

(I-r)

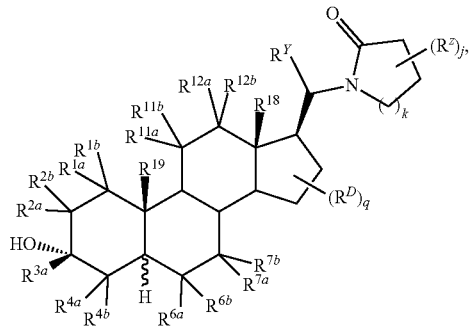

or a pharmaceutically acceptable salt thereof, wherein
k is an integer 1 or 2;
$R^z$ is substituted or unsubstituted alkyl or substituted or unsubstituted aryl; or two $R^z$s on adjacent carbons combine with the intervening atoms to form a substituted or unsubstituted aryl; and
j is an integer 0-6.

In some embodiments, the compound is a compound of Formula (I-v), (I-w), or (I-x):

(I-v)

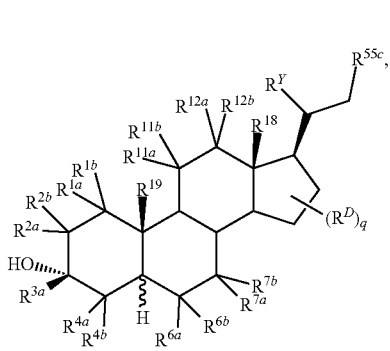

(I-w)

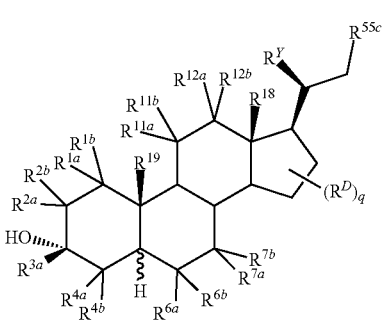

(I-x)

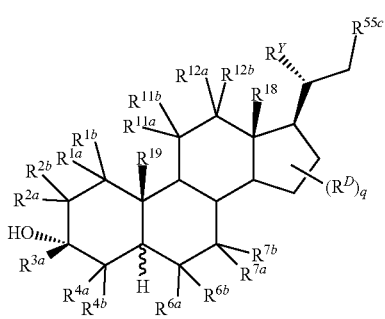

or a pharmaceutically acceptable salt thereof.

In some embodiments, the compound is a compound of Formula (I-Ib), (I-Ic), (I-Id), (I-Ie), (I-Il), (I-Im), (I-In), (I-Ip1), or (I-Ip2):

(I-Ib)

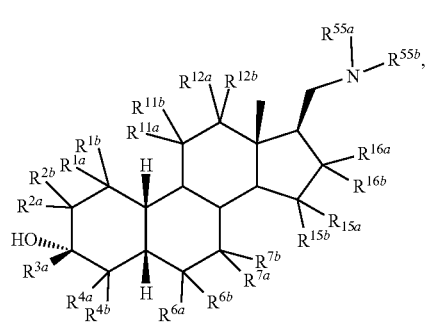

(I-Ic)

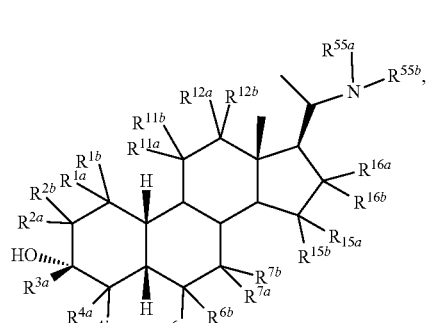

(I-Id)

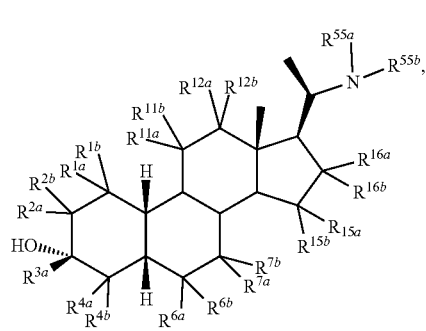

(I-Ie)

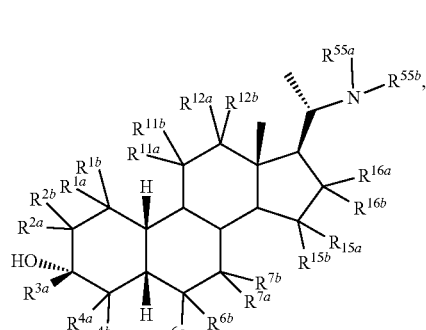

(I-Il)
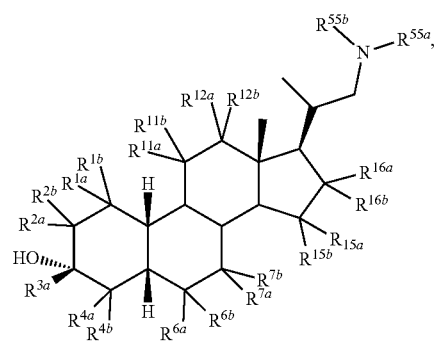
(I-Im)
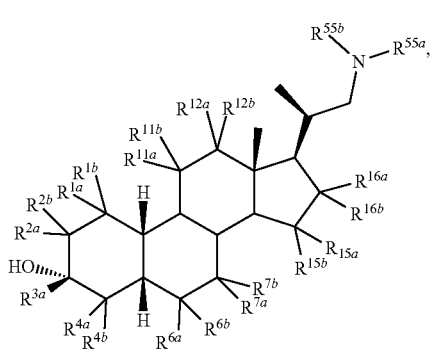
(I-In)
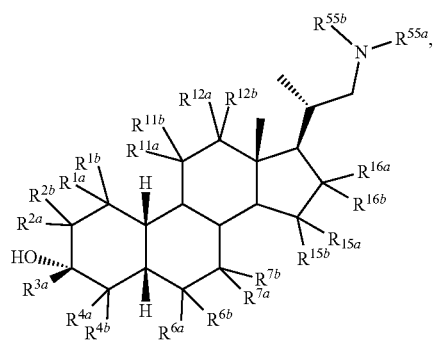
(I-Ip1)
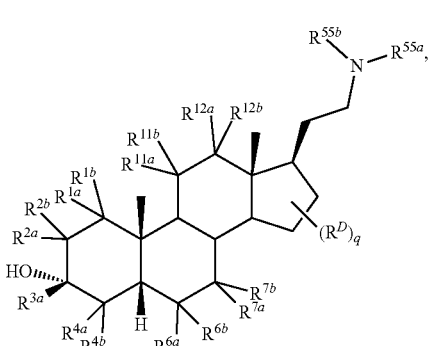
(I-Ip2)
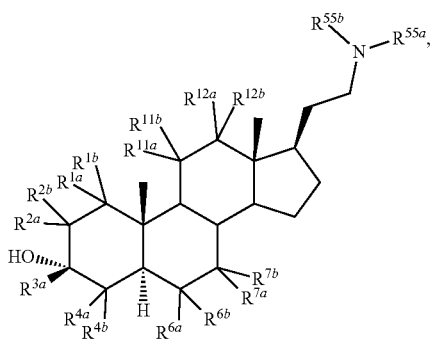
or a pharmaceutically acceptable salt thereof.
In some embodiments, the compound is a compound of Formula (I-If), (I-Ig), or (I-Ih):
(I-If)
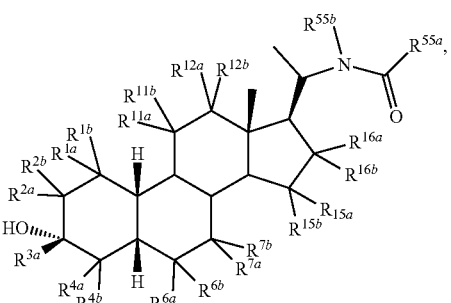
(I-Ig)
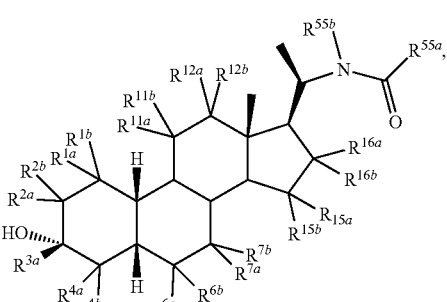
(I-Ih)
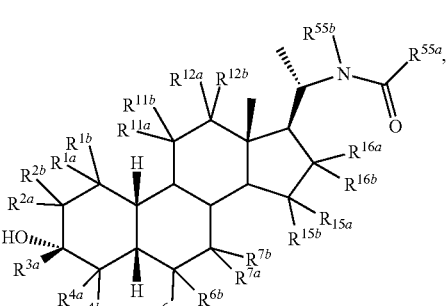
or a pharmaceutically acceptable salt thereof.
In some embodiments, the compound is a compound of Formula (I-Ii), (I-Ij), or (I-Ik):

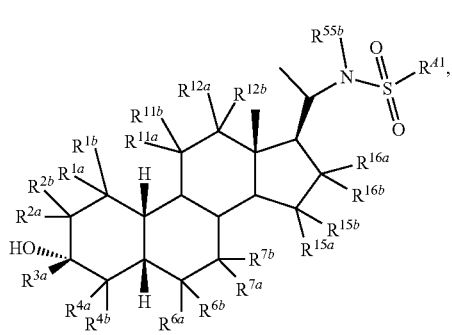
(I-Ii)
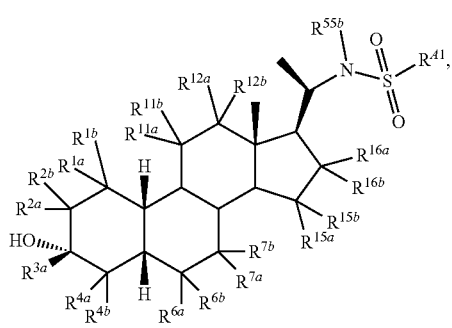
(I-Ij)
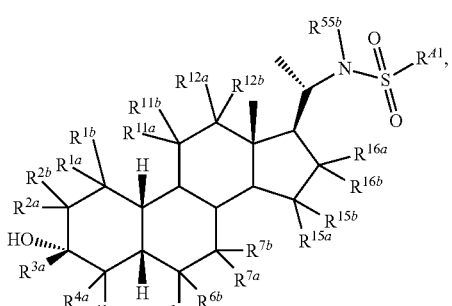
(I-Ik)
or a pharmaceutically acceptable salt thereof.
In some embodiments, the compound is a compound of Formula (I-Io1) or (I-Io2):
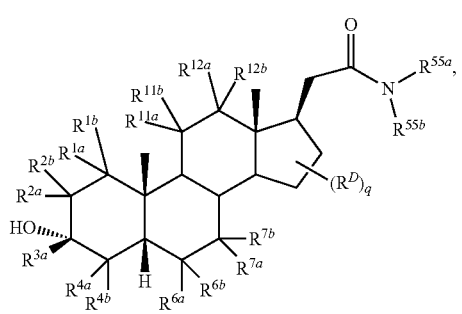
(I-Io1)
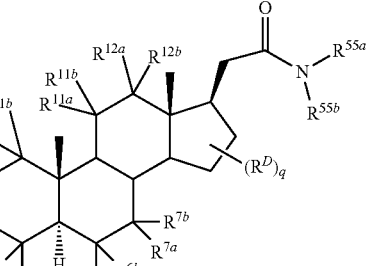
(I-Io2)
or a pharmaceutically acceptable salt thereof.
In some embodiments, the compound is a compound of Formula (I-Iqq), (I-Iq1), (I-Iq2), (I-It1), (I-It2), (I-Iu1), or (I-Iu2):
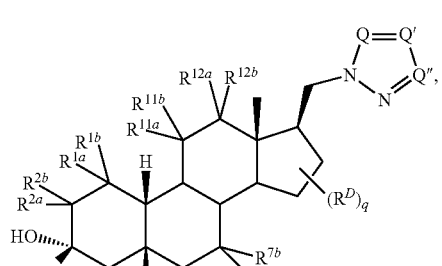
(I-Iqq)
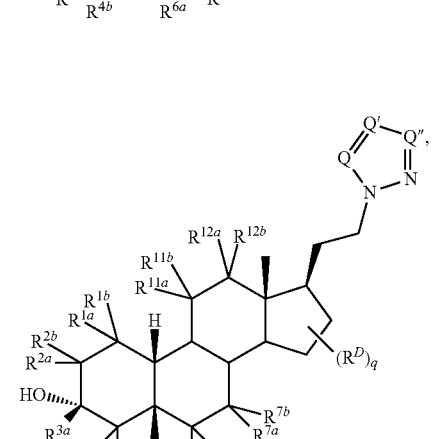
(I-Iq1)
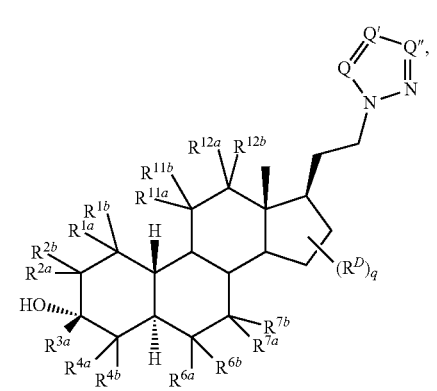
(I-Iq2)

-continued (I-It1)

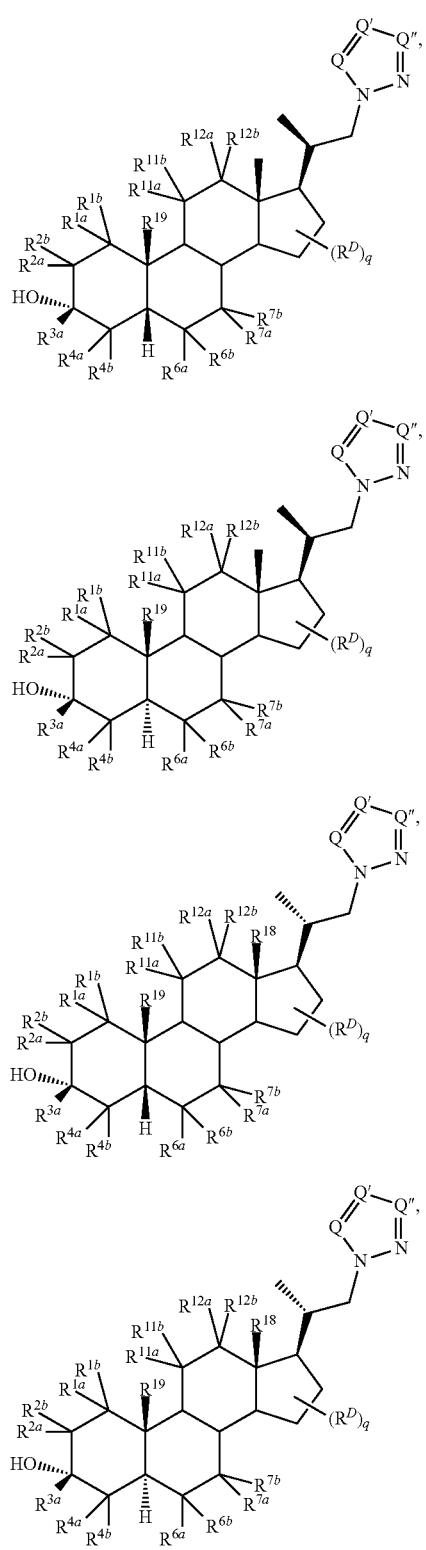

(I-It2)

(I-Iu1)

(I-Iu2)

or a pharmaceutically acceptable salt thereof, wherein
Q, Q', and Q" are each independently CR$^w$ or N;
R$^w$ is hydrogen, cyano, —NH$_2$, or substituted or unsubstituted alkyl; and
at least one of Q, Q', and Q" is CR$^w$.

In some embodiments, the compound is a compound of Formula (I-Irr), (I-Ir1) or (I-Ir2):

(I-Irr)

(I-Ir1)

(I-Ir2)

or a pharmaceutically acceptable salt thereof, wherein
k is an integer 1 or 2;
R$^z$ is substituted or unsubstituted alkyl or substituted or unsubstituted aryl; or two R$^z$s on adjacent carbons combine with the intervening atoms to form a substituted or unsubstituted aryl; and
j an integer 0-6.

In some embodiments, the compound is a compound of Formula (I-Ir3) or (I-Ir4):

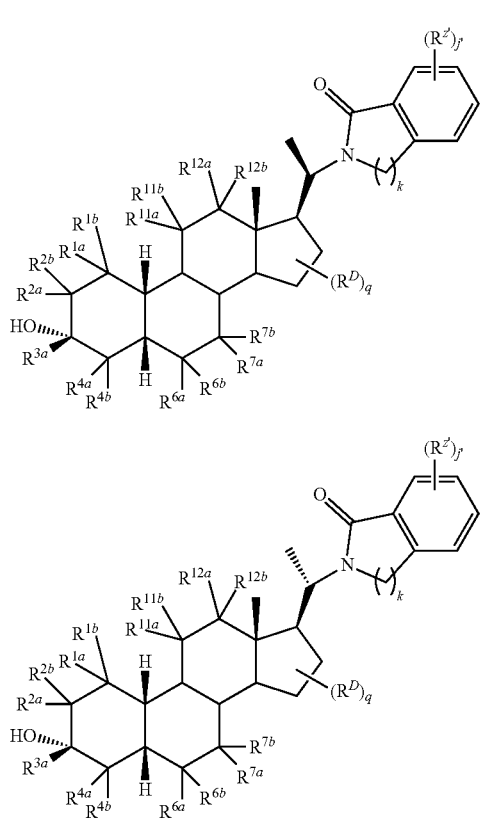

or a pharmaceutically acceptable salt thereof, wherein
k is an integer 1 or 2;
$R^{z'}$ is substituted or unsubstituted alkyl or cyano; and
j' an integer 0-4.

In some embodiments, the compound is a compound of Formula (I-Iw1), (I-Iw2), (I-Ix1), or (I-Ix2):

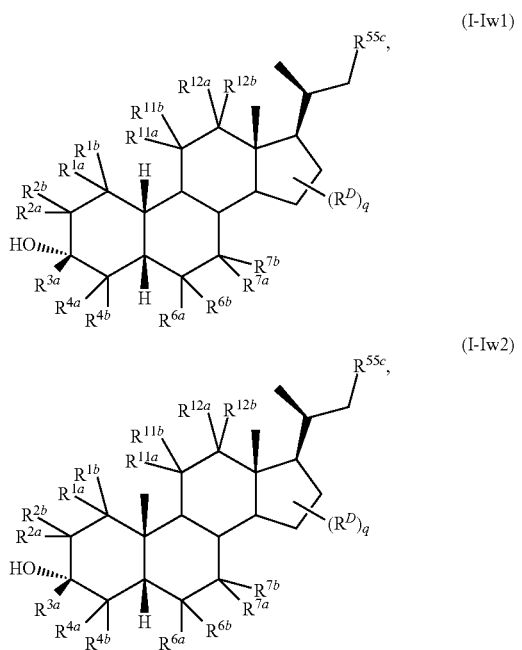

or a pharmaceutically acceptable salt thereof.

In some embodiments, the compound is selected from the group consisting of the compounds identified in Table 1 herein.

Compounds of the present invention as described herein, act, in certain embodiments, as GABA$_A$ receptor modulators. In certain embodiments, the compounds described herein can act as positive allosteric modulators of the GABA receptor e.g., of the GABA$_A$ receptor.

In one embodiment, the compounds described herein (e.g., a compound of Formula I or Table 1) exhibit higher selectivity for modulation of the α4β3δ configuration of GABA$_A$ receptor relative to the α1β2γ2 configuration of GABA$_A$ receptor.

In an aspect, provided herein is a pharmaceutical composition comprising a compound described herein (e.g., a compound of Formula (I)), or a pharmaceutically acceptable salt thereof, and a pharmaceutically acceptable excipient. In certain embodiments, the compound of the present invention is provided in an effective amount in the pharmaceutical composition. In certain embodiments, the compound of the present invention is provided in a therapeutically effective amount. In certain embodiments, the compound of the present invention is provided in a prophylactically effective amount.

In an aspect, provided herein is a pharmaceutically acceptable salt of a compound described herein (e.g., a compound of Formula (I)).

In certain embodiments, the compound is administered orally, subcutaneously, intravenously, or intramuscularly. In certain embodiments, the compound is administered orally. In certain embodiments, the compound is administered chronically. In certain embodiments, the compound is administered continuously, e.g., by continuous intravenous infusion.

Compounds of the present invention as described herein, act, in certain embodiments, as GABA receptor modulators, e.g., effecting the GABA$_A$ receptor in either a positive or negative manner. As modulators of the excitability of the central nervous system (CNS), as mediated by their ability to modulate $GABA_A$ receptor, such compounds are expected to have CNS-activity.

In an aspect, described herein is a method of treating a CNS-related disorder in a subject in need thereof, comprising administering to the subject an effective amount of a compound described herein or a pharmaceutically acceptable salt thereof.

In some embodiments, the CNS-related disorder is a sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, tinnitus, or status epilepticus.

In some embodiments, the CNS-related disorder is depression. In some embodiments, the CNS-related disorder is postpartum depression. In some embodiments, the CNS-related disorder is major depressive disorder. In some embodiments, the major depressive disorder is moderate major depressive disorder. In some embodiments, the major depressive disorder is severe major depressive disorder.

DETAILED DESCRIPTION OF CERTAIN EMBODIMENTS OF THE INVENTION

As generally described herein, the present invention provides compounds designed, for example, to act as GABA receptor modulators. In certain embodiments, such compounds are envisioned to be useful as therapeutic agents for treating a CNS-related disorder (e.g., a disorder as described herein, for example depression, such as post-partum depression or major depressive disorder).

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Isomers, e.g., stereoisomers, can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

"Stereoisomers": It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

As used herein, a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

As used herein, the term "diastereomeric purity" refers to the amount of a compound having the depicted absolute stereochemistry, expressed as a percentage of the total amount of the depicted compound and its diastereomers. The term "diastereomierically pure" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the diastereomer. Methods for determining diastereomeric and enantiomeric purity are well-known in the art. Diastereomeric purity can be determined by any analytical method capable of quantitatively distinguishing between a compound and its diastereomers, such as high performance liquid chromatography (HPLC).

In the compositions provided herein, an enantiomerically pure compound can be present with other active or inactive ingredients. For example, a pharmaceutical composition comprising enantiomerically pure R-position/center/carbon compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

The articles "a" and "an" may be used herein to refer to one or to more than one (i.e. at least one) of the grammatical objects of the article. By way of example "an analogue" means one analogue or more than one analogue.

When a range of values is listed, it is intended to encompass each value and sub-range within the range. For example "$C_{1-6}$alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_5$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl. Common alkyl abbreviations include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$), or i-Bu (—$CH_2CH(CH_3)_2$).

"Alkylene" refers to an alkyl group wherein two hydrogens are removed to provide a divalent radical, and which may be substituted or unsubstituted. Unsubstituted alkylene groups include, but are not limited to, methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), hexylene (—$CH_2CH_2CH_2CH_2CH_2CH_2$—), and the like. Exemplary substituted alkylene groups, e.g., substituted with one or more alkyl (methyl) groups, include but are not limited to, substituted methylene (—$CH(CH_3)$—, —$C(CH_3)_2$—), substituted ethylene (—$CH(CH_3)CH_2$—, —$CH_2CH(CH_3)$—, —$C(CH_3)_2CH_2$—, —$CH_2C(CH_3)_2$—), substituted propylene (—$CH(CH_3)CH_2CH_2$—, —$CH_2CH(CH_3)CH_2$—, —$CH_2CH_2CH(CH_3)$—, —$C(CH_3)_2CH_2CH_2$—, —$CH_2C(CH_3)_2CH_2$—, —$CH_2CH_2C(CH_3)_2$—), and the like. When a range or number of carbons is provided for a particular alkylene group, it is understood that the range or number refers to the range or number of carbons in the linear carbon divalent chain. Alkylene groups may be substituted or unsubstituted with one or more substituents as described herein.

"Alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C$), and the like. Additional examples of alkenyl include heptenyl ($C_7$), octenyl ($C_5$), octatrienyl ($C_5$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C), and the like. Additional examples of alkynyl include heptynyl (C$_7$), octynyl (C$_5$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted C$_{2-10}$ alkynyl. In certain embodiments, the alkynyl group is substituted C$_{2-10}$ alkynyl.

The term "heteroalkyl," as used herein, refers to an alkyl group, as defined herein, which further comprises 1 or more (e.g., 1, 2, 3, or 4) heteroatoms (e.g., oxygen, sulfur, nitrogen, boron, silicon, phosphorus) within the parent chain, wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkyl group refers to a saturated group having from 1 to 10 carbon atoms and 1, 2, 3, or 4 heteroatoms ("heteroC$_{1-10}$ alkyl"). In some embodiments, a heteroalkyl group is a saturated group having 1 to 9 carbon atoms and 1, 2, 3, or 4 heteroatoms ("heteroC$_{1-9}$ alkyl"). In some embodiments, a heteroalkyl group is a saturated group having 1 to 8 carbon atoms and 1, 2, 3, or 4 heteroatoms ("heteroC$_{1-8}$ alkyl"). In some embodiments, a heteroalkyl group is a saturated group having 1 to 7 carbon atoms and 1, 2, 3, or 4 heteroatoms ("heteroC$_{1-7}$ alkyl"). In some embodiments, a heteroalkyl group is a group having 1 to 6 carbon atoms and 1, 2, or 3 heteroatoms ("heteroC$_{1-6}$ alkyl"). In some embodiments, a heteroalkyl group is a saturated group having 1 to 5 carbon atoms and 1 or 2 heteroatoms ("heteroC$_{1-5}$ alkyl"). In some embodiments, a heteroalkyl group is a saturated group having 1 to 4 carbon atoms and 1 or 2 heteroatoms ("heteroC$_{1-4}$ alkyl"). In some embodiments, a heteroalkyl group is a saturated group having 1 to 3 carbon atoms and 1 heteroatom ("heteroC$_{1-3}$ alkyl"). In some embodiments, a heteroalkyl group is a saturated group having 1 to 2 carbon atoms and 1 heteroatom ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("C$_{6-14}$ aryl"). In some embodiments, an aryl group has six ring carbon atoms ("C$_6$ aryl"; e.g., phenyl). In some embodiments, an aryl group has ten ring carbon atoms ("C$_{10}$ aryl"; e.g., naphthyl such as 1-naphthyl and 2-naphthyl). In some embodiments, an aryl group has fourteen ring carbon atoms ("C$_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted C$_{6-14}$ aryl. In certain embodiments, the aryl group is substituted C$_{6-14}$ aryl.

In certain embodiments, an aryl group is substituted with one or more of groups selected from halogen, C$_1$-C$_8$ alkyl, C$_1$-C$_8$ haloalkyl, cyano, hydroxy, C$_1$-C$_8$ alkoxy, and amino.

Examples of representative substituted aryls include the following

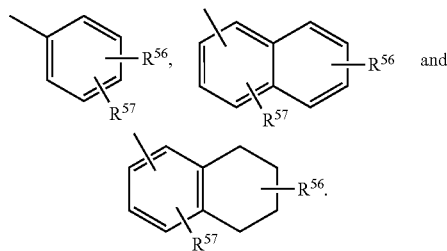

wherein one of R$^{56}$ and R$^{57}$ may be hydrogen and at least one of R$^{56}$ and R$^{57}$ is each independently selected from C$_1$-C$_8$ alkyl, C$_1$-C$_8$ haloalkyl, 4-10 membered heterocyclyl, alkanoyl, C$_1$-C$_8$ alkoxy, heteroaryloxy, alkylamino, arylamino, heteroarylamino, NR$^{58}$COR$^{59}$, NR$^{58}$SOR$^{59}$NR$^{58}$SO$_2$R$^{59}$, COOalkyl, COOaryl, CONR$^{58}$R$^{59}$, CONR$^{58}$OR$^{59}$, NR$^{58}$R$^{59}$, SO$_2$NR$^{58}$R$^{59}$, S-alkyl, SOalkyl, SO$_2$alkyl, Saryl, SOaryl, SO$_2$aryl; or R$^{56}$ and R$^{57}$ may be joined to form a cyclic ring (saturated or unsaturated) from 5 to 8 atoms, optionally containing one or more heteroatoms selected from the group N, O, or S. R$^{60}$ and R$^{61}$ are independently hydrogen, C$_1$-C$_8$ alkyl, C$_1$-C$_4$haloalkyl, C$_3$-C$_{10}$ cycloalkyl, 4-10 membered heterocyclyl, C$_6$-C$_{10}$ aryl, substituted C$_6$-C$_{10}$ aryl, 5-10 membered heteroaryl, or substituted 5-10 membered heteroaryl.

"Fused aryl" refers to an aryl having two of its ring carbon in common with a second aryl or heteroaryl ring or with a carbocyclyl or heterocyclyl ring.

"Heteroaryl" refers to a radical of a 5-10 membered monocyclic or bicyclic 4n+2 aromatic ring system (e.g., having 6 or 10 n electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

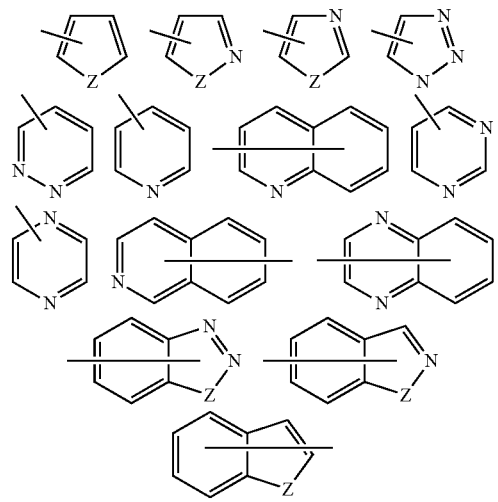

wherein each Z is selected from carbonyl, N, NR$^{65}$, O, and S; and R$^{65}$ is independently hydrogen, C$_1$-C$_8$ alkyl, C$_3$-C$_{10}$ cycloalkyl, 4-10 membered heterocyclyl, C$_6$-C$_{10}$ aryl, and 5-10 membered heteroaryl.

"Carbocyclyl" or "carbocyclic" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 6 ring carbon atoms ("C$_{3-6}$ carbocyclyl"). In some embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted C$_{3-10}$ carbocyclyl. In certain embodiments, the carbocyclyl group is a substituted C$_{3-10}$ carbocyclyl.

In some embodiments, "carbocyclyl" is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted C$_{3-10}$ cycloalkyl. In certain embodiments, the cycloalkyl group is substituted C$_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thioranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a C$_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazine.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g, heteroaryl, cycloalkenyl, e.g, cycloheteroalkenyl, and the like having from 1 to 5, and particularly from 1 to 3 heteroatoms.

"Acyl" refers to a radical —C(O)R$^{20}$, where R$^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein R$^{20}$ is a group other than hydrogen. Representative acyl groups include, but are not limited to, formyl (—CHO), acetyl (—C(=O)CH$_3$), cyclohexylcarbonyl, cyclohexylmethylcarbonyl, benzoyl (—C(=O)Ph), benzylcarbonyl (—C(=O)CH$_2$Ph), C(O)—C$_1$-C$_8$ alkyl, —C(O)—(CH$_2$)$_t$(C$_6$-C$_{10}$ aryl), —C(O)—(CH$_2$)$_t$(5-10 membered heteroaryl), —C(O)—(CH$_2$)$_t$(C$_3$-C$_{10}$ cycloalkyl), and —C(O)—(CH$_2$)$_t$(4-10 membered heterocyclyl), wherein t is an integer from 0 to 4. In certain embodiments, R$^{21}$ is C$_1$-C$_8$ alkyl, substituted with halogen or hydroxy; or C$_3$-C$_{10}$ cycloalkyl, 4-10 membered heterocyclyl, C$_6$-C$_{10}$ aryl, arylalkyl, 5-10 membered heteroaryl or heteroarylalkyl, each of which is substituted with unsubstituted C$_1$-C$_4$alkyl, halogen, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

"Alkoxy" refers to the group —OR$^{29}$ where R$^{29}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

In certain embodiments, R$^{29}$ is a group that has 1 or more substituents, for instance from 1 to 5 substituents, and particularly from 1 to 3 substituents, in particular 1 substituent, selected from the group consisting of amino, substituted amino, C$_6$-C$_{10}$ aryl, aryloxy, carboxyl, cyano, C$_3$-C$_{10}$ cycloalkyl, 4-10 membered heterocyclyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups include, but are not limited to, —O—(CH$_2$)$_t$(C$_6$-C$_{10}$ aryl), —O—(CH$_2$)$_t$(5-10 membered heteroaryl), —O—(CH$_2$)$_t$(C$_3$-C$_{10}$ cycloalkyl), and —O—(CH$_2$)$_t$(4-10 membered heterocyclyl), wherein t is an integer from 0 to 4 and any aryl, heteroaryl, cycloalkyl or heterocyclyl groups present, may themselves be substituted by unsubstituted C$_1$-C$_4$ alkyl, halogen, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. Particular exemplary 'substituted alkoxy' groups are —OCF$_3$, —OCH$_2$CF$_3$, —OCH$_2$Ph, —OCH$_2$-cyclopropyl, —OCH$_2$CH$_2$OH, and —OCH$_2$CH$_2$NMe$_2$.

"Amino" refers to the radical —NH$_2$.

"Oxo group" refers to —C(=O)—.

"Substituted amino" refers to an amino group of the formula —N(R$^{38}$)$_2$ wherein R$^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of R$^{38}$ is not a hydrogen. In certain embodiments, each R$^{38}$ is independently selected from hydrogen, C$_1$-C$_8$ alkyl, C$_3$-C$_8$ alkenyl, C$_3$-C$_8$ alkynyl, C$_6$-C$_{10}$ aryl, 5-10 membered heteroaryl, 4-10 membered heterocyclyl, or C$_3$-C$_{10}$ cycloalkyl; or C$_1$-C$_8$ alkyl, substituted with halogen or hydroxy; C$_3$-C$_8$ alkenyl, substituted with halogen or hydroxy; C$_3$-C$_8$ alkynyl, substituted with halogen or hydroxy, or —(CH$_2$)$_t$(C$_6$-C$_{10}$ aryl), —(CH$_2$)$_t$(5-10 membered heteroaryl), —(CH$_2$)$_t$(C$_3$-C$_{10}$ cycloalkyl), or —(CH$_2$)$_t$(4-10 membered heterocyclyl), wherein t is an integer between 0 and 8, each of which is substituted by unsubstituted C$_1$-C$_4$ alkyl, halogen, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy; or both R$^{38}$ groups are joined to form an alkylene group.

Exemplary "substituted amino" groups include, but are not limited to, —NR$^{39}$—C$_1$-C$_8$ alkyl, —NR$^{39}$—(CH$_2$)$_t$(C$_6$-C$_{10}$ aryl), —NR$^{39}$—(CH$_2$)$_t$(5-10 membered heteroaryl), —NR$^{39}$—(CH$_2$)$_t$(C$_3$-C$_{10}$ cycloalkyl), and —NR$^{39}$—(CH$_2$)$_t$(4-10 membered heterocyclyl), wherein t is an integer from 0 to 4, for instance 1 or 2, each R$^{39}$ independently represents H or C$_1$-C$_8$ alkyl; and any alkyl groups present, may themselves be substituted by halogen, substituted or unsubstituted amino, or hydroxy; and any aryl, heteroaryl, cycloalkyl, or heterocyclyl groups present, may themselves be substituted by unsubstituted C$_1$-C$_4$ alkyl, halogen, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

"Carboxy" refers to the radical —C(O)OH.

"Cyano" refers to the radical —CN.

"Halo" or "halogen" refers to fluoro (F), chloro (Cl), bromo (Br), and iodo (I). In certain embodiments, the halogen group is either fluoro or chloro.

"Haloalkyl" refers to an alkyl radical in which the alkyl group is substituted with one or more halogens. Typical haloalkyl groups include, but are not limited to, trifluoromethyl, difluoromethyl, fluoromethyl, chloromethyl, dichloromethyl, dibromoethyl, tribromomethyl, tetrafluoroethyl, and the like.

"Hydroxy" refers to the radical —OH.

"Nitro" refers to the radical —NO$_2$.

"Thioketo" refers to the group =S.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR—, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR—, —OC(=NR$^{bb}$)R—, —OC(=NR$^{bb}$)OR—, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$_{aa}$ is, independently, selected from C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rad groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_6$-14 aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R is, independently, selected from hydrogen, C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_6$-14 aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ haloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ haloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ haloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH (C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ haloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form O or =S; wherein X is a counterion.

In some embodiments, carbon atom substituents include halogen, —CN, —OH, —OR$^{aa}$, —N(R$^{bb}$)$_2$, —CO$_2$H, —CO$_2$R$^{aa}$, —OC(=O)R$^{aa}$, —C(=O)N(R$^{bb}$)$_2$, —SO$_2$R$^{aa}$, C$_{1-6}$ alkyl, C$_{1-6}$ haloalkyl, C$_{3-10}$ carbocyclyl, 5-6 membered heterocyclyl, phenyl, and 5-6 membered heteroaryl, wherein each instance of R$^{aa}$ is, independently, selected from hydrogen, C$_{1-6}$ alkyl, C$_{1-6}$ haloalkyl, C$_{2-10}$ alkenyl, C$_{2-10}$ alkynyl, C$_{3-10}$ carbocyclyl, 5-6 membered heterocyclyl, phenyl, and 5-6 membered heteroaryl; and each instance of R$^{bb}$ is, independently, selected from hydrogen, C$_{1-6}$ alkyl, C$_{1-6}$ haloalkyl, C$_{2-10}$ alkenyl, C$_{2-10}$ alkynyl, C$_{3-10}$ carbocyclyl, 5-6 membered heterocyclyl, phenyl, and 5-6 membered heteroaryl.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methanesulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

These and other exemplary substituents are described in more detail in the Detailed Description, and Claims. The invention is not intended to be limited in any manner by the above exemplary listing of substituents.

Other Definitions

As used herein, the term "modulation" refers to the inhibition or potentiation of GABA$_A$ receptor function. A "modulator" (e.g., a modulator compound) may be, for example, an agonist, partial agonist, antagonist, or partial antagonist of the GABA$_A$ receptor.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. The term "pharmaceutically acceptable cation" refers to an acceptable cationic counter-ion of an acidic functional group. Such cations are exemplified by sodium, potassium, calcium, magnesium, ammonium, tetraalkylammonium cations, and the like. See, e.g., Berge, et al., *J. Pharm. Sci.* (1977) 66(1): 1-79.

The term "prodrug" is intended to encompass therapeutically inactive compounds that, under physiological conditions, are converted into the therapeutically active agents of the present invention. One method for making a prodrug is to design selected moieties that are hydrolyzed or cleaved at a targeted in vivo site of action under physiological conditions to reveal the desired molecule which then produces its therapeutic effect. In certain embodiments, the prodrug is converted by an enzymatic activity of the subject.

In an alternate embodiment, the present invention provides prodrugs of compound of Formula (I), wherein the prodrug includes a cleavable moiety on the C$_3$ hydroxy as depicted in Formula (I).

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal.

In certain embodiments, the substituent present on an oxygen atom is an oxygen protecting group (also referred to as a hydroxyl protecting group). Oxygen protecting groups include, but are not limited to, —$R^{aa}$, —$N(R^{bb})_2$, —C(=O)$SR^{aa}$, —C(=O)$R^{aa}$, —$CO_2R^{aa}$, —C(=O)$N(R^{bb})_2$, —C(=$NR^{bb}$)$R^{aa}$, —C(=$NR^{bb}$)$OR^{aa}$, —C(=$NR^{bb}$)$N(R^{bb})_2$, —S(=O)$R^{aa}$, —$SO_2R^{aa}$, —$Si(R^{aa})_3$, —$P(R^{cc})_2$, —$P(R^{cc})_3$, —P(=O)$_2R^{aa}$, —P(=O)$(R^{aa})_2$, —P(=O)$(OR^{cc})_2$, —P(=O)$_2N(R^{bb})_2$, and —P(=O)$(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), 2-methoxyethoxymethyl (MEM), benzyl (Bn), triisopropylsilyl (TIPS), t-butyldimethylsilyl (TBDMS), t-butylmethoxyphenylsilyl (TBMPS), methanesulfonate (mesylate), and tosylate (Ts).

In certain embodiments, the substituent present on an sulfur atom is an sulfur protecting group (also referred to as a thiol protecting group). Sulfur protecting groups include, but are not limited to, —$R^{aa}$, —$N(R^{bb})_2$, —C(=O)$SR^{aa}$, —C(=O)$R^{aa}$, —$CO_2R^{aa}$, —C(=O)$N(R^{bb})_2$, —C(=$NR^{bb}$)$R^{aa}$, —C(=$NR^{bb}$)OR—, —C(=$NR^{bb}$)$N(R^{bb})_2$, —S(=O)$R^{aa}$, —$SO_2R^{aa}$, —$Si(R^{aa})_3$, —$P(R^{cc})_2$, —$P(R^{bb})_3$, —P(=O)$_2R^{aa}$, —P(=O)$(R^{aa})_2$, —P(=O)$(OR^{cc})_2$, —P(=O)$_2N(R^{bb})_2$, and —P(=O)$(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

In certain embodiments, the substituent present on a nitrogen atom is an amino protecting group (also referred to herein as a nitrogen protecting group). Amino protecting groups include, but are not limited to, —OH, —$OR^{aa}$, —$N(R^{cc})_2$, —C(=O)$R^{aa}$, —C(=O)$OR^{aa}$, —C(=O)$N(R^{cc})_2$, —S(=O)$_2R^{aa}$, —C(=$NR^{cc}$)$R^{aa}$, —C(=$NR^{cc}$)$OR^{aa}$, —C(=$NR^{cc}$)$N(R^{cc})_2$, —$SO_2N(R^{cc})_2$, —$SO_2R^{cc}$, —$SO_2OR^{cc}$, —$SOR^{aa}$, —C(=S)$N(R^{cc})_2$, —C(=O)$SR^{cc}$, —C(=S)$SR^{cc}$, $C_{1-10}$ alkyl, $C_{2-10}$ alkenyl, $C_{2-10}$ alkynyl, $C_{3-10}$ carbocyclyl, 3-14-membered heterocyclyl, $C_{6-14}$ aryl, and 5-14-membered heteroaryl groups, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R_{aa}$, $R^{bb}$, $R^{cc}$ and $R^{dd}$ are as defined herein. Amino protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary amino protecting groups include, but are not limited to amide groups (e.g., —C(=O)$R^{aa}$), which include, but are not limited to, formamide and acetamide; carbamate groups (e.g., —C(=O)$OR^{aa}$), which include, but are not limited to, 9-fluorenylmethyl carbamate (Fmoc), t-butyl carbamate (BOC), and benzyl carbamate (Cbz); sulfonamide groups (e.g., —S(=O)$_2R^{aa}$), which include, but are not limited to, p-toluenesulfonamide (Ts), methanesulfonamide (Ms), and N-[2-(trimethylsilyl)ethoxy]methylamine (SEM).

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition. In an alternate embodiment, the present invention contemplates administration of the compounds of the present invention as a prophylactic before a subject begins to suffer from the specified disease, disorder or condition.

In general, the "effective amount" of a compound refers to an amount sufficient to elicit the desired biological response, e.g., to treat a CNS-related disorder, is sufficient to induce anesthesia or sedation. As will be appreciated by those of ordinary skill in this art, the effective amount of a compound of the invention may vary depending on such factors as the desired biological endpoint, the pharmacokinetics of the compound, the disease being treated, the mode of administration, and the age, weight, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

Alternative Embodiments

In an alternative embodiment, compounds described herein may also comprise one or more isotopic substitutions. For example, hydrogen may be $^2$H (D or deuterium) or $^3$H (T or tritium); carbon may be, for example, $^{13}$C or $^{14}$C; oxygen may be, for example, $^{18}$O; nitrogen may be, for example, $^{15}$N, and the like. In other embodiments, a particular isotope (e.g., $^3$H, $^{13}$C, $^{14}$C, $^{18}$O, or $^{15}$N) can represent at least 1%, at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, at least 99%, or at least 99.9% of the total isotopic abundance of an element that occupies a specific site of the compound.

Compounds

It should be appreciated that formulas described herein may reference particular carbon atoms, such as C17, C3, C19, etc. These references are based on the position of carbon atoms according to steroid nomenclature known and used in the industry, as shown below:

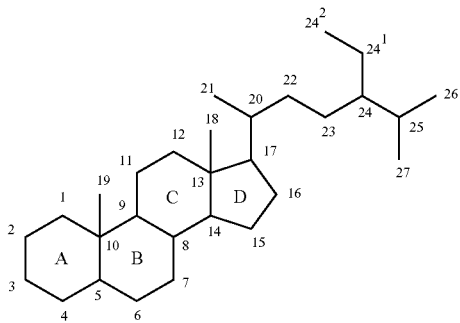

For example, $C_{17}$ refers to the carbon at position 17 and C3 refers to the carbon at position 3.

In an aspect, provided herein is a compound of Formula (I)

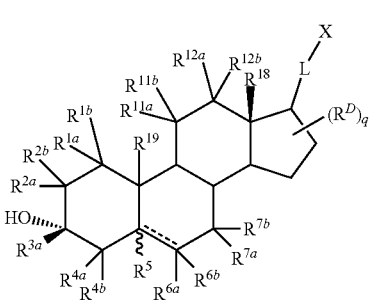

or a pharmaceutically acceptable salt thereof;
wherein:

≡≡≡≡≡ represents a single or double bond, provided if a double bond is present, then one of $R^{6a}$ or $R^{6b}$ is absent and $R^5$ is absent;

L is selected from the group consisting of:

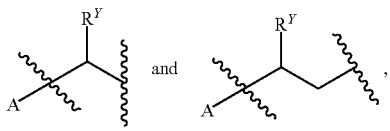

wherein A indicates the point of attachment at C17;

X is selected from the group consisting of —C(O)N($R^{55a}$)($R^{55b}$), —N($R^{55a}$)($R^{55b}$), —N($R^{55b}$)C(O)($R^{55a}$), and $R^{55c}$;

$R^Y$ is each independently hydrogen, cyano, haloalkyl, or unsubstituted alkyl;

$R^{55c}$ is carbon-bound substituted or unsubstituted heteroaryl or substituted or unsubstituted aryl;

$R^{55a}$ and $R^{55b}$ is each independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{41}$, —$N(R^{41})_2$, —$SR^{41}$, —$C(=O)R^{41}$, —$C(=O)OR^{41}$, —$C(=O)SR^{41}$, —$C(=O)N(R^{41})_2$, —$OC(=O)R^{41}$, —$OC(=O)OR^{41}$, —$OC(=O)N(R^{41})_2$, —$OC(=O)SR^{41}$, —$OS(=O)_2R^{41}$, —$OS(=O)_2OR^{41}$, —$OS(=O)_2N(R^{41})_2$, —$N(R^{41})C(=O)R^{41}$, —$N(R^{41})C(=NR^{41})R^{41}$, —$N(R^{41})C(=O)OR^{41}$, —$N(R^{41})C(=O)N(R^{41})_2$, —$N(R^{41})C(=NR^{41})N(R^{41})_2$, —$N(R^{41})S(=O)_2R^{41}$, —$N(R^{41})S(=O)_2OR^{41}$, —$N(R^{41})S(=O)_2N(R^{41})_2$, —$SC(=O)R^{41}$, —$SC(=O)OR^{41}$, —$SC(=O)SR^{41}$, —$SC(=O)N(R^{41})_2$, —$S(=O)_2R^{41}$, —$S(=O)_2OR^{41}$, or —$S(=O)_2N(R^{41})_2$, wherein each instance of $R^{41}$ is independently selected from hydrogen, substituted or unsubstituted alkyl, substituted or unsubstituted alkenyl, substituted or unsubstituted alkynyl, substituted or unsubstituted carbocyclyl, or substituted or unsubstituted heterocyclyl, substituted or unsubstituted aryl, substituted or unsubstituted heteroaryl, an oxygen protecting group when attached to oxygen, a nitrogen protecting group when attached to nitrogen, a sulfur protecting group when attached to sulfur, or two $R^{41}$ groups are taken with the intervening atoms to form a substituted or unsubstituted heterocyclic ring;

or $R^{55a}$ and $R^{55b}$ may join together with the intervening atoms to form a substituted or unsubstituted heterocyclyl or a substituted or unsubstituted heteroaryl;

each of $R^{1a}$, $R^{1b}$, $R^{2a}$, $R^{2b}$, $R^{4a}$, $R^{4b}$, $R^{7a}$, $R^{7b}$, $R^{11a}$, $R^{11b}$, $R^{12a}$, and $R^{12b}$ is independently hydrogen, halogen, cyano, —$NO_2$, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{41}$, —$N(R^{41})_2$, —$SR^{41}$, —$C(=O)R^{41}$, —$C(=O)OR^{41}$, —$C(=O)SR^{41}$, —$C(=O)N(R^{41})_2$, —$OC(=O)R^{41}$, —$OC(=O)OR^{41}$, —$OC(=O)N(R^{41})_2$, —$OC(=O)SR^{41}$, —$OS(=O)_2R^{41}$, —$OS(=O)_2OR^{41}$, —$OS(=O)_2N(R^{41})_2$, —$N(R^{41})C(=O)R^{41}$, —$N(R^{41})C(=NR^{41})R^{41}$, —$N(R^{41})C(=O)OR^{41}$, —$N(R^{41})C(=O)N(R^{41})_2$, —$N(R^{41})C(=NR^{41})N(R^{41})_2$, —$N(R^{41})S(=O)_2R^{41}$, —$N(R^{41})S(=O)_2OR^{41}$, —$N(R^{41})S(=O)_2N(R^{41})_2$, —$SC(=O)R^{41}$, —$SC(=O)OR^{41}$, —$SC(=O)SR^{41}$, —$SC(=O)N(R^{41})_2$, —$S(=O)_2R^{41}$, —$S(=O)_2OR^{41}$, or —$S(=O)_2N(R^{41})_2$, wherein each instance of $R^{41}$ is independently selected from hydrogen, substituted or unsubstituted alkyl, substituted or unsubstituted alkenyl, substituted or unsubstituted alkynyl, substituted or unsubstituted carbocyclyl, or substituted or unsubstituted heterocyclyl, substituted or unsubstituted aryl, substituted or unsubstituted heteroaryl, an oxygen protecting group when attached to oxygen, a nitrogen protecting group when attached to nitrogen, or a sulfur protecting group when attached to sulfur; or $R^{11a}$ and $R^{11b}$ are joined to form an oxo (=O) group; or $R^{12a}$ and $R^{12b}$ are joined to form an oxo (=O) group; or $R^{4a}$ and $R^{4b}$ are joined to form an oxo (=O) group; or $R^{7a}$ and $R^{7b}$ are joined to form an oxo (=O) group; or $R^{2a}$ and $R^{2b}$ are joined to form an oxo (=O) group; or $R^{1a}$ and $R^{1b}$ are joined to form an oxo (=O) group;

$R^{3a}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^5$ is hydrogen or substituted or unsubstituted alkyl;

each of $R^{6a}$ and $R^{6b}$ is hydrogen, halogen, cyano, —$NO_2$, —OH, substituted or unsubstituted alkyl, substituted or unsubstituted alkenyl, or substituted or unsubstituted alkynyl; or $R^{6a}$ and $R^{6b}$ are joined to form an oxo (=O) group;

$R^D$ is independently hydrogen, halogen, —CN, —NO$_2$, oxo, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{C3}$, —N(R$^{C3}$)$_2$, —SR$^{C3}$, —C(=O)R$^{C3}$, —C(=O)OR$^{C3}$, —C(=O)SR$^{C3}$, —C(=O)N(R$^{C3}$)$_2$, —OC(=O)R$^{C3}$, —OC(=O)OR$^{C3}$, —OC(=O)N(R$^{C3}$)$_2$, —OC(=O)SR$^{C3}$, —OS(=O)$_2$R$^{C3}$, —OS(=O)$_2$OR$^{C3}$, —OS(=O)$_2$N(R$^{C3}$)$_2$, —N(R$^{C3}$)C(=O)R$^{C3}$, —N(R$^{C3}$)C(=NR$^{C3}$)R$^{C3}$, —N(R$^{C3}$)C(=O)OR$^{C3}$, —N(R$^{C3}$)C(=O)N(R$^{C3}$)$_2$, —N(R$^{C3}$)C(=NR$^{C3}$)N(R$^{C3}$)$_2$, —N(R$^{C3}$)S(=O)$_2$R$^{C3}$, —N(R$^{C3}$)S(=O)$_2$OR$^{C3}$, —N(R$^{C3}$)S(=O)$_2$N(R$^{C3}$)$_2$, —SC(=O)R$^{C3}$, —SC(=O)OR$^{C3}$, —SC(=O)SR$^{C3}$, —SC(=O)N(R$^{C3}$)$_2$, —S(=O)$_2$R$^{C3}$, —S(=O)$_2$OR$^{C3}$, or —S(=O)$_2$N(R$^{C3}$)$_2$, wherein each instance of R$^{C3}$ is independently selected from hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted carbocyclyl, or substituted or unsubstituted heterocyclyl, an oxygen protecting group when attached to oxygen, a nitrogen protecting group when attached to nitrogen, or a sulfur protecting group when attached to sulfur;

$R^{18}$ is substituted or unsubstituted alkyl;

$R^{19}$ is hydrogen, substituted or unsubstituted alkyl, substituted or unsubstituted alkenyl, or substituted or unsubstituted alkynyl; and q is an integer from 0 to 5;

provided that the compound is not:

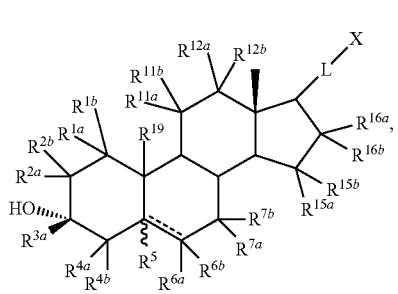

or a pharmaceutically acceptable salt thereof.

In some embodiments, the compound is a compound of Formula (I-I):

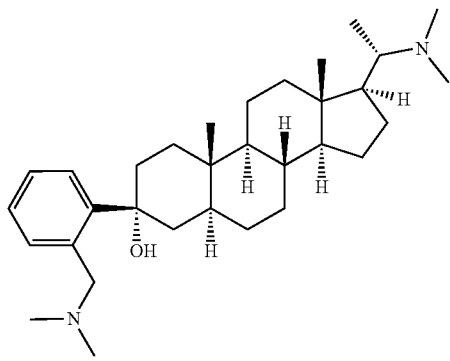

(I-I)

or a pharmaceutically acceptable salt thereof, wherein
each of $R^{15a}$, $R^{15b}$, $R^{16a}$, and $R^{16b}$ is independently hydrogen, halogen, —CN, —NO$_2$, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{C3}$, —N(R$^{C3}$)$_2$, —SR$^{C3}$, —C(=O)R$^{C3}$, —C(=O)OR$^{C3}$, —C(=O)SR$^{C3}$, —C(=O)N(R$^{C3}$)$_2$, —OC(=O)R$^{C3}$, —OC(=O)OR$^{C3}$, —OC(=O)N(R$^{C3}$)$_2$, —OC(=O)SR$^{C3}$, —OS(=O)$_2$R$^{C3}$, —OS(=O)$_2$OR$^{C3}$, —OS(=O)$_2$N(R$^{C3}$)$_2$, —N(R$^{C3}$)C(=O)R$^{C3}$, —N(R$^{C3}$)C(=NR$^{C3}$)R$^{C3}$, —N(R$^{C3}$)C(=O)OR$^{C3}$, —N(R$^{C3}$)C(=O)N(R$^{C3}$)$_2$, —N(R$^{C3}$)C(=NR$^{C3}$)N(R$^{C3}$)$_2$, —N(R$^{C3}$)S(=O)$_2$R$^{C3}$, —N(R$^{C3}$)S(=O)$_2$OR$^{C3}$, —N(R$^{C3}$)S(=O)$_2$N(R$^{C3}$)$_2$, —SC(=O)R$^{C3}$, —SC(=O)OR$^{C3}$, —SC(=O)SR$^{C3}$, —SC(=O)N(R$^{C3}$)$_2$, —S(=O)$_2$R$^{C3}$, —S(=O)$_2$OR$^{C3}$, or —S(=O)$_2$N(R$^{C3}$)$_2$, wherein each instance of R$^{C3}$ is independently selected from hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted carbocyclyl, or substituted or unsubstituted heterocyclyl, an oxygen protecting group when attached to oxygen, a nitrogen protecting group when attached to nitrogen, a sulfur protecting group when attached to sulfur; or $R^{15a}$ and $R^{15b}$ are joined to form an oxo (=O) group; or $R^{16a}$ and $R^{16b}$ are joined to form an oxo (=O) group.

In some embodiments, the compound is a compound of Formula (I-a):

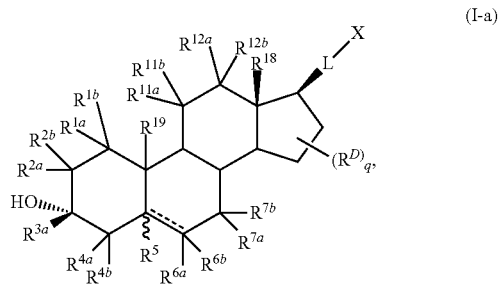

(I-a)

or a pharmaceutically acceptable salt thereof.

In some embodiments, the compound is a compound of Formula (I-Ia):

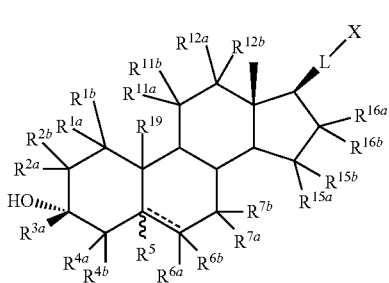

(I-Ia)

or a pharmaceutically acceptable salt thereof.

Groups $R^{55a}$ and $R^{55b}$

In some embodiments, $R^{55a}$ is hydrogen or methyl and $R^{55b}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl.

In some embodiments, $R^{55a}$ and $R^{55b}$ is each independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl.

In some embodiments, $R^{55a}$ and $R^{55b}$ is each independently hydrogen, substituted or unsubstituted carbocyclyl, substituted or unsubstituted heterocyclyl, substituted or unsubstituted aryl, or substituted or unsubstituted heteroaryl.

In some embodiments, $R^{55a}$ and $R^{55b}$ is each independently substituted carbocyclyl, substituted heterocyclyl, substituted aryl, or substituted heteroaryl.

In some embodiments, at least $R^{55a}$ or $R^{55b}$ is other than hydrogen.

In some embodiments, $R^{55a}$ and $R^{55b}$ is each independently hydrogen, substituted or unsubstituted alkyl, substituted or unsubstituted alkenyl, substituted or unsubstituted alkynyl,

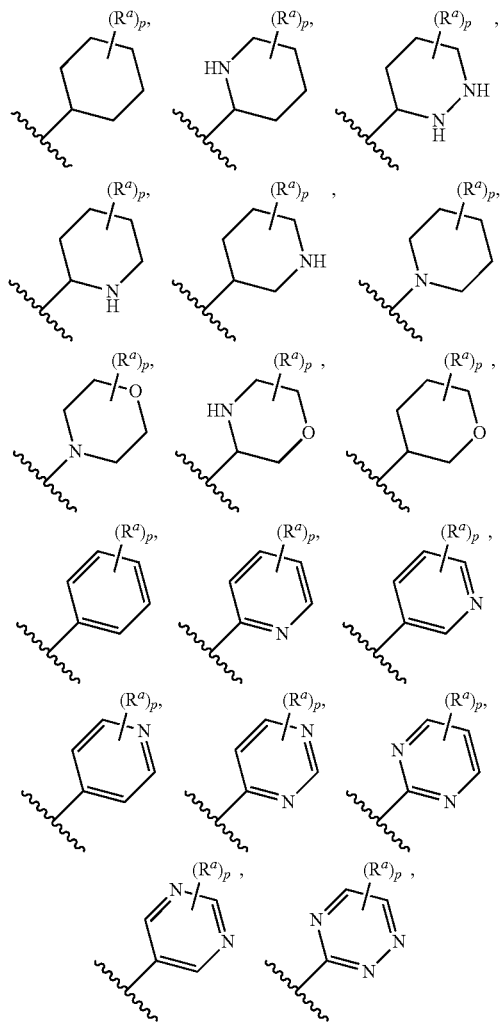

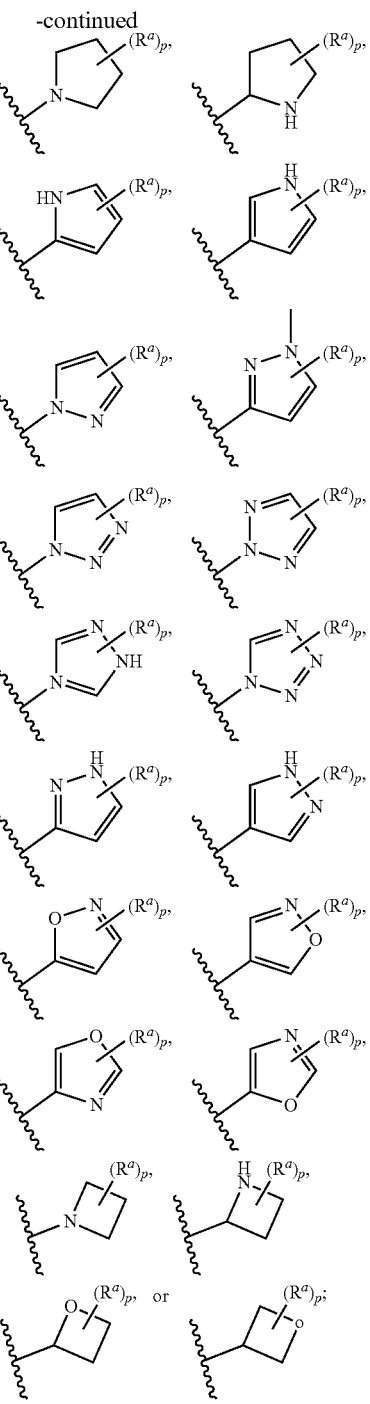

wherein:

each instance of $R^a$ is independently hydrogen, halogen, —$NO_2$, —CN, —$OR^{D4}$, —$N(R^{D4})_2$, —$C(=O)R^{D4}$, —$C(=O)OR^{D4}$, —$C(=O)N(R^{D4})_2$, —$OC(=O)R^{D4}$, —$OC(=O)OR^{D4}$, —$N(R^{D4})C(=O)R^{D4}$, —$OC(=O)N(R^{D4})_2$, —$N(R^{D4})C(=O)OR^{D4}$, —$S(=O)_2R^{D4}$, —$S(=O)_2OR^{D4}$, —$OS(=O)_2R^{D4}$, —$S(=O_2N(R^4)_2$, or —$N(R^{D4})S(=O)_2R^{D4}$, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted 3- to 6-membered heterocyclyl, substituted or unsubstituted $C_{5-10}$ aryl, substituted or unsubstituted 5- to 10-membered heteroaryl;

each instance of $R^{D4}$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted 3- to 6-membered heterocyclyl, substituted or unsubstituted $C_{5-10}$ aryl, substituted or unsubstituted 5- to 10-membered heteroaryl, an oxygen protecting group when attached to oxygen, a nitrogen protecting group when attached to nitrogen, or two $R^{D4}$ groups are taken with the intervening atoms to form a substituted or unsubstituted heterocyclic ring; and p is an integer selected from 0 to 11.

In some embodiments, $R^{55a}$ and $R^{55b}$ is each independently hydrogen, substituted or unsubstituted alkyl, substituted or unsubstituted alkenyl, substituted or unsubstituted alkynyl,

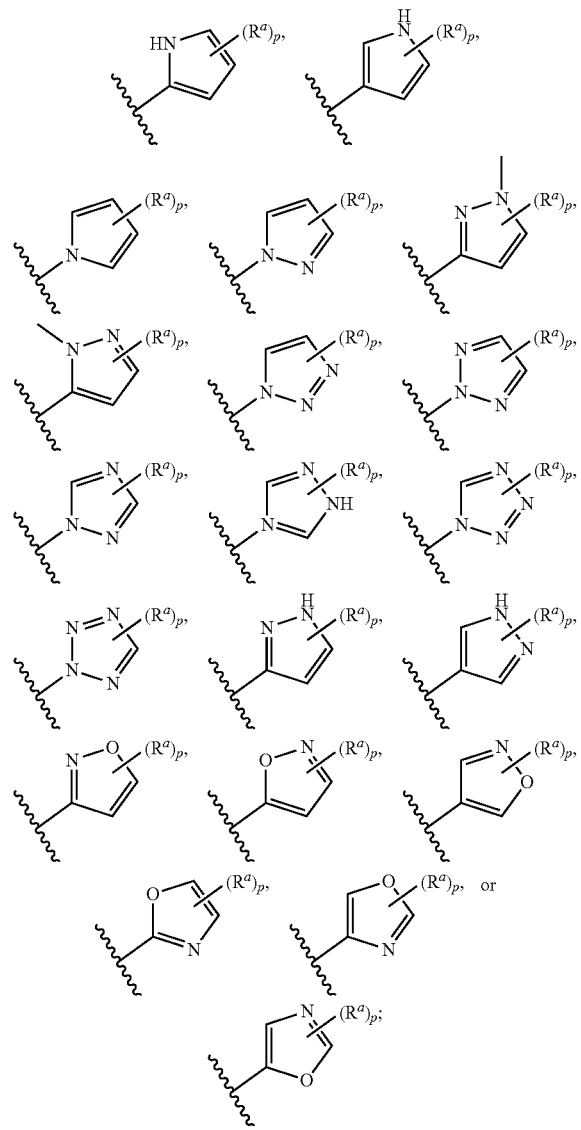

wherein:
each instance of $R^a$ is independently hydrogen, halogen, $-NO_2$, $-CN$, $-OR^{D4}$, $-N(R^{D4})_2$, $-C(=O)R^{D4}$, $-C(=O)OR^{D4}$, $-C(=O)N(R^{D4})_2$, $-OC(=O)R^{D4}$, $-OC(=O)OR^{D4}$, $-N(R^{D4})C(=O)R^{D4}$, $-OC(=O)N(R^{D4})_2$, $-N(R^{D4})C(=O)OR^{D4}$, $-S(=O)_2R^{D4}$, $-S(=O)_2OR^{D4}$, $-OS(=O)_2R^{D4}$, $-S(=O)_2N(R^{D4})_2$, or $-N(R^{D4})S(=O)_2R^{D4}$, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted 3- to 6-membered heterocyclyl, substituted or unsubstituted $C_{5-10}$ aryl, substituted or unsubstituted 5- to 10-membered heteroaryl;

each instance of $R^{D4}$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted 3- to 6-membered heterocyclyl, substituted or unsubstituted $C_{5-10}$ aryl, substituted or unsubstituted 5- to 10-membered heteroaryl, an oxygen protecting group when attached to oxygen, a nitrogen protecting group when attached to nitrogen, or two $R^{D4}$ groups are taken with the intervening atoms to form a substituted or unsubstituted heterocyclic ring; and p is an integer selected from 0 to 3.

In some embodiments, $R^{55a}$ and $R^{55b}$ is each independently hydrogen, substituted or unsubstituted alkyl,

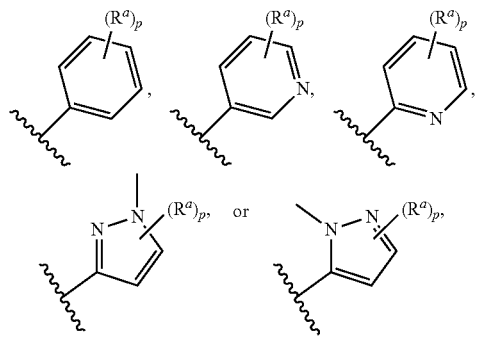

wherein:
each instance of $R^a$ is independently hydrogen, halogen, $-NO_2$, $-CN$, $-OR^{D4}$, $-N(R^{D4})_2$, $-C(=O)R^{D4}$, $-C(=O)OR^{D4}$, $-C(=O)N(R^{D4})_2$, $-OC(=O)R^{D4}$, $-OC(=O)OR^{D4}$, $-N(R^{D4})C(=O)R^{D4}$, $-OC(=O)N(R^{D4})_2$, $-N(R^{D4})C(=O)OR^{D4}$, $-S(=O)_2R^{D4}$, $-S(=O)_2OR^{D4}$, $-OS(=O)_2R^{D4}$, $-S(=O)_2N(R^{D4})_2$, or $-N(R^{D4})S(=O)_2R^{D4}$, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted 3- to 6-membered heterocyclyl, substituted or unsubstituted $C_{5-10}$ aryl, substituted or unsubstituted 5- to 10-membered heteroaryl;

each instance of $R^{D4}$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted 3- to 6-membered heterocyclyl, substituted or unsubstituted $C_{5-10}$ aryl, substituted or unsubstituted 5- to 10-membered heteroaryl, an oxygen protecting group when attached to oxygen, a nitrogen protecting group when attached to nitrogen, or two R$^{D4}$ groups are taken with the intervening atoms to form a substituted or unsubstituted heterocyclic ring; and p is an integer selected from 0 to 5.

In some embodiments, R$^{55a}$ and R$^{55b}$ is independently hydrogen, substituted or unsubstituted alkyl,

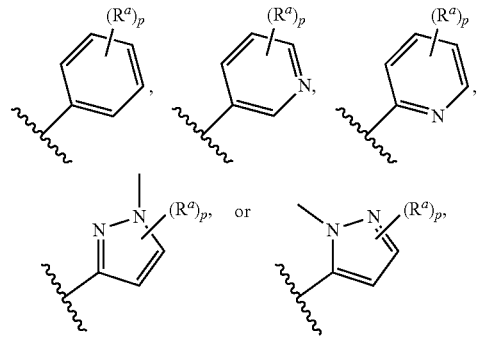

wherein:
each instance of R$^a$ is independently hydrogen, halogen, —CN, —OR$^{D4}$, —N(R$^{D4}$)$_2$, -substituted or unsubstituted C$_{1-6}$ alkyl, substituted or unsubstituted 3- to 6-membered heterocyclyl, substituted or unsubstituted 5- to 10-membered heteroaryl;

each instance of R$^{D4}$ is independently hydrogen or substituted or unsubstituted C$_{1-6}$ alkyl; and p is an integer selected from 0 to 2.

In some embodiments, when R$^a$ is substituted 3- to 6-membered heterocyclyl or substituted 5- to 10-membered heteroaryl, the 3- to 6-membered heterocyclyl or 5- to 10-membered heteroaryl are substituted with one or more of C$_{1-6}$alkyl, cyano, or oxo. For example, in certain embodiments, R$^a$ is a 5- to 6-membered heterocyclyl substituted with one or more of C$_{1-6}$alkyl, cyano, or oxo or a 5- to 6-membered heteroaryl substituted with one or more of C$_{1-6}$alkyl, cyano, or oxo.

In some embodiments, R$^{55a}$ and R$^{55b}$ join together with the intervening atoms to form a substituted or unsubstituted heterocyclyl or substituted or unsubstituted heteroaryl.

In some embodiments, R$^{55a}$ and R$^{55b}$ join together with the intervening atoms to form a substituted or unsubstituted heterocyclyl or substituted or unsubstituted heteroaryl selected from the group consisting of:

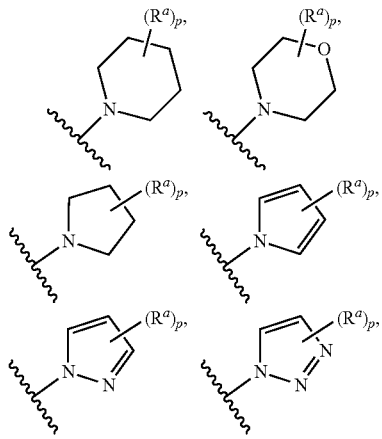

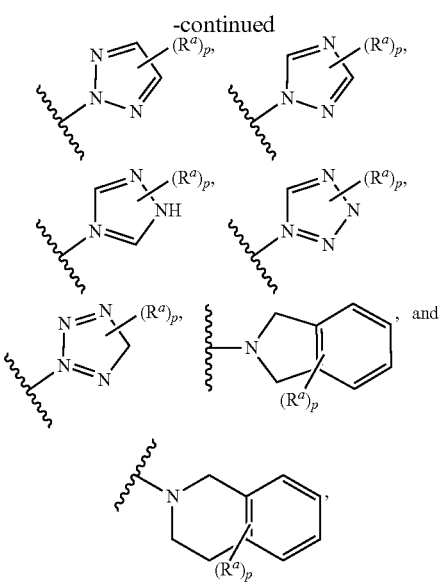

wherein:
each instance of R$^a$ is independently hydrogen, oxo, halogen, —NO$_2$, —CN, —OR$^{D4}$, —N(R$^{D4}$)$_2$, —C(=O)R$^{D4}$, —C(=O)OR$^{D4}$, —C(=O)N(R$^{D4}$)$_2$, —OC(=O)R$^{D4}$, —OC(=O)OR$^{D4}$, —N(R$^{D4}$)C(=O)R$^{D4}$, —OC(=O)N(R$^{D4}$)$_2$, —N(R$^{D4}$)C(=O)OR$^{D4}$, —S(=O)$_2$R$^{D4}$, —S(=O)$_2$OR$^{D4}$, —OS(=O)$_2$R$^{D4}$, —S(=O)$_2$N(R$^{D4}$)$_2$, or —N(R$^{D4}$)S(=O)$_2$R$^{D4}$, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ carbocyclyl, substituted or unsubstituted 3- to 6-membered heterocyclyl, substituted or unsubstituted C$_{5-10}$ aryl, substituted or unsubstituted 5- to 10-membered heteroaryl;

each instance of R$^{D4}$ is independently hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ carbocyclyl, substituted or unsubstituted 3- to 6-membered heterocyclyl, substituted or unsubstituted C$_{5-10}$ aryl, substituted or unsubstituted 5- to 10-membered heteroaryl, an oxygen protecting group when attached to oxygen, a nitrogen protecting group when attached to nitrogen, or two R$^{D4}$ groups are taken with the intervening atoms to form a substituted or unsubstituted heterocyclic ring; and p is an integer selected from 0 to 10.

In some embodiments, R$^{55a}$ and R$^{55b}$ join together with the intervening atoms to form a substituted or unsubstituted heterocyclyl or substituted or unsubstituted heteroaryl selected from the group consisting of:

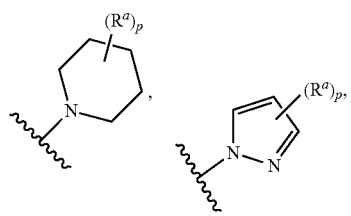

-continued

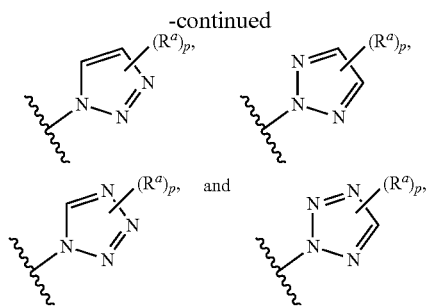

wherein:
each instance of $R^a$ is independently hydrogen, oxo, halogen, —NO$_2$, —CN, —OR$^{D4}$, —N(R$^{D4}$)$_2$, —C(=O)R$^{D4}$, —C(=O)OR$^{D4}$, —C(=O)N(R$^{D4}$)$_2$, —OC(=O)R$^{D4}$, —OC(=O)OR$^{D4}$, —N(R$^{D4}$)C(=O)R$^{D4}$, —OC(=O)N(R$^{D4}$)$_2$, —N(R$^{D4}$)C(=O)OR$^{D4}$, —S(=O)$_2$R$^{D4}$, —S(=O)$_2$OR$^{D4}$, —OS(=O)$_2$R$^{D4}$, —S(=O)$_2$N(R$^{D4}$)$_2$, or —N(R$^{D4}$)S(=O)$_2$R$^{D4}$, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ carbocyclyl, substituted or unsubstituted 3- to 6-membered heterocyclyl, substituted or unsubstituted C$_{5-10}$ aryl, substituted or unsubstituted 5- to 10-membered heteroaryl;
each instance of $R^{D4}$ is independently hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ carbocyclyl, substituted or unsubstituted 3- to 6-membered heterocyclyl, substituted or unsubstituted C$_{5-10}$ aryl, substituted or unsubstituted 5- to 10-membered heteroaryl, an oxygen protecting group when attached to oxygen, a nitrogen protecting group when attached to nitrogen, or two $R^{D4}$ groups are taken with the intervening atoms to form a substituted or unsubstituted heterocyclic ring; and
p is an integer selected from 0 to 10.

In some embodiments, $R^{55a}$ and $R^{55b}$ join together with the intervening atoms to form a substituted or unsubstituted heterocyclyl or substituted or unsubstituted heteroaryl selected from the group consisting of:

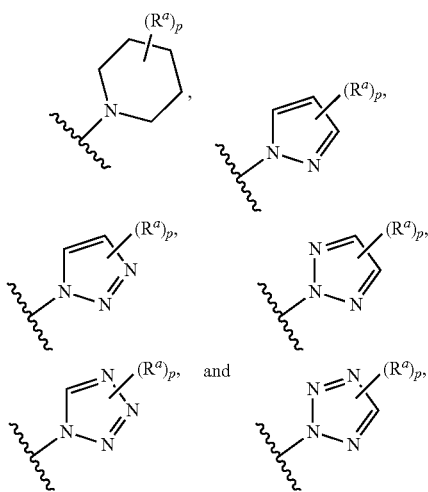

wherein:
each instance of $R^a$ is independently hydrogen, oxo, halogen, —CN, —OR$^{D4}$, —N(R$^{D4}$)$_2$, or substituted or unsubstituted C$_{1-6}$ alkyl;
each instance of $R^{D4}$ is independently hydrogen or substituted or unsubstituted C$_{1-6}$ alkyl; and
p is an integer selected from 0 to 2.

Groups $R^{1a}$ and $R^{1b}$

In some embodiments, $R^{1a}$ and $R^{1b}$ are each independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl.

In some embodiments, $R^{1a}$ and $R^{1b}$ are each independently hydrogen, substituted or unsubstituted carbocyclyl, substituted or unsubstituted heterocyclyl, substituted or unsubstituted aryl, substituted or unsubstituted heteroaryl.

In some embodiments, $R^{1a}$ and $R^{1b}$ are each independently substituted carbocyclyl, substituted heterocyclyl, substituted aryl, or substituted heteroaryl, wherein each is further substituted with substituted carbocyclyl, substituted heterocyclyl, substituted aryl, or substituted heteroaryl.

In some embodiments, $R^{1a}$ and $R^{1b}$ are each independently selected from the group consisting of:

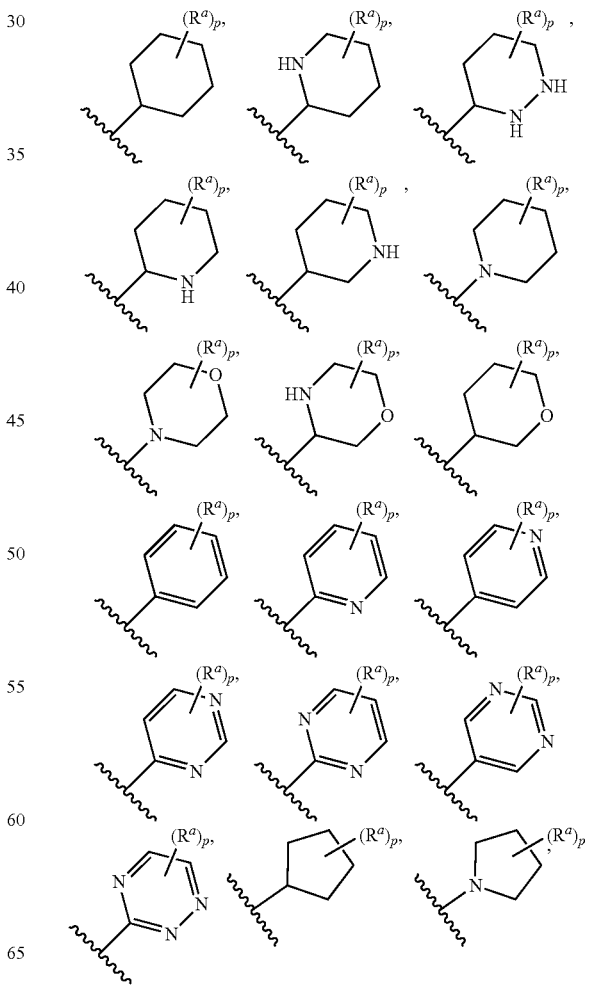

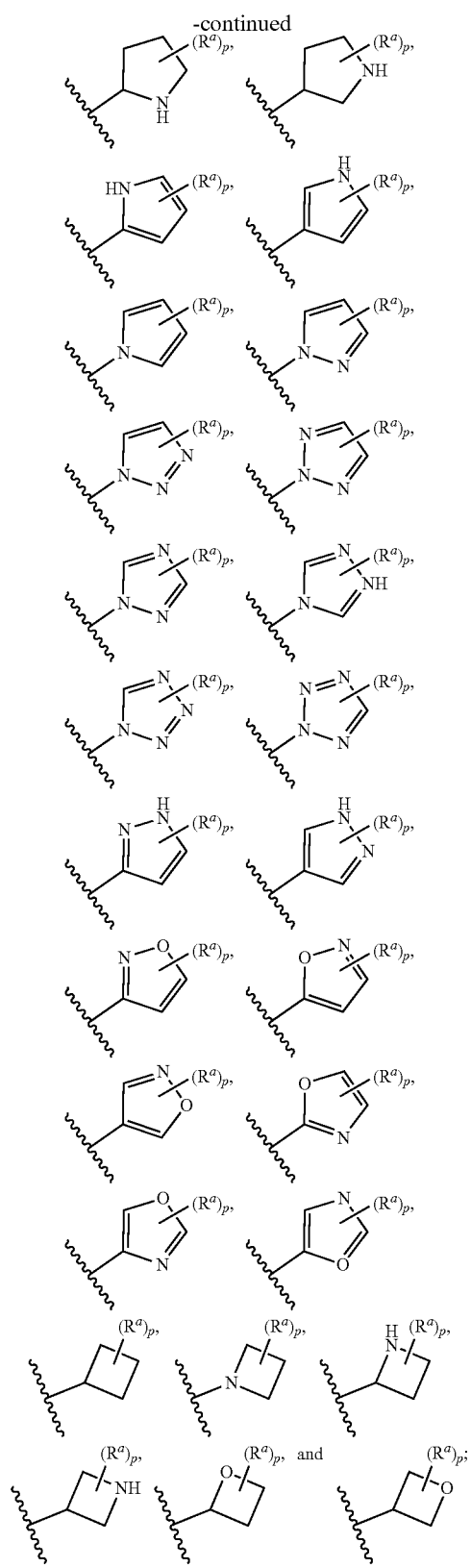

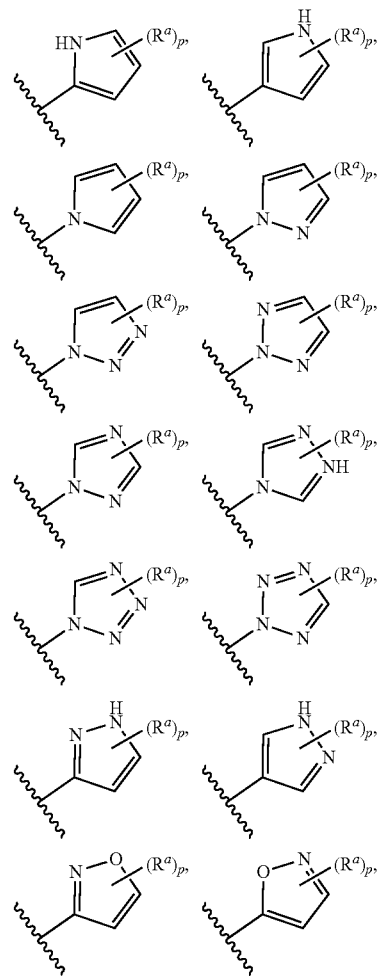

wherein:

each instance of $R^a$ is independently hydrogen, halogen, $-NO_2$, $-CN$, $-OR^{D4}$, $-N(R^{D4})_2$, $-C(=O)R^{D4}$, $-C(=O)OR^{D4}$, $-C(=O)N(R^{D4})_2$, $-OC(=O)R^{D4}$, $-OC(=O)OR^{D4}$, $-N(R^{D4})C(=O)R^{D4}$, $-OC(=O)N(R^{D4})_2$, $-N(R^{D4})C(=O)OR^{D4}$, $-S(=O)_2R^{D4}$, $-S(=O)_2OR^{D4}$, $-OS(=O)_2R^{D4}$, $-S(=O)_2N(R^{D4})_2$, or $-N(R^{D4})S(=O)_2R^{D4}$, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted 3- to 6-membered heterocyclyl, substituted or unsubstituted $C_{5-10}$ aryl, substituted or unsubstituted 5- to 10-membered heteroaryl;

each instance of $R^{D4}$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted 3- to 6-membered heterocyclyl, substituted or unsubstituted $C_{5-10}$ aryl, substituted or unsubstituted 5- to 10-membered heteroaryl, an oxygen protecting group when attached to oxygen, a nitrogen protecting group when attached to nitrogen, or two $R^{D4}$ groups are taken with the intervening atoms to form a substituted or unsubstituted heterocyclic ring; and p is an integer selected from 0 to 11.

In some embodiments, $R^{1a}$ and $R^{1b}$ are each independently selected from the group consisting of:

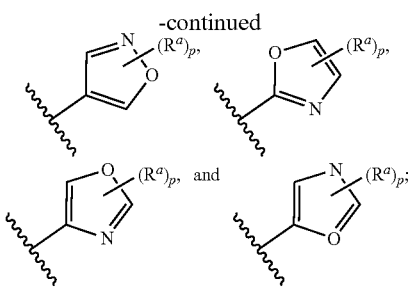

wherein:
each instance of $R^a$ is independently hydrogen, halogen, —NO$_2$, —CN, —OR$^{D4}$, —N(R$^{D4}$)$_2$, —C(=O)R$^{D4}$, —C(=O)OR$^{D4}$, —C(=O)N(R$^{D4}$)$_2$, —OC(=O)R$^{D4}$, —OC(=O)OR$^{D4}$, —N(R$^{D4}$)C(=O)R$^{D4}$, —OC(=O)N(R$^{D4}$)$_2$, —N(R$^{D4}$)C(=O)OR$^{D4}$, —S(=O)$_2$R$^{D4}$, —S(=O)$_2$OR$^{D4}$, —OS(=O)$_2$R$^{D4}$, —S(=O)$_2$N(R$^{D4}$)$_2$, or —N(R$^{D4}$)S(=O)$_2$R$^{D4}$, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted 3- to 6-membered heterocyclyl, substituted or unsubstituted $C_{5-10}$ aryl, substituted or unsubstituted 5- to 10-membered heteroaryl;
each instance of $R^{D4}$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted 3- to 6-membered heterocyclyl, substituted or unsubstituted $C_{5-10}$ aryl, substituted or unsubstituted 5- to 10-membered heteroaryl, an oxygen protecting group when attached to oxygen, a nitrogen protecting group when attached to nitrogen, or two $R^{D4}$ groups are taken with the intervening atoms to form a substituted or unsubstituted heterocyclic ring; and
p is an integer selected from 0 to 11.

In some embodiments, $R^{1a}$ and $R^{1b}$ are both hydrogen.

Groups $R^{2a}$ and $R^{2b}$

In some embodiments, $R^{2a}$ and $R^{2b}$ are each independently hydrogen, halogen, —CN, —NO$_2$, substituted or unsubstituted alkyl, substituted or unsubstituted alkenyl, substituted or unsubstituted alkynyl, —OR$^{E5}$, —OC(=O)R$^{E5}$, —OS(=O)$_2$OR$^{E5}$, —N(R$^{E5}$)$_2$, or —N(R$^{E5}$)C(=O)R$^{E5}$, —N(R$^{E5}$)S(=O)$_2$R$^{E5}$, —N(R$^{E5}$)S(=O)$_2$OR$^{E5}$; wherein each instance of $R^{E5}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two $R^{E5}$ groups are taken with the intervening atoms to form a substituted or unsubstituted heterocyclic ring.

In some embodiments, $R^{2a}$ and $R^{2b}$ are each independently hydrogen, halogen, —CN, —NO$_2$, —OR$^{F6}$, —OC(=O)R$^{F6}$, —N(R$^{F6}$)$_2$, or —N(R$^{F6}$)C(=O)R$^{F6}$; wherein each instance of $R^{F6}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, or two $R^{F6}$ groups are taken with the intervening atoms to form a substituted or unsubstituted heterocyclic ring.

In some embodiments, $R^{2a}$ and $R^{2b}$ are independently hydrogen, —OH, or substituted or unsubstituted $C_{1-6}$ alkyl.

In some embodiments, each of $R^{2a}$ and $R^{2b}$ are independently hydrogen, —OH, $C_{1-6}$ alkyl, $C_{1-6}$ haloalkyl, $C_{1-6}$ alkoxy, or $C_{1-6}$ alkoxyhalo.

In some embodiments, $R^{2a}$ and $R^{2b}$ are independently —CH$_3$, —CH$_2$CH$_3$, —OH, —OCH$_3$, or —CH(CH$_3$)$_2$.

In some embodiments, $R^{2a}$ and $R^{2b}$ are both hydrogen.

In some embodiments, $R^{2a}$ and $R^{2b}$ are joined to form an oxo (=O) group.

Group $R^{3a}$

In some embodiments, $R^{3a}$ is substituted or unsubstituted alkyl, substituted or unsubstituted alkenyl, or substituted or unsubstituted alkynyl.

In some embodiments, $R^{3a}$ is hydrogen, substituted or unsubstituted alkyl, or substituted or unsubstituted carbocyclyl.

In some embodiments, $R^{3a}$ is substituted or unsubstituted carbocyclyl, substituted or unsubstituted heterocyclyl, substituted or unsubstituted aryl, or substituted or unsubstituted heteroaryl.

In some embodiments, $R^{3a}$ is substituted or unsubstituted carbocyclyl. In some embodiments, $R^{3a}$ is cyclopropyl.

In some embodiments, $R^{3a}$ is substituted or unsubstituted alkyl or substituted or unsubstituted carbocyclyl.

In some embodiments, $R^{3a}$ is substituted or unsubstituted $C_{1-6}$alkyl.

In some embodiments, $R^3$ is substituted alkyl. In some embodiments, $R^{3a}$ is unsubstituted alkyl.

In some embodiments, $R^{3a}$ is methyl, ethyl, n-propyl, iso-propyl, n-butyl, iso-butyl. In some embodiments, $R^{3a}$ is methyl. In some embodiments, $R^{3a}$ is ethyl. In some embodiments, $R^{3a}$ is propyl. In some embodiments, $R^{3a}$ is n-butyl.

In some embodiments, $R^{3a}$ is substituted $C_{1-6}$ alkyl.

In some embodiments, $R^{3a}$ is —CH$_2$C$_3$H$_5$.

In some embodiments, $R^{3a}$ is $C_{1-6}$ alkoxy.

In some embodiments, $R^{3a}$ is —CH$_2$OCH$_3$, —CH$_2$CH$_2$OCH$_3$, or —CH$_2$CH$_2$CH$_2$OCH$_3$.

In some embodiments, $R^{3a}$ is —CH$_2$OCH$_2$CH$_3$, —CH$_2$CH$_2$OCH$_2$CH$_3$, or —CH$_2$CH$_2$CH$_2$OCH$_2$CH$_3$.

In some embodiments, $R^{3a}$ is —CH$_2$OCH$_2$CH$_2$CH$_3$, —CH$_2$CH$_2$OCH$_2$CH$_2$CH$_3$, or —CH$_2$CH$_2$CH$_2$OCH$_2$CH$_2$CH$_3$.

Groups $R^{4a}$ and $R^{4b}$

In some embodiments, $R^{4a}$ and $R^{4b}$ is each independently hydrogen, halogen, —CN, —NO$_2$, substituted or unsubstituted alkyl, substituted or unsubstituted alkenyl, substituted or unsubstituted alkynyl, —OR$^{E5}$, —OC(=O)R$^{E5}$, —OS(=O)$_2$OR$^{E5}$, —N(R$^{E5}$)$_2$, or —N(R$^{E5}$)C(=O)R$^{E5}$, —N(R$^{E5}$)S(=O)$_2$R$^{E5}$, —N(R$^{E5}$)S(=O)$_2$OR$^{E5}$; wherein each instance of $R^{E5}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two $R^{E5}$ groups are taken with the intervening atoms to form a substituted or unsubstituted heterocyclic ring.

In some embodiments, $R^{4a}$ and $R^{4b}$ is each independently hydrogen, halogen, —CN, —NO$_2$, —OR$^{F6}$, —OC(=O)R$^{F6}$, —N(R$^{F6}$)$_2$, or —N(R$^{F6}$)C(=O)R$^{F6}$; wherein each instance of $R^{F6}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, or two $R^{F6}$ groups are taken with the intervening atoms to form a substituted or unsubstituted heterocyclic ring.

In some embodiments, $R^{4a}$ and $R^{4b}$ are independently hydrogen, —OH, or substituted or unsubstituted $C_{1-6}$ alkyl.

In some embodiments, each of $R^{4a}$ and $R^{4b}$ are independently hydrogen, —OH, $C_{1-6}$ alkyl, $C_{1-6}$ haloalkyl, $C_{1-6}$ alkoxy, or $C_{1-6}$ alkoxyhalo.

In some embodiments, $R^{4a}$ and $R^{4b}$ are independently —$CH_3$, —$CH_2CH_3$, —OH, —$OCH_3$, or —$CH(CH_3)_2$.

In some embodiments, $R^{4a}$ and $R^{4b}$ are both hydrogen.

In some embodiments, $R^{4a}$ and $R^{4b}$ are joined to form an oxo (=O) group.

Group $R^5$

In some embodiments, $R^5$ is hydrogen or methyl in the cis position, relative to $R^{19}$ or in the trans position, relative to $R^{19}$.

In some embodiments, $R^5$ is hydrogen in the cis position, relative to $R^{19}$ or in the trans position, relative to $R^{19}$. In some embodiments, $R^5$ is hydrogen in the cis position, relative to $R^{19}$. In some embodiments, $R^5$ is hydrogen in the trans position, relative to $R^{19}$.

In some embodiments, $R^5$ is methyl in the cis position, relative to $R^{19}$ or in the trans position, relative to $R^{19}$. In some embodiments, $R^5$ is methyl in the cis position, relative to $R^{19}$. In some embodiments, $R^5$ is methyl in the trans position, relative to $R^{19}$.

Group $R^{6a}$ and $R^{6b}$

In some embodiments, $R^{6a}$ and $R^{6b}$ is independently hydrogen, halogen, substituted or unsubstituted alkyl, substituted or unsubstituted alkenyl, or substituted or unsubstituted alkynyl.

In some embodiments, $R^{6a}$ and $R^{6b}$ is independently hydrogen or substituted alkyl.

In some embodiments, $R^{6a}$ and $R^{6b}$ is independently hydrogen or unsubstituted alkyl.

In some embodiments, $R^{6a}$ is halogen or alkyl and $R^{6b}$ is hydrogen.

In some embodiments, $R^{6a}$ and $R^{6b}$ are both halogen.

In some embodiments, $R^{6a}$ and $R^{6b}$ are both unsubstituted alkyl.

In some embodiments, $R^{6a}$ is hydrogen and $R^{6b}$ is absent.

Groups $R^{7a}$ and $R^{7b}$

In some embodiments, $R^{7a}$ and $R^{7b}$ is each independently hydrogen, halogen, —CN, —$NO_2$, substituted or unsubstituted alkyl, substituted or unsubstituted alkenyl, substituted or unsubstituted alkynyl, —$OR^{E5}$, —$OC(=O)R^{E5}$, —$OS(=O)_2OR^{E5}$, —$N(R^{E5})_2$, or —$N(R^{E5})C(=O)R^{E5}$, —$N(R^{E5})S(=O)_2R^{E5}$, —$N(R^{E5})S(=O)_2OR^{E5}$; wherein each instance of $R^{E5}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two $R^{E5}$ groups are taken with the intervening atoms to form a substituted or unsubstituted heterocyclic ring.

In some embodiments, $R^{7a}$ and $R^{7b}$ is each independently hydrogen, halogen, —CN, —$NO_2$, —$OR^{F6}$, —$OC(=O)R^{F6}$, —$N(R^{F6})_2$, or —$N(R^{F6})C(=O)R^{F6}$; wherein each instance of $R^{F6}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, or two $R^{F6}$ groups are taken with the intervening atoms to form a substituted or unsubstituted heterocyclic ring.

In some embodiments, $R^{7a}$ and $R^{7b}$ are independently hydrogen, —OH, or substituted or unsubstituted $C_{1-6}$ alkyl.

In some embodiments, each of $R^{7a}$ and $R^{7b}$ are independently hydrogen, —OH, $C_{1-6}$ alkyl, $C_{1-6}$ haloalkyl, $C_{1-6}$ alkoxy, or $C_{1-6}$ alkoxyhalo.

In some embodiments, $R^{7a}$ and $R^{7b}$ are independently —$CH_3$, —$CH_2CH_3$, —OH, —$OCH_3$, or —$CH(CH_3)_2$.

In some embodiments, $R^{7a}$ and $R^{7b}$ are both hydrogen.

In some embodiments, $R^{7a}$ and $R^{7b}$ are joined to form an oxo (=O) group.

Groups $R^{11a}$ and $R^{11b}$

In some embodiments, $R^{11a}$ and $R^{11b}$ is each independently hydrogen, halogen, —CN, —$NO_2$, substituted or unsubstituted alkyl, substituted or unsubstituted alkenyl, substituted or unsubstituted alkynyl, —$OR^{E5}$, —$OC(=O)R^{E5}$, —$OS(=O)_2OR^{E5}$, —$N(R^{E5})_2$, or —$N(R^{E5})C(=O)R^{E5}$, —$N(R^{E5})S(=O)_2R^{E5}$, —$N(R^{E5})S(=O)_2OR^{E5}$; wherein each instance of $R^{E5}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two $R^{E5}$ groups are taken with the intervening atoms to form a substituted or unsubstituted heterocyclic ring.

In some embodiments, $R^{11a}$ and $R^{11b}$ is each independently hydrogen, halogen, —CN, —$NO_2$, —$OR^{F6}$, —$OC(=O)R^{F6}$, —$N(R^{F6})_2$, or —$N(R^{F6})C(=O)R^{F6}$; wherein each instance of $R^{F6}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, or two $R^{F6}$ groups are taken with the intervening atoms to form a substituted or unsubstituted heterocyclic ring.

In some embodiments, $R^{11a}$ and $R^{11b}$ are independently hydrogen, —OH, or substituted or unsubstituted $C_{1-6}$ alkyl.

In some embodiments, each of $R^{11a}$ and $R^{11b}$ are independently hydrogen, —OH, $C_{1-6}$ alkyl, $C_{1-6}$ haloalkyl, $C_{1-6}$ alkoxy, or $C_{1-6}$ alkoxyhalo.

In some embodiments, $R^{11a}$ and $R^{11b}$ are independently hydrogen, —OH, or $R^{11a}$ and $R^{11b}$ are joined to form an oxo (=O) group.

In some embodiments, $R^{11a}$ and $R^{11b}$ are independently —$CH_3$, —$CH_2CH_3$, —OH, —$OCH_3$, or —$CH(CH_3)_2$.

In some embodiments, $R^{11a}$ and $R^{11b}$ are both hydrogen.

In some embodiments, $R^{11a}$ and $R^{11b}$ are joined to form an oxo (=O) group.

Groups $R^{12a}$ and $R^{12b}$

In some embodiments, $R^{12a}$ and $R^{12b}$ is each independently hydrogen, halogen, —CN, —$NO_2$, substituted or unsubstituted alkyl, substituted or unsubstituted alkenyl, substituted or unsubstituted alkynyl, —$OR^{E5}$, —$OC(=O)R^{E5}$, —$OS(=O)_2OR^{E5}$, —$N(R^{E5})_2$, or —$N(R^{E5})C(=O)R^{E5}$, —$N(R^{E5})S(=O)_2R^{E5}$, —$N(R^{E5})S(=O)_2OR^{E5}$; wherein each instance of $R^{E5}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two $R^{E5}$ groups are taken with the intervening atoms to form a substituted or unsubstituted heterocyclic ring.

In some embodiments, $R^{12a}$ and $R^{12b}$ is each independently hydrogen, halogen, —CN, —$NO_2$, —$OR^{F6}$, —$OC(=O)R^{F6}$, —$N(R^{F6})_2$, or —$N(R^{F6})C(=O)R^{F6}$; wherein each instance of $R^{F6}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, or two $R^{F6}$ groups are taken with the intervening atoms to form a substituted or unsubstituted heterocyclic ring.

In some embodiments, $R^{12a}$ and $R^{12b}$ are independently hydrogen, —OH, or substituted or unsubstituted $C_{1-6}$ alkyl.

In some embodiments, each of $R^{12a}$ and $R^{12b}$ are independently hydrogen, —OH, $C_{1-6}$ alkyl, $C_{1-6}$ haloalkyl, $C_{1-6}$ alkoxy, or $C_{1-6}$ alkoxyhalo.

In some embodiments, $R^{12a}$ and $R^{12b}$ are independently —CH$_3$, —CH$_2$CH$_3$, —OH, —OCH$_3$, or —CH(CH$_3$)$_2$.

In some embodiments, $R^{12a}$ and $R^{12b}$ are both hydrogen.

In some embodiments, $R^{12a}$ and $R^{12b}$ are joined to form an oxo (=O) group.

Group $R^{19}$

In some embodiments, $R^{19}$ is hydrogen, substituted or unsubstituted alkyl, substituted or unsubstituted alkenyl, or substituted or unsubstituted alkynyl.

In some embodiments, $R^{19}$ is hydrogen or substituted or unsubstituted alkyl.

In some embodiments, $R^{19}$ is substituted alkyl.

In some embodiments, $R^{19}$ is substituted $C_2$-$C_6$ alkyl.

In some embodiments, $R^{19}$ is —CH$_2$OCH$_3$. In some embodiments, $R^{19}$ is —CH$_2$OCH$_2$CH$_3$.

In some embodiments, $R^{19}$ is hydrogen or unsubstituted alkyl.

In some embodiments, $R^{19}$ is unsubstituted alkyl.

In some embodiments, $R^{19}$ is unsubstituted $C_1$-$C_6$ alkyl.

In some embodiments, $R^{19}$ is methyl. In some embodiments, $R^{19}$ is ethyl.

In some embodiments, $R^{19}$ is hydrogen or substituted or unsubstituted $C_1$-$C_6$ alkyl.

In some embodiments, $R^{19}$ is hydrogen, methyl, ethyl, or methoxymethyl.

Group $R^{18}$

In some embodiments, $R^{18}$ is substituted alkyl. In some embodiments, $R^{18}$ is substituted $C_{1-6}$alkyl.

In some embodiments, $R^{18}$ is unsubstituted alkyl. In some embodiments, $R^{18}$ is unsubstituted $C_1$-$C_6$ alkyl. In some embodiments, $R^{18}$ is methyl. In some embodiments, $R^{18}$ is ethyl.

Group $R^D$

In some embodiments, $R^D$ is independently hydrogen, halogen, —CN, —NO$_2$, oxo, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{C3}$, —N(R$^{C3}$)$_2$, —SR$^{C3}$, —C(=O)R$^{C3}$, —C(=O)OR$^{C3}$, —C(=O)SR$^{C3}$, —C(=O)N(R$^{C3}$)$_2$, —OC(=O)R$^{C3}$, —OC(=O)OR$^{C3}$, —OC(=O)N(R$^{C3}$)$_2$, —OC(=O)SR$^{C3}$, —OS(=O)$_2$R$^{C3}$, —OS(=O)$_2$OR$^{C3}$, —OS(=O)$_2$N(R$^{C3}$)$_2$, —N(R$^{C3}$)C(=O)R$^{C3}$, —N(R$^{C3}$)C(=NR$^{C3}$)R$^{C3}$, —N(R$^{C3}$)C(=O)OR$^{C3}$, —N(R$^{C3}$)C(=O)N(R$^{C3}$)$_2$, —N(R$^{C3}$)C(=NR$^{C3}$) N(R$^{C3}$)$_2$, —N(R$^{C3}$)S(=O)$_2$R$^{C3}$, —N(R$^{C3}$)S(=O)$_2$OR$^{C3}$, —N(R$^{C3}$)S(=O)$_2$N(R$^{C3}$)$_2$, —SC(=O)R$^{C3}$, —SC(=O)OR$^{C3}$, —SC(=O)SR$^{C3}$, —SC(=O)N(R$^{C3}$)$_2$, —S(=O)$_2$R$^{C3}$, —S(=O)$_2$OR$^{C3}$, or —S(=O)$_2$N(R$^{C3}$)$_2$, wherein each instance of R$^{C3}$ is independently selected from hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted carbocyclyl, or substituted or unsubstituted heterocyclyl.

In some embodiments, $R^D$ is each independently hydrogen, halogen, —CN, —NO$_2$, oxo, hydroxy, substituted or unsubstituted alkyl, substituted or unsubstituted alkenyl, substituted or unsubstituted alkynyl, or substituted or unsubstituted carbocyclyl.

In some embodiments, $R^D$ is each independently hydrogen, oxo, substituted or unsubstituted alkyl, hydroxy, or substituted or unsubstituted carbocyclyl.

In some embodiments, $R^D$ is independently hydrogen, oxo, methyl, ethyl, hydroxy, or cyclopropyl.

Groups $R^{15a}$ and $R^{15b}$

In some embodiments, each of $R^{15a}$ and $R^{15b}$ is each independently hydrogen, halogen, —CN, —NO$_2$, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{C3}$, —N(R$^{C3}$)$_2$, —SR$^{C3}$, —C(=O)R$^{C3}$, —C(=O)OR$^{C3}$, —C(=O)SR$^{C3}$, —C(=O)N(R$^{C3}$)$_2$, —OC(=O)R$^{C3}$, —OC(=O)OR$^{C3}$, —OC(=O)N(R$^{C3}$)$_2$, —OC(=O)SR$^{C3}$, —OS(=O)$_2$R$^{C3}$, —OS(=O)$_2$OR$^{C3}$, —OS(=O)$_2$N(R$^{C3}$)$_2$, —N(R$^{C3}$)C(=O)R$^{C3}$, —N(R$^{C3}$)C(=NR$^{C3}$)R$^{C3}$, —N(R$^{C3}$)C(=O)OR$^{C3}$, —N(R$^{C3}$)C(=O)N(R$^{C3}$)$_2$, —N(R$^{C3}$)C(=NR$^{C3}$) N(R$^{C3}$)$_2$, —N(R$^{C3}$)S(=O)$_2$R$^{C3}$, —N(R$^{C3}$)S(=O)$_2$OR$^{C3}$, —N(R$^{C3}$)S(=O)$_2$N(R$^{C3}$)$_2$, —SC(=O)R$^{C3}$, —SC(=O)OR$^{C3}$, —SC(=O)SR$^{C3}$, —SC(=O)N(R$^{C3}$)$_2$, —S(=O)$_2$R$^{C3}$, —S(=O)$_2$OR$^{C3}$, or —S(=O)$_2$N(R$^{C3}$)$_2$, wherein each instance of R$^{C3}$ is independently selected from hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted carbocyclyl, or substituted or unsubstituted heterocyclyl, an oxygen protecting group when attached to oxygen, a nitrogen protecting group when attached to nitrogen, a sulfur protecting group when attached to sulfur, or two R$^{C3}$ groups are taken with the intervening atoms to form a substituted or unsubstituted heterocyclic ring; or $R^{15a}$ and $R^{15b}$ are joined to form an oxo (=O) group.

In some embodiments, each of $R^{15a}$ and $R^{15b}$ is each independently hydrogen, halogen, —CN, substituted or unsubstituted alkyl, or substituted or unsubstituted carbocyclyl.

In some embodiments, $R^{15a}$ and $R^{15b}$ are both hydrogen.

In some embodiments, $R^{15a}$ and $R^{15b}$ are joined to form an oxo (=O) group.

In some embodiments, $R^{15a}$ and $R^{15b}$ is each independently hydrogen, substituted or unsubstituted alkyl, or substituted or unsubstituted carbocyclyl. In some embodiments, $R^{15a}$ and $R^{15b}$ is each independently hydrogen, unsubstituted alkyl, or unsubstituted carbocyclyl. In some embodiments, $R^{15a}$ and $R^{15b}$ is each independently hydrogen, methyl, or cyclopropyl.

Groups $R^{16a}$ and $R^{16b}$

In some embodiments, each of $R^{16a}$ and $R^{16b}$ is each independently hydrogen, halogen, —CN, —NO$_2$, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{C3}$, —N(R$^{C3}$)$_2$, —SR$^{C3}$, —C(=O)R$^{C3}$, —C(=O)OR$^{C3}$, —C(=O)SR$^{C3}$, —C(=O)N(R$^{C3}$)$_2$, —OC(=O)R$^{C3}$, —OC(=O)OR$^{C3}$, —OC(=O)N(R$^{C3}$)$_2$, —OC(=O)SR$^{C3}$, —OS(=O)$_2$R$^{C3}$, —OS(=O)$_2$OR$^{C3}$, —OS(=O)$_2$N(R$^{C3}$)$_2$, —N(R$^{C3}$)C(=O)R$^{C3}$, —N(R$^{C3}$)C(=NR$^{C3}$)R$^{C3}$, —N(R$^{C3}$)C(=O)OR$^{C3}$, —N(R$^{C3}$)C(=O)N(R$^{C3}$)$_2$, —N(R$^{C3}$)C(=NR$^{C3}$) N(R$^{C3}$)$_2$, —N(R$^{C3}$)S(=O)$_2$R$^{C3}$, —N(R$^{C3}$)S(=O)$_2$OR$^{C3}$, —N(R$^{C3}$)S(=O)$_2$N(R$^{C3}$)$_2$, —SC(=O)R$^{C3}$, —SC(=O)OR$^{C3}$, —SC(=O)SR$^{C3}$, —SC(=O)N(R$^{C3}$)$_2$, —S(=O)$_2$R$^{C3}$, —S(=O)$_2$OR$^{C3}$, or —S(=O)$_2$N(R$^{C3}$)$_2$, wherein each instance of R$^{C3}$ is independently selected from hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted carbocyclyl, or substituted or unsubstituted heterocyclyl, an oxygen protecting group when attached to oxygen, a nitrogen protecting group when attached to nitrogen, a sulfur protecting group when attached to sulfur, or two $R^{C3}$ groups are taken with the intervening atoms to form a substituted or unsubstituted heterocyclic ring; or $R^{16a}$ and $R^{16b}$ are joined to form an oxo (=O) group.

In some embodiments, each of $R^{16a}$ and $R^{16b}$ is each independently hydrogen, halogen, —CN, substituted or unsubstituted alkyl, or substituted or unsubstituted carbocyclyl.

In some embodiments, $R^{16a}$ and $R^{16b}$ are both hydrogen.

In some embodiments, $R^{16a}$ and $R^{16b}$ are joined to form an oxo (=O) group.

L

In some embodiments, L is

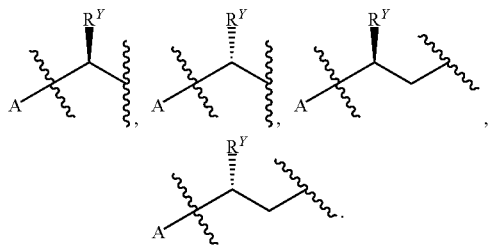

In some embodiments, $R^Y$ is hydrogen, unsubstituted $C_{1-6}$alkyl, unsubstituted $C_{1-6}$haloalkyl, or cyano. In certain embodiments, R is hydrogen, methyl, ethyl, —CF$_3$, or cyano.

In some embodiments, L is

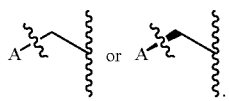

In some embodiments, L is

In some embodiments, L is

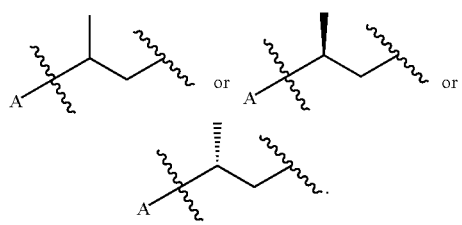

In some embodiments, L is

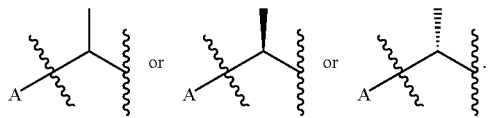

In some embodiments, L is

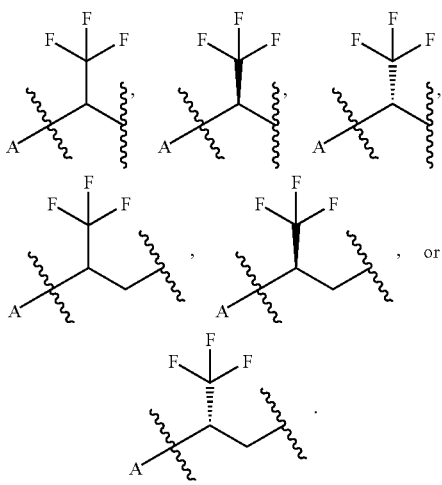

In some embodiments, L is

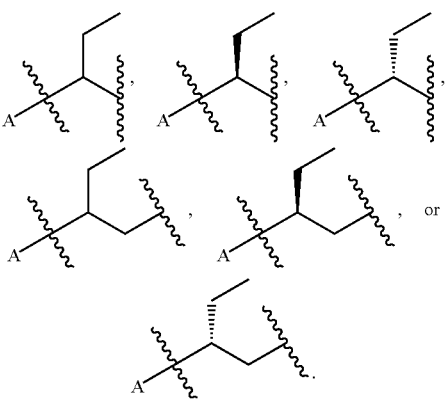

X

In some embodiments, X is —NC(O)($R^{55a}$).
In some embodiments, X is —N($R^{55a}$)($R^{5b}$).
In some embodiments, X is —C(O)N($R^{55a}$)($R^{5b}$).
In some embodiments, X is $R^{55c}$.

Group $R^{55c}$

In some embodiments, $R^{55c}$ is substituted or unsubstituted phenyl or carbon-bound substituted or unsubstituted heteroaryl containing at least one nitrogen in the heteroaryl ring.

In some embodiments, $R^{55c}$ is substituted or unsubstituted phenyl or carbon-bound substituted or unsubstituted heteroaryl selected from the group consisting of pyridyl, isothiazolyl, thiazolyl, pyrimidyl, pyrazinyl, and oxazolyl.

In some embodiments, $R^{55c}$ is selected from the group consisting of:

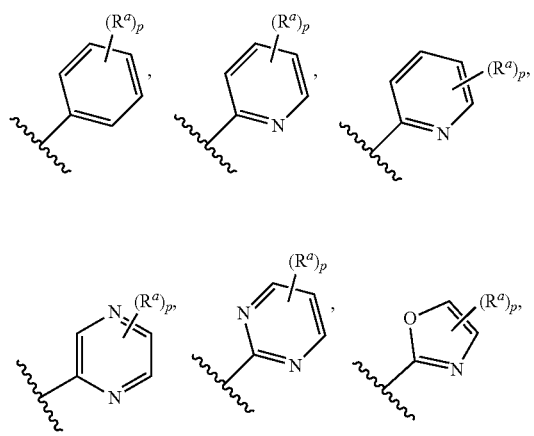

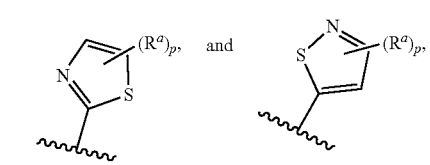

wherein:
each instance of $R^a$ is independently hydrogen, halogen, —CN, —OR$^{D4}$, —N(R$^{D4}$)$_2$, —C(=O)R$^{D4}$, —C(=O)OR$^{D4}$, or substituted or unsubstituted $C_{1-6}$ alkyl;
each instance of $R^{D4}$ is independently hydrogen or substituted or unsubstituted $C_{1-6}$ alkyl; and
p is an integer selected from 0 to 2.

In some embodiments, the compound is a compound of Formula (I-b), (I-c), (I-d), (I-e), (I-l), (I-m), (I-n), or (I-p):

(I-b)

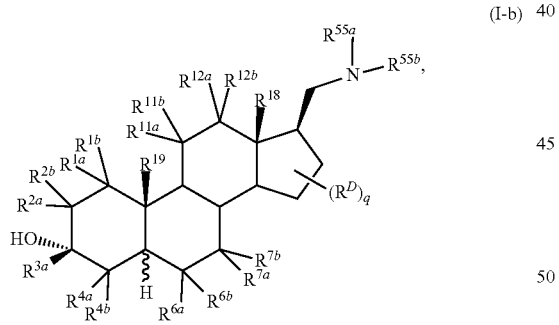

(I-c)

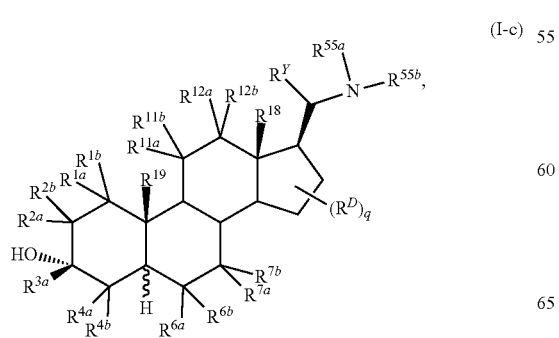

(I-d)

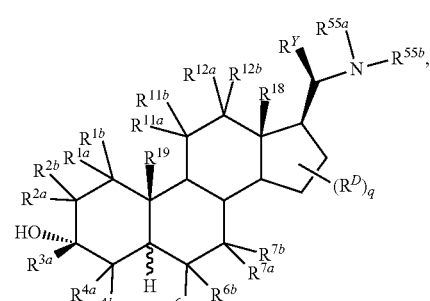

(I-e)

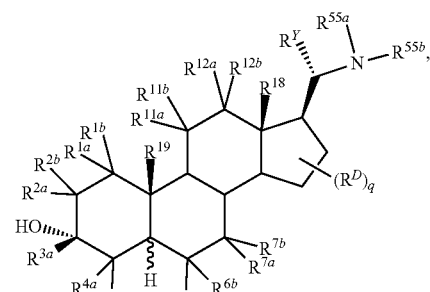

(I-l)

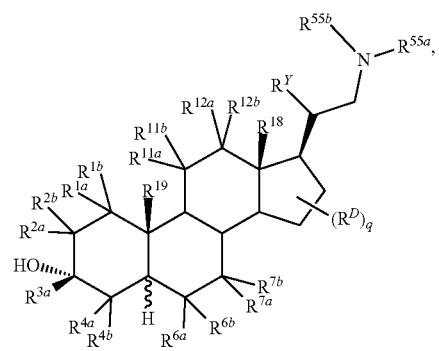

(I-m)

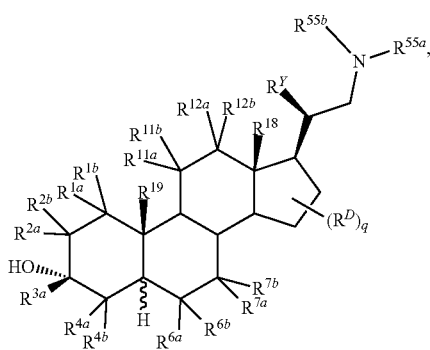

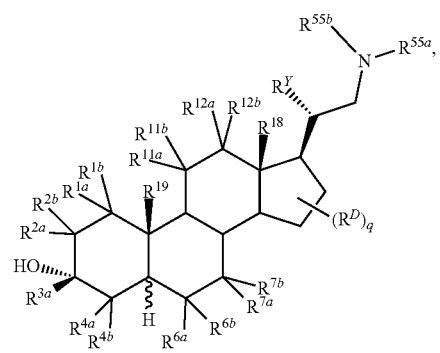
(I-n)
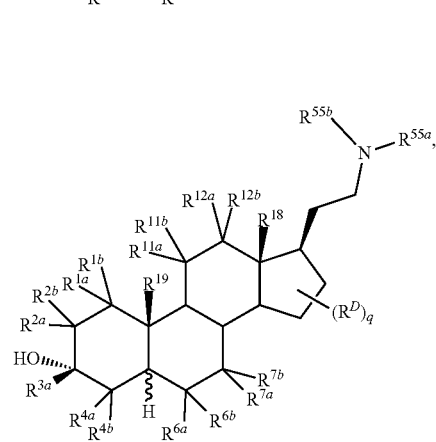
(I-p)
or a pharmaceutically acceptable salt thereof.
In some embodiments, the compound is a compound of Formula (I-f), (I-g), or (I-h):
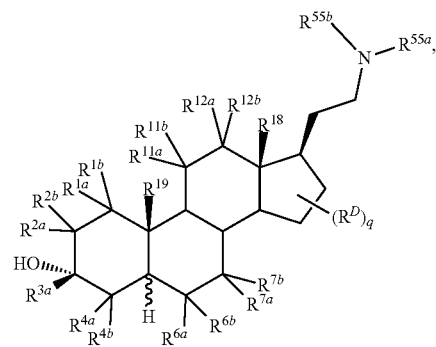
(I-f)
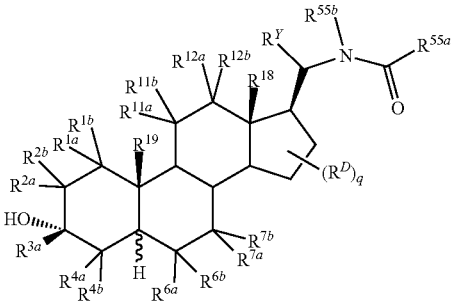
(I-g)
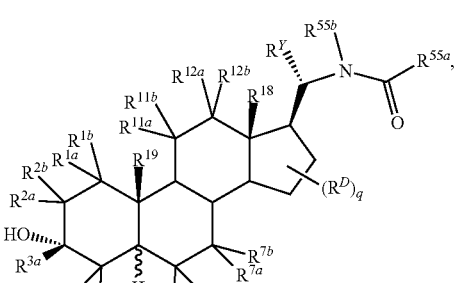
(I-h)
or a pharmaceutically acceptable salt thereof.
In some embodiments, the compound is a compound of Formula (I-i), (I-j), or (I-k):
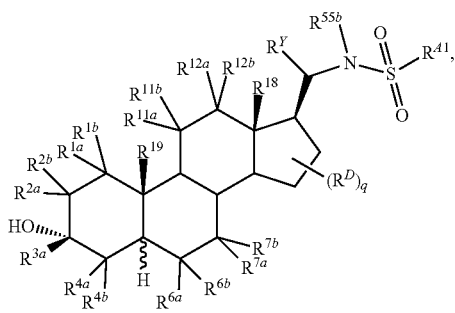
(I-i)
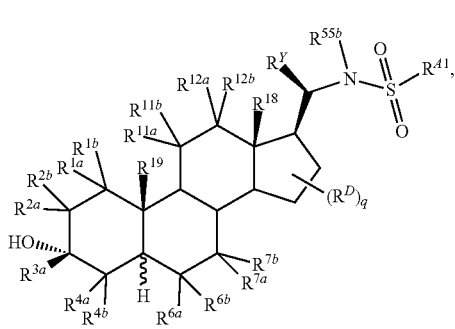
(I-j)
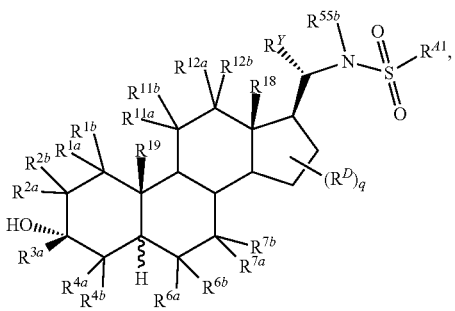
(I-k)
or a pharmaceutically acceptable salt thereof.
In some embodiments, the compound is a compound of Formula (I-o):

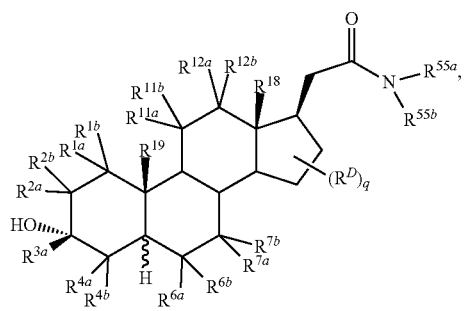
(I-o)

or a pharmaceutically acceptable salt thereof.

In some embodiments, the compound is a compound of Formula (I-qq), (I-q), (I-s), (I-t), or (I-u):

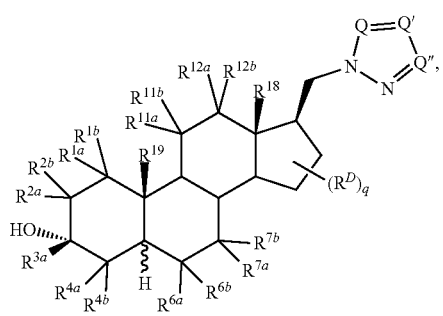
(I-qq)

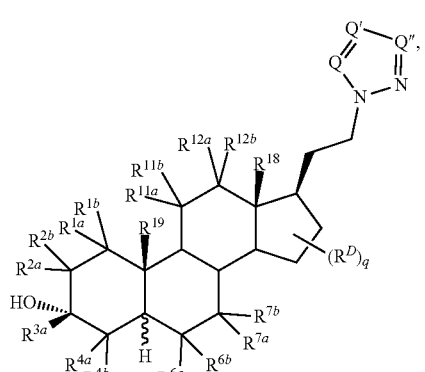
(I-q)

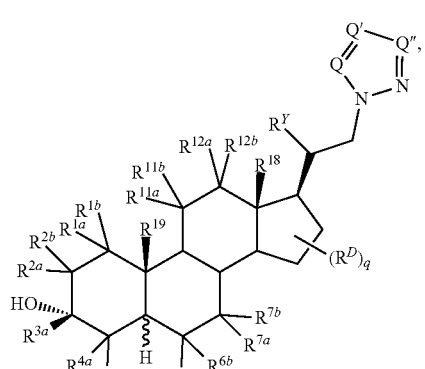
(I-s)

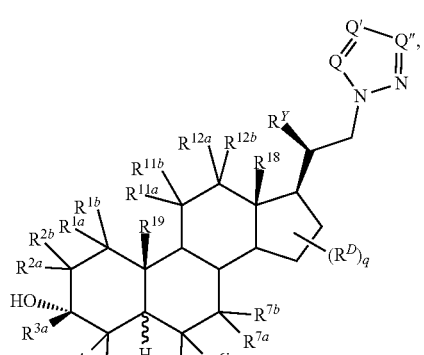
(I-t)

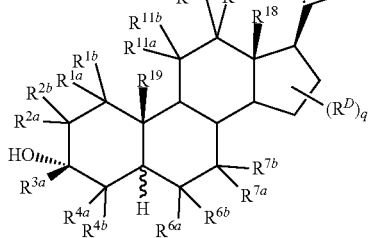
(I-u)

or a pharmaceutically acceptable salt thereof, wherein

Q, Q', and Q" are each independently $CR^w$ or N;

$R^w$ is hydrogen, cyano, —$NH_2$, or substituted or unsubstituted alkyl; and at least one of Q, Q', and Q" is $CR^w$.

In some embodiments, the compound is a compound of Formula (I-r):

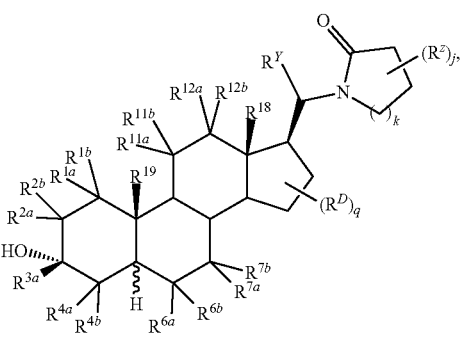
(I-r)

or a pharmaceutically acceptable salt thereof, wherein k is an integer 1 or 2;

$R^z$ is substituted or unsubstituted alkyl or substituted or unsubstituted aryl; or two $R^z$s on adjacent carbons combine with the intervening atoms to form a substituted or unsubstituted aryl; and j is an integer 0-6.

In some embodiments, the compound is a compound of Formula (I-v), (I-w), or (I-x):

(I-v)
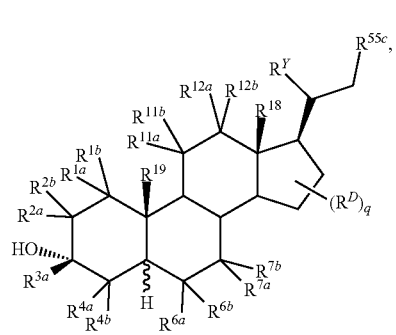
(I-w)
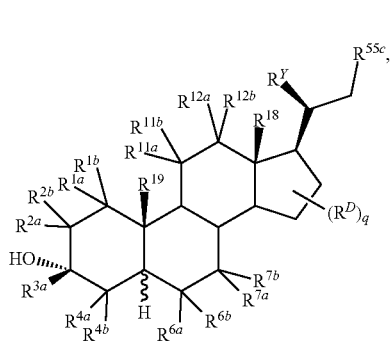
(I-x)
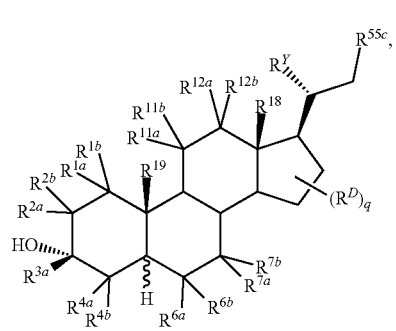
or a pharmaceutically acceptable salt thereof.
In some embodiments, the compound is a compound of Formula (I-Ib), (I-Ic), (I-Id), (I-Ie), (I-Il), (I-Im), (I-In), (I-Ip1), or (I-Ip2):
(I-Ib)
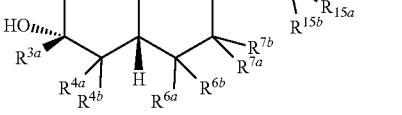
(I-Ic)
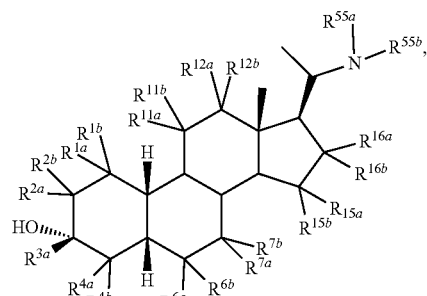
(I-Id)
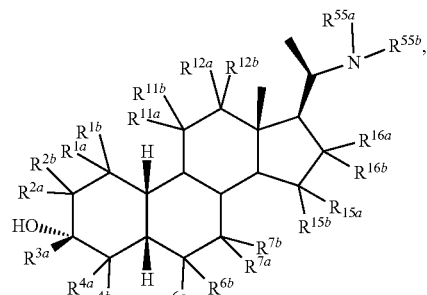
(I-Ie)
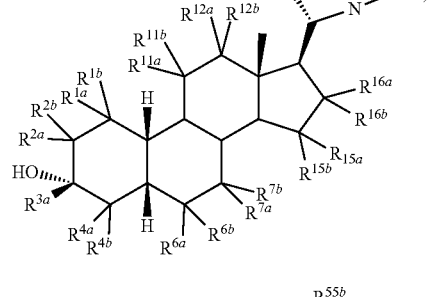
(I-Il)
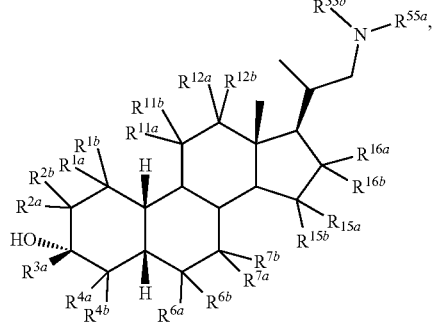
(I-Im)
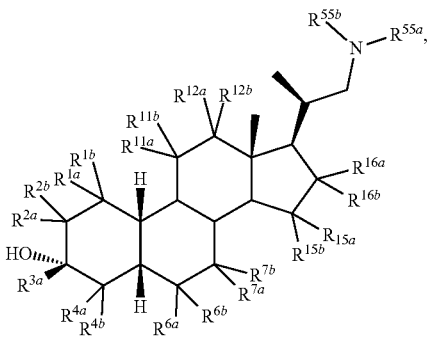

(I-In)
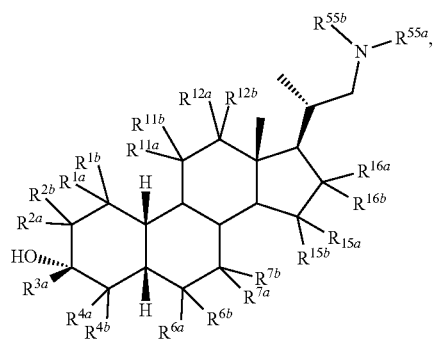
(I-Ip1)
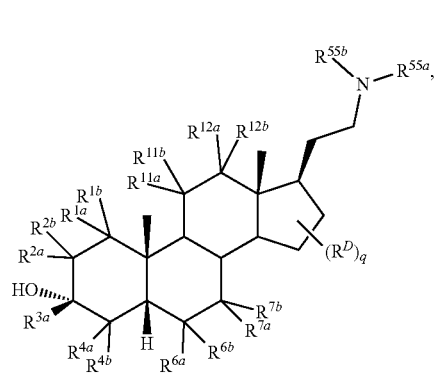
(I-Ip2)
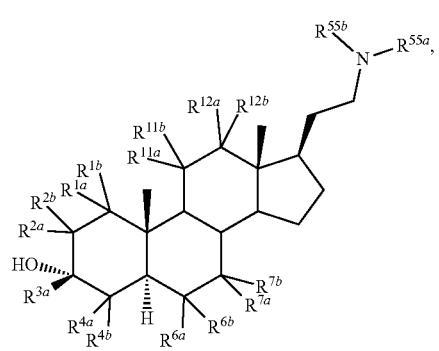
or a pharmaceutically acceptable salt thereof.
In some embodiments, the compound is a compound of Formula (I-If), (I-Ig), or (I-Ih):
(I-If)
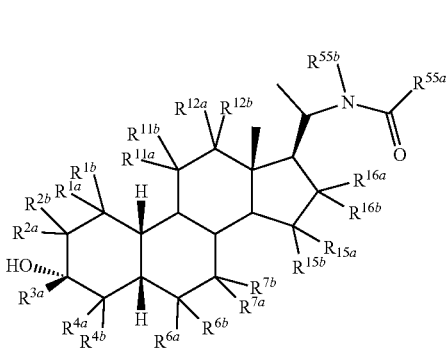
(I-Ig)
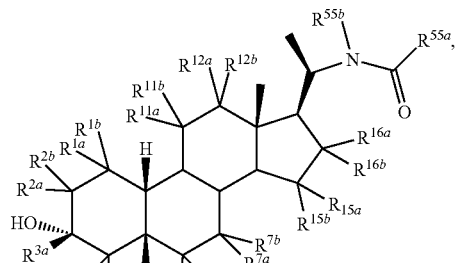
(I-Ih)
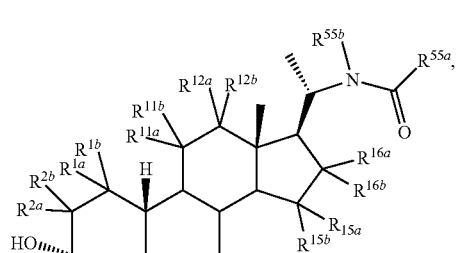
or a pharmaceutically acceptable salt thereof.
In some embodiments, the compound is a compound of Formula (I-Ii), (I-Ij), or (I-Ik):
(I-Ii)
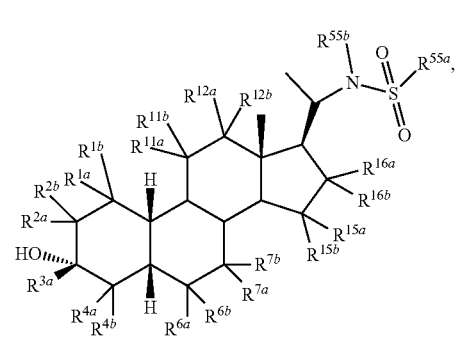
(I-Ij)
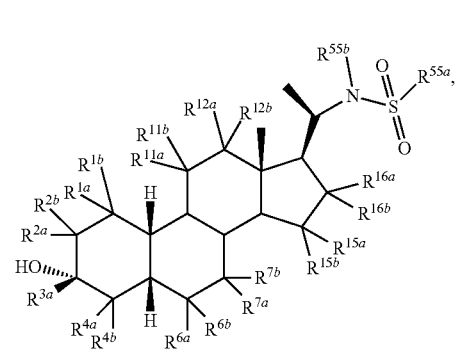

(I-Ik)
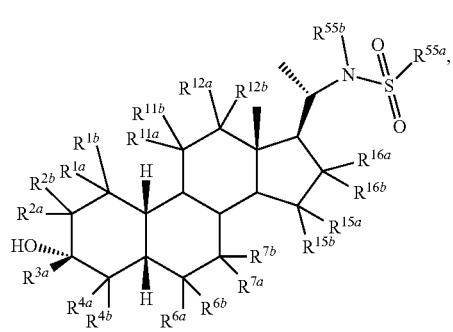
or a pharmaceutically acceptable salt thereof.
In some embodiments, the compound is a compound of Formula (I-Io1) or (I-Io2):
(I-Io1)
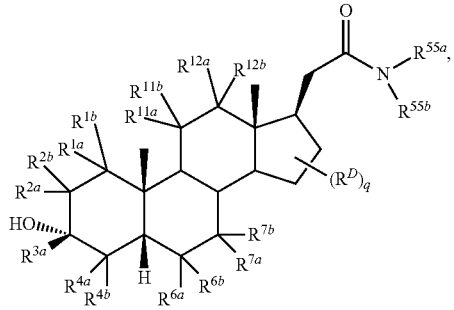
(I-Io2)
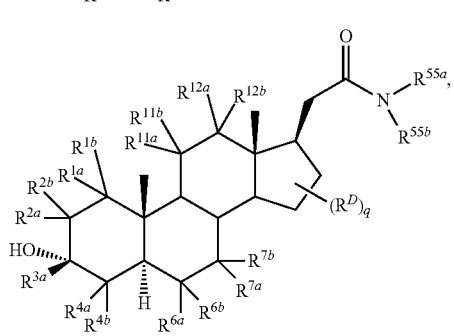
or a pharmaceutically acceptable salt thereof.
In some embodiments, the compound is a compound of Formula (I-Iqq), (I-Iq1), (I-Iq2), (I-It1), (I-It2), (I-Iu1), or (I-Iu2):
(I-Iqq)
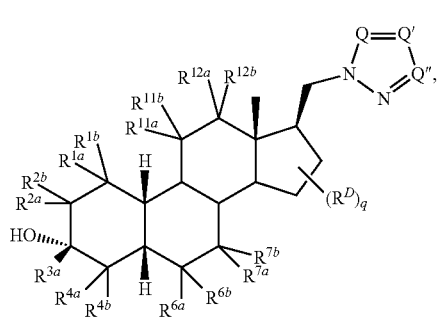
(I-Iq1)
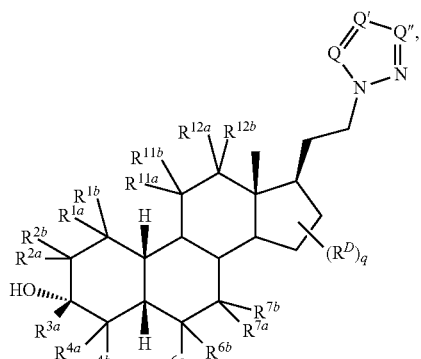
(I-Iq2)
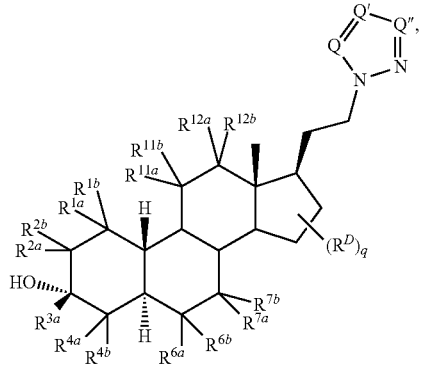
(I-It1)
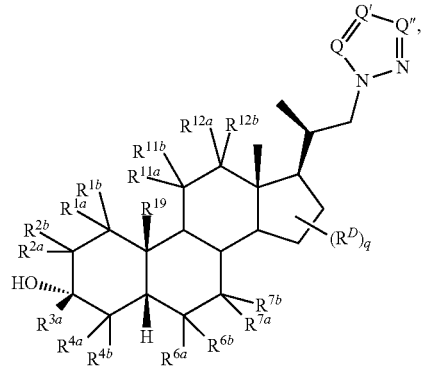
(I-It2)
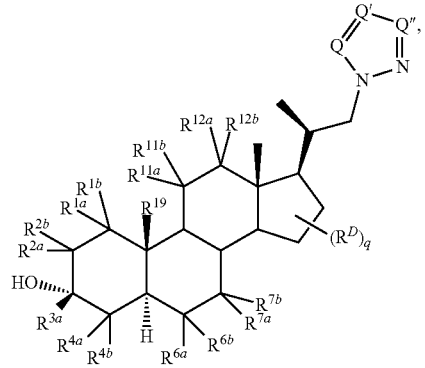

(I-Iu1)

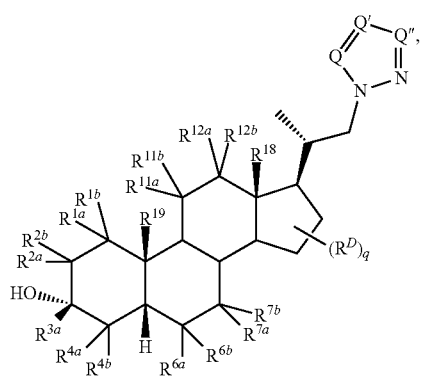

(I-Ir1)

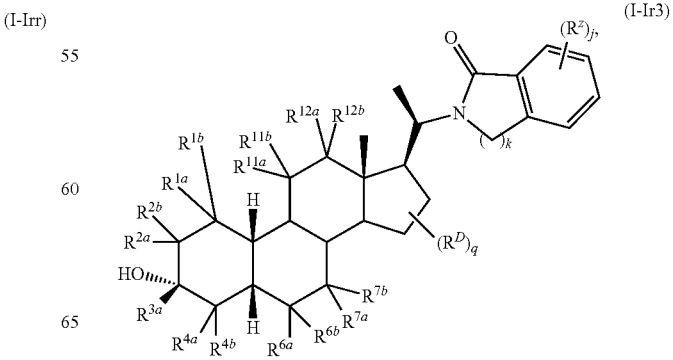

(I-Iu2)

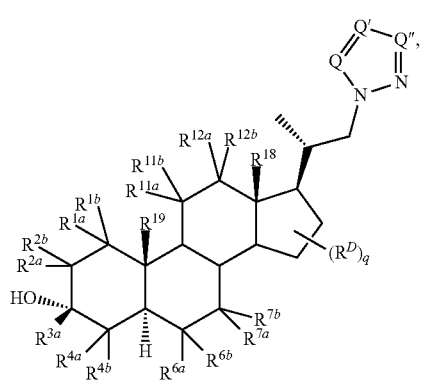

or a pharmaceutically acceptable salt thereof, wherein

Q, Q', and Q" are each independently $CR^w$ or N;

$R^w$ is hydrogen, cyano, —$NH_2$, or substituted or unsubstituted alkyl; and at least one of Q, Q', and Q" is $CR^w$.

In some embodiments, the compound is a compound of Formula (I-Irr), (I-Ir1) or (I-Ir2):

(I-Irr)

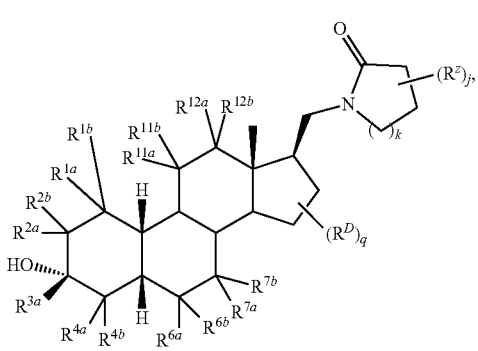

or a pharmaceutically acceptable salt thereof, wherein k is an integer 1 or 2;

$R^z$ is substituted or unsubstituted alkyl or substituted or unsubstituted aryl; or two $R^z$s on adjacent carbons combine with the intervening atoms to form a substituted or unsubstituted aryl; and j an integer 0-6.

In some embodiments, the compound is a compound of Formula (I-Ir3) or (I-Ir4):

(I-Ir3)

-continued

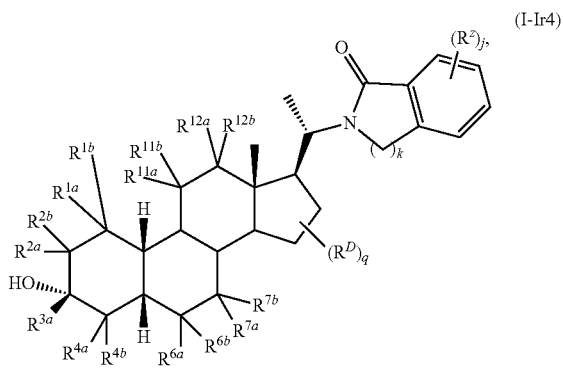
(I-Ir4)

or a pharmaceutically acceptable salt thereof, wherein
k is an integer 1 or 2;
$R^{z'}$ is substituted or unsubstituted alkyl or cyano; and
j' an integer 0-4.

In some embodiments, the compound is a compound of Formula (I-Iw1), (I-Iw2), (I-Ix1), or (I-Ix2):

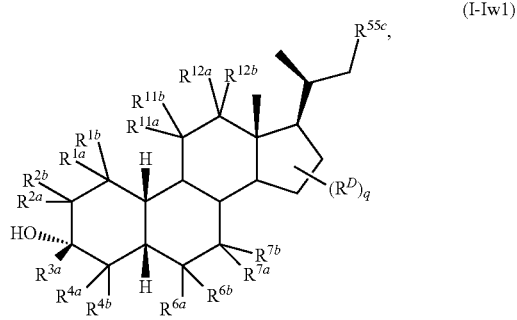
(I-Iw1)

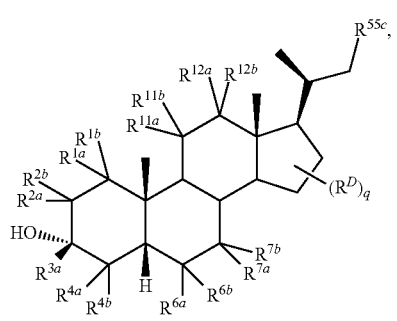
(I-Iw2)

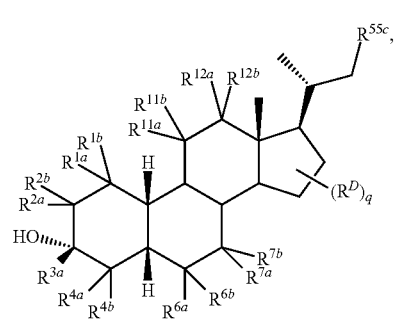
(I-Ix1)

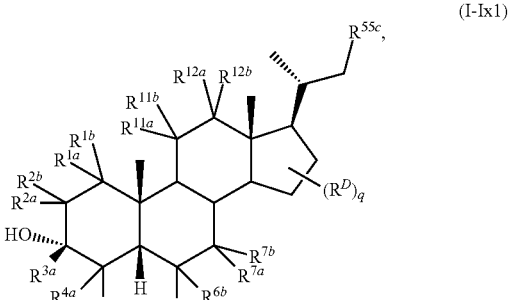
(I-Ix1)

or a pharmaceutically acceptable salt thereof.

It should be appreciated that the stereochemistry at C17 could be depicted in any of the following but equivalent ways:

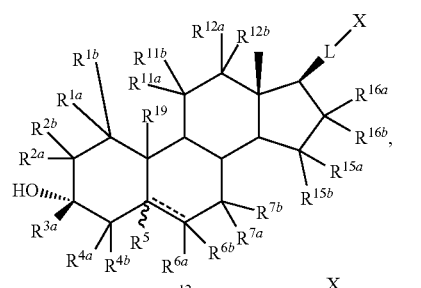

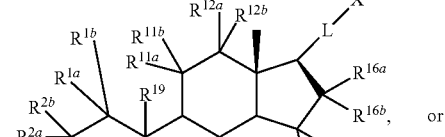
or

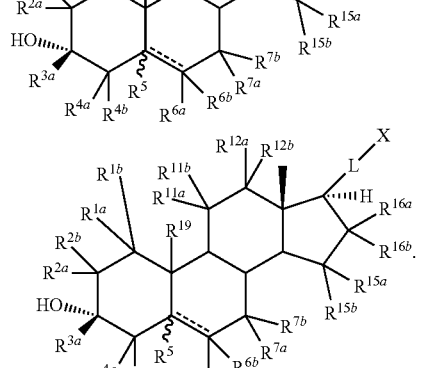

Compounds of the present invention as described herein, act, in certain embodiments, as $GABA_A$ receptor modulators. In certain embodiments, the compounds described herein can act as positive allosteric modulators of the GABA receptor e.g., of the $GABA_A$ receptor.

In one embodiment, the compounds described herein (e.g., a compound of Formula I or Table 1) exhibit higher selectivity for modulation of the α4β3δ configuration of $GABA_A$ receptor relative to the α1β2γ2 configuration of $GABA_A$ receptor.

As modulators of the excitability of the central nervous system (CNS), as mediated by their ability to modulate $GABA_A$ receptor, such compounds are expected to have CNS-activity.

In some embodiments, the compound is selected from the group consisting of the compounds identified in Table 1 below:

TABLE 1

| Example | STRUCTURE |
|---|---|
| 1 | 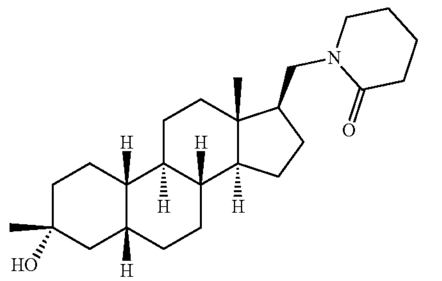 |
| 2 | 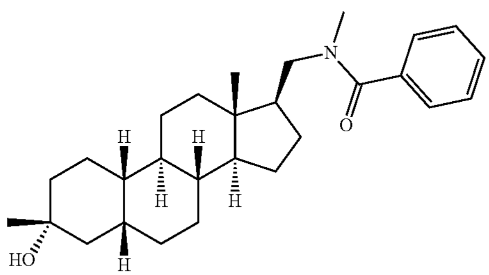 |
| 3 | 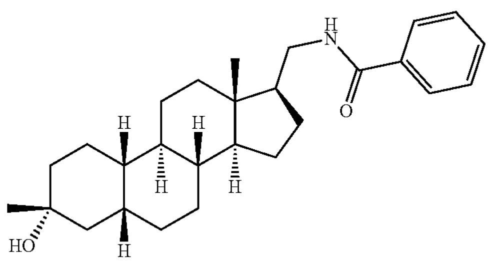 |
| 4 | 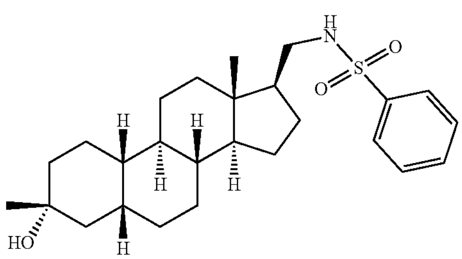 |
| 5 | 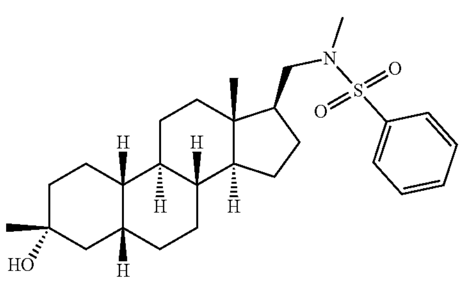 |

TABLE 1-continued
| Example | STRUCTURE |
|---|---|
| 6 | 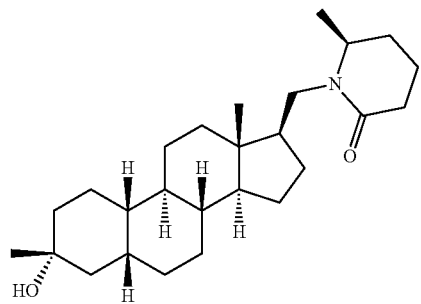 |
| 7 | 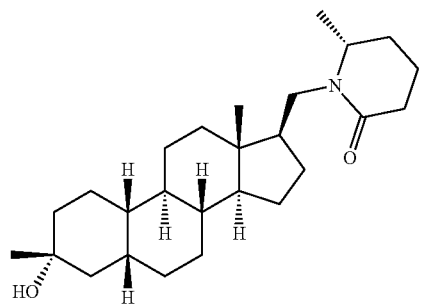 |
| 8 | 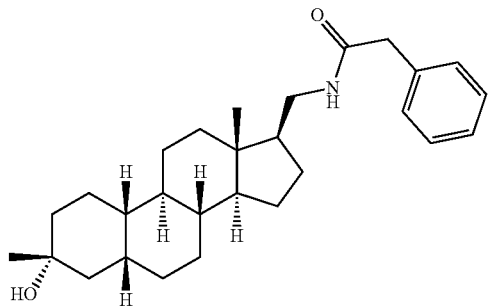 |
| 9 | 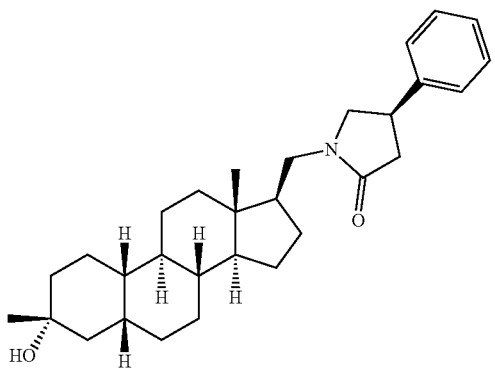 |

TABLE 1-continued

| Example | STRUCTURE |
|---|---|
| 10 | 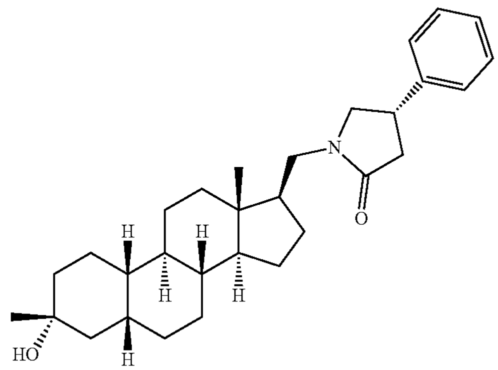 |
| 11 | 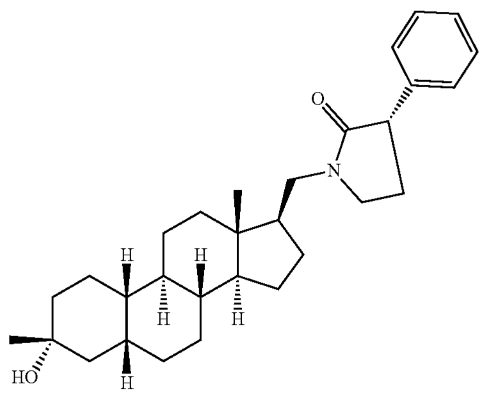 |
| 12 | 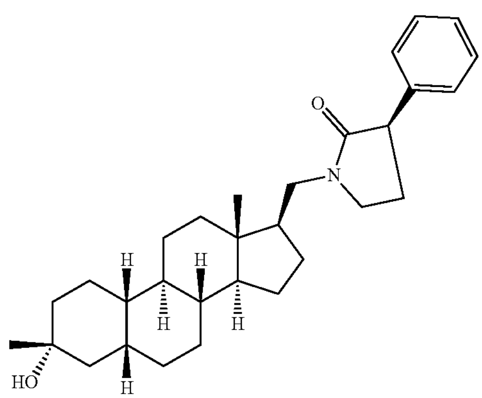 |
| 13 | 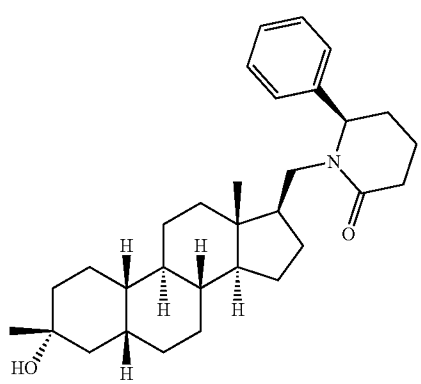 |

TABLE 1-continued
| Example | STRUCTURE |
|---|---|
| 14 | 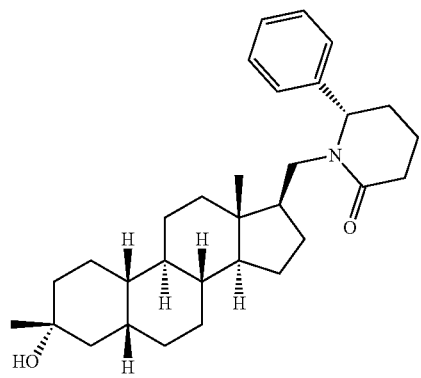 |
| 15 | 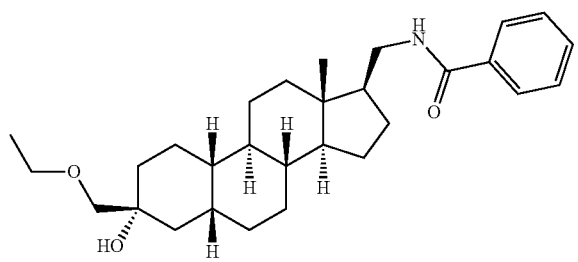 |
| 16 | 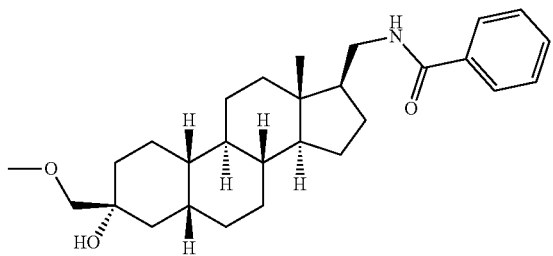 |
| 17 | 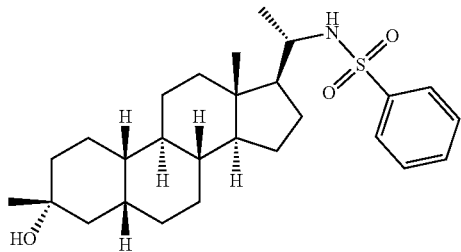 |
| 18 | 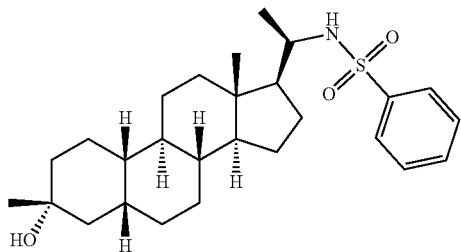 |

TABLE 1-continued
| Example | STRUCTURE |
|---|---|
| 19 | 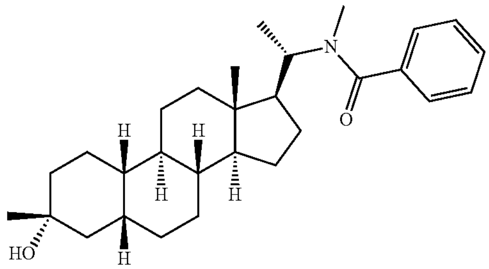 |
| 20 | 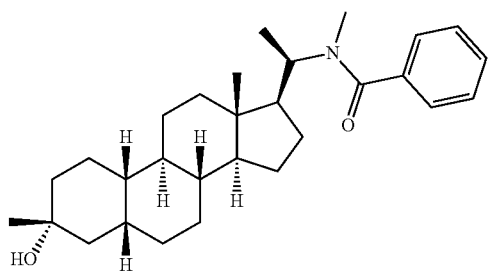 |
| 21 | 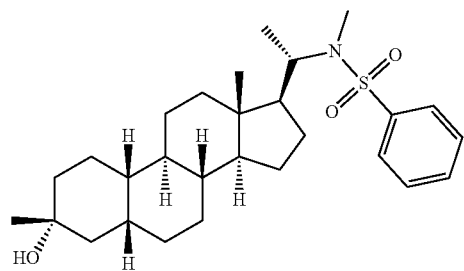 |
| 22 | 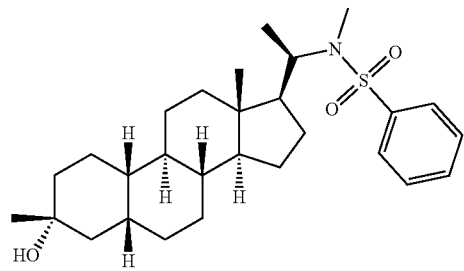 |
| 23 | 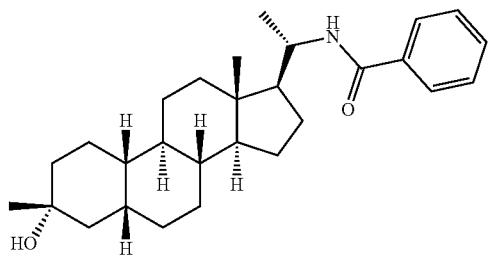 |

TABLE 1-continued

| Example | STRUCTURE |
|---|---|
| 24 | 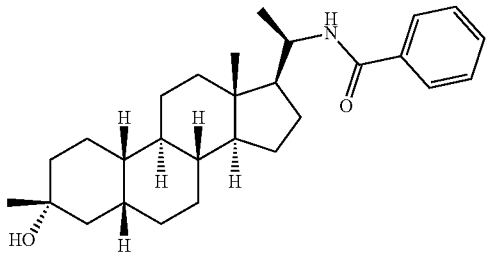 |
| 25 | 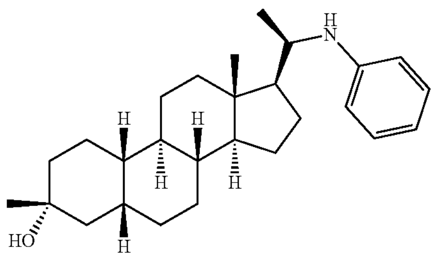 |
| 26 | 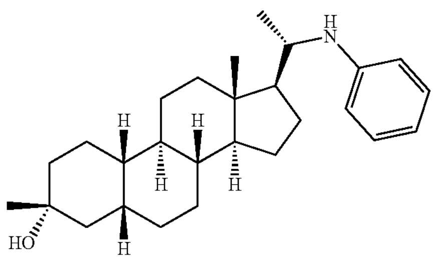 |
| 27 | 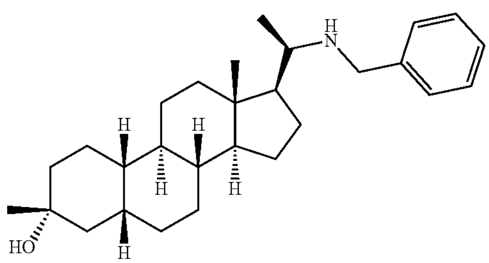 |
| 28 | 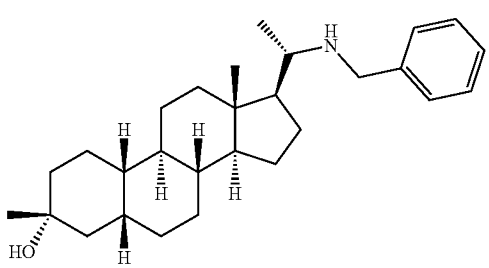 |
| 29 | 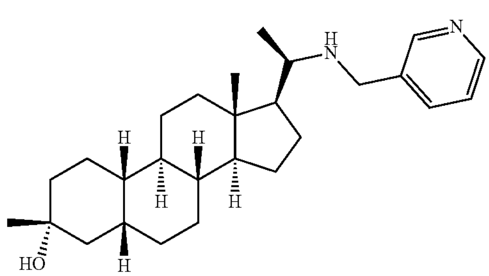 |

TABLE 1-continued
| Example | STRUCTURE |
|---|---|
| 30 | 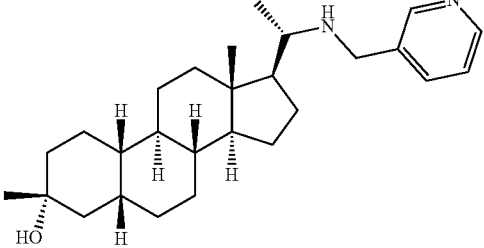 |
| 31 | 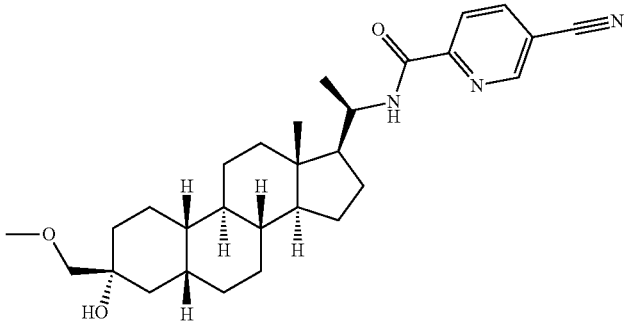 |
| 32 | 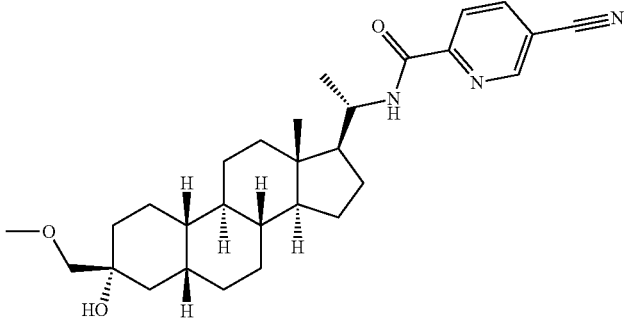 |
| 33 | 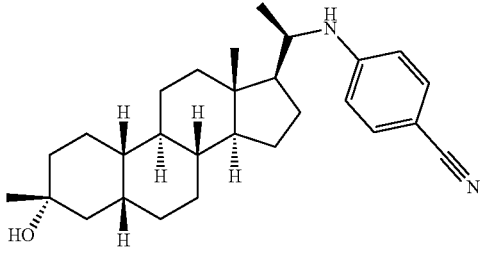 |
| 34 | 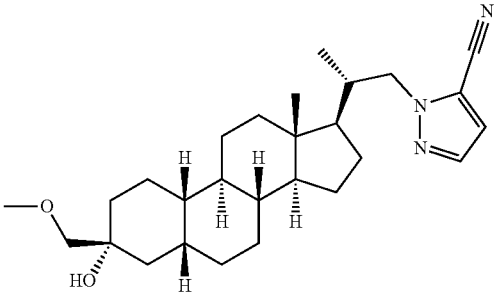 |

TABLE 1-continued
| Example | STRUCTURE |
|---|---|
| 35 | 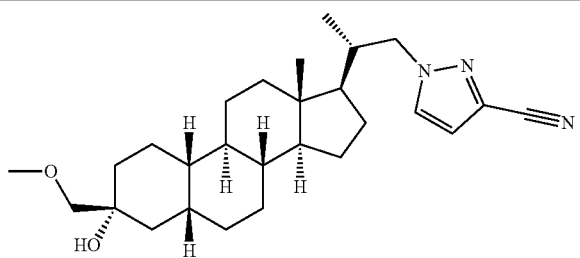 |
| 36 | 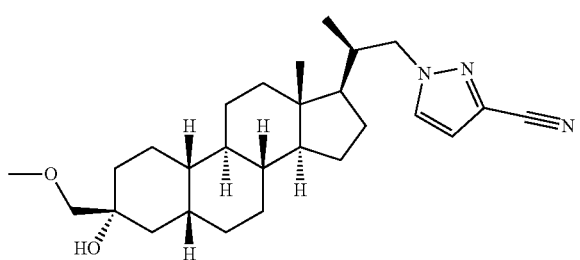 |
| 37 | 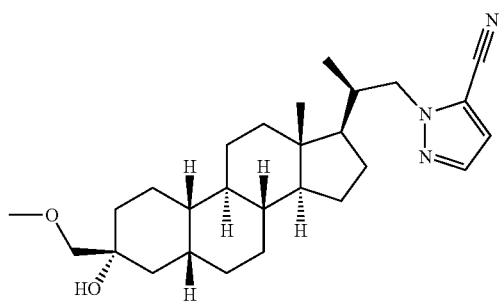 |
| 38 | 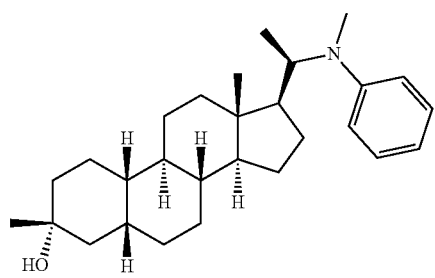 |
| 30 | 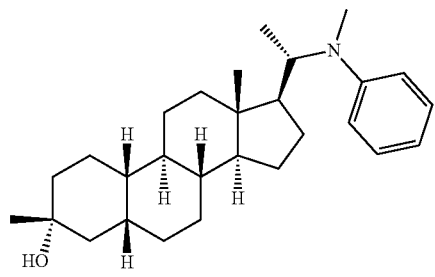 |

TABLE 1-continued

| Example | STRUCTURE |
|---|---|
| 40 | 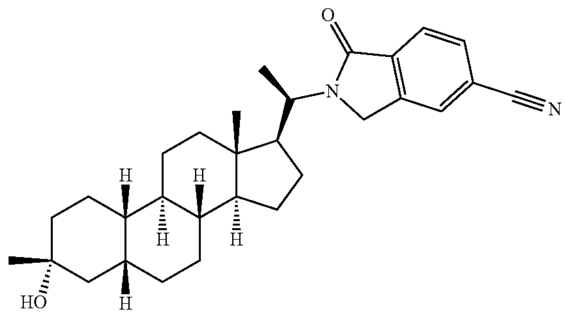 |
| 41 | 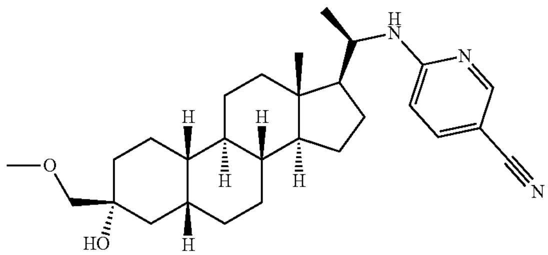 |
| 42 | 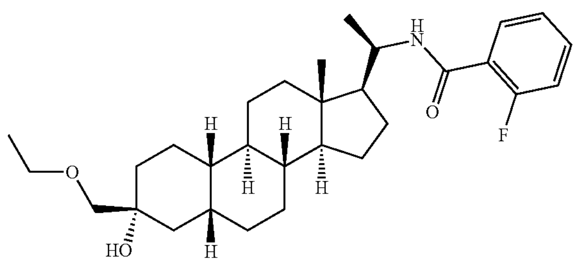 |
| 43 | 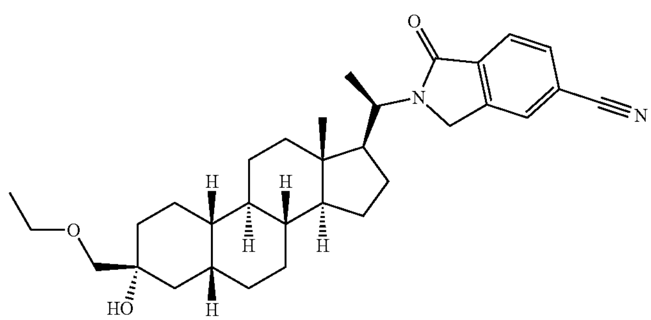 |
| 44 | 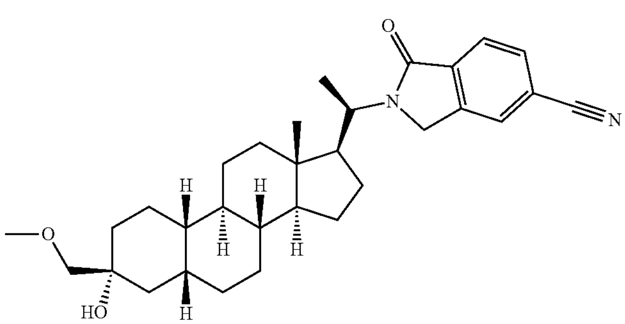 |

TABLE 1-continued

| Example | STRUCTURE |
|---|---|
| 45 | 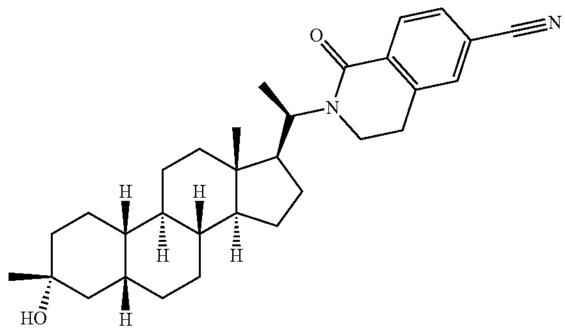 |
| 46 | 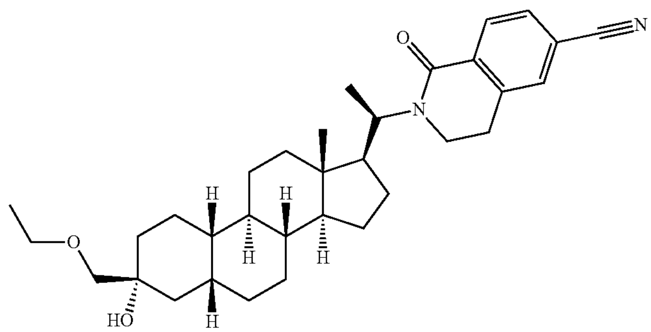 |
| 47 | 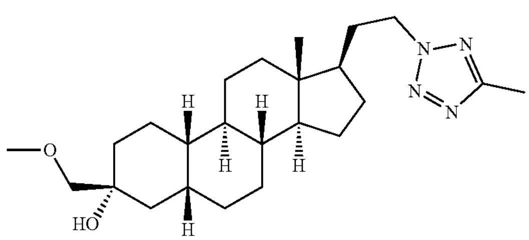 |
| 48 | 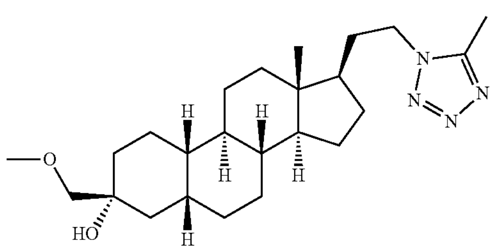 |
| 49 | 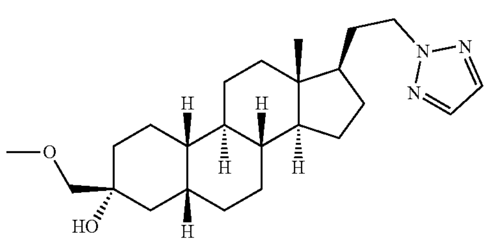 |

TABLE 1-continued

| Example | STRUCTURE |
|---|---|
| 50 | 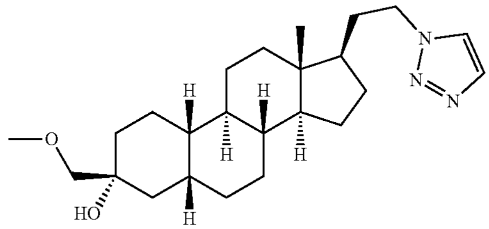 |
| 51 | 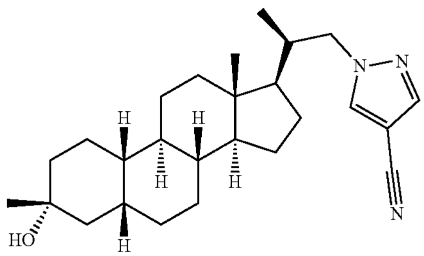 |
| 52 | 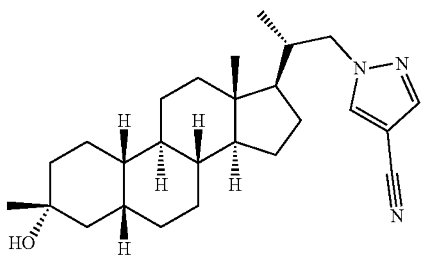 |
| 53 | 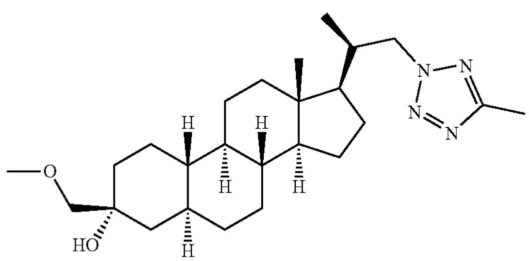 |
| 54 | 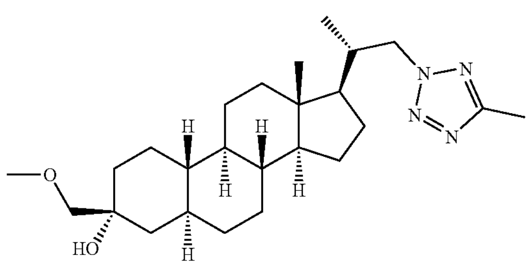 |
| 55 | 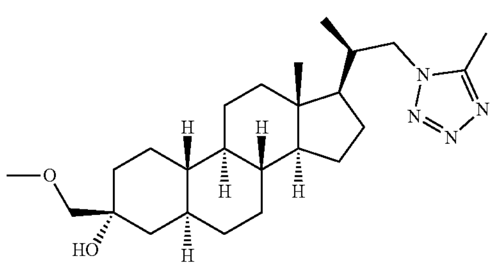 |

TABLE 1-continued

| Example | STRUCTURE |
|---|---|
| 56 | 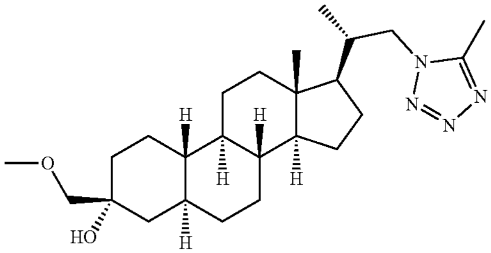 |
| 57 | 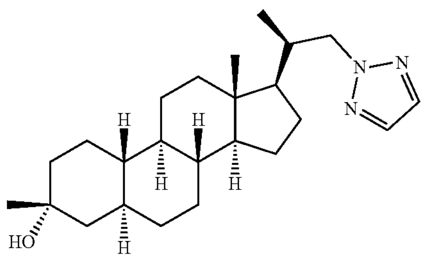 |
| 58 | 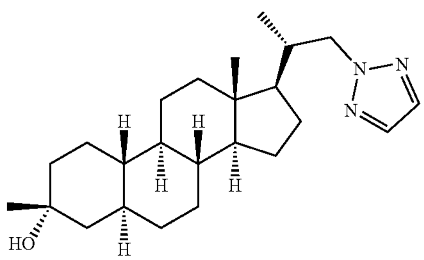 |
| 59 | 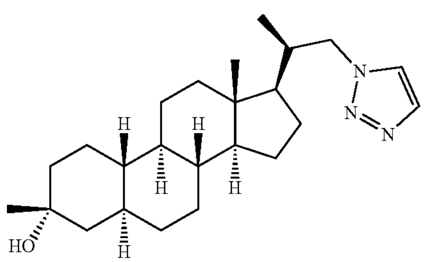 |
| 60 | 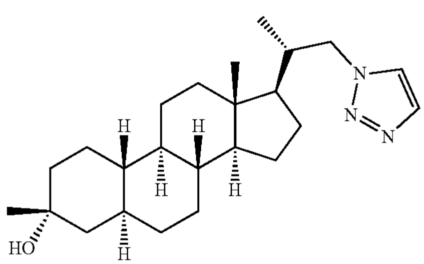 |
| 61 | 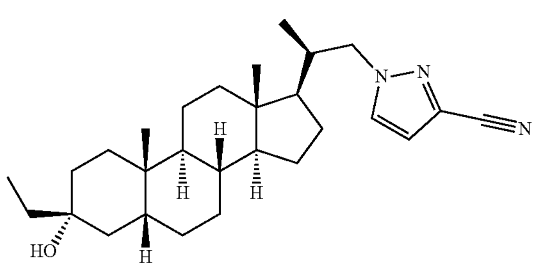 |

TABLE 1-continued
| Example | STRUCTURE |
|---|---|
| 62 | 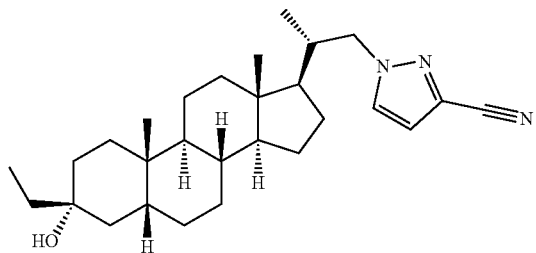 |
| 63 | 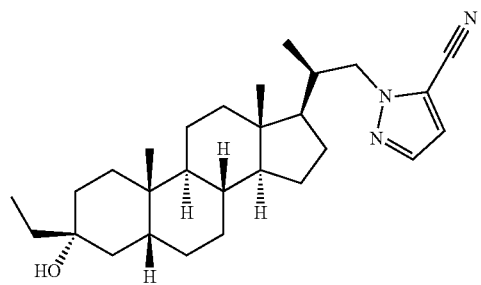 |
| 64 | 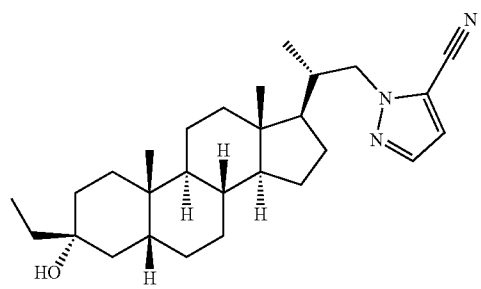 |
| 65 | 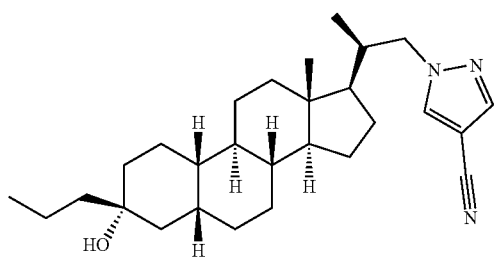 |
| 66 | 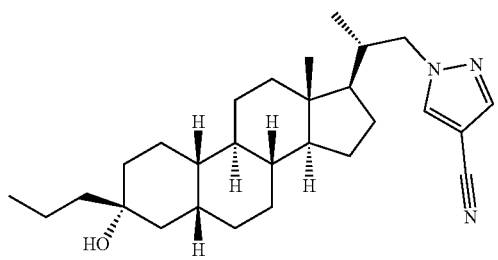 |

TABLE 1-continued
| Example | STRUCTURE |
|---|---|
| 67 | 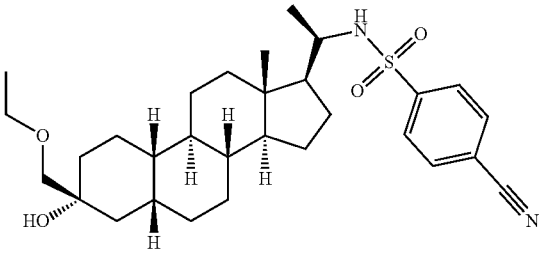 |
| 68 | 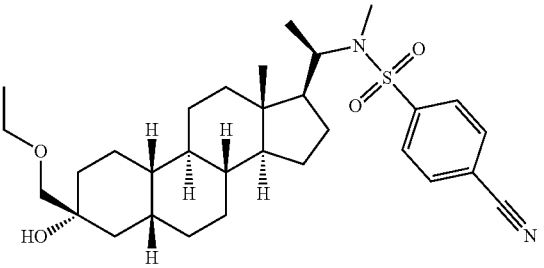 |
| 69 | 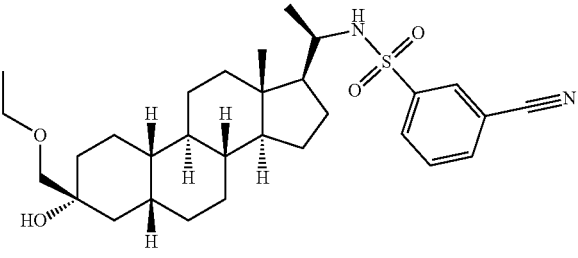 |
| 70 | 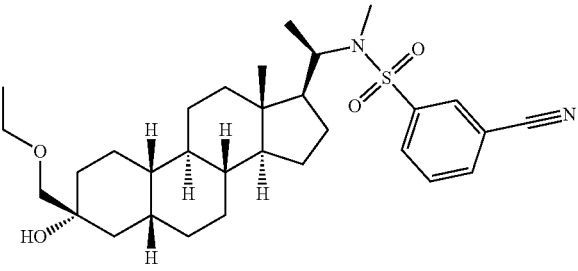 |
| 71 | 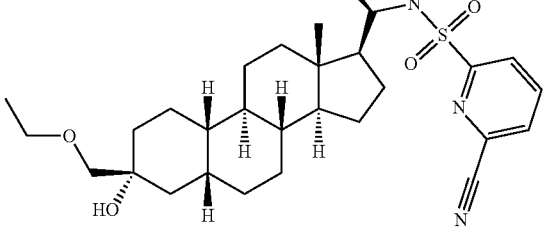 |

TABLE 1-continued
| Example | STRUCTURE |
|---|---|
| 72 | 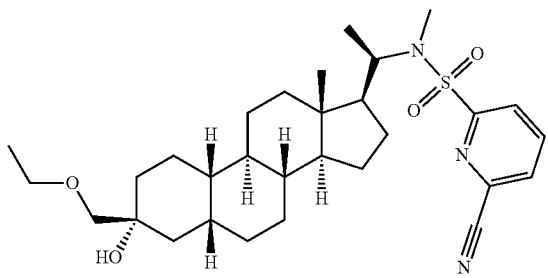 |
| 73 | 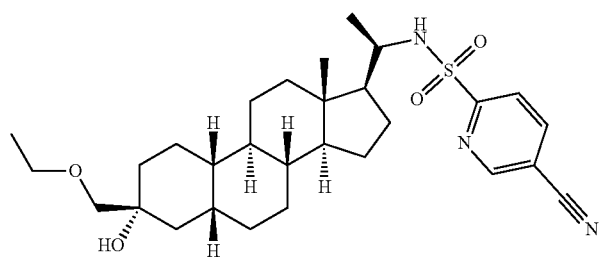 |
| 74 | 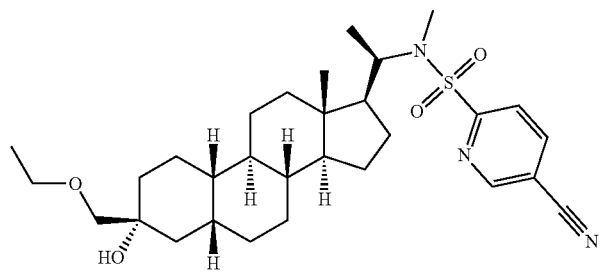 |
| 75 | 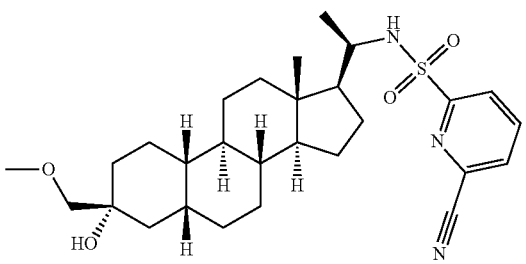 |
| 76 | 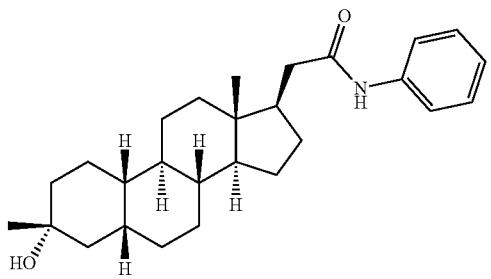 |

TABLE 1-continued
| Example | STRUCTURE |
|---|---|
| 77 | 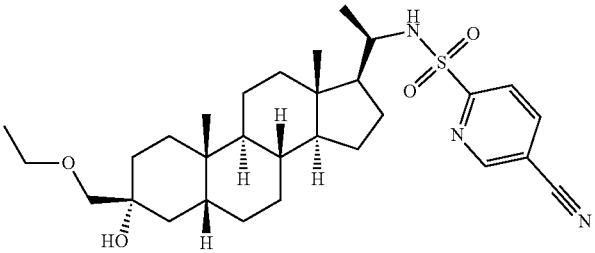 |
| 78 | 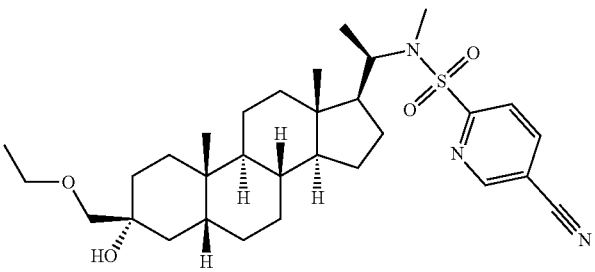 |
| 80 | 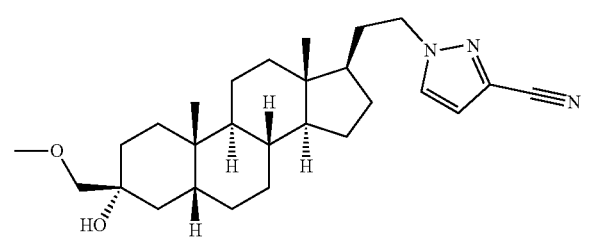 |
| 88 | 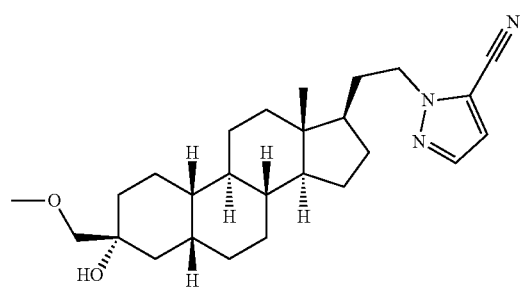 |
| 89 | 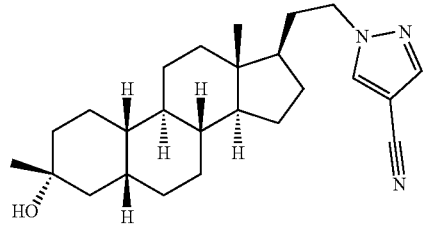 |
| 90 | 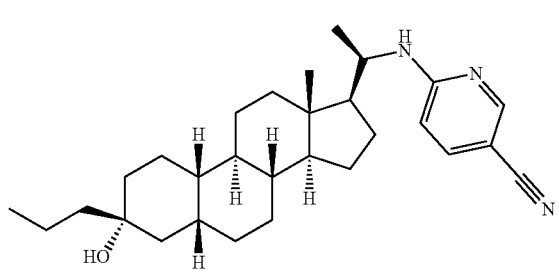 |

TABLE 1-continued

| Example | STRUCTURE |
|---|---|
| 91 | 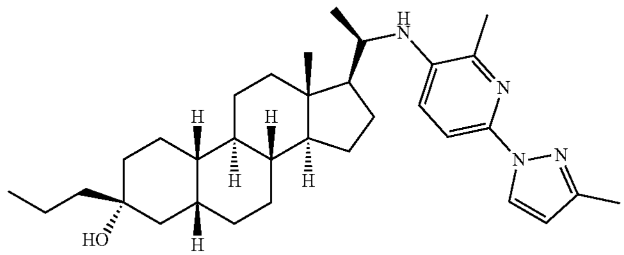 |
| 92 | 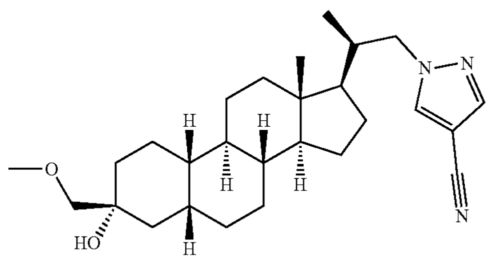 |
| 93 | 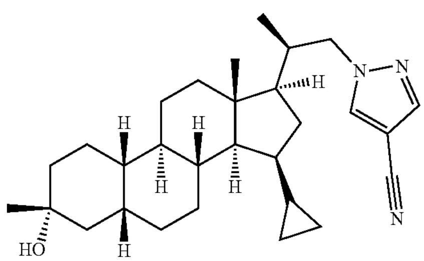 |
| 94 | 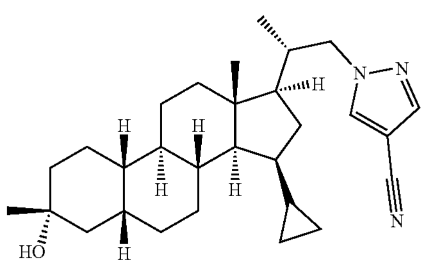 |
| 95 | 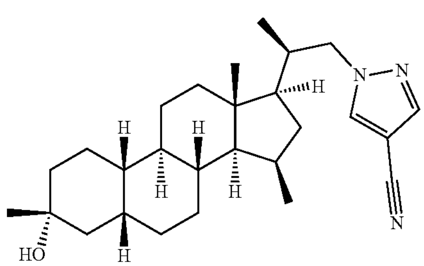 |
| 96 | 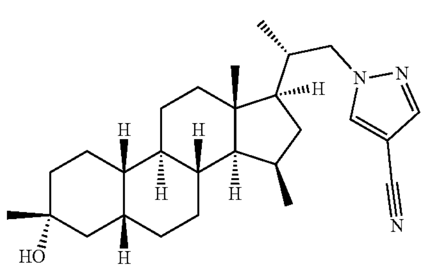 |

TABLE 1-continued
| Example | STRUCTURE |
|---|---|
| 100 | 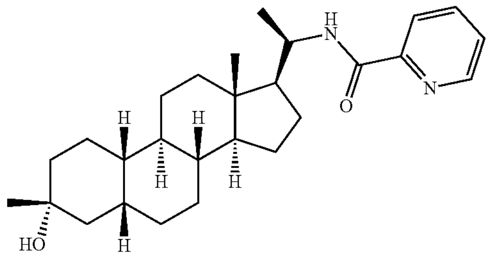 |
| 101 | 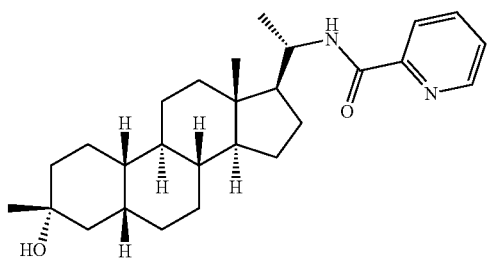 |
| 102 | 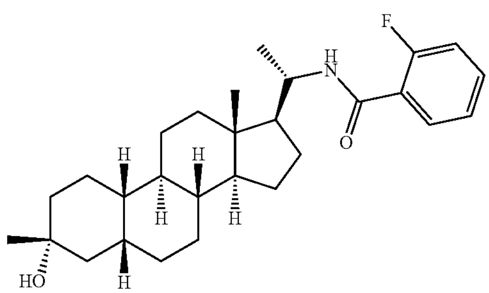 |
| 103 | 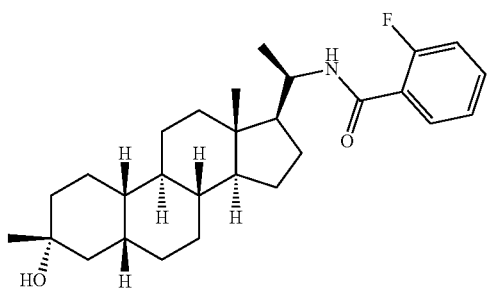 |
| 104 | 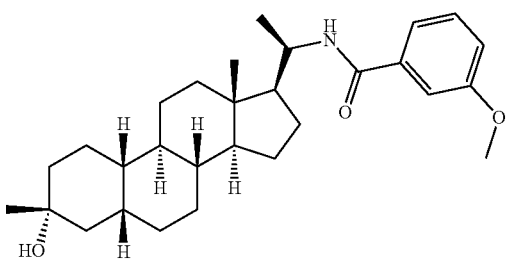 |

TABLE 1-continued
| Example | STRUCTURE |
|---|---|
| 105 | 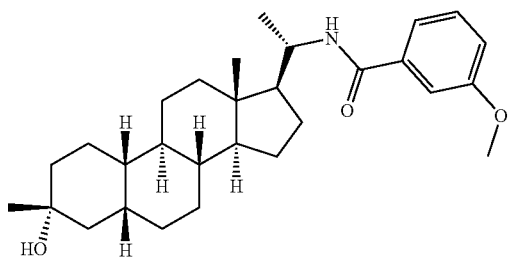 |
| 106 | 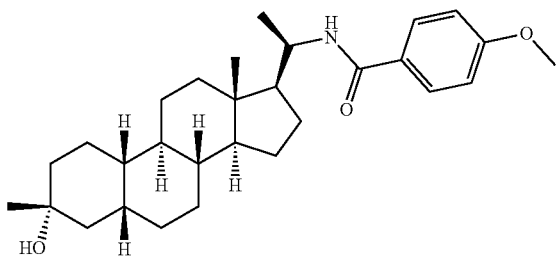 |
| 107 | 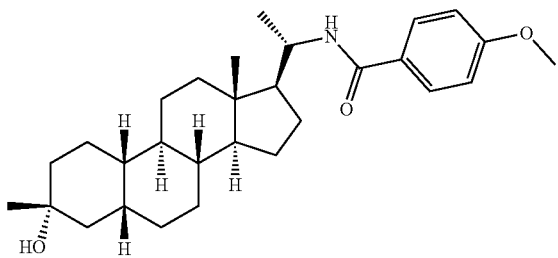 |
| 108 | 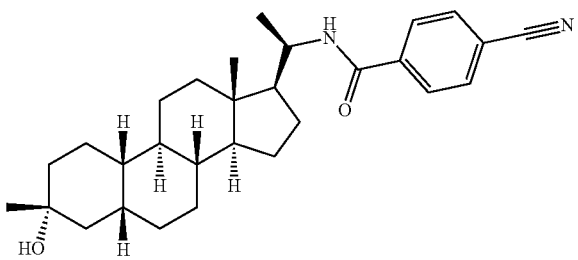 |
| 109 | 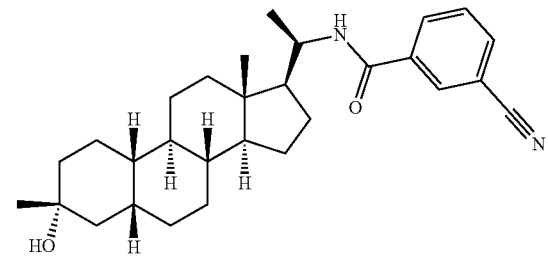 |
| 110 | 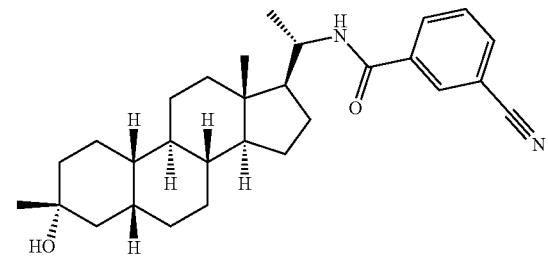 |

TABLE 1-continued

| Example | STRUCTURE |
|---|---|
| 111 | 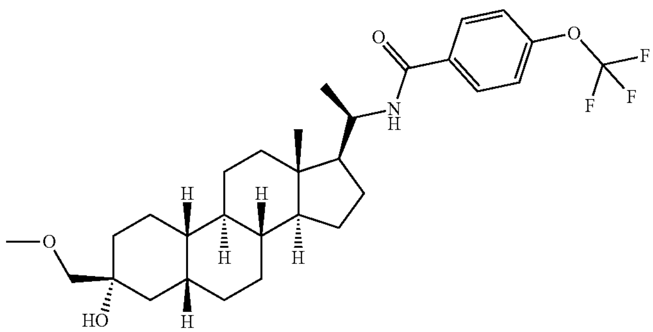 |
| 112 | 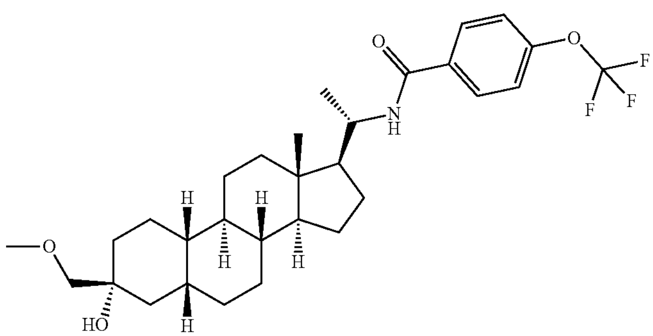 |
| 113 | 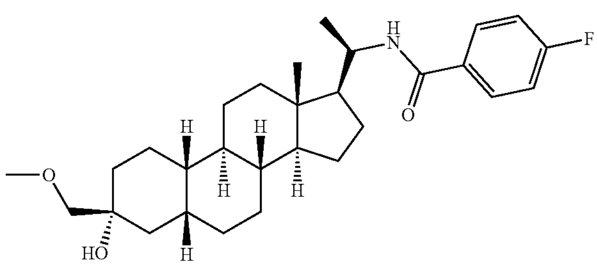 |
| 114 | 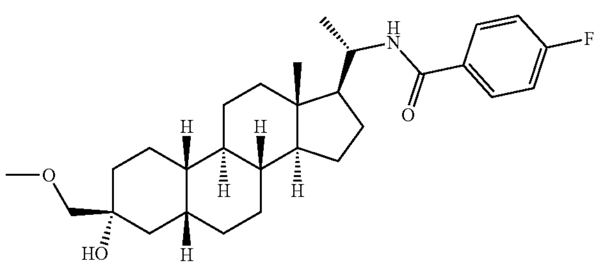 |
| 115 | 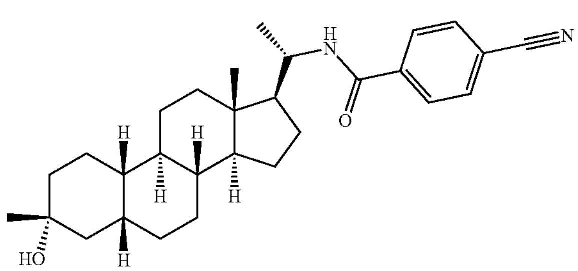 |

TABLE 1-continued
| Example | STRUCTURE |
|---|---|
| 116 | 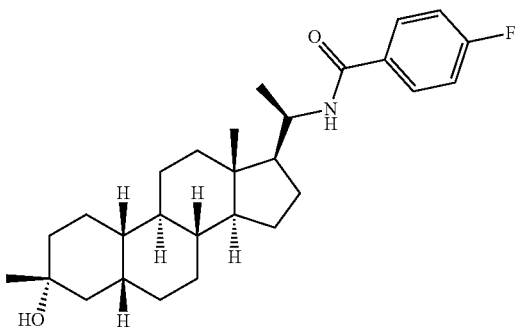 |
| 117 | 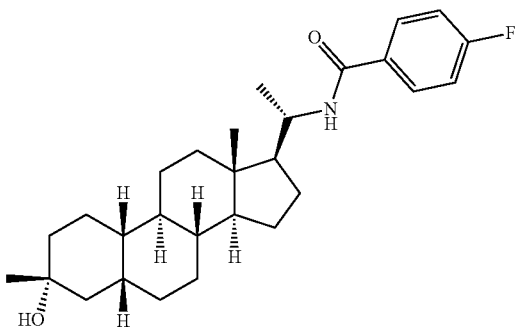 |
| 118 | 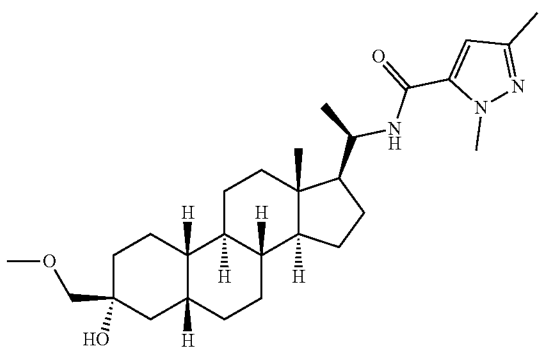 |
| 119 | 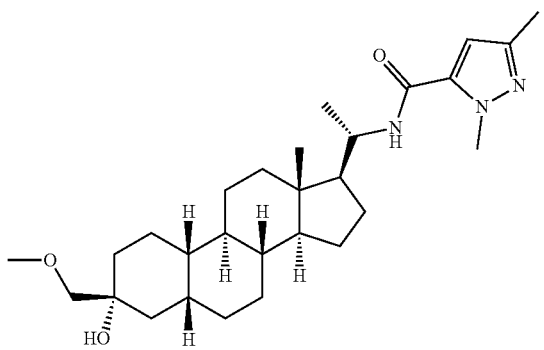 |

TABLE 1-continued
| Example | STRUCTURE |
|---|---|
| 120 | 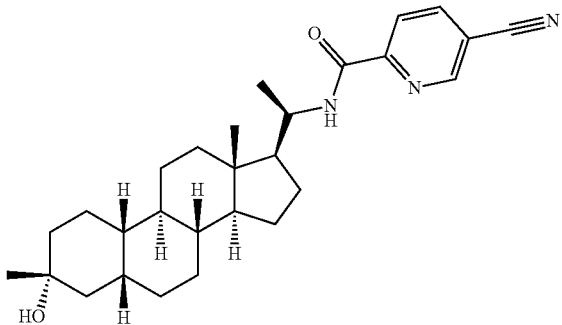 |
| 121 | 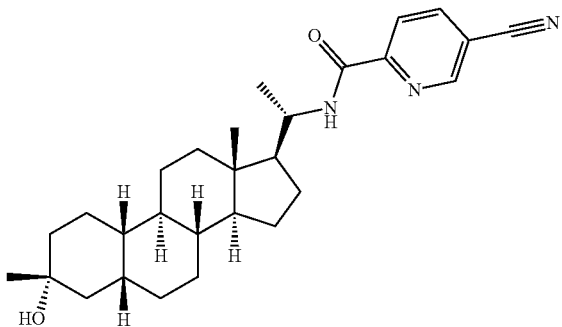 |
| 122 | 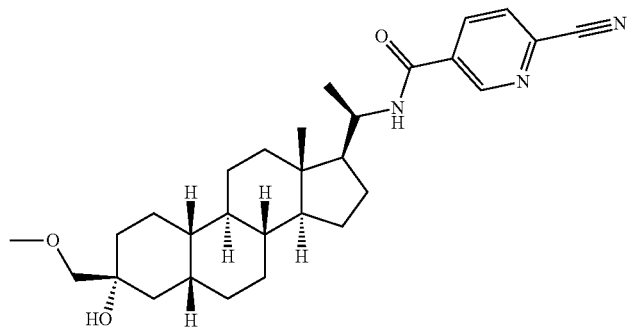 |
| 123 | 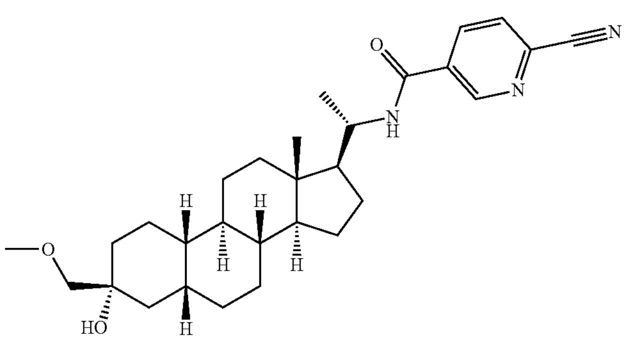 |

TABLE 1-continued
| Example | STRUCTURE |
|---|---|
| 124 | 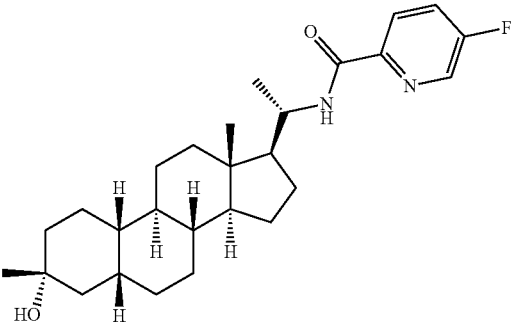 |
| 125 | 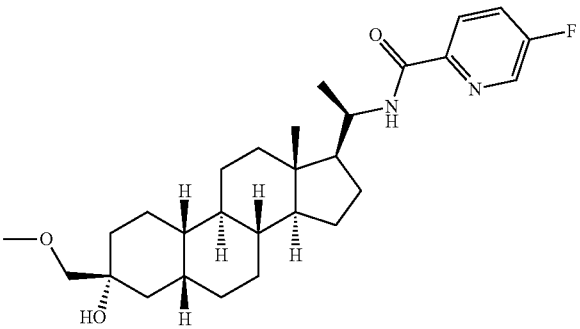 |
| 126 | 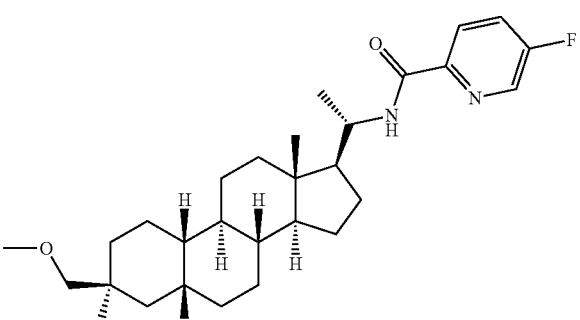 |
| 127 | 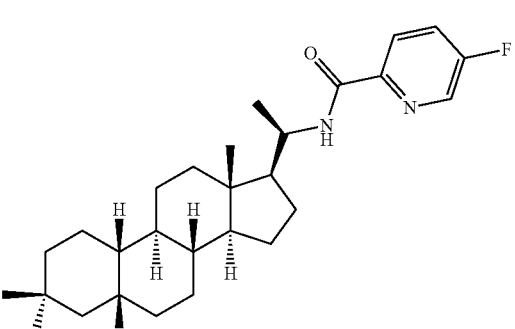 |
| 128 | 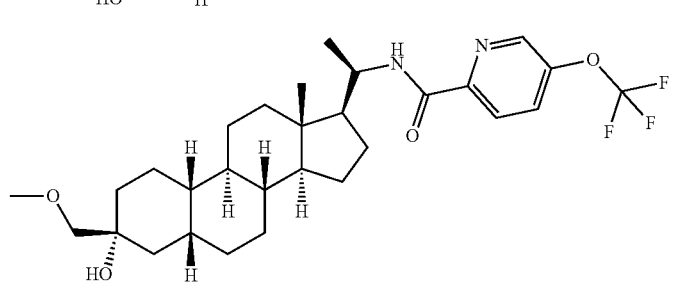 |

TABLE 1-continued
| Example | STRUCTURE |
|---|---|
| 129 | 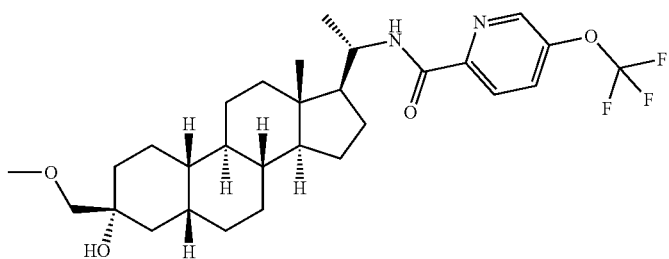 |
| 130 | 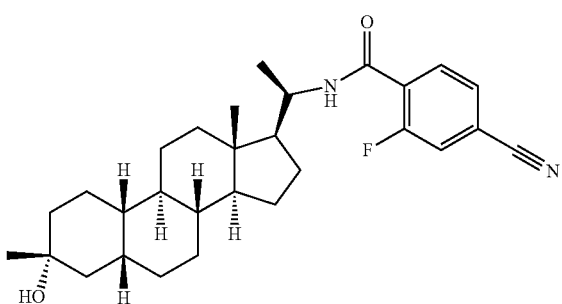 |
| 131 | 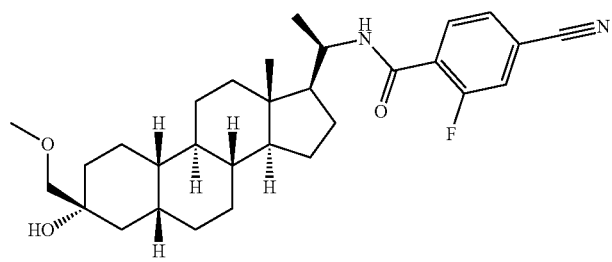 |
| 132 | 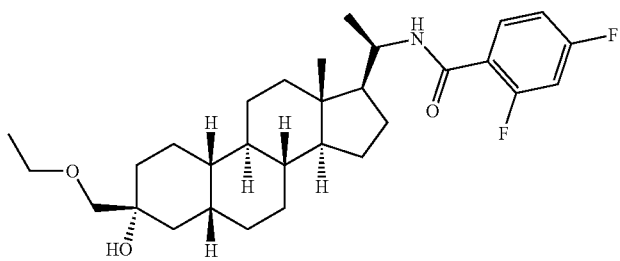 |
| 133 | 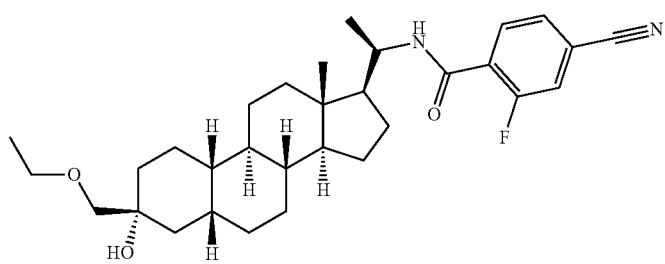 |

TABLE 1-continued
| Example | STRUCTURE |
|---|---|
| 134 | 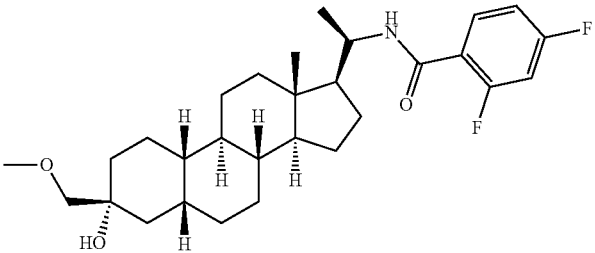 |
| 135 | 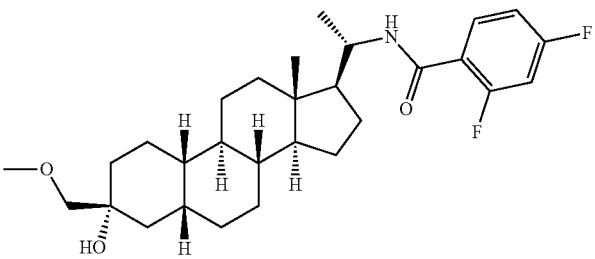 |
| 150 | 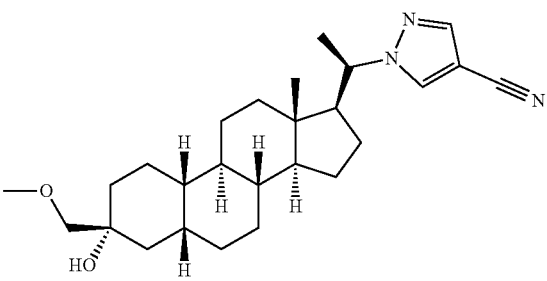 |
| 151 | 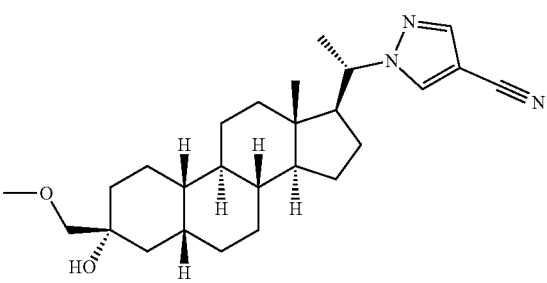 |
| 152 | 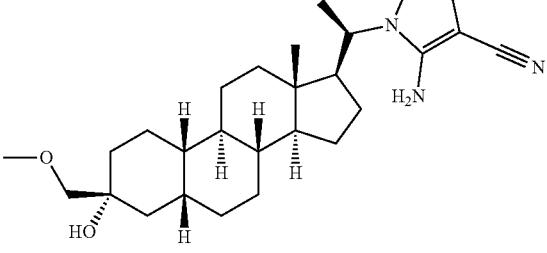 |

TABLE 1-continued
| Example | STRUCTURE |
|---|---|
| 153 | 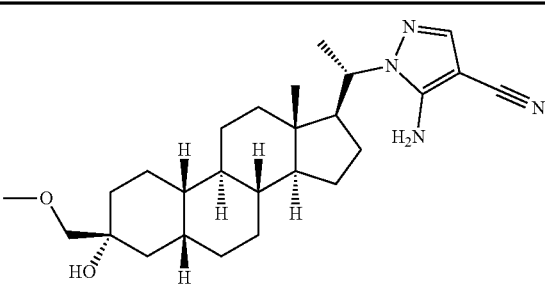 |
| 154 | 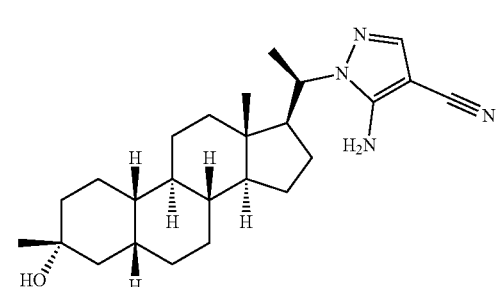 |
| 155 | 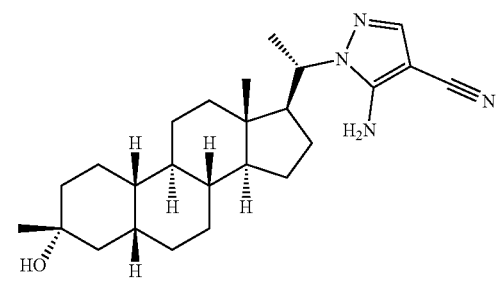 |
| 156 | 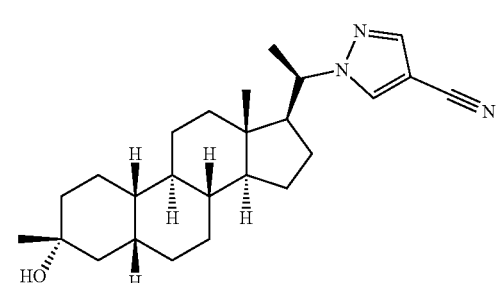 |
| 157 | 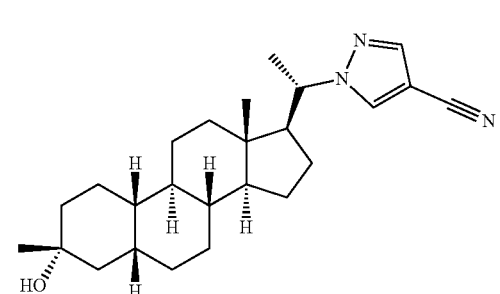 |

TABLE 1-continued

| Example | STRUCTURE |
|---|---|
| 158 | 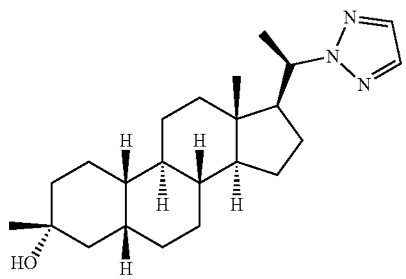 |
| 159 | 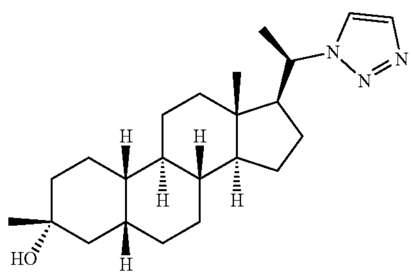 |
| 160 | 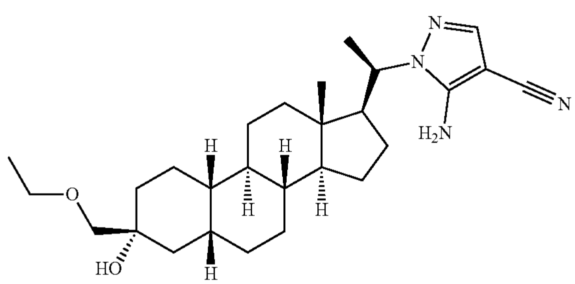 |
| 161 | 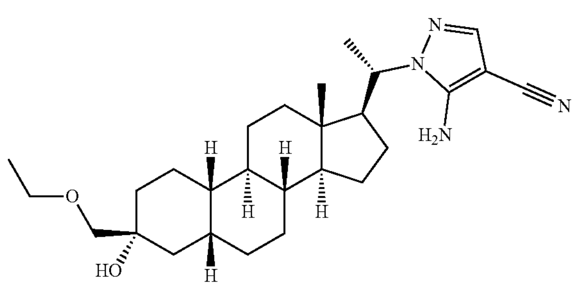 |
| 162 | 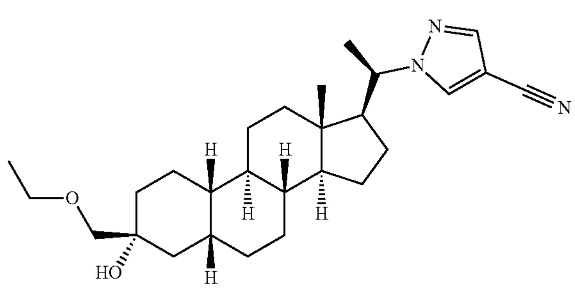 |

TABLE 1-continued
| Example | STRUCTURE |
|---|---|
| 163 | 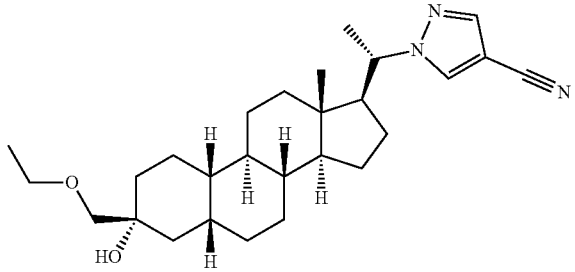 |
| 164 | 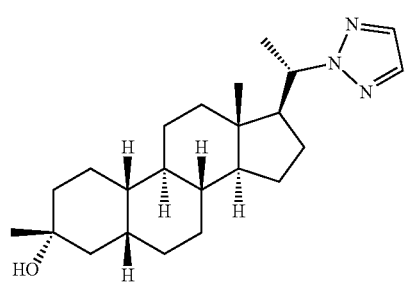 |
| 201 | 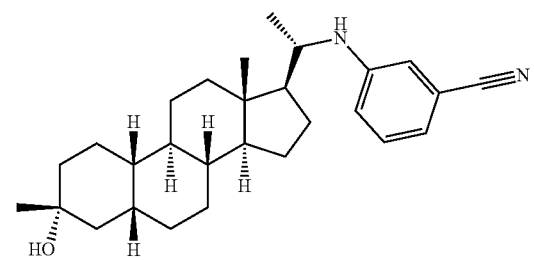 |
| 202 | 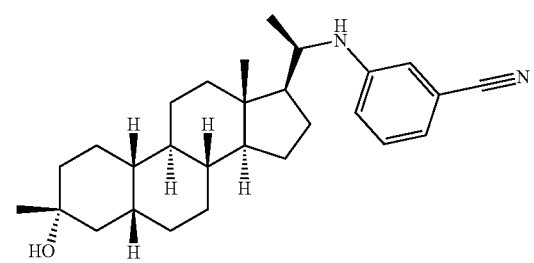 |
| 203 | 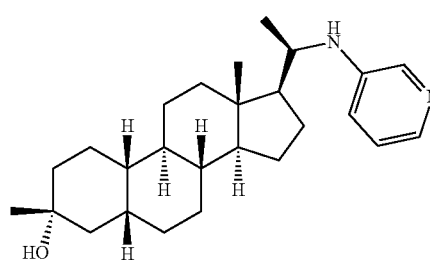 |
| 204 | 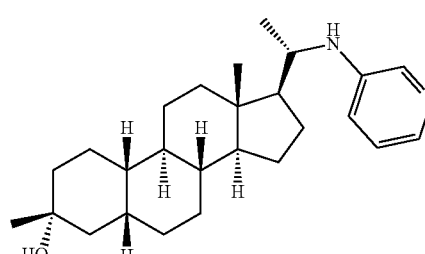 |

TABLE 1-continued
| Example | STRUCTURE |
|---|---|
| 205 | 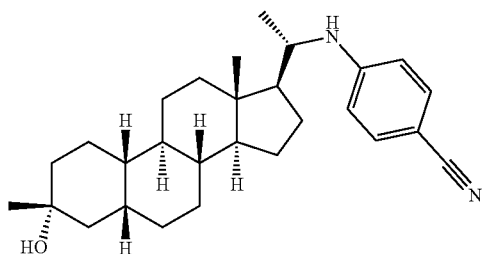 |
| 206 | 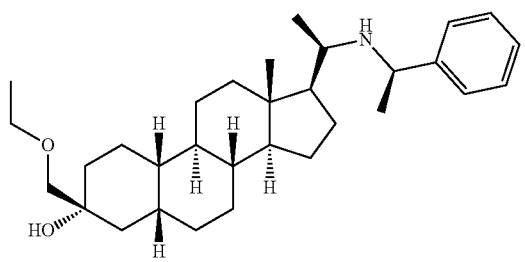 |
| 207 | 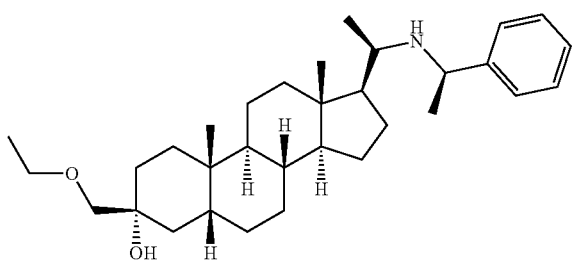 |
| 208 | 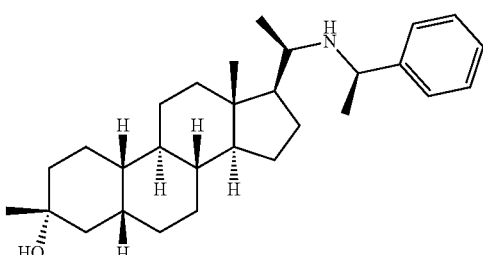 |
| 209 | 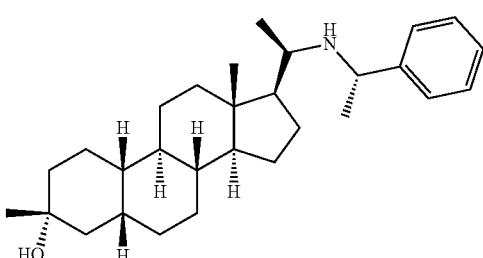 |
| 210 | 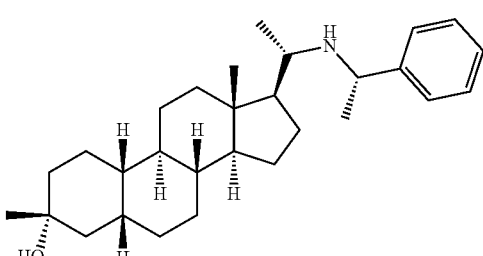 |

TABLE 1-continued
| Example | STRUCTURE |
|---|---|
| 211 | 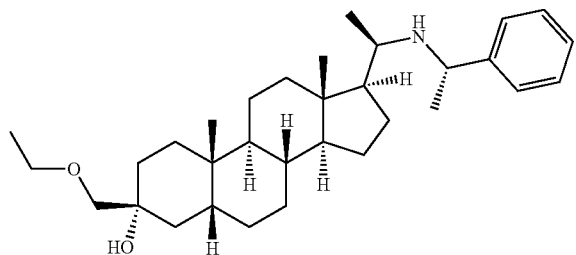 |
| 212 | 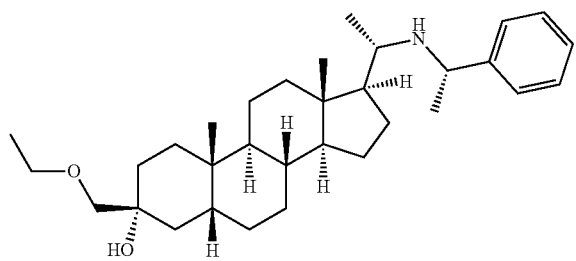 |
| 213 | 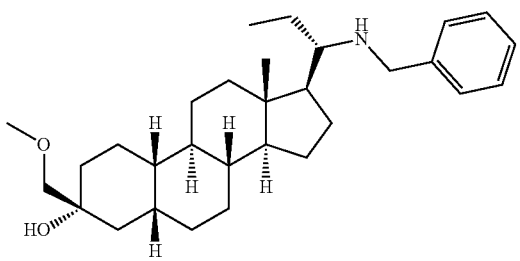 |
| 214 | 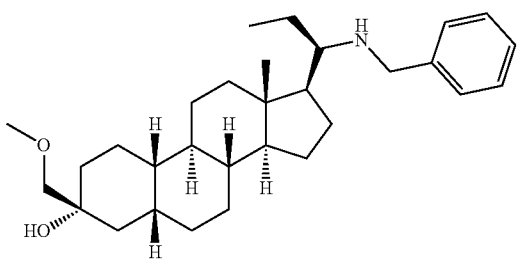 |
| 250 | 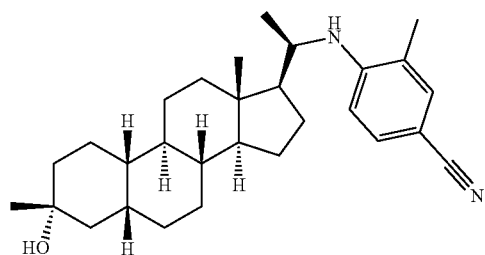 |
| 251 | 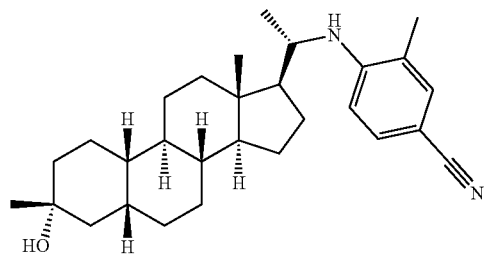 |

TABLE 1-continued
| Example | STRUCTURE |
|---|---|
| 252 | 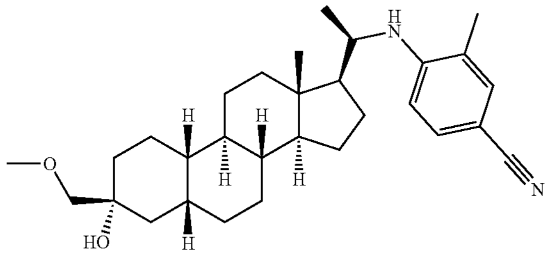 |
| 253 | 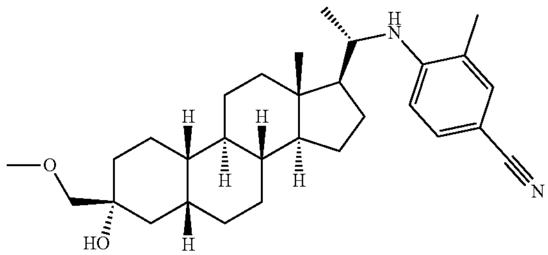 |
| 254 | 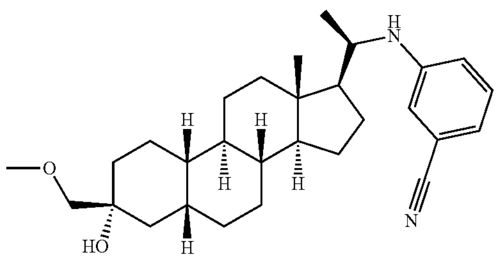 |
| 255 | 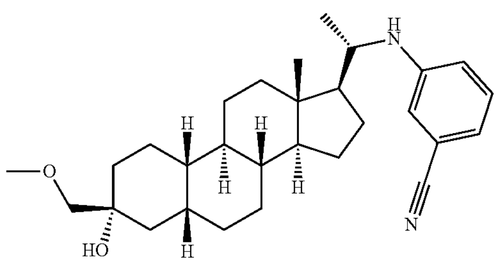 |
| 256 | 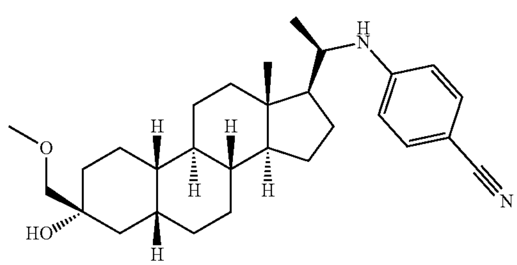 |
| 257 | 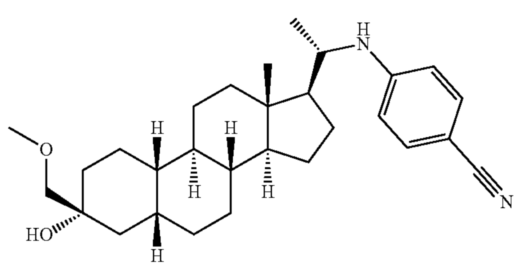 |

TABLE 1-continued
| Example | STRUCTURE |
|---|---|
| 258 | 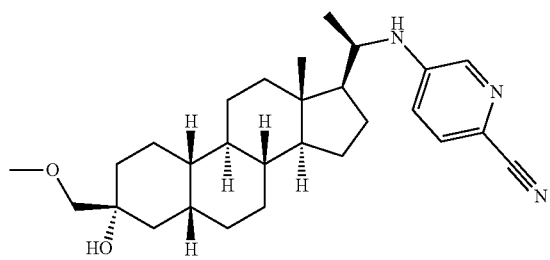 |
| 259 | 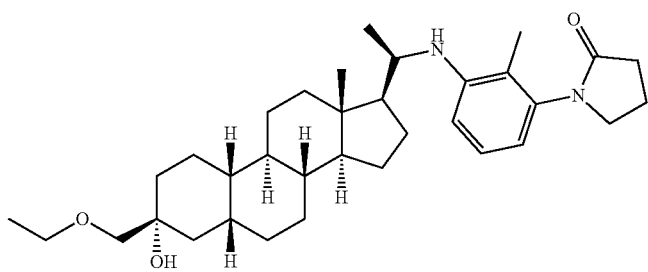 |
| 260 | 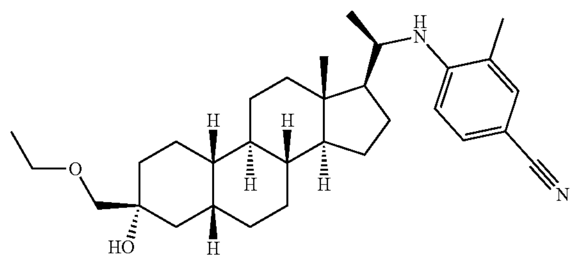 |
| 261 | 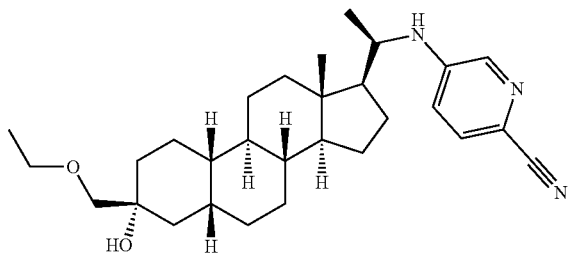 |
| 262 | 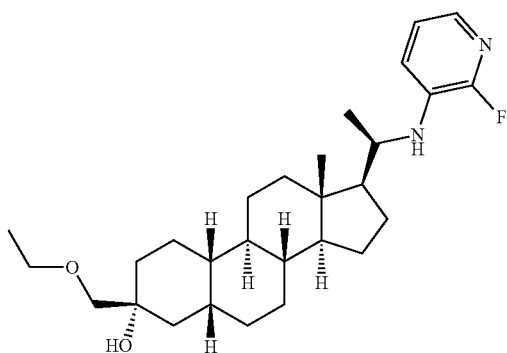 |

TABLE 1-continued
| Example | STRUCTURE |
|---|---|
| 263 | 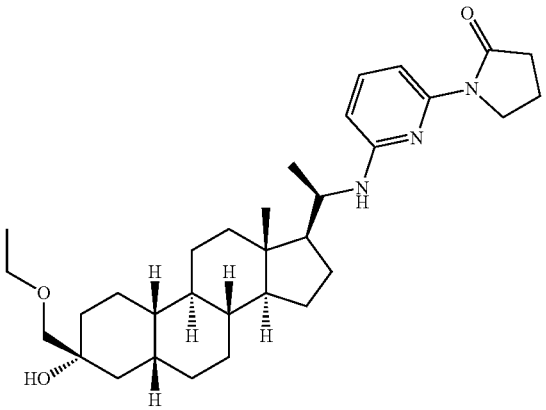 |
| 264 | 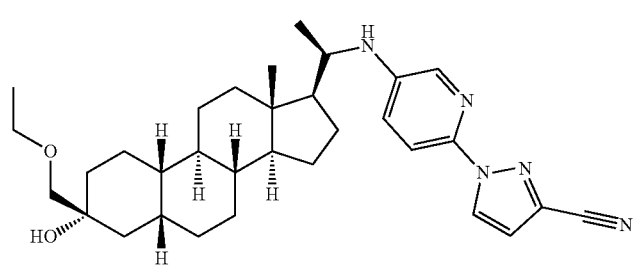 |
| 265 | 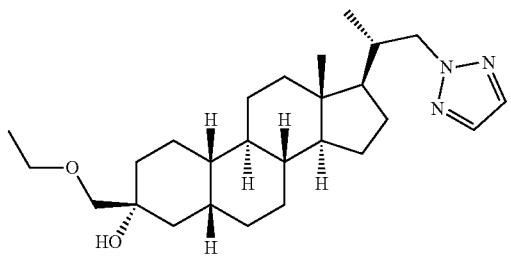 |
| 266 | 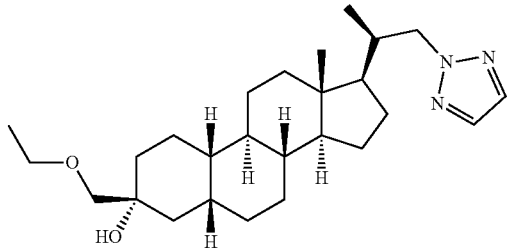 |
| 267 | 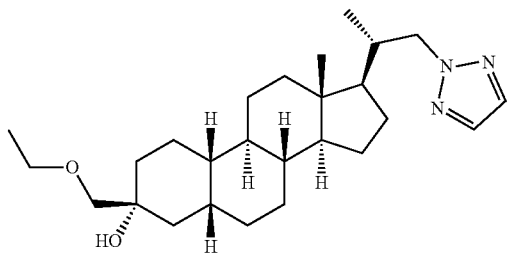 |

TABLE 1-continued
| Example | STRUCTURE |
|---|---|
| 268 | 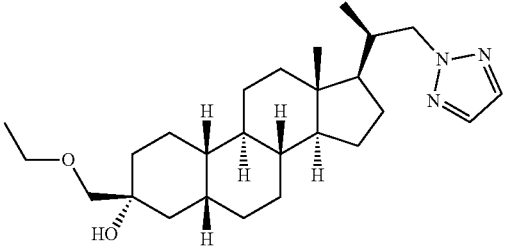 |
| 269 | 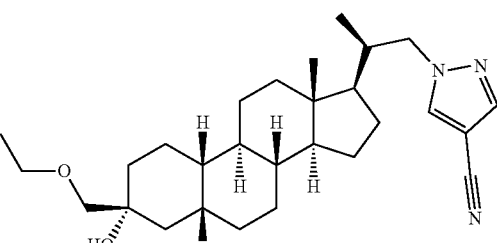 |
| 270 | 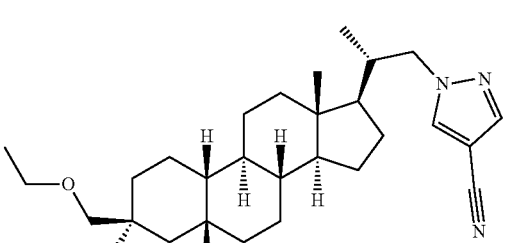 |
| 271 | 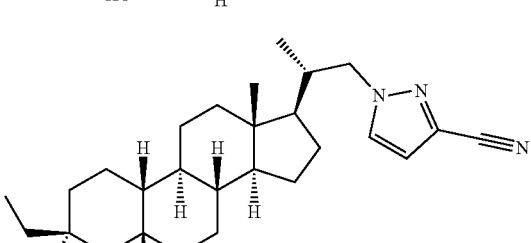 |
| 272 | 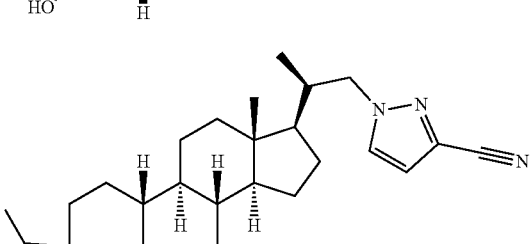 |
| 273 | 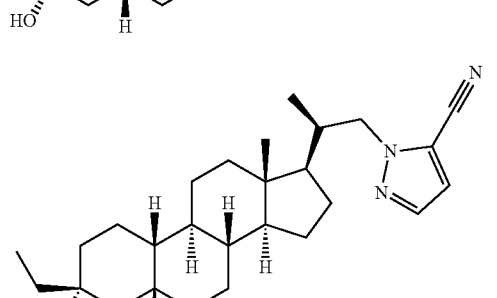 |

TABLE 1-continued
| Example | STRUCTURE |
|---|---|
| 274 | 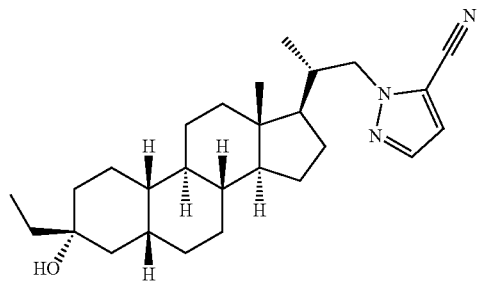 |
| 275 | 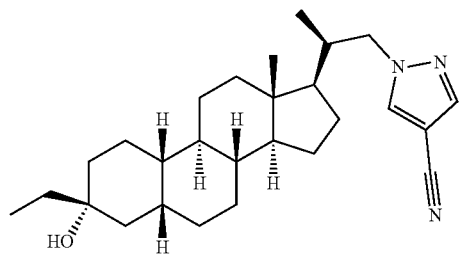 |
| 276 | 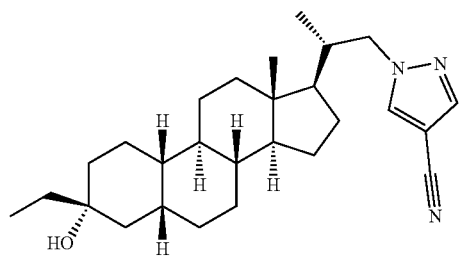 |
| 278 | 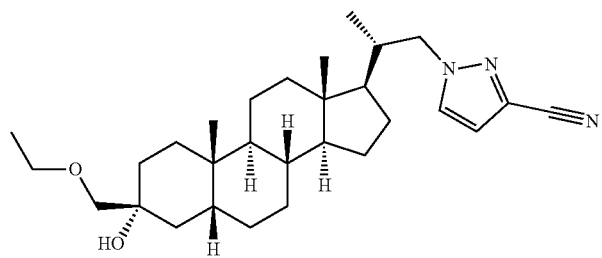 |
| 279 | 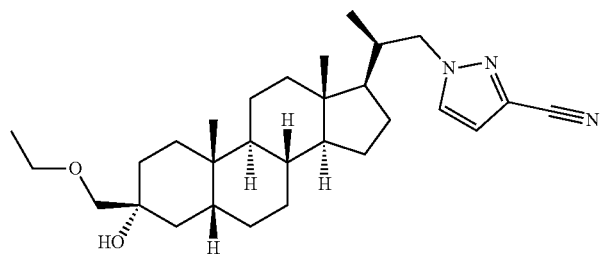 |

TABLE 1-continued
| Example | STRUCTURE |
|---|---|
| 280 | 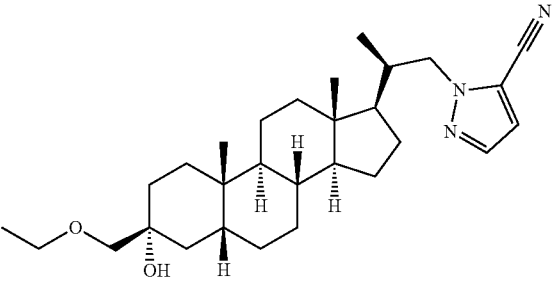 |
| 281 | 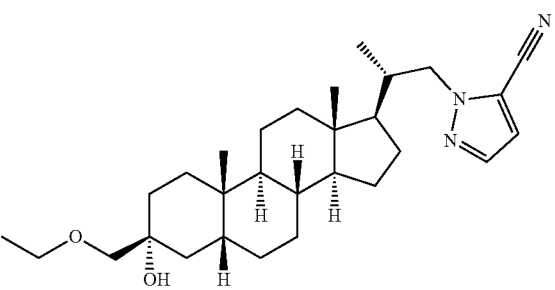 |
| 282 | 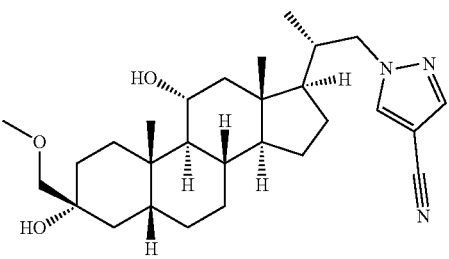 |
| 283 | 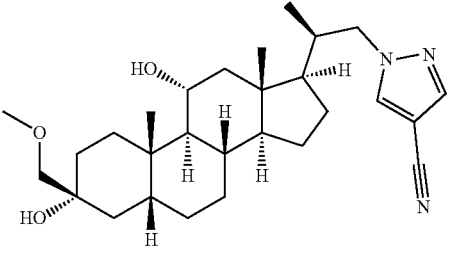 |
| 285 | 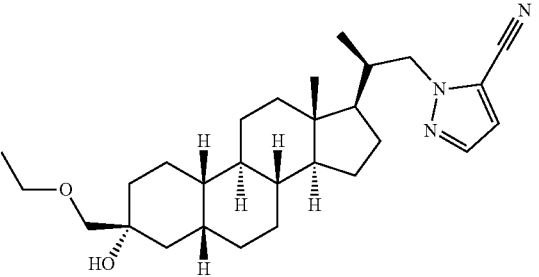 |

TABLE 1-continued
| Example | STRUCTURE |
|---|---|
| 286 | 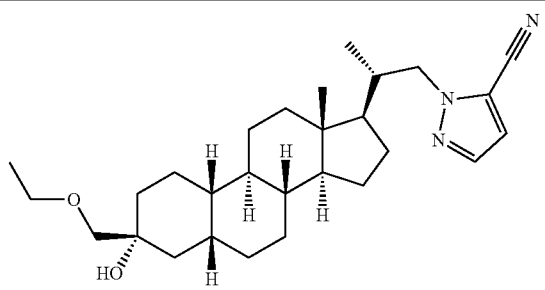 |
| 287 | 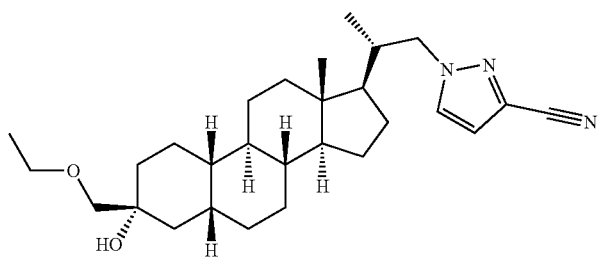 |
| 288 | 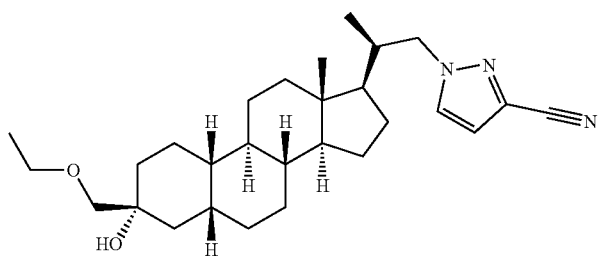 |
| 289 | 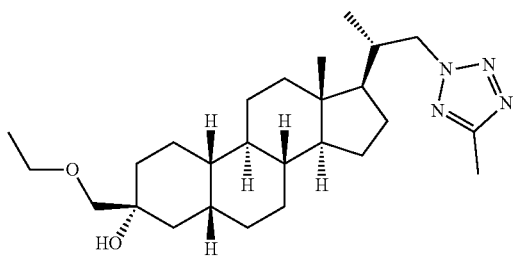 |
| 290 | 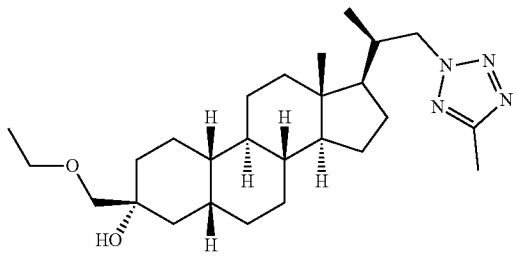 |
| 293 | 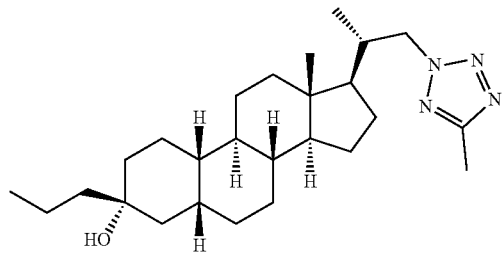 |

TABLE 1-continued
| Example | STRUCTURE |
|---|---|
| 294 | 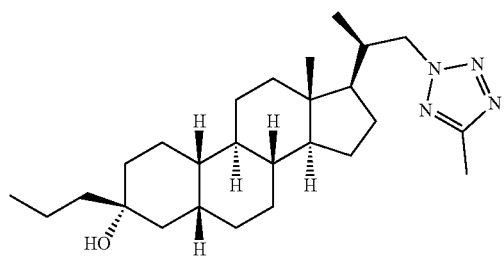 |
| 295 | 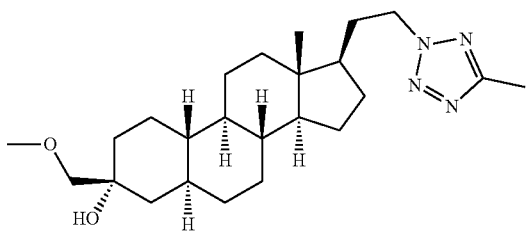 |
| 296 | 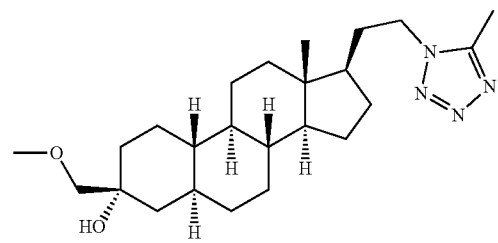 |
| 297 | 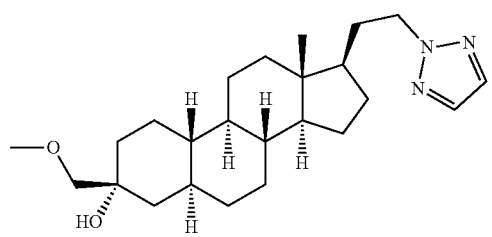 |
| 298 | 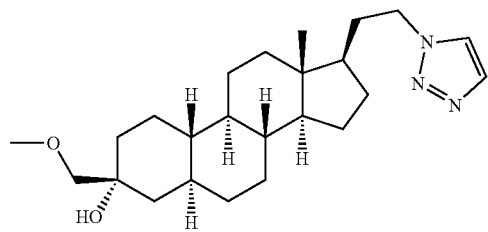 |
| 299 | 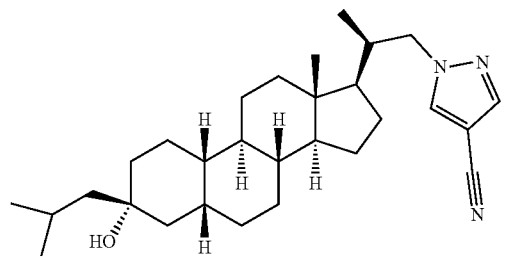 |

TABLE 1-continued
| Example | STRUCTURE |
|---|---|
| 300 | 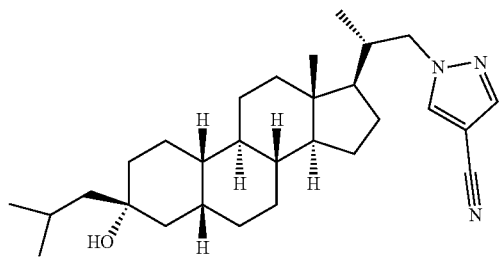 |
| 301 | 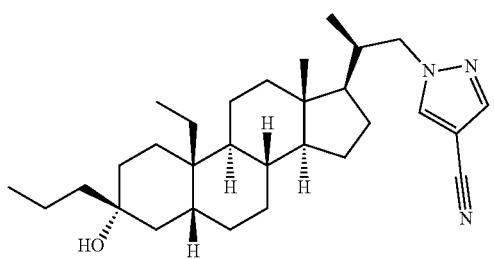 |
| 302 | 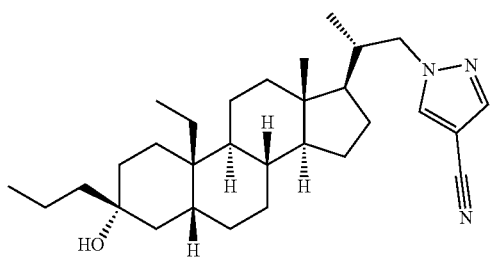 |
| 303 | 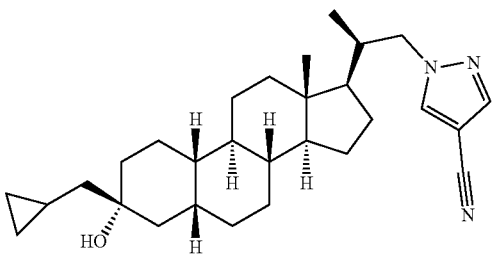 |
| 304 | 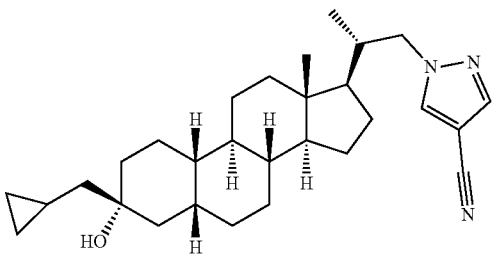 |
| 305 | 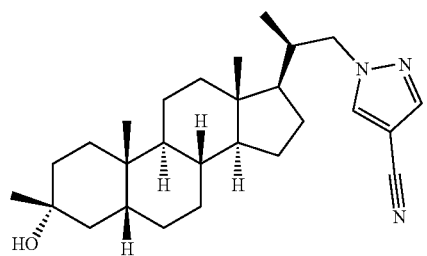 |

TABLE 1-continued
| Example | STRUCTURE |
|---|---|
| 306 | 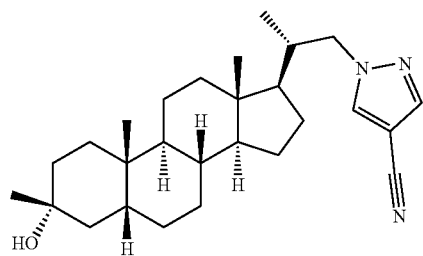 |
| 307 | 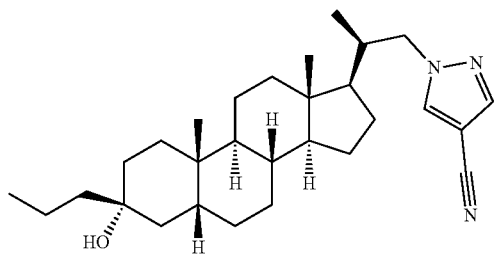 |
| 308 | 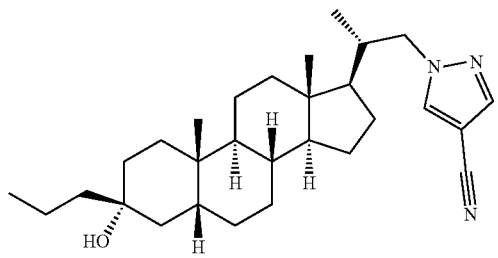 |
| 309 | 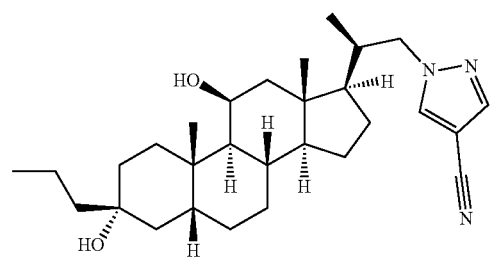 |
| 310 | 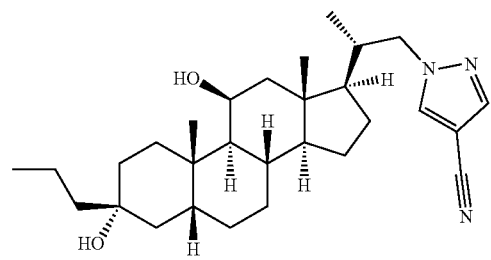 |
| 311 | 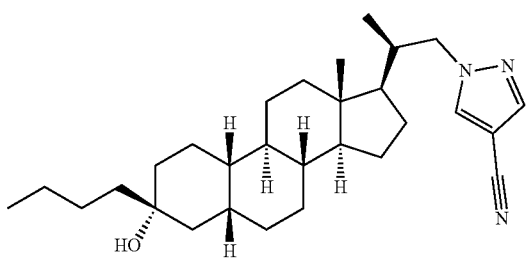 |

TABLE 1-continued
| Example | STRUCTURE |
|---|---|
| 312 | 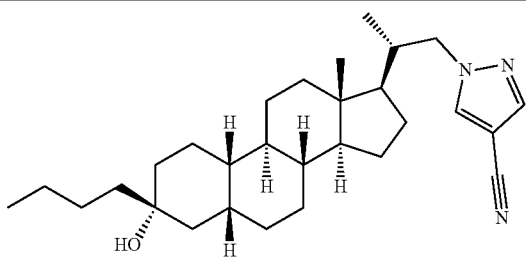 |
| 313 | 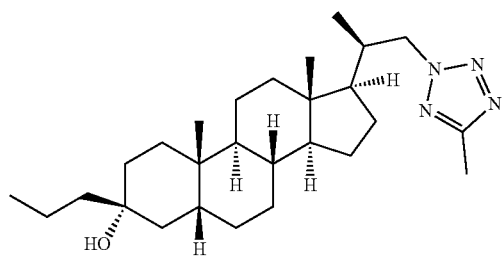 |
| 314 | 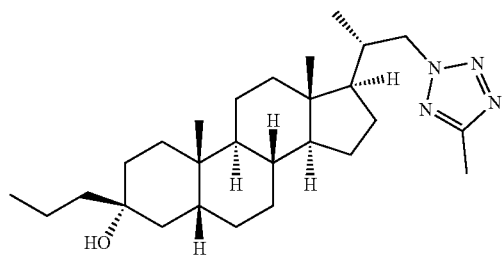 |
| 315 | 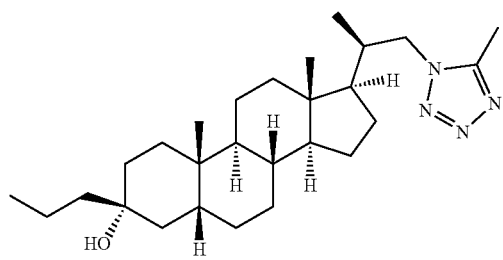 |
| 316 | 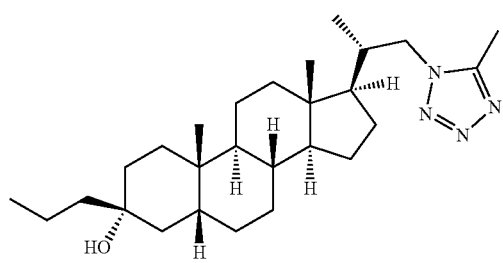 |
| 317 | 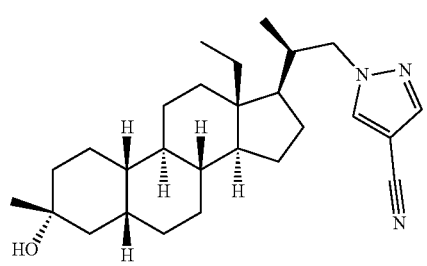 |

TABLE 1-continued
| Example | STRUCTURE |
|---|---|
| 318 | 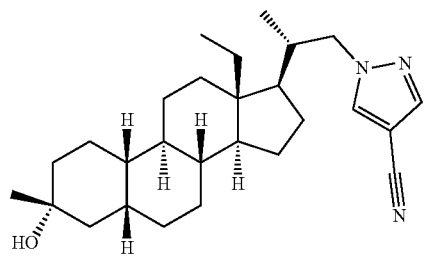 |
| 319 | 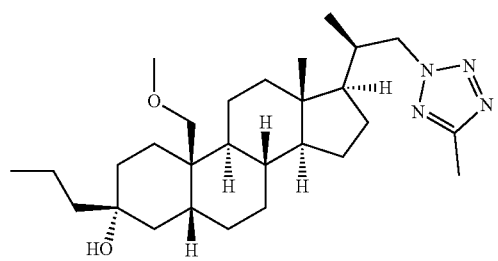 |
| 320 | 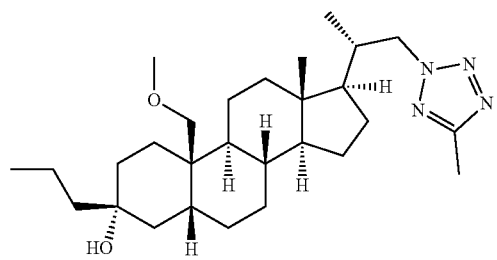 |
| 321 | 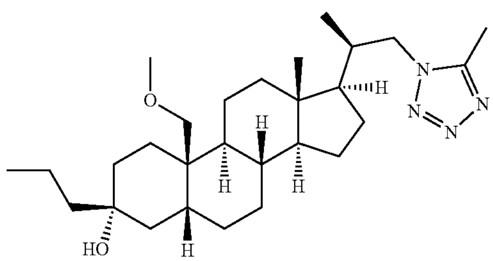 |
| 322 | 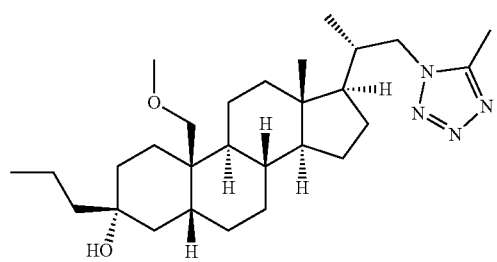 |
| 323 | 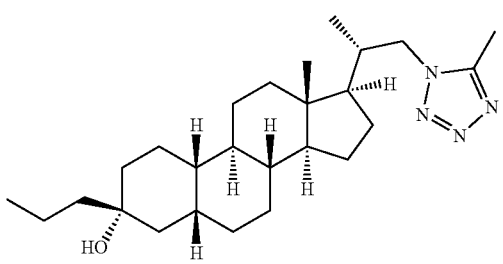 |

TABLE 1-continued

| Example | STRUCTURE |
|---|---|
| 324 | 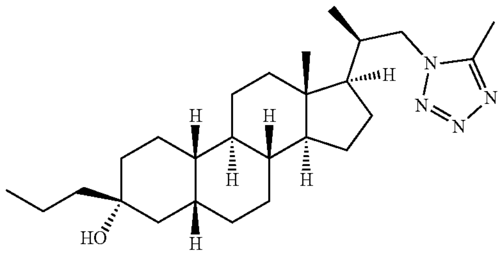 |
| 325 | 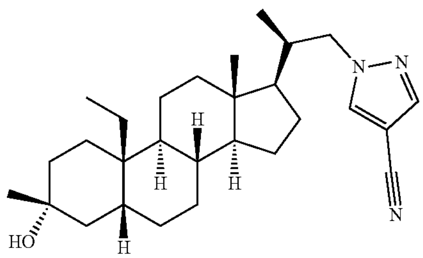 |
| 326 | 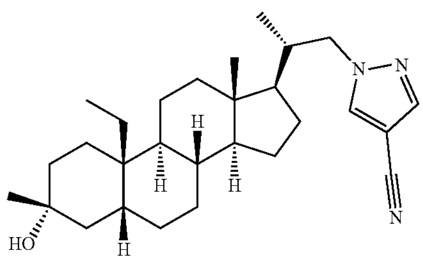 |
| 327 | 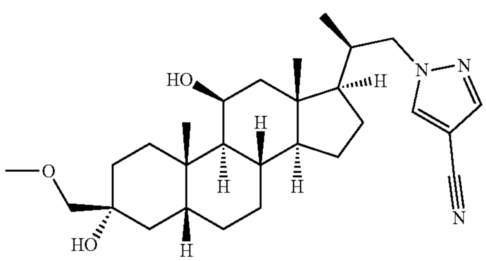 |
| 328 | 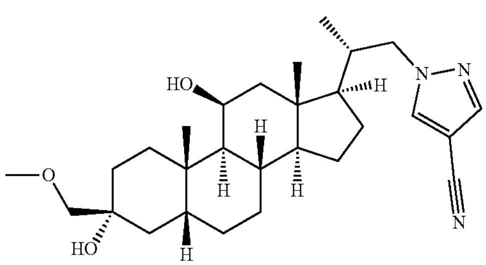 |
| 329 | 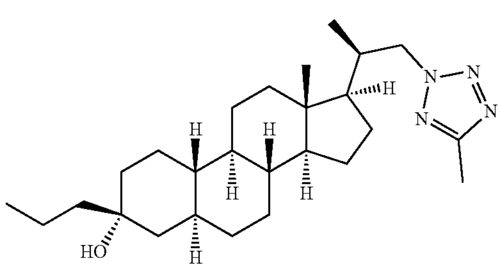 |

TABLE 1-continued
| Example | STRUCTURE |
|---|---|
| 330 | 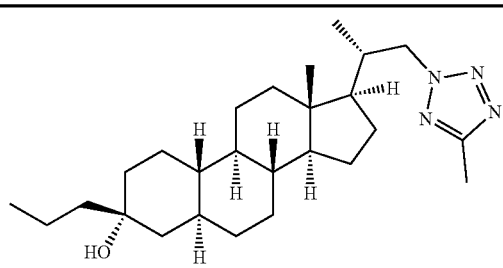 |
| 331 | 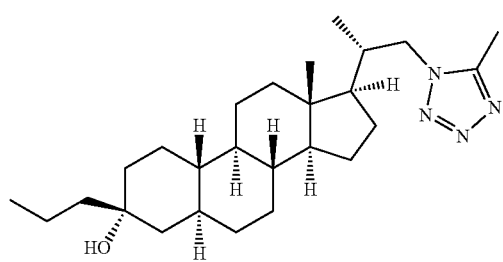 |
| 332 | 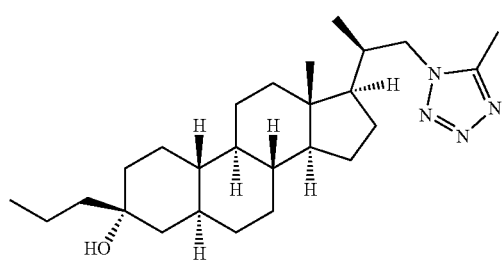 |
| 333 | 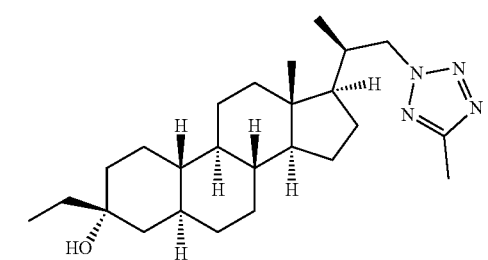 |
| 334 | 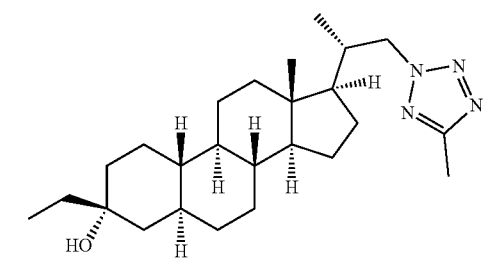 |
| 335 | 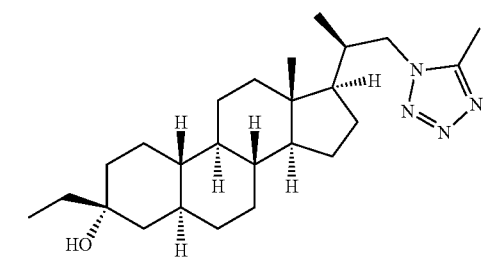 |

US 11,970,514 B2
165                                                              166
TABLE 1-continued
| Example | STRUCTURE |
|---|---|
| 336 | 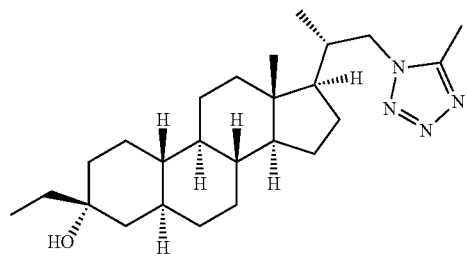 |
| 337 | 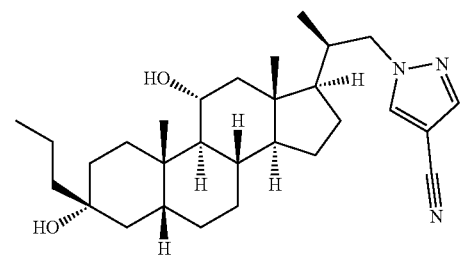 |
| 338 | 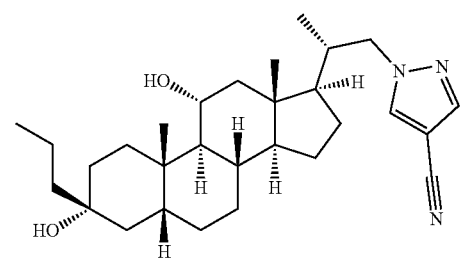 |
| 339 | 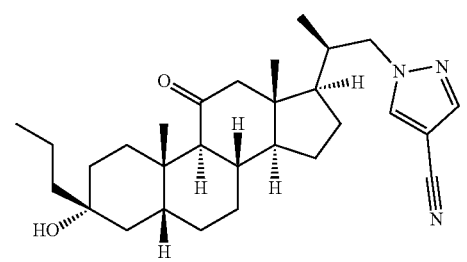 |
| 340 | 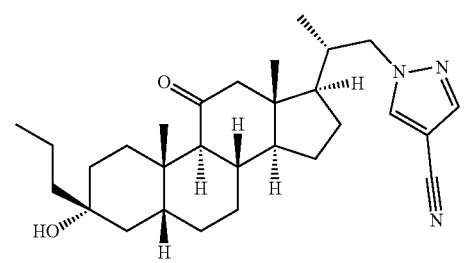 |
| 341 | 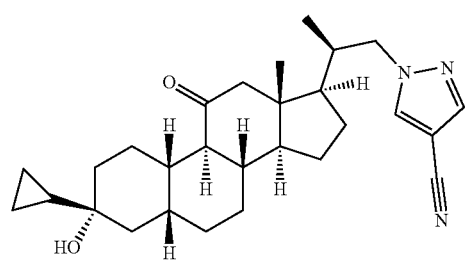 |

TABLE 1-continued
| Example | STRUCTURE |
|---|---|
| 342 | 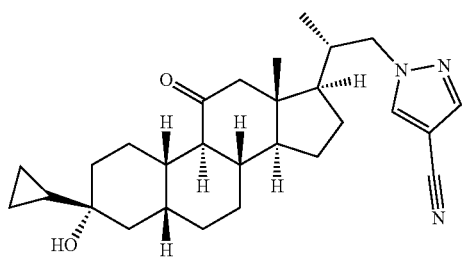 |
| 343 | 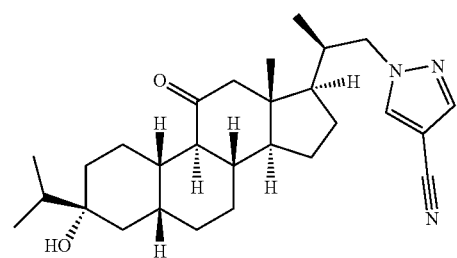 |
| 344 | 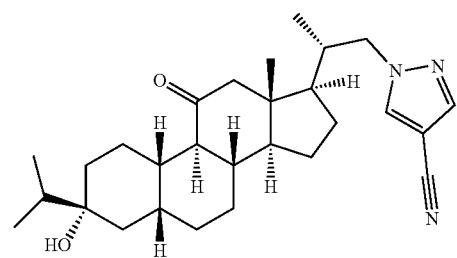 |
| 345 | 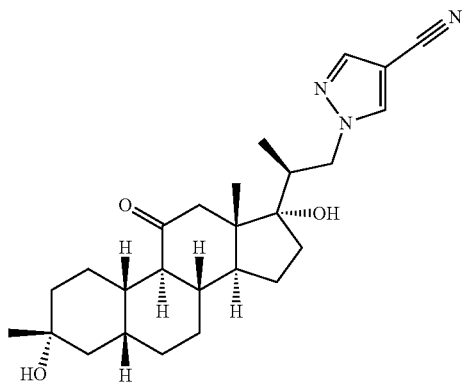 |
| 346 | 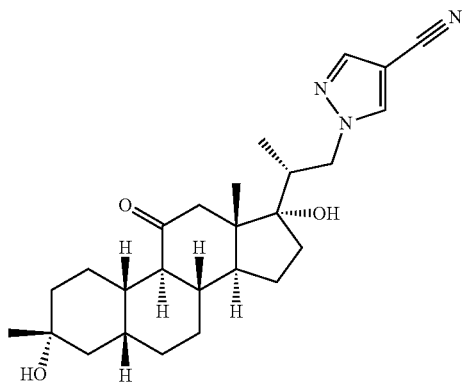 |

TABLE 1-continued
| Example | STRUCTURE |
|---|---|
| 347 | 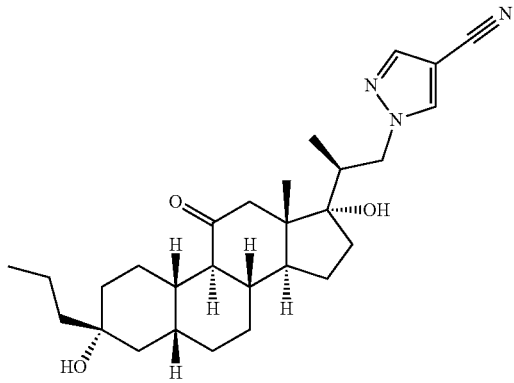 |
| 348 | 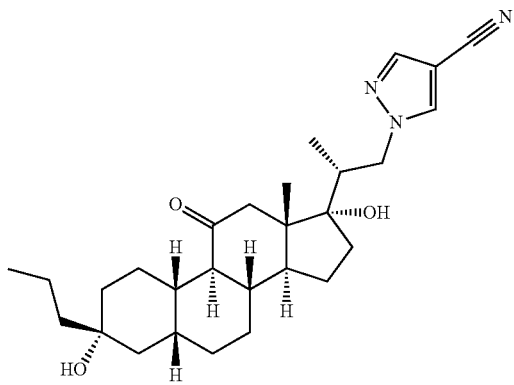 |
| 349 | 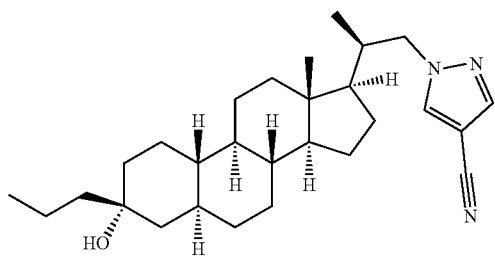 |
| 350 | 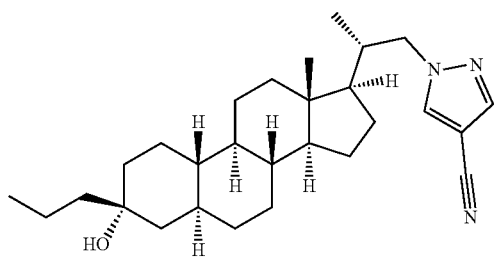 |

TABLE 1-continued
| Example | STRUCTURE |
|---|---|
| 351 | 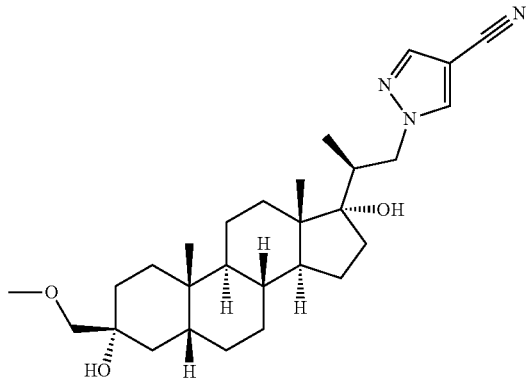 |
| 352 | 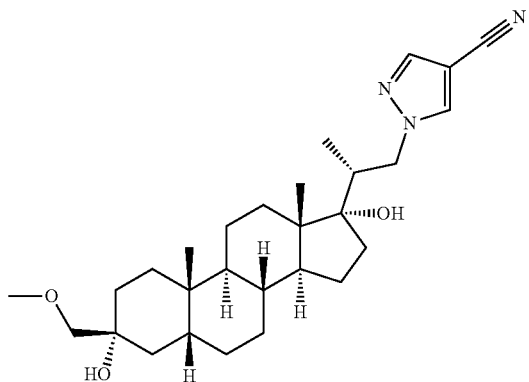 |
| 353 | 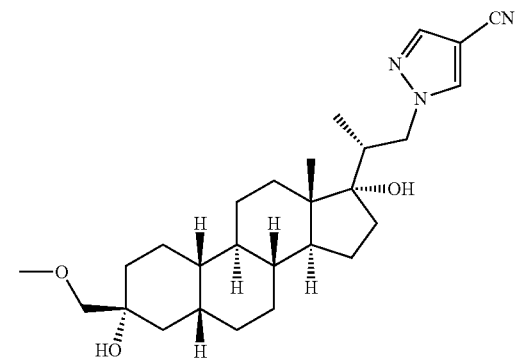 |
| 354 | 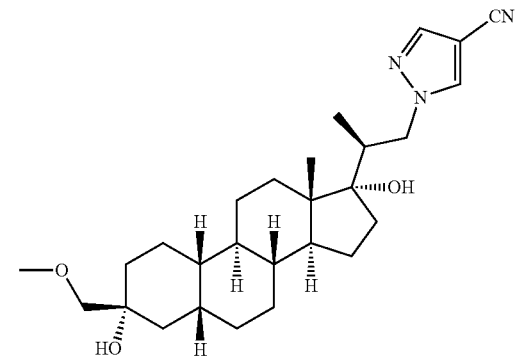 |

TABLE 1-continued
| Example | STRUCTURE |
|---------|-----------|
| 355 | 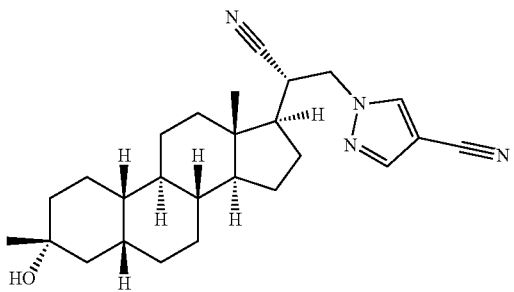 |
| 356 | 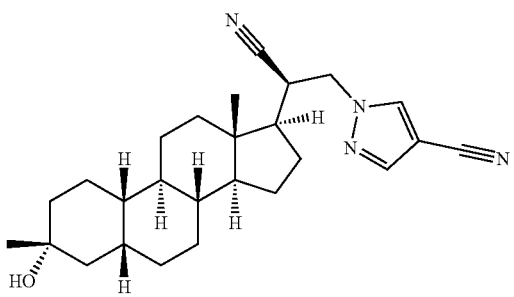 |
| 357 | 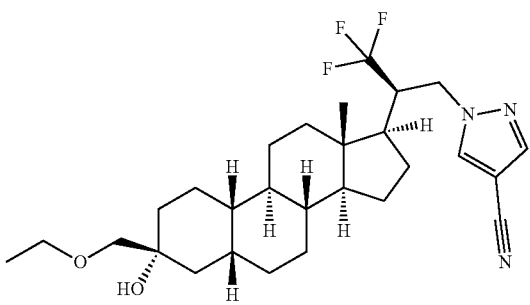 |
| 358 | 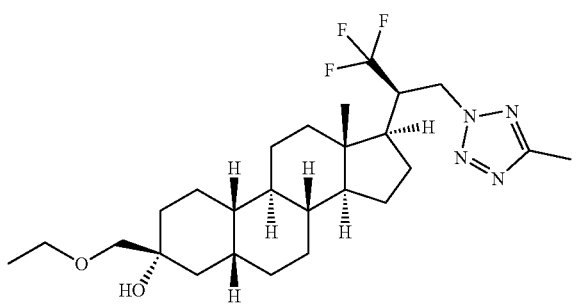 |
| 359 | 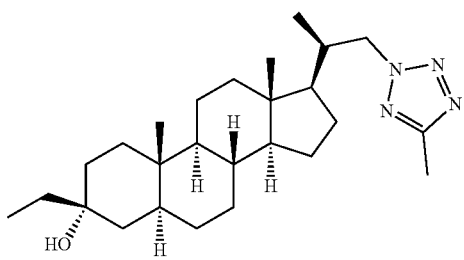 |

TABLE 1-continued
| Example | STRUCTURE |
|---|---|
| 360 | 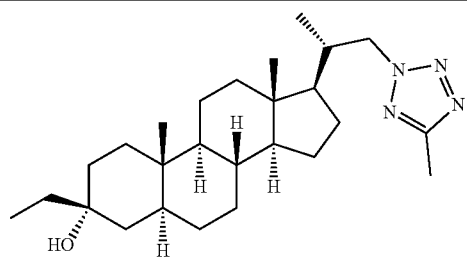 |
| 361 | 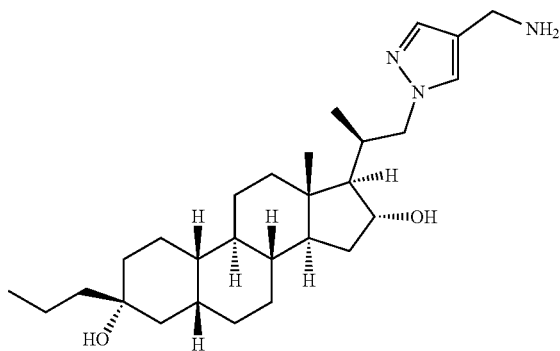 |
| 362 | 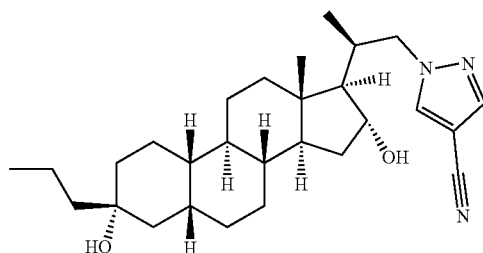 |
| 363 | 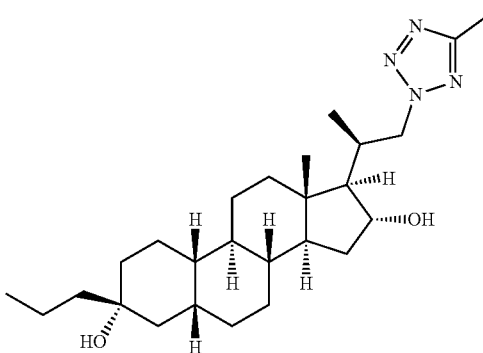 |
| 364 | 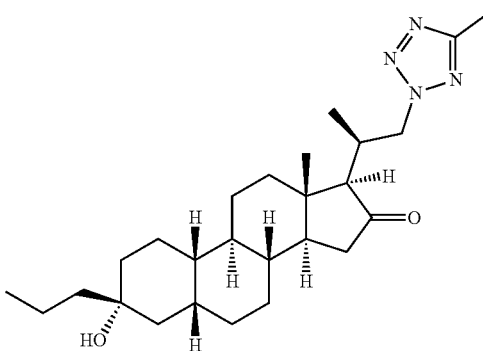 |

TABLE 1-continued
| Example | STRUCTURE |
|---|---|
| 365 | 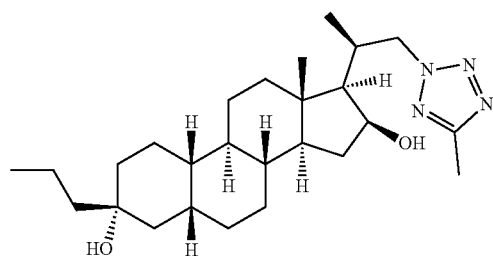 |
| 366 | 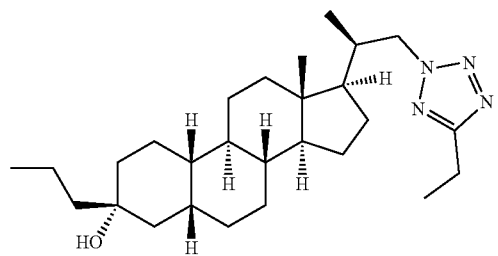 |
| 367 | 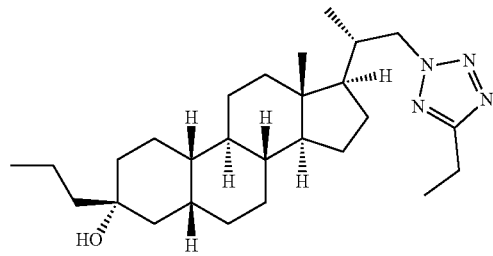 |
| 368 | 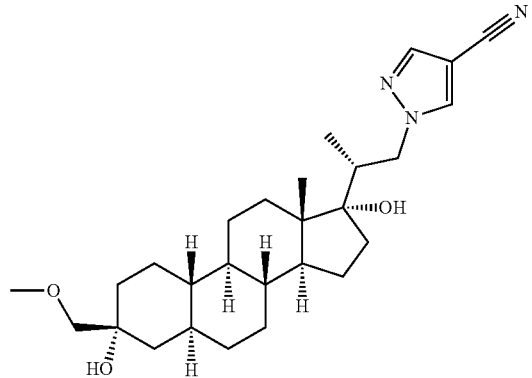 |
| 369 | 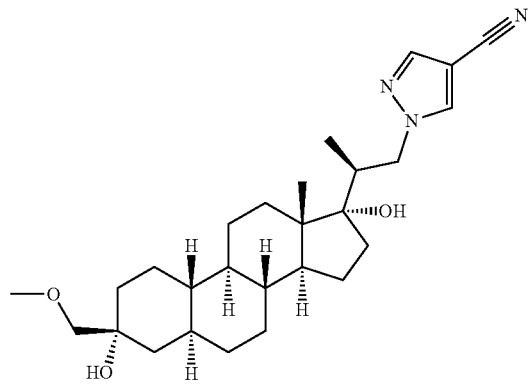 |

TABLE 1-continued

| Example | STRUCTURE |
|---|---|
| 400 | 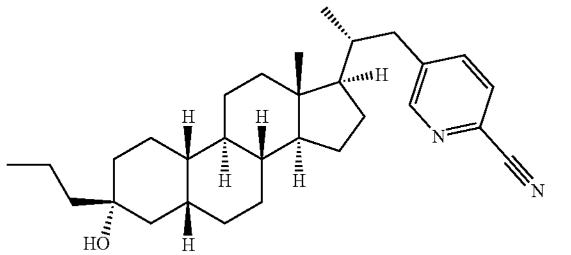 |
| 401 | 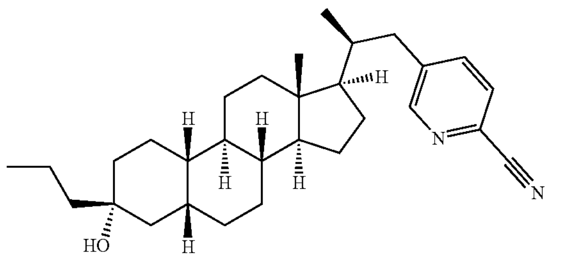 |
| 402 | 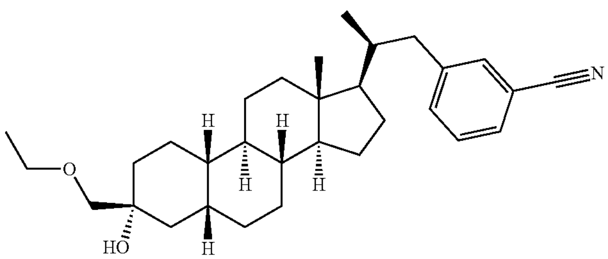 |
| 403 | 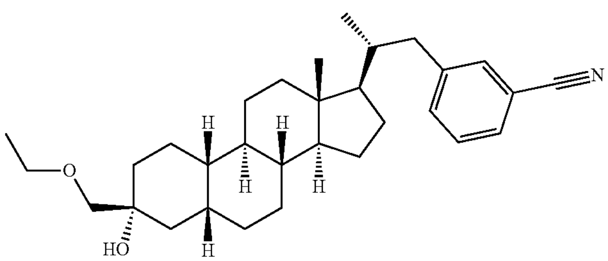 |
| 404 | 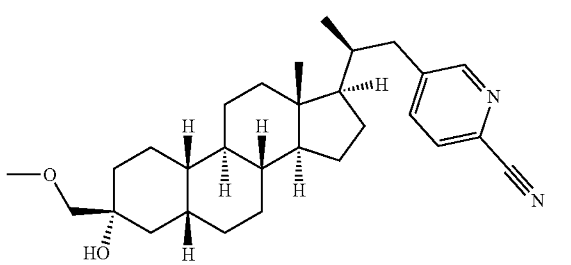 |
| 405 | 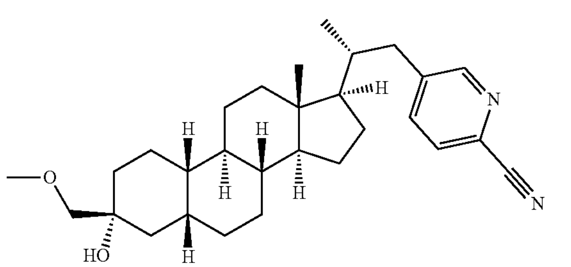 |

TABLE 1-continued

| Example | STRUCTURE |
|---|---|
| 406 | 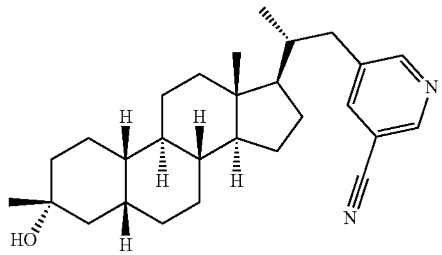 |
| 407 | 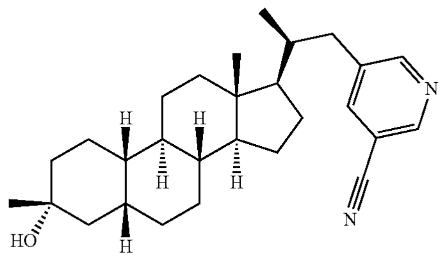 |
| 410 | 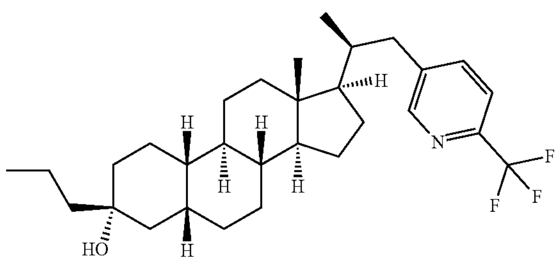 |
| 411 | 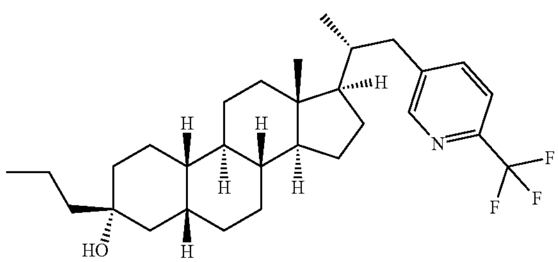 |
| 412 | 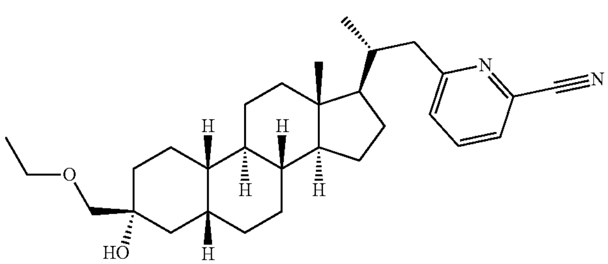 |
| 413 | 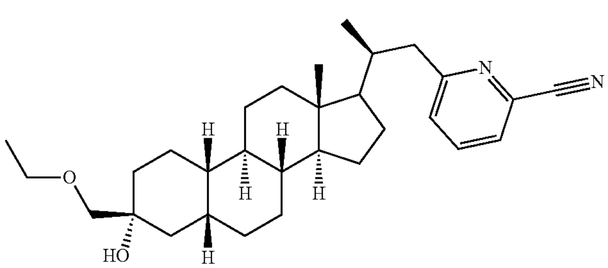 |

TABLE 1-continued
| Example | STRUCTURE |
|---|---|
| 414 | 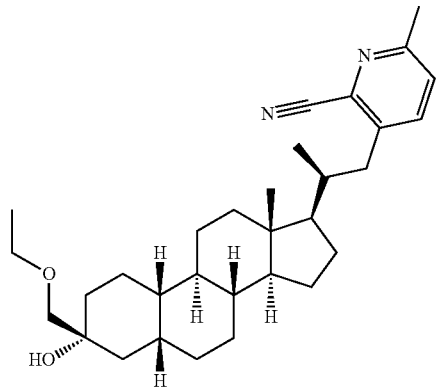 |
| 415 | 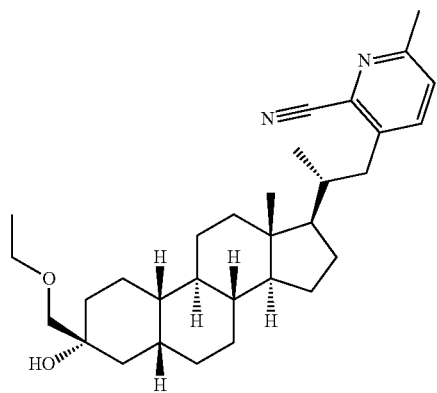 |
| 416 | 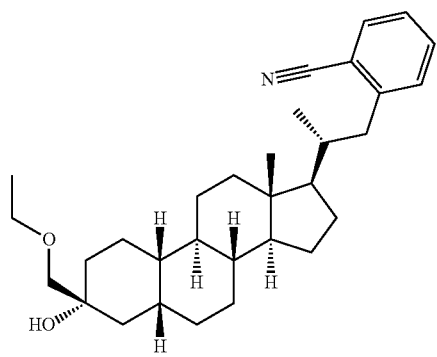 |
| 417 | 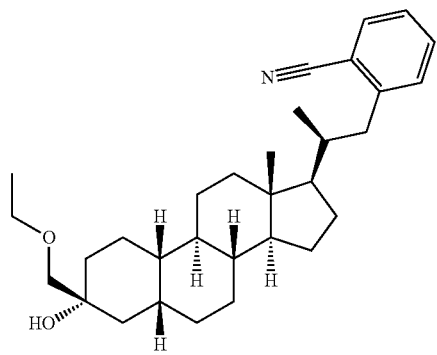 |

TABLE 1-continued
| Example | STRUCTURE |
|---|---|
| 418 | 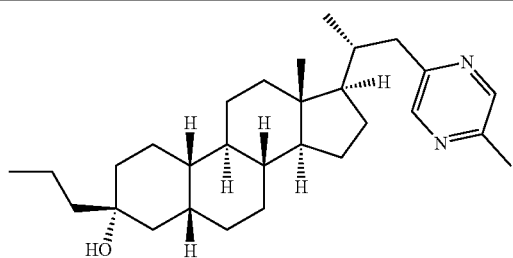 |
| 419 | 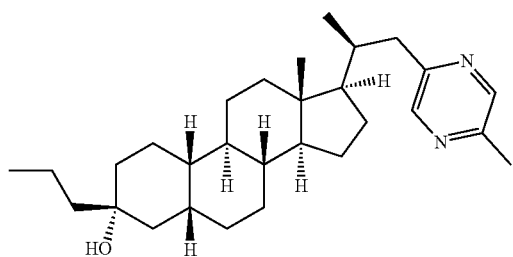 |
| 420 | 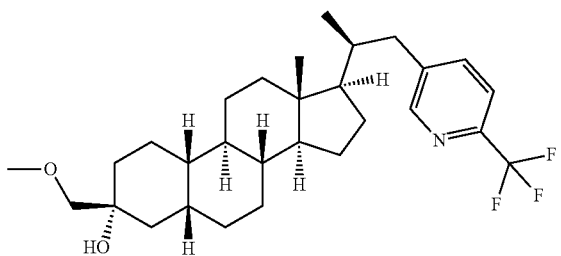 |
| 421 | 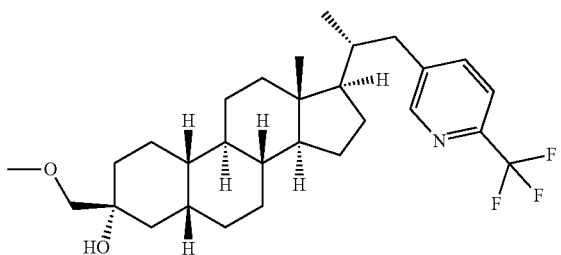 |
| 422 | 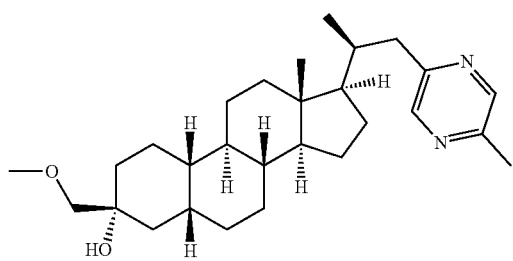 |
| 423 | 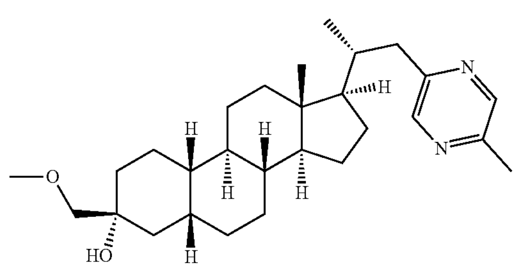 |

TABLE 1-continued
| Example | STRUCTURE |
|---|---|
| 424 | 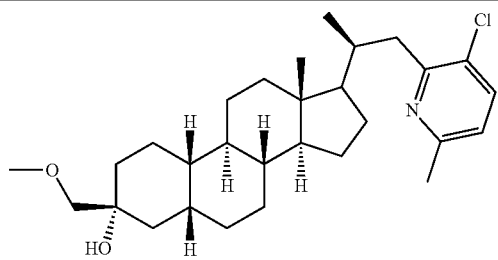 |
| 425 | 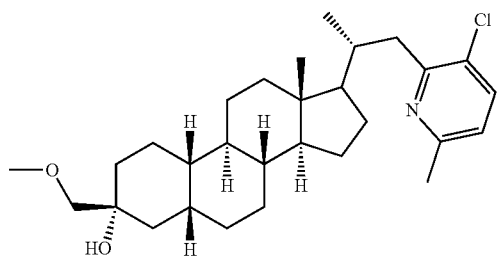 |
| 426 | 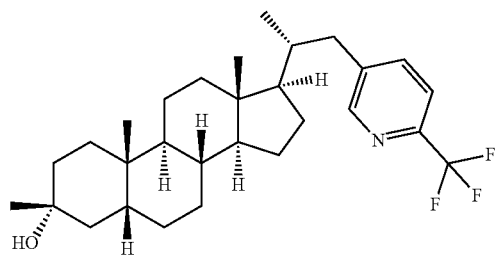 |
| 427 | 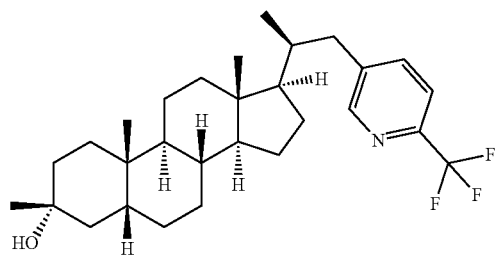 |
| 428 | 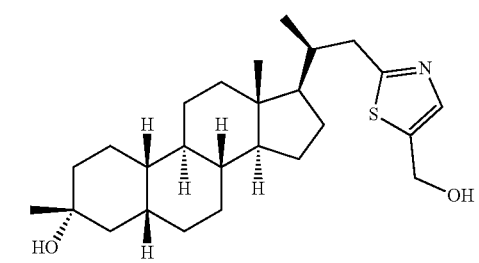 |
| 429 | 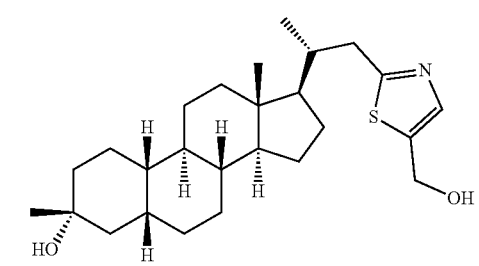 |

TABLE 1-continued
| Example | STRUCTURE |
|---|---|
| 430 | 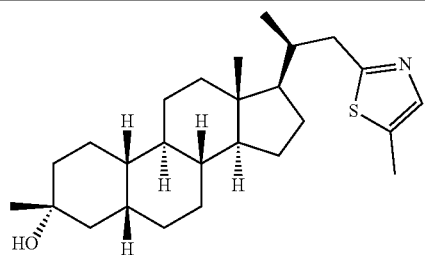 |
| 431 | 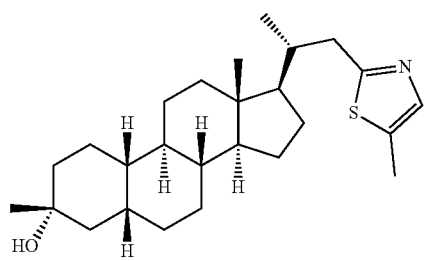 |
| 432 | 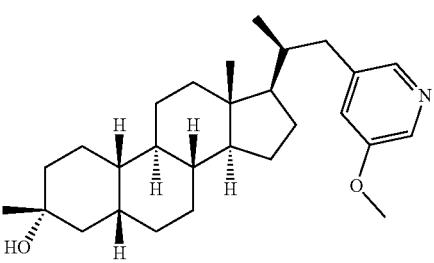 |
| 433 | 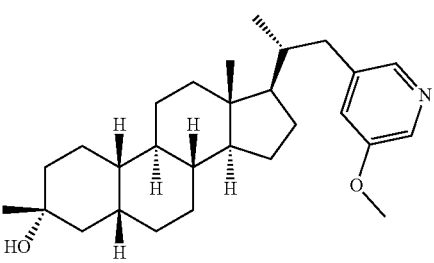 |
| 434 | 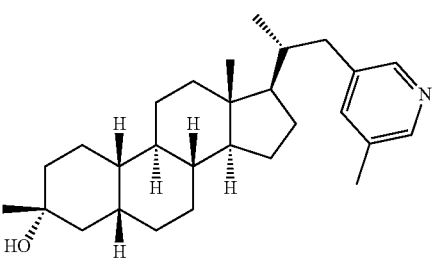 |
| 435 | 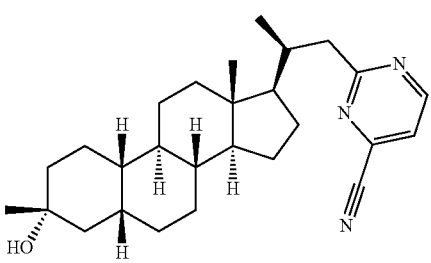 |

TABLE 1-continued
| Example | STRUCTURE |
|---|---|
| 436 | 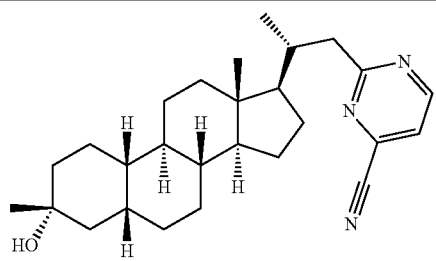 |
| 437 | 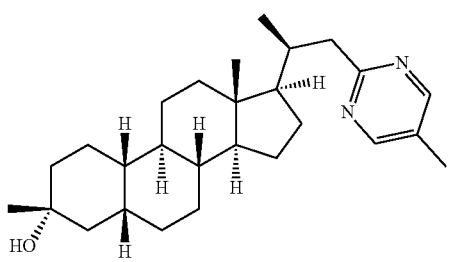 |
| 438 | 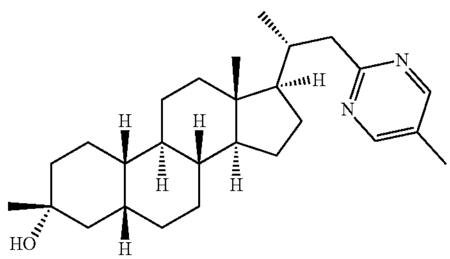 |
| 439 | 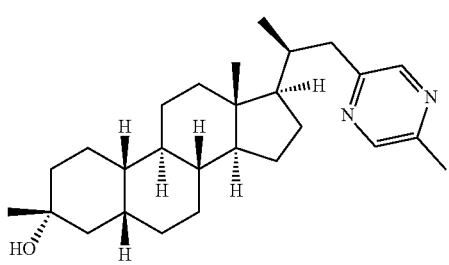 |
| 440 | 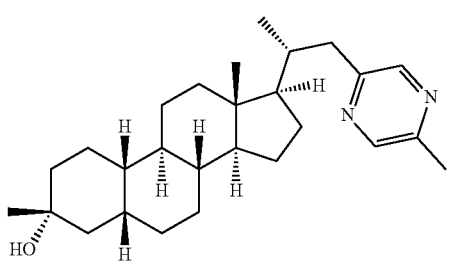 |
| 441 | 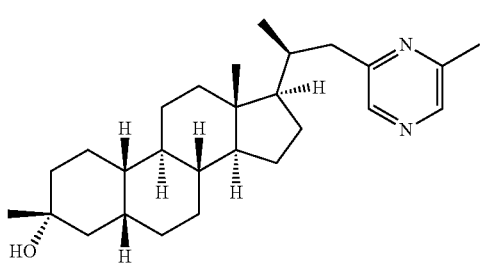 |

TABLE 1-continued
| Example | STRUCTURE |
|---|---|
| 442 | 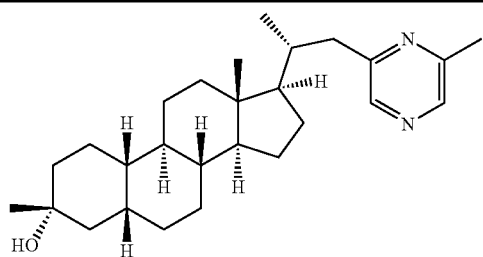 |
| 443 | 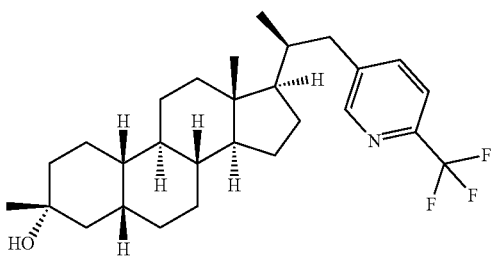 |
| 444 | 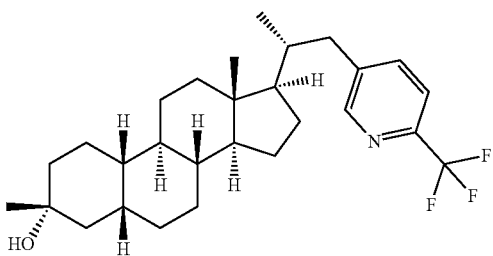 |
| 445 | 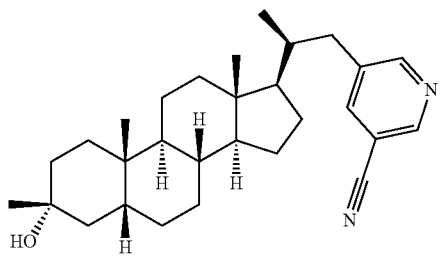 |
| 446 | 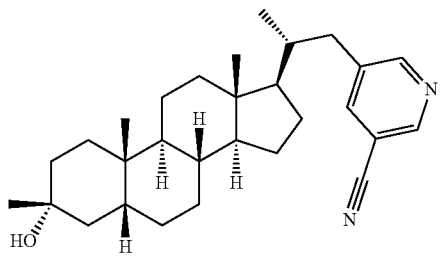 |
| 447 | 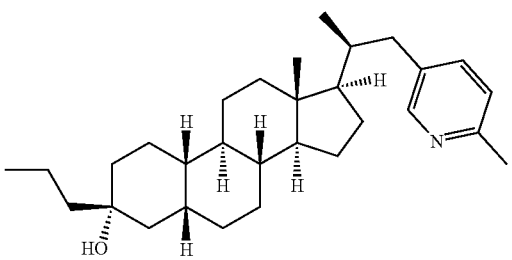 |

TABLE 1-continued
| Example | STRUCTURE |
|---|---|
| 448 | 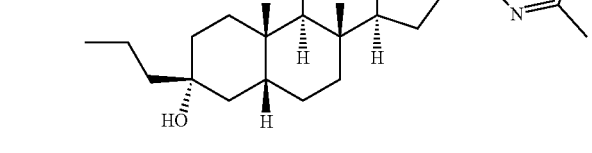 |
| 449 | 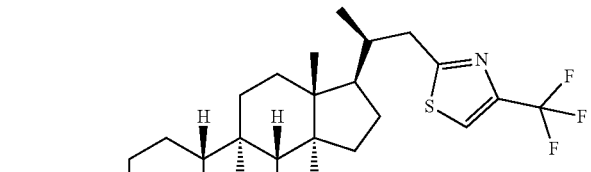 |
| 450 | 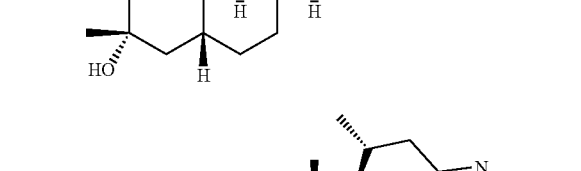 |
| 451 | 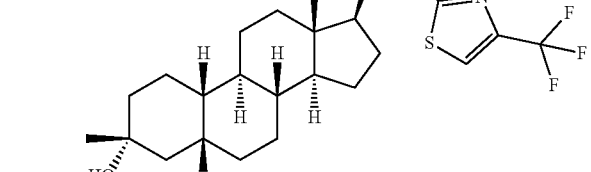 |
| 452 | 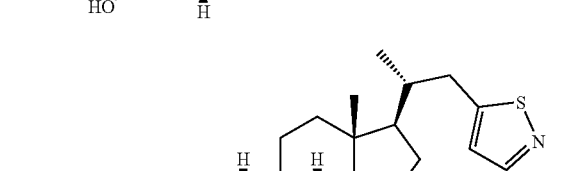 |
| 453 | 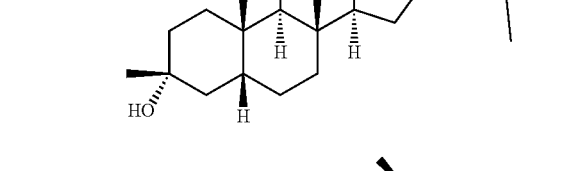 |

TABLE 1-continued
| Example | STRUCTURE |
|---|---|
| 454 | 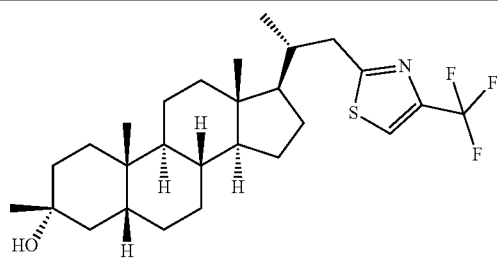 |
| 455 | 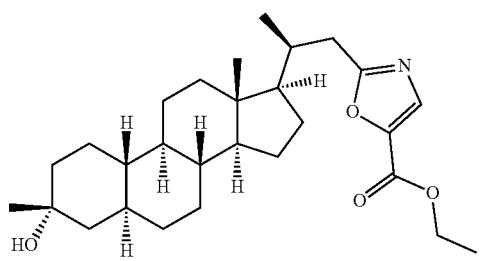 |
| 456 | 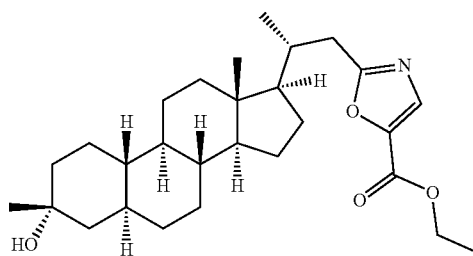 |
| 457 | 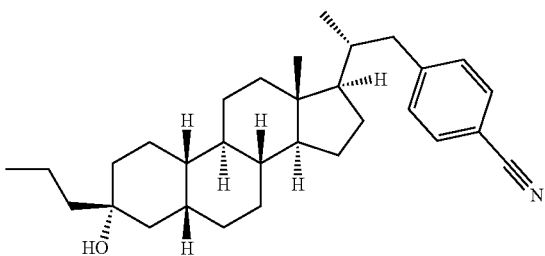 |
| 458 | 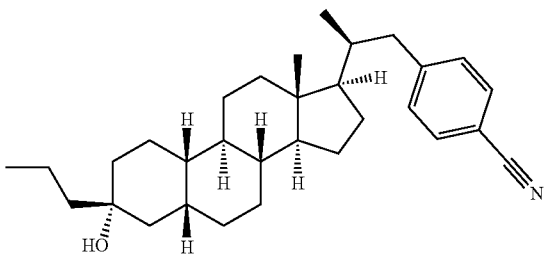 |
| 459 | 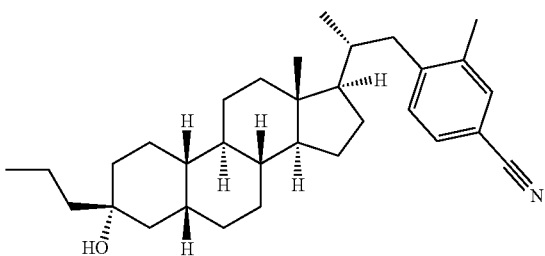 |

TABLE 1-continued
| Example | STRUCTURE |
|---|---|
| 460 | 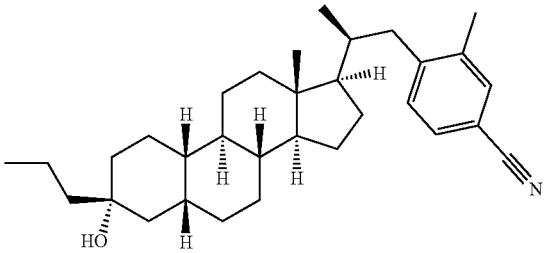 |
| 487 | 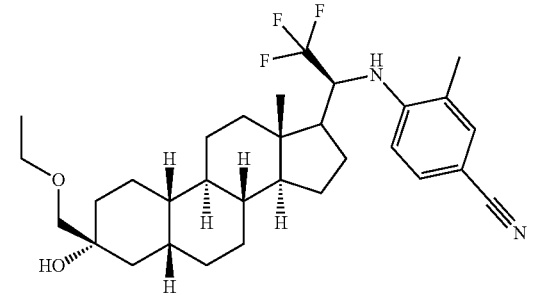 |
| 488 | 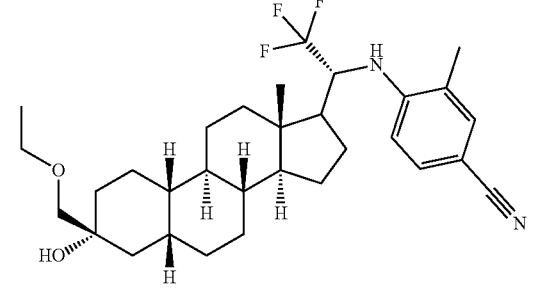 |
| 489 | 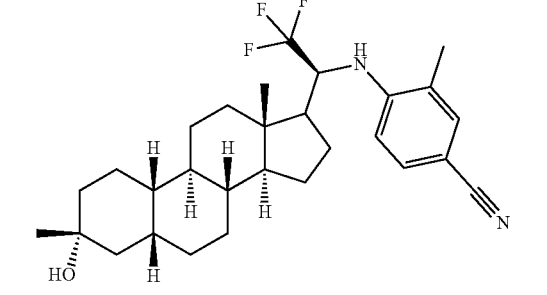 |
| 490 | 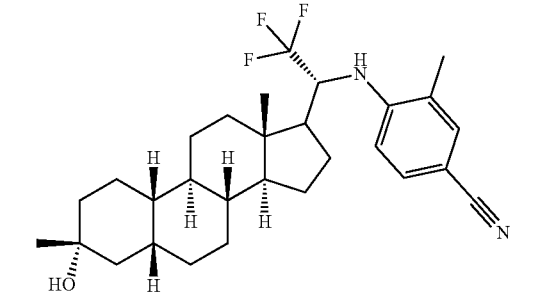 |

TABLE 1-continued

| Example | STRUCTURE |
|---------|-----------|
| 491 | 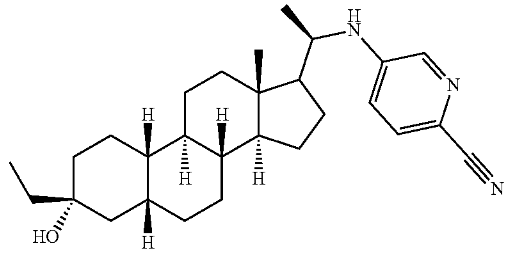 |
| 492 | 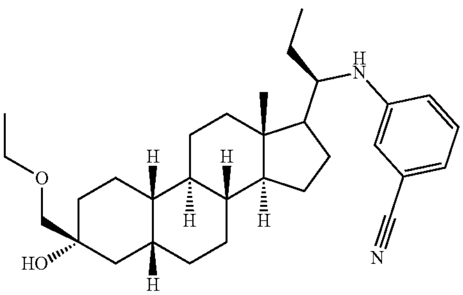 |
| 493 | 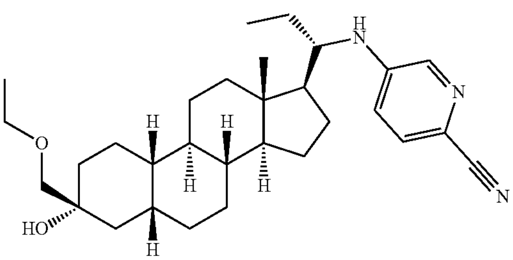 |
| 494 | 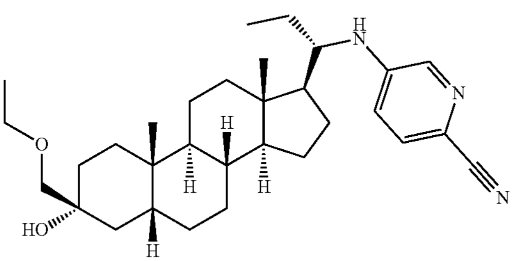 |
| 495 | 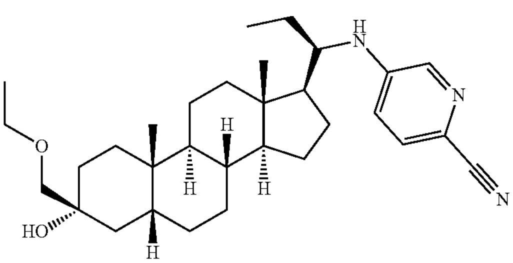 |
| 496 | 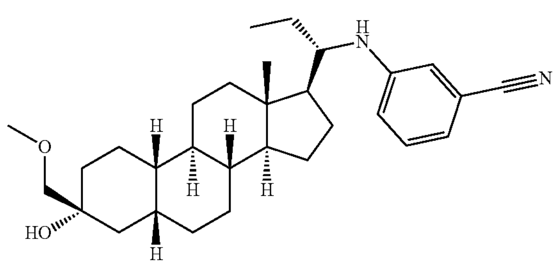 |

TABLE 1-continued
| Example | STRUCTURE |
|---|---|
| 497 | 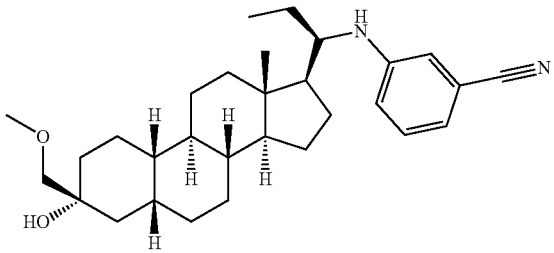 |
| 498 | 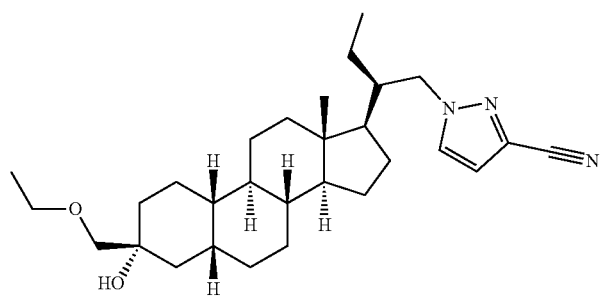 |
| 499 | 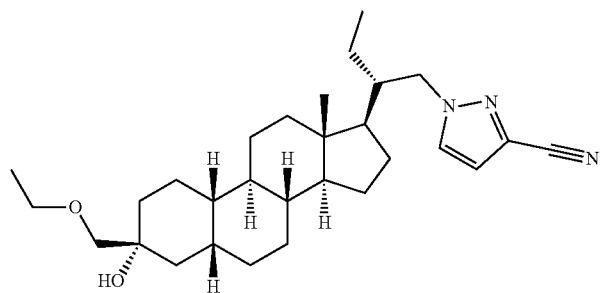 |
| 500 | 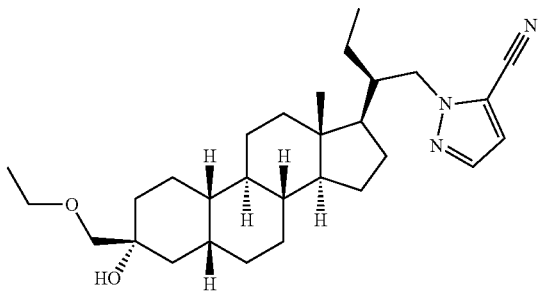 |
| 501 | 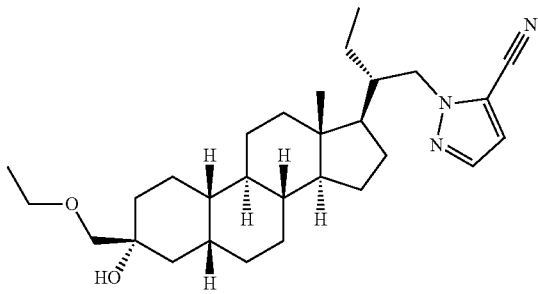 |

TABLE 1-continued

| Example | STRUCTURE |
|---|---|
| 502 | 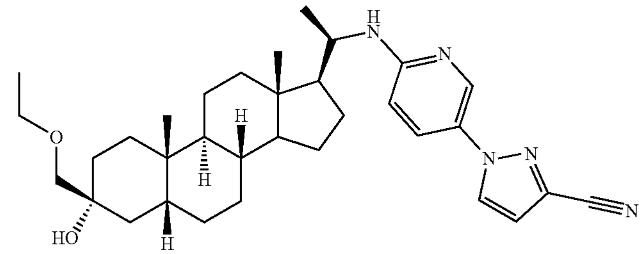 |
| 503 | 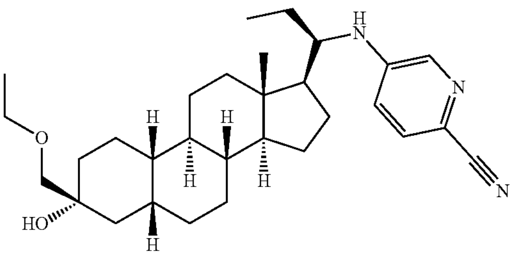 |
| 504 | 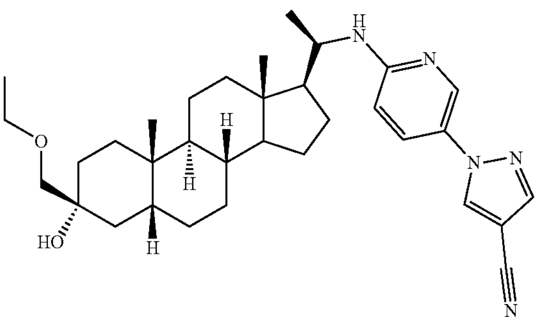 |
| 505 | 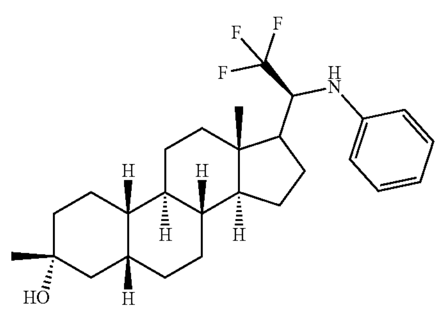 |
| 506 | 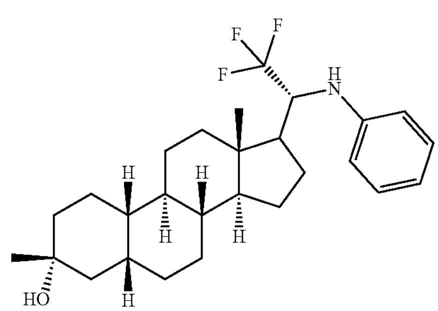 |

Exemplary compounds of the invention may be synthesized from the following known starting materials using methods known to one skilled in the art or certain references, In one aspect, provided herein is a pharmaceutically acceptable salt of a compound described herein (e.g., a compound of Formula (I)).

Pharmaceutical Compositions

In one aspect, provided herein is a pharmaceutical composition comprising a compound described herein (e.g., a compound of Formula (I)) or a pharmaceutically acceptable salt thereof, and a pharmaceutically acceptable excipient. In certain embodiments, the compound of the present invention is provided in an effective amount in the pharmaceutical composition. In certain embodiments, the compound of the present invention is provided in a therapeutically effective amount. In certain embodiments, the compound of the present invention is provided in a prophylactically effective amount.

In certain embodiments, the pharmaceutical composition comprises an effective amount of the active ingredient. In certain embodiments, the pharmaceutical composition comprises a therapeutically effective amount of the active ingredient. In certain embodiments, the pharmaceutical composition comprises a prophylactically effective amount of the active ingredient.

The pharmaceutical compositions provided herein can be administered by a variety of routes including, but not limited to, oral (enteral) administration, parenteral (by injection) administration, rectal administration, transdermal administration, intradermal administration, intrathecal administration, subcutaneous (SC) administration, intravenous (IV) administration, intramuscular (IM) administration, and intranasal administration.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the onset of a CNS-disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc, or may be continued indefinitely, for example, for the rest of the subject's life. In certain embodiments, the chronic administration is intended to provide a constant level of the compound in the blood, e.g., within the therapeutic window over the extended period of time.

The pharmaceutical compositions of the present invention may be further delivered using a variety of dosing methods. For example, in certain embodiments, the pharmaceutical composition may be given as a bolus, e.g., in order to raise the concentration of the compound in the blood to an effective level. The placement of the bolus dose depends on the systemic levels of the active ingredient desired throughout the body, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, preferably from about 0.1 to about 20% by weight, preferably from about 0.1 to about 10% by weight, and more preferably from about 0.5 to about 15% by weight.

Injection dose levels range from about 0.1 mg/kg/hour to at least 20 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 5 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient(s). When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17th edition, 1985, Mack Publishing Company, Easton, Pennsylvania, which is incorporated herein by reference.

The compounds of the present invention can also be administered in sustained release forms or from sustained release drug delivery systems. A description of representative sustained release materials can be found in *Remington's Pharmaceutical Sciences*.

The present invention also relates to the pharmaceutically acceptable acid addition salt of a compound of the present invention. The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

In another aspect, the invention provides a pharmaceutical composition comprising a compound of the present invention and a pharmaceutically acceptable excipient, e.g., a composition suitable for injection, such as for intravenous (IV) administration.

Pharmaceutically acceptable excipients include any and all diluents or other liquid vehicles, dispersion or suspension aids, surface active agents, isotonic agents, preservatives, lubricants and the like, as suited to the particular dosage form desired, e.g., injection. General considerations in the formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21$^{st}$ Edition (Lippincott Williams & Wilkins, 2005).

For example, injectable preparations, such as sterile injectable aqueous suspensions, can be formulated according to the known art using suitable dispersing or wetting agents and suspending agents. Exemplary excipients that can be employed include, but are not limited to, water, sterile saline or phosphate-buffered saline, or Ringer's solution.

In certain embodiments, the pharmaceutical composition further comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, substituted or unsubstituted methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as CAPTISOL®. See, e.g., U.S. Pat. No. 5,376,645. In certain embodiments, the composition comprises hexapropyl-β-cyclodextrin. In a more particular embodiment, the composition comprises hexapropyl-β-cyclodextrin (10-50% in water).

The injectable composition can be sterilized, for example, by filtration through a bacterial-retaining filter, or by incorporating sterilizing agents in the form of sterile solid compositions which can be dissolved or dispersed in sterile water or other sterile injectable medium prior to use.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, response of the individual patient, the severity of the patient's symptoms, and the like.

The compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include pre-filled, pre-measured ampules or syringes of the liquid compositions. In such compositions, the compound is usually a minor component (from about 0.1% to about 50% by weight or preferably from about 1% to about 40% by weight) with the remainder being various vehicles or carriers and processing aids helpful for forming the desired dosing form.

The compounds provided herein can be administered as the sole active agent, or they can be administered in combination with other active agents. In one aspect, the present invention provides a combination of a compound of the present invention and another pharmacologically active agent. Administration in combination can proceed by any technique apparent to those of skill in the art including, for example, separate, sequential, concurrent, and alternating administration.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in *Remington: The Science and Practice of Pharmacy* 21$^{st}$ ed., Lippincott Williams & Wilkins, 2005.

In one aspect, provided is a kit comprising a composition (e.g., a solid composition) comprising a compound of Formula (I).

Methods of Use and Treatment

In an aspect, compounds described herein, e.g., compounds of Formula (I), are envisioned to be useful as therapeutic agents for treating a CNS-related disorder (e.g., sleep disorder, a mood disorder such as depression, a schizophrenia spectrum disorder, a convulsive disorder, epileptogenesis, a disorder of memory and/or cognition, a movement disorder, a personality disorder, autism spectrum disorder, pain, traumatic brain injury, a vascular disease, a substance abuse disorder and/or withdrawal syndrome, or tinnitus) in a subject in need (e.g., a subject with Rett syndrome, Fragile X syndrome, or Angelman syndrome). Exemplary CNS conditions related to GABA-modulation include, but are not limited to, sleep disorders [e.g., insomnia], mood disorders [e.g., depression (e.g., major depressive disorder (MDD)), dysthymic disorder (e.g., mild depression), bipolar disorder (e.g., I and/or II), anxiety disorders (e.g., generalized anxiety disorder (GAD), social anxiety disorder), stress, post-traumatic stress disorder (PTSD), compulsive disorders (e.g., obsessive compulsive disorder (OCD))], schizophrenia spectrum disorders [e.g., schizophrenia, schizoaffective disorder], convulsive disorders [e.g., epilepsy (e.g., status epilepticus (SE)), seizures], disorders of memory and/or cognition [e.g., attention disorders (e.g., attention deficit hyperactivity disorder (ADHD)), dementia (e.g., Alzheimer's type dementia, Lewis body type dementia, vascular type dementia], movement disorders [e.g., Huntington's disease, Parkinson's disease], personality disorders [e.g., anti-social personality disorder, obsessive compulsive personality disorder], autism spectrum disorders (ASD) [e.g., autism, monogenetic causes of autism such as synaptophathy's, e.g., Rett syndrome, Fragile X syndrome, Angelman syndrome], pain [e.g., neuropathic pain, injury related pain syndromes, acute pain, chronic pain], traumatic brain injury (TBI), vascular diseases [e.g., stroke, ischemia, vascular malformations], substance abuse disorders and/or withdrawal syndromes [e.g., addition to opiates, cocaine, and/or alcohol], and tinnitus.

In certain embodiments, CNS-related disorder is a sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, tinnitus, or status epilepticus. In certain embodiments, the CNS-related disorder is depression. In certain embodiments, the CNS-related disorder is postpartum depression. In certain embodiments, the CNS-related disorder is major depressive disorder. In certain embodiments, the major depressive disorder is moderate major depressive disorder. In certain embodiments, the major depressive disorder is severe major depressive disorder.

In an aspect, provided is a method of alleviating or preventing seizure activity in a subject, comprising administering to the subject in need of such treatment an effective amount of a compound of the present invention. In some embodiments, the method alleviates or prevents epileptogenesis.

In yet another aspect, provided is a combination of a compound of the present invention and another pharmacologically active agent. The compounds provided herein can be administered as the sole active agent or they can be administered in combination with other agents. Administration in combination can proceed by any technique apparent to those of skill in the art including, for example, separate, sequential, concurrent and alternating administration.

In another aspect, provided is a method of treating or preventing brain excitability in a subject susceptible to or afflicted with a condition associated with brain excitability, comprising administering to the subject an effective amount of a compound of the present invention to the subject.

In yet another aspect, provided is a method of treating or preventing stress or anxiety in a subject, comprising administering to the subject in need of such treatment an effective amount of a compound of the present invention, or a composition thereof.

In yet another aspect, provided is a method of alleviating or preventing insomnia in a subject, comprising administering to the subject in need of such treatment an effective amount of a compound of the present invention, or a composition thereof.

In yet another aspect, provided is a method of inducing sleep and maintaining substantially the level of REM sleep that is found in normal sleep, wherein substantial rebound insomnia is not induced, comprising administering an effective amount of a compound of the present invention.

In yet another aspect, provided is a method of alleviating or preventing premenstrual syndrome (PMS) or postnatal depression (PND) in a subject, comprising administering to the subject in need of such treatment an effective amount of a compound of the present invention.

In yet another aspect, provided is a method of treating or preventing mood disorders in a subject, comprising administering to the subject in need of such treatment an effective amount of a compound of the present invention. In certain embodiments the mood disorder is depression.

In yet another aspect, provided is a method of cognition enhancement or treating memory disorder by administering to the subject a therapeutically effective amount of a compound of the present invention. In certain embodiments, the disorder is Alzheimer's disease. In certain embodiments, the disorder is Rett syndrome.

In yet another aspect, provided is a method of treating attention disorders by administering to the subject a therapeutically effective amount of a compound of the present invention. In certain embodiments, the attention disorder is ADHD.

In certain embodiments, the compound is administered to the subject chronically. In certain embodiments, the compound is administered to the subject orally, subcutaneously, intramuscularly, or intravenously.

Neuroendocrine Disorders and Dysfunction

Provided herein are methods that can be used for treating neuroendocrine disorders and dysfunction. As used herein, "neuroendocrine disorder" or "neuroendocrine dysfunction" refers to a variety of conditions caused by imbalances in the body's hormone production directly related to the brain. Neuroendocrine disorders involve interactions between the nervous system and the endocrine system. Because the hypothalamus and the pituitary gland are two areas of the brain that regulate the production of hormones, damage to the hypothalamus or pituitary gland, e.g., by traumatic brain injury, may impact the production of hormones and other neuroendocrine functions of the brain. In some embodiments, the neuroendocrine disorder or dysfunction is associated with a women's health disorder or condition (e.g., a women's health disorder or condition described herein). In some embodiments, the neuroendocrine disorder or dysfunction is associated with a women's health disorder or condition is polycystic ovary syndrome.

Symptoms of neuroendocrine disorder include, but are not limited to, behavioral, emotional, and sleep-related symptoms, symptoms related to reproductive function, and somatic symptoms; including but not limited to fatigue, poor memory, anxiety, depression, weight gain or loss, emotional lability, lack of concentration, attention difficulties, loss of lipido, infertility, amenorrhea, loss of muscle mass, increased belly body fat, low blood pressure, reduced heart rate, hair loss, anemia, constipation, cold intolerance, and dry skin.

Neurodegenerative Diseases and Disorders

The methods described herein can be used for treating neurodegenerative diseases and disorders. The term "neurodegenerative disease" includes diseases and disorders that are associated with the progressive loss of structure or function of neurons, or death of neurons. Neurodegenerative diseases and disorders include, but are not limited to, Alzheimer's disease (including the associated symptoms of mild, moderate, or severe cognitive impairment); amyotrophic lateral sclerosis (ALS); anoxic and ischemic injuries; ataxia and convulsion (including for the treatment and prevention and prevention of seizures that are caused by schizoaffective disorder or by drugs used to treat schizophrenia); benign forgetfulness; brain edema; cerebellar ataxia including McLeod neuroacanthocytosis syndrome (MLS); closed head injury; coma; contusive injuries (e.g., spinal cord injury and head injury); dementias including multi-infarct dementia and senile dementia; disturbances of consciousness; Down syndrome; drug-induced or medication-induced Parkinsonism (such as neuroleptic-induced acute akathisia, acute dystonia, Parkinsonism, or tardive dyskinesia, neuroleptic malignant syndrome, or medication-induced postural tremor); epilepsy; fragile X syndrome; Gilles de la Tourette's syndrome; head trauma; hearing impairment and loss; Huntington's disease; Lennox syndrome; levodopa-induced dyskinesia; mental retardation; movement disorders including akinesias and akinetic (rigid) syndromes (including basal ganglia calcification, corticobasal degeneration, multiple system atrophy, Parkinsonism-ALS dementia complex, Parkinson's disease, postencephalitic parkinsonism, and progressively supranuclear palsy); muscular spasms and disorders associated with muscular spasticity or weakness including chorea (such as benign hereditary chorea, drug-induced chorea, hemiballism, Huntington's disease, neuroacanthocytosis, Sydenham's chorea, and symptomatic chorea), dyskinesia (including tics such as complex tics, simple tics, and symptomatic tics), myoclonus (including generalized myoclonus and focal cycloclonus), tremor (such as rest tremor, postural tremor, and intention tremor) and dystonia (including axial dystonia, dystonic writer's cramp, hemiplegic dystonia, paroxysmal dystonia, and focal dystonia such as blepharospasm, oromandibular dystonia, and spasmodic dysphonia and torticollis); neuronal damage including ocular damage, retinopathy or macular degeneration of the eye; neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest; Parkinson's disease; seizure; status epilecticus; stroke; tinnitus; tubular sclerosis, and viral infection induced neurodegeneration (e.g., caused by acquired immunodeficiency syndrome (AIDS) and encephalopathies). Neurodegenerative diseases also include, but are not limited to, neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest. Methods of treating or preventing a neurodegenerative disease also include treating or preventing loss of neuronal function characteristic of neurodegenerative disorder.

Mood Disorders

Also provided herein are methods for treating a mood disorder, for example clinical depression, postnatal depression or postpartum depression, perinatal depression, atypical depression, melancholic depression, psychotic major depression, catatonic depression, seasonal affective disorder, dysthymia, double depression, depressive personality disorder, recurrent brief depression, minor depressive disorder, bipolar disorder or manic depressive disorder, depression caused by chronic medical conditions, treatment-resistant depression, refractory depression, suicidality, suicidal ideation, or suicidal behavior. In some embodiments, the method described herein provides therapeutic effect to a subject suffering from depression (e.g., moderate or severe depression). In some embodiments, the mood disorder is associated with a disease or disorder described herein (e.g., neuroendocrine diseases and disorders, neurodegenerative diseases and disorders (e.g., epilepsy), movement disorders, tremor (e.g., Parkinson's Disease), women's health disorders or conditions).

Clinical depression is also known as major depression, major depressive disorder (MDD), severe depression, unipolar depression, unipolar disorder, and recurrent depression, and refers to a mental disorder characterized by pervasive and persistent low mood that is accompanied by low self-esteem and loss of interest or pleasure in normally enjoyable activities. Some people with clinical depression have trouble sleeping, lose weight, and generally feel agitated and irritable. Clinical depression affects how an individual feels, thinks, and behaves and may lead to a variety of emotional and physical problems. Individuals with clinical depression may have trouble doing day-to-day activities and make an individual feel as if life is not worth living.

Peripartum depression refers to depression in pregnancy. Symptoms include irritability, crying, feeling restless, trouble sleeping, extreme exhaustion (emotional and/or physical), changes in appetite, difficulty focusing, increased anxiety and/or worry, disconnected feeling from baby and/or fetus, and losing interest in formerly pleasurable activities.

Postnatal depression (PND) is also referred to as postpartum depression (PPD), and refers to a type of clinical depression that affects women after childbirth. Symptoms can include sadness, fatigue, changes in sleeping and eating habits, reduced sexual desire, crying episodes, anxiety, and irritability. In some embodiments, the PND is a treatment-resistant depression (e.g., a treatment-resistant depression as described herein). In some embodiments, the PND is refractory depression (e.g., a refractory depression as described herein).

In some embodiments, a subject having PND also experienced depression, or a symptom of depression during pregnancy. This depression is referred to herein as) perinatal depression. In an embodiment, a subject experiencing perinatal depression is at increased risk of experiencing PND.

Atypical depression (AD) is characterized by mood reactivity (e.g., paradoxical anhedonia) and positivity, significant weight gain or increased appetite. Patients suffering from AD also may have excessive sleep or somnolence (hypersomnia), a sensation of limb heaviness, and significant social impairment as a consequence of hypersensitivity to perceived interpersonal rejection.

Melancholic depression is characterized by loss of pleasure (anhedonia) in most or all activities, failures to react to pleasurable stimuli, depressed mood more pronounced than that of grief or loss, excessive weight loss, or excessive guilt.

Psychotic major depression (PMD) or psychotic depression refers to a major depressive episode, in particular of melancholic nature, where the individual experiences psychotic symptoms such as delusions and hallucinations.

Catatonic depression refers to major depression involving disturbances of motor behavior and other symptoms. An individual may become mute and stuporose, and either is immobile or exhibits purposeless or bizarre movements.

Seasonal affective disorder (SAD) refers to a type of seasonal depression wherein an individual has seasonal patterns of depressive episodes coming on in the fall or winter.

Dysthymia refers to a condition related to unipolar depression, where the same physical and cognitive problems are evident. They are not as severe and tend to last longer (e.g., at least 2 years).

Double depression refers to fairly depressed mood (dysthymia) that lasts for at least 2 years and is punctuated by periods of major depression.

Depressive Personality Disorder (DPD) refers to a personality disorder with depressive features.

Recurrent Brief Depression (RBD) refers to a condition in which individuals have depressive episodes about once per month, each episode lasting 2 weeks or less and typically less than 2-3 days.

Minor depressive disorder or minor depression refers to a depression in which at least 2 symptoms are present for 2 weeks.

Bipolar disorder or manic depressive disorder causes extreme mood swings that include emotional highs (mania or hypomania) and lows (depression). During periods of mania the individual may feel or act abnormally happy, energetic, or irritable. They often make poorly thought out decisions with little regard to the consequences. The need for sleep is usually reduced. During periods of depression there may be crying, poor eye contact with others, and a negative outlook on life. The risk of suicide among those with the disorder is high at greater than 6% over 20 years, while self-harm occurs in 30-40%. Other mental health issues such as anxiety disorder and substance use disorder are commonly associated with bipolar disorder.

Depression caused by chronic medical conditions refers to depression caused by chronic medical conditions such as cancer or chronic pain, chemotherapy, chronic stress.

Treatment-resistant depression refers to a condition where the individuals have been treated for depression, but the symptoms do not improve. For example, antidepressants or psychological counseling (psychotherapy) do not ease depression symptoms for individuals with treatment-resistant depression. In some cases, individuals with treatment-resistant depression improve symptoms, but come back. Refractory depression occurs in patients suffering from depression who are resistant to standard pharmacological treatments, including tricyclic antidepressants, MAOIs, SSRIs, and double and triple uptake inhibitors and/or anxiolytic drugs, as well as non-pharmacological treatments (e.g., psychotherapy, electroconvulsive therapy, vagus nerve stimulation and/or transcranial magnetic stimulation).

Post-surgical depression refers to feelings of depression that follow a surgical procedure (e.g., as a result of having to confront one's mortality). For example, individuals may feel sadness or empty mood persistently, a loss of pleasure or interest in hobbies and activities normally enjoyed, or a persistent felling of worthlessness or hopelessness.

Mood disorder associated with conditions or disorders of women's health refers to mood disorders (e.g., depression) associated with (e.g., resulting from) a condition or disorder of women's health (e.g., as described herein).

Suicidality, suicidal ideation, suicidal behavior refers to the tendency of an individual to commit suicide. Suicidal ideation concerns thoughts about or an unusual preoccupation with suicide. The range of suicidal ideation varies greatly, from e.g., fleeting thoughts to extensive thoughts, detailed planning, role playing, incomplete attempts. Symptoms include talking about suicide, getting the means to commit suicide, withdrawing from social contact, being preoccupied with death, feeling trapped or hopeless about a situation, increasing use of alcohol or drugs, doing risky or self-destructive things, saying goodbye to people as if they won't be seen again.

Symptoms of depression include persistent anxious or sad feelings, feelings of helplessness, hopelessness, pessimism, worthlessness, low energy, restlessness, difficulty sleeping, sleeplessness, irritability, fatigue, motor challenges, loss of interest in pleasurable activities or hobbies, loss of concentration, loss of energy, poor self-esteem, absence of positive thoughts or plans, excessive sleeping, overeating, appetite loss, insomnia, self-harm, thoughts of suicide, and suicide attempts. The presence, severity, frequency, and duration of symptoms may vary on a case to case basis. Symptoms of depression, and relief of the same, may be ascertained by a physician or psychologist (e.g., by a mental state examination).

In some embodiments, the method comprises monitoring a subject with a known depression scale, e.g., the Hamilton Depression (HAM-D) scale, the Clinical Global Impression-Improvement Scale (CGI), and the Montgomery-Åsberg Depression Rating Scale (MADRS). In some embodiments, a therapeutic effect can be determined by reduction in Hamilton Depression (HAM-D) total score exhibited by the subject. Reduction in the HAM-D total score can happen within 4, 3, 2, or 1 days; or 96, 84, 72, 60, 48, 24, 20, 16, 12, 10, 8 hours or less. The therapeutic effect can be assessed across a specified treatment period. For example, the therapeutic effect can be determined by a decrease from baseline in HAM-D total score after administering a compound described herein, e.g., a compound of Formula (I) (e.g., 12, 24, or 48 hours after administration; or 24, 48, 72, or 96 hours or more; or 1 day, 2 days, 14 days, 21 days, or 28 days; or 1 week, 2 weeks, 3 weeks, or 4 weeks; or 1 month, 2 months, 6 months, or 10 months; or 1 year, 2 years, or for life).

In some embodiments, the subject has a mild depressive disorder, e.g., mild major depressive disorder. In some embodiments, the subject has a moderate depressive disorder, e.g., moderate major depressive disorder. In some embodiments, the subject has a severe depressive disorder, e.g., severe major depressive disorder. In some embodiments, the subject has a very severe depressive disorder, e.g., very severe major depressive disorder. In some embodiments, the baseline HAM-D total score of the subject (i.e., prior to treatment with a compound described herein, e.g., a compound of Formula (I)) is at least 24. In some embodiments, the baseline HAM-D total score of the subject is at least 18. In some embodiments, the baseline HAM-D total score of the subject is between and including 14 and 18. In some embodiments, the baseline HAM-D total score of the subject is between and including 19 and 22. In some embodiments, the HAM-D total score of the subject before treatment with a compound described herein, e.g., a compound of Formula (I), is greater than or equal to 23. In some embodiments, the baseline score is at least 10, 15, or 20. In some embodiments, the HAM-D total score of the subject after treatment with a compound described herein, e.g., a compound of Formula (I), is about 0 to 10 (e.g., less than 10; 0 to 10, 0 to 6, 0 to 4, 0 to 3, 0 to 2, or 1.8). In some embodiments, the HAM-D total score after treatment with a compound described herein, e.g., a compound of Formula (I), is less than 10, 7, 5, or 3. In some embodiments, the decrease in HAM-D total score is from a baseline score of about 20 to 30 (e.g., 22 to 28, 23 to 27, 24 to 27, 25 to 27, 26 to 27) to a HAM-D total score at about 0 to 10 (e.g., less than 10; 0 to 10, 0 to 6, 0 to 4, 0 to 3, 0 to 2, or 1.8) after treatment with a compound described herein, e.g., a compound of Formula (I). In some embodiments, the decrease in the baseline HAM-D total score to HAM-D total score after treatment with a compound described herein, e.g., a compound of Formula (I), is at least 1, 2, 3, 4, 5, 7, 10, 25, 40, 50, or 100 fold). In some embodiments, the percentage decrease in the baseline HAM-D total score to HAM-D total score after treatment with a compound described herein, e.g., a compound of Formula (I), is at least 50% (e.g., 60%, 70%, 80%, or 90%). In some embodiments, the therapeutic effect is measured as a decrease in the HAM-D total score after treatment with a compound described herein, e.g., a compound of Formula (I), relative to the baseline HAM-D total score (e.g., 12, 24, 48 hours after administration; or 24, 48, 72, 96 hours or more; or 1 day, 2 days, 14 days, or more) is at least 10, 15, or 20 points.

In some embodiments, the method of treating a depressive disorder, e.g., major depressive disorder provides a therapeutic effect (e.g., as measured by reduction in Hamilton Depression Score (HAM-D)) within 14, 10, 4, 3, 2, or 1 days, or 24, 20, 16, 12, 10, or 8 hours or less. In some embodiments, the method of treating the depressive disorder, e.g., major depressive disorder, provides a therapeutic effect (e.g., as determined by a statistically significant reduction in HAM-D total score) within the first or second day of the treatment with a compound described herein, e.g., a compound of Formula (I). In some embodiments, the method of treating the depressive disorder, e.g., major depressive disorder, provides a therapeutic effect (e.g., as determined by a statistically significant reduction in HAM-D total score) within less than or equal to 14 days since the beginning of the treatment with a compound described herein, e.g., a compound of Formula (I). In some embodiments, the method of treating the depressive disorder, e.g., major depressive disorder, provides a therapeutic effect (e.g., as determined by a statistically significant reduction in HAM-D total score) within less than or equal to 21 days since the beginning of the treatment with a compound described herein, e.g., a compound of Formula (I). In some embodiments, the method of treating the depressive disorder, e.g., major depressive disorder, provides a therapeutic effect (e.g., as determined by a statistically significant reduction in HAM-D total score) within less than or equal to 28 days since the beginning of the treatment with a compound described herein, e.g., a compound of Formula (I). In some embodiments, the therapeutic effect is a decrease from baseline in HAM-D total score after treatment with a compound described herein, e.g., a compound of Formula (I) (e.g., treatment with a compound described herein, e.g., a compound of Formula (I), once a day for 14 days). In some embodiments, the HAM-D total score of the subject before treatment with a compound described herein, e.g., a compound of Formula (I), is at least 24. In some embodiments, the HAM-D total score of the subject before treatment with a compound described herein, e.g., a compound of Formula (I), is at least 18. In some embodiments, the HAM-D total score of the subject before treatment with a compound described herein, e.g., a compound of Formula (I), is between and including 14 and 18. In some embodiments, the decrease in HAM-D total score after treating the subject with a compound described herein, e.g., a compound of Formula (I), relative to the baseline HAM-D total score is at least 10. In some embodiments, the decrease in HAM-D total score after treating the subject with a compound described herein, e.g., a compound of Formula (I), relative to the baseline HAM-D total score is at least 15 (e.g., at least 17). In some embodiments, the HAM-D total score associated with treating the subject with a compound described herein, e.g., a compound of Formula (I), is no more than a number ranging from 6 to 8. In some embodiments, the HAM-D total score associated with treating the subject with a compound described herein, e.g., a compound of Formula (I), is no more than 7.

In some embodiments, the method provides therapeutic effect (e.g., as measured by reduction in Clinical Global Impression-Improvement Scale (CGI)) within 14, 10, 4, 3, 2, or 1 days, or 24, 20, 16, 12, 10, or 8 hours or less. In some embodiments, the CNS-disorder is a depressive disorder, e.g., major depressive disorder. In some embodiments, the method of treating the depressive disorder, e.g., major depressive disorder provides a therapeutic effect within the second day of the treatment period. In some embodiments, the therapeutic effect is a decrease from baseline in CGI score at the end of a treatment period (e.g., 14 days after administration).

In some embodiments, the method provides therapeutic effect (e.g., as measured by reduction in Montgomery-Åsberg Depression Rating Scale (MADRS)) within 14, 10, 4, 3, 2, or 1 days, or 24, 20, 16, 12, 10, or 8 hours or less. In some embodiments, the CNS-disorder is a depressive disorder, e.g., major depressive disorder. In some embodiments, the method of treating the depressive disorder, e.g., major depressive disorder provides a therapeutic effect within the second day of the treatment period. In some embodiments, the therapeutic effect is a decrease from baseline in MADRS score at the end of a treatment period (e.g., 14 days after administration).

A therapeutic effect for major depressive disorder can be determined by a reduction in Montgomery-Åsberg Depression Rating Scale (MADRS) score exhibited by the subject. For example, the MADRS score can be reduced within 4, 3, 2, or 1 days; or 96, 84, 72, 60, 48, 24, 20, 16, 12, 10, 8 hours or less. The Montgomery-Åsberg Depression Rating Scale (MADRS) is a ten-item diagnostic questionnaire (regarding apparent sadness, reported sadness, inner tension, reduced sleep, reduced appetite, concentration difficulties, lassitude, inability to feel, pessimistic thoughts, and suicidal thoughts) which psychiatrists use to measure the severity of depressive episodes in patients with mood disorders.

In some embodiments, the method provides therapeutic effect (e.g., as measured by reduction in Edinburgh Postnatal Depression Scale (EPDS)) within 4, 3, 2, 1 days; 24, 20, 16, 12, 10, 8 hours or less. In some embodiments, the therapeutic effect is an improvement measured by the EPDS.

In some embodiments, the method provides therapeutic effect (e.g., as measured by reduction in Generalized Anxiety Disorder 7-Item Scale (GAD-7)) within 4, 3, 2, 1 days; 24, 20, 16, 12, 10, 8 hours or less.

Anxiety Disorders

Provided herein are methods for treating anxiety disorders (e.g., generalized anxiety disorder, panic disorder, obsessive compulsive disorder, phobia, post-traumatic stress disorder). Anxiety disorder is a blanket term covering several different forms of abnormal and pathological fear and anxiety. Current psychiatric diagnostic criteria recognize a wide variety of anxiety disorders.

Generalized anxiety disorder is a common chronic disorder characterized by long-lasting anxiety that is not focused on any one object or situation. Those suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises and peaks in less than ten minutes, can last for several hours and can be triggered by stress, fear, or even exercise; although the specific cause is not always apparent. In addition to recurrent unexpected panic attacks, a diagnosis of panic disorder also requires that said attacks have chronic consequences: either worry over the attacks' potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life threatening illness (i.e. extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions; a much smaller number of sufferers experience only compulsions.

The single largest category of anxiety disorders is that of phobia, which includes all cases in which fear and anxiety is triggered by a specific stimulus or situation. Sufferers typically anticipate terrifying consequences from encountering the object of their fear, which can be anything from an animal to a location to a bodily fluid.

Post-traumatic stress disorder or PTSD is an anxiety disorder which results from a traumatic experience. Post-traumatic stress can result from an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression.

Women's Health Disorders

Provided herein are methods for treating conditions or disorders related to women's health. Conditions or disorders related to women's health include, but are not limited to, gynecological health and disorders (e.g., premenstrual syndrome (PMS), premenstrual dysphoric disorder (PMDD)), pregnancy issues (e.g., miscarriage, abortion), infertility and related disorders (e.g., polycystic ovary syndrome (PCOS)), other disorders and conditions, and issues related to women's overall health and wellness (e.g., menopause).

Gynecological health and disorders affecting women include menstruation and menstrual irregularities; urinary tract health, including urinary incontinence and pelvic floor disorders; and such disorders as bacterial vaginosis, vaginitis, uterine fibroids, and vulvodynia.

Premenstrual syndrome (PMS) refers to physical and emotional symptoms that occur in the one to two weeks before a women's period. Symptoms vary but can include bleeding, mood swings, tender breasts, food cravings, fatigue, irritability, acne, and depression.

Premenstrual dysphoric disorder (PMDD) is a severe form of PMS. The symptoms of PMDD are similar to PMS but more severe and may interfere with work, social activity, and relationships. PMDD symptoms include mood swings, depressed mood or feelings of hopelessness, marked anger, increased interpersonal conflicts, tension and anxiety, irritability, decreased interest in usual activities, difficulty concentrating, fatigue, change in appetite, feeling out of control or overwhelmed, sleep problems, physical problems (e.g., bloating, breast tenderness, swelling, headaches, joint or muscle pain).

Pregnancy issues include preconception care and prenatal care, pregnancy loss (miscarriage and stillbirth), preterm labor and premature birth, sudden infant death syndrome (SIDS), breastfeeding, and birth defects.

Miscarriage refers to a pregnancy that ends on its own, within the first 20 weeks of gestation.

Abortion refers to the deliberate termination of a pregnancy, which can be performed during the first 28 weeks of pregnancy.

Infertility and related disorders include uterine fibroids, polycystic ovary syndrome, endometriosis, and primary ovarian insufficiency.

Polycystic ovary syndrome (PCOS) refers to an endocrine system disorder among women of reproductive age. PCOS is a set of symptoms resulting from an elevated male hormone in women. Most women with PCOS grow many small cysts on their ovaries. Symptoms of PCOS include irregular or no menstrual periods, heavy periods, excess body and facial hair, acne, pelvic pain, difficulty getting pregnant, and patches of thick, darker, velvety skin. PCOS may be associated with conditions including type 2 diabetes, obesity, obstructive sleep apnea, heart disease, mood disorders, and endometrial cancer.

Other disorders and conditions that affect only women include Turner syndrome, Rett syndrome, and ovarian and cervical cancers.

Issues related to women's overall health and wellness include violence against women, women with disabilities and their unique challenges, osteoporosis and bone health, and menopause.

Menopause refers to the 12 months after a woman's last menstrual period and marks the end of menstrual cycles. Menopause typically occurs in a woman's 40s or 50s. Physical symptoms such as hot flashes and emotional symptoms of menopause may disrupt sleep, lower energy, or trigger anxiety or feelings of sadness or loss. Menopause includes natural menopause and surgical menopause, which is a type of induced menopause due to an event such as surgery (e.g., hysterectomy, oophorectomy; cancer). It is induced when the ovaries are gravely damaged by, e.g., radiation, chemotherapy, or other medications.

Epilepsy

The compound of Formula (I), or pharmaceutically acceptable salt, or a pharmaceutically acceptable composition thereof, can be used in a method described herein, for example in the treatment of a disorder described herein such as epilepsy, status epilepticus, or seizure.

Epilepsy is a brain disorder characterized by repeated seizures over time. Types of epilepsy can include, but are not limited to generalized epilepsy, e.g., childhood absence epilepsy, juvenile nyoclonic epilepsy, epilepsy with grand-mal seizures on awakening, West syndrome, Lennox-Gastaut syndrome, partial epilepsy, e.g., temporal lobe epilepsy, frontal lobe epilepsy, benign focal epilepsy of childhood.

Epileptogenesis

The compounds and methods described herein can be used to treat or prevent epileptogenesis. Epileptogenesis is a gradual process by which a normal brain develops epilepsy (a chronic condition in which seizures occur). Epileptogenesis results from neuronal damage precipitated by the initial insult (e.g., status epilepticus).

Status Epilepticus (SE)

Status epilepticus (SE) can include, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges. Convulsive status epilepticus is characterized by the presence of convulsive status epileptic seizures, and can include early status epilepticus, established status epilepticus, refractory status epilepticus, super-refractory status epilepticus. Early status epilepticus is treated with a first line therapy. Established status epilepticus is characterized by status epileptic seizures which persist despite treatment with a first line therapy, and a second line therapy is administered. Refractory status epilepticus is characterized by status epileptic seizures which persist despite treatment with a first line and a second line therapy, and a general anesthetic is generally administered. Super refractory status epilepticus is characterized by status epileptic seizures which persist despite treatment with a first line therapy, a second line therapy, and a general anesthetic for 24 hours or more.

Non-convulsive status epilepticus can include, e.g., focal non-convulsive status epilepticus, e.g., complex partial non-convulsive status epilepticus, simple partial non-convulsive status epilepticus, subtle non-convulsive status epilepticus; generalized non-convulsive status epilepticus, e.g., late onset absence non-convulsive status epilepticus, atypical absence non-convulsive status epilepticus, or typical absence non-convulsive status epilepticus.

The compound of Formula (I) or pharmaceutically acceptable salt, or a pharmaceutically acceptable composition thereof, can also be administered as a prophylactic to a subject having a CNS disorder e.g., a traumatic brain injury, status epilepticus, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges; prior to the onset of a seizure.

Seizure

A seizure is the physical findings or changes in behavior that occur after an episode of abnormal electrical activity in the brain. The term "seizure" is often used interchangeably with "convulsion." Convulsions are when a person's body shakes rapidly and uncontrollably. During convulsions, the person's muscles contract and relax repeatedly.

Based on the type of behavior and brain activity, seizures are divided into two broad categories: generalized and partial (also called local or focal). Classifying the type of seizure helps doctors diagnose whether or not a patient has epilepsy.

Generalized seizures are produced by electrical impulses from throughout the entire brain, whereas partial seizures are produced (at least initially) by electrical impulses in a relatively small part of the brain. The part of the brain generating the seizures is sometimes called the focus.

There are six types of generalized seizures. The most common and dramatic, and therefore the most well-known, is the generalized convulsion, also called the grand-mal seizure. In this type of seizure, the patient loses consciousness and usually collapses. The loss of consciousness is followed by generalized body stiffening (called the "tonic" phase of the seizure) for 30 to 60 seconds, then by violent jerking (the "clonic" phase) for 30 to 60 seconds, after which the patient goes into a deep sleep (the "postictal" or after-seizure phase). During grand-mal seizures, injuries and accidents may occur, such as tongue biting and urinary incontinence.

Absence seizures cause a short loss of consciousness (just a few seconds) with few or no symptoms. The patient, most often a child, typically interrupts an activity and stares blankly. These seizures begin and end abruptly and may occur several times a day. Patients are usually not aware that they are having a seizure, except that they may be aware of "losing time."

Myoclonic seizures consist of sporadic jerks, usually on both sides of the body. Patients sometimes describe the jerks as brief electrical shocks. When violent, these seizures may result in dropping or involuntarily throwing objects.

Clonic seizures are repetitive, rhythmic jerks that involve both sides of the body at the same time.

Tonic seizures are characterized by stiffening of the muscles.

Atonic seizures consist of a sudden and general loss of muscle tone, particularly in the arms and legs, which often results in a fall.

Seizures described herein can include epileptic seizures; acute repetitive seizures; cluster seizures; continuous seizures; unremitting seizures; prolonged seizures; recurrent seizures; status epilepticus seizures, e.g., refractory convulsive status epilepticus, non-convulsive status epilepticus seizures; refractory seizures; myoclonic seizures; tonic seizures; tonic-clonic seizures; simple partial seizures; complex partial seizures; secondarily generalized seizures; atypical absence seizures; absence seizures; atonic seizures; benign Rolandic seizures; febrile seizures; emotional seizures; focal seizures; gelastic seizures; generalized onset seizures; infantile spasms; Jacksonian seizures; massive bilateral myoclonus seizures; multifocal seizures; neonatal onset seizures; nocturnal seizures; occipital lobe seizures; post traumatic seizures; subtle seizures; Sylvan seizures; visual reflex seizures; or withdrawal seizures. In some embodiments, the seizure is a generalized seizure associated with Dravet Syndrome, Lennox-Gastaut Syndrome, Tuberous Sclerosis Complex, Rett Syndrome or PCDH19 Female Pediatric Epilepsy.

Movement Disorders

Also described herein are methods for treating a movement disorder. As used herein, "movement disorders" refers to a variety of diseases and disorders that are associated with hyperkinetic movement disorders and related abnormalities in muscle control. Exemplary movement disorders include, but are not limited to, Parkinson's disease and parkinsonism (defined particularly by bradykinesia), dystonia, chorea and Huntington's disease, ataxia, tremor (e.g., essential tremor), myoclonus and startle, tics and Tourette syndrome, Restless legs syndrome, stiff person syndrome, and gait disorders.

Tremor

The methods described herein can be used to treat tremor, for example the compound of Formula (I) can be used to treat cerebellar tremor or intention tremor, dystonic tremor, essential tremor, orthostatic tremor, parkinsonian tremor, physiological tremor, psychogenic tremor, or rubral tremor. Tremor includes hereditary, degenerative, and idiopathic disorders such as Wilson's disease, Parkinson's disease, and essential tremor, respectively; metabolic diseases (e.g., thyroid-parathyroid-, liver disease and hypoglycemia); peripheral neuropathies (associated with Charcot-Marie-Tooth, Roussy-Levy, diabetes mellitus, complex regional pain syndrome); toxins (nicotine, mercury, lead, CO, Manganese, arsenic, toluene); drug-induced (narcoleptics, tricyclics, lithium, cocaine, alcohol, adrenaline, bronchodilators, theophylline, caffeine, steroids, valproate, amiodarone, thyroid hormones, vincristine); and psychogenic disorders. Clinical tremor can be classified into physiologic tremor, enhanced physiologic tremor, essential tremor syndromes (including classical essential tremor, primary orthostatic tremor, and task- and position-specific tremor), dystonic tremor, parkinsonian tremor, cerebellar tremor, Holmes' tremor (i.e., rubral tremor), palatal tremor, neuropathic tremor, toxic or drug-induced tremor, and psychogenic tremor.

Tremor is an involuntary, at times rhythmic, muscle contraction and relaxation that can involve oscillations or twitching of one or more body parts (e.g., hands, arms, eyes, face, head, vocal folds, trunk, legs).

Cerebellar tremor or intention tremor is a slow, broad tremor of the extremities that occurs after a purposeful movement. Cerebellar tremor is caused by lesions in or damage to the cerebellum resulting from, e.g., tumor, stroke, disease (e.g., multiple sclerosis, an inherited degenerative disorder).

Dystonic tremor occurs in individuals affected by dystonia, a movement disorder in which sustained involuntary muscle contractions cause twisting and repetitive motions and/or painful and abnormal postures or positions. Dystonic tremor may affect any muscle in the body. Dystonic tremors occurs irregularly and often can be relieved by complete rest.

Essential tremor or benign essential tremor is the most common type of tremor. Essential tremor may be mild and nonprogressive in some, and may be slowly progressive, starting on one side of the body but affect both sides within 3 years. The hands are most often affected, but the head, voice, tongue, legs, and trunk may also be involved. Tremor frequency may decrease as the person ages, but severity may increase. Heightened emotion, stress, fever, physical exhaustion, or low blood sugar may trigger tremors and/or increase their severity. Symptoms generally evolve over time and can be both visible and persistent following onset.

Orthostatic tremor is characterized by fast (e.g., greater than 12 Hz) rhythmic muscle contractions that occurs in the legs and trunk immediately after standing. Cramps are felt in the thighs and legs and the patient may shake uncontrollably when asked to stand in one spot. Orthostatic tremor may occurs in patients with essential tremor.

Parkinsonian tremor is caused by damage to structures within the brain that control movement. Parkinsonian tremor is often a precursor to Parkinson's disease and is typically seen as a "pill-rolling" action of the hands that may also affect the chin, lips, legs, and trunk. Onset of parkinsonian tremor typically begins after age 60. Movement starts in one limb or on one side of the body and can progress to include the other side.

Physiological tremor can occur in normal individuals and have no clinical significance. It can be seen in all voluntary muscle groups. Physiological tremor can be caused by certain drugs, alcohol withdrawal, or medical conditions including an overactive thyroid and hypoglycemia. The tremor classically has a frequency of about 10 Hz.

Psychogenic tremor or hysterical tremor can occur at rest or during postural or kinetic movement. Patient with psychogenic tremor may have a conversion disorder or another psychiatric disease.

Rubral tremor is characterized by coarse slow tremor which can be present at rest, at posture, and with intention. The tremor is associated with conditions that affect the red nucleus in the midbrain, classical unusual strokes.

Parkinson's Disease affects nerve cells in the brain that produce dopamine. Symptoms include muscle rigidity, tremors, and changes in speech and gait. Parkinsonism is characterized by tremor, bradykinesia, rigidity, and postural instability. Parkinsonism shares symptoms found in Parkinson's Disease, but is a symptom complex rather than a progressive neurodegenerative disease.

Dystonia is a movement disorder characterized by sustained or intermittent muscle contractions causing abnormal, often repetitive movements or postures. Dystonic movements can be patterned, twisting, and may be tremulous. Dystonia is often initiated or worsened by voluntary action and associated with overflow muscle activation.

Chorea is a neurological disorder characterized by jerky involuntary movements typically affecting the shoulders, hips, and face. Huntington's Disease is an inherited disease that causes nerve cells in the brain to waste away. Symptoms include uncontrolled movements, clumsiness, and balance problems. Huntington's disease can hinder walk, talk, and swallowing.

Ataxia refers to the loss of full control of bodily movements, and may affect the fingers, hands, arms, legs, body, speech, and eye movements.

Myoclonus and Startle is a response to a sudden and unexpected stimulus, which can be acoustic, tactile, visual, or vestibular.

Tics are an involuntary movement usually onset suddenly, brief, repetitive, but non-rhythmical, typically imitating normal behavior and often occurring out of a background of normal activity. Tics can be classified as motor or vocal, motor tics associated with movements while vocal tics associated with sound. Tics can be characterized as simple or complex. For example simple motor tics involve only a few muscles restricted to a specific body part. Tourette Syndrome is an inherited neuropsychiatric disorder with onset in childhood, characterized by multiple motor tics and at least one vocal tic.

Restless Legs Syndrome is a neurologic sensorimotor disorder characterized by an overwhelming urge to move the legs when at rest.

Stiff Person Syndrome is a progressive movement disorder characterized by involuntary painful spasms and rigidity of muscles, usually involving the lower back and legs. Stiff-legged gait with exaggerated lumbar hyperlordosis typically results. Characteristic abnormality on EMG recordings with continuous motor unit activity of the paraspinal axial muscles is typically observed. Variants include "stiff-limb syndrome" producing focal stiffness typically affecting distal legs and feet.

Gait disorders refer to an abnormality in the manner or style of walking, which results from neuromuscular, arthritic, or other body changes. Gait is classified according to the system responsible for abnormal locomotion, and include hemiplegic gait, diplegic gait, neuropathic gait, myopathic gait, parkinsonian gait, choreiform gait, ataxic gait, and sensory gait.

Anesthesia/Sedation

Anesthesia is a pharmacologically induced and reversible state of amnesia, analgesia, loss of responsiveness, loss of skeletal muscle reflexes, decreased stress response, or all of these simultaneously. These effects can be obtained from a single drug which alone provides the correct combination of effects, or occasionally with a combination of drugs (e.g., hypnotics, sedatives, paralytics, analgesics) to achieve very specific combinations of results. Anesthesia allows patients to undergo surgery and other procedures without the distress and pain they would otherwise experience.

Sedation is the reduction of irritability or agitation by administration of a pharmacological agent, generally to facilitate a medical procedure or diagnostic procedure.

Sedation and analgesia include a continuum of states of consciousness ranging from minimal sedation (anxiolysis) to general anesthesia.

Minimal sedation is also known as anxiolysis. Minimal sedation is a drug-induced state during which the patient responds normally to verbal commands. Cognitive function and coordination may be impaired. Ventilatory and cardiovascular functions are typically unaffected.

Moderate sedation/analgesia (conscious sedation) is a drug-induced depression of consciousness during which the patient responds purposefully to verbal command, either alone or accompanied by light tactile stimulation. No interventions are usually necessary to maintain a patent airway. Spontaneous ventilation is typically adequate. Cardiovascular function is usually maintained.

Deep sedation/analgesia is a drug-induced depression of consciousness during which the patient cannot be easily aroused, but responds purposefully (not a reflex withdrawal from a painful stimulus) following repeated or painful stimulation. Independent ventilatory function may be impaired and the patient may require assistance to maintain a patent airway. Spontaneous ventilation may be inadequate. Cardiovascular function is usually maintained.

General anesthesia is a drug-induced loss of consciousness during which the patient is not arousable, even to painful stimuli. The ability to maintain independent ventilatory function is often impaired and assistance is often required to maintain a patent airway. Positive pressure ventilation may be required due to depressed spontaneous ventilation or drug-induced depression of neuromuscular function. Cardiovascular function may be impaired.

Sedation in the intensive care unit (ICU) allows the depression of patients' awareness of the environment and reduction of their response to external stimulation. It can play a role in the care of the critically ill patient, and encompasses a wide spectrum of symptom control that will vary between patients, and among individuals throughout the course of their illnesses. Heavy sedation in critical care has been used to facilitate endotracheal tube tolerance and ventilator synchronization, often with neuromuscular blocking agents.

In some embodiments, sedation (e.g., long-term sedation, continuous sedation) is induced and maintained in the ICU for a prolonged period of time (e.g., 1 day, 2 days, 3 days, 5 days, 1 week, 2 week, 3 weeks, 1 month, 2 months). Long-term sedation agents may have long duration of action. Sedation agents in the ICU may have short elimination half-life.

Procedural sedation and analgesia, also referred to as conscious sedation, is a technique of administering sedatives or dissociative agents with or without analgesics to induce a state that allows a subject to tolerate unpleasant procedures while maintaining cardiorespiratory function.

Examples

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Materials and Methods

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography, HPLC, or supercritical fluid chromatography (SFC). The following schemes are presented with details as to the preparation of representative oxysterols that have been listed herein. The compounds provided herein may be prepared from known or commercially available starting materials and reagents by one skilled in the art of organic synthesis. Exemplary chiral columns available for use in the separation/purification of the enantiomers/diastereomers provided herein include, but are not limited to, CHIRALPAK® AD-10, CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

$^1$H-NMR reported herein (e.g., for the region between δ (ppm) of about 0.5 to about 4 ppm) will be understood to be an exemplary interpretation of the NMR spectrum (e.g., exemplary peak integrations) of a compound.

Exemplary general method for LCMS/LC ELSD: 30-90AB_2 min. Lcm. (Mobile Phase: 1.5 mL/4 L TFA in water (solvent A) and 0.75 mL/4 L TFA in acetonitrile (solvent B), using the elution gradient 30%-90% (solvent B) over 0.9 minutes and holding at 90% for 0.6 minutes at a flow rate of 1.2 mL/min; Column: Xtimate C18 2.1*30 mm, 3 μm; Wavelength: UV 220 nm; Column temperature: 50° C.; MS ionization: ESI; Detector: PDA&ELSD)

Abbreviations: PE: petroleum ether; EtOAc: ethyl acetate; THF: tetrahydrofuran; PCC: pyridinium chlorochromate; TLC: thin layer chromatography; PCC: pyridinium chlorochromate; t-BuOK: potassium tert-butoxide; 9-BBN: 9-borabicyclo[3.3.1]nonane; Pd(t-Bu₃P)₂: bis(tri-tert-butylphosphine)palladium(0); AcCl: acetyl chloride; i-PrMgCl: Isopropylmagnesium chloride; TBSCl: tert-Butyl (chloro)dimethylsilane; (i-PrO)₄Ti: titanium tetraisopropoxide; BHT: 2,6-di-t-butyl-4-methylphenoxide; Me: methyl; i-Pr: iso-propyl; t-Bu: tert-butyl; Ph: phenyl; Et: ethyl; Bz: benzoyl; BzCl: benzoyl chloride; CsF: cesium fluoride; DCC: dicyclohexylcarbodiimide; DCM: dichloromethane; DMAP: 4-dimethylaminopyridine; DMP: Dess-Martin periodinane; EtMgBr: ethylmagnesium bromide; EtOAc: ethyl acetate; TEA: triethylamine; AlaOH: alanine; Boc: t-butoxycarbonyl. Py: pyridine; TBAF: tetra-n-butylammonium fluoride; THF: tetrahydrofuran; TBS: t-butyldimethylsilyl; TMS: trimethylsilyl; TMSCF₃: (Trifluoromethyl)trimethylsilane; Ts: p-toluenesulfonyl; Bu: butyl; Ti(OiPr)₄: tetraisopropoxytitanium; LAH: Lithium Aluminium Hydride; LDA: lithium diisopropylamide; LiOH·H₂O: lithium hydroxide hydrates; MAD: methyl aluminum bis(2, 6-di-t-butyl-4-methylphenoxide); MeCN: acetonitrile; NBS: N-bromosuccinimide; Na₂SO₄: sodium sulfate; Na₂S₂O₃: sodium thiosulfate; MeCN: acetonitrile; MeOH: methanol; Boc: t-butoxycarbonyl; MTBE: methyl tert-butyl ether; K-selectride: Potassium tri(s-butyl)borohydride; 9-BBNdimer: 9-borabicyclo(3.3.1)nonane(dimer); DIPEA: diisopropylethylamine; DMF: dimethylformamide; FA: formic acid; SM: starting material.

Example 1: Synthesis of 1-(((3R,5R,8R,9R,10S,13S,14S,17S)-3-hydroxy-3,13-dimethylhexadecahydro-1H-cyclopenta[a]phenanthren-17-yl)methyl)piperidin-2-one (A7)

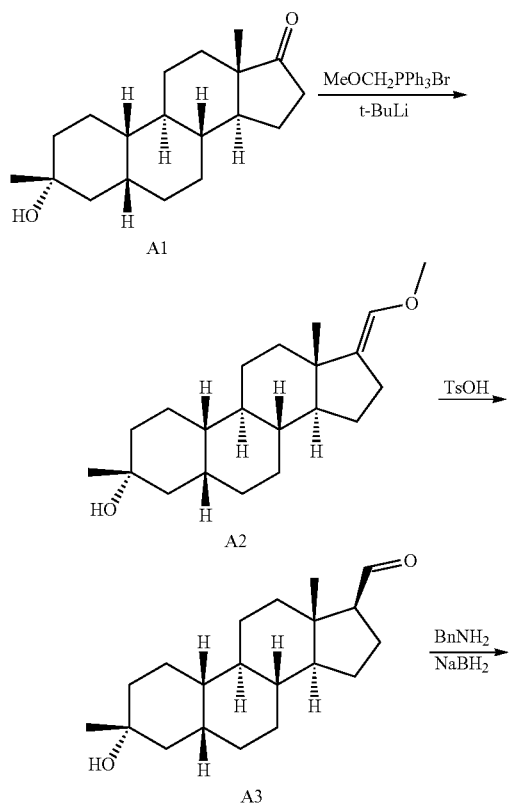

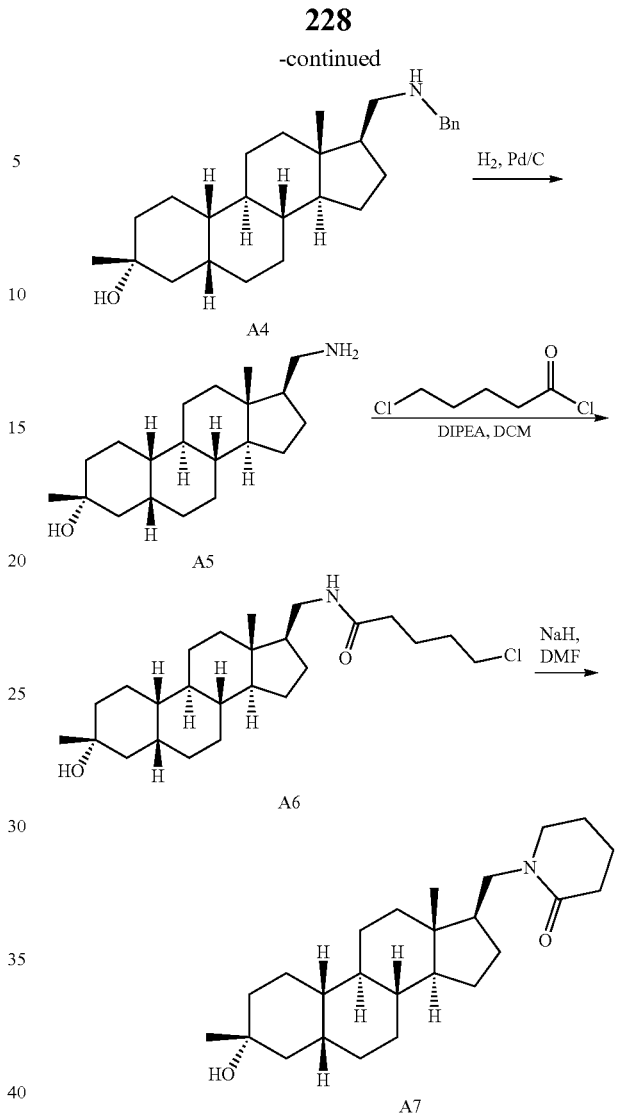

Synthesis of A2

To a solution of chloro(methoxymethyl)triphenylphosphorane (35.3 g, 103 mmol, 3.0 eq) in THF (100 mL) was added t-BuLi (79.2 mL, 103 mmol, 1.3 M in n-hexane, 3.0 eq) at 0° C. After stirring at 0° C. for 1 h, the mixture was added in three portions to A1 (10 g, 34.4 mmol, 1.0 eq) in THF (100 mL). After warming slowly to rt over 12 h, the mixture was treated with NH₄Cl (200 mL, 10%) and extracted with ethyl acetate (3×200 mL). The combined organic solution was washed with brine (300 mL), dried over Na₂SO₄, filtered and concentrated under vacuum to give an oil, which was purified by flash column (0~20% of EtOAc in PE) to give A2 (6.5 g, 59%) as an oil.

¹H NMR (400 MHz, CDCl₃) δ 5.72-5.68 (t, J=2 Hz, 1H), 3.44 (s, 3H), 2.36-2.23 (m, 2H), 2.17-2.07 (m, 1H), 1.92-1.74 (m, 3H), 1.71-1.59 (m, 3H), 1.51-1.35 (m, 7H), 1.34-1.23 (m, 6H), 1.22-1.01 (m, 5H), 0.86 (s, 3H).

Synthesis of A3

To a solution A2 (3 g, 9.41 mmol) in acetone (50 mL) was added p-TsOH (1.75 g, 9.41 mmol). After stirring at 25° C. for 2 h, the reaction was quenched with water (50 mL) and extracted with EtOAc (3×50 mL). The combined organics were washed with NaHCO₃ (100 mL, 10%) and brine (100 mL) and dried over Na₂SO₄, filtered and concentrated. The residue was purified by flash column (0~20% of EtOAc in PE) to give A3 (2.8 g) as an oil.

$^1$H NMR (400 MHz, CDCl$_3$) δ 9.78-9.74 (m, 1H), 2.34-2.23 (m, 1H), 2.18-2.08 (m, 1H), 2.02-1.95 (m, 1H), 1.88-1.61 (m, 9H), 1.49-1.38 (m, 6H), 1.28-1.21 (m, 6H), 1.15-1.06 (m, 3H), 0.94-0.89 (m, 1H), 0.78-0.71 (m, 3H).

Synthesis of A4

To a solution of A3 (1.5 g, 4.92 mmol) in toluene (20 mL) was added phenylmethanamine (1.57 g, 14.7 mmol) and 4-methylbenzenesulfonic acid (137 mg, 0.73 mmol) at 25° C. under N$_2$. After refluxing for 3 h, the reaction mixture was cooled to 25° C. and a suspension of NaBH$_4$ (556 mg, 14.7 mmol) in MeOH (20 mL) was added. After stirring for 1 h, the mixture was poured into water (20 mL) and extracted with EtOAc (3×20 mL). The combined organic solution was washed with NaHCO$_3$ (30 mL, 10%) and brine (20 mL), dried over Na$_2$SO$_4$, filtered and concentrated in vacuum. The residue was purified by flash column (0~20% of EtOAc in PE, 0.5% of NH$_3$·H$_2$O in PE) to give A4 (1 g, 51%) as a solid.

$^1$H NMR (400 MHz, CDCl$_3$) δ 7.32 (s, 2H), 7.31 (s, 2H), 7.25-7.22 (m, 1H), 3.87 (s, 1H), 3.78 (s, 2H), 2.76-2.69 (m, 1H), 2.49-2.42 (m, 1H), 1.93-1.73 (m, 5H), 1.68-1.63 (m, 2H), 1.49-1.35 (m, 6H), 1.34-1.23 (m, 8H), 1.19-0.98 (m, 7H), 0.58 (s, 3H); LC-ELSD/MS purity 90%, MS ESI calcd. for C$_{27}$H$_{42}$NO [M+H]$^+$ 396, found 396.

Synthesis of A5

To a solution of A4 (1 g, 2.52 mmol) in EtOAc (20 mL) was added Pd/C (wet, 10%, 0.45 g) under N$_2$. The suspension was degassed under vacuum and purged with H$_2$ for three times. After stirring under H$_2$ (15 psi) at 25° C. for 12 h, the reaction mixture was filtered through a pad of Celite and washed with EtOAc (3×20 mL). The filtrate was concentrated to give a product (900 mg), which need further hydrogenation. To a solution of the material (900 mg, 2.27 mmol) in EtOAc/MeOH (10 mL/10 mL) was added Pd/C (wet, 10%, 408 mg) under N$_2$. The suspension was degassed under vacuum and purged with H$_2$ for three times. After stirring under H$_2$ (15 psi) at 25° C. for 12 h, the reaction mixture was filtered through a pad of Celite and washed with EtOAc (3×20 mL). The filtrate was concentrated to give a A5 (650 mg) as a solid, which was used without further purification.

$^1$H NMR (400 MHz, CDCl$_3$) δ 2.86-2.78 (m, 1H), 2.57-2.45 (m, 1H), 1.79 (s, 5H), 1.68-1.61 (m, 4H), 1.49-1.36 (m, 8H), 1.28-1.23 (m, 5H), 1.17-1.01 (m, 8H), 0.60 (s, 3H); LC-ELSD/MS purity 99%, MS ESI calcd. for C$_{20}$H$_{36}$NO [M+H]$^+$ 306, found 306.

Synthesis of A6

To a solution of A5 (150 mg, 0.490 mmol) and DIPEA (189 mg, 1.47 mmol) in DCM (2 mL) was added 5-chloropentanoyl chloride (91.1 mg, 0.588 mmol). The mixture was stirred at 30° C. for 1 hr. The reaction mixture was quenched with water (2 mL) and extracted with DCM (3×2 mL). The combined organic layer was dried over anhydrous sodium sulfate, filtered and concentrated. The residue was purified by column chromatography on silica gel (10%-50% of EtOAc in PE) to give A6 (120 mg, 58%) as a solid.

$^1$H NMR (400 MHz, CDCl$_3$) δ 3.57-3.53 (m, 2H), 3.38-3.30 (m, 1H), 3.20-3.10 (m, 1H), 2.22-2.15 (m, 2H), 1.87-1.75 (m, 10H), 1.69-1.61 (m, 4H), 1.54-1.38 (m, 8H), 1.35-1.27 (m, 4H), 1.18-1.02 (m, 7H), 0.66 (s, 3H).

Synthesis of A7

To a solution of A6 (70 mg, 0.165 mmol) in anhydrous DMF (2 mL) was added NaH (60%, 32.8 mg, 0.825 mmol). After stirring at 30° C. for 18 h, the reaction mixture was quenched with ice-water (10 mL) and extracted with EtOAc (2×10 mL). The combined organic solution was washed with 3% LiCl aqueous (2×10 mL) and brine (10 mL), dried over anhydrous sodium sulfate, filtered and concentrated. The residue was purified by column chromatography on silica gel (10%-80% of EtOAc in PE, basified by aqueous ammonia) to give A7 as an oil. The oil was dissolved in MeCN (2 mL), diluted with deionized water (15 mL), concentrated and lyophilized to give A7 (29 mg, 45%) as a solid.

$^1$H NMR (400 MHz, CDCl$_3$) δ 3.57-3.48 (m, 1H), 3.32-3.18 (m, 3H), 2.35 (t, J=6.0 Hz, 2H), 1.89-1.69 (m, 10H), 1.68-1.62 (m, 2H), 1.48-1.36 (m, 7H), 1.35-1.21 (m, 7H), 1.16-0.98 (m, 6H), 0.70 (s, 3H); LC-ELSD/MS purity 99%, MS ESI calcd. for C$_{25}$H$_{42}$NO$_2$ [M+H]$^+$ 388, found 388.

Example 2: Synthesis of N-(((3R,5R,8R,9R,10S, 13S,14S,17S)-3-hydroxy-3,13-dimethylhexadeca-hydro-1H-cyclopenta[a]phenanthren-17-yl)methyl)-N-methylbenzamide (A9)

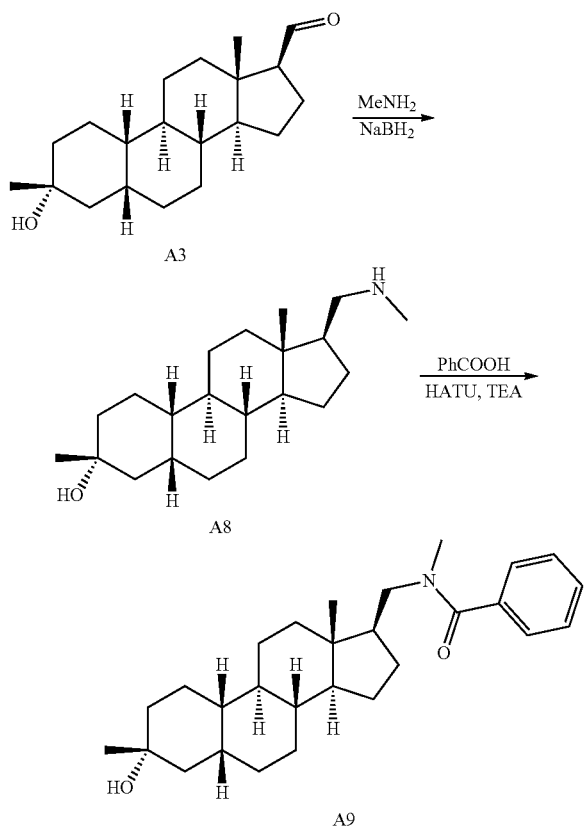

Synthesis of A8

To a solution of A3 (200 mg, 0.65 mmol) in toluene (10 mL) was added methanamine (0.65 mL, 1.31 mmol, 2 M in THF) and 4-methylbenzenesulfonic acid (18.2 mg, 0.098 mmol) at 25° C. under N$_2$. After refluxing at 110° C. for 3 h, the reaction mixture was cooled to 25° C. and a suspension of NaBH$_4$ (74.1 mg, 1.96 mmol) in MeOH (10 mL) was added. After stirring at 25° C. for 1 h, the mixture was poured into water (20 mL) and extracted with EtOAc (3×20 mL). The combined organic solution was washed with NaHCO$_3$ (30 mL, 10%, aqueous) and brine (20 mL), dried over Na$_2$SO$_4$, filtered and concentrated in vacuum. The residue was purified by flash column (0-80% of EtOAc in PE, 0.5% NH$_3$·H$_2$O in PE) to give A8 (160 mg) as an oil.

LC-ELSD/MS purity 95%, MS ESI calcd. for C$_{21}$H$_{38}$NO [M+H]$^+$ 320, found 320.

Synthesis of A9

To a solution of benzoic acid (122 mg, 1 mmol) in DCM (3 mL) was added HATU (285 mg, 0.75 mmol) and Et$_3$N (252 mg, 2.5 mmol) at 25° C. After stirring at 25° C. for 0.5 h, A8 (160 mg, 0.5 mmol) was added. After stirring at 25° C. for 10 h, the residue was diluted with water (10 mL) and then extracted with EtOAc (2×10 mL). The combined organic solution was washed with water (2×10 mL) and brine (10 mL), dried over anhydrous Na$_2$SO$_4$, filtered and concentrated. The residue was purified by flash column (0~50% of EtoAc in PE, 0.1% of NH$_3$·H$_2$O in PE) to give A9 (130 mg) as a solid, which was purified by HPLC (column: Xtimate C18 150*25 mm*5 um), condition: water (0.225% FA)-ACN, gradient: 78-100% B, Gradient Time: 7 mins, 100% B Hold Time: 1 min, flow rate: 25 mL/min) to give A9 (38 mg, 18%) as a solid.

$^1$H NMR (400 MHz, CDCl$_3$) δ 7.42-1.33 (m, 5H), 3.78-3.65 (m, 0.6H), 3.51-3.38 (m, 1.3H), 3.07 (s, 1.5H), 2.92 (s, 1.5H), 1.92-1.76 (m, 5H), 1.65-1.53 (m, 9H), 1.44-1.36 (m, 4H), 1.29-1.22 (m, 5H), 1.13-0.85 (m, 5H), 0.76 (s, 1.6H), 0.32 (s, 1.3H); LC-ELSD/MS purity 99%, MS ESI calcd. for C$_{28}$H$_{42}$NO$_2$ [M+H]$^+$ 424, found 424.

Example 3: Synthesis of N-(((3R,5R,8R,9R,10S,13S,14S,17S)-3-hydroxy-3,13-dimethylhexadecahydro-1H-cyclopenta[a]phenanthren-17-yl)methyl) benzamide (A10)

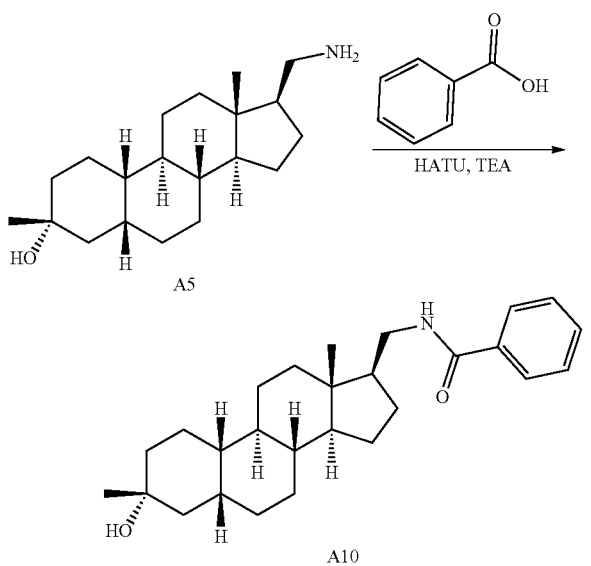

To a solution of benzoic acid (158 mg, 1.3 mmol) in DCM (3 mL) was added HATU (494 mg, 1.3 mmol) and Et$_3$N (330 mg, 3.27 mmol) at 25° C. After stirring for 0.5 h, A5 (200 mg, 0.65 mmol) was added to the reaction mixture. After stirring for 10 h, the mixture was treated by water (10 mL) and extracted with EtOAc (2×10 mL). The combined organic solution was concentrated under vacuum. The residual was resolved in EtOAc and washed with water (2×10 mL), brine (10 mL), dried over anhydrous Na$_2$SO$_4$, filtered and concentrated to give a solid (150 mg). The solid was purified by HPLC (column: Xtimate C18 150*25 mm*5 um), condition: water (0.225% FA)-ACN, gradient: 63-93% B, Gradient Time: 7 mins, 100% B Hold Time: 2 min, flow rate: 25 mL/min) to give A10 (6 mg, 4%) as a solid.

$^1$H NMR (400 MHz, CDCl$_3$) δ 7.77-7.71 (m, 2H), 7.53-7.46 (m, 1H), 7.45-7.39 (m, 2H), 5.99 (s, 1H), 3.61-3.51 (m, 1H), 3.42-3.31 (m, 1H), 2.01-1.79 (m, 5H), 1.69-1.63 (m, 4H), 1.49-1.29 (m, 10H), 1.26 (s, 3H), 1.22-1.04 (m, 6H), 0.72 (m, 3H); LC-ELSD/MS purity 99%, MS ESI calcd. for C$_{27}$H$_{40}$NO$_2$ [M+H]$^+$ 410, found 410.

Example 4: Synthesis of N-(((3R,5R,8R,9R,10S,13S,14S,17S)-3-hydroxy-3,13-dimethylhexadecahydro-1H-cyclopenta[a]phenanthren-17-yl)methyl) benzenesulfonamide (A11)

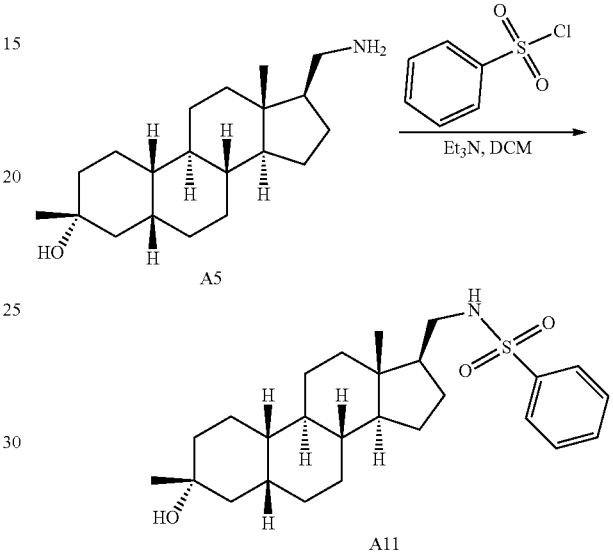

To a solution of A5 (300 mg, 0.9819 mmol) in DCM (10 mL) was added Et$_3$N (247 mg, 2.45 mmol) and benzenesulfonyl chloride (259 mg, 1.47 mmol) at 20° C. After stirring 16 h at 20° C., the reaction mixture was washed with water (3×100 mL). The combined organic solution was dried over Na$_2$SO$_4$, filtered and concentrated to give desired product, which was purified by combi flash (0-15% of EtOAc in PE) to give A11 (180 mg, 41%) as a solid.

$^1$H NMR (400 MHz, CDCl$_3$) δ 7.95-7.85 (m, 2H), 7.65-7.51 (m, 3H), 4.31-4.15 (m, 1H), 3.11-3.00 (m, 1H), 2.85-2.75 (m, 1H), 1.91-1.75 (m, 5H), 1.74-1.59 (m, 3H), 1.45-1.28 (m, 9H), 1.26 (s, 3H), 1.23-0.91 (m, 8H), 0.55 (s, 3H); LC-ELSD/MS purity 99%, MS ESI calcd. for C$_{26}$H$_{38}$NO$_2$S [M+H−H$_2$O]$^+$ 428, found 428.

Example 5: Synthesis of N-(((3R,5R,8R,9R,10S,13S,14S,17S)-3-hydroxy-3,13-dimethylhexadecahydro-1H-cyclopenta[a]phenanthren-17-yl)methyl)-N-methylbenzenesulfonamide (A12)

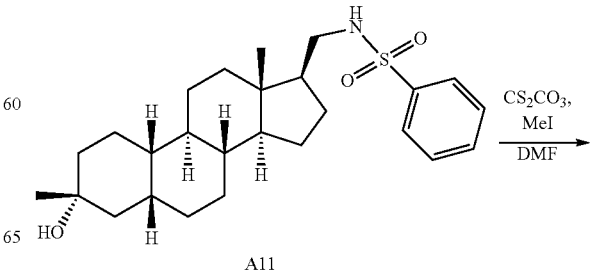

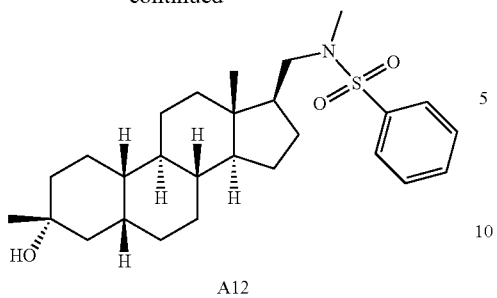

A12

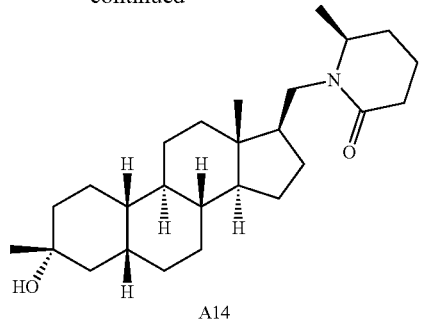

A14

To a solution of A11 (142 mg, 0.3186 mmol) in DMF (5 mL) was added Cs$_2$CO$_3$ (207 mg, 0.6372 mmol) at 20° C. After stirring for 20 mins, MeI (70 mg, 0.4929 mmol) was added. After stirring for 16 h at 20° C., the reaction mixture was added into water (50 mL) and extracted with EtOAc (2×50 mL). The combined organic solution was washed by water (3×100 mL), dried over Na$_2$SO$_4$, filtered and concentrated to give desired product, which was purified by combi-flash (0-15% of EtOAc in PE) to give A12 (64 mg, 44%) as a solid.

$^1$H NMR (400 MHz, CDCl$_3$) δ 7.81-7.75 (m, 2H), 7.55-7.52 (m, 3H), 3.11-3.05 (m, 1H), 2.85-2.75 (m, 1H), 2.69 (s, 3H), 1.91-1.59 (m, 10H), 1.51-1.28 (m, 9H), 1.26 (s, 3H), 1.24-1.01 (m, 6H), 0.71 (s, 3H); LC-ELSD/MS purity 99%, MS ESI calcd. for C$_{27}$H$_{42}$NO$_3$S [M+H]$^+$ 460, found 460.

Examples 6 & 7: Synthesis of (S)-1-(((3R,5R,8R, 9R,10S,13S,14S,17S)-3-hydroxy-3,13-dimethyl-hexadecahydro-1H-cyclopenta[a]phenanthren-17-yl) methyl)-6-methylpiperidin-2-one (A14) & (R)-1-(((3R,5R,8R,9R,10S,13S,14S,17S)-3-hydroxy-3,13-dimethylhexadecahydro-1H-cyclopenta[a] phenanthren-17-yl)methyl)-6-methylpiperidin-2-one (A15)

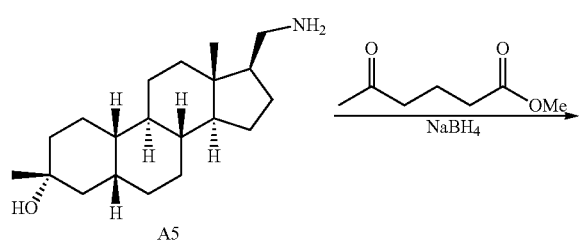

A5

Synthesis of A13

To a solution of A5 (300 mg, 0.981 mmol) in toluene (10 mL) was added methyl 5-oxohexanoate (282 mg, 1.96 mmol). After stirring at 120° C. for 16 h, the reaction was cooled to 25° C. and MeOH (20 ml) and borane sodium hydride (92.6 mg, 2.45 mmol) were added. After 30 min, the mixture was poured into ice-water (50 mL) and extracted with EtOAc (2×30 mL). The combined organic solution was washed with brine (50 mL), dried over Na$_2$SO$_4$, filtered and concentrated in vacuum. The residue was purified by a silica gel column (PE/EtOAc=10/1 to 3/1) to afford A13 (300 mg, 70.5%) as an oil.

$^1$HNMR (400 MHz, CDCl$_3$) δ 3.67 (s, 3H), 2.37-2.31 (m, 2H), 1.96-1.74 (m, 9H), 1.72-1.57 (m, 8H), 1.48-1.37 (m, 9H), 1.30-1.22 (m, 7H), 1.17-1.01 (m, 6H), 0.61 (s, 3H)

Synthesis of A14 & A15

To a solution of A13 (300 mg, 0.691 mmol) in toluene (5 mL) was added trimethylaluminium (1.03 mL, 2 M in toluene) at 25° C. After stirring at 65° C. for 16 h, the mixture was poured into water (30 mL) and extracted with EtOAc (2×20 mL). The combined organic solution was washed with brine (30 mL), dried over Na$_2$SO$_4$, filtered and concentrated. The residue was purified by HPLC separation (column: YMC-Actus Triart C18 100*30 mm*5 um, gradient: 65-95% B, Condition: (water (0.05% HCl)-ACN), flow rate: 25 mL/min) to give A14 (25 mg, 9%) and A16 (30 mg) as solids.

A16 (30 mg) was purified was purified by HPLC separation (column: YMC-Actus Triart C18 100*30 mm*5 um, gradient: 70-100% B, Condition: (water (0.05% HCl)-ACN), flow rate: 25 mL/min) to give A16 (16 mg, 53.5%) as a solid.

A14: $^1$HNMR (400 MHz, CDCl$_3$) δ 4.19-4.13 (m, 1H), 3.57 (s, 1H), 2.74-2.71 (m, 1H), 2.39 (s, 2H), 1.94-1.79 (m, 6H), 1.76-1.57 (m, 9H), 1.51-1.38 (m, 6H), 1.34-1.30 (m, 1H), 1.29-1.24 (m, 5H), 1.22-1.17 (m, 3H), 1.13-1.00 (m, 5H), 0.70 (s, 3H); LC-ELSD/MS purity 99%, MS ESI calcd. for C$_{26}$H$_{44}$NO$_2$ [M+H]$^+$ 402, found 402.

A15: ¹HNMR (400 MHz, CDCl₃) δ 4.23-4.18 (m, 1H), 3.64-3.60 (m, 1H), 2.62-2.57 (m, 1H), 2.40-2.27 (m, 2H), 1.94-1.71 (m, 8H), 1.69-1.59 (m, 5H), 1.47-1.31 (m, 7H), 1.29-1.22 (m, 5H), 1.22-1.16 (m, 4H), 1.14-0.96 (m, 6H), 0.70 (s, 3H); LC-ELSD/MS purity 99%, MS ESI calcd. for $C_{26}H_{44}NO_2$ [M+H]⁺ 402, found 402.

Example 8: Synthesis of N-(((3R,5R,8R,9R,10S,13S,14S,17S)-3-hydroxy-3,13-dimethylhexadeca-hydro-1H-cyclopenta[a]phenanthren-17-yl)methyl)-2-phenylacetamide (A16)

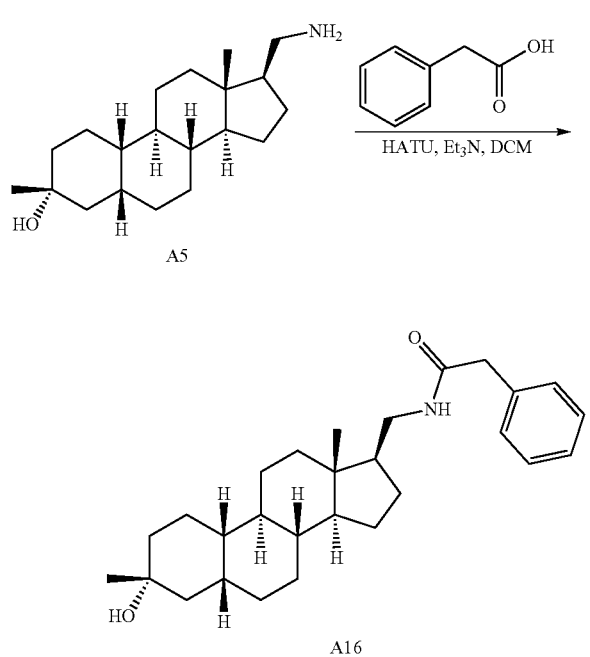

To a suspension of 2-phenylacetic acid (800 mg, 5.88 mmol) and HATU (2.79 g, 7.35 mmol) in DCM (10 mL) under nitrogen at 25° C. was added Et₃N (2.47 g, 24.5 mmol). After stirring at 25° C. for 30 mins, a solution of A5 (1.5 g, 4.90 mmol) was added. After stirring at 25° C. for 18 h, the mixture was quenched by water (10 mL) and extracted with DCM (2×10 mL). The combined organic solution was washed with brine (2×5 mL), dried over Na₂SO₄, filtered and concentrate in vacuum to give A16 (1.41 g). The product (150 mg, 0.354 mmol) was purified by HPLC (Column: YMC-Actus Triart C18 100*30 mm*5 um; Condition: water (0.05% HCl)-ACN; Begin B: 70; End B: 95; Gradient Time (min): 8; 100% B Hold Time (min): 1; FlowRate (ml/min): 25; Injections: 6) to afford A16 (36 mg, 24.1%) as a solid.

¹H NMR (400 MHz, CDCl₃) δ 7.38-7.30 (m, 3H), 7.29-7.23 (m, 2H), 5.20 (s, 1H), 3.56 (s, 2H), 3.28-3.22 (m, 1H), 3.21-3.12 (m, 1H), 1.87-1.77 (m, 3H), 1.76-1.59 (m, 2H), 1.56-1.47 (m, 1H), 1.46-1.31 (m, 9H), 1.30-1.18 (m, 7H), 1.06-0.94 (m, 6H), 0.58 (m, 3H); LC-ELSD/MS purity 99%, MS ESI calcd. for $C_{28}H_{42}NO_2$ [M+H]⁺ 424, found 424.

Examples 9 & 10: Synthesis of (R)-1-(((3R,5R,8R,9R,10S,13S,14S,17S)-3-hydroxy-3,13-dimethyl-hexadecahydro-1H-cyclopenta[a]phenanthren-17-yl)methyl)-4-phenylpyrrolidin-2-one (A18) & (S)-1-(((3R,5R,8R,9R,10S,13S,14S,17S)-3-hydroxy-3,13-dimethylhexadecahydro-1H-cyclopenta[a]phenanthren-17-yl)methyl)-4-phenylpyrrolidin-2-one (A19)

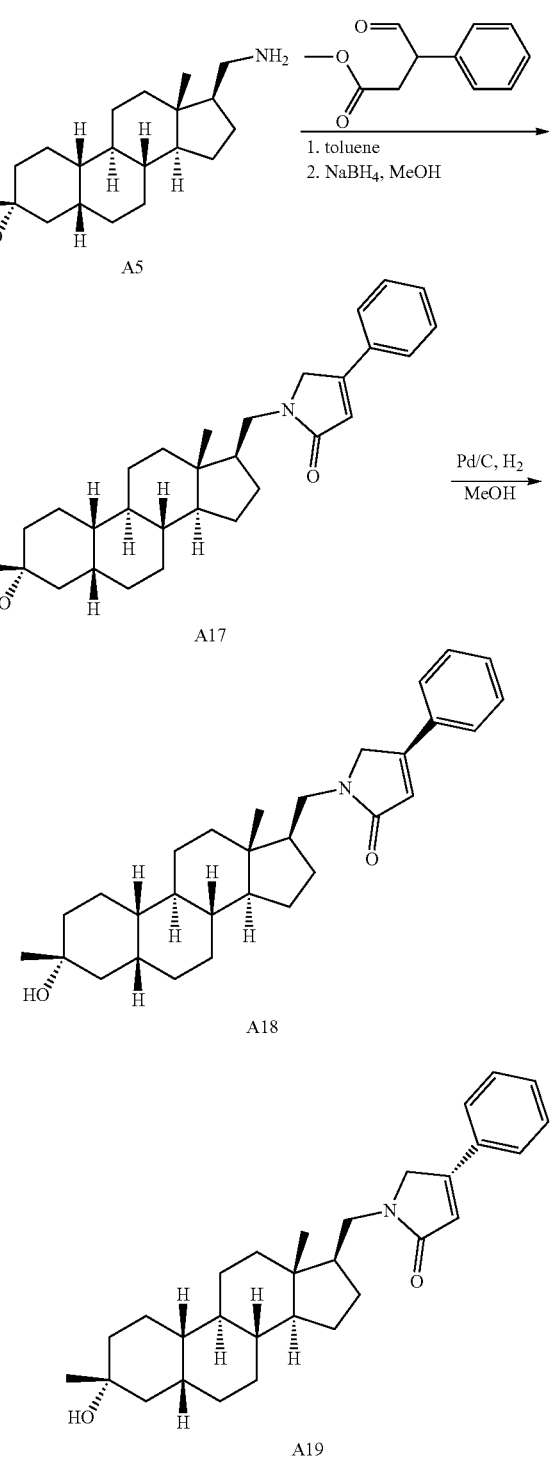

Synthesis of A17

To a solution of A5 (400 mg, 1.30 mmol) in toluene (10 mL) was added benzenepropanoic acid, β-formyl-, methyl ester (499 mg, 2.60 mmol). After stirring at 115° C. for 3 h, the reaction was cooled to 25° C. and MeOH (20 ml) and borane sodium hydride (123 mg, 3.25 mmol) were added. After stirring at 25° C. for 1 h, the mixture was poured into ice-water (50 mL) and extracted with EtOAc (2×30 mL). The combined organic solution was washed with brine (50 mL), dried over $Na_2SO_4$, filtered and concentrated in vacuum. The residue was purified by combi flash (0-20% of EtOAc in PE) to give A17 (190 mg, 33%) as a solid.

$^1$H NMR (400 MHz, $CDCl_3$) δ 7.55-7.41 (m, 5H), 6.44-6.42 (m, 1H), 4.38-4.29 (m, 2H), 3.72-3.62 (m, 1H), 3.41-3.31 (m, 1H), 1.88-1.61 (m, 9H), 1.49-1.35 (m, 8H), 1.28 (s, 3H), 1.24 (s, 3H), 1.19-0.99 (m, 8H).

3.45-3.36 (m, 2H), 3.28-3.22 (m, 1H), 2.84-2.75 (m, 1H), 2.61-2.52 (m, 1H), 1.91-1.59 (m, 10H), 1.51-1.29 (m, 10H), 1.26 (s, 3H), 1.25-0.99 (m, 5H), 0.72 (s, 3H); LC-ELSD/MS purity 99%, MS calcd. for $C_{30}H_{44}NO_2$ $[M+H]^+$ 450, found 450.

Examples 11 & 12: Synthesis of (S)-1-(((3R,5R,8R, 9R,10S,13S,14S,17S)-3-hydroxy-3,13-dimethyl-hexadecahydro-1H-cyclopenta[a]phenanthren-17-yl) methyl)-3-phenylpyrrolidin-2-one (A20) & (R)-1-(((3R,5R,8R,9R,10S,13S,14S,17S)-3-hydroxy-3,13-dimethylhexadecahydro-1H-cyclopenta[a] phenanthren-17-yl)methyl)-3-phenylpyrrolidin-2-one (A21)

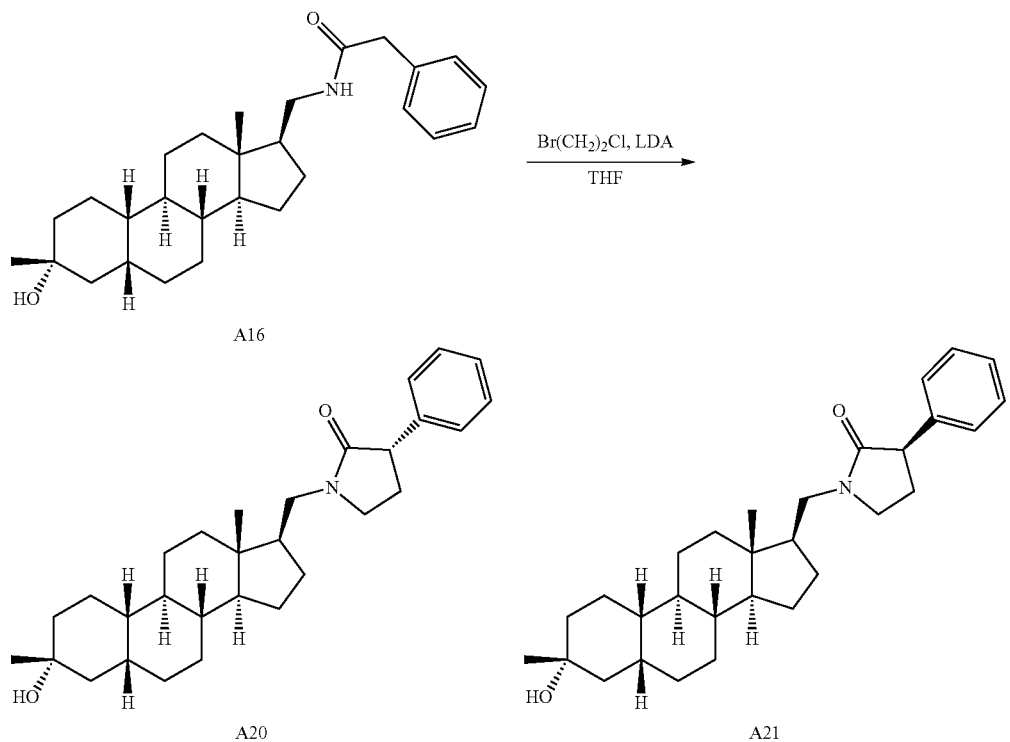

Synthesis of A18 & A19

A solution of A17 (190 mg, 0.4244 mmol) in MeOH (20 mL) was added dried Pd/C (50 mg) and hydrogenated under $H_2$ (15 psi) at 20° C. After stirring for 16 h, the reaction was filtered through a pad of celite and concentrated to give an oil (100 mg, 53%). The oil was purified by SFC (Column: YMC CHIRAL Amylose-C (250 mm*30 mm, 10 um, Condition: 0.1% $NH_3H_2O$ ETOH, Begin B: 55%, End B: 55%) to give A18 (Peak 1, 21 mg, 18%) and A19 (Peak 2, 20 mg, 17%) both as solids.

A18: $^1$H NMR (400 MHz, $CDCl_3$) δ 7.41-7.29 (m, 3H), 7.25-7.20 (m, 2H), 3.76-3.73 (m, 1H), 3.52-3.48 (m, 1H), 3.45-3.41 (m, 1H), 3.40-3.36 (m, 1H), 3.28-3.22 (m, 1H), 2.84-2.75 (m, 1H), 2.61-2.52 (m, 1H), 1.91-1.59 (m, 10H), 1.51-1.29 (m, 10H), 1.26 (s, 3H), 1.25-0.99 (m, 5H), 0.72 (s, 3H); LC-ELSD/MS purity 99%, MS calcd. for $C_{30}H_{44}NO_2$ $[M+H]^+$ 450, found 450.

A19: $^1$H NMR (400 MHz, $CDCl_3$) δ 7.41-7.29 (m, 3H), 7.25-7.20 (m, 2H), 3.76-3.73 (m, 1H), 3.52-3.48 (m, 1H),

A solution of A16 (500 mg, 1.18 mmol) in THF (5 mL) was added to a cold (−78° C.) solution of lithium di-isopropylamide prepared from the addition of n-butyl-lithium in hexane (4.6 mL, 2.5 M, 11.5 mmol) to di-isopropylamine (2 mL, 0.72 g/mL, 14.2 mmol) in THF (5 mL) at −78° C. After stirring at −78° C. for 1 h, 1-bromo-2-chloroethane (507 mg, 3.54 mmol) was added to the reaction mixture. The reaction was warm to 20° C. and stirred for 16 h. After quenching with water (50 mL), the reaction was extracted with EtOAc (2×50 mL). The combined organic solution was washed with brine (100 mL), dried over $Na_2SO_4$, filtered, concentrated and purified by combi flash (0-30% of EtOAc in PE) to give desired product, which was further purified by SFC (Column: YMC CHIRAL Amylose-C (250 mm*30 mm, 10 um, Condition: 0.1% $NH_3H_2O$ ETOH, Begin B: 50%, End B: 50%) to give A20 (Peak 1, 18 mg, 3%) and A21 (Peak 2, 54 mg, 10%) both as solids.

A20: $^1$H NMR (400 MHz, $CDCl_3$) δ 7.35-7.28 (m, 2H), 7.24-7.19 (m, 3H), 3.69-3.61 (m, 1H), 3.49-3.35 (m, 3H), 3.33-3.22 (m, 1H), 2.55-2.45 (m, 2H), 2.17-2.09 (m, 1H), 1.92-1.61 (m, 11H), 1.51-1.31 (m, 7H), 1.27 (s, 3H), 1.21-0.99 (m, 6H), 0.73 (s, 3H). LC-ELSD/MS purity 99%, MS ESI calcd. for $C_{30}H_{44}NO_2$ [M+H]$^+$ 450, found 450.

A21: $^1$H NMR (400 MHz, CDCl$_3$) δ 7.35-7.28 (m, 3H), 7.24-7.19 (m, 2H), 3.69-3.61 (m, 2H), 3.49-3.41 (m, 2H), 3.40-3.35 (m, 1H), 3.33-3.22 (m, 1H), 2.55-2.45 (m, 2H), 2.17-2.09 (m, 1H), 1.92-1.61 (m, 11H), 1.51-1.31 (m, 7H), 1.27 (s, 3H), 1.21-0.99 (m, 6H), 0.71 (s, 3H); LC-ELSD/MS purity 99%, MS ESI calcd. for $C_{30}H_{44}NO_2$ [M+H]$^+$ 450, found 450.

Examples 13 & 14: Synthesis of (R)-1-(((3R,5R,8R,9R,10S,13S,14S,17S)-3-hydroxy-3,13-dimethyl-hexadecahydro-1H-cyclopenta[a]phenanthren-17-yl)methyl)-6-phenylpiperidin-2-one (A22) & (S)-1-(((3R,5R,8R,9R,10S,13S,14S,17S)-3-hydroxy-3,13-dimethylhexadecahydro-1H-cyclopenta[a]phenanthren-17-yl)methyl)-6-phenylpiperidin-2-one (A23)

C. to give solid (410 mg). The material was initially purified by flash column chromatography (ethyl acetate in petroleum ether, 75%) to give a solid (140 mg, 34%) followed by SFC (column: AD (250 mm*30 mm, 5 um)), gradient: 35-35% B (A=0.1% NH3/H2O, B=EtOH), flow rate: 80 mL/min) to give A22 (Peak 1, 50 mg, 36%) and A23 (Peak 2, 40 mg, 29%) as solids.

A22: $^1$HNMR (400 MHz, CDCl$_3$) δ 7.34 (d, J=4.0 Hz, 4H), 7.30-7.27 (m, 1H), 5.32 (s, 1H), 4.70 (s, 1H), 3.40-3.26 (m, 1H), 3.21-3.05 (m, 1H), 2.29 (d, J=3.6 Hz, 1H), 2.24-2.15 (m, 2H), 1.88-1.58 (m, 9H), 1.53-1.28 (m, 11H), 1.26 (s, 4H), 1.18-0.93 (m, 6H), 0.65 (s, 3H); LC-ELSD/MS purity 96.6%. MS ESI calcd. for $C_{31}H_{46}NO_2$ [M+H]$^+$ 464, found 464. Analytical SFC 100% de. (condition: Column: ChiralPak AD-3 150×4.6 mm I.D., 3 um; Gradient: 40% of Ethanol (0.05% DEA) in $C_{02}$; Flow rate: 2.5 mL/min Column temperature:40° C.).

A23: $^1$HNMR (400 MHz, CDCl$_3$) δ 7.34 (d, J=4.4 Hz, 4H), 7.30-7.27 (m, 1H), 5.37-5.29 (m, 1H), 4.74-4.66 (m,

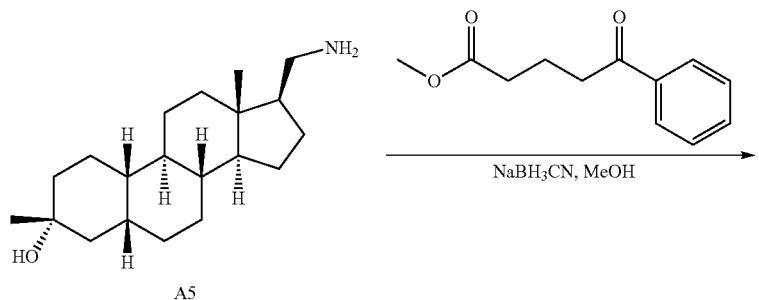

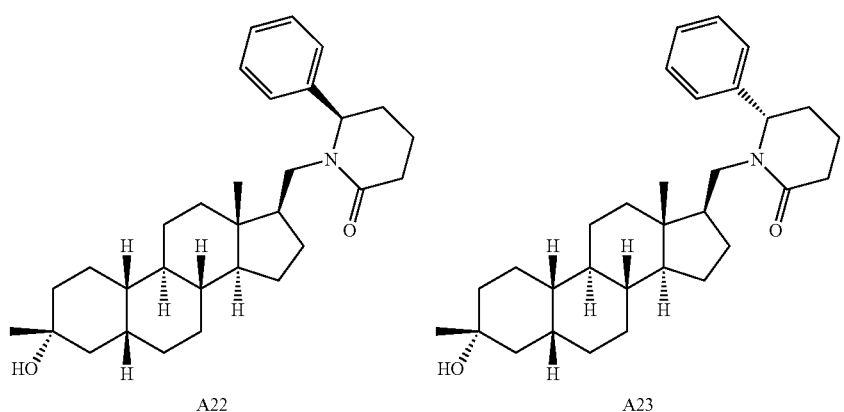

To a stirred solution of A5 (300 mg, 0.9819 mmol) in methanol (40 mL) was added methyl 5-oxo-5-phenylpentanoate (241 mg, 1.17 mmol) and NaCNBH$_3$, (154 mg, 2.45 mmol). The mixture was brought to pH 6 with HOAc (1 mL). After stirring at 70° C. for 48 h, the reaction mixture was extracted with ethyl acetate (2×80 mL). The combined organic solution was washed with brine (100 mL), dried over Na$_2$SO$_4$, filtered and concentrated under vacuum to give a residue, which was triturated in MeCN (20 mL) at 20°

1H), 3.40-3.27 (m, 1H), 3.18-3.10 (m, 1H), 2.30 (s, 1H), 2.24-2.14 (m, 2H), 1.90-1.58 (m, 9H), 1.53-1.28 (m, 11H), 1.26 (s, 4H), 1.19-0.96 (m, 6H), 0.65 (s, 3H); LC-ELSD/MS purity 98.5%. MS ESI calcd. for $C_{31}H_{46}NO_2$ [M+H]$^+$ 464. Analytical SFC 100% de. (condition: Column: ChiralPak AD-3 150×4.6 mm I.D., 3 um; Gradient: 40% of Ethanol (0.05% DEA) in $C_{02}$; Flow rate: 2.5 mL/min Column temperature: 40° C.).

Example 15: Synthesis of N-(((3R,5R,8R,9R,10S,13S,14S,17S)-3-(ethoxymethyl)-3-hydroxy-13-methylhexadecahydro-1H-cyclopenta[a]phenanthren-17-yl)methyl)benzamide (A32)

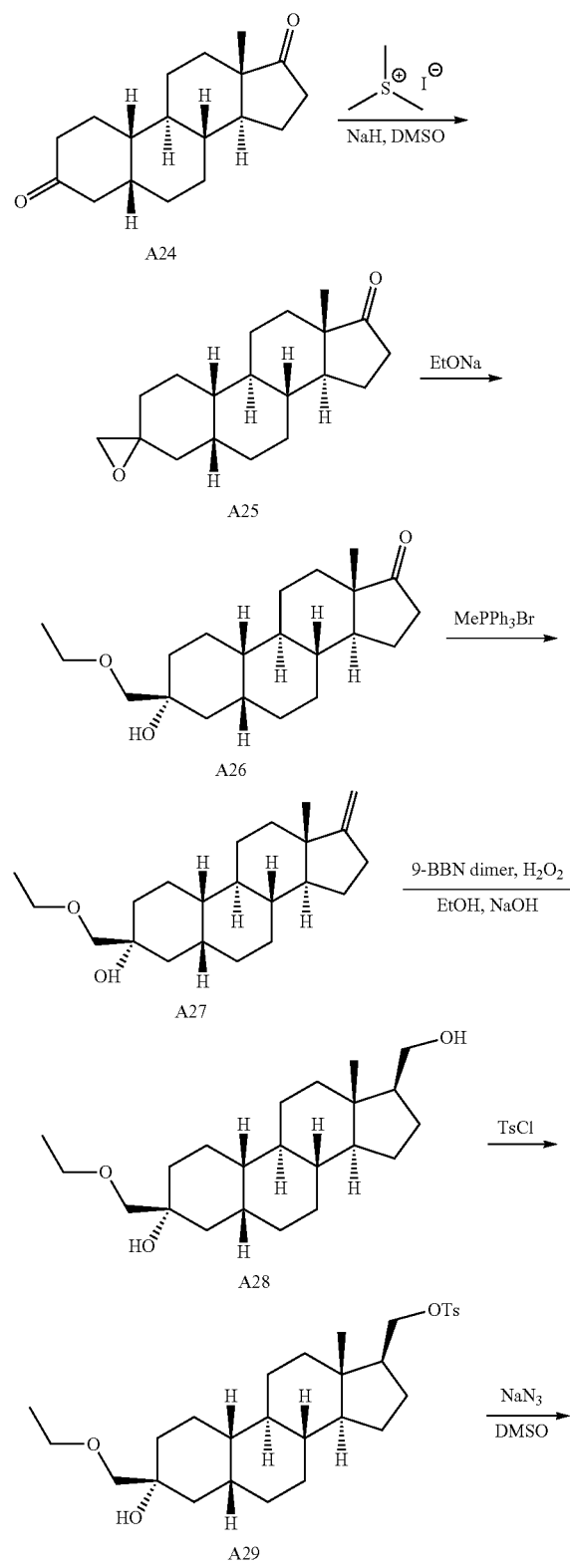

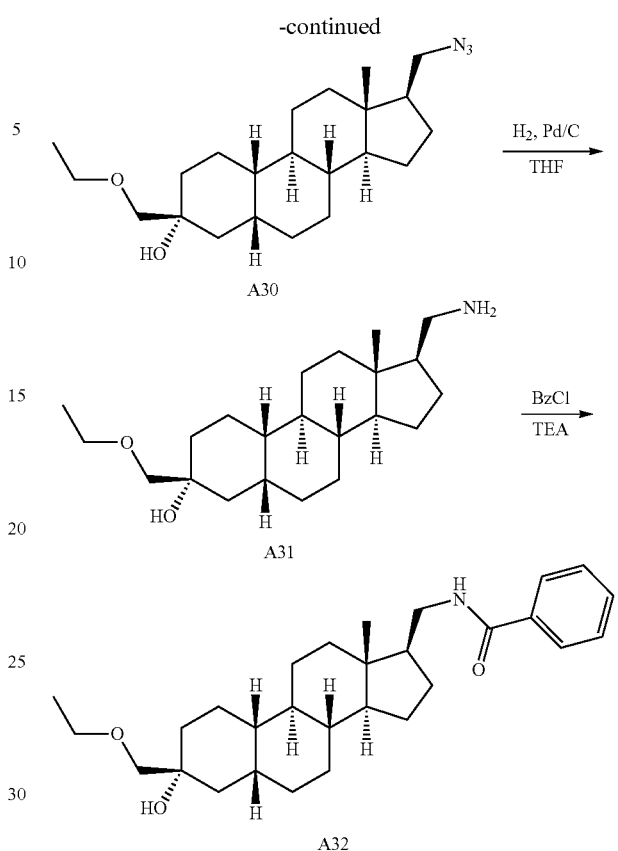

Synthesis of A25

To a stirred solution of iodotrimethyl-4-sulfane (77.9 g, 382 mmol) and NaH (60%, 15.2 g, 382 mmol) in DMSO (900 mL) was added to a solution of estrane-3,17-dione (100 g, 364 mmol) in DMSO (300 mL). After stirring at 15° C. for 16 h, the reaction was treated with water (1000 mL) and extracted with EtOAc (2×1000 mL). The combined organic solution was washed with water (2×1000 mL), brine (1000 mL), dried over anhydrous $Na_2SO_4$, filtered, concentrated in vacuum. The residue was triturated from MeOH (1000 mL) at 65° C. to give filter cake A25a (20 g, 19%) as a solid. The filtrate was concentrated to give A25 (80 g) as an oil. A25 (80.0 g) was triturated from MeOH (300 mL) at 65° C. to give filter cake (15 g, mixture) as a solid, and the filtrate to concentrated to give A25 (65 g) as an oil.

$^1$H NMR (400 MHz, CDCl$_3$) δ 2.65-2.55 (m, 2H), 2.48-2.40 (m, 1H), 2.28-1.50 (m, 11H), 1.50-1.00 (m, 10H), 0.95-0.90 (m, 1H), 0.88 (s, 3H).

Synthesis of A26

To the fresh prepared ethoxysodium (To a solution of ethanol (50 mL) was added Na (8 g, 347 mmol) in five portions at 40° C. under $N_2$ and stirred at 40° C. for 2 h) in ethanol (50 mL) was added A25 (8 g, 27.7 mmol) at 40° C. After stirring at 60° C. for 16 h, the mixture was cooled and poured into water (150 mL) and extracted with EtOAc (2×300 mL). The combined organic solution was washed with brine (150 mL), dried over anhydrous $Na_2SO_4$, filtered and concentrated. The residue was purified by flash column (0~10% of EtOAc in PE) to give A26 (4.9 g, 52.9%, 140 mg for delivery) as an oil.

$^1$H NMR (400 MHz, CDCl$_3$) δ 3.53 (q, J=6.8 Hz, 2H), 3.43 (q, J=9.2 Hz, 2H), 2.70 (s, 1H), 2.48-2.38 (m, 1H), 2.14-1.61 (m, 9H), 1.54-1.03 (m, 16H), 0.86 (s, 3H); LC-

ELSD/MS purity 99%, MS ESI calcd for $C_{19}H_{27}O$ [M−ETOH−H$_2$O+H]$^+$ 271, found 271.

Synthesis of A27

To a mixture of MePPh$_3$Br (9.78 g, 27.4 mmol) in THF (20 mL) was added t-BuOK (3.06 g, 27.4 mmol) at 15° C. under N$_2$. After stirring at 60° C. for 30 min. A27 (4.6 g, 13.7 mmol) in THF (30 mL) was added in portions below 60° C. After stirring at 60 C for 16 h, the reaction mixture was quenched with H$_2$O (100 mL) at 15° C. and extracted with EtOAc (2×200 mL). The combined organic solution was washed with brine (100 mL), dried over anhydrous Na$_2$SO$_4$, filtered and concentrated. The residue was purified by flash column (0~10% of EtOAc in PE) to give A27 (3.7 g, 81.3%) as an oil.

$^1$H NMR (400 MHz, CDCl$_3$) δ 4.66-4.59 (m, 2H), 3.54 (q, J=6.8 Hz, 2H), 3.44 (q, J=9.2 Hz, 2H), 2.69 (s, 1H), 2.54-2.43 (m, 1H), 2.30-2.18 (m, 1H), 1.77 (s, 7H), 1.52-1.07 (m, 17H), 0.78 (s, 3H).

Synthesis of A28

To a solution of A27 (3.7 g, 11.1 mmol) in THF (40 mL) was added 9-BBN dimer (5.41 g, 22.2 mmol) under N$_2$. After stirring at 60° C. for 1 h, the mixture was cooled to 15° C. and ethanol (6.38 mL, 111 mmol) and NaOH (22.2 mL, 5 M, 111 mmol) were added. H$_2$O$_2$ (11.1 mL, 10 M, 111 mmol) was then added dropwise at 25° C. followed by saturated aqueous Na$_2$S$_2$O$_3$ (10 mL). After stirring at 15° C. for another 1 h, the mixture was poured into water (20 mL) and extracted with EtOAc (2×30 mL). The combined organic solution was washed with brine (20 mL), dried over anhydrous Na$_2$SO$_4$, filtered and concentrated. The residue was purified by flash column (0~35% of EtOAc in PE) to give A28 (2.8 g, 71.9%) as a solid.

$^1$H NMR (400 MHz, CDCl$_3$) δ 3.76-3.67 (m, 1H), 3.57-3.50 (m, 3H), 3.46-3.38 (m, 2H), 2.72-2.67 (m, 1H), 1.88-1.72 (m, 5H), 1.68-1.57 (m, 5H), 1.49-1.35 (m, 6H), 1.30-1.01 (m, 12H), 0.65 (s, 3H); LC-ELSD/MS purity 99%, MS ESI calcd for $C_{22}H_{36}O_2$ [M−H$_2$O]$^+$ 333, found 333.

Synthesis of A29

To a solution of A28 (2.7 g, 7.70 mmol) in DCM (30 mL) at 15° C. were added 1-methyl-1H-imidazole (1.26 g, 15.4 mmol), TEA (1.55 g, 15.4 mmol) and then TsCl (2.93 g, 15.4 mmol). After stirring at 15° C. for 2 h, the mixture was washed with water (2×80 mL), brine (80 mL), dried over Na$_2$SO$_4$, filtered and concentrated under vacuum to give A29 (4.7 g) as an oil.

$^1$H NMR (400 MHz, CDCl$_3$) δ 7.79 (d, J=8.0 Hz, 2H), 7.35 (d, J=8.0 Hz, 2H), 4.10-4.03 (m, 1H), 3.97-3.90 (m, 1H), 3.71 (s, 1H), 3.57-3.49 (m, 2H), 3.46-3.38 (m, 2H), 2.46 (s, 3H), 1.84-1.70 (m, 6H), 1.65-1.55 (m, 4H), 1.49-1.33 (m, 6H), 1.23-0.96 (m, 11H), 0.57 (s, 3H).

Synthesis of A30

To a solution of A29 (4.7 g, 9.31 mmol) in DMSO (100 mL) was added NaN$_3$ (1.81 g, 27.9 mmol). After stirring at 70° C. for 16 h, the mixture was cooled and sat.NaHCO$_3$.aq was added until pH>8. The mixture was extracted whit EtOAc (2×100 mL) and the combined organic solution was washed with brine (100 mL), dried over anhydrous Na$_2$SO$_4$, filtered and concentrated under vacuum to give A30 (2.5 g, 72%) as a solid.

$^1$H NMR (400 MHz, CDCl$_3$) δ 3.53 (q, J=7.2 Hz, 2H), 3.46-3.38 (m, 2H), 3.29-3.15 (m, 2H), 2.70 (s, 1H), 1.76 (m, 9H), 1.50-1.32 (m, 7H), 1.20 (m, 11H), 0.62 (s, 3H).

Synthesis of A31

A solution of A30 (2.5 g, 6.65 mmol) in THF (25 mL) with Pd/C (0.2 g, water>50%) was hydrogenated under 15 psi of hydrogen. After 3 h, the mixture was filtered through a pad of celite and the filtrate was concentrated in vacuum to give A31 (1.85 g) as a solid.

$^1$H NMR (400 MHz, CDCl$_3$) δ 3.53 (q, J=6.8 Hz, 2H), 3.46-3.38 (m, 2H), 2.87-2.50 (m, 7H), 1.98-1.56 (m, 9H), 1.38 (m, 7H), 1.20 (t, J=7.2 Hz, 9H), 0.60 (s, 3H); LC-ELSD/MS purity 99%, MS ESI calcd for $C_{22}H_{40}NO_2$ [M+H]$^+$ 350, found 350.

Synthesis of A32

To a solution of A31 (300 mg, 0.858 mmol) in anhydrous DCM (5 mL) was added TEA (260 mg, 2.57 mmol) and BzCl (240 mg, 1.71 mmol) at 25° C. under N$_2$. After stirring for 16 h, the mixture was poured into water (20 mL) and extracted with EtOAc (2×30 mL). The combined organic solution was washed with brine (30 mL), dried over anhydrous Na$_2$SO$_4$, filtered and concentrated. The residue was purified by HPLC (Column: YMC-Actus Triart C18 100×30 mm, 5 um; Condition; water (0.05% HCl)-ACN; Gradient: from 80% to 96% of B in 7.5 min; Flow rate: 25 mL/min; Injections: 8) to give A32 (140 mg, 35.9%) as a solid.

$^1$H NMR (400 MHz, CDCl$_3$) δ 7.77-7.70 (m, 2H), 7.52-7.40 (m, 3H), 6.06-5.91 (m, 1H), 3.53 (d, J=6.8 Hz, 3H), 3.42 (d, J=10.8 Hz, 3H), 1.95-1.74 (m, 5H), 1.69-1.55 (m, 8H), 1.45-1.34 (m, 6H), 1.27-1.04 (m, 10H), 0.72 (s, 3H); LC-ELSD/MS purity 99%, MS ESI calcd for $C_{29}H_{44}NO_3$ [M+H]$^+$ 454, found 454.

Example 16: Synthesis of N-(((3R,5R,8R,9R,10S, 13S,14S,17S)-3-hydroxy-3-(methoxymethyl)-13-methylhexadecahydro-1H-cyclopenta[a] phenanthren-17-yl)methyl)benzamide (A39)

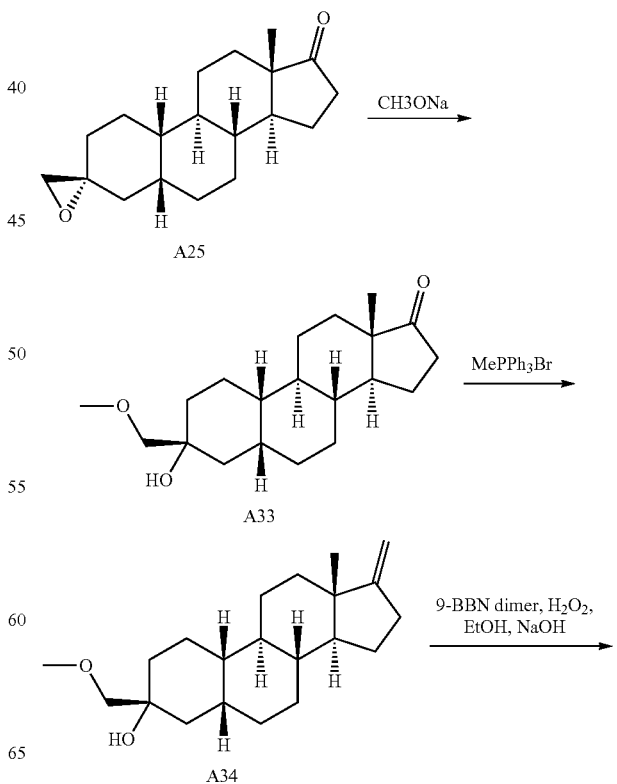

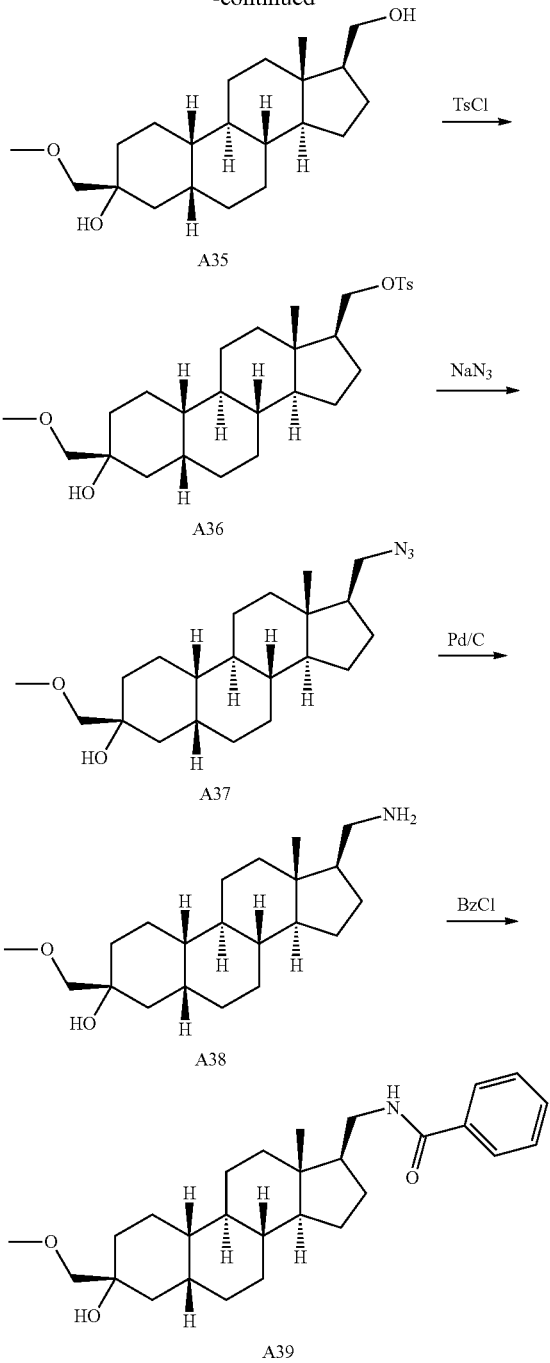

Synthesis of A33

To anhydrous methanol (100 mL) was added Na (6.34 g, 276 mmol) in five portions. The mixture was stirred at 25° C. for 2 h. A25 (8.00 g, 27.7 mmol) in THF (50 mL) was added to the reaction mixture and stirred at 60° C. for 5 h. After the reaction mixture was cooled to 0° C., the reaction mixture was quenched by addition of H$_2$O (100 mL) and extracted with EtOAc (3×100 mL). The combined organic solution was washed with saturated brine (2×100 mL), dried over anhydrous Na$_2$SO$_4$, filtered and concentrated. The residue was purified by flash column (0~30% of EtOAc in PE) to give A333 (5.352 g, 60%) as a solid.

$^1$H NMR (400 MHz, CDCl$_3$) δ 3.45-3.35 (m, 5H), 2.63-2.58 (m, 1H), 2.49-2.40 (m, 1H), 2.13-2.03 (m, 1H), 1.96-1.56 (m, 8H), 1.56-1.00 (m, 13H), 0.86 (s, 3H); LC-ELSD/MS purity 99%, MS ESI calcd. for C$_{20}$H$_{31}$O$_2$ [M−H$_2$O+H]$^+$ 303, found 303

Synthesis of A34

To a mixture of MePPh$_3$Br (11.5 g, 32.4 mmol) in THF (80 mL) was added t-BuOK (3.62 g, 32.4 mmol) at 15° C. under N$_2$. After stirring at 60° C. for 30 min. A33 (5.20 g, 16.2 mmol) in THF (20 mL) was added in portions. After stirring at 60° C. for 16 h, the reaction mixture was quenched with H$_2$O (50 mL) at 15° C. and extracted with EtOAc (3×50 mL). The combined organic solution was washed with saturated brine (2×50 mL), dried over anhydrous Na$_2$SO$_4$, filtered and concentrated. The residue was triturated from CH$_3$OH:H$_2$O=1/1 (100 mL) at 15° C. to give A34 (4.50 g, 87%) as an oil.

$^1$H NMR (400 MHz, CDCl$_3$) δ 4.65-4.58 (m, 2H), 3.45-3.35 (m, 5H), 2.58 (s, 1H), 2.50-2.43 (m, 1H), 2.25-2.13 (m, 1H), 1.88-1.56 (m, 8H), 1.56-1.05 (m, 13H), 0.77 (s, 3H).

Synthesis of A35

The solution of A34 (5.00 g, 15.6 mmol) in THF (50 mL) was added 9-BBN dimer (7.61 g, 31.2 mmol) under N$_2$. After stirring at 60° C. under N$_2$ for 1 h, the mixture was cooled to 15° C. and ethanol (8.97 mL, 156 mmol) and NaOH (31.2 mL, 5 M, 156 mmol) were added. H$_2$O$_2$ (15.6 mL, 10 M, 156 mmol) was then added dropwise at 15° C. After stirring at 60° C. for 1 h, EtOAc (30 mL) and Na$_2$S$_2$O$_3$ (30 mL) were added at 15° C. After stirring for 1 h, the mixture was extracted with EtOAc (3×50 mL). The combined organic solution was washed with brine (50 mL) and dried over anhydrous Na$_2$SO$_4$, filtered and concentrated. The residue was purified by flash column (0~30% of EtOAc in PE) to give A35 (4.50 g) as a solid.

$^1$H NMR (400 MHz, CDCl$_3$) δ 3.75-3.62 (m, 1H), 3.57-3.52 (m, 1H), 3.45-3.35 (m, 5H), 2.58 (brs, 1H), 1.85-1.50 (m, 11H), 1.50-1.00 (m, 14H), 0.65 (s, 3H); LC-ELSD/MS purity 99%, MS ESI calcd. for C$_{21}$H$_{35}$O$_2$ [M−H$_2$O+H]$^+$ 319, found 319.

Synthesis of A36

To a solution of A35 (4.40 g, 13.0 mmol) in DCM (50 mL) at 15° C. were added 1-methyl-1H-imidazole (2.13 g, 26.0 mmol), TEA (2.63 g, 26.0 mmol) and then TsCl (4.95 g, 26.0 mmol). After stirring at 15° C. for 2 h, the mixture was washed with water (2×100 mL), brine (100 mL), dried over Na$_2$SO$_4$, filtered and concentrated under vacuum, which was purified by column (0-20% EtOAc in PE) to give A36 (5.00 g, 78%) as a solid.

$^1$H NMR (400 MHz, CDCl$_3$) δ 7.80-7.77 (m, 2H), 7.37-7.30 (m, 2H), 4.10-4.05 (m, 1H), 3.98-3.92 (m, 1H), 3.42-3.35 (m, 5H), 2.56 (s, 1H), 2.46 (s, 3H), 1.83-1.50 (m, 10H), 1.50-0.92 (m, 14H), 0.56 (s, 3H).

Synthesis of A37

To a solution of A36 (5.00 g, 10.1 mmol) in DMSO (100 mL) was added NaN$_3$ (1.96 g, 30.3 mmol). After stirring at 70° C. for 16 h, the mixture was cooled and aqueous 10% NaHCO$_3$.aq (200 mL) was added until pH>8. The mixture was extracted with EtOAc (2×100 mL) and the combined organic solution was washed with brine 1 (300 mL), dried over anhydrous Na$_2$SO$_4$, filtered and concentrated under vacuum to give A37 (3.50 g, 96%) as an oil.

$^1$H NMR (400 MHz, CDCl$_3$) δ 3.45-3.35 (m, 5H), 3.28-3.13 (m, 2H), 2.60-2.53 (m, 2H), 1.98-1.50 (m, 12H), 1.50-0.95 (m, 11H), 0.63 (s, 3H)

Synthesis of A38

A solution of A37 (1 g, 2.76 mmol) in THF (10 mL) with Pd/C (0.2 g, water>50%) was hydrogenated at 15 psi. After 3 h, the mixture was filtered through a pad of celite and the filtrate was concentrated in vacuum to give A38 (1.08 g) as a solid.

¹H NMR (400 MHz, CDCl₃) δ 8.25 (s, 3H), 3.44-3.34 (m, 5H), 3.07 (s, 1H), 2.87-2.61 (m, 2H), 2.07 (s, 1H), 1.65-1.85 (m, 7H), 1.32-1.51 (m, 7H), 0.98-1.29 (m, 8H), 0.64 (s, 3H).

Synthesis of A39

To a solution of A38 (300 mg, 0.894 mmol) in DCM (5 mL) was added Et₃N (271 mg, 2.68 mmol) and BzCl (250 mg, 1.78 mmol). After stirring at 20° C. for 16 h, the mixture was quenched with H₂O (5 mL) and extracted with DCM (2×2 mL). The combined organic solution was filtered, concentrated (0.53 g) and purified by prep.HPLC (Column: YMC-Actus Triart C18 100*30 mm*5 um; Condition: water (0.05% HCl)-ACN; Begin B: 75; End B: 93; Gradient Time (min): 7; 100% B Hold Time (min): 1; FlowRate (ml/min): 25; Injections: 7) to afford A39 (221 mg, 56%) as a solid.

¹H NMR (400 MHz, CDCl₃) δ 7.77-7.70 (m, 2H), 7.54-7.38 (m, 3H), 6.04-5.95 (m, 1H), 3.60-3.51 (m, 1H), 3.31-3.45 (m, 6H), 2.60 (s, 1H), 1.73-1.95 (m, 5H), 1.6-1.72 (m, 4H), 0.98-1.51 (m, 15H), 0.72 (s, 3H); LC-ELSD/MS purity 99%, MS ESI calcd. for C₂₈H₄₂NO₂ [M+H]⁺ 440, found 440

Examples 17 & 18: Synthesis of N-((S)-1-((3R,5R,8R,9R,10S,13S,14S,17S)-3-hydroxy-3,13-dimethyl-hexadecahydro-1H-cyclopenta[a]phenanthren-17-yl)ethyl)benzenesulfonamide (B4) & N-((R)-1-((3R,5R,8R,9R,10S,13S,14S,17S)-3-hydroxy-3,13-dimethylhexadecahydro-1H-cyclopenta[a]phenanthren-17-yl)ethyl)benzenesulfonamide (B5)

Synthesis of B2

To a solution of KOH (2.61 g, 46.7 mmol) in EtOH (50 mL) was added 19-Norpregnan-20-one, 3-hydroxy-3-methyl-, (3α,5β)-(B1) (5 g, 15.6 mmol) and hydroxylamine.HCl (2.16 g, 31.2 mmol) at 15° C. After stirring for 16 h at 15° C., the reaction was diluted with water (100 mL) and extracted with EtOAc (3×50 mL). The combined organic solution was washed with brine (50 mL), dried over anhydrous Na₂SO₄, filtered and concentrated under vacuum to give B2 (51 g) as an oil.

Synthesis of B3

To a solution of B2 (4 g, 11.9 mmol) in THF (200 mL) was added LiAlH₄ (4.52 g, 119 mmol) at 0° C. After stirring for 16 h at 70° C. the reaction was cooled to 0° C. and H₂O (10 mL and then NaOH (10%, 10 mL) were added. After stirring for 0.5 h at 15° C., the mixture was filtered and the residue was washed with anhydrous THF (2×200 mL). The combined organic solution was concentrated in vacuum to give B3 (4.2 g) as an oil.

Synthesis of B4 & B5

To a solution of B3 (1 g, 3.12 mmol) and TEA (630 mg, 6.24 mmol), 2,6-dimethylpyridine (667 mg, 6.24 mmol) in DCM (10 mL) was added benzenesulfonyl chloride (577 mg, 3.27 mmol) at 0° C. After stirring at rt for 16 h, the mixture was poured in to water (20 mL) and extracted with ethyl acetate (2×20 mL). The combined organic solution was washed with brine (10 mL), dried over Na₂SO₄, filtered, concentrated in vacuum, purified by HPLC ((column: YMC-Actus Triart C18 100*30 mm*5 um), gradient: 75-96% B

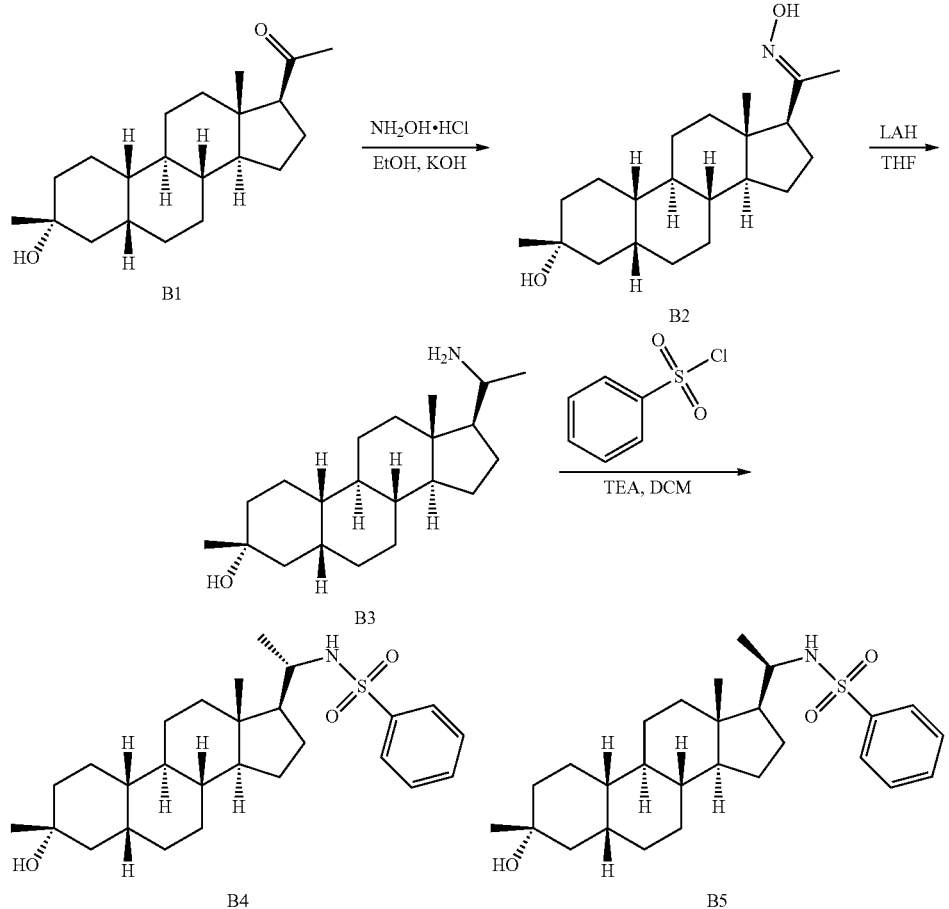

(water (0.05% HCl)-ACN), flow rate: 25 mL/min) and then by SFC (column: YMC CHIRAL Amylose-C (250 mm*30 mm, 10 um, gradient: 40-40% B (0.1% NH3H2O IPA), flow rate: 70 mL/min) to afford B4 (100 mg) and B5 (113 mg, 13%) as solids. B4 (100 mg, 0.2175 mmol) was triturated from H$_2$O (10 mL) at 65° C. to give B4 (78 mg, 78%) as a solid.

B4: $^1$H NMR (400 MHz, CDCl$_3$) $\delta_H$ 7.90-7.80 (m, 2H), 7.65-7.40 (m, 3H), 4.20-4.10 (m, 1H), 3.35-3.30 (m, 1H), 1.85-1.65 (m, 5H), 1.65-1.50 (m, 2H), 1.50-1.25 (m, 7H), 1.25-0.85 (m, 9H), 0.61 (s, 3H); LC-ELSD/MS purity 99%, MS ESI calcd. for C$_{27}$H$_{41}$NO$_3$SNa [M+Na]$^+$ 482, found 482.

B5: $^1$H NMR $\delta_H$ 7.90-7.80 (m, 2H), 7.65-7.40 (m, 3H), 4.20-4.10 (m, 1H), 3.35-3.30 (m, 1H), 2.15-1.95 (m, 1H), 1.80-1.70 (m, 3H), 1.70-1.50 (m, 2H), 1.50-1.20 (m, 15H), 1.20-0.75 (m, 10H), 0.61 (s, 3H); LC-ELSD/MS purity 99%, MS ESI calcd. for C$_{27}$H$_{41}$NO$_3$SNa [M+Na]$^+$ 482, found 482.

Examples 19 & 20: Synthesis of N-((S)-1-((3R,5R,8R,9R,10S,13S,14S,17S)-3-hydroxy-3,13-dimethyl-hexadecahydro-1H-cyclopenta[a]phenanthren-17-yl)ethyl)-N-methylbenzamide (B7) & N-((1R)-1-((3R,5R,9R,10S,13S,14S,17S)-3-hydroxy-3,13-dimethylhexadecahydro-1H-cyclopenta[a]phenanthren-17-yl)ethyl)-N-methylbenzamide (B8)

Synthesis of B6

A solution of B1 (500 mg, 1.6 mmol) in MeNH$_2$ (7.8 mL, 2M in EtOH, 15.6 mmol) was stirred at 25° C. for 10 h. To the reaction mixture was then added NaBH$_4$ (295 mg, 7.8 mmol) at 25° C. The mixture was stirred at 25° C. for 0.5 h, then H$_2$O (20 mL) was added to the reaction mixture and extracted with EtOAc (3×20 mL). The combined organic solution was washed with saturated brine (2×20 mL), dried over anhydrous Na$_2$SO$_4$, filtered and concentrated to give B6 (700 mg) as a solid.

Synthesis of B7 & B8

To a solution of B6 (700 mg, 2.1 mmol) in pyridine (10 mL) was added benzoyl chloride (321 mg, 2.3 mmol). After stirring at 20° C. for 4 h, the reaction mixture was poured into water (20 mL) and extracted with EtOAc (2×20 mL). The combined organic solution was washed with brine (2×20 mL), dried over anhydrous Na$_2$SO$_4$, filtered, concentrated, purified by HPLC ((column: YMC-Actus Triart C18 100*30 mm*5 um), gradient: 70-99% B (water (0.05% HCl)-ACN), flow rate: 25 mL/min) and purified by SFC (column: DAICEL CHIRALPAK AS (250 mm*30 mm, 10 um, gradient: 30-30% B (0.1% NH$_3$H$_2$O ETOH), flow rate: 65 mL/min) to afford B7 (223 mg, 24%) and B8 (78 mg, 9%) as solids.

$^1$H NMR (400 MHz, CDCl$_3$) $\delta_H$ 7.40-7.27 (m, 5H), 4.98-4.80 (m, 0.4H), 3.75-3.60 (m, 0.6H), 2.93 (s, 1.5H), 2.74 (s, 1.5H), 1.95-1.65 (m, 7H), 1.65-1.26 (m, 18H), 1.26-0.85 (m, 6H), 0.83 (s, 1.5H), 0.29 (s, 1.5H); LC-ELSD/MS purity 99%, MS ESI calcd. for C$_{29}$H$_{44}$NO$_2$ [M+H]$^+$ 438, found 438.

$^1$H NMR $\delta_H$ 7.55-7.27 (m, 5H), 4.98-4.80 (m, 0.5H), 3.75-3.60 (m, 0.5H), 2.93 (s, 1.3H), 2.74 (s, 1.8H), 1.95-1.65 (m, 9H), 1.65-1.26 (m, 15H), 1.26-0.95 (m, 7H), 0.95-0.82 (m, 2H), 0.81 (s, 1.8H), 0.26 (s, 1.2H); LC-ELSD/MS purity 99%, MS ESI calcd. for C$_{29}$H$_{44}$NO$_2$ [M+H]$^+$ 438, found 438.

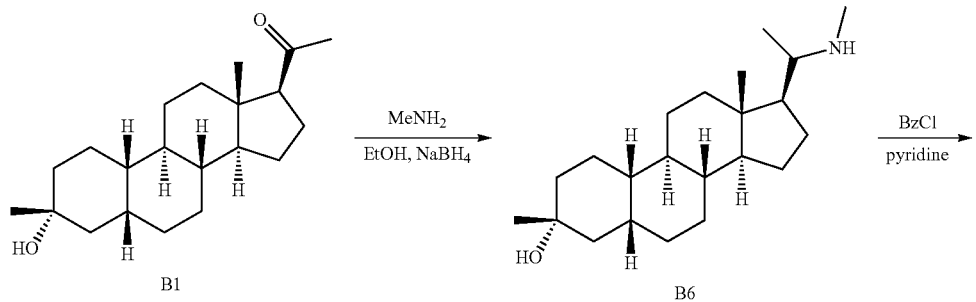

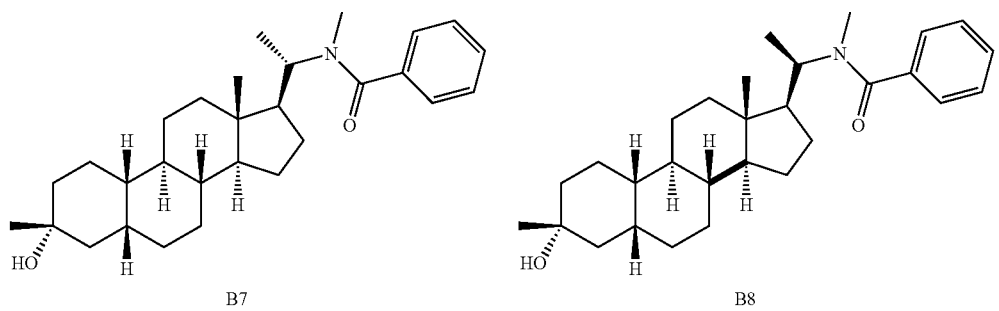

Examples 21 & 22: Synthesis of N-((S)-1-((3R,5R,8R,9R,10S,13S,14S,17S)-3-hydroxy-3,13-dimethyl-hexadecahydro-1H-cyclopenta[a]phenanthren-17-yl)ethyl)-N-methylbenzenesulfonamide (B9) & N-((R)-1-((3R,5R,8R,9R,10S,13S,14S,17S)-3-hydroxy-3,13-dimethylhexadecahydro-1H-cyclopenta[a]phenanthren-17-yl)ethyl)-N-methylbenzenesulfonamide (B10)

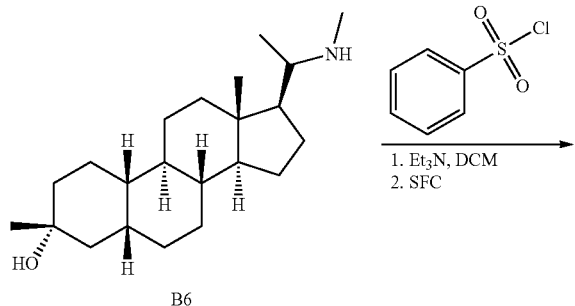

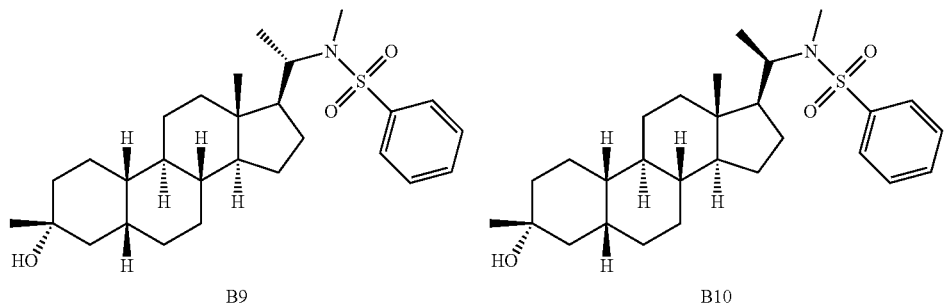

To a solution of B6 (700 mg, 2.2 mmol) and TEA (442 mg, 4.4 mmol), 2,6-dimethylpyridine (468 mg, 4.4 mmol) in DCM (10 mL) was added benzenesulfonyl chloride (404 mg, 2.3 mmol) at 0° C. After stirring at 25° C. for 12 h, the mixture was poured in to water (100 mL) and extracted with ethyl acetate (2×50 mL). The combined organic solution was washed with brine (100 mL), dried over Na$_2$SO$_4$, filtered and concentrated in vacuum, purified by HPLC ((column: YMC-Actus Triart C18 100*30 mm*5 um), gradient: 70-99% B (water (0.05% HCl)-ACN), flow rate: 25 mL/min) and purified by SFC (column: DAICEL CHIRALPAK AS (250 mm*30 mm, 10 um, gradient: 30-30% B (0.1% NH$_3$H$_2$O ETOH), flow rate: 65 mL/min) to afford B10 (195 mg, 32.7%) and B9 (72 mg, 12.0%) as solids.

B9: $^1$H NMR (400 MHz, CDCl$_3$) $\delta_H$ 7.74 (d, J=7.2 Hz, 2H), 7.50-7.39 (m, 3H), 3.89 (dd, J=6.8, 10.8 Hz, 1H), 2.60 (s, 3H), 1.79-1.67 (m, 4H), 1.61-1.48 (m, 4H), 1.46 (s, 7H), 1.29-1.18 (m, 7H), 1.06-0.95 (m, 5H), 0.74 (d, J=6.4 Hz, 3H), 0.67 (s, 3H); LC-ELSD/MS purity 99%, MS ESI calcd. for C$_{28}$H$_{44}$NO$_3$S [M+H]$^+$ 474, found 474.

B10: $^1$H NMR (400 MHz, CDCl$_3$) $\delta_H$ 7.77-7.73 (m, 2H), 7.52-7.41 (m, 3H), 4.01-3.92 (m, 1H), 2.57 (s, 3H), 2.11-2.07 (m, 1H), 1.82-1.71 (m, 3H), 1.59-1.51 (m, 4H), 1.43-1.29 (m, 7H), 1.26-1.13 (m, 7H), 1.04-0.97 (m, 5H), 0.82 (s, 3H), 0.54 (d, J=6.4 Hz, 3H); LC-ELSD/MS purity 99%, MS ESI calcd. for C$_{28}$H$_{44}$NO$_3$S [M+H]$^+$ 474, found 474.

Examples 23 & 24: Synthesis of N-((S)-1-((3R,5R,8R,9R,10S,13S,14S,17S)-3-hydroxy-3,13-dimethyl-hexadecahydro-1H-cyclopenta[a]phenanthren-17-yl)ethyl)benzamide (B11) & N-((R)-1-((3R,5R,8R,9R,10S,13S,14S,17S)-3-hydroxy-3,13-dimethylhexadecahydro-1H-cyclopenta[a]phenanthren-17-yl)ethyl)benzamide (B12)

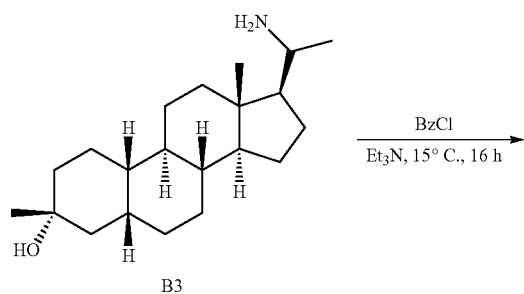

253 254

-continued

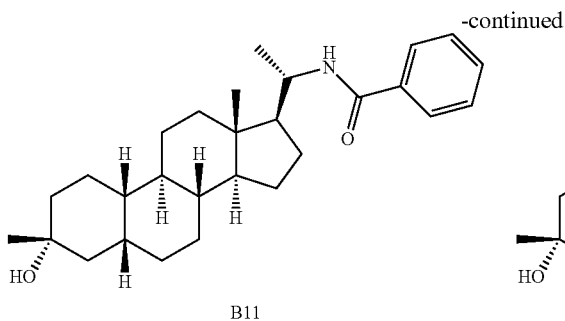
B11

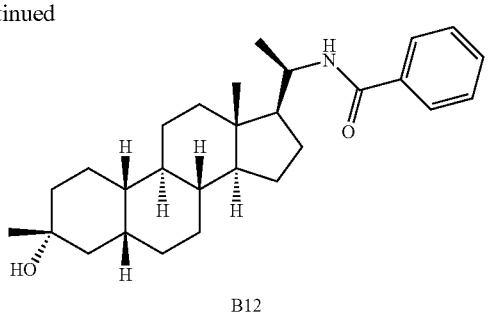
B12

To a solution of B3 (875 mg, 2.7 mmol) in DCM (10 mL) was added benzoyl chloride (574 mg, 4.1 mmol) and TEA (690 mg, 6.8 mmol). After stirring at 15° C. for 16 h, the reaction mixture was poured into water (40 mL) and extracted with EtOAc (2×40 mL). The combined organic solution was washed with water (2×40 mL), dried over anhydrous $Na_2SO_4$, filtered and concentrated. The residue was purified by flash column (0~30% EtOAc in PE) to give a mixture of diastereomers (800 mg, 69.5%). The diastereomers were separated by SFC (Column: Chiralpak AD-3 150iÅ4.6 mm I.D., 3 um, Mobile solution: A: $CO_2$ B: ethanol (0.05% DEA), Gradient: from 5% to 40% of B in 5 min and hold 40% for 2.5 min, then 5% of B for 2.5 min, Flow rate: 2.5 mL/min Column temp.: 35° C., ABPR: 1500 psi) to afford B12 (232 mg, 29.1%) and B11 (279 mg, 35%) as solids.

B12: $^1$H NMR (400 MHz, CDCl$_3$) $\delta_H$ 7.77-7.72 (m, 2H), 7.54-7.34 (d, J=7.5 Hz, 3H), 5.89 (d, J=9.3 Hz, 1H), 4.20 (d, J=5.5 Hz, 1H), 1.95-1.75 (d, J=9.0 Hz, 5H), 1.68-1.58 (m, 3H), 1.48-1.33 (m, 8H), 1.25 (s, 6H), 1.23-1.20 (m, 1H), 1.17 (d, J=6.3 Hz, 3H), 1.14-0.95 (m, 5H), 0.74 (s, 3H); LC-ELSD/MS purity 99%, MS ESI calcd. for $C_{28}H_{42}NO_2$ [M+H]$^+$ 424, found 424.

B11: $^1$H NMR (400 MHz, CDCl$_3$) $\delta_H$ 7.76-7.70 (m, 2H), 7.43 (d, J=7.5 Hz, 3H), 5.88 (d, J=9.0 Hz, 1H), 4.22 (d, J=6.3 Hz, 1H), 1.98-1.75 (s, 5H), 1.68-1.59 (m, 3H), 1.54-1.33 (m, 8H), 1.31-1.02 (m, 15H), 0.77 (s, 3H); LC-ELSD/MS purity 99%, MS ESI calcd. for $C_{28}H_{42}NO_2$ [M+H]$^+$ 424, found 424.

Examples 25 & 26: Synthesis of (3R,5R,8R,9R,10S,13S,14S,17S)-3,13-dimethyl-17-((R)-1-(phenylamino)ethyl)hexadecahydro-1H-cyclopenta[a]phenanthren-3-ol (B14) & (3R,5R,8R,9R,10S,13S,14S,17S)-3,13-dimethyl-17-((S)-1-(phenylamino)ethyl)hexadecahydro-1H-cyclopenta[a]phenanthren-3-ol (B15)

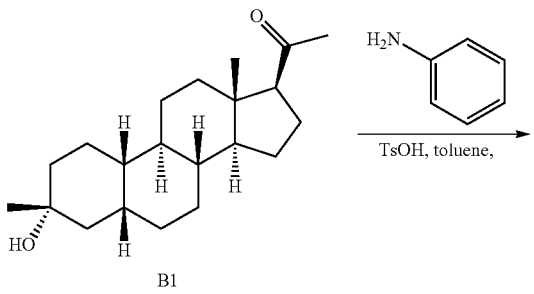
B1

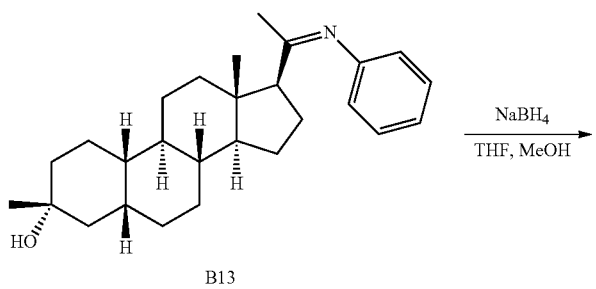
B13

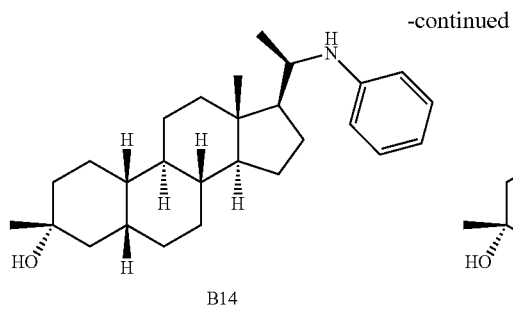

B14

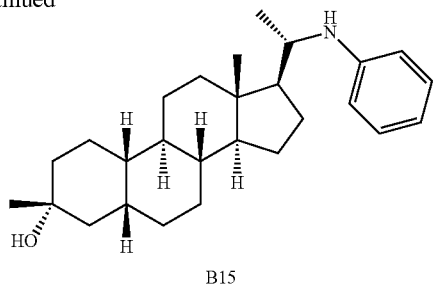

B15

Synthesis of B13

To a solution of B1 (700 mg, 2.2 mmol) and aniline (1.01 g, 10.9 mmol) in toluene (10 mL) were added molecular sieve 4A (2.8 g) and then TsOH (113 mg, 0.6 mmol) at 15° C. After stirring the suspension at 120° C. for 3 h, the mixture was concentrated under vacuum to give B13 (4 g), which was used in the next step without purification.

Synthesis of B14 & B15

To a solution of B13 with molecular sieves (4.0 g) in THF (40 mL) at 20° C. was added NaBH$_4$ (382 mg, 10.1 mmol) and then MeOH (10 mL) dropwise. After stirring at 20° C. for 1 h, the mixture was filtered, and the filtrate was quenched with saturated NH$_4$Cl aqueous (50 mL). The mixture was extracted with DCM (2×50 mL). The combined organic solution was washed with brine (100 mL), dried over Na$_2$SO$_4$, filtered and concentrated and purified by flash column (0~30% EtOAc in PE) to give a mixture of diastereomers (400 mg) that was separated by SFC (Column: Chiralcel OJ-3 150; A4.6 mm I.D., 3 um Mobile solution: A: CO2 B: ethanol (0.05% DEA) Gradient: from 5% to 40% of B in 5 min and hold 40% for 2.5 min, then 5% of B for 2.5 min Flow rate: 2.5 mL/min Column temp.: 35iæ ABPR: 1500 psi) to afford B14 (80 mg, 20%) and B15 (30 mg, 7.51%) as solids.

B14: $^1$H NMR (400 MHz, CDCl$_3$) δ$_H$ 7.15 (br d, J=1.0 Hz, 2H), 6.62 (s, 1H), 6.53 (d, J=7.8 Hz, 2H), 3.39 (br dd, J=6.0, 9.8 Hz, 1H), 2.13-2.04 (m, 1H), 1.80 (s, 4H), 1.68-1.63 (m, 4H), 1.26 (s, 15H), 1.08 (d, J=6.0 Hz, 7H), 1.01-0.93 (m, 2H), 0.66 (s, 3H); LC-ELSD/MS purity 99%, MS ESI calcd. for C$_{27}$H$_{42}$NO [M+H]$^+$ 396, found 396.

B15: $^1$H NMR (400 MHz, CDCl$_3$) δ$_H$ 7.14 (s, 2H), 6.63 (s, 1H), 6.55 (br d, J=8.0 Hz, 2H), 3.37 (br s, 1H), 1.95 (br s, 2H), 1.80 (br s, 3H), 1.69-1.60 (m, 3H), 1.41 (br s, 8H), 1.27 (s, 7H), 1.18 (br d, J=5.8 Hz, 9H), 0.74 (s, 4H); LC-ELSD/MS purity 99%, MS ESI calcd. for C$_{27}$H$_{42}$NO [M+H]$^+$ 396, found 396.

Examples 27 & 28: Synthesis of (3R,5R,8R,9R, 10S,13S,14S,17S)-17-((R)-1-(benzylamino)ethyl)-3, 13-dimethylhexadecahydro-1H-cyclopenta[a] phenanthren-3-ol (B16) & (3R,5R,8R,9R,10S,13S, 14S,17S)-17-((S)-1-(benzylamino)ethyl)-3,13- dimethylhexadecahydro-1H-cyclopenta[a] phenanthren-3-ol (B17)

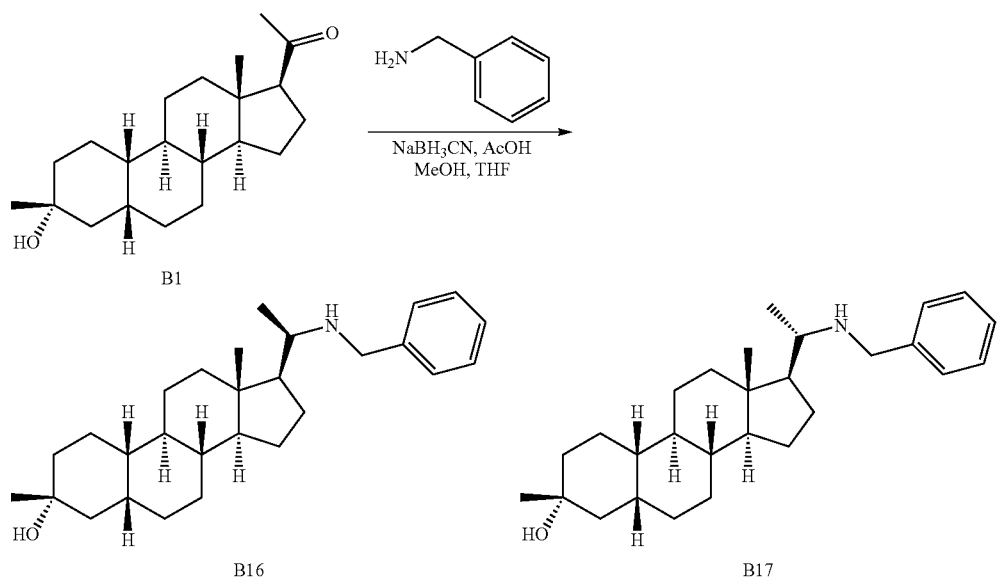

To a solution B1 (8.00 g, 25.1 mmol) in MeOH (100 mL) was added 1-phenylmethanamine (16.0 g, 150 mmol) and the pH of the solution was adjusted to pH 6 with acetic acid (10 mL) and THF (100 mL) at 25° C. under N$_2$. After stirring at 25° C. for 10 min, NaBH$_3$CN (1.48 g, 25.1 mmol) was added. After 1 h at 65° C., the reaction mixture was cooled, diluted with water (200 mL) and extracted with EtOAc (3×200 mL). The combined organic solution was washed with saturated brine (2×200 mL), dried over anhydrous Na$_2$SO$_4$, filtered and concentrated. The residue was purified by flash column (0~10% of DCM in CH₃OH) to give B16 (5.00 g) and B17 (5.00 g) as solids.

B16: ¹H NMR (400 MHz, CDCl₃) δ=7.34-7.21 (m, 5H), 3.93-3.57 (m, 2H), 2.70-2.58 (m, 1H), 2.06-1.98 (m, 1H), 1.95-1.56 (m, 8H), 1.70-1.18 (m, 15H), 1.18-0.95 (m, 8H), 0.62 (s, 3H).

B17: ¹H NMR (400 MHz, CDCl₃) δ=7.34-7.27 (m, 5H), 3.93-3.57 (m, 2H), 2.63-2.52 (m, 1H), 1.95-1.75 (m, 5H), 1.70-1.30 (m, 11H), 1.28-0.95 (m, 16H), 0.65 (s, 3H)

Example 29: Synthesis of N-((R)-1-((3R,5R,8R,9R,10S,13S,14S,17S)-3-hydroxy-3,13-dimethylhexadecahydro-1H-cyclopenta[a]phenanthren-17-yl)ethyl)nicotinamide (B19)

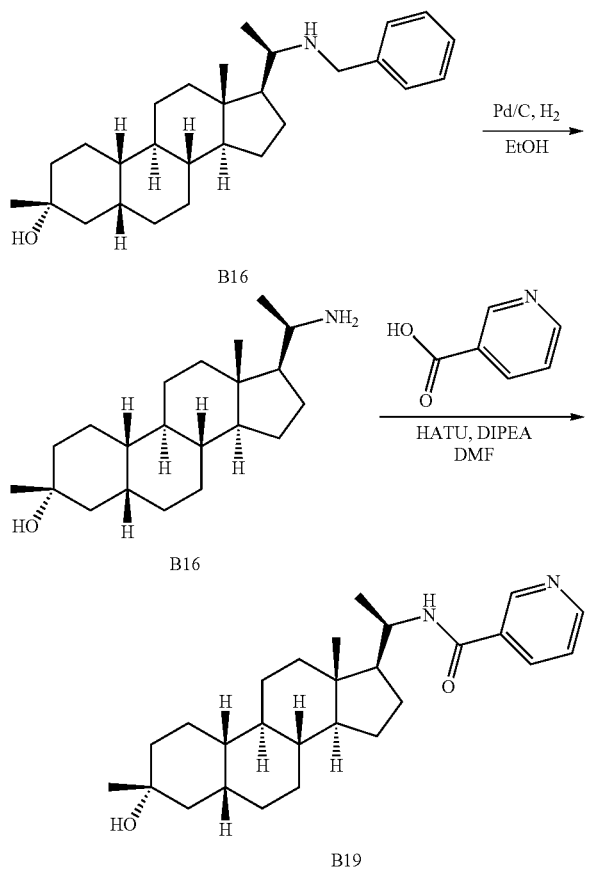

pyridine-3-carboxylic acid (153 mg, 1.25 mmol) was added. After stirring for 16 h at 25° C., the reaction mixture was diluted with EtOAc (10 mL), washed with water (10 mL), 3% of LiCl aqueous (10 mL), water (10 mL) and brine (10 mL), dried over sodium sulfate, filtered and concentrated. The residue was purified by HPLC (Column Agela DuraShell 150 mm_25 mm_5 um; Condition water (0.04% NH₃H₂O+10 mM NH4HCO3)-ACN Begin B 48 End B 78 Gradient Time (min) 8.5; 100% B Hold Time (min) 2 FlowRate (ml/min) 30; Injections 10) to give B19 (48 mg, 18%) as a solid.

¹H NMR (400 MHz, CDCl₃) δ=8.94 (d, J=1.8 Hz, 1H), 8.75-8.70 (m, 1H), 8.11 (td, J=2.0, 7.8 Hz, 1H), 7.40 (dd, J=5.0, 8.3 Hz, 1H), 5.90 (br d, J=9.3 Hz, 1H), 4.41-4.04 (m, 1H), 1.90-1.58 (m, 8H), 1.52-1.30 (m, 10H), 1.30-0.95 (m, 13H), 0.74 (s, 3H); LC-ELSD/MS purity 99%, MS ESI calcd. for C₂₇H₄₁N₂O₂ [M+H]⁺ 425, found 425.

Example 30: Synthesis of N-((S)-1-((3R,5R,8R,9R,10S,13S,14S,17S)-3-hydroxy-3,13-dimethylhexadecahydro-1H-cyclopenta[a]phenanthren-17-yl)ethyl)nicotinamide (B21)

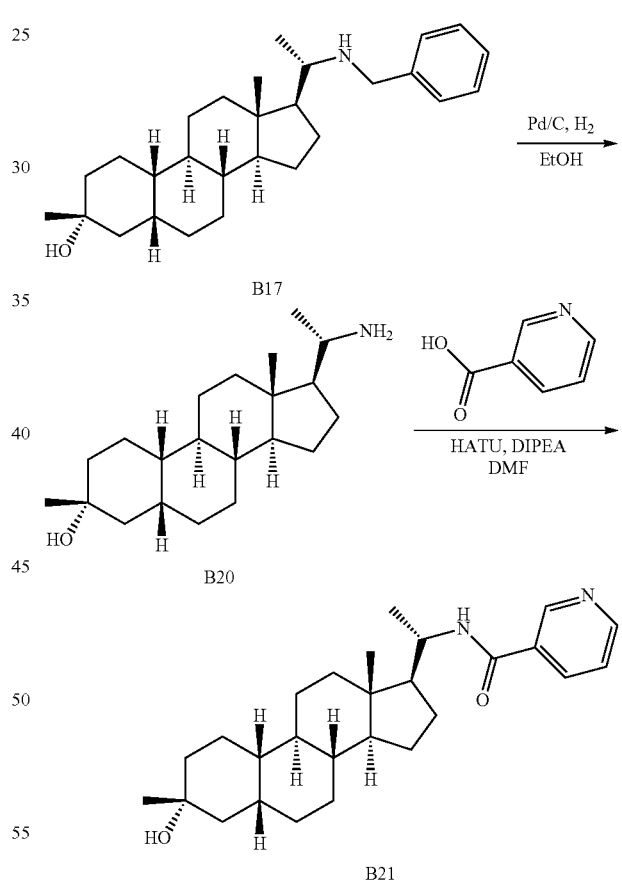

Synthesis of B18

To a solution of B16 (5.00 g, 12.2 mmol) in EtOH (50 mL) was added Pd—C (dry, 500 mg) under N₂. The suspension was degassed under vacuum and purged with H₂ for three times. The mixture was stirred under H₂ (15 psi) at 25° C. for 16 h to give a suspension. The reaction mixture was filtered through a pad of Celite and washed with THF (3×10 mL). The filtrate was concentrated to give B18 (3 g) as a solid.

¹H NMR (400 MHz, CDCl₃) δ=2.90-2.80 (m, 1H), 2.00-1.56 (m, 12H), 1.56-1.12 (m, 18H), 1.00-0.98 (m, 3H), 0.73 (s, 3H).

Synthesis of B19

To a solution of B18 (200 mg, 0.625 mmol) in DMF (3 mL) was added HATU (475 mg, 1.25 mmol) and DIPEA (403 mg, 3.12 mmol). After stirring for 15 mins at 25° C., Synthesis of B20

To a solution of B17 (2.00 g, 4.88 mmol) in EtOH (20 mL) was added Pd—C (dry, 200 mg) under N₂. The suspension was degassed under vacuum and purged with H₂ for three times. The mixture was stirred under H₂ (15 psi) at 25° C. for 16 h to give a suspension. The reaction mixture was filtered through a pad of Celite and washed with THF (3×10 mL). The filtrate was concentrated to give B20 (1.7 g) as a solid.

$^1$H NMR (400 MHz, CDCl$_3$) δ=2.83-2.72 (m, 1H), 2.00-1.75 (m, 7H), 1.56-1.25 (m, 18H), 1.25-0.95 (m, 8H), 0.65 (s, 3H).

Synthesis of B21

To a solution of pyridine-3-carboxylic acid (153 mg, 1.25 mmol) in DMF (5 mL) was added HATU (356 mg, 0.937 mmol) and DIPEA (403 mg, 3.12 mmol). After stirring for 15 mins at 25° C., B20 (200 mg, 0.625 mmol) was added. After stirring for 16 h at 25° C., the reaction mixture was diluted with EtOAc (10 mL), washed with water (10 mL), 3% of LiCl aqueous (10 mL), water (10 mL) and brine (10 mL), dried over sodium sulfate, filtered and concentrated. The residue was purified by prep-HPLC (Column Boston Prime C18 150*30 mm 5 um; Condition water (0.05% ammonia hydroxide v/v)-ACN Begin B 60; End B 90 Gradient Time (min) 8 100% B Hold Time (min) 0.1 FlowRate (ml/min) 25; Injections 8) to give B21 (101 mg, 38%) as a solid.

$^1$H NMR (400 MHz, CDCl$_3$) δ=8.91 (d, J=1.5 Hz, 1H), 8.71 (dd, J=1.6, 4.9 Hz, 1H), 8.08 (d, J=7.8 Hz, 1H), 7.43-7.34 (m, 1H), 5.91 (br d, J=8.8 Hz, 1H), 4.33-4.20 (m, 1H), 2.00-1.75 (m, 5H), 1.70-1.56 (m, 12H), 1.56-1.00 (m, 14H), 0.77 (s, 3H); LC-ELSD/MS purity 99%, MS ESI calcd. for C$_{27}$H$_{41}$N$_2$O$_2$ [M+H]$^+$ 425, found 425.

Examples 31 & 32: Synthesis of 5-cyano-N-((R)-1-((3R,5R,8R,9R,10S,13S,14S,17S)-3-hydroxy-3-(methoxymethyl)-13-methylhexadecahydro-1H-cyclopenta[a]phenanthren-17-yl)ethyl)picolinamide (B25) & 5-cyano-N-((S)-1-((3R,5R,8R,9R,10S,13S,14S,17S)-3-hydroxy-3-(methoxymethyl)-13-methylhexadecahydro-1H-cyclopenta[a]phenanthren-17-yl)ethyl)picolinamide (B26)

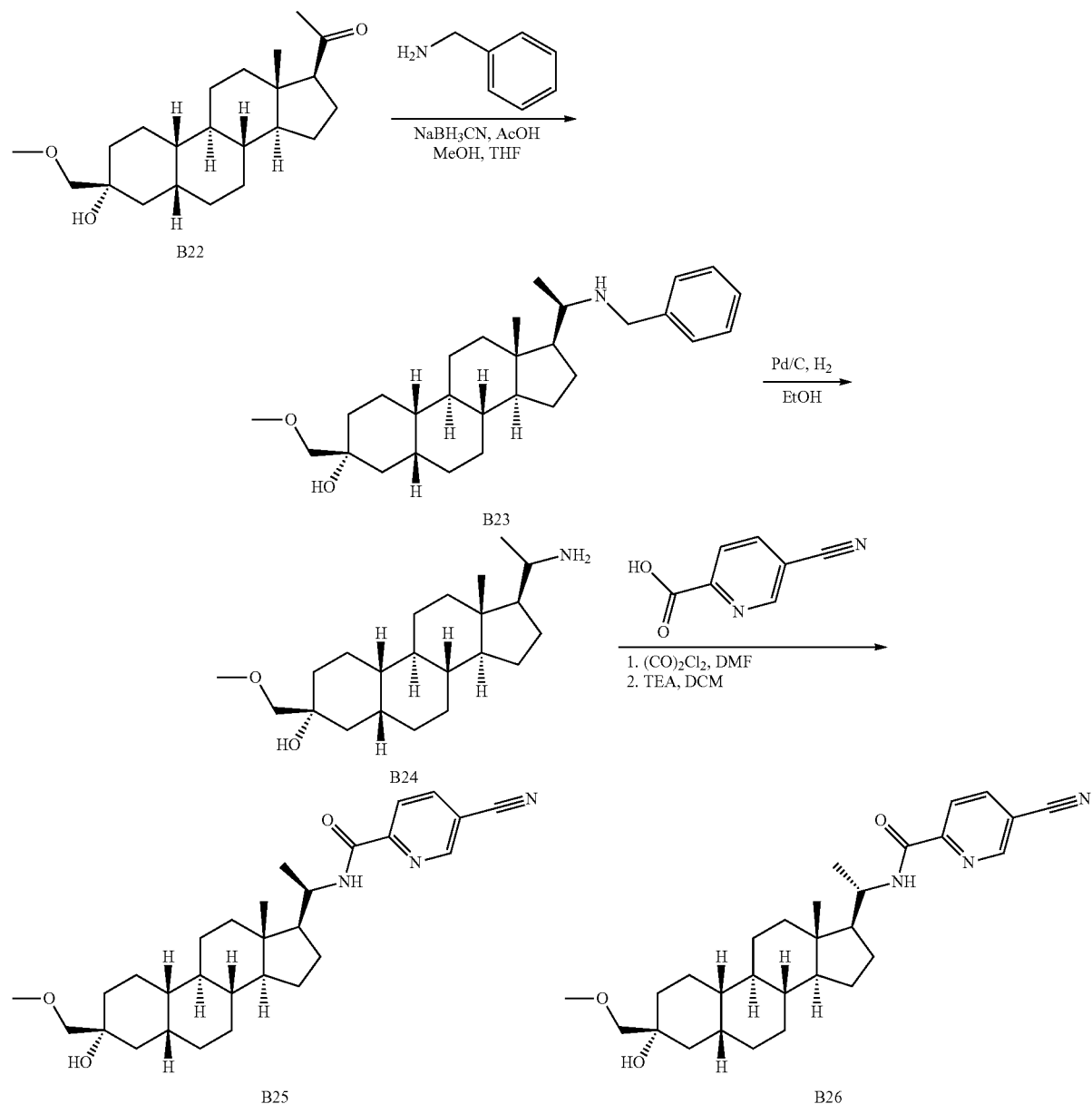

Synthesis of B23

To a solution of B22 (1 g, 2.86 mmol) and 1-phenylmethanamine (1.83 g, 17.1 mmol) in MeOH (15 mL) at 25° C. adjusted to pH 6 (with acetic acid and anhydrous THF) was added after 30 mins NaBH$_3$CN (215 mg, 3.43 mmol). After stirring at 80° C. for 16 h, the solution was diluted with NaHCO$_3$ aqueous (20 mL) and extracted with EtOAc (2×30 mL). The combined organic solution was washed with brine, dried over sodium sulfate, concentrated and purified by column chromatography on silica gel (50-80% of EtOAc in PE) to give desired product (1.09 g) as a solid.

$^1$H NMR (400 MHz, CDCl$_3$) δ 7.36-7.28 (m, 4H), 7.25-7.20 (m, 1H), 3.90-3.86 (m, 1H), 3.63-3.59 (m, 1H), 3.42-3.35 (m, 5H), 2.66-2.53 (m, 1H), 2.04-1.69 (m, 6H), 1.66-1.52 (m, 7H), 1.47-1.30 (m, 8H), 1.28-0.96 (m, 8H), 0.64-0.62 (m, 3H).

Synthesis of B24

To a solution of B23 (1.09 g, 2.47 mmol) in EtOH (10 mL) was added Pd/C (dry, 100 mg). The mixture was stirred under H$_2$ (15 psi) at 25° C. for 16 h. The reaction mixture was filtered through a pad of Celite and washed with MeOH (3×10 mL). The filtrate was concentrated to give B24 (700 mg) as a solid. The product was purified by flash column (2% of MeOH in CH$_2$Cl$_2$) to give B24 (500 mg, 71%) as an oil.

$^1$H NMR (400 MHz, CDCl$_3$) δ 3.42-3.36 (m, 5H), 2.88-2.77 (m, 1H), 2.01-1.71 (m, 6H), 1.70-1.49 (m, 8H), 1.48-1.16 (m, 8H), 1.14-0.97 (m, 8H), 0.72-0.65 (m, 3H).

Synthesis of 25 & 26.

To a solution of 5-cyanopicolinic acid (500 mg, 3.37 mmol) in DCM (30 mL) and DMF (1 mL) was added oxalyl chloride (431 mg, 3.37 mmol) dropwise at 0° C. After stirring at 10° C. for 18 h, DIPEA (147 mg, 1.14 mmol) and B24 (100 mg, 0.286 mmol) were added. After stirring at 25° C. for 48 h, saturated NH$_4$Cl aqueous (50 mL) was added to the mixture and extracted with ethyl acetate (3×30 mL). The combined organic solution was washed with aq. LiCl (3×50 mL), dried over Na$_2$SO$_4$ and filtered concentrated in vacuum. The product was purified by flash column (20% EtOAc in PE) to give a mixture of diastereomers (180 mg) as an oil. The diastereomers were separated by SFC {Column: DAICEL CHIRALPAK AD (250 mm*30 mm, 10 um), Condition: 0.1% NH$_3$H$_2$O ETOH, Begin B: 40%, End B: 40%} and lyophilized to afford B25 (20 mg, Peak 1) and B26 (22 mg, Peak 2) as solids.

B25: $^1$H NMR (400 MHz, CDCl$_3$) δ 8.83 (d, J=1.2 Hz, 1H), 8.34-8.32 (m, 1H), 8.14-8.11 (m, 1H), 7.83 (d, J=9.2 Hz, 1H), 4.15-4.09 (m, 1H), 3.41-3.34 (m, 5H), 2.60 (s, 1H), 1.89-1.68 (m, 5H), 1.67-1.49 (m, 8H), 1.47-1.29 (m, 8H), 1.25-0.85 (m, 6H), 0.68 (s, 3H). LC-ELSD/MS purity 99%, MS ESI calcd. for C$_{29}$H$_{42}$N$_3$O$_3$ [M+H]$^+$ 480, found 480. SFC 100% de.

B26: $^1$H NMR (400 MHz, CDCl$_3$) δ 8.82-8.80 (m, 1H), 8.33-8.31 (m, 1H), 8.13-8.11 (m, 1H), 7.83 (d, J=9.2 Hz, 1H), 4.22-4.13 (m, 1H), 3.42-3.36 (m, 5H), 2.61 (s, 1H), 1.85 (m, 5H), 1.96-1.68 (m, 8H), 1.67-1.53 (m, 5H), 1.51-1.32 (m, 3H), 1.28-1.01 (m, 6H), 0.75 (s, 3H). LC-ELSD/MS purity 99%, MS ESI calcd. for C$_{29}$H$_{42}$N$_3$O$_3$ [M+H]$^+$ 480, found 480. SFC 100% de.

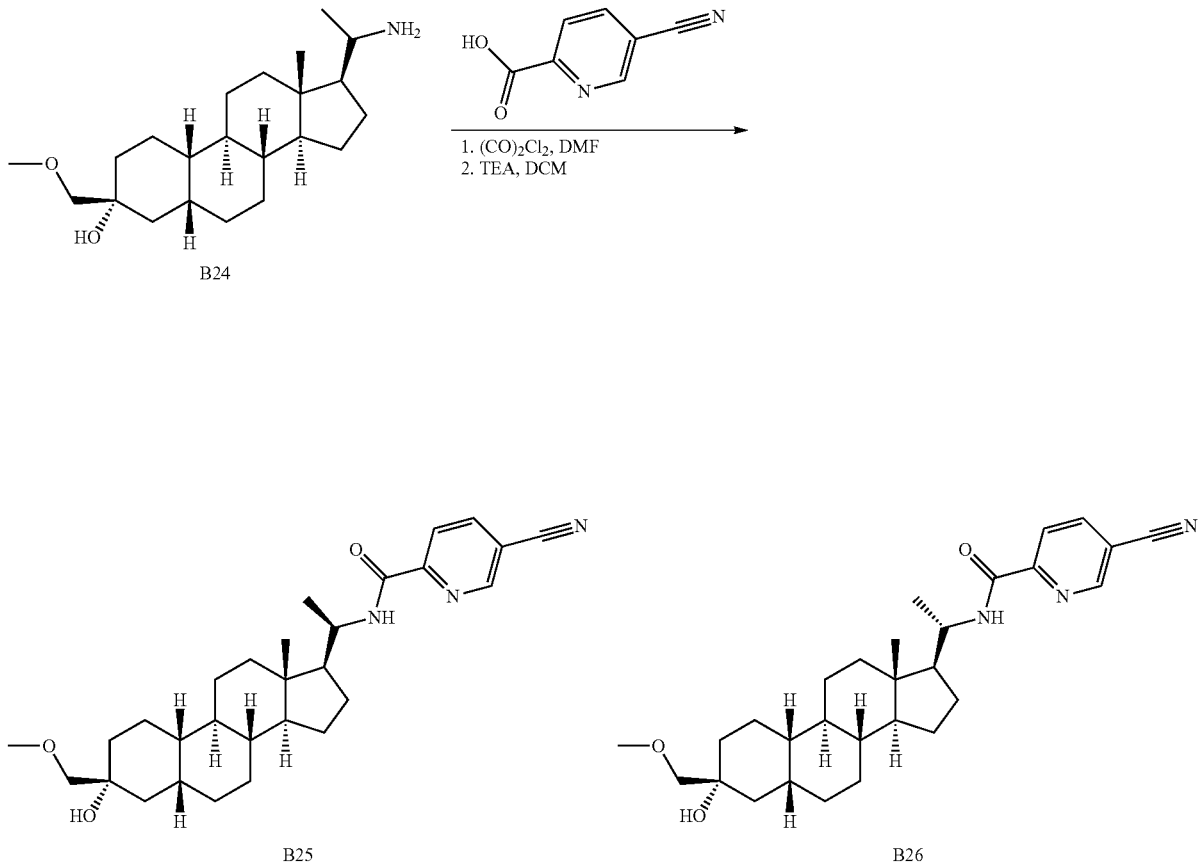

Example 33: Synthesis of 4-(((R)-1-((3R,5R,8R,9R,10S,13S,14S,17S)-3-hydroxy-3,13-dimethylhexadecahydro-1H-cyclopenta[a]phenanthren-17-yl)ethyl)amino)benzonitrile (C1)

Examples 34 to 37: Synthesis of 1-((S)-2-((3R,5R,8R,9R,10S,13S,14S,17R)-3-hydroxy-3-(methoxymethyl)-13-methylhexadecahydro-1H-cyclopenta[a]phenanthren-17-yl)propyl)-1H-pyrazole-5-carbonitrile (C5) (Example 34), 1-((S)-2-((3R,5R,8R,9R,10S,13S,14S,17R)-3-hydroxy-3-(methoxymethyl)-13-methylhexadecahydro-1H-cyclopenta[a]phenanthren-17-yl)propyl)-1H-pyrazole-3-carbonitrile (C6) (Example 35), 1-((R)-2-((3R,5R,8R,9R,10S,13S,14S,17R)-3-hydroxy-3-(methoxymethyl)-13-methylhexadecahydro-1H-cyclopenta[a]phenanthren-17-yl)propyl)-1H-pyrazole-3-carbonitrile (C7) (Example 36), & 1-((R)-2-((3R,5R,8R,9R,10S,13S,14S,17R)-3-hydroxy-3-(methoxymethyl)-13-methylhexadecahydro-1H-cyclopenta[a]phenanthren-17-yl)propyl)-1H-pyrazole-5-carbonitrile (C8) (Example 37)

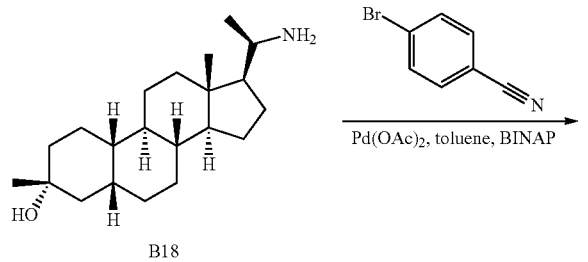

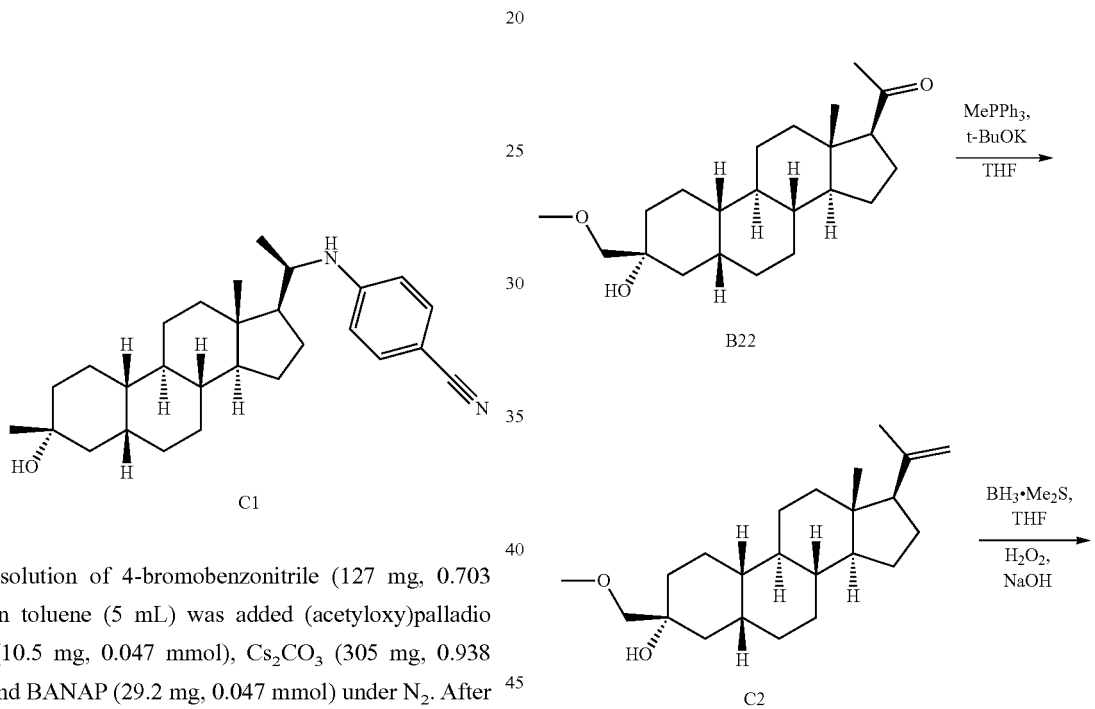

To a solution of 4-bromobenzonitrile (127 mg, 0.703 mmol) in toluene (5 mL) was added (acetyloxy)palladio acetate (10.5 mg, 0.047 mmol), $Cs_2CO_3$ (305 mg, 0.938 mmol) and BANAP (29.2 mg, 0.047 mmol) under $N_2$. After stirring at 25° C. for 20 min, B18 (150 mg, 0.469 mmol) was added and the mixture. After stirring at 110° C. under $N_2$ for 6 h, the reaction was cooled to 25° C. and stirred overnight. The reaction mixture was filtered and concentrated. The residue was purified by HPLC (Column Xtimate C18 150*25 mm*5 um; Condition water (0.225% FA)-ACN Begin B 84; End B 100 Gradient Time (min) 7; 100% B Hold Time (min) 2 FlowRate (ml/min) 25; Injections 5) to afford C1 (80 mg, 41%) as a solid.

$^1$H NMR (400 MHz, $CDCl_3$) δ=7.39 (d, J=8.8 Hz, 2H), 6.47 (d, J=8.8 Hz, 2H), 3.95 (br d, J=8.9 Hz, 1H), 3.51-3.31 (m, 1H), 1.93-1.75 (m, 5H), 1.70-1.53 (m, 2H), 1.49-1.23 (m, 15H), 1.15-0.95 (m, 9H), 0.62 (s, 3H); LCMS purity 99%, MS ESI calcd. for $C_{28}H_{41}N_2O$ [M+H]$^+$ 421, found 421.

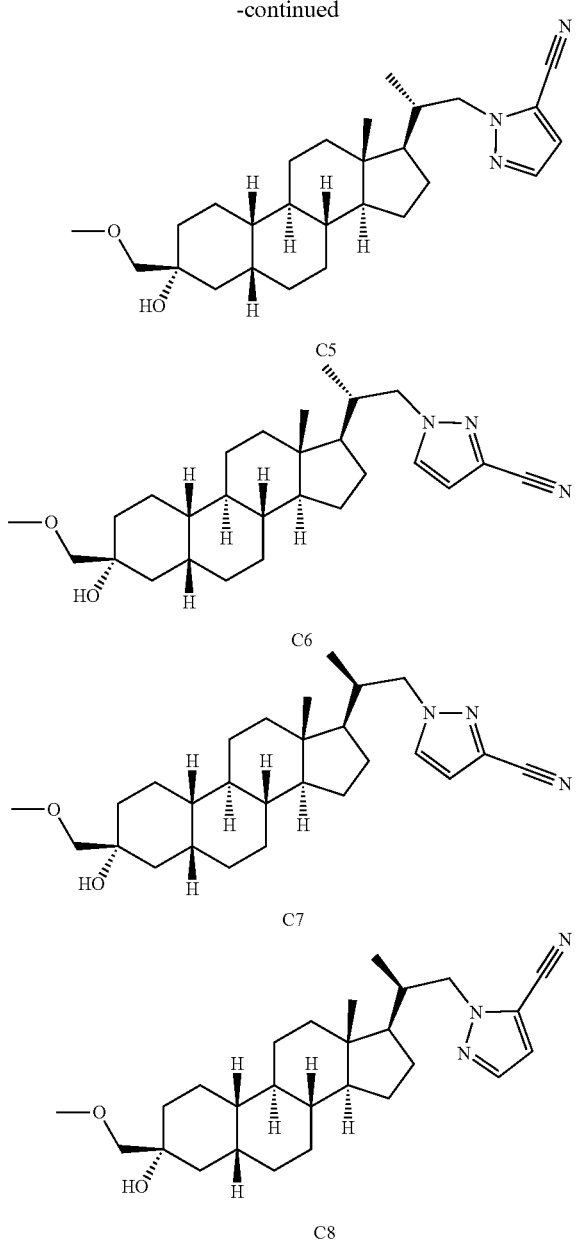

Synthesis of C2

To a solution of MePPh₃Br (12.2 g, 34.0 mmol) in THF (20 mL) was added t-BuOK (2.88 g, 25.8 mmol) at 15° C. After stirring for 1 h at 15° C., B22 (3 g, 8.60 mmol) in THF (20 mL) was added. After stirring at 45° C. for 3 h, the mixture was treated with saturated NH₄Cl (50 mL) and extracted with EtOAc (2×30 mL). The combined organic solution was washed with brine (100 mL), dried over anhydrous Na₂SO₄, filtered and concentrated. The residue was purified by flash column (0~40% of EtOAc in PE) to give C2 (4.5 g, crude) as an oil.

¹H NMR (400 MHz, CDCl₃) δ 4.83 (s, 1H), 4.45 (s, 1H), 3.47-3.31 (m, 5H), 2.61 (s, 1H), 2.05-2.02 (m, 1H), 1.91-1.77 (m, 4H), 1.74 (s, 3H), 1.68-1.52 (m, 5H), 1.49-1.31 (m, 7H), 1.28-1.04 (m, 7H), 0.59-0.50 (n, 3H).

Synthesis of C3

To a solution of C2 (4.5 g, 12.9 mmol) in THF (30 mL) was added BH₃·Me₂S (11.6 mL, 116 mL). After stirring at 15° C. for 1 h, aqueous NaOH (6.16 g, 154 mmol in water) was added at 0° C. followed by hydrogen peroxide (15.4 mL, 10M in water, 154 mmol). After stirring at 78° C. for 3 h, the residue was poured into water (35 mL) and extracted with EtOAc (3×30 mL). The combined organic solution was washed with brine (2×20 mL), dried over anhydrous Na₂SO₄, filtered and concentrated. The residue was triturated from CH₃OH (20 mL) and water (200 mL) to give C3 (4.5 g) as an oil, which was purified by flash column (0~30% of EtOAc in PE) to give C3 (1.7 g, 38%) as a solid.

¹H NMR (400 MHz, CDCl₃) δ 3.77-3.69 (m, 0.6H), 3.62 (dd, J=3.3, 10.5 Hz, 0.4H), 3.40-3.36 (m, 6H), 1.94 (d, 12.5 Hz, 1H), 1.87-1.71 (m, 6H), 1.67-1.52 (m, 4H), 1.49-1.29 (m, 7H), 1.22-0.99 (m, 10H), 0.94 (d, J=6.8 Hz, 2H), 0.66 (s, 3H).

Synthesis of C4

To a solution of C3 (1.3 g, 3.56 mmol) in CH₂Cl₂ (15 mL) at 0° C. was added PPh₃ (1.11 g, 4.27 mmol) and NBS (755 mg, 4.27 mmol). After stirring at 20° C. for 3 h, the reaction mixture was poured into water (20 mL) and extracted with EtOAc (3×30 mL). The combined organic solution was washed with brine (2×20 mL), dried over anhydrous Na₂SO₄, filtered and concentrated. The residue was purified by flash column (0~15% of EtOAc in PE) to give C4 (1.0 g, 59%) as an oil.

¹H NMR (400 MHz, CDCl₃) δ 3.63 (dd, J=3.2, 9.6 Hz, 0.6H), 3.53-3.47 (m, 0.4H), 3.43-3.33 (m, 6H), 1.97-1.87 (m, 1H), 1.86-1.78 (m, 3H), 1.64-1.51 (m, 4H), 1.64-1.51 (m, 4H), 1.48-1.32 (m, 6H), 1.29-1.19 (m, 3H), 1.13-0.95 (m, 8H), 0.67 (s, 3H).

Synthesis of C5, C6, C7 & C8

To a solution of C4 (450 mg, 1.05 mmol) in DMF (10 mL) was added Cs₂CO₃ (682 mg, 2.1 mmol) and 1H-pyrazole-3-carbonitrile (195 mg, 2.1 mmol). After stirring at 85° C. for 12 h, the reaction mixture was diluted with EtOAc (50 mL) and washed by water (20 mL), aq. LiCl (50 mL, 3%) and brine (50 mL), dried over anhydrous Na₂SO₄, filtered and concentrated under vacuum. The residue was purified by flash column (8% of EtOAc in PE) to give C5 & C8 (130 mg) and C6 & C7 (300 mg) as oils.

The mixture of C5 & C8 (130 mg) was purified by SFC (Column: DAICEL CHIRALCEL OJ-H (250 mm*30 mm, 5 um), Condition: 0.1% NH₃·H₂O ETOH, Begin B: 20%, End B: 20%), then concentrated and lyophilized to give C5 (12 mg, Peak 1) and C8 (26 mg, Peak 2), both as solids.

The mixture of C6 & C7 was purified by SFC (Column: DAICEL CHIRALCEL OD-H (250 mm*30 mm, 5 um), Condition: 0.1% NH₃·H₂O ETOH, Begin B: 30%, End B: 30%), then concentrated and lyophilized C6 (83 mg Peak 1) and C7 (97 mg Peak 2), both as solids.

C5: ¹H NMR (400 MHz, CDCl₃) δ 7.57 (d, J=2 Hz, 1H), 6.76 (d, J=2 Hz, 1H), 4.39-4.35 (m, 1H), 3.94-3.88 (m, 1H), 3.42-3.36 (m, 5H), 2.59 (s, 1H), 2.15-1.64 (m, 6H), 1.60-1.52 (m, 8H), 1.49-1.31 (m, 5H), 1.27-0.98 (m, 6H), 0.81 (d, J=6.4 Hz, 3H), 0.71 (s, 3H). LC-ELSD/MS purity 99%, MS ESI calcd. for $C_{27}H_{41}N_3O_2Na$ [M+Na]⁺ 462, found 462. SFC 98.79% de.

C6: ¹H NMR (400 MHz, CDCl₃) δ 7.39 (d, J=2.8 Hz, 1H), 6.65 (d, J=2.4 Hz, 1H), 4.29-4.25 (m, 1H), 3.75-3.69 (m, 1H), 3.42-3.33 (m, 5H), 2.60 (s, 1H), 2.05-1.71 (m, 6H), 1.65-1.55 (m, 6H), 1.48-1.27 (m, 6H), 1.09 (m, 7H), 1.21-0.98 (d, J=6.4 Hz, 3H), 0.70 (s, 3H).

LC-ELSD/MS purity 99%, MS ESI calcd. for $C_{27}H_{41}N_3O_2Na$ [M+Na]⁺ 462, found 462. SFC 100% de.

C7: ¹H NMR (400 MHz, CDCl₃) δ 7.39 (d, J=2.8 Hz, 1H), 6.65 (d, J=2.4 Hz, 1H), 4.53-4.48 (m, 1H), 3.70-3.64 (m, 1H), 3.42-3.36 (m, 5H), 2.61 (s, 1H), 2.16-2.05 (m, 1H), 1.89-1.71 (m, 5H), 1.66-1.52 (m, 7H), 1.49-1.31 (m, 6H), 1.27-1.01 (m, 6H), 0.79 (s, 3H), 0.67 (d, J=6.4 Hz, 3H). LC-ELSD/MS purity 99%, MS ESI calcd. for $C_{27}H_{41}N_3O_2Na$ [M+Na]$^+$ 462, found 462. SFC 100% de.

C8: $^1$H NMR (400 MHz, CDCl$_3$) δ 7.56 (d, J=2 Hz, 1H), 6.77 (d, J=2 Hz, 1H), 4.61-4.57 (m, 1H), 3.93-3.87 (m, 1H), 3.43-3.36 (m, 5H), 2.59 (s, 1H), 2.23-2.14 (m, 1H), 1.93-1.71 (m, 5H), 1.67-1.52 (m, 8H), 1.49-1.31 (m, 5H), 1.28-1.01 (m, 6H), 0.82 (s, 3H), 0.68 (d, J=6.4 Hz, 3H). LC-ELSD/MS purity 99%, MS ESI calcd. for $C_{27}H_{42}N_3O_2$ [M+H]$^+$ 440, found 440. SFC 97% de.

Examples 38 & 39: Synthesis of (3R,5R,8R,9R, 10S,13S,14S,17S)-3,13-dimethyl-17-((R)-1-(methyl (phenyl)amino)ethyl)hexadecahydro-1H-cyclopenta [a]phenanthren-3-ol (C9) & (3R,5R,8R,9R,10S,13S, 14S,17S)-3,13-dimethyl-17-((S)-1-(methyl(phenyl) amino)ethyl)hexadecahydro-1H-cyclopenta[a] phenanthren-3-ol (C10)

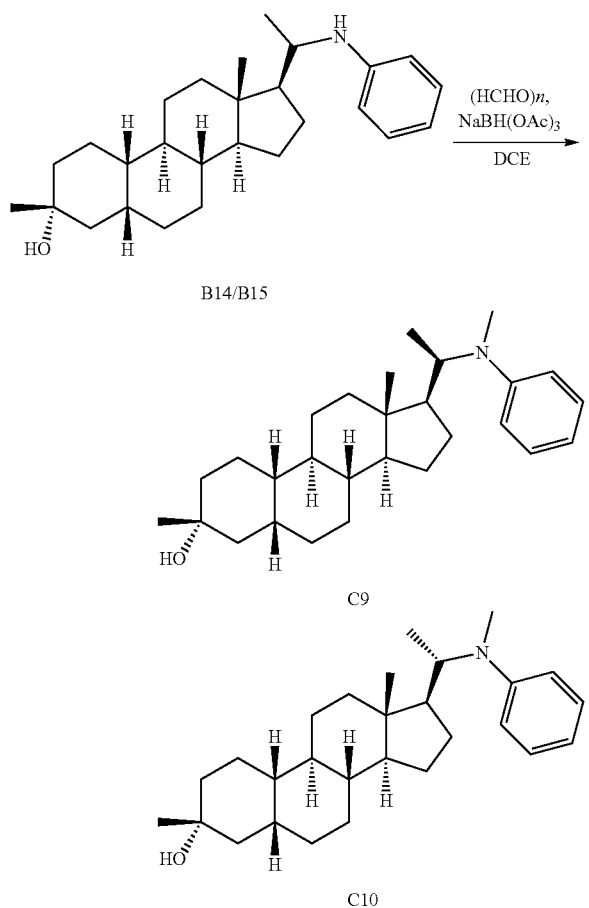

To a solution of B14/B15 (740 mg, 1.87 mmol) and (HCHO)$_n$ (561 mg, 18.7 mmol) in DCE (20 mL) at 25° C. was added NaBH(OAc)$_3$ (470 mg, 7.48 mmol). After stirring at 25° C. for 16 h, additional (HCHO)$_n$ (561 mg, 18.7 mmol) and NaCNBH$_3$ (620 mg) were added. After stirring overnight, the reaction was poured into water (30 mL) and extracted with EtOAc (3×30 mL). The combined organic solution was washed with saturated brine (2×20 mL), dried over anhydrous Na$_2$SO$_4$, filtered and concentrated to give a mixture of C9 & C10 (800 mg) as an oil, which was further purified by prep-HPLC (column: Xbridge 150*30 mm*10 um; Condition water (10 mM NH$_4$HCO$_3$)-ACN from 95% to 100% in 7 min; 100% B Hold Time: 1 min; FlowRat: 25 ml/min) to give mixture of C9 & C10 (260 mg, 0.6346 mmol) as an oil. Purification by SFC (Column: DAICEL CHIRALPAK AD-H (250 mm*30 mm, 5 um), Condition: 0.1% NH$_3$H$_2$O ETOH, Begin B: 40%, End B: 40%, Flow-Rate (ml/min): 50, Injections: 70) to afford C9 (76 mg, Peak 1) and C10 (62 mg, Peak 2) as solids.

C9: $^1$HNMR (400 MHz, CDCl3) δ 7.26-7.20 (m, 2H), 6.79-6.77 (m, 2H), 6.75-6.65 (m, 1H), 3.85-3.77 (m, 1H), 2.65 (s, 3H), 1.81-1.77 (m, 6H), 1.75-1.49 (m, 7H), 1.48-1.31 (m, 6H), 1.30-1.24 (m, 3H), 1.23-1.09 (m, 4H), 1.08-0.96 (m, 5H), 0.64 (s, 3H). LC-ELSD/MS purity 99%, MS ESI calcd. For $C_{28}H_{44}NO$ [M+H]$^+$ 410, found 410. SFC 100% de.

C10: $^1$HNMR (400 MHz, CACl3) δ 7.22-7.18 (m, 2H), 6.75-6.72 (m, 2H), 6.65-6.61 (m, 1H), 3.85-3.79 (m, 1H), 2.69 (s, 3H), 2.00-1.77 (m, 5H), 1.75-1.60 (m, 4H), 1.59-1.50 (m, 7H), 1.49-1.24 (m, 8H), 1.23-1.06 (m, 7H), 0.77 (s, 3H). LC-ELSD/MS purity 99%, MS ESI calcd. For $C_{28}H_{44}NO$ [M+H]$^+$ 410, found 410. SFC 100% de.

Example 40: Synthesis of 2-((R)-1-((3R,5R,8R,9R, 10S,13S,14S,17S)-3-hydroxy-3,13-dimethylhexa-decahydro-1H-cyclopenta[a]phenanthren-17-yl) ethyl)-1-oxoisoindoline-5-carbonitrile (D3)

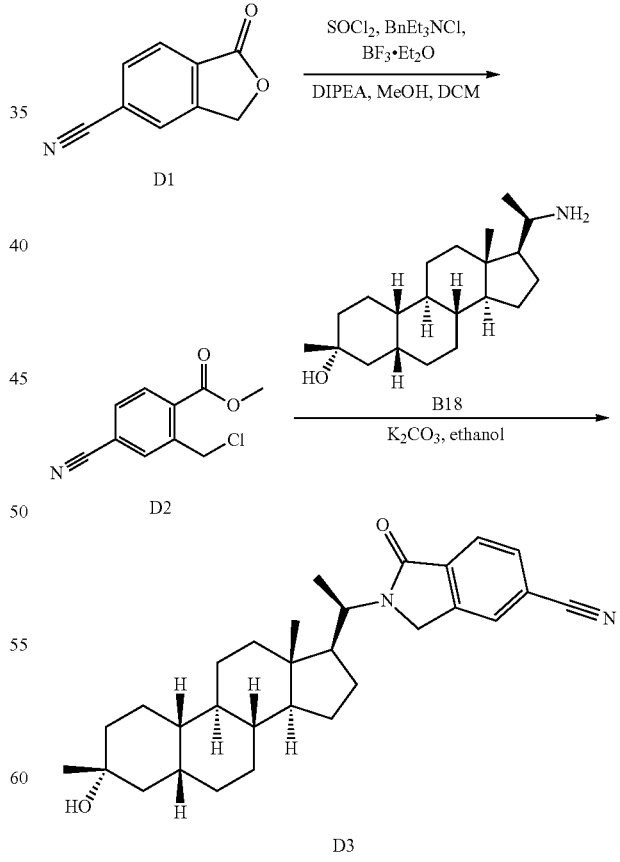

Synthesis of D2

To a mixture of 5-cyanophthalide (1 g, 6.28 mmol) in thionyl chloride (20 mL) was added BF$_3$·Et$_2$O (100 mg, 0.8849 mmol) followed by benzyltriethylammonium chloride (858 mg, 3.77 mmol). After stirring at 90° C. for 72 h, the reaction mixture was cooled and then concentrated in vacuum. The resulting residue was dissolved in dry CH$_2$Cl$_2$ (100 mL), cooled in an ice-EtOH bath for 5 min, and dry MeOH (50 mL) was added dropwise. After adjusting with DIPEA to pH 8, the mixture was concentrated, diluted with EtOAc (300 mL) and filtered. The filtrate was concentrated and purified by silica gel chromatography (3% of ethyl acetate in PE) to afford D2 (1.30 g, 99%) as a solid.

$^1$H NMR (400 MHz, CDCl$_3$) δ$_H$ 8.06 (d, J=8.0 Hz, 1H), 7.90 (d, J=1.0 Hz, 1H), 7.69 (dd, J=1.6, 8.0 Hz, 1H), 5.03 (s, 2H), 3.97 (s, 3H).

Synthesis of D3

A mixture of D2 (392 mg, 1.87 mmol), B18 (300 mg, 0.9388 mmol), and K$_2$CO$_3$ (387 mg, 2.81 mmol) in EtOH (15 mL) was stirred at 25° C. for 1 h. After stirring at 95° C. for 72 h, the reaction mixture was diluted with DCM (100 mL), washed with water (100 mL), brine (100 mL), dried over Na$_2$SO$_4$, filtered and concentrated under vacuum to give a solid, which was purified by prep-HPLC (Column: Xtimate C18 150*25 mm*5 um, Condition: water (0.225% FA)-ACN, Begin B: 82%, End B: 95%, Gradient Time (min): 7, 100% B Hold Time (min): 1, FlowRate (ml/min) 25) to give D3 (110 mg) as a solid. The solid was triturated in hexane (20 mL) to give a solid (87 mg, 20%).

$^1$H NMR (400 MHz, CDCl$_3$) δ$_H$ 7.94 (d, J=8.8 Hz, 1H), 7.78-7.73 (m, 2H), 4.58-4.47 (m, 1H), 4.44-4.34 (m, 2H), 1.90-1.59 (m, 6H), 1.50-1.27 (m, 9H), 1.25-1.20 (m, 8H), 1.19-0.84 (m, 8H), 0.80 (s, 3H); LC-ELSD/MS purity 99%, MS ESI calcd. for C$_{30}$H$_{41}$N$_2$O$_2$ [M+H]$^+$ 461, found 461.

Example 41: Synthesis of 6-(((R)-1-((3R,5R,8R,9R,10S,13S,14S,17S)-3-hydroxy-3-(methoxymethyl)-13-methylhexadecahydro-1H-cyclopenta[a]phenanthren-17-yl)ethyl)amino)nicotinonitrile (E3)

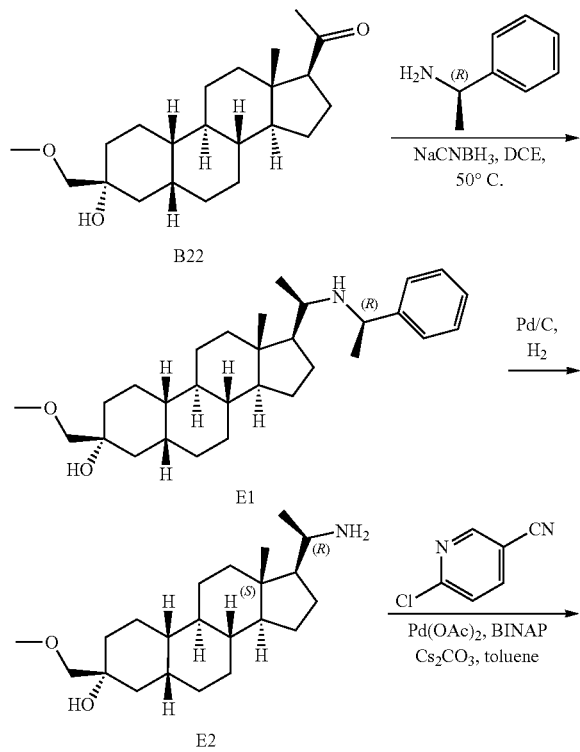

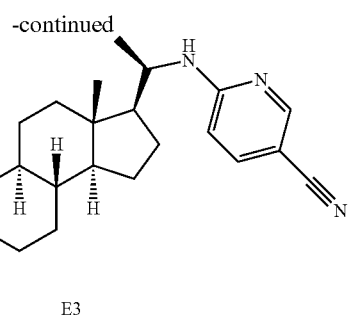

E3

Synthesis of E1

To a solution of B22 (5.00 g, 14.3 mmol) and (1R)-1-phenylethan-1-amine (10.3 g, 85.8 mmol) in DCE (50 mL) was added NaCNBH$_3$ (7.06 g, 114 mmol) at 25° C. After stirring at 50° C. for 16 h, the reaction was quenched with water (50 mL) and extracted with DCM (2×50 mL). The combined organic solution was washed with brine (100 mL), dried over Na$_2$SO$_4$, filtered and concentrated. The residue was purified by flash column (0~20% of EtOAc in PE) to give ST-320-046-009_2 (4.5 g, 69%) as a solid.

$^1$H NMR (400 MHz, CDCl$_3$) δ$_H$ 7.38-7.27 (m, 4H), 7.24-7.16 (m, 1H), 3.89 (q, J=6.3 Hz, 1H), 3.48-3.28 (m, 5H), 2.80-2.66 (m, 1H), 2.56 (s, 1H), 2.23 (br d, J=11.8 Hz, 1H), 1.93-1.55 (m, 9H), 1.40-1.21 (m, 13H), 1.17-1.01 (m, 5H), 0.89 (d, J=6.0 Hz, 3H), 0.78 (s, 3H). % de>99 (by 1H NMR), SFC 100% de.

Synthesis of E2

To a solution of E1 (4.50 g, 9.91 mmol) in EtOH (50 mL) was added Pd—C(dry, 450 mg) under N$_2$. The suspension was degassed under vacuum and purged with H$_2$ for three times. After stirring under H$_2$ (50 psi) at 50° C. for 16 h, the reaction mixture was filtered through a pad of Celite and washed with THF (3×50 mL). The combined filtrate was concentrated to give E2 (3.0 g, 87%) as a solid. The stereochemistry at C20 were assigned based on $^1$H NMR of C21-Me.

$^1$H NMR (400 MHz, CDCl$_3$) δ$_H$ 3.51-3.31 (m, 5H), 2.93-2.72 (m, 1H), 2.01-1.91 (m, 1H), 1.87-1.62 (m, 7H), 1.51-1.03 (m, 19H), 1.00 (d, J=6.0 Hz, 3H), 0.72 (s, 3H).

Synthesis of E3

To a solution of 6-chloropyridine-3-carbonitrile (118 mg, 0.858 mmol) in toluene (2 mL) was added Pd(OAc)$_2$ (9.63 mg, 0.043 mmol), Cs$_2$CO$_3$ (279 mg, 0.858 mmol) and BINAP (26.7 mg, 0.043 mmol) under N$_2$. After stirring at 25° C. for 20 min, E2 (150 mg, 0.429 mmol) was added. After stirring at 110° C. for 32 h, the reaction mixture was filtered and concentrated. The residue was purified by flash column (0~50% of EtOAc in PE) to give a solid. The solid was purified by HPLC (Column Xtimate C18 150*25 mm*5 um; Condition water (0.225% FA)-ACN Begin B 80 End B 100 Gradient Time (min) 7; 100% B Hold Time (min) 1 FlowRate (ml/min) 25) to afford E3 (24 mg, 15% mmol) as a solid.

1H NMR (400 MHz, CDCl$_3$) δ$_H$ 8.34 (d, J=2.0 Hz, 1H), 7.53 (br d, J=7.3 Hz, 1H), 6.29 (d, J=8.8 Hz, 1H), 4.80 (br s, 1H), 3.44-3.22 (m, 5H), 2.63 (br s, 1H), 1.92-1.63 (m, 7H), 1.56-1.27 (m, 10H), 1.26-0.89 (m, 11H), 0.62 (s, 3H). LC-ELSD/MS purity 99%, MS ESI calcd. for C$_{28}$H$_{42}$N$_3$O$_2$ [M+H]$^+$ 452, found 452.

Example 42: Synthesis of N-((R)-1-((3R,5R,8R,9R,10S,13S,14S,17S)-3-(ethoxymethyl)-3-hydroxy-13-methylhexadecahydro-1H-cyclopenta[a]phenanthren-17-yl)ethyl)-2-fluorobenzamide (F9)

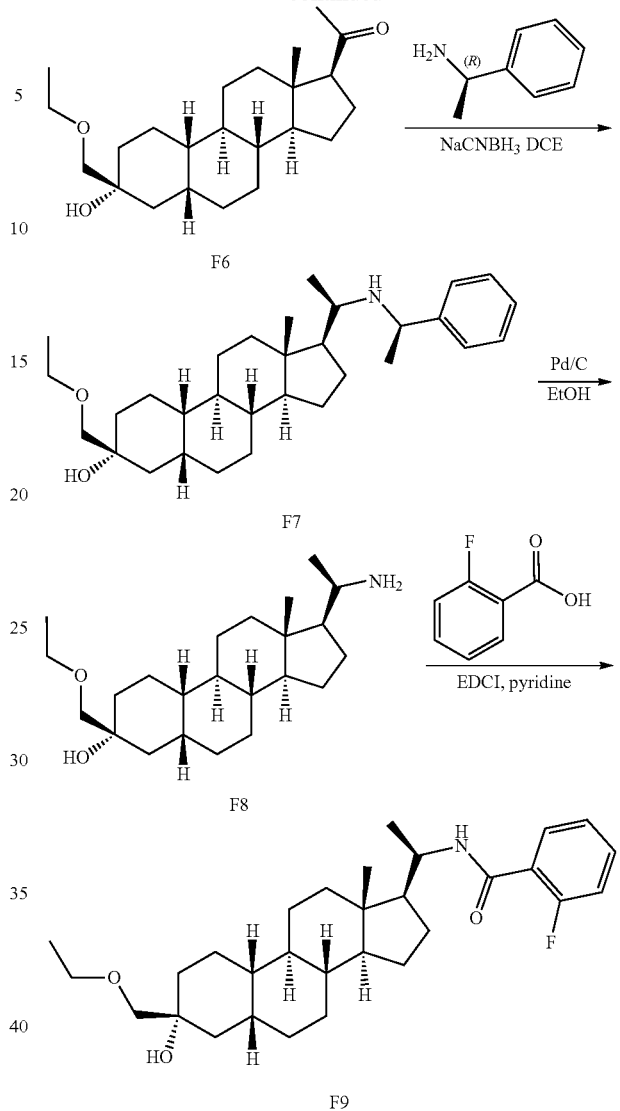

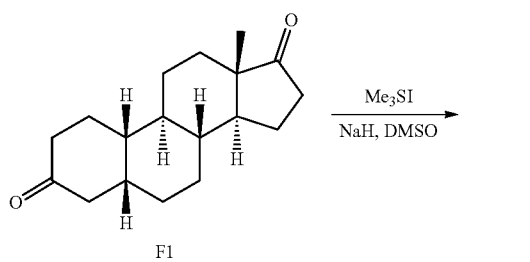

Synthesis of F2

To a stirred solution of trimethylsulfonium iodide (70 g, 343 mmol) in DMSO (200 mL) and THF (100 mL) was added NaH (14 g, 583 mmol) at 0° C. for 2 h under $N_2$. To the mixture was added a solution of estrane-3,17-dione, (5β)-(50 g, 182 mmol) in DMSO (200 mL) and THF (100 mL) at 0° C. After stirring at 25° C. for 16 h, the reaction mixture was poured into $H_2O$ (500 mL) and extracted with EtOAc (2×700 mL). The combined organic solution was washed with water (2×300 mL), brine (300 mL), dried over anhydrous $Na_2SO_4$, filtered and concentrated. The residue was purified by silica gel chromatography (PE/EtOAc=0-9/1 to 4/1) to afford F2 (37 g) as an oil, which was triturated with MeOH (200 mL) at 25° C. to give F2 (27 g, 52%) as a solid.

$^1$H NMR (400 MHz, $CDCl_3$) $\delta_H$ 2.63-2.55 (m, 3H), 2.48-2.40 (m, 1H), 2.27-2.19 (m, 1H), 2.12-1.76 (m, 7H), 1.71-1.64 (m, 2H), 1.53 (m, 8H), 1.18-1.09 (m, 2H), 1.04-0.98 (m, 1H), 0.89-0.87 (m, 3H).

Synthesis of F3

To anhydrous EtOH (200 mL) was added NaH (22.4 g, 933 mmol) at 25° C. in portions. After stirring at 25° C. for 1 h, F2 (27 g, 93.6 mmol) in anhydrous ethanol (100 mL)

was added to the fresh prepared ethoxysodium solution. After stirring at 75° C. for 16 h, the reaction mixture was cooled, quenched with aqueous NH$_4$Cl (200 mL) and extracted with EtOAc (2×300 mL). The combined organic solution was washed with brine (200 mL), dried over anhydrous Na$_2$SO$_4$, filtered, concentrated. The residue was purified by silica gel chromatography (PE/EtOAc=0 to 9/1 to 4/1) to afford F3 (12.2 g, 39%) and F3a (10.4 g, 33%) as oils.

F3: $^1$H NMR (400 MHz, CDCl$_3$) $\delta_H$ 3.53 (q, J=6.8 Hz, 2H), 3.42 (q, J=9.2 Hz, 2H), 2.72 (s, 1H), 2.43 (dd, J=8.2, 19.2 Hz, 1H), 2.13-2.05 (m, 1H), 1.97-1.89 (m, 1H), 1.86-1.74 (m, 5H), 1.66-1.57 (m, 4H), 1.53 (s, 1H), 1.52-1.50 (m, 1H), 1.46-1.27 (m, 7H), 1.20 (t, J=6.8 Hz, 4H), 1.12-1.04 (m, 1H), 0.86 (s, 3H).

Synthesis of F4

To a mixture of EtPPh$_3$Br (39.7 g, 107 mmol) in THF (150 mL) was added t-BuOK (12.0 g, 107 mmol) at 25° C. under N$_2$. After stirring at 25° C. for 30 min, F3 (12 g, 35.8 mmol) in THF (50 mL) was added. After stirring at 75° C. for 16 h, the reaction mixture was diluted with water (200 mL) and extracted with EtOAc (2×300 mL). The combined organic solution was washed with brine (200 mL), dried over anhydrous Na$_2$SO$_4$, filtered and concentrate. The residue was purified by flash column (0~10% of EtOAc in PE) to give F4 (10.4 g, 84%) as an oil.

$^1$H NMR (400 MHz, CDCl$_3$) $\delta_H$ 5.15-5.07 (m, 1H), 3.53 (q, J=6.8 Hz, 2H), 3.43 (q, J=9.2 Hz, 2H), 2.68 (s, 1H), 2.40-2.30 (m, 1H), 2.28-2.13 (m, 2H), 1.87-1.69 (m, 4H), 1.67-1.58 (m, 8H), 1.55-1.35 (m, 7H), 1.28-1.23 (m, 2H), 1.20 (t, J=7.2 Hz, 4H), 1.17-1.06 (m, 3H), 0.87 (s, 1H).

Synthesis of F5

To a solution of F4 (10.4 g, 30.0 mmol) in THF (200 mL) was added 9-BBN dimer (14.6 g, 60.0 mmol) under N$_2$. After stirring at 60° C. under N$_2$ for 1 h, the mixture was cooled to 25° C. and ethanol (30 mL, 30.0 mmol) and NaOH (60.0 mL, 5 M, 300 mmol) were added. After turning clear, H$_2$O$_2$ (30.0 mL, 10 M, 300 mmol) was added dropwise at 25° C. followed by saturated aqueous Na$_2$S$_2$O$_3$ (100 mL). After stirring at 25° C. for another 1 h, the mixture was poured into water (150 mL) and extracted with EtOAc (2×200 mL). The combined organic solution was washed with brine (150 mL), dried over anhydrous Na$_2$SO$_4$, filtered and concentrated. The residue was triturated from MeOH/H$_2$O (100 mL/100 mL) at 25° C. to give F5 (11.6 g) as a solid.

$^1$H NMR (400 MHz, CDCl$_3$) $\delta_H$ 3.52 (q, J=6.8 Hz, 2H), 3.42 (q, J=9.2 Hz, 2H), 1.92-1.74 (m, 7H), 1.66-1.55 (m, 8H), 1.45-1.34 (m, 7H), 1.25 (t, J=6.8 Hz, 3H), 1.23-1.19 (m, 6H), 1.16-1.08 (m, 4H), 0.65 (s, 1H).

Synthesis of F6

To a solution of F5 (11.6 g, 31.8 mmol) in DCM (150 mL) was added silica gel (17 g) and PCC (17.0 g, 79.5 mmol) at 25° C. After stirring at 25° C. for 1 h, the mixture was filtered through a pad of celite and washed with DCM (2×100 mL), filtered and concentrated. The residue was purified by flash column (0~25% of EtOAc in PE) to give F6 (8.5 g, 74%) as an oil.

$^1$H NMR (400 MHz, CDCl$_3$) $\delta_H$ 3.55-3.49 (m, 2H), 3.46-3.37 (m, 2H), 2.79-2.68 (m, 1H), 2.53 (t, J=8.8 Hz, 1H), 2.16-2.11 (m, 1H), 2.10 (s, 3H), 2.02-1.96 (m, 1H), 1.85-1.56 (m, 9H), 1.49-1.35 (m, 7H), 1.27-1.18 (m, 7H), 1.15-1.01 (m, 3H), 0.60 (s, 1H).

Synthesis of F7

To a solution of F6 (12.8 g, 35.3 mmol) and (1R)-1-phenylethan-1-amine (25.5 g, 211 mmol) in DCE (100 mL) at 25° C. was added NaCNBH$_3$ (17.7 g, 282 mmol). After at 50° C. for 16 h, the reaction was diluted with water (300 mL) and extracted with DCM (2×250 mL). The combined organic solution was washed with brine (200 mL), dried over Na$_2$SO$_4$, filtered and concentrated. The residue was triturated from MeOH/H$_2$O (200 mL/200 mL) and purified by flash column (0~10% of EtOAc in PE) to give F7 (8.8 g, 73%) as colorless oil.

$^1$H NMR (400 MHz, CDCl$_3$) $\delta$ 7.36-7.27 (m, 4H), 7.24-7.18 (m, 1H), 3.93-3.85 (m, 1H), 3.57-3.49 (m, 2H), 3.48-3.37 (m, 2H), 2.69 (s, 2H), 2.26-2.18 (m, 1H), 1.89-1.70 (m, 4H), 1.69-1.55 (m, 5H), 1.45-1.31 (m, 6H), 1.28 (d, J=6.4 Hz, 3H), 1.26-1.19 (m, 7H), 1.14-1.01 (m, 5H), 0.89 (d, J=6.0 Hz, 3H), 0.78 (s, 3H). % de>99 (by $^1$H NMR). SFC 100% de.

Synthesis of F8

To a solution of F7 (8.7 g, 18.6 mmol) in EtOH (100 mL) was added Pd—C(dry, 900 mg) and one drop of NH$_3$H$_2$O. After stirring under H$_2$ (50 psi) at 50° C. for 72 h, the reaction mixture was filtered through a pad of Celite and washed with EtOH (3×150 mL). The filtrate was concentrated to give F8 (6.7 g, 99%) as oil. The stereochemistry at C20 were assigned based on $^1$H NMR of C21-Me.

$^1$H NMR (400 MHz, CDCl$_3$) $\delta_H$ 3.56-3.49 (m, 2H), 3.46-3.37 (m, 2H), 2.88-2.79 (m, 1H), 2.00-1.92 (m, 1H), 1.85-1.69 (m, 5H), 1.67-1.54 (m, 8H), 1.49-1.28 (m, 8H), 1.20 (t, J=7.2 Hz, 4H), 1.13-1.04 (m, 4H), 1.01 (d, J=6.0 Hz, 3H), 0.72 (s, 3H).

Synthesis of F9

To a solution of 2-fluorobenzoic acid (77.0 mg, 0.550 mmol) in pyridine (3 mL) at 25° C. was added EDCI (105 mg, 0.550 mmol). After stirring at 25° C. for 30 min. F8 (100 mg, 0.275 mmol) was added. After stirring at 50° C. for 16 h, the mixture was diluted with water (20 mL) and extracted with EtOAc (2×30 mL). The combined organic solution was washed with brine (20 mL), dried over anhydrous Na$_2$SO$_4$, filtered and concentrated. The residue was purified by HPLC (Column: Xtimate C18 150×25 mm; 5 um; Condition: water (0.225% FA)-ACN; Gradient: from 70% to 90% of B in 7 min and hold 100% for 1 min; Flow rate: 25 mL/min) to give F9 (47 mg, 35%) as solid.

$^1$H NMR (400 MHz, CDCl$_3$) $\delta_H$ 8.16-8.10 (m, 1H), 7.49-7.42 (m, 1H), 7.29-7.26 (m, 1H), 7.14-7.07 (m, 1H), 6.68-6.57 (m, 1H), 4.28-4.13 (m, 1H), 3.55-3.49 (m, 2H), 3.45-3.36 (m, 2H), 2.70 (s, 1H), 1.89-1.60 (m, 7H), 1.54-1.23 (m, 10H), 1.22-1.17 (m, 7H), 1.16-0.88 (m, 6H), 0.73 (s, 3H). $^{19}$F NMR (376 MHz, CDCl$_3$) $\delta_F$ −113.67. LC-ELSD/MS purity 99%, MS ESI calcd. for C$_{30}$H$_{45}$FNO$_3$ [M+H]$^+$ 486, found 486.

Example 43: Synthesis of 2-((R)-1-((3R,5R,8R,9R, 10S,13S,14S,17S)-3-(ethoxymethyl)-3-hydroxy-13-methylhexadecahydro-1H-cyclopenta[a] phenanthren-17-yl)ethyl)-1-oxoisoindoline-5-carbonitrile (F10)

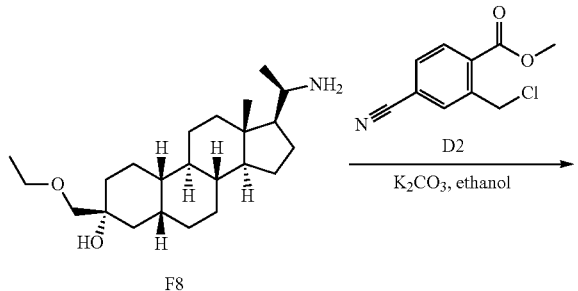

F8

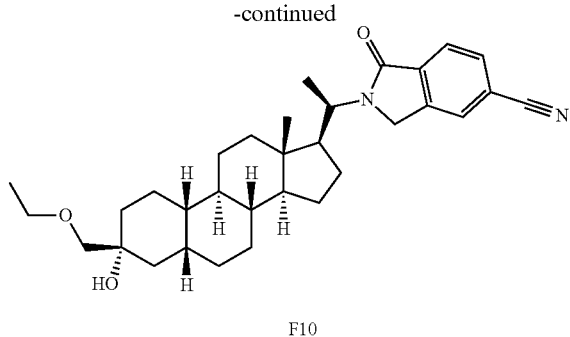

F10

A mixture of D2 (184 mg, 0.88 mmol), F8 (160 mg, 0.44 mmol), and K$_2$CO$_3$ (182 mg, 1.32 mmol) in EtOH (15 mL) was stirred at 25° C. for 1 h. After stirring at 95° C. for 16 h, the reaction mixture was diluted with DCM (100 mL), washed with water (100 mL), brine (100 mL), dried over Na$_2$SO$_4$, filtered and concentrated under vacuum to give a solid. The residue was purified by prep-HPLC (Condition: water (0.225% FA)-ACN, Begin B: 80, End B: 100, Gradient Time (min): 7, 100% B Hold Time (min): 0, FlowRate (ml/min): 25) to give F10 (11 mg, 5%) as a solid.

$^1$H NMR (400 MHz, CDCl$_3$) δ$_H$ 7.94 (d, 1H), 7.81-7.68 (m, 2H), 4.60-4.45 (m, 1H), 4.39 (d, J=2.0 Hz, 2H), 3.61-3.46 (m, 2H), 3.44-3.29 (m, 2H), 2.71 (s, 1H), 1.88-1.55 (m, 7H), 1.53-1.36 (m, 7H), 1.34-1.25 (m, 3H), 1.24-1.14 (m, 9H), 1.14-0.82 (m, 4H), 0.80 (s, 3H). LC-ELSD/MS purity 99%, MS ESI calcd. for C$_{32}$H$_{45}$N$_2$O$_3$ [M+H]$^+$ 505, found 505.

Example 44: Synthesis of 2-((R)-1-((3R,5R,8R,9R, 10S,13S,14S,17S)-3-hydroxy-3-(methoxymethyl)- 13-methylhexadecahydro-1H-cyclopenta[a] phenanthren-17-yl)ethyl)-1-oxoisoindoline-5- carbonitrile (F11)

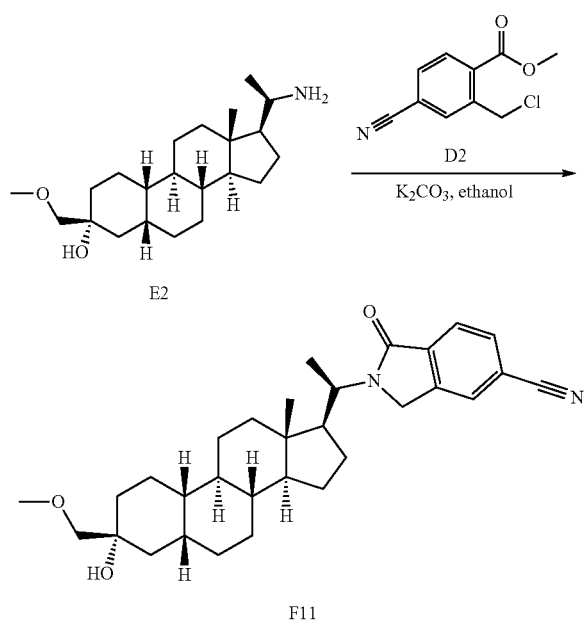

A mixture of D2 (345 mg, 1.65 mmol), E2 (300 mg, 0.825 mmol), and K$_2$CO$_3$ (340 mg, 2.47 mmol) in EtOH (15 mL) was stirred at 25° C. for 1 h. After stirring at 95° C. for 72 h, the reaction mixture was diluted with DCM (100 mL), washed with water (100 mL), brine (100 mL), dried over Na$_2$SO$_4$, filtered and concentrated under vacuum to give F11 (500 mg) as a solid, which was purified by prep-HPLC (Condition: water (0.225% FA)-ACN, Begin B: 69, End B: 99, Gradient Time (min): 7, 100% B Hold Time (min): 1, FlowRate (ml/min): 25) to give F11 (95 mg, 19%) as a solid.

$^1$H NMR (400 MHz, CDCl$_3$) δ$_H$ 7.93 (m, 1H), 7.81-7.71 (m, 2H), 4.63-4.33 (m, 3H), 3.45-3.26 (m, 5H), 2.59 (s, 1H), 1.90-1.65 (m, 6H), 1.57-1.35 (m, 7H), 1.34-1.27 (m, 2H), 1.24-1.09 (m, 8H), 1.08-0.84 (m, 4H), 0.79 (s, 3H). LC-ELSD/MS purity 99%, MS ESI calcd. for C$_{31}$H$_{43}$N$_2$O$_3$ [M+H]$^+$ 491, found 491.

Example 45: Synthesis of 2-((R)-1-((3R,5R,8R,9R, 10S,13S,14S,17S)-3-hydroxy-3,13-dimethylhexa- decahydro-1H-cyclopenta[a]phenanthren-17-yl) ethyl)-1-oxo-1,2,3,4-tetrahydroisoquinoline-6- carbonitrile (F13)

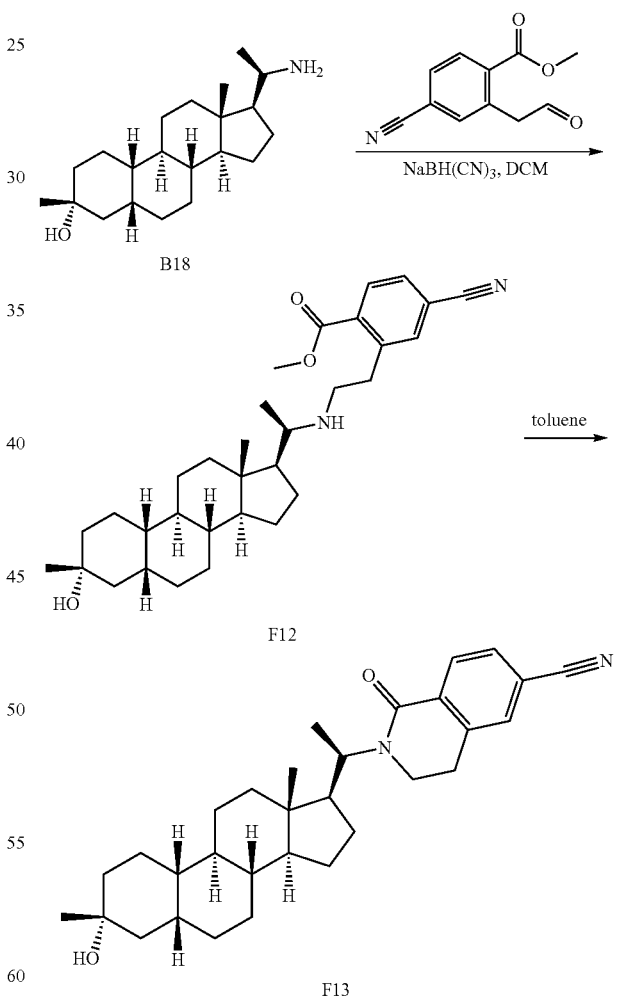

Synthesis of F12

To a solution of B18 (300 mg, 0.938 mmol) and benzoic acid, 4-cyano-2-(2-oxoethyl)-, methyl ester (379 mg, 1.87 mmol) in DCE (6 mL) and CH$_3$OH (6 mL) was added NaCNBH$_3$ (176 mg, 2.81 mmol) and acetic acid (168 mg, 2.81 mmol) at 25° C. under N₂. After stirring at rt for 16 h, the mixture was poured into water (20 mL) and extracted with DCM (3×20 mL). The combined organic solution was washed with brine (2×20 mL), dried over anhydrous Na₂SO₄, filtered and concentrated to give F12 (300 mg) as an oil, used directly for the next step.

Synthesis of F13

A solution of F12 (300 mg, 0.592 mmol) in toluene (20 mL) was stirred at 110° C. for 16 h. The reaction mixture was concentrated and purified by HPLC (Column Xtimate C18 150*25 mm*5 um Condition water (0.225% FA)-ACN Begin B 80 End B 100 Gradient Time (min) 7 100% B Hold Time (min) 2; FlowRate (ml/min) 25) to afford F13 (72 mg, 26%) as a solid.

1H NMR (400 MHz, CDCl₃) δ$_H$ 8.19 (d, J=8.1 Hz, 1H), 7.62 (d, J=8.0 Hz, 1H), 7.48 (s, 1H), 4.93 (br s, 1H), 3.72-3.31 (m, 2H), 3.19-3.01 (m, 1H), 2.91 (br d, J=16.1 Hz, 1H), 1.87-1.62 (m, 7H), 1.54-1.21 (m, 14H), 1.18-0.88 (m, 9H), 0.79 (s, 3H). LC-ELSD/MS purity 99%, MS ESI calcd. for $C_{31}H_{43}N_2O_2$ [M+H]⁺ 475, found 475.

Example 46: Synthesis of 2-((R)-1-((3R,5R,8R,9R, 10S,13S,14S,17S)-3-(ethoxymethyl)-3-hydroxy-13-methylhexadecahydro-1H-cyclopenta[a]phenanthren-17-yl)ethyl)-1-oxo-1,2,3,4-tetrahydroisoquinoline-6-carbonitrile (15)

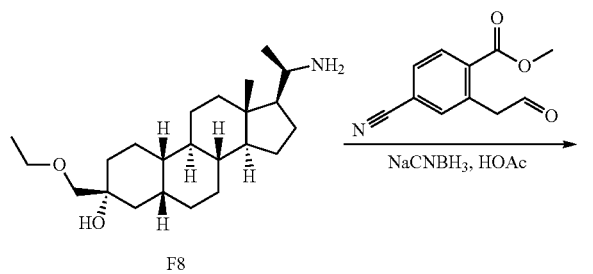

F8

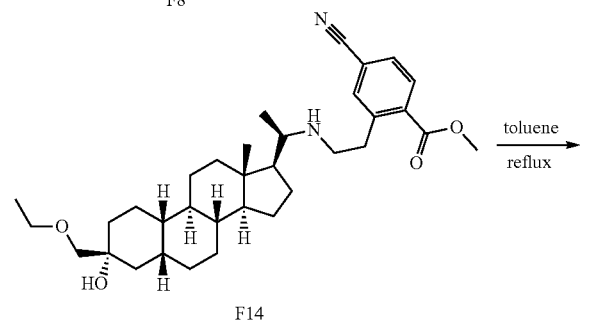

F14

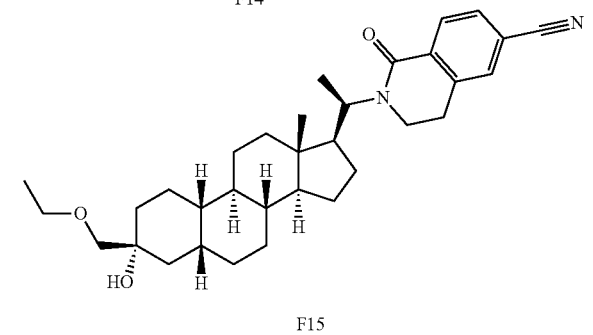

F15

Synthesis of F14

To a solution of F8 (100 mg, 1.23 mmol) and benzoic acid, 4-cyano-2-(2-oxoethyl)-, methyl ester (250 mg, 1.23 mmol) in CH₃OH/DCE (2/2 mL) was added acetic acid (88.2 mg, 1.47 mmol) and NaBH₃CN (92.3 mg, 1.47 mmol) in one portion at 25° C. under N₂. After stirring at rt for 16 h, the reaction was combined with another batch prepared from 100 mg of F8 and poured into aqueous NaHCO₃ (20 mL). The aqueous solution was extracted with DCM (2×50 mL). The combined organic solution was washed with brine (2×30 mL), dried over anhydrous Na₂SO₄, filtered and concentrated to give F14 (600 mg) as an oil. LC-ELSD/MS purity 82%, MS ESI calcd. for $C_{30}H_{51}N_2O_4$ [M+H]⁺ 551, found 551.

Synthesis of F15

A solution of F14 (580 mg, 1.05 mmol) in toluene (20 mL) was refluxed for 16 h. The reaction mixture was concentrated and purified by HPLC (Column Xtimate C18 150*25 mm*5 um Condition water (0.225% FA)-ACN Begin B 90 End B 100 Gradient Time (min) 7 100% B Hold Time (min) 0; FlowRate (ml/min) 30) to afford F15 (42 mg, 8%) as a solid.

¹H NMR (400 MHz, CDCl₃) δ$_H$ 8.19 (d, J=7.6 Hz, 1H), 7.62 (d, J=7.6 Hz, 1H), 7.48 (s, 1H), 5.00-4.90 (m, 1H), 3.59-3.30 (m, 6H), 3.17-3.02 (m, 1H), 2.98-2.91 (m, 1H), 0.76-0.70 (m, 1H), 1.83-1.70 (m, 4H), 1.68-1.54 (m, 8H), 1.43-1.24 (m, 7H), 1.25-1.15 (m, 4H), 1.15-1.07 (m, 6H), 1.15-0.90 (m, 1H), 0.79 (s, 3H). LC-ELSD/MS purity 99%, MS ESI calcd. for C33H47N2O3 [M+H]⁺ 519, found 519.

Examples 47 & 48: Synthesis of (3R,5R,8R,9R, 10S,13R,14S,17R)-3-(methoxymethyl)-13-methyl-17-(2-(5-methyl-2H-tetrazol-2-yl)ethyl)hexadecahydro-1H-cyclopenta[a]phenanthren-3-ol (G5) & (3R,5R,8R,9R,10S,13R,14S,17R)-3-(methoxymethyl)-13-methyl-17-(2-(5-methyl-1H-tetrazol-1-yl)ethyl)hexadecahydro-1H-cyclopenta[a]phenanthren-3-ol (G6)

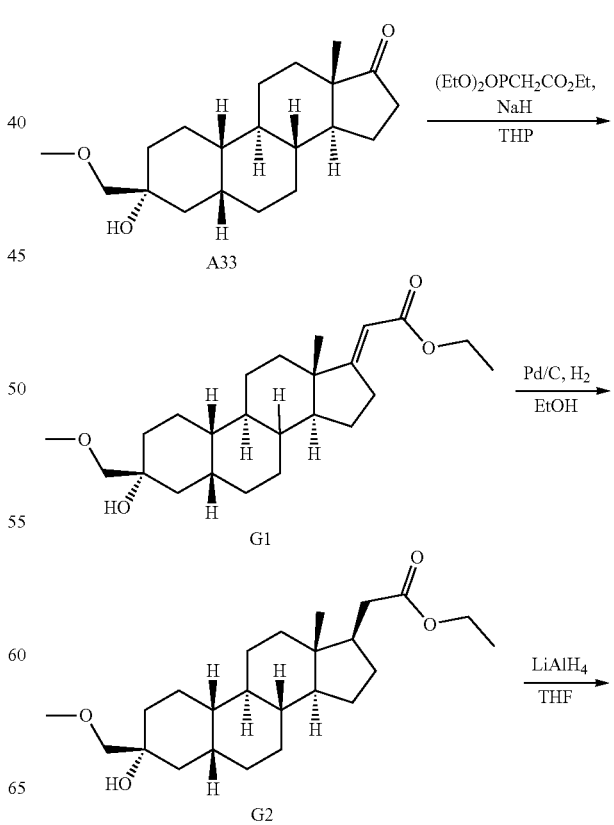

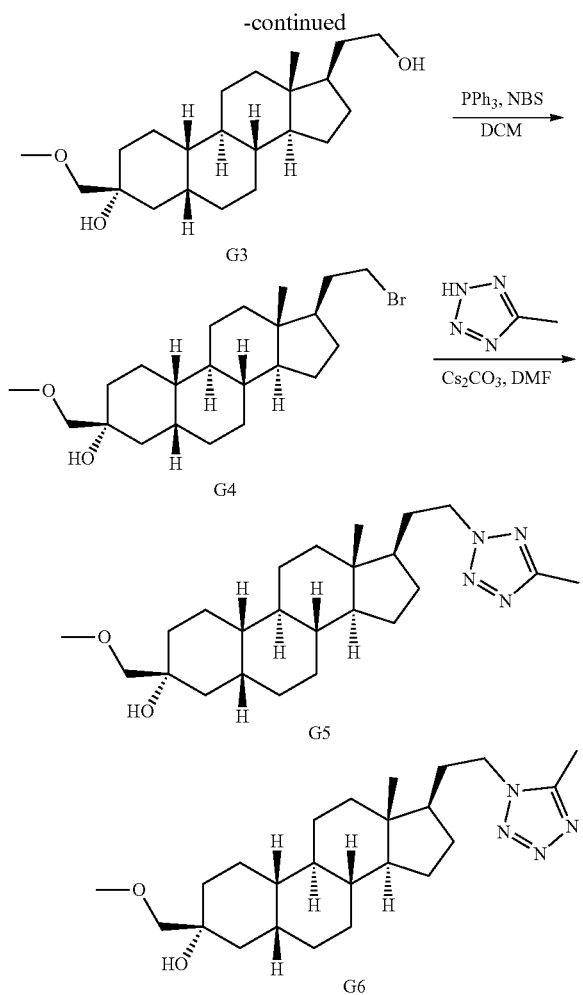

Synthesis of G1

To a stirred solution of sodium hydride (1.23 g, 30.8 mmol, 60% in oil) in THF (75 mL) and was added ethyl 2-(diethoxyphosphanyl) (7.32 g, 32.7 mmol) at 40° C. After stirring for 30 min under $N_2$, A33 (3.0 g, 9.4 mmol) was added. After stirring at 65° C. for 4 h, the mixture was cooled and concentrated under reduced pressure at 40° C. The mixture was poured into ice-water (100 mL) and extracted with EtOAc (3×100 mL). The combined organic solution was washed with saturated brine (2×100 mL), dried over anhydrous $Na_2SO_4$, filtered and concentrated. The residue was purified by flash column (0~20% of EtOAc in PE) to give G1 (2.9 g, 79%) as an oil.

$^1$H NMR (400 MHz, CDCl$_3$) $\delta_H$ 5.51 (t, J=2.4 Hz, 1H), 4.19-4.05 (m, 2H), 3.43-3.29 (m, 5H), 2.85-2.78 (m, 2H), 2.60 (s, 1H), 1.98-1.75 (m, 7H), 1.68-1.00 (m, 15H), 0.88-0.84 (m, 2H), 0.83-0.78 (m, 3H)

Synthesis of G2

To a solution of G1 (2.9 g, 7.42 mmol) in EtOH (50 mL) was added Pd—C(wet, 10%, 3 g) under $N_2$. The suspension was degassed under vacuum and purged with $H_2$ for three times. The mixture was stirred under $H_2$ (15 psi) at 25° C. for 12 h to give a suspension. The reaction mixture was filtered through a pad of Celite and washed with EtOH (3×50 mL). The filtrate was concentrated to give G2 (2.7 g), used directly for the next step.

LC-ELSD/MS purity 99%, MS ESI calcd. for $C_{24}H_{39}O_3$ [M−H$_2$O+H]$^+$ 375, found 375.

Synthesis of G3

To a solution of G2 (2.7 g, 6.9 mmol) in THF (50 mL) was added lithium aluminum hydride (390 mg, 10.3 mmol) in one portion at 20° C. under $N_2$. After stirring at 20° C. for 12 h, $H_2O$ (2 mL) was added and 1 M HCl was added until pH to 5. The aqueous solution was extracted with EtOAc (3×10 mL). The combined organic solution was washed with saturated brine (2×20 mL), dried over anhydrous $Na_2SO_4$, filtered and concentrated. The residue was purified by flash column (0~50% of EtOAc in PE) to give G3 (2.2 g, 92%) as a solid.

$^1$H NMR (400 MHz, CDCl$_3$) $\delta_H$ 3.73-3.57 (m, 2H), 3.43-3.35 (m, 5H), 2.59 (s, 1H), 1.90-1.71 (m, 7H), 1.52-1.19 (m, 13H), 1.18-0.97 (m, 7H), 0.59 (s, 3H).

Synthesis of G4

To a solution of G3 (2.2 g, 6.3 mmol) in CH$_2$Cl$_2$ (20 mL) at 0° C. were added PPh$_3$ (1.9 g, 7.5 mmol) and NBS (1.3 g, 7.5 mmol). After stirring at rt for 4 h, the reaction mixture was diluted with water (100 mL) and extracted with EtOAc (3×30 mL). The combined organic solution was washed with saturated brine (2×20 mL), dried over anhydrous $Na_2SO_4$, filtered and concentrated. The residue was purified by flash column (0~15% of EtOAc in PE) to give G4 (1.1 g, 30%) as an oil.

$^1$H NMR (400 MHz, CDCl$_3$) $\delta_H$ 3.51-3.26 (m, 7H), 2.58 (s, 1H), 2.01-1.53 (m, 12H), 1.49-0.94 (m, 14H), 0.59 (s, 3H).

Synthesis of G5 & G6

To a solution of G4 (250 mg, 0.6 mmol) in DMF (5 mL) was added Cs$_2$CO$_3$ (390 mg, 1.2 mmol) and 5-methyl-2H-1,2,3,4-tetrazole (100 mg, 1.2 mmol). After stirring at 85° C. for 12 h, the reaction mixture was diluted with water (100 mL) and extracted with EtOAc (3×20 mL). The combined organic solution was washed with brine (2×50 mL), dried over Na$_2$SO$_4$, filtered, concentrated and purified by flash column (0~30% of EtOAc in DCM) to give G5 (90 mg, 45%) as a solid and G6 (40 mg, 20%) as a solid.

G5: $^1$H NMR (400 MHz, CDCl$_3$) $\delta_H$ 4.61-4.44 (m, 2H), 3.44-3.36 (m, 5H), 2.56 (s, 1H), 2.53 (s, 3H), 2.16-2.07 (m, 1H), 1.90-1.61 (m, 9H), 1.50-0.97 (m, 16H), 0.61 (s, 3H). The structure was confirmed by HMBC. LC-ELSD/MS purity 99%, MS ESI calcd. for $C_{24}H_{39}N_4O$ [M−H$_2$O+H]$^+$ 399, found 399.

G6: $^1$H NMR (400 MHz, CDCl$_3$) $\delta_H$ 4.22 (t, J=8.0 Hz, 2H), 3.45-3.34 (m, 5H), 2.64-2.55 (m, 4H), 2.06-1.96 (m, 1H), 1.87-1.62 (m, 9H), 1.51-1.01 (m, 16H), 0.60 (s, 3H). The structure was confirmed by HMBC. LC-ELSD/MS purity 99%, MS ESI calcd. for $C_{24}H_{39}N_4O$ [M−H$_2$O+H]$^+$ 399, found 399.

Examples 49 & 50: Synthesis of (3R,5R,8R,9R, 10S,13R,14S,17R)-17-(2-(2H-1,2,3-triazol-2-yl)ethyl)-3-(methoxymethyl)-13-methylhexadecahydro-1H-cyclopenta[a]phenanthren-3-ol (G7) & (3R,5R, 8R,9R,10S,13R,14S,17R)-17-(2-(1H-1,2,3-triazol-1-yl)ethyl)-3-(methoxymethyl)-13-methylhexadecahydro-1H-cyclopenta[a]phenanthren-3-ol (G8)

Examples 51 & 52: Synthesis of 1-((R)-2-((3R,5R, 8R,9R,10S,13S,14S,17R)-3-hydroxy-3,13-dimethylhexadecahydro-1H-cyclopenta[a]phenanthren-17-yl)propyl)-1H-pyrazole-4-carbonitrile (H7) & 1-((S)-2-((3R,5R,8R,9R,10S,13S,14S,17R)-3-hydroxy-3,13-dimethylhexadecahydro-1H-cyclopenta[a]phenanthren-17-yl)propyl)-1H-pyrazole-4-carbonitrile (H8)

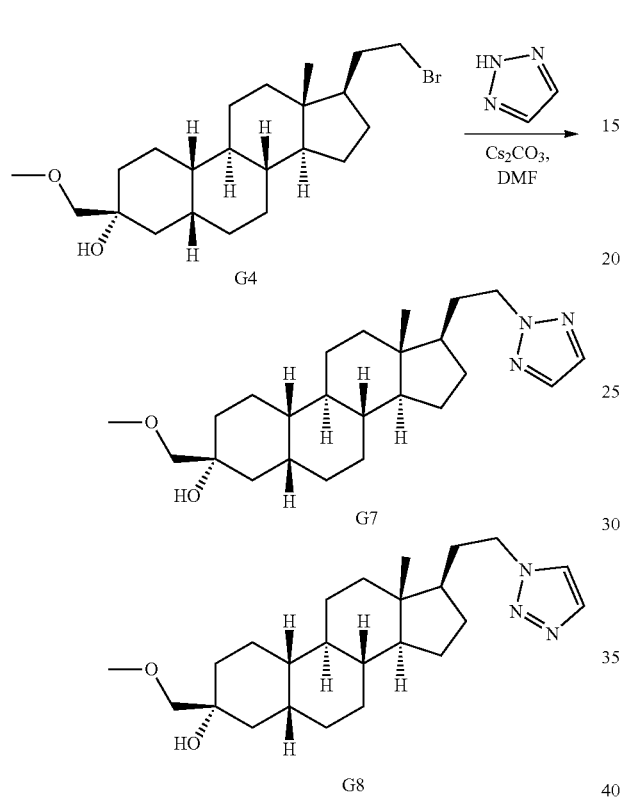

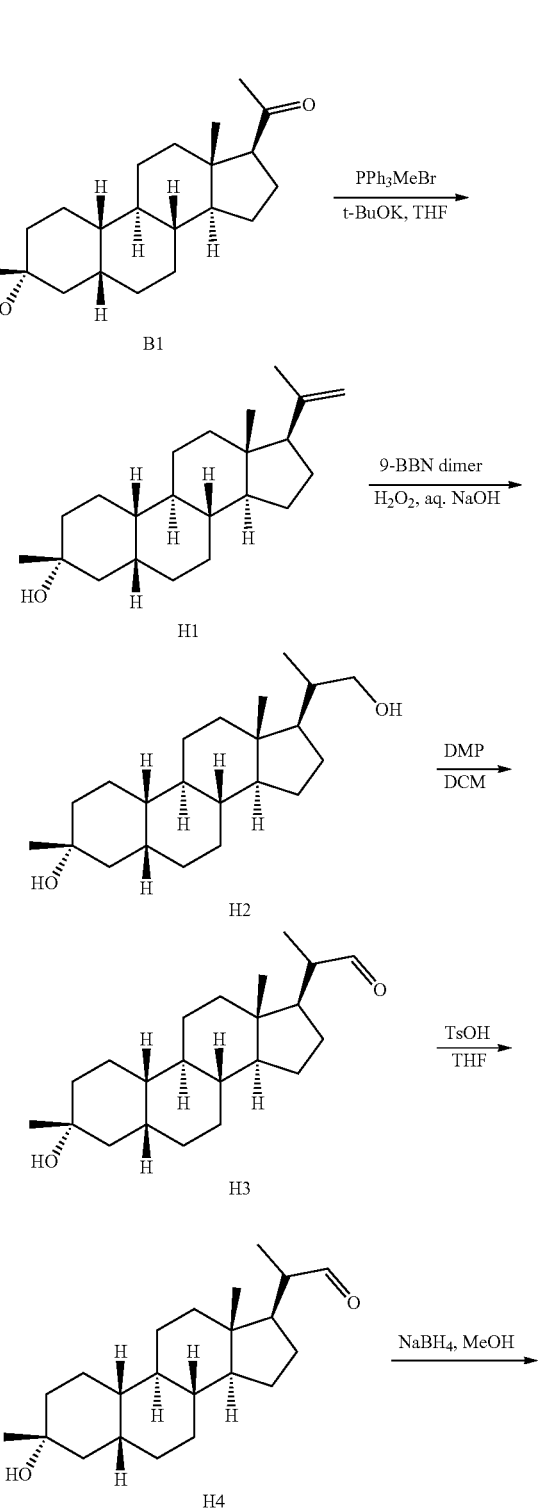

To a solution of G4 (200 mg, 0.48 mmol) in DMF (5 mL) was added $Cs_2CO_3$ (315 mg, 0.97 mmol) and 2H-1,2,3-triazole (66.8 mg, 0.97 mmol). After stirring 85° C. for 12 h, the mixture was diluted with water (100 mL) and extracted with EtOAc (3×20 mL). The combined organic solution was washed with brine (2×50 mL), dried over anhydrous $Na_2SO_4$, filtered and concentrated, and purified by flash column (0~30% of EtOAc in DCM) to give G7 (82 mg, 41%) as a solid and G8 (40 mg, 32%, Rf=0.20, PE/EtOAc=3/1) as a solid.

G7: $^1$H NMR (400 MHz, $CDCl_3$) $\delta_H$ 7.58 (s, 2H), 4.52-4.35 (m, 2H), 3.42-3.35 (m, 5H), 2.58 (s, 1H), 2.16-2.05 (m, 1H), 1.85-1.68 (m, 6H), 1.59-0.98 (m, 19H), 0.60 (s, 3H). LC-ELSD/MS purity 99%, MS ESI calcd. for $C_{24}H_{40}N_3O_2$ $[M+H]^+$ 402, found 402.

G8: $^1$H NMR (400 MHz, $CDCl_3$) $\delta_H$ 7.70 (s, 1H), 7.53 (s, 1H), 4.46-4.27 (m, 2H), 3.45-3.29 (m, 5H), 2.57 (s, 1H), 2.09-2.00 (m, 1H), 1.88-1.80 (m, 2H), 1.69-1.59 (m, 8H), 1.42-1.01 (m, 15H), 0.60 (s, 3H). LC-ELSD/MS purity 99%, MS ESI calcd. for $C_{24}H_{40}N_3O_2$ $[M+H]^+$ 402, found 402.

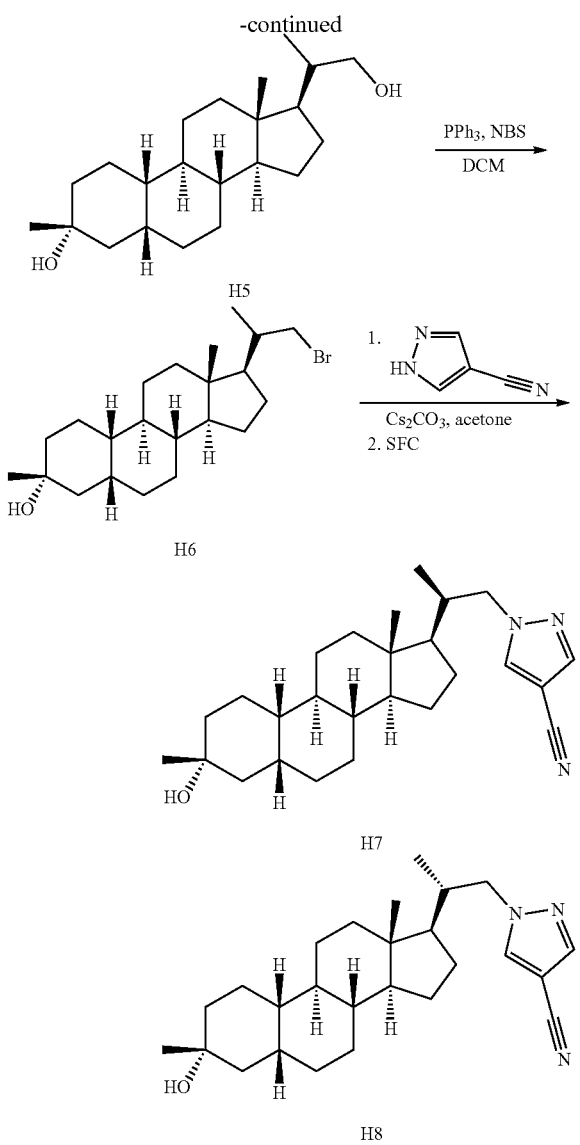

Synthesis of H₁

To a mixture of MePPh₃Br (16.6 g, 46.7 mmol) in THF (150 mL) was added t-BuOK (5.24 g, 46.7 mmol) at 25° C. under N₂. After stirring at 50° C. for 30 min, B1 (5 g, 15.6 mmol) was added. After stirring at 50° C. for 2 h, the reaction mixture was quenched with 10% NH₄Cl aqueous (300 mL) at 25° C. and extracted with EtOAc (2×200 mL). The combined organic solution was concentrated and triturated with MeOH/H₂O (1:1, 300 mL) to give H1 (4.8 g, 97.3%) as a solid.

¹H NMR (400 MHz, CDCl₃) δ$_H$ 4.84 (s, 1H), 4.70 (s, 1H), 2.03 (t, J=9.2 Hz, 1H), 1.90-1.78 (m, 4H), 1.75 (s, 3H), 1.72-1.59 (m, 5H), 1.50-1.24 (m, 12H), 1.23-0.98 (m, 6H), 0.57 (s, 3H).

Synthesis of H₂

To a solution of H1 (4.8 g, 15.1 mmol) in THF (100 mL) was added 9-BBN dimer (7.3 g, 30.2 mmol). After stirring at 45° C. for 16 h, ethanol (10 mL) at 15° C., followed by NaOH aqueous (30.1 mL, 5.0 M, 151 mmol) were added at 0° C. Hydrogen peroxide (15 mL, 10 M, 151 mmol) was then added dropwise at 0° C. After stirring at 78° C. for 1 h, the mixture as cooled to 15° C. and water (150 mL) was added. After stirring at 25° C. for 20 min, the solid was filtered and washed with water (2×10 mL), dried under vacuum to give H₂ (4.3 g).

Note: The ratio of 21-α-Me and 21-β-Me is 4:1 based on H-NMR.

¹H NMR (400 MHz, CDCl₃) δ$_H$ 3.77-3.59 (m, 1H), 3.48-3.30 (m, 1H), 1.96 (td, J=3.2, 12.4 Hz, 1H), 1.89-1.76 (m, 4H), 1.58-1.34 (m, 8H), 1.33-1.14 (m, 12H), 1.09-0.93 (m, 8H), 0.68 (s, 3H).

Synthesis of H₃

To a solution of H2 (2 g, 5.97 mmol) in DCM (20 mL) was added DMP (5.04 g, 11.9 mmol) in portions. After stirring at 25° C. for 30 min, the mixture was quenched by saturated NaHCO₃ aqueous (200 mL), The aqueous solution was extracted with DCM (2×150 mL). The combined organic solution was washed with saturated Na₂S₂O₃ aqueous (200 mL), brine (200 mL) dried over Na₂SO₄, filtered and concentrated. The residue was purified by flash column (0~20% of EtOAc in PE) to give H3 (1 g, 50.5%) as an oil.

Note: The ratio of 21-α-Me and 21-β-Me is 4:1 based on H-NMR.

¹H NMR (400 MHz, CDCl₃) δ$_H$ 9.56 (d, J=3.2 Hz, 0.8H), 9.52 (d, J=3.2 Hz, 0.2H), 2.59-2.17 (m, 2H), 2.04 (s, 1H), 1.94-1.80 (m, 5H), 1.68-1.60 (m, 4H), 1.50-1.27 (m, 12H), 1.14-1.03 (m, 8H), 0.71-0.66 (m, 3H).

Synthesis of H₄

To a solution of H3 (1 g, 3 mmol) in THF (20 mL) was added TsOH (1.03 g, 6 mmol). After stirring at 25° C. for 16 h, the mixture was added H₂O (100 mL) and extracted with EtOAc (2×100 mL). The combined organic solution was washed with saturated NaHCO₃ (200 mL), brine (200 mL), dried over anhydrous Na₂SO₄, filtered and concentrated to give H₄ (1 g), which was used as is.

Note: The ratio of 21-α-Me and 21-β-Me is 2:3 based on H-NMR.

¹H NMR (400 MHz, CDCl₃) δ$_H$ 9.56 (d, J=3.2 Hz, 0.4H), 9.52 (d, J=4.8 Hz, 0.6H), 2.59-2.18 (m, 2H), 1.94-1.80 (m, 5H), 1.68-1.61 (m, 5H), 1.46-1.24 (m, 12H), 1.12-1.02 (m, 8H), 0.71-0.66 (m, 3H).

Synthesis of H₅

To a solution of H4 (1 g) in MeOH (10 mL) was added NaBH₄ (226 mg, 6 mmol). After stirring at 25° C. for 16 h, the reaction mixture was quenched by saturated NH₄Cl (150 mL) and extracted with EtOAc (3×100 mL). The combined organic solution was washed with brine (200 mL), dried over anhydrous Na₂SO₄, filtered and concentrated to give H5 (1 g) as a solid, which was used as is.

¹H NMR (400 MHz, CDCl₃) δ$_H$ 3.79-3.58 (m, 1H), 3.49-3.33 (m, 1H), 1.96-1.78 (m, 5H), 1.55-1.35 (m, 9H), 1.33-1.17 (m, 11H), 1.09-0.92 (m, 8H), 0.68 (s, 3H).

Synthesis of H₆

To a solution of H5 (1 g, 2.98 mmol) in DCM (10 mL) at 0° C. was added PPh₃ (936 mg, 3.57 mmol) and NBS (635 mg, 3.57 mmol). After stirring at 25° C. for 1 h, the reaction mixture was poured into water (50 mL) and extracted with DCM (3×50 mL). The combined organic solution was washed with saturated brine (100 mL), dried over anhydrous Na₂SO₄, filtered and concentrated. The residue was purified by flash column (0~10% of EtOAc in PE) to give H6 (640 mg, 54.2%) as an oil.

¹H NMR (400 MHz, CDCl₃) δ$_H$ 3.63 (dd, J=2.8, 9.6 Hz, 0.6H), 3.50 (dd, J=2.8, 9.6 Hz, 0.4H), 3.41-3.29 (m, 1H), 1.95-1.75 (m, 5H), 1.69-1.60 (m, 4H), 1.45-1.23 (m, 14H), 1.11-0.96 (m, 9H), 0.69-0.67 (m, 1H).

Synthesis of H7 & H8

To a solution of H6 (640 mg, 1.61 mmol) in acetone (10 mL) was added Cs₂CO₃ (1.58 g, 4.83 mmol) and 1H-pyrazole-4-carbonitrile (224 mg, 2.41 mmol). After stirring at 55° C. for 12 h, the reaction mixture was added water (100 mL) and extracted with EtOAc (2×80 mL). The combined organic solution dried over Na$_2$SO$_4$, filtered, concentrated and purified by flash column (0~25% of EtOAc in PE) to give a mixture of H7 & H8 (500 mg) as oil. The diastereomers (350 mg, 0.85 mmol) were separated by SFC (Column: DAICEL CHIRALPAKIC AS-H (250 mm*30 mm, 5 um); Condition: 0.1% NH$_3$H$_2$O ETOH; Begin B: 30%; End B: 30%; FlowRate (ml/min): 65) to give H7 (156 mg, 44.6%) and H8 (120 mg, 34.3%), both as solids.

H7: $^1$H NMR (400 MHz, CDCl$_3$) $\delta_H$ 7.80 (s, 1H), 7.75 (s, 1H), 4.49 (dd, J=4.4, 13.6 Hz, 1H), 3.66 (dd, J=10.8, 13.2 Hz, 1H), 2.17-2.04 (m, 1H), 1.91-1.73 (m, 5H), 1.70-1.60 (m, 3H), 1.50-1.25 (m, 13H), 1.22-1.00 (m, 7H), 0.79 (s, 3H), 0.68 (d, J=6.4 Hz, 3H). LC-ELSD/MS purity 99%, analytic SFC: 100% de, MS ESI calcd. for C$_{26}$H$_{39}$N$_3$O [M+H]$^+$ 410.3, found 410.3.

H8: $^1$H NMR (400 MHz, CDCl$_3$) $\delta_H$ 7.79 (s, 1H), 7.75 (s, 1H), 4.25 (dd, J=4.0, 13.2 Hz, 1H), 3.72 (dd, J=9.6, 13.6 Hz, 1H), 2.07-1.77 (m, 6H), 1.70-1.60 (m, 3H), 1.50-1.25 (m, 13H), 1.21-1.00 (m, 7H), 0.81 (d, J=6.4 Hz, 3H), 0.71 (s, 3H). LC-ELSD/MS purity 99%, analytic SFC: 97.08% de, MS ESI calcd. for C$_{26}$H$_{39}$N$_3$O [M+H]$^+$ 410.3, found 410.3.

Examples 53-56: Synthesis of (3R,5S,8R,9R,10S, 13S,14S,17R)-3-(methoxymethyl)-13-methyl-17-((R)-1-(5-methyl-2H-tetrazol-2-yl)propan-2-yl)hexadecahydro-1H-cyclopenta[a]phenanthren-3-ol (H20), (3R,5S,8R,9R,10S,13S,14S,17R)-3-(methoxymethyl)-13-methyl-17-((S)-1-(5-methyl-2H-tetrazol-2-yl)propan-2-yl)hexadecahydro-1H-cyclopenta[a]phenanthren-3-ol (H21), (3R,5S,8R, 9R,10S,13S,14S,17R)-3-(methoxymethyl)-13-methyl-17-((R)-1-(5-methyl-1H-tetrazol-1-yl) propan-2-yl)hexadecahydro-1H-cyclopenta[a] phenanthren-3-ol (H22) & (3R,5S,8R,9R,10S,13S, 14S,17R)-3-(methoxymethyl)-13-methyl-17-((S)-1-(5-methyl-1H-tetrazol-1-yl)propan-2-yl) hexadecahydro-1H-cyclopenta[a]phenanthren-3-ol (H23)

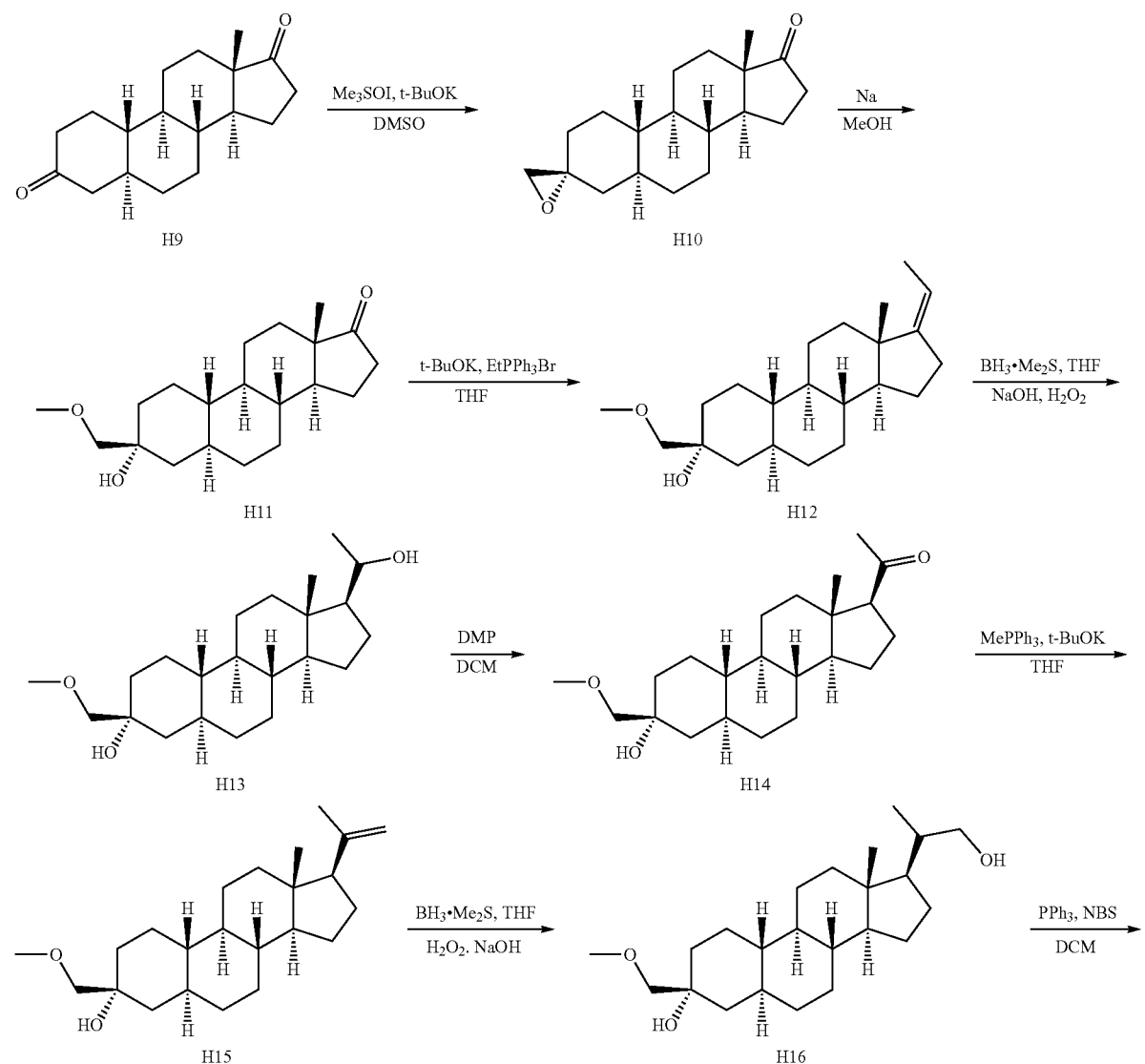

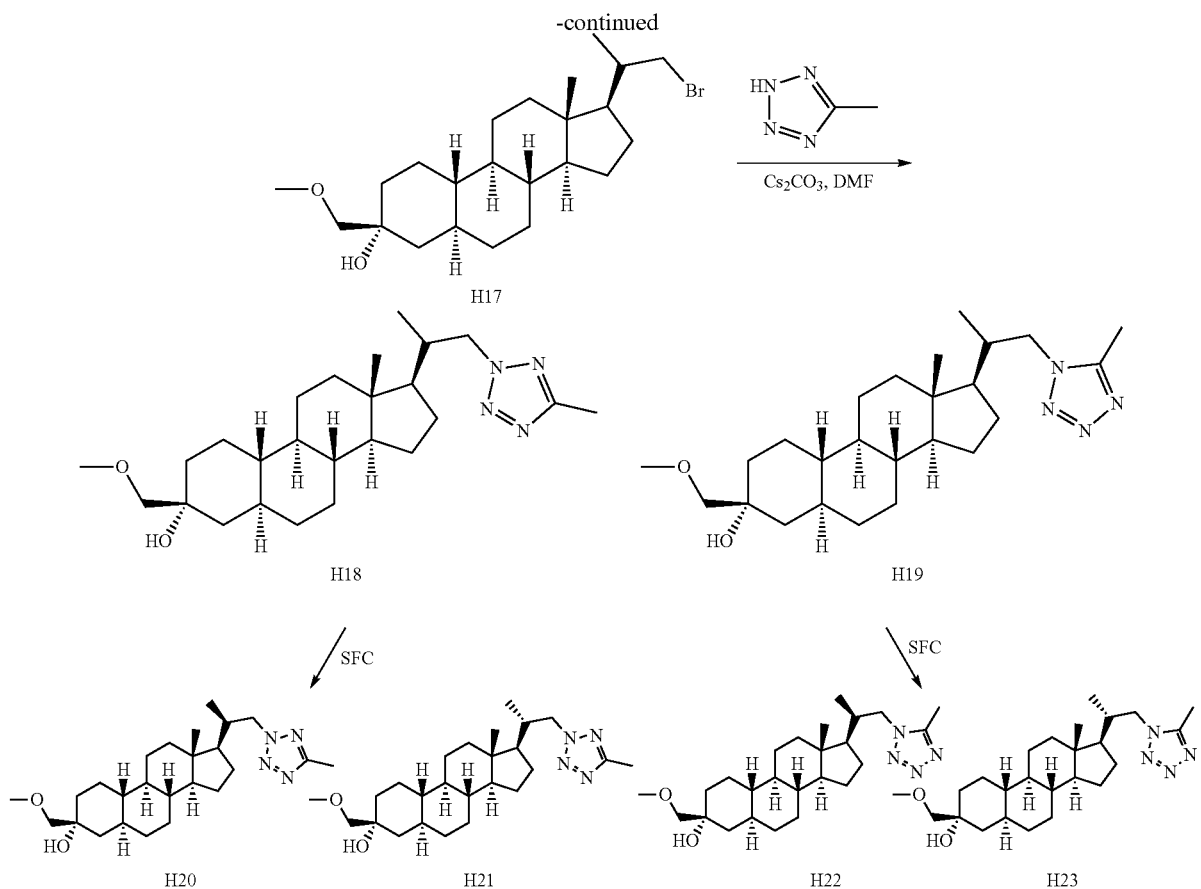

Synthesis of H10

To a solution of trimethylsulfoxonium iodide (4.2 g, 19.1 mmol) in DMSO (50 mL) was added t-BuOK (2.14 g, 19.1 mmol). After stirring at 60° C. for 1 h under $N_2$, (5α)-estrane-3,17-dione (5 g, 18.2 mmol, CAS: 5696-58-2) was added. After stirring at 25° C. for 2 h, the reaction was diluted with water (200 mL) and extracted with EtOAc (2×200 mL). The combined organic solution was washed with brine (300 mL), dried over anhydrous $Na_2SO_4$, filtered, and concentrated in vacuum to afford H10 (5 g, 95.4%) as a solid $^1$H NMR (400 MHz, CDCl$_3$) $\delta_H$ 2.67-2.61 (m, 2H), 2.44 (dd, J=8.4, 19.2 Hz, 1H), 2.13-2.03 (m, 1H), 2.00-1.74 (m, 6H), 1.70-1.61 (m, 2H), 1.55-1.40 (m, 2H), 1.38-0.99 (m, 9H), 0.92-0.71 (m, 5H).

Synthesis of H11

To anhydrous MeOH (100 mL) was added Na (1.19 g, 51.9 mmol) at 25° C. in portions. After 30 min, H10 (5 g, 17.3 mmol) was added. After stirring at 60° C. for 16 h, the reaction was diluted with water (200 ml) and concentrated to remove most of the solvent. The mixture was extracted with EtOAc (2×200 mL). The combined organic solution was washed with brine (2×100 mL), dried over anhydrous $Na_2SO_4$, filtered, concentrated to give H11 (5.5 g, 99.2%) as a solid.

$^1$H NMR (400 MHz, CDCl$_3$) $\delta_H$ 3.38 (s, 3H), 3.18 (s, 2H), 2.43 (dd, J=8.4, 19.2 Hz, 1H), 2.12-2.03 (m, 1H), 1.96-1.72 (m, 6H), 1.64-1.45 (m, 5H), 1.36-1.19 (m, 5H), 1.15-0.97 (m, 4H), 0.87 (s, 3H), 0.80-0.68 (m, 2H).

Synthesis of H12

To a mixture of EtPPh$_3$Br (19.0 g, 51.3 mmol) in THF (150 mL) was added t-BuOK (5.75 g, 51.3 mmol) at 25° C. under $N_2$. After stirring at 50° C. for 30 min, H11 (5.5 g, 17.1 mmol) was added in portions below 50° C. After stirring at 40° C. for 2 h, the reaction mixture was quenched with 10% NH$_4$Cl aqueous (300 mL) at 25° C. and extracted with EtOAc (2×200 mL). The combined organic solution was concentrated and purified by trituration with MeOH/H$_2$O (1:1, 150 mL) to give H12 (5 g, 88.0%) as a solid.

$^1$H NMR (400 MHz, CDCl$_3$) $\delta_H$ 5.15-5.06 (m, 1H), 3.38 (s, 3H), 3.18 (s, 2H), 2.42-2.30 (m, 1H), 2.26-2.13 (m, 2H), 2.07-1.97 (m, 1H), 1.86-1.63 (m, 8H), 1.58-1.36 (m, 4H), 1.27-0.95 (m, 9H), 0.87 (s, 3H), 0.78-0.65 (m, 2H).

Synthesis of H13

To a solution of H12 (5 g, 15.0 mmol) in THF (100 mL) was added BH$_3$·Me$_2$S (7.5 mL, 10 M, 75.0 mmol). After stirring at 25° C. for 2 h, EtOH (10 mL) followed by NaOH (30 mL, 5 M) and H$_2$O$_2$ (15 mL, 10 M) were added dropwise. After stirring at 60° C. for 1 h, the mixture was quenched by Na$_2$S$_2$O$_3$ (400 mL, 10%) and extracted with EtOAc (2×300 mL). The combined organic solution was washed with brine (300 mL), dried over Na$_2$SO$_4$, filtered and concentrated to give H13 (5.25 g) as a solid.

$^1$H NMR (400 MHz, CDCl$_3$) $\delta_H$ 3.86-3.78 (m, 1H), 3.73-3.61 (m, 1H), 3.36 (s, 3H), 3.16 (s, 2H), 2.17-1.96 (m, 1H), 1.89-1.66 (m, 7H), 1.52-1.34 (m, 5H), 1.19 (d, J=6.4 Hz, 3H), 1.16-0.83 (m, 10H), 0.81-0.56 (m, 5H).

Synthesis of H14

To a solution of H13 (5.25 g, 14.9 mmol) in DCM (100 mL) was added DMP (12.6 g, 29.8 mmol) in portions. After stirring at 25° C. for 1 h, the mixture was quenched by saturated NaHCO₃ aqueous (300 mL) and extracted with DCM (2×250 mL). The combined organic solution was washed with saturated Na₂S₂O₃ aqueous (400 mL), brine (300 mL) dried over Na₂SO₄, filtered and concentrated. The residue was purified by flash column (0~15% of EtOAc in PE) to give H14 (4 g, 77.0%) as a solid.

¹H NMR (400 MHz, CDCl₃) δ$_H$ 3.38 (s, 3H), 3.18 (s, 2H), 2.53 (t, J=8.8 Hz, 1H), 2.19-2.12 (m, 1H), 2.11 (s, 3H), 2.02-1.94 (m, 1H), 1.87-1.68 (m, 4H), 1.64-1.54 (m, 4H), 1.48-1.35 (m, 2H), 1.29-0.92 (m, 10H), 0.81-0.64 (m, 2H), 0.61 (s, 3H).

Synthesis of H15

To a mixture of MePPh₃Br (12.2 g, 34.2 mmol) in THF (100 mL) was added t-BuOK (3.83 g, 34.2 mmol) at 25° C. under N₂. After stirring at 50° C. for 30 min, H14 (4 g, 11.4 mmol) was added. After stirring at 50° C. for 3 h, the reaction mixture was quenched with 10% NH₄Cl aqueous (300 mL) at 25° C. and extracted with EtOAc (2×300 mL). The combined organic solution was concentrated. The residue was purified by trituration with MeOH/H₂O (1:1, 200 mL) to give H₁₅ (3.5 g, 88.6%) as a solid.

¹H NMR (400 MHz, CDCl₃) δ$_H$ 4.84 (s, 1H), 4.69 (s, 1H), 3.38 (s, 3H), 3.18 (s, 2H), 2.08-2.01 (m, 1H), 1.85-1.68 (m, 9H), 1.62-1.34 (m, 4H), 1.26-0.94 (m, 11H), 0.75-0.63 (m, 2H), 0.56 (s, 3H).

Synthesis of H16

To a solution of H15 (3.5 g, 10.0 mmol) in THF (80 mL) was added BH₃·Me₂S (5.0 mL, 10 M, 50.0 mmol). After stirring at 25° C. for 1 h, EtOH (10 mL) followed by NaOH (20 mL, 5 M) and H₂O₂ (10 mL, 10 M) were added dropwise. After stirring at 60° C. for 1 h, the mixture was extracted with EtOAc (2×200 mL), washed with Na₂S₂O₃ (300 mL, 10%), brine (150 mL), dried over Na₂SO₄, filtered and concentrated. The residue was purified by flash column (0~30% of EtOAc in PE) to H16 (3.1 g, 85.1%) as a solid.

¹H NMR (400 MHz, CDCl₃) δ$_H$. 3.71-3.53 (m, 1H), 3.43-3.24 (m, 1H), 3.32 (s, 3H), 3.11 (s, 2H), 1.98-1.85 (m, 1H), 1.81-1.61 (m, 5H), 1.54-1.45 (m, 4H), 1.39-1.04 (m, 8H), 1.02-0.73 (m, 10H), 0.88-0.55 (m, 5H).

Synthesis of H17

To a solution of H16 (600 mg, 1.64 mmol) in DCM (8 mL) at 0° C. was added PPh₃ (514 mg, 1.96 mmol) and NBS (348 mg, 1.96 mmol). After stirring at 25° C. for 2 h, the reaction mixture was diluted with water (100 mL) and extracted with DCM (2×80 mL). The combined organic solution was washed with brine (50 mL), dried over anhydrous Na₂SO₄, filtered and concentrated. The residue was purified by flash column (0~15% of EtOAc in PE) to give H17 (700 mg, 99.8%) as an oil.

¹H NMR (400 MHz, CDCl₃) δ$_H$ 3.68-3.47 (m, 1H), 3.41-3.30 (m, 4H), 3.18 (s, 2H), 2.03-1.58 (m, 10H), 1.45-1.11 (m, 7H), 1.11-0.88 (m, 10H), 0.75-0.62 (m, 5H).

Synthesis of H18 & H19

To a solution of H17 (300 mg, 0.71 mmol) in DMF (8 mL) was added Cs₂CO₃ (684 mg, 2.1 mmol) and 5-methyl-2H-1,2,3,4-tetrazole (88.2 mg, 1.05 mmol). After stirring at 85° C. for 4 h, the reaction mixture was diluted with water (200 mL) and extracted with EtOAc (2×150 mL). The combined organic solution was dried over Na₂SO₄, filtered and concentrated. The residue was purified by flash column (5~60% of EtOAc in PE) to give H18 (200 mg, 66.2%) and H19 (90 mg, 29.8%, Rf=0.1 (PE:EtOAc=3:1)) both as solids.

H18: ¹H NMR (400 MHz, CDCl₃) δ$_H$ 4.82-4.46 (m, 1H), 4.33-4.18 (m, 1H), 3.38 (s, 3H), 3.18 (s, 2H), 2.53 (s, 3H), 2.29-2.07 (m, 1H), 2.04-1.59 (m, 9H), 1.55-1.19 (m, 6H), 1.18-0.88 (m, 8H), 0.88-0.80 (m, 3H), 0.77-0.65 (m, 5H).

H19: ¹H NMR (400 MHz, CDCl₃) δ$_H$ 4.63-4.20 (m, 1H), 3.93-3.78 (m, 1H), 3.39 (s, 3H), 3.18 (s, 2H), 2.54 (s, 3H), 2.18-1.84 (m, 4H), 1.82-1.60 (m, 6H), 1.47-1.36 (m, 2H), 1.30-0.91 (m, 12H), 0.85-0.79 (m, 3H), 0.77-0.64 (m, 5H).

Synthesis of H20 & H21

H18 (200 mg, 0.46 mmol) was separated into C21 diastereomers by SFC (Column: DAICEL CHIRALPAK IC (250 mm*30 mm, 5 um); Condition: 0.1% NH₃H₂O IPA; Begin B: 45%; End B: 45%; FlowRate (ml/min): 50) to give H₂O (62 mg, 31.1%) and H21 (104 mg, 52.2%) both as solids. The configurations of C20 in these two compounds were referred to the paper "Chem. Rev. 2014, 114, 6349-6382". The peak of C21-β-Me in H-NMR is in higher field than C21-α-Me.

H20: ¹H NMR (400 MHz, CDCl₃) δ$_H$ 4.76 (dd, J=4.4, 13.2 Hz, 1H), 4.23 (dd, J=10.4, 13.2 Hz, 1H), 3.38 (s, 3H), 3.18 (s, 2H), 2.53 (s, 3H), 2.29-2.15 (m, 1H), 2.01 (s, 1H), 1.93-1.62 (m, 7H), 1.59-1.55 (m, 2H), 1.47-1.19 (m, 6H), 1.15-0.93 (m, 7H), 0.81 (s, 3H), 0.76-0.65 (m, 5H); LC-ELSD/MS purity 99%; analytical SFC: 96.46%; MS ESI calcd. for C₂₅H₄₂N₄O₂ [M+H]⁺ 431.3, found 431.3.

H21: ¹H NMR (400 MHz, CDCl₃) δ$_H$ 4.52 (dd, J=4.0, 13.2 Hz, 1H), 4.28 (dd, J=9.2, 13.2 Hz, 1H), 3.38 (s, 3H), 3.18 (s, 2H), 2.53 (s, 3H), 2.20-2.07 (m, 1H), 2.02-1.87 (m, 3H), 1.77-1.58 (m, 7H), 1.48-1.36 (m, 2H), 1.26-0.95 (m, 11H), 0.85 (d, J=6.8 Hz, 3H), 0.76-0.63 (m, 5H). LC-ELSD/MS purity 99%; analytical SFC: 95.38%; MS ESI calcd. for C₂₅H₄₂N₄O₂ [M+H]⁺ 431.3, found 431.3.

Synthesis of H22 & H23

H19 (90 mg, 0.46 mmol) was separated into C21 diastereomers by prep-HPLC (Column: Xtimate C18 150*25 mm*5 um; Condition: water (0.04% NH₃H₂O+10 mM NH₄HCO₃)— ACN; Begin B: 55%; End B: 85%; Gradient Time (min): 7.5; 100% B Hold Time (min): 2; FlowRate (ml/min): 30) to give H22 (27 mg, 30%) and H23 (12 mg, 13.3%)(P1) both as solids. The configurations of C20 in these two compounds were referred to the paper "Chem. Rev. 2014, 114, 6349-6382". The peak of C21-β-Me in H-NMR is in higher field than C21-α-Me.

H22: ¹H NMR (400 MHz, CDCl₃) δ$_H$ 4.54 (dd, J=4.4, 14.0 Hz, 1H), 3.83 (dd, J=11.2, 13.6 Hz, 1H), 3.39 (s, 3H), 3.19 (s, 2H), 2.55 (s, 3H), 2.19-2.07 (m, 1H), 2.01 (s, 1H), 1.92-1.60 (m, 8H), 1.48-1.18 (m, 7H), 1.16-0.94 (m, 7H), 0.82 (s, 3H), 0.76-0.64 (m, 5H); LC-ELSD/MS purity 99%; 100% de based on H-NMR; MS ESI calcd. for C₂₅H₄₂N₄O₂ [M+H]⁺ 431.3, found 431.3.

H23: ¹H NMR (400 MHz, CDCl₃) δ$_H$ 4.28 (dd, J=3.6, 13.6 Hz, 1H), 3.86 (dd, J=10.4, 13.6 Hz, 1H), 3.38 (s, 3H), 3.18 (s, 2H), 2.54 (s, 3H), 2.15-1.79 (m, 4H), 1.77-1.64 (m, 5H), 1.60-1.55 (m, 2H), 1.47-1.36 (m, 2H), 1.29-0.95 (m, 11H), 0.82 (d, J=6.8 Hz, 3H), 0.76-0.65 (m, 5H); LC-ELSD/MS purity 99%; 100% de based on H-NMR; MS ESI calcd. for C₂₅H₄₂N₄O₂ [M+H]⁺ 431.3, found 431.3.

Example 57-60: Synthesis of (3R,5S,8R,9R,10S, 13S,14S,17R)-17-((R)-1-(2H-1,2,3-triazol-2-yl)propan-2-yl)-3,13-dimethylhexadecahydro-1H-cyclopenta[a]phenanthren-3-ol (H33), (3R,5S,8R,9R,10S, 13S,14S,17R)-17-((S)-1-(2H-1,2,3-triazol-2-yl)propan-2-yl)-3,13-dimethylhexadecahydro-1H-cyclopenta[a]phenanthren-3-ol (H34), (3R,5S,8R, 9R,10S,13S,14S,17R)-17-((R)-1-(1H-1,2,3-triazol-1-yl)propan-2-yl)-3,13-dimethylhexadecahydro-1H-cyclopenta[a]phenanthren-3-ol (H35) & (3R,5S,8R, 9R,10S,13S,14S,17R)-17-((S)-1-(1H-1,2,3-triazol-1-yl)propan-2-yl)-3,13-dimethylhexadecahydro-1H-cyclopenta[a]phenanthren-3-ol (H36)

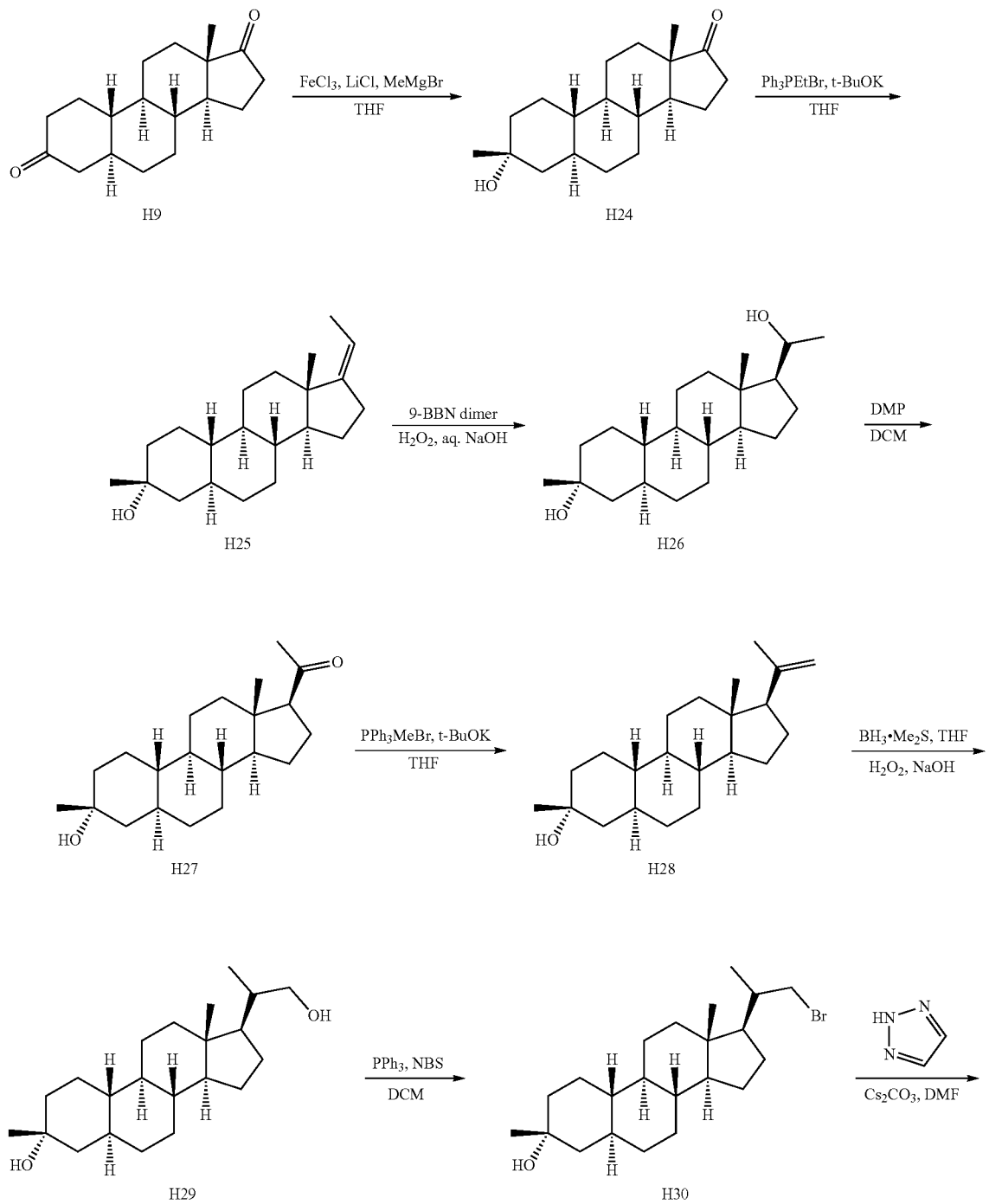

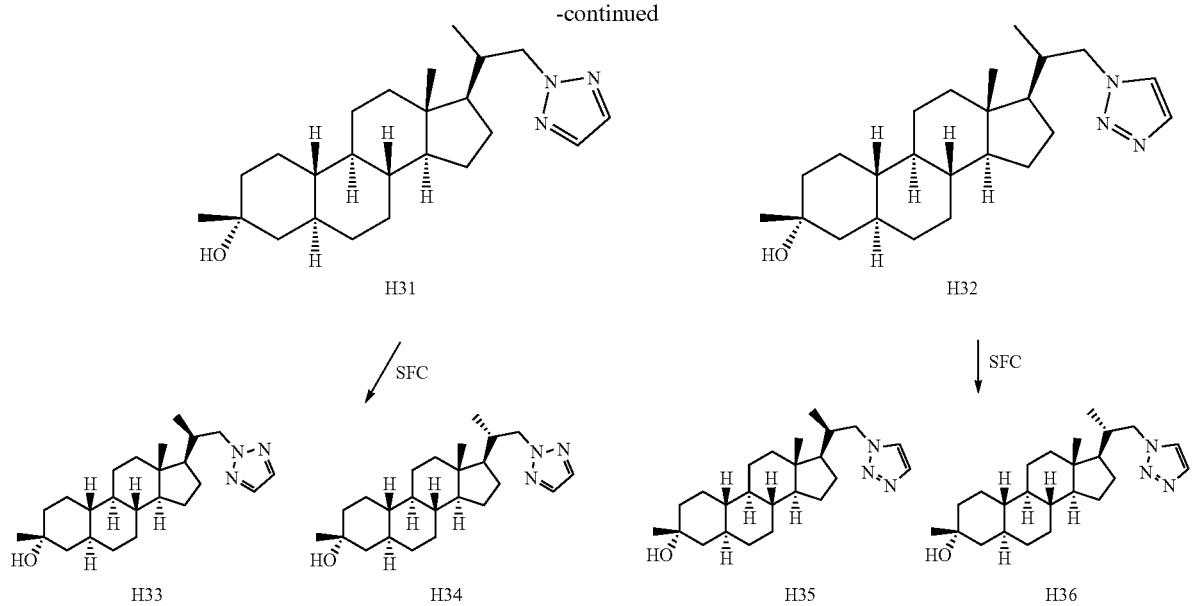

Synthesis of H24

A suspension of LiCl (12.9 g, 305 mmol, anhydrous) in THF (600 mL, anhydrous) was stirred at 25° C. under $N_2$. After 30 mins, $FeCl_3$ (19.4 g, 120 mmol, anhydrous) was added and the mixture was cooled to −30° C. before adding MeMgBr (145 mL, 3M in diethyl ether, 436 mmol) dropwise at −30° C. After stirring at −30° C. for 10 mins, H9 (20 g, 72.8 mmol) was added. After stirring at −15° C. for 2 h, citric acid (500 mL, 10% aq.) was added and the mixture was extracted with EtOAc (2×300 mL). The combined organic solution was washed with saturated brine (300 mL), dried over anhydrous $Na_2SO_4$, filtered and concentrated in vacuum to give H24 (20 g, 95%) as a solid.

$^1$H NMR (400 MHz, $CDCl_3$) $\delta_H$ 2.43 (dd, J=8.8, 19.2 Hz, 1H), 2.14-2.00 (m, 1H), 1.97-1.85 (m, 2H), 1.81-1.72 (m, 3H), 1.71-1.44 (m, 5H), 1.40-1.16 (m, 8H), 1.15-0.98 (m, 5H), 0.87 (s, 3H), 0.80-0.64 (m, 2H)

Synthesis of H25

To a mixture of $PPh_3EtBr$ (50.8 g, 137 mmol) in THF (200 mL) was added t-BuOK (15.3 g, 137 mmol) at 25° C. under $N_2$. After stirring at 40° C. for 30 min, H24 (20 g, 68.6 mmol) was added. After stirring at 40° C. for 3 h, the reaction mixture was quenched with saturated $NH_4Cl$ aqueous (300 mL) at 20° C. and extracted with EtOAc (2×500 mL). The combined organic solution was concentrated and purified by trituration with $MeOH/H_2O$ (1:1, 1 L) at reflux to give $H_{25}$ (20 g, 96.1%) as a solid.

$^1$H NMR (400 MHz, $CDCl_3$) $\delta_H$ 5.15-5.05 (m, 1H), 2.43-2.09 (m, 3H), 1.86-1.47 (m, 10H), 1.47-1.40 (m, 2H), 1.38-1.27 (m, 2H), 1.22-0.94 (m, 11H), 0.88 (s, 3H), 0.77-0.60 (m, 2H)

Synthesis of $H_{26}$

To a solution of $H_{25}$ (20.0 g, 66.1 mmol) in anhydrous THF (200 mL) was added 9-BBN dimer (48.3 g, 198 mmol) at 25° C. under $N_2$. After stirring at 50° C. for 2 h, the mixture was cooled and quenched by EtOH (37.8 mL, 660 mmol) at 0° C. NaOH (26.4 g in 132 mL water, 5 M, 660 mmol) was then added very slowly followed by $H_2O_2$ (66.0 mL, 10 M, 660 mmol) maintain inner temperature below 30° C. After stirring at 50° C. for 1 h, the mixture was poured into sat. $Na_2S_2O_3$ (500 mL), stirred for 30 mins and extracted with EtOAc (2×300 mL). The combined organic solution was dried over $Na_2SO_4$, filtered and concentrated in vacuum to give H26 (50 g), which was purified by trituration in methanol/$H_2O$ (1:1) (500 mL) at 25° C. for 16 h to give H26 (20 g, 40.3%) as a solid.

Synthesis of H27

To a solution of H26 (10 g, 31.1 mmol) in DCM (100 mL) was added DMP (65.7 g, 155 mmol) at 25° C. After stirring at 25° C. for 1 h, the mixture was washed with a mixed solution of $NaHCO_3$ (500 mL, sat.) and $Na_2S_2O_3$ (2×500 mL, sat.), dried over $Na_2SO_4$, filtered, concentrated in vacuum and purified by flash column (15~35% EtOAc in PE) to give H27 (7 g, 70.7%) as a solid.

$^1$H NMR (400 MHz, $CDCl_3$) $\delta_H$ 2.53 (t, J=8.8 Hz, 1H), 2.23-1.94 (m, 6H), 1.89-1.72 (m, 2H), 1.70-1.50 (m, 5H), 1.46-0.91 (m, 15H), 0.77-0.63 (m, 2H), 0.61 (s, 3H).

Synthesis of H28

To a mixture of $MePPh_3Br$ (6.71 g, 18.8 mmol) in THF (25 mL) was added t-BuOK (2.10 g, 18.8 mmol) at 25° C. under $N_2$. After stirring at 50° C. for 30 min, H27 (3.0 g, 9.4 mmol) was added. After stirring 50° C. for 2 h, the reaction mixture was quenched with saturated $NH_4Cl$ aqueous (50 mL) at 25° C. and extracted with EtOAc (2×200 mL). The combined organic solution was dried over $Na_2SO_4$, filtered, concentrated and purified by flash column (0~20% of EtOAc in PE) to give H28 (2.2 g, 74.0%) as a solid.

$^1$H NMR (400 MHz, $CDCl_3$) $\delta_H$ 4.84 (s 1H), 4.70 (s, 1H), 2.08-1.99 (m, 1H), 1.80-1.62 (m, 10H), 1.60-1.51 (m, 3H), 1.37-0.94 (m, 15H), 0.75-0.62 (m, 2H), 0.57 (s, 3H)

Synthesis of H29

To a solution of H28 (2.2 g, 6.95 mmol) in THF (20 mL) was added $BH_3 \cdot Me_2S$ (3.46 mL, 10 M, 34.7 mmol). After stirring at 25° C. for 16 h, EtOH (4 mL, 69.5 mmol) was added dropwise followed by NaOH (2.77 g in 13.9 mL water, 69.5 mmol) and $H_2O_2$ (6.95 mL, 10 M, 69.5 mmol). After stirring at 60° C. for 3 h, the reaction mixture was quenched by $Na_2SO_3$ (100 mL, 10%) and extracted with EtOAc (2×200 mL). The combined organic solution was dried over $Na_2SO_4$, filtered and concentrated and purified by flash column (0~30% of EtOAc in PE) to give H29 (2.7 g) as a solid.

¹H NMR (400 MHz, CDCl₃) δ_H 3.83-3.57 (m, 1H), 3.50-3.30 (m, 1H), 2.00-1.62 (m, 7H), 1.56-1.48 (m, 3H), 1.19 (s, 10H), 1.12-0.91 (m, 11H), 0.68 (s, 5H)

Synthesis of H30

To a solution of H29 (500 mg, 1.5 mmol) in DCM (8 mL) at 0° C. was added PPh₃ (584 mg, 2.2 mmol) and NBS (396 mg, 2.2 mmol). After stirring at 25° C. for 2 h, the reaction mixture was diluted water (100 mL) and extracted with DCM (2×80 mL). The combined organic solution was washed with saturated brine (50 mL), dried over anhydrous Na₂SO₄, filtered and concentrated. The residue was purified by flash column (0~15% of EtOAc in PE) to give H30 (400 mg, 67.5%) as an oil.

¹H NMR (400 MHz, CDCl₃) δ_H 3.67-3.47 (m, 1H), 3.40-3.30 (m, 1H), 1.95-1.50 (m, 11H), 1.38-1.23 (m, 6H), 1.20 (s, 3H), 1.16-0.95 (m, 10H), 0.71-0.60 (m, 5H)

Synthesis of H31-H36

To a solution of H30 (400 mg, 1.0 mmol) in DMF (10 mL) was added Cs₂CO₃ (977 mg, 3.0 mmol) and 2H-1,2,3-triazole (103 mg, 1.5 mmol). After stirring at 80° C. for 16 h, the reaction mixture was diluted with water (50 mL) and extracted with EtOAc (2×50 mL). The combined organic solution was dried over Na₂SO₄, filtered, concentrated and purified by flash column (5~90% of EtOAc in PE) to give H31 (170 mg, 44.1%) and H32 (170 mg, 44.1%) both as solids The C21 diastereomers of H31 (170 mg) were separated by SFC (column: DAICEL CHIRALPAK ADH (250 mm*30 mm, 5 um), gradient: 40-40% B (water (0.1% NH₃H₂O IPA), flow rate: 50 mL/min) to give H33 (20 mg, 11.8%) and H34 (74 mg, 43.7%) both as solids.

H34: ¹H NMR (400 MHz, CDCl₃) δ_H 7.58 (s, 2H), 4.52-4.44 (m, 1H), 4.18-4.07 (m, 1H), 2.22-2.08 (m, 1H), 2.04-1.89 (m, 2H), 1.79-1.61 (m, 5H), 1.53-1.26 (m, 4H), 1.21-0.90 (m, 15H), 0.81 (d, J=6.8 Hz, 3H), 0.72 (s, 3H), 0.68-0.60 (m, 2H); LCMS 30-90AB_2 min_E. purity ≥99%, MS ESI calcd. for C₂₄H₄₀N₃O [M+H]⁺ 386.3, found 386.3.

H33: ¹H NMR (400 MHz, CDCl₃) δ_H 7.58 (s, 2H), 4.75-4.67 (m, 1H), 4.12-4.03 (m, 1H), 2.30-2.17 (m, 1H), 1.95-1.72 (m, 4H), 1.69-1.61 (m, 3H), 1.53-1.51 (m, 1H), 1.39-1.17 (m, 10H), 1.13-0.91 (m, 8H), 0.82 (s, 3H), 0.66 (d, J=6.8 Hz, 5H); LCMS 30-90AB_2 min_E. purity ≥99%, MS ESI calcd. for C₂₄H₄₀N₃O [M+H]⁺ 386.3, found 386.3.

The C21 diastereomers of H32 (170 mg) was purified by SFC (column: DAICEL CHIRALPAK AD (250 mm*30 mm, 10 um), gradient: 45-45% B (0.1% NH₃H₂O ETOH), flow rate: 70 mL/min) to give H35 (39 mg, 23.0%) and H36 (36 mg, 21.3%) both as a solid.

H35: ¹H NMR (400 MHz, CDCl₃) δ_H 7.70 (s, 1H), 7.50 (s, 1H), 4.72-4.63 (m, 1H), 4.02-3.93 (m, 1H), 2.17-2.05 (m, 1H), 1.94-1.60 (m, 7H), 1.54-1.51 (m, 1H), 1.40-1.18 (m, 10H), 1.16-0.97 (m, 8H), 0.82 (s, 3H), 0.75-0.62 (m, 5H); LCMS 30-90AB_2 min_E. purity ≥99%, MS ESI calcd. for C₂₄H₄₀N₃O [M+H]⁺ 386.3, found 386.3.

H36: ¹H NMR (400 MHz, CDCl₃) δ_H 7.70 (s, 1H), 7.50 (s, 1H), 4.46-4.38 (m, 1H), 4.11-4.02 (m, 1H), 2.07-1.88 (m, 3H), 1.79-1.60 (m, 5H), 1.55-1.24 (m, 5H), 1.21-0.92 (m, 13H), 0.84 (d, J=6.4 Hz, 3H), 0.72 (s, 3H), 0.70-0.61 (m, 2H); LCMS 30-90AB_2 min_E. purity ≥99%, MS ESI calcd. for C₂₄H₄₀N₃O [M+H]⁺ 386.3, found 386.3.

Examples 61-64: Synthesis of 1-((R)-2-((3R,5R,8R, 9S,10S,13S,14S,17R)-3-ethyl-3-hydroxy-10,13-dimethylhexadecahydro-1H-cyclopenta[a]phenanthren-17-yl)propyl)-1H-pyrazole-3-carbonitrile (J8), 1-((S)-2-((3R,5R,8R,9S,10S,13S,14S,17R)-3-ethyl-3-hydroxy-10,13-dimethylhexadecahydro-1H-cyclopenta[a]phenanthren-17-yl)propyl)-1H-pyrazole-3-carbonitrile (J9), 1-((R)-2-((3R,5R,8R,9S,10S,13S, 14S,17R)-3-ethyl-3-hydroxy-10,13-dimethylhexadecahydro-1H-cyclopenta[a]phenanthren-17-yl)propyl)-1H-pyrazole-5-carbonitrile (J10) & 1-((S)-2-((3R,5R,8R,9S,10S, 13S,14S,17R)-3-ethyl-3-hydroxy-10,13-dimethylhexadecahydro-1H-cyclopenta[a]phenanthren-17-yl)propyl)-1H-pyrazole-5-carbonitrile (J11)

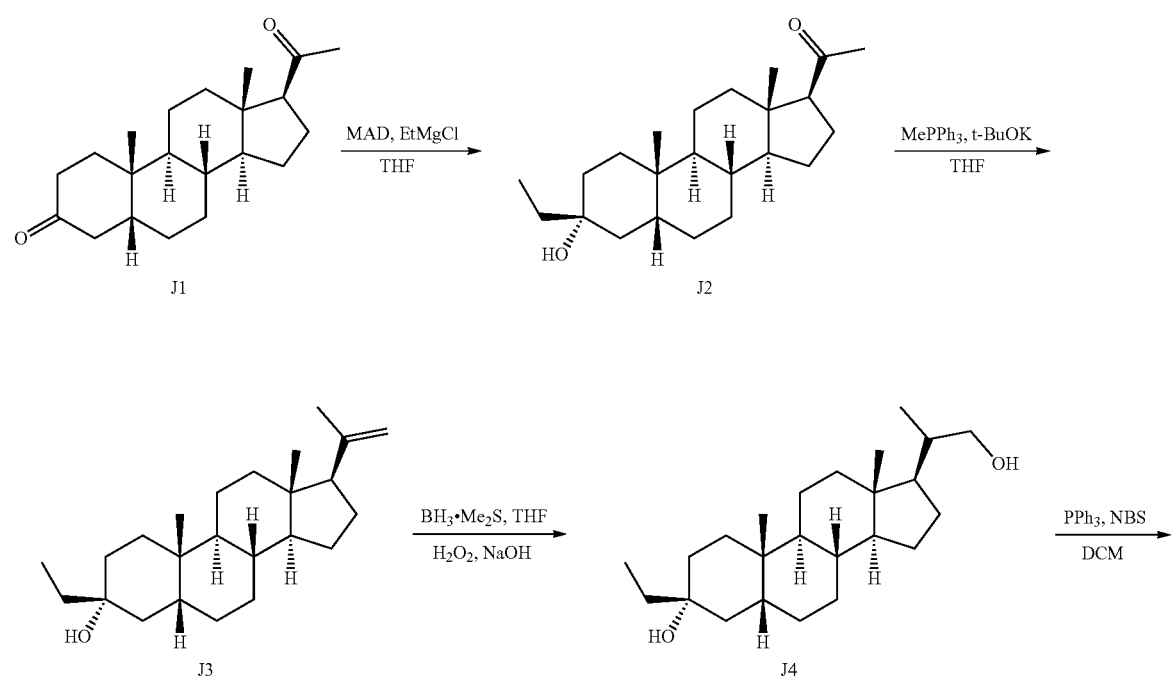

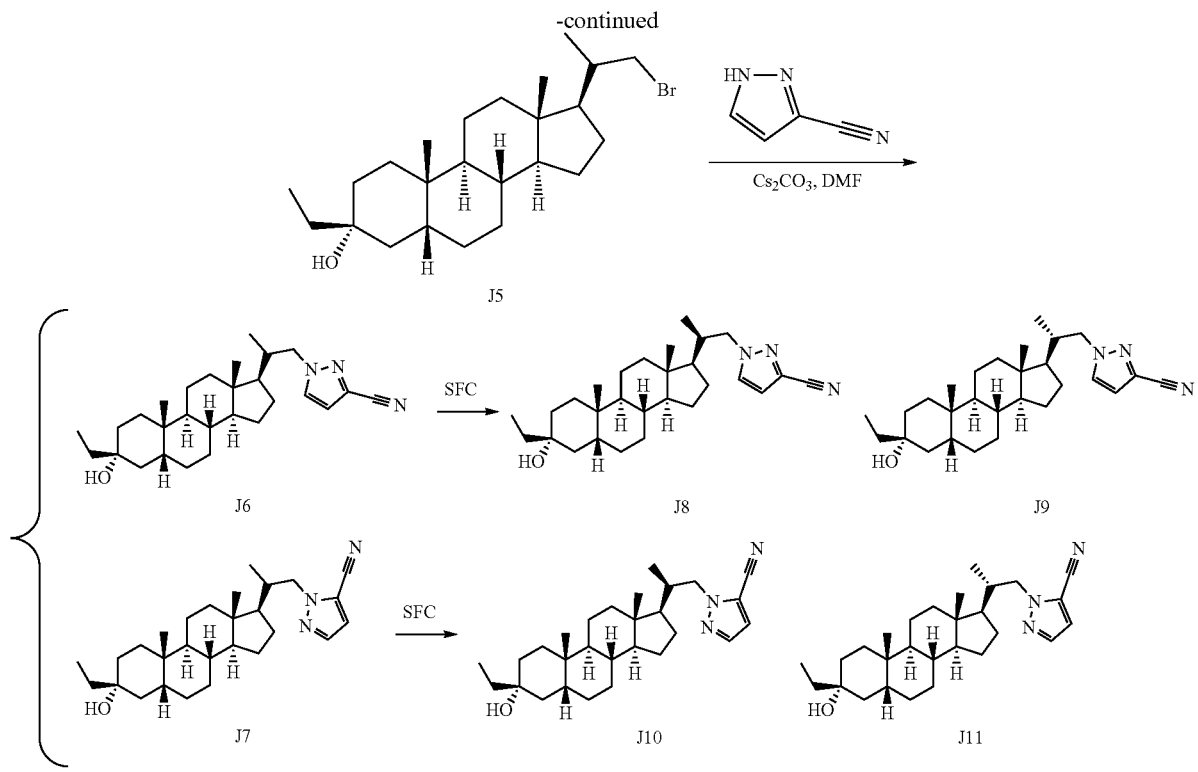

Synthesis of J2

To a solution of 2, 6-di-tert-butyl-4-methylphenol (22.5 g, 102 mmol) in toluene (50 mL) was added dropwise AlMe$_3$ (25.5 mL, 51.0 mmol, 2 M in toluene) at 0° C. The mixture was stirred at 25° C. for 1 h and used directly as MAD solution. To the MAD (51.0 mmol) was added a solution of J1 (5 g, 15.7 mmol) in DCM (25 mL) dropwise at −70° C. After stirring at −70° C. for 1 h under N$_2$, bromo(ethyl) magnesium (15.6 mL, 47.0 mmol, 3M in ethyl ether) was added dropwise at −70° C. The resulting solution was stirred at −70° C. for another 1 h. The reaction mixture was poured into saturated aqueous citric acid (50 mL) at below 10° C. followed by adding ice-water (60 mL) and stirred for another 10 min. The aqueous solution was extracted with EtOAc (2×40 mL). The combined organic solution was washed with brine (20 mL), dried over anhydrous Na$_2$SO$_4$, filtered and concentrated. The residue was purified by flash column (10% of EtOAc in PE) to give J2 (3.7 g) as a solid.

$^1$H NMR (400 MHz, CDCl$_3$) $\delta_H$ 2.57-2.49 (m, 1H), 2.22-2.09 (m, 4H), 2.03-1.96 (m, 1H), 1.94-1.79 (m, 2H), 1.73-1.62 (m, 3H), 1.61-1.33 (m, 12H), 1.24-0.96 (m, 6H), 0.93 (s, 3H), 0.88 (t, J=7.6 Hz, 3H), 0.59 (s, 3H).

Synthesis of J3

To a suspension of MePh$_3$PBr (3.07 g, 8.64 mmol) in THF (25 mL) was added t-BuOK (967 mg, 8.64 mmol). After stirring at 40° C. for 10 min, the mixture was slowly added dropwise to a solution of J2 (1.5 g, 4.32 mmol) in THF (15 mL) at 20° C. After stirring for 30 min, the reaction was quenched with sat.NH$_4$Cl (50 mL) and extracted with EtOAc (3×50 mL). The combined organic solution was washed with sat. NH$_4$Cl (50 mL), dried over Na$_2$SO$_4$, filtered, concentrated and purified by combi-flash (0~25% of EtOAc in PE) to give J3 (1.2 g) as a solid.

$^1$H NMR (400 MHz, CDCl$_3$) $\delta_H$ 4.84 (s, 1H), 4.70 (s, 1H), 2.07-1.98 (m, 1H), 1.94-1.79 (m, 3H), 1.75 (s, 3H), 1.73-1.60 (m, 3H), 1.53-1.32 (m, 8H), 1.29-1.14 (m, 9H), 0.93 (s, 3H), 0.90-0.86 (m, 5H), 0.55 (s, 3H).

Synthesis of J4

To a solution of J3 (1.2 g, 3.48 mmol) in THF (20 mL) was added BH$_3$/Me$_2$S (1.73 mL, 10 M, 17.4 mmol) dropwise at 25° C. under N$_2$. After stirring at 25° C. for 2 h, the mixture was cooled to 0° C. and treated with EtOH (1.60 g, 34.8 mmol), NaOH (6.95 mL, 5M, 34.8 mmol) and then H$_2$O$_2$ (3.47 mL, 10 M, 34.8 mmol) slowly maintain inner temperature below 0° C. When the inner temperature no longer rises, the mixture was poured into water (30 mL) and stirred for 30 mins. The suspension was extracted with EtOAc (2×30 mL). The combined organic solution was wash with water (2×30 mL), dried over anhydrous Na$_2$SO$_4$, filtered, concentrated and purified by flash column (0~30% of EtOAc in PE) to give J4 (915 mg) as an oil.

$^1$H NMR (400 MHz, CDCl$_3$) $\delta_H$ 3.80-3.58 (m, 1H), 3.52-3.32 (m, 1H), 2.99 (s, 2H), 1.99-1.77 (m, 4H), 1.73-1.57 (m, 4H), 1.51-1.33 (m, 7H), 1.31-1.12 (m, 9H), 1.07-0.94 (m, 5H), 0.93 (s, 3H), 0.87 (t, J=7.2 Hz, 3H), 0.66 (s, 3H).

Synthesis of J5

To a solution of J4 (458 mg, 1.26 mmol) in DCM (10 mL) at 0° C. was added PPh$_3$ (495 mg, 1.89 mmol) and NBS (336 mg, 1.89 mmol). After stirring at 25° C. for 2 h, the reaction was diluted with water (10 mL) and extracted with DCM (2×15 mL). The combined organic solution was washed with brine (2×15 mL), dried over anhydrous Na$_2$SO$_4$, filtered and concentrated. The residue was purified by flash column (0~10% of EtOAc in PE) to give J5 (440 mg) as an oil.

$^1$H NMR (400 MHz, CDCl$_3$) $\delta_H$ 3.66-3.47 (m, 1H), 3.40-3.28 (m, 1H), 1.97-1.77 (m, 4H), 1.73-1.62 (m, 2H), 1.56-1.43 (m, 4H), 1.42-1.24 (m, 11H), 1.23-0.95 (m, 9H), 0.93 (s, 3H), 0.87 (t, J=7.2 Hz, 3H), 0.66 (d, J=2.8 Hz, 3H).

Synthesis of J6 & J7

To a solution of J5 (390 mg, 0.916 mmol) in DMF (10 mL) was added $Cs_2CO_3$ (594 mg, 1.83 mmol) and 1H-pyrazole-3-carbonitrile (170 mg, 1.83 mmol). After stirring at 85° C. for 12 h, the reaction was washed by water and aq. LiCl (30 mL, 5%), brine (30 mL), dried over anhydrous $Na_2SO_4$, filtered and concentrated under vacuum. The residue was purified by flash column (30% of EtOAc in PE) to give J6 (286 mg, 71%) and J7 (54 mg, 13%) both as oils.

J6: LC-ELSD/MS MS ESI calcd for $C_{28}H_{42}N_3$ $[M-H_2O+H]^+$ 420, found 420; $C_{28}H_{43}N_3ONa$ $[M+Na]^+$ 460, found 460.

J7: LC-ELSD/MS MS ESI calcd. for $C_{28}H_{42}N_3$ $[M-H_2O+H]^+$ 420, found 420; $C_{28}H_{43}N_3ONa$ $[M+Na]^+$ 460, found 460.

Synthesis of J8 & J9

J6 (286 mg, 0.653 mmol) was purified by SFC (Column: Chiralcel OD-3 50×4.6 mm I.D., 3 um; Mobile solution: A: $CO_2$ B: ethanol (0.05% DEA) Gradient: from 5% to 40% of B in 2 min and hold 40% for 1.2 min, then 5% of B for 0.8 min; Flow rate: 4 mL/min) to afford J9 (72.7 mg, 25.5%) and J8 (99.3 mg, 34.8%) as solids.

The C20-Me diastereomers were assigned based on $^1$H NMR of $C_{21}$-Me.

J8: $^1$H NMR (400 MHz, $CDCl_3$) $\delta_H$ 7.39 (d, J=2.4 Hz, 1H), 6.65 (d, J=2.4 Hz, 1H), 4.49 (dd, J=4.8, 13.3 Hz, 1H), 3.69 (dd, J=10.4, 13.3 Hz, 1H), 2.18-2.05 (m, 1H), 1.93-1.78 (m, 4H), 1.72-1.57 (m, 4H), 1.51-1.33 (m, 8H), 1.31-1.09 (m, 9H), 1.05-0.97 (m, 1H), 0.94 (s, 3H), 0.88 (t, J=7.6 Hz, 3H), 0.77 (s, 3H), 0.67 (d, J=6.4 Hz, 3H). LC-ELSD/MS purity 99%, MS ESI calcd. for $C_{28}H_{42}N_3$ $[M-H_2O+H]^+$ 420, found 420; $C_{28}H_{43}N_3ONa$ $[M+Na]^+$ 460, found 460. SFC 99.91% de.

J9: $^1$H NMR (400 MHz, $CDCl_3$) $\delta_H$ 7.32 (d, J=2.4 Hz, 1H), 6.58 (d, J=2.4 Hz, 1H), 4.20 (dd, J=4.0, 13.4 Hz, 1H), 3.67 (dd, J=10, 13.4 Hz, 1H), 2.01-1.72 (m, 5H), 1.66-1.51 (m, 4H), 1.43-1.27 (m, 8H), 1.24-1.02 (m, 9H), 0.97-0.89 (m, 1H), 0.86 (s, 3H), 0.81 (t, J=7.2 Hz, 3H), 0.73 (d, J=6.4 Hz, 3H), 0.63 (s, 3H). LC-ELSD/MS purity 99%, MS ESI calcd. for $C_{28}H_{42}N_3$ $[M-H_2O+H]^+$ 420, found 420; $C_{28}H_{43}N_3ONa$ $[M+Na]^+$ 460, found 460; $C_{28}H_{43}N_3ONa$ $[M+Na]^+$ 460, found 460. SFC 100% de.

Synthesis of J10 & J11

J7 (54 mg, 0.123 mmol) was purified by SFC (Column: Chiralpak AD-3 50×4.6 mm I.D., 3 um; Mobile solution: A: $CO_2$ B: ethanol (0.05% DEA) Gradient: from 5% to 40% of B in 2 min and hold 40% for 1.2 min, then 5% of B for 0.8 min; Flow rate: 4 mL/min) to afford J10 (20.8 mg, 39%) and J11 (17.2 mg, 32%) as solids.

The C20-Me diastereomers were assigned based on $^1$H NMR of C21-Me.

J10: $^1$H NMR (400 MHz, $CDCl_3$) $\delta_H$ 7.56 (d, J=2.0 Hz, 1H), 6.78 (d, J=2.0 Hz, 1H), 4.59 (dd, J=4.8, 13.2 Hz, 1H), 3.90 (dd, J=11.2, 13.2 Hz, 1H), 2.19 (br d, J=9.6 Hz, 1H), 1.95-1.80 (m, 4H), 1.73-1.57 (m, 4H), 1.51-1.34 (m, 7H), 1.32-1.08 (m, 10H), 1.05-0.96 (m, 1H), 0.94 (s, 3H), 0.88 (t, J=7.6 Hz, 3H), 0.81 (s, 3H), 0.68 (d, J=6.4 Hz, 3H). LC-ELSD/MS purity 99%, MS ESI calcd. for $C_{28}H_{42}N_3$ $[M-H_2O+H]^+$ 420, found 420; $C_{28}H_{43}N_3ONa$ $[M+Na]^+$ 460, found 460. SFC 99.72% de J11: $^1$H NMR (400 MHz, $CDCl_3$) $\delta_H$=7.57 (d, J=2.4 Hz, 1H), 6.77 (d, J=2.0 Hz, 1H), 4.37 (dd, J=4.0, 13.4 Hz, 1H), 3.91 (dd, J=10.4, 13.6 Hz, 1H), 2.19-2.05 (m, 1H), 1.99-1.79 (m, 4H), 1.72-1.57 (m, 4H), 1.51-1.34 (m, 7H), 1.31-1.07 (m, 10H), 1.04-0.96 (m, 1H), 0.93 (s, 3H), 0.88 (t, J=7.2 Hz, 3H), 0.81 (s, 3H), 0.70 (s, 3H). LC-ELSD/MS purity 99%, MS ESI calcd. for $C_{28}H_{42}N_3$ $[M-H_2O+H]^+$ 420, found 420; $C_{28}H_{44}N_3O$ $[M+H]^+$ 438, found 438. SFC 99.93% de.

Examples 65 & 66: Synthesis of 1-((R)-2-((3R,5R, 8R,9R,10S,13S,14S,17R)-3-hydroxy-13-methyl-3-propylhexadecahydro-1H-cyclopenta[a]phenanthren-17-yl)propyl)-1H-pyrazole-4-carbonitrile (K8) & 1-((S)-2-((3R,5R,8R,9R,10S,13S,14S,17R)-3-hydroxy-13-methyl-3-propylhexadecahydro-1H-cyclopenta[a]phenanthren-17-yl)propyl)-1H-pyrazole-4-carbonitrile (K9)

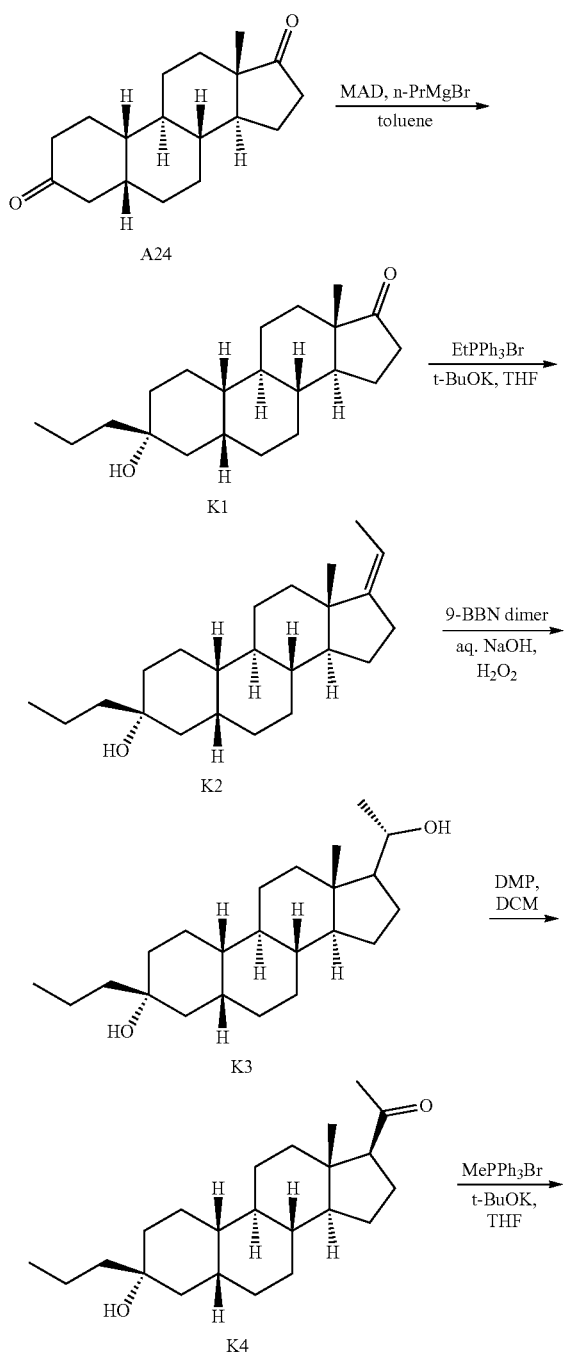

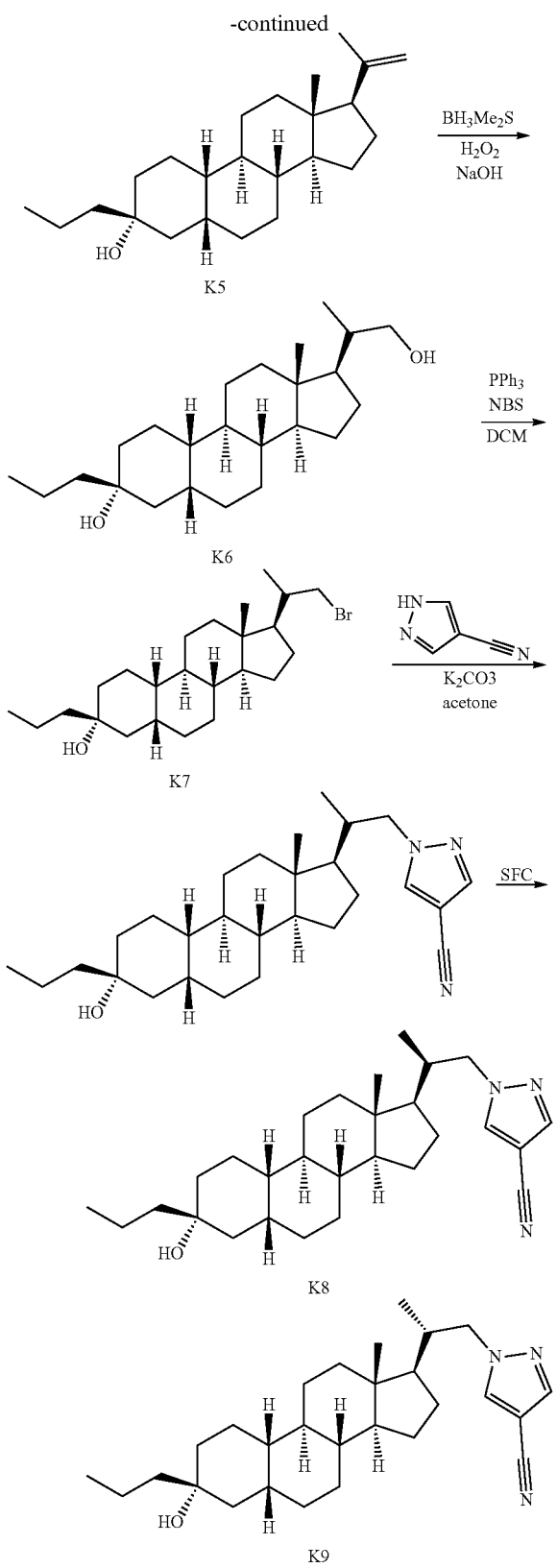

The mixture was stirred at 25° C. for 1 h and used directly as a solution of MAD. To the MAD (54 mmol in 30 mL toluene) solution was added a solution of A24 (5 g, 18.2 mmol) in toluene (20 mL) dropwise at −60° C. After stirring at −60° C. for 1 h under $N_2$, n-prMgBr (27.3 mL, 54.6 mmol, 2M in THF) was added drop wise at −60° C. After stirring at −60° C. for another 4 h, the reaction mixture was poured into saturated aqueous citric acid (100 mL) below 10° C. and extracted with EtOAc (2×100 mL). The combined organic solution was dried over $Na_2SO_4$, filtered and concentrated in vacuum. The residue was purified by a silica gel column (PE/EtOAc=0-20%) to give K1 (3.83 g, 66.1%) as a solid.

$^1$H NMR (400 MHz, $CDCl_3$) $\delta_H$ 2.49-2.37 (m, 1H), 2.31-1.98 (m, 2H), 1.97-1.87 (m, 1H), 1.86-1.73 (m, 4H), 1.72-1.60 (m, 2H), 1.55-1.45 (m, 5H), 1.45-1.27 (m, 10H), 1.27-1.00 (m, 4H), 0.93 (t, J=7.2 Hz, 3H), 0.87 (s, 3H).

Synthesis of K2

To a mixture of $EtPPh_3Br$ (26.5 g, 71.4 mmol) in THF (50 mL) was added t-BuOK (8.01 g, 71.4 mmol) at 15° C. under $N_2$. After stirring at 50° C. for 30 min. K1 (3.8 g, 11.9 mmol) was added in portions below 40° C. After stirring at 40° C. for 1 h, the reaction mixture was quenched with 10% $NH_4Cl$ aqueous (100 mL) at 15° C. and extracted with EtOAc (500 mL). The combined organic solution was concentrated under vacuum and was purified by trituration with $MeOH/H_2O$ (1:1, 300 mL) at reflux to give K2 (4.5) as an oil.

$^1$H NMR (400 MHz, $CDCl_3$) $\delta_H$ 5.10 (d, J=7.2 Hz, 1H), 2.41-2.09 (m, 4H), 1.78-1.71 (m, 3H), 1.66-1.63 (m, 3H), 1.56-1.51 (m, 3H), 1.50-1.42 (m, 3H), 1.37-1.29 (m, 6H), 1.21-1.00 (m, 6H), 0.93 (t, J=7.28 Hz, 3H), 0.87 (s, 3H).

Synthesis of K3

To a solution of K2 (4.5 g, 13.6 mmol) in THF (50 mL) was added 9-BBN dimer (9.95 g, 40.8 mmol) at 15° C. After stirring at 40° C. for 1 h, ethanol (6.21 g, 135 mmol) was added at 15° C. followed by aqueous NaOH (27 mL, 5M, 135 mmol) at −10° C. and finally $H_2O_2$ (13.5 mL, 10 M, 135 mmol) dropwise. After stirring at 80° C. for 1 h, the reaction was quenched with sat. $Na_2S_2O_3$ (50 mL). After stirring for 30 min, the mixture was extracted with EtOAc (100 mL). The combined organic solution was washed with saturated brine (2×100 mL), dried over anhydrous $Na_2SO_4$, concentrated under vacuum and purified by silica gel chromatography (PE/EtOAc=10 to 20%) to give K3 (3.2 g, 67.5%) as a solid.

$^1$H NMR (400 MHz, $CDCl_3$) $\delta_H$ 3.74-3.66 (m, 1H), 1.85-1.60 (m, 10H), 1.49-1.29 (m, 13H), 1.22 (d, J=6 Hz, 3H), 1.16-1.00 (m, 7H), 0.93 (t, J=7.2 Hz, 3H), 0.66 (s, 3H).

LC-ELSD/MS purity 99%, MS ESI calcd. for $C_{23}H_{40}O_2$ $[M+H-2H_2O]^+$ 313.3, found 313.3.

Synthesis of K4

To a solution of K3 (3.1 g, 8.89 mmol) in DCM (30 mL) was added Dess-martin periodane (7.5 g, 17.7 mmol) at 25° C. After stirring for 10 min, the mixture was quenched by saturated $NaHCO_3/Na_2S_2O_3$ aqueous (1:1, 375 mL) at 25° C. The organic solution was separated and washed with saturated $NaHCO_3/Na_2S_2O_3$ aqueous (1:1, 375 mL), brine (200 mL), dried over $Na_2SO_4$, filtered and concentrated under vacuum, to give K4 (4 g) as a solid.

$^1$H NMR (400 MHz, $CDCl_3$) $\delta_H$ 2.40 (d, J=12.80 Hz, 1H), 2.11 (s, 3H), 1.93-1.81 (m, 4H), 1.72-1.63 (m, 8H), 1.50-1.41 (m, 8H), 1.13-1.02 (m, 6H), 0.94-0.91 (m, 3H), 0.62 (s, 3H).

Synthesis of K5

To a mixture of $MePPh_3Br$ (12.3 g, 34.5 mmol) in THF (50 mL) was added t-BuOK (3.87 g, 34.5 mmol) at 15° C. under $N_2$. After stirring at 50° C. for 30 min, K4 (4 g, 11.5 mmol) was added in portions below 50° C. After stirring at Synthesis of K1

To a solution of 2,6-di-tert-butyl-4-methylphenol (24 g, 108 mmol) in toluene (30 mL) under nitrogen at 0° C. was added $AlMe_3$ (2 M in toluene, 27 mL, 54 mmol) dropwise.

50° C. for 1 h, the reaction mixture was quenched with 10% NH₄Cl aqueous (100 mL) at 15° C. and extracted with EtOAc (200 mL). The combined organic solution was concentrated under vacuum and purified by silica gel chromatography (PE/EtOAc=0 to 5%) to give K5 (600 mg, 15.1%) as a solid.

¹H NMR (400 MHz, CDCl₃) δ_H 4.84 (s, 1H), 4.69 (s, 1H) 2.04-1.99 (m, 2H), 1.86-1.76 (m, 3H), 1.75 (s, 3H), 1.74-1.57 (m, 6H), 1.56-1.50 (m, 2H), 1.49-1.28 (m, 10H), 1.23-0.97 (m, 6H), 0.93 (t, J=7.2 Hz, 3H), 0.56 (s, 3H).

Synthesis of K6

To a solution of K5 (600 mg, 1.74 mmol) in THF (5 mL) was added BH₃·Me₂S (0.87 mL, 8.7 mmol, 10 M) dropwise at 0° C. After stirring at 25° C. for 3 h, the reaction mixture was cooled to 0° C. and ethanol (800 mg, 17.4 mmol) followed by NaOH aqueous (1.73 mL, 17.4 mmol, 5 M) and finally H₂O₂ (1.73 mL, 17.4 mmol) were added. After stirring at 70° C. for 1 h, the mixture was extracted with EtOAc (2×50 mL). The combined organic solution was washed with saturated Na₂S₂O₃ aqueous (2×20 mL), brine (50 mL), dried over Na₂SO₄, filtered and evaporated to give K6 (620 mg) as an oil.

¹H NMR (400 MHz, CDCl₃) δ_H 3.85-3.58 (m, 1H), 3.52-3.29 (m, 1H), 2.01-1.71 (m, 5H), 1.71-1.58 (m, 4H), 1.51-1.12 (m, 17H), 1.11-0.98 (m, 6H), 0.97-0.90 (m, 5H), 0.68 (s, 3H).

Synthesis of K7

To a solution of K6 (620 mg, 1.7 mmol) in DCM (10 mL) at 0° C. was added PPh₃ (668 mg, 2.55 mmol) and NBS (453 mg, 2.55 mmol). After stirring at 25° C. for 2 h, the reaction was diluted with water (50 mL) and extracted with DCM (2×80 mL). The combined organic solution was washed with saturated brine (50 mL), dried over anhydrous Na₂SO₄, filtered and concentrated. The residue was purified by flash column (0~15% of EtOAc in PE) to give K7 (385 mg, 67.5%) as an oil.

¹H NMR (400 MHz, CDCl₃) δ_H 3.67-3.45 (m, 1H), 3.34 (s, 1H), 1.97-1.72 (m, 5H), 1.72-1.50 (m, 7H), 1.49-1.28 (m, 12H), 1.22-1.16 (m, 1H), 1.15-1.03 (m, 5H), 1.00 (d, J=6.4 Hz, 3H), 0.92 (t, J=7.2 Hz, 3H), 0.68 (s, 3H).

Synthesis of K8 & K9

To a solution of K7 (200 mg, 0.47 mmol) in acetone (5 mL) were added 1H-pyrazole-4-carbonitrile (52.5 mg, 0.56 mmol) and K₂CO₃ (129 mg, 0.94 mmol). After stirring at 25° C. for 14 h, the mixture was diluted with water (40 mL) and extracted with EtOAc (2×50 mL). The combined organic solution was dried over Na₂SO₄, filtered, concentrated and purified by flash column (20~50% of EtOAc in PE) to give a mixture of K8 & K9 (100 mg) as a solid.

The diastereomers were separated by SFC (Column: DAICEL CHIRALCEL OD-H (250 mm*30 mm, 5 um), Condition: 0.1% NH₃H₂O EtOH, Begin B: 30%, End B: 30%, FlowRate (ml/min): 50) to afford K8 (43 mg, 43%) and K9 (30 mg, 30%) as solids. The C20-Me diastereomers were assigned based on ¹H NMR of C21-Me.

K8: ¹H NMR (400 MHz, CDCl₃) δ_H 7.75 (s, 1H), 7.80 (s, 1H), 4.50 (dd, J=13.2, 4.39 Hz, 1H), 3.66 (dd, J=13.2, 10.00 Hz, 1H), 2.18-2.02 (m, 1H), 1.87-1.76 (m, 3H), 1.68-1.59 (m, 3H), 1.50-1.41 (m, 3H), 1.41-1.18 (m, 14H), 1.18-1.00 (m, 6H), 0.93 (t, J=7.2 Hz, 3H), 0.79 (s, 3H), 0.68 (d, J=6.4 Hz, 3H).

LC-ELSD/MS 30-90AB_2 min_E, purity 99%, 100% de based on H-NMR; MS ESI calcd. for C₂₈H₄₃N₃O [M+H–H₂O]⁺ 420.3, found 420.3.

K9: ¹H NMR (400 MHz, CDCl₃) δ_H 7.79 (s, 1H), 7.75 (s, 1H), 4.19-4.32 (m, 1H), 3.72 (dd, J=13.13, 9.2 Hz, 1H), 1.87-2.08 (m, 3H), 1.59-1.84 (m, 6H), 1.22-1.51 (m, 14H), 1.00-1.20 (m, 7H), 0.93 (t, J=7.2 Hz, 3H), 0.81 (d, J=6.4 Hz, 3H), 0.71 (s, 3H).

LC-ELSD/MS 30-90AB_2 min_E, purity 99%, purity 99%, 100% de based on H-NMR; MS ESI calcd. for C₂₈H₄₃N₃O [M+H–H₂O]⁺ 420.3, found 420.3.

Examples 67 & 68: Synthesis of 4-cyano-N-((R)-1-((3R,5R,8R,9R,10S,13S,14S,17S)-3-(ethoxymethyl)-3-hydroxy-13-methylhexadecahydro-1H-cyclopenta[a]phenanthren-17-yl)ethyl)benzenesulfonamide (67) & 4-cyano-N-((R)-1-((3R,5R,8R,9R,10S,13S,14S,17S)-3-(ethoxymethyl)-3-hydroxy-13-methyl-hexadecahydro-1H-cyclopenta[a]phenanthren-17-yl)ethyl)-N-methylbenzenesulfonamide (68)

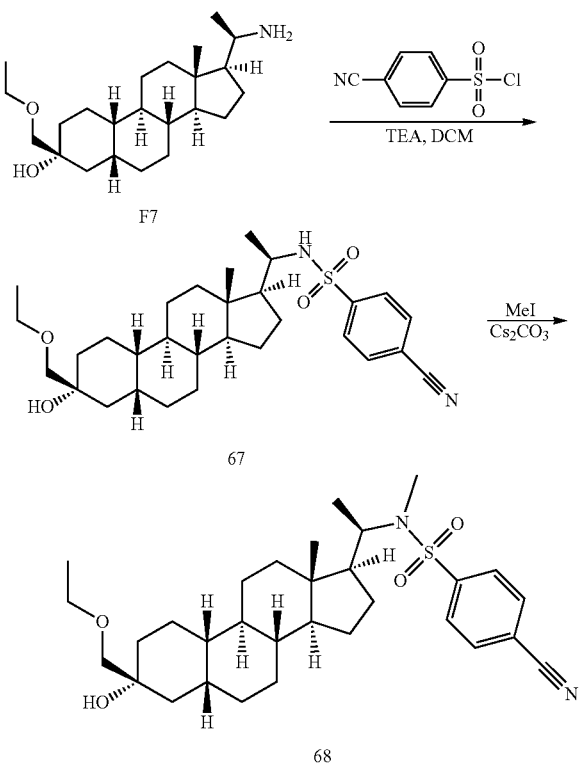

Synthesis of 67

To a solution of F7 (300 mg, 0.825 mmol) in DCM (5 mL) was added Et₃N (208 mg, 2.06 mmol) and 4-cyanobenzene-1-sulfonyl chloride (247 mg, 1.23 mmol) at 25° C. After stirring at 25° C. for 16 h, the resulting colorless solution was washed with water (3×100 mL). The organic layer was dried over anhydrous Na₂SO₄, filtered and concentrated. The residue was purified by flash column (30% of EtOAc in PE) to give 67 (398 mg) as a solid.

¹H NMR (400 MHz, CDCl₃) δ_H 8.00-7.98 (m, 2H), 7.81-7.79 (m, 2H), 4.27 (d, J=8.8 Hz, 1H), 3.53 (q, J=6.8 Hz, 2H), 3.45-3.38 (m, 3H), 2.73 (s, 1H), 1.99-1.96 (m, 1H), 1.82-1.66 (m, 4H), 1.63-1.50 (m, 7H), 1.47-1.13 (m, 10H), 1.11-0.83 (m, 8H), 0.56 (s, 3H). LC-ELSD/MS purity 99%, MS ESI calcd. for C₃₀H₄₄N₂O₄SNa [M+Na]⁺ 551, found 551.

Synthesis of 68

To a solution of 67 (150 mg, 0.283 mmol) in DMF (3 mL) was added Cs₂CO₃ (184 mg, 0.566 mmol). After stirring for 20 mins at 25° C., MeI (60.1 mg, 0.424 mmol) was added to the reaction mixture. After stirring at 25° C. for 16 h, the resulting mixture was poured into water (50 mL) and extracted with EtOAc (2×50 mL). The combined organic layer was washed with water (3×100 mL), dried over anhydrous Na$_2$SO$_4$, filtered and concentrated. The residue was purified by pre-HPLC (column: Xtimate C18 150*25 mm*5 um, condition: water (0.225% FA)-ACN, Begin B: 77, End B: 100) to give 68 (89 mg, 58%) as a solid.

$^1$H NMR (400 MHz, CDCl$_3$) δ$_H$ 7.94-7.92 (m, 2H), 7.81-7.79 (m, 2H), 4.07-3.99 (m, 1H), 3.53 (q, J=6.8 Hz, 2H), 3.46 (q, J=9.2 Hz, 2H), 2.73-2.66 (m, 4H), 2.10-2.07 (m, 1H), 1.85-1.47 (m, 10H), 1.44-1.18 (m, 10H), 1.14-0.99 (m, 6H), 0.86 (s, 3H), 0.64 (d, J=6.4 Hz, 3H).

LC-ELSD/MS purity 99%, MS ESI calcd. for C$_{31}$H$_{45}$N$_2$O$_3$S [M+H–H$_2$O]$^+$ 525, found 525.

The following examples were synthesized similar to Examples 67 & 68 with the listed sulfonyl chloride or alkylating agent and an appropriate SM.

| Ex | SM | Sulfonyl chloride/ alkylating agent | STRUCTURE | Analytical |
|---|---|---|---|---|
| 69 | F8 | 3-cyanobenzene-1-sulfonyl chloride | 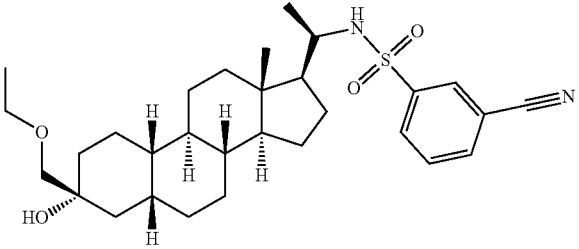 | 1H NMR (400 MHz, CDCl$_3$) δ$_H$ 8.17 (s, 1H), 8.11 (d, J = 8 Hz, 1H), 7.84 (d, J = 8 Hz, 1H), 7.65 (t, J = 8 Hz, 1H), 4.28 (d, J = 8.8 Hz, 1H), 3.53 (q, J = 6.8 Hz, 2H), 3.43 (q, J = 9.2 Hz, 3H), 2.73 (s, 1H), 2.00-1.97 (m, 1H), 1.84-1.65 (m, 3H), 1.63-1.50 (m, 7H), 1.47-1.30 (m, 5H), 1.29-1.12 (m, 5H), 1.09-0.87 (m, 9H), 0.57 (s, 3H). LC-ELSD/MS purity 99%, MS ESI calcd. for C$_{30}$H$_{44}$N$_2$O$_4$SNa [M + Na]$^+$ 551, found 551. |
| 70 | 69 | MeI | 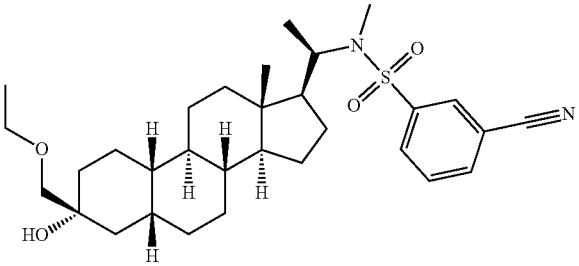 | $^1$H NMR (400 MHz, CDCl$_3$) δ$_H$ 8.11 (s, 1H), 8.05 (d, J = 8 Hz, 1H), 7.85 (d, J = 8 Hz, 1H), 7.65 (t, J = 8 Hz, 1H), 4.07-4.00 (m, 1H), 3.53 (q, J = 6.8 Hz, 2H), 3.43 (q, J = 9.2 Hz, 3H), 2.71-2.66 (m, 4H), 2.10-2.05 (m, 1H), 1.84-1.47 (m, 9H), 1.44-1.18 (m, 10H), 1.14-1.00 (m, 6H), 0.86 (s, 3H), 0.65 (d, J = 6.8 Hz, 3H). LC-ELSD/MS purity 99%, MS ESI calcd. for C$_{31}$H$_{45}$N$_2$O$_3$S [M + H – H$_2$O]$^+$ 525, found 525. |
| 71 | F8 | 6-cyanopyridine-2-sulfonyl chloride | 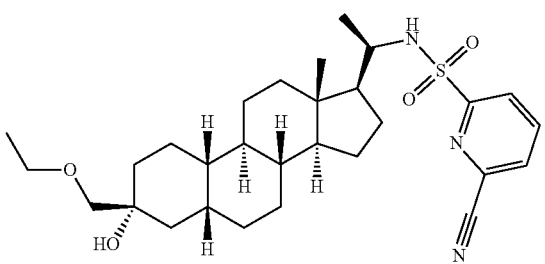 | $^1$H NMR (400 MHz, CDCl$_3$) δ$_H$ 8.23-8.19 (m, 1H), 8.10-8.05 (m, 1H), 7.87-7.83 (m, 1H), 4.63 (d, J = 9.2 Hz, 1H), 3.53 (q, J = 7.2 Hz, 3H), 3.47-3.39 (m, 2H), 2.23-2.16 (m, 1H), 1.87-1.57 (m, 9H), 1.49-1.30 (m, 8H), 1.21 (t, J = 6.8 Hz, 4H), 1.16-0.98 (m, 6H), 0.93 (d, J = 6.4 Hz, 3H), 0.69 (s, 3H). LC-ELSD purity 99%, MS ESI calcd. for C$_{29}$H$_{42}$N$_3$O$_4$S [M – H]$^+$ 528, found 528. |
| 72 | 71 | MeI | 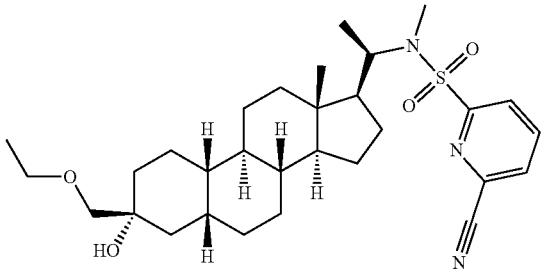 | $^1$H NMR (400 MHz, CDCl$_3$) δ$_H$ 8.20-8.17 (m, 1H), 8.09-8.04 (m, 1H), 7.85-7.82 (m, 1H), 4.13-4.05 (m, 1H), 3.56-3.50 (m, 2H), 3.47-3.39 (m, 2H), 2.84 (s, 3H), 2.73-2.67 (m, 1H), 2.15-2.08 (m, 1H), 1.87-1.74 (m, 3H), 1.68-1.56 (m, 4H), 1.49-1.25 (m, 9H), 1.21 (t, J = 6.8 Hz, 4H), 1.16-1.04 (m, 6H), 0.88-0.86 (m, 3H), 0.85 (s, 3H). LC-ELSD/MS purity 99%, MS ESI calcd. for C$_{30}$H$_{45}$N$_3$O$_4$SNa [M + Na]$^+$ 566, found 566. |

| Ex | SM | Sulfonyl chloride/ alkylating agent | STRUCTURE | Analytical |
|---|---|---|---|---|
| 73 | F8 | 5-cyanopyridine-2-sulfonyl chloride | 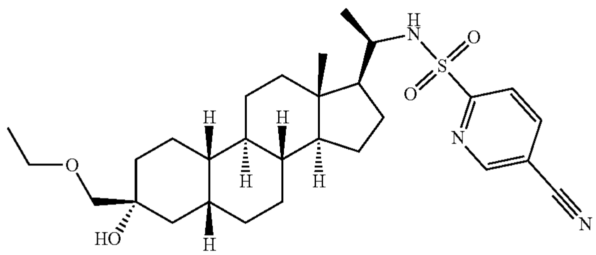 | ¹H NMR (400 MHz, CDCl₃) δ$_H$ 8.96 (dd, J = 0.8, 2.0 Hz, 1H), 8.22-8.17 (m, 1H), 8.16-8.10 (m, 1H), 4.62 (d, J = 9.2 Hz, 1H), 3.53 (q, J = 6.8 Hz, 3H), 3.49-3.36 (m, 2H), 2.73 (br s, 1H), 2.22-2.06 (m, 1H), 1.90-1.57 (m, 7H), 1.36 (br s, 8H), 1.21 (t, J = 7.2 Hz, 11H), 0.87 (d, J = 6.4 Hz, 3H), 0.65-0.65 (m, 1H), 0.69 (s, 2H). LC-ELSD/MS purity 99%, MS ESI calcd. for C₂₉H₄₂N₃O₃S [M − H₂O + H]⁺ 512.3 found 512.3. |
| 74 | 73 | MeI | 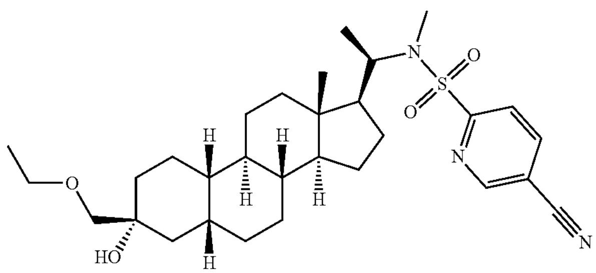 | ¹H NMR (400 MHz, CDCl₃) δ$_H$ 8.95 (s, 1H), 8.26-7.96 (m, 2H), 4.15-4.02 (m, 1H), 3.53 (q, J = 7.2 Hz, 2H), 3.48-3.37 (m, 2H), 2.83 (s, 3H), 2.71 (br s, 1H), 2.10 (br d, J = 11.6 Hz, 1H), 1.90-1.50 (m, 7H), 1.50-1.15 (m, 12H), 1.15-1.00 (m, 7H), 0.85 (s, 3H), 0.79 (br d, J = 6.8 Hz, 3H). LC-ELSD/MS purity 99%, MS ESI calcd. for C₃₀H₄₄N₃O₃S [M − H₂O + H]⁺ 526.3 found 526.3. |
| 75 | E2 | 6-cyanopyridine-2-sulfonyl chloride | 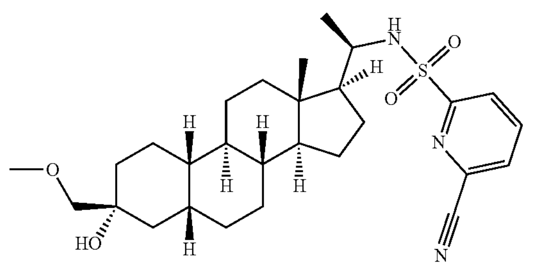 | ¹H NMR (400 MHz, CDCl₃) δ$_H$ 8.23-8.19 (m, 1H), 8.11-8.05 (m, 1H), 7.87-7.83 (m, 1H), 4.68-4.62 (m, 1H), 3.58-3.47 (m, 1H), 3.39 (s, 5H), 2.64-2.56 (m, 1H), 2.23-2.15 (m, 1H), 1.87-1.80 (m, 1H), 1.78-1.59 (m, 5H), 1.48-1.31 (m, 8H), 1.27-1.02 (m, 9H), 0.92 (d, J = 6.4 Hz, 3H), 0.69 (s, 3H). LC-ELSD purity 99%, MS ESI calcd. for C₂₈H₄₀N₃O₄S [M − H]⁺ 514, found 514. |

Example 76: Synthesis of 2-((3R,5R,8R,9R,10S,13R,14S,17R)-3-hydroxy-3,13-dimethylhexadecahydro-1H-cyclopenta[a]phenanthren-17-yl)-N-phenylacetamide (76)

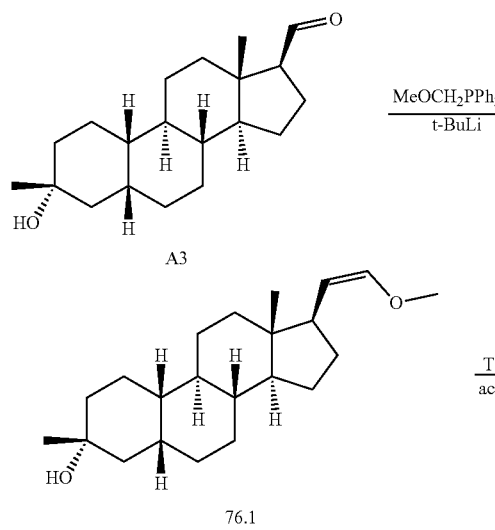
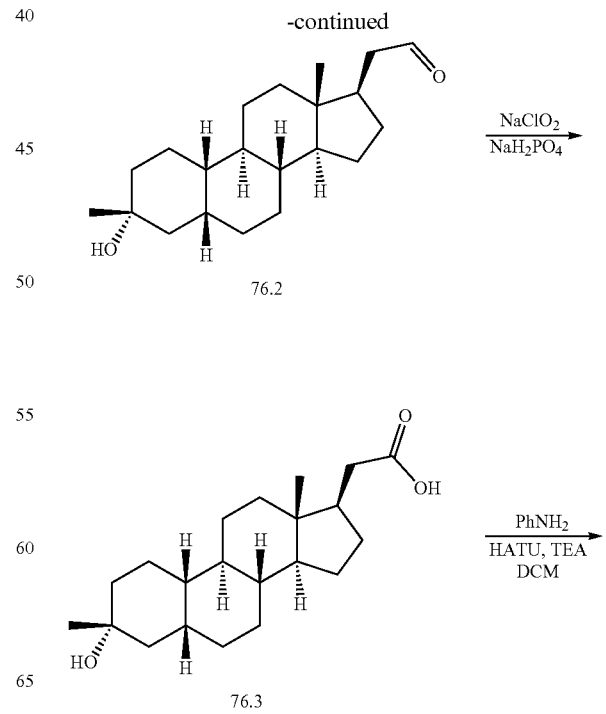

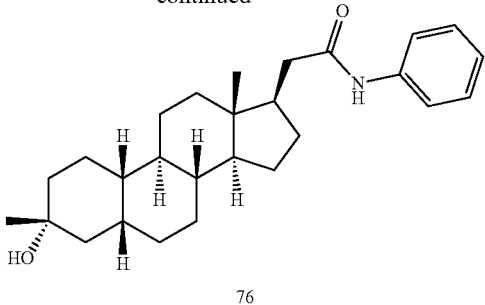

76

Synthesis of 76.1

To a solution of bromo (methoxymethyl) triphenyl-λ⁵-phosphane (3.81 g, 9.8 mmol) in THF (20 mL) was added tert-butyllithium (7.5 mL, 9.8 mmol, 2.5 M in n-hexane) at 0° C. After stirring at 0° C. for 1 h, A3 (1 g, 3.3 mmol) in THF (10 mL) was added at 0° C. After stirred at 15° C. for 1 h, the mixture was treated with NH₄Cl (20 mL, 10%) and extracted with EtOAc (2×40 mL). The combined organic phase was washed with brine (40 mL), dried over anhydrous Na₂SO₄, filtered and concentrated. The residue was purified by flash column (0~13% of EtOAc in PE) to give 76.1 (840 mg, 77.0%) as an oil.

¹H NMR (400 MHz, CDCl3) δ$_H$ 6.22 (d, J=12.4 Hz, 0.6H), 5.93 (d, J=6.4 Hz, 0.4H), 4.67-4.60 (m, 0.6H), 4.27-4.22 (m, 0.4H), 3.53 (d, J=10.0 Hz, 3H), 1.80 (br s, 5H), 1.68-1.59 (m, 4H), 1.49-1.21 (m, 16H), 1.19-0.91 (m, 7H), 0.59 (d, J=5.2 Hz, 3H).

Synthesis of 76.2

To a solution 76.1 (840 g, 2.5 mmol) in acetone (15 mL) was added TsOH (6.50 g, 37.8 mmol) at 15° C. After stirring at 15° C. for 10 mins, the mixture was poured into water (20 mL) and extracted with DCM (2×40 mL). The combined organic phase was washed with NaHCO₃ (20 mL), brine (20 mL), dried over anhydrous Na₂SO₄, filtered and concentrated. The residue was purified by flash column (0~15% of EtOAc in PE) to give 76.2 (550 mg, 27.6%) as a solid ¹H NMR (400 MHz, CDCl₃) δ$_H$ 9.76 (t, J=2.4 Hz, 1H), 2.52-2.44 (m, 1H), 2.28-2.18 (m, 1H), 1.99-1.76 (m, 5H), 1.70-1.60 (m, 4H), 1.50-1.36 (m, 6H), 1.33-1.23 (m, 8H), 1.17-1.01 (m, 6H), 0.93-0.78 (m, 2H), 0.60 (s, 3H).

Synthesis of 76.3

To a solution of 76.2 (550 mg, 1.7 mmol) in acetone (7.5 mL) and 2-methyl-2-butene (2 mL) was added dropwise aqueous NaH₂PO₄ (1.03 g, 8.6 mmol) and NaClO₂ (777 mg, 8.6 mmol) in water (5 mL) at 0° C. After stirring at 15° C. for 2 h, the resulting colorless solution was poured into water (20 mL) and filtered. The filter cake was washed with water (50 mL) and concentrated to afford 76.3 (390 mg, 67.8%) as a solid.

¹H NMR (400 MHz, CDCl₃) δ$_H$ 2.45-2.34 (m, 1H), 2.17-2.08 (m, 1H), 2.00-1.75 (m, 5H), 1.71-1.58 (m, 4H), 1.26 (s, 19H), 0.60 (s, 3H).

Synthesis of 76

To a solution of 76.3 (150 mg, 0.45 mmol) in DCM (3 mL) was added HATU (340 mg, 0.9 mmol), TEA (225 mg, 2.2 mmol) and aniline (83.4 mg, 0.9 mmol) at 25° C. After stirring at 25° C. for 16 h, the mixture was poured into water (15 mL), the aqueous phase was extracted with EtOAc (2×30 mL). The combined organic phase was washed with brine (20 mL), dried over anhydrous Na₂SO₄, filtered and concentrated. The residue was triturated from MeCN (5 mL) at 15° C., then washed with HCl (5 ml) and NaHCO₃ (5 ml) to give 76 (130 mg, 71.0%) as a solid.

¹H NMR (400 MHz, CDCl3) δ$_H$ 7.50 (br d, J=8.0 Hz, 2H), 7.32 (t, J=7.6 Hz, 2H), 7.13-7.06 (m, 2H), 2.45 (dd, J=4.8, 14.0 Hz, 1H), 2.17-2.09 (m, 1H), 2.05-1.72 (m, 6H), 1.70-1.63 (m, 3H), 1.50-1.24 (m, 14H), 1.18-1.00 (m, 6H), 0.64 (s, 3H). LCMS Rt=1.189 min in 2 min chromatography, 30-90AB_2 min_E.M (Mobile Phase: 1.5 mL/4LTFA in water (solvent A) and 0.75 mL/4LTFA in acetonitrile (solvent B), using the elution gradient 30%-90% (solvent B) over 0.9 minutes and holding at 90% for 0.6 minutes at a flow rate of 1.2 mL/min; Column: Xtimate C18 2.1*30 mm, 3 □m; Wavelength: UV 220 nm; Column temperature: 50° C.; MS ionization: ESI; Detector: PDA&ELSD), purity 99%, MS ESI calcd for C₂₇H₄₀NO₂ [M+H]⁺ 410, found 410.

Examples 77 & 78: Synthesis of 5-cyano-N-((R)-1-((3R,5R,8R,9S,10S,13S,14S,17S)-3-(ethoxymethyl)-3-hydroxy-10,13-dimethylhexadecahydro-1H-cyclopenta[a]phenanthren-17-yl)ethyl)-N-methylpyridine-2-sulfonamide (77) & 5-cyano-N-((R)-1-((3R,5R,8R,9S,10S,13S,14S,17S)-3-(ethoxymethyl)-3-hydroxy-10,13-dimethylhexadecahydro-1H-cyclopenta[a]phenanthren-17-yl)ethyl)pyridine-2-sulfonamide (78)

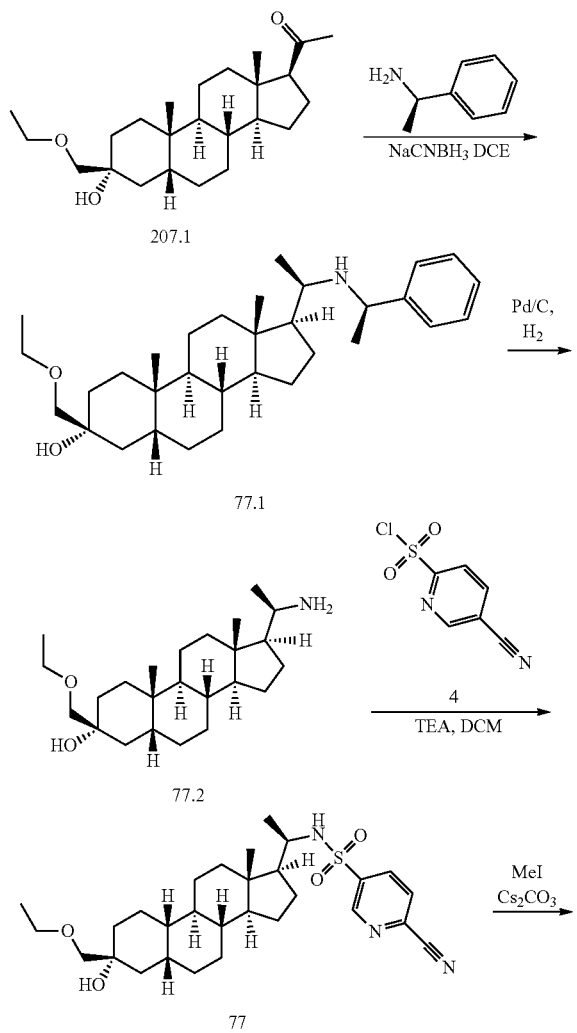

311

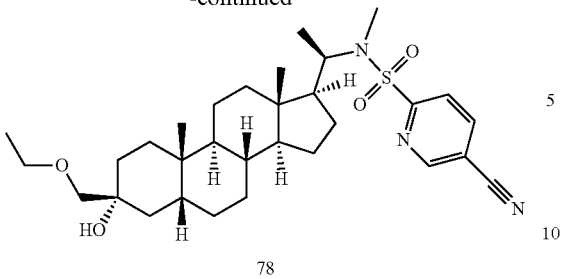

78

Synthesis of 77.1

To a solution of 207.1 (3.6 g, 9.92 mmol) and (1R)-1-phenylethan-1-amine (7.21 g, 59.4 mmol) in DCE (40 mL) at 25° C. under $N_2$, then $NaCNBH_3$ (4.91 g, 79.3 mmol) was added. After stirring at 50° C. for 16 h, the reaction was quenched with water (50 mL), extracted with DCM (2×50 mL). The combined organic phase was washed with 10% HCl (2×100 mL), saturated $NaHCO_3$ (100 mL), brine (100 mL), dried over $Na_2SO_4$, filtered and concentrated to give 77.1 (5 g) as oil.

Synthesis of 77.2

To a solution of 77.1 (2.5 g, 5.18 mmol) in EtOH (50 mL) was added Pd—C(dry, 500 mg) and one drop $NH_3H_2O$. The mixture was stirred under $H_2$ (50 psi) at 50° C. for 48 h to give a suspension. The reaction mixture was filtered through a pad of Celite and washed with EtOH (3×50 mL). The filtrate was concentrated. The residue was purified by flash column (0-5% of MeOH in DCM) to give 77.2 (1.3 g, 66.6%) as oil.

$^1$H NMR (400 MHz, $CDCl_3$) $\delta_H$ 3.53 (q, J=7.0 Hz, 2H), 3.46-3.35 (m, 2H), 2.90-2.76 (m, 1H), 2.01-1.64 (m, 6H), 1.61-1.34 (m, 11H), 1.32-0.97 (m, 15H), 0.93 (s, 3H), 0.70 (s, 3H).

Synthesis of 77

To a solution of 77.2 (300 mg, 0.794 mmol) and 5-cyanopyridine-2-sulfonyl chloride (320 mg, 1.58 mmol) in DCM (10 mL) was added TEA (801 mg, 7.94 mmol) at 15° C. to give a solution. After 15 mins, the mixture was poured into water (30 mL), stirred for 20 mins, and then extracted with DCM (3×20 mL). The combined organic phase was washed with brine (2×50 mL), dried over anhydrous $Na_2SO_4$, filtered and concentrated. The residue was purified by flash column (0~20% of EtOAc in PE) to give 77 (58 mg, 13.4%) as a solid.

$^1$H NMR (400 MHz, $CDCl_3$) $\delta_H$ 8.96 (s, 1H), 8.22-8.16 (m, 1H), 8.15-8.10 (m, 1H), 4.63 (d, J=9.1 Hz, 1H), 3.59-3.48 (m, 3H), 3.47-3.36 (m, 2H), 2.74 (s, 1H), 2.17 (br d, J=11.4 Hz, 1H), 1.97-1.59 (m, 5H), 1.51-1.28 (m, 8H), 1.25-0.97 (m, 12H), 0.93 (s, 3H), 0.86 (d, J=6.3 Hz, 3H), 0.68 (s, 3H). LC-ELSD/MS purity 99%, MS ESI calcd. for $C_{30}H_{44}N_3O_3S$ $[M+H-H_2O]^+$ 526.3 found 526.3.

Synthesis of 78

To a solution of 77 (100 mg, 0.184 mmol) in DMF (3 mL) was added MeI (65.2 mg, 0.459 mmol) and $Cs_2CO_3$ (120 mg, 0.367 mmol). After stirring at 25° C. for 16 h, the mixture was poured into water (20 mL) and extracted with EtOAc (2×20 mL). The combined organic phase was washed with brine (20 mL), dried over anhydrous $Na_2SO_4$, filtered and concentrated. The residue was purified by flash column (0~20% of EtOAc in PE) to give 78 (22.2 mg, 21.7%) as a solid. $^1$H NMR (400 MHz, $CDCl_3$) $\delta_H$ 8.95 (s, 1H), 8.21-8.14 (m, 1H), 8.12-8.03 (m, 1H), 4.23-3.91 (m, 1H), 3.53 (q, J=6.9 Hz, 2H), 3.48-3.33 (m, 2H), 2.82 (s, 3H), 2.72 (s, 1H), 2.11 (br d, J=12.3 Hz, 1H), 1.99-1.78 (m, 2H), 1.76-1.58 (m, 4H), 1.38 (br d, J=13.1 Hz, 8H), 1.21 (br t, J=6.9 Hz, 9H), 0.94 (s, 3H), 0.84 (s, 3H), 0.79 (d, J=6.5 Hz, 3H).

LC-ELSD/MS purity 99%, MS ESI calcd. for $C_{31}H_{46}N_3O_3S$ $[M+H-H_2O]^+$ 540.3 found 540.3.

Examples 87 & 88: Synthesis of 1-(2-((3R,5R,8R,9R,10S,13R,14S,17R)-3-hydroxy-3-(methoxymethyl)-13-methylhexadecahydro-1H-cyclopenta[a]phenanthren-17-yl)ethyl)-1H-pyrazole-3-carbonitrile (87) & 1-(2-((3R,5R,8R,9R,10S,13R,14S,17R)-3-hydroxy-3-(methoxymethyl)-13-methylhexadecahydro-1H-cyclopenta[a]phenanthren-17-yl)ethyl)-1H-pyrazole-5-carbonitrile (88)

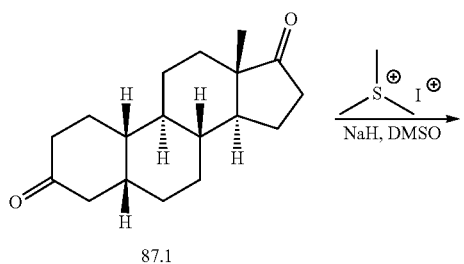

87.1

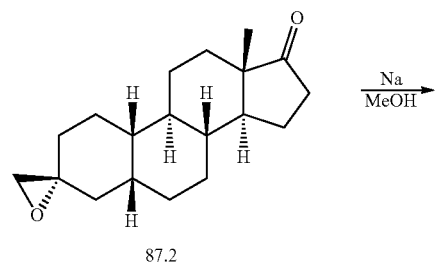

87.2

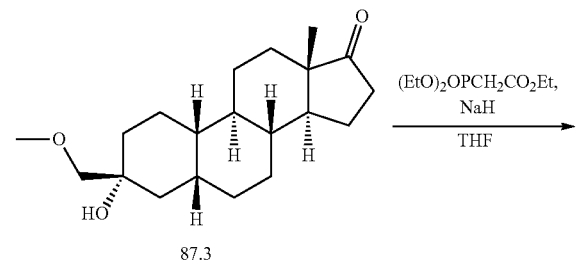

87.3

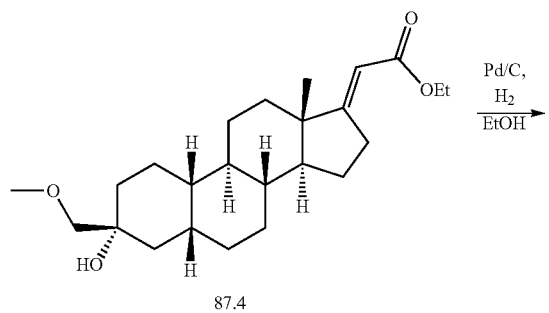

87.4

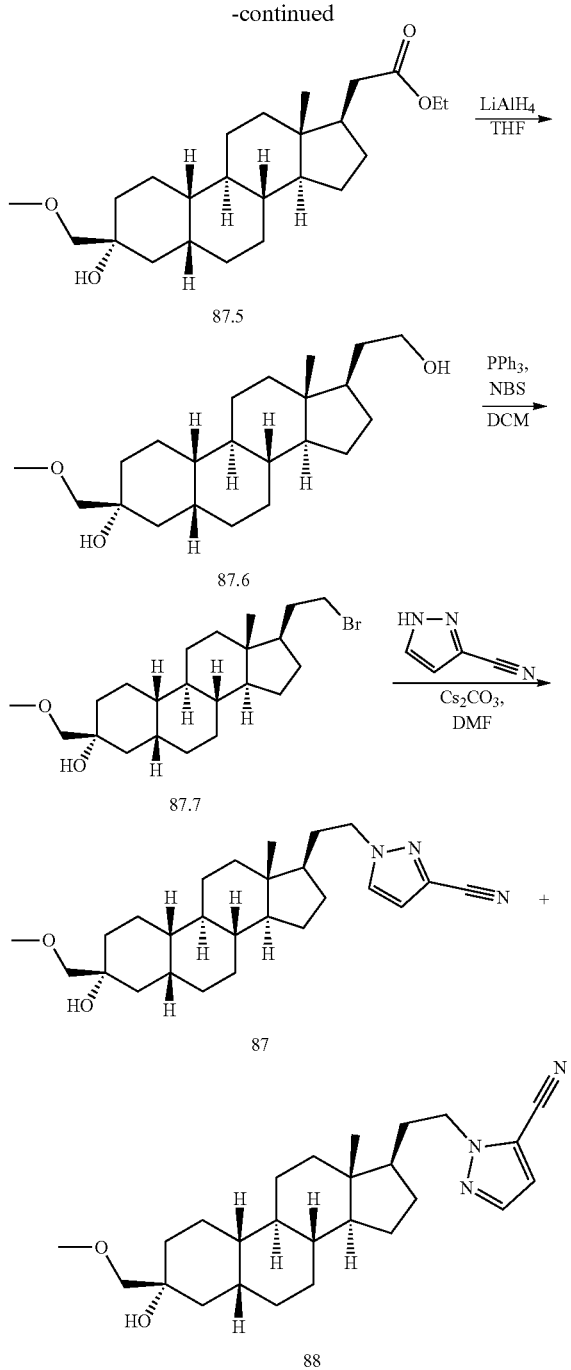

¹H NMR (400 MHz, CDCl₃) δ 2.67-2.37 (m, 2H), 2.28-2.13 (m, 2H), 2.12-2.04 (m, 1H), 1.99-1.89 (m, 1H), 1.88-1.72 (m, 4H), 1.70-1.60 (m, 2H), 1.58-1.43 (m, 5H), 1.41-1.04 (m, 8H), 0.92-0.82 (m, 3H)

Synthesis of 87.3

Na (21.5 g, 935 mmol) was added into MeOH (250 mL) at 25° C. in portions. After stirring at 25° C. for 2 h under N₂, 87.2 (45 g, 156 mmol) in MeOH (150 mL) was added. After stirring at 75° C. for 12 h, the resulting solution was cooled to 25° C. and poured into water (400 mL). The aqueous phase was extracted with EtOAc (3×400 mL). The combined organic phase was washed with brine (2×200 mL), dried over anhydrous Na₂SO₄, filtered and concentrated. The residue was purified by flash column (0~15% of EtOAc in PE) to give 87.3 (30 g) as an oil and C₃ epimer (12 g, 24.0%) as a solid. 87.3 was re-purified by flash column [0~5% of EtOAc in PE and DCM (1:1)] to give 87.3 (9 g, 30%) as an oil.

¹H NMR (400 MHz, CDCl₃) δ 3.47-3.31 (m, 5H), 2.42 (dd, J=8.4, 19.2 Hz, 1H), 2.12-2.02 (m, 1H), 1.96-1.89 (m, 1H), 1.86-1.67 (m, 6H), 1.60-1.41 (m, 7H), 1.38-1.17 (m, 7H), 1.10-1.00 (m, 1H), 0.85 (s, 3H).

Synthesis of 87.4

To a stirred solution of NaH (2.05 g, 51.4 mmol, 60% in oil) in THF (40 mL) were added ethyl 2-(diethoxyphosphanyl (8.73 g, 39.0 mmol) at 25° C. for 10 mins under N₂ followed by 87.3 (5 g, 15.6 mmol). After stirring at 65° C. for 12 h, the mixture was cooled to room temperature and concentrated. The residue was poured into ice-water (v/v=1/1) (50 mL), stirred for 20 mins and extracted with EtOAc (3×100 mL). The combined organic phase was washed with brine (2×100 mL), dried over anhydrous Na₂SO₄, filtered and concentrated. The residue was purified by flash column (0~50% of EtOAc in PE) to give 87.4 (280 mg, 4.6%) as an oil.

¹H NMR (400 MHz, CDCl₃) δ_H 5.52 (t, J=2.4 Hz, 1H), 4.20-4.09 (m, 2H), 3.46-3.35 (m, 6H), 2.82 (dt, J=3.1, 6.0 Hz, 2H), 2.67-2.54 (m, 1H), 1.89-1.73 (m, 7H), 1.66-1.56 (m, 5H), 1.36-1.22 (m, 9H), 0.98-0.84 (m, 2H), 0.81 (s, 3H).

Synthesis of 87.5

To a solution of 87.4 (280 mg, 0.71 mmol) in EtOH (10 mL) was added Pd/C (wet, 10%, 600 mg) under N₂. The suspension was degassed under vacuum and purged with H₂ for three times. After stirring under H₂ (15 psi) at 25° C. for 12 h, the resulting suspension was filtered through a pad of Celite and washed with EtOH (3×10 mL). The filtrate was concentrated to give 87.5 (250 mg, 96%) as an oil.

¹H NMR (400 MHz, CDCl₃) δ_H 4.11 (q, J=6.8 Hz, 2H), 3.72 (q, J=6.8 Hz, 2H), 3.42-3.37 (m, 5H), 2.35 (dd, J=4.8, 14.4 Hz, 1H), 2.09 (dd, J=9.8, 14.4 Hz, 1H), 1.83-1.74 (m, 4H), 1.69-1.56 (m, 5H), 1.45-1.34 (m, 6H), 1.27-1.22 (m, 6H), 1.12-1.04 (m, 4H), 0.59 (s, 3H).

Synthesis of 87.6

To a solution of 87.5 (250 mg, 0.63 mmol) in THF (5 mL) was added LiAlH₄ (36.2 mg, 0.95 mmol) in one portion at 20° C. under N₂. After stirring at 20° C. for 12 h, H₂O (2 ml) was added to the resulting gray suspension and the mixture was acidified with 1 M HCl to pH ~5. The aqueous phase was extracted with EtOAc (3×10 mL). The combined organic phase was washed with brine (2×20 mL), dried over anhydrous Na₂SO₄, filtered and concentrated. The residue was purified by flash column (0~50% of EtOAc in PE) to give 87.6 (200 mg, 90%) as a solid.

¹H NMR (400 MHz, CDCl₃) δ_H 4.72 (d, J=3.2 Hz, 1H), 4.68 (d, J=2.4 Hz, 1H), 3.72-3.57 (m, 2H), 3.46-3.33 (m, 6H), 2.76-2.44 (m, 1H), 1.93-1.74 (m, 5H), 1.69-1.52 (m, 7H), 1.46-1.33 (m, 7H), 1.16-1.03 (m, 5H), 0.59 (s, 3H).

Synthesis of 87.2

To a solution of NaH (8.00 g, 60%, 200 mmol) in DMSO (100 mL) was added a solution of trimethylsulfonium iodide (40.7 g, 200 mmol) in THF (100 mL) dropwise at 0° C. over 30 mins under N₂. The resulting mixture was added into a solution of 87.1 (50 g, 182 mmol) in DMSO (100 mL). After stirring at 25° C. for 12 h, the resulting suspension was poured into ice-water (v/v=1/1) (400 mL), stirred for 20 mins and extracted with EtOAc (3×400 mL). The combined organic phase was washed with brine (2×200 mL), dried over anhydrous Na₂SO₄, filtered and concentrated. The residue was triturated from MeOH (300 mL) at 25° C. to give 87.2 (45 g) as a solid.

Synthesis of 87.7

To a solution of 87.6 (200 mg, 0.57 mmol) in DCM (5 mL) at 0° C. was added PPh₃ (179 mg, 0.68 mmol) and NBS (116 mg, 0.68 mmol). After stirring at 20° C. for 12 h, the resulting solution was poured into water (20 mL) and extracted with EtOAc (3×30 mL). The combined organic phase was washed with brine (2×20 mL), dried over anhydrous Na₂SO₄, filtered and concentrated. The residue was purified by flash column (0~15% of EtOAc in PE) to give 87.7 (120 mg, 51%) as an oil.

¹H NMR (400 MHz, CDCl₃) $\delta_H$ 3.49-3.29 (m, 6H), 2.58 (s, 1H), 1.96-1.75 (m, 4H), 1.60-1.50 (m, 9H), 1.45-1.04 (m, 14H), 0.59 (s, 3H).

Synthesis of 87 & 88

To a solution of 87.7 (120 mg, 0.2902 mmol) in DMF (5 mL) were added Cs₂CO₃ (190 mg, 0.5804 mmol) and 1H-pyrazole-3-carbonitrile (54 mg, 0.5804 mmol) at 25° C. After stirring at 85° C. for 12 h, the resulting mixture was cooled to 25° C., poured into water (10 mL). and extracted with EtOAc (3×10 mL). The combined organic phase was washed with brine (2×20 mL), dried over anhydrous Na₂SO₄, filtered and concentrated. The residue was purified by flash column (0~50% of EtOAc in PE) to give 87 (48.4 mg, 39%) as a solid and 88, which was further purified by SFC (Column: DAICEL CHIRALCEL OD-H (250 mm*30 mm, 5 um), Flow Rate (mL/min): 40) to afford 87 (4.1 mg, 3.3%) as a solid.

87: ¹H NMR (400 MHz, CDCl₃) $\delta_H$ 7.44 (d, J=2.4 Hz, 1H), 6.65 (d, J=2.4 Hz, 1H), 4.23-4.07 (m, 2H), 3.43-3.34 (m, 5H), 2.59 (brs, 1H), 2.04-1.94 (m, 1H), 1.88-1.73 (m, 4H), 1.67-1.56 (m, 9H), 1.50-1.35 (m, 5H), 1.28-1.18 (m, 3H), 1.09-0.96 (m, 4H), 0.60 (s, 3H). LC-ELS/MS purity 99%, MS ESI calcd. for C₂₆H₃₉N₃O₂Na [M+Na]⁺ 448.3, found 448.3.

88: ¹H NMR (400 MHz, CDCl₃) $\delta_H$ 7.56 (d, J=2.4 Hz, 1H), 6.77 (d, J=2.0 Hz, 1H), 4.37-4.21 (m, 2H), 3.46-3.34 (m, 5H), 2.57 (brs, 1H), 2.15-2.01 (m, 1H), 1.92-1.73 (m, 4H), 1.72-1.61 (m, 6H), 1.49-1.36 (m, 5H), 1.30-1.17 (m, 4H), 1.15-0.94 (m, 6H), 0.60 (s, 3H). LC-ELSD/MS purity 99%, MS ESI calcd. for C₂₆H₄₀N₃O₂ [M+H]⁺ 426.3, found 426.3.

Example 89: 1-(2-((3R, 5R, 8R, 9R, 10S, 13R, 14S, 17R)-3-hydroxy-3, 13-dimethylhexadecahydro-1H-cyclopenta[a]phenanthren-17-yl) ethyl)-1H-pyrazole-4-carbonitrile

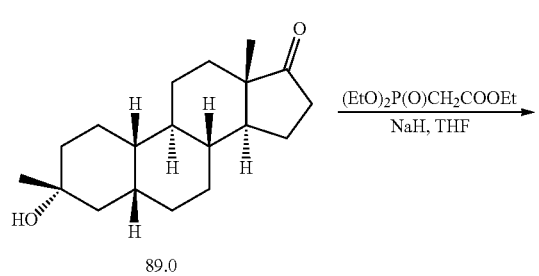

89.0

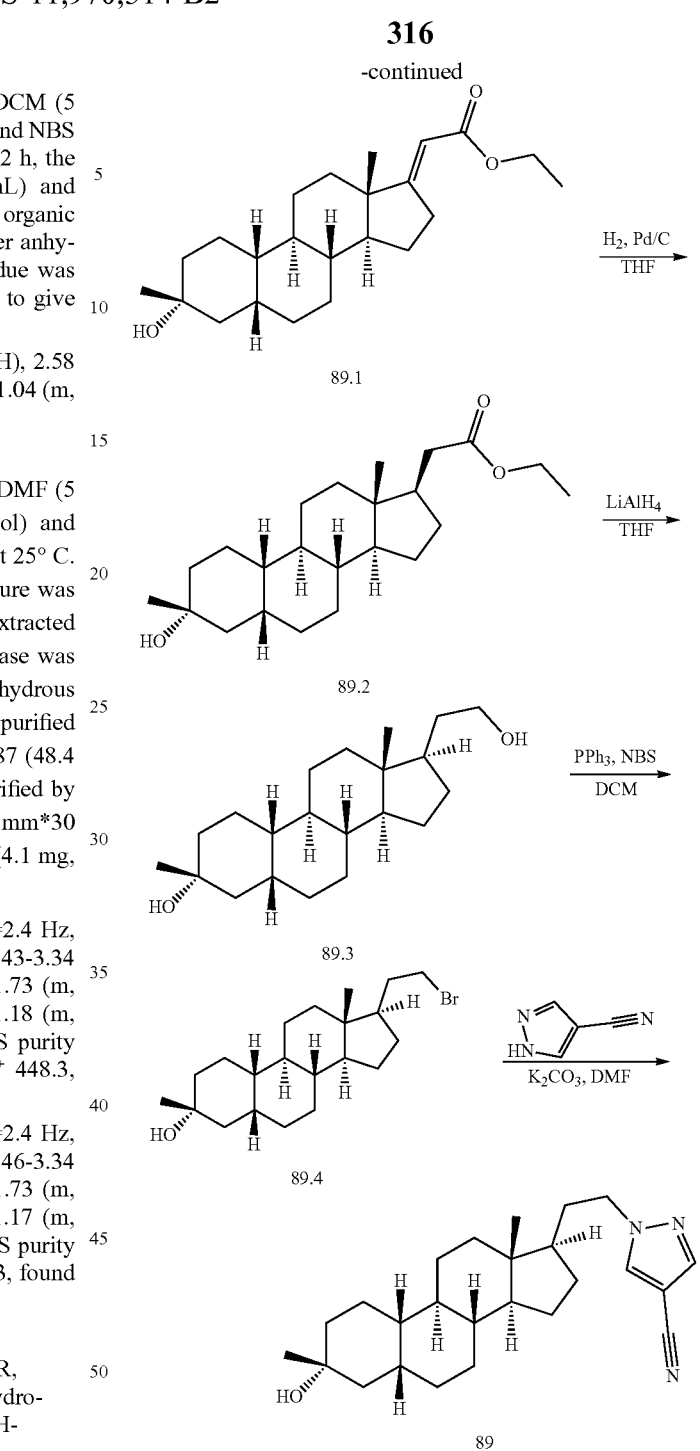

Synthesis of 89.1

To a suspension of NaH (2.75 g, 60%, 68.8 mmol) in THF (60 mL) was added (EtO)₂P(O)CH₂COOEt (15.4 g, 68.8 mmol) dropwise at 0° C. After stirring at 20° C. for 10 min, a solution of 89.0 (10 g, 34.4 mmol) in THF (20 mL) was added dropwise at 20° C. After stirring at 70° C. for 16 h, the reaction mixture was poured into NH₄Cl (200 mL, 10% aq) and extracted with EtOAc (200 mL). The organic layer was separated, dried over Na₂SO₄, filtered, concentrated. The residue was purified by flash column (0-20% EtOAc in PE) to give 89.1 (12 g, 97%) as an oil. ¹H NMR (400 MHz, CDCl₃) $\delta_H$ 5.52 (t, J=2.4 Hz, 1H), 4.15 (q, J=7.2 Hz, 2H), 2.90-2.75 (m, 2H), 1.95-1.60 (m, 5H), 1.50-1.25 (m, 18H), 1.20-1.05 (m, 4H), 0.82 (s, 3H).

Synthesis of 89.2

To a solution of 89.1 (12 g, 33.2 mmol) in THF (150 mL) was added Pd/C (2 g, dry, 10%) under N$_2$. After stirring under H$_2$ (40 psi) at 40° C. for 24 h, the reaction mixture was filtered through a pad of celite which was then washed with THF (3×50 mL). The combined filtrate was concentrated to give 89.2 (11.7 g, 97.5%) as an oil. $^1$H NMR (400 MHz, CDCl$_3$) δ$_H$ 4.11 (q, J=6.8 Hz, 2H), 2.35 (dd, J=5.2, 14.4 Hz, 1H), 2.10 (dd, J=10.0, 14.8 Hz, 1H), 2.00-1.75 (m, 6H), 1.70-1.50 (m, 3H), 1.50-1.35 (m, 6H), 1.35-1.25 (m, 10H), 1.20-0.95 (m, 6H), 0.59 (s, 3H).

Synthesis of 89.3

To a suspension of LiAlH$_4$ (6.0 g, 158 mmol) in THF (120 mL) was added a solution of 89.2 (11.1 g, 30.6 mmol) in THF (30 mL) at 0° C. under N$_2$. After stirring at 0° C. for 10 min, to the mixture was added water/THF (6 mL/200 mL) dropwise followed by NaOH (6 mL, 10% aq.) and water (18 mL). The mixture was filtered and the precipitate was washed with THF (3×100 mL). The combined filtrate was concentrated and triturated in DCM (50 mL) to give 89.3 (9 g, 92%) as a solid.

$^1$H NMR (400 MHz, CDCl$_3$) δ$_H$ 3.75-3.55 (m, 2H), 1.90-1.60 (m, 9H), 1.50-1.15 (m, 16H) 1.15-0.90 (m, 6H), 0.59 (s, 3H).

Synthesis of 89.4

To a solution of 89.3 (300 mg, 0.935 mmol) in DCM (8 mL) at 0° C. was added PPh$_3$ (487 mg, 1.86 mmol) and NBS (331 mg, 1.86 mmol). After stirring at 25° C. for 3 h to give a solution, the mixture was poured into water (20 mL) and extracted with DCM (3×20 mL). The combined organic phase was washed with brine (2×50 mL), dried over anhydrous Na$_2$SO$_4$, filtered and concentrated. The residue was purified by flash column (0~30% of EtOAc in PE) to give 89.4 (310 mg) as oil.

$^1$H NMR (400 MHz, CDCl$_3$) δ$_H$ 3.49-3.41 (m, 1H), 3.37-3.27 (m, 1H), 2.02-1.91 (m, 1H), 1.89-1.78 (m, 4H), 1.74-1.61 (m, 6H), 1.49-1.35 (m, 7H), 1.34-1.28 (m, 2H), 1.26 (s, 3H), 1.23-1.18 (m, 1H), 1.15-1.02 (m, 6H), 0.59 (s, 3H).

Synthesis of 90

To a solution of 89.4 (310 mg, 0.808 mmol) in DMF (5 mL) were added 1H-pyrazole-4-carbonitrile (222 mg, 1.61 mmol) and K$_2$CO$_3$ (75.2 mg, 0.808 mmol). After stirring at 50° C. for 16 h, the mixture was treated with water (20 mL) and extracted with EtOAc (2×20 mL). The combined organic phase was washed with brine (20 mL), dried over anhydrous Na$_2$SO$_4$, filtered and concentrated. The residue was purified by flash column (0~30% of EtOAc in PE) to give 90 (200 mg, 62.6%) as a solid.

1H NMR (400 MHz, CDCl$_3$) δ$_H$ 7.79 (s, 1H), 7.78 (s, 1H), 4.22-4.04 (m, 2H), 2.05-1.97 (m, 1H), 1.89-1.76 (m, 4H), 1.72-1.59 (m, 6H), 1.50-1.28 (m, 8H), 1.26 (s, 5H), 1.23-1.20 (m, 1H), 1.09-0.96 (m, 5H), 0.60 (s, 3H). LC-ELSD/MS purity >99%, MS ESI calcd. for C$_{25}$H$_{37}$N$_3$O [M−H$_2$O+H]$^+$ 378.3, found 378.3.

Example 90: Synthesis of 6-(((R)-1-((3R,5R,8R,9R, 10S,13S,14S,17S)-3-hydroxy-13-methyl-3-propyl-hexadecahydro-1H-cyclopenta[a]phenanthren-17-yl) ethyl)amino)nicotinonitrile (90)

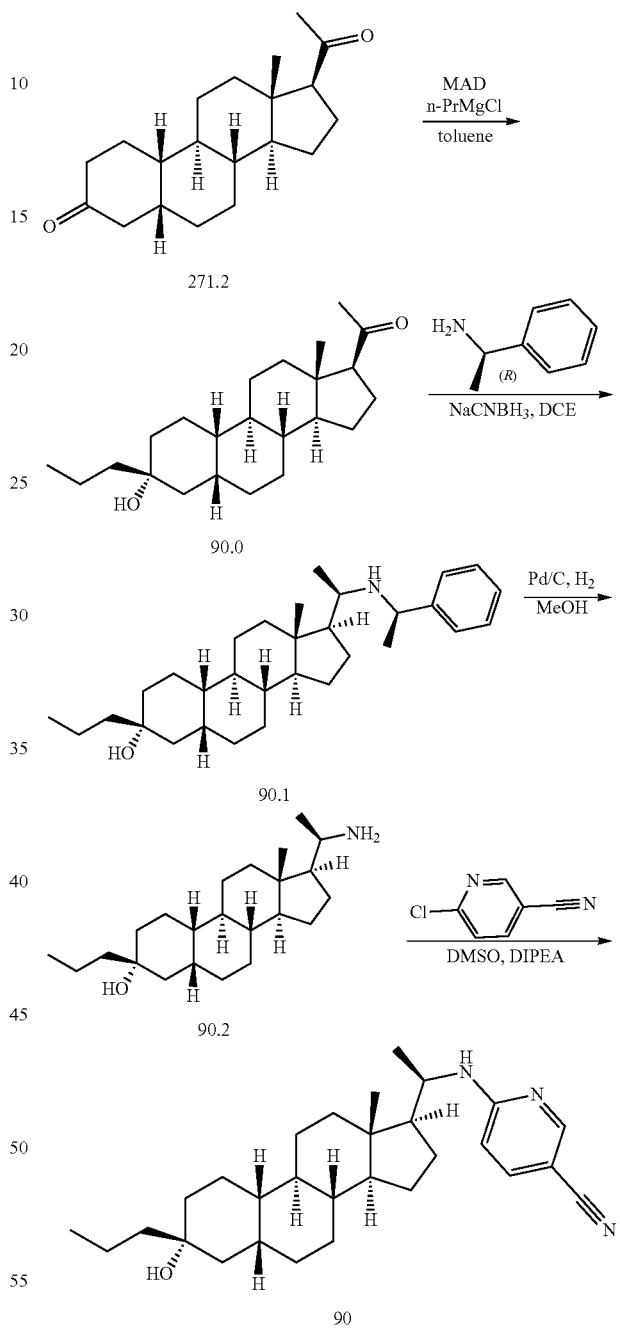

Synthesis of 90.0

To a solution of 2,6-di-tert-butyl-4-methylphenol (13.1 g, 59.6 mmol) in toluene (20 mL) was added AlMe$_3$ (14.9 mL, 29.8 mmol, 2 M in toluene) dropwise at 0° C. After stirring at 25° C. for 30 min. To the MAD solution was added a solution of 271.2 (3 g, 9.91 mmol) in anhydrous toluene (40 mL) dropwise at −70° C. After stirring at −70° C. for 1 h under N$_2$, n-PrMgCl (14.8 mL, 29.7 mmol, 2 M in diethyl ether) was added drop wise at −70° C. The resulting solution was stirred at −70° C. for another 2 h to give a solution. The reaction mixture was poured into saturated aqueous citric acid (100 mL) at below 10° C. and extracted with EtOAc (2×100 mL). The combined organic layer was dried over Na$_2$SO$_4$, filtered and concentrated in vacuum. The product was purified by flash column (0~10% of EtOAc in PE) to give 90.0 (1.7 g, 49%) as a solid.

$^1$H NMR (400 MHz, CDCl$_3$) δ$_H$ 2.53 (t, J=8 Hz, 1H), 2.16-2.11 (m, 4H), 2.04-1.98 (m, 1H), 1.83-1.52 (m, 3H), 1.50-1.30 (m, 5H), 1.27-1.02 (m, 10H), 0.97-0.77 (m, 11H), 0.61 (s, 3H).

Synthesis of 90.1

To a solution of 90.0 (1.8 g, 5.2 mmol) and (1R)-1-phenylethan-1-amine (3.76 g, 31.1 mmol) in DCE (30 mL) at 20° C. was added NaBH$_3$CN (2.6 g, 41.5 mmol) at 20° C. The suspension was stirred at 50° C. for 16 h. The reaction was quenched with water (50 mL), extracted with DCM (2×50 mL). The combined organic phase was washed with brine (50 mL), dried over Na$_2$SO$_4$, filtered and concentrated under vacuum to give the product, which was purified by flash column (0~30% of EtOAc in PE) to give 90.1 (2.7 g) as oil.

$^1$H NMR (400 MHz, CDCl$_3$) δ$_H$ 7.37-7.28 (m, 4H), 7.24-7.17 (m, 1H), 3.89 (q, J=6.4 Hz, 1H), 2.76-2.64 (m, 1H), 2.22 (d, J=12.4 Hz, 1H), 1.87-1.50 (m, 10H), 1.49-1.32 (m, 9H), 1.30-1.21 (m, 7H), 1.16-1.01 (m, 6H), 0.93 (t, J=7.3 Hz, 3H), 0.88 (d, J=6.0 Hz, 3H), 0.78 (s, 3H).

Synthesis of 90.2

To a solution of 90.1 (2.7 g, 5.97 mmol) and Pd/C (300 mg, 10% Palladium on carbon, 10% water dry) in MeOH (50 mL) at 20° C. was hydrogenated under 50 psi of hydrogen at 50° C. for 16 h. The reaction mixture was filtered through a pad of Celite and washed with MeOH (3×100 mL). The filtrate was concentrated to give 90.2 (1.4 g, 67.6%) as a solid.

$^1$H NMR (400 MHz, CDCl$_3$) δ$_H$ 2.91-2.77 (m, 1H), 2.01-1.92 (m, 1H), 1.80-1.51 (m, 10H), 1.49-1.27 (m, 12H), 1.23-1.04 (m, 8H), 1.00 (d, J=6.4 Hz, 3H), 0.93 (t, J=7.2 Hz, 3H), 0.73 (s, 3H).

Synthesis of 90

To a solution of 90.2 (100 mg, 0.3 mmol) in DMSO (3 mL) at 20° C. under N$_2$ were added 6-chloropyridine-3-carbonitrile (79.6 mg, 0.6 mmol) and DIPEA (74.3 mg, 0.6 mmol). After stirring at 120° C. for 16 h, the mixture was extracted with EtOAc (3×50 mL). The combined organic phase was washed with water (3×20 mL), brine (50 mL), dried over anhydrous Na$_2$SO$_4$, filtered and concentrated in vacuum. The residue was purified by flash column (10%-30% of EtOAc in PE) to give 90 (88.7 mg, 68.7%) as a solid.

$^1$H NMR (400 MHz, CDCl$_3$) δ$_H$ 8.34 (d, J=2.0 Hz, 1H), 7.53 (d, J=8.8 Hz, 1H), 6.29 (d, J=9.2 Hz, 1H), 4.89-4.69 (m, 1H), 3.95-3.72 (m, 1H), 1.92-1.70 (m, 5H), 1.68-1.58 (m, 3H), 1.54-1.21 (m, 16H), 1.17-0.98 (m, 8H), 0.93 (t, J=7.2 Hz, 3H), 0.63 (s, 3H). LC-ELSD/MS purity 99%, analytic SFC: 100% de. MS ESI calcd. for C$_{29}$H$_{44}$N$_3$O [M+H]$^+$ 450.3, found 450.3.

Example 91: Synthesis of (3R,5R,8R,9R,10S,13S, 14S,17S)-13-methyl-17-((R)-1-((2-methyl-6-(3-methyl-1H-pyrazol-1-yl)pyridin-3-yl)amino)ethyl)-3-propylhexadecahydro-1H-cyclopenta[a] phenanthren-3-ol (91)

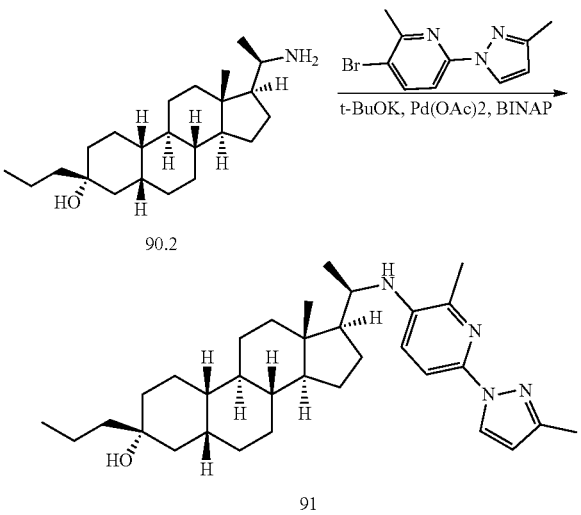

To a solution of 90.2 (100 mg, 0.3 mmol), 3-bromo-2-methyl-6-(3-methyl-1H-pyrazol-1-yl)pyridine (145 mg, 0.6 mmol), BINAP (17.9 mg, 0.03 mmol) and t-BuOK (64.5 mg, 0.6 mmol) in toluene (3 mL) was added Pd(OAc)$_2$ (6.45 mg, 0.03 mmol) under N$_2$. The mixture was stirred at 110° C. under microwave for 18 h to give a solution. Water (10 mL) was added into the solution. The mixture was extracted with EtOAc (3×20 mL). The combined organic phase was washed with water (3×20 mL), brine (50 mL), dried over anhydrous Na$_2$SO$_4$, filtered, concentrated in vacuum. The residue was purified by flash column (10%-30% of EtOAc in PE) to give 91 (40.6 mg, 27.2%) as a solid.

$^1$H NMR (400 MHz, CDCl$_3$) δ$_H$ 8.26 (d, J=2.4 Hz, 1H), 7.56 (d, J=8.4 Hz, 1H), 6.92 (d, J=8.4 Hz, 1H), 6.17 (d, J=2.4 Hz, 1H), 3.47-3.35 (m, 1H), 3.33-3.24 (m, 1H), 2.36 (d, J=3.2 Hz, 6H), 2.14-2.06 (m, 1H), 1.95-1.58 (m, 8H), 1.52-1.20 (m, 17H), 1.09 (d, J=6.0 Hz, 4H), 1.05-0.97 (m, 2H), 0.93 (t, J=7.2 Hz, 3H), 0.66 (s, 3H). LC-ELSD/MS purity 99%, MS ESI calcd. for C$_{33}$H$_{51}$N$_4$O [M+H]$^+$ 519.4, found 519.4.

Example 92: Synthesis of 1-((R)-2-((3R, 5R, 8R, 9R, 10S, 13S, 14S, 17R)-3-hydroxy-3-(methoxymethyl)-13-methylhexadecahydro-1H-cyclopenta[a] phenanthren-17-yl) propyl)-1H-pyrazole-4-carbonitrile (92)

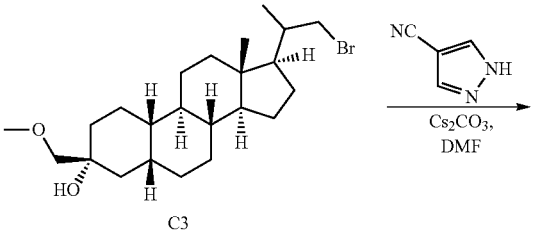

-continued

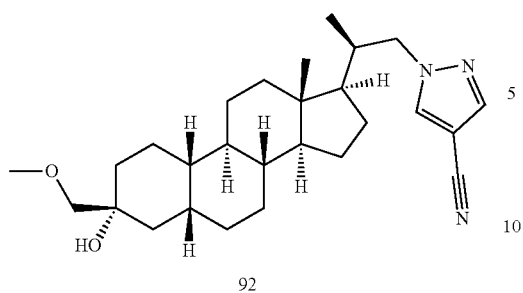

92

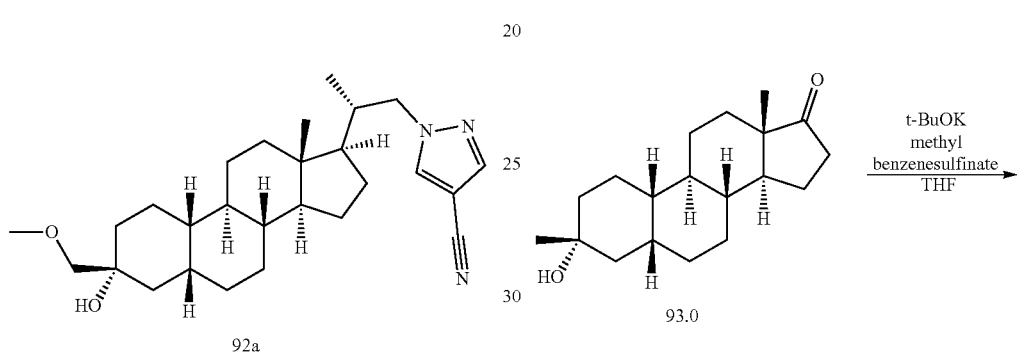

92a

To a solution of C3 (90 mg, 0.2105 mmol) and Cs₂CO₃ (137 mg, 0.421 mmol) in DMF (3 mL) was added 1H-pyrazole-4-carbonitrile (39.1 mg, 0.421 mmol) at 25° C. under N₂. After stirring at 80° C. for 16 h, the solution was cooled to 25° C., poured into water (100 mL) and extracted with EtOAc (3×100 mL). The combined organic phase was washed with brine (2×50 mL), dried over anhydrous Na₂SO₄, filtered and concentrated. The residue was purified by SFC (Column: DAICEL CHIRALCEL OD-H (250 mm*30 mm, 5 um) condition: 0.1% NH₃H₂O EtOH, flow rate: 40 mL/min) to give 92 (Peak 1, Rt=1.533 min, 30 mg) as a solid and 92a (Peak 2, Rt=1.936 min, 20 mg) as a solid. 92 was re-purified by HPLC separation (column: Xtimate C18 150*25 mm*5 um, gradient: 85-100% condition: water (0.225% FA)-ACN, flow rate: 25 mL/min) to give 92 (7 mg) as a solid.

$^1$H NMR (400 MHz, CDCl₃) $\delta_H$ 7.77 (d, J=18 Hz, 2H), 4.50 (dd, J=4.4, 13.2 Hz, 1H), 3.65 (dd, J=11.2, 13.2 Hz, 1H), 3.46-3.34 (m, 5H), 2.61 (s, 1H), 2.17-2.03 (m, 1H), 2.17-2.03 (m, 1H), 1.93-1.73 (m, 5H), 1.66 (br s, 1H), 1.55-1.29 (m, 8H), 1.26-0.99 (m, 9H), 0.79 (s, 3H), 0.67 (d, J=6.4 Hz, 3H). LC-ELSD/MS purity 99%, MS ESI calcd. for $C_{27}H_{40}N_3O$ [M+H−H2O]⁺ 422.3, found 422.3

Example 93-64: Synthesis of 1-((R)-2-((3R,5R,8R, 9R,10S,13R,14S,15S,17R)-15-cyclopropyl-3-hydroxy-3,13-dimethylhexadecahydro-1H-cyclopenta [a]phenanthren-17-yl)propyl)-1H-pyrazole-4-carbonitrile (93) & 1-((S)-2-((3R,5R,8R,9R,10S, 13R,14S,15S,17R)-15-cyclopropyl-3-hydroxy-3,13-dimethylhexadecahydro-1H-cyclopenta[a] phenanthren-17-yl)propyl)-1H-pyrazole-4-carbonitrile (94)& 1-((R)-2-((3R,5R,8R,9R,10S,13S, 14S,15S,17S)-15-cyclopropyl-3-hydroxy-3,13-dimethylhexadecahydro-1H-cyclopenta[a] phenanthren-17-yl)-2-hydroxypropyl)-1H-pyrazole-4-carbonitrile (628)& 1-((S)-2-((3R,5R,8R,9R,10S, 13S,14S,15S,17S)-15-cyclopropyl-3-hydroxy-3,13-dimethylhexadecahydro-1H-cyclopenta[a] phenanthren-17-yl)-2-hydroxypropyl)-1H-pyrazole-4-carbonitrile (629)

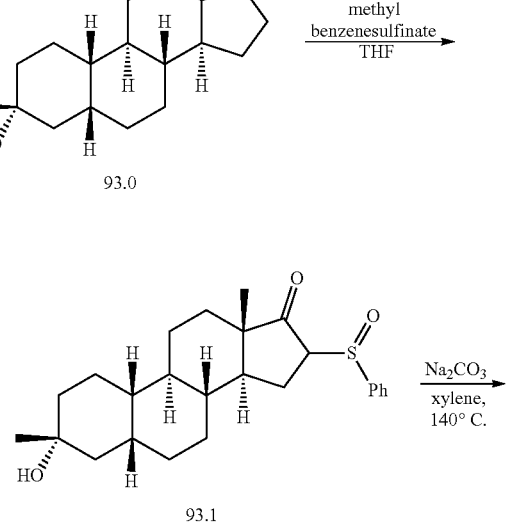

93.0

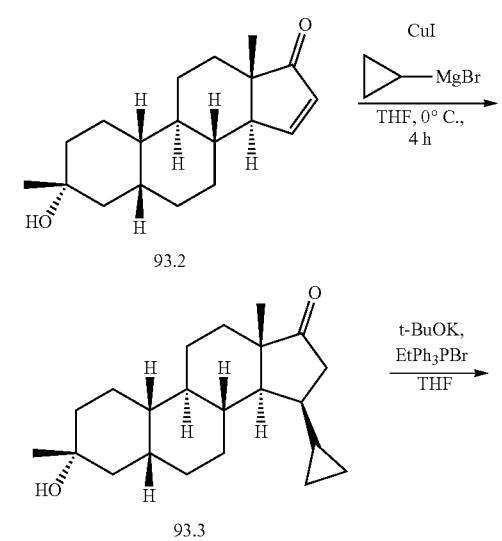

93.1

93.2

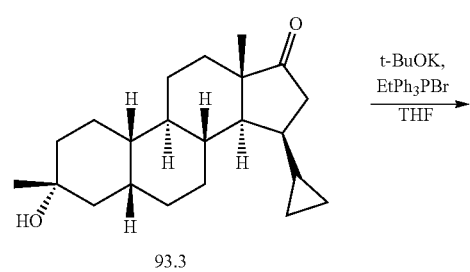

93.3

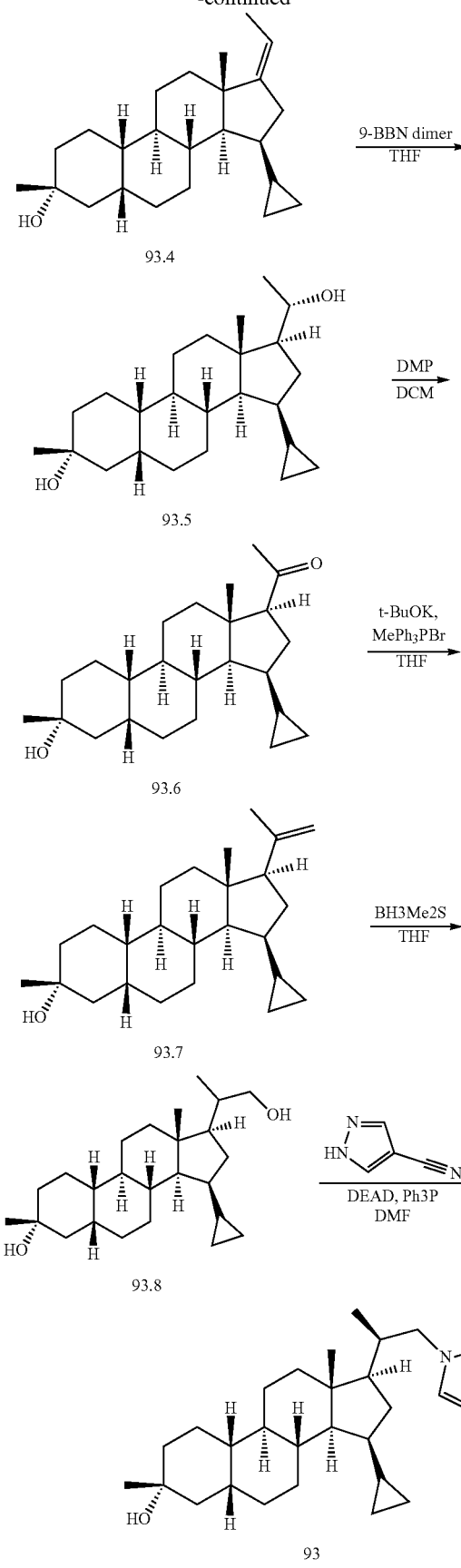
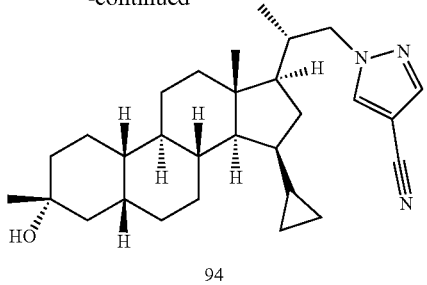

Synthesis of 93.1

To a solution of t-BuOK (6.17 g, 55.0 mmol) in THF (150 mL) was added 93.0 (8 g, 27.5 mmol) at 25° C. under $N_2$. After stirring at 25° C. for 10 min, methyl benzenesulfinate (8.59 g, 55.0 mmol) was added. After stirring at 30° C. for another 30 min, the mixture was quenched with $H_2O$ (200 mL) and extracted with EtOAc (200×3 mL). The organic layer was dried over $Na_2SO_4$, filtered and concentrated in vacuum to give 93.1 (16 g) as oil.

$^1H$ NMR (400 MHz, $CDCl_3$) $\delta_H$ 7.74-7.44 (m, 8H), 3.53-3.44 (m, 1H), 3.26 (dd, J=8.2, 9.9 Hz, 1H), 2.41-2.35 (m, 1H), 1.81 (br s, 1H), 1.56-1.30 (m, 15H), 1.23-1.01 (m, 4H), 0.98 (s, 1H), 0.93 (s, 2H).

Synthesis of 93.2

To a mixture of 93.1 (16 g, 38.5 mmol) in xylene (200 mL) was added $Na_2CO_3$ (61.1 g, 577 mmol) in portions. After stirring at 140° C. under $N_2$ for 12 h, the mixture was filtered and concentrated. The residue was purified by flash column (0~15% of EtOAc in PE) to give 93.2 (4.3 g) as a solid.

$^1H$ NMR (400 MHz, $CDCl_3$) $\delta_H$ 7.55-7.51 (m, 1H), 6.03 (dd, J=3.1, 5.9 Hz, 1H), 2.37 (br d, J=10.3 Hz, 1H), 1.85 (br s, 5H), 1.72 (br s, 2H), 1.62-1.34 (m, 9H), 1.33-1.23 (m, 6H), 1.08 (s, 3H).

Synthesis of 93.3

To a solution of bromo (cyclopropyl) magnesium (6.14 g, 84.6 ml, 42.3 mmol, 0.5 M in THF) in THF (150 mL) was added CuI (8.05 g, 42.3 mmol) at 0° C. under $N_2$. After stirring at 0° C. for 1 h, 93.2 (3.5 g, 12.1 mmol) was added. After stirring at 0° C. for another 3 h, the residue was poured into $NH_4Cl$ (50 mL) and extracted with EtOAc (3×50 mL). The combined organic phase was washed with brine (2×50 mL), dried over anhydrous $Na_2SO_4$, filtered, concentrated. The residue was purified by flash column (0~30% of EtOAc in PE) to give 93.3 (3.8 g) as a solid.

$^1H$ NMR (400 MHz, $CDCl_3$) $\delta_H$ 2.47-2.39 (m, 1H), 2.38-2.27 (m, 1H), 1.96-1.69 (m, 8H), 1.63-1.48 (m, 6H), 1.45-1.43 (m, 1H), 1.40-1.31 (m, 3H), 1.30-1.27 (m, 4H), 1.26-1.18 (m, 1H), 1.11 (s, 4H), 0.95 (br d, J=8.3 Hz, 1H), 0.70-0.62 (m, 1H), 0.47 (s, 1H), 0.24-0.03 (m, 2H).

LC-ELSD/MS purity 99%, MS ESI calcd. for $C_{22}H_{33}N_3O$ $[M-H_2O+H]^+$ 313.3 found 313.3.

Synthesis of 93.4

To a mixture of $EtPPh_3Br$ (20.6 g, 55.5 mmol) in THF (100 mL) was added t-BuOK (6.22 g, 55.5 mmol) at 25° C. under $N_2$. After stirring at 45° C. for 30 min, 93.3 (3.7 g, 11.1 mmol) was added below 45° C. After stirring at 45° C. for another 16 h, the reaction mixture was quenched with 10% $NH_4Cl$ aqueous (40 mL) at 25° C. and extracted with EtOAc (2×30 mL). The combined organic phase was dried over $Na_2SO_4$, filtered, concentrated. The residue was purified by flash column (0~20% of EtOAc in PE) to give 93.4 (3.7 g) as a solid.

¹H NMR (400 MHz, CDCl₃) δ_H 5.18-5.07 (m, 1H), 2.46-2.36 (m, 1H), 2.31-2.15 (m, 2H), 1.84 (br d, J=6.8 Hz, 4H), 1.77-1.63 (m, 4H), 1.59-1.30 (m, 12H), 1.29-1.27 (m, 4H), 1.19-1.08 (m, 5H), 0.86-0.77 (m, 1H), 0.58-0.49 (m, 1H), 0.40-0.31 (m, 1H), 0.13-0.00 (m, 2H).

Synthesis of 93.5

To a solution of 93.4 (700 mg, 2.04 mmol) in anhydrous THF (15 mL) was added BH₃·Me₂S (1.01 ml, 10.2 mmol) at 25° C. under N₂. After stirring at 25° C. for 12 h, the resulting mixture was treated sequentially with ethanol (3.09 mL, 61.2 mmol) at 25° C., NaOH aqueous (12.2 mL, 5.0 M, 61.2 mmol) and H₂O₂ (6.13 mL, 30% in water, 61.2 mmol) dropwise at 0° C. After stirring at 50° C. for 1 h, the mixture was cooled, poured into Na₂S₂O₃ (50 mL, sat. aq.) and extracted with EtOAc (2×50 mL). The combined organic phase was washed with brine (30 mL), dried over anhydrous Na₂SO₄, filtered and concentrated in vacuum. The residue was purified by flash column (15~25% of EtOAc in PE) to give 93.5 (560 mg) as a solid.

¹H NMR (400 MHz, CDCl₃) δ_H 3.82-3.74 (m, 1H), 2.24 (td, J=9.2, 13.5 Hz, 1H), 2.02 (s, 1H), 1.85 (br d, J=6.5 Hz, 5H), 1.92-1.58 (m, 1H), 1.92-1.58 (m, 1H), 1.41 (br d, J=3.3 Hz, 9H), 1.28 (s, 5H), 1.24 (d, J=6.3 Hz, 4H), 1.18-1.01 (m, 4H), 0.92-0.78 (m, 4H), 0.57 (br dd, J=3.9, 7.7 Hz, 1H), 0.42-0.32 (m, 1H), 0.16-0.02 (m, 2H). LC-ELSD/MS purity 99%, MS ESI calcd. for C₂₄H₃₇ [M−2H₂O+H]⁺ 325.3 found 325.3.

Synthesis of 93.6

To a mixture of 93.5 (460 mg, 1.27 mmol) in DCM (30 mL) was added DMP (1.61 g, 3.81 mmol) in portions. After stirring at 20° C. for 30 min, the mixture was quenched with NaHCO₃ (20 mL) and Na₂S₂O₃ (20 mL) and extracted with DCM (2×30 mL) The organic phase was washed with Na₂S₂O₃ (2×20 mL, sat.), brine (30 mL, sat), dried over Na₂SO₄, filtered and concentrated. The residue was purified by flash column (0~15% of EtOAc in PE) to give 93.6 (310 mg) as a solid.

¹H NMR (400 MHz, CDCl₃) δ_H 2.44 (dd, J=8.8, 10.5 Hz, 1H), 2.14 (s, 4H), 2.02-1.92 (m, 3H), 1.85 (br d, J=6.8 Hz, 2H), 1.76-1.65 (m, 2H), 1.38 (br s, 12H), 1.29 (s, 4H), 1.17-1.04 (m, 2H), 0.87-0.77 (m, 1H), 0.85 (s, 3H), 0.62-0.52 (m, 1H), 0.46-0.35 (m, 1H), 0.17-0.01 (m, 2H). LC-ELSD/MS purity 99%, MS ESI calcd. for C₂₄H₃₇O [M−H₂O+H]⁺ 341.3 found 341.3.

Synthesis of 93.7

To a suspension of Ph₃PMeBr (3.08 g, 8.64 mmol) in THF (20 mL) was added t-BuOK (969 mg, 8.64 mmol) at 20° C. under N₂. After stirring for 30 min at 50° C., a solution of 93.6 (310 mg, 0.864 mmol) in THF (5 mL) was added dropwise to the resulting suspension. After stirring at 50° C. for 2 h under N₂, the reaction mixture was poured into 10% NH₄Cl (50 mL) and extracted with EtOAc (40 mL×3). The combined organic phase was washed with brine (40 mL), dried over anhydrous Na₂SO₄, filtered and concentrated. The residue was purified by flash column (0~10% of EtOAc in PE) to give 93.7 (300 mg) as a solid.

¹H NMR (400 MHz, CDCl₃) δ_H 4.86 (s, 1H), 4.74 (s, 1H), 2.03-1.79 (m, 7H), 1.78 (s, 3H), 1.76-1.60 (m, 3H), 1.51-1.27 (m, 13H), 1.23-0.98 (m, 4H), 0.78 (s, 4H), 0.58 (br s, 1H), 0.45-0.32 (m, 1H), 0.17-0.03 (m, 1H), 0.17-0.03 (m, 1H).

Synthesis of 93.8

To a solution of 93.7 (200 mg, 0.560 mmol) in THF (10 mL) was added BH₃·Me₂S (0.559 mL, 10M, 5.59 mmol) at 50° C. After stirring for 16 h, to the resulting mixture was added ethanol (1.95 m, NaOH (6.70 mL, 5M in water, 33.5 mmol) at 0° C. and hydrogen peroxide (3.32 mL, 10 M in water, 33.5 mmol) dropwise at 0° C. After stirring at 80° C. for 1 h, the mixture was added into water (100 ml) and extracted with EtOAc (2×100 mL). The organic layer was washed with saturated Na₂S₂O₃ (100 ml), brine (100 mL), dried over anhydrous Na₂SO₄, filtered and concentrated in vacuum to give 93.8 (100 mg) as a solid.

¹H NMR (400 MHz, CDCl₃) δ_H 3.81-3.33 (m, 2H), 2.21-2.07 (m, 1H), 2.02-1.52 (m, 10H), 1.51-1.44 (m, 3H), 1.39-1.29 (m, 5H), 1.28 (s, 4H), 1.07 (br d, J=6.5 Hz, 7H), 0.97 (d, J=6.8 Hz, 2H), 0.90 (s, 4H), 0.61-0.52 (m, 1H), 0.43-0.27 (m, 1H), 0.17-0.14 (m, 2H).

Synthesis of 93 & 94

To a solution of 93.8 (100 mg, 0.277 mmol) and 1H-pyrazole-4-carbonitrile (51.5 mg, 0.554 mmol) in DMF (5 mL) were added Ph₃P (288 mg, 1.10 mmol) and DEAD (191 mg, 1.10 mmol). After stirring at 25° C. for 16 h, the mixture was poured into ice-water (30 mL) and extracted with EtOAc (3×20 mL). The combined organic phase was washed with brine (2×50 mL), dried over anhydrous Na₂SO₄, filtered and concentrated. The residue was purified by SFC (Column: DAICEL CHIRALCEL OD-H (250 mm*30 mm, 5 um); Condition: 0.1% NH₃H₂O ETOH; Begin B: 45%; End B: 45%) to afford 94 (30.6 mg, 25.7%, Rt=1.540 min) as a solid and 93 (30.2 mg, 25.3%, Rt=1.957 min) as a solid.

93: ¹H NMR (400 MHz, CDCl₃) δ_H 7.81 (s, 1H), 7.76 (s, 1H), 4.48 (dd, J=4.8, 13.3 Hz, 1H), 3.70 (dd, J=10.3, 13.3 Hz, 1H), 2.23-2.08 (m, 2H), 2.04-1.93 (m, 1H), 1.85 (br d, J=7.0 Hz, 4H), 1.77-1.59 (m, 1H), 1.51-1.37 (m, 7H), 1.29 (s, 8H), 1.16-1.05 (m, 4H), 1.00 (s, 3H), 0.80 (br s, 1H), 0.72 (d, J=6.5 Hz, 3H), 0.58 (br s, 1H), 0.42-0.31 (m, 1H), 0.00-0.00 (m, 1H), 0.16-0.08 (m, 2H). LC-ELSD/MS purity 99%, MS ESI calcd. for C₂₉H₄₂N₃ [M−H₂O+H]⁺ 432.3 found 432.3. SFC 100% de.

94: ¹H NMR (400 MHz, CDCl₃) δ_H 7.81 (s, 1H), 7.78 (s, 1H), 4.30 (dd, J=3.8, 13.3 Hz, 1H), 3.73 (dd, J=9.9, 13.4 Hz, 1H), 2.26 (td, J=9.2, 13.3 Hz, 1H), 2.14-2.03 (m, 1H), 1.84 (br d, J=6.8 Hz, 6H), 1.64-1.59 (m, 2H), 1.39 (br d, J=10.8 Hz, 8H), 1.53-1.33 (m, 1H), 1.29-1.22 (m, 5H), 1.08 (br d, J=10.5 Hz, 4H), 0.94 (s, 3H), 0.82 (d, J=6.5 Hz, 4H), 0.59 (td, J=3.8, 7.9 Hz, 1H), 0.44-0.31 (m, 1H), 0.19-0.07 (m, 2H). LC-ELSD/MS purity 99%, MS ESI calcd. for C₂₉H₄₂N₃ [M−H₂O+H]⁺ 432.4 found 432.4. SFC 96% de.

Example 95 & 96: Synthesis of 1-((R)-2-((3R,5R,8R,9R,10S,13R,14S,15R,17R)-3-hydroxy-3,13,15-trimethylhexadecahydro-1H-cyclopenta[a]phenanthren-17-yl)propyl)-1H-pyrazole-4-carbonitrile (95) & 1-((S)-2-((3R,5R,8R,9R,10S,13R,14S,15R,17R)-3-hydroxy-3,13,15-trimethylhexadecahydro-1H-cyclopenta[a]phenanthren-17-yl)propyl)-1H-pyrazole-4-carbonitrile (96)

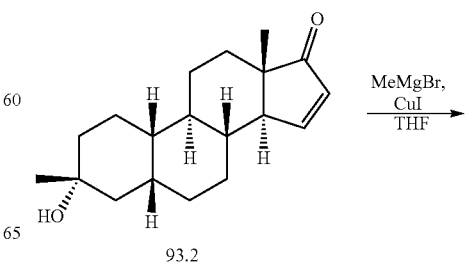

93.2

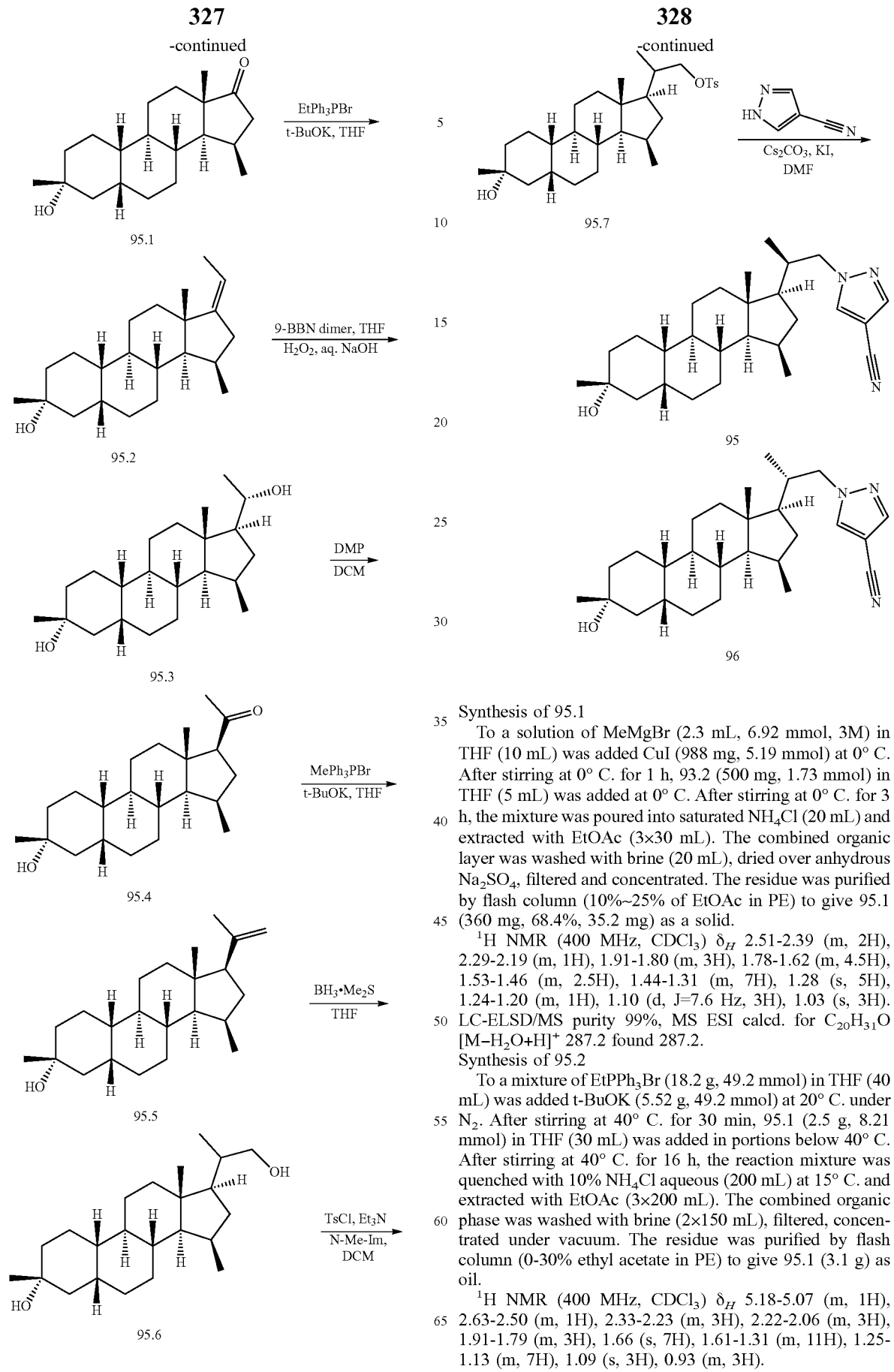

Synthesis of 95.1

To a solution of MeMgBr (2.3 mL, 6.92 mmol, 3M) in THF (10 mL) was added CuI (988 mg, 5.19 mmol) at 0° C. After stirring at 0° C. for 1 h, 93.2 (500 mg, 1.73 mmol) in THF (5 mL) was added at 0° C. After stirring at 0° C. for 3 h, the mixture was poured into saturated NH$_4$Cl (20 mL) and extracted with EtOAc (3×30 mL). The combined organic layer was washed with brine (20 mL), dried over anhydrous Na$_2$SO$_4$, filtered and concentrated. The residue was purified by flash column (10%~25% of EtOAc in PE) to give 95.1 (360 mg, 68.4%, 35.2 mg) as a solid.

$^1$H NMR (400 MHz, CDCl$_3$) δ$_H$ 2.51-2.39 (m, 2H), 2.29-2.19 (m, 1H), 1.91-1.80 (m, 3H), 1.78-1.62 (m, 4.5H), 1.53-1.46 (m, 2.5H), 1.44-1.31 (m, 7H), 1.28 (s, 5H), 1.24-1.20 (m, 1H), 1.10 (d, J=7.6 Hz, 3H), 1.03 (s, 3H). LC-ELSD/MS purity 99%, MS ESI calcd. for C$_{20}$H$_{31}$O [M–H$_2$O+H]$^+$ 287.2 found 287.2.

Synthesis of 95.2

To a mixture of EtPPh$_3$Br (18.2 g, 49.2 mmol) in THF (40 mL) was added t-BuOK (5.52 g, 49.2 mmol) at 20° C. under N$_2$. After stirring at 40° C. for 30 min, 95.1 (2.5 g, 8.21 mmol) in THF (30 mL) was added in portions below 40° C. After stirring at 40° C. for 16 h, the reaction mixture was quenched with 10% NH$_4$Cl aqueous (200 mL) at 15° C. and extracted with EtOAc (3×200 mL). The combined organic phase was washed with brine (2×150 mL), filtered, concentrated under vacuum. The residue was purified by flash column (0-30% ethyl acetate in PE) to give 95.1 (3.1 g) as oil.

$^1$H NMR (400 MHz, CDCl$_3$) δ$_H$ 5.18-5.07 (m, 1H), 2.63-2.50 (m, 1H), 2.33-2.23 (m, 3H), 2.22-2.06 (m, 3H), 1.91-1.79 (m, 3H), 1.66 (s, 7H), 1.61-1.31 (m, 11H), 1.25-1.13 (m, 7H), 1.09 (s, 3H), 0.93 (m, 3H).

Synthesis of 95.3

To a solution of 95.2 (2.6 g, 8.21 mmol) in anhydrous THF (30 mL) was added 9-BBN dimer (4.00 g, 16.4 mmol) at 25° C. under $N_2$. After stirring at 40° C. for 16 h, to the resulting mixture was added ethanol (4.53 g, 98.5 mmol) at 25° C., followed by NaOH aqueous (19.7 mL, 5.0 M, 98.5 mmol) and $H_2O_2$ (9.85 mL, 10 M, 98.5 mmol) dropwise at 0° C. After stirring at 80° C. for 1 h, the mixture was cooled, poured into $Na_2S_2O_3$ (100 mL, sat. aq.) and extracted with EtOAc (2×150 mL). The organic phase was washed with brine (2×100 mL), dried over anhydrous $Na_2SO_4$, filtered and concentrated in vacuum. The residue was purified by flash column (15-40% EtOAc in PE) to give 95.3 (2.6 g, 94.8%) as a solid $^1$H NMR (400 MHz, CDCl$_3$) $\delta_H$ 3.86-3.65 (m, 1H), 2.38-2.26 (m, 1H), 2.20-2.07 (m, 1H), 1.91-1.52 (m, 11H), 1.50-1.37 (m, 6H), 1.29-1.24 (m, 8H), 1.19-0.98 (m, 5H), 0.93 (m, 3H), 0.82 (s, 3H).

Synthesis of 95.4

To a solution of 95.3 (2.6 g, 7.77 mmol) in DCM (30 mL) was added Dess-martin (6.57 g, 15.5 mmol) at 25° C. After stirring at 25° C. for 10 min, the mixture was quenched with saturated NaHCO$_3$ aqueous (100 mL) at 10° C. The DCM phase was separated and washed with saturated NaHCO$_3$/Na$_2$S$_2$O$_3$ aqueous (1:1, 3×100 mL), brine (2×50 mL), dried over Na$_2$SO$_4$, filtered and concentrated under vacuum. The residue was purified by flash column (0~30% of EtOAc in PE) to give 95.4 (1 g, 38.7%) as a solid.

$^1$H NMR (400 MHz, CDCl$_3$) $\delta_H$ 2.49 (dd, J=8.8, 10.8 Hz, 1H), 2.22-2.13 (m, 1H), 2.11 (s, 3H), 2.09-2.00 (m, 1H), 1.97-1.79 (m, 5H), 1.75-1.59 (m, 3H), 1.51-1.29 (m, 9H), 1.28 (s, 4H), 1.25-0.99 (m, 3H), 0.96 (d, J=7.2 Hz, 3H), 0.78 (s, 3H). LC-ELSD/MS purity: 99%, MS ESI calcd. for $C_{22}H_{36}O_2$ [M−H$_2$O+H]$^+$ 315.3, found $C_{22}H_{36}O_2$ [M−H$_2$O+H]$^+$ 315.2.

Synthesis of 95.5

To a mixture of MePPh$_3$Br (2.24 g, 6.30 mmol) in THF (27 mL) was added t-BuOK (706 mg, 6.30 mmol) at 20° C. under N$_2$. After stirring at 50° C. for 30 min, 95.4 (700 mg, 2.10 mmol) in THF (3 mL) was added in portions below 50° C. After stirring at 50° C. for 16 h, the reaction mixture was quenched with 10% NH$_4$Cl aqueous (20 mL) at 15° C. and extracted with EtOAc (3×20 mL). The combined organic phase was washed with brine (2×20 mL), dried over anhydrous Na$_2$SO$_4$, filtered and concentrated under vacuum. The residue was purified by flash column (0-20% of ethyl acetate in PE) to give 95.5 (620 mg, 89.3%) as a solid.

$^1$H NMR (400 MHz, CDCl$_3$) $\delta_H$ 4.84 (s, 1H), 4.71 (s, 1H), 2.16-1.95 (m, 3H), 1.91-1.77 (m, 4H), 1.76 (s, 3H), 1.69-1.58 (m, 3H), 1.49-1.39 (m, 5H), 1.37-1.28 (m, 4H), 1.27 (s, 4H), 1.24-0.99 (m, 6H), 0.95 (d, J=7.2 Hz, 3H), 0.91-0.82 (m, 2H), 0.72 (s, 3H).

Synthesis of 95.6

To a solution of 95.5 (300 mg, 0.9075 mmol) in THF (5 mL) was added BH$_3$-Me$_2$S (544 μL, 10M, 5.44 mmol) at 25° C. After stirring at 45° C. for 16 h, the resulting mixture was treated with ethanol (1.25 g, 27.2 mmol) at 15° C. and by NaOH aqueous (5.43 mL, 5.0 M, 27.2 mmol) at 0° C. Hydrogen peroxide (2.71 mL, 10 M, 27.2 mmol) was then added dropwise at 0° C. After stirring at 78° C. for 1 h, the mixture was cooled to 15° C. and Na$_2$S$_2$O$_3$ (20 mL, sat. aq.) was added. The aqueous layer was extracted with EtOAc (3×20 mL). The organic phase was washed with brine (50 mL), dried over anhydrous Na$_2$SO$_4$, filtered and concentrated. The residue was purified by flash column (0-40% of EtOAc in PE) to give 95.6 (450 mg) as a solid.

$^1$H NMR (400 MHz, CDCl$_3$) $\delta_H$ 3.75-3.59 (m, 1H), 3.51-3.34 (m, 1H), 2.33-2.16 (m, 1H), 2.15-1.99 (m, 1H), 1.95-1.79 (m, 3H), 1.72-1.55 (m, 6H), 1.51-1.36 (m, 5H), 1.27 (s, 4H), 1.24-1.08 (m, 6H), 1.05 (br d, J=6.8 Hz, 3H), 0.96 (d, J=6.8 Hz, 2H), 0.90 (dd, J=2.0, 7.2 Hz, 3H), 0.84 (s, 3H).

Synthesis of 95.7

To a solution of 95.6 (250 mg, 0.7172 mmol) in DCM (5 mL) were added N-Me-imidazole (87.8 mg, 1.07 mmol), TEA (144 mg, 1.43 mmol) and TsCl (203 mg, 1.07 mmol). After stirring at 20° C. for 1 h, the mixture was washed with water (5 mL) and extracted with DCM (3×20 mL). The organic phase was washed with brine (50 mL), dried over anhydrous Na$_2$SO$_4$, filtered and concentrated. The residue was purified by flash column (0-40% of EtOAc in PE) to give 95.7 (240 mg, 66.6%) as a solid.

$^1$H NMR (400 MHz, CDCl$_3$) $\delta_H$ 7.79 (dd, J=2.4, 8.4 Hz, 2H), 7.34 (dd, J=2.4, 8.4 Hz, 2H), 4.18-4.07 (m, 1H), 4.01-3.94 (m, 1H), 3.82-3.74 (m, 1H), 2.45 (s, 3H), 2.23-2.05 (m, 1H), 1.88-1.76 (m, 4H), 1.73-1.55 (m, 3H), 1.53-1.32 (m, 7H), 1.29-1.23 (m, 6H), 1.23-1.01 (m, 6H), 1.00-0.93 (m, 3H), 0.90-0.84 (m, 5H), 0.80-0.71 (m, 3H).

Synthesis of 95 & 96

To a solution of 95.7 (240 mg, 0.4773 mmol) in DMF (5 mL) were added 4-cyano-pyrazole (53.3 mg, 0.5727 mmol), KI (79.2 mg, 0.4773 mmol) and Cs$_2$CO$_3$ (465 mg, 1.43 mmol). After stirring at 120° C. for 16 h, the mixture was quenched with water (5 mL) and extracted with EtOAc (50 mL×3). The organic phase was washed with brine (30 mL×2), dried over Na$_2$SO$_4$, filtered and concentrated under vacuum. The residue was purified by column (0%-55% of EtOAc in PE) to give a mixture of diastereomers. The diastereomers were separated by SFC (column: DAICEL CHIRALCEL OD-H (250 mm*30 mm, 5 um); Mobile phase: A: CO$_2$ B: 0.1% NH$_3$H$_2$O ETOH; gradient: from 40% to 40% of B, Flow Rate (ml/min): 60) to give 96 (51.5 mg, 21.5%) and 95 (65.7 mg, 27.4%) as a solid.

95: $^1$H NMR (400 MHz, CDCl$_3$) $\delta_H$ 7.80 (s, 1H), 7.76 (s, 1H), 4.27 (dd, J=3.76, 13.30 Hz, 1H), 3.72 (dd, J=9.91, 13.43 Hz, 1H), 2.43-2.27 (m, 1H), 2.22-1.98 (m, 2H), 1.93-1.79 (m, 4H), 1.73-1.53 (m, 6H), 1.51-1.36 (m, 5H), 1.27 (s, 3H), 1.22-1.00 (m, 7H), 0.94 (d, J=7.2 Hz, 3H), 0.87 (s, 3H), 0.80 (d, J=6.5 Hz, 2H). LC-ELSD/MS purity: 99%, MS ESI calcd. for $C_{27}H_{41}N_3O$ [M−H$_2$O+H]$^+$ 406.3, found $C_{27}H_{41}N_3O$ [M−H$_2$O+H]$^+$ 406.3.

96: $^1$H NMR (400 MHz, CDCl$_3$) $\delta_H$ 7.80 (s, 1H), 7.75 (s, 1H), 4.47 (dd, J=4.5, 13.3 Hz, 1H), 3.68 (dd, J=10.4, 13.2 Hz, 1H), 2.28-2.06 (m, 3H), 1.88-1.57 (m, 8H), 1.51-1.34 (m, 6H), 1.27 (s, 4H), 1.21-1.02 (m, 7H), 0.97-0.89 (m, 6H), 0.69 (d, J=6.8 Hz, 3H). LC-ELSD/MS purity: 99%, MS ESI calcd. for $C_{27}H_{41}N_3O$ [M−H$_2$O+H]$^+$ 406.3, found $C_{27}H_{41}N_3O$ [M−H2O+H]$^+$ 406.3.

The following examples were synthesized similar to Examples 29, 30, 31, or 32 with the listed acid and appropriate SM. In the case of B24 as SM, the diastereomeric products were separated by SFC (e.g. Column: DAICEL CHIRALPAK AS-H (250 mm*30 mm, 5 um), Condition: 0.1% NH$_3$H$_2$O EtOH, Begin B: 30%, End B 30%) yielding both diastereomers after separation. The diastereomers were assigned based on 1H NMR of C21-Me.

| Example | SM | acid | STRUCTURE | Analytical |
|---|---|---|---|---|
| 100 | B18 | pyridine-2-carboxylic acid | 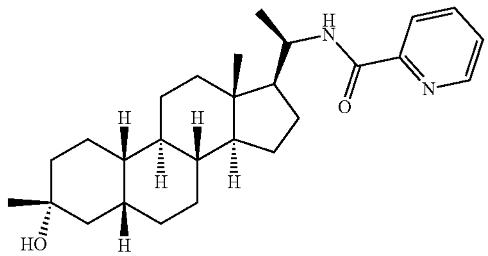 | ¹H NMR (400 MHz, CDCl3) δ$_H$ 8.55 (d, J = 4.0 Hz, 1H), 8.21 (d, J = 7.6 Hz, 1H), 7.95 (d, J = 9.6 Hz, 1H), 7.84 (dt, J = 2.0, 8.0 Hz, 1H), 7.43-7.38 (m, 1H), 4.19-4.07 (m, 1H), 1.86-1.74 (m, 5H), 1.67-1.46 (m, 4H), 1.45-1.31 (m, 7H), 1.31-1.19 (m, 6H), 1.19 (d, J = 6.4 Hz, 3H), 1.16-0.86 (m, 6H), 0.71 (s, 3H); LC-ELSD/MS purity 95%, MS ESI calcd. for $C_{27}H_{41}N_2O_2$ [M + H]⁺ 425, found 425. |
| 101 | B20 | pyridine-2-carboxylic acid | 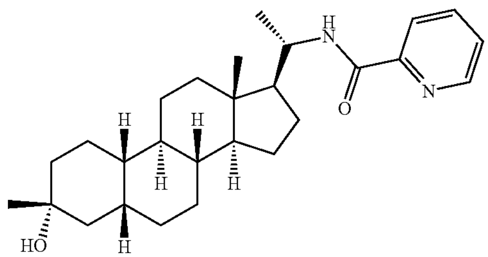 | ¹H NMR (400 MHz, CDCl3) δ$_H$ 8.53 (d, J = 4.0 Hz, 1H), 8.19 (d, J = 8.0 Hz, 1H), 7.93 (d, J = 9.2 Hz, 1H), 7.83 (dt, J = 1.6, 7.6 Hz, 1H), 7.43-7.38 (m, 1H), 4.24-4.14 (m, 1H), 1.99-1.93 (m, 1H), 1.89-1.79 (m, 4H), 1.68-1.57 (m, 7H), 1.50-1.37 (m, 7H), 1.29-1.26 (m, 7H), 1.14-1.02 (m, 5H), 0.77 (s, 3H); LC-ELSD/MS purity 99%, MS ESI calcd. for $C_{27}H_{41}N_2O_2$ [M + H]⁺ 425, found 425. |
| 102 | B20 | 2-fluoro-benzoic acid | 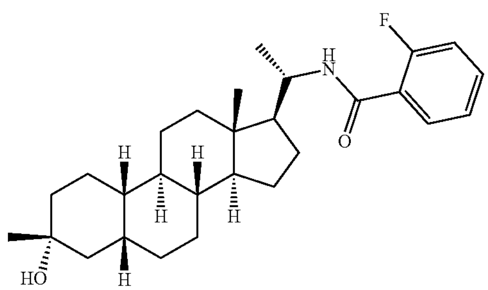 | ¹H NMR (400 MHz, CDCl3) δ 8.15-7.95 (m 1H), 7.51-7.36 (m, 1H), 7.26-7.20 (m, 1H), 7.16-7.03 (m, 1H), 7.02-7.00 (m, 1H), 4.25-4.20 (m, 1H), 2.00-1.75 (m, 4H), 1.71-1.54 (m, 5H), 1.53-1.35 (m, 7H), 1.33-1.18 (m, 10H), 1.17-1.00 (m, 5H), 0.75 (s, 3H); LCMS purity 99%, MS ESI calcd. For C28H40FNO2 [M + H]⁺ 442, found 442. |
| 103 | B18 | 2-fluoro-benzoic acid | 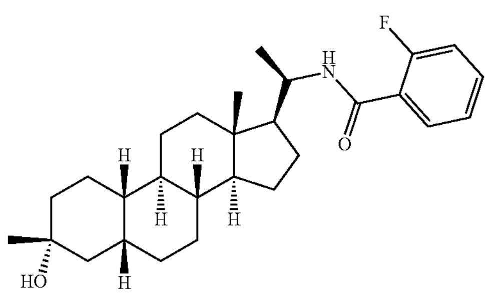 | ¹H NMR (400 MHz, CDCl3) δ 8.28-8.24 (m 1H), 7.65-7.52 (m, 1H), 7.39-7.40 (m 1H), 7.26-7.24 (m, 1H), 6.85-6.65 (m, 1H), 4.46-4.21 (m, 1H), 2.05-1.93 (m, 5H), 1.81-1.66 (m, 4H), 1.60-1.52 (m, 7H), 1.43-1.29 (m, 10H), 1.27-1.08 (m, 5H), 0.86 (s, 3H); LCMS purity 98%, MS ESI calcd. For C28H40FNO2 [M + H]⁺ 442, found 442 |
| 104 | B18 | 3-methoxy-benzoic acid | 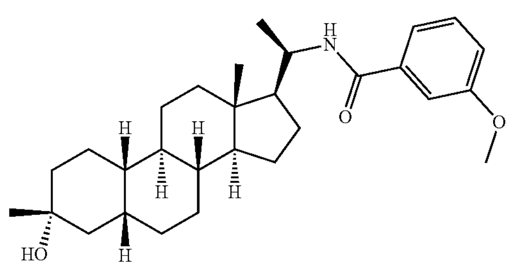 | ¹H NMR (400 MHz, CDCl3) δ 7.37-7.31 (m, 2 H), 7.23-7.21 (m, 1 H), 7.04-6.99 (m, 1 H), 5.89-5.86 (m, 1 H), 4.22-4.18 (m, 1 H), 3.85 (s, 3H), 1.89-1.64 (m, 5 H), 1.63-1.48 (m, 3 H), 1.50-1.39 (m, 8 H), 1.38-1.15 (m, 10 H), 1.14-0.95 (m, 5 H), 0.74 (s, 3 H); LCMS purity 99%, MS ESI calcd. For C29H43NO3 [M + H]⁺ 454, found 454.3 |

-continued

| Example | SM | acid | STRUCTURE | Analytical |
|---|---|---|---|---|
| 105 | B20 | 3-methoxy-benzoic acid | 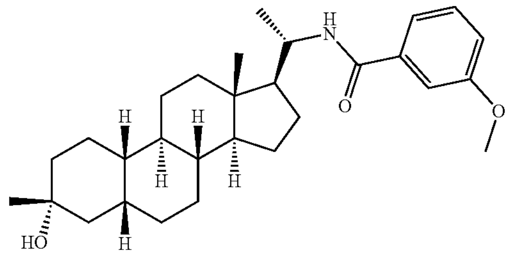 | $^1$H NMR (400 MHz, CDCl3) δ 7.34-7.30 (m, 2 H), 7.23-7.20 (m, 1 H), 7.04-6.98 (m, 1 H), 5.95-5.80 (m, 1 H), 4.27-4.12 (m, 1 H), 3.85 (s, 3H), 1.98-1.77 (m, 4 H), 1.75-1.60 (m, 4 H), 1.55-1.33 (m, 8 H), 1.32-1.15 (m, 10 H), 1.14-0.98 (m, 5 H), 0.77 (s, 3 H); LCMS purity 99%, MS ESI calcd. For C29H43NO3 [M + H]$^+$ 454, found 454.3 |
| 106 | B18 | 4-methoxy-benzoic acid | 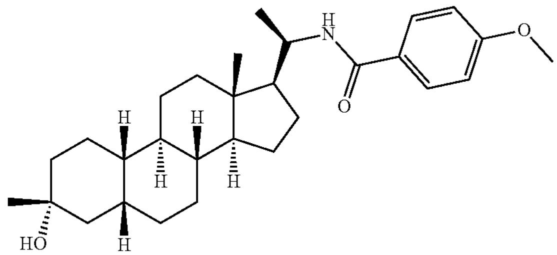 | $^1$H NMR (400 MHz, CDCl3) δ 7.76-7.65 (m, 2 H), 6.98-6.88 (m, 2 H), 5.84-5.76 (m, 1 H), 4.24-4.11 (m, 1 H), 3.84 (s, 3 H), 1.92-1.72 (m, 5 H), 1.70-1.58 (m, 3 H), 1.49-1.32 (m, 8 H), 1.31-1.23 (m, 6 H), 1.22-1.09 (m, 6 H), 1.08-0.90 (m, 3 H), 0.73 (s, 3 H); LCMS purity 99%, MS ESI calcd. For $C_{29}H_{43}NO_3$ [M + H]$^+$ 454, found 454 |
| 107 | B20 | 4-methoxy-benzoic acid | 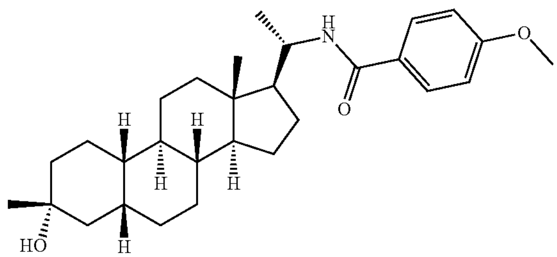 | $^1$H NMR (400 MHz, CDCl3) δ 7.73-7.68 (m, 2 H), 6.96-6.88 (m, 2 H), 5.84-5.76 (m, 1 H), 4.27-4.15 (m, 1 H), 3.84 (s, 3 H), 1.78-1.98 (m, 5 H), 1.73-1.58 (m, 3 H) 1.53-1.30 (m, 9 H), 1.29-1.22 (m, 8 H), 1.21-1.01 (m, 6 H), 0.76 (s, 3 H); LCMS purity 99%, MS ESI calcd. For C29H43NO3 [M + H]$^+$ 454, found 454 |
| 108 | B18 | 4-cyano-benzoic acid | 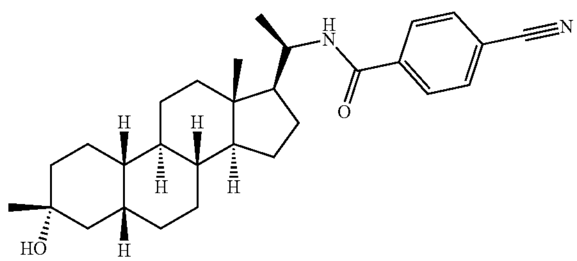 | $^1$H NMR (400 MHz, CDCl$_3$) δ 7.89-7.82 (m, 2H), 7.77-7.71 (m, 2H), 5.94-5.87 (m, 1H), 4.25-4.15 (m, 1H), 1.89-1.74 (m, 5H), 1.72-1.55 (m, 5H), 1.48-1.34 (m, 8H), 1.29-1.15 (m, 8H), 1.15-0.95 (m, 5H), 0.74 (s, 3H); LCMS purity 99%, MS ESI calcd. For $C_{29}H_{41}N_2O_2$ [M + H]$^+$ 449, found 449. |
| 109 | B18 | 3-cyano-benzoic acid | 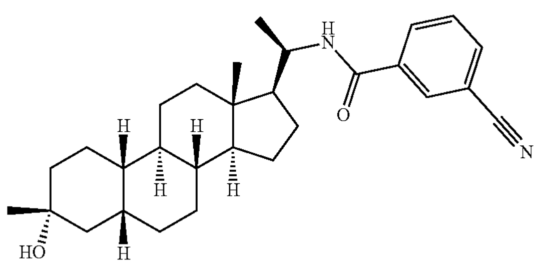 | $^1$H NMR (400 MHz, CDCl3) δ$_H$ 8.06-7.95 (m, 2H), 7.78 (d, 1H), 7.61-7.55 (m, 1H), 5.88 (d, 1H), 4.25-4.14 (m, 1H), 1.90-1.74 (m, 5H), 1.71-1.59 (m, 3H), 1.50-1.34 (m, 9H), 1.33-1.27 (m, 2H), 1.26 (s, 3H), 1.24-1.21 (m, 1H), 1.19 (d, 3H), 1.16-0.97 (m, 5H), 0.74 (s, 3H); LCMS MS ESI calcd. for $C_{29}H_{41}N_2O_2$ [M + H]+ 449, found 449. |
| 110 | B20 | 3-cyano-benzoic acid | 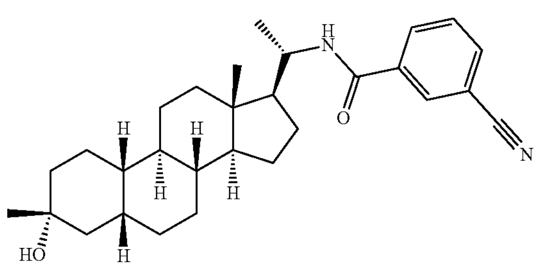 | H NMR (400 MHz, CDCl3) δ 8.03-7.93 (m, 2H), 7.77 (d, 1H), 7.60-7.53 (m, 1H), 5.91 (d, 1H), 4.29-4.14 (m, 1H), 1.95 (d, 1H), 1.90-1.76 (m, 4H), 1.71-1.52 (m, 6H), 1.51-1.31 (m, 8H), 1.28 (s, 3H), 1.27-1.22 (m, 3H), 1.19-0.99 (m, 6H), 0.77 (s, 3H); LCMS MS ESI calcd. for $C_{29}H_{41}N_2O_2$ [M + H]+ 449, found 449. |

| Example | SM | acid | STRUCTURE | Analytical |
|---|---|---|---|---|
| 111 | B24 | (trifluoro methoxy) benzoic acid | 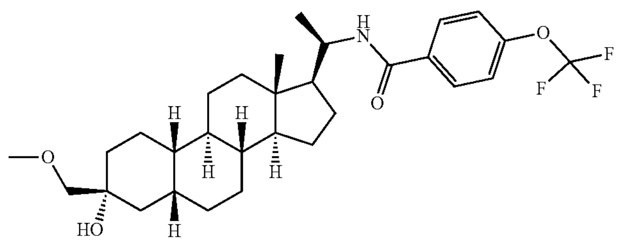 | B38: ¹H NMR (400 MHz, CDCl3) δ 7.77 (d, J = 8.8 Hz, 2H), 7.27-7.24 (m, 2H), 5.84 (d, J = 9.2 Hz, 1H), 4.18 (br s, 1H), 3.45-3.35 (m, 5H), 2.00-1.52 (m, 9H), 1.52-1.25 (m, 8H), 1.25-1.00 (m, 11H), 0.76 (s, 3H). LC-ELSD/MS purity 99%, MS ESI calcd. for $C_{30}H_{43}F_3NO_4$ [M + H]⁺ 538, found 538. SFC 100% de. |
| 112 | | | 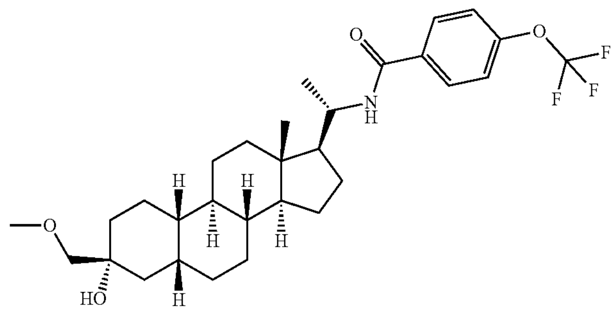 | ¹H NMR (400 MHz, CDCl3) δ 7.77 (d, J = 8.8 Hz, 2H), 7.27-7.24 (m, 2H), 5.87 (d, J = 8.8 Hz, 1H), 4.17 (br s, 1H), 3.45-3.35 (m, 5H), 2.62 (s, 1H), 1.85-1.56 (m, 9H), 1.50-1.25 (m, 8H), 1.25-0.95 (m, 10H), 0.73 (s, 3H). LC-ELSD/MS purity 99%, MS ESI calcd. for $C_{30}H_{43}F_3NO_4$ [M + H]⁺ 538, found 538. SFC 100% de. |
| 113 | B24 | 4-fluoro-benzoic acid | 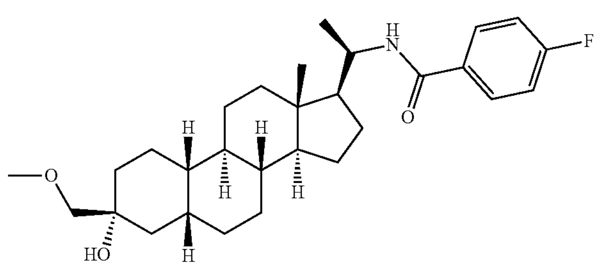 | ¹H NMR (400 MHz, CDCl3) δ 7.77-7.73 (m, 2H), 7.10 (T, J = 8.4 Hz, 2H), 5.86 (d, J = 8.8 Hz, 1H), 4.20-4.14 (m, 1H), 3.41-3.34 (m, 5H), 2.63 (s, 1H), 1.84-1.53 (m, 10H), 1.47-1.29 (m, 8H), 1.23-0.93 (m, 9H), 0.72 (s, 3H). LC-ELSD/MS purity 99%, MS ESI calcd. for $C_{29}H_{43}FNO_3$ [M + H]⁺ 472, found 472. SFC 96.96% de. |
| 114 | | | 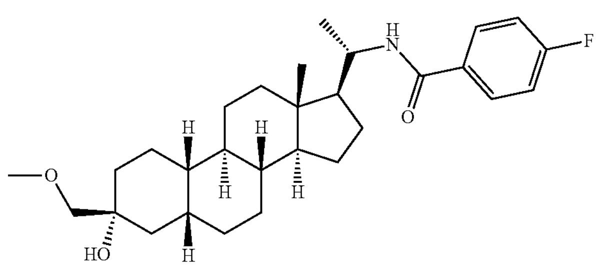 | ¹H NMR (400 MHz, CDCl3) δ 7.75-7.71 (m, 2H), 7.10 (t, J = 8.4 Hz, 2H), 5.86 (d, J = 8.8 Hz, 1H), 4.23-4.14 (m, 1H), 3.42-3.36 (m, 5H), 2.63 (s, 1H), 1.95-1.56 (m, 10H), 1.50-1.32 (m, 8H), 1.28-1.00 (m, 9H), 0.75 (s, 3H). LC-ELSD/MS purity 99%, MS ESI calcd. for $C_{29}H_{43}FNO_3$ [M + H]⁺ 472, found 472. SFC 95.44% de. |
| 115 | B20 | 4-cyano-benzoic acid | 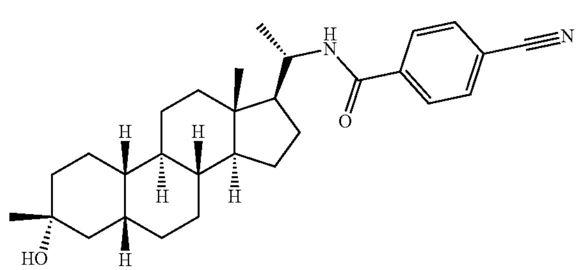 | ¹H NMR (400 MHz, CDCl3) δ_H 7.85-7.79 (m, 2H), 7.76-7.70 (m, 2H), 5.92 (br d, J = 8.8 Hz, 1H), 4.26-4.15 (m, 1H), 1.98-1.90 (m, 1H), 1.88-1.77 (m, 4H), 1.69-1.54 (m, 7H), 1.49-1.38 (m, 7H), 1.27 (t, J = 3.6 Hz, 7H), 1.20-1.06 (m, 5H), 0.77 (s, 3H); LCMS purity 99%, MS ESI calcd. for C29H41N2O2 [M + H]+ 449, found 449. |

| Example | SM | acid | STRUCTURE | Analytical |
|---|---|---|---|---|
| 116 | B24 | 4-fluoro-benzoic acid | 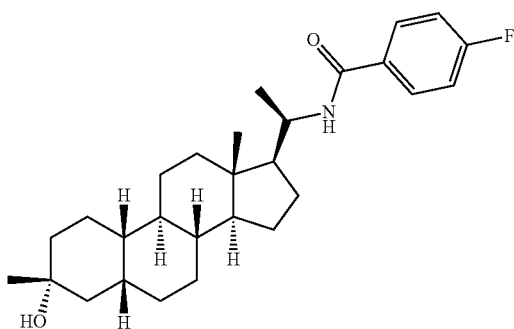 | $^1$H NMR (400 MHz, CDCl$_3$) $\delta_H$ 7.75 (dd, J = 5.3, 8.8 Hz, 2H), 7.10 (t, J = 8.5 Hz, 2H), 5.84 (br d, J = 9.0 Hz, 1H), 4.30-4.08 (m, 1H), 1.83-1.79 (m, 5H), 1.70-1.54 (m, 4H), 1.49-1.22 (m, 14H), 1.22-1.01 (m, 8H), 0.73 (s, 3H). $^{19}$F NMR (376 MHz, CDCl$_3$): $\delta_F$ −108.682. LC-ELSG/MS purity 99%, MS ESI calcd. For C$_{28H41}$FNO$_2$ [M + H]$^+$ 442, found 442. SFC 98.25% de. |
| 117 | | | 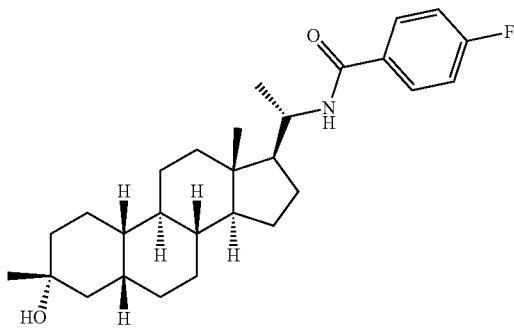 | $^1$H NMR (400 MHz, CDCl3) $\delta_H$ 7.81-7.64 (m, 2H), 7.09 (t, J = 8.7 Hz, 2H), 5.83 (br d, J = 8.5 Hz, 1H), 4.31-4.10 (m, 1H), 1.94 (br d, J = 12.3 Hz, 1H), 1.89-1.75 (m, 4H), 1.51-1.40 (m, 6H), 1.50-1.40 (m, 5H), 1.33-1.22 (m, 9H), 1.20-0.99 (m, 6H), 0.76 (s, 3H). $^{19}$F NMR (376 MHz, CDCl$_3$): $\delta_F$ −108.774. LC-ELSG/MS purity 99%, MS ESI calcd. For C$_{28H41}$FNO$_2$ [M + H]$^+$ 442, found 442. SFC 95.16% de |
| 118 | B24 | 1,3-dimethyl-1H-pyrazole-5-carboxylic acid | 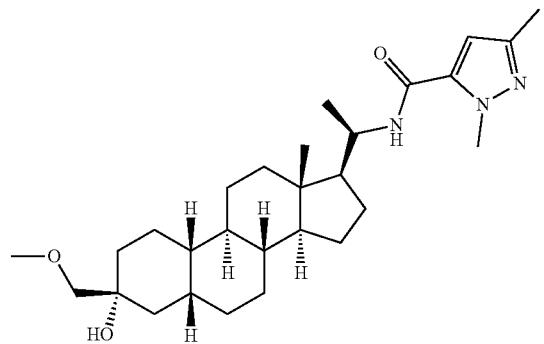 | $^1$H NMR (400 MHz, CDCl$_3$) $\delta_H$ 6.17 (s, 1H), 5.68 (br d, J = 9.3 Hz, 1H), 4.11-4.02 (m, 4H), 3.46-3.30 (m, 5H), 2.62 (br s, 1H), 2.26 (s, 3H), 1.88-1.69 (m, 6H), 1.62-1.56 (m, 5H), 1.46-0.94 (m, 16H), 0.71 (s, 3H). LC-ELSD/MS purity 99%, MS ESI calcd. For C$_{28H46}$N$_3$O$_3$ [M + H]$^+$ 472, found 472. SFC 99.4% de. |
| 119 | | | 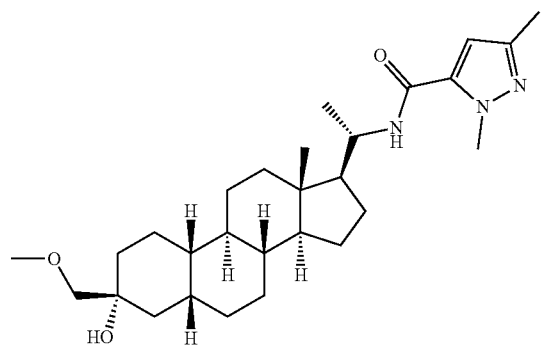 | $^1$H NMR (400 MHz, CDCl3) $\delta_H$ 6.20 (s, 1H), 5.71 (br d, J = 9.0 Hz, 1H), 4.19-4.02 (m, 4H), 3.47-3.32 (m, 5H), 2.25 (s, 3H), 1.96-1.88 (m, 1H), 1.86-1.65 (m, 7H), 1.51-0.98 (m, 20H), 0.74 (s, 3H). LC-ELSD/MS purity 99%, MS ESI calcd. For C$_{28}$H$_{46}$N$_3$O$_3$ [M + H]$^+$ 472, found 472. SFC 98.62% de. |

| Example | SM | acid | STRUCTURE | Analytical |
|---|---|---|---|---|
| 120 | B24 | 5-cyano-pyridine-2-carboxylic acid | 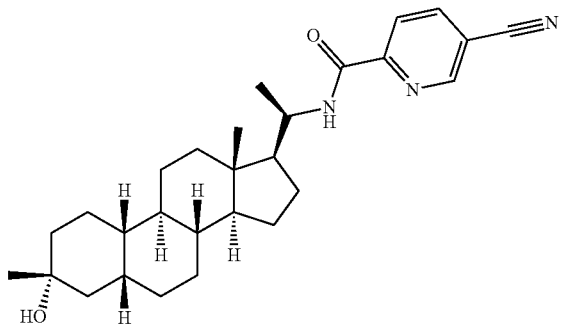 | B47: ¹H NMR (400 MHz, CDCl₃) δ$_H$ 8.83 (d, J = 1.0 Hz, 1 H), 8.34 (d, J = 8.0 Hz, 1 H), 8.13 (dd, J = 2.0, 8.4 Hz, 1 H), 7.85 (d, J = 9.2 Hz, 1 H), 4.20-4.04 (m, 1 H), 1.84 (s, 1 H), 1.82-1.71 (m, 1 H), 1.82-1.68 (m, 4 H), 1.48-1.31 (m, 10 H), 1.28-1.22 (m, 6 H), 1.19 (d, J = 6.4 Hz, 4 H), 1.22-1.17 (m, 1 H), 1.14-1.09 (m, 2 H), 0.99-0.82 (m, 2 H), 0.69 (s, 3 H). LC-ELSD/MS purity 99% MS ESI calcd. For C$_{27}$H$_{40}$N$_4$O$_3$ [M + H]⁺ 450, found 450. SFC 99.5% de |
| 121 | | | 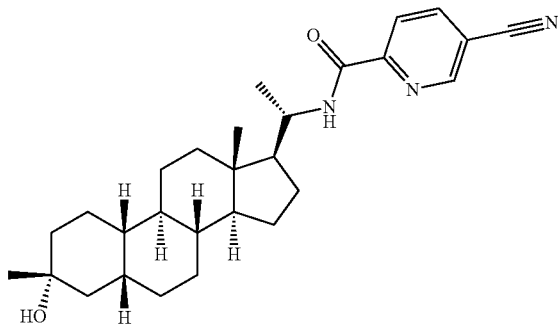 | ¹H NMR (400 MHz, CHLOROFORM-d) Shift = 8.81 (d, J = 1.2 Hz, 1H), 8.32 (d, J = 8.0 Hz, 1H), 8.13 (dd, J = 2.0, 8.0 Hz, 1H), 7.83 (d, J = 9.2 Hz, 1H), 4.28-4.10 (m, 1H), 1.95 (d, J = 12.4 Hz, 1H), 1.89-1.77 (m, 4H), 1.70-1.62 (m, 2H), 1.55-1.35 (m, 10H), 1.32-1.22 (m, 10H), 1.19-0.99 (m, 6H), 0.76 (s, 3H). LC-ELSD/MS purity 99% MS ESI calcd. For C$_{27}$H$_{40}$N$_4$O$_3$ [M + H]⁺ 450, found 450. SFC 99.3% de |
| 122 | B24 | 6-cyano-pyridine-3-carboxylic | 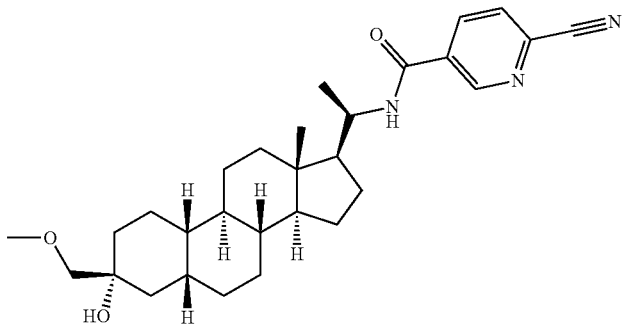 | ¹H NMR (400 MHz, CDCl₃) δ$_H$ 9.02 (d, J = 1.6 Hz, 1H), 8.24 (dd, J = 2.4, 8.0 Hz, 1H), 7.79 (d, J = 8.0 Hz, 1H), 5.99 (br d, J = 9.2 Hz, 1H), 4.36-4.06 (m, 1H), 3.46-3.31 (m, 5H), 2.64 (s, 1H), 1.90-1.81 (m, 1H), 1.81-1.72 (m, 4H), 1.65 (br d, J = 4.8 Hz, 2H), 1.51-1.29 (m, 9H), 1.29-1.19 (m, 5H), 1.13 (br d, J = 9.6 Hz, 3H), 1.09-0.93 (m, 3H), 0.73 (s, 3H); LC-ELSD/MS purity 99%, MS ESI calcd. for C29H40N3O2 [M + H]+ 462, found 462 |
| 123 | | | 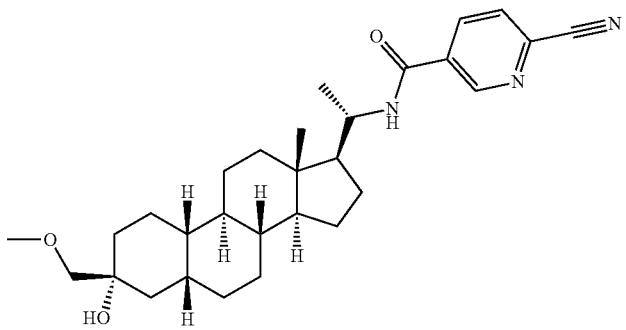 | ¹H NMR (400 MHz, CDCl₃) δ$_H$ 8.92 (d, J = 1.6 Hz, 1H), 8.14 (dd, J = 2.0, 8.0 Hz, 1H), 7.71 (d, J = 8.0 Hz, 1H), 5.90 (br d, J = 8.8 Hz, 1H), 4.30-4.08 (m, 1H), 3.40-3.27 (m, 5H), 2.56 (s, 1H), 1.87 (br d, J = 12.3 Hz, 1H), 1.81-1.67 (m, 4H), 1.61 (br s, 2H), 1.44-1.25 (m, 9H), 1.25-1.15 (m, 5H), 1.14-1.05 (m, 3H), 1.04-0.93 (m, 3H), 0.70 (s, 3H); LC-ELSD/MS purity 99%, MS ESI calcd. for C29H41N3O2 [M + H]+ 462, found 462. |

-continued

| Example | SM | acid | STRUCTURE | Analytical |
|---|---|---|---|---|
| 124 | B20 | 5-fluoro-pyridine-2-carboxylic acid | 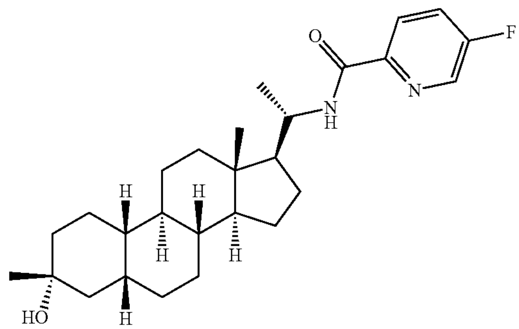 | 1HNMR (400 MHz, CHLOROFORM-d) δ 8.36 (d, J = 2.8 Hz, 1H), 8.23 (dd, J = 4.6, 8.7 Hz, 1H), 7.74 (br d, J = 9.0 Hz, 1H), 7.52 (dt, J = 2.8, 8.3 Hz, 1H), 4.26-4.00 (m, 1H), 1.96 (br d, J = 12.5 Hz, 1H), 1.90-1.66 (m, 5H), 1.52-1.20 (m, 20H), 1.20-0.94 (m, 5H), 0.76 (s, 3H). 19F NMR (376 MHz, CHLOROFORM-d) δ −123.06 (s, 1F). LC-ELSD/MS purity 99%, MS ESI calcd. for C27H40FN2O2 [M + H]+ 443, found 443. |
| 125 | B24 | 5-fluoro-pyridine-2-carboxylic acid | 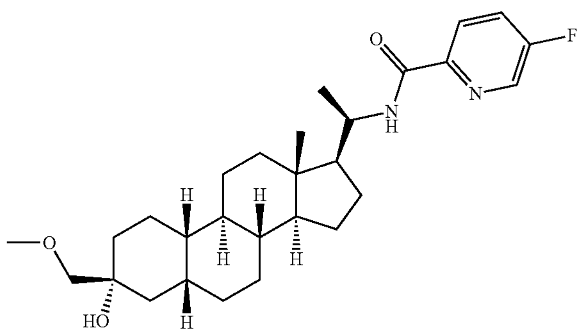 | $^1$H NMR (400 MHz, CDCl3) δ 8.39-8.36 (m, 1H), 8.23-8.21 (m, 1H), 7.80-7.71 (m, 1H), 7.52 (m, 1H), 4.22-4.03 (m, 1H), 3.47-3.30 (m, 6H), 2.60 (m, 1H), 1.62-1.92 (m, 7H), 1.54-1.32 (m, 8H), 1.30-1.16 (m, 6H), 1.14-0.87 (m, 5H), 0.70 (s, 3H). LC-ELSD/MS purity 99%, MS ESI calcd. For $C_{28}H_{42}FN_2O_3$ [M + H]$^+$ 473, found 473. SFC 99% de. |
| 126 | | | 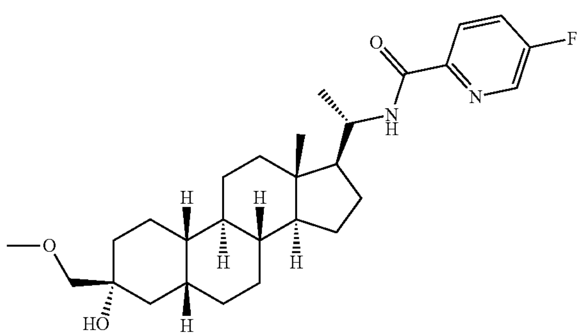 | $^1$H NMR (400 MHz, CDCl3) δ 8.39-8.36 (m, 1H), 8.23-8.21 (m, 1H), 7.80-7.71 (m, 1H), 7.52 (m, 1H), 4.22-4.03 (m, 1H), 3.47-3.30 (m, 6H), 2.60 (m, 1H), 1.62-1.92 (m, 7H), 1.54-1.32 (m, 10H), 1.30-1.16 (m, 6H), 1.14-0.87 (m, 5H), 0.76 (s, 3H). LC-ELSD/MS purity 99% MS ESI calcd. For $C_{28}H_{42}FN_2O_3$ [M+H]$^+$ 473, found 473. SFC 99% de. |
| 127 | B18 | 5-fluoro-pyridine-2-carboxylic acid | 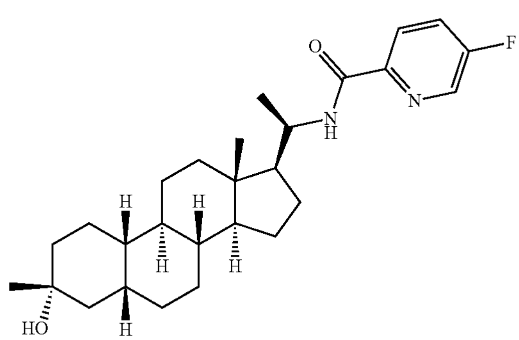 | $^1$H NMR (400 MHz, CDCl$_3$) δ 8.38 (m, 1H), 8.28-8.19 (m, 1H), 7.79-7.72 (m, 1H), 7.57-7.47 (m, 1H), 4.18-4.04 (m, 1H), 1.90-1.73 (m, 5H), 1.69-1.59 (m, 7H), 1.49-1.39 (m, 3H), 1.34-1.22 (m, 7H), 1.21-1.15 (m, 4H), 1.14-0.87 (m, 5H), 0.70 (s, 3H). LC-ELSD/MS purity 99%, MS ESI calcd. For $C_{27}H_{40}FN_2O_2$ [M + H]$^+$ 443, found 443. |
| 128 | B24 | 5-(trifluoromethoxy)pyridine-2-carboxylic acid | 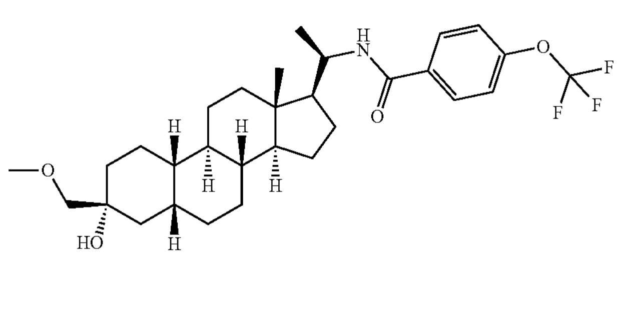 | $^1$H NMR (400 MHz, CDCl$_3$) δ$_H$ 8.47 (d, J = 2.8 Hz, 1H), 8.28 (d, J = 8.8 Hz, 1H), 7.77 (d, J = 9.2 Hz, 1H), 7.69-7.66 (m, 1H), 4.15-4.06 (m, 1H), 3.43-3.34 (m, 5H), 2.59 (s, 1H), 1.89-1.69 (m, 5H), 1.66-1.51 (m, 7H), 1.48-1.29 (m, 8H), 1.27-1.09 (m, 5H), 1.06-0.85 (m, 2H), 0.69 (s, 3H). $^{19}$F NMR (367 MHz, CDCl$_3$) δ −57.98. LC-ELSD/MS purity 99%, MS ESI calcd. for |

-continued

| Example | SM | acid | STRUCTURE | Analytical |
|---|---|---|---|---|
| | | | | $C_{29}H_{42}F_3N_2O_4$ [M + H]$^+$ 539, found 539. SFC 100% de. |
| 129 | | | 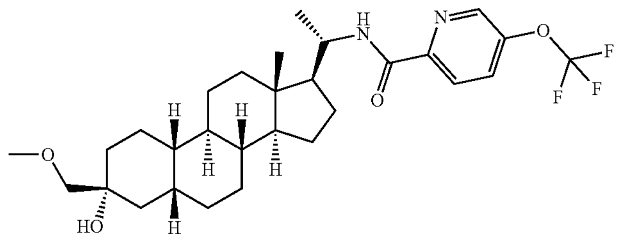 | $^1$H NMR (400 MHz, CDCl$_3$) $\delta_H$ 8.45 (d, J = 2.8 Hz, 1H), 8.27 (d, J = 8.8 Hz, 1H), 7.78 (d, J = 9.2 Hz, 1H), 7.69-7.67 (m, 1H), 4.15-4.06 (m, 1H), 3.43-3.34 (m, 5H), 2.60 (s, 1H), 1.97-1.71 (m, 5H), 1.68-1.53 (m, 7H), 1.52-1.32 (m, 8H), 1.27-0.99 (m, 7H), 0.76 (s, 3H). $^{19}$F NMR (367 MHz, CDCl$_3$) $\delta$ −58.03. LC-ELSD/MS purity 99%, MS ESI calcd. for $C_{29}H_{42}F_3N_2O_4$ [M + H]$^+$ 539, found 539. SFC 95.4% de. |
| 130 | B18 | 4-cyano-2-fluoro-benzoic acid | 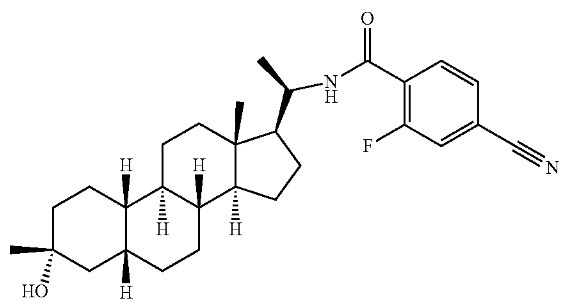 | $^1$H NMR (400 MHz, CDCl$_3$) $\delta_H$ 8.25 (t, J = 7.6 Hz, 1H), 7.59-7.55 (m, 1H), 7.46-7.42 (m, 1H), 6.60-6.52 (m, 1H), 4.25-4.16 (m, 1H), 1.90-1.75 (m, 5H), 1.70-1.56 (m, 3H), 1.56-1.30 (m, 8H), 1.30-0.95 (m, 15H), 0.72 (s, 3H). $^{19}$F NMR (376 MHz, CDCl$_3$) $\delta_F$ −111.418. LC-ELSD/MS purity 99%, MS ESI calcd. for $C_{29}H_{40}FN_2O_2$ [M + H]$^+$ 467, found 467. SFC 100% de. |
| 131 | E2 | 4-cyano-2-fluoro-benzoic acid | 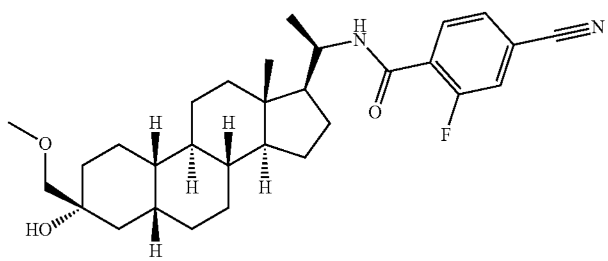 | $^1$H NMR (400 MHz, CDCl$_3$) $\delta_H$ 8.25 (t, J = 8.0 Hz, 1H), 7.57 (dd, J = 1.2, 8.0 Hz, 1H), 7.44 (dd, J = 1.2, 11.2 Hz, 1H), 6.60-6.51 (m, 1H), 4.25-4.15 (m, 1H), 3.42-3.35 (m, 5H), 2.61 (s, 1H), 1.87-1.60 (m, 7H), 1.50-1.23 (m, 10H), 1.19 (d, J = 6.4 Hz, 4H), 1.12 (m, 6H), 0.72 (s, 3H). $^{19}$F NMR (376 MHz, CDCl$_3$) $\delta_F$ −111.34. LC-ELSD/MS purity 99%, MS ESI calcd. for $C_{30}H_{42}FN_2O_3$ [M + H]$^+$ 497, found 497. |
| 132 | F8 | 2,4-difluoro-benzoic acid | 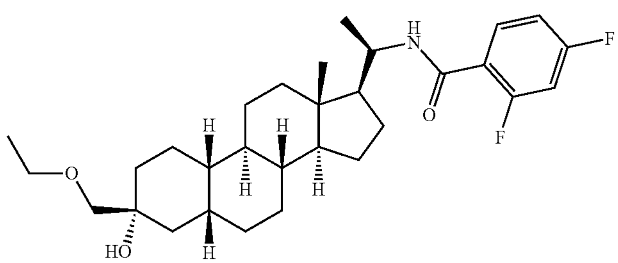 | $^1$H NMR (400 MHz, CDCl$_3$) $\delta_H$ 8.20-8.13 (m, 1H), 7.02-6.96 (m, 1H), 6.89-6.82 (m, 1H), 6.56-6.47 (m, 1H), 4.24-4.14 (m, 1H), 3.55-3.49 (m, 2H), 3.45-3.37 (m, 2H), 2.71 (s, 1H), 1.86-1.59 (m, 8H), 1.50-1.28 (m, 9H), 1.22-1.17 (m, 7H), 1.16-0.90 (m, 6H), 0.72 (s, 3H). $^{19}$F NMR (376 MHz, CDCl$_3$) $\delta_F$ −104.56, −104.59, −109.37, −109.40. LC-ELSD/MS purity 99%, MS ESI calcd. for $C_{30}H_{44}F_2NO_3$ [M + H]$^+$ 504, found 504; SFC 99% de. |
| 133 | F8 | 4-cyano-2-fluoro-benzoic acid | 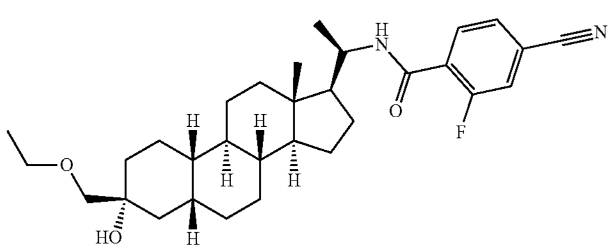 | $^1$H NMR (400 MHz, CDCl$_3$) $\delta_H$ 8.25 (t, J = 8.0 Hz, 1H), 7.57 (dd, J = 1.2, 8.0 Hz, 1H), 7.44 (d, J = 11.2 Hz, 1H), 6.60-6.51 (m, 1H), 4.26-4.14 (m, 1H), 3.55-3.49 (m, 2H), 3.45-3.37 (m, 2H), 2.72 (s, 1H), 1.85-1.73 (m, 4H), 1.67-1.61 (m, 3H), 1.49-1.33 (m, 10H), 1.22-1.18 (m, 7H), 1.15-1.09 (m, 3H), 1.07-0.94 (m, 3H), 0.72 (s, 3H). $^{19}$F NMR (376 MHz, CDCl$_3$) $\delta_F$ −111.32. LC-ELSD/MS purity 99%, MS ESI calcd. for $C_{31}H_{44}FN_2O_3$ [M + H]$^+$ 511, found 511. |

| Example | SM | acid | STRUCTURE | Analytical |
|---|---|---|---|---|
| 134 | B24 | 2,4-difluoro-benzoic acid | 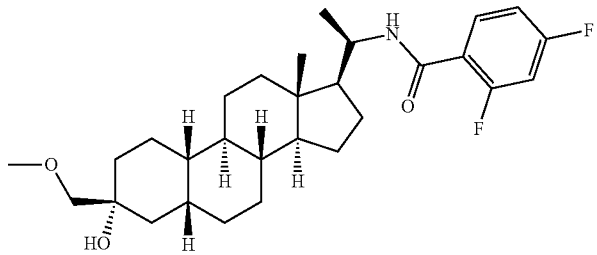 | $^1$H NMR (400 MHz, CDCl$_3$) δ$_H$ 8.16-8.02 (m, 1H), 7.05-6.93 (m, 1H), 6.92-6.76 (m, 1H), 6.60-6.43 (m, 1H), 4.27-4.10 (m, 1H), 3.47-3.27 (m, 5H), 2.60 (s, 1H), 1.87-1.62 (m, 7H), 1.58-1.26 (m, 10H), 1.25-0.91 (m, 10H), 0.72 (s, 3H). $^{19}$F NMR (376 MHz, CDCl$_3$) δ$_F$ -104.54, -109.40. LC-ELSD/MS purity 99%, MS ESI calcd. for C$_{29}$H$_{42}$F$_2$NO$_3$ [M + H]+ 490, found 490. SFC 100% de |
| 135 | | | 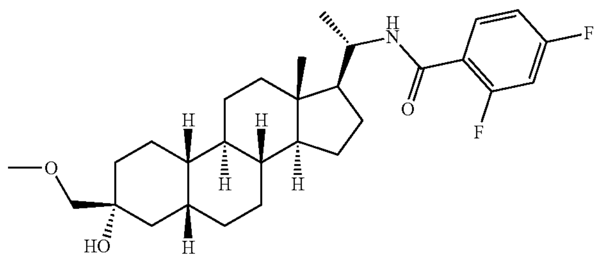 | $^1$H NMR (400 MHz, CDCl$_3$) δ$_H$ 8.17-8.02 (m, 1H), 7.06-6.93 (m, 1H), 6.90-6.78 (m, 1H), 6.53-6.35 (m, 1H), 4.29-4.12 (m, 1H), 3.45-3.33 (m, 5H), 2.62 (s, 1H), 1.98-1.90 (m, 1H), 1.89-1.66 (m, 5H), 1.58-1.30 (m, 10H), 1.30-0.98 (m, 11H), 0.75 (s, 3H). $^{19}$F NMR (376 MHz, CDCl$_3$) δ$_F$ -104.74, -109.75. LC-ELSD/MS purity 99%, MS ESI calcd. for C$_{29}$H$_{42}$F$_2$NO$_3$ [M + H]+ 490, found 490. SFC 98% de |

Examples 150-153: Synthesis of 1-((R)-1-((3R, 5R, 8R, 9R, 10S, 13S, 14S, 17S)-3-hydroxy-3-(methoxymethyl)-13-methylhexadecahydro-1H-cyclopenta[a]phenanthren-17-yl) ethyl)-1H-pyrazole-4-carbonitrile (150) & 1-((S)-1-((3R,5R,8R,9R,10S,13S,14S,17S)-3-hydroxy-3-(methoxymethyl)-13-methylhexadecahydro-1H-cyclopenta[a]phenanthren-17-yl)ethyl)-1H-pyrazole-4-carbonitrile (151)& 5-amino-1-((R)-1-((3R,5R,8R,9R,10S,13S,14S,17S)-3-hydroxy-3-(methoxymethyl)-13-methylhexadecahydro-1H-cyclopenta[a]phenanthren-17-yl)ethyl)-1H-pyrazole-4-carbonitrile (152) & 5-amino-1-((S)-1-((3R,5R,8R,9R,10S,13S,14S,17S)-3-hydroxy-3-(methoxymethyl)-13-methylhexadecahydro-1H-cyclopenta[a]phenanthren-17-yl)ethyl)-1H-pyrazole-4-carbonitrile (153)

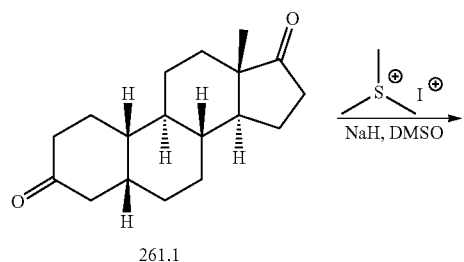

261.1

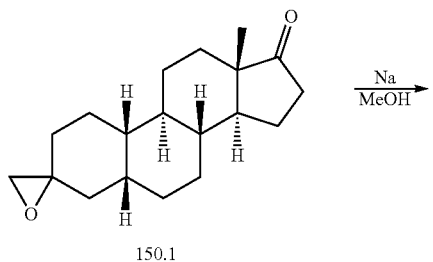

150.1

-continued

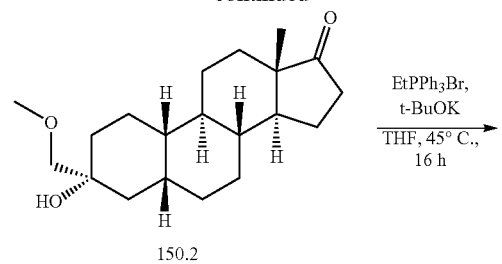

150.2

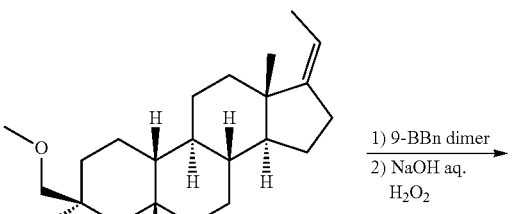

150.3

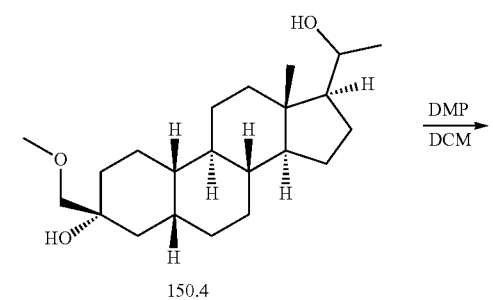

150.4

347

-continued

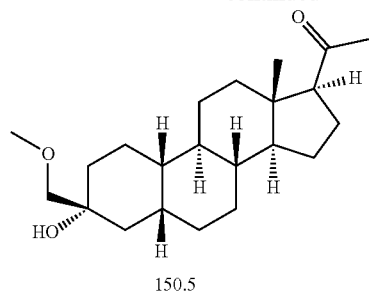
150.5

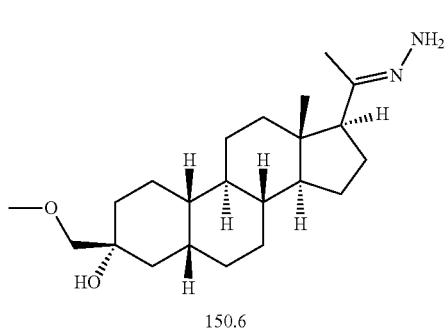
150.6

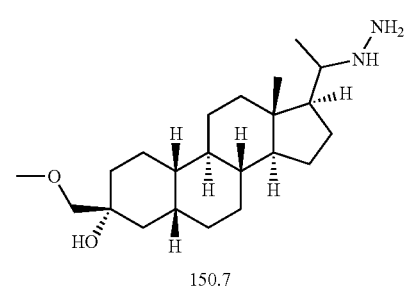
150.7

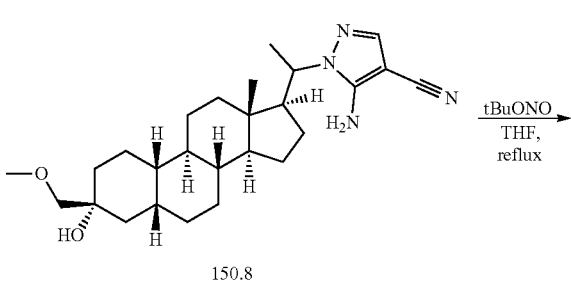
150.8

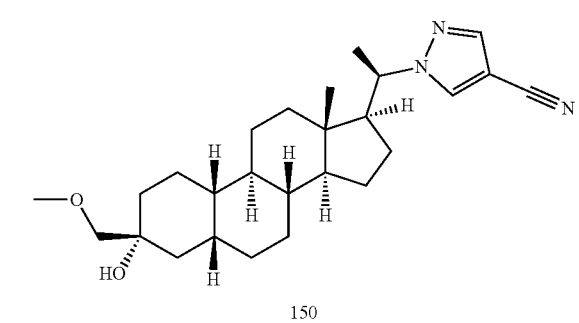
150

348

-continued

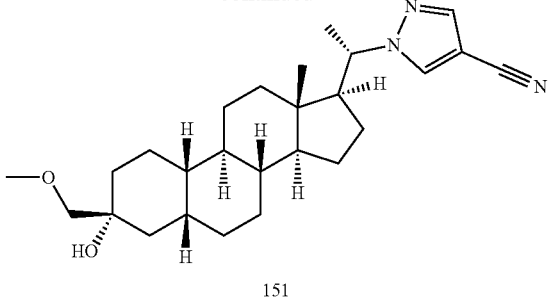
151

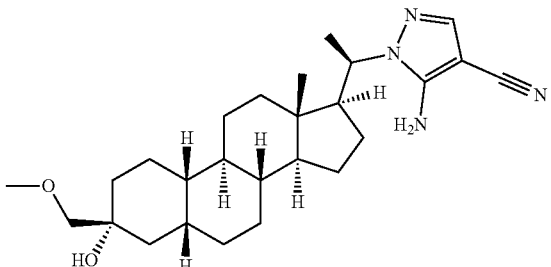
150.8

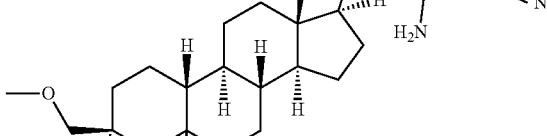
152

153

Synthesis of 150.1

To a solution of NaH (8.00 g, 200 mmol, 60% in oil) in DMSO (100 mL) was added a solution of trimethylsulfonium iodide (40.7 g, 200 mmol) in THF (100 mL) dropwise at 0° C. After stirring for 30 mins under $N_2$, 261.1 (50 g, 182 mmol) in DMSO (100 mL) was added. After stirring at 25° C. for another 12 h, the mixture was poured into ice-water (w/w=1/1, 400 mL), stirred for 20 min, and extracted with EtOAc (3×400 mL). The combined organic phase was washed with brine (2×200 mL), dried over anhydrous $Na_2SO_4$, filtered and concentrated. The residue was triturated with MeOH (300 mL) at 25° C. and the mother liquid was concentrated to give 150.1 (45 g) as a solid.

$^1$H NMR (400 MHz, CDCl$_3$) δ$_H$ 2.67-2.37 (m, 2H), 2.28-2.13 (m, 2H), 2.12-2.04 (m, 1H), 1.99-1.89 (m, 1H), 1.88-1.72 (m, 4H), 1.70-1.60 (m, 2H), 1.58-1.43 (m, 5H), 1.41-1.04 (m, 8H), 0.92-0.82 (m, 3H)

Synthesis of 150.2

Na (21.5 g, 935 mmol) was added into MeOH (250 mL) at 25° C. in portions. After stirring at 25° C. for 2 h under $N_2$, 150.1 (45 g, 156 mmol) in MeOH (150 mL) was added. After stirring at 75° C. for 12 h, the mixture was poured into water (400 mL) and extracted with EtOAc (3×400 mL). The combined organic phase was washed with brine (2×200 mL), dried over anhydrous $Na_2SO_4$, filtered and concentrated. The residue was purified by flash column (0~15% of EtOAc in PE) to give 150.2 (30 g) as oil. The 150.2 (30 g) was purified by flash column [0~5% of EtOAc in PE and DCM (1:1)] to give 150.2 (9 g, 30%) as oil.

$^1$H NMR (400 MHz, $CDCl_3$) $\delta_H$ 3.47-3.31 (m, 5H), 2.42 (dd, J=8.4, 19.2 Hz, 1H), 2.12-2.02 (m, 1H), 1.96-1.89 (m, 1H), 1.86-1.67 (m, 6H), 1.60-1.41 (m, 7H), 1.38-1.17 (m, 7H), 1.10-1.00 (m, 1H), 0.85 (s, 3H).

Synthesis of 150.3

To a suspension of $EtPPh_3Br$ (30.0 g, 84.0 mmol) in THF (100 mL) was added t-BuOK (9.40 g, 84.0 mmol) at 25° C. under $N_2$. After stirring for 1 h, 150.2 (9 g, 28.0 mmol) in THF (50 mL) was added at 25° C. After stirring at 40° C. for 3 h, the solution was combined with two batches prepared from 9 g and 18 g respectively of 150.2. The mixture was poured into $NH_4Cl$ (200 mL, aq.) and extracted with EtOAc (3×200 mL). The combined organic phase was washed with brine (2×100 mL), dried over anhydrous $Na_2SO_4$, filtered and concentrated. The residue was triturated from MeOH (300 mL) and water (300 mL) at 25° C. to give 150.3 (30 g) as oil.

$^1$H NMR (400 MHz, $CDCl_3$) $\delta_H$ 5.17-5.05 (m, 1H), 3.46-3.32 (m, 5H), 2.59 (brs, 1H), 2.43-2.12 (m, 4H), 1.90-1.79 (m, 2H), 1.77-1.69 (m, 7H), 1.67-1.61 (m, 4H), 1.43-1.32 (m, 3H), 1.23-1.03 (m, 6H), 0.87 (s, 3H).

Synthesis of 150.4

To a solution of 150.3 (30 g) in THF (150 mL) was added 9-BBN dimer (43.9 g, 180 mmol) at 25° C. After stirring for 1 h, the reaction mixture was sequentially treated with NaOH (108 mL, 5M in water, 541 mmol) at 0° C. and hydrogen peroxide (54.1 mL, 541 mmol) dropwise at 0° C. After stirring at 78° C. for 3 h, the reaction mixture was quenched with saturated aqueous $Na_2S_2O_3$ (100 mL) and ice-water (300 mL), stirred for 20 min and then extracted with EtOAc (3×250 mL). The combined organic phase was washed with brine (2×250 mL), dried over anhydrous $Na_2SO_4$, filtered and concentrated. The residue was triturated from $CH_3OH$ (100 mL) and water (500 mL) at 25° C. to give 150.4 (35 g) as oil, which was purified by flash column (0~15% of EtOAc in PE) to give 150.4 (12 g) as a solid.

$^1$H NMR (400 MHz, $CDCl_3$) $\delta_H$ 3.74-3.66 (m, 1H), 3.43-3.36 (m, 5H), 2.60 (s, 1H), 1.95-1.71 (m, 6H), 1.64 (s, 4H), 1.60-1.44 (m, 6H), 1.35-1.19 (m, 6H), 1.16-1.08 (m, 4H), 0.92-0.80 (m, 1H), 0.75 (s, 1H), 0.65 (s, 3H).

Synthesis of 150.5

To a solution of 150.4 (12 g) in DCM (100 mL) was added DMP (33.1 g, 78.2 mmol) in one portion at 25° C. After stirring at 35° C. for 30 min, the residue was diluted with $NaHCO_3$ (100 mL) and filtered. The mixture was washed with $Na_2SO_3$ and $NaHCO_3$ (3:1) in water (100 mL). The aqueous phase was extracted with DCM (100 mL). The combined organic phase was washed with brine (2×100 mL), dried over anhydrous $Na_2SO_4$, filtered and concentrated. The residue was purified by flash column (0~15% of EtOAc in PE) to give 150.5 (5 g, 42%) as a solid.

$^1$H NMR (400 MHz, $CDCl_3$) $\delta$ 3.45-3.34 (m, 5H), 2.62 (s, 1H), 2.59-2.46 (m, 1H), 2.26-2.13 (m, 1H), 2.13-2.09 (m, 1H), 2.11 (s, 3H), 2.03-1.97 (m, 1H), 2.03-1.97 (m, 1H), 1.83 (d, J=15.2 Hz, 1H), 1.78-1.63 (m, 5H), 1.52-1.33 (m, 5H), 1.31-1.00 (m, 8H), 0.61 (s, 3H).

Synthesis of 150.6

To a solution of 150.5 (2.9 g, 8.3 mmol) in EtOH (30 mL) were added $Et_3N$ (3.5 mL) and hydrazine hydrate (4.16 g, 83.2 mmol) at 25° C. After stirring at 75° C. for 12 h, the solution was concentrated. The residue was diluted with water (30 mL) and extracted with EtOAc (3×20 mL). The combined organic layer was washed with brine (30 mL), dried over anhydrous $Na_2SO_4$, filtered and concentrated to give 150.6 (3 g, 99%) as an oil.

$^1$H NMR (400 MHz, $CDCl_3$) $\delta_H$ 4.91 (brs, 2H), 3.50-3.30 (m, 5H), 2.60 (s, 1H), 2.30-2.10 (m, 2H), 1.90-1.50 (m, 10H), 1.50-0.95 (m, 15H), 0.57 (s, 3H).

Synthesis of 150.7

To a solution of 150.6 (3 g, 8.3 mmol) in MeOH (30 mL) were added AcOH (990 mg, 16.5 mmol) and $NaBH_3CN$ (5.20 g, 82.6 mmol) at 25° C. After stirring at 75° C. for 12 h, the solution was concentrated. The residue was diluted with water (30 mL) and extracted with EtOAc (3×20 mL). The combined organic layer was washed with brine (30 mL), dried over anhydrous $Na_2SO_4$, filtered and concentrated to give 150.7 (3 g, 99%) as oil, which was used directly for the next step without further purification.

Synthesis of 152 & 153

To a solution of 150.7 (3 g, 8.2 mmol) in EtOH (50 mL) were added TEA (2.48 g, 24.6 mmol) and 2-(ethoxymethylidene) propanedinitrile (1.2 g, 9.9 mmol) at 25° C. After stirring at 75° C. for 16 h, the mixture was concentrated in vacuum and the residue was purified by flash column (20-40% of EtOAc in PE) to give 150.8 (3 g, 82.8%) as solid. 150.8 (500 mg, 1.1 mmol) was purified by Prep-HPLC (Column: Agela DuraShell 150 mm_25 mm_5 m; Condition: water (0.04% $NH_3H_2O$+10 mM $NH_4HCO_3$)-ACN; Begin B: 42; End B: 72; Gradient Time (min): 7.5; 100% B Hold Time (min): 2) to afford 152 (48.8 mg, 10%) as a solid and 153 (200 mg) as solid. 153 (200 mg, 0.5 mmol) was further purified by SFC (Column: DAICEL CHIRALPAK AD (250 mm*30 mm, 10 um); Condition: 0.1% $NH_3H_2O$ EtOH; Begin B: 50; End B: 50) to afford 153 (83.2 mg, 42%) as solid.

152: $^1$H NMR (400 MHz, $CDCl_3$) $\delta_H$ 7.48 (s, 1H), 4.18 (s, 2H), 4.00-3.80 (m, 1H), 3.50-3.30 (m, 5H), 2.55 (s, 1H), 2.18 (q, J=10.0 Hz, 1H), 1.95-1.85 (m, 1H), 1.80-1.60 (m, 4H), 1.50-1.15 (m, 11H), 1.10-0.75 (m, 9H), 0.69 (s, 3H), 0.46 (d, J=12.4 Hz, 1H). LC-ELSD/MS purity ≥99%, 100% de based on H-NMR; MS ESI calcd. for $C_{26}H_{41}N_4O_2$ [M+H]$^+$ 441.3, found 441.3.

153: $^1$H NMR (400 MHz, $CDCl_3$) $\delta_H$ 7.51 (s, 1H), 4.18 (s, 2H), 4.00-3.80 (m, 1H), 3.50-3.30 (m, 5H), 2.60 (s, 1H), 2.15-2.00 (m, 1H), 1.95-1.90 (m, 1H), 1.85-1.65 (m, 5H), 1.50-0.95 (m, 20H), 0.77 (s, 3H). LC-ELSD/MS purity ≥99%, 100% de based on H-NMR; MS ESI calcd. for $C_{26}H_{41}N_4O_2$ [M+H]$^+$ 441.3, found 441.3.

Synthesis of 150 & 151

To a solution of 150.8 (1.5 g, 3.4 mmol) in THF (20 mL) was added tert-butyl nitrite (419 mg, 4.1 mmol) at 25° C. After stirring at 75° C. for 16 h, the mixture was poured into water (50 mL) and extracted with DCM (2×30 mL). The combined organic layers were washed with brine (50 mL), dried over anhydrous $Na_2SO_4$ and concentrated in vacuum to give 150 & 151 (1 g) as solid. The diastereomers were purified by prep-HPLC (Column: Agela DuraShell 150 mm_25 mm_5 um; Condition: water (0.04% $NH_3H_2O$+10 mM $NH_4HCO_3$)-ACN; Begin B: 55; End B: 85; Gradient Time (min): 7.5; 100% B Hold Time (min): 2) to afford 150 & 151 (200 mg, 20%) as a solid. The diastereomers were separated by SFC (Column: DAICEL CHIRALPAK AD-H (250 mm*30 mm, 5 um) Condition: 0.1% $NH_3H_2O$ EtOH; Begin B: 40; End B: 40; Gradient Time (min): 7.5; 100% B Hold Time (min): 2) to afford 150 (12 mg, 6%, Rt=1.616 min, de=100%) as a solid and 151 (43.7 mg, 22%, Rt=1.867 min, de=99.92%) as a solid.

150: $^1$H NMR (400 MHz, CDCl$_3$) $\delta_H$ 7.78 (s, 1H), 7.75 (s, 1H), 4.40-4.20 (m, 1H), 3.50-3.30 (m, 5H), 2.56 (s, 1H), 2.00-1.60 (m, 6H), 1.50-0.95 (m, 18H), 0.90-0.60 (m, 5H), 0.20-0.10 (m, 1H).

LC-ELSD/MS purity ≥99%, analytic SFC: 100% de; MS ESI calcd. for C$_{26}$H$_{40}$N$_3$O$_2$ [M+H]$^+$ 426.3, found 426.3.

151: $^1$H NMR (400 MHz, CDCl$_3$) $\delta_H$ 7.80-7.75 (m, 2H), 4.30-4.10 (m, 1H), 3.50-3.30 (m, 5H), 2.61 (s, 1H), 2.00-1.65 (m, 8H), 1.60-1.30 (m, 10H), 1.30-0.95 (m, 9H), 0.76 (s, 3H).

LC-ELSD/MS purity ≥99%, analytic SFC: 100% de; MS ESI calcd. for C$_{26}$H$_{40}$N$_3$O$_2$ [M+H]$^+$ 426.3, found 426.3.

Examples 154-157: Synthesis of 1-((R)-1-((3R,5R,8R,9R,10S,13S,14S,17S)-3-hydroxy-3,13-dimethyl-hexadecahydro-1H-cyclopenta[a]phenanthren-17-yl)ethyl)-1H-pyrazole-4-carbonitrile (156) & 1-((S)-1-((3R,5R,8R,9R,10S,13S,14S,17S)-3-hydroxy-3,13-dimethylhexadecahydro-1H-cyclopenta[a]phenanthren-17-yl)ethyl)-1H-pyrazole-4-carbonitrile (157) 5-amino-1-((R)-1-((3R,5R,8R,9R,10S,13S,14S,17S)-3-hydroxy-3,13-dimethylhexadecahydro-1H-cyclopenta[a]phenanthren-17-yl)ethyl)-1H-pyrazole-4-carbonitrile (154) & 5-amino-1-((S)-1-((3R,5R,8R,9R,10S,13S,14S,17S)-3-hydroxy-3,13-dimethylhexadecahydro-1H-cyclopenta[a]phenanthren-17-yl)ethyl)-1H-pyrazole-4-carbonitrile (155)

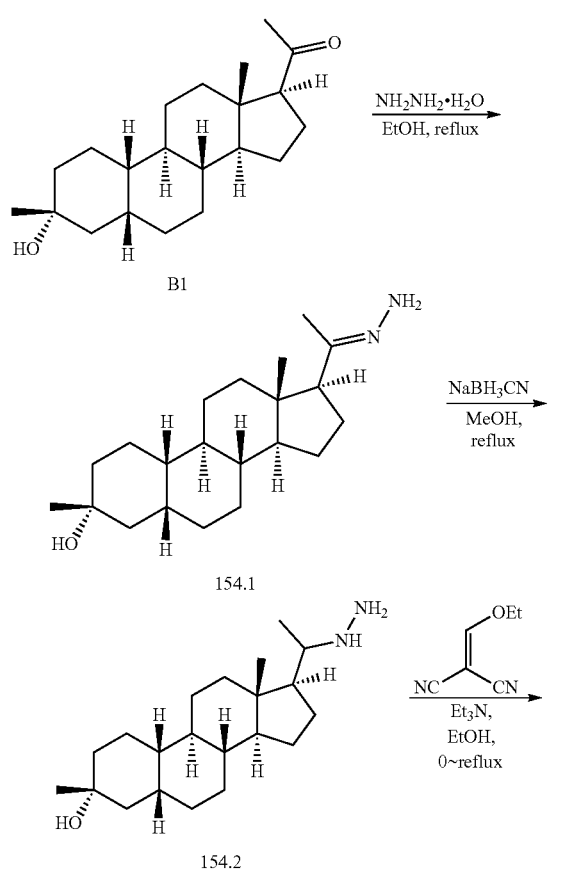

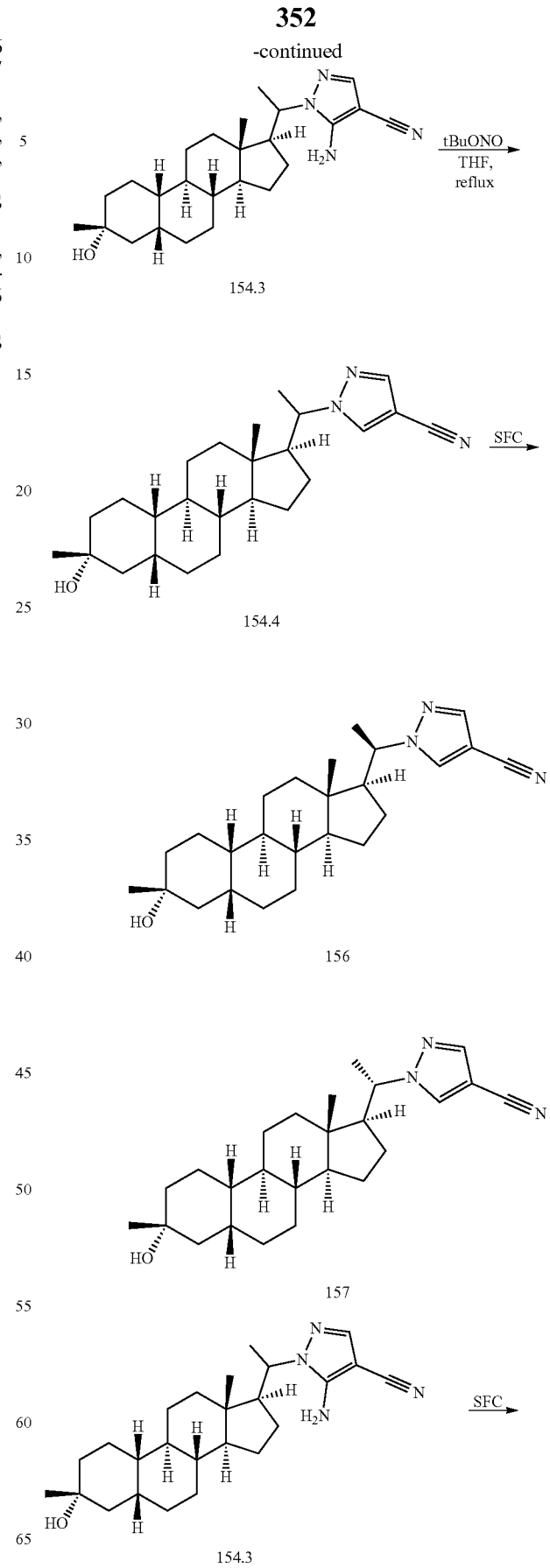

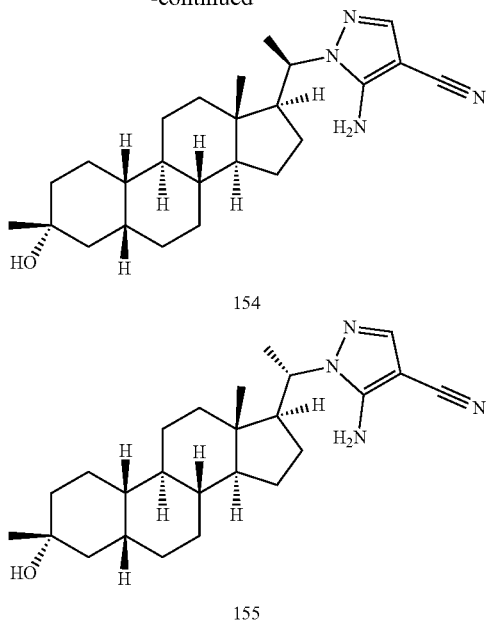

154

155

Synthesis of 154.1

To a solution of B1 (2 g, 6.3 mmol) in ethanol (20 mL) were added Et$_3$N (3.5 mL) and hydrazine hydrate (3.13 g, 62.6 mmol) at 25° C. After stirring at 75° C. for 12 h, the reaction mixture was concentrated, diluted with water (30 mL) and extracted with EtOAc (3×20 mL). The combined organic layer was washed with brine (30 mL), dried over anhydrous Na$_2$SO$_4$, filtered and concentrated to give 154.1 (1.8 g, 87%) as oil.

Synthesis of 154.2

To a solution of 154.1 (1.8 g, 5.4 mmol) in MeOH (20 mL) was added NaBH$_3$CN (3.39 g, 54.0 mmol) at 25° C. After stirring at 75° C. for 12 h, the solution was concentrated, diluted with water (30 mL) and extracted with EtOAc (3×20 mL). The combined organic layer was washed with brine (30 mL), dried over anhydrous Na$_2$SO$_4$, filtered and concentrated to give 154.2 (1.6 g, 89%) as a solid.

Synthesis of 154 & 155

To a solution of 154.2 (1.6 g, 4.8 mmol) in EtOH (20 mL) were added Et$_3$N (1.98 mL) and 2-(ethoxymethylidene)propanedinitrile (699 mg, 5.73 mmol) at 25° C. After stirring at 85° C. for 16 h, the solution was concentrated, diluted with water (30 mL) and extracted with EtOAc (3×20 mL). The combined organic layer was washed with brine (30 mL), dried over anhydrous Na$_2$SO$_4$, filtered and concentrated to give 154.3 (1.6 g, 81%) as a solid. 154.3 (1.0 g) was purified by pre-HPLC (Column HT C18 Highload 150 mm*25 mm*5 μm, Condition water (0.04% NH$_3$H$_2$O+10 mM NH$_4$HCO$_3$)—CH$_3$CN, Begin B: 50%, End B: 80%) to afford 154.3 (200 mg) as a solid.

154.3 (200 mg) was separated by SFC (Column: Waters UPCC with PDA Detector) to afford 154 (60 mg, P1, Rt=3.321 min) as a solid and 155 (30 mg, P2, Rt=3.669 min) as a solid. 154 (60 mg) was further purified by pre-HPLC (Column Xtimate C18 150*25 mm*5 μm, Condition: water (10 mM NH$_4$HCO$_3$)—CH$_3$CN, Begin B 52%, End B 82%) to afford 154 (18.1 mg, Rt=3.319 min, de=100%) as a solid.

155 (30 mg) was further purified by pre-HPLC (Column Xtimate C18 150*25 mm*5 μm, Condition water (10 mM NH$_4$HCO$_3$)—CH$_3$CN, Begin B 52%, End B 82%) to afford 155 (9.2 mg, Rt=3.676 min, de=96.3%) as a solid.

154: $^1$H NMR (400 MHz, CDCl$_3$) δ$_H$ 7.48 (s, 1H), 4.18 (s, 2H), 3.96-3.85 (m, 1H), 2.25-2.15 (m, 1H), 1.95-1.60 (m, 5H), 1.51-1.22 (m, 11H), 1.25-0.76 (m, 13H), 0.70 (s, 3H), 0.52-0.45 (m, 1H). LC-ELSD/MS purity 99%, analytic SFC: 100% de. MS ESI calcd. for C$_{25}$H$_{39}$N$_4$O [M+H]$^+$ 411.3 found 411.3.

155: $^1$H NMR (400 MHz, CDCl$_3$) δ$_H$ 7.51 (s, 1H), 4.20-4.05 (m, 2H), 3.95-3.82 (m, 1H), 2.14-2.05 (m, 1H), 2.00-1.75 (m, 5H), 1.75-1.60 (m, 2H), 1.52-1.35 (m, 11H), 1.35-1.00 (m, 12H), 0.78 (s, 3H). LC-ELSD/MS purity 99%, analytic SFC: 96.3% de. MS ESI calcd. for C$_{25}$H$_{39}$N$_4$O [M+H]$^+$ 411.3 found 411.3.

Synthesis of 156 & 157

To a solution of 154.3 (1 g, 2.4 mmol) in THF (20 mL) was added tert-butyl nitrite (300 mg, 2.9 mmol) at 25° C. After stirring at 75° C. for 16 h, the mixture was poured into water (50 mL) and extracted with DCM (2×30 mL). The combined organic layers were washed with brine (50 mL), dried over anhydrous Na$_2$SO$_4$ and concentrated. The product was purified by flash column (10-30% of EtOAc in PE) at 25° C. to afford 154.4 (800 mg) as solid. 154.4 was further purified by pre-HPLC (Column HT C18 Highload 150 mm*25 mm*5 μm, Condition water (0.04% NH$_3$H$_2$O+10 mM NH$_4$HCO$_3$)—CH$_3$CN, Begin B 60, End B 90) to afford 154.4 (200 mg, 25%) as a solid.

The diastereomers were separated by SFC (Column: Chiralpak AD-3 150×4.6 mm I.D., 3 μm, Mobile phase: 40% of ethanol (0.05% DEA) in CO$_2$) to afford 156 (60 mg, P1, Rt=2.049 min) as a solid and 157 (30 mg, P2, Rt=2.466 min) as a solid.

156 (60 mg) was further purified by pre-HPLC (Column Xtimate C18 150*25 mm*5 μm, Condition water (10 mM NH$_4$HCO$_3$)—CH$_3$CN, Begin B 59%, End B 89%) to afford 156 (19.5 mg, Rt=2.057 min, de=100%) as a solid.

157 (30 mg) was further purified by pre-HPLC (Column Xtimate C18 150*25 mm*5 μm, Condition water (10 mM NH$_4$HCO$_3$)—CH$_3$CN, Begin B 59%, End B 89%) to afford 157 (13.2 mg, Rt=2.495 min, de=100%) as a solid.

156: $^1$H NMR (400 MHz, CDCl$_3$) δ$_H$ 7.78 (s, 1H), 7.75 (s, 1H), 4.25-4.35 (m, 1H), 2.02-1.88 (m, 2H), 1.81-1.64 (m, 4H), 1.50-1.20 (m, 11H), 0.86-0.65 (m, 5H), 0.20-0.12 (m, 1H). LC-ELSD/MS purity 99%, analytic SFC: 100% de. MS ESI calcd. for C$_{25}$H$_{38}$N$_3$O [M+H]$^+$ 396.3 found 396.3.

157: $^1$H NMR (400 MHz, CDCl$_3$) δ$_H$ 7.78-7.74 (m, 2H), 4.24-4.12 (m, 1H), 2.01-1.79 (m, 5H), 1.73-1.61 (m, 2H), 1.55-1.24 (m, 10H), 1.29-1.00 (m, 14H), 0.77 (s, 3H). LC-ELSD/MS purity 99%, analytic SFC: 100% de. MS ESI calcd. for C$_{25}$H$_{38}$N$_3$O [M+H]+ 396.3 found 396.3.

Examples 158 & 159: Synthesis of (3R,5R,8R,9R,10S,13S,14S,17S)-17-((R)-1-(2H-1,2,3-triazol-2-yl)ethyl)-3,13-dimethylhexadecahydro-1H-cyclopenta[a]phenanthren-3-ol (158) & (3R,5R,8R,9R,10S,13S,14S,17S)-17-((R)-1-(1H-1,2,3-triazol-1-yl)ethyl)-3,13-dimethylhexadecahydro-1H-cyclopenta[a]phenanthren-3-ol (159)

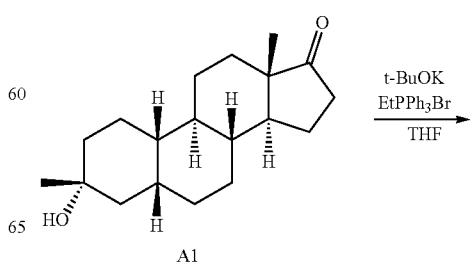

A1

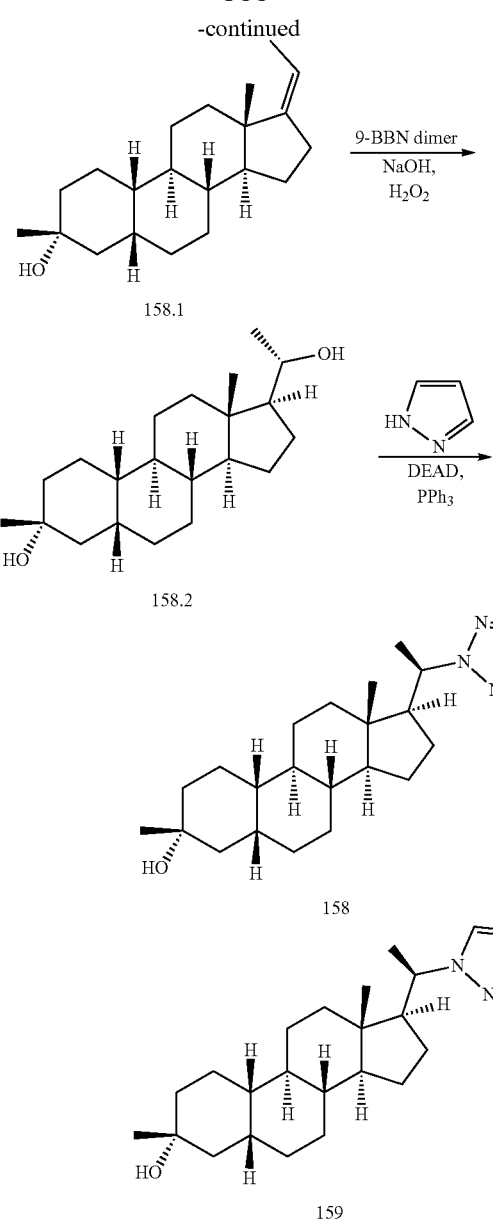

Synthesis of 158.1

To a mixture of EtPPh$_3$Br (38.2 g, 103 mmol) in THF (100 mL) was added t-BuOK (11.5 g, 103 mmol) at 25° C. under N$_2$. After stirring at 40° C. for 30 min, A1 (10 g, 34.4 mmol) was added in portions below 40° C. After stirring at 40° C. for 1 h, the reaction mixture was quenched with 10% NH$_4$Cl aqueous (100 mL) and extracted with EtOAc (2×100 mL). The combined organic layers were washed with brine (200 mL), dried over anhydrous Na$_2$SO$_4$, filter and concentrated under vacuum to give a solid. The solid was purified by trituration with MeOH/H$_2$O (1:1, 100 mL) at reflux to give 158.1 (13.7 g) as oil.

$^1$H NMR (400 MHz, CDCl$_3$) δ$_H$ 5.11 (q, J=7.2 Hz, 1H), 2.40-2.30 (m, 1H), 2.29-2.17 (m, 2H), 1.90-1.77 (m, 3H), 1.74-1.68 (m, 1H), 1.65 (br d, J=7.2 Hz, 3H), 1.62-1.58 (m, 1H), 1.48-1.35 (m, 6H), 1.35-1.26 (m, 3H), 1.26 (s, 3H), 1.24-1.18 (m, 2H), 1.18-1.05 (m, 4H), 0.87 (s, 3H)

Synthesis of 158.2

To a solution of 158.1 (4 g, 13.2 mmol) in THF (40 mL) was added 9-BBN dimer (6.38 g, 26.4 mmol) at 0° C. After stirring at 25° C. for 1 h, the reaction mixture was sequentially treated with ethanol (23 mL) at 25° C., NaOH aqueous (26.4 mL, 5 M, 132 mmol) at 0° C. and H$_2$O$_2$ (22.4 g, 30%, 198 mmol) dropwise. After stirring at 70° C. for 1 h, the reaction mixture was quenched with saturated aqueous Na$_2$S$_2$O$_3$ (50 mL), stirred at 0° C. for 10 minutes, and diluted with water (50 mL). The suspension was stirred at 25° C. for 1 h, filtered, washed with water (2×40 mL), dried under vacuum to give 158.2 (3.5 g) as a solid.

$^1$H NMR (400 MHz, CDCl$_3$) δ$_H$ 3.79-3.65 (m, 1H), 1.99-1.79 (m, 5H), 1.74-1.59 (m, 3H), 1.57-1.52 (m, 2H), 1.50-1.28 (m, 9H), 1.26 (s, 3H), 1.22 (d, J=6.4 Hz, 3H), 1.20-0.99 (m, 7H), 0.66 (s, 3H).

Synthesis of 158 & 159

To a solution of 158.2 (1 g, 3.1 mmol) in THF (10 mL) were added 2H-1,2,3-triazole (257 mg, 3.7 mmol), triphenylphosphine (1.63 g, 6.2 mmol) and diisopropyl azodicarboxylate (1.08 g, 6.2 mmol) at 0° C. After stirring at 25° C. for 12 h, the mixture was poured into water (20 mL) and extracted with EtOAc (2×20 mL). The combined organic layer was washed with brine (2×20 mL), dried over anhydrous Na$_2$SO$_4$, filtered and concentrated. The residue was purified by flash column (0~10% of EtOAc in PE) to give 158 (80 mg) and 159 (40 mg) both as oil.

158 (80 mg) was further purified by pre-HPLC (Method: SAGE-TJF-019-P1I; Column: Xtimate C18 150*25 mm*5 um; Condition: water (0.225% FA)-ACN; Begin B: 70%; End B: 100%) to afford 158 (34.2 mg, 43%) as a solid.

159 (40 mg) was further purified by pre-HPLC (Method: SAGE-TJF-019-P1H; Column: Xtimate C18 150*25 mm*5 um; Condition: water (0.225% FA)-ACN; Begin B: 90%; Begin B: 100%)) to afford 159 (4.7 mg, 12%) as a solid.

158: $^1$H NMR (400 MHz, CDCl$_3$) δ$_H$ 7.54 (s, 2H), 4.75-4.60 (m, 1H), 2.20-2.08 (m, 1H), 1.99-1.85 (m, 1H), 1.84-1.60 (m, 6H), 1.53-1.50 (m, 1H), 1.47 (d, J=6.8 Hz, 3H), 1.45-1.23 (m, 9H), 1.22 (s, 3H), 1.20-0.95 (m, 5H), 0.76 (s, 3H), 0.70-0.55 (m, 1H), −0.01--0.09 (m, 1H). LC-ELSD/MS purity 99%, MS ESI calcd. for C$_{23}$H$_{38}$N$_3$O [M+H]$^+$ 372.3, found 372.3.

159: $^1$H NMR (400 MHz, CDCl$_3$) δ$_H$ 7.71 (d, J=0.8 Hz, 1H), 7.59 (d, J=1.2 Hz, 1H), 5.12-4.96 (m, 1H), 2.42-2.12 (m, 4H), 2.10-2.00 (m, 2H), 1.90-1.75 (m, 6H), 1.74-1.59 (m, 5H), 1.52-1.50 (m, 1H), 1.43 (s, 3H), 1.40-1.34 (m, 1H), 1.32-1.02 (m, 9H), 0.74 (s, 3H). LC-ELSD/MS purity 99%, MS ESI calcd. for C$_{23}$H$_{36}$N$_3$ [M−H$_2$O+H]$^+$ 354.3, found 354.3.

Examples 160-163: Synthesis of 5-amino-1-((R)-1-((3R,5R,8R,9R,10S,13S,14S,17S)-3-(ethoxymethyl)-3-hydroxy-13-methylhexadecahydro-1H-cyclopenta[a]phenanthren-17-yl)ethyl)-1H-pyrazole-4-carbonitrile (160) & 5-amino-1-((S)-1-((3R,5R,8R,9R,10S,13S,14S,17S)-3-(ethoxymethyl)-3-hydroxy-13-methylhexadecahydro-1H-cyclopenta[a]phenanthren-17-yl)ethyl)-1H-pyrazole-4-carbonitrile (161) & 1-((R)-1-((3R,5R,8R,9R,10S,13S,14S,17S)-3-(ethoxymethyl)-3-hydroxy-13-methylhexadecahydro-1H-cyclopenta[a]phenanthren-17-yl)ethyl)-1H-pyrazole-4-carbonitrile (162) & 1-((S)-1-((3R,5R,8R,9R,10S,13S,14S,17S)-3-(ethoxymethyl)-3-hydroxy-13-methylhexadecahydro-1H-cyclopenta[a]phenanthren-17-yl)ethyl)-1H-pyrazole-4-carbonitrile (163)

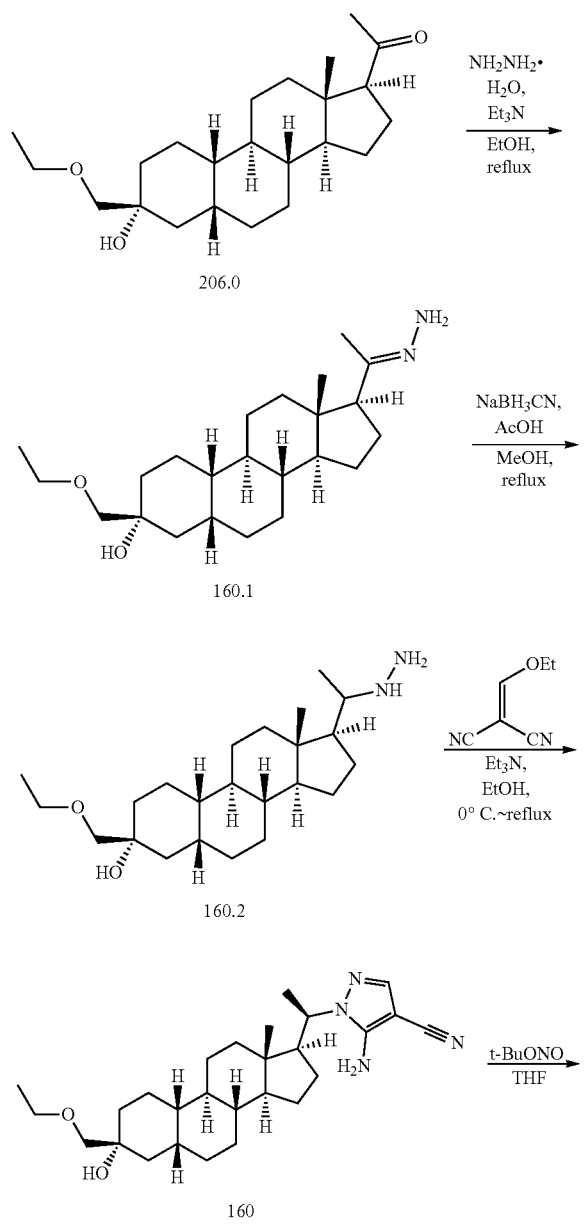

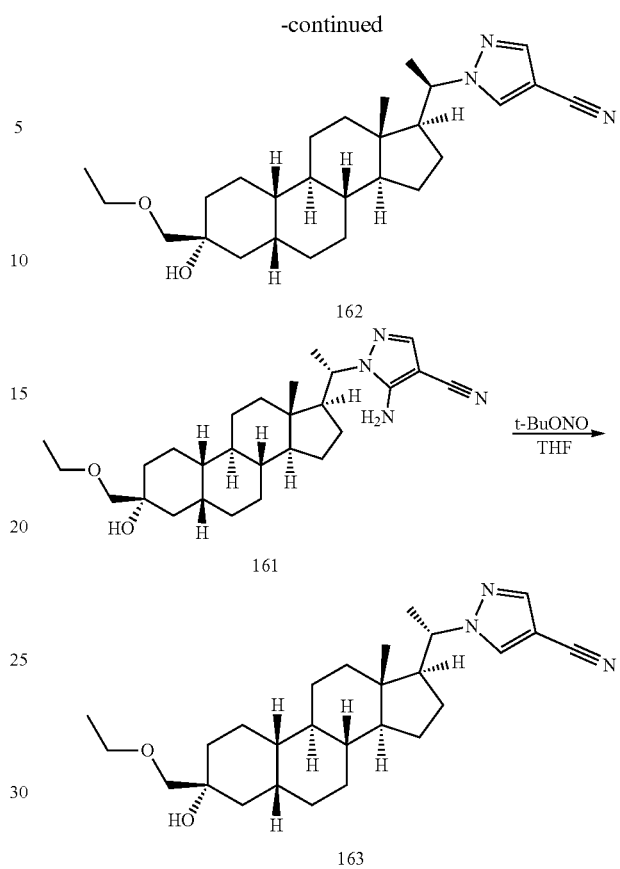

Synthesis of 160.1

To a solution of 206.0 (1.55 g, 4.3 mmol) in ethanol (5 mL) was added Et$_3$N (1.8 mL) and hydrazine hydrate (2.50 g, 42.6 mmol) at 25° C. After stirring at 80° C. for 12 h, the solution was concentrated. The residue was diluted with water (50 mL) and extracted with EtOAc (3×30 mL). The combined organic layer was washed with brine (30 mL), dried over anhydrous Na$_2$SO$_4$, filtered and concentrated to give 160.1 (1.6 g) as oil. The 160.1 (1.6 g) was purified by flash column (EtOAc in PE=20~50%) to afford 160.1 (1.4 g, 87%) as a solid.

$^1$H NMR (400 MHz, CDCl$_3$) δ$_H$ 4.90 (br, s, 2H), 3.52 (q, J=6.8 Hz, 2H), 3.42 (q, J=9.2 Hz, 2H), 2.71 (br, s, 1H), 2.29-2.09 (m, 2H), 1.90-1.55 (m, 14H), 1.50-1.25 (m, 7H), 1.25-0.95 (m, 7H), 0.56 (s, 3H).

Synthesis of 160.2

To a solution of 160.1 (1.4 g, 3.7 mmol) in MeOH (5 mL) was added AcOH (445 mg, 7.4 mmol) and NaBH$_3$CN (2.33 g, 37.1 mmol) at 25° C. After stirring at 75° C. for 12 h, the solution was concentrated. The residue was diluted with water (30 mL) and extracted with EtOAc (3×20 mL). The combined organic layer was washed with saturated brine (30 mL), dried over anhydrous Na$_2$SO$_4$, filtered and concentrated to give 160.2 (1.2 g, 86%) as an oil, which was used to next step directly.

Synthesis of 160 & 161

To a solution of 160.2 (600 mg, 1.6 mmol) in EtOH (5 mL) were added Et$_3$N (479 mg, 4.7 mmol) and 2-(ethoxymethylene) propanedinitrile (230 mg, 1.9 mmol) at 25° C. After stirring at 75° C. for 16 h, the mixture was concentrated in vacuum and the residue was purified by flash column (20-40% of EtOAc in PE) to give a mixture of 160

& 161 (200 mg) as a solid. The diastereomers (200 mg) was purified by pre-HPLC (Column: Waters Xbridge 150*25 mm*5 um; Condition: water (10 Mm $NH_4HCO_3$)-ACN; Begin B: 50%; End 80%) to give a mixture of 160 & 161 (50 mg) as a solid. The diastereomers (50 mg) were separated by SFC (Column: DAICEL CHIRALPAK AD-H (250 mm*30 mm, 5 um); Condition: Neu-ETOH; Begin B: 45%; End 45%) to give 160 (8.2 mg, 16%) and 161 (9.8 mg, 19%) as a solid.

160: $^1$H NMR (400 MHz, $CDCl_3$) $\delta_H$ 7.48 (s, 1H), 4.18 (s, 2H), 3.98-3.85 (m, 1H), 3.51 (q, J=6.8 Hz, 2H), 3.45-3.35 (m, 2H), 2.67 (s, 1H), 2.29-2.09 (m, 1H), 2.00-1.68 (m, 4H), 1.54-1.30 (m, 11H), 1.27-0.78 (m, 13H), 0.69 (s, 3H), 0.53-0.40 (m, 1H). LC-ELSD/MS: purity 99%, analytic SFC: 99.26% de; MS ESI calcd. for $C_{27}H_{43}N_4O_2$ [M+H]$^+$ 455.3, found 455.4.

161: $^1$H NMR (400 MHz, $CDCl_3$) $\delta_H$ 7.51 (s, 1H), 4.14 (s, 2H), 3.96-3.80 (m, 1H), 3.53 (q, J=7.2 Hz, 2H), 3.42 (q, J=9.6 Hz, 2H), 2.71 (s, 1H), 2.13-2.04 (m, 1H), 1.97-1.89 (m, 1H), 1.87-1.61 (m, 6H), 1.48-1.35 (m, 10H), 1.26-0.96 (m, 12H), 0.77 (s, 3H). LC-ELSD/MS: purity 99%, analytic SFC: 95.96% de; MS ESI calcd. for $C_{27}H_{43}N_4O_2$ [M+H]$^+$ 455.3, found 455.3.

Synthesis of 162

To a solution of 160 (16 mg, 0.035 mmol) in THF (2 mL) was added tert-butyl nitrite (4.34 mg, 0.042 mmol) at 15° C. After stirring at 75° C. for 16 h, the mixture was poured into water (10 mL) and extracted with DCM (2×10 mL). The combined organic layers were washed with brine (30 mL), dried over anhydrous $Na_2SO_4$ and concentrated in vacuum. The residue was purified by flash column (0~30% of EtOAc in PE) to give 162 (15 mg) as oil. 162 (15 mg) was purified again by flash column (0~30% of EtOAc in PE) to give 162 (6.1 mg, 41%) as a solid.

$^1$H NMR (400 MHz, $CDCl_3$) $\delta_H$ 7.79 (s, 1H), 7.75 (s, 1H), 4.30-4.22 (m, 1H), 3.51 (q, J=7.2 Hz, 2H), 3.40 (dd, J=9.2 Hz, 24.8 Hz, 2H), 2.68 (s, 1H), 1.95-1.65 (m, 6H), 1.55-1.45 (m, 2H), 1.42 (d, J=6.8 Hz, 3H), 1.39-1.22 (m, 7H), 1.22-1.17 (m, 4H), 1.15-0.71 (m, 7H), 0.71 (s, 3H), 0.17-0.10 (m, 1H). LC-ELSD/MS: purity 99%, MS ESI calcd. for $C_{27}H_{41}N_3O_2$ [M+H]$^+$ 440.3, found 440.3.

Synthesis of 163

To a solution of 161 (25 mg, 0.055 mmol) in THF (2 mL) was added t-BuONO (6.80 mg, 0.066 mmol) at 15° C. After stirring at 75° C. for 16 h, the mixture was poured into water (10 mL) and extracted with DCM (2×10 mL). The combined organic layers were washed with brine (50 mL), dried over anhydrous $Na_2SO_4$ and concentrated in vacuum. The residue was purified by flash column (0~20% of EtOAc in PE) to give 163 (2 mg, 8%) as a solid.

$^1$H NMR (400 MHz, $CDCl_3$) $\delta_H$ 7.76 (s, 2H), 4.25-4.10 (m, 1H), 3.53 (q, J=7.2 Hz, 2H), 3.42 (dd, J=9.6 Hz, 19.2 Hz, 2H), 2.72 (s, 1H), 1.95-1.60 (m, 9H), 1.52-1.50 (m, 3H), 1.49-1.23 (m, 9H), 1.22-1.18 (m, 4H), 1.17-1.01 (m, 5H), 0.76 (s, 3H). LC-ELSD/MS: purity 98%, MS ESI calcd. for $C_{27}H_{41}N_3O_2$ [M+H]$^+$ 440.3, found 440.3.

Example 164: Synthesis of (3R,5R,8R,9R,10S,13S, 14S,17S)-17-((S)-1-(2H-1,2,3-triazol-2-yl)ethyl)-3, 13-dimethylhexadecahydro-1H-cyclopenta[a]phenanthren-3-ol (164)

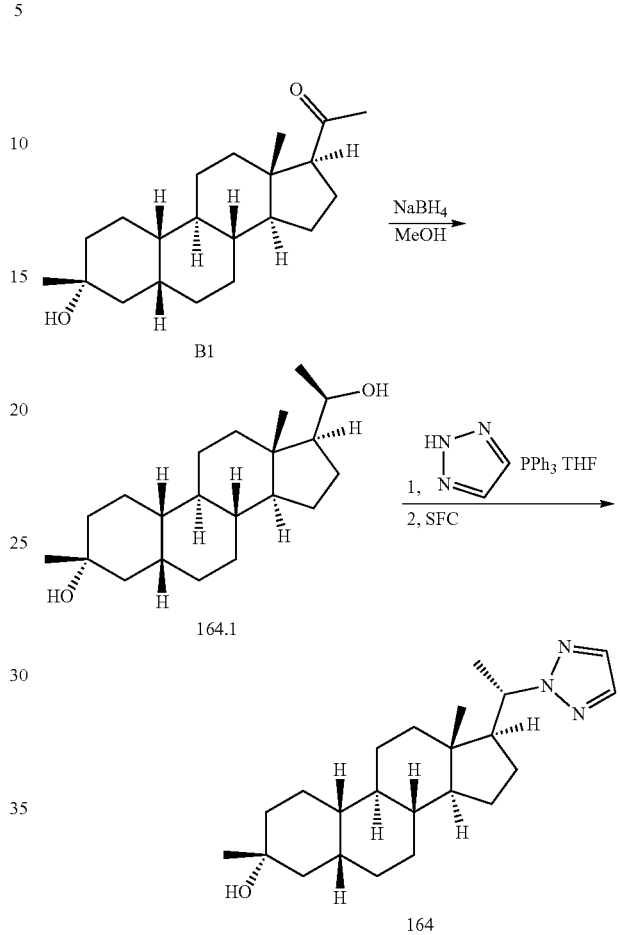

Synthesis of 164.1

To a solution of B1 (2.0 g, 6.28 mmol) in MeOH (20 mL) was added $NaBH_4$ (355 mg, 9.4 mmol) at 25° C. After stirring at 25° C. for 2 h, the mixture was poured into water (200 mL) and extracted with EtOAc (2×100 mL). The organic layer was washed with brine (2×100 mL), dried over anhydrous $Na_2SO_4$, filtered and concentrated in vacuum to give 164.1 (2 g, 99%) (including 10% 21-down-Me isomer) as a solid.

$^1$H NMR (400 MHz, $CDCl_3$) $\delta_H$ 3.78-3.67 (m, 1H), 2.12-1.96 (m, 1H), 1.90-1.76 (m, 3H), 1.70-1.54 (m, 9H), 1.51-1.30 (m, 8H), 1.22 (m, 2H), 1.16-0.99 (m, 9H), 0.75 (s, 3H).

Synthesis of 164

To a solution of 164.1 (500 mg, 1.6 mmol), triphenylphosphane (608 mg, 2.3 mmol) and 2H-1,2,3-triazole (138 mg, 2.0 mmol) in THF (10 mL) was added DIAD (469 mg, 2.3 mmol) at 0° C. After stirring at 25° C. for 16 h, the reaction mixture was concentrated and purified by flash column (0-45% of EtOAc in PE) to give 164 (20 mg). 164 (20 mg) was further purified by SFC (Column: DAICEL CHIRALPAK AD-H (250 mm*30 mm, 5 um); condition: 0.1% $NH_3H_2O$ ETOH; Begin B: 40%; End B: 40%) to afford 164 (4.3 mg, 22%, P2, Rt=1.926 min) as a solid.

$^1$H NMR (400 MHz, $CDCl_3$) $\delta_H$ 7.55 (s, 2H), 4.68-4.57 (m, 1H), 2.10 (q, J=9.2 Hz, 1H), 1.98 (d, J=12.8 Hz, 1H), 1.92-1.57 (m, 6H), 1.53-1.29 (m, 10H), 1.26 (s, 6H), 1.21-0.98 (m, 7H), 0.78 (s, 3H). LCMS: purity 96%, analytic SFC: 99.82% de. MS ESI calcd. for $C_{23}H_{37}N_3O$ $[M+H]^+$ 372.3, found 372.3.

The following examples were synthesized similar to Examples 25 & 26 with the listed aniline or to Examples 27 & 28 with the listed amine and appropriate SM. In the case of diasteriomeric products, typically the diastereomeric isomers were separated by SFC (e.g. Column: DAICEL CHIRALPAK AS-H (250 mm*30 mm, 5 um), Condition: 0.1% $NH_3H_2O$ EtOH, Begin B: 30%, End B 30%) or prep-HPLC (column: DuraShell 150*25 mm*5 um; Condition: water (10 mM $NH_4HCO_3$)-ACN; 75%-95% in 7 min. FlowRate: 25 mL/min) yielding both diastereomers after separation. The diastereomers were assigned based on 1H NMR of C21-Me.

| Example | SM | Aniline/amine | STRUCTURE | Analytical |
|---|---|---|---|---|
| 201 | B1 | 3-aminobenzonitrile | 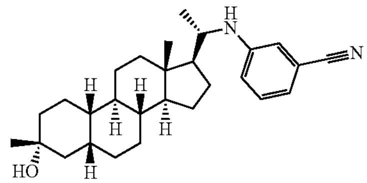 | $^1$H NMR (400 MHz, CDCl3) $\delta_H$ 7.17 (t, J = 8.0 Hz, 1H), 6.88 (d, J = 7.2 Hz, 1H), 6.76-6.67 (m, 2H), 3.63 (s, 1H), 3.34 (s, 1H), 1.99-1.78 (m, 4H), 1.70-1.58 (m, 3H), 1.47 (d, J = 14.8 Hz, 2H), 1.43-1.29 (m, 9H), 1.27 (s, 3H), 1.24-1.20 (m, 1H), 1.18 (d, J = 6.0 Hz, 3H), 1.16-1.00 (m, 6H), 0.75 (s, 3H). LC-ELSD/MS purity 99%, MS ESI calcd. for $C_{28}H_{41}N_2O$ $[M + H]^+$ 421, found 421. SFC 100% de. |
| 202 | | | 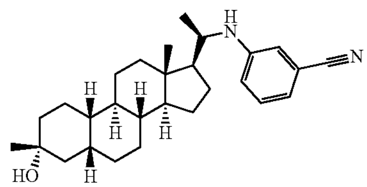 | $^1$H NMR (400 MHz, CDCl3) $\delta_H$ 7.18 (t, J = 8.0 Hz, 1H), 6.88 (d, J = 7.6 Hz, 1H), 6.75-6.65 (m, 2H), 3.61 (s, 1H), 3.36 (s, 1H), 1.99-1.93 (m, 1H), 1.90-1.76 (m, 4H), 1.69-1.54 (m, 5H), 1.50-1.28 (m, 10H), 1.26 (s, 3H), 1.22-1.12 (m, 3H), 1.09 (d, J = 6.0 Hz, 3H), 1.06-0.93 (m, 2H), 0.63 (s, 3H). LC-ELSD/MS purity 99%, MS ESI calcd. for $C_{28}H_{41}N_2O$ $[M + H]^+$ 421, found 421. SFC 100% de. |
| 203 | B1 | pyridin-3-amine | 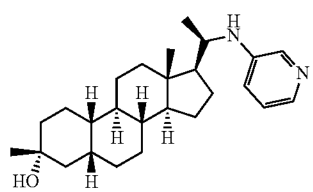 | $^1$H NMR (400 MHz, CDCl$_3$) $\delta$ = 7.97-7.92 (m, 1H), 7.91-7.85 (m, 1H), 7.09-7.01 (m, 1H), 6.85-6.73 (m, 1H), 3.44-3.31 (m, 2H), 2.07-1.96 (m, 1H), 1.87-1.77 (m, 3H), 1.52-1.34 (m, 8H), 1.32-1.17 (m, 10H), 1.15-0.94 (m, 9H), 0.65 (s, 3H); LCMS purity 99%, MS ESI calcd. for $C_{26}H_{41}N_2O$ $[M + H]^+$ 397, found 397; analytical SFC 100% de, |
| 204 | | | 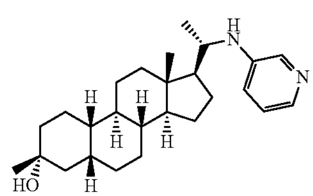 | $^1$H NMR (400 MHz, CDCl$_3$) $\delta$ = 7.95 (d, J = 2.8 Hz, 1H), 7.88 (d, J = 3.5 Hz, 1H), 7.08-7.01 (m, 1H), 6.85-6.77 (m, 1H), 3.52-3.39 (m, 1H), 3.39-3.28 (m, 1H), 1.99-1.89 (m, 2H), 1.88-1.78 (m, 3H), 1.69-1.66 (m, 1H), 1.51-1.46 (m, 1H), 1.46-1.33 (m, 8H), 1.32-1.25 (m, 7H), 1.24-1.20 (m, 1H), 1.20-1.17 (m, 3H), 1.15-1.01 (m, 5H), 0.74 (s, 3H); LCMS purity 99%, MS ESI calcd. for $C_{26}H_{41}N_2O$ $[M + H]^+$ 397, found 397; analytical SFC 97% de, |

-continued

| Example | SM | Aniline/amine | STRUCTURE | Analytical |
|---------|----|--|-----------|------------|
| 205 | B1 | 4-aminobenzonitrile | 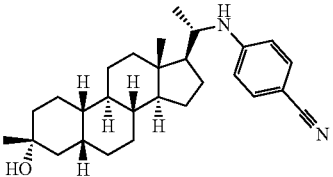 | $^1$H NMR (400 MHz, CDCl$_3$) δ 7.54-7.30 (m, 2H), 6.51-6.43 (m, 2H), 4.01-3.92 (m, 1H), 3.50-3.38 (m, 1H), 2.08-1.78 (m, 3H), 1.78-1.48 (m, 9H), 1.47-1.33 (m, 7H), 1.26-1.16 (m, 7H), 1.15-1.02 (m, 5 H), 0.74 (s, 3H). LC-ELSD/MS purity 99%, MS ESI calcd. for C$_{28}$H$_{41}$N$_2$O[M + H]$^+$ 421, found 421. SFC 99% de. |
| 206 | | (1R)-1-phenylethan-1-amine | 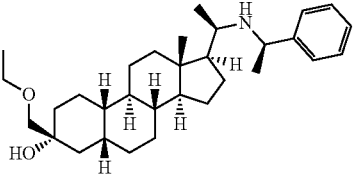 | $^1$H NMR (400 MHz, CDCl$_3$) δ$_H$ 7.36-7.27 (m, 4H), 7.24-7.18 (m, 1H), 3.92-3.86 (m, 1H), 3.57-3.50 (m, 2H), 3.48-3.38 (m, 2H), 2.75-2.66 (m, 2H), 2.26-2.18 (m, 1H), 1.88-1.71 (m, 4H), 1.69-1.54 (m, 7H), 1.50-1.31 (m, 7H), 1.28 (d, J = 6.8 Hz, 3H), 1.21 (t, J = 7.2 Hz, 4H), 1.13-1.01 (m, 5H), 0.89 (d, J = 6.0 Hz, 3H), 0.78 (s, 3H). LC-ELSD/MS purity 99%, MS ESI calcd. for C$_{31}$H$_{50}$NO$_2$ [M + H]$^+$ 468, found 468. SFC 100% de. |
| 207 | | (1R)-1-phenylethan-1-amine | 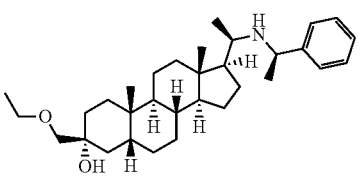 | $^1$H NMR (400 MHz, CDCl$_3$) δ$_H$ 7.40-7.28 (m, 4H), 7.25-7.18 (m, 1H), 3.95-3.85 (m, 1H), 3.57-3.48 (m, 2H), 3.47-3.35 (m, 2H), 2.77-2.64 (m, 2H), 2.30-2.10 (m 1H), 2.01-1.68 (m, 3H), 1.66-1.40 (m, 10H), 1.31-1.04 (m, 14H), 1.03-1.82 (m, 8H), 0.75 (s, 3H). LC-ELSD/MS purity 99%, MS ESI calcd. for C$_{32}$H$_{52}$NO$_2$ [M + H]$^+$ 482, found 482. |
| 208 | B1 | (1R)-1-phenylethan-1-amine | 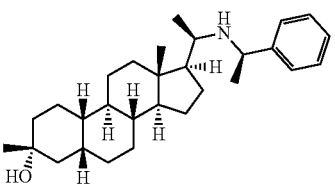 | $^1$H NMR (400 MHz, CDCl3) δ$_H$ 7.37-7.27 (m, 4H), 7.24-7.18 (m, 1H), 3.89 (m, 1H), 2.81-2.63 (m, 1H), 2.30-2.15 (m, 1H), 1.88 (m, 1H), 1.83-1.53 (m, 6H), 1.52-1.31 (m, 8H), 1.31-1.27 (m, 5H), 1.26 (s, 3H), 1.25-1.17 (m, 3H), 1.15-1.01 (m, 5H), 0.89 (m, 3H), 0.78 (s, 3H). LC-ELSD/MS purity 99%, MS ESI calcd. for C$_{29}$H$_{46}$NO [M + H]$^+$ 424, found 424. %. de >99 (by 1H NMR) |

-continued

| Example | SM | Aniline/amine | STRUCTURE | Analytical |
|---|---|---|---|---|
| 209 | B1 | (1S)-1-phenylethan-1-amine | 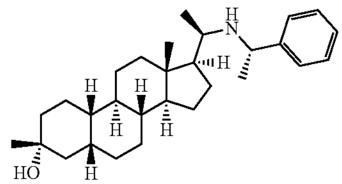 | ¹H NMR (400 MHz, CDCl₃) δ$_H$ 7.36-7.27 (m, 4H), 7.23 (s, 1H), 3.95-3.85 (m, 1H), 2.29-2.20 (m, 1H), 2.16-2.08 (m, 1H), 1.87-1.75 (m, 1H), 1.82-1.48 (m, 9H), 1.48-1.32 (m, 10H), 1.26 (s, 6H), 1.13-1.02 (m, 4H), 0.95 (d, J = 6.0 Hz, 4H), 0.40 (s, 3H). LC-ELSD/MS purity 99%, MS ESI calcd. for C₂₉H₄₆NO [M + H]⁺ 424, found 424. SFC 100% de. |
| 210 | | | 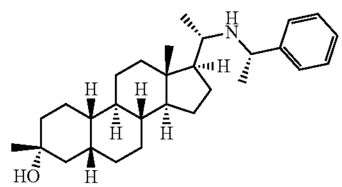 | ¹H NMR (400 MHz, CDCl₃) δ$_H$ 7.36-7.27 (m, 4H), 7.20 (s, 1H), 3.78-3.84 (m, 1H), 2.71-2.53 (m, 1H), 2.12-1.72 (m, 5H), 1.69-1.55 (m, 3H), 1.41-1.38 (m, 8H), 1.31-1.22 (m, 10H), 1.10-1.06 (m, 6H), 0.98-0.94 (m, 3H), 0.68 (s, 3H). LC-ELSD/MS purity 99%, MS ESI calcd. for C₂₉H₄₅NO [M + H]⁺ 424, found 424. SFC 99.82% de. |
| 211 | | (1S)-1-phenylethan-1-amine | 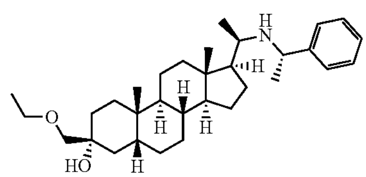 | ¹H NMR (400 MHz, CDCl₃) δ$_H$ 7.35-7.26 (m, 4H), 7.25-7.19 (m, 1H), 3.92-3.85 (m, 1H), 3.56-3.48 (m, 2H), 3.47-3.36 (m, 2H), 2.71-2.67 (m, 1H), 2.30-2.15 (m, 2H), 1.97-1.87 (m, 1H), 1.82-1.63 (m, 3H), 1.55-1.46 (m, 7H), 1.34-1.17 (m, 13H), 1.16-0.98 (m, 4H), 0.98-0.89 (m, 7H), 0.39 (s, 3H). LC-ELSD/MS purity 99%, MS ESI calcd. for C₃₂H₅₂NO₂ [M + H]⁺ 482, found 482. SFC 100% de. |
| 212 | | | 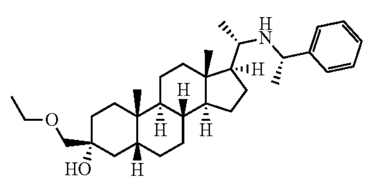 | ¹H NMR (400 MHz, CDCl₃) δ$_H$ 7.36-7.27 (m, 4H), 7.23-7.17 (m, 1H), 3.85-3.78 (m, 1H), 3.57-3.49 (m, 2H), 3.46-3.36 (m, 2H), 2.68-2.54 (m, 2H), 2.05-1.75 (m, 4H), 1.70-1.51 (m, 10H), 1.31-1.18 (m, 10H), 1.17-0.98 (m, 5H), 0.98-0.88 (m, 7H), 0.65 (s, 3H). LC-ELSD/MS purity 99%, MS ESI calcd. for C₃₂H₅₂NO₂ [M + H]⁺ 482, found 482. SFC 96.7% de. |

Examples 213&214: Synthesis of (3R,5R,8R,9R,10S,13S,14S,17S)-17-((S)-1-(benzylamino)propyl)-3-(methoxymethyl)-13-methylhexadecahydro-1H-cyclopenta[a]phenanthren-3-ol (213)& (3R,5R,8R,9R,10S,13S,14S,17S)-17-((R)-1-(benzylamino)propyl)-3-(methoxymethyl)-13-methylhexadecahydro-1H-cyclopenta[a]phenanthren-3-ol (214)

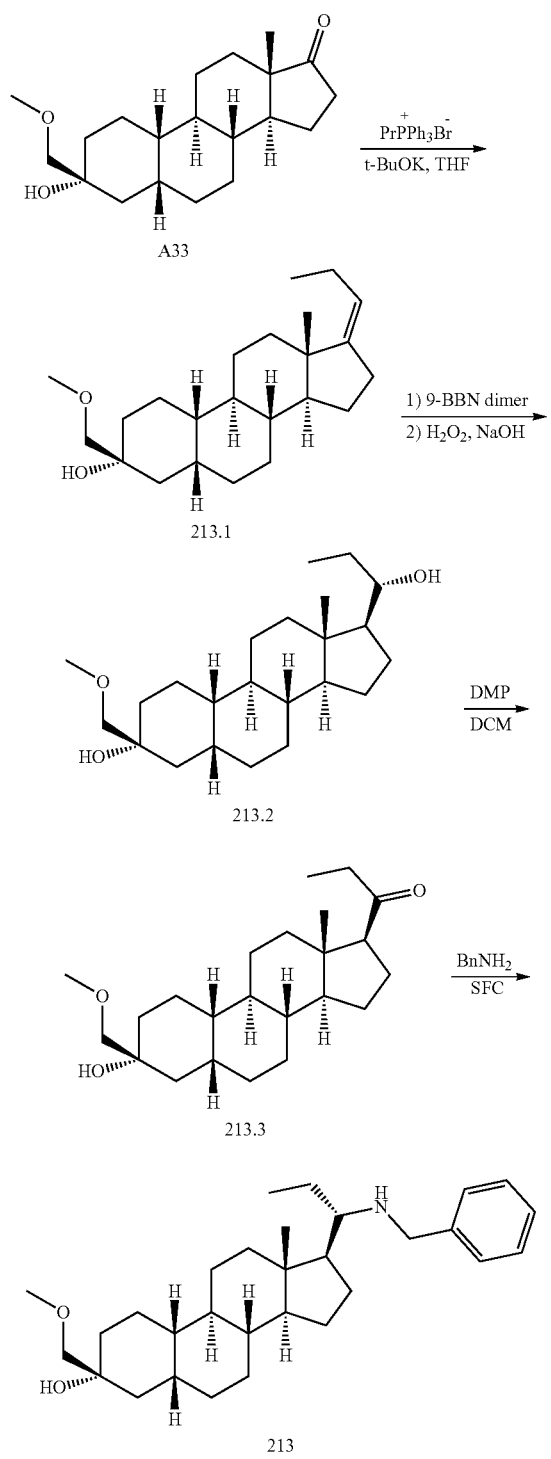

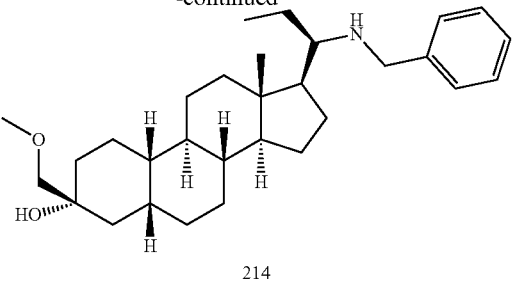

214

Synthesis of 213.1

To a suspension of triphenyl(propyl)phosphonium bromide (23.5 g, 61.1 mmol) in THF (50 mL) was added t-BuOK (6.84 g, 61.1 mmol) at 25° C. under $N_2$. After stirring at 60° C. for 1 h, A33 (3.3 g, 10.2 mmol) in THF (20 mL) was added to the mixture at 60° C. After stirring at 60° C. for 16 h, $NH_4Cl$ (100 mL) was added to the resulting solution. The organic layer was separated, dried over anhydrous $Na_2SO_4$, filtered and concentrated. The residue was purified by flash column (0-5% of EtOAc in PE) to give 213.1 (5.8 g) as an oil.

$^1$H NMR (400 MHz, CDCl3) $\delta_H$ 5.00 (t, J=6.8 Hz, 1H), 3.42-3.36 (m, 5H), 2.57 (s, 1H), 2.39-1.95 (m, 5H), 1.85-1.52 (m, 10H), 1.49-0.99 (m, 10H), 0.92 (t, J=7.6 Hz, 3H), 0.86 (s, 3H).

Synthesis of 213.2

To a solution of 213.1 (5.8 g, 16.7 mmol) in anhydrous THF (50 mL) was added 9-BBN dimer (10.1 g, 41.7 mmol) under $N_2$. After stirring at 60° C. for 16 h, the mixture was cooled, quenched by EtOH (30 mL) at 0° C. NaOH (16.6 mL, 5M, 83.4 mmol) was added very slowly. After addition, $H_2O_2$ (16.6 mL, 166 mmol, 10 M) was added slowly until the inner temperature no longer rises. After stirring at 70° C. for 2 h, the mixture was cooled and poured into water (50 mL) and extracted with EtOAc (3×60 mL). The organic layer was dried over anhydrous $Na_2SO_4$, filtered and concentrated. The residue was purified by flash column (10%~20% of EtOAc in PE) to give 213.2 (5.8 g, 95%) as an oil. $^1$H NMR (400 MHz, CDCl$_3$) $\delta_H$ 3.53-3.48 (m, 1H), 3.42-3.36 (m, 5H), 2.57 (s, 1H), 1.87-1.51 (m, 10H), 1.48-1.30 (m, 8H), 1.27-0.98 (m, 12H), 0.67 (s, 3H). LC-ELSD/MS purity 99%, MS ESI calcd. for $C_{23}H_{37}O$ [M−2H$_2$O+H]$^+$ 329 found 329.

Synthesis of 213.3

To a solution of 213.2 (5.7 g, 15.6 mmol) in DCM (30 mL) was added DMP (13.2 g, 31.2 mmol) at 25° C. After stirring at 25° C. for 1 h, the resulting solution was quenched with NaHCO$_3$ (50 mL) and extracted with EtOAc (3×30 mL). The combined organic layer was washed with Na$_2$S$_2$O$_3$ (3×30 mL, sat.), brine (50 mL), dried over anhydrous Na$_2$SO$_4$, filtered and concentrated. The residue was purified by column (10% of EtOAc in PE) to give 213.3 (5.83 g) as an oil. $^1$H NMR (400 MHz, CDCl$_3$) $\delta_H$3.42-3.36 (m, 5H), 2.60 (s, 1H), 2.52 (t, J=8.8 Hz, 1H), 2.40-1.92 (m, 4H), 1.86-1.51 (m, 8H), 1.50-1.30 (m, 7H), 1.29-0.94 (m, 9H), 0.59 (s, 3H). LC-ELSD/MS purity 99%, MS ESI calcd. for $C_{23}H_{37}O_2$ [M−H$_2$O+H]$^+$ 345 found 345.

Synthesis of 213 & 214

A mixture of 213.3 (1.5 g, 4.13 mmol), TsOH (39.7 mg, 0.231 mmol) and 1-phenylmethanamine (2.2 g, 20.6 mmol) and Ti (OCH$_2$CH$_3$)$_4$ (4.69 g, 20.6 mmol) in toluene (20 mL) was stirred at 110° C. for 16 h to give colorless solution. MeOH (10 mL) was added into the mixture followed by NaBH$_4$ (1.25 g). After stirring at 25° C. for 2 h, water (20 mL) was added to the resulting colorless solution and extracted with EtOAc (3×30 mL). The combined organic phase was washed with water (3×30 mL), brine (50 mL), dried over anhydrous Na$_2$SO$_4$, filtered and concentrated. The residue was purified by column (5% 50% of EtOAc in PE) to give 2.09 g of diastereomers, which was separated by SFC (Column: DAICEL CHIRALCEL OJ (250 mm*50 mm, 10 um), Condition: 0.1% NH$_3$H$_2$O ETOH, Begin B: 20%, End B: 20%) to give 214 (700 mg, Peak 2) and 213 (450 mg, Peak 1) as oils. 213 (80 mg, 0.176 mmol) was further purified by SFC (Column: DAICEL CHIRALCEL OJ-H (250 mm*30 mm, 5 um), Condition: 0.1% NH$_3$H$_2$O ETOH, Begin B: 15%, End B: 15%) to give 213 (38 mg, 88%, Rt=2.182 min) as a solid. 214 (75 mg, 0.165 mmol) was further purified by SFC (Column: DAICEL CHIRALCEL OJ-H (250 mm*30 mm, 5 um), Condition: 0.1% NH$_3$H$_2$O ETOH, Begin B: 15%, End B: 15%) to give 214 (35 mg, Rt=2.519 min) as a solid.

213: $^1$H NMR (400 MHz, CDCl$_3$) $\delta_H$ 7.36-7.29 (m, 4H), 7.24-7.21 (m, 1H), 3.78-3.67 (m, 2H), 3.43-3.36 (m, 5H), 2.60 (s, 1H), 2.50-2.46 (m, 1H), 1.87-1.50 (m, 11H), 1.49-1.21 (m, 10H), 1.20-0.86 (m, 9H), 0.79 (s, 3H). LC-ELSD/MS purity 99%, MS ESI calcd. for C$_{30}$H$_{48}$NO$_2$ [M+H]$^+$ 454 found 454. SFC 100% de.

214: $^1$H NMR (400 MHz, CDCl$_3$) $\delta_H$ 7.36-7.29 (m, 4H), 7.24-7.21 (m, 1H), 3.83-3.77 (m, 1H), 3.62-3.58 (m, 1H), 3.42-3.36 (m, 5H), 2.65-2.55 (m, 2H), 2.14-2.06 (m, 1H), 1.86-1.50 (m, 10H), 1.49-1.16 (m, 10H), 1.14-0.79 (m, 9H), 0.66 (s, 3H). LC-ELSD/MS purity 99%, MS ESI calcd. for C$_{30}$H$_{48}$NO$_2$ [M+H]$^+$ 454 found 454. SFC 96.78% de.

The following examples were synthesized similar to Example 33 with the listed aryl halide and appropriate SM. In the case of diasteriomeric products, typically the diastereomeric isomers were separated by SFC (e.g. Column: DAICEL CHIRALPAK AS-H (250 mm*30 mm, 5 um), Condition: 0.1% NH$_3$H$_2$O EtOH, Begin B: 30%, End B 30%) or prep-HPLC (column: DuraShell 150*25 mm*5 um; Condition: water (10 mM NH$_4$HCO$_3$)-ACN; 75%-95% in 7 min. FlowRate: 25 mL/min) yielding both diastereomers after separation. The diastereomers were assigned based on 1H NMR of C21-Me.

| Example | SM | Aryl halide | STRUCTURE | Analytical |
|---|---|---|---|---|
| 250 | B18 | 4-bromo-3-methyl-benzonitrile | 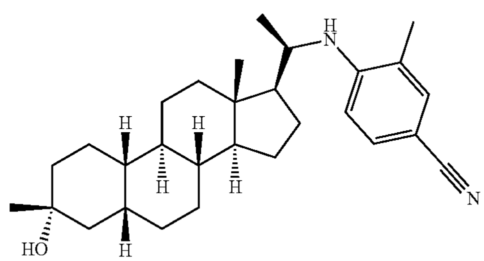 | $^1$HNMR (400 MHz, CDCl3) δ 7.37 (dd, J = 1.8, 8.5 Hz, 1H), 6.54 (d, J = 8.5 Hz, 1H), 3.53-3.47 (m, 1H), 2.08 (s, 3H), 1.95-1.56 (m, 8H), 1.56-1.15 (m, 16H), 1.15-0.90 (m, 9H), 0.63 (s, 3H), LC-ELSD/MS purity 99%, MS ESI calcd. for C$_{29}$H$_{42}$N$_2$O [M + H]$^+$ 435, found 435. SFC 99.84% de |
| 251 | | | 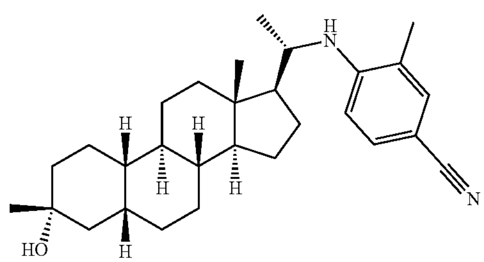 | $^1$HNMR (400 MHz, CDCl3) δ 7.37 (dd, J = 1.9, 8.4 Hz, 1H), 6.54 (d, J = 8.5 Hz, 1H), 3.53-3.47 (m, 1H), 2.08 (s, 3H), 2.01-1.56 (m, 6H), 1.54-1.15 (m, 17H), 1.15-1.00 (m, 10H), 0.75 (s, 3H). LC-ELSD/MS purity 99%, MS ESI calcd. for C$_{29}$H$_{42}$N$_2$O [M + H]$^+$ 435, found 435. SFC 99.66% de |
| 252 | B24 | 4-bromo-3-methyl-benzonitrile | 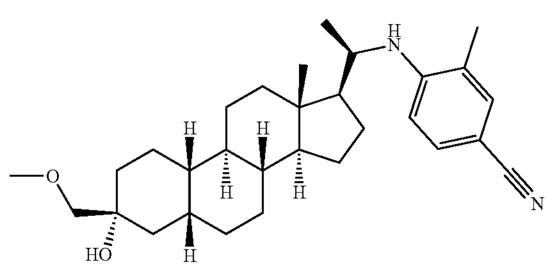 | $^1$H NMR (400 MHz, CDCl$_3$) $\delta_H$ 7.37 (dd, J = 1.9, 8.5 Hz, 1H), 7.28-7.26 (m, 1H), 6.53 (d, J = 8.6 Hz, 1H), 3.50 (br dd, J = 6.2, 10.1 Hz, 1H), 3.43-3.33 (m, 5H), 2.08 (s, 3H), 2.03-1.65 (m, 8H), 1.57-1.22 (m, 13H), 1.18-0.92 (m, 8H), 0.63 (s, 3H). LC-ELSD/MS purity 99%, MS ESI calcd. for C$_{30}$H$_{45}$N$_2$O$_2$ [M + H]$^+$ 465, found 465. SFC 100% de. |
| 253 | | | 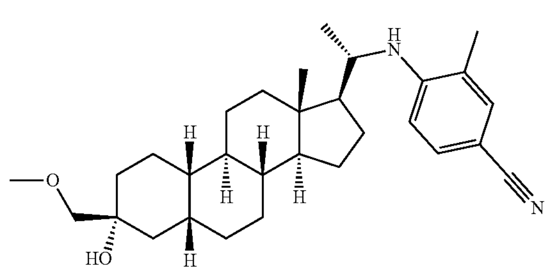 | $^1$H NMR (400 MHz, CDCl$_3$) $\delta_H$ 7.38-7.33 (m, 1H), 7.29-7.24 (m, 1H), 6.53 (d, J = 8.6 Hz, 1H), 3.58-3.24 (m, 6H), 2.08 (s, 3H), 2.01-1.63 (m, 8H), 1.55-1.33 (m, 10H), 1.29-0.98 (m, 11H), 0.74 (s, 3H). LC-ELSD/MS purity 99%, MS ESI calcd. for C$_{30}$H$_{45}$N$_2$O$_2$ [M + H]$^+$ 467, found 467. SFC 100% de. |

-continued

| Example | SM | Aryl halide | STRUCTURE | Analytical |
|---|---|---|---|---|
| 254 | B24 | 3-bromo-benzonitrile | 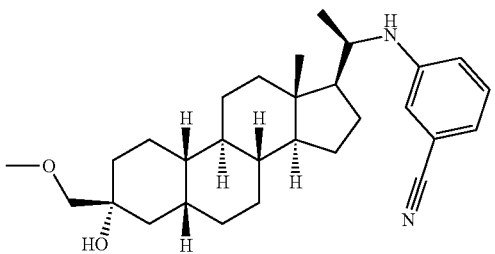 | ¹H NMR (400 MHz, CDCl₃) $\delta_H$ 7.21-7.17 (m, 1H), 6.91-6.89 (m, 1H), 6.76-6.71 (m, 2H), 3.67 (d, J = 9.6 Hz, 1H), 3.45-3.32 (m, 5 H), 2.63 (s, 1H), 1.98-1.70 (m, 6H), 1.68-1.53 (m, 5H), 1.54-1.33 (m, 7H), 1.30-1.02 (m, 10H), 0.76 (s, 3H). LC-ELSD/MS purity 99%, MS ESI calcd. for $C_{29}H_{43}N_2O_2$ [M + H]⁺ 451, found 451. SFC 100% de. |
| 255 | | | 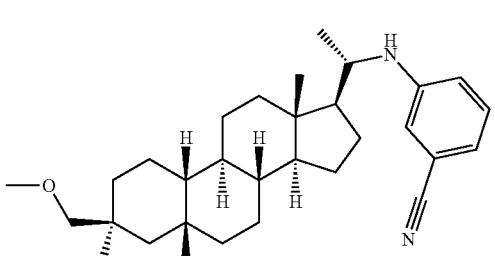 | ¹H NMR (400 MHz, CDCl₃) $\delta_H$ 7.19-7.15 (m, 1H), 6.88-6.86 (m, 1H), 6.72-6.67 (m, 2H), 3.62 (d, J = 8.4 Hz, 1H), 3.41-3.33 (m, 5 H), 2.62 (s, 1H), 1.98-1.70 (m, 6H), 1.68-1.51 (m, 5H), 1.50-1.29 (m, 7H), 1.26-0.94 (m, 10H), 0.63 (s, 3H). LC-ELSD/MS purity 99%, MS ESI calcd. for $C_{29}H_{43}N_2O_2$ [M + H]⁺ 451, found 451. SFC 100% de. |
| 256 | B24 | 4-bromo-benzonitrile | 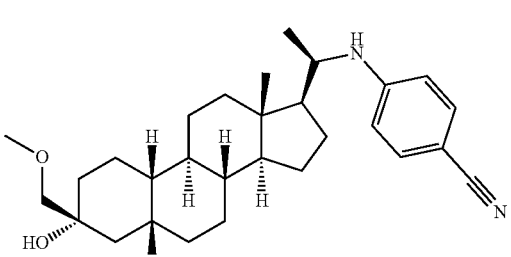 | ¹H NMR (400 MHz, CDCl₃) $\delta_H$ 7.39 (d, J = 8.8 Hz, 2H), 6.47 (d, J = 8.8 Hz, 2H), 3.45-3.38 (m, 6H), 1.94-1.74 (m, 5H), 1.68-1.59 (m, 5H), 1.49-1.18 (m, 14H), 1.11 (d, J = 6.4 Hz, 3H), 1.05-0.96 (m, 2H), 0.62 (s, 3H). LC-ELSD/MS purity 99%, MS ESI calcd. for $C_{29}H_{43}N_2O_2$ [M + H]⁺ 451, found 451. SFC 99% de. |
| 257 | | | 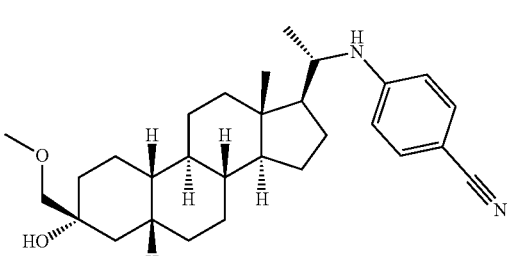 | ¹H NMR (400 MHz, CDCl₃) $\delta_H$ 7.38 (d, J = 8.8 Hz, 2H), 6.49 (d, J = 8.9 Hz, 2H), 3.42-3.38 (m, 6H), 1.97-1.75 (m, 5H), 1.68-1.59 (m, 5H), 1.45-1.32 (m, 10H), 1.19 (d, J = 6.4 Hz, 3H), 1.15-1.03 (m, 6H), 0.74 (s, 3H). LC-ELSD/MS purity 99%, MS ESI calcd. for $C_{29}H_{43}N_2O_2$ [M + H]⁺ 451, found 451. SFC 99% de. |
| 258 | E2 | 5-bromopyridine-2-carbonitrile | 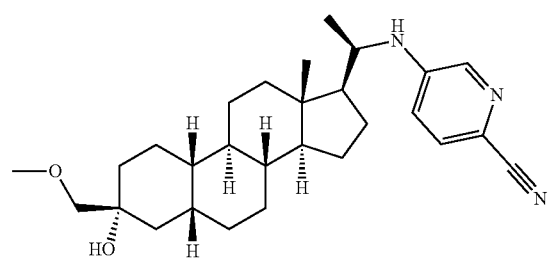 | ¹H NMR (400 MHz, CDCl₃) $\delta_H$ 7.97-7.91 (m, 1H), 7.45-7.38 (m, 1H), 6.78-6.70 (m, 1H), 4.15-4.06 (m, 1H), 3.46-3.31 (m, 6H), 2.66-2.57 (m, 1H), 1.97-1.68 (m, 6H), 1.68-1.61 (m, 5H), 1.39-1.34 (m, 3H), 1.34-1.24 (m, 3H), 1.24-1.18 (m, 4H), 1.18-0.96 (m, 6H), 0.74-0.68 (s, 3H). LC-ELSD/MS purity 99%, MS ESI calcd. for $C_{28}H_{42}N_3O_2$ [M + H]+ 452, found 452. |

-continued

| Example | SM | Aryl halide | STRUCTURE | Analytical |
|---|---|---|---|---|
| 259 | F8 | 1-(3-bromo-2-methylphenyl)pyrrolidin-2-one | 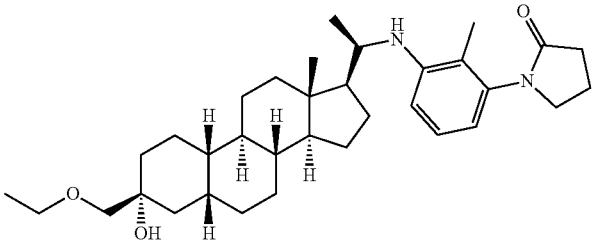 | $^1$H NMR (400 MHz, CDCl$_3$) $\delta_H$ 7.14-7.05 (m, 1H), 6.58-6.43 (m, 2H), 3.75-3.62 (m, 2H), 3.58-3.33 (m, 6H), 2.75-2.68 (s, 1H), 2.61-2.53 (m, 2H), 2.25-2.08 (s, 3H), 1.95-1.71 (m, 7H), 1.70-1.59 (m, 4H), 1.50-1.29 (m, 8H), 1.26-1.16 (m, 5H), 1.15-0.90 (m, 8H), 0.68-0.60 (s, 3H). LC-ELSD/MS purity 99%, MS ESI calcd. for C$_{34}$H$_{53}$N$_2$O$_3$ [M + H]+ 537, found 537. |
| 260 | F8 | 4-bromo-3-methylbenzonitrile | 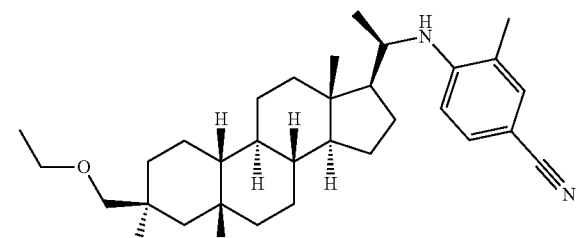 | $^1$H NMR (400 MHz, CDCl$_3$) $\delta_H$ 7.38 (d, J = 8.8 Hz, 1H), 7.30 (s, 1H), 6.63 (d, J = 8.8 Hz, 1H), 5.22 (d, J = 9.6 Hz, 1H), 4.13 (s, 1H), 3.59-3.50 (m, 2H), 3.47-3.41 (m, 3H), 2.68-2.65 (m, 1H), 2.34-2.31 (m, 1H), 2.07 (s, 3H), 1.82-1.45 (m, 9H), 1.38-1.22 (m, 8H), 1.18-1.14 (m, 2H), 1.09 (t, J = 6.8 Hz, 4H), 1.04 (d, J = 6.0 Hz, 3H), 0.98-0.84 (m, 2H), 0.54 (s, 3H). LC-ELSD/MS purity 99%, MS ESI calcd. for C$_{31}$H$_{47}$N$_2$O$_2$ [M + H]$^+$ 479, found 479. |
| 261 | F8 | 5-bromopyridine-2-carbonitrile | 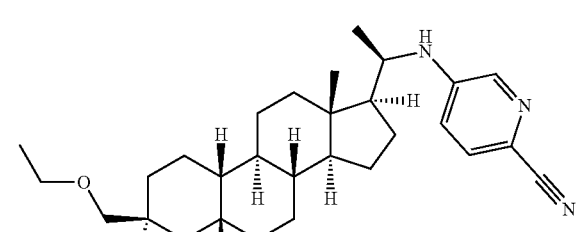 | $^1$H NMR (400 MHz, CDCl3) $\delta_H$ 7.95-7.93 (m, 1H), 7.46-7.42 (m, 1H), 6.77-6.72 (m, 1H), 4.07-4.02 (m, 1H), 3.56-3.50 (m, 2H), 3.46-3.38 (m, 3H), 2.74 (s, 1H), 1.91-1.73 (m, 4.5H), 1.69-1.56 (m, 4.5H), 1.51-1.29 (m, 9H), 1.27-1.18 (m, 6H), 1.15-1.12 (m, 4H), 1.07-0.97 (m, 2H), 0.62 (s, 3H). LC-ELSD/MS purity 99%, MS ESI calcd. for C$_{29}$H$_{44}$N$_3$O$_2$ [M + H]$^+$ 466.3 found 466.3. |
| 262 | F8 | 3-bromo-2-fluoropyridine | 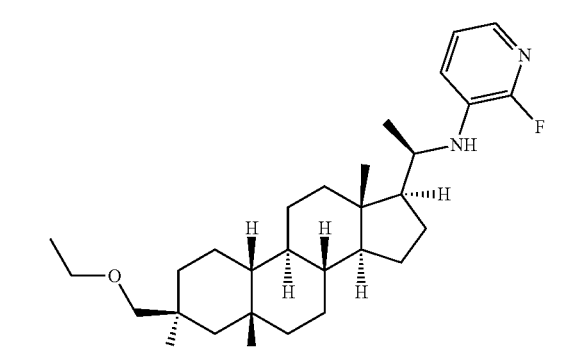 | $^1$H NMR (400 MHz, CDCl$_3$) $\delta_H$ 7.39-7.34 (m, 1H), 7.01-6.95 (m, 1H), 6.92-6.84 (m, 1H), 3.84-3.74 (m, 1H), 3.57-3.48 (m, 2H), 3.47-3.38 (m, 2H), 3.37-3.27 (m, 1H), 2.71 (s, 1H), 2.06-1.99 (m, 1H), 1.93-1.71 (m, 4H), 1.69-1.59 (m, 3H), 1.50-1.16 (m, 14H), 1.15-0.92 (m, 8H), 0.63 (s, 3H). $^{19}$F NMR (400 MHz, CDCl$_3$) $\delta_F$ −87.63. LCMS purity >99% MS ESI calcd. for C$_{28}$H$_{44}$FN$_2$O$_2$ [M + H]$^+$ 459, found 459. |

| Example | SM | Aryl halide | STRUCTURE | Analytical |
|---|---|---|---|---|
| 263 | F8 | 1-(6-bromopyridin-2-yl)pyrrolidin-2-one | 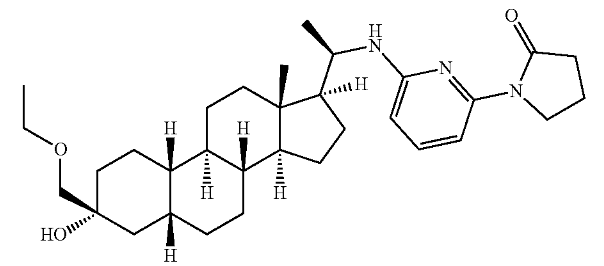 | $^1$H NMR (400 MHz, CDCl$_3$) $\delta_H$ 7.52 (d, J = 8 Hz, 1H), 7.28 (t, J = 8 Hz, 1H), 6.04 (d, J = 8 Hz, 1H), 4.11-3.98 (m, 3H), 3.79-3.69 (m, 1H), 3.53 (q, J = 7.2 Hz, 2H), 3.42 (q, J = 8.4 Hz, 2H), 2.71 (s, 1H), 2.61 (t, J = 8.4 Hz, 2H), 2.10-1.96 (m, 3H), 1.89-1.51 (m, 10H), 1.48-1.16 (m, 11H), 1.13-0.91 (m, 8H), 0.64 (s, 3H). LC-ELSD/MS purity 99%, MS ESI calcd. for C$_{32}$H$_{50}$N$_3$O$_3$ [M + H]$^+$ 524, found 524. |
| 264 | F8 | 1-(5-bromopyridin-2-yl)-1H-pyrazole-3-carbonitrile | 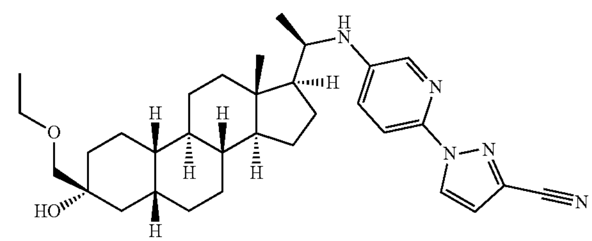 | $^1$H NMR (400 MHz, CDCl$_3$) $\delta_H$ 8.44 (s, 1H), 7.76 (d, J = 8.4 Hz, 1H), 7.71 (s, 1H), 6.97 (br d, J = 9.6 Hz, 1H), 6.79 (s, 1H), 3.63 (br d, J = 9.6 Hz, 1H), 3.57-3.48 (m, 2H), 3.46-3.39 (m, 2H), 2.74 (s, 1H), 1.98 (br d, J = 12.5 Hz, 1H), 1.88-1.56 (m, 9H), 1.52-1.30 (m, 9H), 1.29-0.93 (m, 12H), 0.65 (s, 3H). LC-ELSD/MS purity 99%, MS ESI calcd. for C$_{32}$H$_{44}$N$_5$O [M − H$_2$O + H]$^+$ 514.3 found 514.3. |

Examples 265-268: Synthesis of (3R,5R,8R,9R,10S,13S,14S,17R)-17-((S)-1-(2H-1,2,3-triazol-2-yl)propan-2-yl)-3-(ethoxymethyl)-13-methylhexadecahydro-1H-cyclopenta[a]phenanthren-3-ol (265) & (3R,5R,8R,9R,10S,13S,14S,17R)-17-((R)-1-(2H-1,2,3-triazol-2-yl)propan-2-yl)-3-(ethoxymethyl)-13-methylhexadecahydro-1H-cyclopenta[a]phenanthren-3-ol (266) & (3R,5R,8R,9R,10S,13S,14S,17R)-17-((S)-1-(1H-1,2,3-triazol-1-yl)propan-2-yl)-3-(ethoxymethyl)-13-methylhexadecahydro-1H-cyclopenta[a]phenanthren-3-ol (267) & (3R,5R,8R,9R,10S,13S,14S,17R)-17-((R)-1-(1H-1,2,3-triazol-1-yl)propan-2-yl)-3-(ethoxymethyl)-13-methylhexadecahydro-1H-cyclopenta[a]phenanthren-3-ol (268)

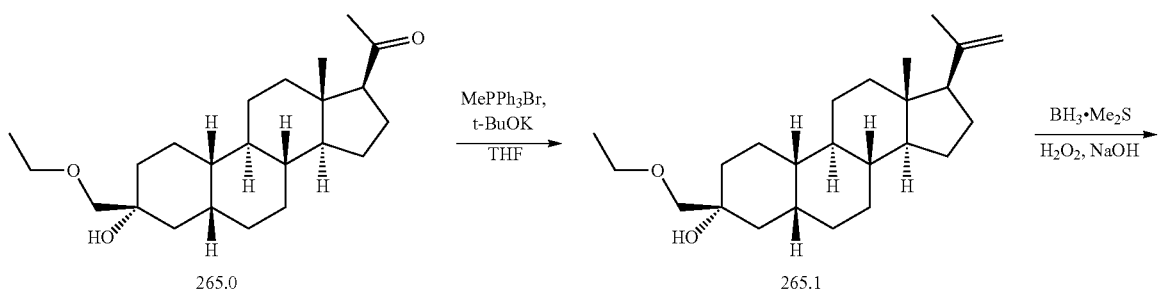

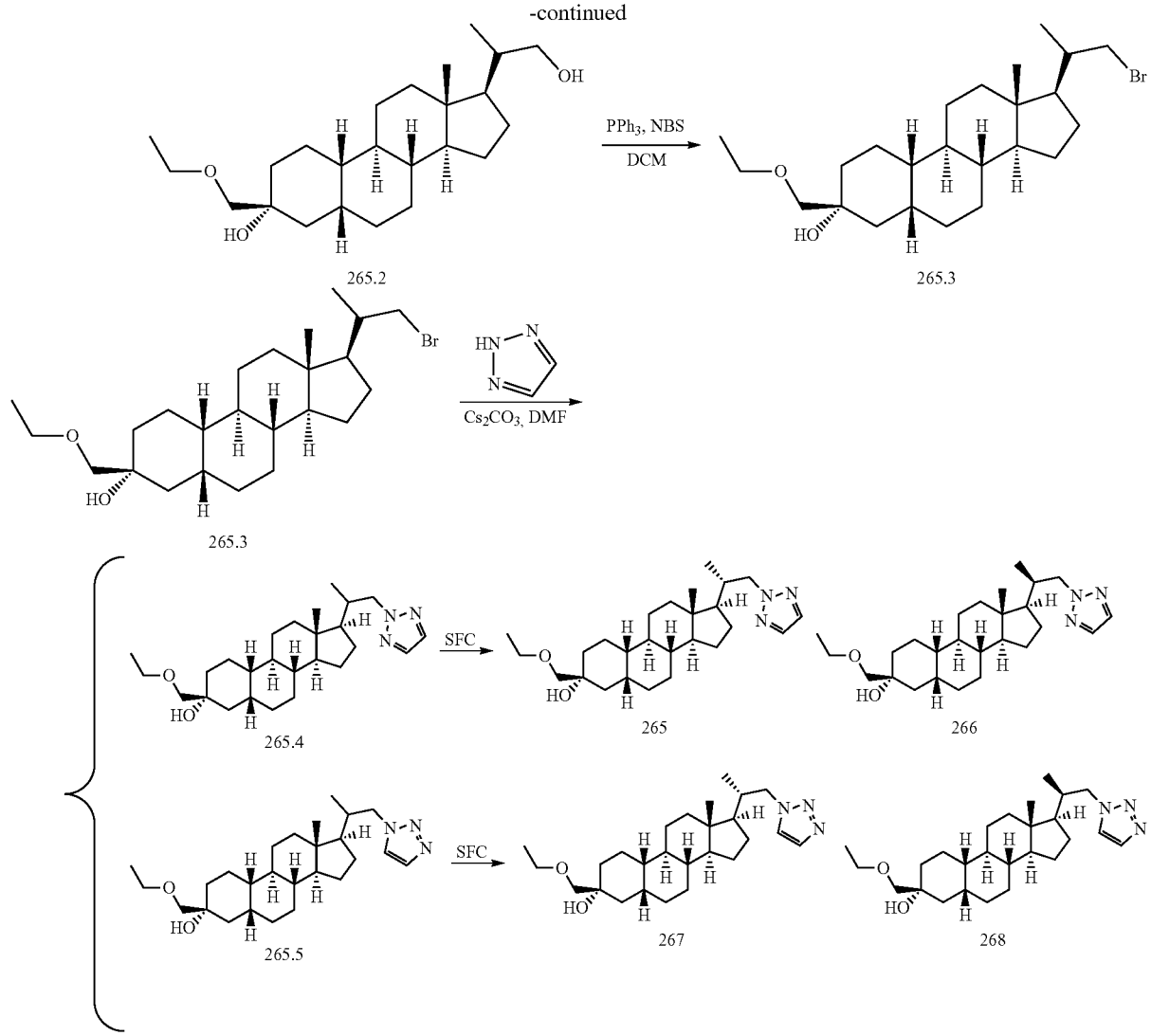

Synthesis of 265.1

To a solution of t-BuOK (833 mg, 7.4 mmol) in THF (15 mL) was added MePPh$_3$Br (2.65 g, 7.4 mmol) at 15° C. After stirring at 40° C. for 0.5 h, a solution of 265.0 (900 mg, 2.5 mmol) in THF (5 mL) was added into the reaction. After stirring at 40° C. for 16 h, the resulting mixture was poured into water (100 mL) and extracted with EtOAc (2×50 mL). The combined organic phase was washed with brine (2×100 mL), dried over anhydrous Na$_2$SO$_4$, filtered and concentrated. The product was purified by flash column (0~30% of EtOAc in PE) to give 265.1 (500 mg, 62%) as an oil.

$^1$H NMR (400 MHz, CDCl$_3$) $\delta_H$ 4.84 (s, 1H), 4.70 (s, 1H), 3.53 (q, J=6.8 Hz, 2H), 3.45 (q, J=9.2 Hz, 2H), 2.70 (s, 1H), 2.10-1.97 (m, 1H), 1.87-1.69 (m, 8H), 1.68-1.61 (m, 3H), 1.57 (s, 5H), 1.46-1.34 (m, 5H), 1.31-1.10 (m, 8H), 0.56 (m, 3H).

Synthesis of 265.2

To a solution of 265.1 (500 mg, 1.3 mmol) in THF (5 mL) was added BH$_3$·Me$_2$S (0.414 mL, 10 M, 4.1 mmol) at 15° C. After stirring at 45° C. for 1 h, the resulting mixture was diluted with ethanol (630 mg, 13.7 mmol) at 15° C., followed by aqueous NaOH solution (2.74 mL, 5.0 M, 13.7 mmol) at 15° C. and H$_2$O$_2$ (1.37 mL, 10 M, 13.7 mmol) dropwise at 15° C. After stirring at 80° C. for 1 h, the reaction mixture was cooled to 15° C., poured into water (50 mL) and extracted with EtOAc (2×50 mL). The combined organic layer was washed with brine (2×100 mL), dried over anhydrous Na$_2$SO$_4$, filtered and concentrated. The residue was purified by flash column (0~30% of EtOAc in PE) to give 265.2 (500 mg, 95%) as a solid.

$^1$H NMR (400 MHz, CDCl$_3$) $\delta_H$ 3.77-3.61 (m, 1H), 3.53 (q, J=7.2 Hz, 2H), 3.48-3.32 (m, 3H), 2.59-2.26 (m, 1H), 2.00-1.70 (m, 8H), 1.51-1.33 (m, 10H), 1.15 (m, 3H), 0.98-0.92 (m, 3H), 0.90-0.76 (m, 8H), 0.68 (s, 3H).

Synthesis of 265.3

To a solution of 265.2 (200 mg, 0.5 mmol) in DCM (10 mL) were added PPh$_3$ (275 mg, 1.0 mmol) and NBS (186 mg, 1.0 mmol) at 0° C. After stirring at 25° C. for 1 h, the mixture was poured into water (50 mL) and extracted with DCM (2×50 mL). The combined organic layer was washed with brine (100 mL), dried over anhydrous Na$_2$SO$_4$, filtered and concentrated. The residue was purified by flash column (0~20% of EtOAc in PE) to give 265.3 (150 mg, 0.5 mmol, 70%) as a solid.

Synthesis of 265.4 & 265.5

To a solution of 265.3 (150 mg, 0.5 mmol) in DMF (1 mL) were added CsCO$_3$ (220 mg, 0.7 mmol) and 2H-1,2,3- triazole (23.4 mg, 0.2 mmol) at 0° C. After stirring at 85° C. for 12 h, the resulting mixture was cooled to 25° C., diluted with water (10 mL) and extracted with EtOAc (3×20 mL). The combined organic phase was washed with water (3×30 mL), brine (30 mL), dried over anhydrous Na$_2$SO$_4$, filtered and concentrated to give 265.4 & 265.5 (120 mg) as an oil. The residue was purified by flash column (0~45% of EtOAc in PE) to give 265.4 (80 mg, 67%, Rf=0.5, PE/EtOAc=1/1) as a solid and 265.5 (40 mg, 34%, Rf=0.4, PE/EtOAc=1/1) as a solid.

Separation of 265 and 266

The 265.4 (80 mg) was separated by SFC ((Column: DAICEL CHIRALCEL OD-H (250 mm*30 mm, 5 □m); condition: 0.1% NH$_3$H$_2$O EtOH; Begin B: 40%; End B: 40%) to afford 265 (5.1 mg, 6%) as a solid and 266 (23 mg, 29%) as a solid.

265: $^1$H NMR (400 MHz, CDCl$_3$) $\delta_H$ 7.59 (s, 2H), 4.47 (dd, J=4.0, 13.6 Hz, 1H), 4.12 (dd, J=9.6, 13.2 Hz, 1H), 3.52 (q, J=6.8 Hz, 2H), 3.42 (q, J=9.6 Hz, 2H), 2.69 (s, 1H), 2.20-1.70 (m, 7H), 1.53-1.31 (m, 8H), 1.30-1.15 (m, 8H), 1.15-1.00 (m, 5H), 0.81 (d, J=6.4 Hz, 3H), 0.71 (s, 3H). LC-ELSD/MS purity 99%, 100% de based on H-NMR. MS ESI calcd. for C$_{26}$H$_{42}$N$_3$O [M–H$_2$O+H]$^+$ 412.3, found 412.3.

266: $^1$H NMR (400 MHz, CDCl$_3$) $\delta_H$ 7.59 (s, 2H), 4.70 (dd, J=4.4, 13.2 Hz, 1H), 4.08 (dd, J=10.8, 12.9 Hz, 1H), 3.53 (q, J=6.8 Hz, 2H), 3.42 (q, J=9.2 Hz, 2H), 2.70 (s, 1H), 2.31-2.15 (m, 1H), 1.95-1.61 (m, 8H), 1.54-1.31 (m, 8H), 1.30-1.16 (m, 7H), 1.14-0.99 (m, 5H), 0.81 (s, 3H), 0.66 (d, J=6.4 Hz, 3H). LC-ELSD/MS purity 99%, 100% de based on H-NMR. MS ESI calcd. for C$_{26}$H$_{42}$N$_3$O [M–H$_2$O+H]$^+$ 412.3, found 412.3.

Separation of 267 and 268

The 265.5 (40 mg) was separated by SFC ((Column: DAICEL CHIRALCEL OD-H (250 mm*30 mm, 5□m); condition: 0.1% NH$_3$H$_2$O EtOH; Begin B: 40%; End B: 40%) to afford 267 (7.6 mg, 19%) as a solid and 268 (15 mg, 38%) as a solid.

267: $^1$H NMR (400 MHz, CDCl$_3$) $\delta_H$ 7.70 (s, 1H), 7.50 (s, 1H), 4.44 (dd, J=3.6, 13.8 Hz, 1H), 4.03 (dd, J=9.6, 13.6 Hz, 1H), 3.52 (q, J=6.8 Hz, 2H), 3.42 (q, J=9.2 Hz, 2H), 2.71 (s, 1H), 2.09-1.68 (m, 7H), 1.51-1.28 (m, 9H), 1.23-0.99 (m, 12H), 0.84 (d, J=6.4 Hz, 3H), 0.71 (s, 3H). LC-ELSD/MS purity 99%, 100% de based on H-NMR. MS ESI calcd. C$_{26}$H$_{44}$N$_3$O$_2$ [M+H]$^+$ 430.3, found 430.3.

268: $^1$H NMR (400 MHz, CDCl$_3$) $\delta_H$ 7.70 (s, 1H), 7.50 (s, 1H), 4.68 (d, J=10.8 Hz, 1H), 4.05-3.83 (m, 1H), 3.54-3.52 (m, 2H), 3.46-3.40 (q, J=9.2 Hz), 2.72 (s, 1H), 1.97-1.73 (m, 5H), 1.53-1.32 (m, 9H), 1.31-1.17 (m, 8H), 1.16-0.96 (m, 6H), 0.81 (s, 3H), 0.70 (d, J=6.4 Hz, 3H). LC-ELSD/MS purity 99%, 100% de based on H-NMR. MS ESI calcd. for C$_{26}$H$_{44}$N$_3$O$_2$ [M+H]$^+$ 430.3, found 430.3.

Examples 269 & 270: Synthesis of 1-((R)-2-((3R, 5R,8R,9R,10S,13S,14S,17R)-3-(ethoxymethyl)-3-hydroxy-13-methylhexadecahydro-1H-cyclopenta[a]phenanthren-17-yl)propyl)-1H-pyrazole-4-carbonitrile (269) & 1-((S)-2-((3R,5R,8R,9R,10S, 13S,14S,17R)-3-(ethoxymethyl)-3-hydroxy-13-methylhexadecahydro-1H-cyclopenta[a]phenanthren-17-yl)propyl)-1H-pyrazole-4-carbonitrile (270)

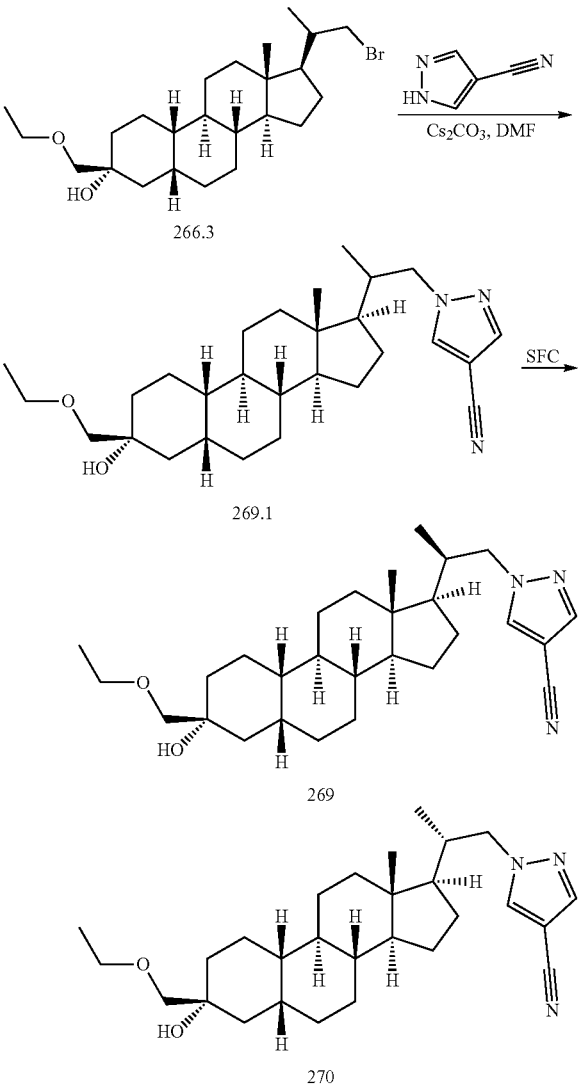

To a solution of 265.3 (150 mg, 0.5 mmol) in DMF (1 mL) were added CsCO$_3$ (220 mg, 0.7 mmol) and 1H-pyrazole-4-carbonitrile (47.2 mg, 0.5 mmol) at 0° C. After stirring at 85° C. for 12 h, the reaction mixture was diluted with water (10 mL) and extracted with EtOAc (3×20 mL). The combined organic phase was washed with water (3×30 mL), brine (30 mL), dried over anhydrous Na$_2$SO$_4$, filtered and concentrated to give 269.1 (153 mg) as an oil. The residue was purified by flash column (0~50% of EtOAc in PE) and then by pre-HPLC (Column: Waters Xbridge 150*25 5u); condition: water (10 mM NH$_4$HCO$_3$)-ACN; Begin B: 70%; End B: 100%) to afford 269.1 (50 mg, 50%) as a solid. The diastereomers were separated by SFC (Column: DAICEL CHIRALPAK AS-H (250 mm*30 mm, 5□m); condition: 0.1% NH$_3$H$_2$O EtOH; Begin B: 30%; End B: 30%) to afford 269 (13.9 mg, 22%) and 270 (12.7 mg, 34%) as solids.

269: $^1$H NMR (400 MHz, CDCl$_3$) $\delta_H$ 7.80 (s, 1H), 7.75 (s, 1H), 4.50 (dd, J=4.4, 13.2 Hz, 1H), 3.70-3.60 (m, 1H), 3.53 (q, J=7.2 Hz, 2H), 3.43 (q, J=9.2 Hz, 2H), 2.72 (s, 1H), 2.20-2.02 (m, 1H), 1.93-1.63 (m, 7H), 1.53-1.29 (m, 8H), 1.27-1.00 (m, 12H), 0.79 (s, 3H), 0.67 (d, J=6.4 Hz, 3H). LC-ELSD/MS purity 99%, analytic SFC: 100% de. MS ESI calcd. for C$_{28}$H$_{42}$N$_3$O [M−H$_2$O+H]$^+$ 436.3, found 436.3.

270: $^1$H NMR (400 MHz, CDCl$_3$) $\delta_H$ 7.80 (s, 1H), 7.75 (s, 1H), 4.26 (dd, J=3.2, 13.6 Hz, 1H), 3.80-3.63 (m, 1H), 3.52 (q, J=6.8 Hz, 2H), 3.41 (q, J=9.2 Hz, 2H), 2.71 (s, 1H), 2.10-1.62 (m, 8H), 1.52-1.29 (m, 8H), 1.27-0.96 (m, 12H), 0.80 (d, J=6.4 Hz, 3H), 0.71 (s, 3H). LC-ELSD/MS purity 99%, analytic SFC: 92.94% de. MS ESI calcd. for C$_{28}$H$_{42}$N$_3$O [M−H$_2$O+H]$^+$ 436.3, found 436.3.

Examples 271-274: Synthesis of 1-((S)-2-((3R,5R, 8R,9R,10S,13S,14S,17R)-3-ethyl-3-hydroxy-13-methylhexadecahydro-1H-cyclopenta[a] phenanthren-17-yl)propyl)-1H-pyrazole-3-carbonitrile (271) & 1-((R)-2-((3R,5R,8R,9R,10S, 13S,14S,17R)-3-ethyl-3-hydroxy-13-methylhexadecahydro-1H-cyclopenta[a] phenanthren-17-yl)propyl)-1H-pyrazole-3-carbonitrile (272) & 1-((R)-2-((3R,5R,8R,9R,10S, 13S,14S,17R)-3-ethyl-3-hydroxy-13-methylhexadecahydro-1H-cyclopenta[a] phenanthren-17-yl)propyl)-1H-pyrazole-5-carbonitrile (273) & 1-((S)-2-((3R,5R,8R,9R,10S, 13S,14S,17R)-3-ethyl-3-hydroxy-13-methylhexadecahydro-1H-cyclopenta[a] phenanthren-17-yl)propyl)-1H-pyrazole-5-carbonitrile (274)

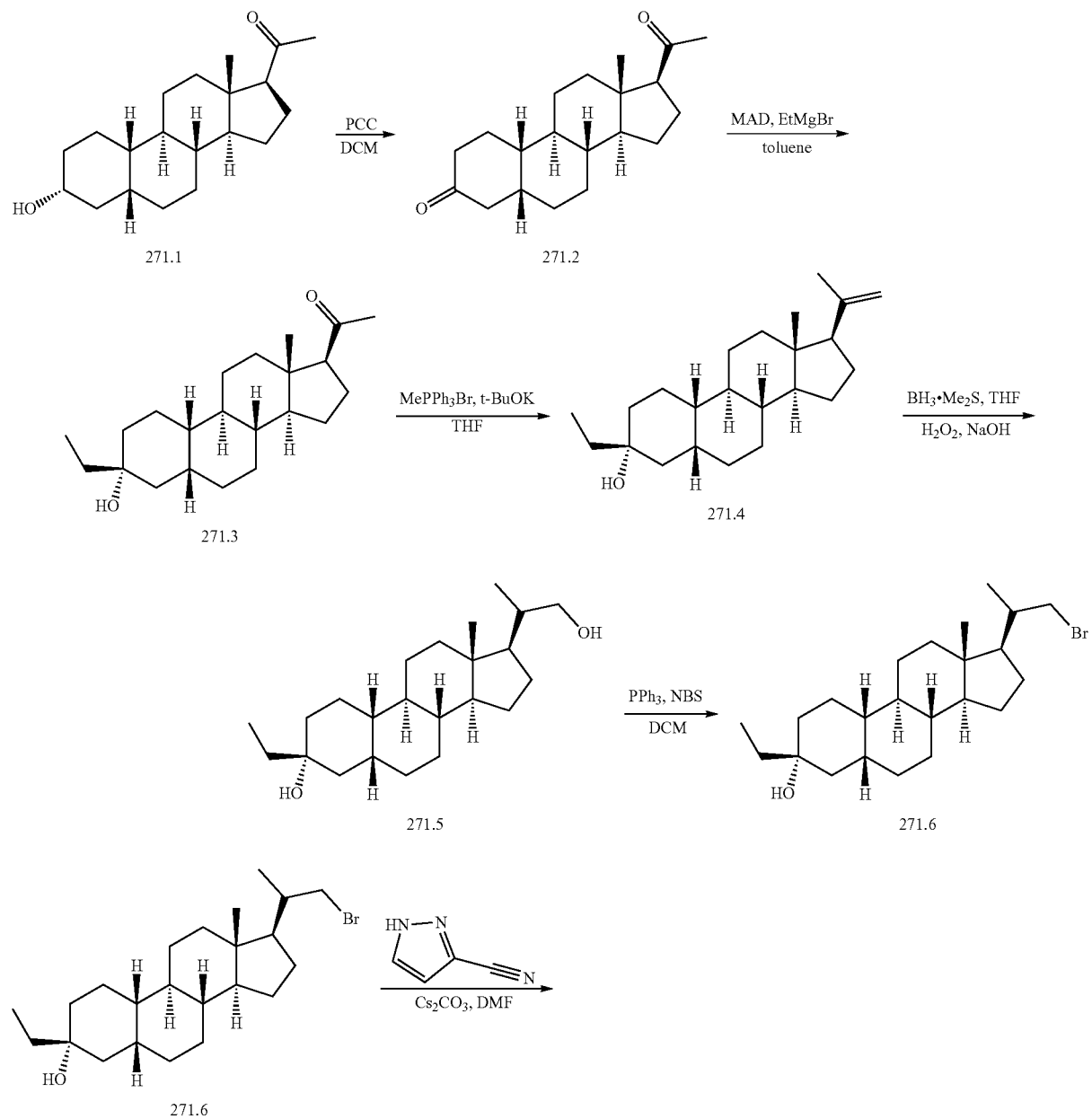

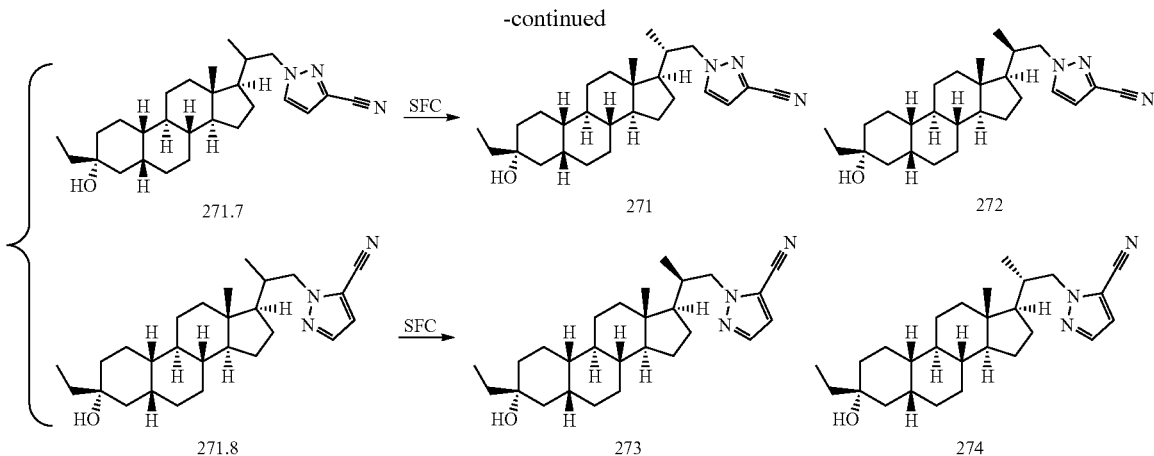

Synthesis of 271.2

To a solution of 271.1 (3.5 g, 11.4 mmol) in DCM (50 mL) was added PCC (4.9 g, 22.8 mmol) at 25° C. After stirring at 25° C. for 2 h, the resulting mixture was filtered, and the filter cake was washed with DCM (2×50 mL). The combined filtrate was concentrated. The residue was purified by silica gel column eluted with PE/EtOAc=6/1 to afford 271.2 (2.8 g, 77%) as a solid.

$^1$H NMR (400 MHz, CDCl$_3$) δ 2.65-2.50 (m, 2H), 2.25-2.01 (m, 9H), 1.80-1.66 (m, 4H), 1.65-1.55 (m, 2H), 1.54-1.44 (m, 4H), 1.43-1.31 (m, 1H), 1.30-1.11 (m, 5H), 0.65 (s, 3H).

Synthesis of 271.3

To a solution of BHT (12 g, 54.4 mmol) in toluene (120 mL) under N$_2$ at 0° C. was added trimethylaluminum (2 M in toluene, 14 mL, 28 mmol) dropwise. After stirring at 25° C. for 1 h, a solution of 271.2 (6 g, 19.8 mmol) in DCM (60 mL) was added dropwise at −70° C. After stirring at −70° C. for 1 h under N$_2$, EtMgBr (20 mL, 60 mmol, 3M in ethyl ether) was added dropwise at −70° C. After stirring at −70° C. for another 1 h, the reaction mixture was poured into citric acid (600 mL, sat.) at 10° C. and extracted with DCM (2×800 mL). The combined organic layer was dried over anhydrous Na$_2$SO$_4$, filtered and concentrated. The residue was triturated by PE to give 271.3 (3.83 g, 58%) as a solid.

$^1$H NMR (400 MHz, CDCl$_3$) δ$_H$ 2.56-2.50 (m, 1H), 2.24-2.10 (m, 4H), 2.07-1.99 (m, 1H), 1.89-1.51 (m, 9H), 1.50-1.20 (m, 12H), 1.19-1.00 (m, 3H), 0.98-0.80 (m, 3H), 0.61 (s, 3H).

Synthesis of 271.4

To a suspension of MePh$_3$PBr (6.4 g, 18.0 mmol) in THF (50 mL) was added t-BuOK (2.01 g, 18.0 mmol). After stirring at 40° C. for 10 mins, the mixture was slowly added dropwise to a solution of 271.3 (3 g, 9.02 mmol) in THF (30 mL) at 20° C. for 30 mins. After the addition, the mixture was quenched with sat. NH$_4$Cl (100 mL) and extracted with EtOAc (3×100 mL). The combined organic phase was washed with sat. NH$_4$Cl (100 mL), dried over anhydrous Na$_2$SO$_4$, filtered, concentrated and purified by flash column (0~25% of EtOAc in PE) to give 271.4 (2.445 g, 82%) as a solid.

$^1$H NMR (400 MHz, CDCl$_3$) δ$_H$ 4.84 (s, 1H), 4.69 (s, 1H), 2.02-1.53 (m, 13H), 1.50-1.33 (m, 4H), 1.32-1.11 (m, 11H), 1.10-0.99 (m, 2H), 0.85-0.80 (m, 3H), 0.56 (s, 3H).

Synthesis of 271.5

To a solution of 271.4 (2.44 g, 7.38 mmol) in THF (20 mL) was added BH$_3$/Me$_2$S (2.8 g, 10 M, 36.9 mmol) dropwise at 25° C. under N$_2$. After stirring at 25° C. for 2 h, the mixture was cooled and quenched sequentially with EtOH (3.39 g, 73.8 mmol) at 0° C., NaOH (14.7 mL, 5 M, 73.8 mmol) slowly and finally H$_2$O$_2$ (7.38 mL, 10 M, 73.8 mmol) dropwise until the reaction temperature no longer rises. After the reaction temperature remained below 0° C., the mixture was poured into water (30 mL), stirred for 30 mins. and extracted with EtOAc (2×30 mL). The combined organic solution was washed with water (2×30 mL), dried over anhydrous Na$_2$SO$_4$, filtered, concentrated and purified by flash column (0~30% of EtOAc in PE) to give 271.5 (2.257 g, 87%) as an oil.

$^1$H NMR (400 MHz, CDCl$_3$) δ$_H$ 3.76-3.71 (m, 1H), 3.47-3.36 (m, 1H), 1.98-1.74 (m, 5H), 1.73-1.50 (m, 5H), 1.49-1.32 (m, 5H), 1.31-1.20 (m, 9H), 1.16-1.00 (m, 5H), 0.98-0.79 (m, 6H), 0.67 (s, 3H).

Synthesis of 271.6

To a solution of 271.5 (1.2 g, 3.44 mmol) in DCM (10 mL) at 0° C. were added PPh$_3$ (1.35 g, 5.15 mmol) and NBS (916 mg, 5.15 mmol). After stirring at 25° C. for 2 h, the reaction was diluted with water (10 mL) and extracted with DCM (2×15 mL). The combined organic phase was washed with brine (2×15 mL), dried over anhydrous Na$_2$SO$_4$, filtered and concentrated. The residue was purified by flash column (0~10% of EtOAc in PE) to give 271.6 (1.006 g, 71%) as an oil.

$^1$H NMR (400 MHz, CDCl$_3$) δ$_H$ 3.61-3.48 (m, 1H), δ 3.39-3.34 (m, 1H), 2.03-1.83 (m, 2H), 1.82-1.60 (m, 6H), 1.59-1.51 (m, 6H), 1.50-120 (m, 13H), 1.19-0.91 (m, 4H), 0.90-0.78 (m, 3H), 0.67 (s, 3H).

Synthesis of 271.7 & 271.8

To a solution of 271.6 (1 g, 2.43 mmol) in DMF (10 mL) was added Cs$_2$CO$_3$ (1.57 g, 4.86 mmol) and 1H-pyrazole-3-carbonitrile (452 mg, 4.86 mmol) at 25° C. After stirring at 85° C. for 12 h, the reaction mixture was diluted with water (20 mL) and extracted with EtOAc (3×20 mL). The combined organic phase was washed with water (30 mL) and aq. LiCl (30 mL, 5%), brine (30 mL), dried over anhydrous Na$_2$SO$_4$, filtered and concentrated. The residue was purified by flash column (0~30% of EtOAc in PE) to give 271.7 (544 mg, 53%) and 271.8 (163 mg, 16%) both as oils.

271.7: $^1$H NMR (400 MHz, CDCl$_3$) δ$_H$ 7.70-7.68 (m, 1H), 6.77-6.75 (m, 1H), 4.61-4.33 (m, 1H), 3.99-3.77 (m, 1H), 2.26-2.09 (m, 4H), 2.08-1.78 (m, 4H), 1.77-1.56 (m, 5H), 1.50-1.25 (m, 8H), 1.24-1.20 (m, 5H), 1.19-1.00 (m, 5H), 0.99-0.75 (m, 3H), 0.74-0.65 (m, 3H).

271.8: ¹H NMR (400 MHz, CDCl₃) δ_H 7.68-7.67 (m, 1H), 7.40-7.26 (m, 1H), 6.77-6.64 (m, 1H), 4.53-4.24 (m, 1H), 3.78-3.66 (m, 1H), 2.24-2.11 (m, 1H), 2.00-1.74 (m, 6H), 1.73-1.56 (m, 6H), 1.50-1.25 (m, 9H), 1.24-1.09 (m, 5H), 0.99-0.80 (m, 3H), 0.79-0.76 (m, 3H), 0.74-0.65 (m, 3H).

Separation of 271 & 272

271.7 (544 mg, 1.28 mmol) was separated by SFC (column: DAICEL CHIRALCEL OJ-H (250 mm*30 mm, 5 um), condition: 0.1% NH₃H₂O ETOH, Begin B: 20%, End B: 20%, FlowRate (ml/min): 60, Injections: 80) to give 271 (97.6 mg, 18%) and 272 (182.9 mg, 33%) as a solid. The two diastereomers were assigned based on ¹H NMR of C21-Me (C21-down-Me is at more downfield than C21-up isomer).

271: ¹H NMR (400 MHz, CDCl₃) δ_H 7.40-7.39 (m, 1H), 6.66-6.64 (m, 1H), 4.30-4.24 (m, 1H), 3.78-3.71 (m, 1H), 1.93-1.74 (m, 3H), 1.80-1.68 (m, 3H), 1.67-1.52 (m, 7H), 1.50-1.25 (m, 7H), 1.24-1.00 (m, 8H), 0.99-0.80 (m, 3H), 0.78-0.75 (m, 3H), 0.71 (s, 3H). LC-ELSD/MS purity 99%, MS ESI calcd. for C₂₇H₄₂N₃O [M+H]⁺ 424, found 424. SFC 100% de.

272: ¹H NMR (400 MHz, CDCl₃) δ_H 7.40-7.38 (m, 1H), 6.66-6.64 (m, 1H), 4.53-4.47 (m, 1H), 3.73-3.66 (m, 1H), 2.17-2.10 (m, 1H), 1.90-1.68 (m, 5H), 1.67-1.51 (m, 5H), 1.50-1.25 (m, 11H), 1.24-1.20 (m, 2H), 1.19-1.00 (m, 4H), 0.90-0.80 (m, 3H), 0.79 (s, 3H), 0.69-0.66 (m, 3H). LC-ELSD/MS purity 99%, MS ESI calcd. for C₂₇H₄₂N₃O [M+H]⁺ 424, found 424. SFC 99.84% de.

Separation of 273 & 274

271.8 (163 mg, 0.384 mmol) was separated by SFC (column: DAICEL CHIRALPAK AD-H (250 mm*30 mm, 5 um), condition: 0.1% NH₃H₂O IPA, Begin B: 40%, End B: 40%, FlowRate (ml/min): 50, Injections: 100) to give 273 (70 mg) as a solid and 274 (53 mg) as a solid. The 273 (70 mg) was re-purified by SFC (column: DAICEL CHIRALCEL OJ-H (250 mm*30 mm, 5 um), condition: 0.1% NH₃H₂O ETOH, Begin B: 15%, End B: 15%; FlowRate (ml/min): 60) to give 273 (21.8 mg) as a solid. The 274 (53 mg) was re-purified by SFC (column: DAICEL CHIRALCEL OJ-H (250 mm*30 mm, 5 um), condition: 0.1% NH₃H₂O ETOH, Begin B: 15%, End B: 15%, FlowRate (ml/min): 60, Injections: 45) to give 274 (19.8 mg) as a solid. The two diastereomers were assigned based on ¹H NMR of C21-Me (C21-down-Me is at more downfield than C21-up isomer).

273: ¹H NMR (400 MHz, CDCl₃) δ_H 7.57-7.56 (m, 1H), 6.78-6.77 (m, 1H), 4.63-4.57 (m, 1H), 3.94-3.87 (m, 1H), 2.22-2.18 (m, 1H), 1.90-1.81 (m, 2H), 1.80-1.63 (m, 3H), 1.62-1.58 (m, 5H), 1.50-1.48 (m, 2H), 1.47-1.20 (m, 10H), 1.19-1.00 (m, 5H), 0.95-0.78 (m, 6H), 0.70-0.67 (m, 3H). LC-ELSD/MS purity 99%, MS ESI calcd. for C₂₇H₄₂N₃O [M+H]⁺ 424, found 424. SFC 100% de.

274: ¹H NMR (400 MHz, CDCl₃) δ_H 7.58-7.56 (m, 1H), 6.78-6.76 (m, 1H), 4.40-4.35 (m, 1H), 3.95-3.88 (m, 1H), 2.11-1.97 (m, 1H), 1.94-1.77 (m, 2H), 1.75-1.63 (m, 3H), 1.62-1.58 (m, 5H), 1.50-1.48 (m, 3H), 1.47-1.20 (m, 9H), 1.19-1.00 (m, 5H), 0.97-0.76 (m, 6H), 0.72 (s, 3H).

LC-ELSD/MS purity 99%, MS ESI calcd. for C₂₇H₄₂N₃O [M+H]⁺ 424, found 424. SFC 100% de.

Examples 275-276: Synthesis of 1-((R)-2-((3R,5R, 8R,9R,10S,13S,14S,17R)-3-ethyl-3-hydroxy-13-methylhexadecahydro-1H-cyclopenta[a]phenanthren-17-yl)propyl)-1H-pyrazole-4-carbonitrile (275) & 1-((S)-2-((3R,5R,8R,9R,10S, 13S,14S,17R)-3-ethyl-3-hydroxy-13-methylhexadecahydro-1H-cyclopenta[a]phenanthren-17-yl)propyl)-1H-pyrazole-4-carbonitrile (276)

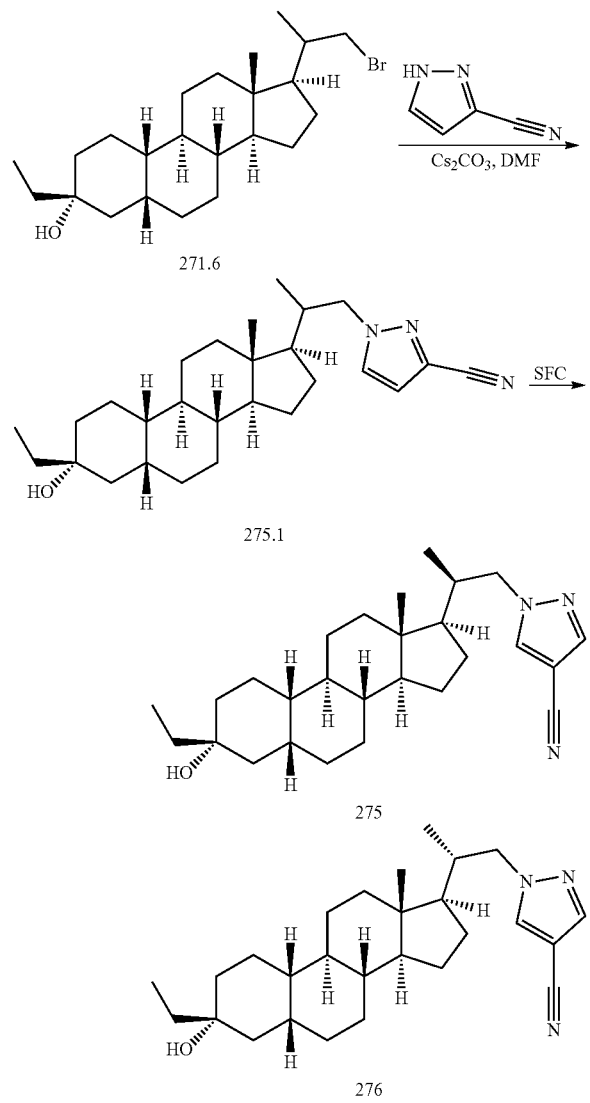

Synthesis of 275.1

To a solution of 271.6 (333 mg, 0.81 mmol) in DMF (5 mL) was added Cs₂CO₃ (523 mg, 1.61 mmol) and 1H-pyrazole-3-carbonitrile (82.7 mg, 0.89 mmol) at 25° C. After stirring at 85° C. for 12 h, the resulting colorless solution was diluted with EtOAc (50 mL) and washed with water (50 mL), brine (50 mL), dried over anhydrous Na₂SO₄, filtered and concentrated. The residue was purified by flash column (0~20% EtOAc in PE) to give 275.1 (200 mg, 58%) as a solid.

¹H NMR (400 MHz, CDCl₃) δ_H 7.80-7.75 (m, 2H), 4.52-4.23 (m, 1H), 3.76-3.62 (m, 1H), 2.10-2.04 (m, 1H), 2.03-1.73 (m, 5H), 1.72-1.50 (m, 5H), 1.49-1.23 (m, 8H), 1.22-1.00 (m, 8H), 0.95-0.83 (m, 4H), 0.82-0.76 (m, 3H), 0.75-0.67 (m, 3H).

Separation of 275 & 276

275.1 (200 mg) was separated by SFC (DAICEL CHIRALCEL OD-H (250 mm*30 mm, 5 um), Condition: 0.1% NH$_3$H$_2$O ETOH Begin B: 35% End B: 35% FlowRate (ml/min): 50) to give 276 (68 mg, 34%, Peak 2, Rt=1.835 min) and 275 (53 mg, 27%, Peak 1, Rt=1.529 min) as solids. The two diastereomers were assigned based on $^1$H NMR of C21-Me (C21-down-Me is at more downfield than C21-up isomer).

275: $^1$H NMR (400 MHz, CDCl$_3$) $\delta_H$ 7.80-7.75 (m, 2H), 4.28-4.23 (m, 1H), 3.76-3.69 (m, 1H), 2.05-1.92 (m, 3H), 1.90-1.75 (m, 3H), 1.74-1.55 (m, 5H), 1.54-1.24 (m, 10H), 1.23-0.98 (m, 7H), 0.95-0.83 (m, 3H), 0.82-0.81 (m, 3H), 0.71 (s, 3H). LC-ELSD/MS purity 99%, analytic SFC: 99.82% de; MS ESI calcd. for C$_{27}$H$_{40}$N$_3$ [M+H−H$_2$O]$^+$ 406, found 406; C$_{27}$H$_{41}$N$_3$ONa [M+Na]$^+$ 446.3, found 446.3.

276: $^1$H NMR (400 MHz, CDCl$_3$) $\delta_H$ 7.80-7.75 (m, 2H), 4.52-4.47 (m, 1H), 3.69-3.62 (m, 1H), 2.13-2.07 (m, 1H), 1.90-1.75 (m, 5H), 1.74-1.55 (m, 5H), 1.54-1.48 (m, 3H), 1.47-1.25 (m, 6H), 1.24-1.23 (m, 3H), 1.22-1.00 (m, 5H), 0.95-0.80 (m, 3H), 0.79 (s, 3H), 0.69-0.67 (m, 3H). LC-ELSD/MS purity 99%, analytic SFC: 99.70% de; MS ESI calcd. for C$_{27}$H$_{40}$N$_3$ [M+H−H2O]$^+$ 406, found 406; C$_{27}$H$_{41}$N$_3$ONa [M+Na]$^+$ 446.3, found 446.3.

Examples 278-281: Synthesis of 1-((S)-2-((3R,5R,8R,9S,10S,13S,14S,17R)-3-(ethoxymethyl)-3-hydroxy-10,13-dimethylhexadecahydro-1H-cyclopenta[a]phenanthren-17-yl)propyl)-1H-pyrazole-3-carbonitrile (278) & 1-((R)-2-((3R,5R,8R,9S,10S,13S,14S,17R)-3-(ethoxymethyl)-3-hydroxy-10,13-dimethylhexadecahydro-1H-cyclopenta[a]phenanthren-17-yl)propyl)-1H-pyrazole-3-carbonitrile (279) & 1-((R)-2-((3R,5R,8R,9S,10S,13S,14S,17R)-3-(ethoxymethyl)-3-hydroxy-10,13-dimethylhexadecahydro-1H-cyclopenta[a]phenanthren-17-yl)propyl)-1H-pyrazole-5-carbonitrile (280) & 1-((S)-2-((3R,5R,8R,9S,10S,13S,14S,17R)-3-(ethoxymethyl)-3-hydroxy-10,13-dimethylhexadecahydro-1H-cyclopenta[a]phenanthren-17-yl)propyl)-1H-pyrazole-5-carbonitrile (281)

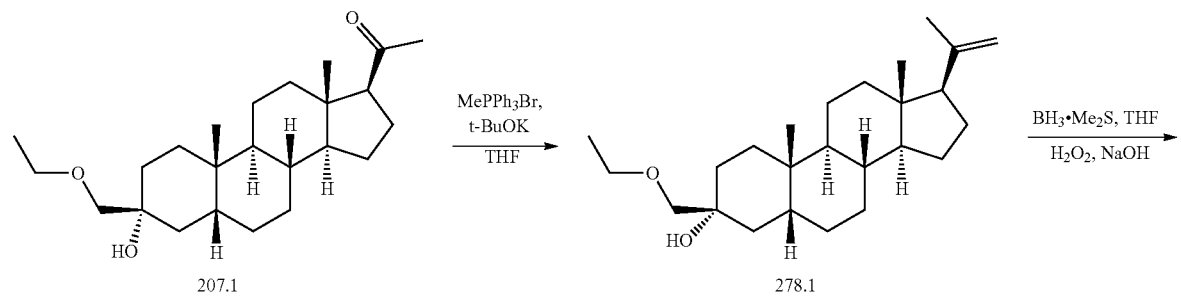

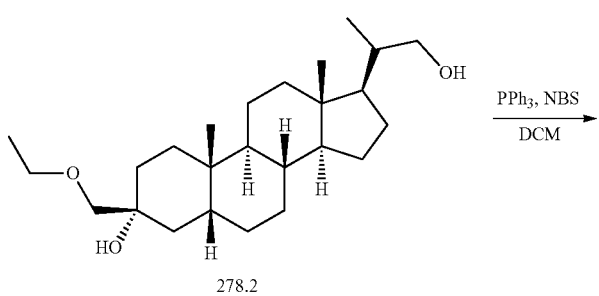

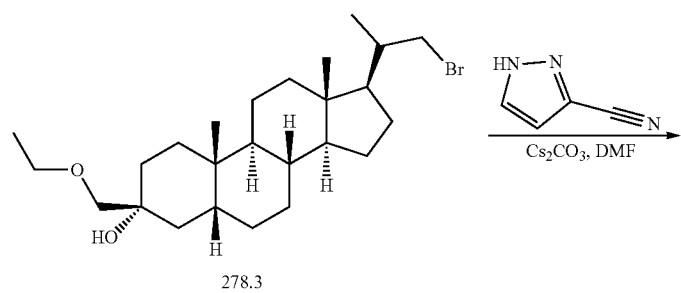

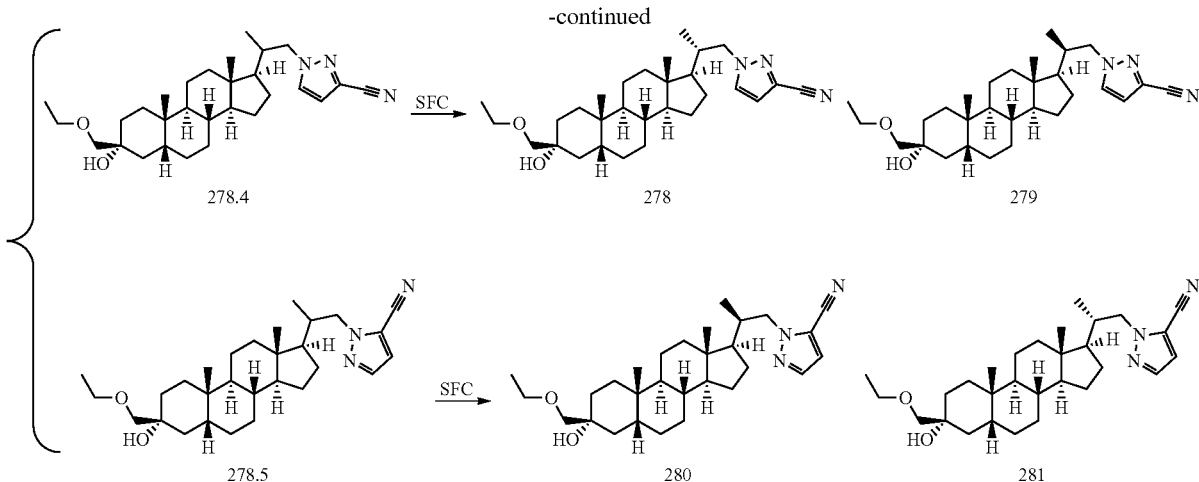

Synthesis of 278.1

To a solution of MePPh₃Br (2.59 g, 7.95 mmol) in THF (30 mL) was added t-BuOK (892 mg, 7.95 mmol) at 25° C. After stirring at 25° C. for 1 h, 207.1 (1 g, 2.65 mmol) in THF (10 mL) was added at 25° C. After stirring at 50° C. for 3 h, the mixture was treated with NH₄Cl (20 mL, sat) and extracted with EtOAc (2×30 mL). The combined organic phase was washed with brine (10 mL), dried over anhydrous Na₂SO₄, filtered and concentrated. The residue was triturated from MeOH (30 mL) and water (30 mL) at 25° C. to give 278.1 (900 mg) as an oil.

$^1$H NMR (400 MHz, CDCl₃) $\delta_H$ 4.88-4.65 (m, 2H), 3.59-3.34 (m, 4H), 2.10-1.96 (m, 2H), 1.85-1.63 (m, 9H), 1.52-1.34 (m, 6H), 1.29-1.17 (m, 9H), 1.02-0.89 (m, 7H), 0.63-0.50 (m, 3H).

Synthesis of 278.2

To a solution of 278.1 (900 mg, 2.40 mmol) in THF (20 mL) was added BH₃·Me₂S (2.15 mL, 21.5 mmol) at 25° C. After stirring for 1 h, the reaction was sequentially treated with NaOH (1.91 g, 47.9 mmol in water) at 0° C. and H₂O₂ (4.79 mL, 10 M in water, 47.9 mmol) also at 0° C. After stirring at 70° C. for 1 h, the resulting colourless solution was cooled to 25° C., poured into water (50 mL) and extracted with EtOAc (3×30 mL). The combined organic phase was washed with brine (2×20 mL), dried over anhydrous Na₂SO₄, filtered and concentrated. The residue was purified by flash column (0~30% of EtOAc in PE) to give 278.2 (380 mg, 40%) as a solid.

$^1$H NMR (400 MHz, CDCl₃) $\delta_H$ 3.78-3.61 (m, 1H), 3.58-3.31 (m, 5H), 2.00-1.77 (m, 5H), 1.72-1.67 (m, 1H), 1.62-1.47 (m, 5H), 1.44-1.34 (m, 5H), 1.32-1.17 (m, 9H), 1.12-1.00 (m, 4H), 0.97-0.88 (m, 6H), 0.66 (s, 3H)

Synthesis of 278.3

To a solution of 278.2 (330 mg, 0.8404 mmol) in DCM (10 mL) at 0° C. was added PPh₃ (262 mg, 1.00 mmol) and NBS (177 mg, 1.00 mmol). After stirring at 25° C. for 3 h, the resulting solution was poured into water (50 mL) and extracted with DCM (3×50 mL). The combined organic phase was washed with brine (2×50 mL), dried over anhydrous Na₂SO₄, filtered and concentrated. The residue was purified by flash column (0~15% of EtOAc in PE) to give 278.3 (309 mg, 81%) as an oil.

$^1$H NMR (400 MHz, CDCl₃) $\delta_H$ 3.63 (br d, J=9.6 Hz, 0.5H), 3.57-3.26 (m, 5.5H), 2.68 (s, 1H), 1.94-1.65 (m, 6H), 1.50 (br d, J=12.0 Hz, 2H), 1.41-1.15 (m, 17H), 1.08 (br d, J=5.2 Hz, 4H), 0.98-0.91 (m, 4H), 0.66 (s, 3H)

Synthesis of 278.4 & 278.5

To a solution of 278.3 (309 mg, 0.6805 mmol) and Cs₂CO₃ (443 mg, 1.36 mmol) in DMF (3 mL) was added 1H-pyrazole-3-carbonitrile (126 mg, 1.36 mmol) at 25° C. under N₂. After stirring at 80° C. for 16 h, the resulting solution was cooled to 25° C., poured into water (100 mL) and extracted with EtOAc (3×100 mL). The combined organic phase was washed with brine (2×50 mL), dried over anhydrous Na₂SO₄, filtered and concentrated. The residue was purified by flash column (0~15% of EtOAc in PE) to give 278.4 (180 mg, 57%) and 278.5 (90 mg, 28%) both as oils.

Separation of 278 and 279

278.4 was purified by SFC (column: DAICEL CHIRALCEL OD-H (250 mm*30 mm, 5 um), gradient: 30% condition: 0.1% NH₃H₂O ETOH, flow rate: 60 mL/min) to give 278 (23 mg, Peak 1, Rt=1.618 min) and 279 (30 mg, Peak 2, Rt=2.275 min) both as solids.

278: $^1$H NMR (400 MHz, CDCl₃) $\delta_H$ 7.39 (d, J=2.0 Hz, 1H), 6.65 (d, J=2.4 Hz, 1H), 4.28 (dd, J=3.6, 13.6 Hz, 1H), 3.72 (dd, J=10.0, 13.2 Hz, 1H), 3.59-3.31 (m, 4H), 2.70 (s, 1H), 2.09-1.98 (m, 1H), 1.97-1.76 (m, 4H), 1.74-1.58 (m, 3H), 1.53-1.30 (m, 10H), 1.23-1.08 (m, 8H), 1.02-0.90 (m, 4H), 0.79 (d, J=6.4 Hz, 3H), 0.69 (s, 3H). LC-ELSD/MS purity 99%, MS ESI calcd. for C₂₉H₄₄N₃O [M+H−H₂O]⁺ 450, found 450; C₂₉H₄₅N₃O₂Na [M+Na]⁺ 490, found 490. SFC 100% de 279: $^1$H NMR (400 MHz, CDCl₃) $\delta_H$ 7.39 (d, J=2.4 Hz, 1H), 6.65 (d, J=2.4 Hz, 1H), 4.49 (dd, J=4.8, 13.2 Hz, 1H), 3.68 (dd, J=10.8, 13.2 Hz, 1H), 3.58-3.36 (m, 4H), 2.71 (s, 1H), 2.19-2.05 (m, 1H), 2.00-1.77 (m, 4H), 1.70 (br d, J=14.4 Hz, 1H), 1.64-1.55 (m, 4H), 1.47-1.33 (m, 6H), 1.30-1.08 (m, 10H), 1.03-0.92 (m, 4H), 0.77 (s, 3H), 0.67 (d, J=6.4 Hz, 3H).

LC-ELSD/MS purity 99%, MS ESI calcd. for C₂₉H₄₄N₃O [M+H−H₂O]⁺ 450, found 450; C₂₉H₄₅N₃O₂Na [M+Na]⁺ 490, found 490. SFC 100% de

Separation of 280 and 281

278.5 was purified by SFC (column: DAICEL CHIRALPAK AD-H (250 mm*30 mm, 5 um), gradient: 25% condition: 0.1% NH₃H₂O ETOH, flow rate: 50 mL/min) to give 280 (5 mg, Peak 1, Rt=1.036 min) and 281 (1.6 mg, Rt=1.223 min) both as solids.

280: $^1$H NMR (400 MHz, CDCl₃) $\delta_H$ 7.56 (d, J=2.4 Hz, 1H), 6.77 (d, J=2.4 Hz, 1H), 4.58 (dd, J=4.8, 13.2 Hz, 1H), 3.90 (dd, J=10.8, 13.2 Hz, 2H), 3.59-3.35 (m, 5H), 2.70 (s, 1H), 2.19 (br s, 2H), 2.00-1.76 (m, 5H), 1.70 (br d, J=14.8 Hz, 4H), 1.48-1.31 (m, 7H), 1.28-1.08 (m, 6H), 1.03-0.91 (m, 4H), 0.80 (s, 3H), 0.69 (d, J=6.8 Hz, 3H). LC-ELSD/MS purity 99%, MS ESI calcd. for $C_{29}H_{46}N_3O_2$ $[M+H]^+$ 468, found 468; $C_{29}H_{45}N_3O$ $[M+H-H_2O]^+$ 450, found 450; $C_{29}H_{45}N_3O_2Na$ $[M+Na]^+$ 490, found 490. SFC 100% de 281: $^1$H NMR (400 MHz, CDCl$_3$) $\delta_H$ 7.57 (d, J=2.0 Hz, 1H), 6.77 (d, J=2.0 Hz, 1H), 4.37 (dd, J=3.6, 13.2 Hz, 1H), 3.91 (dd, J=10.4, 13.8 Hz, 1H), 3.58-3.34 (m, 5H), 2.69 (s, 1H), 2.11 (br d, J=10.8 Hz, 1H), 2.00-1.76 (m, 5H), 1.70 (br d, J=14.8 Hz, 3H), 1.50-1.31 (m, 7H), 1.29-1.07 (m, 9H), 1.03-0.89 (m, 4H), 0.81 (d, J=6.5 Hz, 3H), 0.70 (s, 3H). LC-ELSD/MS purity 99%, MS ESI calcd. for $C_{29}H_{44}N_3O$ $[M+H-H_2O]^+$ 450, found 450. SFC 100% de Examples 282 & 283: Synthesis of 1-((S)-2-((3R, 5R,8S,9S,10S,11R,13S,14S,17R)-3,11-dihydroxy-3-(methoxymethyl)-10,13-dimethylhexadecahydro-1H-cyclopenta[a]phenanthren-17-yl)propyl)-1H-pyrazole-4-carbonitrile (282) & 1-((R)-2-((3R,5R, 8S,9S,10S,11R,13S,14S,17R)-3,11-dihydroxy-3-(methoxymethyl)-10,13-dimethylhexadecahydro-1H-cyclopenta[a]phenanthren-17-yl)propyl)-1H-pyrazole-4-carbonitrile (283)

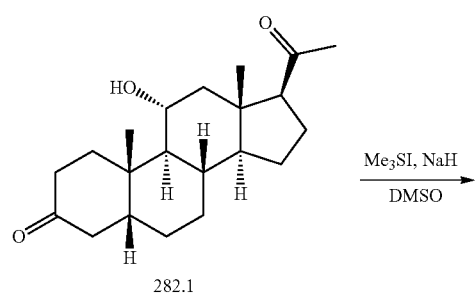

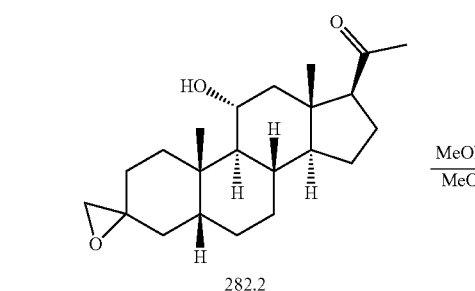

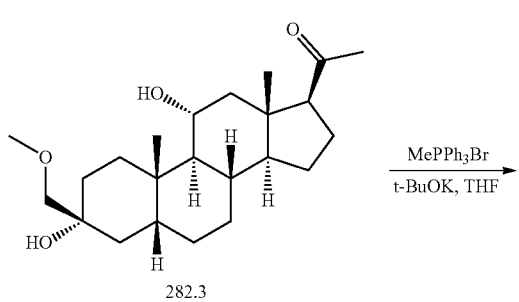

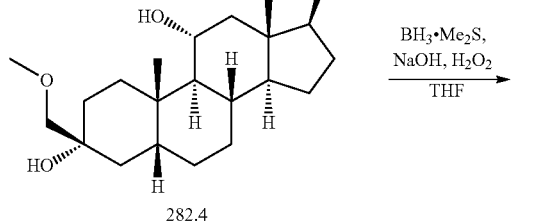

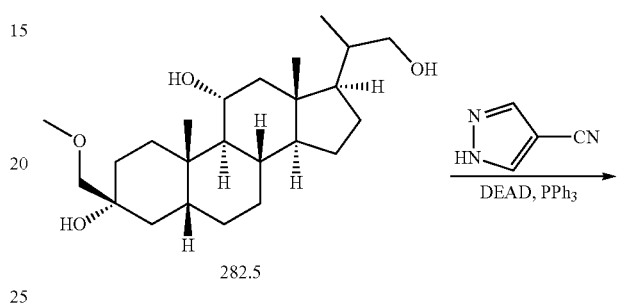

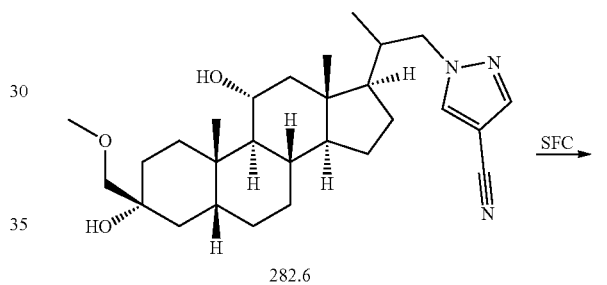

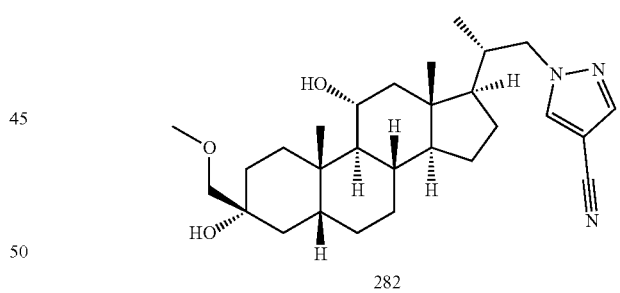

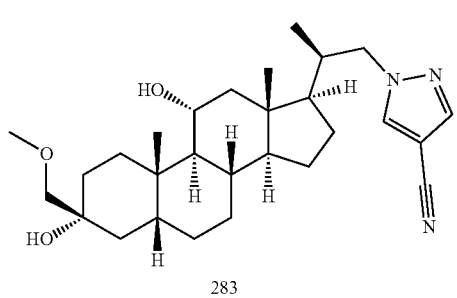

Synthesis of 282.2

To a solution of Me$_3$S (7.95 g, 39.0 mmol) in DMSO (30 mL) was added sodium hydride (935 mg, 39.0 mmol). After stirring at 0° C. for 30 min under N$_2$, a solution of 282.1 (5 g, 15.0 mmol) in DMSO (20 mL) was added. After stirring at 25° C. for 3 h under N$_2$, the mixture was quenched with NH$_4$C (100 mL, sat.) and extracted with EtOAc (2×75 mL). The combined organic layers were washed with brine (150 mL), dried over anhydrous Na$_2$SO$_4$, filtered and concentrated to give 282.2 (5 g, 96.3%) as oil.

$^1$H NMR (400 MHz, CDCl$_3$) δ$_H$ 4.02-3.85 (m, 1H), 2.78-2.50 (m, 4H), 2.48-2.18 (m, 3H), 2.17-2.13 (m, 1H), 2.12 (d, J=2.4 Hz, 3H), 1.90-1.59 (m, 6H), 1.58-1.27 (m, 8H), 1.20-1.13 (m, 2H), 1.12-1.07 (m, 3H), 0.97 (s, 3H), 0.62 (d, J=10.0 Hz, 3H).

Synthesis of 282.3

To a solution of 282.2 (11 g, 31.7 mmol) in MeOH (100 mL) was added MeONa (8.53 g, 158 mmol) at 25° C. After stirring at 60° C. for 16 h, the mixture was added quenched with NH$_4$Cl (60 mL, sat) and extracted with DCM (3×30 mL). The combined organic phase was washed with brine (2×30 mL), dried over anhydrous Na$_2$SO$_4$, filtered and concentrated. The residue was purified by flash column (20~40% of EtOAc in PE) to give 282.3 (3.3 g, 27.4%) as an oil.

$^1$H NMR (400 MHz, CDCl$_3$) δ$_H$ 3.90 (td, J=10.4, 15.6 Hz, 1H), 3.43-3.33 (m, 6H), 3.16 (s, 1H), 2.80-2.62 (m, 1H), 2.60-2.45 (m, 2H), 2.33-2.27 (m, 1H), 2.23-2.15 (m, 1H), 2.12 (s, 3H), 2.08-2.03 (m, 1H), 1.93-1.83 (m, 1H), 1.82-1.75 (m, 1H), 1.74-1.58 (m, 8H), 1.57-1.33 (m, 7H), 1.21-1.12 (m, 4H), 1.05 (s, 3H), 1.01-0.86 (m, 4H), 0.84-0.68 (m, 1H), 0.60 (d, J=2.0 Hz, 3H).

Synthesis of 282.4

To a mixture of MePPh$_3$Br (9.32 g, 26.1 mmol) in THF (80 mL) was added t-BuOK (2.92 g, 26.1 mmol) at 15° C. under N$_2$. After stirring at 15° C. for 30 mins, 282.3 (3.3 g, 8.71 mmol) in THF (20 mL) was added. After stirring at 40° C. for 2 h, the resulting suspension was poured into NH$_4$Cl (150 mL) and extracted with EtOAc (2×100 mL). The combined organic phase was washed with brine (20 mL), dried over anhydrous Na$_2$SO$_4$, filtered and concentrated. The residue was refluxed in MeOH (80 mL) at 70° C. for 30 mins, cooled to 15° C., added water (80 mL), filtered and concentrated to give 282.4 (1.6 g, 48.7%) as a solid.

$^1$H NMR (400 MHz, CDCl$_3$) δ$_H$ 4.85 (s, 1H), 4.70 (s, 1H), 3.95-3.80 (m, 1H), 3.39 (s, 5H), 3.21-3.12 (m, 1H), 2.66-2.58 (m, 1H), 2.55-2.46 (m, 1H), 2.26-2.06 (m, 3H), 1.98-1.80 (m, 2H), 1.75 (s, 3H), 1.72-1.66 (m, 4H), 1.57-1.49 (m, 1H), 1.47-1.33 (m, 4H), 1.32-1.28 (m, 1H), 1.21-1.09 (m, 4H), 1.06 (s, 2H), 1.01-0.82 (m, 4H), 0.56 (d, J=3.2 Hz, 3H).

Synthesis of 282.5

To a solution of 282.4 (600 mg, 1.59 mmol) in THF (10 mL) was added BH$_3$·Me$_2$S (0.477 mL, 4.77 mmol, 10 M) at 0° C. After stirring at 20° C. for 12 h, the resulting mixture was sequentially treated with ethanol (10 mL), NaOH aqueous (3.18 mL, 5.0 M) at 0° C. and then hydrogen peroxide (1.90 mL, 10 M) dropwise at 0° C. After the addition was complete, the reaction mixture was quenched with saturated aqueous Na$_2$S$_2$O$_3$ (30 mL) and extracted with EtOAc (2×30 mL). The combined organic phase was washed with brine (2×20 mL), dried over anhydrous Na$_2$SO$_4$, filtered and concentrated to give 282.5 (750 mg) as an oil.

$^1$H NMR (400 MHz, CDCl$_3$) δ$_H$ 3.96-3.79 (m, 1H), 3.76-3.70 (m, 1H), 3.65-3.59 (m, 1H), 3.51-3.41 (m, 1H), 3.40-3.34 (m, 5H), 3.24-3.15 (m, 1H), 2.50 (br d, J=14.0 Hz, 1H), 2.31-2.12 (m, 2H), 1.96-1.76 (m, 3H), 1.73-1.55 (m, 7H), 1.51-1.48 (m, 1H), 1.47-1.32 (m, 5H), 1.30-1.29 (m, 1H), 1.23-1.13 (m, 4H), 1.11-0.99 (m, 5H), 0.98-0.84 (m, 5H), 0.80-0.71 (m, 1H), 0.68 (d, J=3.6 Hz, 3H).

Synthesis of 282 & 283

To a solution of 282.5 (750 mg, 1.90 mmol) in DMF (10 mL) were added Ph$_3$P (996 mg, 3.80 mmol), DEAD (212 mg, 2.28 mmol) and 1H-pyrazole-4-carbonitrile (598 mg, 2.28 mmol) 0° C. After stirring at 20° C. for 16 h, the mixture was poured into water (10 mL) and extracted with EtOAc (2×20 mL). The combined organic phase was washed with brine (10 mL), dried over anhydrous Na$_2$SO$_4$, filtered and concentrated to give 282.6 (400 mg) as oil, which was purified by pre-HPLC (Welch Xtimate C18 150×25 mm, 5 □m; Condition: water (0.225% FA)-ACN; Gradient: from 52% to 82% of B in 8.5 min and hold 100% for 2 min; Flow rate: 30 mL/min) to afford 283 (60 mg) and 282 (20 mg) both as solids.

282 (20 mg) was further purified by SFC (Column: DAICEL CHIRALPAK AD-H 250 mm×30 mm, 5 □m; Condition: 0.1% NH$_3$H$_2$O ETOH; Gradient: from 45% to 45% of B; Flow rate: 50 mL/min; Column temperature: 35° C.) to afford 282 (6.6 mg, 33%) as a solid.

283 (60 mg) was further purified by SFC (Column: DAICEL CHIRALPAK AD-H 250 mm×30 mm, 5 □m; Condition: 0.1% NH$_3$H$_2$O ETOH; Gradient: from 40% to 40% of B; Flow rate: 50 mL/min; Column temperature: 35° C.) to afford 283 (8.4 mg, 14%) as a solid.

282: $^1$H NMR (400 MHz, CDCl$_3$) δ$_H$ 7.80 (s, 1H), 7.75 (s, 1H), 4.24 (dd, J=3.6, 13.6 Hz, 1H), 3.84 (br s, 1H), 3.74-3.68 (m, 1H), 3.41-3.39 (m, 5H), 2.62 (s, 1H), 2.49 (br d, J=14.4 Hz, 1H), 2.25 (dd, J=4.8, 12 Hz, 1H), 2.05-1.95 (m, 2H), 1.94-1.77 (m, 3H), 1.68-1.62 (m, 3H), 1.40 (br d, J=16 Hz, 5H), 1.26-1.16 (m, 6H), 1.06 (s, 3H), 1.01-0.95 (m, 1H), 0.89-0.85 (m, 1H), 0.83 (d, J=6.4 Hz, 3H), 0.71 (s, 3H). LC-ELSD/MS purity 99%, MS ESI calcd. for C$_{26}$H$_{37}$N$_3$ [M−2H$_2$O−MeOH]$^+$ 402.3 found 402.3. SFC 99.32% de.

283: $^1$H NMR (400 MHz, CDCl$_3$) δ$_H$ 7.80 (s, 1H), 7.75 (s, 1H), 4.50 (dd, J=4.4, 13.2 Hz, 1H), 3.92-3.82 (m, 1H), 3.70-3.63 (m, 1H), 3.43-3.39 (m, 5H), 2.63 (s, 1H), 2.51-2.44 (m, 1H), 2.19 (dd, J=4.9, 11.7 Hz, 1H), 2.15-2.06 (m, 1H), 1.89 (br d, J=13.6 Hz, 3H), 1.64 (br s, 4H), 1.44-1.32 (m, 5H), 1.29-1.17 (m, 5H), 1.07 (s, 4H), 1.05-0.96 (m, 1H), 0.90-0.86 (m, 1H), 0.79 (s, 3H), 0.67 (d, J=6.4 Hz, 3H). LC-ELSD/MS purity 99%, MS ESI calcd. for C$_{26}$H$_{37}$N$_3$ [M−2H$_2$O−MeOH]$^+$ 402.3 found 402.3 SFC 100% de.

Examples 285-290: Synthesis of 1-((R)-2-((3R,5R,8R,9R,10S,13S,14S,17R)-3-(ethoxymethyl)-3-hydroxy-13-methylhexadecahydro-1H-cyclopenta[a]phenanthren-17-yl)propyl)-1H-pyrazole-5-carbonitrile (285) &1-((S)-2-((3R,5R,8R,9R,10S,13S,14S,17R)-3-(ethoxymethyl)-3-hydroxy-13-methylhexadecahydro-1H-cyclopenta[a]phenanthren-17-yl)propyl)-1H-pyrazole-5-carbonitrile (286) & 1-((S)-2-((3R,5R,8R,9R,10S,13S,14S,17R)-3-(ethoxymethyl)-3-hydroxy-13-methylhexadecahydro-1H-cyclopenta[a]phenanthren-17-yl)propyl)-1H-pyrazole-3-carbonitrile (287) & 1-((R)-2-((3R,5R,8R,9R,10S,13S,14S,17R)-3-(ethoxymethyl)-3-hydroxy-13-methylhexadecahydro-1H-cyclopenta[a]phenanthren-17-yl)propyl)-1H-pyrazole-3-carbonitrile (288)

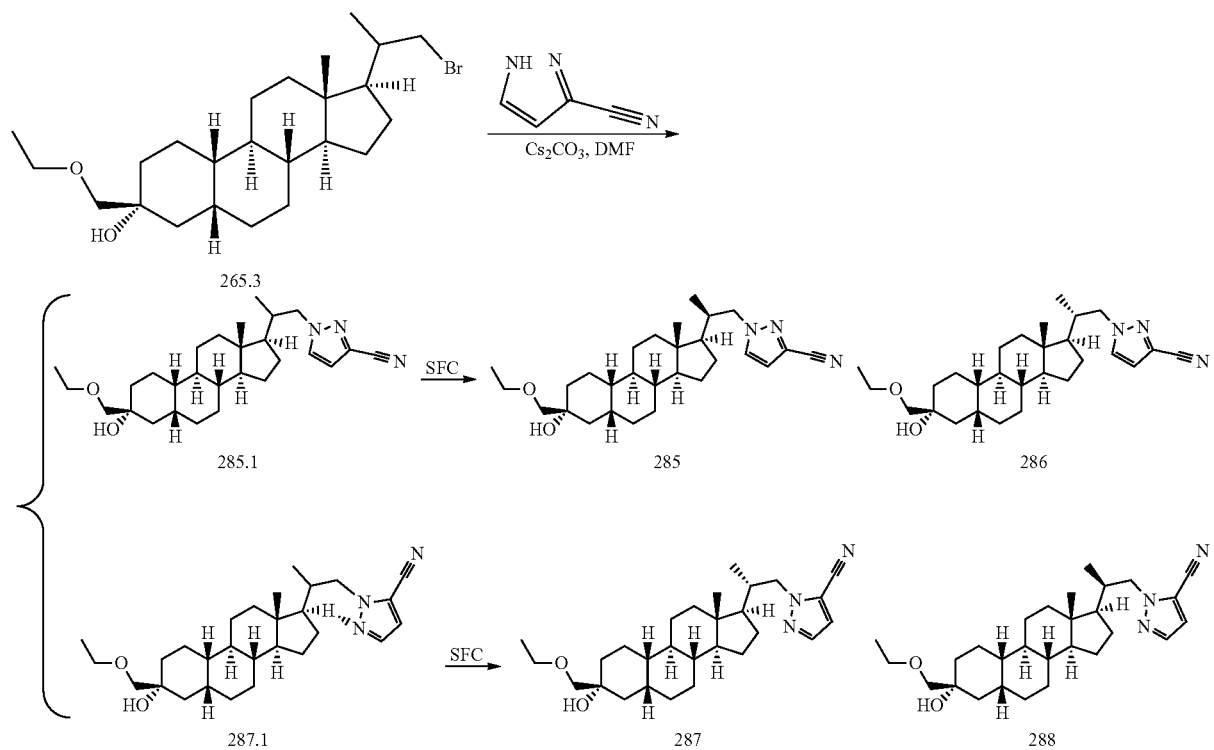

Synthesis of 285.1 & 287.1

To a solution of 265.3 (400 mg, 0.906 mmol) in DMF (10 mL) was added 1H-pyrazole-3-carbonitrile (168 mg, 1.81 mmol) and Cs$_2$CO$_3$ (589 mg, 1.81 mmol) at 25° C. After stirring at 60° C. for 4 h, the mixture was cooled to 25° C., poured into water (20 mL) and extracted with EtOAc (2×50 mL). The combined organic phase was washed with brine (20 mL), dried over anhydrous Na$_2$SO$_4$, filtered and concentrated. The residue was purified by flash column (0~10%~20% of EtOAc in PE) to give 285.1 (50 mg, 12.1%) as a solid and 287.1 (400 mg, 97.3%) as an oil.

285.1: $^1$H NMR (400 MHz, CDCl$_3$) $\delta_H$ 7.60-7.53 (m, 1H), 6.80-6.74 (m, 1H), 4.64-4.56 (m, 0.5H), 4.41-4.34 (m, 0.5H), 3.96-3.85 (m, 1H), 3.57-3.49 (m, 2H), 3.48-3.38 (m, 2H), 2.79-2.60 (m, 1H), 2.25-2.06 (m, 1H), 2.00-1.73 (m, 4H), 1.70-1.57 (m, 4H), 1.51-1.34 (m, 7H), 1.30-1.17 (m, 7H), 1.15-0.98 (m, 5H), 0.85-0.79 (m, 3H), 0.74-0.65 (m, 3H).

287.1: $^1$H NMR (400 MHz, CDCl$_3$) $\delta_H$ 7.43-7.36 (m, 1H), 6.65 (s, 1H), 4.55-4.47 (m, 0.6H), 4.31-4.24 (m, 0.4H), 3.79-3.64 (m, 1H), 3.58-3.49 (m, 2H), 3.48-3.39 (m, 2H), 2.99-2.88 (m, 1H), 2.22-2.01 (m, 2H), 1.97-1.70 (m, 9H), 1.67-1.57 (m, 3H), 1.50-1.34 (m, 4H), 1.27-1.18 (m, 5H), 1.13-1.03 (m, 5H), 0.79 (s, 3H), 0.72-0.65 (m, 3H).

Separation of 285 & 286

285.1 (50 mg, 0.110 mmol) was purified by SFC (Column: YMC CHIRAL Amylose-C 250×30 mm, 10 um; Condition: 0.1% NH$_3$H$_2$O ETOH; Gradient: from 45% to 45% B; Flow rate: 80 mL/min; Column temperature: 35° C.) to afford 285 (Peak 1, Rt=1.315 min, 21.7 mg, 43.4%) and 286 (Peak 2, Rt=2.181 min, 15.4 mg, 30.8%) as solids. The two diastereomers were assigned based on $^1$H NMR of C21-Me (C21-down-Me is at more downfield than C21-up isomer).

285: $^1$H NMR (400 MHz, CDCl$_3$) $\delta_H$ 7.58-7.54 (m, 1H), 6.79-6.76 (m, 1H), 4.64-4.55 (m, 1H), 3.95-3.86 (m, 1H), 3.57-3.49 (m, 2H), 3.47-3.38 (m, 2H), 2.70 (s, 1H), 2.26-2.12 (m, 1H), 1.93-1.70 (m, 5H), 1.69-1.57 (m, 4H), 1.50-1.32 (m, 7H), 1.29-1.18 (m, 6H), 1.15-1.02 (m, 5H), 0.82 (s, 3H), 0.68 (d, J=6.4 Hz, 3H). LC-ELSD/MS purity 99%, MS ESI calcd. for C$_{28}$H$_{42}$N$_3$O [M–H$_2$O+H]$^+$ 436.3 found 436.3. SFC 100% de.

286: $^1$H NMR (400 MHz, CDCl$_3$) $\delta_H$ 7.57 (s, 1H), 6.77 (s, 1H), 4.41-4.34 (m, 1H), 3.96-3.87 (m, 1H), 3.56-3.49 (m, 2H), 3.47-3.38 (m, 2H), 2.69 (s, 1H), 2.17-2.05 (m, 1H), 2.00-1.90 (m, 2H), 1.84-1.75 (m, 3H), 1.66-1.61 (m, 3H), 1.50-1.35 (m, 8H), 1.25-1.18 (m, 6H), 1.14-1.01 (m, 5H), 0.81 (d, J=6.4 Hz, 3H), 0.72 (s, 3H). LC-ELSD/MS purity 99%, MS ESI calcd. for C$_{28}$H$_{42}$N$_3$O [M–H$_2$O+H]$^+$ 436.3 found 436.3. SFC 99% de.

Separation of 287 & 288

287.1 (400 mg, 0.909 mmol) was purified by SFC (Column: DAICEL CHIRALCEL OD-H 250×30 mm, 5 um;

Condition: 0.1% NH$_3$H$_2$O ETOH; Gradient: from 30% to 30% B; Flow rate: 60 mL/min; Column temperature: 35° C.) to afford 288 (Peak 1, Rt=1.449 min, 67 mg, 16.2%) and 287 (Peak 2, Rt=1.639 min, 106.6 mg, 25.7%) as solids. The two diastereomers were assigned based on $^1$H NMR of C21-Me (C21-down-Me is at more downfield than C21-up isomer).

287: $^1$H NMR (400 MHz, CDCl$_3$) $\delta_H$ 7.57 (s, 1H), 6.77 (s, 1H), 4.41-4.34 (m, 1H), 3.96-3.87 (m, 1H), 3.56-3.49 (m, 2H), 3.47-3.38 (m, 2H), 2.69 (s, 1H), 2.17-2.05 (m, 1H), 2.00-1.90 (m, 2H), 1.84-1.75 (m, 3H), 1.66-1.61 (m, 3H), 1.50-1.35 (m, 8H), 1.25-1.18 (m, 6H), 1.14-1.01 (m, 5H), 0.81 (d, J=6.4 Hz, 3H), 0.72 (s, 3H). LC-ELSD/MS purity 99%, MS ESI calcd. for C$_{28}$H$_{42}$N$_3$O [M–H$_2$O+H]$^+$ 436.3 found 436.3. SFC 100% de.

288: $^1$H NMR (400 MHz, CDCl$_3$) $\delta_H$ 7.58-7.54 (m, 1H), 6.79-6.76 (m, 1H), 4.64-4.55 (m, 1H), 3.95-3.86 (m, 1H), 3.57-3.49 (m, 2H), 3.47-3.38 (m, 2H), 2.70 (s, 1H), 2.26-2.12 (m, 1H), 1.93-1.70 (m, 5H), 1.69-1.57 (m, 4H), 1.50-1.32 (m, 7H), 1.29-1.18 (m, 6H), 1.15-1.02 (m, 5H), 0.82 (s, 3H), 0.68 (d, J=6.4 Hz, 3H). LC-ELSD/MS purity 99%, MS ESI calcd. for C$_{28}$H$_{42}$N$_3$O [M–H$_2$O+H]$^+$ 436.3 found 436.3. analytic SFC 100% de.

Example 289 & 290: Synthesis of (3R,5R,8R,9R, 10S,13S,14S,17R)-3-(ethoxymethyl)-13-methyl-17-((S)-1-(5-methyl-2H-tetrazol-2-yl)propan-2-yl)hexadecahydro-1H-cyclopenta[a]phenanthren-3-ol (289) & (3R,5R,8R,9R,10S,13S,14S,17R)-3-(ethoxymethyl)-13-methyl-17-((R)-1-(5-methyl-2H-tetrazol-2-yl)propan-2-yl)hexadecahydro-1H-cyclopenta[a]phenanthren-3-ol (290)

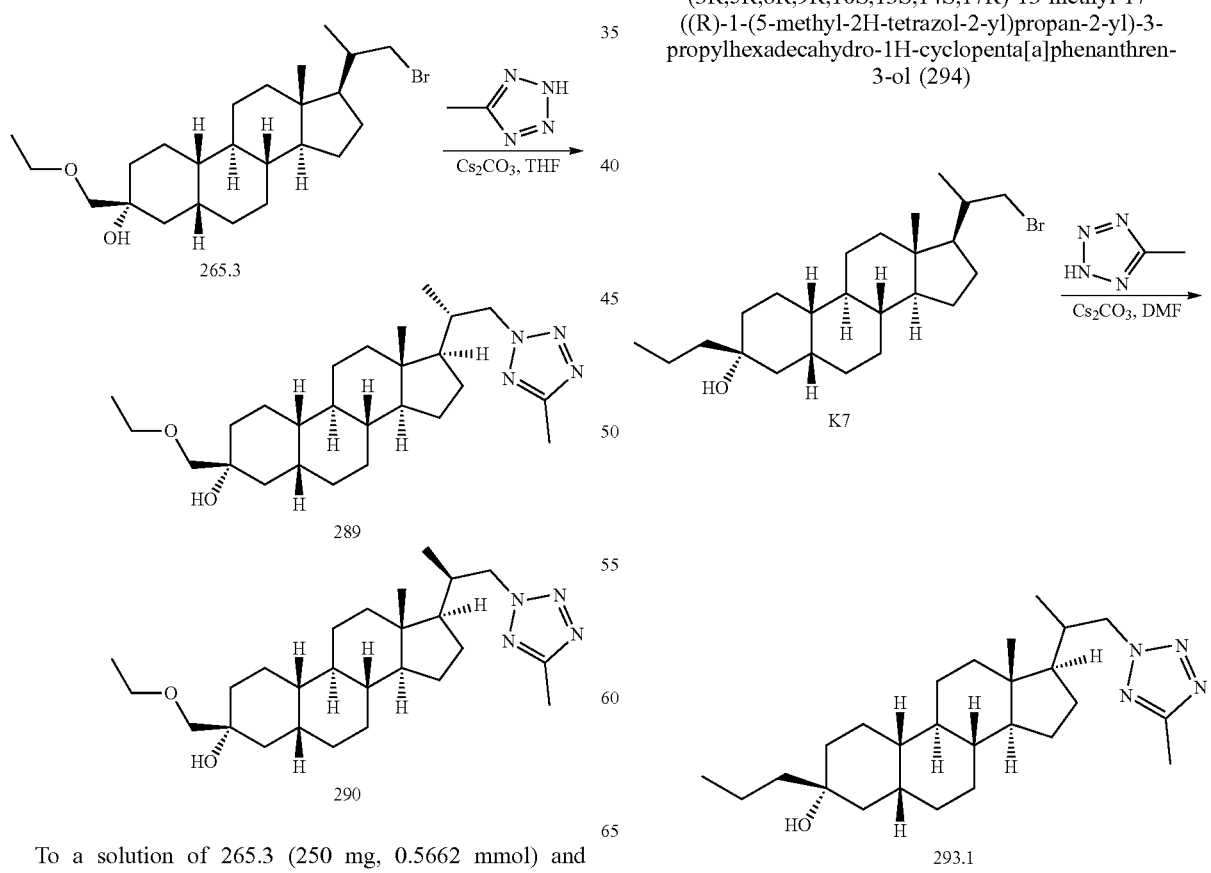

To a solution of 265.3 (250 mg, 0.5662 mmol) and Cs$_2$CO$_3$ (368 mg, 1.13 mmol) in DMF (10 mL) was added 5-methyl-2H-1,2,3,4-tetrazole (71.4 mg, 0.8493 mmol) at 15° C. under N$_2$. After stirring at 80° C. for 16 h, the resulting solution was cooled to 15° C., poured into water (30 mL) and extracted with EtOAc (3×20 mL). The combined organic phase was washed with brine (2×50 mL), dried over anhydrous Na$_2$SO$_4$, filtered and concentrated. The residue was purified by flash column (0~15% of EtOAc in PE) to give mixture of diastereomers (160 mg, 63%), which were separated by SFC (Condition: 0.1% NH$_3$H$_2$O ETOH; Begin B: 40%; End B: 40%; FlowRate (ml/min): 80) to give 290 (Peak 2, 30 mg, 18%, Rt=4.166 min) and 289 (Peak 1, 16.6 mg, 10%, Rt=2.713 min) as solids.

289: $^1$H NMR (400 MHz, CDCl$_3$) $\delta_H$ 4.53 (dd, J=3.6, 13.2 Hz, 1H), 4.28 (dd, J=9.2, 13.2 Hz, 1H), 3.53 (q, J=6.8 Hz, 2H), 3.46-3.38 (m, 2H), 2.69 (s, 1H), 2.54 (s, 3H), 2.14 (td, J=6.4, 10.0 Hz, 1H), 2.05-1.88 (m, 2H), 1.86-1.52 (m, 7H), 1.51-1.29 (m, 6H), 1.28-1.00 (m, 12H), 0.85 (d, J=6.4 Hz, 3H), 0.72 (s, 3H). LC-ELSD/MS purity 97%, MS ESI calcd. for C$_{26}$H$_{43}$N$_4$O [M–H$_2$O+H]$^+$ 427.3, found 427.3.

290: $^1$H NMR (400 MHz, CDCl$_3$) $\delta_H$ 4.75 (dd, J=4.4, 13.2 Hz, 1H), 4.80-4.70 (m, 1H), 4.24 (dd, J=10.8, 13.2 Hz, 1H), 3.53 (q, J=6.8 Hz, 2H), 3.43 (q, J=9.2 Hz, 2H), 2.54 (s, 3H), 2.30-2.15 (m, 1H), 1.95-1.72 (m, 5H), 1.71-1.55 (m, 5H), 1.51-1.17 (m, 12H), 1.16-0.98 (m, 5H), 0.81 (s, 3H), 0.71 (d, J=6.4 Hz, 3H). LC-ELSD/MS purity 99%, MS ESI calcd. for C$_{26}$H$_{43}$N$_4$O [M–H$_2$O+H]$^+$ 427.3, found 427.3.

Examples 293 & 294: Synthesis of (3R,5R,8R,9R, 10S,13S,14S,17R)-13-methyl-17-((S)-1-(5-methyl-2H-tetrazol-2-yl)propan-2-yl)-3-propylhexadecahydro-1H-cyclopenta[a]phenanthren-3-ol (293) & (3R,5R,8R,9R,10S,13S,14S,17R)-13-methyl-17-((R)-1-(5-methyl-2H-tetrazol-2-yl)propan-2-yl)-3-propylhexadecahydro-1H-cyclopenta[a]phenanthren-3-ol (294)

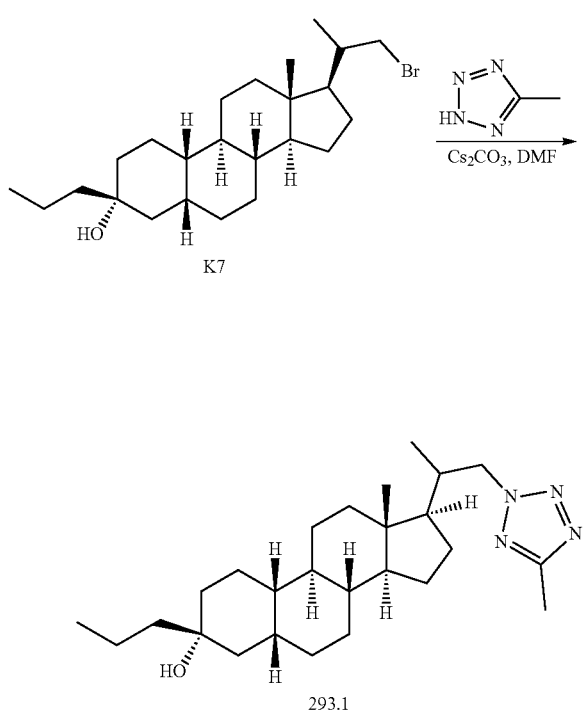

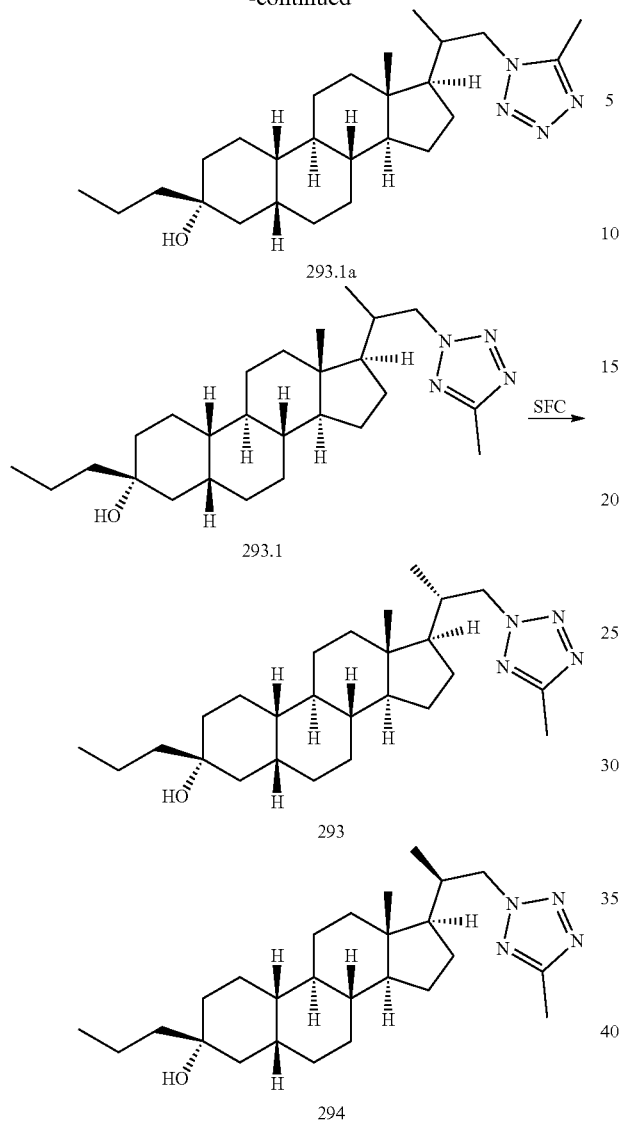

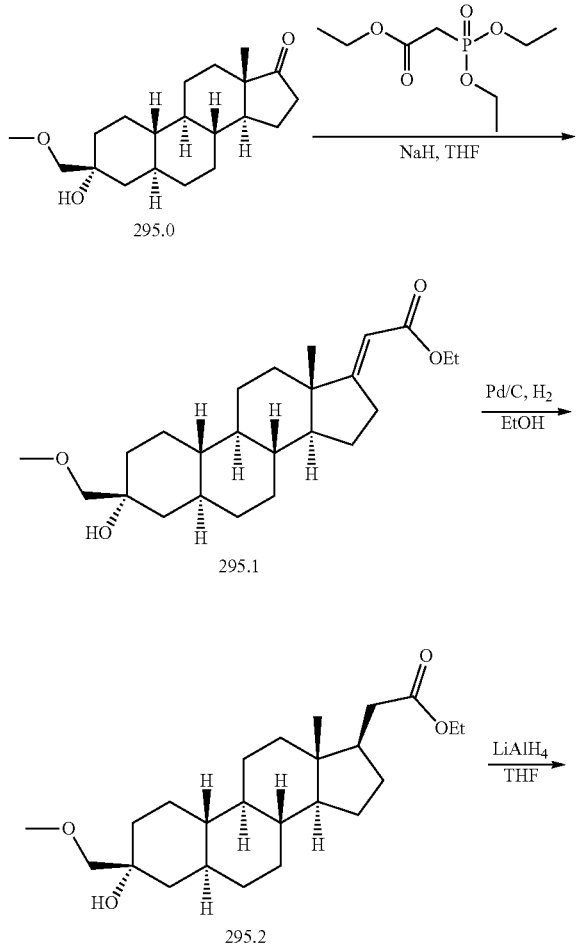

Synthesis of 293.1

To a solution of K7 (185 mg, 0.43 mmol) in DMF (10 mL) were added $Cs_2CO_3$ (283 mg, 0.87 mmol) and 5-methyl-2H-1,2,3,4-tetrazole (73.1 mg, 0.87 mmol). After stirring at 80° C. for 16 h, the mixture was added into saturated $NH_4Cl$ (100 mL) and extracted with EtOAc (3×30 mL). The combined organic layer was washed with water (2×100 mL), brine (100 mL), dried over anhydrous $Na_2SO_4$, filtered and concentrated. The residue was purified by flash column (0~50% of EtOAc in PE) to give 293.1 (100 mg, 54%) and 293.1a (60 mg, 32%) both as oils.

293.1: $^1$H NMR (400 MHz, CDCl$_3$) $\delta_H$ 4.80-4.70 (m, 1H), 4.56-4.44 (m, 1H), 4.35-4.15 (m, 1H), 2.53 (s, 3H), 2.30-2.10 (m, 1H), 1.99-1.59 (m, 9H), 1.52-1.22 (m, 12H), 1.20-0.90 (m, 10H), 0.88-0.80 (m, 3H), 0.75-0.66 (m, 3H).

293.1a: $^1$H NMR (400 MHz, CDCl$_3$) $\delta_H$ 4.60-4.50 (m, 1H), 4.35-4.25 (m, 1H), 3.90-3.75 (m, 1H), 2.55 (d, J=2.4 Hz, 3H), 2.08-1.59 (m, 9H), 1.52-1.22 (m, 13H), 1.20-1.02 (m, 7H), 0.98-0.90 (m, 3H), 0.84-0.78 (m, 3H), 0.76-0.65 (m, 3H).

Synthesis of 293 & 294

The diastereomeric mixture 293.1 (100 mg, 0.23 mmol) was separated by SFC (Column: DAICEL CHIRALCEL OD-H (250 mm*30 mm, 5 μm), Condition: 0.1% $NH_3H_2O$ ETOH, Begin B: 45%, End B: 45%, FlowRate (ml/min): 60) to give 293 (24 mg, 24%, Rt=4.068) and 294 (39 mg, 39%, Rt=5.548) both as solids.

293: $^1$H NMR (400 MHz, CDCl$_3$) $\delta_H$ 4.52 (dd, J=4.0 Hz, 13.2 Hz, 1H), 4.35-4.24 (m, 1H), 2.54 (s, 3H), 2.20-1.90 (m, 3H), 1.89-1.59 (m, 6H), 1.52-1.26 (m, 11H), 1.25-1.02 (m, 10H), 0.98-0.92 (m, 3H), 0.91-0.80 (m, 3H), 0.72 (s, 3H). LC-ELSD/MS purity 99%, MS ESI calcd. for $C_{26}H_{43}N_4$ [M+H−H$_2$O]$^+$ 411.3, found 411.3, SFC: 100% de.

294: $^1$H NMR (400 MHz, CDCl$_3$) $\delta_H$ 4.75 (dd, J=4.4 Hz, 13.2 Hz, 1H), 4.30-4.18 (m, 1H), 2.53 (s, 3H), 2.30-2.18 (m, 1H), 1.95-1.59 (m, 8H), 1.52-1.28 (m, 13H), 1.26-1.02 (m, 8H), 0.98-0.90 (m, 3H), 0.81 (s, 3H), 0.76-0.66 (m, 3H). LC-ELSD/MS purity 99%, MS ESI calcd. for $C_{26}H_{43}N_4$ [M+H−H$_2$O]$^+$ 411.3, found 411.3, SFC: 100% de.

Examples 295-296: Synthesis of (3R,5S,8R,9R,10S,13R,14S,17R)-3-(methoxymethyl)-13-methyl-17-(2-(5-methyl-2H-tetrazol-2-yl)ethyl)hexadecahydro-1H-cyclopenta[a]phenanthren-3-ol (295) & (3R,5S,8R,9R,10S,13R,14S,17R)-3-(methoxymethyl)-13-methyl-17-(2-(5-methyl-1H-tetrazol-1-yl)ethyl)hexadecahydro-1H-cyclopenta[a]phenanthren-3-ol (296)

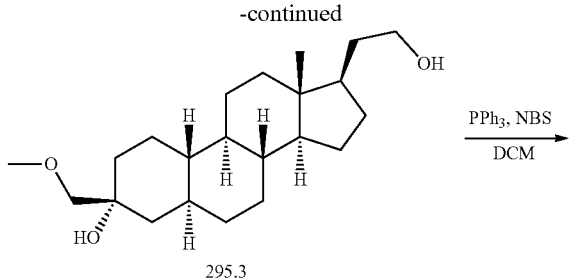

295.3

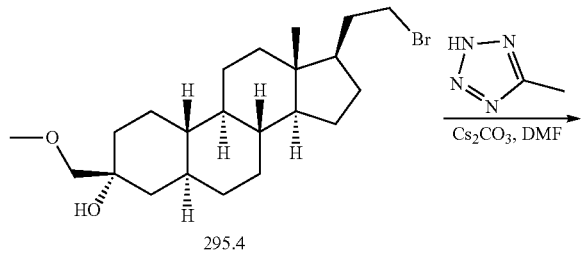

295.4

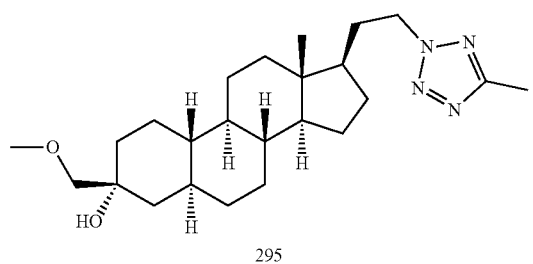

295

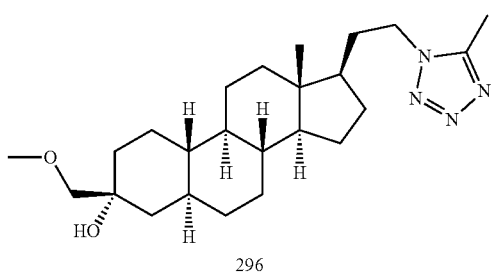

296

Synthesis of 295.1

To a stirred solution of NaH (2.05 g, 51.4 mmol, 60% in mineral oil) in THF (100 mL) and was added ethyl 2-(diethoxyphosphanyl)acetate (12.2 g, 54.5 mmol) at 25° C. After stirring at 40° C. for 30 mins under $N_2$, 295.0 (5 g, 15.6 mmol) was added. After stirring at 65° C. for 16 h, the resulting mixture was cooled to 25° C. and poured into $NH_4Cl$ (100 mL, sat.). The aqueous layer was extracted with EtOAc (3×60 mL). The combined organic phase was washed with brine (2×100 mL), dried over anhydrous $Na_2SO_4$, filtered and concentrated. The residue was purified by flash column (0~10% of EtOAc in PE) to give 295.1 (5 g, 82%) as an oil.

$^1$H NMR (400 MHz, $CDCl_3$) $\delta_H$ 5.52 (s, 1H), 4.20-4.05 (m, 2H), 3.39 (s, 3H), 3.19 (s, 2H), 2.85-2.75 (m, 2H), 2.01 (s, 1H), 1.95-1.59 (m, 8H), 1.52-1.25 (m, 9H), 1.24-0.95 (m, 5H), 0.82 (s, 3H), 0.80-0.65 (m, 2H). LC-ELSD/MS purity 99%, MS ESI calcd. for $C_{24}H_{39}O_4$ [M+H]$^+$ 391.3, found 391.3.

Synthesis of 295.2

A mixture of 295.1 (4.8 g, 12.2 mmol) and wet Pd/C (1 g, 10%) in EtOH (100 mL) was stirred at 25° C. for 16 h under $H_2$. The mixture was filtered, and the mother liquor was concentrated to give 295.2 (4 g, 84%) as an oil.

$^1$H NMR (400 MHz, $CDCl_3$) $\delta_H$ 4.20-4.05 (m, 2H), 3.38 (s, 3H), 3.18 (s, 2H), 2.40-2.30 (m, 1H), 2.15-1.60 (m, 9H), 1.52-1.25 (m, 9H), 1.20-0.90 (m, 9H), 0.80-0.63 (m, 2H), 0.60 (s, 3H).

Synthesis of 295.3

To a solution of 295.2 (3.9 g, 9.9 mmol) in THF (100 mL) was added $LiAlH_4$ (376 mg, 9.9 mmol) at 25° C. After stirring at 25° C. for 30 mins, HCl (50 mL, 1 M) was added to the mixture. The aqueous layer was extracted with EtOAc (3×50 mL). The combined organic layer was washed with $NaHCO_3$ (100 mL, sat.), brine (100 mL), dried over anhydrous $Na_2SO_4$, filtered and concentrated to give 295.3 (3.4 g, 98%) as a solid.

$^1$H NMR (400 MHz, $CDCl_3$) $\delta_H$ 3.75-3.58 (m, 2H), 3.38 (s, 3H), 3.18 (s, 2H), 2.00 (s, 1H), 1.95-1.59 (m, 9H), 1.50-1.20 (m, 7H), 1.19-0.95 (m, 9H), 0.75-0.65 (m, 2H), 0.59 (s, 3H).

LC-ELSD/MS purity 99%, MS ESI calcd. for $C_{22}H_{37}O_2$ [M−$H_2O$+H]$^+$ 333.3, found 333.3.

Synthesis of 295.4

To a solution of 295.3 (800 mg, 2.3 mmol) in DCM (20 mL) were added $PPh_3$ (1.19 g, 4.6 mmol) and NBS (811 mg, 4.6 mmol) at 0° C. After stirring at 25° C. for 16 h, the mixture was poured into water (100 mL) and extracted with DCM (2×50 mL). The combined organic layer was washed with brine (100 mL), dried over anhydrous $Na_2SO_4$, filtered and concentrated. The residue was purified by flash column (0-5% of EtOAc in PE) to give 295.4 (800 mg, 85%) as an oil.

$^1$H NMR (400 MHz, $CDCl_3$) $\delta_H$ 3.49-3.22 (m, 5H), 3.18 (s, 2H), 1.99-1.59 (m, 10H), 1.50-1.20 (m, 7H), 1.19-0.65 (m, 10H), 0.60 (s, 3H).

Synthesis of 295 & 296

To a solution of 295.4 (300 mg, 0.73 mmol) in DMF (10 mL) were added $Cs_2CO_3$ (472 mg, 1.5 mmol) and 5-methyl-1,2,3,4-tetrazole (121 mg, 1.5 mmol). After stirring at 80° C. for 16 h, the mixture was poured into water (100 mL) and extracted with EtOAc (3×50 mL). The combined organic layer was washed with LiCl (2×100 mL, 4% in water), brine (100 mL), dried over anhydrous $Na_2SO_4$, filtered and concentrated. The residue was purified by flash column (0~40% of EtOAc in PE) to give 295 (94 mg, 31%) and 296 (77 mg, 25%) both as solids.

295: $^1$H NMR (400 MHz, $CDCl_3$) $\delta_H$ 4.60-4.40 (m, 2H), 3.38 (s, 3H), 3.18 (s, 2H), 2.53 (s, 3H), 2.20-1.95 (m, 2H), 1.95-1.59 (m, 9H), 1.52-0.90 (m, 14H), 0.78-0.64 (m, 2H), 0.61 (s, 3H). LC-ELSD/MS purity 99%, MS ESI calcd. for $C_{24}H_{41}N_4O_2$ [M+H]$^+$ 417.3, found 417.3.

296: $^1$H NMR (400 MHz, $CDCl_3$) $\delta_H$ 4.22 (t, J=8.0 Hz, 2H), 3.38 (s, 3H), 3.18 (s, 2H), 2.55 (s, 3H), 2.14-1.97 (m, 2H), 1.95-1.59 (m, 9H), 1.52-0.90 (m, 14H), 0.78-0.64 (m, 2H), 0.61 (s, 3H). LC-ELSD/MS purity 99%, MS ESI calcd. for $C_{24}H_{41}N_4O_2$ [M+H]$^+$ 417.3, found 417.3.

Examples 297&298: Synthesis of (3R,5S,8R,9R, 10S,13R,14S,17R)-17-(2-(2H-1,2,3-triazol-2-yl) ethyl)-3-(methoxymethyl)-13-methylhexadecahydro-1H-cyclopenta[a]phenanthren-3-ol (297) & (3R,5S, 8R,9R,10S,13R,14S,17R)-17-(2-(1H-1,2,3-triazol-1-yl)ethyl)-3-(methoxymethyl)-13-methylhexadecahydro-1H-cyclopenta[a] phenanthren-3-ol (298)

Examples 299 & 300: Synthesis of 1-((R)-2-((3S, 5R,8R,9R,10S,13S,14S,17R)-3-hydroxy-3-isobutyl-13-methylhexadecahydro-1H-cyclopenta[a] phenanthren-17-yl)propyl)-1H-pyrazole-4-carbonitrile (299) & 1-((S)-2-((3S,5R,8R,9R,10S, 13S,14S,17R)-3-hydroxy-3-isobutyl-13-methylhexadecahydro-1H-cyclopenta[a] phenanthren-17-yl)propyl)-1H-pyrazole-4-carbonitrile (300)

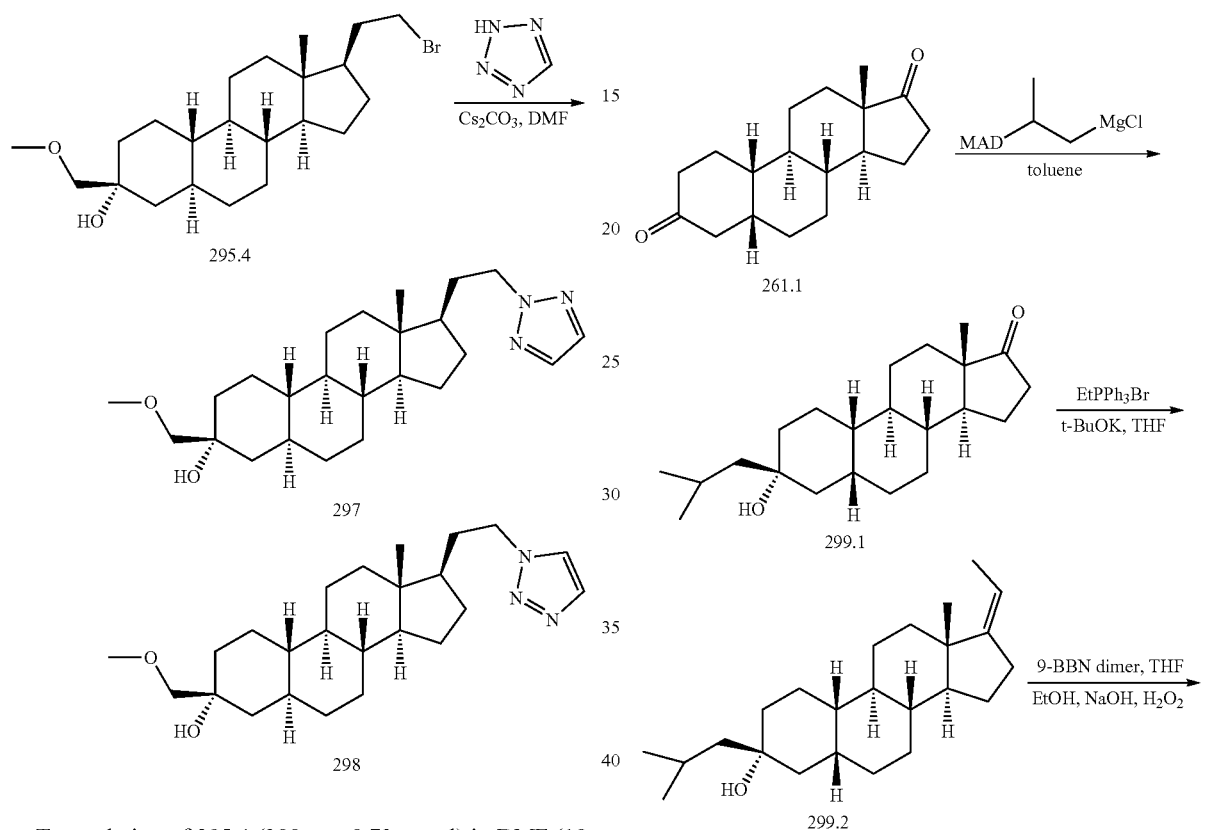

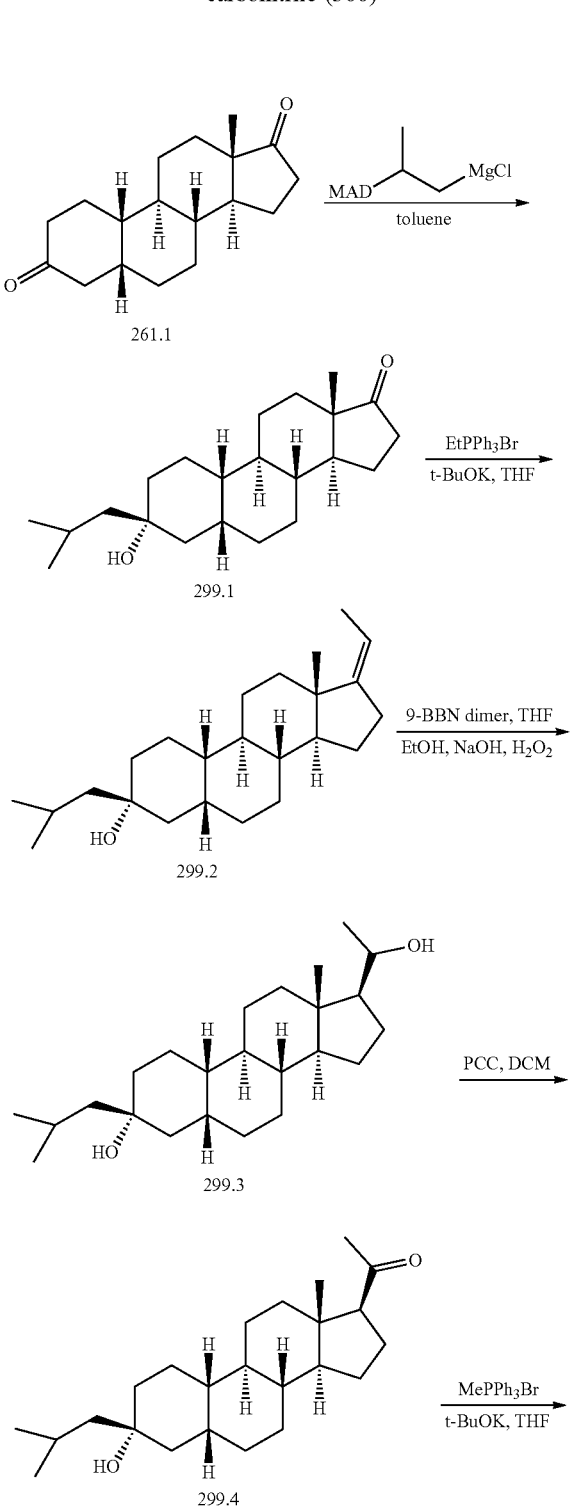

To a solution of 295.4 (300 mg, 0.73 mmol) in DMF (10 mL) were added Cs$_2$CO$_3$ (472 mg, 1.5 mmol) and 2H-1,2,3-triazole (100 mg, 1.5 mmol). After stirring at 80° C. for 16 h, the mixture was added into water (100 mL) and extracted with EtOAc (3×50 mL). The combined organic layer was washed with LiCl (2×100 mL, 4% in water), brine (100 mL), dried over anhydrous Na$_2$SO$_4$, filtered and concentrated. The residue was purified by flash column (0~40% of EtOAc in PE) to give 297 (50 mg, 17%) and 298 (65 mg, 22%) both as solids.

297: $^1$H NMR (400 MHz, CDCl$_3$) $\delta_H$ 7.58 (s, 2H), 4.50-4.31 (m, 2H), 3.38 (s, 3H), 3.18 (s, 2H), 2.15-2.05 (m, 1H), 1.98 (s, 1H), 1.90-1.59 (m, 9H), 1.50-0.85 (m, 14H), 0.75-0.64 (m, 2H), 0.61 (s, 3H). LC-ELSD/MS purity 99%, MS ESI calcd. for C$_{24}$H$_{40}$N$_3$O$_2$ [M+H]$^+$ 402.3, found 402.3.

298: $^1$H NMR (400 MHz, CDCl$_3$) $\delta_H$ 7.70 (s, 1H), 7.53 (s, 1H), 4.48-4.25 (m, 2H), 2.10-1.98 (m, 2H), 1.95-1.59 (m, 9H), 1.50-0.90 (m, 14H), 0.75-0.64 (m, 2H), 0.61 (s, 3H). LC-ELSD/MS purity 99%, MS ESI calcd. for C$_{24}$H$_{40}$N$_3$O$_2$ [M+H]$^+$ 402.3, found 402.3.

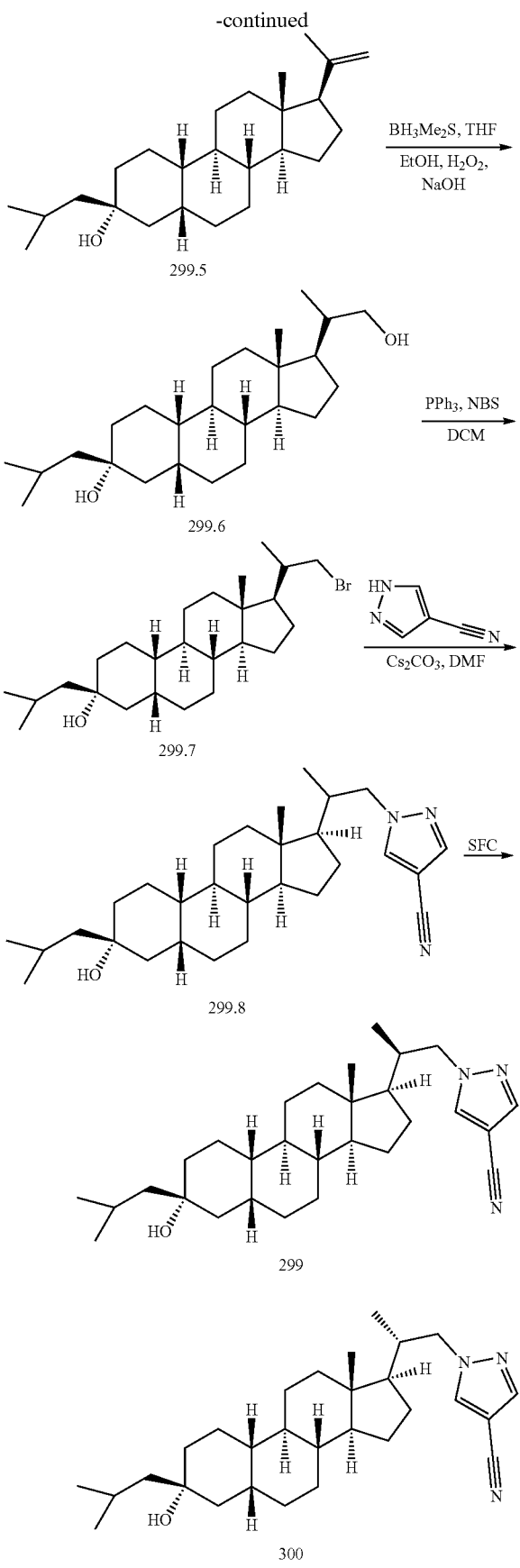

Synthesis of 299.1

To a solution of 2,6-di-tert-butyl-4-methylphenol (48.2 g, 218 mmol) in toluene (300 mL) was added dropwise AlMe₃ (54.4 mL, 109 mmol, 2 M in toluene) at 0° C. After stirring at 30° C. for 30 min, the MAD solution was cooled to −70° C. and a solution of 261.1 (10 g, 36.4 mmol) in DCM (20 mL) was added dropwise at −70° C. After stirring at −70° C. for 1 h under N₂, isobutylmagnesium chloride (54.5 mL, 109 mmol, 2 M in THF) was added dropwise at −70° C. After stirring at −70° C. for 4 h, the reaction mixture was poured into saturated aqueous citric acid (300 mL) at 10° C. and extracted with EtOAc (2×200 mL). The combined organic layer was dried over Na₂SO₄, filtered and concentrated in vacuum. The product was purified by flash column (0-30% of EtOAc in PE) to give product 299.1 (8.2 g, 67%) as oil.

¹H NMR (400 MHz, CDCl₃) δ$_H$ 2.44 (dd, J=8.0, 18.8 Hz, 1H), 2.14-2.01 (m, 1H), 1.98-1.89 (m, 1H), 1.86-1.60 (m, 8H), 1.56-1.34 (m, 10H), 1.20-1.07 (m, 3H), 0.97 (d, J=6.8 Hz, 6H), 0.90-0.82 (m, 6H).

Synthesis of 299.2

To a suspension of Ph₃PEtBr (17.8 g, 48.0 mmol) in anhydrous THF (150 mL) was added t-BuOK (5.37 g, 48.0 mmol) at 25° C. under N₂. After stirring at 50° C. for 30 mins, a solution of 299.1 (8 g, 24.0 mmol) in anhydrous THF (50 mL) was added dropwise. After stirring at 50° C. for 16 h, the mixture was poured into saturated NH₄Cl (500 mL), stirred for 10 mins. and extracted with EtOAc (2×200 mL). The combined organic phase was washed with brine (2×200 mL), filtered and concentrated. The residue was purified by flash column (0-30% of EtOAc in PE) to give 299.2 (6 g, 72.6%) as oil.

¹H NMR (400 MHz, CDCl₃) δ$_H$ 5.19-5.04 (m, 1H), 2.40-2.14 (m, 3H), 1.88-1.59 (m, 10H), 1.52-1.37 (m, 7H), 1.35-1.02 (m, 11H), 0.97 (dd, J=1.6, 6.8 Hz, 6H), 0.87 (s, 3H).

Synthesis of 299.3

To a solution of 299.2 (6.0 g, 17.4 mmol) in THF (70 mL) was added 9-BBN dimer (4.24 g, 34.8 mmol) at 20° C. After stirring at 50° C. for 16 h, the reaction was cooled to 0° C. and sequentially treated with ethanol (19.8 ml, 347 mmol), NaOH (69.4 mL, 5 M, 347 mmol) slowly, and finally H₂O₂ (34.7 mL, 347 mmol, 30%) slowly below 15° C. After stirring at 75° C. for 1 h, the reaction mixture was poured into saturated aqueous Na₂S₂O₃ (500 mL) at 0° C. and stirred at 0° C. for 1 h. The reaction was checked by potassium iodide-starch test paper to confirm excess H₂O₂ was destroyed. The mixture was extracted with EtOAc (2×200 mL). The combined organic layer was washed with brine (2×500 mL), drive over anhydrous Na₂SO₄, filtered and concentrated in vacuum to give the product 299.3 (7.2 g) as a solid.

Synthesis of 299.4

To a solution of 299.3 (7.0 g, 19.3 mmol) in DCM (300 mL) and was added PCC (12.4 g, 57.9 mmol) and silica gel (14 g). After stirring at 25° C. for 2 h, the precipitate was filtered and the filtrate was concentrated under vacuum. The residue was purified by flash column (0-30% of EtOAc in PE) to give product 299.4 (3.5 g, 50.3%) as a solid.

¹H NMR (400 MHz, CDCl₃) δ$_H$ 2.54 (t, J=8.8 Hz, 1H), 2.11 (s, 3H), 2.04-1.96 (m, 1H), 1.87-1.59 (m, 8H), 1.55-1.32 (m, 11H), 1.30-1.02 (m, 7H), 0.97 (dd, J=1.2, 6.4 Hz, 6H), 0.61 (s, 3H).

Synthesis of 299.5

To a mixture of MePPh₃Br (5.9 g, 16.6 mmol) in THF (50 mL) was added t-BuOK (1.9 g, 16.6 mmol) at 15° C. under N₂. After stirring at 50° C. for 30 mins, 299.4 (2 g, 5.5 mmol) was added in portions below 50° C. After stirring at 50° C. for 1 h, the reaction mixture was quenched with 10%

NH₄Cl aqueous (200 mL) at 15° C. and extracted with EtOAc (300 mL). The combined organic phase was concentrated under vacuum to give a solid, which was purified by silica gel chromatography (PE/EtOAc=20/1 to 5/1) to afford 299.5 (1.7 g, 85.8%) as a solid.

¹H NMR (400 MHz, CDCl₃) $\delta_H$ 4.84 (s, 1H), 4.70 (s, 1H), 2.07-2.00 (m, 1H), 1.86-1.65 (m, 12H), 1.52-1.32 (m, 10H), 1.29-1.06 (m, 8H), 0.97 (dd, J=0.8, 6.8 Hz, 6H), 0.57 (s, 3H).

Synthesis of 299.6

To a solution of 299.5 (1 g, 2.78 mmol) in THF (20 mL) was added borane dimethylsulfide (0.84 mL, 10 M 8.34 mmol). After stirring at 45° C. for 1 h, the reaction mixture was sequentially diluted with ethanol (1.91 g, 41.7 mmol) at 15° C., followed by NaOH aqueous (8.3 mL, 5.0 M, 41.7 mmol) at 15° C. and finally H₂O₂ (4.2 mL, 10 M, 41.7 mmol) dropwise at 15° C. After stirring at 78° C. for 1 h, the reaction mixture was quenched with saturated aqueous Na₂S₂O₃ (500 mL) at 0° C. and stirred at 0° C. for 1 h. The reaction was checked by potassium iodide-starch test paper to confirm excess H₂O₂ was destroyed. The mixture was cooled and added to water (1000 mL). The mixture was filtered. The filter cake was washed with water (3×500 mL), dried under vacuum to give 299.6 (1 g) as a solid.

¹H NMR (400 MHz, CDCl₃) $\delta_H$ 3.77-3.60 (m, 1H), 3.49-3.32 (m, 1H), 2.00-1.53 (m, 12H), 1.50-1.27 (m, 12H), 1.25-0.98 (m, 12H), 0.95-0.77 (m, 3H), 0.68 (s, 3H).

Synthesis of 299.7

To a solution of 299.6 (500 mg, 1.32 mmol) in DCM (5 mL) at 0° C. was added PPh₃ (519 mg, 1.98 mmol) and NBS (352 mg, 1.98 mmol). After stirring at 20° C. for 2 h to give a solution, the reaction mixture was added water (50 mL) and extracted with DCM (2×50 mL). The combined organic phase was washed with brine (100 mL), dried over anhydrous Na₂SO₄, filtered and concentrated. The residue was purified by flash column (0~15% of EtOAc in PE) to give 299.7 (400 mg, 68.9%) as a oil.

¹H NMR (400 MHz, CDCl₃) $\delta_H$ 3.66-3.47 (m, 1H), 3.42-3.29 (m, 1H), 1.96-1.72 (m, 6H), 1.69-1.58 (m, 3H), 1.52-1.39 (m, 5H), 1.37-1.16 (m, 10H), 1.15-0.99 (m, 8H), 0.97 (dd, J=1.6, 6.8 Hz, 6H), 0.70-0.67 (m, 3H).

Synthesis of 299.8

To a solution of 299.7 (400 mg, 910 μmol) and 1H-pyrazole-4-carbonitrile (101 mg, 1.09 mmol) in DMF (10 mL) was added Cs₂CO₃ (592 mg, 1.82 mmol) at 20° C. under N₂. After stirring at 80° C. for 16 h, the reaction mixture was quenched with saturated aq. NH₄Cl solution (50 mL) and extracted with EtOAc (2×30 mL). The combined organic phase was washed with brine (50 mL), dried over anhydrous Na₂SO₄, filtered and concentrated. The residue was purified by flash column (0-30% of EtOAc in PE) to give the product 299.8 (260 mg, 63.2%) as a solid.

¹H NMR (400 MHz, CDCl₃) $\delta_H$ 7.80 (s, 1H), 7.75 (s, 1H), 4.49 (dd, J=4.4, 13.2 Hz, 1H), 4.25 (dd, J=4.0, 14.0 Hz, 1H), 3.78-3.59 (m, 2H), 2.17-2.01 (m, 1H), 1.96-1.60 (m, 10H), 1.49-1.27 (m, 11H), 1.22-1.08 (m, 5H), 1.00-0.95 (m, 6H), 0.83-0.78 (m, 3H), 0.73-0.66 (m, 3H).

Synthesis of 299 & 300

299.8 was separated by SFC Column: DAICEL CHIRALCEL OJ-H (250 mm*30 mm, 5 um); condition: 0.1% NH₃H₂O EtOH; Begin B: 25%; End B: 25%) to afford 299 (121.7 mg, 48.5%, Rt=3.217 min) as a solid and 300 (78.2 mg, 31.4%, Rt=2.963 min) as a solid.

299: ¹H NMR (400 MHz, CDCl₃) $\delta_H$ 7.80 (s, 1H), 7.75 (s, 1H), 4.56-4.42 (m, 1H), 3.71-3.59 (m, 1H), 2.17-2.07 (m, 1H), 1.91-1.58 (m, 10H), 1.52-1.31 (m, 12H), 1.26-1.12 (m, 6H), 0.99-0.95 (m, 6H), 0.79 (s, 3H), 0.68 (d, J=6.4 Hz, 3H). LC-ELSD/MS: purity 99%, analytic SFC: 98.1% de; MS ESI calcd. for C₂₉H₄₄N₃ [M−H₂O+H]⁺ 434.3, found 434.3. SFC 100% de.

300: ¹H NMR (400 MHz, CDCl₃) $\delta_H$ 7.79 (s, 1H), 7.75 (s, 1H), 4.26 (dd, J=4.0, 13.6 Hz, 1H), 3.77-3.67 (m, 1H), 2.05-1.90 (m, 3H), 1.83-1.60 (m, 8H), 1.49-1.33 (m, 9H), 1.29-1.06 (m, 9H), 0.98-0.95 (m, 6H), 0.81 (d, J=6.4 Hz, 3H), 0.71 (s, 3H). LC-ELSD/MS: purity 99%, analytic SFC: 100% de; MS ESI calcd. for C₂₉H₄₄N₃ [M−H₂O+H]⁺ 434.3, found 434.3. SFC 100% de.

Examples 301 & 302: Synthesis of 1-((R)-2-((3R, 5R,8S,9S,10S,13S,14S,17R)-10-ethyl-3-hydroxy-13-methyl-3-propylhexadecahydro-1H-cyclopenta[a]phenanthren-17-yl)propyl)-1H-pyrazole-4-carbonitrile (301) & 1-((S)-2-((3R,5R,8S,9S,10S, 13S,14S,17R)-10-ethyl-3-hydroxy-13-methyl-3-propylhexadecahydro-1H-cyclopenta[a]phenanthren-17-yl)propyl)-1H-pyrazole-4-carbonitrile (302)

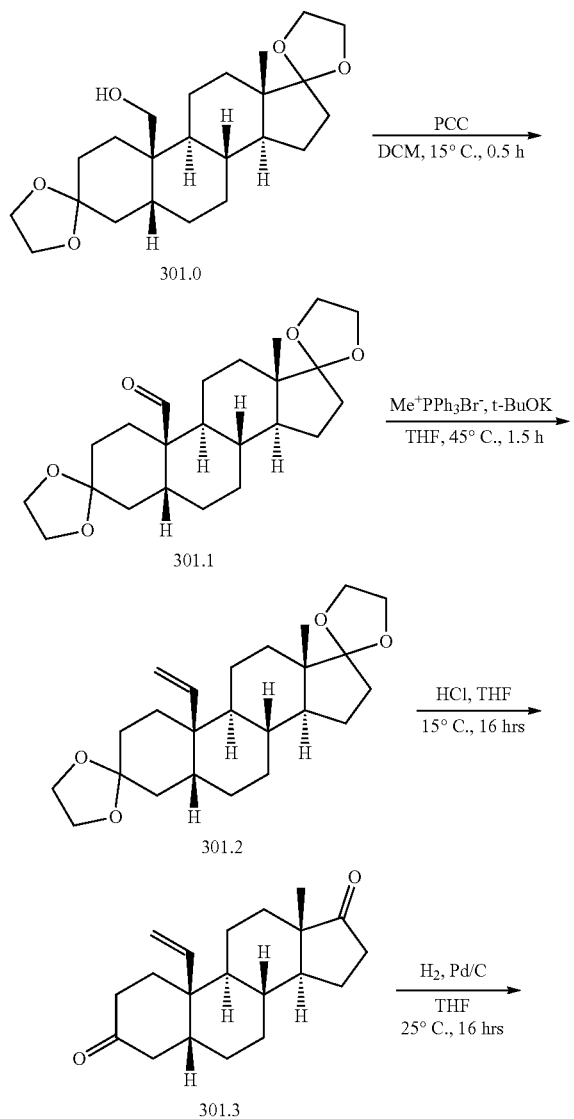

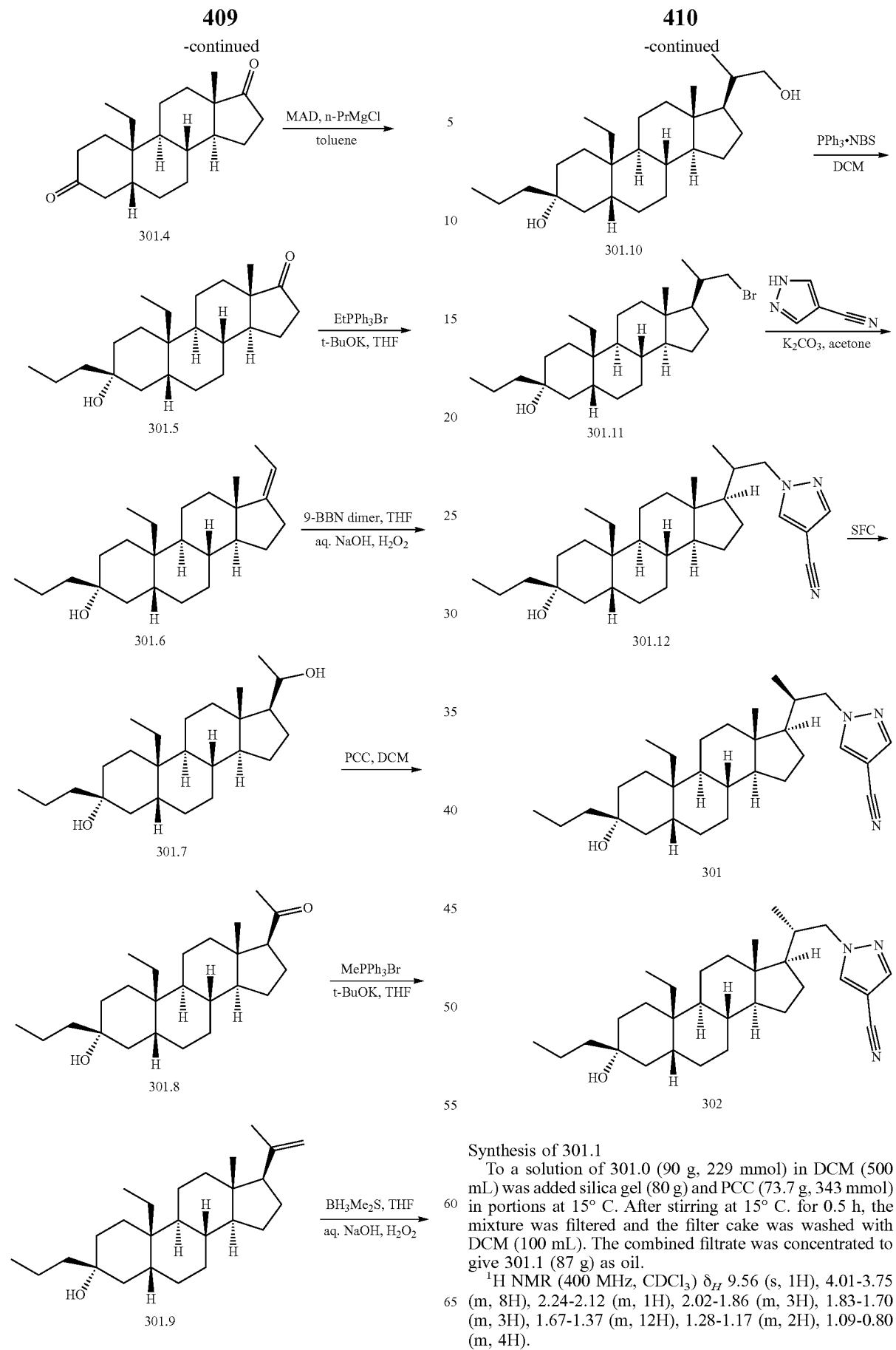
Synthesis of 301.1
To a solution of 301.0 (90 g, 229 mmol) in DCM (500 mL) was added silica gel (80 g) and PCC (73.7 g, 343 mmol) in portions at 15° C. After stirring at 15° C. for 0.5 h, the mixture was filtered and the filter cake was washed with DCM (100 mL). The combined filtrate was concentrated to give 301.1 (87 g) as oil.
$^1$H NMR (400 MHz, CDCl$_3$) $\delta_H$ 9.56 (s, 1H), 4.01-3.75 (m, 8H), 2.24-2.12 (m, 1H), 2.02-1.86 (m, 3H), 1.83-1.70 (m, 3H), 1.67-1.37 (m, 12H), 1.28-1.17 (m, 2H), 1.09-0.80 (m, 4H).

Synthesis of 301.2

To a suspension of MePPh$_3$Br (145 g, 408 mmol) in THF (300 mL) was added t-BuOK (45.7 g, 408 mmol) at 15° C. After stirring at 45° C. for 0.5 h, a solution of 301.1 (80 g, 204 mmol) in THF (200 mL) was added at 45° C. After stirring at 45° C. for 1 h, the mixture was diluted with PE (300 mL) and filtered. The filtrate was concentrated to give 301.2 (200 g) as oil. 301.2 (600 g) was treated with PE (1 L) and stirred for 16 h. The suspension was filtered and the filtrate was concentrated to give 301.2 (252 g) as oil.

$^1$H NMR (400 MHz, CDCl$_3$) $\delta_H$ 6.30 (dd, J=11.2, 17.6 Hz, 1H), 5.15-4.96 (m, 2H), 3.94-3.81 (m, 8H), 2.02-1.73 (m, 7H), 1.58-1.35 (m, 13H), 1.22-1.14 (m, 2H), 0.81 (s, 3H).

Synthesis of 301.3

To a solution of 301.2 (100 g, 257 mmol) in THF (1 L) was added 12 M HCl (107 mL, 1285 mmol). After stirring at 15° C. for 16 h, the reaction mixture was diluted with H$_2$O (800 mL), treated with solid Na$_2$CO$_3$ (200 g) until pH=9, and extracted with EtOAc (3×500 mL). The combined organic layers were dried over Na$_2$SO$_4$, filtered and concentrated to give the product (100 g). The product (200 g) was purified by flash column (0-30% of EtOAc in PE) to give the product 301.3 (80 g, 40.2%) as a solid.

$^1$H NMR (400 MHz, CDCl$_3$) $\delta_H$ 6.31 (dd, J=11.2, 17.6 Hz, 1H), 5.19 (d, J=11.2 Hz, 1H), 5.09 (d, J=17.6 Hz, 1H), 2.71 (t, J=15.2 Hz, 1H), 2.46 (dd, J=8.8, 19.2 Hz, 1H), 2.37-2.21 (m, 2H), 2.17-2.06 (m, 4H), 2.00-1.83 (m, 3H), 1.71-1.51 (m, 7H), 1.40-1.26 (m, 4H), 0.87 (s, 3H).

Synthesis of 301.4

To a mixture of 301.3 (80 g, 266 mmol) in THF (1 L) was added Pd—C(wet, 50%, 10 g) under N$_2$. The suspension was degassed under vacuum and purged with H$_2$ for three times. After hydrogenating at 30 psi of hydrogen at 25° C. for 16 h, the reaction mixture was filtered through a pad of Celite and washed with THF (3×200 mL). The filtrate was concentrated to give the product 301.4 (80 g, 99.5%) as a solid.

$^1$H NMR (400 MHz, CDCl$_3$) $\delta_H$ 2.68 (t, J=13.6 Hz, 1H), 2.46 (dd, J=8.8, 19.2 Hz, 1H), 2.38-2.27 (m, 1H), 2.24-2.16 (m, 1H), 2.13-2.06 (m, 2H), 2.01-1.92 (m, 1H), 1.88-1.69 (m, 6H), 1.65-1.51 (m, 4H), 1.44-1.16 (m, 7H), 0.88 (s, 3H), 0.81 (t, J=7.6 Hz, 3H).

Synthesis of 301.5

To a solution of 2,6-di-tert-butyl-4-methylphenol (40.1 g, 182 mmol) in toluene (100 mL) was added dropwise AlMe$_3$ (45.6 mL, 91.2 mmol, 2M in toluene) at 0° C. The mixture was stirred at 20° C. for 30 mins to give a MAD solution. To the MAD (91.2 mmol in 145 mL toluene) solution was added a solution of 301.4 (9.2 g, 30.4 mmol) in DCM (50 mL) dropwise at −70° C. After stirring at −70° C. for 1 h under N$_2$, n-PrMgCl (45.6 mL, 91.2 mmol, 2 M in THF) was added dropwise at −70° C. The resulting solution was stirred at −70° C. for another 2 h. The reaction mixture was poured into saturated aqueous citric acid (300 mL) below 10° C. and extracted with EtOAc (2×300 mL). The combined organic layer was dried over Na$_2$SO$_4$, filtered and concentrated. The residue was purified by flash column (0-25% of EtOAc in PE) to give 301.5 (6.2 g, 59%) as a solid.

$^1$H NMR (400 MHz, CDCl$_3$) $\delta_H$ 2.51-2.37 (m, 1H), 2.15-2.00 (m, 1H), 1.97-1.61 (m, 8H), 1.54-1.45 (m, 6H), 1.41-1.18 (m, 13H), 0.94 (t, J=7.2 Hz, 3H), 0.85 (s, 3H), 0.81 (t, J=7.6 Hz, 3H).

Synthesis of 301.6

To a suspension of Ph$_3$PEtBr (19.2 g, 51.9 mmol) in anhydrous THF (100 mL) was added t-BuOK (5.81 g, 51.9 mmol) at 25° C. under N$_2$. After stirring at 50° C. for 30 mins, a solution of 301.5 (6 g, 17.3 mmol) in anhydrous THF (50 mL) was added dropwise. After stirring at 50° C. for 16 h, the mixture was poured into saturated NH$_4$Cl (300 mL), stirred for 10 mins. and extracted with EtOAc (2×200 mL). The combined organic phase was washed with brine (2×200 mL), filtered and concentrated. The residue was purified by flash column (0-20% of EtOAc in PE) to give the product 301.6 (5.6 g, 90%) as oil.

$^1$H NMR (400 MHz, CDCl$_3$) $\delta_H$ 5.18-4.95 (m, 1H), 2.41-2.11 (m, 3H), 1.88 (t, J=12.8 Hz, 1H), 1.81-1.71 (m, 1H), 1.67-1.59 (m, 6H), 1.54-1.39 (m, 9H), 1.36-1.25 (m, 7H), 1.20-1.13 (m, 3H), 0.94 (t, J=7.2 Hz, 3H), 0.89-0.83 (m, 5H), 0.79 (t, J=7.6 Hz, 3H).

Synthesis of 301.7

To a solution of 301.6 (5.5 g, 15.3 mmol) in THF (80 mL) under N$_2$ was added 9-BBN dimer (7.46 g, 30.6 mmol). After stirring at 20° C. for 16 h, ethanol (14.0 g, 306 mmol) was added, followed by NaOH aqueous (45.8 mL, 5.0M, 229 mmol) at 0° C. Hydrogen peroxide (25.9 g, 229 mmol, 30% in H$_2$O) was then added dropwise at 0° C. After stirring at 70° C. for 1 h, the mixture was cooled to 15° C., diluted with water (200 mL) and saturated aqueous Na$_2$SO$_3$ (200 mL). The aqueous phase was extracted with EtOAc (2×200 mL). The combined organic phase was washed with brine (200 mL), dried over anhydrous Na$_2$SO$_4$, filtered and concentrated to give the product. The product was triturated from MeCN (30 mL) to give 301.7 (6.5 g) as a solid.

Synthesis of 301.8

To a mixture of 301.7 (6 g, 15.9 mmol) and silica gel (10 g) in DCM (150 mL) was added PCC (8.53 g, 39.7 mmol) in portions. After stirring at 20° C. for 1 h, the reaction mixture was filtered and eluted with DCM (2×50 mL). The filtrate was concentrated. The residue was purified by flash column (0-20% of EtOAc in PE) to give 301.8 (4.2 g, 70%) as a solid.

$^1$H NMR (400 MHz, CDCl$_3$) $\delta_H$ 2.53 (t, J=8.8 Hz, 1H), 2.22-2.09 (m, 4H), 2.05-1.97 (m, 1H), 1.93-1.84 (m, 1H), 1.78-1.59 (m, 6H), 1.53-1.10 (m, 20H), 0.95 (t, J=7.2 Hz, 3H), 0.79 (t, J=7.6 Hz, 3H), 0.59 (s, 3H).

Synthesis of 301.9

To a suspension of MePPh$_3$Br (1.14 g, 3.20 mmol) in anhydrous THF (10 mL) was added t-BuOK (537 mg, 4.80 mmol) at 25° C. under N$_2$. After stirring at 50° C. for 30 mins, a solution of 301.8 (600 mg, 1.60 mmol) in anhydrous THF (5 mL) was added dropwise. After stirring at 50° C. for 16 h, the mixture was poured into saturated NH$_4$Cl (30 mL), stirred for 10 mins. and extracted with EtOAc (2×20 mL). The combined organic phase was washed with brine (2×30 mL), filtered and concentrated. The residue was purified by flash column (0-20% of EtOAc in PE) to 301.9 (580 mg, 97%) as a solid.

$^1$H NMR (400 MHz, CDCl$_3$) $\delta_H$ 4.84 (s, 1H), 4.69 (s, 1H), 2.03-1.80 (m, 3H), 1.76-1.60 (m, 9H), 1.52-1.34 (m, 10H), 1.29-1.13 (m, 11H), 0.94 (t, J=7.2 Hz, 3H), 0.78 (t, J=7.6 Hz, 3H), 0.54 (s, 3H).

Synthesis of 301.10

To a solution of 301.9 (580 mg, 1.55 mmol) in THF (15 mL) was added BH$_3$·Me$_2$S (465 μL, 4.65 mmol, 10M) at 20° under N$_2$. After stirring at 20° C. for 16 h, the resulting mixture was treated with ethanol (1.42 g, 31.0 mmol) at 15° C. and NaOH aqueous (4.64 mL, 5.0 M, 23.2 mmol) at 0° C. Hydrogen peroxide (2.62 g, 23.2 mmol, 30% in H$_2$O) was then added dropwise at 0° C. After stirring at 70° C. for 1 h, the mixture was cooled to 15° C., diluted with water (50 mL) and saturated aqueous Na$_2$SO$_3$ (50 mL). The reaction was then checked by potassium iodide-starch test paper to confirm excess H$_2$O$_2$ was destroyed (did not changed to blue). The aqueous phase was extracted with EtOAc (2×50 mL). The combined organic phase was washed with brine (50 mL), dried over anhydrous Na₂SO₄, filtered and concentrated to give 301.10 (600 mg) as a solid.

¹H NMR (400 MHz, CDCl₃) δ_H 3.77-3.59 (m, 1H), 3.48-3.29 (m, 1H), 2.99 (s, 1H), 1.97-1.72 (m, 4H), 1.64-1.58 (m, 3H), 1.52-1.25 (m, 17H), 1.19-1.01 (m, 9H), 0.97-0.92 (m, 4H), 0.78 (t, J=7.6 Hz, 3H), 0.66 (s, 3H)

Synthesis of 301.11

To a solution of 301.10 (600 mg, 1.53 mmol) in DCM (15 mL) at 0° C. was added PPh₃ (600 mg, 2.29 mmol) and NBS (407 mg, 2.29 mmol). After stirring at 20° C. for 2 h, the reaction mixture was diluted with water (20 mL) and extracted with DCM (2×20 mL). The combined organic phase was washed with brine (20 mL), dried over anhydrous Na₂SO₄, filtered and concentrated. The residue was purified by flash column (0-15% of EtOAc in PE) to give 301.11 (500 mg, 72%) as oil.

¹H NMR (400 MHz, CDCl₃) δ_H 3.66-3.46 (m, 1H), 3.40-3.26 (m, 1H), 1.91-1.73 (m, 4H), 1.64-1.45 (m, 9H), 1.40-1.24 (m, 12H), 1.20-0.98 (m, 9H), 0.94 (t, J=7.2 Hz, 3H), 0.78 (t, J=7.4 Hz, 3H), 0.71-0.61 (m, 3H).

Synthesis of 301.12

To a solution of 301.11 (500 mg, 1.10 mmol) and 1H-pyrazole-4-carbonitrile (112 mg, 1.21 mmol) in DMF (10 mL) was added Cs₂CO₃ (721 mg, 2.20 mmol) at 20° C. under N₂. After stirring at 80° C. for 16 h, the reaction mixture was quenched with saturated aq. NH₄Cl solution (50 mL) and extracted with EtOAc (2×30 mL). The combined organic phase was washed with brine (50 mL), dried over anhydrous Na₂SO₄, filtered and concentrated. The residue was purified by flash column (0-30% of EtOAc in PE) to give the product 301.12 (250 mg, 49%) as a solid.

¹H NMR (400 MHz, CDCl₃) δ_H 7.84-7.69 (m, 2H), 4.54-4.20 (m, 1H), 3.79-3.57 (m, 1H), 2.03-1.58 (m, 8H), 1.53-1.09 (m, 23H), 0.94 (t, J=7.6 Hz, 3H), 0.83-0.75 (m, 6H), 0.72-0.65 (m, 3H).

Separation of 301 & 302

301.12 (250 mg) was separated by SFC (Column: DAICEL CHIRALCEL OJ-H (250 mm*30 mm, 5 um)); condition: 0.1% NH₃H₂O EtOH; Begin B: 25%; End B: 25%) to afford 301 (58.7 mg, 23%, Rt=3.254 min) and 302 (70.3 mg, 28%, Rt=2.949 min) as solids.

301: ¹H NMR (400 MHz, CDCl₃) δ 7.80 (s, 1H), 7.75 (s, 1H), 4.48 (dd, J=4.8, 13.6 Hz, 1H), 3.65 (dd, J=10.8, 13.6 Hz, 1H), 2.16-2.05 (m, 1H), 1.94-1.58 (m, 8H), 1.53-1.31 (m, 12H), 1.30-1.03 (m, 10H), 0.94 (t, J=7.2 Hz, 3H), 0.82-0.75 (m, 6H), 0.67 (d, J=6.8 Hz, 3H). LC-ELSD/MS purity 99%, analytic SFC: 97.72% de. MS ESI calcd. for $C_{30}H_{46}N_3$ [M+H−H₂O]⁺ 448.4, found 448.4. SFC 100% de.

302: ¹H NMR (400 MHz, CDCl₃) δ 7.79 (s, 1H), 7.75 (s, 1H), 4.25 (dd, J=4.0, 13.6 Hz, 1H), 3.72 (dd, J=10.0, 13.6 Hz, 1H), 2.06-1.83 (m, 4H), 1.80-1.70 (m, 1H), 1.69-1.57 (m, 4H), 1.53-1.32 (m, 12H), 1.30-1.11 (m, 10H), 0.94 (t, J=7.2 Hz, 3H), 0.82-0.75 (m, 6H), 0.69 (s, 3H). LC-ELSD/MS purity 99%, analytic SFC: 98.04% de. MS ESI calcd. for $C_{30}H_{46}N_3$ [M+H−H₂O]⁺ 448.4, found 448.4. SFC 100% de.

Examples 303 & 304: Synthesis of 1-((R)-2-((3S,5R,8R,9R,10S,13S,14S,17R)-3-(cyclopropylmethyl)-3-hydroxy-13-methylhexadecahydro-1H-cyclopenta[a]phenanthren-17-yl)propyl)-1H-pyrazole-4-carbonitrile (303) & 1-((S)-2-((3S,5R,8R,9R,10S,13S,14S,17R)-3-(cyclopropylmethyl)-3-hydroxy-13-methylhexadecahydro-1H-cyclopenta[a]phenanthren-17-yl)propyl)-1H-pyrazole-4-carbonitrile (304)

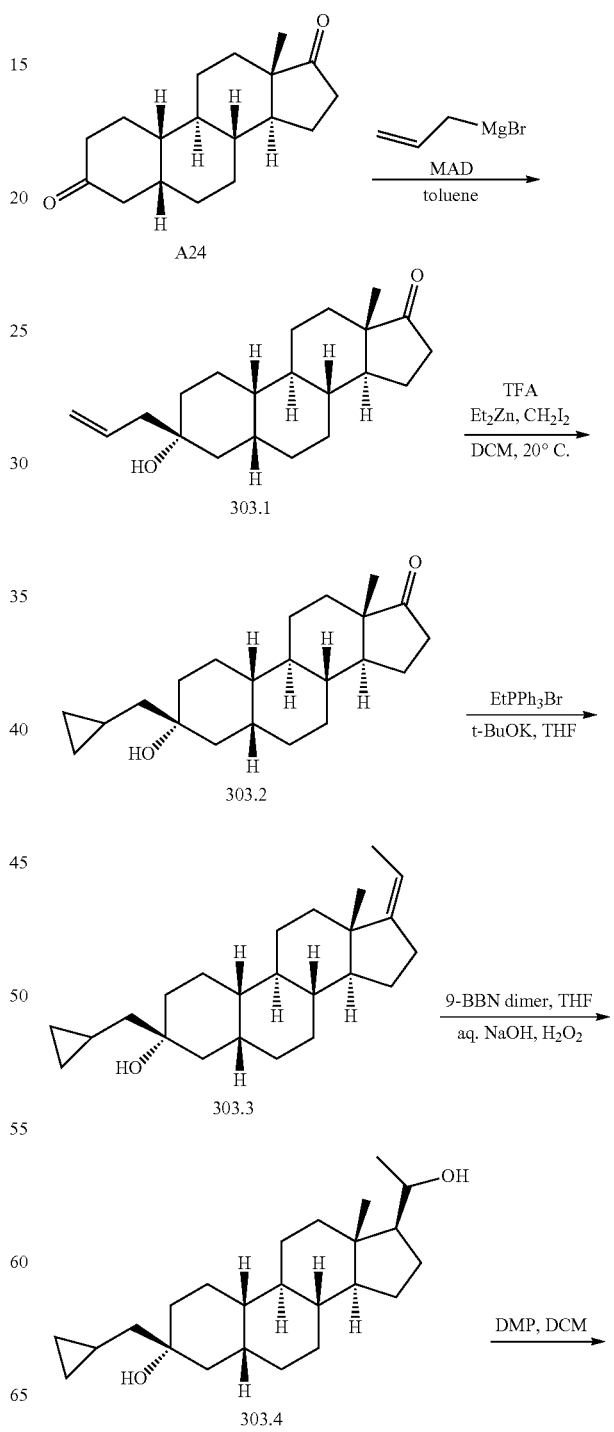

415
-continued

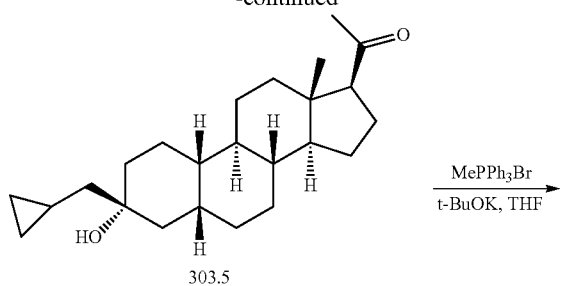
303.5

MePPh₃Br
t-BuOK, THF →

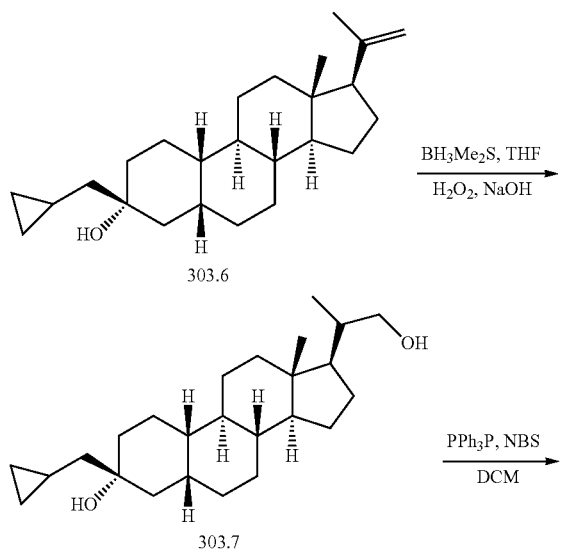
303.6

BH₃Me₂S, THF
H₂O₂, NaOH →

303.7

PPh₃P, NBS
DCM →

303.8

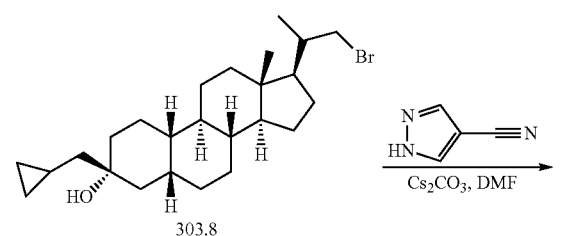

303.9

SFC →

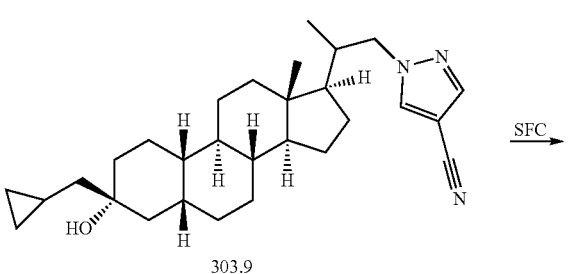
303

416
-continued

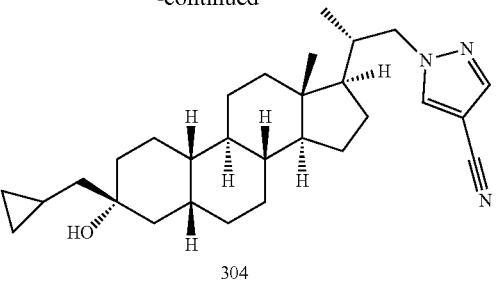
304

Synthesis of 303.1

To a MAD (72.8 mmol in 100 mL toluene) solution was added a solution of A24 (10 g, 36.4 mmol) in DCM (30 mL) dropwise at −70° C. under $N_2$. After stirring at −70° C. for 1 h, bromo(prop-2-en-1-yl)magnesium (36.4 mL, 36.4 mmol, 1M) was added dropwise. After stirring at −70° C. for 3 h, the reaction mixture was poured into 20% aqueous citric acid (200 mL) at 10° C. and extracted with EtOAc (2×200 mL). The combined organic layer was dried over $Na_2SO_4$, filtered and concentrated in vacuum. The residue was purified by a silica gel column (PE/EtOAc=30-40%) to give 303.1 (8.8 g, 77%) as a solid.

$^1$H NMR (400 MHz, CDCl$_3$) $\delta_H$ 5.96-5.80 (m, 1H), 5.25-5.08 (m, 2H), 2.53-2.35 (m, 3H), 2.16-2.04 (m, 1H), 2.00-1.64 (m, 7H), 1.55-1.38 (m, 5H), 1.36-1.24 (m, 5H), 1.22-1.02 (m, 5H), 0.87 (s, 3H).

Synthesis of 303.2

To a solution of Et$_2$Zn (37.8 mL, 1M in hexane) in DCM (120 mL) at 0° C. were added CF$_3$COOH (3.59 g, 31.5 mmol) dropwise over a period of 0.5 h under $N_2$, followed by CH$_2$I$_2$ (10.1 g, 37.8 mmol) dropwise over a period of 15 mins, finally a solution of 303.1 (2 g, 6.31 mmol) in DCM (30 mL). After stirring at 0° C. for 1 h and warming to 20° C. for 12 h, the mixture was combined with another batch (from 2.0 g of 303.1) and added into saturated NH$_4$Cl (200 mL). The aqueous layer was extracted with DCM (3×50 mL). The combined organic layer was washed with brine (200 mL), dried over anhydrous Na$_2$SO$_4$, filtered and concentrated. The residue was purified by flash column (0-30% of EtOAc in PE) to give 303.2 (2.5 g) as a solid.

$^1$H NMR (400 MHz, CDCl$_3$) $\delta_H$ 2.44 (dd, J=8.4, 19.2 Hz, 1H), 2.15-1.90 (m, 2H), 1.88-1.59 (m, 8H), 1.52-1.36 (m, 6H), 1.35-1.00 (m, 9H), 0.87 (s, 3H), 0.80-0.70 (m, 1H), 0.55-0.45 (m, 2H), 0.15-0.05 (m, 2H). LC-ELSD/MS purity 99%, MS ESI calcd. for C$_{22}$H$_{33}$O [M+H−H$_2$O]$^+$ 313.3, found 313.3.

Synthesis of 303.3

To a solution of EtPh$_3$PBr (10.7 g, 29.0 mmol) in THF (25 mL) was added t-BuOK (3.25, 29.0 mmol) at 15° C. under $N_2$. After stirring at 50° C. for 30 minutes, a solution of 303.2 (2.4 g, 7.26 mmol) in THF (25 mL) was added to the reaction below 50° C. After stirring at 50° C. for 3 h, the mixture was added into saturated NH$_4$Cl (150 mL) and extracted with EtOAc (3×50 mL). The combined organic layer was washed with brine (100 mL), dried over anhydrous Na$_2$SO$_4$, filtered and concentrated. The residue was purified by flash column (0-10% of EtOAc in PE) to give 303.3 (2 g, 81%) as oil.

$^1$H NMR (400 MHz, CDCl$_3$) $\delta_H$ 5.15-5.05 (m, 1H), 2.45-2.08 (m, 3H), 1.90-1.65 (m, 9H), 1.60-1.20 (m, 11H), 1.19-1.00 (m, 6H), 0.87 (s, 3H), 0.85-0.74 (m, 1H), 0.55-0.45 (m, 2H), 0.15-0.05 (m, 2H).

Synthesis of 303.4

To a solution of 303.3 (2 g, 5.83 mmol) in THF (30 mL) was added 9-BBN dimer (4.21 g, 17.4 mmol) at 45° C. After stirring for 16 h. the reaction mixture was sequentially treated with EtOH (20 mL) at 15° C., NaOH (23.2 mL, 5M, 116 mmol) at 0° C. and finally by $H_2O_2$ (13.1 g, 30%, 116 mmol). After stirring at 70° C. for 2 h, the reaction was diluted with water (150 mL) and then saturated $Na_2S_2O_3$ (100 mL). The mixture was filtered and the filter cake was washed with water (2×50 mL) and concentrated to give 303.4 (2.05 g, 98%) as a solid.

$^1$H NMR (400 MHz, CDCl$_3$) δ$_H$ 3.78-3.62 (m, 1H), 1.98-1.58 (m, 10H), 1.52-1.25 (m, 11H), 1.23-1.00 (m, 10H), 0.82-0.70 (m, 1H), 0.66 (s, 3H), 0.55-0.45 (m, 2H), 0.15-0.05 (m, 2H).

Synthesis of 303.5

To a solution of 303.4 (2.1 g, 5.82 mmol) in DCM (40 mL) was added DMP (4.91 g, 11.6 mmol) at 30° C. After stirring for 1 h, the mixture was added into saturated NaHCO$_3$ (200 mL) and extracted with DCM (3×50 mL). The combined organic layer was washed with saturated Na$_2$S$_2$O$_3$ (2×200 mL), brine (200 mL), dried over anhydrous Na$_2$SO$_4$, filtered and concentrated to give 303.5 (2 g) as oil. 303.5 (1 g) was purified by flash column (0-30% of EtOAc in PE) to give 303.5 (450 mg, 45%) as a solid.

$^1$H NMR (400 MHz, CDCl$_3$) δ$_H$ 2.54 (t, J=8.8 Hz, 1H), 2.20-2.13 (m, 1H), 2.12 (s, 3H), 2.05-1.96 (m, 1H), 1.90-1.60 (m, 9H), 1.55-1.30 (m, 9H), 1.28-1.00 (m, 6H), 0.80-0.70 (m, 1H), 0.61 (s, 3H), 0.55-0.45 (m, 2H), 0.15-0.05 (m, 2H). LC-ELSD/MS purity 99%, MS ESI calcd. for $C_{24}H_{37}O$ [M+H–H$_2$O]$^+$ 341.3, found 341.3.

Synthesis of 303.6

To a solution of MePh$_3$PBr (2.97 g, 8.34 mmol) in THF (20 mL) was added t-BuOK (934 mg, 8.34 mmol) at 15° C. under N$_2$. After stirring at 50° C. for 30 minutes, a solution of 303.5 (1 g, 2.78 mmol) was added to the reaction mixture below 50° C. After stirring at 50° C. for 1 h, the mixture was added into saturated NH$_4$Cl (100 mL) and extracted with EtOAc (3×30 mL). The combined organic layer was washed with brine (100 mL), dried over anhydrous Na$_2$SO$_4$, filtered and concentrated. The residue was purified by flash column (0-5% of EtOAc in PE) to give 303.6 (600 mg, 61%) as oil.

$^1$H NMR (400 MHz, CDCl$_3$) δ$_H$ 4.84 (s, 1H), 4.70 (s, 1H), 2.10-2.00 (m, 1H), 1.89-1.59 (m, 13H), 1.52-1.26 (m, 9H), 1.25-0.95 (m, 6H), 0.93-0.70 (m, 2H), 0.57 (s, 3H), 0.55-0.45 (m, 2H), 0.15-0.05 (m, 2H).

Synthesis of 303.7

To a solution of 303.6 (600 mg, 1.68 mmol) in THF (10 mL) was added BH$_3$Me$_2$S (0.5 mL, 10M in THF, 5.00 mmol) at 15° C. After stirring at 15° C. for 16 h, the reaction mixture was sequentially treated with EtOH (10 mL) at 15° C., NaOH (6.72 mL. 5M in water, 33.6 mmol) at 0° C. and finally H$_2$O$_2$ (3.80 g, 30%, 33.6 mmol) dropwise. After stirring at 70° C. for 2 h, the mixture was added into water (100 mL), stirred for 30 minutes, and filtered. The filter cake was washed with water (2×50 mL), saturated Na$_2$S$_2$O$_3$ (100 mL) and concentrated to give 303.7 (550 mg, 87%) as a solid.

$^1$H NMR (400 MHz, CDCl$_3$) δ$_H$ 3.80-3.60 (m, 1H), 3.52-3.30 (m, 1H), 2.00-1.59 (m, 11H), 1.52-1.10 (m, 13H), 1.08-0.75 (m, 9H), 0.69 (s, 3H), 0.55-0.45 (m, 2H), 0.15-0.05 (m, 2H).

Synthesis of 303.8

To a solution of 303.7 (500 mg, 1.33 mmol) in DCM (10 mL) was added NBS (473 mg, 2.66 mmol) and Ph$_3$P (697 mg, 2.66 mmol) at 0° C. under N$_2$. After stirring at 15° C. for 2 h, the mixture was concentrated and purified by flash column (0-10% of EtOAc in PE) to give 303.8 (450 mg) as a solid.

$^1$H NMR (400 MHz, CDCl$_3$) δ$_H$ 3.68-3.50 (m, 1H), 3.42-3.30 (m, 1H), 2.00-1.59 (m, 9H), 1.52-1.20 (m, 13H), 1.18-0.95 (m, 6H), 0.93-0.70 (m, 4H), 0.68 (s, 3H), 0.55-0.45 (m, 2H), 0.15-0.05 (m, 2H).

Synthesis of 303.9

To a solution of 303.8 (450 mg) in DMF (10 mL) were added Cs$_2$CO$_3$ (535 mg, 2.04 mmol) and 1H-pyrazole-4-carbonitrile (189 mg, 2.04 mmol) at 15° C. under N$_2$. After stirring at 80° C. for 2 h, the mixture was added into saturated NH$_4$Cl (100 mL) and extracted with EtOAc (3×30 mL). The combined organic layer was washed with water (2×200 mL), brine (200 mL), dried over anhydrous Na$_2$SO$_4$, filtered and concentrated. The residue was purified by flash column (0-30% of EtOAc in PE) to give 303.9 (240 mg, 52%) as oil.

$^1$H NMR (400 MHz, CDCl$_3$) δ$_H$ 7.80 (s, 1H), 7.75 (s, 1H), 4.55-4.22 (m, 1H), 3.75-3.60 (m, 1H), 2.18-2.07 (m, 1H), 1.99-1.59 (m, 10H), 1.52-1.28 (m, 10H), 1.23-1.00 (m, 7H), 0.85-0.65 (m, 7H), 0.55-0.45 (m, 2H), 0.15-0.05 (m, 2H).

Synthesis of 303 & 304

303.9 (240 mg, 0.53) was separated by SFC (Column: DAICEL CHIRALCEL OD (250 mm*30 mm, 10□m), Condition: 0.1% NH$_3$H$_2$O ETOH, Begin B: 45, End B: 45, FlowRate (ml/min): 70) to give 304 (rt=1.627 min, 77.0 mg, 32%) and 303 (rt=2.135 min, 111.0 mg, 46%) both as solids.

303: $^1$H NMR (400 MHz, CDCl$_3$) δ$_H$ 7.80 (s, 1H), 7.75 (s, 1H), 4.55-4.45 (m, 1H), 3.20-3.10 (m, 1H), 2.16-2.04 (m, 1H), 1.95-1.59 (m, 10H), 1.52-1.30 (m, 8H), 1.29-1.00 (m, 9H), 0.79 (s, 3H), 0.78-0.70 (m, 1H), 0.67 (d, J=6.8 Hz, 3H), 0.55-0.45 (m, 2H), 0.15-0.05 (m, 2H).

LC-ELSD/MS purity 99%, analytic SFC: 99.88% de. MS ESI calcd. for $C_{29}H_{42}N_3$ [M+H–H$_2$O]$^+$ 432.3, found 432.3. SFC 100% de.

304: $^1$H NMR (400 MHz, CDCl$_3$) δ$_H$ 7.80 (s, 1H), 7.76 (s, 1H), 4.30-4.20 (m, 1H), 3.80-3.65 (m, 1H), 2.10-1.59 (m, 11H), 1.52-1.26 (m, 9H), 1.24-1.00 (m, 8H), 0.80 (d, J=6.8 Hz, 3H), 0.78-0.72 (m, 1H), 0.71 (s, 3H), 0.55-0.45 (m, 2H), 0.15-0.05 (m, 2H). LC-ELSD/MS purity 99%, analytic SFC: 97.94% de. MS ESI calcd. for $C_{29}H_{42}N_3$ [M+H–H$_2$O]$^+$ 432.3, found 432.3. SFC 100% de.

Examples 305 & 306: Synthesis of 1-((R)-2-((3R, 5R,8R,9S,10S,13S,14S,17R)-3-hydroxy-3,10,13-trimethylhexadecahydro-1H-cyclopenta[a] phenanthren-17-yl)propyl)-1H-pyrazole-4-carbonitrile (305) & 1-((S)-2-((3R,5R,8R,9S,10S, 13S,14S,17R)-3-hydroxy-3,10,13-trimethylhexadecahydro-1H-cyclopenta[a] phenanthren-17-yl)propyl)-1H-pyrazole-4-carbonitrile (306)

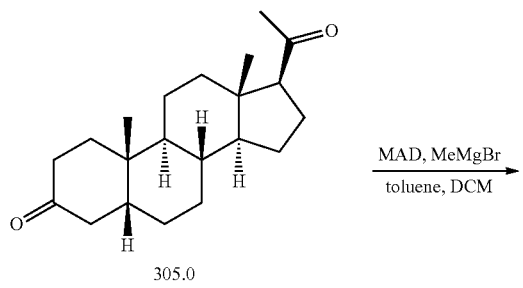

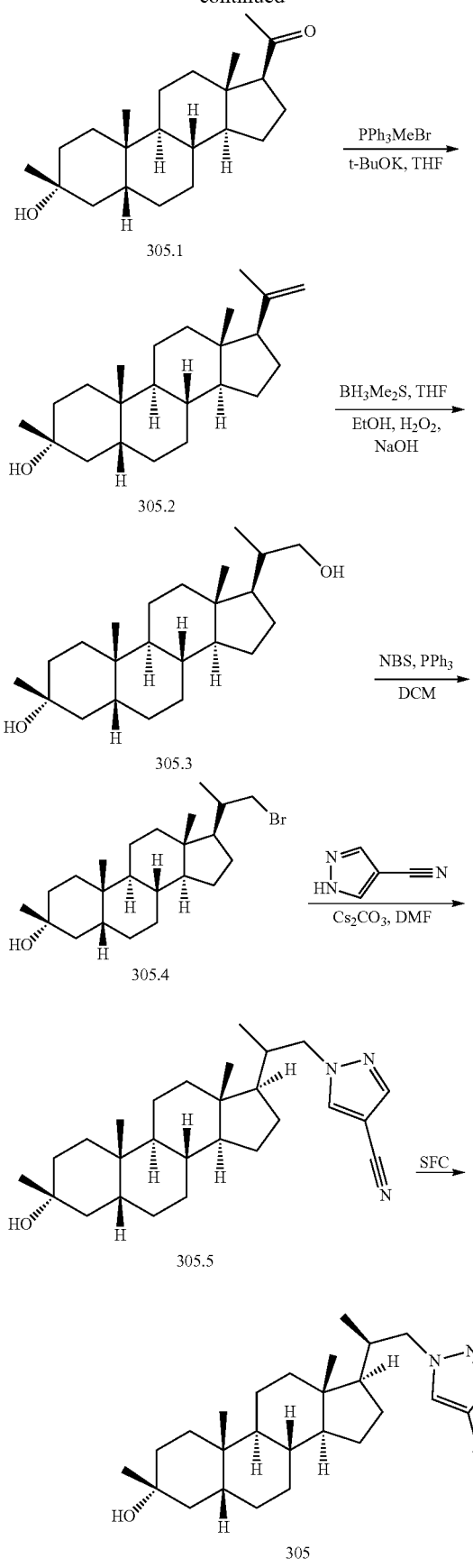

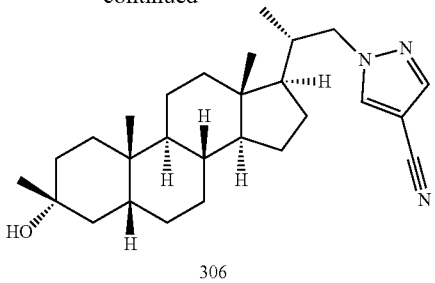

Synthesis of 305.1

To a solution of 2, 6-di-t-butyl-p-cresol (butylated hydroxytoluene) (48.0 g, 218 mmol) in toluene (150 mL) under $N_2$ at 0° C. was added trimethylaluminum (2 M in toluene, 54.5 mL, 109 mmol) dropwise. After stirring at 15° C. for 30 mins, a solution of 305.0 (10 g, 36.4 mmol) in DCM (100 mL) was added dropwise to the above solution under $N_2$ at −78° C. After stirring at −78° C. for 30 mins, MeMgBr (36.3 mL, 109 mmol, 3M in ether) was added dropwise to the reaction mixture. After stirring at −78° C. for 0.5 h, the reaction mixture was poured to ice-cooled aqueous citric acid (400 mL) and extracted with EtOAc (2×400 mL). The combined organic layer was washed with brine (2×500 mL), dried over anhydrous $Na_2SO_4$, filtered and concentrated. The residue was purified by flash column (0~40% of EtAOc in PE) to give 305.1 (4.1 g, 39.0%) as a solid.

$^1$H NMR (400 MHz, $CDCl_3$) $\delta_H$ 2.52 (t, J=9.2 Hz, 1H), 2.20-2.13 (m, 1H), 2.11 (s, 3H), 2.05-1.80 (m, 4H), 1.76-1.40 (m, 12H), 1.26 (s, 3H), 1.25-1.01 (m, 6H), 0.94 (s, 3H), 0.59 (s, 3H).

Synthesis of 305.2

To a solution of $MePh_3PBr$ (13.1 g, 36.9 mmol) in THF (100 mL) was added t-BuOK (4.14 g, 36.9 mmol) at 15° C. After stirring at 50° C. for 0.5 h, a solution of 305.1 (4.1 g, 12.3 mmol) in THF (10 mL) was added into the reaction mixture below 50° C. After stirring at 60° C. for 1 h, the mixture was added into $NH_4Cl$ (100 mL, sat.) and extracted with EtOAc (2×100 mL). The combined organic layer was washed with brine (2×200 mL), dried over anhydrous $Na_2SO_4$, filtered and concentrated. The residue was triturated from $MeOH/H_2O$ (160 mL/160 mL) at 15° C. to give 305.2 (4.0 g, 98.5%) as a solid.

$^1$H NMR (400 MHz, $CDCl_3$) $\delta_H$ 4.84-4.83 (m, 1H), 4.70-4.69 (m, 1H), 2.03-1.76 (m, 5H), 1.75-1.72 (m, 3H), 1.70-1.40 (m, 11H), 1.25 (s, 3H), 1.23-1.00 (m, 8H), 0.94 (s, 3H), 0.54 (s, 3H).

Synthesis of 305.3

To a solution of 305.2 (2 g, 6.05 mmol) in THF (50 mL) was added $BH_3Me_2S$ (3.02 mL, 10M, 30.2 mmol) at 15° C. After stirring for 1 h, the reaction was sequentially treated with EtOH (50 mL) at 15° C., NaOH (24.2 mL, 5M in water, 121 mmol) at 0° C. and finally $H_2O_2$ (12.1 mL, 10 M in water, 121 mmol) at 0° C. After stirring at 70° C. for 2 h, the resulting colorless solution was poured into water (200 ml) and stirred for 1 h at 15° C. The solid was filtered and washed with water (2×50 mL), the mother liquid was quenched with aqueous $Na_2S_2O_3$ (250 mL, sat.). The solid was dissolved in DCM (100 mL) and washed with $Na_2S_2O_3$ (100 ml sat.), brine (100 mL), dried over anhydrous $Na_2SO_4$ and concentrated to give 305.3 (2 g, 95.2%) as a solid.

$^1$H NMR (400 MHz, $CDCl_3$) $\delta_H$ 3.79-3.58 (m, 1H), 3.51-3.31 (m, 1H), 2.01-1.68 (m, 5H), 1.54-1.26 (m, 11H), 1.25 (s, 3H), 1.23-1.06 (m, 8H), 1.04-0.94 (m, 6H), 0.92-0.76 (m, 2H), 0.66 (s, 3H)

Synthesis of 305.4

To a solution of 305.3 (800 mg, 2.29 mol) in DCM (10 mL) at 0° C. were added PPh₃ (899 mg, 3.43 mmol) and NBS (610 mg, 3.43 mmol). After stirring at 15° C. for 2 h, water (20 mL) was added to the resulting solution and extracted with DCM (2×20 mL). The combined organic phase was washed with brine (2×50 mL), dried over anhydrous Na₂SO₄, filtered and concentrated. The residue was purified by flash column (0~10% of EtOAc in PE) to give 305.4 (860 mg, 91.2%) as an oil.

¹H NMR (400 MHz, CDCl₃) $\delta_H$ 3.70-3.40 (m, 1H), 3.35-3.25 (m, 1H), 2.01-1.60 (m, 13H), 1.59-1.40 (m, 4H), 1.39-1.25 (m, 3H), 1.24-1.15 (m, 4H), 1.09-0.95 (m, 6H), 0.94 (s, 3H), 0.90-0.68 (m, 1H), 0.67-0.64 (m, 3H).

Synthesis of 305.5

To a solution of 305.4 (860 mg, 2.09 mmol) in DMF (10 mL) were added Cs₂CO₃ (1.36 g, 4.18 mmol) and 1H-pyrazole-4-carbonitrile (389 mg, 4.18 mmol). After stirring at 80° C. for 20 h, the mixture was poured into NH₄Cl (50 mL, sat.), stirred for 10 mins and filtered. The filter cake was washed with water (2×30 ml) to give 305.5 (810 mg, 91.5%) as a solid.

¹H NMR (400 MHz, CDCl₃) $\delta_H$ 7.79 (s, 1H), 7.75 (s, 1H), 4.50-4.20 (m, 1H), 3.75-3.60 (m, 1H), 2.2-2.1 (m, 1H), 1.95-1.60 (m, 12H), 1.40-1.35 (m, 2H), 1.30-1.25 (m, 3H), 1.20-1.01 (m, 10H), 0.98-0.80 (m, 3H), 0.79-0.70 (m, 3H), 0.69-0.65 (m, 3H).

Synthesis of 305 & 306

305.5 (810 mg, 1.91 mmol) was separated by SFC (Column: DAICEL CHIRALPAK AD-H (250 mm*30 mm, 5 um); Condition: 0.1% NH₃H₂O IPA; Begin B: 30%; End B: 30%) to give 305 (348.7 mg, 43.0%) and 306 (203.8 mg, 25.0%) both as solids.

305: ¹H NMR (400 MHz, CDCl₃) $\delta_H$ 7.80 (s, 1H), 7.75 (s, 1H), 4.48 (dd, J=3.6 Hz, 13.2 Hz, 1H), 3.66 (dd, J=10.8 Hz, 1.6 Hz, 1H), 2.20-1.57 (m, 7H), 1.53-1.27 (m, 9H), 1.26 (s, 3H), 1.25-0.96 (m, 9H), 0.95 (s, 3H), 0.77 (s, 3H), 0.67 (d, J=6.4 Hz, 3H). LC-ELSD/MS: purity 99%, analytic SFC: 99% de; MS ESI calcd. for C₂₇H₄₁N₃O [M−H₂O+H]⁺ 406.3, found 406.3.

306: ¹H NMR (400 MHz, CDCl₃) $\delta_H$ 7.80 (s, 1H), 7.75 (s, 1H), 4.25 (dd, J=3.6 Hz, 13.2 Hz, 1H), 3.71 (dd, J=9.2 Hz, 13.2 Hz, 1H), 2.2-1.60 (m, 7H), 1.5-1.3 (m, 9H), 1.26 (s, 3H), 1.25-0.95 (m, 9H), 0.94 (s, 3H), 0.81 (d, J=6.4 Hz, 3H), 0.69 (s, 3H). LC-ELSD/MS: purity 98%, analytic SFC: 99% de; MS ESI calcd. for C₂₇H₄₁N₃O [M−H₂O+H]⁺ 406.3, found 406.3. MS ESI calcd. for C₂₇H₄₁N₃O [M+H]⁺ 424.3, found 424.3.

Examples 307 & 308: Synthesis of 1-((R)-2-((3R,5R,8R,9S,10S,13S,14S,17R)-3-hydroxy-10,13-dimethyl-3-propylhexadecahydro-1H-cyclopenta[a]phenanthren-17-yl)propyl)-1H-pyrazole-4-carbonitrile (307) & 1-((S)-2-((3R,5R,8R,9S,10S,13S,14S,17R)-3-hydroxy-10,13-dimethyl-3-propylhexadecahydro-1H-cyclopenta[a]phenanthren-17-yl)propyl)-1H-pyrazole-4-carbonitrile (308)

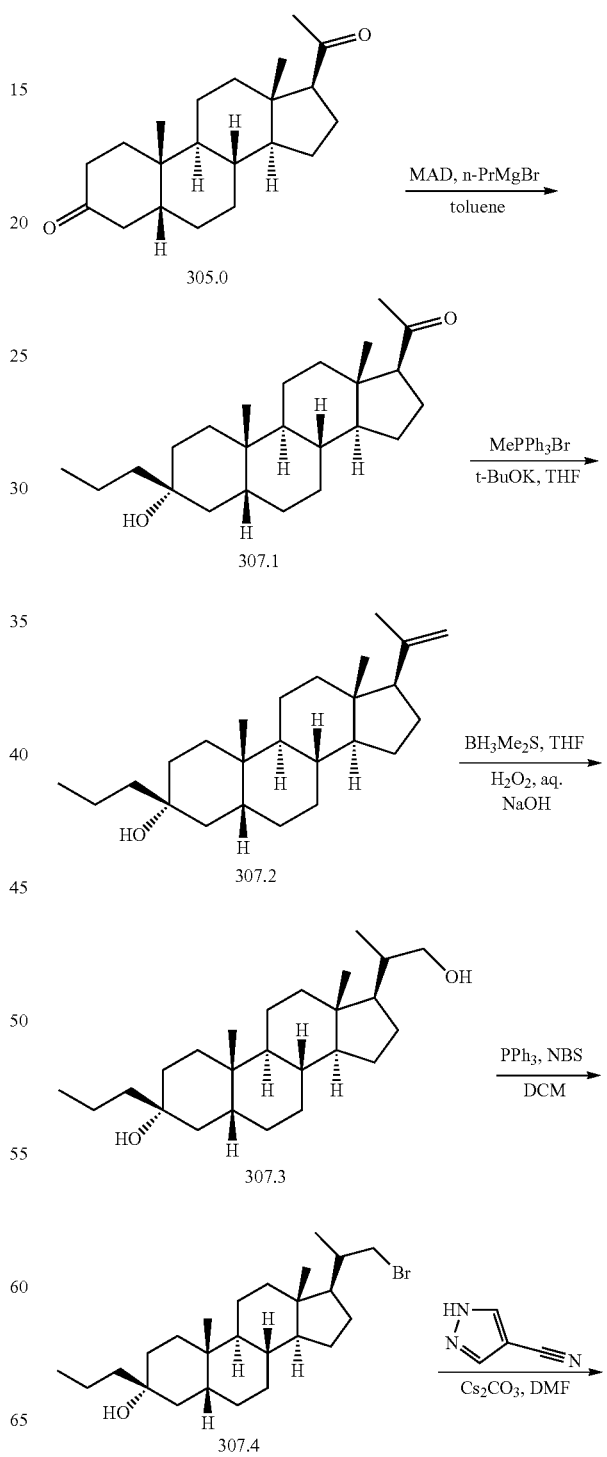

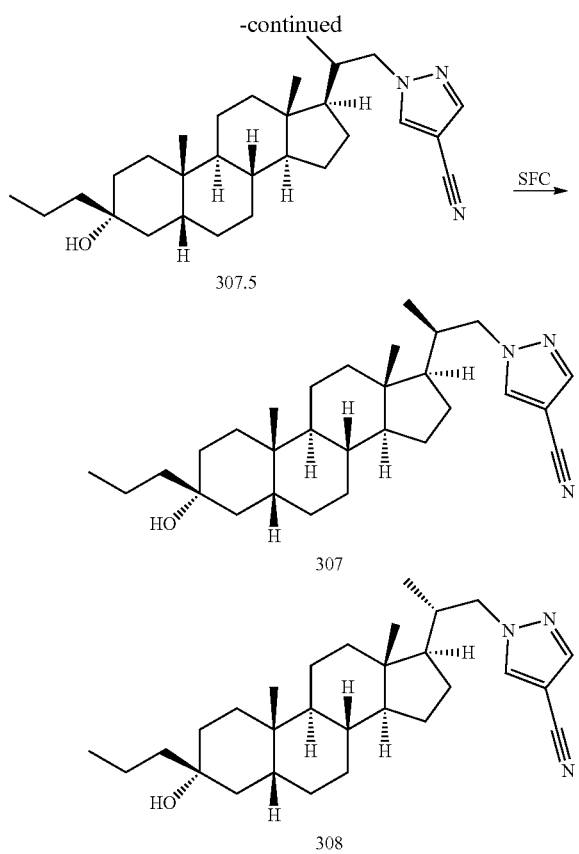

Synthesis of 307.1

To a solution of 2,6-di-t-butyl-p-cresol (butylated hydroxytoluene) (33.5 g, 152 mmol) in toluene (100 mL) under nitrogen at 0° C. was added trimethylaluminum (2 M in toluene, 38 mL, 76 mmol) dropwise. After stirring at 20° C. for 1 h, a solution of 305.0 (8.0 g, 25.2 mmol) in toluene (50 mL) was added to the above solution dropwise under $N_2$ at −70° C. After stirring at −70° C. for 1 h, to the resulting mixture was added n-PrMgCl (37.8 mL, 75.6 mmol, 2M in THF) dropwise. After stirring at −70° C. for 0.5 h, the reaction mixture was poured to ice-cooled aqueous citric acid (500 mL) and extracted with EtOAc (2×500 mL). The combined organic layer was washed with brine (2×300 mL), dried over anhydrous $Na_2SO_4$, filtered and concentrated. The residue was combined with another solution of the product to be purified by flash column (0~25% of EtOAc in PE) to give 307.1 (5.9 g, 52%) as a solid.

$^1$H NMR (400 MHz, CDCl$_3$) δ$_H$ 2.53 (t, J=8.8 Hz, 1H), 2.19-2.13 (m, 1H), 2.11 (s, 3H), 2.06-1.64 (m, 6H), 1.54-1.36 (m, 11H), 1.32-1.00 (m, 9H), 0.96-0.91 (m, 6H), 0.59 (s, 3H).

Synthesis of 307.2

To a solution of PPh$_3$MeBr (17.4 g, 48.9 mmol) in THF (100 mL) was added t-BuOK (5.48 g, 48.9 mmol). After stirring at 50° C. for 0.5 h, a solution of 307.1 (5.9 g, 16.3 mmol) in THF (50 mL) was added at 50° C. After stirring at 50° C. for 12 h, the mixture was poured into NH$_4$Cl (200 mL, sat.) and extracted with EtOAc (2×100 mL). The combined organic phase was washed with brine (2×100 mL), dried over anhydrous Na$_2$SO$_4$, filtered and concentrated. The residue was purified by flash column (0~5% of EtOAc in PE) to give 307.2 (5.2 g, 89%) as a solid.

$^1$H NMR (400 MHz, CDCl$_3$) δ$_H$ 4.84 (s, 1H), 4.69 (s, 1H), 2.06-1.98 (m, 1H), 1.92-1.80 (m, 3H), 1.75 (s, 3H), 1.73-1.46 (m, 8H), 1.45-0.97 (m, 16H), 0.96-0.90 (m, 6H), 0.54 (s, 3H).

Synthesis of 307.3

To a solution of 307.2 (2.0 g, 5.57 mmol) in THF (20 mL) was added BH$_3$·Me$_2$S (1.67 mL, 10 M, 16.7 mmol) at 0° C. After stirring at 20° C. for 16 h, the reaction mixture was sequentially treated with EtOH (5 mL) at 20° C., aq. NaOH (16.7 mL, 5 M, 83.5 mmol) and finally by H$_2$O$_2$ (8.35 mL, 83.5 mmol, 10M). After stirring at 70° C. for 1 h, the reaction mixture was cooled to 20° C., poured into Na$_2$S$_2$O$_3$ (100 mL, sat.) and extracted with EtOAc (2×100 mL). The combined organic layer was washed with saturated Na$_2$S$_2$O$_3$ (100 mL), brine (100 mL), dried over anhydrous Na$_2$SO$_4$, filtered and concentrated to give 307.3 (2.1 g) as a solid.

$^1$H NMR (400 MHz, CDCl$_3$) δ$_H$ 3.73 (dd, J=3.6, 10.8 Hz, 0.6H), 3.64 (dd, J=3.3, 10.4 Hz, 0.4H), 3.45 (dd, J=7.2, 10.8 Hz, 0.6H), 3.35 (dd, J=7.2, 10.4 Hz, 0.4H), 1.98-1.54 (m, 8H), 1.45-1.18 (m, 17H), 1.17-1.01 (m, 6H), 0.97-0.91 (m, 8H), 0.66 (s, 3H).

Synthesis of 307.4

To a solution of 307.3 (500 mg, 1.32 mmol) in DCM (20 mL) at 0° C. was added PPh$_3$ (519 mg, 1.98 mmol) and NBS (352 mg, 1.98 mmol). After stirring at 20° C. for 2 h, the reaction mixture was diluted with water (50 mL) and extracted with DCM (2×100 mL). The combined organic phase was washed with brine (100 mL), dried over anhydrous Na$_2$SO$_4$, filtered and concentrated. The residue was purified by flash column (0~20% of EtOAc in PE) to give 307.4 (500 mg, 86.2%) as a solid.

$^1$H NMR (400 MHz, CDCl$_3$) δ$_H$ 3.62 (dd, J=3.2, 10.0 Hz, 0.6H), 3.49 (dd, J=3.2, 10.0 Hz, 0.4H), 3.40-3.30 (m, 1H), 1.98-1.50 (m, 10H), 1.50-1.15 (m, 15H), 1.15-0.95 (m, 7H), 0.93-0.85 (m, 6H), 0.66 (s, 3H).

Synthesis of 307 & 308

To a solution of 307.4 (500 mg, 1.13 mmol) in DMF (20 mL) were added Cs$_2$CO$_3$ (736 mg, 2.26 mmol) and 1H-pyrazole-4-carbonitrile (210 mg, 2.26 mmol). After stirring at 80° C. for 16 h, the mixture was added to saturated NH$_4$Cl (100 mL) and extracted with EtOAc (3×100 mL). The combined organic layer was washed with LiCl (100 mL, 3% in water), brine (2×100 mL), dried over anhydrous Na$_2$SO$_4$, filtered and concentrated. The residue was purified by flash column (0~30% of EtOAc in PE) to afford to give 307.5 as a solid. The residue was purified by SFC (Column: DAICEL CHIRALPAK AD (250 mm*30 mm, 10 um); Condition: 0.1% NH$_3$H$_2$O IPA; Begin B: 35%; End B: 35%; Flow Rate (ml/min): 60) to give 307 (181.7 mg, 35.2%) and 308 (141.8 mg, 27.6%) both as solids.

307: $^1$H NMR (400 MHz, CDCl$_3$) δ$_H$ 7.80 (s, 1H), 7.75 (s, 1H), 4.55-4.41 (m, 1H), 3.73-3.57 (m, 1H), 2.17-2.04 (m, 1H), 1.93-1.78 (m, 4H), 1.71-1.58 (m, 2H), 1.53-1.29 (m, 13H), 1.29-0.97 (m, 9H), 0.97-0.91 (m, 6H), 0.77 (s, 3H), 0.67 (d, J=6.4 Hz, 3H). LC-ELSD/MS: purity 99%, analytic SFC: 100% de; MS ESI calcd. for C$_{29}$H$_{44}$N$_3$ [M−H$_2$O+H]$^+$ 434.3, found 434.3.

308: $^1$H NMR (400 MHz, CDCl$_3$) δ$_H$ 7.80 (s, 1H), 7.75 (s, 1H), 4.29-4.21 (m 1H), 3.76-3.67 (m, 1H), 2.06-1.64 (m, 7H), 1.51-1.28 (m, 13H), 1.27-0.96 (m, 9H), 0.96-0.90 (m, 6H), 0.80 (d, J=6.8 Hz, 3H), 0.69 (s, 3H). LC-ELSD/MS:

purity 99%, analytic SFC: 100% de; MS ESI calcd. for $C_{29}H_{44}N_3$ $[M-H_2O+H]^+$ 434.3, found 434.3.

Examples 309 & 310: Synthesis of 1-((R)-2-((3R,5R,8S,9S,10S,11S,13S,14S,17R)-3,11-dihydroxy-10,13-dimethyl-3-propylhexadecahydro-1H-cyclopenta[a]phenanthren-17-yl)propyl)-1H-pyrazole-4-carbonitrile (309) & 1-((S)-2-((3R,5R,8S,9S,10S,11S,13S,14S,17R)-3,11-dihydroxy-10,13-dimethyl-3-propylhexadecahydro-1H-cyclopenta[a]phenanthren-17-yl)propyl)-1H-pyrazole-4-carbonitrile (310)

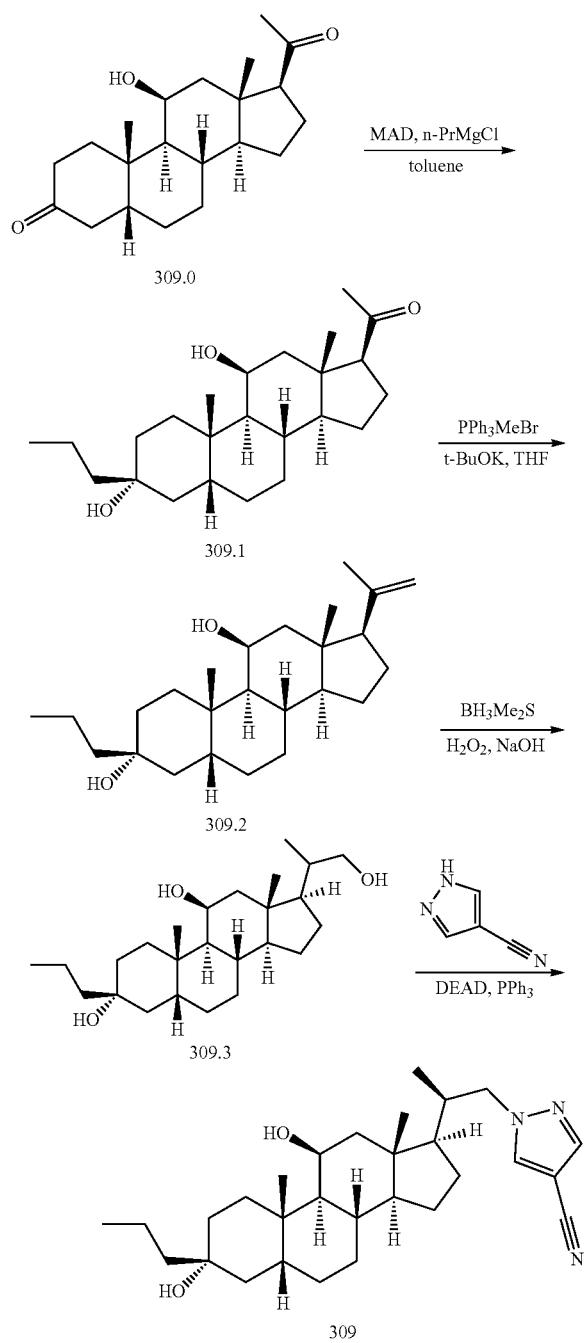

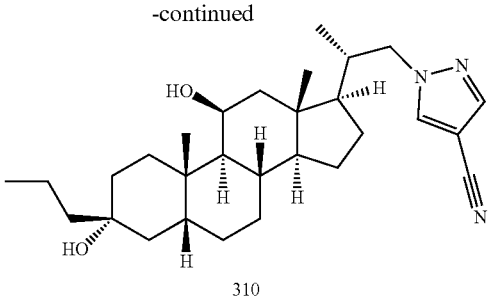

Synthesis of 309.1

To a solution of 2, 6-di-tert-butyl-4-methylphenol (1.03 g, 4.68 mmol) in toluene (5 mL) was added dropwise AlMe₃ (1.17 mL, 2.34 mmol, 2 M in toluene) at 0° C. under N₂. After stirring at 25° C. for 30 mins, to the fresh prepared MAD (2.34 mmol) solution under N₂ at −70° C. was added a solution of 309.0 (260 mg, 0.781 mmol) in toluene (5 mL) dropwise. After stirring at −70° C. for an h, chloro(propyl)magnesium (1.17 mL, 2.34 mmol, 2M in THF) was added to the mixture dropwise. After stirring at −70° C. for 0.5 h, the reaction mixture was poured to ice-cooled aqueous citric acid (20 mL) and extracted with ethyl acetate (2×30 mL). The combined organic layers were washed with brine (2×20 mL), dried over anhydrous Na₂SO₄, filtered and concentrated. The residue was purified by flash column (0-60% of ethyl acetate in PE) to give 309.1 (130 mg, 44.2%) as a solid. 309.1 (130 mg, 0.345 mmol) was further purified by pre-HPLC (Column: Welch Xtimate C18 150*25 mm*5 um; Condition: water (0.225% FA)-ACN; Begin B: 58%; End B: 88%) to afford 309.1 (45.2 mg, 35.0%) as a solid.

¹H NMR (400 MHz, CDCl₃) $\delta_H$ 4.26 (br s, 1H), 2.45 (t, J=9.2 Hz, 1H), 2.22-2.14 (m, 2H), 2.12 (s, 3H), 1.91-1.79 (m, 3H), 1.77-1.67 (m, 3H), 1.64 (br dd, J=8.0, 3.6 Hz, 2H), 1.60 (br d, J=3.0 Hz, 1H), 1.55-1.52 (m, 2H), 1.44 (br dd, J=14.4, 3.2 Hz, 1H), 1.40-1.37 (m, 1H), 1.37-1.30 (m, 4H), 1.29-1.20 (m, 3H), 1.19 (s, 3H), 1.17 (br d, J=4.0 Hz, 1H), 1.13 (br d, J=4.0 Hz, 1H), 1.02 (br d, J=3.6 Hz, 1H), 0.95 (t, J=7.2 Hz, 3H), 0.83 (s, 3H). LC-ELSD/MS purity 99%, MS ESI calcd. for $C_{24}H_{40}O_3$ $[M-2H_2O+H]^+$ 341.3 found 341.3.

Synthesis of 309.2

To a suspension of MePPh₃Br (1.37 g, 3.86 mmol) in anhydrous THF (10 mL) was added t-BuOK (433 mg, 3.86 mmol) at 25° C. under N₂. After stirring at 60° C. for 30 mins, a solution of 309.1 (730 mg, 1.93 mmol) in anhydrous THF (5 mL) was added dropwise. After stirring at 60° C. for 16 h, the mixture was cooled, poured into ice-water (50 mL), stirred for 10 mins, and extracted with EtOAc (2×50 mL). The combined organic phase was washed with brine (2×50 mL), dried over anhydrous Na₂SO₄, filtered and concentrated. The residue was purified by flash column (0~10% of EtOAc in PE) to give 309.2 (540 mg) as oil.

¹H NMR (400 MHz, CDCl₃) $\delta_H$ 4.84 (s, 1H), 4.71 (s, 1H), 4.21 (br d, J=2.8 Hz, 1H), 2.04-1.96 (m, 2H), 1.94-1.78 (m, 4H), 1.75 (s, 3H), 1.74-1.64 (m, 3H), 1.61 (br d, J=3.2 Hz, 1H), 1.57-1.79 (m, 4H), 1.48-1.43 (m, 1H), 1.43-1.30 (m, 5H), 1.23-1.10 (m, 7H), 0.94 (t, J=7.2 Hz, 3H), 0.79 (s, 3H).

Synthesis of 309.3

To a solution of 309.2 (540 mg, 1.44 mmol) in THF (20 mL) was added BH₃·Me₂S (0.719 mL, 10 M, 7.19 mmol) at 25° C. After stirring at 25° C. for 16 h, the reaction was sequentially treated with EtOH (2.50 mL, 43.1 mmol) at 25° C., NaOH (8.62 mL, 5.0 M, 43.1 mmol) at 0° C., and finally by H₂O₂ (4.30 mL, 43.1 mmol, 30% in water). After stirring at 70° C. for 1 h, the mixture was poured into water (100 mL) and extracted with EtOAc (2×200 mL). The combined organic layer was washed with saturated Na$_2$S$_2$O$_3$ (200 mL), brine (200 mL), dried over anhydrous Na$_2$SO$_4$, filtered and concentrated to give 309.3 (460 mg) as colorless oil. The residue was dissolved in DCM (10 mL), washed with NH$_4$Cl (10%, 5×50 mL), brine (2×50 mL), dried over anhydrous Na$_2$SO$_4$, filtered and concentrated to give 309.3 (240 mg) as a solid.

Synthesis of 309 & 310

To a solution of 309.3 (240 mg, 0.611 mmol), Ph$_3$P (799 mg, 3.05 mmol) and 1H-pyrazole-4-carbonitrile (113 mg, 1.22 mmol) in DMF (10 mL) was added DEAD (531 mg, 0.480 mL, 3.05 mmol). After stirring at 25° C. for 16 h, the mixture was poured into water (30 mL). The aqueous phase was extracted with EtOAc (2×50 mL). The combined organic phase was washed with brine (30 mL), dried over anhydrous Na$_2$SO$_4$, filtered, concentrated. The residue was purified by prep-HPLC (Column: Welch Xtimate C18 150*25 mm*5 um; Condition: water (0.04% NH$_3$·H$_2$O)-ACN; Begin B: 60%; End B: 90%) to afford 310 (29.2 mg) as a solid and 309 (49.2 mg) as a solid.

309: $^1$H NMR (400 MHz, CDCl$_3$) $\delta_H$ 7.79 (s, 1H), 7.75 (s, 1H), 4.23 (dd, J=13.6, 3.6 Hz, 1H), 4.17 (br s, 1H), 3.73 (dd, J=13.6, 9.2 Hz, 1H), 2.10 (dd, J=14.0, 2.6 Hz, 1H), 2.05-1.96 (m, 1H), 1.95-1.86 (m, 2H), 1.86-1.76 (m, 3H), 1.75-1.64 (m, 2H), 1.54-1.51 (m, 2H), 1.45-1.25 (m, 10H), 1.22 (br d, J=6.8 Hz, 1H), 1.18 (s, 3H), 1.17-1.04 (m, 5H), 1.01 (d, J=4.0 Hz, 1H), 0.96-0.92 (m, 6H), 0.83 (d, J=6.4 Hz, 3H). LC-ELSD/MS purity 99%, MS ESI calcd. for C$_{29}$H$_{42}$N$_3$ [M−2H$_2$O+H]$^+$ 432.3 found 432.3.

310: $^1$H NMR (400 MHz, CDCl$_3$) $\delta_H$ 7.80 (s, 1H), 7.76 (s, 1H), 4.49 (dd, J=13.2, 4.4 Hz, 1H), 4.20 (br s, 1H), 3.67 (dd, J=13.2, 10.8 Hz, 1H), 2.16-2.01 (m, 2H), 1.94-1.64 (m, 7H), 1.60 (d, J=3.2 Hz, 1H), 1.54-1.51 (m, 2H), 1.46-1.25 (m, 10H), 1.22 (br d, J=5.6 Hz, 1H), 1.19 (s, 3H), 1.18-1.06 (m, 5H), 1.04 (d, J=4.0 Hz, 1H), 1.01 (s, 3H), 0.99-0.89 (m, 4H), 0.67 (d, J=6.4 Hz, 3H). LC-ELSD/MS purity 99%, MS ESI calcd. for C$_{29}$H$_{42}$N$_3$ [M−2H$_2$O+H]$^+$ 432.3 found 432.3.

Examples 311 & 312: Synthesis of 1-((R)-2-((3R,5R,8R,9R,10S,13S,14S,17R)-3-butyl-3-hydroxy-13-methylhexadecahydro-1H-cyclopenta[a]phenanthren-17-yl)propyl)-1H-pyrazole-4-carbonitrile (311) (3R,5R,8R,9R,10S,13S,14S,17R)-3-butyl-3-hydroxy-13-methylhexadecahydro-1H-cyclopenta[a]phenanthren-17-yl)propyl)-1H-pyrazole-4-carbonitrile (312)

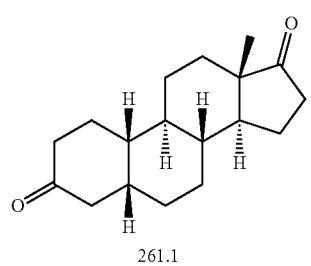

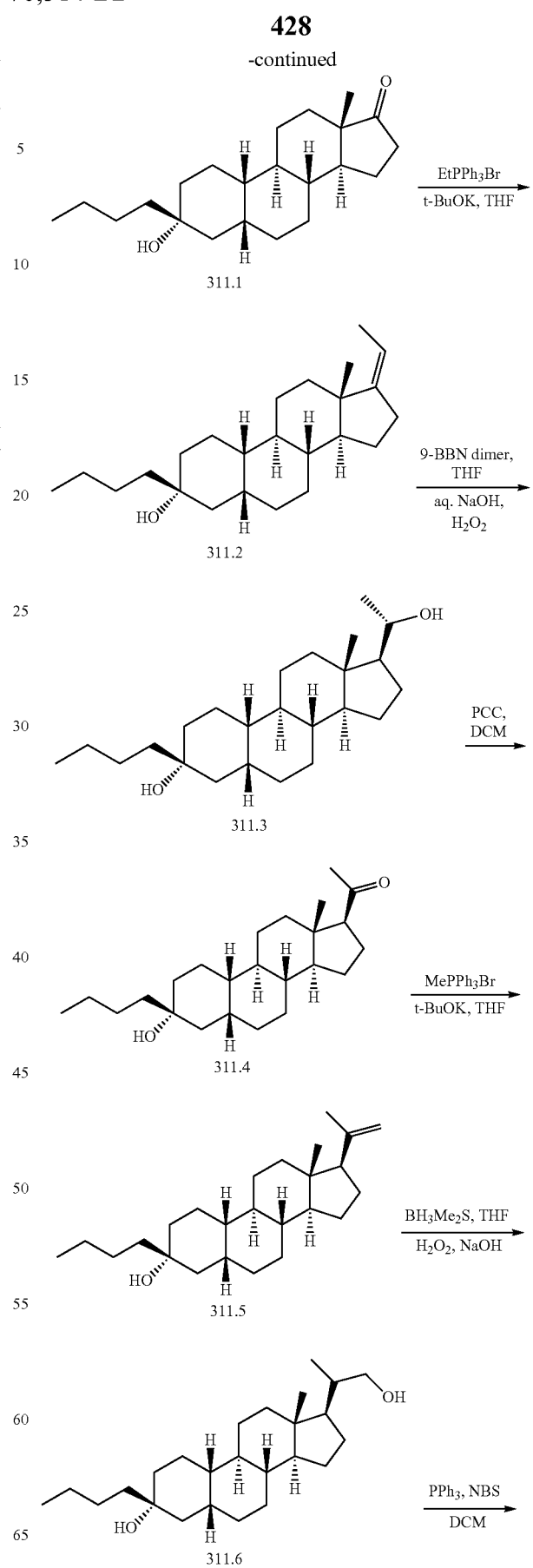

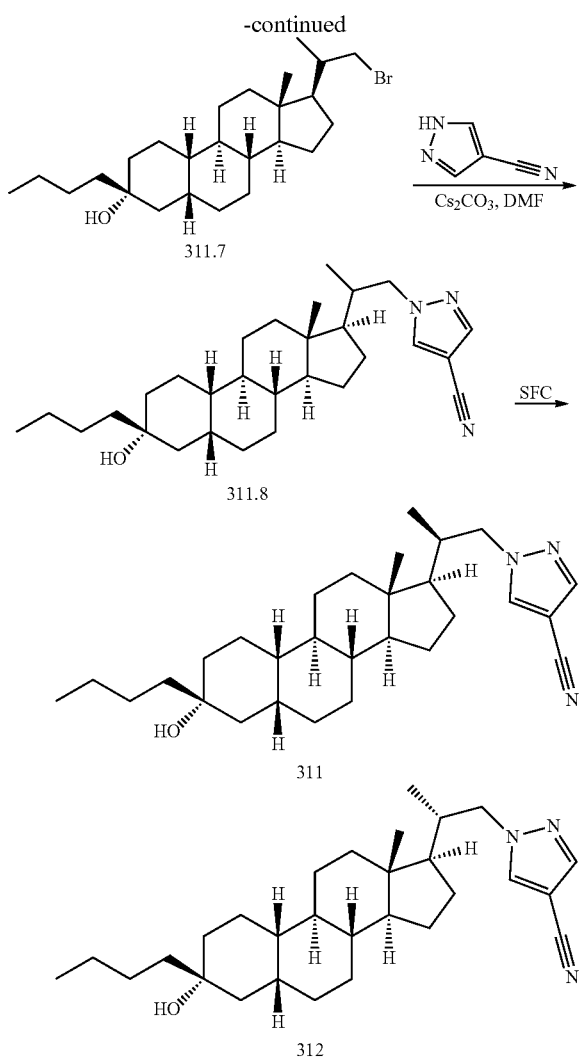

Synthesis of 311.1

To the fresh prepared MAD (109 mmol) solution in toluene (500 mL) was added 261.1 (10 g, 36.4 mmol) in DCM (50 mL) dropwise at −70° C. After stirring at −70° C. for 1 h under $N_2$, n-BuMgCl (54.5 mL, 109 mmol, 2M) was added dropwise at −70° C. After stirring at −70° C. for another 4 h, the reaction mixture was poured into saturated aqueous citric acid (1000 mL) at 10° C. and extracted with EtOAc (2×500 mL). The combined organic layer was dried over $Na_2SO_4$, filtered and concentrated in vacuum to give the product which was purified by flash column (0~40% of EtOAc in PE) to give 311.1 (10 g, 82.6%) as a solid.

$^1$H NMR (400 MHz, $CDCl_3$) $\delta_H$ 2.47-2.38 (m, 1H), 2.14-2.01 (m, 1H), 1.98-1.88 (m, 1H), 1.85-1.64 (m, 6H), 1.59-1.41 (m, 7H), 1.37-1.01 (m, 14H), 0.96-0.89 (m, 3H), 0.86 (s, 3H).

Synthesis of 311.2

To a mixture of $EtPPh_3Br$ (26.7 g, 72.0 mmol) in THF (120 mL) was added t-BuOK (8.07 g, 72.0 mmol) at 25° C. under $N_2$. After stirring at 40° C. for 30 mins, 311.1 (12.0 g, 36.0 mmol) was added at 40° C. After stirring at 40° C. for 3 h, the reaction mixture was quenched with saturated $NH_4Cl$ aqueous (200 mL) at 25° C. and extracted with EtOAc (2×100 mL). The combined organic phase was concentrated under vacuum to give a solid, which was purified by trituration with $MeOH/H_2O$ (1:1, 150 mL) to give 311.2 (12 g) as a solid.

$^1$H NMR (400 MHz, $CDCl_3$) $\delta_H$ 5.22-5.03 (m, 1H), 2.42-2.12 (m, 3H), 1.85-1.68 (m, 4H), 1.67-1.62 (m, 4H), 1.57-1.42 (m, 8H), 1.36-1.07 (m, 14H), 0.92 (t, J=6.8 Hz, 3H), 0.87 (s, 3H)

Synthesis of 311.3

To a solution of 311.2 (12 g, 34.8 mmol) in THF (150 mL) under $N_2$ was added 9-BBN dimer (16.9 g, 69.6 mmol) at 15° C. After stirring at 45° C. for 16 h, the resulting mixture was treated sequentially with ethanol (19.8 mL, 347 mmol) at 15° C., NaOH aqueous (69.4 mL, 5.0 M, 347 mmol) at 0° C. and then hydrogen peroxide (34.7 mL, 10 M, 347 mmol) dropwise at 15° C. After stirring at 70° C. for 1 h, the reaction was cooled to 15° C. and added into the water (200 mL) and saturated aqueous $Na_2S_2O_3$ (200 mL). The aqueous phase was extracted with EtOAc (2×200 mL). The combined organic phase was washed with brine (200 mL), dried over anhydrous $Na_2SO_4$, filtered and concentrated to give the product, which was purified by trituration with $H_2O$ (250 mL) at 20° C. to give 311.3 (15.1 g) as a solid.

$^1$H NMR (400 MHz, $CDCl_3$) $\delta_H$ 3.81-3.53 (m, 1H), 1.97-1.59 (m, 1H), 1.97-1.58 (m, 9H), 1.51-1.25 (m, 15H), 1.23-1.03 (m, 11H), 0.92 (t, J=6.8 Hz, 3H), 0.66 (s, 3H). LC-ELSD/MS purity 99%, MS ESI calcd. for $C_{24}H_{39}$ $[M-2H_2O+H]^+$ 327.3, found 327.3.

Synthesis of 311.4

To a solution of 311.3 (15 g, 41.3 mmol) in DCM (200 mL) at 0° C. was added silica gel (18 g) and PCC (17.7 g, 82.6 mmol). After stirring at 20° C. for 3 h, PE (100 mL) was added to the reaction mixture. The resulting mixture was filtered through a pad of silica gel and the filter cake was washed with DCM (400 mL). The filtrate was concentrated and the residue was purified by flash column (0-30% of EtOAc in PE) to give 311.4 (10 g, 67.5%) as a solid.

$^1$H NMR (400 MHz, $CDCl_3$) $\delta_H$ 2.54 (t, J=8.8 Hz, 1H), 2.20-2.13 (m, 1H), 2.12 (s, 3H), 2.03-1.97 (m, 1H), 1.83-1.60 (m, 7H), 1.49-1.26 (m, 15H), 1.25-1.04 (m, 6H), 0.92 (t, J=6.4 Hz, 3H), 0.61 (s, 3H). LC-ELSD/MS purity 99%, MS ESI calcd. for $C_{24}H_{39}O$ $[M-H_2O+H]^+$ 343.3, found 343.3.

Synthesis of 311.5

To a mixture of $MePPh_3Br$ (5.93 g, 16.6 mmol) in THF (30 mL) was added t-BuOK (1.86 g, 16.6 mmol) at 25° C. under $N_2$. After stirring at 50° C. for 30 mins, 311.4 (3 g, 8.31 mmol) was added at 50° C. After stirring at 50° C. for 16 h, the reaction mixture was quenched with saturated $NH_4Cl$ aqueous (100 mL) at 25° C. and extracted with EtOAc (2×100 mL). The combined organic phase was concentrated under vacuum to give a solid, which was purified by flash column (0~30% of EtOAc in PE) to give 311.5 (1.2 g, 40.2%) as a solid $^1$H NMR (400 MHz, $CDCl_3$) $\delta_H$ 4.84 (s, 1H), 4.70 (s, 1H), 2.05 (s, 2H), 1.85-1.57 (s, 13H), 1.50-1.20 (m, 16H), 1.18-1.02 (m, 4H), 0.92 (t, J=6.4 Hz, 3H), 0.57 (s, 3H).

Synthesis of 311.6

To a solution of 311.5 (1.2 g, 3.34 mmol) in THF (10 mL) was added $BH_3Me_2S$ (1.67 mL, 10 M, 16.7 mmol). After stirring at 25° C. for 16 h under $N_2$, the reaction mixture was sequentially treated with EtOH (1.91 mL, 33.4 mmol), NaOH (1.33 g in 6.68 mL water, 33.4 mmol) and $H_2O_2$ (3.34 mL, 10 M, 33.4 mmol) dropwise. After stirring at 70° C. for 2 h, the reaction mixture was quenched by $Na_2SO_3$ (100 mL, 10%) and extracted with EtOAc (2×200 mL). The combined organic layer was dried over $Na_2SO_4$, filtered and concentrated. The residue was purified by flash column (0~30% of EtOAc in PE) to give 311.6 (1.2 g, 96.0%) as a solid.

¹H NMR (400 MHz, CDCl₃) δ$_H$ 3.79-3.59 (m, 1H), 3.50-3.32 (m, 1H), 1.99-1.59 (m, 8H), 1.50-1.14 (m, 18H), 1.11-1.01 (m, 5H), 0.96 (s, 1H), 0.94 (s, 1H), 0.92 (t, J=6.4 Hz, 3H), 0.68 (s, 3H).

Synthesis of 311.7

To a solution of 311.6 (300 mg, 0.8 mmol) in DCM (5 mL) at 0° C. was added PPh₃ (312 mg, 1.2 mmol) and NBS (211 mg, 1.2 mmol). After stirring at 20° C. for 2 h, the reaction was diluted with water (20 mL) and extracted with DCM (2×20 mL). The combined organic phase was washed with brine (20 mL), dried over anhydrous Na₂SO₄, filtered and concentrated. The residue was purified by flash column (0~15% of EtOAc in PE) to give 311.7 (270 mg, 77.1%) as oil.

¹H NMR (400 MHz, CDCl₃) δ$_H$ 3.42-3.29 (m, 1H), 1.96-1.42 (m, 15H), 1.36-1.23 (m, 13H), 1.14-0.98 (m, 8H), 0.95-0.89 (m, 3H), 0.70-0.65 (m, 3H).

Synthesis of 311.8

To a solution of 311.7 (300 mg, 0.7 mmol) in DMF (5 mL) were added Cs₂CO₃ (443 mg, 1.4 mmol) and 1H-pyrazole-4-carbonitrile (126 mg, 1.4 mmol). After stirring at 80° C. for 16 h under N₂, the mixture was added into saturated NH₄Cl (20 mL) and extracted with EtOAc (3×50 mL). The combined organic layer was washed with LiCl (50 mL, 3% in water), brine (2×100 mL), dried over anhydrous Na₂SO₄, filtered and concentrated. The residue was purified by flash column (0~30% of EtOAc in PE) to give 311.8 (200 mg, 72.2%) as a solid.

Separation of 311 & 312

The diastereomeric mixture 311.8 (400 mg, 0.9 mmol) was separated by SFC (Column: DAICEL CHIRALCEL OD-H (250 mm*30 mm, 5 um); Condition: 0.1% NH₃H₂O ETOH; Begin B: 40%; End B: 40%; Flow Rate (ml/min): 60) to give 311 (86.5 mg, 21.6%) and 312 (58.2 mg, 14.5%) both as solids.

311: ¹H NMR (400 MHz, CDCl₃) δ$_H$ 7.80 (s, 1H), 7.75 (s, 1H), 4.50 (dd, J=4.4, 13.6 Hz, 1H), 3.70-3.60 (m, 1H), 2.18-2.05 (m, 1H), 1.91-1.57 (m, 9H), 1.49-1.25 (m, 14H), 1.24-1.03 (m, 7H), 0.92 (t, J=6.4 Hz, 3H), 0.79 (s, 3H), 0.68 (d, J=6.8 Hz, 3H). LC-ELSD/MS purity 99%, analytic SFC: 100% de, MS ESI calcd. for C₂₉H₄₄N₃ [M−H₂O+H]⁺ 434.3, found 434.3. SFC 100% de.

312: ¹H NMR (400 MHz, CDCl₃) δ$_H$ 7.80 (s, 1H), 7.75 (s, 1H), 4.26 (dd, J=4.0, 13.6 Hz, 1H), 3.76-3.67 (m, 1H), 2.08-1.88 (m, 3H), 1.83-1.57 (m, 6H), 1.50-1.21 (m, 15H), 1.20-0.99 (m, 7H), 0.92 (t, J=6.8 Hz, 3H), 0.81 (d, J=6.8 Hz, 3H), 0.71 (s, 3H). LC-ELSD/MS purity 99%, analytic SFC: 100% de, MS ESI calcd. for C₂₉H₄₄N₃ [M−H₂O+H]⁺ 434.3, found 434.3. SFC 100% de.

Examples 313-316: Synthesis of (3R,5R,8R,9S,10S,13S,14S,17R)-10,13-dimethyl-17-((R)-1-(5-methyl-2H-tetrazol-2-yl)propan-2-yl)-3-propylhexadecahydro-1H-cyclopenta[a]phenanthren-3-ol (313) & (3R,5R,8R,9S,10S,13S,14S,17R)-10,13-dimethyl-17-((S)-1-(5-methyl-2H-tetrazol-2-yl)propan-2-yl)-3-propylhexadecahydro-1H-cyclopenta[a]phenanthren-3-ol (314) & (3R,5R,8R,9S,10S,13S,14S,17R)-10,13-dimethyl-17-((R)-1-(5-methyl-1H-tetrazol-1-yl)propan-2-yl)-3-propylhexadecahydro-1H-cyclopenta[a]phenanthren-3-ol (315) & (3R,5R,8R,9S,10S,13S,14S,17R)-10,13-dimethyl-17-((S)-1-(5-methyl-1H-tetrazol-1-yl)propan-2-yl)-3-propylhexadecahydro-1H-cyclopenta[a]phenanthren-3-ol (316)

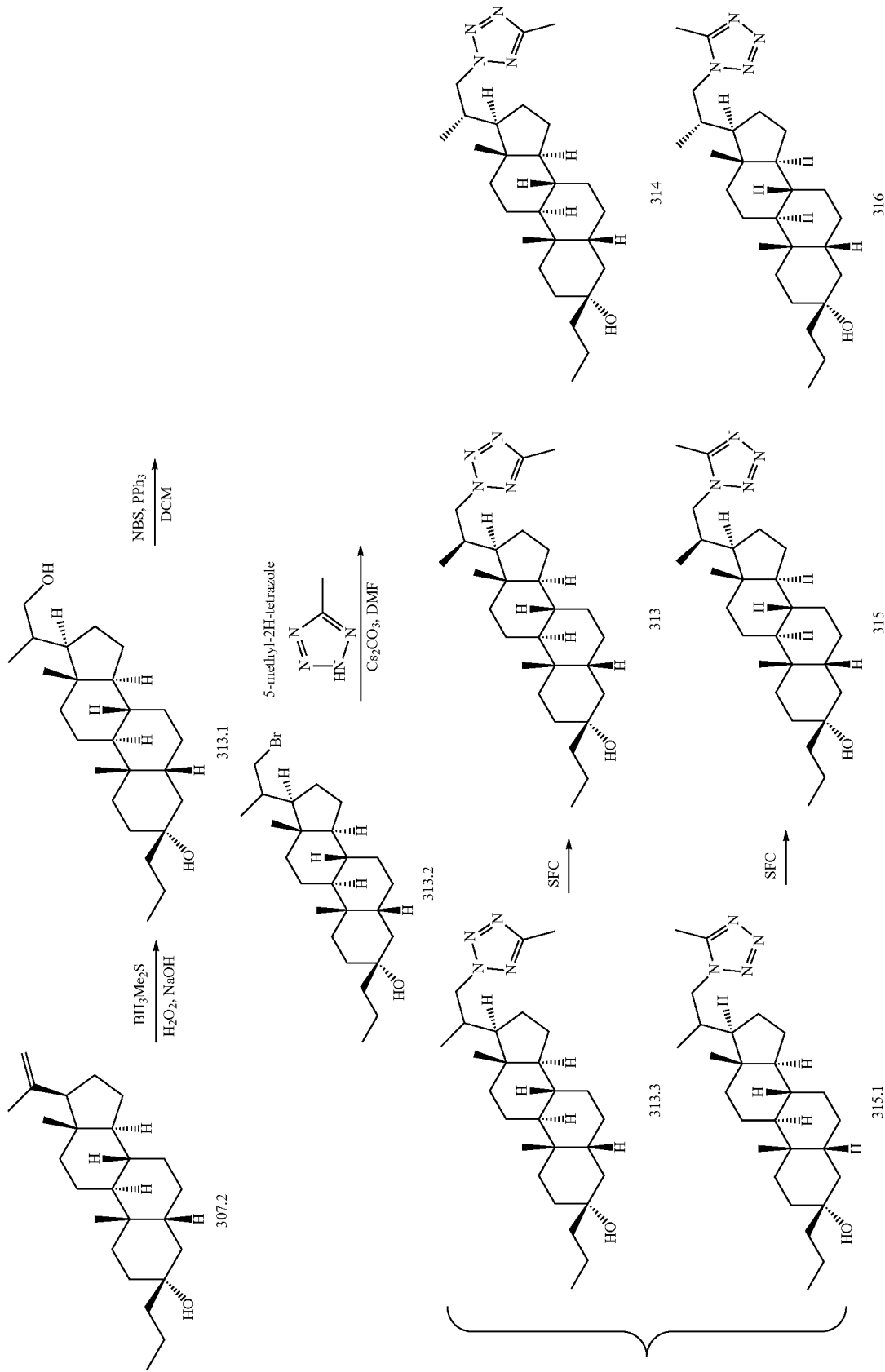

Synthesis of 313.1

To a solution of 307.2 (1.5 g, 4.2 mmol) in THF (15 mL) was added BH$_3$·Me$_2$S (2.09 mL, 20.9 mmol, 10 M) dropwise at 0° C. After stirring at 25° C. for 3 h, the reaction mixture was cooled to 0° C. and sequentially treated with ethanol (1.92 g, 41.8 mmol) dropwise at 0° C. NaOH aqueous (6.26 mL, 62.6 mmol, 10 M) dropwise followed by H$_2$O$_2$ (6.26 mL, 62.6 mmol) at 0° C. After stirring at 70° C. for 1 h, the mixture was extracted with EtOAc (2×25 mL). The combined organic phase was washed with saturated Na$_2$S 203 aqueous (2×30 mL), brine (30 mL), dried over Na$_2$SO$_4$, filtered and evaporated to give 313.1 (1.8 g) as solid.

$^1$H NMR (400 MHz, CDCl$_3$) $\delta_H$ 3.76-3.69 (m, 1H), 3.50-3.32 (m, 1H), 1.94-1.75 (m, 4H), 1.72-1.65 (m, 2H), 1.60-1.29 (m, 11H), 1.28-1.14 (m, 9H), 1.13-1.00 (m, 5H), 0.99-0.85 (m, 8H), 0.66 (s, 3H).

Synthesis of 313.2

To a solution of 313.1 (1.8 g, 4.77 mmol) in DCM (20 mL) was added PPh$_3$ (1.87 g, 7.15 mmol) and NBS (1.27 g, 7.15 mmol) at 0° C. After stirring at 25° C. for 2 h, the reaction was added to water (20 mL) and extracted with DCM (2×20 mL). The combined organic phase was washed with brine (20 mL), dried over anhydrous Na$_2$SO$_4$, filtered and concentrated. The residue was purified by flash column (0~25% of EtOAc in PE) to give 313.2 (1 g, 47.8%) as an oil.

$^1$H NMR (400 MHz, CDCl$_3$) $\delta_H$ 3.65-3.50 (m, 1H), 3.40-3.33 (m, 1H), 1.90-1.76 (m, 4H), 1.75-1.65 (m, 2H), 1.64-1.51 (m, 8H), 1.49-1.21 (m, 10H), 1.19-1.01 (m, 6H), 1.00-0.84 (m, 8H), 0.66 (s, 3H).

Synthesis of 313.3 & 315.1

To a solution of 313.2 (1 g, 2.27 mmol) in DMF (8 mL) were added Cs$_2$CO$_3$ (1.47 g, 4.54 mmol) and 5-methyl-2H-1,2,3,4-tetrazole (381 mg, 4.54 mmol). After stirring at 80° C. for 16 h, the mixture was added into saturated NH$_4$Cl (20 mL) and extracted with EtOAc (3×20 mL). The combined organic layer was washed with water (2×20 mL), brine (20 mL), dried over anhydrous Na$_2$SO$_4$, filtered and concentrated. The residue was purified by flash column (0~100% of EtOAc in PE) to give 313.3 (735 mg) and 315.1 (287 mg) both as colorless oil.

313.3: $^1$H NMR (400 MHz, CDCl$_3$) $\delta_H$ 4.77-4.50 (m, 1H), 4.32-4.23 (m, 1H), 2.53 (m, 3H), 2.26-2.08 (m, 1H), 2.03-1.78 (m, 4H), 1.71-1.62 (m, 2H), 1.56-1.08 (m, 9H), 1.06-1.02 (m, 9H), 1.00-0.90 (m, 8H), 0.89-0.80 (m, 5H), 0.75-0.58 (s, 3H).

315.1: $^1$H NMR (400 MHz, CDCl$_3$) $\delta_H$ 4.56-4.50 (m, 1H), 4.32-3.75 (m, 1H), 2.95 (s, 3H), 2.88 (s, 3H), 2.54 (s, 3H), 2.28-2.16 (m, 1H), 1.93-1.79 (m, 4H), 1.73-1.31 (m, 10H), 1.28-1.01 (m, 9H), 1.00-0.90 (m, 5H), 0.89-0.80 (m, 3H), 0.75-0.58 (s, 3H).

Separation of 313 & 314

313.3 (735 mg) was separated by SFC (DAICEL CHIRALCEL OD-H (250 mm*30 mm, 5 um), Condition: 0.1% NH$_3$H$_2$O ETOH, Begin B: 40%, End B: 40%, FlowRate (ml/min): 50) to afford 313 (352.1 mg, 47.9%) and 314 (202.6 mg, 27.5%) both as solids.

313: $^1$H NMR (400 MHz, CDCl$_3$) $\delta_H$ 4.56-4.50 (m, 1H), 4.32-4.23 (m, 1H), 2.53 (m, 3H), 2.20-2.08 (m, 1H), 2.03-1.78 (m, 4H), 1.71-1.62 (m, 2H), 1.56-1.08 (m, 11H), 1.06-1.02 (m, 11H), 1.00-0.90 (m, 6H), 0.89-0.80 (m, 3H), 0.70 (s, 3H). LC-ELSD/MS purity 99%, MS ESI calcd. for C$_{27}$H$_{45}$N$_4$ [M–H$_2$O+H]$^+$ 425 found 425. SFC 100% de.

314: $^1$H NMR (400 MHz, CDCl$_3$) $\delta_H$ 4.56-4.50 (m, 1H), 4.32-4.24 (m, 1H), 2.53 (s, 3H), 2.28-2.16 (m, 1H), 1.93-1.79 (m, 4H), 1.73-1.58 (m, 2H), 1.57-1.31 (m, 11H), 1.28-1.01 (m, 11H), 1.00-0.90 (m, 6H), 0.89-0.80 (m, 3H), 0.70 (s, 3H). LC-ELSD/MS purity 99%, MS ESI calcd. for C$_{27}$H$_{45}$N$_4$ [M–H$_2$O+H]$^+$ 425 found 425. SFC 100% de.

Separation of 315 & 316

315.1 (287 mg) was separated by SFC (DAICEL CHIRALCEL OD-H (250 mm*30 mm, 5 um), Condition: 0.1% NH$_3$H$_2$O ETOH, Begin B: 35%, End B: 35%, FlowRate (ml/min): 50) to afford 315 (83.7 mg, 29.2%) and 316 (67.8 mg, 23.7%) both as solids.

315: $^1$H NMR (400 MHz, CDCl$_3$) $\delta_H$ 4.32-4.27 (m, 1H), 3.90-3.80 (m, 1H), 2.55 (s, 3H), 2.20-1.80 (m, 5H), 1.78-1.59 (m, 2H), 1.50-1.25 (m, 12H), 1.24-1.05 (m, 10H), 1.02-0.95 (m, 6H), 0.82 (d, J=6.5 Hz, 3H), 0.70 (s, 3H). LC-ELSD/MS purity 99%, MS ESI calcd. for C$_{27}$H$_{45}$N$_4$ [M–H$_2$O+H]$^+$ 425 found 425. SFC 100% de.

316: $^1$H NMR (400 MHz, CDCl$_3$) $\delta_H$ 4.56-4.49 (m, 1H), 3.90-3.79 (m, 1H), 2.55 (s, 3H), 2.19-2.06 (m, 1H), 1.94-1.79 (m, 4H), 1.73-1.60 (m, 2H), 1.51-1.32 (m, 13H), 1.28-0.98 (m, 9H), 0.97-0.91 (m, 6H), 0.80 (s, 3H), 0.73-0.67 (m, 3H). LC-ELSD/MS purity 99%, MS ESI calcd. for C$_{27}$H$_{45}$N$_4$ [M–H$_2$O+H]$^+$ 425 found 425. SFC 100% de.

Examples 317 & 318: Synthesis of 1-((R)-2-((3R,5R,8R,9R,10S,13S,14S,17R)-13-ethyl-3-hydroxy-3-methylhexadecahydro-1H-cyclopenta[a]phenanthren-17-yl)propyl)-1H-pyrazole-4-carbonitrile (317) & 1-((S)-2-((3R,5R,8R,9R,10S,13S,14S,17R)-13-ethyl-3-hydroxy-3-methylhexadecahydro-1H-cyclopenta[a]phenanthren-17-yl)propyl)-1H-pyrazole-4-carbonitrile (318)

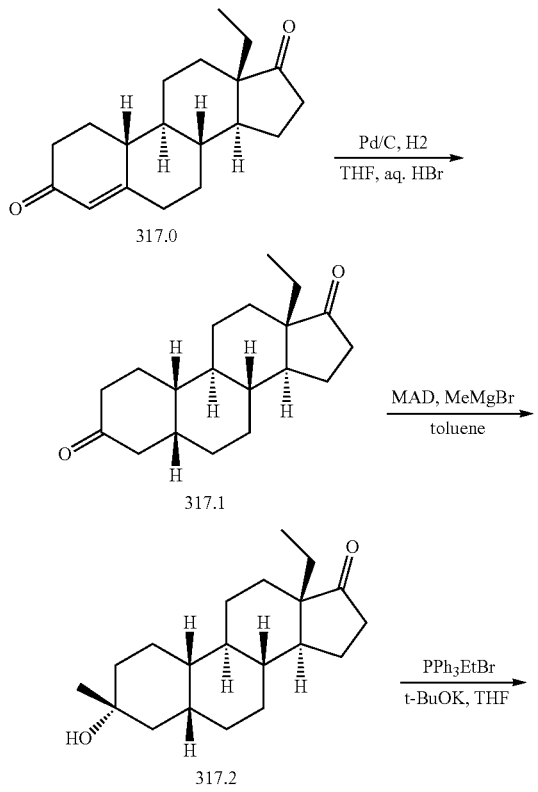

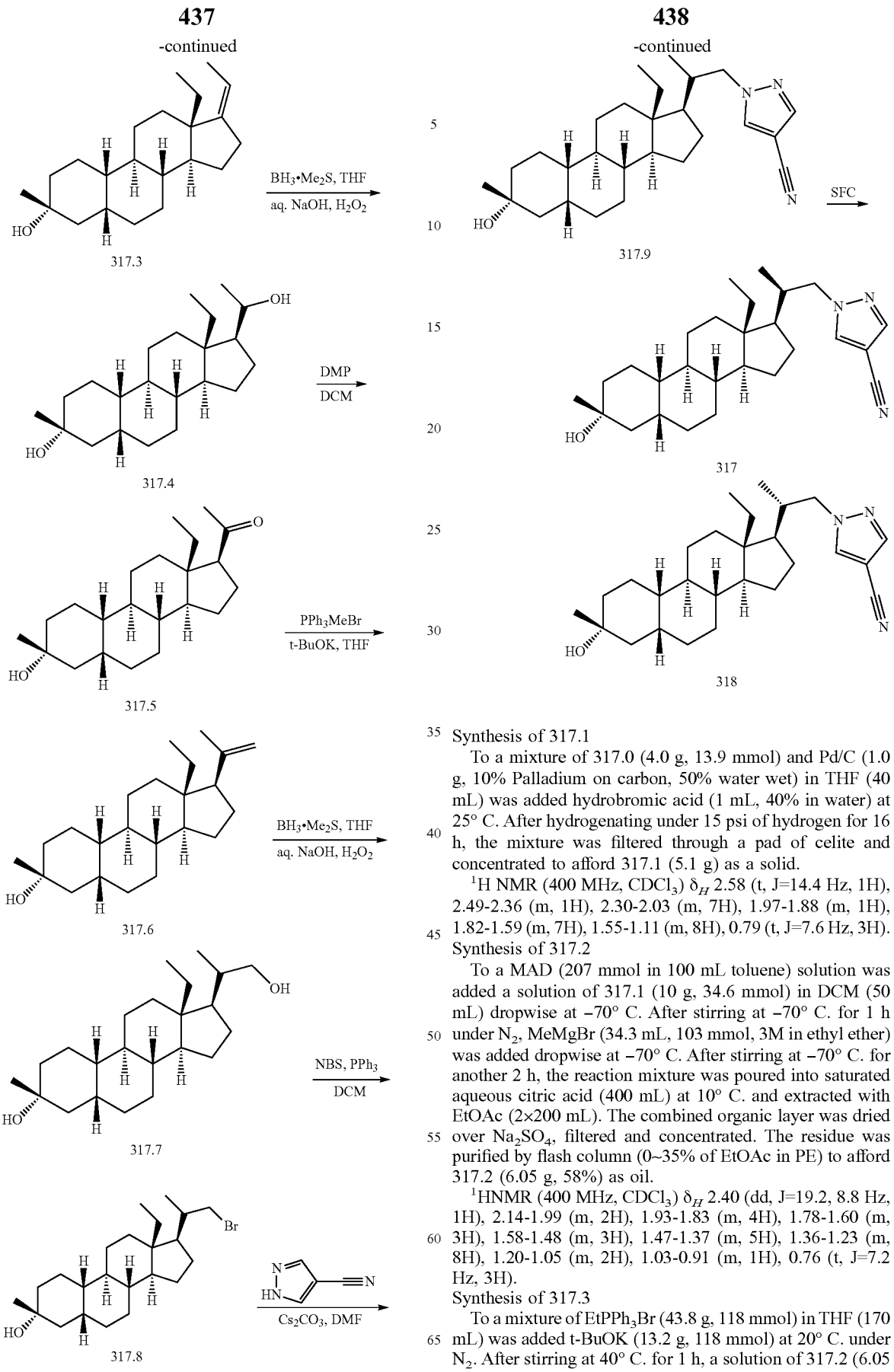

Synthesis of 317.1

To a mixture of 317.0 (4.0 g, 13.9 mmol) and Pd/C (1.0 g, 10% Palladium on carbon, 50% water wet) in THF (40 mL) was added hydrobromic acid (1 mL, 40% in water) at 25° C. After hydrogenating under 15 psi of hydrogen for 16 h, the mixture was filtered through a pad of celite and concentrated to afford 317.1 (5.1 g) as a solid.

$^{1}$H NMR (400 MHz, CDCl$_3$) $\delta_H$ 2.58 (t, J=14.4 Hz, 1H), 2.49-2.36 (m, 1H), 2.30-2.03 (m, 7H), 1.97-1.88 (m, 1H), 1.82-1.59 (m, 7H), 1.55-1.11 (m, 8H), 0.79 (t, J=7.6 Hz, 3H).

Synthesis of 317.2

To a MAD (207 mmol in 100 mL toluene) solution was added a solution of 317.1 (10 g, 34.6 mmol) in DCM (50 mL) dropwise at −70° C. After stirring at −70° C. for 1 h under N$_2$, MeMgBr (34.3 mL, 103 mmol, 3M in ethyl ether) was added dropwise at −70° C. After stirring at −70° C. for another 2 h, the reaction mixture was poured into saturated aqueous citric acid (400 mL) at 10° C. and extracted with EtOAc (2×200 mL). The combined organic layer was dried over Na$_2$SO$_4$, filtered and concentrated. The residue was purified by flash column (0~35% of EtOAc in PE) to afford 317.2 (6.05 g, 58%) as oil.

$^{1}$HNMR (400 MHz, CDCl$_3$) $\delta_H$ 2.40 (dd, J=19.2, 8.8 Hz, 1H), 2.14-1.99 (m, 2H), 1.93-1.83 (m, 4H), 1.78-1.60 (m, 3H), 1.58-1.48 (m, 3H), 1.47-1.37 (m, 5H), 1.36-1.23 (m, 8H), 1.20-1.05 (m, 2H), 1.03-0.91 (m, 1H), 0.76 (t, J=7.2 Hz, 3H).

Synthesis of 317.3

To a mixture of EtPPh$_3$Br (43.8 g, 118 mmol) in THF (170 mL) was added t-BuOK (13.2 g, 118 mmol) at 20° C. under N$_2$. After stirring at 40° C. for 1 h, a solution of 317.2 (6.05 g, 19.8 mmol) in THF (20 mL) was added at 40° C. After stirring at 40° C. for 36 h, the reaction mixture was quenched with 10% NH$_4$Cl aqueous (100 mL) at 20° C. and extracted with EtOAc (2×100 mL). The combined organic phase was washed with brine (20 mL) dried over anhydrous Na$_2$SO$_4$, filtered and concentrated. The residue was purified by flash column (0~12% of EtOAc in PE) to give 317.3 (5.2 g, 83%) as oil $^1$HNMR (400 MHz, CDCl$_3$) δ$_H$ 5.23-5.15 (m, 1H), 2.46-2.30 (m, 2H), 2.22-2.08 (m, 1H), 1.90-1.78 (m, 3H), 1.71-1.63 (m, 5H), 1.56-1.40 (m, 7H), 1.34-1.22 (m, 9H), 1.20-0.92 (m, 5H), 0.83 (t, J=7.2 Hz, 3H).

Synthesis of 317.4

To a solution of 317.3 (4.2 g, 3.15 mmol) in THF (60 mL) was added BH$_3$Me$_2$S (3.95 mL, 39.5 mmol, 10M) at 0° C. After stirring at 20° C. for 12 h, the reaction mixture was sequentially treated with ethanol (13.8 mL) at 15° C., NaOH aqueous (47.7 mL, 5.0 M) at 0° C. and finally hydrogen peroxide (23.7, 10 M) dropwise at 0° C. After stirring at 78° C. for 1 h, the reaction mixture was cooled to 15° C. The aqueous phase was collected and treated with saturated aqueous Na$_2$S$_2$O$_3$ (80 mL). The aqueous phase was extracted with EtOAc (2×100 mL). The combined organic phase was washed with brine (2×30 mL), dried over anhydrous Na$_2$SO$_4$, filtered and concentrated to give 317.4 (4.6 g) as a solid.

$^1$HNMR (400 MHz, CDCl$_3$) δ$_H$ 3.88-3.69 (m, 1H), 2.32-2.09 (m, 1H), 1.93-1.75 (m, 4H), 1.71-1.61 (m, 5H), 1.50-1.24 (m, 17H), 1.18-1.03 (m, 5H), 0.99-0.80 (m, 5H).

Synthesis of 317.5

To a solution of 317.4 (5.6 g, 16.7 mmol) in DCM (200 mL) at 10° C. was added DMP (14.1 g, 33.4 mmol). After stirring at 20° C. for 30 minutes, the mixture was quenched by saturated NaHCO$_3$ aqueous (50 mL) and saturated Na$_2$S$_2$O$_3$ (50 mL) at 10° C. The DCM phase was separated and washed with saturated NaHCO$_3$/Na$_2$S$_2$O$_3$ aqueous (1:1, 2×30 mL), brine (20 mL), dried over Na$_2$SO$_4$, filtered and concentrated. The residue was purified by flash column (0~25% of EtOAc in PE) to give 317.5 (4.15 g, 75%) as a solid.

$^1$HNMR (400 MHz, CDCl$_3$) δ$_H$ 2.50-2.42 (m, 1H), 2.34-2.17 (m, 5H), 1.89-1.78 (m, 3H), 1.75-1.58 (m, 4H), 1.50-1.36 (m, 6H), 1.33-1.03 (m, 13H), 0.96-0.81 (m, 1H), 0.62 (t, J=7.6 Hz, 3H).

Synthesis of 317.6

To a mixture of MePPh$_3$Br (17.7 g, 49.6 mmol) in THF (80 mL) was added t-BuOK (5.55 g, 49.6 mmol) at 20° C. under N$_2$. After stirring at 50° C. for 1 h, a solution of 317.5 (4.15 g, 12.4 mmol) in THF (10 mL) was added at 50° C. After stirring at 50° C. for 12 h, the reaction mixture was quenched with 10% NH$_4$Cl aqueous (50 mL) at 20° C. and extracted with EtOAc (2×80 mL). The combined organic phase was washed with brine (30 mL) dried over anhydrous Na$_2$SO$_4$, filtered and concentrated. The residue was purified by flash column (0~12% of EtOAc in PE) to give 317.6 (2.85 g, 70%) as oil.

$^1$HNMR (400 MHz, CDCl$_3$) δ$_H$ 4.80 (s, 1H), 4.77 (s, 1H), 2.24-2.19 (m, 1H), 1.99-1.94 (m, 1H), 1.92-1.80 (m, 6H), 1.66-1.57 (m, 4H), 1.50-1.33 (m, 7H), 1.30-1.23 (m, 7H), 1.19-0.97 (m, 6H), 0.91-0.81 (m, 1H), 0.74 (t, J=7.6 Hz, 3H).

Synthesis of 317.7

To a solution of 317.6 (1.0 g, 3.02 mmol) in THF (10 mL) was added BH$_3$Me$_2$S (1.20 mL, 12.0 mmol, 10 M) at 0° C. After stirring at 20° C. for 12 h, the resulting mixture was treated sequentially with ethanol (3.16 mL) at 15° C., NaOH aqueous (10.8 mL, 5.0 M) at 0° C., and finally hydrogen peroxide (5.43 mL, 10 M) dropwise at 0° C. After stirring at 78° C. for 1 h, the mixture was cooled to 15° C. and quenched with saturated aqueous Na$_2$S$_2$O$_3$ (30 mL). The aqueous phase was extracted with EtOAc (2×60 mL). The combined organic phase was washed with brine (2×30 mL), dried over anhydrous Na$_2$SO$_4$, filtered and concentrated. The residue was purified by flash column (0~30% of EtOAc in PE) to give 317.7 (1.0 g) as a solid.

$^1$H NMR (400 MHz, CDCl$_3$) δ$_H$ 3.88-3.60 (m, 1H), 3.45-3.33 (m, 1H), 2.28-2.12 (m, 1H), 1.89-1.70 (m, 4H), 1.68-1.56 (m, 4H), 1.50-1.16 (m, 17H), 1.14-1.02 (m, 5H), 0.99-0.82 (m, 7H)

Synthesis of 317.8

To a solution of 317.7 (500 mg, 1.43 mmol) in DCM (10 mL) was added triphenylphosphine (561 mg, 2.14 mmol) and NBS (380 mg, 2.14 mmol) at 0° C. under N$_2$. After stirring at 15° C. for 2 h. The mixture was concentrated. The residue was purified by flash column (0~13% of EtOAc in PE) to give 317.8 (300 mg, 51%) as a solid.

$^1$H NMR (400 MHz, CDCl$_3$) 3.75-3.48 (m, 1H), 3.40-3.31 (m, 1H), 2.25-2.12 (m, 1H), 1.93-1.76 (m, 5H), 1.68-1.59 (m, 2H), 1.50-1.22 (m, 16H), 1.20-0.99 (m, 9H), 0.94-0.83 (m, 4H).

Synthesis of 317.9

To a solution of 317.8 (360 mg, 0.87 mmol) in DMF (8 mL) were added 1H-pyrazole-4-carbonitrile (161 mg, 1.74 mmol) and Cs$_2$CO$_3$ (566 mg, 1.74 mmol) at 20° C. under N$_2$. After stirring at 80° C. for 12 h, the mixture was diluted with H$_2$O (15 mL) and extracted with EtOAc (3×30 mL). The combined organic phase was washed with H$_2$O (2×30 mL) and brine (30 mL), dried over anhydrous Na$_2$SO$_4$, filtered and concentrated. The residue was purified by flash column (0~25% of EtOAc in PE) to give 317.9 (300 mg) as a solid.

$^1$H NMR (400 MHz, CDCl$_3$) 7.80 (s, 1H), 7.75 (s, 1H), 4.65-4.26 (m, 1H), 3.72-3.60 (m, 1H), 2.30-2.12 (m, 2H), 1.90-1.75 (m, 4H), 1.70-1.57 (m, 3H), 1.51-1.35 (m, 8H), 1.32-1.20 (m, 8H), 1.14-1.01 (m, 6H), 0.98-0.80 (m, 4H), 0.71-0.63 (m, 2H).

Separation of 317 & 318

317.9 (300 mg) was separated by SFC (column: DuraShell 150*25 mm*5 um, A; CO$_2$; B: 0.1% NH$_3$H$_2$O EtOH; gradient: 25-25%, flow rate: 60 mL/min.) to give 317 (89.3 mg, 30%) as a solid and 318 (118.0 mg, 39%) as a solid.

317: $^1$H NMR (400 MHz, CDCl$_3$) δ$_H$ 7.80 (s, 1H), 7.75 (s, 1H), 4.60 (dd, J=13.6, 4.0 Hz, 1H), 3.67 (dd, J=13.6, 10.4 Hz, 1H), 2.31-2.15 (m, 2H), 1.88-1.75 (m, 4H), 1.70-1.56 (m, 3H), 1.52-1.35 (m, 8H), 1.33-1.16 (m, 8H), 1.14-0.84 (m, 9H), 0.68 (d, J=6.8 Hz, 3H). LC-ELSD/MS: purity 99%, analytic SFC: 99.78% de; MS ESI calcd. for C$_{27}$H$_{40}$N$_3$ [M−H$_2$O+H]$^+$ 406.3, found 406.3; MS ESI calcd. for C$_{27}$H$_{42}$N$_3$O [M+H]$^+$ 424.3, found 424.3. SFC 100% de.

318: $^1$H NMR (400 MHz, CDCl$_3$) δ$_H$ 7.80 (s, 1H), 7.75 (s, 1H), 4.29 (dd, J=13.2, 4.0 Hz, 1H), 3.67 (dd, J=13.2, 9.6 Hz, 1H), 2.27-2.10 (m, 2H), 1.94-1.75 (m, 4H), 1.68-1.57 (m, 3H), 1.50-1.32 (m, 8H), 1.30-0.95 (m, 13H), 0.93-0.81 (m, 7H). LC-ELSD/MS: purity 99%, analytic SFC: 99.36% de; MS ESI calcd. for C$_{27}$H$_{40}$N$_3$ [M−H$_2$O+H]$^+$ 406.3, found 406.3. SFC 100% de.

Examples 319-322: Synthesis of (3R,5R,8S,9S,10R, 13S,14S,17R)-10-(methoxymethyl)-13-methyl-17-((R)-1-(5-methyl-2H-tetrazol-2-yl)propan-2-yl)-3-propylhexadecahydro-1H-cyclopenta[a]phenanthren-3-ol (319) & (3R,5R,8S,9S,10R,13S,14S,17R)-10-(methoxymethyl)-13-methyl-17-((S)-1-(5-methyl-2H-tetrazol-2-yl)propan-2-yl)-3-propylhexadecahydro-1H-cyclopenta[a]phenanthren-3-ol (320) & (3R,5R,8S,9S,10R,13S,14S,17R)-10-(methoxymethyl)-13-methyl-17-((R)-1-(5-methyl-1H-tetrazol-1-yl)propan-2-yl)-3-propylhexadecahydro-1H-cyclopenta[a]phenanthren-3-ol (321) & (3R,5R,8S,9S,10R,13S,14S,17R)-10-(methoxymethyl)-13-methyl-17-((S)-1-(5-methyl-1H-tetrazol-1-yl)propan-2-yl)-3-propylhexadecahydro-1H-cyclopenta[a]phenanthren-3-ol (322)

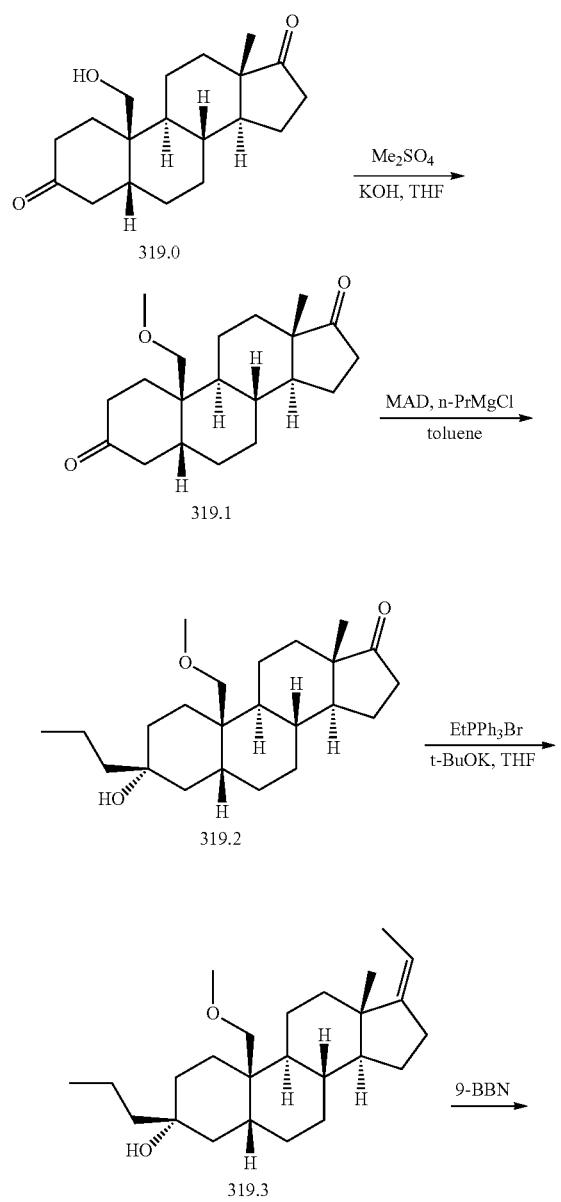

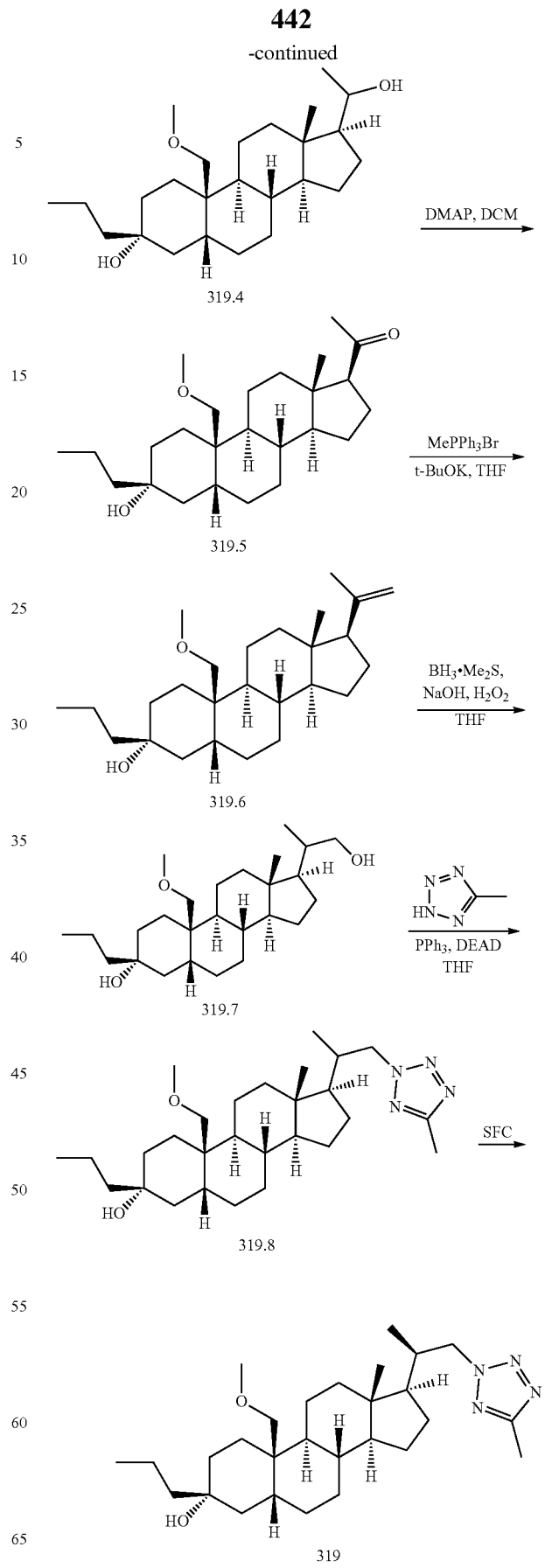

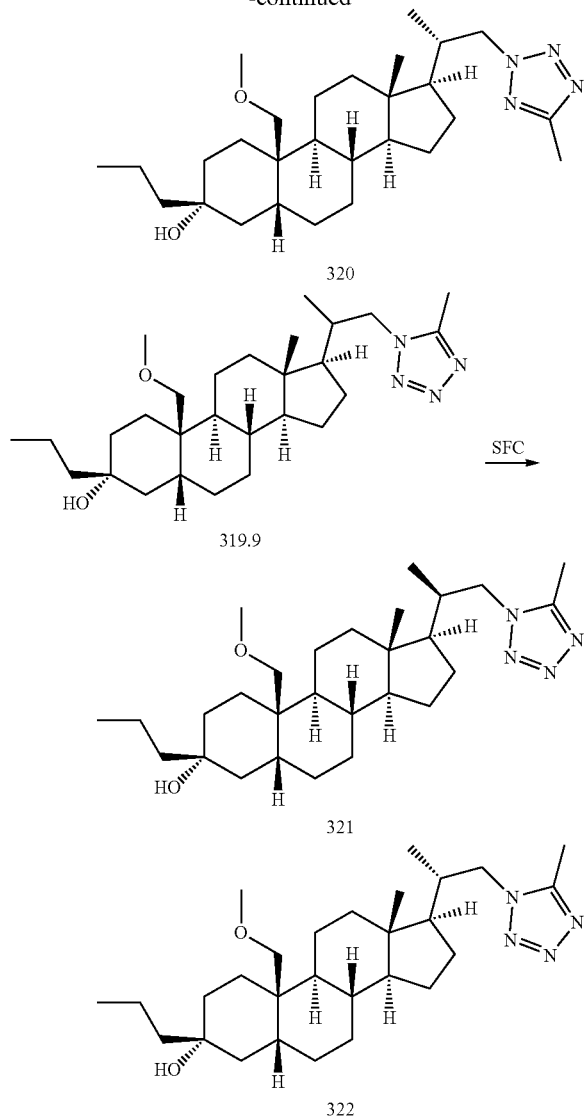

Synthesis of 319.1

To a solution of 319.0 (30 g, 98.5 mmol) in THF (200 mL) was added KOH (16.5 g, 295 mmol) and Me$_2$SO$_4$ (25.2 g, 197 mmol) at 0° C. After stirring at 25° C. for 16 h under N$_2$, the mixture was quenched with water (300 mL) and extracted with EtOAc (3×500 mL). The combined organic layers were washed with brine (1 L), dried over anhydrous Na$_2$SO$_4$, filtered and evaporated. The residue was purified by flash column (0~15% of EtOAc in PE) to afford 319.1 (21.4 g, 68%) as a solid.

$^1$H NMR (400 MHz, CDCl$_3$) δ$_H$ 3.61-3.58 (d, J=9.2 Hz, 3H), 3.35-3.33 (m, 4H), 2.66-2.58 (m, 1H), 2.50-2.43 (m, 1H), 2.37-1.81 (m, 11H), 1.77-1.05 (m, 7H), 0.89 (s, 3H).

Synthesis of 319.2

To a solution of 2,6-di-tert-butyl-4-methylphenol (42.7 g, 194 mmol) in toluene (70 mL) was added dropwise AlMe$_3$ (48.5 mL, 97.1 mmol, 2 M in toluene) at 0° C. After stirring at 25° C. for 30 mins, to the MAD solution was added a solution of 319.1 (10 g, 31.4 mmol) in anhydrous toluene (200 mL) dropwise at −70° C. After stirring at −70° C. for 1 h under N$_2$, n-PrMgCl (47 mL, 94.1 mmol, 2 M in diethyl ether) was added dropwise at −70° C. After stirring at −70° C. for another 2 h, the reaction mixture was poured into saturated aqueous citric acid (500 mL) at 0° C. and extracted with EtOAc (2×500 mL). The combined organic layer was dried over anhydrous Na$_2$SO$_4$, filtered and concentrated in vacuum. The residue was purified by flash column (0~20% of EtOAc in PE) to give 319.2 (7.4 g, 65%) as a solid.

$^1$H NMR (400 MHz, CDCl$_3$) δ$_H$ 3.55-3.53 (d, J=9.2 Hz, 1H), 3.33 (s, 3H), 3.22-3.20 (d, J=9.2 Hz, 1H), 2.47-2.40 (m, 1H), 2.12-2.03 (m, 1H), 1.96-1.61 (m, 7H), 1.54-1.39 (m, 9H), 1.37-1.15 (m, 9H), 0.93 (t, J=7.2 Hz, 3H), 0.85 (s, 3H).

Synthesis of 319.3

To a suspension of EtPPh$_3$Br (30.2 g, 81.6 mmol) in THF (150 mL) was added t-BuOK (9.15 g, 81.6 mmol) at 15° C. under N$_2$. After stirring at 45° C. for 30 mins, 319.2 (7.4 g, 20.4 mmol) in THF (50 mL) was added. After stirring at 45° C. for 16 h, the resulting suspension was poured into water (200 mL) and extracted with EtOAc (3×250 mL). The combined organic layer was concentrated. The residue was purified by column (0~5% of EtOAc in PE) to give 319.3 (8.4 g) as an oil.

$^1$H NMR (400 MHz, CDCl$_3$) δ$_H$ 5.13-5.07 (m, 1H), 3.58-3.55 (d, J=9.2 Hz, 1H), 3.33 (s, 3H), 3.20-3.18 (d, J=9.2 Hz, 1H), 2.38-2.12 (m, 3H), 1.90-1.67 (m, 4H), 1.64-1.54 (m, 6H), 1.48-1.22 (m, 13H), 1.21-1.08 (m, 4H), 0.93 (t, J=7.2 Hz, 3H), 0.85 (s, 3H).

Synthesis of 319.4

To a solution of 319.3 (8.4 g, 22.4 mmol) in THF (150 mL) was added 9-BBN dimmer (21.8 g, 89.6 mmol) at 25° C. under N$_2$. After stirring at 40° C. for 16 h, the reaction mixture was cooled and quenched with EtOH (20.9 g, 448 mmol) at 0° C., followed by adding NaOH (89.6 mL, 5 M, 448 mmol) very slowly. After addition, H$_2$O$_2$ (53.7 mL, 537 mmol, 10 M in water) was added slowly until the reaction temperature no longer rises and the reaction temperature was maintained below 30° C. After stirring at 80° C. for another 2 h, the aqueous phase was extracted with EtOAc (2×350 mL). The combined organic phase was washed with saturated Na$_2$S$_2$O$_3$ (2×100 mL), brine (150 mL), drive over anhydrous Na$_2$SO$_4$, filtered and concentrated. The residue was purified by column (0~20% of EtOAc in PE) to give 319.4 (7.86 g) as a solid.

$^1$H NMR (400 MHz, CDCl$_3$) δ$_H$ 3.72-3.65 (m, 1H), 3.56-3.54 (d, J=9.2 Hz, 1H), 3.32 (s, 3H), 3.18-3.16 (d, J=9.2 Hz, 1H), 1.95-1.72 (m, 5H), 1.70-1.49 (m, 5H), 1.48-1.23 (m, 13H), 1.21-1.04 (m, 9H), 0.93 (t, J=6.8 Hz, 3H), 0.64 (s, 3H).

Synthesis of 319.5

To a solution of 319.4 (7.36 g, 18.7 mmol) in DCM (150 mL) was added DMP (15.8 g, 37.4 mmol). After stirring at 25° C. for 1 h, the mixture was quenched with NaHCO$_3$ (300 mL) and Na$_2$S$_2$O$_3$ (300 mL). The mixture was extracted with DCM (2×300 mL) and the organic layer was washed with Na$_2$S$_2$O$_3$ (2×100 mL, sat.), brine (300 mL, sat.), dried over Na$_2$SO$_4$, filtered and concentrated in vacuum to give 319.5 (11 g) as an oil.

$^1$H NMR (400 MHz, CDCl$_3$) δ$_H$ 3.54-3.52 (d, J=9.2 Hz, 1H), 3.32 (s, 3H), 3.19-3.17 (d, J=9.2 Hz, 1H), 2.52 (t, J=8.8 Hz, 1H), 2.26-1.63 (m, 15H), 1.49-1.08 (m, 15H), 0.93 (t, J=7.2 Hz, 3H), 0.59 (s, 3H). LC-ELSD/MS purity 99%, MS ESI calcd. for C$_{25}$H$_{41}$O$_2$ [M−H$_2$O+H]$^+$ 373.3, found 373.3, C$_{24}$H$_{37}$O [M−MeOH−H$_2$O+H]$^+$ 341.3, found 341.3.

Synthesis of 319.6

To a suspension of MePh$_3$BrP (14.6 g, 40.9 mmol) in anhydrous THF (100 mL) was added t-BuOK (4.58 g, 40.9 mmol) at 25° C. under N$_2$. After stirring at 60° C. for 30 mins, a solution of 319.5 (3.2 g, 8.19 mmol) in anhydrous THF (30 mL) was added dropwise at 25° C. After stirring at 60° C. for 16 h, the resulting suspension was poured into saturated NH₄Cl (100 mL) and extracted with EtOAc (2×100 mL). The combined organic phase was washed with brine (200 mL), filtered and concentrated. The residue was purified by flash column (0~5% of EtOAc in PE) to give 319.6 (2.8 g) as an oil.

$^1$H NMR (400 MHz, CDCl₃) δ$_H$ 4.84 (s, 1H), 4.69 (s, 1H), 3.58-3.56 (d, J=8.8 Hz, 1H), 3.33 (s, 3H), 3.18-3.16 (d, J=9.2 Hz, 1H), 2.04-1.99 (m, 1H), 1.87-1.65 (m, 7H), 1.59-1.37 (m, 6H), 1.36-1.02 (m, 13H), 0.93 (t, J=6.8 Hz, 3H), 0.89-0.83 (m, 4H), 0.54 (s, 3H).

Synthesis of 319.7

To a solution of 319.6 (1 g, 2.57 mmol) in THF (10 ml) was added BH₃·Me₂S (2.05 mL, 20.5 mmol, 10M) at 0° C. After stirring at 15° C. for 16 h, the reaction mixture was cooled and sequentially treated with EtOH (718 mg, 51.3 mmol) at 0° C., NaOH (10.2 mL, 51.3 mmol, 5M) very slowly and finally H₂O₂ (6.15 mL, 61.6 mmol) slowly until the reaction temperature no longer rises and the reaction temperature was maintained below 30° C. After stirring at 80° C. for another 1 h, saturated aqueous Na₂S₂O₃ (50 mL) was added and the mixture was stirred at 0° C. for another 1 h. The aqueous phase was extracted with EtOAc (3×50 mL). The combined organic phase was washed with saturated Na₂S₂O₃ (100 mL), brine (100 mL), drive over anhydrous Na₂SO₄, filtered and concentrated to give 319.7 (800 mg) as a solid.

$^1$H NMR (400 MHz, CDCl₃) δ$_H$ 3.75-3.60 (m, 1H), 3.57-3.55 (m, 1H), 3.46-3.36 (m, 1H), 3.33 (s, 3H), 3.18-3.16 (d, J=8.8 Hz, 1H), 1.97-1.58 (m, 7H), 1.52-1.27 (m, 9H), 1.25-1.02 (m, 12H), 0.95-0.73 (m, 8H), 0.66 (s, 3H).

Synthesis of 319.8 & 319.9

To a solution of 319.7 (400 mg, 0.983 mmol) and 5-methyl-2H-1,2,3,4-tetrazole (123 mg, 1.47 mmol) in THF (5 mL) were added Ph₃P (411 mg, 1.57 mmol) and DEAD (273 mg, 1.57 mmol) at 0° C. After stirring at 25° C. for 16 h, the mixture was poured into ice-water (50 mL) and extracted with EtOAc (3×50 mL). The combined organic phase was washed with brine (2×50 mL), dried over anhydrous Na₂SO₄, filtered and concentrated. The residue was purified by flash column (0~50% of EtOAc in PE) to give 319.8 (350 mg) and 319.9 (100 mg) both as oils.

Separation of 319 & 320

319.8 (350 mgl) was separated by SFC (Column: DAICEL CHIRALPAK AD (250 mm*30 mm, 10 um); Condition: 0.1% NH₃H₂O IPA; Begin B: 40%; End B: 40%) to give 319 (Peak 2, 149.9 mg, Rt=2.912 min, 43%) and 320 (Peak 1, 121.3 mg, Rt=1.369 min, 35%) both as solids.

319.9 (100 mg) was further purified by HPLC (Column: Welch Xtimate C18 150*25 mm*5 um; Condition: water (0.05% NH₃H₂O)-ACN; Begin B: 70; End B: 100; Gradient Time (min): 8.5; 100% B Hold Time (min): 2; FlowRate (ml/min): 30; Injections: 8) to give 50 mg as a solid, which was separated by SFC (Column: DAICEL CHIRALPAK AD (250 mm*30 mm, 10 um); Condition: 0.1% NH₃H₂O ETOH; Begin B: 30%; End B: 30%) to give 321 (Peak 1, 8.2 mg, Rt=1.443 min, 16%) and 322 (Peak 2, 15.1 mg, Rt=1.638 min, 30%) both as solids.

319: $^1$H NMR (400 MHz, CDCl₃) δ$_H$ 4.75-4.70 (m, 1H), 4.26-4.20 (m, 1H), 3.57-3.54 (d, J=9.2 Hz, 1H), 3.33 (s, 3H), 3.20-3.18 (d, J=8.8 Hz, 1H), 2.53 (s, 3H), 2.25-2.17 (m, 1H), 1.91-1.58 (m, 10H), 1.53-1.26 (m, 14H), 1.24-1.06 (m, 6H), 0.93 (t, J=6.8 Hz, 3H), 0.79 (s, 3H), 0.71-0.70 (d, J=6.4 Hz, 1H). LC-ELSD/MS purity 99%, MS ESI calcd. for C₂₈H₄₇O [M−H₂O+H]⁺ 455.4, found 455.4. SFC 100% de.

320: $^1$H NMR (400 MHz, CDCl₃) δ$_H$ 4.54-4.50 (m, 1H), 4.31-4.25 (m, 1H), 3.56-3.54 (d, J=9.2 Hz, 1H), 3.30 (s, 3H), 3.18-3.16 (d, J=8.8 Hz, 1H), 2.53 (s, 3H), 2.17-2.08 (m, 1H), 2.04-1.62 (m, 9H), 1.52-1.27 (m, 12H), 1.25-1.06 (m, 7H), 0.93 (t, J=7.2 Hz, 3H), 0.85-0.83 (d, J=6.8 Hz, 3H), 0.70 (s, 3H). LC-ELSD/MS purity 99%, MS ESI calcd. for C₂₈H₄₇O [M−H₂O+H]⁺ 455.4, found 455.4. SFC 100% de.

321: $^1$H NMR (400 MHz, CDCl₃) δ$_H$ 4.53-4.49 (m, 1H), 3.85-3.79 (m, 1H), 3.55-3.53 (d, J=9.2 Hz, 1H), 3.33 (s, 3H), 3.21-3.19 (d, J=9.2 Hz, 1H), 2.54 (s, 3H), 2.16-2.09 (m, 1H), 1.89-1.61 (m, 7H), 1.53-1.38 (m, 9H), 1.36-1.09 (m, 12H), 0.94 (t, J=7.2 Hz, 3H), 0.80 (s, 3H), 0.71-0.69 (d, J=6.8 Hz, 3H). LC-ELSD/MS purity 99%, MS ESI calcd. for C₂₈H₄₇O [M−H₂O+H]⁺ 455.4, found 455.4. SFC 100% de.

322: $^1$H NMR (400 MHz, CDCl₃) δ$_H$ 4.31-4.26 (m, 1H), 3.87-3.81 (m, 1H), 3.56-3.54 (d, J=8.8 Hz, 1H), 3.33 (s, 3H), 3.19-3.17 (d, J=8.8 Hz, 1H), 2.54 (s, 3H), 2.10-1.62 (m, 8H), 1.53-1.27 (m, 13H), 1.24-1.07 (m, 7H), 0.94 (t, J=7.2 Hz, 3H), 0.82-0.80 (d, J=6.4 Hz, 3H), 0.70 (s, 3H). LC-ELSD/MS purity 99%, MS ESI calcd. for C₂₈H₄₇O [M−H₂O+H]⁺ 455.4, found 455.4. SFC 100% de.

Examples 323 & 324: (3R,5R,8R,9R,10S,13S,14S,17R)-13-methyl-17-(1-(5-methyl-1H-tetrazol-1-yl)propan-2-yl)-3-propylhexadecahydro-1H-cyclopenta[a]phenanthren-3-ol (323)& (3R,5R,8R,9R,10S,13S,14S,17R)-13-methyl-17-(1-(5-methyl-1H-tetrazol-1-yl)propan-2-yl)-3-propylhexadecahydro-1H-cyclopenta[a]phenanthren-3-ol (324)

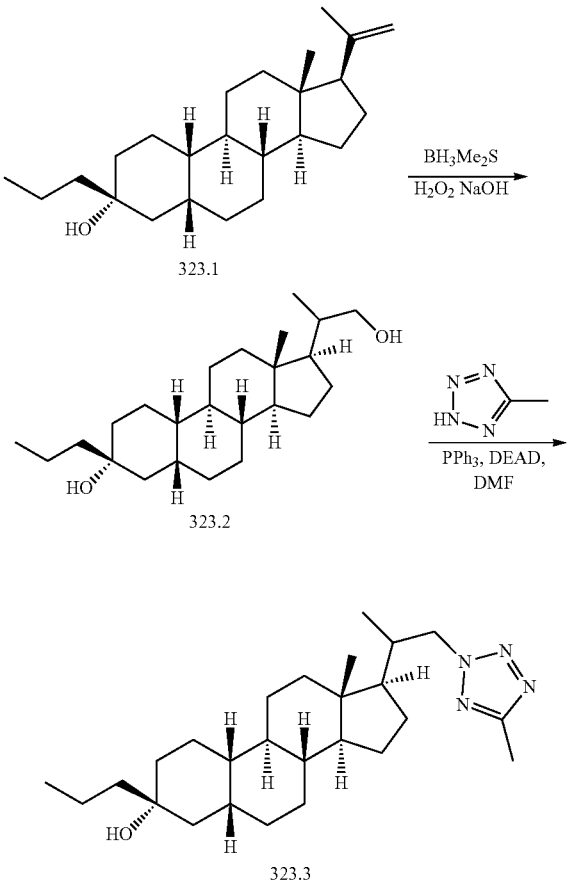

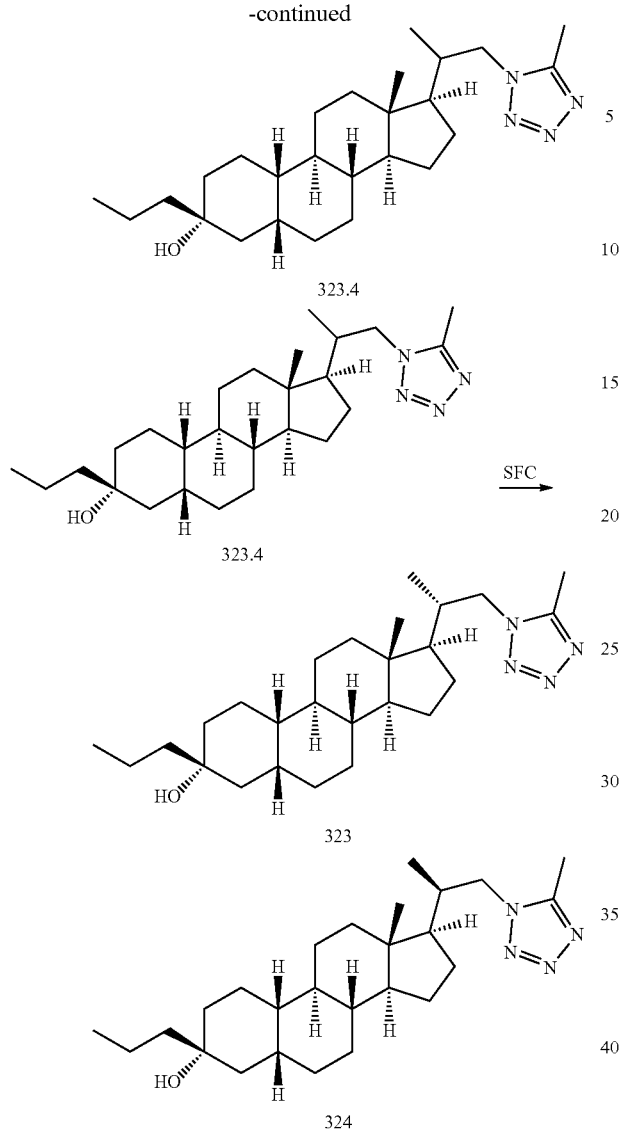

323.4

323.4 → SFC

323

324

Synthesis of 323.2

To a solution of 323.1 (600 mg, 1.74 mmol) in THF (5 mL) was added BH$_3$·Me$_2$S (0.87 mL, 8.7 mmol, 10 M) dropwise at 0° C. After stirring at 25° C. for 3 h, the reaction mixture was cooled to 0° C. and sequentially treated with ethanol (800 mg, 17.4 mmol) at 0° C., NaOH aqueous (1.73 mL, 17.4 mmol, 5 M) dropwise and finally by H$_2$O$_2$ (1.73 mL, 17.4 mmol) at 0° C. After stirring at 70° C. for 1 h, the mixture was extracted with EtOAc (2×50 mL). The combined organic phase was washed with saturated Na$_2$S$_2$O$_3$ aqueous (2×20 mL), brine (50 mL), dried over Na$_2$SO$_4$, filtered and evaporated to give 323.2 (620 mg) as an oil.

$^1$H NMR (400 MHz, CDCl$_3$) δ$_H$ 3.85-3.58 (m, 1H), 3.52-3.29 (m, 1H), 2.01-1.71 (m, 5H), 1.71-1.58 (m, 4H), 1.51-1.12 (m, 17H), 1.11-0.98 (m, 6H), 0.97-0.90 (m, 5H), 0.68 (s, 3H).

Synthesis of 323.3 & 323.4

To a solution of 323.1 (24 g, 66.1 mmol) and 5-methyl-2H-1,2,3,4-tetrazole (8.33 g, 99.1 mmol) in DMF (500 mL) were added Ph$_3$P (27.5 g, 105 mmol) and DEAD (18.2 g, 105 mmol). After stirring at 25° C. for 16 h, the mixture was poured into water (500 mL) and extracted with EtOAc (2×250 mL). The combined organic phase was washed with brine (250 mL), dried over anhydrous Na$_2$SO$_4$, filtered and concentrated. The residue was purified by flash column (0~50% of EtOAc in PE) to give 323.3 (16.2 g, 57%) and 323.4 (10 g) both as solids.

Separation of 324 & 325

323.4 was triturated from MeOH/H$_2$O=1:1 (240 mL) at 25° C. and separated by SFC (Column: DAICEL CHIRALCEL OD 250 mm×50 mm, 10 um; Condition: 0.1% NH$_3$H$_2$O ETOH; Gradient: from 40% to 40% of B; Flow rate: 200 mL/min; Column temperature: 40° C.) to afford 323 (1569.1 mg, 23%) and 324 (2304.6 mg, 33.9%) both as solid.

323: $^1$H NMR (400 MHz, CDCl$_3$) δ$_H$ 4.33-4.24 (m, 1H), 3.91-3.80 (m, 1H), 2.55 (s, 3H), 2.12-2.01 (m, 1H), 2.01-1.91 (m, 2H), 1.82-1.61 (m, 6H), 1.56-1.51 (m, 2H), 1.49-1.42 (m, 3H), 1.40-1.29 (m, 8H), 1.27-1.01 (m, 8H), 0.93 (t, J=7.2 Hz, 3H), 0.82 (d, J=6.4 Hz, 3H), 0.71 (s, 3H). LC-ELSD/MS purity 99%, MS ESI calcd. for C$_{26}$H$_{43}$N$_4$ [M−H$_2$O+H]$^+$ 411.3 found 411.3 analytic SFC 100% de.

324: $^1$H NMR (400 MHz, CDCl$_3$) δ$_H$ 4.54 (dd, J=4.4, 13.6 Hz, 1H), 3.84 (dd, J=11.2, 13.6 Hz, 1H), 2.55 (s, 3H), 2.20-2.04 (m, 1H), 1.91-1.62 (m, 8H), 1.55-1.44 (m, 4H), 1.41-1.24 (m, 12H), 1.16_1.04 (m, 5H), 0.93 (t, J=7.2 Hz, 3H), 0.82 (s, 3H), 0.70 (d, J=6.4 Hz, 3H).

LC-ELSD/MS purity 99%, MS ESI calcd. for C$_{26}$H$_{43}$N$_4$ [M−H$_2$O+H]$^+$ 411.3 found 411.3 analytic SFC 100% de.

Examples 325 & 326: 1-((S)-2-((3R,5R,8S,9S,10S,13S,14S,17R)-10-ethyl-3-hydroxy-3,13-dimethylhexadecahydro-1H-cyclopenta[a]phenanthren-17-yl)propyl)-1H-pyrazole-4-carbonitrile (325) & 1-((R)-2-((3R,5R,8S,9S,10S,13S,14S,17R)-10-ethyl-3-hydroxy-3,13-dimethylhexadecahydro-1H-cyclopenta[a]phenanthren-17-yl)propyl)-1H-pyrazole-4-carbonitrile (326)

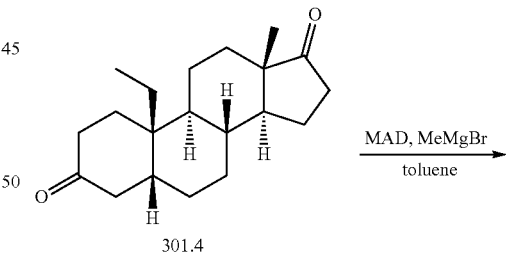

301.4 → MAD, MeMgBr / toluene

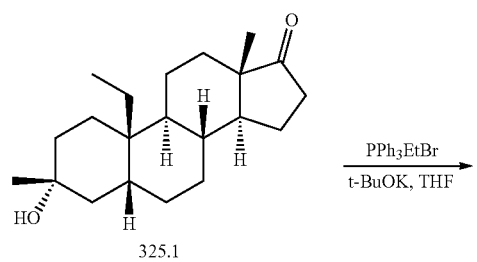

325.1 → PPh$_3$EtBr / t-BuOK, THF

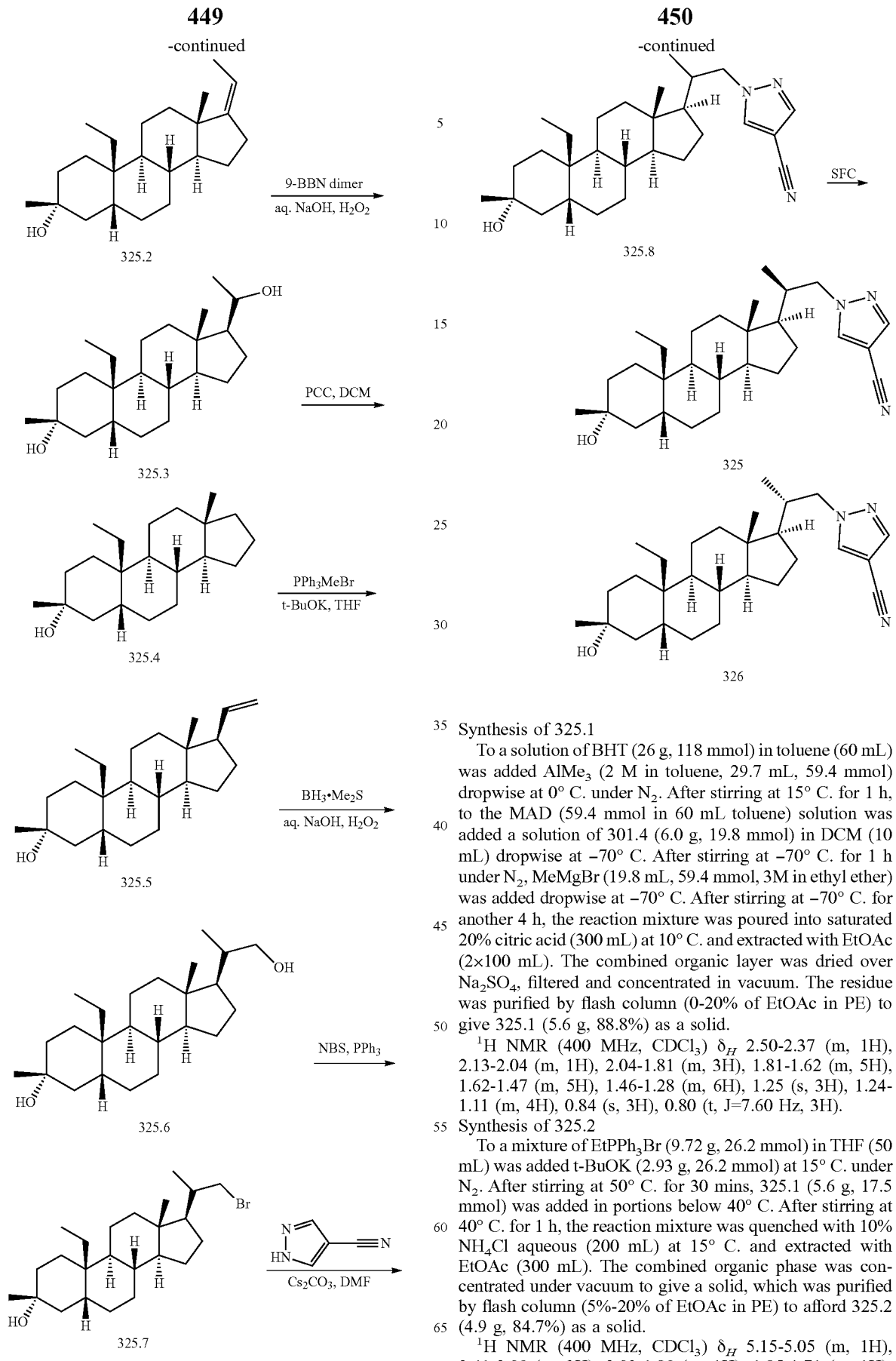

Synthesis of 325.1

To a solution of BHT (26 g, 118 mmol) in toluene (60 mL) was added AlMe₃ (2 M in toluene, 29.7 mL, 59.4 mmol) dropwise at 0° C. under N₂. After stirring at 15° C. for 1 h, to the MAD (59.4 mmol in 60 mL toluene) solution was added a solution of 301.4 (6.0 g, 19.8 mmol) in DCM (10 mL) dropwise at −70° C. After stirring at −70° C. for 1 h under N₂, MeMgBr (19.8 mL, 59.4 mmol, 3M in ethyl ether) was added dropwise at −70° C. After stirring at −70° C. for another 4 h, the reaction mixture was poured into saturated 20% citric acid (300 mL) at 10° C. and extracted with EtOAc (2×100 mL). The combined organic layer was dried over Na₂SO₄, filtered and concentrated in vacuum. The residue was purified by flash column (0-20% of EtOAc in PE) to give 325.1 (5.6 g, 88.8%) as a solid.

$^1$H NMR (400 MHz, CDCl₃) $\delta_H$ 2.50-2.37 (m, 1H), 2.13-2.04 (m, 1H), 2.04-1.81 (m, 3H), 1.81-1.62 (m, 5H), 1.62-1.47 (m, 5H), 1.46-1.28 (m, 6H), 1.25 (s, 3H), 1.24-1.11 (m, 4H), 0.84 (s, 3H), 0.80 (t, J=7.60 Hz, 3H).

Synthesis of 325.2

To a mixture of EtPPh₃Br (9.72 g, 26.2 mmol) in THF (50 mL) was added t-BuOK (2.93 g, 26.2 mmol) at 15° C. under N₂. After stirring at 50° C. for 30 mins, 325.1 (5.6 g, 17.5 mmol) was added in portions below 40° C. After stirring at 40° C. for 1 h, the reaction mixture was quenched with 10% NH₄Cl aqueous (200 mL) at 15° C. and extracted with EtOAc (300 mL). The combined organic phase was concentrated under vacuum to give a solid, which was purified by flash column (5%-20% of EtOAc in PE) to afford 325.2 (4.9 g, 84.7%) as a solid.

$^1$H NMR (400 MHz, CDCl₃) $\delta_H$ 5.15-5.05 (m, 1H), 2.41-2.09 (m, 3H), 2.03-1.89 (m, 1H), 1.85-1.71 (m, 1H), 1.70-1.59 (m, 6H), 1.59-1.37 (m, 9H), 1.37-1.27 (m, 3H), 1.25 (s, 3H), 1.22-1.04 (m, 5H), 0.85 (s, 3H), 0.79 (t, J=7.6 Hz, 3H).

Synthesis of 325.3

To a solution of 325.2 (4.9 g, 14.8 mmol) in THF (50 mL) was added 9-BBN dimer (10.8 g, 44.4 mmol) at 15° C. After stirring at 40° C. for 1 h, the reaction was sequentially treated with ethanol (6.8 g, 148 mmol) at 15° C., NaOH aqueous (29.5 mL, 5M, 148 mmol) at −10° C. and finally by $H_2O_2$ (14.7 mL, 10 M, 148 mmol) dropwise. After stirring at 80° C. for 1 h, the reaction was quenched with aqueous sat. $Na_2S_2O_3$ (50 mL), stirred for 30 mins and extracted with EtOAc (100 mL). The combined organic phase was washed with brine (2×100 mL), dried over anhydrous $Na_2SO_4$, concentrated under vacuum to give 325.3 (11 g) as a solid.

$^1$H NMR (400 MHz, CDCl$_3$) $\delta_H$ 3.77-3.62 (m, 1H), 2.03-1.91 (m, 3H), 1.83-1.71 (m, 5H), 1.57-1.45 (m, 12H), 1.24 (s, 3H), 1.21 (d, J=6.40 Hz, 3H), 1.18-0.94 (m, 7H), 0.81-0.76 (m, 3H), 0.64 (s, 3H).

Synthesis of 325.4

To a solution of 325.3 (5.15 g, 14.8 mmol) in DCM (100 mL) was added silica gel (10 g) and PCC (6.36 g, 29.6 mmol) at 0° C. After stirring at 15° C. for 3 h, the suspension was filtered and the filter cake was washed with DCM (2×100 mL). The combined filtrate was concentrated under vacuum to give a solid, which was purified by flash column (PE/EtOAc=20/1 to 4/1) to afford 325.4 (2.8 g, 54.6%) as a solid.

$^1$H NMR (400 MHz, CDCl$_3$) $\delta_H$ 2.60-2.45 (m, 1H) 2.28-2.12 (m, 1H), 2.11 (s, 3H), 2.03-1.91 (m, 2H), 1.82-1.59 (m, 6H), 1.54-1.28 (m, 10H), 1.25 (s, 3H), 1.24-1.03 (m, 6H), 0.79 (t, J=7.60 Hz, 3H), 0.59 (s, 3H).

Synthesis of 325.5

To a mixture of MePPh$_3$Br (4.5 g, 12.6 mmol) in THF (20 mL) was added t-BuOK (1.41 g, 12.6 mmol) at 15° C. under N$_2$. After stirring at 50° C. for 30 mins, 325.4 (2.2 g, 6.34 mmol) was added in portions below 50° C. After stirring at 50° C. for 1 h, the reaction mixture was quenched with 10% NH$_4$Cl aqueous (100 mL) at 15° C. and extracted with EtOAc (100 mL). The combined organic phase was concentrated under vacuum to give a solid. The residue was purified by silica gel chromatography (PE/EtOAc=20/1 to 5/1) to afford 325.5 (1.6 g, 73.3%) as a solid.

$^1$H NMR (400 MHz, CDCl$_3$) $\delta_H$ 4.84 (s, 1H), 4.69 (s, 1H), 2.04-1.90 (m, 2H), 1.87-1.76 (m, 2H), 1.75 (s, 3H), 1.73-1.57 (m, 5H), 1.53-1.26 (m, 9H), 1.25 (s, 3H), 1.23-0.82 (m, 8H), 0.79 (t, J=7.60 Hz, 3H), 0.54 (s, 3H).

Synthesis of 325.6

To a solution of 325.5 (400 mg, 1.16 mmol) in THF (10 mL) was added BH$_3$Me$_2$S (0.348 mL, 10 M in DMS, 3.48 mmol) at 15° C. After stirring at 15° C. for 16 h, the reaction was treated sequentially with EtOH (533 mg, 11.6 mmol) at 15° C., NaOH (2.32 mL. 5M in water, 11.6 mmol) at 0° C. and finally by H$_2$O$_2$ (1.2 mL, 10 M, 11.6 mmol) dropwise. After stirring at 80° C. for 1 h, the reaction mixture was quenched with sat. Na$_2$S$_2$O$_3$ (50 mL), stirred for 30 mins. and extracted with EtOAc (100 mL). The combined organic phase was washed with brine (2×100 mL), dried over anhydrous Na$_2$SO$_4$ and concentrated under vacuum to give 325.6 (400 mg, 95.2%) as a solid.

$^1$H NMR (400 MHz, CDCl$_3$) $\delta_H$ 3.75-3.70 (m, 1H), 3.48-3.40 (m, 1H), 2.01-1.71 (m, 6H), 1.70-1.58 (m, 4H), 1.50-1.37 (m, 5H), 1.34-1.28 (m, 2H), 1.24 (s, 3H), 1.22-0.98 (m, 11H), 0.95 (d, J=6.80 Hz, 3H), 0.79 (t, J=7.60 Hz, 3H), 0.66 (s, 3H).

Synthesis of 325.7

To a solution of 325.6 (400 mg, 1.1 mmol) in DCM (10 mL) was added PPh$_3$ (432 mg, 1.65 mmol) and NBS (293 mg, 1.65 mmol) at 0° C. After stirring at 20° C. for 2 h, the mixture was added into water (50 mL) and extracted with DCM (2×50 mL). The combined organic phase was washed with brine (100 mL), dried over anhydrous Na$_2$SO$_4$, filtered and concentrated. The residue was purified by flash column (0~15% of EtOAc in PE) to give 325.7 (400 mg, 85.4%) as oil.

$^1$H NMR (400 MHz, CDCl$_3$) $\delta_H$ 3.66-3.47 (m, 1H), 3.41-3.28 (m, 1H), 2.03-1.71 (m, 5H), 1.71-1.59 (m, 3H), 1.56-1.49 (m, 2H), 1.48-1.28 (m, 12H), 1.24 (s, 3H), 1.23-1.10 (m, 5H), 1.07 (d, J=6.40 Hz, 2H), 1.00 (d, J=6.40 Hz, 2H), 0.79 (t, J=7.60 Hz, 3H), 0.67-0.65 (m, 3H).

Synthesis of 325.8

To a solution of 325.7 (200 mg, 0.47 mmol) in DMF (10 mL) were added Cs$_2$CO$_3$ (306 mg, 0.94 mmol) and 1H-pyrazole-4-carbonitrile (65.6 mg, 0.705 mmol). After stirring at 80° C. for 3 h under N$_2$, the mixture was added into saturated NH$_4$Cl (100 mL) and extracted with EtOAc (3×100 mL). The combined organic layer was washed with LiCl (100 mL, 5% in water), brine (2×100 mL), dried over anhydrous Na$_2$SO$_4$, filtered and concentrated. The residue was purified by flash column (0~30% of EtOAc in PE) to afford 325.8 (200 mg, 97.5%) as a solid.

$^1$H NMR (400 MHz, CDCl$_3$) $\delta_H$ 7.80 (s, 1H), 7.76 (s, 1H), 4.57-4.19 (m, 1H), 3.78-3.52 (m, 1H), 2.19-2.05 (m, 1H), 2.04-1.71 (m, 6H), 1.57-1.32 (m, 11H), 1.25 (s, 3H), 1.22-1.01 (m, 9H), 0.79 (s, 3H), 0.77 (s, 3H), 0.64-0.70 (m, 3H).

Synthesis of 325 & 326

325.8 (200 mg, 0.46 mmol) was separated by SFC (Column: DAICEL CHIRALPAK AD (250 mm*50 mm, 10 um), Condition: 0.1% NH$_3$H$_2$O IPA, Begin B: 30%, End B: 30%, FlowRate (ml/min): 70) to afford 325 (60 mg, 30.1%) as a solid and 326 (65 mg, 32.6%) as a solid.

325: $^1$H NMR (400 MHz, CDCl$_3$) $\delta_H$ 7.80 (s, 1H), 7.75 (s, 1H), 4.48 (dd, J=13.40, 4.40 Hz, 1H), 3.65 (dd, J=13.20, 10.80 Hz, 1H), 2.16-2.02 (m, 1H), 2.00-1.56 (m, 8H), 1.54-1.43 (m, 2H), 1.43-1.27 (m, 8H), 1.25 (s, 3H), 1.24-1.02 (m, 8H), 0.84-0.74 (m, 6H), 0.67 (d, J=6.60 Hz, 3H). LC-ELSD/MS: purity >99%; analytic SFC: 99.28% de; MS ESI calcd. for C$_{28}$H$_{42}$N$_3$ [M−H$_2$O+H]$^+$ 420.3, found 420.3. SFC 100% de.

326: $^1$H NMR (400 MHz, CDCl$_3$) $\delta_H$ 7.80 (s, 1H), 7.75 (s, 1H), 4.25 (dd, J=13.40, 3.60 Hz, 1H), 3.72 (dd, J=13.40, 9.60 Hz, 1H), 2.10-1.86 (m, 4H), 1.84-1.59 (m, 4H), 1.55-1.49 (m, 2H), 1.49-1.26 (m, 9H), 1.25 (s, 3H), 1.22-1.04 (m, 8H), 0.82-0.75 (m, 6H), 0.69 (s, 3H). LC-ELSD/MS: purity >99%; analytic SFC: 100% de; MS ESI calcd. for C$_{28}$H$_{42}$N$_3$ [M−H$_2$O+H]$^+$ 420.3, found 420.3. SFC 100% de.

Examples 327 & 328: 1-((R)-2-((3R,5R,8S,9S,10S,11S,13S,14S,17R)-3,11-dihydroxy-3-(methoxymethyl)-10,13-dimethylhexadecahydro-1H-cyclopenta[a]phenanthren-17-yl)propyl)-1H-pyrazole-4-carbonitrile (327) & 1-((S)-2-((3R,5R,8S,9S,10S,11S,13S,14S,17R)-3,11-dihydroxy-3-(methoxymethyl)-10,13-dimethylhexadecahydro-1H-cyclopenta[a]phenanthren-17-yl)propyl)-1H-pyrazole-4-carbonitrile (328)

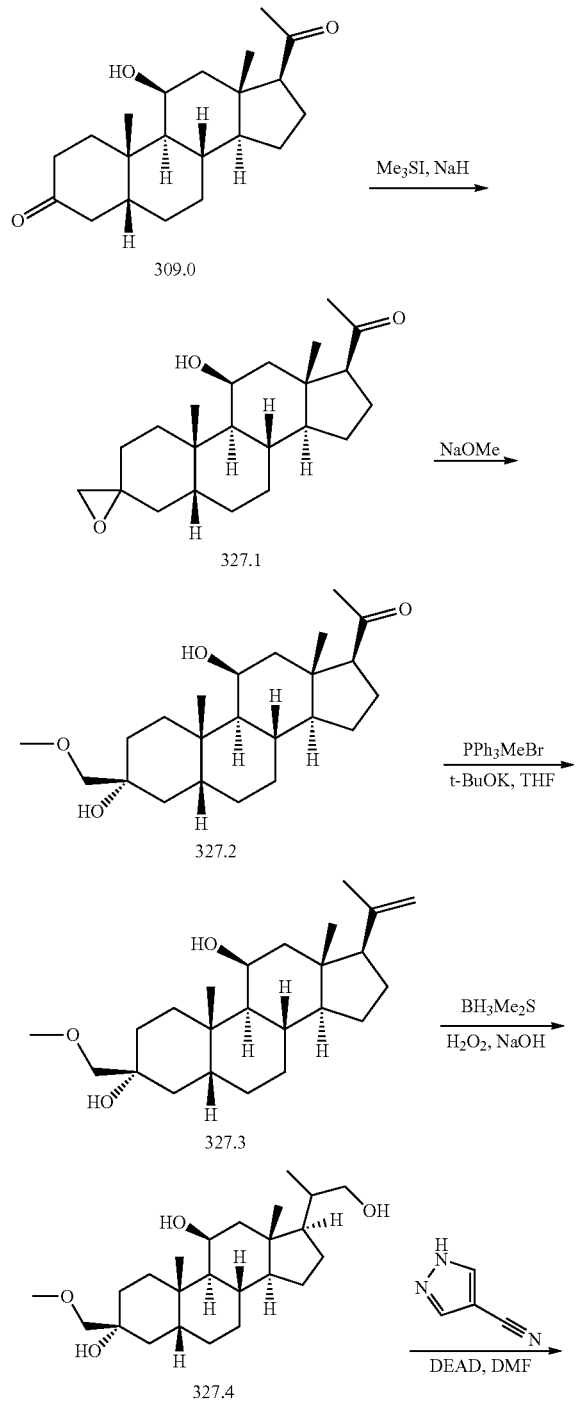

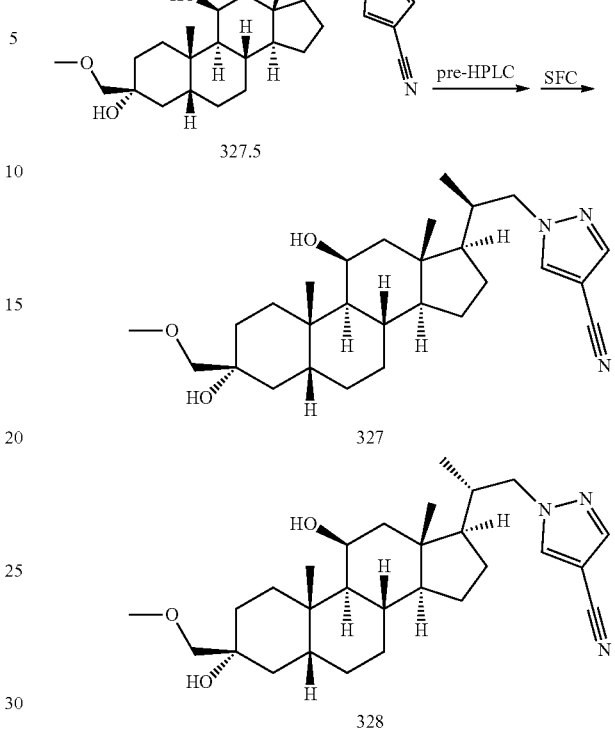

Synthesis of 327.1

To a solution of Me$_3$SI (2.75 g, 13.5 mmol) in THF (30 mL) and DMSO (30 mL) was added NaH (540 mg, 13.5 mmol, 60%) at 0° C. in portions under N$_2$. After stirring at 0° C. for 1 h, to the resulting mixture was added a solution of 309.0 (3 g, 9.02 mmol) in DMSO (30 mL). After stirring at 25° C. for another 2 h, the resulting suspension was poured into water (200 mL), the aqueous phase was extracted with EtOAc (2×300 mL). The combined organic phase was washed with brine (200 mL), dried over anhydrous Na$_2$SO$_4$, filtered and concentrated. The residue was purified by flash column (0~15% of EtOAc in PE) to give 327.1 (1.4 g) as oil.

Synthesis of 327.2

To a solution of 327.1 (820 mg, 2.36 mmol) in MeOH (15 mL) was added MeONa (1.27 g, 23.6 mmol). After stirring at 50° C. for 16 h, the reaction mixture was combined with another batch prepared from 1.4 g of 327.1, poured into water (100 mL) and extracted with ethyl acetate (2×150 mL). The combined organic layers were washed with saturated aqueous NH$_4$Cl (100 mL), brine (100 mL), dried over anhydrous Na$_2$SO$_4$, filtered and concentrated. The residue, which was combined with 530 mg of 327.2, and purified by flash column (0~40% ethyl acetate in PE) to give 327.2 (870 mg) as oil.

Synthesis of 327.3

To a suspension of MePh$_3$PBr (6.68 g, 18.7 mmol) in anhydrous THF (50 mL) was added t-BuOK (2.09 g, 18.7 mmol) at 25° C. under N$_2$. After stirring at 60° C. for 30 mins, a solution of 327.2 (710 mg, 1.87 mmol) in anhydrous THF (10 mL) was added dropwise. After stirring at 60° C. for 16 h, the mixture was cooled and poured into ice-water (100 mL), stirred for 10 mins. and extracted with EtOAc (2×150 mL). The combined organic phase was washed with brine (2×100 mL), filtered and concentrated. The residue was purified by flash column (0~25% of EtOAc in PE) to give 327.3 (290 mg) as a solid.

Synthesis of 327.4

To a solution of 327.3 (290 mg, 0.770 mmol) in THF (15 mL) was added BH$_3$Me$_2$S (0.384 mL, 10 M, 3.84 mmol) at 25° C. After stirring at 25° C. for 16 h, the reaction was sequentially treated with EtOH (1.33 mL, 23.0 mmol) at 25° C., NaOH (4.60 mL, 5.0 M, 23.0 mmol) at 0° C., and H$_2$O$_2$ (2.30 mL, 23.0 mmol, 30% in water) dropwise. After stirring at 70° C. for 1 h, the mixture was poured into water (80 mL) and extracted with EtOAc (2×100 mL). The combined organic layer was washed with saturated Na$_2$S$_2$O$_3$ (100 mL), brine (100 mL), dried over anhydrous Na$_2$SO$_4$, filtered and concentrated to give 327.4 (320 mg) as oil.

Synthesis of 327.5

To a solution of 327.4 (320 mg, 0.810 mmol) in DMF (10 mL) were added Ph$_3$P (1.06 g, 4.05 mmol), DEAD (705 mg, 0.637 mL, 4.05 mmol) and 1H-pyrazole-4-carbonitrile (149 mg, 1.61 mmol) at 0° C. After stirring at 25° C. for 16 h, the mixture was poured into water (30 mL) and extracted with EtOAc (2×50 mL). The combined organic phase was washed with brine (30 mL), dried over anhydrous Na$_2$SO$_4$, filtered and concentrated.

Separation of 327 & 328

325.5 was separated by pre-HPLC (Column: Welch Xtimate C18 150*25 mm*5 um; Condition: water (0.05% NH$_3$H$_2$O)-ACN; Begin B: 55%; End B: 85%) to afford 327 (20 mg) and 450 (60 mg) both as solids. 327 (60 mg) was repurified by SFC (Column: DAICEL CHIRALCEL OD-H (250 mm*30 mm, 5 um); Condition: 0.1% NH$_3$H$_2$O ETOH; Begin B: 45%; End B: 45%; Flow Rate (ml/min): 50) to give 327 (Peak 3, Rt=4.125 min, 7 mg, 11.7%) as a solid. 328 (95 mg) was repurified by SFC (Column: DAICEL CHIRALCEL OD (250 mm*30 mm, 10 um); Condition: 0.1% NH$_3$H$_2$O ETOH; Begin B: 60%; End B: 60%; Flow Rate (ml/min): 80) to give 328 (Peak 2, Rt=6.567 min, 27 mg, 28.4%) as a solid.

327: $^1$H NMR (400 MHz, CDCl$_3$) $\delta_H$ 7.80 (s, 1H), 7.76 (s, 1H), 4.53-4.47 (m, 1H), 4.19 (br s, 1H), 3.70-3.62 (m, 1H), 3.44-3.36 (m, 5H), 2.69 (s, 1H), 2.16-2.01 (m, 2H), 1.94-1.80 (m, 4H), 1.79-1.65 (m, 3H), 1.50-1.22 (m, 7H), 1.18 (s, 4H), 1.17-1.07 (m, 4H), 1.06-1.03 (m, 1H), 1.00 (s, 3H), 0.67 (d, J=6.4 Hz, 3H). LC-ELSD/MS purity 99%, MS ESI calcd. for C$_{28}$H$_{40}$N$_3$O [M−2H$_2$O+H]$^+$ 434.3 found 434.3. SFC 100% de.

328: $^1$H NMR (400 MHz, CDCl$_3$) $\delta_H$ 7.80 (s, 1H), 7.75 (s, 1H), 4.27-4.16 (m, 2H), 3.77-3.68 (m, 1H), 3.40 (s, 5H), 2.04-1.96 (m, 1H), 1.94-1.79 (m, 4H), 1.78-1.63 (m, 3H), 1.56-1.53 (m, 1H), 1.48-1.38 (m, 4H), 1.30-1.22 (m, 2H), 1.18 (s, 4H), 1.13-1.06 (m, 3H), 1.02-0.97 (m, 1H), 0.92 (s, 3H), 0.82 (d, J=6.4 Hz, 3H). LC-ELSD/MS purity 99%, MS ESI calcd. for C$_{28}$H$_{40}$N$_3$O [M−2H$_2$O+H]$^+$ 434.3 found 434.3. SFC 100% de.

Example 329-332: Synthesis of (3R,5S,8R,9R,10S,13S,14S,17R)-13-methyl-17-((R)-1-(5-methyl-2H-tetrazol-2-yl)propan-2-yl)-3-propylhexadecahydro-1H-cyclopenta[a]phenanthren-3-ol (329) & (3R,5S,8R,9R,10S,13S,14S,17R)-13-methyl-17-((S)-1-(5-methyl-2H-tetrazol-2-yl)propan-2-yl)-3-propylhexadecahydro-1H-cyclopenta[a]phenanthren-3-ol (330) & (3R,5S,8R,9R,10S,13S,14S,17R)-13-methyl-17-((S)-1-(5-methyl-1H-tetrazol-1-yl)propan-2-yl)-3-propylhexadecahydro-1H-cyclopenta[a]phenanthren-3-ol (331) & (3R,5S,8R,9R,10S,13S,14S,17R)-13-methyl-17-((R)-1-(5-methyl-1H-tetrazol-1-yl)propan-2-yl)-3-propylhexadecahydro-1H-cyclopenta[a]phenanthren-3-ol (332)

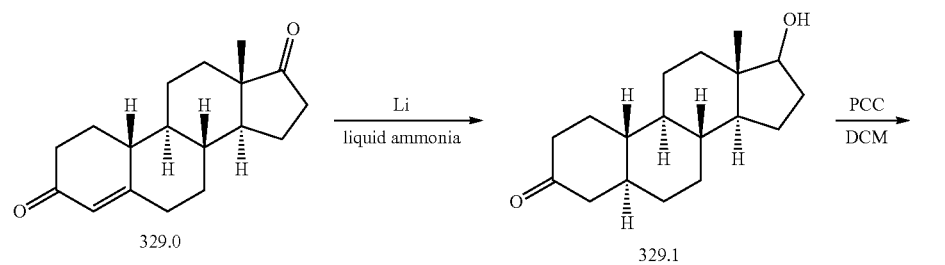

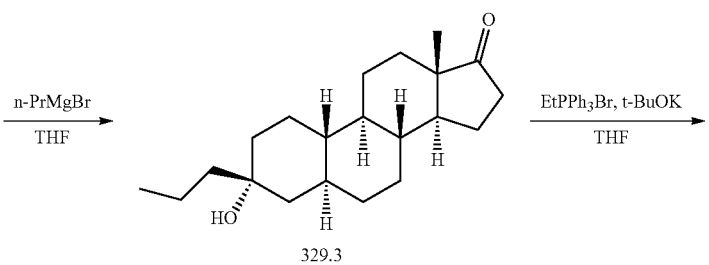

-continued
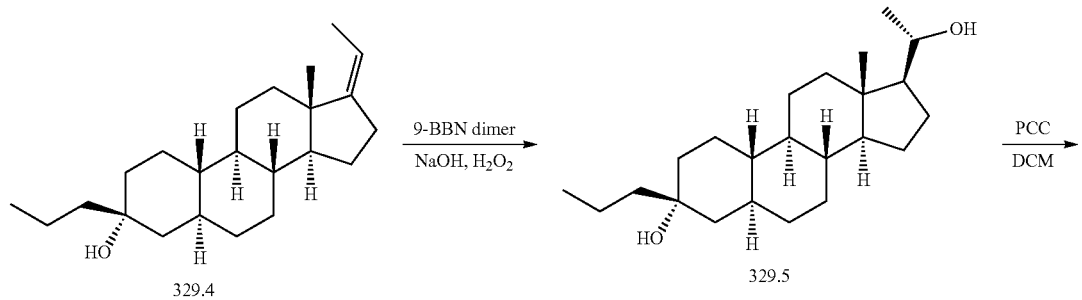
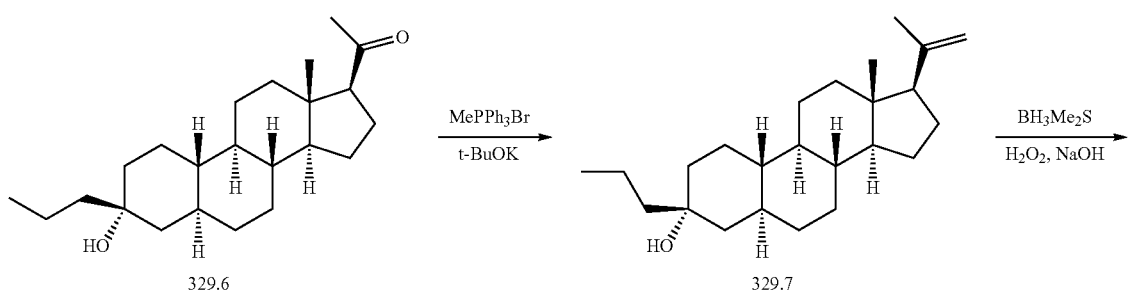
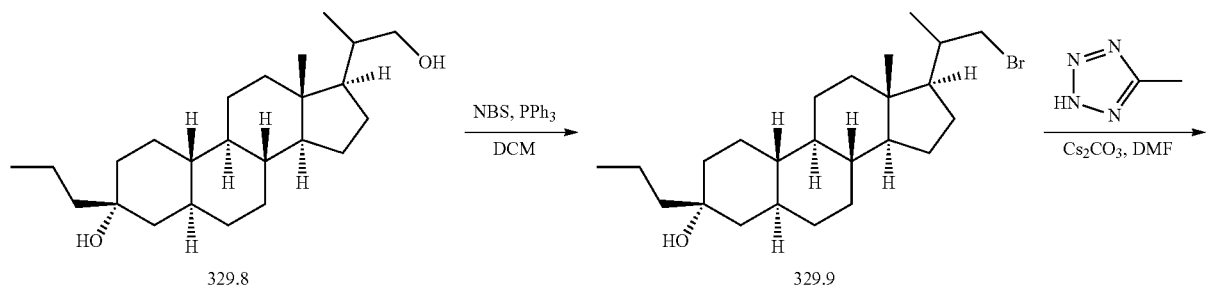
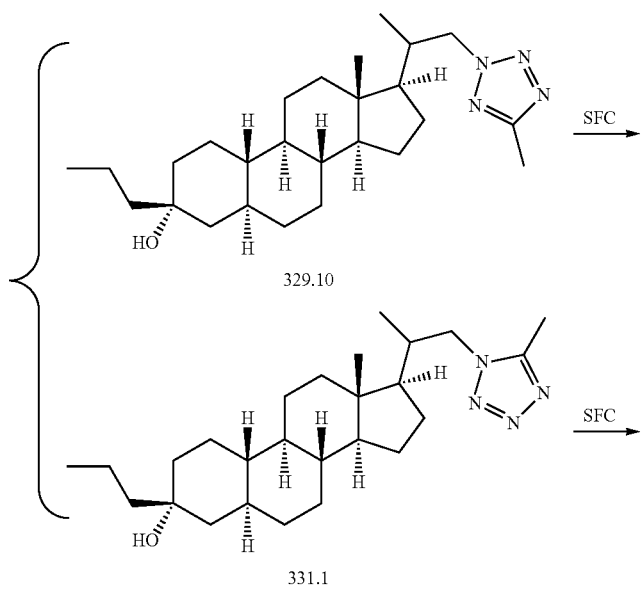

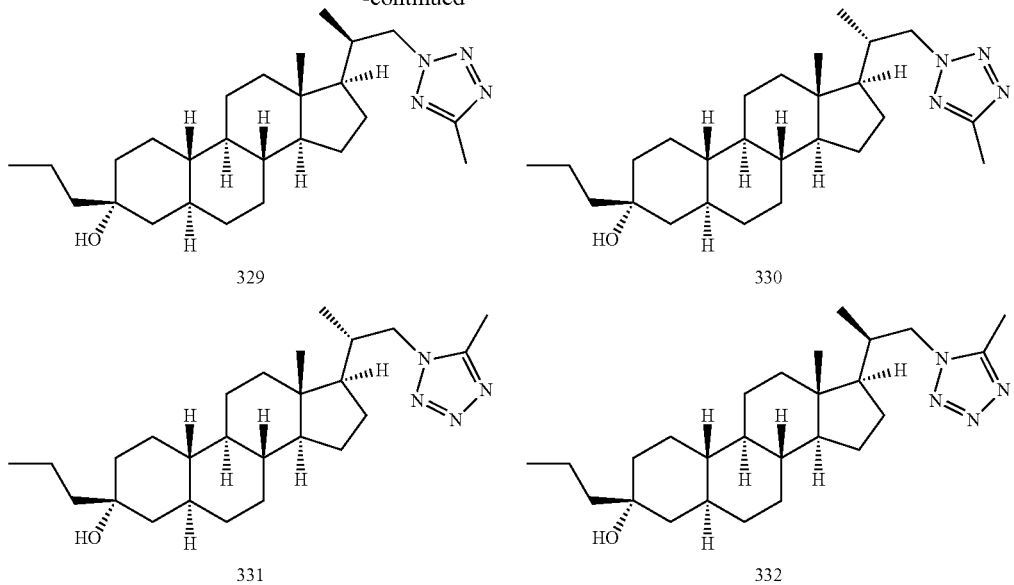

Synthesis of 329.1

Lithium (7.27 g, 915 mmol) was added to fresh prepared liquid ammonia (500 mL) in portions at −70° C. under $N_2$. After stirring at −70° C. for 1 h, a solution of 329.0 (50 g, 183 mmol) and t-butanol (27 g, 366 mmol) in THF (500 mL) was added below −60° C. After stirring at −70° C. for 1 h, ammonium chloride (500 g) was added, then the mixture was warmed to 25° C. After stirring for 16 h, the reaction mixture was added $H_2O$ (1 L) and extracted with EtOAc (3×500 mL). The combined organic solution was washed with 1 M HCl (2×500 mL), saturated $NaHCO_3$ aqueous (500 mL), brine (1 L), dried over $Na_2SO_4$ and concentrated under vacuum to give 329.1 (97 g) as oil.

$^1$H NMR (400 MHz, $CDCl_3$) $\delta_H$ 3.75-3.55 (m, 1H), 2.50-2.00 (m, 10H), 2.00-1.25 (m, 8H), 1.25-0.60 (m, 9H).

Synthesis of 329.2

To a solution of 329.1 (100 g, 361 mmol) in DCM (1000 mL) were added silica gel (116 g) and PCC (116 g, 541 mmol) at 0° C. After stirring at 25° C. for 2 h, PE (1000 mL) was added to the reaction mixture. The resulting mixture was filtered through a pad of silica gel and the filter cake was washed with DCM (2000 mL). The filtrate was concentrated to give 329.2 (90 g) as oil. $^1$H NMR (400 MHz, $CDCl_3$) $\delta_H$ 2.55-2.02 (m, 8H), 2.02-1.39 (m, 8H), 1.39-0.69 (m, 10H).

Synthesis of 329.3

To a solution of 329.2 (15 g, 54.6 mmol) in THF (200 mL) was added n-PrMgCl (81.5 mL, 163 mmol, 2M in THF) dropwise at −60° C. under $N_2$. After stirring at −60° C. for 2 h, the reaction mixture was poured into saturated aqueous $NH_4Cl$ (100 mL) at 0° C. and extracted with EtOAc (2×200 mL). The combined organic layer was dried over $Na_2SO_4$, filtered and concentrated. The residue was triturated from MeCN (50 mL) at 80° C. to give 329.3 (7 g, 40.4%) as a solid.

$^1$H NMR (400 MHz, $CDCl_3$) $\delta_H$ 2.44 (dd, J=8.4, 19.2 Hz, 1H), 2.14-2.00 (m, 1H), 1.99-1.84 (m, 2H), 1.83-1.71 (m, 3H), 1.70-1.44 (m, 5H), 1.43-1.12 (m, 10H), 1.11-0.99 (m, 4H), 0.97-0.90 (m, 3H), 0.88 (s, 3H), 0.81-0.66 (m, 2H).

Synthesis of 329.4

To a mixture of $EtPPh_3Br$ (24.3 g, 65.6 mmol) in THF (80 mL) was added t-BuOK (7.36 g, 65.6 mmol) at 15° C. under $N_2$. After stirring for 30 mins, 329.3 (7 g, 21.9 mmol) in THF (20 mL) was added. After stirring at 40° C. for 1 h, the mixture was poured into $NH_4Cl$ (50 mL) and extracted with EtOAc (2×100 mL). The combined organic phase was washed with brine (100 mL), dried over anhydrous $Na_2SO_4$, filtered and concentrated. The residue was heated at 70° C. in MeOH (50 mL) for 30 minutes, cooled to room temperature, poured into water (50 mL), filtered to give 329.4 (11 g) as a solid.

$^1$H NMR (400 MHz, $CDCl_3$) $\delta_H$ 5.24-4.98 (m, 1H), 2.45-2.30 (m, 1H), 2.28-2.11 (m, 2H), 1.88-1.74 (m, 2H), 1.73-1.57 (m, 7H), 1.55-1.48 (m, 2H), 1.44-1.25 (m, 6H), 1.24-0.96 (m, 9H), 0.95-0.90 (m, 3H), 0.88 (s, 3H), 0.78-0.62 (m, 2H).

Synthesis of 329.5

To a solution of 329.4 (6 g, 18.1 mmol) in anhydrous THF (60 mL) was added 9-BBN dimer (13.2 g, 54.3 mmol) at 15° C. under $N_2$. After stirring at 60° C. for 2 h, the mixture was cooled and treated sequentially with EtOH (15 mL), NaOH (15 mL, 5M, 75.5 mmol) very slowly and $H_2O_2$ (22.6 mL, 226 mmol, 10 M) slowly below 30° C. After stirring at 60° C. for 2 h, the mixture was cooled, poured into water (50 mL) and extracted with EtOAc (2×50 mL). The combined organic layer was dried over $Na_2SO_4$, filtered and concentrated in vacuum. The product was purified by flash column (20~25% of EtOAc in PE) to give 329.5 (6.1 g, 52.8%) as a solid.

$^1$H NMR (400 MHz, $CDCl_3$) $\delta_H$ 3.86-3.57 (m, 1H), 1.98-1.81 (m, 2H), 1.81-1.70 (m, 2H), 1.70-1.60 (m, 3H), 1.57-1.48 (m, 3H), 1.42-1.25 (m, 7H), 1.23 (d, J=6.0 Hz, 3H), 1.17-0.96 (m, 9H), 0.95-0.89 (m, 3H), 0.67 (s, 5H).

Synthesis of 329.6

To a solution of 329.5 (6.1 g, 17.5 mmol) in DCM (50 mL) was added PCC (11.2 g, 52.5 mmol) and silica gel (15 g) at 25° C. After stirring at 25° C. for 1 h, the reaction mixture was filtered and the residue was washed with DCM (2×20 mL). The combined filtrate was concentrated in vacuum. The residue was purified by flash column (15-20% of EtOAc in PE) to give 329.6 (3 g, 49.5%) as a solid.

¹H NMR (400 MHz, CDCl₃) $\delta_H$ 2.55 (t, J=8.8 Hz, 1H), 2.12 (s, 4H), 2.00 (td, J=3.2, 12.0 Hz, 1H), 1.89-1.73 (m, 2H), 1.59 (br d, J=2.8 Hz, 1H), 1.55-1.50 (m, 1H), 1.49-1.16 (m, 10H), 1.15-0.97 (m, 6H), 0.96-0.90 (m, 3H), 0.81-0.65 (m, 2H), 0.62 (s, 3H).

Synthesis of 329.7

To a mixture of MePPh₃Br (9.25 g, 25.9 mmol) in THF (40 mL) was added t-BuOK (2.9 g, 25.9 mmol) at 15° C. under N₂. After stirring 30 mins, 329.6 (3 g, 8.65 mmol) in THF (10 mL) was added. After stirring at 40° C. for 2 h, the mixture was poured into NH₄Cl.aq (150 mL) and extracted with EtOAc (2×200 mL). The combined organic phase was washed with brine (20 mL), dried over anhydrous Na₂SO₄, filtered and concentrated. The residue was heated in MeOH (500 mL) at 70° C. for 30 minutes, cooled to room temperature, added water (300 mL), filtered and concentrated to give 329.7 (3 g, 100%) as a solid.

¹H NMR (400 MHz, CDCl₃) $\delta_H$ 4.85 (s, 1H), 4.71 (s, 1H), 2.11-1.98 (m, 1H), 1.76 (s, 7H), 1.71-1.64 (m, 3H), 1.64-1.53 (m, 3H), 1.39 (d, J=3.6 Hz, 4H), 1.14 (br s, 12H), 0.95-0.88 (m, 3H), 0.77-0.62 (m, 2H), 0.58 (s, 3H).

Synthesis of 329.8

To a solution of 329.7 (2.6 g, 7.54 mmol) in THF (30 mL) was added BH₃.Me₂S (2.26 mL, 22.6 mmol, 10M) at 0° C. under N₂. After stirring at 20° C. for 3 h, the reaction mixture was treated sequentially with ethanol (6.50 mL, 113 mmol) at 0° C., NaOH aqueous (22.6 mL, 5.0 M, 113 mmol), and then hydrogen peroxide (11.3 mL, 10 M, 113 mmol) dropwise. After 1 hr, the reaction was quenched with Na₂S₂O₃ (30 mL), stirred for 10 minutes and extracted with EtOAc (2×50 mL). The combined organic phase was washed with brine (50 mL), dried over anhydrous Na₂SO₄, filtered and concentrated. The residue was purified by flash column (0~25% of EtOAc in PE) to give 329.8 (3.1 g) as a solid.

¹H NMR (400 MHz, CDCl₃) $\delta_H$ 3.79-3.58 (m, 1H), 3.54-3.29 (m, 1H), 1.88-1.58 (m, 10H), 1.56-1.47 (m, 2H), 1.38 (d, J=3.6 Hz, 4H), 1.34-1.23 (m, 3H), 1.22-1.15 (m, 2H), 1.14-0.97 (m, 9H), 0.95 (d, J=6.8 Hz, 2H), 0.93-0.89 (m, 3H), 0.68 (s, 5H).

Synthesis of 329.9

To a solution of 329.8 (500 mg, 1.37 mmol) in DCM (5 mL) were added PPh₃ (574 mg, 2.19 mmol) and NBS (387 mg, 2.19 mmol) at 0° C. under N₂, After stirring at 25° C. for 3 h, the mixture was concentrated and purified by flash column (0~3% of EtOAc in PE) to give 329.9 (560 mg, 96.2%) as a solid.

¹H NMR (400 MHz, CDCl₃) $\delta_H$ 3.68-3.47 (m, 1H), 3.41-3.30 (m, 1H), 1.96-1.70 (m, 5H), 1.67-1.47 (m, 7H), 1.38 (d, J=3.2 Hz, 4H), 1.35-1.22 (m, 6H), 1.16-0.99 (m, 6H), 0.99-0.86 (m, 6H), 0.68 (s, 5H).

Synthesis of 329.10 and 331.1

To a solution of 329.9 (560 mg, 1.31 mmol) in DMF (10 mL) were added 5-methyl-2H-1,2,3,4-tetrazole (164 mg, 1.96 mmol) and Cs₂CO₃ (2.13 g, 6.55 mmol) at 20° C. under N₂. After stirring at 120° C. for 2 h, the reaction mixture was diluted with water (100 mL) and extracted with ethyl acetate (3×150 mL). The combined organic layers were washed with brine (150 mL), dried over anhydrous Na₂SO₄, filtered and concentrated under vacuum to dryness. The residue was purified by flash column (0-100% ethyl acetate in PE) to give 329.10 (390 mg, 69.5%) and 331.1 (170 mg, 30.3%) both as solids.

Separation of 329.10

329.10 (390 mg, 0.909 mmol) was separated by SFC (Column: DAICEL CHIRALPAK AD (250 mm*30 mm, 10 um); Condition: 0.1% NH₃H₂O ETOH; Begin: B 60%; End B: 60%; Flow Rate (ml/min): 80) to give 329 (Peak 2, Rt=1.828 min, 207.5 mg, 53.2%) as a solid and 3330 (Peak 1, Rt=1.680 min, 95.6 mg, 24.5%) as a solid. The stereochemistry at C20 was assigned based on ¹H NMR of C21-Me (C18-Me with C21-down-Et is at more downfield than C21-up isomer).

329: ¹HNMR (400 MHz, CDCl₃) $\delta_H$ 4.77 (dd, J=13.2, 4.4 Hz, 1H), 4.24 (dd, J=13.2, 10.0 Hz, 1H), 2.54 (s, 3H), 2.31-2.15 (m, 1H), 1.93-1.82 (m, 2H), 1.82-1.72 (m, 2H), 1.65 (ddd, J=9.2, 6.4, 2.4 Hz, 2H), 1.59 (s, 1H), 1.58-1.48 (m, 2H), 1.39 (d, J=3.2 Hz, 3H), 1.37-1.32 (m, 2H), 1.31-1.18 (m, 3H), 1.18-1.09 (m, 5H), 1.08-1.02 (m, 2H), 0.99 (br dd, J=12.4, 5.2 Hz, 2H), 0.92 (br s, 3H), 0.82 (s, 3H), 0.71 (d, J=6.4 Hz, 4H), 0.66 (br d, J=3.2 Hz, 1H). LC-ELSD/MS purity 99%, MS ESI calcd. for C₂₆H₄₄N₄O [M+H]⁺ 429.3, found 429.3. SFC 100% de.

330: ¹HNMR (400 MHz, CDCl₃) $\delta_H$ 4.53 (dd, J=13.2, 3.6 Hz, 1H), 4.29 (dd, J=13.2, 9.2 Hz, 1H), 2.54 (s, 3H), 2.21-2.08 (m, 1H), 2.05-1.89 (m, 2H), 1.74 (br dd, J=12.8, 2.8 Hz, 2H), 1.70-1.57 (m, 4H), 1.53-1.57 (m, 1H), 1.52-1.40 (m, 2H), 1.39 (d, J=3.2 Hz, 3H), 1.35-1.24 (m, 2H), 1.23-1.16 (m, 2H), 1.13 (s, 2H), 1.12-1.00 (m, 5H), 0.99-0.95 (m, 1H), 0.92 (br s, 3H), 0.86 (d, J=6.8 Hz, 3H), 0.73 (s, 3H), 0.71-0.63 (m, 2H). LC-ELSD/MS purity 99%, MS ESI calcd. for C₂₆H₄₄N₄O [M+H]⁺ 429.3, found 429.4. SFC 100% de.

Separation of 331 & 332

331.1 (170 mg, 0.396 mmol) was separated by SFC (Column: DAICEL CHIRALCEL OJ-H (250 mm*30 mm, 5 um); Condition: 0.1% NH₃H₂O ETOH; Begin: B 20%; End B: 20%; Flow Rate (ml/min): 60) to give 331 (Peak 1, Rt=2.220 min, 30.9 mg, 18.2%) as a solid and 332 (Peak 2, Rt=2.354 min, 62.9 mg, 37.2%) as a solid. The stereochemistry at $C_{20}$ was assigned based on ¹H NMR of $C_{21}$-Me ($C_{18}$-Me with $C_{21}$-down-Et is at more downfield than $C_{21}$-up isomer).

331: ¹HNMR (400 MHz, CDCl₃) $\delta_H$ 4.29 (dd, J=13.6, 3.6 Hz, 1H), 3.87 (dd, J=13.6, 10.4 Hz, 1H), 2.55 (s, 3H), 2.11-1.91 (m, 3H), 1.75 (br d, J=14.4 Hz, 2H), 1.71-1.61 (m, 3H), 1.60-1.50 (m, 3H), 1.49-1.42 (m, 1H), 1.39 (br d, J=3.2 Hz, 4H), 1.34-1.22 (m, 3H), 1.20-1.14 (m, 2H), 1.12 (s, 2H), 1.10-0.97 (m, 5H), 0.92 (br s, 3H), 0.84 (d, J=6.4 Hz, 3H), 0.74-0.62 (m, 5H). LC-ELSD/MS purity 99%, MS ESI calcd. for C₂₆H₄₄N₄O [M+H]⁺ 429.3, found 429.4. SFC 100% de.

332: ¹H NMR (400 MHz, CDCl₃) $\delta_H$ 4.55 (dd, J=13.6, 4.4 Hz, 1H), 3.85 (dd, J=13.6, 11.2 Hz, 1H), 2.56 (s, 3H), 2.20-2.07 (m, 1H), 1.94-1.83 (m, 2H), 1.82-1.72 (m, 2H), 1.69-1.62 (m, 3H), 1.61-1.50 (m, 3H), 1.39 (br d, J=3.6 Hz, 4H), 1.35 (br dd, J=10.0, 3.2 Hz, 2H), 1.32-1.27 (m, 2H), 1.26-1.21 (m, 1H), 1.20-1.13 (m, 2H), 1.12 (s, 2H), 1.10-0.96 (m, 4H), 0.93 (br s, 3H), 0.83 (s, 3H), 0.76-0.64 (m, 5H). LC-ELSD/MS purity 99%, MS ESI calcd. for C₂₆H₄₄N₄O [M+H]⁺ 429.3, found 429.4. SFC 100% de.

Examples 333-336: Synthesis of (3R,5S,8R,9R,10S, 13S,14S,17R)-3-ethyl-13-methyl-17-((R)-1-(5-methyl-2H-tetrazol-2-yl)propan-2-yl)hexadecahydro-1H-cyclopenta[a]phenanthren-3-ol (333) & (3R,5S,8R,9R,10S,13S,14S,17R)-3-ethyl-13-methyl-17-((S)-1-(5-methyl-2H-tetrazol-2-yl)propan-2-yl)hexadecahydro-1H-cyclopenta[a]phenanthren-3-ol (334) & (3R,5S,8R,9R,10S,13S,14S,17R)-3-ethyl-13-methyl-17-((R)-1-(5-methyl-1H-tetrazol-1-yl)propan-2-yl)hexadecahydro-1H-cyclopenta[a]phenanthren-3-ol (335) & (3R,5S,8R,9R,10S,13S,14S,17R)-3-ethyl-13-methyl-17-((S)-1-(5-methyl-1H-tetrazol-1-yl)propan-2-yl)hexadecahydro-1H-cyclopenta[a]phenanthren-3-ol (336)

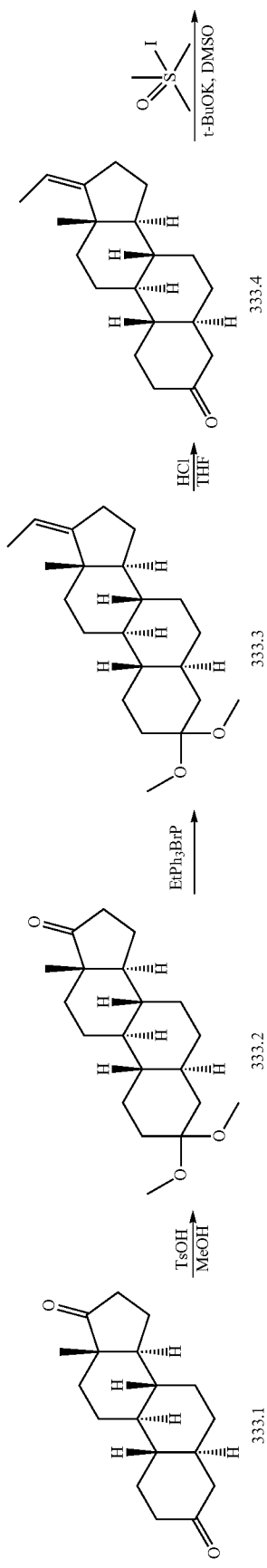
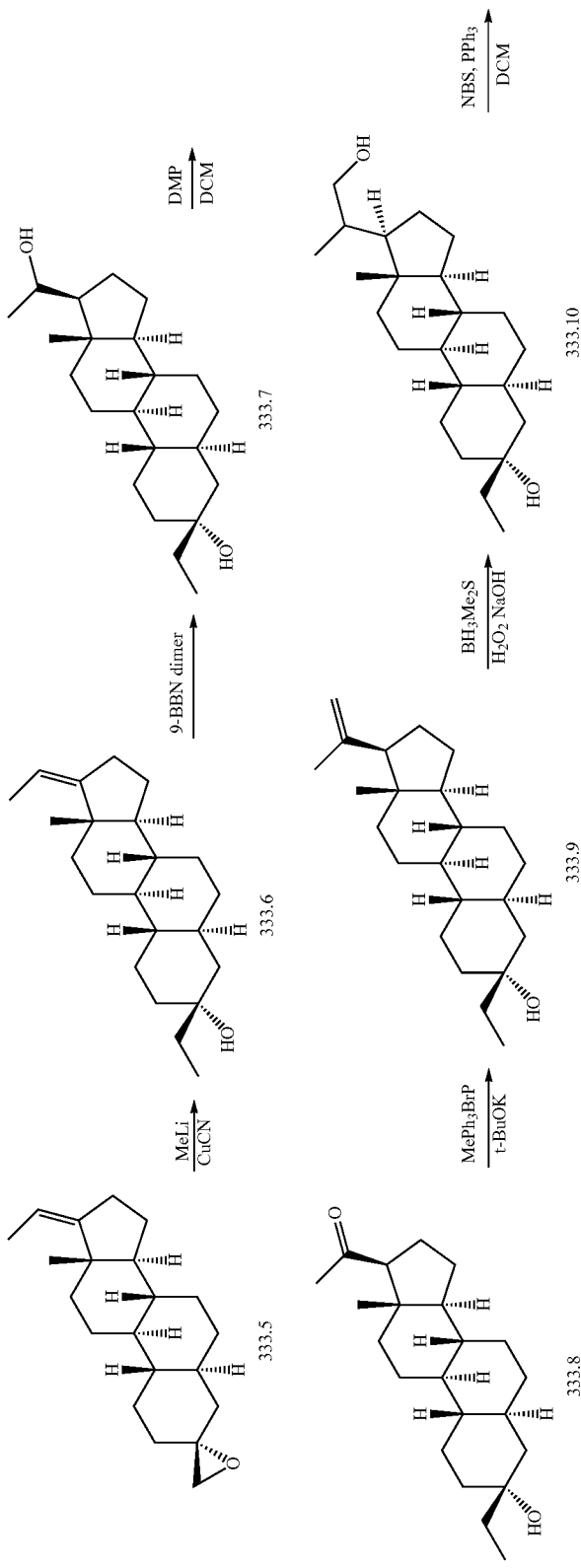

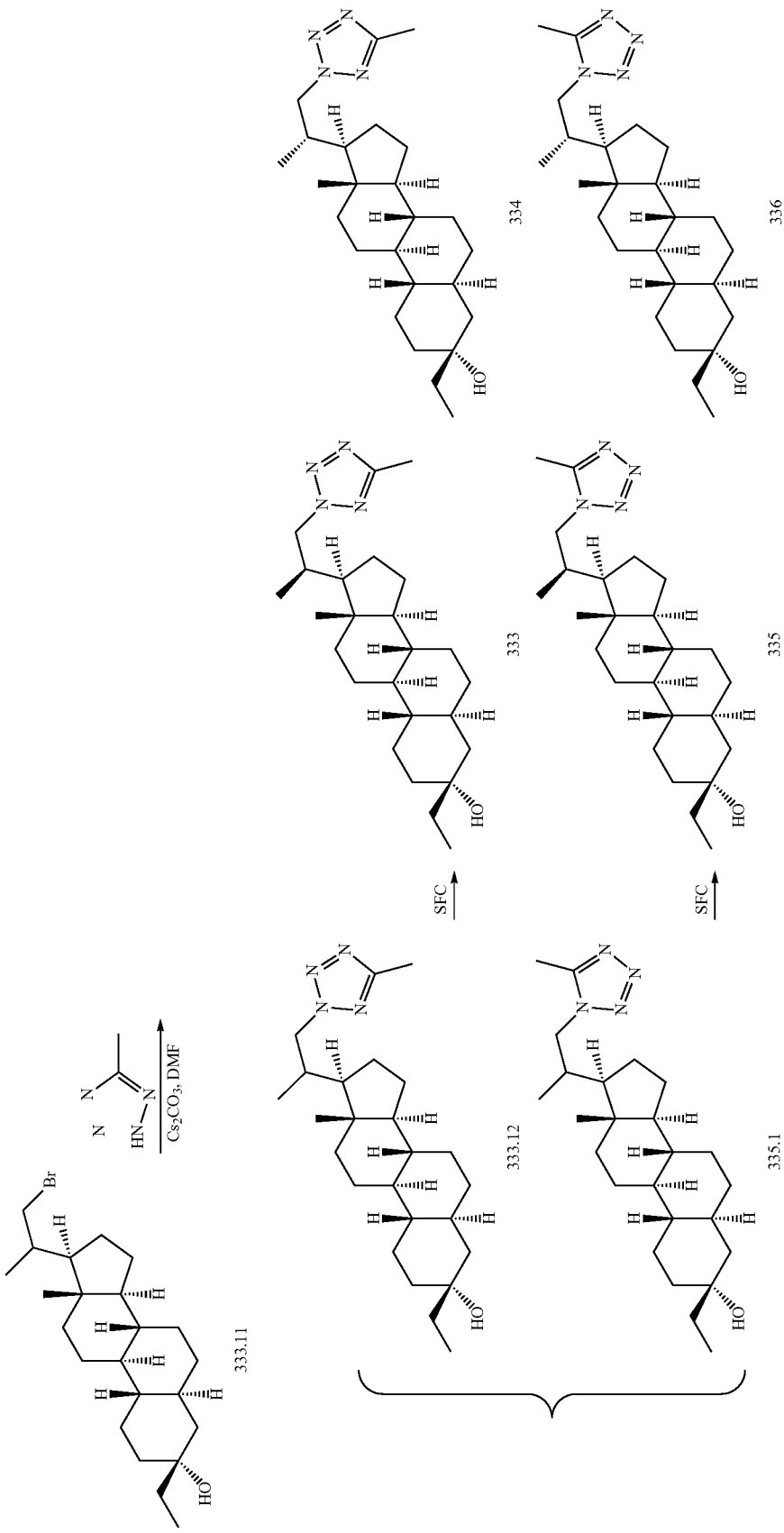

Synthesis of 333.2

To a solution of 333.1 (51.5 g, 187 mmol) in MeOH (600 mL) was added 4-methylbenzenesulfonic acid (6.44, 37.4 mmol) at 25° C. under $N_2$. After stirring at 55° C. for 16 h, $Et_3N$ (20 mL) was added, and the mixture was filtered to afford 333.2 (57 g) as a solid.

$^1$H NMR (400 MHz, $CDCl_3$) $\delta_H$ 3.49 (d, J=5.6 Hz, 1H), 3.20 (s, 3H), 3.14 (s, 3H), 2.48-2.38 (m, 1H), 2.12-2.01 (m, 2H), 1.96-1.90 (m, 2H), 1.88-1.74 (m, 4H), 1.68-1.62 (m, 1H), 1.56-1.44 (m, 1H), 1.35-1.20 (m, 5H), 1.13-0.95 (m, 5H), 0.87 (s, 1H), 0.80-0.68 (m, 2H).

Synthesis of 333.3

To a mixture of $EtPPh_3Br$ (98.7 g, 266 mmol) in THF (250 mL) was added t-BuOK (29.8 g, 266 mmol) at 15° C. under $N_2$. After stirred at 15° C. for 30 mins, 333.2 (28.5 g, 88.9 mmol) in THF (50 mL) was added. After stirring at 40° C. for 2 h, the mixture was poured into $NH_4Cl$.aq (150 mL) and extracted with EtOAc (2×200 mL). The combined organic phase was washed with brine (20 mL), dried over anhydrous $Na_2SO_4$, filtered and concentrated. The residue was heated in MeOH (500 mL) at 70° C. for 30 minutes, cooled to room temperature, diluted with water (300 mL), filtered and concentrated to give 333.3 (25.5 g) as a solid.

$^1$H NMR (400 MHz, $CDCl_3$) $\delta_H$ 5.15-5.07 (m, 1H), 3.20 (s, 3H), 3.14 (s, 3H), 2.41-2.31 (m, 1H), 2.27-2.12 (m, 2H), 2.10-2.02 (m, 1H), 1.91 (td, J=3.2, 13.2 Hz, 1H), 1.85-1.76 (m, 2H), 1.71-1.58 (m, 6H), 1.57-1.48 (m, 3H), 1.30-1.13 (m, 6H), 1.11-0.93 (m, 5H), 0.87 (s, 3H), 0.75-0.67 (m, 2H).

Synthesis of 333.4

To a solution of 333.3 (51 g, 153 mmol) in THF (500 mL) was added HCl (153 mL, 1 M, 153 mmol) at 15° C. After stirring for 2 h, the mixture was poured into aq $NaHCO_3$ (400 mL) and extracted with EtOAc (2×300 mL). The combined organic phase was washed with brine (200 mL), dried over anhydrous $Na_2SO_4$, filtered and concentrated to give 333.4 (42 g, 95.8%) as a solid.

$^1$H NMR (400 MHz, $CDCl_3$) $\delta_H$ 5.16-5.08 (m, 1H), 2.42-2.17 (m, 7H), 2.09 (t, J=13.2 Hz, 1H), 1.88-1.79 (m, 2H), 1.76-1.63 (m, 6H), 1.59 (s, 1H), 1.56-1.40 (m, 2H), 1.28-1.16 (m, 8H), 1.04-0.94 (m, 1H), 0.90 (s, 1H), 0.78-0.69 (m, 1H).

Synthesis of 333.5

To solution of $Me_3SIO$ (47.9 g, 218 mmol) in DMSO (300 mL) and THF (300 mL) was added NaH (5.23 g, 218 mmol) at 0° C. under $N_2$. After stirring for 1 h, 333.4 (42 g, 146 mmol) in THF (200 mL) was added. After stirring at 25° C. for 3 h, the reaction mixture was poured into water (1000 mL), stirred at 25° C. for 3 h and filtered to give 333.5 (48 g) as a solid.

$^1$H NMR (400 MHz, $CDCl_3$) $\delta_H$ 5.15-5.07 (m, 1H), 2.64-2.61 (m, 5H), 2.41-2.30 (m, 1H), 2.27-2.11 (m, 2H), 2.00-1.92 (m, 1H), 1.91-1.80 (m, 2H), 1.67-1.60 (m, 5H), 1.56-1.50 (m, 1H), 1.45-1.35 (m, 1H), 1.30-1.10 (m, 8H), 1.07-0.95 (m, 2H), 0.89 (s, 3H), 0.84-0.72 (m, 2H).

Synthesis of 333.6

To a suspension of CuCN (3.92 g, 43.8 mmol) in THF (40 mL) was added MeLi (54.7 mL, 87.6 mmol, 1.6M) at −70° C. under $N_2$. After stirring at −70° C. for 1 h, 333.6 (4.4 g, 14.6 mmol) in THF (10 mL) was added at −70° C. After stirring at 25° C. for 2 h, the reaction was slowly poured into 10% $NH_4Cl$ (20 mL) and extracted with EtOAc (2×50 mL). The combined organic phase was washed with brine (20 mL), dried over anhydrous $Na_2SO_4$, filtered and concentrated to give 333.6 (4.4 g) as a solid.

1H NMR (400 MHz, $CDCl_3$) δ 5.14-5.08 (m, 1H), 2.39-2.10 (m, 3H), 1.85-1.39 (m, 10H), 1.39-0.94 (m, 13H), 0.94-0.60 (m, 9H).

Synthesis of 333.7

To a solution of 333.6 (4.4 g, 13.3 mmol) in anhydrous THF (50 mL) was added 9-BBN dimer (8.03 g, 33.2 mmol) at 25° C. under $N_2$. After stirring at 60° C. for 16 h, the mixture was cooled and sequentially treated with EtOH (20 mL) at 0° C., NaOH (2.66 g, 13.3 mL, 5M, 66.5 mmol) very slowly and $H_2O_2$ (13.3 mL, 133 mmol, 10 M in water) slowly until the reaction temperature no longer rises and the reaction temperature was maintained below 30° C. After stirring at 60° C. for 2 h, the mixture was cooled, quenched with $Na_2S_2O_3$ (100 mL, sat. aq.) and extracted with EtOAc (3×100 mL). The combined organic layer was dried over $Na_2SO_4$, filtered and concentrated in vacuum. The residue was purified by column (5%-30% of EtOAc in PE) to give 333.7 (10 g) as a solid.

1H NMR (400 MHz, $CDCl_3$) $\delta_H$ 3.74-3.66 (m, 1H), 1.96-1.39 (m, 13H), 1.39-1.00 (m, 14H), 1.00-0.85 (m, 5H), 0.75-0.57 (m, 5H).

Synthesis of 333.8

To a solution of 333.7 (1.3 g, 3.88 mmol) in DCM (20 mL) was added DMP (3.29 g, 7.76 mmol). After stirring at 25° C. for 1 h, the mixture was quenched with $NaHCO_3$ (50 mL) and extracted with EtOAc (3×30 mL). The organic layer was washed with $Na_2S_2O_3$ (3×30 mL, sat.), brine (50 mL), dried over $Na_2SO_4$, filtered and concentrated in vacuum. The residue was purified by column (5%-30% of EtOAc in PE) to give to give 333.8 (1.16 g, 90%) as a solid.

1H NMR (400 MHz, $CDCl_3$) $\delta_H$ 2.53 (t, J=8.8 Hz, 1H), 2.21-1.53 (m, 9H), 1.53-1.10 (m, 10H), 1.10-0.63 (m, 13H), 0.61 (s, 3H).

Synthesis of 333.9

To a mixture of $MePPh_3Br$ (2.48 g, 6.96 mmol) in THF (40 mL) was added t-BuOK (779 mg, 6.96 mmol) at 25° C. under $N_2$. After stirring at 50° C. for 30 mins, 333.8 (1.16 g, 3.48 mmol) in THF (10 mL) was added. After stirring at 50° C. for 18 h, the reaction mixture was quenched with water (40 mL) at 25° C. and extracted with EtOAc (2×50 mL). The combined organic phase was washed with water (3×10 mL), brine (30 mL), dried over anhydrous $Na_2SO_4$, filtered and concentrated in vacuum. The residue was purified by column (2% of EtOAc in PE) to give 333.9 (620 mg, 54%) as a solid.

1H NMR (400 MHz, $CDCl_3$) $\delta_H$ 4.84 (s, 1H), 4.70 (s, 1H), 2.08-1.57 (m, 10H), 1.57-1.06 (m, 13H), 1.06-0.52 (m, 13H).

Synthesis of 333.10

To a solution of 333.9 (2.9 g, 8.77 mmol) in THF (25 mL) was added $BH_3Me_2S$ (4.38 mL, 43.8 mmol, 10 M) at 0° C. under $N_2$. After stirring at 15° C. for 16 h, the reaction was sequentially treated with EtOH (20 mL), NaOH (17.5 mL, 87.7 mmol, 5M) at 0° C., and finally $H_2O_2$ (8.77 mL, 87.7 mmol, 10M) dropwise. After stirring at 60° C. for 1 h, the mixture was added into water (50 mL) and extracted with EtOAc (3×50 mL). The combined organic layer was washed with saturated $Na_2S_2O_3$ (100 mL), brine (100 mL), dried over anhydrous $Na_2SO_4$, filtered and concentrated. The residue was purified by column (0-30% of EtOAc in PE) to give 333.10 (3.2 g) as a solid.

$^1$H NMR (400 MHz, $CDCl_3$) $\delta_H$ 3.74-3.71 (m, 1H), 3.65-3.61 (m, 0.5H), 3.48-3.43 (m, 1H), 3.37-3.33 (m, 0.5H), 1.97-1.57 (m, 8H), 1.57-1.38 (m, 8H), 1.38-1.08 (m, 8H), 1.08-0.83 (m, 8H), 0.74-0.58 (m, 5H).

Synthesis of 333.11

To a solution of 333.10 (1 g, 2.86 mmol) in DCM (20 mL) at 0° C. were added $PPh_3$ (1.12 g, 4.29 mmol) and NBS (763 mg, 4.29 mmol) at 25° C. under $N_2$. After stirring for 2 h, the reaction was diluted with water (20 mL) and extracted with DCM (2×20 mL). The combined organic phase was washed with brine (20 mL), dried over anhydrous Na₂SO₄, filtered and concentrated. The residue was purified by flash column (0-5% of EtOAc in PE) to give 333.11 (1.2 g) as oil.

¹H NMR (400 MHz, CDCl₃) δ$_H$ 3.65-3.62 (m, 0.6H), 3.52-3.49 (m, 0.4H), 3.39-3.31 (m, 1H), 2.35 (s, 1H), 1.93-1.44 (m, 10H), 1.44-1.01 (m, 12H), 1.01-0.59 (m, 14H).

Synthesis of 333.12 & 335.1

To a solution of 333.11 (1.2 g, 2.91 mmol) in DMF (10 mL) were added Cs₂CO₃ (1.89 g, 5.82 mmol) and 5-methyl-2H-1,2,3,4-tetrazole (489 mg, 5.82 mmol) at 25° C. under N₂. After stirring at 80° C. for 16 h, the mixture was added into saturated NH₄Cl (20 mL) and extracted with EtOAc (3×20 mL). The combined organic layer was washed with water (2×30 mL), brine (50 mL), dried over anhydrous Na₂SO₄, filtered and concentrated. The residue was purified by column (0-100% of EtOAc in PE) to give 333.12 (700 mg) and 335.1 (300 mg) as solids.

333.12: ¹H NMR (400 MHz, CDCl₃) δ$_H$ 4.77-4.73 (m, 0.6H), 4.53-4.49 (m, 0.4H), 4.31-4.20 (m, 1H), 2.52 (s, 1H), 2.25-1.39 (m, 14H), 1.39-0.91 (m, 13H), 0.91-0.55 (m, 12H). LC-ELSD/MS purity 99%, MS ESI calcd. for C₂₅H₄₃N₄O [M+H]⁺ 415. found 415.

335.1: ¹H NMR (400 MHz, CDCl₃) δ$_H$ 4.56-4.52 (m, 0.6H), 4.30-4.26 (m, 0.4H), 3.89-3.80 (m, 1H), 2.55 (s, 1H), 2.17-1.39 (m, 14H), 1.39-0.94 (m, 13H), 0.94-0.59 (m, 12H). LC-ELSD/MS purity 99%, MS ESI calcd. for C₂₅H₄₃N₄O [M+H]⁺ 415. found 415.

Separation of 333 & 334

333.12 (700 mg, 1.68 mmol) was separated by SFC (Column: DAICEL CHIRALCEL OJ-H (250 mm*30 mm, 5 um), Condition: 0.1% NH₃H₂O ETOH, Begin B: 15%, End B: 15%) to give 333 (430 mg, 62%, Rt=1.786 min) and 334 (230 mg, 33%, Rt=1.593 min) as solids. The two diastereomers were assigned based on ¹H NMR of C21-Me (C21-down-Me is at more downfield than C21-up isomer).

333: ¹H NMR (400 MHz, CDCl₃) δ$_H$ 4.78-4.73 (m, 1H), 4.26-4.20 (m, 1H), 2.53 (s, 1H), 2.26-2.17 (m, 1H), 1.90-1.57 (m, 10H), 1.57-1.07 (m, 14H), 1.07-0.62 (m, 14H). LC-ELSD/MS purity 99%, MS ESI calcd. for C₂₅H₄₃N₄O [M+H]⁺ 415, found 415. analytic SFC 98.46% de.

334: ¹H NMR (400 MHz, CDCl₃) δ$_H$ 4.54-4.49 (m, 1H), 4.31-4.25 (m, 1H), 2.53 (s, 1H), 2.19-1.90 (m, 3H), 1.76-1.40 (m, 10H), 1.40-0.95 (m, 14H), 0.95-0.60 (m, 12H). LC-ELSD/MS purity 99%, MS ESI calcd. for C₂₅H₄₃N₄O [M+H]⁺ 415, found 415. analytic SFC 99.82% de.

Separation of 335 & 336

335.1 (300 mg, 0.7235 mmol) was separated by SFC (Column: DAICEL CHIRALCEL OD (250 mm*30 mm, 10 um), Condition: 0.1% NH₃H₂O ETOH, Begin B: 30%, End B: 30%) to give 335 (170 mg, 57%, Rt=1.705 min) and 336 (130 mg, 43%, Rt=1.574 min) as solids.

335: ¹H NMR (400 MHz, CDCl₃) δ$_H$ 4.56-4.51 (m, 1H), 3.86-3.80 (m, 1H), 2.54 (s, 1H), 2.17-2.07 (m, 1H), 1.91-1.52 (m, 10H), 1.52-1.03 (m, 14H), 1.03-0.62 (m, 14H). LC-ELSD/MS purity 99%, MS ESI calcd. for C₂₅H₄₃N₄O [M+H]⁺ 415 found 415. analytic SFC 98.04% de.

336: ¹H NMR (400 MHz, CDCl₃) δ$_H$ 4.30-4.26 (m, 1H), 3.89-3.83 (m, 1H), 2.54 (s, 1H), 2.09-1.91 (m, 3H), 1.77-1.56 (m, 10H), 1.56-1.11 (m, 10H), 1.11-0.79 (m, 5H), 0.79-0.61 (m, 5H). LC-ELSD/MS purity 99%, MS ESI calcd. for C₂₅H₄₃N₄O [M+H]⁺ 415 found 415. analytic SFC 97.44% de.

Examples 337 & 338: Synthesis of 1-((R)-2-((3R,5R,8S,9S,10S,11R,13S,14S,17R)-3,11-dihydroxy-10,13-dimethyl-3-propylhexadecahydro-1H-cyclopenta[a]phenanthren-17-yl)propyl)-1H-pyrazole-4-carbonitrile (337) & 1-((S)-2-((3R,5R,8S,9S,10S,11R,13S,14S,17R)-3,11-dihydroxy-10,13-dimethyl-3-propylhexadecahydro-1H-cyclopenta[a]phenanthren-17-yl)propyl)-1H-pyrazole-4-carbonitrile (338)

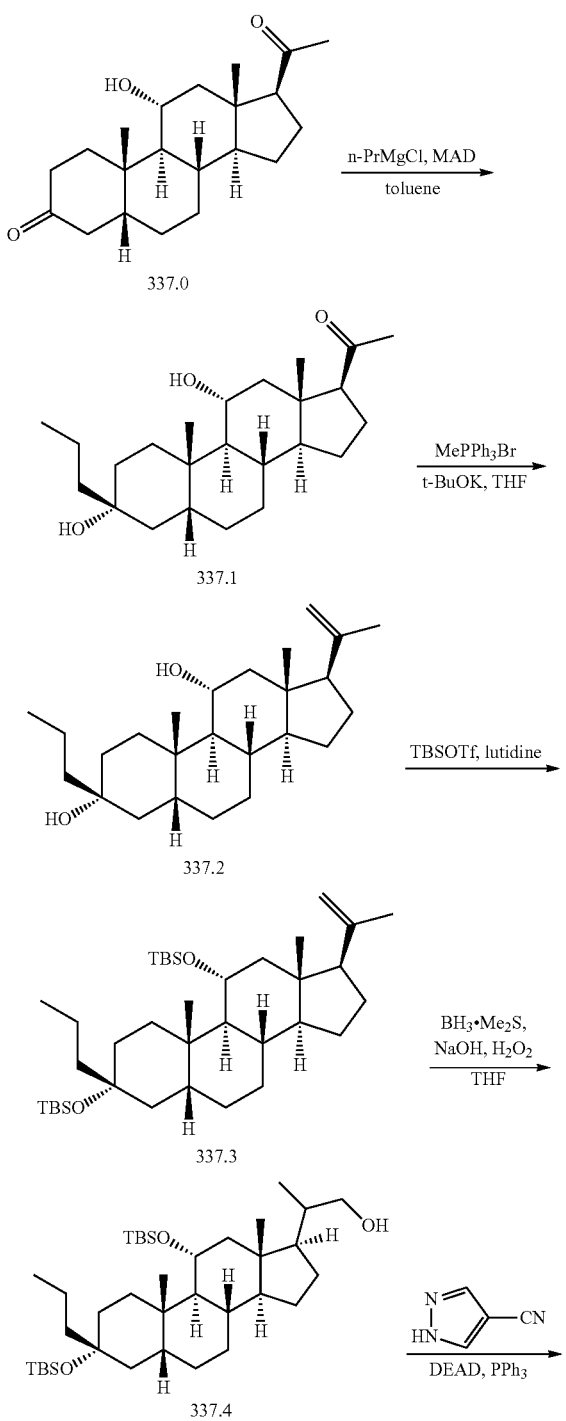

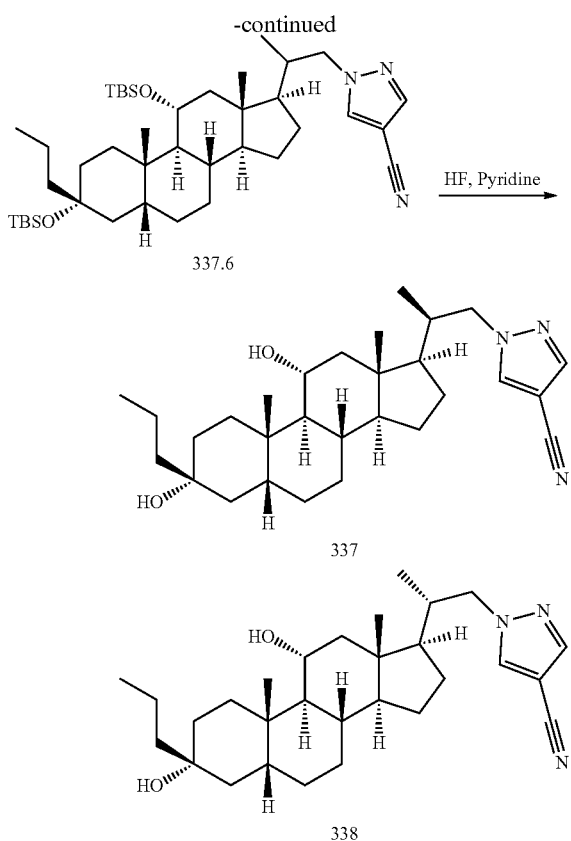

Synthesis of 337.1

To a solution of BHT (39.6 g, 179 mmol) in toluene (150 mL) was added AlMe$_3$ (2 M in toluene, 44.7 mL, 89.5 mmol) dropwise at 0° C. under N$_2$. The mixture was stirred at 20° C. for 1 h and used directly as a solution of MAD without further purification. To the fresh prepared MAD (90 mmol) solution was added a solution of 337.0 (10 g, 30.0 mmol) in DCM (80 mL) dropwise at −70° C. under N$_2$. After stirring at −70° C. for 1 h, n-PrMgCl (45 mL, 90 mmol, 2M in ethyl ether) was added dropwise at −70° C. After stirring at −70° C. for another 2 h, the reaction mixture was poured into saturated aqueous citric acid (200 mL) at 10° C. and extracted with EtOAc (2×100 mL). The combined organic layer was dried over Na$_2$SO$_4$, filtered and concentrated. The residue was purified by flash column (0-30% of EtOAc in PE) to afford 337.1 (2.8 g, 25%) as a solid.

$^1$H NMR (400 MHz, CDCl$_3$) δ$_H$ 3.97-3.75 (m, 1H), 2.55 (t, J=8.9 Hz, 1H), 2.49-2.41 (m, 1H), 2.32 (dd, J=5.0, 11.8 Hz, 1H), 2.22-2.08 (m, 4H), 1.93-1.78 (m, 2H), 1.74-1.58 (m, 4H), 1.55-1.30 (m, 10H), 1.29-1.13 (m, 6H), 1.06 (s, 3H), 1.00-0.86 (m, 4H), 0.61 (s, 3H).

Synthesis of 337.2

To a suspension of MePh$_3$PBr (5.28 g, 14.8 mmol) in anhydrous THF (20 mL) was added t-BuOK (2.91 g, 26.0 mmol) at 15° C. under N$_2$. After stirring at 60° C. for 30 mins, a solution of 337.1 (2.8 g, 7.43 mmol) in anhydrous THF (20 mL) was added dropwise. After stirring for 16 h, the mixture was cooled and poured into ice-water (50 mL), stirred for 10 mins. and extracted with EtOAc (2×50 mL). The combined organic phase was washed with brine (2×50 mL), filtered and concentrated. The residue was purified by flash column (0~50% of EtOAc in PE) to give 337.2 (2 g, 71.9%) as a solid.

$^1$H NMR (400 MHz, CDCl$_3$) δ$_H$ 4.86 (s, 1H), 4.70 (s, 1H), 3.85 (br s, 1H), 2.47 (br d, J=14.3 Hz, 1H), 2.18 (dd, J=5.0, 11.8 Hz, 1H), 2.10-2.04 (m, 1H), 1.95-1.77 (m, 3H), 1.74-1.48 (m, 9H), 1.47-1.12 (m, 13H), 1.10-0.98 (m, 4H), 0.93 (t, J=7.2 Hz, 3H), 0.93-0.80 (m, 1H), 0.55 (s, 3H).

Synthesis of 337.3

To a solution of 337.2 (2 g, 5.33 mmol) in DCM (20 mL) were added 2,6-dimethylpyridine (2.56 g, 23.9 mmol) and TBSOTf (5.63 g, 21.3 mmol) at 0° C. dropwise under N$_2$. After stirring at 25° C. for 1 h, the reaction mixture was quenched by water (50 mL) and extracted with DCM (2×30 mL). The combined organic layer was washed with brine (50 mL) and dried over Na$_2$SO$_4$, filtered and concentrated in vacuum. The residue was purified by column (0~1% of EtOAc in PE) to give 337.3 (1.8 g, 56%) as oil.

Synthesis of 337.4

To a solution of 337.3 (1.8 g, 2.98 mmol) in THF (40 ml) was added BH$_3$·Me$_2$S (0.894 mL, 8.94 mmol) at 0° C. under N$_2$. After stirring at 25° C. for 16 h, the reaction mixture was cooled to 0° C. and sequentially treated with NaOH (5.96 mL, 5M, 29.8 mmol) and then H$_2$O$_2$ (2.97 mL, 29.8 mmol, 1.13 g/mL, 30% in water) slowly until the reaction temperature no longer rises and the reaction temperature was maintained below 30° C. After stirring at 50° C. for 1 h, the reaction was quenched with saturated aqueous Na$_2$S$_2$O$_3$ (30 mL) and stirred at 0° C. for another 1 h. The aqueous phase was extracted with EtOAc (3×30 mL). The combined organic phase was washed with saturated Na$_2$S$_2$O$_3$ (2×50 mL), brine (2×50 mL), drive over anhydrous Na$_2$SO$_4$ filtered and concentrated to give 337.4 (1.2 g) as a solid.

Synthesis of 337.5

To a solution of 337.4 (150 mg, 0.2414 mmol) in DMF (5 mL) were added Ph$_3$P (101 mg, 0.3682 mmol), DEAD (67.2 mg, 0.3862 mmol) and 1H-pyrazole-4-carbonitrile (33.7 mg, 0.3621 mmol) at 20° C. under N$_2$. After stirring for 16 h, the mixture was poured into water (10 mL) and extracted with EtOAc (2×20 mL). The combined organic phase was washed with brine (10 mL), dried over anhydrous Na$_2$SO$_4$, filtered and concentrated to give 337.5 (120 mg) as a solid.

Synthesis of 337 & 338

To a solution of 337.5 (700 mg, 1.00 mmol) in THF (10 mL) was added HF-Py (5 mL, 30% in Py) at 20° C. under N$_2$. After stirring for 16 h, the reaction mixture was neutralized with 5% NaOH (30 mL) and water (20 mL). The mixture was filtered and the filter cake was washed with water (2×10 mL) and dried. The residue was purified by flash column (0~30% of EtOAc in PE) and further purified by SFC (Column DAICEL CHIRALCEL OD (250 mm*50 mm, 10 um), Condition 0.1% NH$_3$H$_2$O EtOH Begin B: 35 End B: 35 Gradient Time (min), 100% B Hold Time (min), FlowRate (ml/min) 70) to afford 338 (70 mg, 11.7%) and 337 (100 mg, 16.7%) as solids. The two diastereomers were assigned based on 1H NMR of C21-Me (C21-down-Me is at more downfield than C21-up isomer).

337: $^1$H NMR (400 MHz, CDCl$_3$) δ$_H$ 7.80 (s, 1H), 7.75 (s, 1H), 4.24 (dd, J=3.8, 13.5 Hz, 1H), 3.97-3.77 (m, 1H), 3.72 (dd, J=9.5, 13.5 Hz, 1H), 2.45 (br d, J=14.3 Hz, 1H), 2.25 (dd, J=4.8, 11.9 Hz, 1H), 2.07-1.75 (m, 4H), 1.58 (s, 3H), 1.25 (s, 14H), 1.19-1.03 (m, 8H), 0.94 (t, J=7.3 Hz, 3H), 0.83 (d, J=6.5 Hz, 3H), 0.71 (s, 3H). LC-ELSD/MS purity 99%, MS ESI calcd. for C$_{29}$H$_{42}$N$_3$ [M−2H$_2$O+H]$^+$ 432.3 found 432.3. SFC: 99% de.

338: $^1$H NMR (400 MHz, CDCl$_3$) δ$_H$ 7.80 (s, 1H), 7.75 (s, 1H), 4.49 (dd, J=4.5, 13.3 Hz, 1H), 3.89 (br s, 1H), 3.66 (dd, J=10.5, 13.3 Hz, 1H), 2.51-2.38 (m, 1H), 2.19 (dd, J=4.9, 11.7 Hz, 1H), 2.11 (br d, J=5.5 Hz, 1H), 1.94-1.76 (m, 3H), 1.69-1.57 (m, 4H), 1.45-1.24 (m, 12H), 1.22-1.01 (m, 9H), 0.94 (br t, J=7.3 Hz, 3H), 0.79 (s, 3H), 0.68 (d, J=6.5 Hz, 3H). LC-ELSD/MS purity 99%, MS ESI calcd. for C$_{29}$H$_{42}$N$_3$ [M−2H$_2$O+H]$^+$ 432.3 found 432.3. SFC: 99% de.

Example 339: 1-((S)-2-((3R,5R,8S,9S,10S,13S,14S,17R)-3-hydroxy-10,13-dimethyl-11-oxo-3-propyl-hexadecahydro-1H-cyclopenta[a]phenanthren-17-yl)propyl)-1H-pyrazole-4-carbonitrile (339)

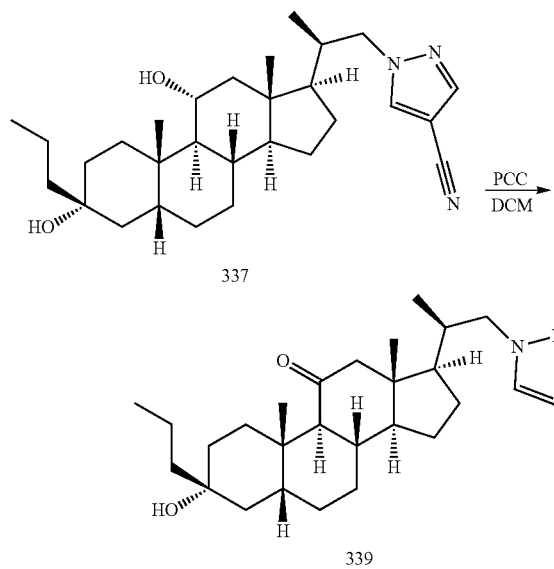

337

339

To a solution of 337 (100 mg, 0.2138 mmol) in DCM (10 mL) was added silica gel (100 mg) and PCC (91.9 mg, 0.4276 mmol) in at 25° C. under $N_2$. After stirring at 25° C. for 30 mins, the reaction mixture was filtered through a pad of silica and washed with DCM (3×10 mL). The filtrate was concentrated. The residue was purified by flash column (0~30% of EtOAc in PE) to give 339 (31 mg, 31.1%) as a solid.

$^1$H NMR (400 MHz, CDCl$_3$) $\delta_H$ 7.80 (s, 1H), 7.74 (s, 1H), 4.33 (dd, J=4.8, 13.5 Hz, 1H), 3.68 (dd, J=9.9, 13.3 Hz, 1H), 2.51 (br d, J=9.5 Hz, 1H), 2.45-2.38 (m, 2H), 2.34-2.26 (m, 1H), 2.10 (br s, 1H), 1.75 (br d, J=14.1 Hz, 6H), 1.52-1.21 (m, 15H), 1.18 (s, 3H), 1.06 (dt, J=3.5, 14.6 Hz, 1H), 0.94 (t, J=7.3 Hz, 3H), 0.73 (s, 3H), 0.70 (d, J=6.6 Hz, 3H). LC-ELSD/MS purity 99%, MS ESI calcd. for $C_{29}H_{42}N_3O$ [M−H$_2$O+H]$^+$ 448.3 found 448.3.

Example 340: Synthesis of 1-((R)-2-((3R,5R,8S,9S,10S,13S,14S,17R)-3-hydroxy-10,13-dimethyl-11-oxo-3-propylhexadecahydro-1H-cyclopenta[a]phenanthren-17-yl)propyl)-1H-pyrazole-4-carbonitrile (340)

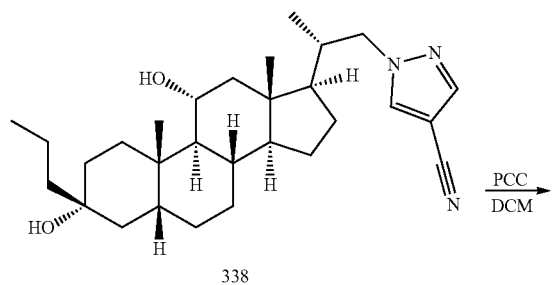

338

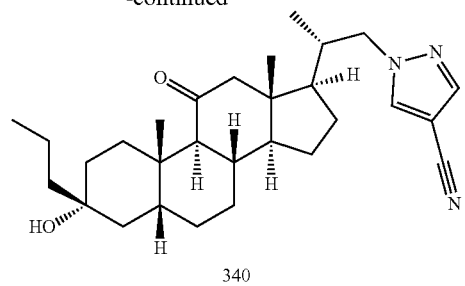

340

To a solution of 338 (60 mg, 0.1282 mmol) in DCM (10 mL) was added silica (100 mg) and PCC (55.1 mg, 0.2564 mmol) in at 25° C. under $N_2$. After stirring at 25° C. for 30 mins, the reaction mixture was filtered through a pad of silica and washed with DCM (3×10 mL). The filtrate was concentrated. The residue was purified by flash column (0~30% of EtOAc in PE) to give 340 (4.3 mg, 7.2%) as a solid.

$^1$H NMR (400 MHz, CDCl$_3$) $\delta_H$ 7.80 (s, 1H), 7.75 (s, 1H), 4.23 (dd, J=3.8, 13.6 Hz, 1H), 3.77 (dd, J=9.1, 13.5 Hz, 1H), 2.53-2.46 (m, 2H), 2.41 (br d, J=14.5 Hz, 1H), 2.28 (d, J=12.1 Hz, 1H), 2.12-1.94 (m, 2H), 1.92-1.66 (m, 5H), 1.52-1.22 (m, 15H), 1.17 (s, 3H), 1.07 (br dd, J=3.4, 14.7 Hz, 1H), 0.93 (t, J=7.2 Hz, 3H), 0.79 (d, J=6.6 Hz, 3H), 0.66 (s, 3H).

LC-ELSD/MS purity 99%, MS ESI calcd. for $C_{29}H_{42}N_3O$ [M−H$_2$O+H]$^+$ 448.4 found 448.4.

Examples 341 & 342: Synthesis of 1-((R)-2-((3R,5R,8R,9R,10S,13S,14S,17R)-3-cyclopropyl-3-hydroxy-13-methylhexadecahydro-1H-cyclopenta[a]phenanthren-17-yl)propyl)-1H-pyrazole-4-carbonitrile (341) & 1-((S)-2-((3R,5R,8R,9R,10S,13S,14S,17R)-3-cyclopropyl-3-hydroxy-13-methylhexadecahydro-1H-cyclopenta[a]phenanthren-17-yl)propyl)-1H-pyrazole-4-carbonitrile (342)

Synthesis of 341.1

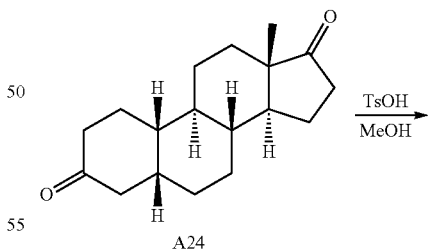

A24

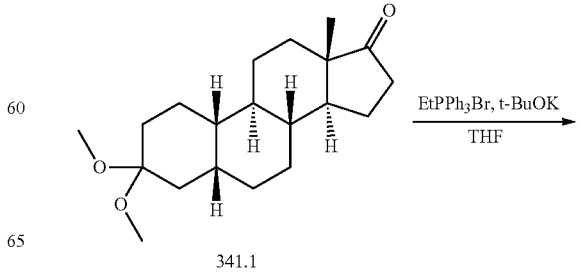

341.1

477
-continued
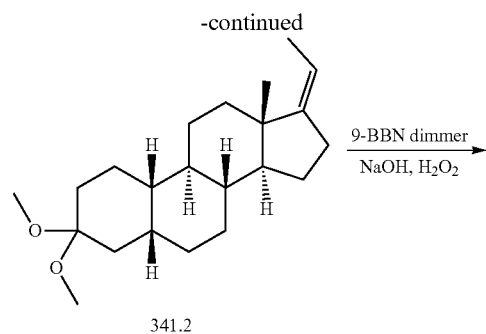
341.2
9-BBN dimmer
NaOH, H$_2$O$_2$
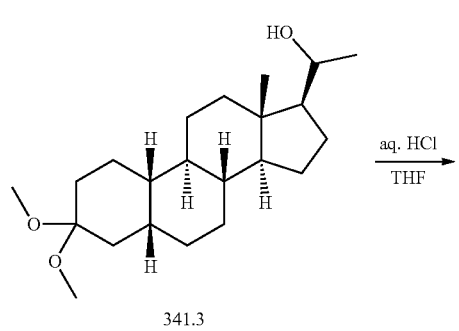
341.3
aq. HCl
THF
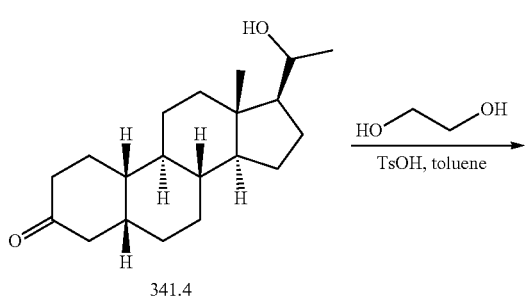
341.4
HO—CH$_2$CH$_2$—OH
TsOH, toluene
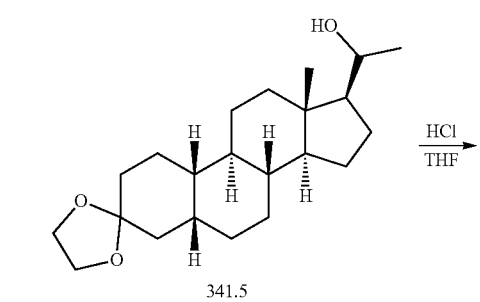
341.5
HCl
THF
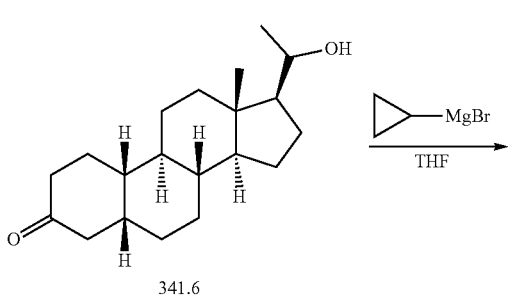
341.6
cyclopropyl-MgBr
THF
478
-continued
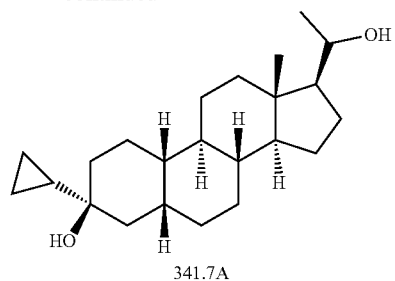
341.7A
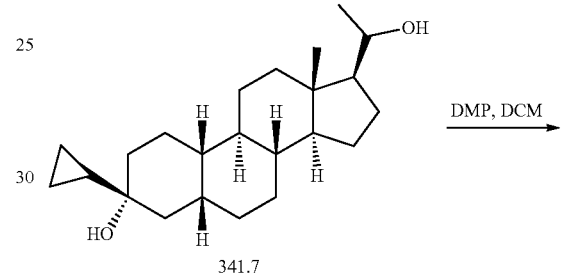
341.7
DMP, DCM
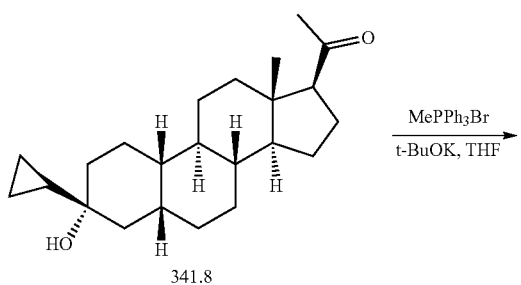
341.8
MePPh$_3$Br
t-BuOK, THF
341.9
BH$_3$Me$_2$S
H$_2$O$_2$, NaOH
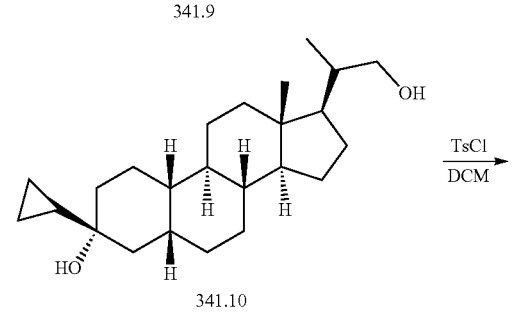
341.10
TsCl
DCM

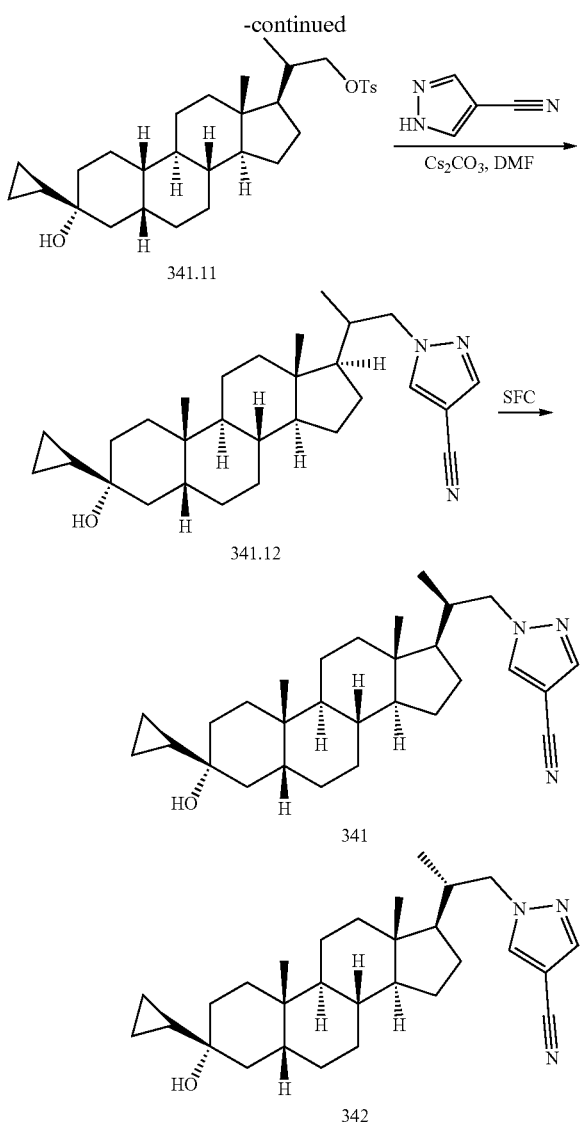

To a solution of A24 (300 g, 1093 mmol) in MeH (2 L) was added 4-methylbenzenesulfonic acid (18.7 g, 109 mmol) at 20° C. under N. After stirring at 65° C. for 1 h, the reaction mixture was cooled and the precipitate was collected by filtration and washed with methanol (2×300 mL) to give 341.1 (230 g) as a solid.

$^1$H NMR (400 MHz, CDCl$_3$) δ$_H$ 3.19 (s, 3H), 3.14 (s, 3H), 2.60-2.39 (m, 2H), 2.25-2.00 (2H), 1.97-1.90 (m, 2H), 1.86-1.75 (m, 6H), 1.70-1.60 (m, 5H), 1.56-1.49 (m, 4H), 1.47-1.35 (m, 10H), 1.30-1.22 (m, 5H), 1.15-1.00 (m, 2H), 0.86 (s, 3H).

Synthesis of 341.2

To a suspension of EtPPh$_3$Br (798 g, 2.15 mol) in THF (1.5 L) was added t-BuOK (241 g, 2.15 mol) at 20° C. under N$_2$. After stirring at 50° C. for 30 mins, a solution of 341.1 (230 g, 717 mmol) in THF (500 mL) was added. After stirring at 50° C. for 16 h, the mixture was cooled to 25° C., quenched with sat NH$_4$Cl (500 mL) and extracted with EtOAc (2×500 mL). The combined organic phase was washed with brine (2×500 mL), dried over anhydrous Na$_2$SO$_4$, filtered and concentrated in vacuum to give the product. The solid was suspended in methanol (1 L) and water (1 L). The solid was collected by filtration and the filter cake was dried to afford 341.2 (290 g) as a solid.

$^1$H NMR (400 MHz, CDCl$_3$) δ$_H$ 3.19 (s, 3H), 3.14 (s, 3H), 2.40-2.10 (m, 4H), 1.95-1.35 (m, 13H), 1.33-1.05 (m, 10H), 0.87 (s, 3H).

Synthesis of 341.3

To a solution of 341.2 (275 g, 826 mmol) in THF (2 L) was added 9-BBN dimer (402 g, 1.65 mol) at 20° C. under N$_2$. After stirring at 50° C. for 2 h, the mixture was cooled to 0° C. and sequentially treated with ethanol (379 g, 8.26 mol) and NaOH (1.65 L, 5 M, 8.26 mol) dropwise. After the addition was completed, H$_2$O$_2$ (825 mL, 8.26 mol, 30%) was added slowly and the reaction temperature was maintained below 15° C. After stirred at 75° C. for 1 h, the reaction was quenched with saturated aqueous Na$_2$S$_2$O$_3$ (260 mL) and stirred at 0° C. for another 1 h. The mixture was cooled and added into water (2 L). The mixture was filtered and the filter cake was washed with water (3×700 mL), dried under vacuum to give 341.3 (285 g) as a solid.

$^1$H NMR (400 MHz, CDCl$_3$) δ$_H$ 3.17-3.09 (m, 6H), 1.96-1.77 (m, 8H), 1.64-1.29 (m, 11H), 1.24-0.91 (m, 10H), 0.63 (s, 3H).

Synthesis of 341.4

To a solution of 341.3 (285 g, 813 mmol) in THF (3 L) was added aq HCl (1.62 L, 1.62 mol, 1 M) at 20° C. After stirring for 1 h, the mixture was treated with water (700 mL) and extracted with DCM (2×500 mL). The combined organic phase was washed with brine (2×500 mL), dried over anhydrous Na$_2$SO$_4$, filtered, concentrated to afford 341.4 (280 g) as a solid.

$^1$H NMR (400 MHz, CDCl$_3$) δ$_H$ 3.75-3.65 (m, 1H), 2.65-2.55 (m, 1H), 2.30-2.10 (m, 1H), 2.00-1.80 (m, 5H), 1.75-1.42 (m, 10H), 1.40-1.28 (m, 4H), 1.29-1.15 (m, 7H), 0.66 (s, 3H).

Synthesis of 341.5

To a solution of 341.4 (14 g, 45.9 mmol) in toluene (200 mL) was added TsOH (787 mg, 4.6 mmol) and ethane-1,2-diol (28.4 g, 458 mol) at 20° C. under N$_2$. After stirring at 120° C. for 4 h, the mixture was poured into water (100 mL) and extracted with ethyl acetate (2×100 mL). The combined organic layers was washed with brine (100 mL), dried over Na$_2$SO$_4$, filtered and concentrated in vacuum. The residue was purified by flash column (5-10% EtOAc in PE) to give 341.5 (8 g, 50%) as a solid.

$^1$H NMR (400 MHz, CDCl$_3$) δ$_H$ 3.93 (s, 4H), 3.76-3.63 (m, 1H), 2.03-1.95 (m, 1H), 1.93-1.80 (m, 4H), 1.64-1.58 (m, 3H), 1.56-1.48 (m, 2H), 1.44-1.30 (s, 6H), 1.27-0.95 (m, 12H), 0.66 (s, 3H).

Synthesis of 341.6

A solution of 341.5 (10 g, 28.6 mmol) and aq. HCl (28.6 mL, 2 M, 57.2 mmol) in THF (30 mL) was stirred at 20° C. for 16 h. The mixture was added into saturated NaHCO$_3$ (200 mL). The aqueous layer was extracted with EtOAc (3×100 mL). The combined organic layer was washed with brine (150 mL), dried over anhydrous Na$_2$SO$_4$, filtered and concentrated to give 341.6 (8 g) as a solid.

$^1$H NMR (400 MHz, CDCl$_3$) δ$_H$ 3.80-3.70 (m, 1H), 2.59 (t, J=14.0 Hz, 1H), 2.25-2.08 (m, 5H), 1.99-1.80 (m, 2H), 1.75-1.30 (m, 13H), 1.28-1.08 (m, 7H), 0.69 (s, 3H).

Synthesis of 341.7, 341.7A

To a solution of 341.6 (3.0 g, 9.9 mmol) was added bromo(cyclopropyl)magnesium (59.0 mL, 29.5 mmol, 0.5 M) in THF (30 mL) at 70° C. under N$_2$. After stirring at 70° C. for 4 h, the mixture was cooled to 25° C., poured into saturated NH$_4$Cl (100 mL) and extracted with DCM (3×50 mL). The combined organic phase was washed with brine (2×100 mL), dried over anhydrous Na$_2$SO$_4$, filtered and concentrated. The residue was purified by flash column (5~25% of EtOAc in PE) to give mixture 341.7A (2.4 g, 70.3%) and 341.7 (700 mg, 20.5%), both as solids.

341.7A: $^1$H NMR (400 MHz, CDCl$_3$) $\delta_H$ 3.77-3.60 (m, 1H), 1.96-1.78 (m, 2H), 1.75-1.49 (m, 8H), 1.43-1.28 (m, 5H), 1.24-1.19 (m, 4H), 1.17-0.98 (m, 8H), 0.96-0.79 (m, 2H), 0.66 (s, 3H), 0.38-0.26 (m, 4H).

341.7: $^1$H NMR (400 MHz, CDCl$_3$) $\delta_H$ 3.77-3.61 (m, 1H), 2.27-2.11 (m, 1H), 2.01-1.75 (m, 6H), 1.72-1.36 (m, 14H), 1.34-0.99 (m, 18H), 0.90-0.81 (m, 1H), 0.67 (s, 3H), 0.42-0.29 (m, 4H).

Synthesis of 341.8

To a solution of 341.7 (700 mg, 2.01 mmol) in DCM (30 mL) was added DMP (1.27 g, 3.01 mmol) at 20° C. After stirring for 5 mins, the mixture was quenched with NaHCO$_3$ (20 mL, saturated) and Na$_2$S$_2$O$_3$ (20 mL, saturated). The organic layer was separated, dried over Na$_2$SO$_4$, filtered and concentrated. The residue was purified by flash column (0~30% EtOAc in PE) to give 341.8 (300 mg, 43.3%) as a solid.

$^1$H NMR (400 MHz, CDCl$_3$) $\delta_H$ 2.64-2.48 (m, 2H), 2.21-2.15 (m, 2H), 2.12 (s, 3H), 2.10-1.96 (m, 3H), 1.84-1.59 (m, 8H), 1.37-1.07 (m, 11H), 0.62 (s, 3H), 0.43-0.32 (m, 4H).

Synthesis of 341.9

To a mixture of MePPh$_3$Br (1.39 g, 3.9 mmol) in THF (6 mL) was added t-BuOK (437 mg, 3.90 mmol) at 20° C. under N$_2$. After stirring at 40° C. for 30 mins, 341.8 (450 mg, 1.30 mmol) was added at 40° C. After stirring at 40° C. for 3 h, the mixture was quenched with saturated NH$_4$Cl aqueous (50 mL) at 20° C. and extracted with EtOAc (3×50 mL). The combined organic phase was washed with water (2×50 mL), dried over anhydrous Na$_2$SO$_4$, filtered and concentrated. The residue was purified by flash column (0~15% of EtOAc in PE) to give 341.9 (300 mg, 67.4%) as a solid.

$^1$H NMR (400 MHz, CDCl$_3$) $\delta_H$ 4.85 (s, 1H), 4.70 (s, 1H), 2.03-1.97 (m, 1H), 1.89-1.77 (m, 3H), 1.76 (s, 3H), 1.73-1.63 (m, 4H), 1.52-1.39 (m, 6H), 1.37-1.00 (m, 11H), 0.83 (s, 1H), 0.57 (s, 1H), 0.43-0.30 (m, 4H).

Synthesis of 341.10

To a solution of 341.9 (300 mg, 0.9 mmol) in THF (5 mL) was added BH$_3$·Me$_2$S (300 µL, 10 M, 2.99 mmol) at 20° C. under N$_2$. After stirring for 1 h, the reaction was sequentially treated dropwise with EtOH (600 µL, 10.4 mmol), NaOH (349 mg in 1.75 mL water, 5 M, 8.75 mmol) and H$_2$O$_2$ (900 µL, 10 M, 9.0 mmol). After stirring at 70° C. for 2 h, the mixture was quenched by Na$_2$S$_2$O$_3$ (50 mL, 10%) and extracted with EtOAc (50 mL). The organic layer was separated, dried over Na$_2$SO$_4$, filtered and concentrated in vacuum to give 341.10 (300 mg) as a solid.

$^1$H NMR (400 MHz, CDCl$_3$) $\delta_H$ 3.81-3.58 (m, 1H), 3.50-3.33 (m, 1H), 1.91-1.76 (m, 4H), 1.51-1.37 (m, 7H), 1.33-1.20 (m, 8H), 1.14-1.01 (m, 7H), 0.95 (d, J=6.8 Hz, 2H), 0.91-0.79 (m, 3H), 0.69 (s, 3H), 0.44-0.29 (m, 4H).

Synthesis of 341.11

To a solution of 341.10 (300 mg, 0.83 mmol) in DCM (5 mL) were added N-methylimidazole (101 mg, 1.24 mmol), TEA (251 mg, 2.49 mmol) and TsCl (316 mg, 1.66 mmol) at 20° C. under N$_2$. After stirring for 0.5 h, the mixture was poured into water (20 mL) and extracted with EtOAc (2×30 mL). The combined organic phase was washed with water (2×20 mL), dried over anhydrous Na$_2$SO$_4$, filtered, concentrated and to give 341.11 (500 mg) as oil.

Synthesis of 341.12

To a solution of 341.11 (500 mg, 0.97 mmol) in DMF (10 mL) were added Cs$_2$CO$_3$ (632 mg, 1.94 mmol), 4-cyanopyrazole (180 mg, 1.94 mmol) and KI (161 mg, 0.97 mmol) at 20° C. under N$_2$. After stirring at 80° C. for 16 h, the mixture was diluted with EtOAc (2×30 mL) and washed with water (30 mL), LiCl (5%, 30 mL aq.), dried over Na$_2$SO$_4$, filtered and concentrated. The residue was purified by flash column (5-30% EtOAc in PE)) to give 341.12 (220 mg, 52.0%) as a solid.

$^1$H NMR (400 MHz, CDCl$_3$) $\delta_H$ 7.80 (s, 1H), 7.75 (s, 1H), 4.62-4.19 (m, 1H), 3.79-3.61 (m, 1H), 2.19-2.06 (m, 1H), 2.03-1.76 (m, 5H), 1.72-1.59 (m, 3H), 1.52-1.28 (m, 10H), 1.22-1.03 (m, 7H), 0.87-0.78 (m, 4H), 0.73-0.66 (m, 3H), 0.43-0.29 (m, 4H).

Separation of 341 & 342

341.12 (220 mg, 0.5049 mmol) was separated by SFC (column: DAICEL CHIRALCEL OD-H (250 mm*30 mm, 5 um); Mobile phase: A: CO$_2$ B: 0.1% NH$_3$H$_2$O EtOH; gradient: from 40% to 40% of B, FlowRate (ml/min): 60) to give 341 (75.9 mg, 34.6%) and 342 (70 mg, 31.8%) both as solids. 342 (70 mg, 0.1606 mmol) was further purified by flash column (0~30% EtOAc in PE) to give 342 (41.9 mg, 59.5%) as a solid.

341: $^1$H NMR (400 MHz, CDCl$_3$) $\delta_H$ 7.80 (s, 1H), 7.75 (s, 1H), 4.56-4.45 (m, 1H), 3.75-3.60 (m, 1H), 2.18-2.06 (m, 1H), 2.04-1.95 (m, 1H), 1.92-1.76 (m, 4H), 1.72-1.59 (m, 3H), 1.52-1.19 (m, 12H), 1.16-1.03 (m, 5H), 0.85 (s, 1H), 0.80 (s, 3H), 0.64 (d, J=6.5 Hz, 3H), 0.42-0.33 (m, 4H). LC-ELSD/MS purity 99%, analytic SFC: 99.82% de, MS ESI calcd. for C$_{28}$H$_{40}$N$_3$ [M−H$_2$O+H]$^+$ 418.3, found 418.3.

342: $^1$H NMR (400 MHz, CDCl$_3$) $\delta_H$ 7.80 (s, 1H), 7.75 (s, 1H), 4.31-4.21 (m, 1H), 3.78-3.67 (m, 1H), 2.08-1.75 (m, 6H), 1.71-1.59 (m, 3H), 1.52-1.20 (m, 12H), 1.18-1.03 (m, 6H), 0.81 (d, J=6.8 Hz, 3H), 0.72 (s, 3H), 0.42-0.29 (m, 4H). LC-ELSD/MS purity 99%, analytic SFC: 100% de, MS ESI calcd. for C$_{28}$H$_{40}$N$_3$ [M−H$_2$O+H]$^+$ 418.3, found 418.3.

Examples 343 & 344: Synthesis of 1-((R)-2-((3R, 5R,8R,9R,10S,13S,14S,17R)-3-hydroxy-3-isopropyl-13-methylhexadecahydro-1H-cyclopenta[a]phenanthren-17-yl)propyl)-1H-pyrazole-4-carbonitrile (343) & 1-((S)-2-((3R,5R,8R,9R,10S, 13S,14S,17R)-3-hydroxy-3-isopropyl-13-methylhexadecahydro-1H-cyclopenta[a]phenanthren-17-yl)propyl)-1H-pyrazole-4-carbonitrile (344)

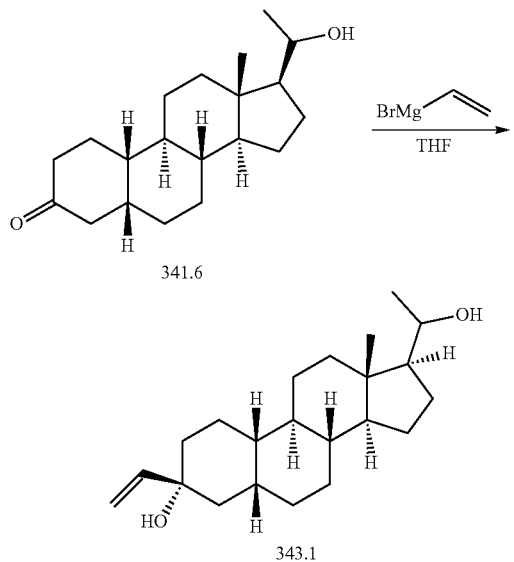

483
-continued
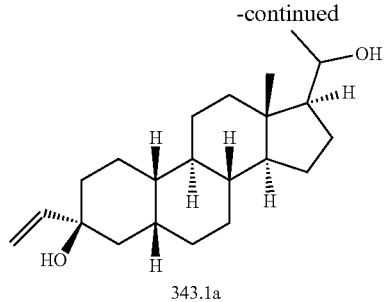
343.1a
TBSCl, imidazole
DCM
→
484
-continued
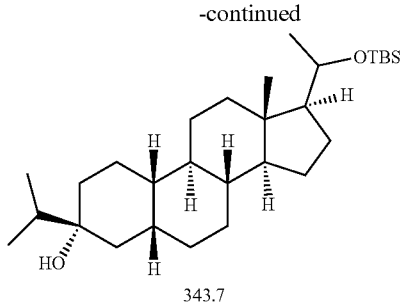
343.7
TBAF
THF
→
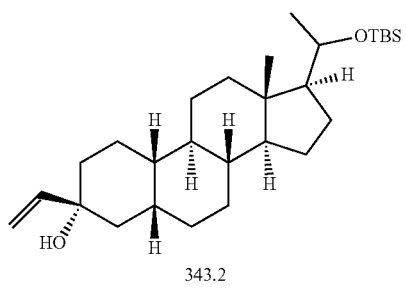
343.2
m-CPBA
DCM
→
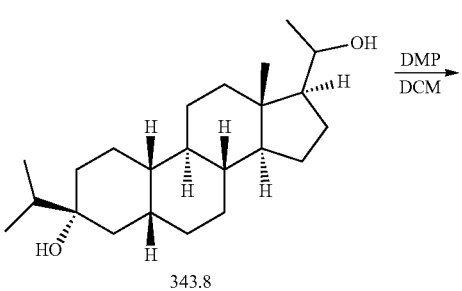
343.8
DMP
DCM
→
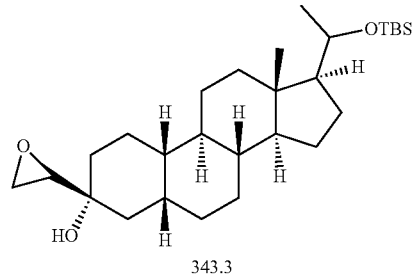
343.3
LiAlH₄
THF
→
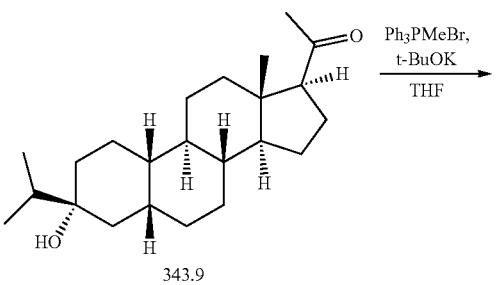
343.9
Ph₃PMeBr,
t-BuOK
THF
→
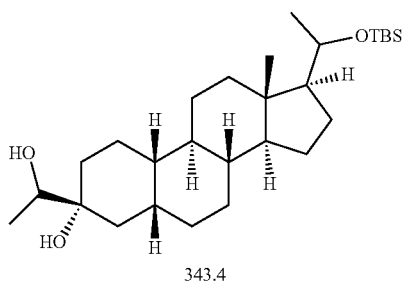
343.4
DMSO, (COCl)₂
Et₃N, DCM
→
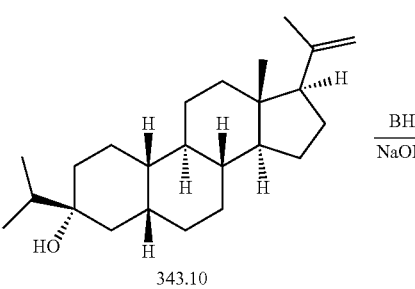
343.10
BH₃Me₂S
NaOH, H₂O₂
→
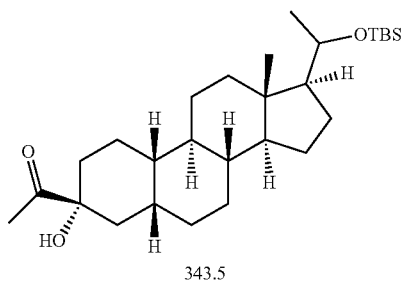
343.5
Ph₃PMeBr,
t-BuOK
THF
→
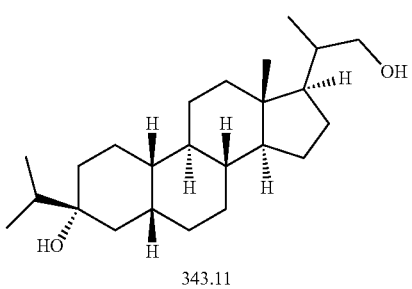
343.11
Ph₃P, NBS
DCM
→
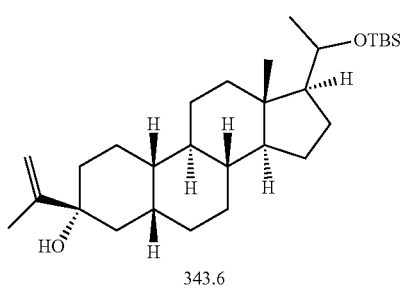
343.6
Pd/C, H₂
THF
→
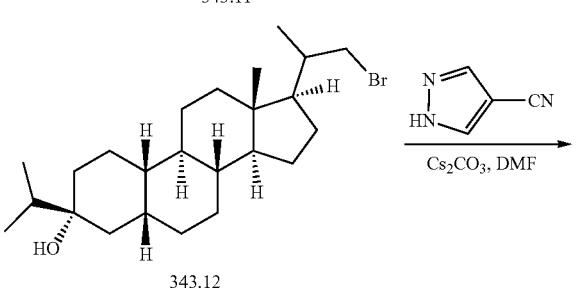
343.12
Cs₂CO₃, DMF
→

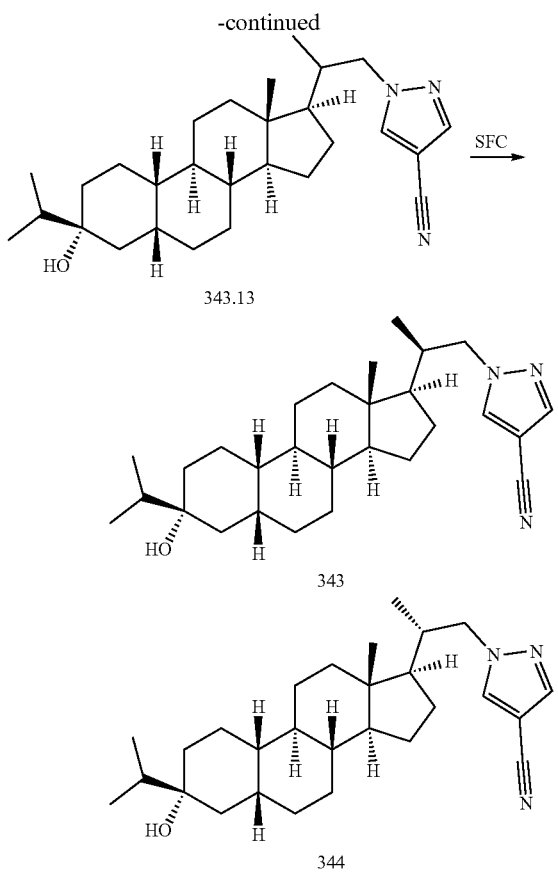

Synthesis of 343.1 & 343.1A

To a solution of 341.6 (4 g, 13.1 mmol) in THF (60 mL) was added CH$_2$CHMgBr (24.5 mL, 1.6 M, 39.3 mmol) at 0° C. under N$_2$. After stirring at 15° C. for 2 h, the mixture was added into saturated NH$_4$Cl (100 mL) and extracted with EtOAc (3×50 mL). The combined organic layer was washed with brine (100 mL), dried over anhydrous Na$_2$SO$_4$, filtered and concentrated. The residue was purified by flash column (0-30% of EtOAc in PE) to give 343.1 (1.5 g) and 343.1a (800 mg, 18%) both as solids.

343.1a: $^1$H NMR (400 MHz, CDCl$_3$) δ$_H$ 5.94 (dd, J=10.8 Hz, 17.6 Hz, 1H), 5.23 (dd, J=1.6 Hz, 17.6 Hz, 1H), 5.00 (dd, J=1.6 Hz, 10.8 Hz, 1H), 3.80-3.70 (m, 1H), 2.20-2.10 (m, 1H), 1.95-1.59 (m, 9H), 1.52-1.30 (m, 6H), 1.28-1.00 (m, 13H), 0.67 (s, 3H).

343.1: $^1$H NMR (400 MHz, CDCl$_3$) δ$_H$ 6.12 (dd, J=10.8 Hz, 17.2 Hz, 1H), 5.32 (dd, J=1.2 Hz, 17.6 Hz, 1H), 5.15 (dd, J=1.2 Hz, 10.8 Hz, 1H), 3.75-3.65 (m, 1H), 2.00-1.75 (m, 6H), 1.70-1.59 (m, 3H), 1.52-1.25 (m, 9H), 1.22 (d, J=6.4 Hz, 3H), 1.20-1.00 (m, 8H), 0.66 (s, 3H).

Synthesis of 343.2

To a solution of 343.1 (800 mg, 2.4 mmol) in DCM (20 mL) were added imidazole (570 mg, 8.4 mmol) and TBSCl (1.08 g, 7.2 mmol) at 15° C. under N$_2$. After stirring at 15° C. for 16 h, the mixture was filtered. The filtrate was washed with NH$_4$Cl (50 mL) and the aqueous layer was extracted with DCM (2×30 mL). The combined organic layer was washed with brine (100 mL), dried over anhydrous Na$_2$SO$_4$, filtered and concentrated. The residue was purified by flash column (0-5% of EtOAc in PE) to give 343.2 (1.2 g) as oil.

$^1$H NMR (400 MHz, CDCl$_3$) δ$_H$ 6.12 (dd, J=10.4 Hz, 16.8 Hz, 1H), 5.31 (d, J=17.6 Hz, 1H), 5.15 (d, J=10.8 Hz, 1H), 3.80-3.60 (m, 1H), 2.00-1.59 (m, 9H), 1.52-0.90 (m, 19H), 0.89-0.87 (m, 9H), 0.64 (s, 3H), 0.05-0.04 (m, 6H).

Synthesis of 343.3

To a solution of 343.2 (1 g, 2.2 mmol) and NaHCO$_3$ (561 mg, 6.7 mmol) in DCM (30 mL) was added m-CPBA (1.35 g, 85%, 6.7 mmol) at 20° C. under N$_2$. After stirring at 20° C. for 16 h, the mixture was quenched by saturated NaHCO$_3$ aqueous (100 mL) and extracted with DCM (2×50 mL). The combined DCM phase was washed with saturated NaHCO$_3$/Na$_2$S$_2$O$_3$ aqueous (1:1, 2×100 mL), brine (100 mL), dried over Na$_2$SO$_4$, filtered and concentrated. The residue was purified by flash column (0-15% of EtOAc in PE) to give 343.3 (550 mg, 53%) as a solid.

$^1$H NMR (400 MHz, CDCl$_3$) δ$_H$ 3.75-3.60 (m, 1H), 3.39 (s, 1H), 2.95-2.85 (m, 1H), 2.80-2.70 (m, 1H), 2.10-1.59 (m, 9H), 1.52-1.20 (m, 10H), 1.18-0.95 (m, 9H), 0.90-0.85 (m, 9H), 0.65 (s, 3H), 0.05-0.04 (m, 6H).

Synthesis of 343.4

To a solution of 343.3 (550 mg, 1.2 mmol) in THF (10 mL) was added LiAlH$_4$ (134 mg, 3.5 mmol) at 20° C. under N$_2$. After stirring for 1 h, HCl (30 mL, 1.0 M) was added to the mixture and extracted with EtOAc (3×30 mL). The combined organic layer was washed with saturated NaHCO$_3$ (100 mL), brine (100 mL), dried over anhydrous Na$_2$SO$_4$, filtered and concentrated to give 343.4 (600 mg) as a solid.

$^1$H NMR (400 MHz, CDCl$_3$) δ$_H$ 4.10-4.00 (m, 1H), 3.75-3.60 (m, 1H), 1.95-1.55 (m, 13H), 1.52-1.28 (m, 8H), 1.25-0.95 (m, 11H), 0.90-0.87 (m, 9H), 0.64 (s, 3H), 0.05-0.35 (m, 6H).

Synthesis of 343.5

To a solution of oxalic dichloride (244 mg, 1.9 mmol) in DCM (5 mL) was added DMSO (301 mg, 3.9 mmol) at −70° C. under N$_2$. After stirring for 30 minutes, a solution of 343.4 (450 mg, 0.97 mmol) in DCM (5 mL) was added. After stirring at −70° C. for 30 minutes. Et$_3$N (979 mg, 9.7 mmol) was added at −70° C. After stirring at 15° C. for 16 h, the mixture was added into water (50 mL) and extracted with DCM (3×20 mL). The combined organic layer was washed with brine (50 mL), dried over anhydrous Na$_2$SO$_4$, filtered and concentrated. The residue was purified by flash column (0-10% of EtOAc in PE) to give 343.5 (280 mg, 63%) as a solid.

$^1$H NMR (400 MHz, CDCl$_3$) δ$_H$ 3.72-3.60 (m, 1H), 2.25 (s, 3H), 1.95-1.59 (m, 10H), 1.52-0.95 (m, 18H), 0.90-0.87 (m, 9H), 0.63 (s, 3H), 0.05-0.04 (m, 6H).

Synthesis of 343.6

To a solution of MePh$_3$PBr (1.38 g, 3.9 mmol) in THF (5 mL) was added t-BuOK (434 mg, 3.9 mmol) at 15° C. under N$_2$. After stirring at 50° C. for 1 h, 343.5 (300 mg, 0.65 mmol) in THF (5 mL) was added below 15° C. After stirring at 60° C. for 3 h, the mixture was added into saturated NH$_4$Cl (100 mL) and extracted with EtOAc (3×30 mL). The combined organic layer was washed with brine (100 mL), dried over anhydrous Na$_2$SO$_4$, filtered and concentrated. The residue was purified by flash column (0-10% of EtOAc in PE) to give 343.6 (240 mg, 81%) as a solid.

$^1$H NMR (400 MHz, CDCl$_3$) δ$_H$ 5.01 (d, J=7.6 Hz, 2H), 3.75-3.60 (m, 1H), 2.00-1.80 (m, 4H), 1.79 (s, 3H), 1.75-1.59 (m, 4H), 1.52-1.20 (m, 11H), 1.18-0.95 (m, 9H), 0.90-0.87 (m, 9H), 0.63 (s, 3H), 0.05-0.04 (m, 6H).

Synthesis of 343.7

To a solution of 343.6 (190 mg, 0.41 mmol) in THF (5 mL) was added Pd/C (50 mg, 10% in water) at 20° C. under H$_2$. After stirring for 16 h, the mixture was filtered and the filtrate was concentrated to give 343.7 (190 mg, 100%) as an oil.

¹H NMR (400 MHz, CDCl₃) δ_H 3.72-3.60 (m, 1H), 2.15-2.05 (m, 1H), 1.95-1.59 (m, 9H), 1.52-1.20 (m, 10H), 1.18-0.95 (m, 9H), 0.94-0.87 (m, 15H), 0.63 (s, 3H), 0.05-0.04 (m, 6H).

Synthesis of 343.8

To a solution of 343.7 (240 mg, 0.52 mmol) in THF (10 mL) was added TBAF (815 mg, 2.6 mmol) at 20° C. under N₂, After stirring at 55° C. for 16 h, the mixture was added into saturated NH₄Cl (100 mL) and extracted with EtOAc (3×30 mL). The combined organic layer was washed with brine (100 mL), dried over anhydrous Na₂SO₄, filtered and concentrated. The residue was purified by flash column (0~50% of EtOAc in PE) to give 343.8 (150 mg, 83%) as a solid.

¹H NMR (400 MHz, CDCl₃) δ_H 3.75-3.65 (m, 1H), 2.15-2.05 (m, 1H), 2.00-1.60 (m, 8H), 1.52-1.25 (m, 11H), 1.22 (d, J=6.4 Hz, 3H), 1.20-1.00 (m, 7H), 0.90 (d, J=0.8 Hz, 3H), 0.88 (d, J=0.8 Hz, 3H), 0.66 (s, 3H).

Synthesis of 343.9

To a solution of 343.8 (150 mg, 0.43 mmol) in DCM was added DMP (364 mg, 0.86 mmol) (10 mL). After stirring at 40° C. for 1 h, the mixture was added into saturated NaHCO₃ (50 mL) and extracted with DCM (3×20 mL). The combined organic layer was washed with saturated Na₂S₂O₃ (2×50 mL), brine (50 mL), dried over anhydrous Na₂SO₄, filtered and concentrated. The residue was purified by flash column (0-15% of EtOAc in PE) to give 343.9 (140 mg, 94%) as a solid.

¹H NMR (400 MHz, CDCl₃) δ_H 2.54 (t, J=9.2 Hz, 1H), 2.20-2.12 (m, 1H), 2.11 (s, 3H), 2.10-2.00 (m, 2H), 1.90-1.60 (m, 9H), 1.50-1.00 (m, 13H), 0.90 (s, 3H), 0.88 (s, 3H), 0.61 (s, 3H).

LC-ELSD/MS 30-90AB_2 min_E, purity 99%, MS ESI calcd. for C₂₃H₃₇O [M−H₂O+H]⁺ 329.3, found 329.3.

Synthesis of 343.10

To a solution of MePh₃PBr (667 mg, 1.9 mmol) in THF (10 mL) was added t-BuOK (209 mg, 1.9 mmol) at 15° C. under N₂. After stirring at 50° C. for 1 h, 343.9 (130 mg, 0.38 mmol) was added below 50° C. After stirring at 50° C. for 2 h, the mixture was added into saturated NH₄Cl (50 mL) and extracted with EtOAc (3×20 mL). The combined organic layer was washed with brine (50 mL), dried over anhydrous Na₂SO₄, filtered and concentrated. The residue was purified by flash column (0-10% of EtPAc in PE) to give 343.10 (100 mg, 78%) as a solid.

¹H NMR (400 MHz, CDCl₃) δ_H 4.84 (s, 1H), 4.70 (s, 1H), 2.15-1.95 (m, 2H), 1.85-1.59 (m, 12H), 1.52-0.95 (m, 15H), 0.89 (d, J=0.8 Hz, 3H), 0.88 (s, 3H), 0.57 (s, 3H).

Synthesis of 343.11

To a solution of 343.10 (100 mg, 0.29 mmol) in THF (5 mL) was added BH₃Me₂S (0.29 mL, 10 M, 2.90 mmol) at 20° C. under N₂. After stirring at 20° C. for 16 h, the reaction mixture was sequentially treated with EtOH (5 mL) at 15° C., NaOH (4 mL, 5 M, 20.0 mmol) at 0° C., and finally H₂O₂ (2.30 g, 20.3 mmol, 30%) dropwise. After stirring at 70° C. for 1 h, the mixture was added into water (50 mL) and extracted with EtOAc (3×20 mL). The combined organic layer was washed with saturated Na₂S₂O₃ (2×50 mL), brine (100 mL), dried over anhydrous Na₂SO₄, filtered and concentrated to give 343.11 (100 mg) as a solid.

¹H NMR (400 MHz, CDCl₃) δ_H 3.75-3.60 (m, 1H), 3.50-3.35 (m, 1H), 2.15-1.70 (m, 6H), 1.52-1.17 (m, 16H), 1.15-0.95 (m, 9H), 0.89 (s, 3H), 0.88 (s, 3H), 0.68 (s, 3H).

Synthesis of 343.12

To a solution of 343.11 (100 mg, 0.28 mmol) in DCM (10 mL) were added NBS (98.1 mg, 0.55 mmol) and PPh3 (144 mg, 0.55 mmol) at 0° C. under N₂. After stirring at 20° C. for 1 h, the mixture was concentrated. The residue was purified by flash column (0-5% of EtOAc in PE) to give 343.12 (60 mg, 51%) as colorless oil.

¹H NMR (400 MHz, CDCl₃) δ_H 3.65-3.45 (m, 1H), 3.40-3.30 (m, 1H), 2.15-2.02 (m, 1H), 1.95-1.59 (m, 9H), 1.52-1.21 (m, 13H), 1.20-0.96 (m, 7H), 0.89 (s, 3H), 0.88 (s, 3H), 0.68 (s, 3H).

Synthesis of 343 & 344

To a solution of 343.12 (60 mg, 0.14 mmol) were added Cs₂CO₃ (138 mg, 0.42 mmol) and 1H-pyrazole-4-carbonitrile (39.3 mg, 0.42 mmol) at 20° C. under N₂. After stirring at 80° C. for 16 h, the mixture was added into saturated NH₄Cl (50 mL) and extracted with EtOAc (3×20 mL). The combined organic layer was washed with water (2×50 mL), brine (50 mL), dried over anhydrous Na₂SO₄, filtered and concentrated. The residue was purified by flash column (0-30% of EtOAc in PE) to give 369.13 (50 mg, 81%) as a solid.

369.13 (50 mg, 0.11 mmol) was separated by SFC (Column: DAICEL CHIRALCEL OD-H (250 mm*30 mm, 5 m), Condition: 0.1% NH₃H₂O EtOH, Begin B: 35%, End B: 35%, FlowRate (ml/min): 50) to give 343 (9.1 mg, P1, rt=1.452, 18%) and 344 (17.0 mg, P2, rt=1.646, 34%) both as solids.

343: ¹H NMR (400 MHz, CDCl₃) δ_H 7.80 (s, 1H), 7.75 (s, 1H), 4.50 (dd, J=4.0 Hz, 12.8 Hz, 1H), 3.65 (dd, J=10.8 Hz, 13.6 Hz, 1H), 2.15-2.05 (m, 2H), 1.90-1.59 (m, 10H), 1.52-1.00 (m, 15H), 0.90 (s, 3H), 0.88 (s, 3H), 0.79 (s, 3H), 0.68 (d, J=6.4 Hz, 3H). LC-ELSD/MS purity 99%, analytic SFC: 99.44% de; MS ESI calcd. for C₂₈H₄₂N₃ [M−H₂O+H]⁺ 420.3, found 420.3. SFC 100% de.

344: ¹H NMR (400 MHz, CDCl₃) δ_H 7.79 (s, 1H), 7.75 (s, 1H), 4.25 (dd, J=3.6 Hz, 13.6 Hz, 1H), 3.72 (dd, J=9.2 Hz, 13.2 Hz, 1H), 2.15-1.59 (m, 11H), 1.52-1.00 (m, 16H), 0.89 (d, J=1.6 Hz, 3H), 0.87 (d, J=1.2 Hz, 3H), 0.80 (d, J=6.4 Hz, 3H), 0.71 (s, 3H). LC-ELSD/MS purity 99%, analytic SFC: 99.24% de; MS ESI calcd. for C₂₈H₄₂N₃ [M−H₂O+H]⁺ 420.3, found 420.3. SFC 100% de.

Examples 345 & 346: Synthesis of 1-((S)-2-((3R, 5R,8R,9R,10S,13S,14S,17S)-3,17-dihydroxy-3,13-dimethylhexadecahydro-1H-cyclopenta[a]phenanthren-17-yl)propyl)-1H-pyrazole-4-carbonitrile (345) & 1-((R)-2-((3R,5R,8R,9R,10S,13S,14S,17S)-3,17-dihydroxy-3,13-dimethylhexadecahydro-1H-cyclopenta[a]phenanthren-17-yl)propyl)-1H-pyrazole-4-carbonitrile (346)

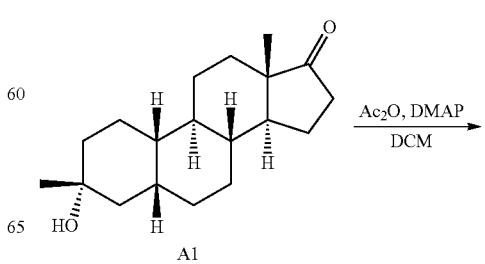

A1

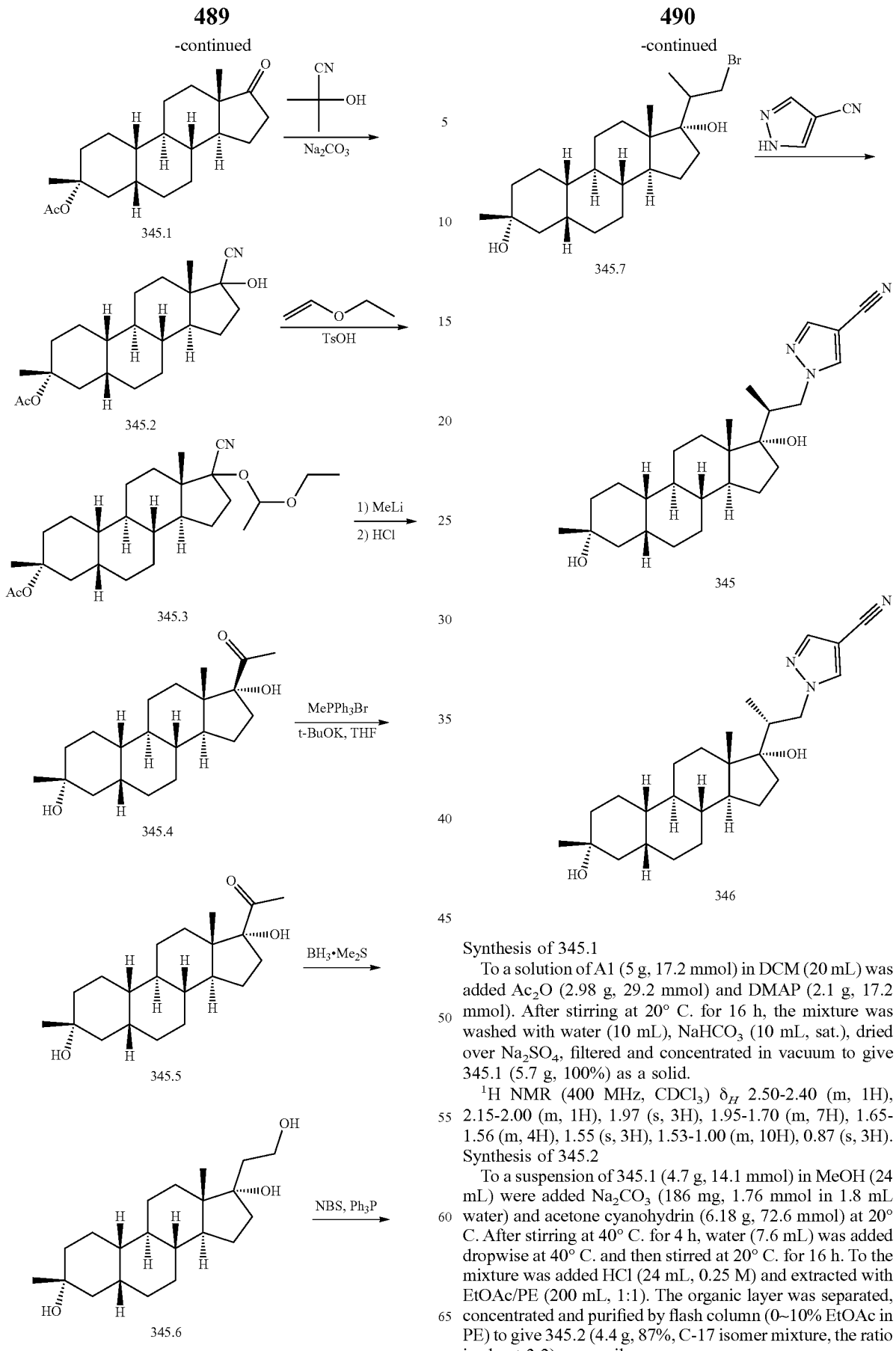

Synthesis of 345.1

To a solution of A1 (5 g, 17.2 mmol) in DCM (20 mL) was added Ac₂O (2.98 g, 29.2 mmol) and DMAP (2.1 g, 17.2 mmol). After stirring at 20° C. for 16 h, the mixture was washed with water (10 mL), NaHCO₃ (10 mL, sat.), dried over Na₂SO₄, filtered and concentrated in vacuum to give 345.1 (5.7 g, 100%) as a solid.

$^1$H NMR (400 MHz, CDCl₃) $\delta_H$ 2.50-2.40 (m, 1H), 2.15-2.00 (m, 1H), 1.97 (s, 3H), 1.95-1.70 (m, 7H), 1.65-1.56 (m, 4H), 1.55 (s, 3H), 1.53-1.00 (m, 10H), 0.87 (s, 3H).

Synthesis of 345.2

To a suspension of 345.1 (4.7 g, 14.1 mmol) in MeOH (24 mL) were added Na₂CO₃ (186 mg, 1.76 mmol in 1.8 mL water) and acetone cyanohydrin (6.18 g, 72.6 mmol) at 20° C. After stirring at 40° C. for 4 h, water (7.6 mL) was added dropwise at 40° C. and then stirred at 20° C. for 16 h. To the mixture was added HCl (24 mL, 0.25 M) and extracted with EtOAc/PE (200 mL, 1:1). The organic layer was separated, concentrated and purified by flash column (0~10% EtOAc in PE) to give 345.2 (4.4 g, 87%, C-17 isomer mixture, the ratio is about 3:2) as an oil.

Synthesis of 345.3

To a solution of 345.2 (1.5 g, 4.17 mmol) in THF (10 mL) was added ethoxyethene (3.0 g, 41.7 mmol) and TsOH (7.2 mg, 0.042 mmol). After stirring at 30° C. for 2 h, the reaction was treated with TEA (2 drops) and concentrated in vacuum. The residue was purified by flash column (0~8% EtOAc in PE) to give 345.3 (1.6 g, 89%) as an oil.

Synthesis of 345.4

To a solution of 345.3 (1.5 g, 3.5 mmol) in THF (30 mL) was added MeLi (21.6 mL, 1.6 M, 34.7 mmol). After stirring at 20° C. for 4 h, the mixture was quenched by HCl (40 mL, 1 M) and extracted with EtOAc (50 mL). The organic layer was separated, dried over $Na_2SO_4$, filtered, concentrated. The residue was purified by flash column (0~40% EtOAc in PE) to give 345.4, which was purified by flash column (20~40% EtOAc in PE) to give 345.4 (160 mg).

345: $^1$H NMR (400 MHz, $CDCl_3$) $\delta_H$, 2.66 (s, 1H), 2.35-2.20 (m, 4H), 1.85-1.50 (m, 10H), 1.50-1.30 (m, 9H), 1.25 (s, 3H), 1.20-0.95 (m, 4H), 0.93 (s, 3H). LC-ELSD/MS purity 99%, MS ESI calcd. for $C_{21}H_{31}$ $[M+H-2H_2O]^+$ 299, found 299.

Synthesis of 345.5

To a suspension of $MePh_3PBr$ (29.4 g, 83.2 mmol) in anhydrous THF (50 mL) was added t-BuOK (9.33 g, 83.2 mmol) at 25° C. under $N_2$. After stirring at 60° C. for 30 min, a solution of 345.4 (3.5 g, 10.4 mmol) in anhydrous THF (10 mL) was dropwise. After stirring for 16 h, the mixture was cooled, poured into ice-water (50 mL), stirred for 10 min and extracted with EtOAc (2×50 mL). The combined organic phase was washed with brine (2×50 mL), filtered and concentrated. The residue was purified by flash column (0~30% of EtOAc in PE) to give 345.5 (2.8 g, 60.4%) as a solid.

$^1$H NMR (400 MHz, $CDCl_3$) $\delta_H$ 4.97 (s, 1H), 4.93-4.89 (m, 1H), 2.39 (ddd, J=3.5, 11.6, 14.7 Hz, 1H), 1.94-1.70 (m, 12H), 1.53-1.24 (m, 16H), 1.23-1.01 (m, 4H), 0.64 (s, 3H)

Synthesis of 345.6

To a solution of 345.5 (300 mg, 0.9021 mmol) in anhydrous THF (5 mL) was added $BH_3 \cdot Me_2S$ (20.451 mL, 4.51 mmol) at 25° C. under $N_2$. After stirring at 25° C. for 4 h, the mixture was treated sequentially with EtOH (828 mg, 18.0 mmol) at 0° C. and NaOH (3.6 mL, 5M, 18.0 mmol) very slowly. After addition, $H_2O_2$ (1.8 mL, 18.0 mmol, 10 M in water) was added slowly until the reaction temperature no longer rises and the reaction temperature was maintained below 30° C. After stirring at 60° C. for 2 h, the mixture was added $Na_2S_2O_3$ (10 mL, sat. aq.) at 0° C. and extracted with EtOAc (3×10 mL). The combined organic phase was washed with brine (2×20 mL), dried over anhydrous $Na_2SO_4$, filtered and concentrated. The residue was purified by flash column (0~30% of EtOAc in PE) to give 345.6 (200 mg, 63.2%) as a solid.

$^1$H NMR (400 MHz, $CDCl_3$) $\delta_H$ 4.18 (br d, J=10.8 Hz, 1H), 3.59 (br d, J=7.8 Hz, 1H), 2.62 (s, 1H), 2.34 (br s, 1H), 1.90-1.60 (m, 11H), 1.51-1.23 (m, 13H), 1.17 (d, J=7.3 Hz, 7H), 0.76 (s, 3H). LC-ELSD/MS purity 99%, MS ESI calcd. for $C_{22}H_{35}O$ $[M+H-2H_2O]^+$ 315.3 found 315.3.

Synthesis of 345.7

To a solution of 345.6 (100 mg, 0.2852 mmol) in DCM (5 mL) at 0° C. were added $PPh_3$ (149 mg, 0.5704 mmol) and NBS (100 mg, 0.5704 mmol). After stirring at 25° C. for 3 h, the mixture was poured into water (20 mL) and extracted with DCM (3×20 mL). The combined organic phase was washed with brine (2×50 mL), dried over anhydrous $Na_2SO_4$, filtered and concentrated. The residue was purified by flash column (0~30% of EtOAc in PE) to give 345.7 (65 mg, 55.5%) as colorless oil.

Synthesis of 345 & 346

To a solution of 345.7 (200 mg, 0.4837 mmol) in DMF (1 mL) were added $Cs_2CO_3$ (253 mg, 0.9674 mmol) and 1H-pyrazole-4-carbonitrile (90.0 mg, 0.9674 mmol). After stirring at 80° C. for 1 h, the reaction was combined with another 4 batches prepared from 50 mg of 380.7 respectively. The mixture was added into saturated $NH_4Cl$ (100 mL) and extracted with EtOAc (3×30 mL). The combined organic layer was washed with water (2×50 mL), LiCl (2×50 mL, 5% in water), brine (50 mL), dried over anhydrous $Na_2SO_4$, filtered and concentrated. The residue was purified by flash column (0~20% of EtOAc in PE) to give 345 (65 mg) as an oil and 346 (27.1 mg, 13.2%) as solid. 345 was re-purified by SFC (Column DAICEL CHIRALPAK AS (250 mm*30 mm, 10 um) Condition 0.1% $NH_3 \cdot H_2O$ EtOH Begin B 30% End B 30% Gradient Time (min) 100% B Hold Time (min) FlowRate (ml/min) 60) to afford 345 (36.0 mg, 55.4%) as solid.

345: $^1$H NMR (400 MHz, $CDCl_3$) $\delta_H$ 7.81 (s, 1H), 7.75 (s, 1H), 4.47 (dd, J=4.1, 13.7 Hz, 1H), 3.99 (dd, J=10.0, 13.6 Hz, 1H), 2.56-2.31 (m, 1H), 2.02-1.58 (m, 12H), 1.48-1.05 (m, 16H), 0.91 (s, 3H), 0.74 (d, J=6.5 Hz, 3H). LC-ELSD/MS purity 99%, MS ESI calcd. for $C_{26}H_{36}N_3$ $[M+H-2H_2O]^+$ 390.3 found 390.3. SFC 100% de.

346: $^1$H NMR (400 MHz, $CDCl_3$) $\delta_H$ 7.81 (s, 1H), 7.75 (s, 1H), 4.47 (dd, J=4.1, 13.7 Hz, 1H), 3.99 (dd, J=10.0, 13.6 Hz, 1H), 2.56-2.31 (m, 1H), 2.02-1.58 (m, 12H), 1.48-1.05 (m, 16H), 0.91 (s, 3H), 0.74 (d, J=6.5 Hz, 3H). LC-ELSD/MS purity 99%, MS ESI calcd. for $C_{26}H_{38}N_3O$ $[M+H-H_2O]^+$ 408.3 found 408.3. SFC 100% de.

Examples 347 & 348: Synthesis of 1-((S)-2-((3R,5R,8R,9R,10S,13S,14S,17S)-3,17-dihydroxy-13-methyl-3-propylhexadecahydro-1H-cyclopenta[a]phenanthren-17-yl)propyl)-1H-pyrazole-4-carbonitrile (347) & 1-((R)-2-((3R,5R,8R,9R,10S,13S,14S,17S)-3,17-dihydroxy-13-methyl-3-propylhexadecahydro-1H-cyclopenta[a]phenanthren-17-yl)propyl)-1H-pyrazole-4-carbonitrile (348)

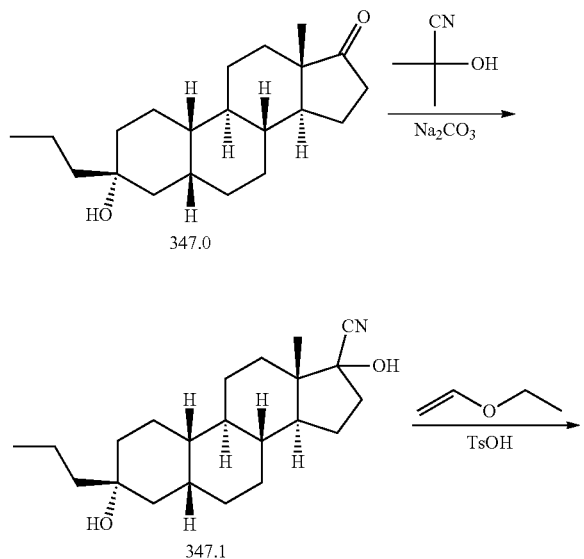

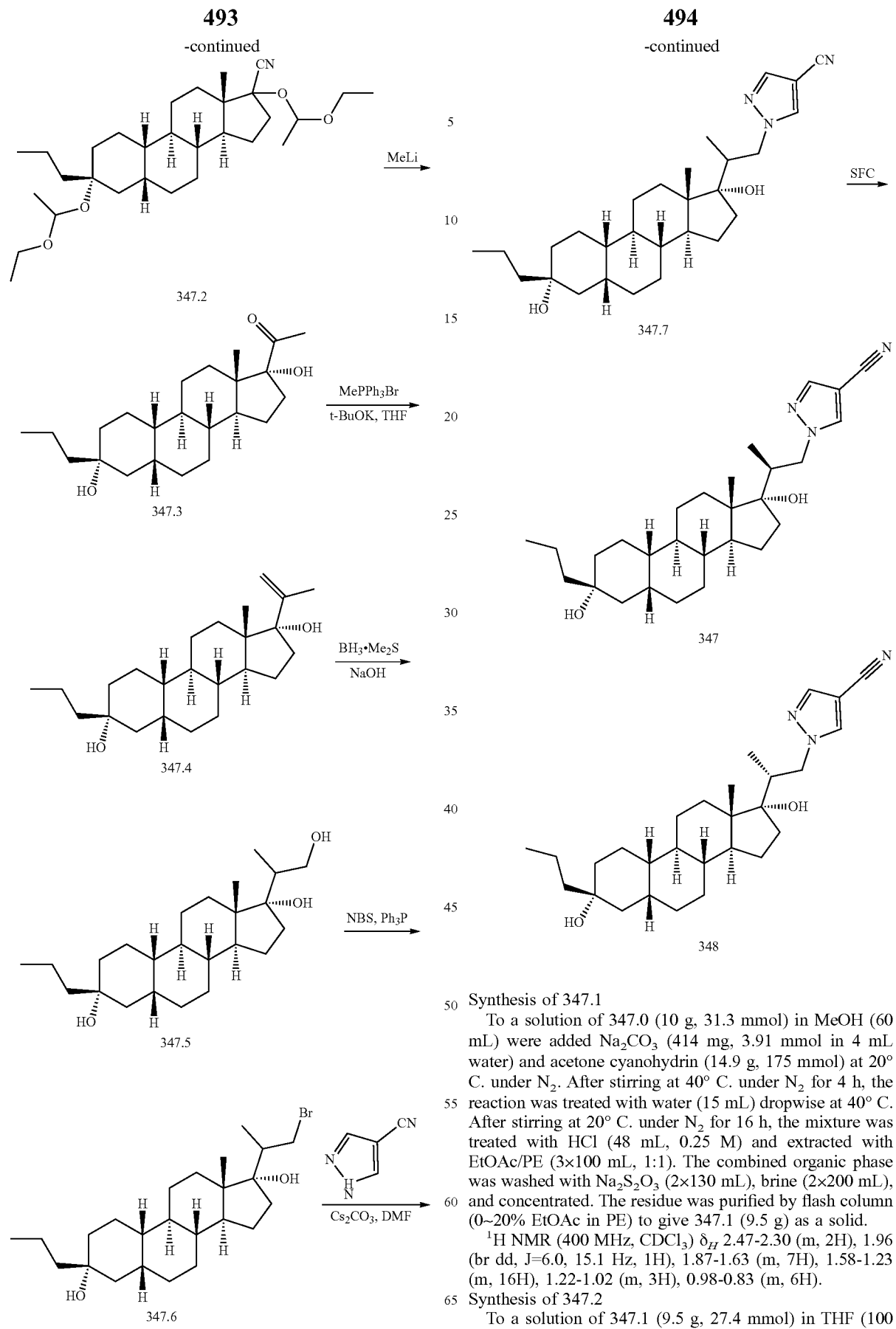

Synthesis of 347.1

To a solution of 347.0 (10 g, 31.3 mmol) in MeOH (60 mL) were added Na$_2$CO$_3$ (414 mg, 3.91 mmol in 4 mL water) and acetone cyanohydrin (14.9 g, 175 mmol) at 20° C. under N$_2$. After stirring at 40° C. under N$_2$ for 4 h, the reaction was treated with water (15 mL) dropwise at 40° C. After stirring at 20° C. under N$_2$ for 16 h, the mixture was treated with HCl (48 mL, 0.25 M) and extracted with EtOAc/PE (3×100 mL, 1:1). The combined organic phase was washed with Na$_2$S$_2$O$_3$ (2×130 mL), brine (2×200 mL), and concentrated. The residue was purified by flash column (0~20% EtOAc in PE) to give 347.1 (9.5 g) as a solid.

$^1$H NMR (400 MHz, CDCl$_3$) δ$_H$ 2.47-2.30 (m, 2H), 1.96 (br dd, J=6.0, 15.1 Hz, 1H), 1.87-1.63 (m, 7H), 1.58-1.23 (m, 16H), 1.22-1.02 (m, 3H), 0.98-0.83 (m, 6H).

Synthesis of 347.2

To a solution of 347.1 (9.5 g, 27.4 mmol) in THF (100 mL) was added ethoxyethene (19.7 g, 274 mmol) and TsOH (47.1 mg, 0.2739 mmol). After stirring at 30° C. for 2 h, the mixture was treated with TEA (2 drops) and concentrated in vacuum. The residue was purified by flash column (0~8% EtOAc in PE) to give 347.2 (15 g) as an oil.

Synthesis of 347.3

To a solution of 347.2 (7.5 g, 15.3 mmol) in THF (50 mL) was added MeLi (47.8 mL, 1.6 M, 76.5 mmol) at 0° C. under $N_2$. After stirring at 25° C. for 4 h, the mixture was quenched with $NH_4Cl$ (40 mL) and extracted with EtOAc (50 mL). The organic layer was separated, dried over $Na_2SO_4$, filtered, concentrated. The residue was purified by flash column (0~40% EtOAc in PE) to give 347.3 (5 g) as a solid. To a solution of 347.3 (5 g) in MeOH (50 mL) was added HCl (49.3 mL, 1 M, 49.3 mmol) at 25° C. under $N_2$. After stirring at 25° C. for 1 h, the reaction was extracted with EtOAc (3×40 mL). The combined organic phase was washed with saturated aqueous $Na_2CO_3$ (50 mL), brine (2×50 mL), dried over anhydrous $Na_2SO_4$, filtered and concentrated to give 347.3 (2.5 g, 70%) as a solid.

$^1$H NMR (400 MHz, $CDCl_3$) $\delta_H$ 2.73-2.55 (m, 2H), 2.26 (s, 3H), 1.84-1.59 (m, 9H), 1.52-1.24 (m, 15H), 1.22-1.01 (m, 3H), 0.93 (t, J=7.2 Hz, 3H), 0.72 (s, 3H). LC-ELSD/MS purity 99%, MS ESI calcd. for $C_{23}H_{35}O$ $[M+H-2H_2O]^+$ 327.3 found 327.3.

Synthesis of 347.4

To a suspension of $MePh_3PBr$ (19.5 g, 55.1 mmol) in anhydrous THF (50 mL) was added t-BuOK (6.18 g, 55.1 mmol) at 25° C. under $N_2$. After stirring at 60° C. for 30 min, a solution of 347.3 (2.5 g, 6.89 mmol) in anhydrous THF (30 mL) was dropwise. After stirring at 60° C. for 16 h, the mixture was cooled, poured into ice-water (50 mL), stirred for 10 min and extracted with EtOAc (2×50 mL). The combined organic phase was washed with brine (2×50 mL), dried over anhydrous $Na_2SO_4$, filtered, concentrated. The residue was purified by flash column (0~20% of EtOAc in PE) to give 347.4 (1.5 g, 60%) as a solid.

$^1$H NMR (400 MHz, $CDCl_3$) $\delta_H$ 4.91 (s, 1H), 5.00-4.76 (m, 1H), 2.55-2.30 (m, 1H), 1.94-1.83 (m, 6H), 1.78-1.61 (m, 6H), 1.53-1.30 (m, 13H), 1.29-1.00 (m, 6H), 0.93 (t, J=7.3 Hz, 3H), 0.76-0.61 (m, 3H).

Synthesis of 347.5

To a solution of 347.4 (1.5 g, 4.15 mmol) in anhydrous THF (30 mL) was added $BH_3 \cdot Me_2S$ (2.07 mL, 20.7 mmol, 10M) at 25° C. under $N_2$. After stirring at 25° C. for 4 h, the reaction was sequentially treated with EtOH (3.81 g, 83.0 mmol) at 0° C. and then NaOH (16.6 mL, 5M, 83.0 mmol) very slowly. After addition, $H_2O_2$ (8.30 mL, 83.0 mmol, 10 M in water) was added slowly until the reaction temperature no longer rises and the reaction temperature was maintained below 30° C. After stirring at 60° C. for 2 h, the mixture was diluted with $Na_2S_2O_3$ (50 mL, sat. aq.) at 0° C. and extracted with EtOAc (3×50 mL). The combined organic phase was washed with brine (2×50 mL), dried over anhydrous $Na_2SO_4$, filtered and concentrated. The residue was purified by flash column (20~50% of EtOAc in PE) to give 347.5 (730 mg) as a solid.

Synthesis of 347.6

To a solution of 347.5 (300 mg, 0.7923 mmol) in DCM (10 mL) at 0° C. were added $PPh_3$ (414 mg, 1.58 mmol) and NBS (278 mg, 1.58 mmol). After stirring at 25° C. for 3 h, the mixture was poured into water (20 mL) and extracted with DCM (3×20 mL). The combined organic phase was washed with brine (2×50 mL), dried over anhydrous $Na_2SO_4$, filtered and concentrated. The residue was purified by flash column (0~30% of EtOAc in PE) to give 347.6 (65 mg, 18.6%) as a solid.

Synthesis of 347.7

To a solution of 347.6 (65 mg, 0.1472 mmol) in DMF (0.5 mL) were added $Cs_2CO_3$ (77.2 mg, 0.2944 mmol) and 1H-pyrazole-4-carbonitrile (27.4 mg, 0.2944 mmol). After stirring at 80° C. for 1 h, the mixture was poured into water (20 mL) and extracted with DCM (3×20 mL). The combined organic phase was washed with brine (2×50 mL), dried over anhydrous $Na_2SO_4$, filtered and concentrated. The mixture was purified by HPLC (Column YMC Triart C18 150*25 mm*5 um Condition water (10 mM $NH_4HCO_3$)-ACN Begin B: 73% End B: 100% Gradient Time (min) 9.5; Flow Rate (ml/min) 30) to afford 347.7 (15 mg, 22.4%) as solid.

Separation of 347 & 348

347.7 (15 mg, 0.033 mmol) was separated by SFC (Column DAICEL CHIRALCEL OD-H (250 mm*30 mm, 5 um) Condition 0.1% $NH_3H_2O$ EtOH Begin B 35%; End B 35% Gradient Time (min) 100% B Hold Time (min) FlowRate (ml/min) 50) to afford 348 (2 mg, 13.4%, Rt=min) as solid and 347 (2.5 mg, 16.7%) as solid.

347: $^1$H NMR (400 MHz, $CDCl_3$) $\delta_H$ 7.81 (s, 1H), 7.75 (s, 1H), 4.47 (dd, J=4.1, 13.4 Hz, 1H), 3.99 (dd, J=10.0, 13.6 Hz, 1H), 2.51-2.38 (m, 1H), 1.99-1.66 (m, 10H), 1.47-1.24 (m, 14H), 1.22-1.05 (m, 5H), 0.97-0.90 (m, 6H), 0.74 (d, J=6.8 Hz, 3H). LC-ELSD/MS purity 99%, MS ESI calcd. for $C_{28}H_{40}N_3$ $[M+H-2H_2O]^+$ 418.3 found 418.3. SFC 100% de.

348: $^1$H NMR (400 MHz, $CDCl_3$) $\delta_H$ 7.81 (s, 1H), 7.77 (s, 1H), 4.35 (dd, J=4.3, 14.1 Hz, 1H), 4.04 (dd, J=9.5, 13.8 Hz, 1H), 2.41 (s, 1H), 2.03-1.93 (m, 1H), 1.83-1.67 (m, 5H), 1.52-1.43 (m, 9H), 1.38-1.02 (m, 13H), 0.93 (t, J=7.2 Hz, 4H), 0.80 (s, 3H), 0.77 (d, J=6.8 Hz, 3H). LC-ELSD/MS purity 99%, MS ESI calcd. for $C_{28}H_{42}N_3O$ $[M+H-H_2O]^+$ 436.3 found 436.3. SFC 100% de.

Examples 349 & 350: 1-((R)-2-((3R,5S,8R,9R,10S,13S,14S,17R)-3-hydroxy-13-methyl-3-propylhexadecahydro-1H-cyclopenta[a]phenanthren-17-yl)propyl)-1H-pyrazole-4-carbonitrile (349) & 1-((S)-2-((3R,5S,8R,9R,10S,13S,14S,17R)-3-hydroxy-13-methyl-3-propylhexadecahydro-1H-cyclopenta[a]phenanthren-17-yl)propyl)-1H-pyrazole-4-carbonitrile (350)

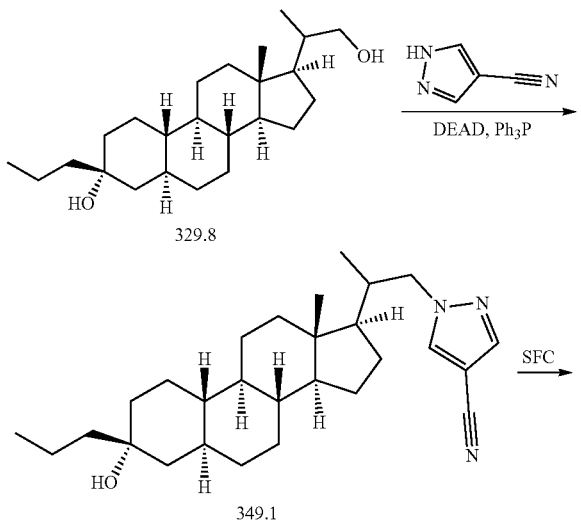

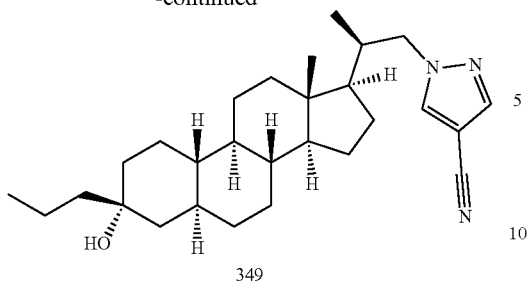

349

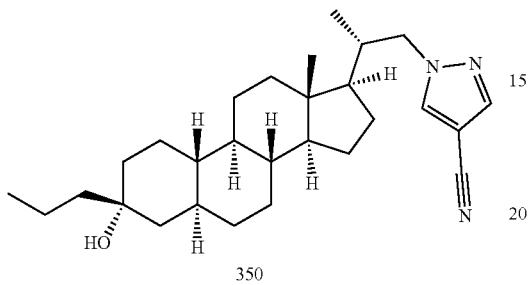

350

Synthesis of 349.1

To a solution of 329.8 (150 mg, 0.4136 mmol) in DMF (2 mL) were added Ph₃P (173 mg, 0.6617 mmol), DEAD (115 mg, 0.6617 mmol) and 1H-pyrazole-4-carbonitrile (57.7 mg, 0.6204 mmol) at 0° C. After stirring at 20° C. for 16 h, the mixture was poured into water (10 mL) and extracted with EtOAc (2×20 mL). The combined organic phase was washed with brine (10 mL), dried over anhydrous Na₂SO₄, filtered and concentrated. The residue was purified by flash column (0~15% of EtOAc in PE) to give 349.1 (200 mg) as a solid.

¹H NMR (400 MHz, CDCl₃) δ$_H$ 7.79 (s, 1H), 7.75 (s, 1H), 4.35-4.28 (m, 1H), 4.21 (q, J=7.2 Hz, 3H), 2.18-2.06 (m, 1H), 1.95-1.70 (m, 5H), 1.67-1.60 (m, 5H), 1.55-1.48 (m, 4H), 1.40-1.37 (m, 4H), 1.36-1.31 (m, 3H), 1.30-1.25 (m, 6H), 1.22-0.97 (m, 10H), 0.94-0.89 (m, 1H), 0.93-0.89 (m, 3H), 0.83-0.78 (m, 3H), 0.73-0.63 (m, 5H).

Separation of 349 & 350

349.1 (200 mg) was separated by SFC (Column: DAICEL CHIRALCEL OJ-H 250 mm×30 mm, 5 um; Condition: 0.1% NH₃H₂O ETOH; Gradient: from 20% to 20% of B; Flow rate: 60 mL/min; Column temperature: 40° C.) to afford 349 (79.0 mg, 39.6%, Rt=2.418 min) as a solid and 350 (33.0 mg, 16.5%, Rt=2.141 min) as a solid.

349: ¹H NMR (400 MHz, CDCl₃) δ$_H$ 7.79 (s, 1H), 7.75 (s, 1H), 4.51 (dd, J=4.0, 13.2 Hz, 1H), 3.70-3.61 (m, 1H), 2.16-2.05 (m, 1H), 1.90-1.71 (m, 4H), 1.67-1.59 (m, 3H), 1.54-1.48 (m, 2H), 1.41-1.28 (m, 7H), 1.27-0.96 (m, 11H), 0.94-0.89 (m, 3H), 0.80 (s, 3H), 0.68 (d, J=6.4 Hz, 5H). LC-ELSD/MS purity 99%, MS ESI calcd. for C₂₈H₄₄N₃O [M+H]⁺ 438.3 found 438.3. SFC 99% de.

350: ¹H NMR (400 MHz, CDCl₃) δ$_H$ 7.79 (s, 1H), 7.75 (s, 1H), 4.25 (dd, J=4.0, 13.6 Hz, 1H), 3.76-3.68 (m, 1H), 2.07-1.87 (m, 3H), 1.78-1.69 (m, 2H), 1.68-1.59 (m, 3H), 1.54-1.48 (m, 2H), 1.38 (d, J=3.6 Hz, 5H), 1.34-1.24 (m, 2H), 1.19-0.94 (m, 11H), 0.93-0.89 (m, 3H), 0.81 (d, J=6.4 Hz, 3H), 0.71 (s, 1H), 0.70-0.62 (m, 2H). LC-ELSD/MS purity 99%, MS ESI calcd. for C₂₈H₄₄N₃O [M+H]⁺ 438.3 found 438.3. SFC 99% de.

Examples 351 & 352: Synthesis of 1-((S)-2-((3R,5R,8R,9S,10S,13S,14S,17S)-3,17-dihydroxy-3-(methoxymethyl)-10,13-dimethylhexadecahydro-1H-cyclopenta[a]phenanthren-17-yl)propyl)-1H-pyrazole-4-carbonitrile (351) & 1-((R)-2-((3R,5R,8R,9S,10S,13S,14S,17S)-3,17-dihydroxy-3-(methoxymethyl)-10,13-dimethylhexadecahydro-1H-cyclopenta[a]phenanthren-17-yl)propyl)-1H-pyrazole-4-carbonitrile (352)

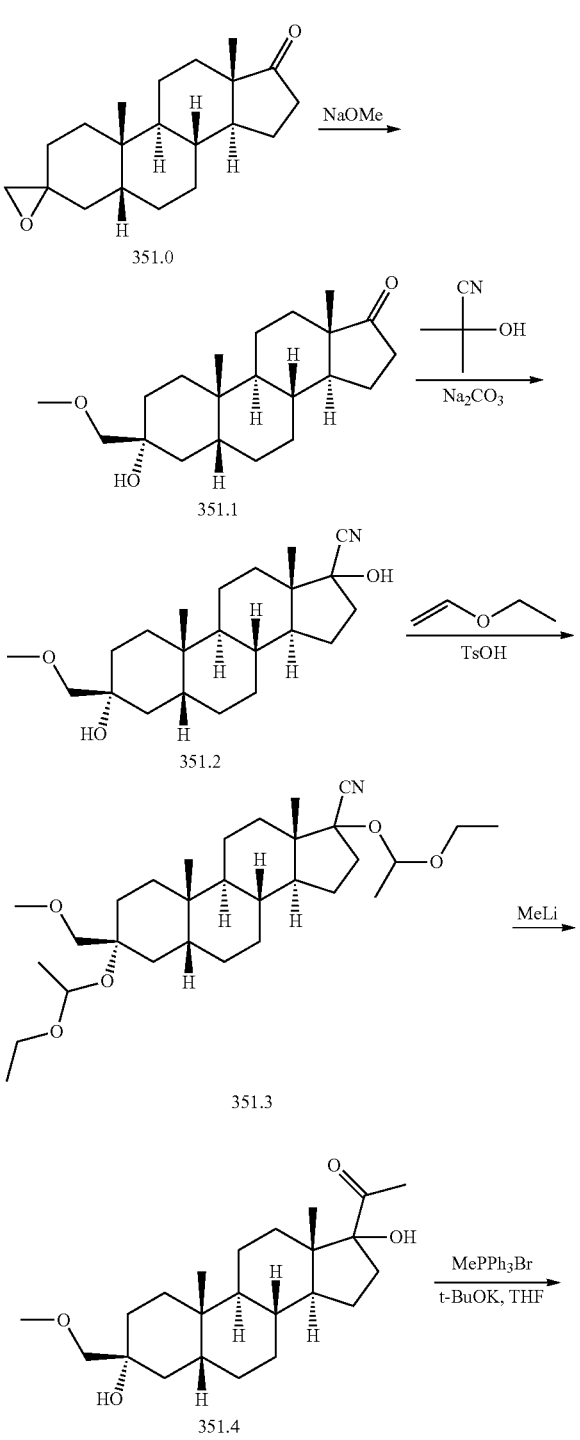

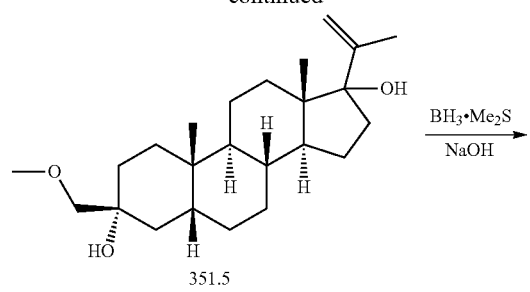
351.5

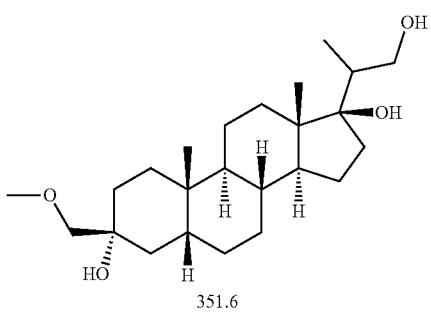
351.6

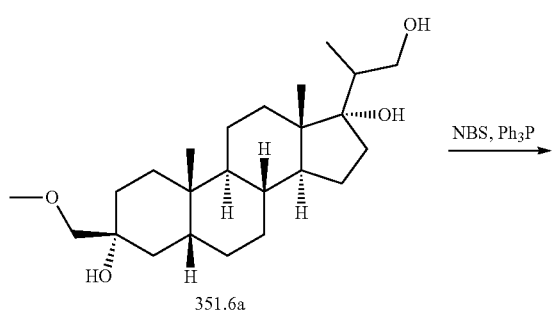
351.6a

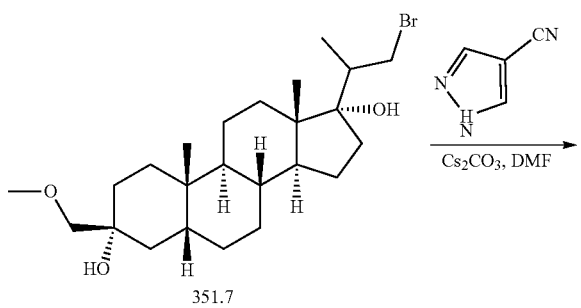
351.7

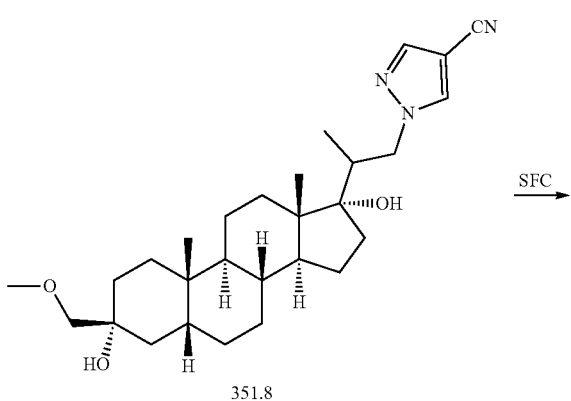
351.8

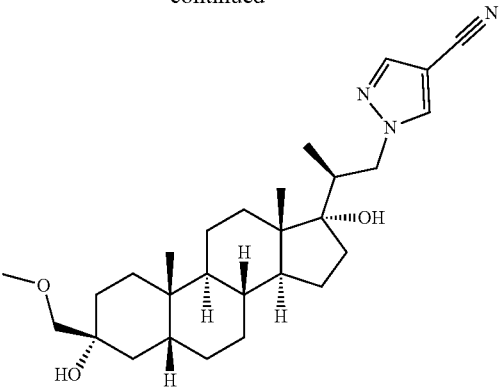
351

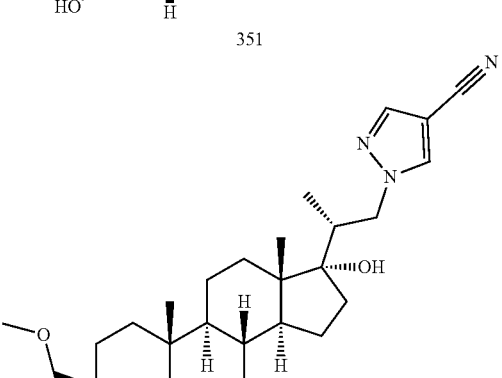
352

Synthesis of 351.1

To a solution of 351.0 (30 g, 99.1 mmol) in methanol (300 mL) was added MeONa (32.0 g, 594 mmol) at 25° C. After stirring at 60° C. for 16 h, the mixture was poured into water (600 mL) and extracted with EtOAc (2×600 mL). The combined organic layer was washed with saturated $Na_2S_2O_3$ (400 mL), brine (400 mL), dried over anhydrous $Na_2SO_4$, filtered and concentrated. The residue was purified by flash column (0~16% EtOAc in PE) to give 351.1 (12 g) as oil.

$^1$H NMR (400 MHz, CDCl$_3$) $\delta_H$ 3.52-3.33 (m, 5H), 2.62 (s, 1H), 2.43 (br dd, J=8.4, 19.2 Hz, 1H), 2.14-2.06 (m, 1H), 1.98-1.68 (m, 7H), 1.62-1.28 (m, 13H), 0.98-0.93 (m, 3H), 0.89-0.81 (m, 3H).

Synthesis of 351.2

To a suspension of 351.1 (9.1 g, 27.2 mmol) in MeOH (50 mL) were added $Na_2CO_3$ (3.50 mL, 3.40 mmol, 0.97 M) and 2-hydroxy-2-methylpropanenitrile (11.4 g, 135 mmol) at 20° C. After stirring at 40° C. for 4 h, water (14.6 mL) was added dropwise at 40° C. After stirring at 20° C. for 16 h, the mixture was quenched with HCl (50 mL, 0.25 M) and extracted with EtOAc/PE (100 mL, 1:1). The combined organic layer was washed with saturated $Na_2S_2O_3$ (50 mL, sat.), dried over anhydrous $Na_2SO_4$, filtered and concentrated. The residue was purified by flash column (0~30% of EtOAc in PE) to give 351.2 (6.24 g) as oil.

$^1$H NMR (400 MHz, CDCl$_3$) $\delta_H$ 3.47-3.31 (m, 5H), 2.68-2.61 (m, 1H), 2.59 (s, 1H), 2.53-2.38 (m, 1H), 2.15-1.64 (m, 9H), 1.56-1.15 (m, 14H), 0.97-0.91 (m, 3H), 0.89-0.79 (m, 3H).

Synthesis of 351.3

To a solution of 351.2 (5.36 g, 14.8 mmol) in THF (35 mL) were added ethoxyethene (10.6 g, 148 mmol) and TsOH (25.4 mg, 0.1480 mmol). After stirring at 30° C. for 2 h, the mixture was treated with TEA (7 drops) and concentrated in vacuum. The residue was purified by flash column (0~8% of EtOAc in PE) to give 351.3 (6.5 g) as oil.

$^1$H NMR (400 MHz, CDCl$_3$) δ$_H$ 5.15-4.97 (m, 2H), 3.81-3.45 (m, 11H), 3.38-3.26 (m, 4H), 2.61-2.42 (m, 1H), 2.20-1.63 (m, 12H), 1.42-1.14 (m, 14H), 0.96-0.94 (m, 3H), 0.93 (d, J=6.4 Hz, 3H), 0.84 (d, J=2.4 Hz, 1H).

Synthesis of 351.4

To a solution of 351.3 (3.3 g, 6.52 mmol) in THF (45 mL) was added MeLi (36.6 mL, 1.6 M, 58.6 mmol) at 0° C. After stirring at 20° C. for 4 h, the mixture was quenched by HCl (40 mL, 1 M) and extracted with EtOAc (50 mL). The organic layer was separated, dried over anhydrous Na$_2$SO$_4$, filtered and concentrated. The residue was purified by flash column (0~40% EtOAc in PE) to give 351.4 (1.2 g) as oil.

$^1$H NMR (400 MHz, CDCl$_3$) δ$_H$ 3.48-3.30 (m, 5H), 2.70-2.64 (m, 1H), 2.59 (br d, J=16.8 Hz, 2H), 2.34-2.17 (m, 3H), 2.04 (s, 1H), 1.98-1.64 (m, 7H), 1.55-1.14 (m, 12H), 1.02-0.92 (m, 4H), 0.68 (s, 3H).

Synthesis of 351.5

To a mixture of MePPh$_3$Br (18.0 g, 50.6 mmol) in THF (100 mL) was added t-BuOK (5.66 g, 50.6 mmol) at 25° C. under N$_2$. After stirring at 50° C. for 30 mins, 351.4 (2.4 g, 6.33 mmol) in THF (20 mL) was added at 25° C. After stirring at 60° C. for 3 h, the reaction mixture was cooled, poured into ice water (100 mL) and extracted with EtOAc (100 mL×2). The combined organic layer was dried over anhydrous Na$_2$SO$_4$, filtered and concentrated. The residue was purified by flash column (0~30% of EtOAc in PE) to give 351.5 (2.13 g) as solid.

$^1$H NMR (400 MHz, CDCl$_3$) δ$_H$=4.97 (s, 1H), 4.92-4.88 (m, 1H), 4.81 (d, J=7.2 Hz, 1H), 3.44-3.31 (m, 6H), 2.57-2.49 (m, 1H), 2.38 (ddd, J=3.6, 11.6, 14.8 Hz, 1H), 1.98-1.80 (m, 6H), 1.80-1.65 (m, 4H), 1.54-1.30 (m, 6H), 1.29-1.05 (m, 5H), 0.98-0.91 (m, 4H), 0.72 (s, 1H), 0.61 (s, 3H).

Synthesis of 351.6 & 351.6a

To a solution of 351.5 (1 g, 2.65 mmol) in THF (35 mL) was added BH$_3$Me$_2$S (1.32 mL, 10M, 13.2 mmol) at 25° C. After stirring at 25° C. for 16 h, the reaction was treated with EtOH (2.30 mL, 39.7 mmol) at 25° C., NaOH (7.94 mL, 5.0M, 39.7 mmol) at 0° C., and H$_2$O$_2$ (3.98 mL, 39.7 mmol, 30% in water) dropwise. After stirring at 70° C. for 1 h, the reaction was quenched with saturated aqueous Na$_2$S$_2$O$_3$ (20 mL). After stirring at 0° C. for another 1 h, the reaction was checked by potassium iodide-starch test paper to confirm excess H$_2$O$_2$ was destroyed (did not changed to blue) and extracted with EtOAc (2×30 mL). The combined organic layer was washed with brine (40 mL), dried over anhydrous Na$_2$SO$_4$, filtered and concentrated. The residue was purified by flash column (0~50% of EtOAc in PE) to give 351.6 (673 mg) as a solid and 351.6a (132 mg) as oil.

351.6: $^1$H NMR (400 MHz, CDCl$_3$) δ$_H$ 4.17 (br d, J=10.4 Hz, 1H), 3.57 (br d, J=7.2 Hz, 1H), 3.44-3.32 (m, 5H), 3.03-2.91 (m, 1H), 2.63 (br d, J=16.4 Hz, 2H), 2.49 (br s, 1H), 1.99-1.62 (m, 12H), 1.55-1.30 (m, 7H), 1.17 (d, J=6.8 Hz, 3H), 1.14-0.99 (m, 2H), 0.98-0.92 (m, 4H), 0.79-0.70 (m, 3H).

351.6a: $^1$H NMR (400 MHz, CDCl$_3$) δ$_H$ 4.23-4.11 (m, 1H), 3.66-3.51 (m, 1H), 3.42-3.33 (m, 5H), 2.56 (d, J=2.8 Hz, 2H), 2.37 (dd, J=3.6, 6.1 Hz, 1H), 1.98-1.63 (m, 9H), 1.52-1.19 (m, 12H), 1.17 (d, J=6.8 Hz, 3H), 1.13-0.97 (m, 2H), 0.94 (s, 3H), 0.74 (s, 3H). LC-ELSD/MS purity 99%, MS ESI calcd for C$_{24}$H$_{39}$O$_2$ [M−2H$_2$O+H]$^+$ 359.3, found 359.3, C$_{23}$H$_{35}$O [M−MeOH−2H$_2$O+H]$^+$ 327.3, found 327.3.

Synthesis of 351.7

To a solution of 351.6a (321.5 mg, 0.8134 mmol) in DCM (15 mL) at 0° C. was added PPh$_3$ (424 mg, 1.62 mmol) and NBS (288 mg, 1.62 mmol). After stirring at 25° C. for 30 mins, the reaction was worked up with another bather. The mixture was poured into water (40 mL) and extracted with DCM (3×40 mL). The combined organic phase was washed with brine (2×50 mL), dried over anhydrous Na$_2$SO$_4$, filtered and concentrated. The residue was purified by flash column (0~30% of EtOAc in PE) to give 351.7 (650 mg) as oil.

$^1$H NMR (400 MHz, CDCl$_3$) δ$_H$ 3.78-3.68 (m, 1H), 3.44-3.34 (m, 7H), 2.76 (s, 1H), 2.57 (br s, 1H), 2.18-2.07 (m, 1H), 1.97-1.75 (m, 5H), 1.62-1.36 (m, 15H), 1.17-1.14 (m, 3H), 0.99-0.86 (m, 4H), 0.77 (s, 3H).

Synthesis of 351.8

To a solution of 351.7 (260 mg, 0.5862 mmol) in DMF (5 mL) were added Cs$_2$CO$_3$ (459 mg, 1.75 mmol) and 1H-pyrazole-4-carbonitrile (108 mg, 1.17 mmol). After stirring at 80° C. for 16 h, the mixture was added into saturated NH$_4$Cl (10 mL) and extracted with EtOAc (3×30 mL). The combined organic layer was washed with water (2×50 mL), LiCl (2×50 mL, 5% in water), brine (50 mL), dried over anhydrous Na$_2$SO$_4$, filtered and concentrated. The residue was purified by flash column (0~50% of EtOAc in PE) to give 351.8 (71 mg) as a solid.

$^1$H NMR (400 MHz, CDCl$_3$) δ$_H$ 7.82-7.79 (m, 1H), 7.77-7.73 (m, 1H), 4.52-4.38 (m, 1H), 4.04-3.92 (m, 1H), 3.42-3.33 (m, 5H), 2.68-2.58 (m, 1H), 2.52-2.35 (m, 1H), 1.97-1.77 (m, 6H), 1.70-1.37 (m, 15H), 1.21-1.08 (m, 2H), 1.03-0.97 (m, 1H), 0.95 (s, 3H), 0.90-0.86 (m, 3H), 0.75-0.70 (m, 2H).

Separation of 351 & 352

351.8 (650 mg, 1.38 mmol) was separated by SFC (Column: Phenomenex-Cellulose-2 (250 mm*30 mm, 5 um); Condition: 0.1% NH$_3$H$_2$O MEOH) to give 351 (52.8 mg, 8.14%, Rt=2.396 min) as a solid and 352 (38.0 mg, 5.86%, Rt=1.992 min) as a solid.

351: $^1$H NMR (400 MHz, CDCl$_3$) δ$_H$ 7.81 (s, 1H), 7.75 (s, 1H), 4.46 (dd, J=4.0, 13.5 Hz, 1H), 3.98 (dd, J=10.0, 13.4 Hz, 1H), 3.43-3.33 (m, 5H), 2.61 (s, 1H), 2.51-2.37 (m, 1H), 2.00-1.62 (m, 9H), 1.54-1.07 (m, 13H), 1.03-0.97 (m, 1H), 0.95 (s, 3H), 0.88 (s, 3H), 0.73 (d, J=6.8 Hz, 3H). LC-ELSD/MS purity 99%, MS ESI calcd for C$_{27}$H$_{36}$N$_3$ [M−CH$_3$OH−2H$_2$O+H]$^+$ 402.2, found 402.2.

352: $^1$H NMR (400 MHz, CDCl$_3$) δ$_H$ 7.83 (s, 1H), 7.79 (s, 1H), 4.37 (dd, J=4.0, 13.6 Hz, 1H), 4.05 (dd, J=9.6, 13.6 Hz, 1H), 3.48-3.38 (m, 5H), 2.62 (s, 1H), 2.49-2.36 (m, 1H), 2.07-1.62 (m, 10H), 1.55-1.13 (m, 12H), 1.05-0.99 (m, 1H), 0.99-0.94 (m, 3H), 0.83-0.73 (m, 6H). LC-ELSD/MS purity 99%, MS ESI calcd for C$_{28}$H$_{42}$N$_3$O$_2$ [M−H$_2$O+H]$^+$ 452.2, found 452.2.

The following examples were synthesized similar to Examples 351 & 352 with the listed SM in place of 351.0.

| Example | SM | STRUCTURE | Analytical |
|---|---|---|---|
| 353 | Spiro[estrane-3,2'-oxiran]-17-one, (5β)- | 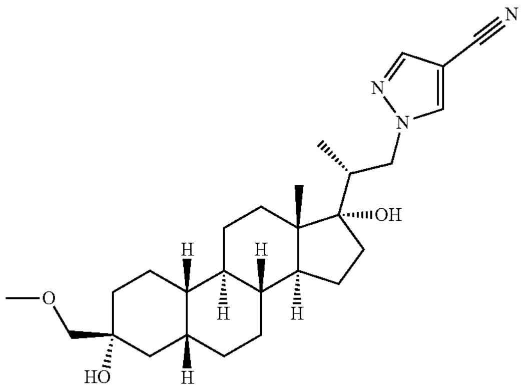 | ¹H NMR (400 MHz, CDCl₃) δ$_H$ 7.81 (s, 1H), 7.77 (s, 1H), 4.35 (dd, J = 3.8, 13.6 Hz, 1H), 4.03 (dd, J = 9.7, 13.7 Hz, 1H), 3.44-3.35 (m, 5H), 2.57 (s, 1H), 2.41 (br s, 1H), 2.05-1.93 (m, 1H), 1.86-1.65 (m, 8H), 1.52-0.99 (m, 15H), 0.80 (s, 3H), 0.79-0.76 (m, 1H), 0.77 (d, J = 6.8 Hz, 2H). LC-ELSD/MS purity 99%, MS ESI calcd for C₂₇H₄₀N₃O₂ [M − H₂O + H]⁺ 438.3, found 438.3, C₂₆H₃₄N₃ [M − CH₃OH − 2H₂O + H]⁺ 388.2, found 388.2. |
| 354 | Spiro[estrane-3,2'-oxiran]-17-one, (5β)- | 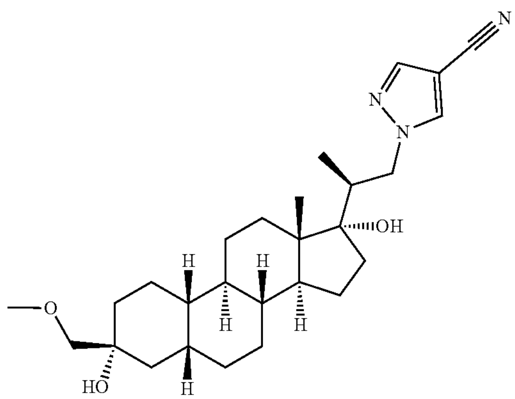 | ¹H NMR (400 MHz, CDCl₃) δ$_H$ 7.81 (s, 1H), 7.75 (s, 1H), 4.47 (dd, J = 4.3, 13.6 Hz, 1H), 3.98 (dd, J = 10.2, 13.9 Hz, 1H), 3.42-3.35 (m, 5H), 2.57 (s, 1H), 2.44 (s, 1H), 1.93 (br t, J = 11.9 Hz, 1H), 1.87-1.62 (m, 9H), 1.46-1.05 (m, 14H), 0.91 (s, 3H), 0.74 (d, J = 6.8 Hz, 3H). LC-ELSD/MS purity 99%, MS ESI calcd for C₂₇H₄₀N₃O₂ [M − H₂O + H]⁺ 438.3, found 438.3, C₂₆H₃₄N₃ [M − MeOH − 2H₂O + H]⁺ 388.2, found 388.2. |

Examples 355 & 356: Synthesis of 1-((S)-2-cyano-2-((3R,5R,8R,9R,10S,13S,14S,17R)-3-hydroxy-3,13-dimethylhexadecahydro-1H-cyclopenta[a]phenanthren-17-yl)ethyl)-1H-pyrazole-4-carbonitrile (355) & 1-((R)-2-cyano-2-((3R,5R,8R,9R,10S,13S,14S,17R)-3-hydroxy-3,13-dimethylhexadecahydro-1H-cyclopenta[a]phenanthren-17-yl)ethyl)-1H-pyrazole-4-carbonitrile (356)

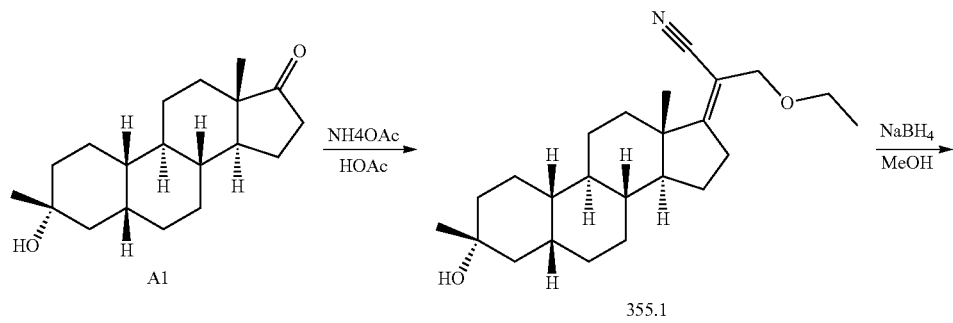

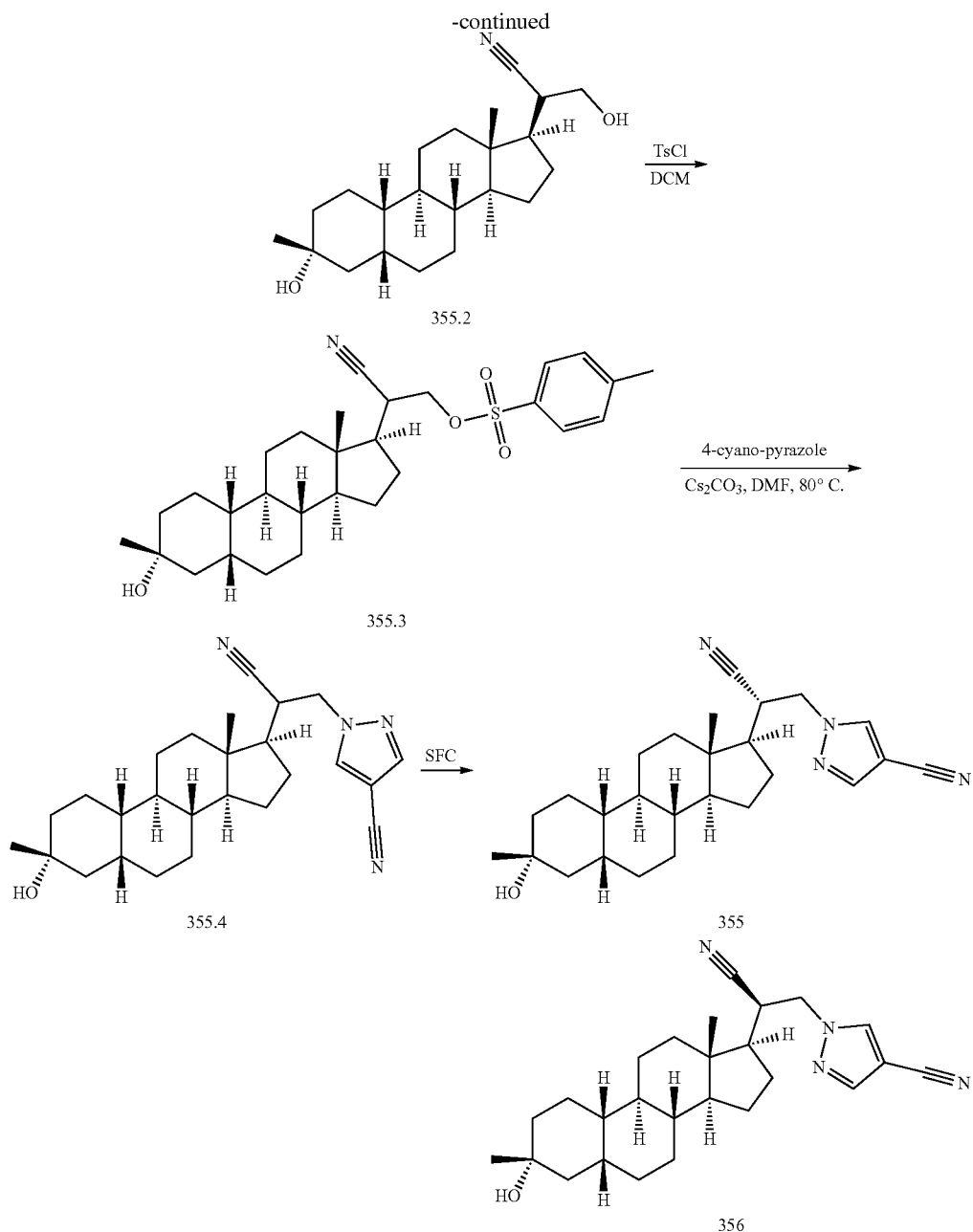

Synthesis of 355.1

To a solution of A1 (3 g, 10.3 mmol) in toluene (50 mL) were added ammonium acetate (2.38 g, 30.9 mmol), acetic acid (6.18 g, 103 mmol) and ethyl 2-isocyanoacetate (2.33 g, 20.6 mmol) at 25° C. under $N_2$. After stirring at 140° C. for 18 h, the reaction mixture was quenched with $NH_4Cl$ (50 mL, sat) at 20° C. and extracted with EtOAc (2×50 mL). The combined organic phase was washed with brine (100 mL), dried over anhydrous $Na_2SO_4$, filtered and concentrated. The residue was purified by flash column (0~20% of EtOAc in PE) to give 355.1 (3.5 g) as a solid.

$^1$H NMR (400 MHz, $CDCl_3$) $\delta_H$ 4.26 (q, J=7.2 Hz, 2H), 3.23-3.07 (m, 1H), 3.02-2.68 (m, 2H), 1.92-1.72 (m, 5H), 1.68-1.37 (m, 11H), 1.36-1.23 (m, 12H), 1.22-1.10 (m, 3H), 1.01 (s, 3H)

Synthesis of 355.2

To a solution of 355.1 (500 mg, 1.29 mmol) in MeOH (15 mL) was added $NaBH_4$ (488 mg, 12.9 mmol) at 25° C. under $N_2$. After stirring at 25° C. for 3 h, the reaction mixture was quenched with $NH_4Cl$ (50 mL, sat) at 20° C. and extracted with EtOAc (2×50 mL). The combined organic phase was washed with brine (100 mL), dried over anhydrous $Na_2SO_4$, filtered and concentrated. The residue was purified by flash column (0~20% of EtOAc in PE) to give 355.2 (433 mg, 97.3%) as a solid.

$^1$H NMR (400 MHz, $CDCl_3$) $\delta_H$ 3.91-3.64 (m, 2H), 2.88-2.79 (m, 1H), 2.09-2.03 (m, 1H), 2.03-1.77 (m, 4H), 1.77-1.63 (m, 5H), 1.53-1.36 (m, 6H), 1.34-1.17 (m, 8H), 1.15-0.98 (m, 5H), 0.82-0.69 (m, 3H)

Synthesis of 355.3

To a solution of 355.2 (430 mg, 1.24 mmol) in DCM (5 mL) were added N-methylimidazole (152 mg, 1.86 mmol), TEA (375 mg, 3.72 mmol) and TsCl (472 mg, 2.48 mmol). After stirring at 25° C. for 1 h, the mixture was poured into NaHCO$_3$ (10 mL, sat.) and extracted with DCM (2×30 mL). The combined organic phase was washed with water (2×20 mL), dried over anhydrous Na$_2$SO$_4$, filtered and concentrated to give 355.3 (650 mg) as oil.

$^1$H NMR (400 MHz, CDCl$_3$) δ$_H$ 7.85-7.79 (m, 2H), 7.46-7.35 (m, 2H), 7.09-7.02 (m, 1H), 6.90-6.85 (m, 1H), 4.09-3.92 (m, 1H), 3.70 (s, 2H), 3.05-2.61 (m, 1H), 2.46 (s, 3H), 2.21 (br s, 1H), 2.00-1.74 (m, 4H), 1.56-1.33 (m, 7H), 1.26 (s, 7H), 1.14-1.00 (m, 5H), 0.71 (s, 3H), 0.24-0.05 (m, 1H)

Synthesis of 355.4

To a solution of 355.3 (650 mg, 1.30 mmol) in DMF (15 mL) were added Cs$_2$CO$_3$ (847 mg, 2.60 mmol) and 4-cyanopyrazole (242 mg, 2.60 mmol). After stirring at 80° C. for 16 h, the mixture was diluted with EtOAc (2×30 mL). The combined organic solution was washed with water (30 mL), LiCl (5%, 30 mL aq.), dried over Na$_2$SO$_4$, filtered and concentrated. The residue was purified by flash column (5-30% EtOAc in PE) to give 355.4 (330 mg, 60.4%) as a solid.

Separation of 355 & 356

355.4 (330 mg, 07845 mmol) was separated by SFC (column: cDAICEL CHIRALPAK AD (250 mm*30 mm, 10 um)); Mobile phase: A: CO$_2$ B: 0.1% NH$_3$H$_2$O EtOH; gradient: from 55% to 55% of B, FlowRate (ml/min): 80) to give 355 (138 mg) and 356 (91 mg) both as solids. 355 (138 mg, 0.3281 mmol) was further purified by SFC (DAICEL CHIRALPAK AD-H (250 mm*30 mm, 5 um)); Mobile phase: A: CO$_2$ B: 0.1% NH$_3$H$_2$O EtOH; gradient: from 45% to 45% of B, FlowRate (ml/min): 50) to give 355 (93 mg, 67.8%) as a solid.

355: $^1$H NMR (400 MHz, CDCl$_3$) δ$_H$ 7.99 (s, 1H), 7.85 (s, 1H), 4.47-4.36 (m, 1H), 4.26-4.14 (m, 1H), 3.04-2.91 (m, 1H), 2.30-2.20 (m, 1H), 2.14-1.94 (m, 1H), 1.89-1.77 (m, 3H), 1.74-1.61 (m, 3H), 1.52-1.36 (m, 7H), 1.26 (s, 7H), 1.20-1.00 (m, 6H), 0.77 (s, 3H). LC-ELSD/MS purity 99%, analytic SFC: 100% de; MS ESI calcd. for C$_{26}$H$_{35}$N$_4$ [M−H$_2$O+H]$^+$ 403.3 found 403.3

356: $^1$H NMR (400 MHz, CDCl$_3$) δ$_H$ 7.96 (s, 1H), 7.86 (s, 1H), 4.51-4.35 (m, 1H), 3.39-3.26 (m, 1H), 1.97-1.89 (m, 1H), 1.87-1.59 (m, 8H), 1.53-1.36 (m, 7H), 1.26 (s, 8H), 1.16-1.01 (m, 5H), 0.81 (s, 3H). LC-ELSD/MS purity 99%, analytic SFC: 100% de; MS ESI calcd. for C$_{26}$H$_{35}$N$_4$ [M−H$_2$O+H]$^+$ 403.3 found 403.3

Example 357: Synthesis of 1-((R)-2-((3R,5R,8R,9R,10S,13S,14S,17R)-3-(ethoxymethyl)-3-hydroxy-13-methylhexadecahydro-1H-cyclopenta[a]phenanthren-17-yl)-3,3,3-trifluoropropyl)-1H-pyrazole-4-carbonitrile (357)

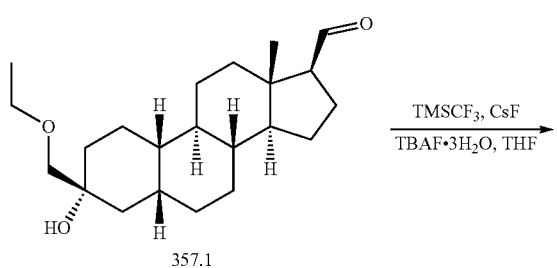

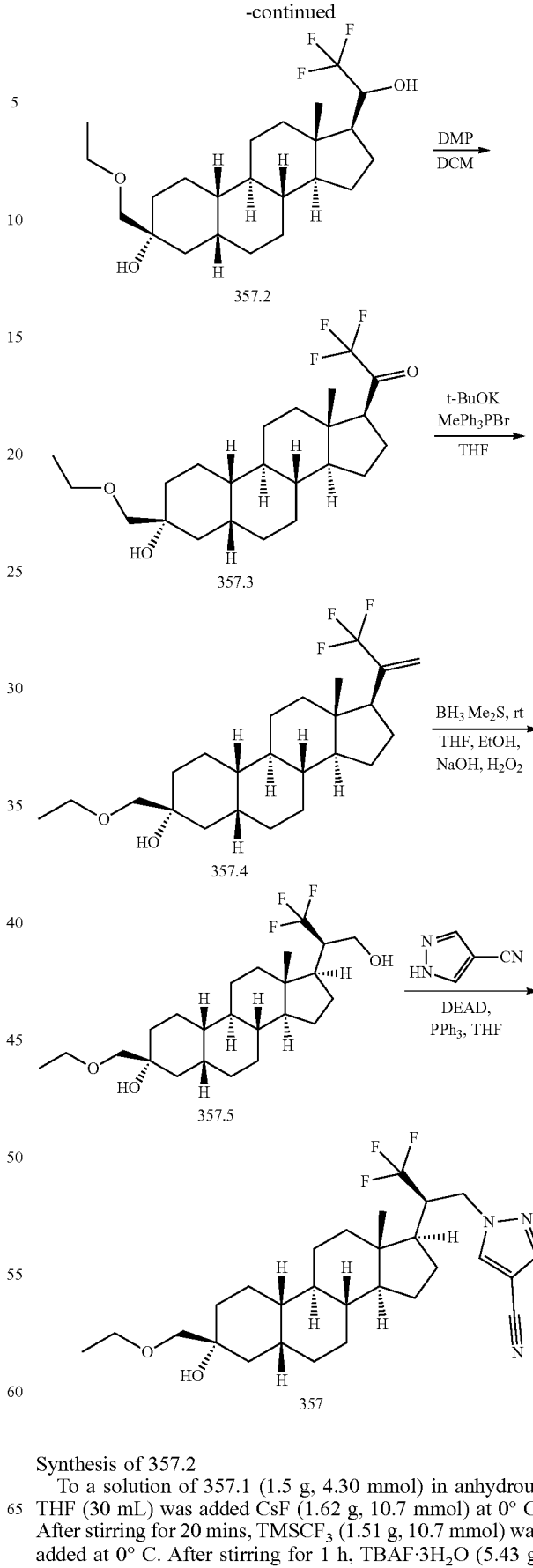

Synthesis of 357.2

To a solution of 357.1 (1.5 g, 4.30 mmol) in anhydrous THF (30 mL) was added CsF (1.62 g, 10.7 mmol) at 0° C. After stirring for 20 mins, TMSCF$_3$ (1.51 g, 10.7 mmol) was added at 0° C. After stirring for 1 h, TBAF·3H$_2$O (5.43 g, 17.2 mmol) was added. After stirring at 50° C. for another 1 h, the reaction mixture was poured into ice-water (50 mL), stirred for 10 mins and extracted with EtOAc (2×30 mL). The combined organic phase was washed with brine (2×20 mL), dried over anhydrous Na$_2$SO$_4$, filtered and concentrated in vacuum to give 357.2 (1.7 g) as a solid.
Synthesis of 357.3

To a solution of 357.2 (1.7 g, 4.06 mmol) in DCM (50 mL) was added DMP (4.28 g, 10.1 mmol) at 25° C. After stirring at 35° C. for 1 h, the reaction mixture was quenched with saturated NaHCO$_3$/Na$_2$S$_2$O$_3$ (50 mL/50 mL) and extracted with DCM (2×30 mL). The combined organic layer was washed with aqueous saturated NaHCO$_3$/Na$_2$S$_2$O$_3$ (50 mL/50 mL), brine (30 mL), dried over anhydrous Na$_2$SO$_4$, filtered and concentrated to give 357.3 (1.25 g) as a solid.
Synthesis of 357.4

To a mixture of MePPh$_3$Br (10.7 g, 30.2 mmol) in THF (40 mL) was added t-BuOK (3.38 g, 30.2 mmol) at 25° C. under N$_2$. After stirring at 50° C. for 1 h, a solution of 357.3 (2.1 g, 5.04 mmol) in THF (8 mL) was added at 25° C. After stirring at 25° C. for 1 h, the reaction mixture was quenched with 10% NH$_4$Cl aqueous (100 mL) at 20° C. and extracted with EtOAc (2×50 mL). The combined organic phase was washed with brine (20 mL) dried over anhydrous Na$_2$SO$_4$, filtered and concentrated. The residue was purified by flash column (0~10% of EtOAc in PE) to give 357.4 (1.7 g, 82%) as an oil $^1$HNMR (400 MHz, CDCl$_3$) $\delta_H$ 5.87-5.81 (m, 1H), 5.44-5.40 (m, 1H), 3.53 (q, J=6.8 Hz, 2H), 3.47-3.37 (m, 2H), 2.68 (s, 1H), 2.32 (t, J=9.6 Hz, 1H), 1.98-1.59 (m, 10H), 1.51-1.34 (m, 6H), 1.26-1.11 (m, 8H), 1.09-0.99 (m, 2H), 0.63 (s, 3H). $^{19}$FNMR (377 MHz, CDCl$_3$) $\delta_F$ −66.89 (s, 3F)
Synthesis of 357.5

To a solution of 357.4 (720 mg, 1.7 mmol) in THF (20 mL) was added BH$_3$Me$_2$S (6.92 mL, 6.92 mmol, 1M in THF) at 0° C. After stirring at 50° C. for 12 h, the reaction mixture was sequentially treated with ethanol (2.42 mL) at 15° C., NaOH aqueous (8.3 mL, 5.0 M) at 0° C. and hydrogen peroxide (4.15 mL, 10 M, 3.07 mmol) dropwise at 0° C. After stirring at 78° C. for 1 h, the mixture was cooled to 15° C. and quenched with saturated aqueous Na$_2$S$_2$O$_3$ (100 mL). The reaction was checked by potassium iodide-starch test paper to confirm excess H$_2$O$_2$ was destroyed (did not changed to blue). The aqueous phase was extracted with EtOAc (2×100 mL). The combined organic phase was washed with brine (2×50 mL), dried over anhydrous Na$_2$SO$_4$, filtered and concentrated. The residue was purified by flash column (0~30% of EtOAc in PE) to afford 357.5 (330 mg, 44%) as a solid $^1$HNMR (400 MHz, CDCl$_3$) $\delta_H$ 4.03-3.96 (m, 1H), 3.91-3.83 (m, 1H), 3.53 (q, J=6.8 Hz, 2H), 3.42 (q, J=9.2 Hz, 2H), 2.80-2.51 (m, 1H), 2.23-2.11 (m, 1H), 1.95-1.77 (m, 5H), 1.72-1.55 (m, 6H), 1.51-1.32 (m, 8H), 1.23-1.00 (m, 9H), 0.72 (s, 3H)

$^{19}$FNMR (377 MHz, CDCl$_3$) $\delta_F$ −64.17 (s, 3F)
Synthesis of 357

To a solution of 357.5 (80 mg, 0.18 mmol) in DMP were added 1H-pyrazole-4-carbonitrile (25.8 mg, 0.28 mmol), DEAD (64.3 mg, 0.37 mmol) and PPh$_3$ (96.8 mg, 0.37 mmol) at 0° C. After stirring at 15° C. for 12 h, the mixture was concentrated. The residue was purified by flash column (0~30% of EtOAc in PE) to give 357 (70 mg, 75%) as a solid.

$^1$HNMR (400 MHz, CDCl$_3$) $\delta_H$ 7.81 (s, 1H), 7.80 (s, 1H), 4.60-4.53 (m, 1H), 4.23-4.17 (m, 1H), 3.53 (q, J=7.2 Hz, 2H), 3.47-3.38 (m, 2H), 2.95-2.85 (m, 1H), 2.72 (s, 1H), 2.04-1.97 (m, 1H), 1.92-1.74 (m, 4H), 1.73-1.57 (m, 6H), 1.52-1.35 (m, 6H), 1.31-1.13 (m, 8H), 1.13-1.06 (m, 2H), 0.84 (s, 3H). LC-ELSD/MS: purity 99%; MS ESI calcd. for C$_{28}$H$_{39}$F$_3$N$_3$O [M−H2O+H]$^+$ 490.3, found 490.3.

Example 358: Synthesis of (3R,5R,8R,9R,10S,13S,14S,17R)-3-(ethoxymethyl)-13-methyl-17-((R)-1,1,1-trifluoro-3-(5-methyl-2H-tetrazol-2-yl)propan-2-yl)hexadecahydro-1H-cyclopenta[a]phenanthren-3-ol (358)

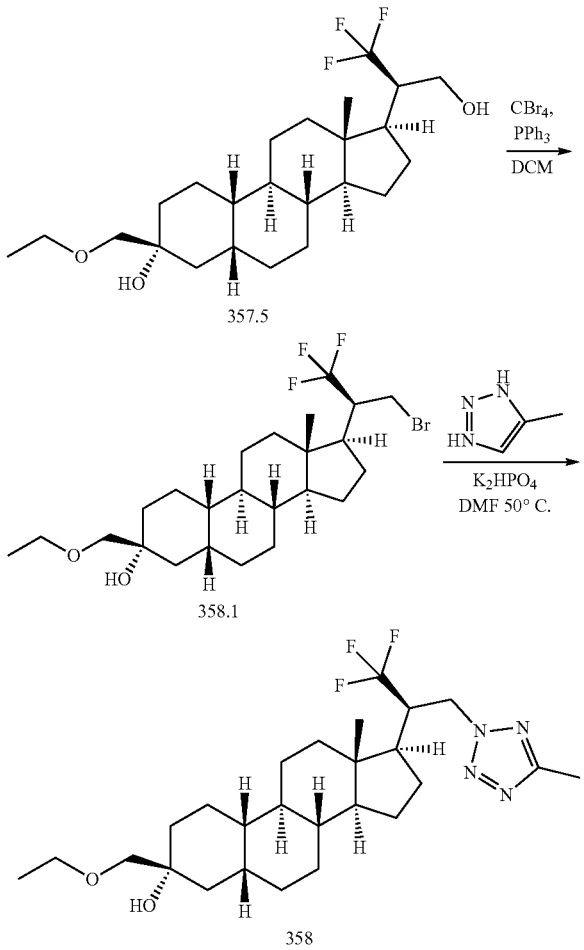

Synthesis of 358.1

To a solution of 357.5 (370 mg, 0.86 mmol) in DCM (5 mL) were added triphenylphosphine (335 mg, 1.28 mmol) and CBr$_4$ (424 mg, 1.28 mmol) at 15° C. After stirring at 40° C. for 1 h, the mixture was concentrated. The residue was purified by flash column (0~30% of EtOAc in PE) to give 358.1 (0.26 g, 61%) as a solid.

$^1$HNMR (400 MHz, CDCl$_3$) $\delta_H$ 3.73-3.65 (m, 1H), 3.59-3.49 (m, 3H), 3.47-3.37 (m, 2H), 2.77-2.58 (m, 1H), 2.56-2.42 (m, 1H), 1.95-1.80 (m, 4H), 1.72-1.36 (m, 13H), 1.30-0.99 (m, 10H), 0.71 (s, 3H). $^{19}$FNMR (377 MHz, CDCl$_3$) $\delta_F$ −64.47 (s, 3F)
Synthesis of 358

To a solution of 358.1 (130 mg, 0.26 mmol) in DMF (3 mL) were added 5-methyl-1H-1,2,3,4-tetrazole (44.1 mg, 0.52 mmol) and K$_2$HPO$_4$ (119 mg, 0.52 mmol) at 20° C. After stirring at 50° C. for 12 h, the mixture was diluted with H₂O (10 mL) and extracted with EtOAc (3×10 mL). The combined organic phase was washed with brine (5 mL), dried over anhydrous Na₂SO₄, filtered and concentrated. The residue was purified by flash column (0~30% of EtOAc in PE) to give 358 (50 mg, 38%) as a solid.

¹HNMR (400 MHz, CDCl₃) δ_H 4.83-4.73 (m, 2H), 3.53 (q, J=7.2 Hz, 2H), 3.42 (q, J=9.2 Hz, 2H), 3.12-3.02 (m, 1H), 2.71 (s, 1H), 2.54 (s, 3H), 1.96-1.86 (m, 2H), 1.83-1.75 (m, 3H), 1.73-1.64 (m, 4H), 1.63-1.60 (m, 1H), 1.52-1.35 (m, 6H), 1.29-1.13 (m, 8H), 1.12-1.00 (m, 3H), 0.83 (s, 3H). LC-ELSD/MS: purity 99%; MS ESI calcd. for C₂₆H₄₀F₃N₄O [M−H2O+H]⁺ 481.3, found 481.3.

Examples 359 & 360: (3R,5S,8R,9S,10S,13S,14S,17R)-3-ethyl-10,13-dimethyl-17-((R)-1-(5-methyl-2H-tetrazol-2-yl)propan-2-yl)hexadecahydro-1H-cyclopenta[a]phenanthren-3-ol (359) & (3R,5S,8R,9S,10S,13S,14S,17R)-3-ethyl-10,13-dimethyl-17-((S)-1-(5-methyl-2H-tetrazol-2-yl)propan-2-yl)hexadecahydro-1H-cyclopenta[a]phenanthren-3-ol (360)

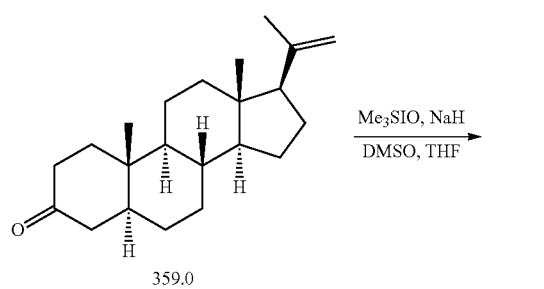

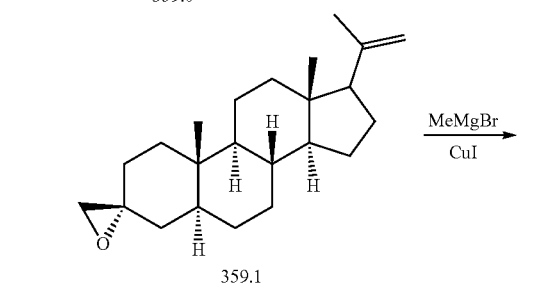

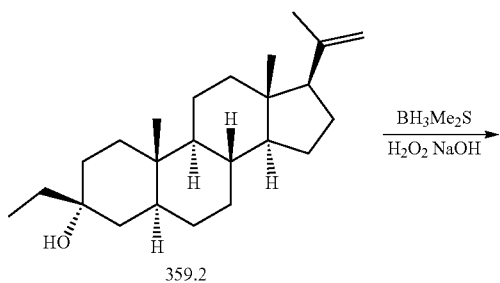

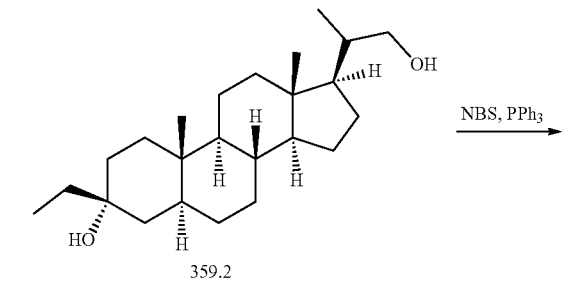

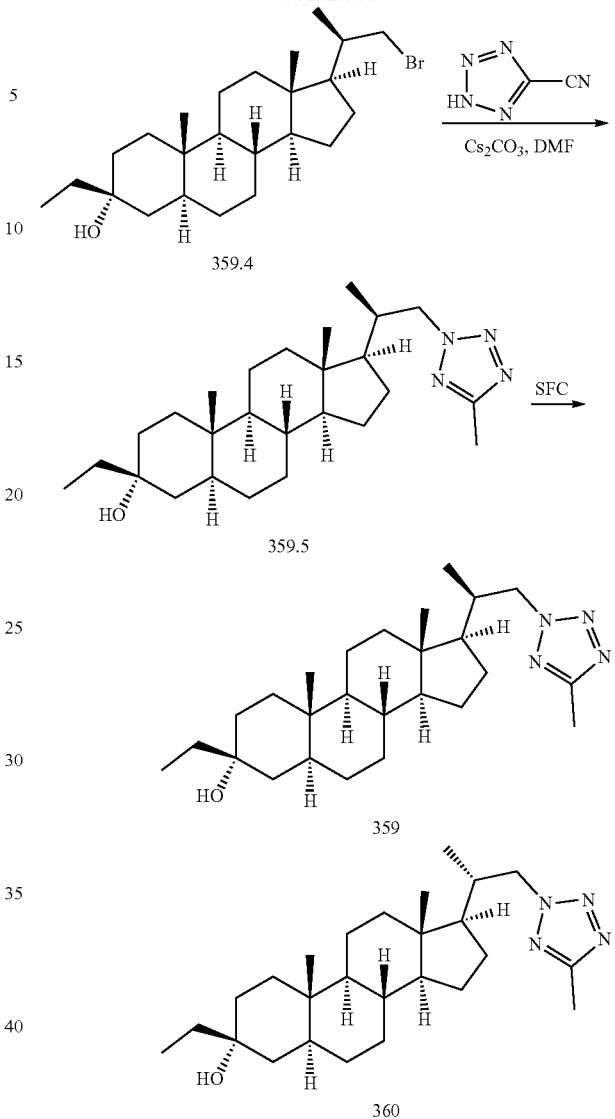

Synthesis of 359.1

To a solution of Me₃SIO (3.12 g, 14.2 mmol) in DMSO (30 mL) and THF (30 mL) was added NaH (340 mg, 14.2 mmol) at 0° C. under N₂. After stirring for 1 h, 359.0 (3 g, 9.53 mmol) in DMSO (30 mL) was added. After stirring at 25° C. for 3 h, the reaction mixture was poured into water (200 mL). The reaction mixture was filtered to give 359.1 (3.3 g) as a solid.

¹H NMR (400 MHz, CDCl₃) δ_H 4.84 (s, 1H), 4.70 (s, 1H), 2.64-2.59 (m, 2H), 2.06-1.98 (m, 2H), 1.88-1.79 (m, 2H), 1.75 (s, 3H), 1.71-1.65 (m, 3H), 1.60-1.52 (m, 3H), 1.35-1.12 (m, 8H), 1.00-0.76 (m, 8H), 0.57 (s, 3H).

Synthesis of 359.2

To a solution of 359.1 (4.3 g, 13 mmol) in THF (40 mL) and CuI (371 mg, 1.95 mmol) cooled to 0° C. was added MeMgBr (13 mL, 3 M, 39 mmol). After stirring at 0° C. for 1 h, the mixture was poured into water (30 mL) and extracted with EtOAc (2×40 mL). The combined organic phase was washed with brine (40 mL), dried over anhydrous Na₂SO₄, filtered and concentrated. The residue was purified by flash column (0~7% of EtOAc in PE) to give 359.2 (3.5 g, 78.2%) as a solid.

¹H NMR (400 MHz, CDCl₃) δ_H 4.84 (s, 1H), 4.70 (s, 1H), 2.15-1.95 (m, 1H), 1.80-1.75 (m, 1H), 1.74-1.60 (m, 4H), 1.59-1.40 (m, 9H), 1.39-1.02 (m, 10H), 1.00-0.78 (m, 7H), 0.74 (s, 3H), 0.56 (s, 3H).

Synthesis of 359.3

To a solution of 359.2 (3.5 g, 10.1 mmol) in THF (40 mL) was added BH₃·Me₂S (5.04 mL, 50.4 mmol, 10 M) dropwise at 0° C. After stirring at 25° C. for 3 h, the reaction mixture was cooled to 0° C. and sequentially treated dropwise with ethanol (4.6 g, 100 mmol), NaOH aqueous (15 mL, 151 mmol, 10 M) and finally with H₂O₂ (15 mL, 151 mmol). After stirring at 70° C. for 1 h, the mixture was extracted with EtOAc (2×40 mL). The combined organic phase was washed with saturated Na₂S₂O₃ aqueous (2×40 mL), brine (40 mL), dried over Na₂SO₄, filtered and evaporated to give 359.3 (3.5 g) as a solid.

¹H NMR (400 MHz, CDCl₃) δ_H 3.75-3.68 (m, 1H), 3.50-3.42 (m, 1H), 1.70-1.60 (m, 8H), 1.59-1.30 (m, 7H), 1.29-1.05 (m, 10H), 1.04-1.00 (m, 3H), 0.99-0.78 (m, 6H), 0.77-0.68 (s, 3H), 0.67 (s, 3H).

Synthesis of 359.4

To a solution of 359.3 (3.5 g, 9.65 mmol) in DCM (35 mL) at 0° C. were added PPh₃ (3.77 g, 14.4 mmol) and NBS (2.56 g, 14.4 mmol). After stirring at 25° C. for 2 h, the reaction mixture was added to water (35 mL) and extracted with DCM (2×35 mL). The combined organic phase was washed with brine (35 mL), dried over anhydrous Na₂SO₄, filtered and concentrated. The residue was purified by flash column (0~30% of EtOAc in PE) to give 359.4 (2 g, 48.7%) as oil.

¹H NMR (400 MHz, CDCl₃) δ_H 3.65-3.33 (m, 2H), 1.90-1.75 (m, 2H), 1.74-1.28 (m, 9H), 1.27-1.15 (m, 7H), 1.14-1.00 (m, 7H), 0.99-0.78 (m, 8H), 0.77-0.68 (s, 3H), 0.67 (s, 3H).

Synthesis of 359.5

To a solution of 359.4 (700 mg, 1.64 mmol) in DMF (5 mL) were added Cs₂CO₃ (1.06 g, 3.28 mmol) and 5-methyl-2H-1,2,3,4-tetrazole (275 mg, 3.28 mmol). After stirring at 80° C. for 16 h, the mixture was added into saturated NH₄Cl (10 mL) and extracted with EtOAc (3×10 mL). The combined organic layer was washed with LiCl aq. (5% in water, 2×10 mL), dried over anhydrous Na₂SO₄, filtered and concentrated. The residue was purified by flash column (0-35% of EtOAc in PE) to give 359.5 (400 mg, 56.8%) as oil.

¹H NMR (400 MHz, CDCl₃) δ_H 4.78-4.20 (m, 2H), 2.53 (s, 3H), 2.26-1.75 (m, 2H), 1.70-1.48 (m, 10H), 1.45-1.20 (m, 10H), 1.20-1.03 (m, 5H), 1.00-0.85 (m, 3H), 0.74 (s, 3H), 0.70 (s, 3H), 0.69-0.65 (m, 3H).

Separation of 359 & 360

359.5 (567 mg, 1.32 mmol) was separated by SFC (Column: DAICEL CHIRALCEL OD (250 mm*30 mm, 10 um), Condition: 0.1% NH₃H₂O ETOH, Begin B: 30%, End B: 30%, FlowRate (ml/min): 70) to afford 359 (304.1 mg, 53.8%) and 360 (184.2 mg, 32.5%) as solids.

359: ¹H NMR (400 MHz, CDCl₃) δ_H 4.78-4.73 (m, 1H), 4.28-4.20 (m, 1H), 2.53 (s, 3H), 2.26-2.20 (m, 1H), 2.00-1.75 (m, 2H), 1.70-1.48 (m, 10H), 1.45-1.20 (m, 10H), 1.20-1.03 (m, 4H), 1.00-0.85 (m, 3H), 0.74 (s, 3H), 0.70 (s, 3H), 0.69-0.65 (m, 3H). LC-ELSD/MS purity 99%, MS ESI calcd. for C₂₆H₄₅N₄O [M+H]⁺ 429 found 429. SFC 99% de.

360: ¹H NMR (400 MHz, CDCl₃) δ_H 4.56-4.24 (m, 2H), 2.53 (s, 3H), 2.45-1.88 (m, 3H), 1.55-1.51 (m, 2H), 1.50-1.26 (m, 10H), 1.25-1.00 (m, 12H), 0.88-0.85 (m, 3H), 0.84-0.80 (m, 3H), 0.73 (s, 3H), 0.71 (s, 3H). LC-ELSD/MS purity 99%, MS ESI calcd. for C₂₆H₄₅N₄O [M+H]⁺ 429 found 429. SFC 99% de.

Examples 361: Synthesis of (3R,5R,8R,9R,10S,13S,14S,16R,17R)-17-((R)-1-(4-(aminomethyl)-1H-pyrazol-1-yl)propan-2-yl)-13-methyl-3-propylhexadecahydro-1H-cyclopenta[a]phenanthrene-3,16-diol (361)

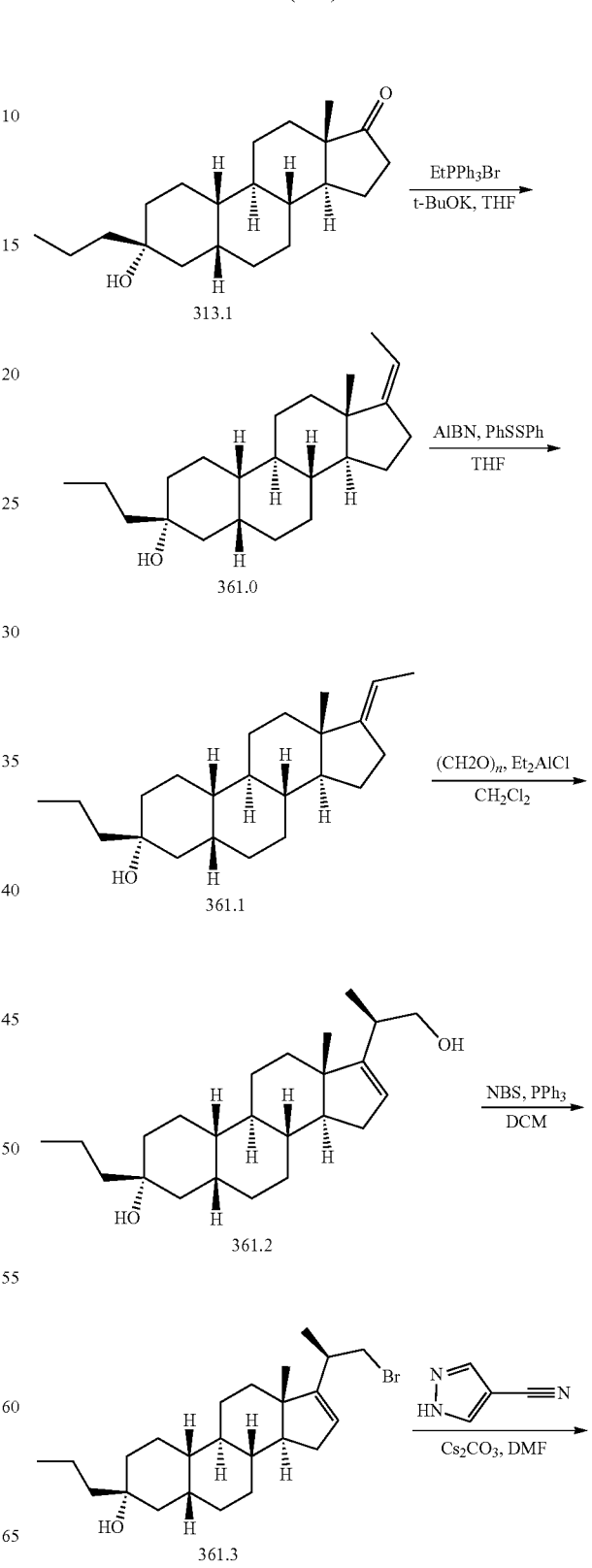

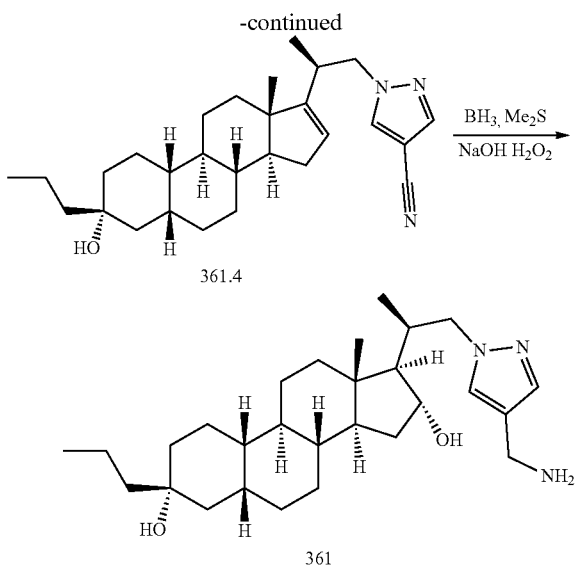

Synthesis of 361.0

To a mixture of EtPPh$_3$Br (26.5 g, 71.4 mmol) in THF (50 mL) was added t-BuOK (8.01 g, 71.4 mmol) at 15° C. under N$_2$. After stirring at 50° C. for 30 min, 313.1 (3.8 g, 11.9 mmol) was added in portions below 40° C. After stirring at 40° C. for another 1 hour to give a suspension, the reaction mixture was quenched with 10% NH$_4$Cl aqueous (100 mL) at 15° C. and extracted with EtOAc (500 mL). The combined organic phase was concentrated under vacuum to give a solid, which was purified by trituration with MeOH/H$_2$O (1:1, 300 mL) at reflux to give 361.0 (4.5 g) as oil.

$^1$H NMR (400 MHz, CDCl$_3$) δ$_H$ 5.10 (d, J=7.2 Hz, 1H), 2.41-2.09 (m, 4H), 1.78-1.71 (m, 3H), 1.66-1.63 (m, 3H), 1.56-1.51 (m, 3H), 1.50-1.42 (m, 3H), 1.37-1.29 (m, 6H), 1.21-1.00 (m, 6H), 0.93 (t, J=7.28 Hz, 3H), 0.87 (s, 3H).

Synthesis of 361.1

Under nitrogen gas protection, a 250 mL three-necked flask was charged with dry THF (100 mL), 361.0 (5.5 g, 16.6 mmol), AIBN (1.0 g, 6.14 mmol) and (PhS)$_2$ (1.41 g, 6.46 mmol). After stirring at 65° C. for 24 h, the reaction mixture was poured into EtOAc (200 mL) and washed with NaClO (150 mL). The organic phase was concentrated. The residue was purified by flash column (0~10% of EtOAc in PE) to give 361.1 (5.07 g) as a solid.

$^1$H NMR (400 MHz, CDCl$_3$) δ$_H$ 5.10-4.96 (m, 1H), 2.36-2.14 (m, 2H), 1.72 (s, 9H), 1.57-1.38 (m, 10H), 1.30-1.00 (m, 10H), 0.93 (t, J=7.2 Hz, 3H), 0.73 (s, 3H).

Synthesis of 361.2

To a stirred solution of (CH$_2$O)$_n$(1.14 g, 38.2 mmol) in DCM (20 mL) was added Et$_2$AlCl (63.8 mL, 63.8 mmol, 1M) dropwise at −78° C. After mins under N$_2$, 361.1 (5.07 g, 15.3 mmol) was added at −78° C. After stirring at 25° C. for 12 h, the mixture was quenched with ice-water (20 mL) at 0° C. and extracted with EtOAc (3×200 mL). The combined organic phase was washed with brine (2×20 mL), dried over anhydrous Na$_2$SO$_4$, filtered and concentrated. The residue was purified by flash column (0~25% of EtOAc in PE) to give 361.2 (2.68 g) as a solid.

$^1$H NMR (400 MHz, CDCl$_3$) δ$_H$ 5.46 (br s, 1H), 3.60-3.50 (m, 1H), 3.49-3.40 (m, 1H), 2.46-2.33 (m, 1H), 2.08 (ddd, J=2.8, 6.4, 14.8 Hz, 1H), 1.89-1.61 (m, 7H), 1.55-1.28 (m, 15H), 1.28-1.14 (m, 4H), 1.14-1.10 (m, 3H), 0.98-0.88 (m, 3H), 0.79 (s, 3H). LC-ELSD/MS purity 99%, MS ESI calcd for C$_{24}$H$_{39}$O$_1$ [M−H$_2$O+H]$^+$ 343.3, found 343.3,

Synthesis of 361.3

To a solution of 361.2 (1.65 g, 4.57 mmol) in DCM (70 mL) at 0° C. were added PPh$_3$ (2.39 g, 9.14 mmol) and NBS (1.62 g, 9.14 mmol). After stirring at 25° C. for 0.5 h, the resulting solution was combined with another batch prepared from 1 g of 361.2 to work-up. The mixture was poured into water (20 mL). The aqueous phase was extracted with DCM (3×20 mL). The combined organic phase was washed with brine (2×50 mL), dried over anhydrous Na$_2$SO$_4$, filtered and concentrated. The residue was purified by flash column (0~10% of EtOAc in PE) to give 361.3 (2.37 g) as a solid.

$^1$H NMR (400 MHz, CDCl$_3$) δ$_H$ 5.51-5.38 (m, 1H), 4.81 (br d, J=2.4 Hz, 1H), 3.50 (dd, J=4.0, 9.8 Hz, 1H), 3.18 (t, J=9.2 Hz, 1H), 2.98 (br d, J=15.2 Hz, 1H), 2.59-2.43 (m, 1H), 2.19-2.07 (m, 1H), 1.90-1.63 (m, 10H), 1.56-1.43 (m, 9H), 1.42-1.28 (m, 12H), 0.96-0.91 (m, 6H), 0.80-0.72 (m, 3H).

Synthesis of 361.4

To a solution of 361.3 (1 g, 2.36 mmol) in DMF (20 mL) were added Cs$_2$CO$_3$ (1.85 g, 7.08 mmol) and 1H-pyrazole-4-carbontrile (439 mg, 4.72 mmol). After stirring at 80° C. for 16 h, the reaction was diluted with water (10 mL) and extracted with EtOAc (3×10 mL). The combined organic phase was washed with water (3×10 mL) brine (30 mL), dried over anhydrous Na$_2$SO$_4$, filtered and concentrated. The residue was purified by column (5%~30% of EtOAc in PE) to give 361.4 (550 mg) as a solid.

1H NMR (400 MHz, MeOD) δ$_H$ 8.36-8.20 (m, 3H), 8.03-7.85 (m, 3H), 4.27-4.22 (m, 1H), 4.06-3.99 (m, 1H), 2.80-2.75 (m, 1H), 2.12-2.05 (m, 1H), 1.81-1.35 (m, 10H), 1.35-0.97 (m, 15H), 0.92 (t, J=7.2 Hz, 3H), 0.81 (s, 3H).

Synthesis of 361

To a solution of 361.4 (550 mg, 1.26 mmol) in THF (20 mL) was added BH$_3$-Me$_2$S (0.63 mL, 6.3 mmol, 10 M) dropwise at 0° C. After stirring at 25° C. for 3 h, the resulting colorless suspension was cooled to 0° C. and sequentially treated dropwise at 0° C. with ethanol (579 mg), NaOH aqueous (2.52 mL, 5 M) and H$_2$O$_2$ (1.26 mL, 10 M). After stirring at 70° C. for 1 h, the resulting colorless suspension was washed with saturated Na$_2$S$_2$O$_3$ (50 mL), brine (100 mL), dried over anhydrous Na$_2$SO$_4$, filtered and concentrated. The residue was purified by pre-HPLC (column: Xtimate C18 150×25 mm×5 um, condition: water (0.225% FA)-ACN, Begin B: 70, End B: 100) to give 361 (100 mg) as oil. 361 (100 mg, 0.2184 mmol) was purified by SFC (Column: DAICEL CHIRALCEL OD (250 mm×30 mm, 10 um), Condition: 0.1% NH$_3$H$_2$O ETOH, Begin B: 40%, End B: 40%) to give 361 (11 mg, 92%) as a solid.

1H NMR (400 MHz, DMSO) δ$_H$ 7.49 (s, 1H), 7.30 (s, 1H), 4.47 (d, J=5.2 Hz, 1H), 4.18-4.13 (m, 1H), 3.99-3.91 (m, 2H), 3.68-3.55 (m, 3H), 2.13-2.05 (m, 2H), 1.87-1.54 (m, 8H), 1.54-1.25 (m, 10H), 1.25-0.90 (m, 9H), 0.84 (t, J=7.2 Hz, 3H), 0.75 (d, J=6.8 Hz, 3H), 0.69 (s, 3H). LC-ELSD/MS purity 99%, MS ESI calcd. for C$_{28}$H$_{48}$N$_3$O$_2$ [M+H]$^+$ 458 found 458.

Example 362: Synthesis of 1-((R)-2-((3R,5R,8R,9R,10S,13S,14S,16R,17R)-3,16-dihydroxy-13-methyl-3-propylhexadecahydro-1H-cyclopenta[a]phenanthren-17-yl)propyl)-1H-pyrazole-4-carbonitrile (362)

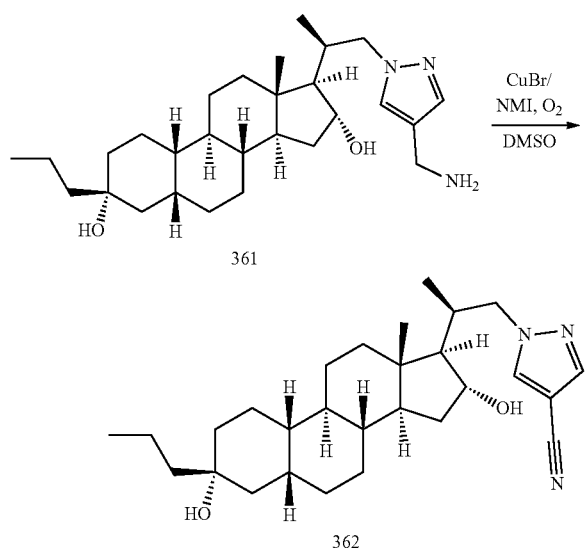

To a 10 mL eggplant type Schlenk flask were added CuBr$_2$ (1.2 mg, 0.005462 mmol), 361 (25 mg, 0.05462 mmol) and a solution of NMI (1.34 mg, 0.01638 mmol) in DMSO (5 mL). The flask was evacuated and purged with oxygen for three times before the flask was attached to a balloon filled with oxygen. After stirring at 100° C. for 24 h, the reaction mixture was cooled, diluted with water (10 mL) and extracted with EtOAc (3×15 mL). The combined organic solution was concentrated and purified by column (10%~60% of PE in EtOAc) to give 362 (2 mg) as a solid.

$^1$H NMR (400 MHz, DMSO) $\delta_H$ 7.18 (d, J=3.6 Hz, 2H), 4.36-4.31 (m, 1H), 4.24 (t, J=7.2 Hz, 1H), 3.86-3.81 (m, 1H), 2.34-2.24 (m, 1H), 1.82-1.56 (m, 10H), 1.56-1.43 (m, 5H), 1.43-1.05 (m, 10H), 1.05-0.85 (m, 9H), 0.74 (s, 3H). LC-ELSD/MS purity 99%, MS ESI calcd. for C$_{28}$H$_{44}$N$_3$O$_2$ [M+H]$^+$ 454 found 454.

Example 363: Synthesis of (3R,5R,8R,9R,10S,13S,14S,16R,17R)-13-methyl-17-((R)-1-(5-methyl-2H-tetrazol-2-yl)propan-2-yl)-3-propylhexadecahydro-1H-cyclopenta[a]phenanthrene-3,16-diol (363)

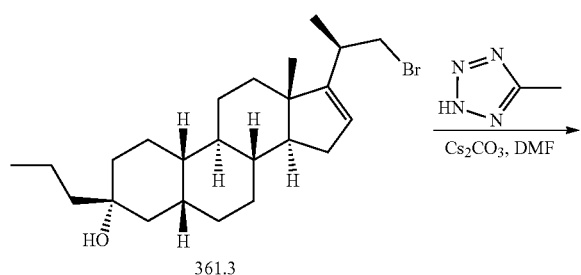

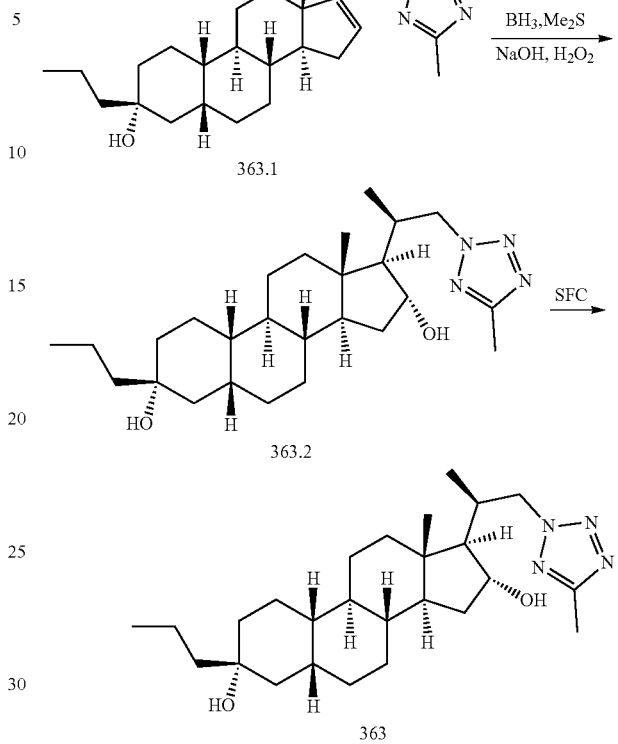

Synthesis of 363.1

To a solution of 361.3 (1.72 g, 4.06 mmol) in DMF (5 mL) were added Cs$_2$CO$_3$ (3.17 g, 12.1 mmol) and 5-methyl-2H-1, 2, 3, 4-tetrazole (682 mg, 8.12 mmol). After stirring at 80° C. for 16 h, the mixture was poured into saturated NH$_4$Cl (10 mL) and extracted with EtOAc (3×30 mL). The combined organic layer was washed with water (2×50 mL), LiCl (2×50 mL, 5% in water), brine (50 mL), dried over anhydrous Na$_2$SO$_4$, filtered and concentrated. The residue was purified by flash column (0~50% of EtOAc in PE) to give 363.1 (500 mg) as a solid. 363.1 (500 mg, 1.17 mmol) was purified by SFC (Column: Phenomenex-Cellulose-2 (250 mm*30 mm, 5 um); Condition 0.1% NH$_3$H$_2$O MEOH) to give 363.1 (280 mg, 56.1%) as a solid.

$^1$H NMR (400 MHz, CDCl$_3$) $\delta_H$ 5.50 (br s, 1H), 4.56 (dd, J=4.8, 13.2 Hz, 1H), 4.36 (dd, J=9.6, 13.2 Hz, 1H), 2.89 (br s, 1H), 2.54 (s, 3H), 2.07 (br d, J=18.4 Hz, 1H), 1.82 (br s, 7H), 1.28 (s, 15H), 1.24-1.11 (m, 3H), 1.04 (d, J=6.8 Hz, 3H), 0.93 (t, J=7.2 Hz, 3H), 0.80 (s, 3H). LC-ELSD/MS purity 99%, MS ESI calcd for C$_{26}$H$_{41}$N$_4$ [M−H$_2$O+H]$^+$ 409.3, found 409.3.

Synthesis of 363.2

To a solution of 361.1 (200 mg, 0.4687 mmol) in THF (5 mL) was added BH$_3$Me$_2$S (140 μL, 10 M, 1.40 mmol) at 25° C. After stirring at 25° C. for 16 h, the reaction mixture was sequentially treated with EtOH (0.272 mL 4.68 mmol) at 25° C., NaOH (0.936 mL, 5.0 M, 4.68 mmol) at 0° C., and H$_2$O$_2$ (116 μL, 1.17 mmol, 30% in water). After stirring at 70° C. for an 1 h, the reaction was quenched saturated aqueous Na$_2$S$_2$O$_3$ (20 mL) and stirred at 0° C. for another 1 h. The reaction was checked by potassium iodide-starch test paper to confirm excess H$_2$O$_2$ was destroyed (did not changed to blue). The aqueous phase was extracted with EtOAc (2×30 mL). The combined organic layer was washed with brine (40 mL), dried over anhydrous Na$_2$SO$_4$, filtered and concentrated. The residue was purified by flash column (0~50% of EtOAc in PE) to give 363.2 (116 mg) as a solid.

$^1$H NMR (400 MHz, CDCl$_3$) δ$_H$ 4.70 (dd, J=5.2, 13.2 Hz, 1H), 4.34 (dd, J=9.2, 13.2 Hz, 1H), 4.25-4.17 (m, 1H), 2.54 (s, 3H), 2.40 (td, J=7.2, 14.4 Hz, 1H), 1.85-1.62 (m, 10H), 1.55-1.43 (m, 7H), 1.42-0.99 (m, 18H), 0.97-0.90 (m, 6H), 0.78 (s, 3H).

Synthesis of 363

363.2 (110 mg, 0.2473 mmol) was purified by SFC (Column: DAICEL CHIRALPAK AD (250 mm*30 mm, 10 um); Condition: 0.1% NH$_3$H$_2$O IPA) to give 363 (72.7 mg, 66.6%) as a solid.

$^1$H NMR (400 MHz, CDCl$_3$) δ$_H$ 4.70 (dd, J=4.8, 13.2 Hz, 1H), 4.34 (dd, J=9.2, 13.2 Hz, 1H), 4.20 (br d, J=6.4 Hz, 1H), 2.54 (s, 3H), 2.49-2.36 (m, 1H), 1.84-1.60 (m, 7H), 1.54-1.42 (m, 6H), 1.40-1.00 (m, 15H), 0.96-0.89 (m, 6H), 0.78 (s, 3H). LC-ELSD/MS purity 99%, MS ESI calcd for C$_{26}$H$_{41}$N$_4$ [M−2H$_2$O+H]$^+$ 409.3, found 409.3.

Example 364: Synthesis of (3R,5R,8R,9R,10S,13S, 14S,17R)-3-hydroxy-13-methyl-17-((R)-1-(5-methyl-2H-tetrazol-2-yl)propan-2-yl)-3-propyltetradecahydro-1H-cyclopenta[a]phenanthren-16 (2H)-one (364)

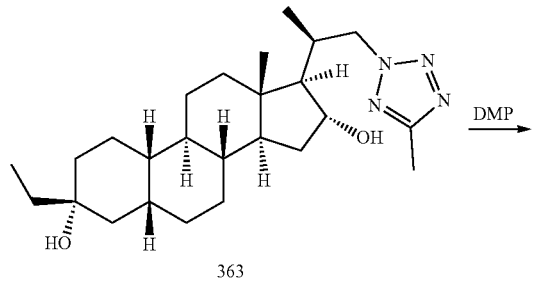

To a solution of 363 (40 mg, 0.08995 mmol) in DCM (3 mL) was added DMP (76.2 mg, 0.1799 mmol). After stirring at 25° C. for 2 h, the mixture was quenched with sat. NaHCO$_3$:Na$_2$S$_2$O$_3$ (v:v=1:1, 10 mL) and extracted with DCM (2×20 mL). The combined organic phase was washed with brine (20 mL), dried over anhydrous Na$_2$SO$_4$, filtered and concentrated. The residue was purified by flash column (0~25% of EtOAc in PE) to give 364 (29.6 mg, 74.3%) as a solid.

$^1$H NMR (400 MHz, CDCl$_3$) δ$_H$ 4.67 (dd, J=7.6, 13.1 Hz, 1H), 4.52 (dd, J=7.6, 13.2 Hz, 1H), 2.54 (s, 3H), 2.51-2.40 (m, 1H), 2.23 (dd, J=7.6, 17.9 Hz, 1H), 1.88-1.62 (m, 8H), 1.53-1.10 (m, 17H), 1.07 (d, J=6.8 Hz, 4H), 0.93 (t, J=7.2 Hz, 3H), 0.86 (s, 3H). LC-ELSD/MS purity 99%, MS ESI calcd for C$_{26}$H$_{42}$N$_4$O$_2$Na [M+Na]$^+$ 465.3, found 465.3, C$_{26}$H$_{41}$N$_4$O [M−H$_2$O+H]$^+$ 425.4, found 425.4.

Example 365: Synthesis of (3R,5R,8R,9R,10S,13S, 14S,16S,17R)-13-methyl-17-((R)-1-(5-methyl-2H-tetrazol-2-yl)propan-2-yl)-3-propylhexadecahydro-1H-cyclopenta[a]phenanthrene-3,16-diol (365)

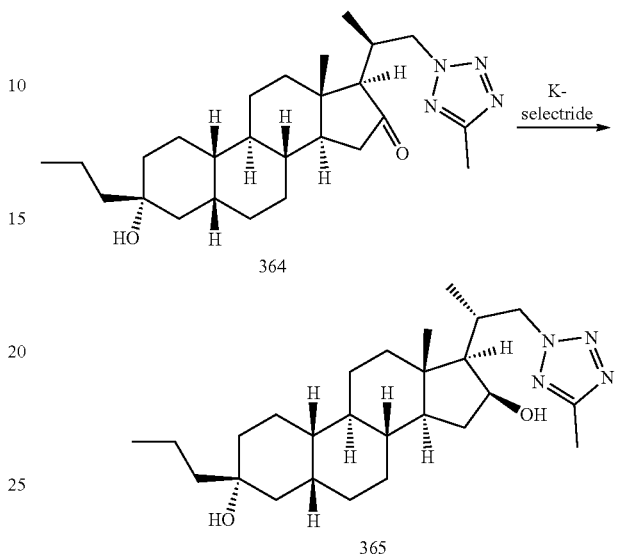

To a solution of 364 (110 mg, 0.248 mmol) in THF (10 mL) was added K-selectride dropwise (1.24 mL, 1.24 mmol 1M in THF) at −70° C. under N$_2$. After the addition, the mixture was allowed to warm to 20° C. slowly. The mixture was quenched with 10% NH$_4$Cl (30 mL) and extracted with EtOAc (2×15 mL). The combined organic phase was washed with 10% NH$_4$Cl (30 mL), dried over Na$_2$SO$_4$, filtered, concentrated and purified by flash column (0~30% of EtOAc in PE) to give 365 (30.2 mg, 27.4%) as a solid.

$^1$H NMR (400 MHz, CDCl$_3$) δ$_H$ 4.84 (dd, J=4.2, 13.1 Hz, 1H), 4.45-4.30 (m, 2H), 2.70 (s, 1H), 2.54 (s, 3H), 2.39-2.23 (m, 1H), 1.90 (br d, J=12.8 Hz, 1H), 1.83-1.56 (m, 6H), 1.51-1.21 (m, 14H), 1.20-1.09 (m, 4H), 1.04 (s, 3H), 0.94 (s, 3H), 0.83 (d, J=6.4 Hz, 3H). LC-ELSD/MS purity 99%, MS ESI calcd for C$_{26}$H$_{40}$N$_4$ [M−2H$_2$O+H]$^+$ 409.3, found 409.3.

Examples 366 & 367: Synthesis of (3R,5R,8R,9R, 10S,13S,14S,17R)-17-((R)-1-(5-ethyl-2H-tetrazol-2-yl)propan-2-yl)-13-methyl-3-propylhexadecahydro-1H-cyclopenta[a]phenanthren-3-ol (366)& (3R,5R, 8R,9R,10S,13S,14S,17R)-17-((S)-1-(5-ethyl-2H-tetrazol-2-yl)propan-2-yl)-13-methyl-3-propylhexadecahydro-1H-cyclopenta[a]phenanthren-3-ol (367)

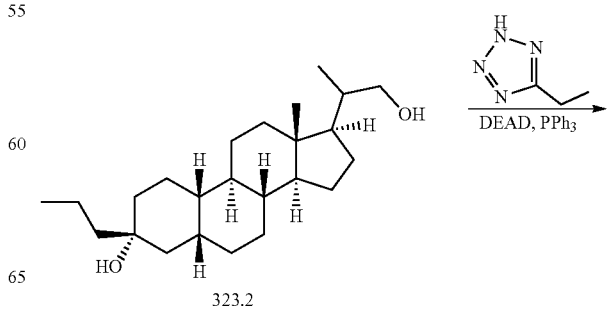

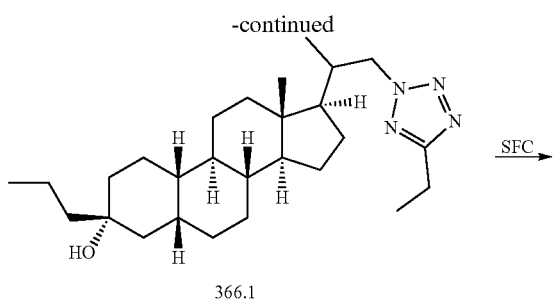

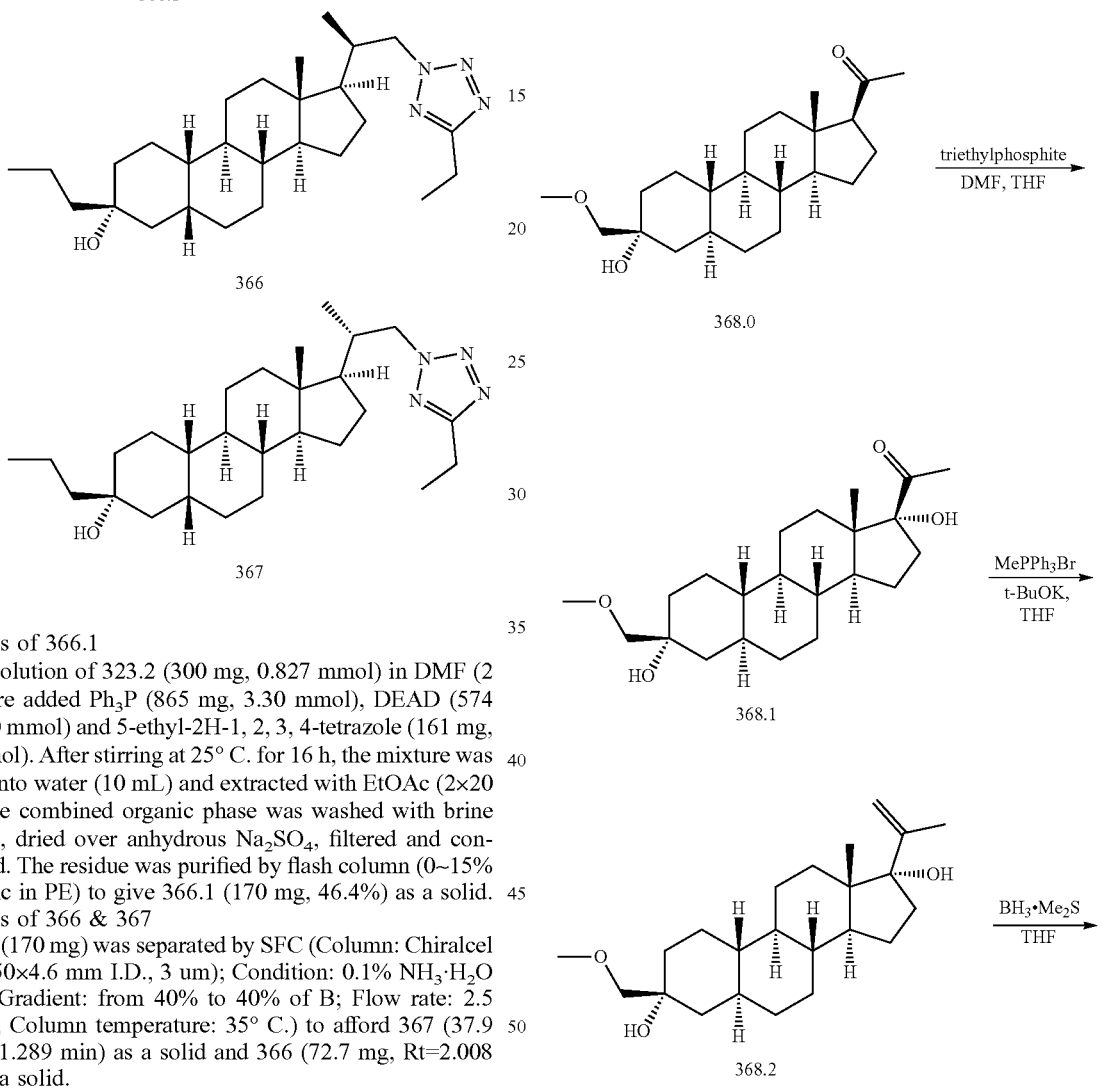

Examples 368 & 369: Synthesis of 1-((R)-2-((3R, 5S,8R,9R,10S,13S,14S,17S)-3,17-dihydroxy-3-(methoxymethyl)-13-methylhexadecahydro-1H-cyclopenta[a]phenanthren-17-yl)propyl)-1H-pyrazole-4-carbonitrile (368) & 1-((S)-2-((3R,5S,8R,9R,10S, 13S,14S,17S)-3,17-dihydroxy-3-(methoxymethyl)-13-methylhexadecahydro-1H-cyclopenta[a]phenanthren-17-yl)propyl)-1H-pyrazole-4-carbonitrile (369)

Synthesis of 366.1

To a solution of 323.2 (300 mg, 0.827 mmol) in DMF (2 mL) were added Ph₃P (865 mg, 3.30 mmol), DEAD (574 mg, 3.30 mmol) and 5-ethyl-2H-1, 2, 3, 4-tetrazole (161 mg, 1.65 mmol). After stirring at 25° C. for 16 h, the mixture was poured into water (10 mL) and extracted with EtOAc (2×20 mL). The combined organic phase was washed with brine (10 mL), dried over anhydrous Na₂SO₄, filtered and concentrated. The residue was purified by flash column (0~15% of EtOAc in PE) to give 366.1 (170 mg, 46.4%) as a solid.

Synthesis of 366 & 367

366.1 (170 mg) was separated by SFC (Column: Chiralcel OD-3 150×4.6 mm I.D., 3 um); Condition: 0.1% NH₃·H₂O ETOH; Gradient: from 40% to 40% of B; Flow rate: 2.5 mL/min; Column temperature: 35° C.) to afford 367 (37.9 mg, Rt=1.289 min) as a solid and 366 (72.7 mg, Rt=2.008 min) as a solid.

366: $^1$H NMR (400 MHz, CDCl₃) $\delta_H$ 4.75 (dd, J=4.4, 13.2 Hz, 1H), 4.25 (dd, J=10.4, 13.1 Hz, 1H), 2.91 (q, J=8 Hz, 2H), 2.27-2.19 (m, 1H), 1.93-1.62 (m, 8H), 1.56-1.51 (m, 2H), 1.49-1.44 (m, 2H), 1.36 (br t, J=8.0 Hz, 13H), 1.27-1.20 (m, 2H), 1.14-1.03 (m, 5H), 0.93 (t, J=7.2 Hz, 3H), 0.81 (s, 3H), 0.70 (d, J=6.4 Hz, 3H). LC-ELSD/MS purity 99%, MS ESI calcd. for C₂₇H₄₅N₄ [M–H₂O+H]⁺ 425.4, found 425.4. SFC 99% de.

367: $^1$H NMR (400 MHz, CDCl₃) $\delta_H$ 4.53 (dd, J=13.3 Hz, 4.0 Hz, 1H), 4.29 (dd, J=13.2 Hz, 9.6 Hz, 1H), 2.91 (q, J=8.0 Hz, 2H), 2.10-2.18 (m, 1H), 1.91-2.02 (m, 2H), 1.61-1.82 (m, 6H), 1.43-1.49 (m, 3H), 1.21-1.41 (m, 14H), 0.98-1.20 (m, 7H), 0.93 t, J=7.3 Hz, 3H), 0.84 (d, J=6.4 Hz, 3H), 0.72 (s, 3H). LC-ELSD/MS purity 99%, MS ESI calcd. for C₂₇H₄₅N₄ [M–H₂O+H]⁺ 425.4, found 425.4. SFC 99% de

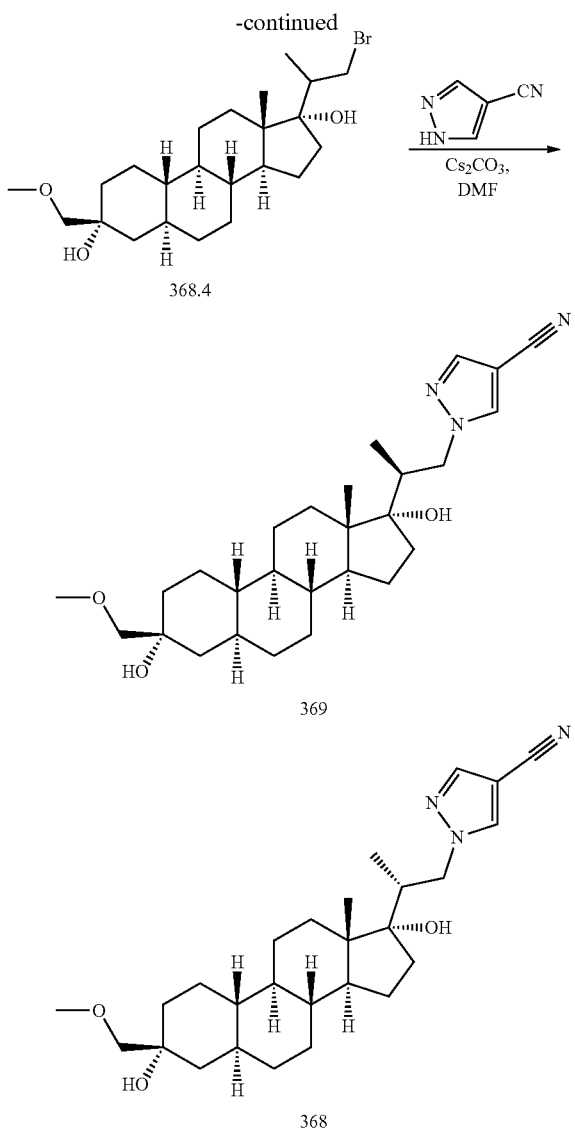

Synthesis of 368.1

A suspension of NaH (228 mg, 60% in oil, 5.72 mmol) in a mixture of t-butanol (2.5 mL) and DMF (3 mL) was stirred under N$_2$ at −25° C. To the stirred suspension was added triethylphosphite (142 mg, 0.842 mmol) and 368.0 (1 g, 2.86 mmol) in a mixture of anhydrous THF (10 mL) and DMF (1 mL). After stirring at −25° C. for 2 h, the reaction mixture was neutralized with acetic acid and diluted with DCM (100 mL) and water (50 mL). The aqueous layer was separated and extracted with DCM (2×100 mL). The combined organic layers were washed with brine (100 mL), dried over anhydrous Na$_2$SO$_4$, filtered and concentrated under vacuum. The residue was purified by column (0-20% EtOAc in PE) to give 368.1 (600 mg) as a solid, which was further purified by SFC (Column: DAICEL CHIRALCEL OD (250 mm×30 mm, 10 um); Condition: 0.1% NH$_3$H$_2$O ETOH; Begin B: 20%; End B: 20%) to afford 688.1 (180 mg, 45%) as a solid.

1H NMR (400 MHz, CDCl$_3$) δ$_H$ 3.38 (s, 3H), 3.18 (s, 2H), 2.71-2.59 (m, 2H), 2.26 (s, 3H), 2.06-1.92 (m, 1H), 1.89-1.59 (m, 10H), 1.49-0.94 (m, 10H), 0.72 (s, 5H).

Synthesis of 368.2

To a mixture of MePPh$_3$Br (1.76 g, 4.93 mmol) in THF (15 mL) was added t-BuOK (552 mg, 4.93 mmol) at 25° C. under N$_2$. After stirring at 25° C. for 30 mins, 368.1 (180 mg, 0.493 mmol) in THF (5 mL) was added. After stirring at 60° C. for 3 h, the reaction mixture was cooled, poured to NH$_4$Cl (50 ml) and extracted with EtOAc (2×50 mL). The combined organic layer was dried over anhydrous sodium sulfate, filtered and concentrated. The residue was purified by flash column (0~10% of EtOAc in PE) to give 368.2 (140 mg) as a solid.

1H NMR (400 MHz, CDCl$_3$) δ$_H$ 4.98 (s, 1H), 4.91 (d, J=1.3 Hz, 1H), 3.38 (s, 3H), 3.18 (s, 2H), 2.39 (ddd, J=3.4, 11.6, 14.6 Hz, 1H), 1.83 (s, 5H), 1.79-1.62 (m, 6H), 1.61-1.60 (m, 1H), 1.54-1.34 (m, 4H), 1.29-0.94 (m, 9H), 0.81-0.65 (m, 2H), 0.64 (s, 3H).

Synthesis of 368.3

To a solution of 368.2 (140 mg, 0.386 mmol) in THF (5 mL) was added BH$_3$Me$_2$S (0.0772 mL, 10M, 0.772 mmol) at 25° C. After stirring at 50° C. for 16 h, the reaction mixture was sequentially treated with EtOH (0.337 mL, 5.79 mmol) at 0° C., NaOH (1.15 mL, 5.0 M, 5.79 mmol) and H$_2$O$_2$ (0.577 mL, 5.79 mmol, 30% in water) dropwise. After stirring at 70° C. for 1 h, the mixture was poured into water (30 mL) and extracted with EtOAc (2×30 mL). The combined organic layer was washed with saturated Na$_2$S$_2$O$_3$ (30 mL), brine (30 mL), dried over anhydrous Na$_2$SO$_4$, filtered and concentrated to give 368.3 (50 mg) as a solid.

1H NMR (400 MHz, CDCl$_3$) δ$_H$ 4.06-4.00 (m, 1H), 3.67-3.54 (m, 1H), 3.38 (s, 3H), 3.18 (s, 2H), 2.04 (s, 1H), 1.87-1.61 (m, 1H), 1.48-1.34 (m, 3H), 1.29-1.11 (m, 10H), 1.29-1.11 (m, 10H), 1.03-0.98 (m, 3H), 0.91-0.84 (m, 2H), 0.76 (s, 5H).

Synthesis of 368.4

To a solution of 368.3 (50 mg, 0.131 mmol) in DCM (5 mL) at 0° C. were added PPh$_3$ (68.7 mg, 0.262 mmol) and NBS (46.1 mg, 0.262 mmol). After stirring at 25° C. for 2 h, the mixture was poured into water (20 mL) and extracted with DCM (3×20 mL). The combined organic phase was washed with brine (2×50 mL), dried over anhydrous Na$_2$SO$_4$, filtered and concentrated. The residue was purified by flash column (0~30% of EtOAc in PE) to give 368.4 (100 mg) as a solid.

1H NMR (400 MHz, CDCl$_3$) δ$_H$ 3.79-3.58 (m, 1H), 3.38 (s, 3H), 3.18 (s, 2H), 1.42 (br s, 1H), 1.31-1.20 (m, 6H), 1.11 (br d, J=6.3 Hz, 5H), 0.99 (br s, 4H), 0.93-0.83 (m, 4H), 0.81-0.59 (m, 5H), 0.07 (d, J=1.8 Hz, 7H), 0.14-0.01 (m, 1H).

Synthesis of 368 & 369

To a solution of 368.4 (100 mg, 0.225 mmol) in DMF (5 mL) were added Cs$_2$CO$_3$ (177 mg, 0.675 mmol) and 1H-pyrazole-4-carbontrile (41.8 mg, 0.450 mmol). After stirring at 80° C. for 16 h, the reaction mixture was added into saturated NH$_4$Cl (50 mL) and extracted with EtOAc (3×50 mL). The combined organic layer was washed with LiCl (100 mL, 5% in water), brine (2×100 mL), dried over anhydrous Na$_2$SO$_4$, filtered and concentrated. The residue was purified by SFC (Column: Welch Xtimate C18 150*25 mm*5 um; Condition: water (0.05% NH$_3$H$_2$O)-ACN; Begin B: 60%; End B: 90%) to afford 368 (2.5 mg, 2%) as a solid and 369 (1.1 mg, 1%) as a solid.

368: $^1$H NMR (400 MHz, CDCl$_3$) δ$_H$ 7.79 (d, J=15.1 Hz, 2H), 4.42-4.27 (m, 1H), 4.10-3.95 (m, 1H), 3.39 (s, 3H), 3.18 (s, 2H), 2.46-2.35 (m, 1H), 2.03-1.94 (m, 2H), 1.86-1.79 (m, 1H), 1.77-1.69 (m, 4H), 1.68-1.59 (m, 5H), 1.29-0.95 (m, 11H), 0.81 (s, 3H), 0.77 (d, J=6.8 Hz, 3H), 0.74-0.66 (m, 2H). LC-ELSD/MS purity 99%, MS ESI calcd. for C$_{27}$H$_{40}$N$_3$O$_2$ [M−H$_2$O+H]$^+$ 438.3 found 438.3.

369: $^1$H NMR (400 MHz, CDCl$_3$) δ$_H$ 7.82-7.72 (m, 2H), 4.54-4.40 (m, 1H), 4.05-3.88 (m, 1H), 3.39 (s, 3H), 3.19 (s,

2H), 2.50-2.37 (m, 1H), 2.04-1.61 (m, 9H), 1.60 (s, 2H), 1.25 (s, 13H), 0.91 (s, 3H), 0.74 (br d, J=6.5 Hz, 4H). LC-ELSD/MS purity 99%, MS ESI calcd. for $C_{27}H_{40}N_3O_2$ $[M-H_2O+H]^+$ 438.3 found 438.3.

Examples 400 & 401: Synthesis of 5-((S)-2-((3R, 5R,8R,9R,10S,13R,14S,17R)-3-hydroxy-13-methyl-3-propylhexadecahydro-1H-cyclopenta[a] phenanthren-17-yl)propyl)picolinonitrile (401) & 5-((R)-2-((3R,5R,8R,9R,10S,13R,14S,17R)-3-hydroxy-13-methyl-3-propylhexadecahydro-1H-cyclopenta[a]phenanthren-17-yl)propyl)picolinonitrile (400)

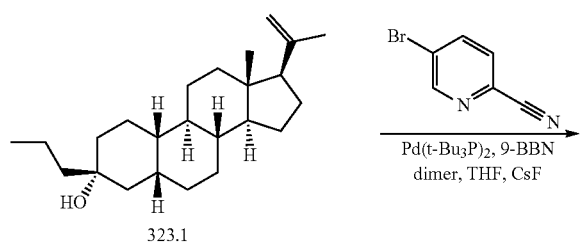

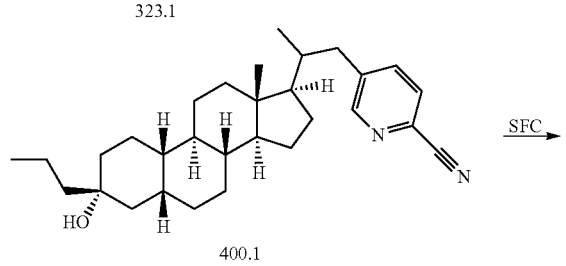

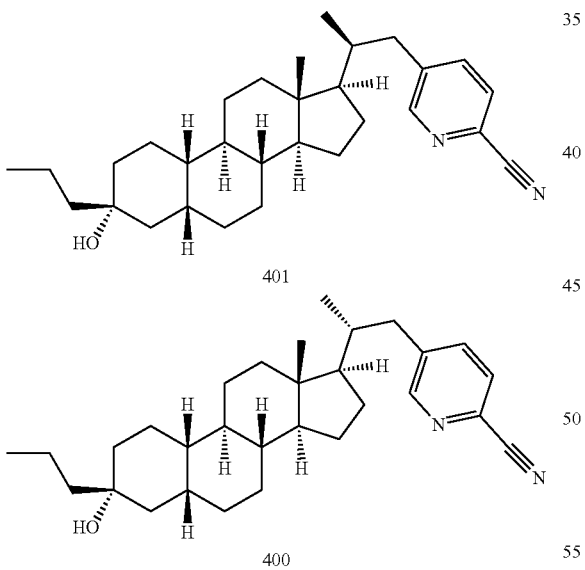

Synthesis of 400.1
To a solution of 323.1 (500 mg, 1.45 mmol) in THF (15 mL) was added 9-BBN dimer (529 mg, 2.17 mmol) at 15° C. under $N_2$. After stirring at 75° C. for 3 h, 6-bromopyridine-2-carbonitrile (625 mg, 3.42 mmol), CsF (516 mg, 3.42 mmol) and Pd(t-Bu3P)$_2$ (87.3 mg, 0.171 mmol) were added. After stirring at 75° C. for 16 h, the mixture was poured into ice-water (50 mL) and extracted with EtOAc (3×40 mL). The combined organic phase was washed with brine (2×100 mL), dried over anhydrous $Na_2SO_4$, filtered and concentrated. The residue was purified by flash column (0~30% of EtOAc in PE) to give 400.1 (600 mg) as a solid.
Separation of 400 & 401
400.1 (400 mg, 0.8914 mmol) was separated by SFC (Column DAICEL CHIRALPAK AD (250 mm*30 mm, 10 um) Condition 0.1% $NH_3H_2O$ ETOH Begin B 55% End B 55% Gradient Time (min) 100% B Hold Time (min) Flow Rate (ml/min) 80) to afford 400 (129.5 mg, 32.3%, Peak 1, Rt=0.860 min) as a solid and 401 (25.6 mg, 6.41%, Peak 2, Rt=2.286 min) as a solid.
400: $^1H$ NMR (400 MHz, CDCl$_3$) $\delta_H$ 8.50 (s, 1H), 7.66-7.53 (m, 2H), 2.93 (dd, J=3.2, 13.4 Hz, 1H), 2.21 (dd, J=10.4, 13.6 Hz, 1H), 2.09-1.90 (m, 2H), 1.83-1.59 (m, 7H), 1.55-1.26 (m, 14H), 1.25-0.99 (m, 7H), 0.93 (t, J=7.2 Hz, 3H), 0.80 (d, J=6.4 Hz, 3H), 0.70 (s, 3H).
LC-ELSD/MS purity 99%, MS ESI calcd. for $C_{30}H_{43}N_2$ $[M-H_2O+H]^+$ 431.3, found 431.3. SFC 99% de.
401: $^1H$ NMR (400 MHz, CDCl$_3$) $\delta_H$ 8.50 (s, 1H), 7.71-7.48 (m, 2H), 3.19 (dd, J=3.6, 13.6 Hz, 1H), 2.18 (dd, J=11.2, 13.6 Hz, 1H), 1.98 (d, J=12.4 Hz, 1H), 1.91-1.58 (m, 8H), 1.53-1.19 (m, 16H), 1.15-1.00 (m, 5H), 0.93 (t, J=7.2 Hz, 3H), 0.79 (s, 3H), 0.69 (d, J=6.4 Hz, 3H). LC-ELSD/MS purity 99%, MS ESI calcd. for $C_{30}H_{43}N_2$ $[M-H_2O+H]^+$ 431.4, found 431.4. SFC 100% de.

Examples 402 & 403: Synthesis of 3-((S)-2-((3R, 5R,8R,9R,10S,13R,14S,17R)-3-(ethoxymethyl)-3-hydroxy-13-methylhexadecahydro-1H-cyclopenta[a] phenanthren-17-yl)propyl)benzonitrile (402) & 3-((R)-2-((3R,5R,8R,9R,10S,13R,14S,17R)-3-(ethoxymethyl)-3-hydroxy-13-methylhexadecahydro-1H-cyclopenta[a]phenanthren-17-yl)propyl) benzonitrile (403)

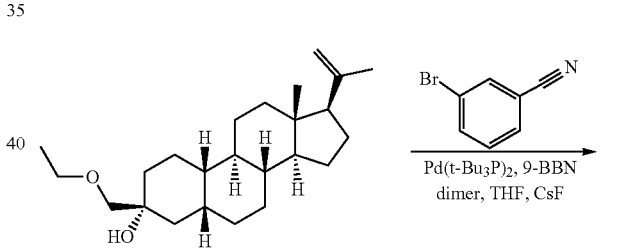

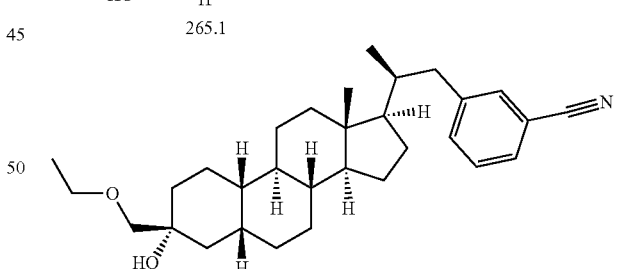

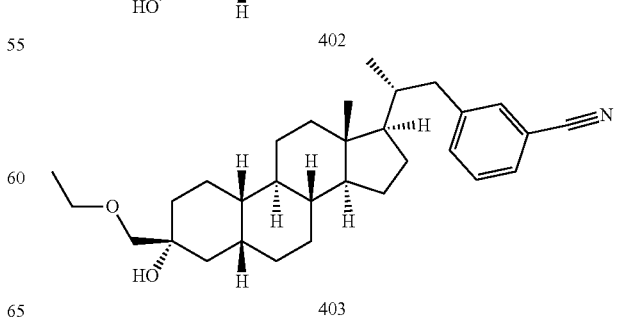

To a solution of 265.1 (300 mg, 0.831 mmol) in THF (15 mL) under N₂ at 15° C. was added 9-BBN dimer (202 mg, 0.831 mmol). After stirring at 75° C. for 3 h, the reaction mixture was cooled to 15° C. and 3-bromobenzonitrile (302 mg, 1.66 mmol), CsF (252 mg, 1.66 mmol) and Pd(t-Bu3P)₂ (42.4 mg, 83.1 mmol) were added to the mixture. After stirring at 75° C. for 16 h, the reaction was cooled, quenched with water (30 mL), and extracted with EtOAc (3×30 mL). The combined organic layer was dried over anhydrous Na₂SO₄, filtered through a pad of silica gel and concentrated. The residue was purified by flash column (0~30% of EtOAc in PE) to give a solid. The diastereomers were separated by SFC (Column DAICEL CHIRALPAK AD (250 mm*30 mm, 10 um); Condition 0.1% NH₃H₂O ETOH Begin B 55% End B 55% Gradient Time (min) 100% B Hold Time (min) FlowRate (ml/min) 70) to afford 402 (13.1 mg, 4%, Rt=2.613 min) and 403 (95.1 mg, 28%, Rt=1.596 min) both as solids. The two diastereomers were assigned based on ¹H NMR of C21-Me (C21-down-Me is at more downfield than C21-up isomer).

402: ¹H NMR (400 MHz, CDCl₃) δ_H 7.49 (br s, 1H), 7.44 (s, 1H), 7.38 (br d, J=4.3 Hz, 2H), 3.56 (q, J=6.6 Hz, 2H), 3.50-3.39 (m, 2H), 3.20 (br d, J=13.3 Hz, 1H), 2.73 (br s, 1H), 2.16-2.08 (m, 1H), 2.02 (br d, J=11.5 Hz, 1H), 1.92-1.65 (m, 4H), 1.53-1.27 (m, 12H), 1.25-1.08 (m, 11H), 0.82 (s, 3H), 0.70 (br d, J=6.3 Hz, 3H). LC-ELSD/MS purity 99%, MS ESI calcd. for C₃₁H₄₅NO₂Na [M+Na]⁺ 486.3 found 486.3. SFC: 100% de.

403: ¹H NMR (400 MHz, CDCl₃) δ_H 7.49-7.45 (m, 1H), 7.42 (s, 1H), 7.36 (d, J=5.0 Hz, 2H), 3.53 (q, J=7.0 Hz, 2H), 3.42 (q, J=9.3 Hz, 2H), 2.91 (dd, J=2.9, 13.4 Hz, 1H), 2.70 (s, 1H), 2.11 (dd, J=10.5, 13.6 Hz, 1H), 2.04-1.91 (m, 2H), 1.87-1.61 (m, 7H), 1.52-1.26 (m, 8H), 1.24-1.01 (m, 11H), 0.78 (d, J=6.3 Hz, 3H), 0.70 (s, 3H). LC-ELSD/MS purity 99%, MS ESI calcd. for C₃₁H₄₅NO₂Na [M+Na]⁺ 486.3 found 486.3. SFC: 100% de.

Examples 404 & 405: Synthesis of 5-((S)-2-((3R,5R,8R,9R,10S,13R,14S,17R)-3-hydroxy-3-(methoxymethyl)-13-methylhexadecahydro-1H-cyclopenta[a]phenanthren-17-yl)propyl)picolinonitrile (404) & 5-((R)-2-((3R,5R,8R,9R,10S,13R,14S,17R)-3-hydroxy-3-(methoxymethyl)-13-methylhexadecahydro-1H-cyclopenta[a]phenanthren-17-yl)propyl)picolinonitrile (405)

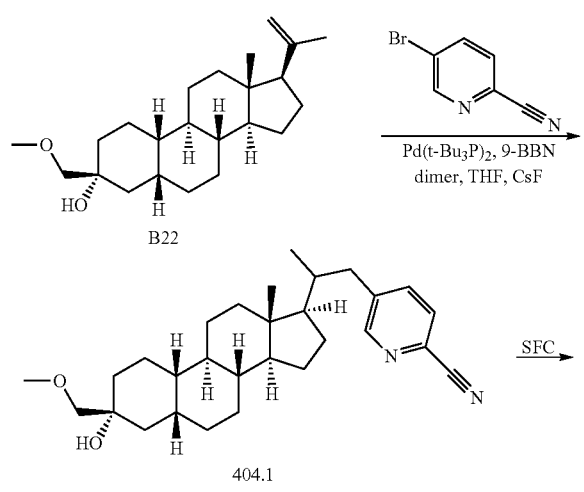

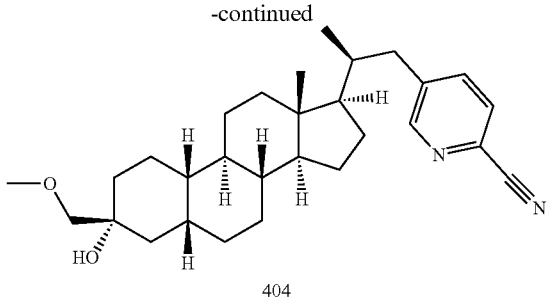

404

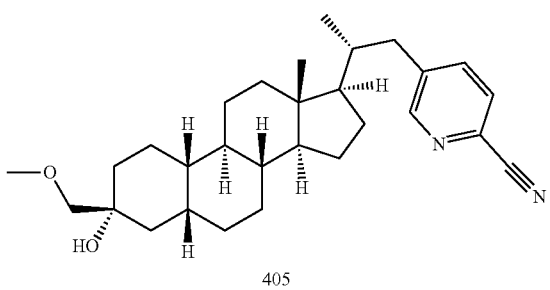

405

Synthesis of 404.1

To solution of B22 (500 mg, 1.44 mmol) in THF (15 mL) under nitrogen atmosphere at 15° C. was added 9-BBN dimer (524 mg, 2.15 mmol). After stirring at 55° C. for 3 h, 5-bromopyridine-2-carbonitrile (523 mg, 2.86 mmol), CsF (431 mg, 2.86 mmol) and Pd(t-Bu3P)₂ (72.9 mg, 0.1430 mmol) were added to the mixture. After stirring at 55° C. for 16 h, the mixture was quenched by H₂O (40 mL) and extracted with EtOAc (50 mL). The organic layer was separated, dried over Na₂SO₄, filtered, concentrated and purified by flash column (0~25% EtOAc in PE) to give 404.1 (85 mg) as a solid.

LC-ELSD/MS purity 99%, MS ESI calcd for C₂₉H₄₁N₂O [M−H₂O+H]⁺ 450.3, found 450.3.

Synthesis of 404 & 405

404.1 (480 mg, 0.9723 mmol) was purified by SFC (Column DAICEL CHIRALPAK AD (250 mm*30 mm, 10 um); Condition 0.1% NH₃H₂O IPA) to give 404 (17.6 mg, 7.04%, Rt=2.394 min) and 405 (142.1 mg, 56.8%, Rt=0.842 min) both as solids.

404: ¹H NMR (400 MHz, CDCl₃) δ_H 8.50 (s, 1H), 7.63-7.49 (m, 2H), 3.43-3.35 (m, 5H), 3.27-3.12 (m, 1H), 2.60 (s, 1H), 2.27-2.10 (m, 1H), 1.98 (br d, J=12.4 Hz, 1H), 1.91-1.61 (m, 8H), 1.45-1.05 (m, 16H), 0.79 (s, 3H), 0.69 (d, J=6.8 Hz, 3H). LC-ELSD/MS purity 99%, MS ESI calcd for C₂₉H₄₁N₂O [M−H₂O+H]⁺ 433.3, found 433.3.

405: ¹H NMR (400 MHz, CDCl₃) δ_H 8.50 (s, 1H), 7.63-7.49 (m, 2H), 3.43-3.33 (m, 5H), 2.93 (dd, J=3.2, 13.3 Hz, 1H), 2.59 (s, 1H), 2.20 (dd, J=10.4, 13.6 Hz, 1H), 2.11-1.64 (m, 8H), 1.46-0.95 (m, 17H), 0.80 (d, J=6.4 Hz, 3H), 0.70 (s, 3H). LC-ELSD/MS purity 99%, MS ESI calcd for C₂₉H₄₁N₂O [M−H₂O+H]⁺ 433.3, found 433.3.

Examples 406 & 407: Synthesis of 5-((R)-2-((3R,5R,8R,9R,10S,13R,14S,17R)-3-hydroxy-3,13-dimethylhexadecahydro-1H-cyclopenta[a]phenanthren-17-yl)propyl)nicotinonitrile (406) & 5-((S)-2-((3R,5R,8R,9R,10S,13R,14S,17R)-3-hydroxy-3,13-dimethylhexadecahydro-1H-cyclopenta[a]phenanthren-17-yl)propyl)nicotinonitrile (407)

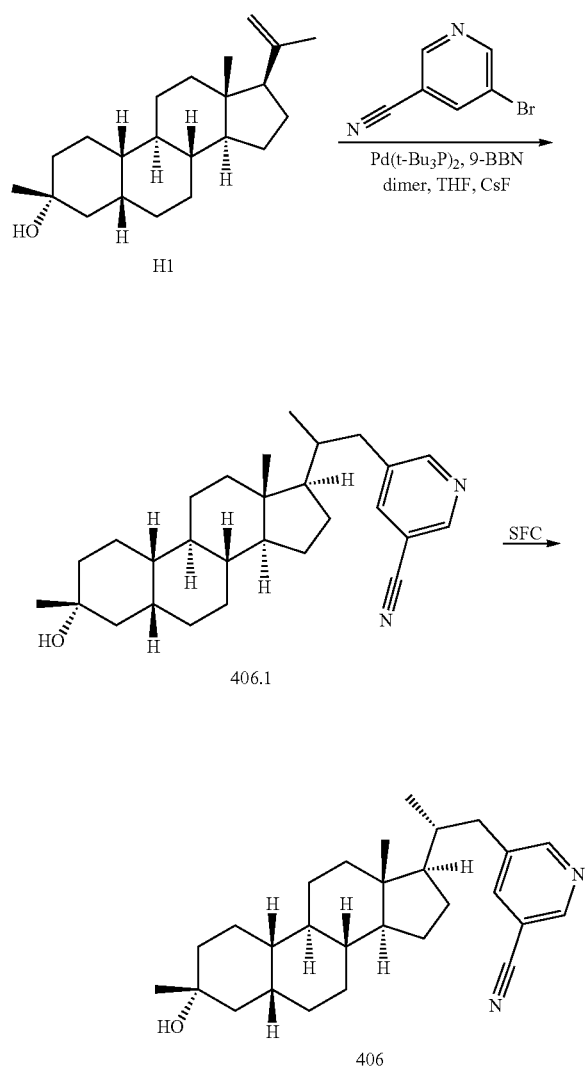

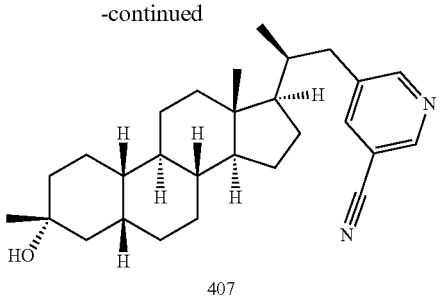

Synthesis of 406.1

To solution of H1 (400 mg, 1.26 mmol) in dioxane (10 mL) under nitrogen atmosphere at 15° C. was added 9-BBN dimmer (461 mg, 1.89 mmol). After stirring 75° C. for 3 h, 5-bromopyridine-3-carbonitrile (461 mg, 2.52 mmol), CsF (380 mg, 2.52 mmol) and Pd(t-Bu3P)$_2$ (64.3 mg, 126 µmol) were added. After stirring at 75° C. for 16 h, the reaction was cooled, quenched with water (30 mL), and extracted with EtOAc (3×30 mL). The combined organic layer was dried over anhydrous sodium sulfate, filtered and concentrated to give the product. The product was purified by flash column (0~50% of EtOAc in PE) to give 406.1 as a solid.

Separation of 406 & 407

406.1 was separated by SFC (Column: DAICEL CHIRALCEL OJ-H (250 mm*30 mm, 5 um)); condition: 0.1% NH$_3$H$_2$O ETOH IPA; Begin B: 20%; End B: 30%) to afford 406 (122.8 mg, 40.8%, P1, Rt=2.761 min) 407 (38.2 mg, 12.7%, P2, Rt=3.092 min) both as solids.

406: $^1$H NMR (400 MHz, CDCl$_3$) δ$_H$ 8.71 (d, J=1.6 Hz, 1H), 8.59 (d, J=2.0 Hz, 1H), 7.72 (t, J=1.6 Hz, 1H), 2.91 (dd, J=2.8, 14.6 Hz, 1H), 2.19 (dd, J=10.4, 14.0 Hz, 1H), 2.06-1.91 (m, 2H), 1.88-1.78 (m, 3H), 1.72-1.59 (m, 4H), 1.52-1.33 (m, 8H), 1.31-1.09 (m, 12H), 0.81 (d, J=6.8 Hz, 3H), 0.70 (s, 3H). LC-ELSD/MS: purity >99%, analytic SFC: 98.36% de, MS ESI calcd. for C$_{28}$H$_{41}$N$_2$O [M+H]$^+$ 421.3, found 421.3.

407: $^1$H NMR (400 MHz, CDCl$_3$) δ$_H$ 8.71 (d, J=1.6 Hz, 1H), 8.59 (d, J=1.6 Hz, 1H), 7.72 (s, 1H), 3.17 (dd, J=3.6, 13.6 Hz, 1H), 2.16 (dd, J=11.2, 13.6 Hz, 1H), 2.02-1.96 (m, 1H), 1.89-1.79 (m, 4H), 1.71-1.59 (m, 4H), 1.51-1.35 (m, 10H), 1.31-1.15 (m, 10H), 0.80 (s, 3H), 0.70 (d, J=6.4 Hz, 3H) LC-ELSD/MS: purity >99%, analytic SFC: 96.36% de, MS ESI calcd. for C$_{28}$H$_{39}$N$_2$ [M−H$_2$O+H]$^+$ 403.3, found 403.3.

The following examples were synthesized similar to Examples 400-407 with the listed bromide and appropriate SM. The diastereomers were assigned based on 1H NMR of

| Example | SM | Br | STRUCTURE | Analytical |
|---|---|---|---|---|
| 410 | 323.1 | 5-bromo-2-(trifluoromethyl)pyridine | 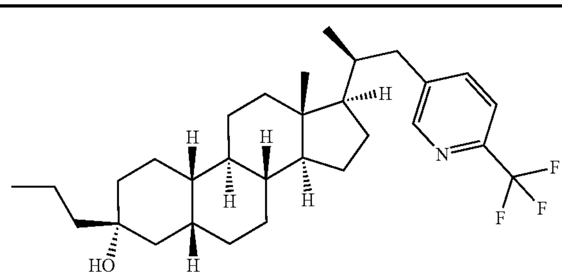 | $^1$H NMR (400 MHz, CDCl$_3$)) δ$_H$ 8.50 (s, 1H), 7.77-7.47 (m, 2H), 3.20 (dd, J = 3.6, 13.8 Hz, 1H), 2.19 (dd, J = 11.2, 13.4 Hz, 1H), 2.01 (br d, J = 12.4 Hz, 1H), 1.92-1.64 (m, 7H), 1.50-1.25 (m, 15H), 1.18-1.00 (m, 6H), 0.93 (t, J = 7.2 Hz, 4H), 0.80 (s, 3H), 0.70 (d, J = 6.4 Hz, 3H). LC-ELSD/MS purity 99%, MS ESI calcd. for C$_{30}$H$_{43}$F$_3$N [M − H$_2$O + H]+ 474.3, found 474.3. SFC 100% de. |

| Example | SM | Br | STRUCTURE | Analytical |
|---|---|---|---|---|
| 411 | | | 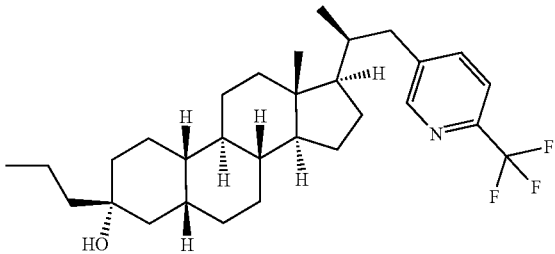 | ¹H NMR (400 MHz, CDCl₃) δ$_H$ 8.50 (s, 1H), 7.69-7.54 (m, 2H), 2.93 (dd, J = 2.8, 13.6 Hz, 1H), 2.21 (dd, J = 10.4, 13.6 Hz, 1H), 2.08-1.91 (m, 2H), 1.85-1.59 (m, 7H), 1.55-1.23 (m, 15H), 1.22-0.98 (m, 7H), 0.93 (t, J = 7.2 Hz, 3H), 0.81 (d, J = 6.4 Hz, 3H), 0.70 (s, 3H). LC-ELSD/MS purity 99%, MS ESI calcd. for $C_{30}H_{43}F_3N$ [M − H₂O + H]⁺ 474.3, found 474.3. SFC 100% de. |
| 412 | 265.1 | 6-bromo-picolino-nitrile | 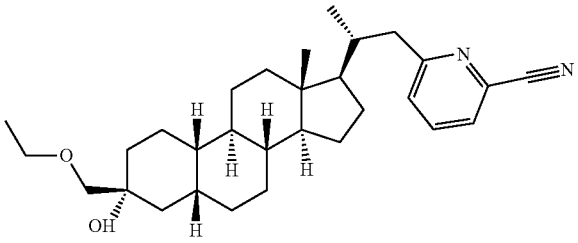 | ¹H NMR (400 MHz, CDCl₃) δ$_H$ 7.74-7.65 (m, 1H), 7.51 (d, J = 7.5 Hz, 1H), 7.31 (d, J = 8.0 Hz, 1H), 3.53 (q, J = 7.0 Hz, 2H), 3.43 (q, J = 9.3 Hz, 2H), 3.04 (dd, J = 3.4, 13.4 Hz, 1H), 2.69 (br s, 1H), 2.37 (dd, J = 10.4, 13.2 Hz, 1H), 2.03-1.59 (m, 10H), 1.51-1.25 (m, 8H), 1.23-0.93 (m, 11H), 0.80 (d, J = 6.5 Hz, 3H), 0.72 (s, 3H). LC-ELSD/MS purity 99%, MS ESI calcd. for $C_{30}H_{45}N_2O_2$ [M + H]⁺ 465.3 found 465.3. SFC: 100% de. |
| 413 | 265.1 | 6-bromo-picolino-nitrile | 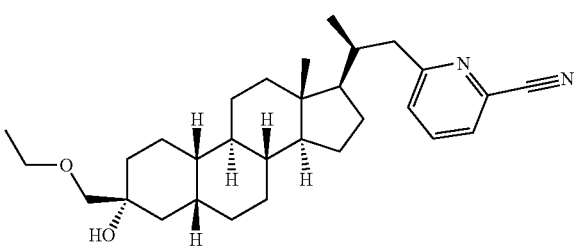 | ¹H NMR (400 MHz, CDCl₃) δ$_H$ 7.74-7.62 (m, 1H), 7.50 (d, J = 7.5 Hz, 1H), 7.31 (d, J = 7.8 Hz, 1H), 3.53 (q, J = 7.0 Hz, 2H), 3.43 (q, J = 9.2 Hz, 2H), 3.28 (dd, J = 4.0, 13.2 Hz, 1H), 2.70 (s, 1H), 2.38 (dd, J = 10.8, 13.2 Hz, 1H), 1.99 (br d, J = 13.2 Hz, 2H), 1.92-1.71 (m, 4H), 1.67-1.60 (m, 3H), 1.51-1.29 (m, 8H), 1.28-1.02 (m, 11H), 0.80 (s, 3H), 0.69 (d, J = 6.5 Hz, 3H). LC-ELSD/MS purity 99%, MS ESI calcd. for $C_{30}H_{45}N_2O_2$ [M + H]⁺ 465.3 found 465.3. SFC: 100% de. |
| 414 | 265.1 | 3-bromo-6-methyl-picolino-nitrile | 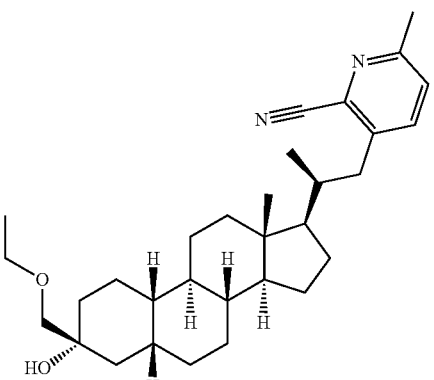 | ¹H NMR (400 MHz, CDCl₃) δ$_H$ 7.48 (d, J = 8.0 Hz, 1H), 7.28 (s, 1H), 3.53 (q, J = 6.9 Hz, 2H), 3.43 (q, J = 9.1 Hz, 2H), 3.28 (dd, J = 4.1, 13.4 Hz, 1H), 2.70 (br s, 1H), 2.56 (s, 3H), 2.35 (dd, J = 11.2, 13.4 Hz, 1H), 2.02 (br d, J = 12.3 Hz, 1H), 1.90-1.61 (m, 8H), 1.52-1.18 (m, 15H), 1.13-1.04 (m, 4H), 0.84 (s, 3H), 0.70 (d, J = 6.5 Hz, 3H). LC-ELSD/MS calcd. for $C_{31}H_{45}N_2O$ [M + H − H₂O]⁺ 461.3 found 461.3. SFC: 99% de. |
| 415 | 265.1 | 3-bromo-6-methyl-picolino-nitrile | 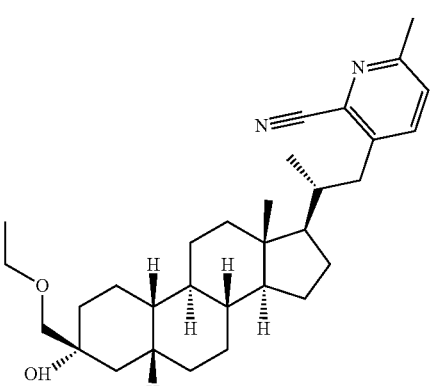 | ¹H NMR (400 MHz, CDCl₃) δ$_H$ 7.51 (d, J = 8.0 Hz, 1H), 7.30 (s, 1H), 3.55 (q, J = 7.0 Hz, 2H), 3.45 (q, J = 9.1 Hz, 2H), 3.16-3.02 (m, 1H), 2.72 (br s, 1H), 2.59 (s, 3H), 2.33 (dd, J = 10.9, 13.7 Hz, 1H), 2.10-1.96 (m, 2H), 1.89-1.61 (m, 8H), 1.23 (br t, J = 7.0 Hz, 18H), 0.83 (d, J = 6.5 Hz, 3H), 0.72 (s, 3H). LC-ELSD/MS purity 99%, MS ESI calcd. for $C_{31}H_{45}N_2O$ [M + H − H₂O]⁺ 461.3 found 461.3. SFC: 99% de. |

| Example | SM | Br | STRUCTURE | Analytical |
|---|---|---|---|---|
| 416 | 265.1 | 2-bromo-benzo-nitrile | 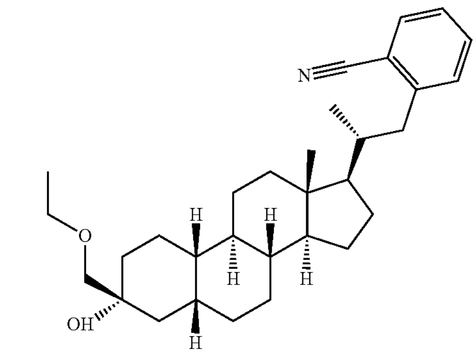 | ¹H NMR (400 MHz, CDCl₃) $\delta_H$ 7.59 (s, 1H), 7.49 (s, 1H), 7.30-7.27 (m, 1H), 7.25 (br s, 1H), 3.53 (q, J = 6.9 Hz, 2H), 3.43 (q, J = 9.2 Hz, 2H), 3.13 (dd, J = 3.0, 13.3 Hz, 1H), 2.31 (dd, J = 11.2, 13.2 Hz, 1H), 2.09-1.91 (m, 2H), 1.86-1.57 (m, 10H), 1.52-1.17 (m, 14H), 1.16-0.94 (m, 6H), 0.71 (s,3H). LC-ELSD/MS purity 99%, MS ESI calcd. for C₂₉H₃₈N [M − EtOH − H₂O + H]⁺ 400.3 found 400.3. SFC: 100% de. |
| 417 | 265.1 | 2-bromo-benzo-nitrile | 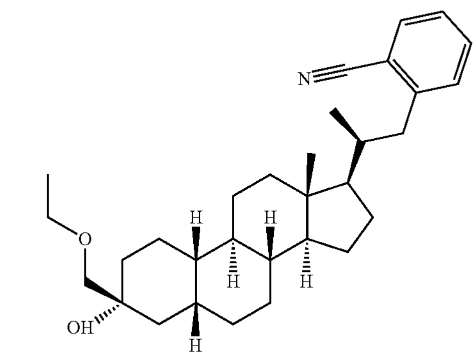 | ¹H NMR (400 MHz, CDCl₃) $\delta_H$ 7.62 (d, J = 7.4 Hz, 1H), 7.54-7.48 (m, 1H), 7.32-7.29 (m, 1H), 7.27 (s, 1H), 3.56 (q, J = 7.0 Hz, 2H), 3.45 (q, J = 9.2 Hz, 2H), 3.34 (dd, J = 4.2, 13.4 Hz, 1H), 2.72 (s, 1H), 2.49-2.34 (m, 1H), 2.06 (br d, J = 12.1 Hz, 1H), 1.97-1.60 (m, 9H), 1.53-1.26 (m, 9H), 1.23 (t, J = 6.9 Hz, 4H), 1.20-1.01 (m, 5H), 0.87 (s, 3H), 0.71 (d, J = 6.5 Hz, 3H). LC-ELSD/MS purity 99%, MS ESI calcd. for C₂₉H₃₈N [M − EtOH − H₂O + H]⁺ 400.3 found 400.3. SFC: 100% de. |
| 418 | 323.1 | 2-bromo-5-methyl-pyrazine | 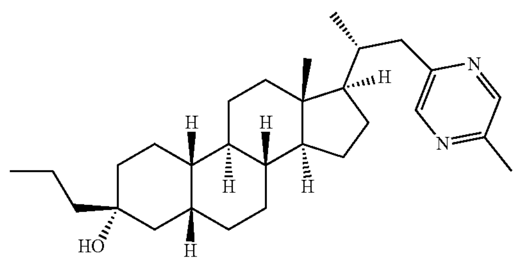 | ¹H NMR (400 MHz, CDCl₃) $\delta_H$ 0.71 (s, 3H) 0.82 (d, J = 6.53 Hz, 3H) 0.93 (t, J = 7.28 Hz, 3H) 1.13-0.99 (m, 5H) 1.25-1.13 (m, 3H) 1.34 (br s, 7H) 1.46-1.36 (m, 5H) 1.55-1.4 (m, 4H) 1.74-1.67 (m, 1H) 1.81-1.74 (m, 2H) 1.91-1.81 (m, 1H) 1.99-1.91 (m, 2H) 2.32 (dd, J = 13.43, 10.16 Hz, 1H) 2.52 (s, 3H) 3.00-2.94 (m, 1H) 8.27 (d, J = 1.25 Hz, 1H) 8.38 (s, 1H). LC-ELSD/MS purity 99%, MS ESI calcd. for C₂₉H₄₇N₂O [M + H]⁺ 439.4 found 439.4. |
| 419 | | | 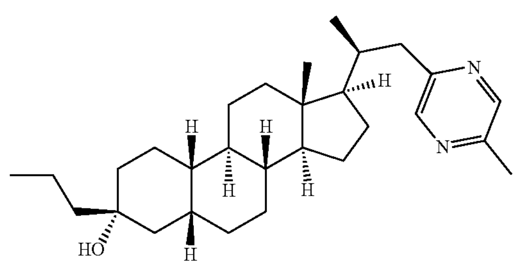 | LC-ELSD/MS purity 99%, MS ESI calcd. for C₂₉H₄₇N₂O [M + H]⁺ 439.4 found 439.4. |
| 420 | B22 | 5-bromo-2-(trifluoro-methyl)pyridine | 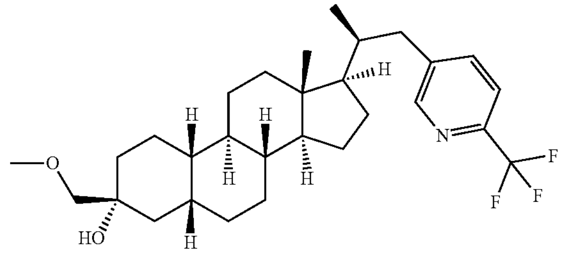 | ¹H NMR (400 MHz, CDCl₃) $\delta_H$ 8.50 (s, 1H), 7.60 (s, 2H), 3.43-3.33 (m, 5H), 3.20 (br d, J = 16.8 Hz, 1H), 2.60 (s, 1H), 2.19 (dd, J = 11.2, 13.6 Hz, 1H), 2.01 (br d, J = 12.8 Hz, 1H), 1.92-1.60 (m, 9H), 1.42-1.05 (m, 15H), 0.84-0.84 (m, 1H), 0.80 (s, 3H), 0.70 (d, J = 6.4 Hz, 3H). LC-ELSD/MS purity 99%, MS ESI calcd for C₂₉H₄₁F₃NO [M − H₂O + H]⁺ 476.3, found 476.3. |

-continued

| Example | SM | Br | STRUCTURE | Analytical |
|---|---|---|---|---|
| 421 | | | 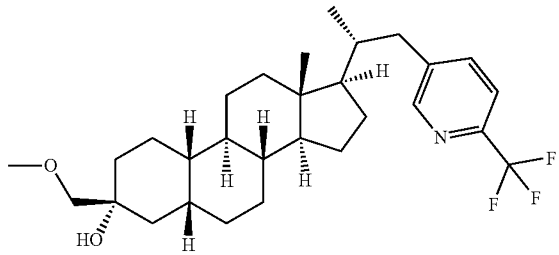 | $^1$H NMR (400 MHz, CDCl$_3$) δ$_H$ 8.50 (s, 1H), 7.60 (s, 2H), 3.43-3.33 (s, 5H), 2.98-2.90 (m, 1H), 2.64-2.55 (m, 1H), 2.25-2.16 (m, 1H), 2.08-1.91 (m, 2H), 1.87-1.59 (m, 8H), 1.49-0.93 (m, 15H), 0.81 (d, J = 6.4 Hz, 3H), 0.70 (s, 3H). LC-ELSD/MS purity 99%, MS ESI calcd for C$_{29}$H$_{41}$F$_3$NO [M − H$_2$O + H]$^+$ 476.3, found 476.3. |
| 422 | B22 | 2-bromo-5-methyl-pyrazine | 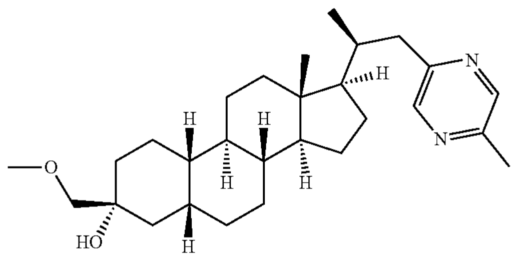 | $^1$H NMR (400 MHz, CDCl$_3$) δ$_H$ 8.37 (s, 1H), 8.27 (s, 1H), 3.43-3.35 (m, 5H), 3.21 (br d, J = 10.0 Hz, 1H), 2.59 (s, 1H), 2.52 (s, 3H), 2.37-2.26 (m, 1H), 2.06-1.74 (m, 7H), 1.42-0.96 (m, 18H), 0.81 (s, 3H), 0.70 (d, J = 6.4 Hz, 3H). LC-ELSD/MS purity 99%, MS ESI calcd for C$_{28}$H$_{45}$N$_2$O$_2$ [M + H]$^+$ 441.3, found 441.3. |
| 423 | | | 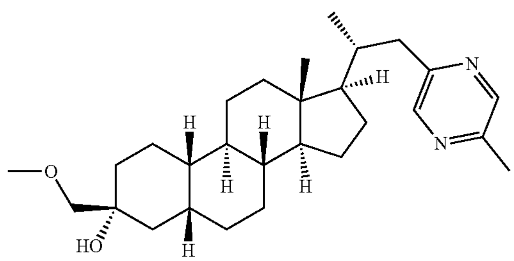 | $^1$H NMR (400 MHz, CDCl$_3$) δ$_H$ 8.40 (s, 1H), 8.30 (s, 1H), 3.45-3.38 (m, 5H), 2.99 (dd, J = 2.8, 13.2 Hz, 1H), 2.60 (s, 1H), 2.55 (s, 3H), 2.34 (dd, J = 10.4, 13.4 Hz, 1H), 2.07-1.68 (m, 7H), 1.53-0.96 (m, 18H), 0.84 (d, J = 6.4 Hz, 3H), 0.73 (s, 3H). LC-ELSD/MS purity 99%, MS ESI calcd for C$_{28}$H$_{45}$N$_2$O$_2$ [M + H]$^+$ 441.3, found 441.3. |
| 424 | B22 | 2,3-dichloro-6-methyl-pyridine | 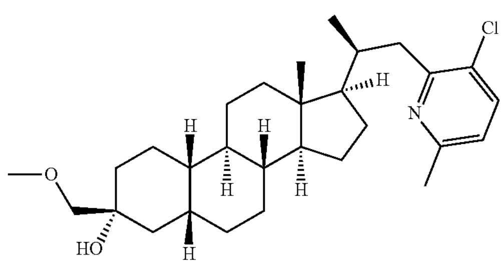 | $^1$H NMR (400 MHz, CDCl$_3$) δ$_H$ 7.47 (d, J = 8.4 Hz, 1H), 6.91 (d, J = 8.4 Hz, 1H), 3.43-3.36 (m, 5H), 3.33 (dd, J = 4.7, 12.8 Hz, 1H), 2.60-2.52 (m, 2H), 2.50 (s, 3H), 2.19-1.99 (m, 2H), 1.91-1.59 (m, 7H), 1.50-1.03 (m, 16H), 0.82 (s, 3H), 0.69 (d, J = 6.6 Hz, 3H). LC-ELSD/MS purity 99%, MS ESI calcd. for C$_{29}$H$_{45}$ClNO$_2$ [M + H]$^+$ 474.3 found 474.3. SFC: 100% de. |
| 425 | | | 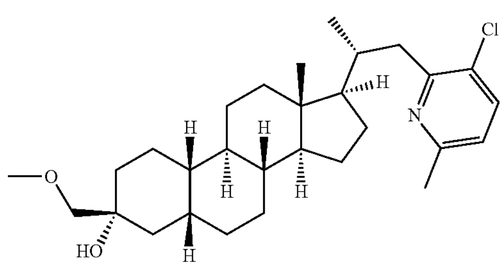 | $^1$H NMR (400 MHz, CDCl$_3$) δ$_H$ 7.48 (d, J = 8.4 Hz, 1H), 6.91 (d, J = 8.0 Hz, 1H), 3.43-3.36 (m, 5H), 3.03 (dd, J = 4.7, 12.8 Hz, 1H), 2.70-2.50 (m, 2H), 2.50 (s, 3H), 2.30-2.20 (m, 1H), 1.85-1.59 (m, 13H), 1.56-1.03 (m, 18H), 0.80 (s, 3H), 0.75 (d, J = 6.8 Hz, 3H). LC-ELSD/MS purity 99%, MS ESI calcd. for C$_{29}$H$_{45}$ClNO$_2$ [M + H]$^+$ 474.3 found 474.3. SFC: 100% de. |
| 426 | 305.2 | 5-bromo-2-(trifluoro-methyl)pyridine | 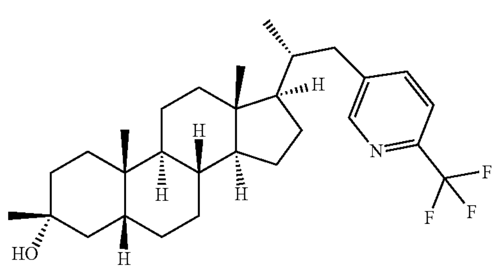 | $^1$H NMR (400 MHz, CDCl$_3$) δ$_H$ 8.50 (s, 1 H), 7.57-7.65 (m, 2 H), 2.98-2.88 (m, 1 H), 2.26-2.16 (m, 1 H), 1.56-2.06 (m, 8 H), 1.35-1.50 (m, 8 H), 1.00-1.26 (m, 12 H), 0.94 (s, 3 H), 0.81 (d, J = 6.4 Hz, 3 H), 0.68 (s, 3 H). LC-ELSD/MS: purity 99%, analytic SFC: 100% de; MS ESI calcd. for C$_{29}$H$_{41}$F$_3$N [M − H2O + H]$^+$ 460.3, found 460.3. |

-continued

| Example | SM | Br | STRUCTURE | Analytical |
|---|---|---|---|---|
| 427 | | | 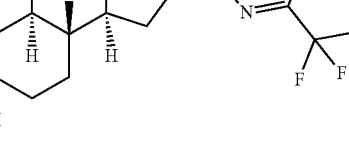 | $^1$H NMR (400 MHz, CDCl$_3$) δ$_H$ 8.50 (s, 1 H), 7.57-7.64 (m, 2 H), 3.25-3.10 (m, 1 H), 2.24-2.13 (m, 1 H), 1.63-2.06 (m, 8 H), 1.37-1.50 (m, 8 H), 1.05-1.26 (m, 12 H), 0.96 (s, 3 H), 0.78 (s, 3 H), 0.70 (d, J = 6.4 Hz, 3 H). LC-ELSD/MS: purity 99%, analytic SFC: 99% de; MS ESI calcd. for C$_{29}$H$_{41}$F$_3$N [M − H2O + H]$^+$ 460.3, found 460.3. |
| 428 | H1 | (2-bromo-thiazol-5-yl) methanol | 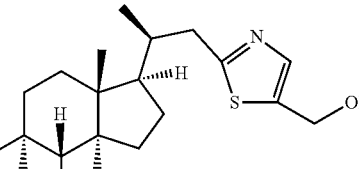 | $^1$H NMR(400 MHz, CDCl$_3$) δ$_H$ 7.03 (s, 1H), 4.74 (s, 2H), 3.36 (dd, J = 3.6, 14.4 Hz, 1H), 2.64 (dd, J = 10.0, 13.6 Hz, 1H), 2.29-2.20 (m, 1H), 2.02-1.92 (m, 2H), 1.89-1.76 (m, 4H), 1.51-1.33 (m, 8H), 1.32-1.02 (m, 15H), 0.83 (d, J = 6.4 Hz, 3H), 0.78 (s, 3H). LC-ELSD/MS: purity >99%, analytic SFC: 100% de. MS ESI calcd. for C$_{26}$H$_{42}$NO$_2$S [M + H]$^+$ 432.3, found 432.3. |
| 429 | | | 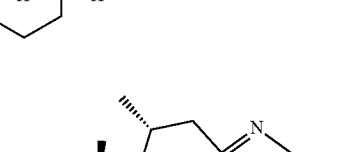 | $^1$H NMR(400 MHz, CDCl$_3$) δ$_H$ 7.03 (s, 1H), 4.74 (d, J = 6.0 Hz, 2H), 3.12 (dd, J = 3.2, 14.4 Hz, 1H), 2.63 (dd, J = 10.4, 14.8 Hz, 1H), 2.34-2.25 (m, 1H), 2.02-1.77 (m, 6H), 1.65-1.60 (m, 2H), 1.52-1.20 (m, 15H), 1.18-1.00 (m, 6H), 0.94 (d, J = 6.8 Hz, 3H), 0.72 (s, 3H). LC-ELSD/MS: purity >99%, analytic SFC: 99.28% de. MS ESI calcd. for C$_{26}$H$_{42}$NO$_2$S [M + H]$^+$ 432.3, found 432.3. |
| 430 | H1 | 2-bromo-5-methyl-thiazole | 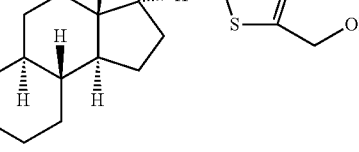 | $^1$H NMR (400 MHz, CDCl$_3$) δ$_H$ 7.28 (s, 1H), 3.35-3.26 (m, 1H), 2.61-2.51 (m, 1H), 2.42 (s, 3H), 2.00-1.76 (m, 7H), 1.68-1.58 (m, 3H), 1.49-1.32 (m, 8H), 1.30-1.09 (m, 11H), 0.83 (d, J = 6.4 Hz, 3H), 0.77 (s, 3H). LC-ELSD/MS: purity >99%, 100% de based on H-NMR. MS ESI calcd. for C$_{26}$H$_{42}$NOS [M + H]$^+$ 416.3, found 416.3. |
| 431 | | | 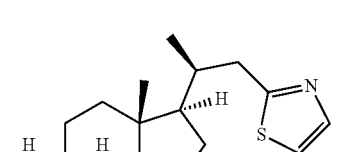 | $^1$H NMR (400 MHz, CDCl$_3$) δ$_H$ 7.29 (s, 1H), 3.06 (dd, J = 3.2, 14.4 Hz, 1H), 2.63-2.53 (m, 1H), 2.42 (s, 3H), 2.01-1.77 (m, 7H), 1.50-1.32 (m, 9H), 1.31-1.05 (m, 13H), 0.94 (d, J = 6.4 Hz, 3H), 0.72 (s, 3H). LC-ELSD/MS: purity >99%, analytic SFC: 100% de.MS ESI calcd. for C$_{26}$H$_{42}$NOS [M + H]$^+$ 416.3, found 416.3. |
| 432 | H1 | 3-bromo-5-methoxy pyridine | 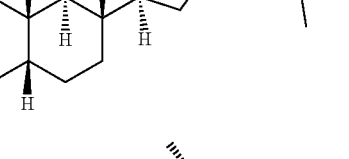 | $^1$H NMR (400 MHz, CDCl$_3$) δ$_H$ 8.13 (d, J = 2.8 Hz, 1H), 8.02 (s, 1H), 6.96 (s, 1H), 3.86 (s, 3H), 3.11 (dd, J = 4.0, 13.6 Hz, 1H), 2.12-1.98 (m, 2H), 1.90-1.78 (m, 4H), 1.70-1.60 (m, 3H), 1.51-1.36 (m, 7H), 1.32-1.23 (m, 9H), 1.13-1.02 (m, 5H), 0.80 (s, 3H), 0.70 (d, J = 6.4 Hz, 3H). LC-ELSD/MS: purity >99%, analytic SFC: 98.80% de. MS ESI calcd. for C$_{28}$H$_{44}$NO$_2$ [M + H]$^+$ 426.3, found 426.3. |

-continued

| Example | SM | Br | STRUCTURE | Analytical |
|---|---|---|---|---|
| 433 | | | 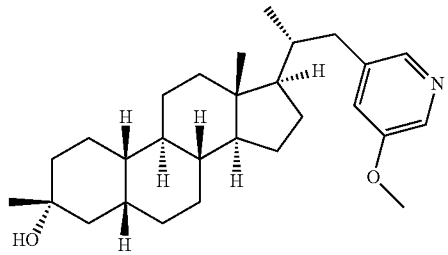 | $^1$H NMR (400 MHz, CDCl$_3$) $\delta_H$ 8.13 (d, J = 2.4 Hz, 1H), 8.02 (s, 1H), 6.96 (s, 1H), 3.86 (s, 3H), 2.85 (dd, J = 2.8, 13.6 Hz, 1H), 2.14-1.92 (m, 3H), 1.89-1.68 (m, 4H), 1.52-1.30 (m, 9H), 1.27-1.02 (m, 14H), 0.81 (d, J = 6.4 Hz, 3H), 0.70 (s, 3H). LC-ELSD/MS: purity >99%, analytic SFC: 95.04% de. MS ESI calcd. for C$_{28}$H$_{44}$NO$_2$ [M + H]$^+$ 426.3, found 426.3. |
| 434 | H1 | 3-bromo-5-methyl-pyridine | 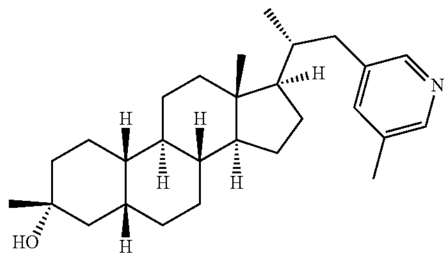 | $^1$H NMR (400 MHz, CDCl$_3$) $\delta_H$ 8.25 (s, 1H), 8.19 (s, 1H), 2.83 (d, J = 12.0 Hz, 1H), 2.31 (s, 3H), 2.09-1.92 (m, 3H), 1.88-1.75 (m, 3H), 1.65-1.59 (m, 3H), 1.51-1.32 (m, 8H), 1.32-1.00 (m, 14H), 0.80 (d, J = 6.4 Hz, 3H), 0.70 (s, 3H). LC-ELSD/MS: purity >99%, analytic SFC: 99.84% de. MS ESI calcd. for C$_{28}$H$_{44}$NO [M + H]$^+$ 410.3, found 410.3. |
| 435 | H1 | 2-bromo-pyrimidine-4-carbonitrile | 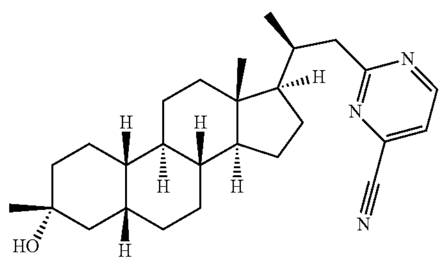 | $^1$H NMR (400 MHz, CDCl$_3$) $\delta_H$ 8.88 (d, J = 4.8 Hz, 1H), 7.44 (d, J = 4.8 Hz, 1H), 3.44 (dd, J = 4.0, 13.2 Hz, 1H), 2.63 (dd, J = 10.4, 13.2 Hz, 1H), 2.20-2.10 (m, 1H), 2.02-1.95 (m, 1H), 1.90-1.77 (m, 4H), 1.68-1.59 (m, 3H), 1.51-1.32 (m, 8H), 1.29-1.06 (m, 12H), 0.81 (s, 3H), 0.73 (d, J = 6.4 Hz, 3H). LC-ELSD/MS: purity >99%, analytic SFC: 99.02% de. MS ESI calcd. for C$_{27}$H$_{40}$N$_3$O [M + H]$^+$ 422.3, found 422.3. |
| 436 | | | 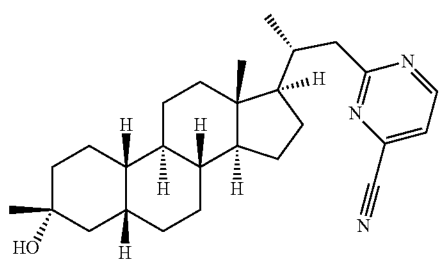 | $^1$H NMR (400 MHz, CDCl$_3$) $\delta_H$ 8.88 (d, J = 4.8 Hz, 1H), 7.44 (d, J = 4.4 Hz, 1H), 3.18 (dd, J = 3.6, 13.2 Hz, 1H), 2.64 (dd, J = 10.4, 13.6 Hz, 1H), 2.18-2.06 (m, 1H), 2.01-1.90 (m, 2H), 1.88-1.78 (m, 3H), 1.69-1.58 (m, 3H), 1.51-1.34 (m, 8H), 1.33-1.08 (m, 12H), 0.85 (d, J = 6.4 Hz, 3H), 0.73 (s, 3H). LC-ELSD/MS: purity >99%, analytic SFC: 100% de. MS ESI calcd. for C$_{27}$H$_{37}$N$_3$ [M − H$_2$O + H]$^+$ 404.3, found 404.3. |
| 437 | H1 | 2-bromo-5-methyl-pyrimidine | 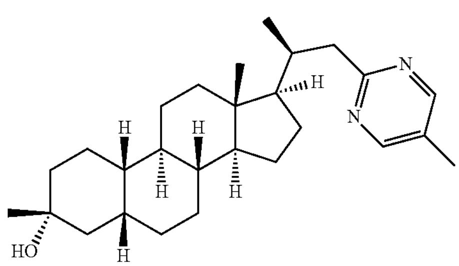 | $^1$H NMR (400 MHz, CDCl$_3$) $\delta_H$ 8.49 (s, 2H), 3.35 (dd, J = 4.0, 12.8 Hz, 1H), 2.51 (dd, J = 10.8, 13.2 Hz, 1H), 2.27 (s, 3H), 2.18-2.06 (m, 1H), 2.05-1.97 (m, 1H), 1.91-1.77 (m, 4H), 1.91-1.77 (m, 4H), 1.50-1.31 (m, 8H), 1.30-1.07 (m, 11H), 0.81 (s, 3H), 0.72 (d, J = 7.8 Hz, 3H). LC-ELSD/MS: purity >99%, analytic SFC: 98.90% de. MS ESI calcd. for C$_{27}$H$_{43}$N$_2$O [M + H]$^+$ 411.3, found 411.3. |
| 438 | | | 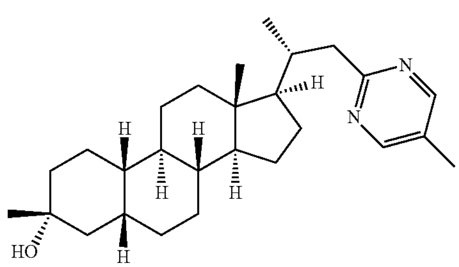 | $^1$H NMR (400 MHz, CDCl$_3$) $\delta_H$ 8.49 (s, 2H), 3.16-3.07 (m, 1H), 2.50 (dd, J = 10.8, 13.2 Hz, 1H), 2.27 (s, 3H), 2.14-2.02 (m, 1H), 2.01-1.89 (m, 2H), 1.88-1.77 (m, 3H), 1.67-1.60 (m, 2H), 1.50-1.31 (m, 8H), 1.30-1.02 (m, 13H), 0.84 (d, J = 6.4 Hz, 3H), 0.73 (s, 3H). LC-ELSD/MS: purity >99%, analytic SFC: 100% de. MS ESI calcd. for C$_{27}$H$_{43}$N$_2$O [M + H]$^+$ 411.3, found 411.3. |

-continued

| Example | SM | Br | STRUCTURE | Analytical |
|---|---|---|---|---|
| 439 | H1 | 2-bromo-5-methyl-pyrazine | 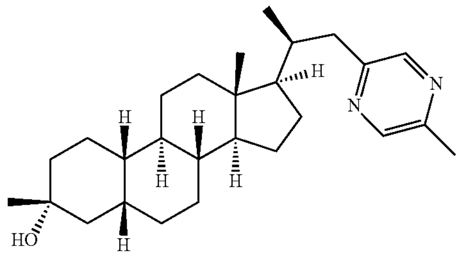 | $^1$H NMR (400 MHz, CDCl$_3$) δ$_H$ 8.38 (s, 1H), 8.27 (d, J = 1.2 Hz, 1H), 3.21 (dd, J = 4.0, 13.2 Hz, 1H), 2.52 (s, 3H), 2.31 (dd, J = 10.8, 13.6 Hz, 1H), 2.05-1.74 (m, 7H), 1.68-1.58 (m, 3H), 1.46-1.36 (m, 6H), 1.32-1.24 (m, 8H), 1.12-1.02 (m, 5H), 0.81 (s, 3H), 0.70 (d, J = 6.4 Hz, 3H). LC-ELSD/MS: purity >99%, analytic SFC: 100% de. MS ESI calcd. for C$_{27}$H$_{43}$N$_2$O [M + H]$^+$ 411.4 found 411.4 |
| 440 | | | 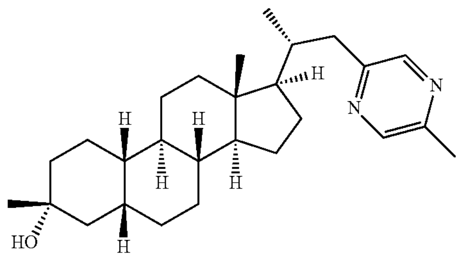 | $^1$H NMR (400 MHz, CDCl$_3$) δ$_H$ 8.38 (s, 1H), 8.27 (d, J = 0.8 Hz, 1H), 2.96 (dd, J = 3.2, 13.2 Hz, 1H), 2.52 (s, 3H), 2.31 (dd, J = 10.4, 13.6 Hz, 1H), 2.04-1.77 (m, 6H), 1.67-1.62 (m, 2H), 1.51-1.30 (m, 8H), 1.28-0.97 (m, 13H), 0.82 (d, J = 6.4 Hz, 3H), 0.71 (s, 3H). LC-ELSD/MS: purity >99%, analytic SFC: 100% de. MS ESI calcd. for C$_{27}$H$_{43}$N$_2$O [M + H]$^+$ 411.3 found 411.3 |
| 441 | B1 | 2-bromo-6-methyl-pyrazine | 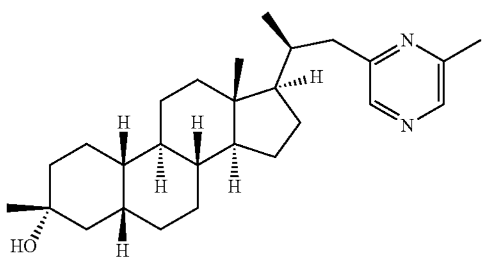 | $^1$H NMR (400 MHz, CDCl$_3$) δ$_H$ 8.24 (s, 1H), 8.20 (s, 1H), 3.26-3.18 (m, 1H), 2.53 (s, 3H), 2.37-2.27 (m, 1H), 2.07-1.73 (m, 7H), 1.48-1.34 (m, 7H), 1.30-1.20 (m, 9H), 1.14-1.00 (m, 6H), 0.81 (s, 3H), 0.71 (d, J = 6.4 Hz, 3H). LC-ELSD/MS: purity >99%, analytic SFC: 98.22% de. MS ESI calcd. for C$_{27}$H$_{43}$N$_2$O [M + H]$^+$ 411.3 found 411.3 |
| 442 | | | 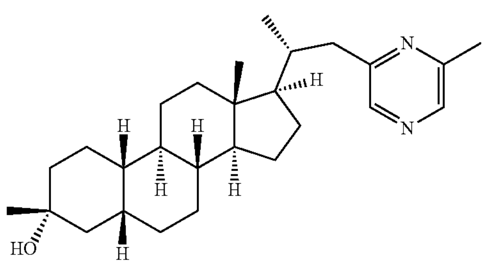 | $^1$H NMR (400 MHz, CDCl$_3$) δ$_H$ 8.24 (s, 1H), 8.20 (s, 1H), 2.98 (dd, J = 3.2, 13.2 Hz, 1H), 2.53 (s, 3H), 2.31 (dd, J = 10.4, 13.6 Hz, 1H), 2.02-1.77 (m, 7H), 1.50-1.33 (m, 8H), 1.31-1.19 (m, 8H), 1.17-1.00 (m, 6H), 0.82 (d, J = 6.4 Hz, 3H), 0.71 (s, 3H). LC-ELSD/MS: purity >99%, analytic SFC: 100% de. MS ESI calcd. for C$_{27}$H$_{43}$N$_2$O [M + H]$^+$ 411.3 found 411.3 |
| 443 | H1 | 5-bromo-2-(trifluoromethyl) pyridine | 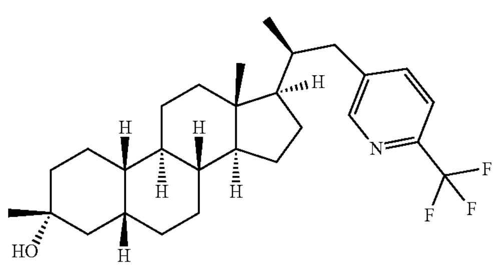 | $^1$H NMR (400 MHz, CDCl$_3$) δ$_H$ 8.50 (s, 1H), 7.64-7.54 (m, 2H), 3.23-3.16 (m, 1H), 2.22-2.15 (m, 1H), 2.06-1.95 (m, 1H), 1.89-1.59 (m, 8H), 1.51-1.34 (m, 7H), 1.33-1.07 (m, 13H), 0.80 (s, 3H), 0.70 (d, J = 6.8 Hz, 3H). LC-ELSD/MS: purity >99%, analytic SFC: 99.26% de. MS ESI calcd. for C$_{28}$H$_{39}$F$_3$N [M − H$_2$O + H]$^+$ 446.3 found 446.3 |
| 444 | | | 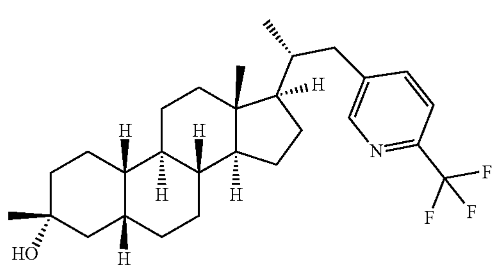 | $^1$H NMR (400 MHz, CDCl$_3$) δ$_H$ 8.50 (s, 1H), 7.68-7.55 (m, 2H), 2.97-2.88 (m, 1H), 2.26-2.16 (m, 1H), 2.08-1.59 (m, 9H), 1.51-1.33 (m, 7H), 1.32-0.98 (m, 13H), 0.81 (d, J = 6.4 Hz, 3H), 0.70 (s, 3H). LC-ELSD/MS: purity >99%, analytic SFC: 98.24% de. MS ESI calcd. for C$_{28}$H$_{39}$F$_3$N [M − H$_2$O + H]$^+$ 446.3 found 446.3 |

-continued

| Example | SM | Br | STRUCTURE | Analytical |
|---|---|---|---|---|
| 445 | 305.2 | 5-bromo-pyridine-3-carbonitrile | 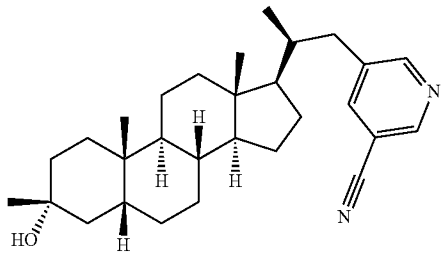 | $^1$H NMR (400 MHz, CDCl$_3$) $\delta_H$ 8.71 (d, J = 2.0 Hz, 1H), 8.59 (d, J = 1.8 Hz, 1H), 7.72 (s, 1H), 3.16 (dd, J = 3.8, 13.8 Hz, 1H), 2.16 (dd, J = 11.0, 13.6 Hz, 1H), 2.03-1.67 (m, 7H), 1.51-1.31 (m, 10H), 1.26 (s, 3H), 1.24-1.04 (m, 8H), 0.96 (s, 3H), 0.78 (s, 3H), 0.70 (d, J = 6.4 Hz, 3H). LC-ELSD/MS: purity 99%, analytic SFC: 92.6% de; MS ESI calcd. for C$_{29}$H$_{41}$N$_2$ [M − H2O + H]$^+$ 417.3, found 417.3. |
| 446 | | | 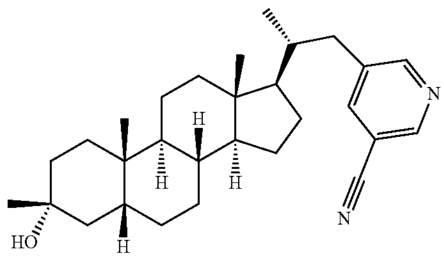 | $^1$H NMR (400 MHz, CDCl$_3$) $\delta_H$ 8.72 (d, J = 1.8 Hz, 1H), 8.59 (d, J = 2.0 Hz, 1H), 7.72 (t, J = 1.8 Hz, 1H), 2.96-2.86 (m, 1H), 2.24-2.13 (m, 1H), 2.06-1.61 (m, 8H), 1.54-1.37 (m, 9H), 1.26 (s, 3H), 1.22-0.99 (m, 8H), 0.94 (s, 3H), 0.80 (d, J = 6.4 Hz, 3H), 0.69 (s, 3H). LC-ELSD/MS: purity 99%, analytic SFC: 100% de; MS ESI calcd. for C$_{29}$H$_{41}$N$_2$ [M − H$_2$O + H]$^+$ 417.3, found 417.3; MS ESI calcd. for C$_{29}$H$_{43}$N$_2$O [M + H]$^+$ 435.3, found 435.3. |
| 447 | 323.1 | 5-bromo-2-methyl-pyridine | 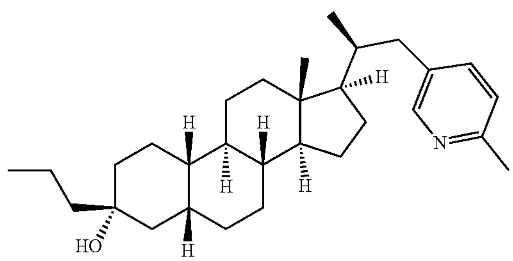 | $^1$H NMR (400 MHz, CDCl$_3$) $\delta_H$ 8.27 (d, J = 2.0 Hz, 1H), 7.35 (br d, J =7.6 Hz, 1H), 7.06 (d, J = 8.0 Hz, 1H), 3.14-3.01 (m, 1H), 2.53 (s, 3H), 2.11-1.99 (m, 2H), 1.91-1.62 (m, 8H), 1.49-1.17 (m, 16H), 1.14-0.99 (m, 5H), 0.93 (t, J =7.2 Hz, 3H), 0.79 (s, 3H), 0.69 (d, J = 6.4 Hz, 3H). LC-ELSD/MS purity 99%, MS ESI calcd for C$_{30}$H$_{48}$NO [M + H]$^+$ 438.4, found 438.4. SFC 95% de. |
| 448 | | | 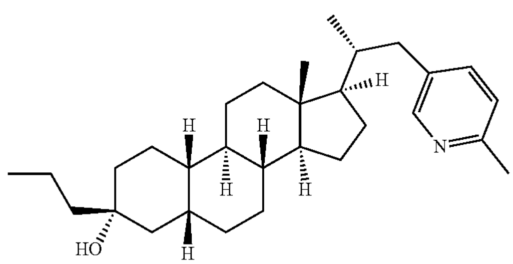 | $^1$H NMR (400 MHz, CDCl$_3$) $\delta_H$ 8.29 (d, J = 2.0 Hz, 1H), 7.37 (dd, J = 2.0, 7.6 Hz, 1H), 7.08 (d, J = 8.0 Hz, 1H), 2.91-2.78 (m, 1H), 2.54 (s, 3H), 2.09 (dd, J = 10.2, 13.6 Hz, 1H), 2.06-1.94 (m, 2H), 1.88-1.62 (m, 7H), 1.55-1.28 (m, 14H), 1.26-1.01 (m, 8H), 0.96 (t, J = 7.2 Hz, 3H), 0.82 (d, J = 6.4 Hz, 3H), 0.71 (s, 3H). LC-ELSD/MS purity 99%, MS ESI calcd for C$_{30}$H$_{48}$NO [M + H]$^+$ 438.4, found 438.4. SFC 100% de. |
| 449 | B1 | 2-bromo-4-(trifluoro-methyl)-1,3-thiazole | 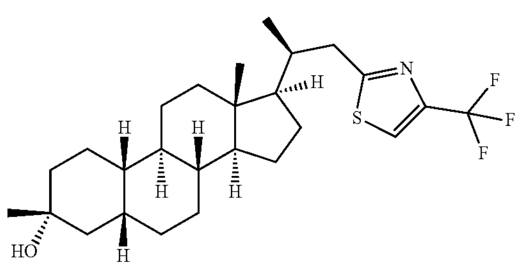 | $^1$H NMR (400 MHz, CDCl$_3$) $\delta_H$ 7.62 (s, 1H), 3.39 (dd, J = 3.6, 14.4 Hz, 1H), 2.73 (dd, J = 10.8, 14.4 Hz, 1H), 2.03-1.79 (m, 6H), 1.69-1.59 (m, 3H), 1.45-1.25 (m, 14H), 1.17-1.00 (m, 6H), 0.84 (d, J = 6.4 Hz, 3H), 0.78 (s, 3H). LC-ELSD/MS: purity >99%, analytic SFC: 100% de, MS ESI calcd. for C$_{26}$H$_{39}$F$_3$NOS [M + H]$^+$ 470.3, found 470.3. |
| 450 | | | 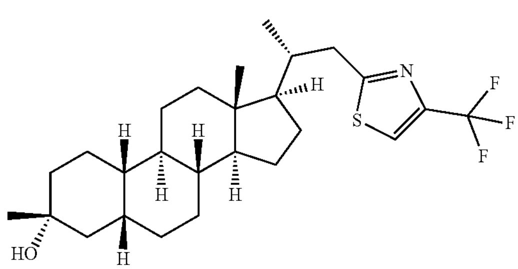 | $^1$H NMR (400 MHz, CDCl$_3$) $\delta_H$ 7.62 (s, 1H), 3.16 (dd, J = 3.6, 14.4 Hz, 1H), 2.71 (dd, J = 10.4, 14.8 Hz, 1H), 1.99-1.78 (m, 6H), 1.66-1.58 (m, 3H), 1.50-1.33 (m, 8H), 1.29-1.07 (m, 12H), 0.95 (d, J = 6.8 Hz, 3H), 0.72 (s, 3H)LC-ELSD/MS: purity >99%, analytic SFC: 100% de, MS ESI calcd. for C$_{26}$H$_{39}$F$_3$NOS [M + H]$^+$ 470.2, found 470.2. |

-continued

| Example | SM | Br | STRUCTURE | Analytical |
|---|---|---|---|---|
| 451 | B1 | 5-iodo-3-methyl-1,2-thiazole | 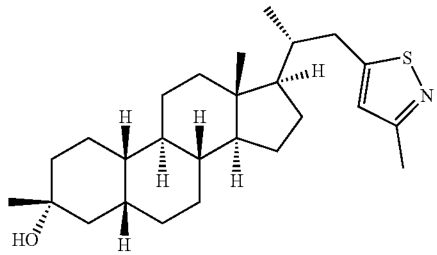 | $^1$H NMR (400 MHz, CDCl$_3$) $\delta_H$ 6.72 (s, 1H), 3.02-2.94 (m, 1H), 2.56 (dd, J = 9.4, 14.7 Hz, 1H), 2.45 (s, 3H), 2.00-1.63 (m, 8H), 1.49-1.32 (m, 8H), 1.26 (s, 5H), 1.19-1.02 (m, 7H), 0.93 (d, J = 6.8 Hz, 3H), 0.70 (s, 3H). LC-ELSD/MS: purity 99%, analytic SFC: 98.2% de; MS ESI calcd. for C$_{26}$H$_{42}$NOS [M + H]$^+$ 416.3, found 416.3. |
| 452 | | | 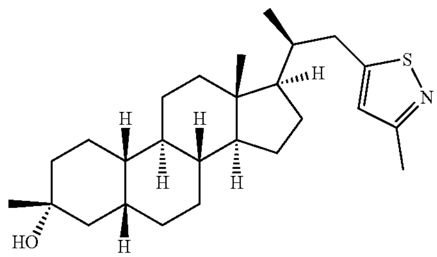 | LC-ELSD/MS: analytic SFC: 98.2% de; MS ESI calcd. for C$_{26}$H$_{42}$NOS [M + H]$^+$ 416.3, found 416.3. |
| 453 | 305.2 | 2-bromo-4-(trifluoro-methyl)-1,3-thiazole | 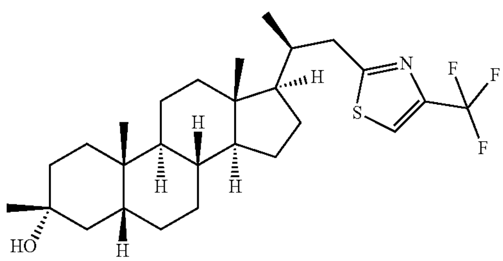 | $^1$H NMR (400 MHz, CDCl$_3$) $\delta_H$ 7.62 (s, 1H), 3.43-3.34 (m, 1H), 2.77-2.68 (m, 1H), 1.99-1.63 (m, 7H), 1.46-1.33 (m, 9H), 1.27-1.07 (m, 12H), 0.95 (s, 3H), 0.84 (d, J = 6.4 Hz, 3H), 0.76 (s, 3H). LC-ELSD/MS: purity 99%, analytic SFC: 94.3% de; MS ESI calcd. for C$_{27}$H$_{41}$F$_3$NOS [M + H]$^+$ 484.3, found 484.3. |
| 454 | | | 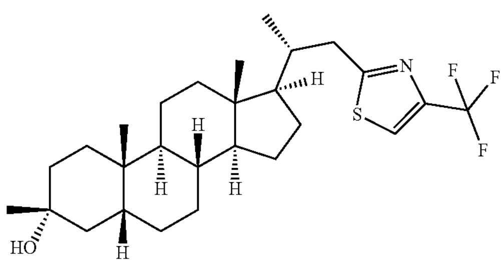 | $^1$H NMR (400 MHz, CDCl$_3$) $\delta_H$ 7.62 (s, 1H), 3.21-3.12 (m, 1H), 2.77-2.65 (m, 1H), 1.98-1.61 (m, 7H), 1.47-1.34 (m, 9H), 1.26-1.07 (m, 12H), 0.96-0.93 (m, 6H), 0.70 (s, 3H). LC-ELSD/MS: purity 99%, analytic SFC: 99.9% de; MS ESI calcd. for C$_{27}$H$_{41}$F$_3$NOS [M + H]$^+$ 484.3, found 484.3. |
| 455 | B1 | ethyl 2-chloro-oxazole-5-carboxy-late | 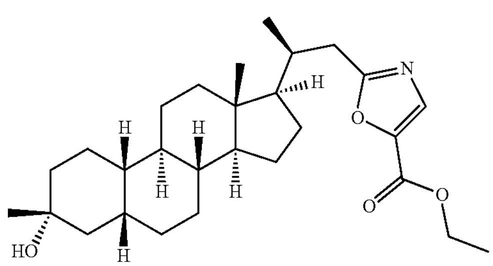 | $^1$H NMR (400 MHz, CDCl$_3$) $\delta_H$ 7.65 (s, 1H), 4.37 (q, J = 7.1 Hz, 2H), 3.17 (dd, J = 3.9, 14.7 Hz, 1H), 2.56 (dd, J = 10.5, 14.8 Hz, 1H), 2.05-1.76 (m, 8H), 1.56-1.30 (m, 8H), 1.30-1.15 (m, 8H), 1.11-0.98 (m, 7H), 0.84 (d, J = 6.5 Hz, 3H), 0.76 (s, 3H), 0.65 (s, 1H). LC-ELSD/MS purity 99%, MS ESI calcd. for C$_{28}$H$_{44}$NO$_4$ [M + H]$^+$ 458.3 found 458.3. SFC: 99% de. |
| 456 | | | 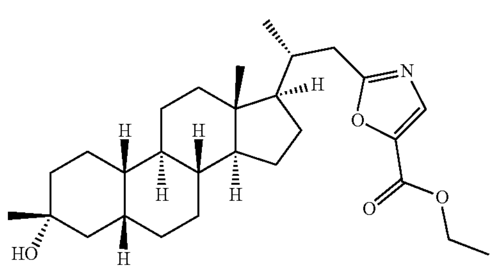 | $^1$H NMR (400 MHz, CDCl$_3$) $\delta_H$ 7.65 (s, 1H), 4.38 (q, J = 7.2 Hz, 2H), 2.93 (dd, J = 3.6, 14.7 Hz, 1H), 2.55 (dd, J = 9.8, 14.8 Hz, 1H), 2.17-1.74 (m, 6H), 1.62 (br d, J = 10.8 Hz, 2H), 1.49-1.25 (m, 17H), 1.21-0.99 (m, 7H), 0.95 (d, J = 6.8 Hz, 3H), 0.75-0.67 (m, 1H), 0.71 (s, 2H). LC-ELSD/MS purity 99%, MS ESI calcd. for C$_{28}$H$_{44}$NO$_4$ [M + H]$^+$ 458.3 found 458.3. |

-continued

| Example | SM | Br | STRUCTURE | Analytical |
|---|---|---|---|---|
| 457 | 323.1 | 4-bromo-benzo-nitrile | 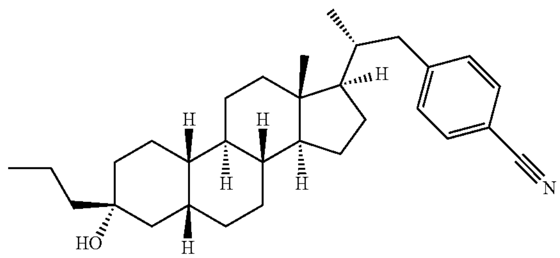 | $^1$H NMR (400 MHz, CDCl$_3$) $\delta_H$ 7.55 (d, J = 8.0 Hz, 2H), 7.23 (d, J = 8.0 Hz, 2H), 2.93 (dd, J = 3.2, 13.3 Hz, 1H), 2.18-2.11 (m, 1H), 2.03-1.93 (m, 2H), 1.82-1.60 (m, 7H), 1.58-1.43 (m, 6H), 1.39-1.27 (m, 8H), 1.20-1.00 (m, 7H), 0.93 (t, J = 7.2 Hz, 3H), 0.78 (d, J = 6.4 Hz, 3H), 0.69 (s, 3H). LC-ELSD/MS purity 99%, MS ESI calcd for C$_{31}$H$_{44}$N [M − H$_2$O + H]$^+$ 430.4, found 430.4. SFC 100% de. |
| 458 | | | 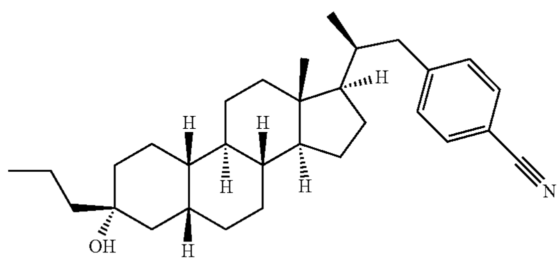 | LC-ELSD/MS MS ESI calcd for C$_{31}$H$_{44}$N [M − H$_2$O + H]$^+$ 430.4, found 430.4. SFC 100% de. |
| 459 | 323.1 | 4-bromo-3-methyl-benzo-nitrile | 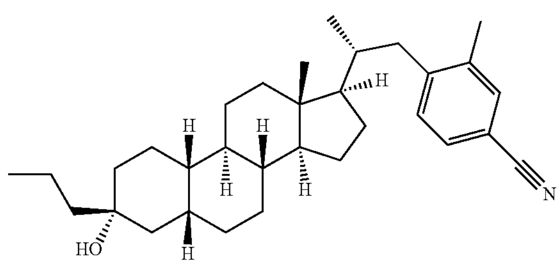 | $^1$H NMR (400 MHz, CDCl$_3$) $\delta_H$ 7.42-7.38 (m, 2H), 7.16 (d, J = 7.6 Hz, 1H), 2.91 (dd, J = 3.2, 13.4 Hz, 1H), 2.33 (s, 3H), 2.19-2.12 (m, 1H), 2.05-1.95 (m, 2H), 1.83-1.60 (m, 7H), 1.50-1.26 (m, 13H), 1.26-0.98 (m, 8H), 0.94 (t, J = 7.2 Hz, 3H), 0.77 (d, J = 6.4 Hz, 3H), 0.69 (s, 3H). LC-ELSD/MS purity 99%, MS ESI calcd for C$_{32}$H$_{46}$N [M − H$_2$O + H]$^+$ 444.4, found 444.4. SFC 100% de. |
| 460 | | | 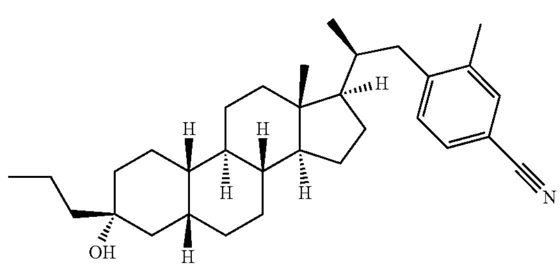 | $^1$H NMR (400 MHz, CDCl$_3$) $\delta_H$ 7.42-7.37 (m, 2H), 7.16 (d, J = 7.6 Hz, 1H), 3.10 (dd, J = 4.4, 13.6 Hz, 1H), 2.33 (s, 3H), 2.22 (dd, J = 11.2, 13.2 Hz, 1H), 2.03-1.97 (m, 1H), 1.87-1.60 (m, 8H), 1.52-1.44 (m, 3H), 1.41-1.19 (m, 13H), 1.13-1.02 (m, 5H), 0.94 (t, J = 7.2 Hz, 3H), 0.79 (s, 3H), 0.66 (d, J = 6.4 Hz, 3H). LC-ELSD/MS purity 99%, MS ESI calcd for C$_{32}$H$_{46}$N [M − H$_2$O + H]$^+$ 444.4, found 444.4. SFC 99% de. |

Examples 487 & 488: Synthesis of 4-(((S)-1-((3R,5R,8R,9R,10S,13S,14S,17S)-3-(ethoxymethyl)-3-hydroxy-13-methylhexadecahydro-1H-cyclopenta[a]phenanthren-17-yl)-2,2,2-trifluoroethyl)amino)-3-methylbenzonitrile (487) & 4-(((R)-1-((3R,5R,8R,9R,10S,13S,14S,17S)-3-(ethoxymethyl)-3-hydroxy-13-methylhexadecahydro-1H-cyclopenta[a]phenanthren-17-yl)-2,2,2-trifluoroethyl)amino)-3-methylbenzonitrile (488)

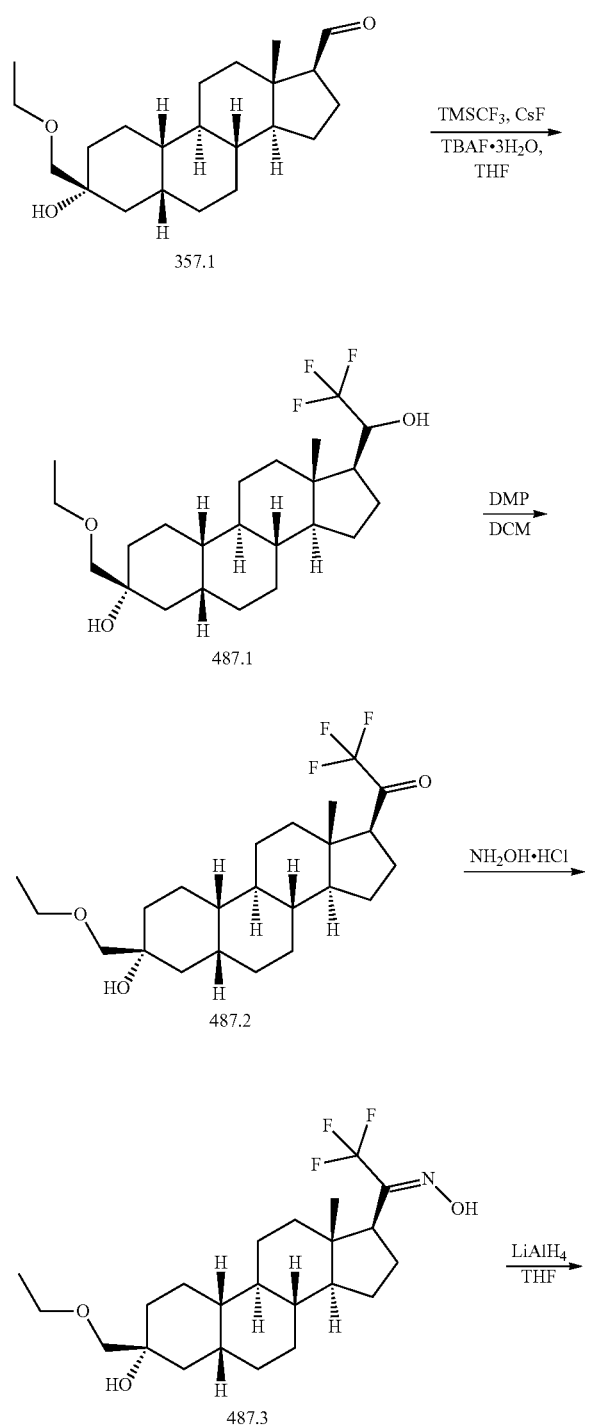

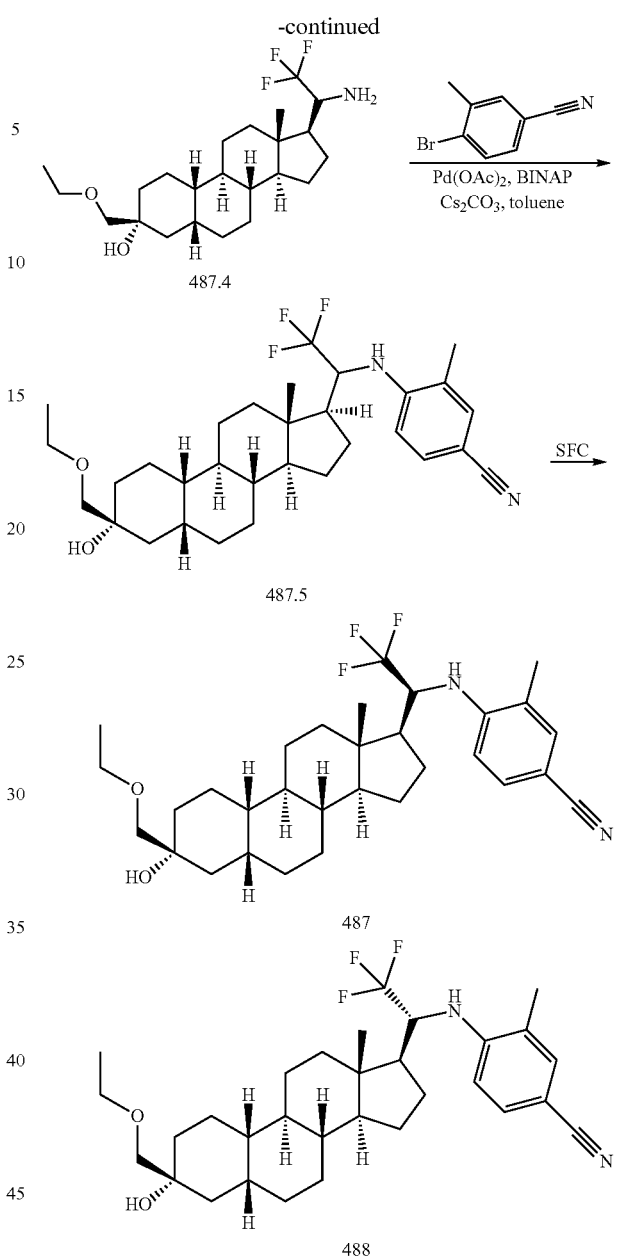

Synthesis of 487.1

To a solution of 357.1 (1.5 g, 4.30 mmol) in anhydrous THF (30 mL) was added CsF (1.62 g, 10.7 mmol) at 0° C., After stirring for 20 mins, TMSCF$_3$ (1.51 g, 10.7 mmol) was added at 0° C. After stirring for 1 h, TBAF·3H$_2$O (5.43 g, 17.2 mmol) was added. After stirring at 50° C. for another 1 h, the reaction mixture was poured into ice-water (50 mL), stirred for 10 mins. The and extracted with EtOAc (2×30 mL). The combined organic phase was washed with brine (2×20 mL), dried over anhydrous Na$_2$SO$_4$, filtered and concentrated in vacuum to give 487.1 (1.7 g) as a solid.

Synthesis of 487.2

To a solution of 487.1 (1.7 g, 4.06 mmol) in DCM (50 mL) was added DMP (4.28 g, 10.1 mmol) at 25° C. After stirring at 35° C. for 1 h, the reaction mixture was quenched with saturated NaHCO$_3$/Na$_2$S$_2$O$_3$ (50 mL/50 mL). The organic was separated and the aqueous was extracted with DCM (2×30 mL). The combined organic layer was washed with aqueous saturated NaHCO₃/Na₂S₂O₃ (50 mL/50 mL), brine (30 mL), dried over anhydrous Na₂SO₄, filtered and concentrated to give 487.2 (1.25 g) as a solid.

¹H NMR (400 MHz, CDCl₃) δ 3.55-3.48 (m, 2H), 3.48-3.30 (m, 2H), 3.30-2.90 (m, 1H), 2.72 (s, 1H), 2.20-2.05 (m, 1H), 1.90-1.50 (m, 8H), 1.50-1.25 (m, 10H), 1.25-0.85 (m, 7H), 0.72 (m, 3H). ¹⁹F NMR (376 MHz, CDCl₃) δ −78.68. LC-ELSD/MS 99%, MS ESI calcd. for C₂₃H₃₅F3O₃Na [M+Na]⁺ 439, found 439.

Synthesis of 487.3

To a solution of 487.2 (600 mg, 1.44 mmol) and CH₃CH₂ONa (234 mg, 3.45 mmol) in EtOH (10 mL) was added hydroxylamine hydrochloride (200 mg, 2.88 mmol) at 25° C. After stirring at 25° C. for 16 h, the mixture was diluted with water (100 mL) and extracted with EtOAc (3×100 mL). The combined organic solution was dried over anhydrous Na₂SO₄, filtered and concentrated to give 487.3 (0.58 g) as a solid.

¹H NMR (400 MHz, CDCl₃) δ$_H$ 3.56-3.49 (m, 2H), 3.47-3.35 (m, 3H), 2.62-2.57 (m, 2H), 2.19-2.08 (m, 2H), 1.85-1.32 (m, 9H), 1.26-1.15 (m, 7H), 1.12-0.75 (m, 8H), 0.65 (s, 3H).

Synthesis of 487.4

To a mixture of 487.3 (480 mg, 1.11 mmol) in THF (10 mL) was added LiAlH₄ (252 mg, 6.66 mmol) at 0° C. After stirred at reflux for 6 h, the mixture was diluted with water (100 mL) and NaOH (15%, 100 mL) and extracted with EtOAc (3×100 mL). The combined organic solution was dried over anhydrous Na₂SO₄, filtered and concentrated. The residue was purified by column chromatography on silica gel (PE:EtOAc=4:1) to give 487.4 (300 mg) as an oil.

¹H NMR (400 MHz, CDCl₃) δ$_H$ 3.56-3.48 (m, 2H), 3.47-3.37 (m, 2H), 3.26-3.17 (m, 1H), 2.90-2.47 (m, 1H), 1.86-1.55 (m, 11H), 1.49-1.33 (m, 6H), 1.28-1.23 (m, 2H), 1.20 (t, J=7.2 Hz, 4H), 1.15-1.09 (m, 2H), 1.06 (d, J=8.8 Hz, 3H), 0.90-0.80 (m, 1H), 0.72 (s, 3H). ¹⁹F NMR (376.5 MHz, CDCl₃) δ$_F$ −77.258.

Synthesis of 487.5

To a solution of 487.4 (150 mg, 0.359 mmol), 4-bromobenzonitrile (105 mg, 0.538 mmol), BINAP (44.6 mg, 0.0718 mmol) and Cs₂CO₃ (348 mg, 1.07 mmol) in toluene (6 mL) was added Pd(OAc)₂ (16.1 mg, 0.0718 mmol) at 25° C. under N₂. After stirring at 110° C. for 16 h, the resulting suspension was filtered through a pad of Celite and washed with EtOAc (3×20 mL). The filtrate was concentrated. The residue was purified by flash column (0~25% of EtOAc in PE) to give 487.5 (120 mg) as a solid.

¹H NMR (400 MHz, CDCl₃) δ$_H$ 7.43-7.40 (m, 1H), 7.34-7.32 (m, 1H), 6.66 (d, J=8.4 Hz, 1H), 4.03-3.93 (m, 1H), 3.92-3.86 (m, 1H), 3.52 (q, J=7.2 Hz, 2H), 3.41 (q, J=9.2 Hz, 2H), 2.73 (s, 1H), 2.17-2.15 (m, 3H), 1.98-1.89 (m, 1H), 1.81-1.72 (m, 6H), 1.66-1.58 (m, 3H), 1.51-1.45 (m, 1H), 1.43 (s, 3H), 1.36 (d, J=9.6 Hz, 4H), 1.20 (t, J=7.2 Hz, 4H), 1.17-0.87 (m, 5H), 0.63 (s, 3H). ¹⁹F NMR (376.5 MHz, CDCl₃) δ$_F$ −72.898.

Separation 487 & 488

487.5 (120 mg, 0.225 mmol) was separated by SFC (Column: DAICEL CHIRALPAK AD-H 250×30 mm I.D., 5 um; Condition: 0.1% NH₃H₂O ETOH; Gradient: from 35% to 35% of B; Flow rate: 50 mL/min; Column temperature: 40° C.) to afford 487 (56.3 mg, 47%, Peak 1, Rt=3.648 min) as a solid and 488 (10 mg, Peak 2, Rt=5.086 min) as an oil.

487: ¹H NMR (400 MHz, CDCl₃) δ$_H$ 7.44-7.39 (m, 1H), 7.35-7.31 (m, 1H), 6.68-6.63 (m, 1H), 4.04-3.94 (m, 1H), 3.92-3.85 (m, 1H), 3.57-3.48 (m, 2H), 3.46-3.36 (m, 2H), 2.72 (s, 1H), 2.15 (s, 3H), 2.01-1.88 (m, 1H), 1.81-1.57 (m, 10H), 1.50-1.33 (m, 6H), 1.31-1.23 (m, 2H), 1.20 (t, J=7.2 Hz, 4H), 1.16-0.90 (m, 4H), 0.63 (s, 3H). LC-ELSD/MS purity 99%, MS ESI calcd. for C₃₁H₄₂F3N₂O [M−H₂O+H]⁺ 415.3 found 415.3. SFC 100% de. ¹⁹F NMR (376.5 MHz, CDCl₃) δ$_F$ −72.900.

488: ¹H NMR (400 MHz, CDCl₃) δ$_H$ 7.46-7.41 (m, 1H), 7.35-7.31 (m, 1H), 6.69 (d, J=8.4 Hz, 1H), 4.14-4.01 (m, 2H), 3.56-3.49 (m, 2H), 3.46-3.38 (m, 2H), 2.71 (s, 1H), 2.17 (s, 3H), 1.96-1.87 (m, 2H), 1.84-1.74 (m, 5H), 1.73-1.66 (m, 1H), 1.64-1.57 (m, 3H), 1.50-1.35 (m, 6H), 1.20 (t, J=7.2 Hz, 8H), 1.07-0.96 (m, 2H), 0.52 (s, 3H). LC-ELSD/MS purity 99%, MS ESI calcd. for C₃₁H₄₂F₃N₂O [M−H₂O+H]⁺ 415.3 found 415.3. ¹⁹F NMR (376.5 MHz, CDCl₃) δ$_F$ −74.694.

Examples 489 & 490: Synthesis of 3-methyl-4-(((S)-2,2,2-trifluoro-1-((3R,5R,8R,9R,10S,13S,14S, 17S)-3-hydroxy-3,13-dimethylhexadecahydro-1H-cyclopenta[a]phenanthren-17-yl)ethyl)amino) benzonitrile (489) & 3-methyl-4-(((R)-2,2,2-trifluoro-1-((3R,5R,8R,9R,10S,13S,14S,17S)-3-hydroxy-3,13-dimethylhexadecahydro-1H-cyclopenta[a]phenanthren-17-yl)ethyl)amino) benzonitrile (490)

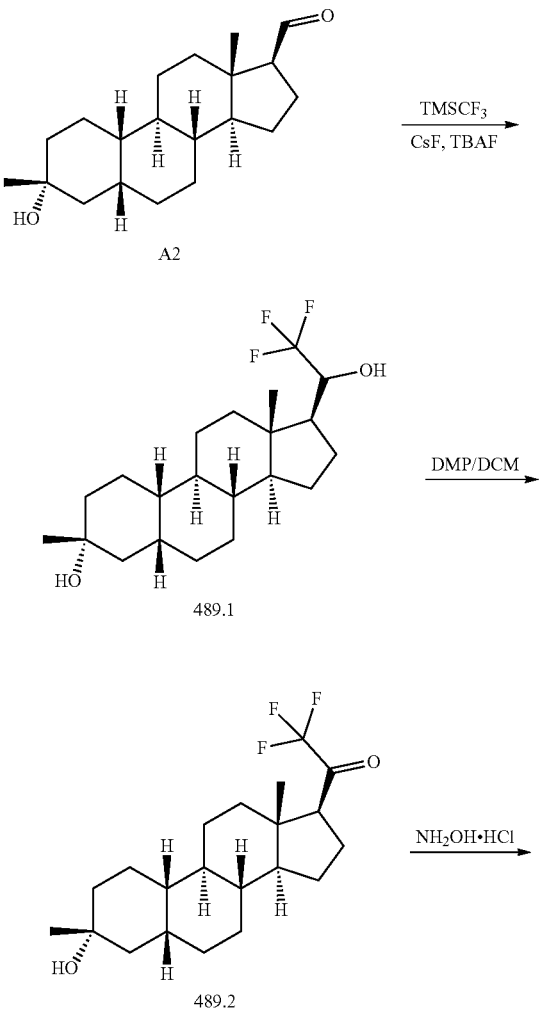

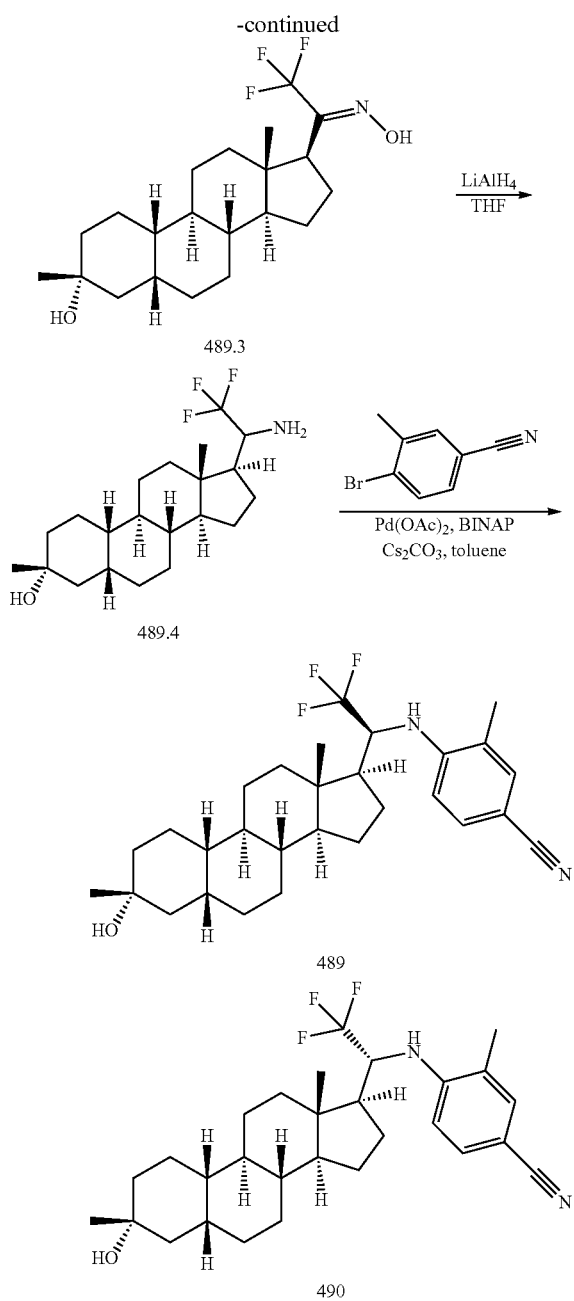

Synthesis of 489.1

To a solution of A2 (9.5 g, 31.2 mmol), CsF (4.73 g, 31.2 mmol) in THF (300 mL) was added TMSCF$_3$ (13.2 g, 93.5 mmol) at 0° C. under N$_2$. After stirring at 0° C. for 1 h, TBAF (40.7 g, 156 mmol) was added. After stirring at 20° C. for 16 h, the mixture was poured into water (50 mL) and concentrated to remove THF. The residue was extracted with EtOAc (2×400 mL). The combined organic phase was washed with brine (250 mL), dried over anhydrous Na$_2$SO$_4$, filtered and concentrated. The residue was purified by flash column (0%~9% of EtOAc in PE) to give 489.1 (4.0 g, 94%) as a solid.

$^1$H NMR (400 MHz, CDCl$_3$) $\delta_H$ 4.02 (br d, J=7.2 Hz, 1H), 2.09-1.83 (m, 4H), 1.78-1.65 (m, 8H), 1.51-1.34 (m, 8H), 1.26 (s, 3H), 1.14-0.92 (m, 6H), 0.73 (s, 3H).

Synthesis of 489.2

To a solution of 489.1 (500 mg, 1.33 mmol) in DCM (20 mL) at 0° C. was added DMP (1.40 g, 3.32 mmol). After stirring at 25° C. for 16 h, the mixture was poured into brine (15 mL) and extracted with EtOAc (30 mL×3). The combined organic phase was dried over anhydrous Na$_2$SO$_4$, filtered and concentrated. The residue was triturated from CH$_3$CN (20 mL) at 25° C. to give 489.2 (500 mg) as a solid.

$^1$H NMR (400 MHz, CDCl$_3$) $\delta_H$ 2.95 (s, 1H), 2.62-2.49 (m, 1H), 2.04 (s, 2H), 1.80 (m, 6H), 1.51-1.20 (m, 13H), 1.09 (br s, 4H), 0.88 (s, 1H), 0.75-0.68 (m, 3H).

Synthesis of 489.3

To a solution of 489.2 (1 g, 2.68 mmol) and EtONa (558 mg, 8.04 mmol) in EtOH (30 mL) was added hydroxylamine hydrochloride (372 mg, 5.36 mmol) at 25° C. After stirring at 40° C. for 24 h, the mixture was diluted with water (100 mL) and extracted with EtOAc (3×100 mL). The combined organic solution was dried over anhydrous Na$_2$SO$_4$, filtered and concentrated to give 489.3 (900 mg, 87%) as a solid.

$^1$H NMR (400 MHz, CDCl$_3$) $\delta_H$ 3.80-3.60 (m, 1H), 2.22-1.63 (m, 17H), 1.53-0.96 (m, 10H), 0.81-0.57 (m, 4H).

Synthesis of 489.4

To a mixture of 489.3 (900 mg, 2.32 mmol) in THF (10 mL) was added LiAlH$_4$ (527 mg, 13.9 mmol) at 25° C. After stirring at 80° C. for 6 h, the reaction was combined with another batch prepared from 300 mg of 489.3 to work-up. The mixture was diluted with water (20 mL) and EtOAc (50 mL). The mixture was then treated with NaOH (20 mL, 15%) and water (50 mL). The resulting mixture was filtered and concentrated. The residue was washed with HCl (20 mL, 1 M) and EtOAc (20 mL). The aqueous phase was adjusted with NaOH (30 mL, 2 M) to pH 13 and extracted with EtOAc (2×50 mL). The combined organic layer was concentrated. The residue was purified by flash column (0~15% of EtOAc in PE) to give 489.4 (240 mg, 30%) as a solid.

$^1$H NMR (400 MHz, CDCl$_3$) $\delta_H$ 3.94-3.81 (m, 1H), 3.29-3.00 (m, 1H), 2.23 (td, J=3.2, 12.4 Hz, 1H), 2.10 (td, J=3.2, 12.8 Hz, 1H), 1.90-1.75 (m, 10H), 1.68-1.58 (m, 8H), 1.44-1.37 (m, 8H), 1.10-1.04 (m, 8H), 0.78 (d, J=4.4 Hz, 4H), 0.73 (s, 2H).

Synthesis of 489 & 490

To a solution of 489.4 (180 mg, 0.482 mmol), 4-bromo-3-methylbenzonitrile (141 mg, 0.723 mmol), BINAP (59.9 mg, 0.0964 mmol) and (Cs$_2$CO$_3$ 469 mg, 1.44 mmol) in toluene (2 mL) was added Pd(OAc)$_2$ (21.6 mg, 0.09638 mmol) at 25° C. under N$_2$. After stirring at 110° C. for 16 h, the mixture was poured into water (20 mL) and extracted with EtOAc (2×50 mL). The combined organic phase was washed with brine (20 mL), dried over anhydrous Na$_2$SO$_4$, filtered and concentrated. The residue was purified by flash column (0~30% of EtOAc in PE) to give 490 (59 mg) and 489 (40 mg) both as solids. 489 (39.9 mg, 0.0816 mmol) was further purified by SFC (Column DAICEL CHIRALCEL OD-H (250 mm*30 mm, 5 um); Condition 0.1% NH$_3$H$_2$O ETOH; FlowRate (ml/min): 50) to give 489 (20.7 mg, 52.0%) as a solid. 490 (59 mg, 0.120 mmol) was further purified by SFC (Column DAICEL CHIRALCEL OJ-H (250 mm*30 mm, 5 um); Condition Neu-ETOH; FlowRate (ml/min) 60) to give 490 (19.7 mg, 33.6%) as a solid.

489: $^1$H NMR (400 MHz, CDCl$_3$) $\delta_H$ 7.42 (d, J=8.4 Hz, 1H), 7.33 (s, 1H), 6.66 (d, J=8.8 Hz, 1H), 4.06-3.94 (m, 1H), 3.88 (br d, J=9.6 Hz, 1H), 3.72 (br d, J=5.2 Hz, 1H), 2.15 (s, 3H), 1.94 (br s, 1H), 1.81-1.72 (m, 5H), 1.61 (br d, J=13.6 Hz, 3H), 1.51-1.34 (m, 6H), 1.32-1.18 (m, 9H), 1.13-0.90 (m, 3H), 0.63 (s, 3H). LC-ELSD/MS purity 99%, MS ESI calcd for C$_{29}$H$_{38}$F3N$_2$ [M−H$_2$O+H]$^+$ 471, found 471;

$C_{29}H_{40}F_3N_2O$ [M+H]$^+$ 489, found 489; $C_{29}H_{39}F_3N_2ONa$ [M+H]$^+$ 511, found 511. $^{19}F$ NMR (376.5 MHz, CDCl$_3$) $\delta_F$ −72.917.

490: $^1H$ NMR (400 MHz, CDCl$_3$) $\delta_H$ 7.49-7.38 (m, 1H), 7.33 (s, 1H), 6.69 (d, J=8.4 Hz, 1H), 4.18-4.00 (m, 2H), 2.17 (s, 3H), 1.98-1.74 (m, 7H), 1.73-1.58 (m, 3H), 1.51-1.29 (m, 8H), 1.26 (s, 4H), 1.23-0.94 (m, 6H), 0.52 (s, 3H). LC-ELSD/MS purity 99%, MS ESI calcd for $C_{29}H_{38}F_3N_2$ [M−H$_2$O+H]$^+$ 471, found 471; $C_{29}H_{40}F_3N_2O$ [M+H]$^+$ 489, found 489; $C_{29}H_{39}F_3N_2ONa$ [M+H]$^+$ 511, found 511. $^{19}F$ NMR (376.5 MHz, CDCl$_3$) $\delta_F$ −74.722.

Example 491: Synthesis of 5-(((R)-1-((3R,5R,8R,9R,10S,13S,14S,17S)-3-ethyl-3-hydroxy-13-methyl-hexadecahydro-1H-cyclopenta[a]phenanthren-17-yl)ethyl)amino)picolinonitrile (491)

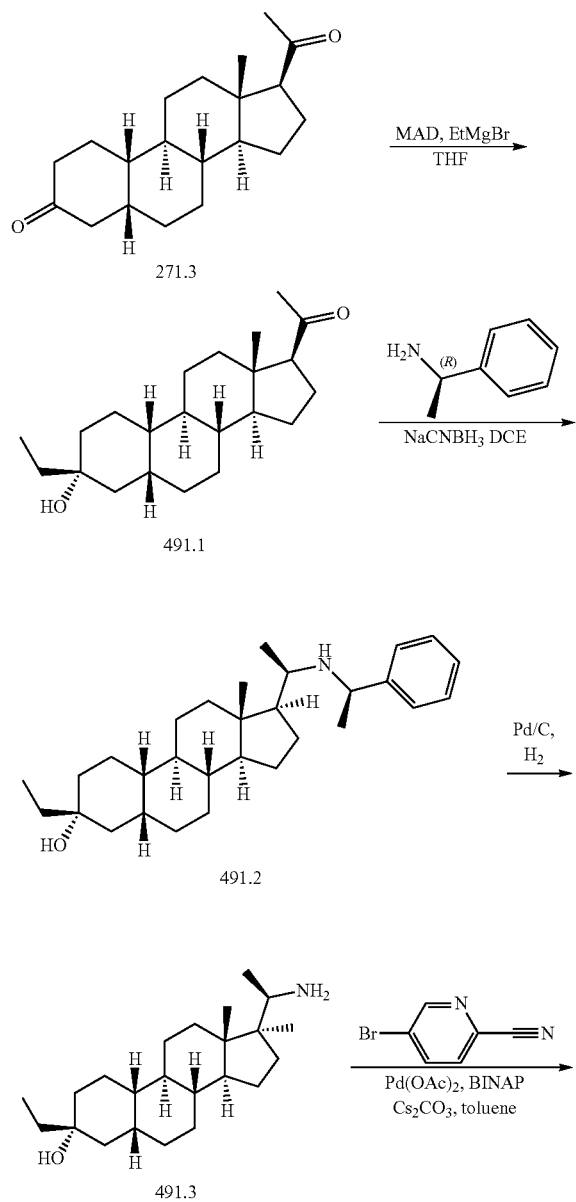

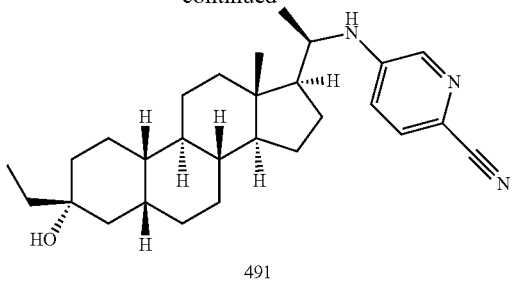

Synthesis of 491.1

To a solution of BHT (9.2 g, 41.7 mmol) in toluene (60 mL) under N$_2$ at 0° C. was added trimethylaluminum (2 M in toluene, 10.4 mL, 20.8 mmol) dropwise. After stirring at 25° C. for 1 h, a solution of 271.3 (2.1 g, 6.94 mmol) in toluene (10 mL) at −70° C. was added dropwise to the above solution. After stirring at −70° C. for 1 h under N$_2$, EtMgBr (6.93 mL, 20.8 mmol, 3 M in ethyl ether) was added dropwise at −70° C. After stirring at −70° C. for 1 h, the reaction mixture was poured into aqueous citric acid (30 mL, sat.) at 10° C. and extracted with DCM (2×30 mL). The combined organic layer was dried over anhydrous Na$_2$SO$_4$, filtered and concentrated. The residue was purified by flash column (0~30% of EtOAc in PE) to give 491.1 (1.76 g, 76%) as a solid.

$^1H$ NMR (400 MHz, CDCl$_3$) $\delta_H$ 2.58-2.55 (m, 1H), 2.19-2.15 (m, 4H), 2.13-2.00 (m, 1H), 1.78-1.60 (m, 10H), 1.59-1.51 (m, 8H), 1.50-1.25 (m, 3H), 1.24-1.00 (m, 3H), 0.91 (t, J=7.6, 3H), 0.63 (s, 3H).

Synthesis of 491.2

To a solution of 491.1 (1.76 g, 5.29 mmol) in DCE (15 mL) with (1R)-1-phenylethan-1-amine (3.84 g, 31.7 mmol) at 25° C. was added NaCNBH$_3$ (2.65 g, 42.3 mmol) at 25° C. After stirring at 50° C. for 16 h, the reaction mixture was quenched with water (15 mL) and extracted with DCM (2×15 mL). The combined organic phase was washed with brine (15 mL), dried over anhydrous Na$_2$SO$_4$, filtered, and concentrated. The residue was purified by flash column (0~30% of EtOAc in PE) to give 491.2 (2.54 g) as a solid, which was re-purified by flash column (0~30% of EtOAc in PE) to give 491.2 (2 g, 79%) as a solid.

$^1H$ NMR (400 MHz, CDCl$_3$) $\delta_H$ 7.27-7.15 (m, 5H), 4.08-4.01 (m, 1H), 4.00-3.60 (m, 1H), 2.45-2.43 (m, 1H), 2.42-2.17 (m, 1H), 2.00-1.98 (m, 2H), 1.97-1.96 (m, 2H), 1.95-1.75 (m, 2H), 1.75-1.48 (m, 6H), 1.47-1.18 (m, 13H), 1.17-0.96 (m, 6H), 0.95-0.81 (m, 4H), 0.80-0.70 (m, 3H).

Synthesis of 491.3

To a solution of 491.2 (1 g, 2.28 mmol) in EtOH (10 mL) was added dry Pd—C (800 mg, 10%) under N$_2$. The suspension was degassed under vacuum and purged with H$_2$ for three times. After stirring under H$_2$ (50 psi) at 50° C. for 48 h, the resulting suspension was filtered through a pad of Celite and washed with THF (3×40 mL). The filtrate was concentrated. The residue was purified by flash column (5~100% of EtOAc in PE) to give 491.3 (308 mg, 31%) as a solid.

$^1H$ NMR (400 MHz, CDCl$_3$) $\delta_H$ 3.75-3.70 (m, 1H), 2.05-2.04 (m, 1H), 1.76-1.72 (m, 1H), 1.71-1.51 (m, 8H), 1.50-1.21 (m, 12H), 1.20-1.00 (m, 10H), 0.88 (t, J$_1$=7.2, J$_2$=7.6, 3H), 0.75 (s, 3H).

Synthesis of 491

To a mixture of 491.3 (300 mg, 0.899 mmol), 5-bromopyridine-2-carbonitrile (327 mg, 1.79 mmol), BINAP (55.9 mg, 0.0897 mmol) and Cs$_2$CO$_3$ (583 mg, 1.79 mmol) in toluene (5 mL) was added Pd(OAc)$_2$ (20.1 mg, 0.0895 mmol) at 25° C. under N$_2$. After stirring at 120° C. for 18 h, the resulting suspension was diluted with water (10 mL) and extracted with EtOAc (2×10 mL). The combined organic layers was concentrated and purified twice by flash column (0~20% of EtOAc in PE) to give 491 (150 mg) as a solid, which was further purified by pre-HPLC(Column: Xtimate C18 150*25 mm*5 um), Condition: water (10 mM NH$_4$HCO$_3$)-ACN, Begin B: 65%, End B: 95%, Gradient Time (min): 9.5, 100% B Hold Time (min): 2, Flow Rate (ml/min): 25) to afford 491 (66.2 mg, 74%) as a solid.

$^1$H NMR (400 MHz, CDCl$_3$) δ$_H$ 7.94 (d, J=2.4, 1H), 7.44 (d, J=8.4, 1H), 6.77-6.73 (m, 1H), 4.15-4.00 (m, 1H), 3.50-3.83 (m, 1H), 1.95-1.80 (m, 2H), 1.79-1.52 (m, 8H), 1.51-1.20 (m, 12H), 1.18-0.91 (m, 8H), 0.88 (t, J=7.2, 3H), 0.62 (s, 3H). LC-ELSD/MS purity 99%; MS ESI calcd. for C$_{28}$H$_{42}$N$_3$O [M+H]$^+$ 436, found 436.

Example 492: Synthesis of 3-(((R)-1-((3R,5R,8R, 9R,10S,13S,14S,17S)-3-(ethoxymethyl)-3-hydroxy-13-methylhexadecahydro-1H-cyclopenta[a]phenanthren-17-yl)propyl)amino)benzonitrile (492)

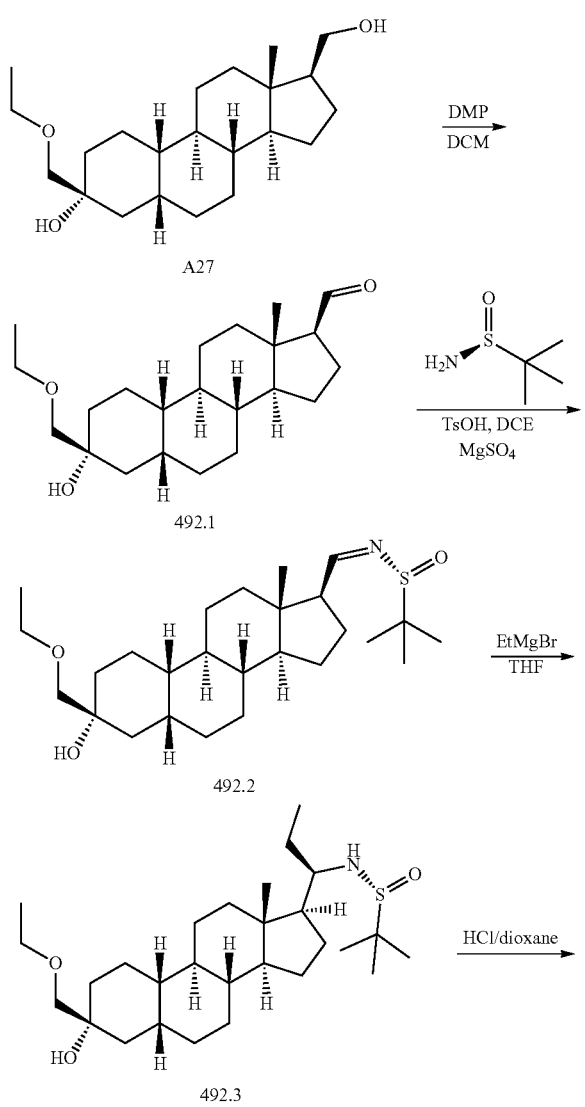

Synthesis of 492.1

To a solution of A27 (9, 25.6 mmol) in DCM (100 mL) was added PCC (11.0 g, 51.2 mmol) and silica gel (15 g) at 25° C. After stirring at 25° C. for 2 h, the reaction mixture was filtered and the residue was washed with DCM (2×100 mL). The combined filtrate was concentrated. The residue was purified by flash column (0~20% of EtOAc in PE) to give 492.1 (3.1 g, 35%) as a solid.

$^1$H NMR (400 MHz, CDCl$_3$) δ 9.72-9.66 (m, 1H), 3.50-3.42 (m, 2H), 3.42-3.30 (m, 2H), 2.30-2.20 (m, 1H), 2.15-1.80 (m, 4H), 1.80-1.50 (m, 2H), 1.50-1.25 (m, 8H), 1.25-1.00 (m, 12H), 0.90 (s, 1H), 0.75 (s, 3H).

Synthesis of 492.2

To a mixture of (R)-2-methylpropane-2-sulfinamide (2.07 g, 17.1 mmol), pyridinium toluene-4-sulfonate (179 mg, 0.715 mmol) and MgSO$_4$ (8.58 g, 71.5 mmol) in DCE (200 mL) was added 492.1 (5 g, 14.3 mmol) at 25° C. After stirring at 50° C. for 16 h, the mixture was poured into water (100 mL) and extracted with EtOAc (2×150 mL). The combined organic phase was washed with brine (100 mL), dried over anhydrous Na$_2$SO$_4$, filtered and concentrated. The residue was purified by flash column (0~10% of EtOAc in PE) to give 492.2 (2.54 g, 39%) as a solid.

$^1$H NMR (400 MHz, CDCl$_3$) δ$_H$ 8.03 (d, J=5.6 Hz, 1H), 3.53 (q, J=6.8 Hz, 2H), 3.42 (q, J=9.2 Hz, 2H), 2.55-2.45 (m, 1H), 2.05-1.50 (m, 14H), 1.50-1.20 (m, 9H), 1.20-0.95 (m, 13H), 0.74 (s, 3H).

Synthesis of 492.3

To a solution of 492.2 (700 mg, 1.54 mmol) in THF (10 mL) was added EtMgBr (1.53 mL, 3M, 4.62 mmol) at −78° C. under N$_2$. After stirring at −78° C. for 15 mins and warming to 25° C. for 30 mins, the reaction was quenched by saturated NH$_4$Cl aq. (30 mL) and extracted by EtOAc (3×20 mL). The combined organic phase was dried over Na$_2$SO$_4$ and concentrated to give 492.3 (703.7 mg). The product was used to next step directly. The stereochemistry at C$_{20}$ was assigned based on the mechanism of Ellman reaction.

Synthesis of 492.4

To a solution of 492.3 (703.7 mg, 1.45 mmol) in dioxane (7 mL) was added HCl/dioxane (1.08 mL, 4M, 0.165 mL) at 25° C. After stirring at 25° C. for 2 h, the reaction mixture was combined with another batch prepared from 106 mg of 492.3, poured into saturated NaHCO₃. The resulting mixture was extracted with DCM (3×20 mL). The combined organic phase was dried over anhydrous Na₂SO₄ and concentrated. The residue was purified by flash column (0~20% MeOH in DCM) to give 492.4 (302.6 mg) as an oil.

¹H NMR (400 MHz, CDCl₃) $\delta_H$ 3.52 (q, J=7.2 Hz, 2H), 3.41 (q, J=9.2 Hz, 2H), 2.76-2.65 (m, 1H), 2.25-1.50 (m, 13H), 1.50-1.10 (m, 14H), 1.10-0.85 (m, 8H), 0.67 (s, 3H).

Synthesis of 492

A mixture of 492.4 (100 mg, 0.WXR-36 mmol), 3-bromobenzonitrile (96.1 mg, 0.528 mmol), BINAP (49.2 mg, 0.079 mmol) and cesium carbonate (172 mg, 0.528 mmol) in toluene (1.5 mL) was sparged with N₂ for 2 mins, then Pd(OAc)₂ (17.7 mg, 0.079 mmol) was added at 25° C. After stirring at 110° C. for 16 h, the resulting suspension was combined with another batch prepared from 30 mg of 492.4, filtered through a pad of Celite and washed with EtOAc (3×10 mL). The filtrate was concentrated. The residue was purified by flash column (0~20% of EtOAc in PE) to give 492 (40 mg) as an oil. The 494 (40.0 mg, 0.835 mmol) was further purified by HPLC (Column Xtimate C18 150*25 mm*5 um; Condition water (0.225% FA)-ACN Begin B 95 End B 100 Gradient Time (min) 7 100% B Hold Time (min) 1 FlowRate (ml/min) 25) to afford 492 (7.00 mg, 6%) as a solid.

¹H NMR (400 MHz, CDCl₃) $\delta_H$ 7.16 (br t, J=7.7 Hz, 1H), 6.85 (br d, J=7.4 Hz, 1H), 6.78-6.68 (m, 2H), 3.53 (q, J=6.9 Hz, 2H), 3.48-3.38 (m, 2H), 3.33 (br s, 1H), 1.97-1.61 (m, 9H), 1.50-1.30 (m, 11H), 1.30-0.96 (m, 11H), 0.86 (t, J=7.3 Hz, 3H), 0.72 (s, 3H). LC-ELSD/MS purity 99%, MS ESI calcd. for $C_{31}H_{47}N_2O_2$ [M+H]⁺ 479.3 found 479.3.

Example 493: Synthesis of 5-(((S)-1-((3R,5R,8R, 9R,10S,13S,14S,17S)-3-(ethoxymethyl)-3-hydroxy-13-methylhexadecahydro-1H-cyclopenta[a]phenanthren-17-yl)propyl)amino)picolinonitrile (493)

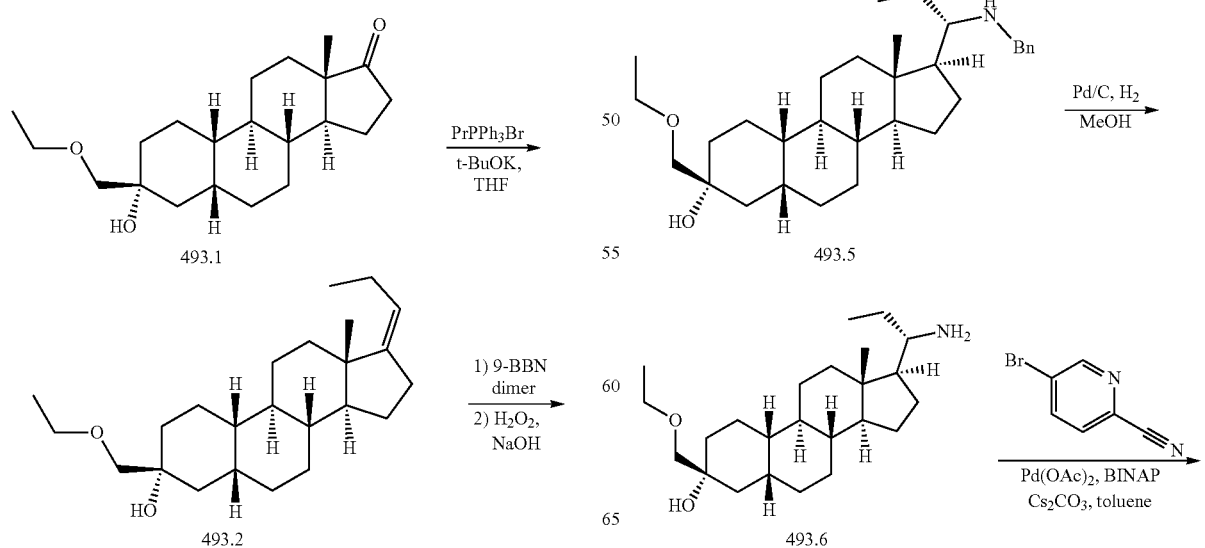

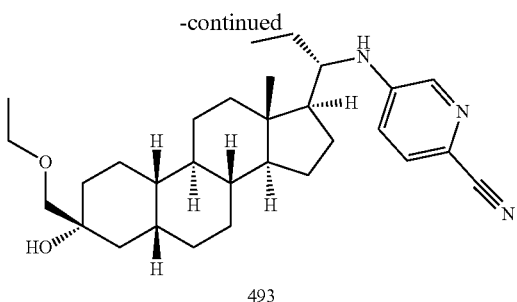

493

Synthesis of 493.2

To a mixture of bromotriphenylpropylphosphane (45.8 g, 119 mmol) in THF (200 mL) was added t-BuOK (13.3 g, 19 mmol) at 15° C. under $N_2$. After stirring at 50° C. for 6 h, 493.1 (10 g, 29.8 mmol) was added in portions at 50° C. After stirring at 50° C. for 16 h, the resulting suspension was quenched with 10% $NH_4Cl$ aqueous (400 mL) at 15° C. and extracted with EtOAc (300 mL). The combined organic phase was concentrated. The residue was purified by flash column (0~10% of EtOAc in PE) to give 493.2 (6 g, 56%) as an oil.

$^1$H NMR (400 MHz, $CDCl_3$) $\delta_H$ 5.01 (t, J=7.2 Hz, 1H), 3.61-3.35 (m, 4H), 2.68 (s, 1H), 2.44-2.28 (m, 1H), 2.26-1.96 (m, 4H), 1.88-1.67 (m, 5H), 1.51-1.41 (m, 4H), 1.30-1.03 (m, 12H), 0.99-0.89 (m, 4H), 0.88-0.84 (m, 4H).

Synthesis of 493.3

To a solution of 493.2 (6 g, 16.6 mmol) in THF (100 mL) was added 9-BBN dimmer (8.10 g, 33.2 mmol) at 15° C. After stirring at 60° C. for 6 h, the reaction mixture was cooled and sequentially treated with EtOH (20 mL) at 0° C. and NaOH (49.8 mL, 5M, 249 mmol). After addition, $H_2O_2$ (33.2 mL, 332 mmol, 10 M in water) was added slowly until the inner temperature did not increased any more and the inner temperature was maintained below 15° C. After stirring at 80° C. for another 2 h, the aqueous phase was extracted with ethyl acetate (3×100 mL). The combined organic phase was washed with saturated $Na_2S_2O_3$ (2×50 mL), brine (2×100 mL), dried over anhydrous $Na_2SO_4$, filtered and concentrated. The residue was purified by flash column (15% of ethyl acetate in PE) to give 493.3 (5 g, 80%) as a solid.

$^1$H NMR (400 MHz, $CDCl_3$) $\delta_H$ 3.59-3.36 (m, 5H), 2.72-2.66 (m, 1H), 1.90-1.70 (m, 5H), 1.67-1.52 (m, 7H), 1.49-1.30 (m, 8H), 1.28-1.02 (m, 10H), 0.99-0.90 (m, 3H), 0.67 (s, 3H).

Synthesis of 493.4

To a solution of 493.3 (4 g, 10.5 mmol) in DCM (100 mL) was added DMP (8.90 g, 21.0 mmol) at 15° C. After stirring at 45° C. for 30 mins, the resulting colourless solution was poured into $NaHCO_3$.aq (50 mL) and extracted with EtOAc (3×30 mL). The combined organic solution was washed with $Na_2S_2O_3$.aq (50 mL), brine (2×20 mL), dried over anhydrous $Na_2SO_4$, filtered and concentrated. The residue was purified by flash column (0~15% of EtOAc in PE) to give 493.4 (2.8 g, 71%) as an oil.

$^1$H NMR (400 MHz, $CDCl_3$) $\delta_H$ 3.59-3.34 (m, 4H), 2.52 (t, J=8.8 Hz, 1H), 2.43-2.32 (m, 2H), 2.21-2.10 (m, 1H), 1.94 (td, J=3.3, 12.3 Hz, 1H), 1.86-1.54 (m, 8H), 1.52-1.34 (m, 7H), 1.30-1.14 (m, 7H), 1.08-0.98 (m, 6H), 0.64-0.53 (m, 3H).

Synthesis of 493.5 & 493.5a

To a suspension 493.4 (3.2 g, 8.49 mmol) in toluene (50 mL) were added TsOH (73.0 mg, 0.4245 mmol), 1-phenyl-methanamine (4.54 g, 42.4 mmol), and $Ti(OCH(CH_3)_2)_4$ (12.0 g, 42.4 mmol). After stirring at 115° C. for 16 h, the reaction was concentrated. To the residue (4.1 g, 8.80 mmol) in MeOH (50 mL) was added $NaBH_4$ (563 mg, 17.5 mmol) at 15° C. After stirring at 15° C. for 16 h, the resulting colorless solution was poured into water (400 mL) and extracted with EtOAc (3×400 mL). The combined organic phase was washed with brine (2×200 mL), dried over anhydrous $Na_2SO_4$, filtered and concentrated. The residue was purified by flash column (0~35% of EtOAc in PE) to give 493.5 (0.45 g) as an oil and 493.5a (3.35 g) as an oil.

493.5: $^1$H NMR (400 MHz, $CDCl_3$) $\delta_H$ 7.39-7.30 (m, 4H), 7.25-7.20 (m, 1H), 3.83 (br d, J=11.2 Hz, 1H), 3.62 (br d, J=12.8 Hz, 1H), 3.53 (q, J=7.2 Hz, 2H), 3.46-3.38 (m, 2H), 2.79-2.52 (m, 2H), 1.96-1.72 (m, 6H), 1.70-1.56 (m, 7H), 1.46-1.30 (m, 8H), 1.20 (t, J=7.2 Hz, 5H), 1.06-0.97 (m, 4H), 0.93 (t, J=7.6 Hz, 3H), 0.69-0.62 (m, 3H).

494.5a: $^1$H NMR (400 MHz, $CDCl_3$) $\delta_H$ 7.36-7.31 (m, 4H), 7.24-7.18 (m, 1H), 3.82-3.77 (m, 1H), 3.60 (d, J=12.8 Hz, 1H), 3.57-3.49 (m, 2H), 3.46-3.37 (m, 2H), 2.77-2.65 (m, 1H), 2.65-2.57 (m, 1H), 2.12 (br d, J=12.4 Hz, 1H), 1.87-1.54 (m, 12H), 1.50-1.32 (m, 10H), 1.22-0.96 (m, 12H), 0.87 (t, J=7.6 Hz, 3H), 0.79 (s, 1H), 0.67 (s, 3H).

Synthesis of 493.6

To a solution of 493.5 (0.4 g, 0.855 mmol) in EtOH (10 mL) was added Pd/C (wet, 10%, 0.4 g) under $N_2$. The suspension was degassed under vacuum and purged with $H_2$ for three times. After stirring under $H_2$ (50 psi) at 25° C. for 12 h, the resulting suspension was filtered through a pad of Celite and washed with EtOH (3×15 mL). The filtrate was concentrated. The residue was purified by flash column (0~10% of MeOH in DCM) to give 493.6 (322 mg) as a solid, which was purified by flash column (0~10% of MeOH in DCM) to give 493.6 (96 mg) as an oil.

$^1$H NMR (400 MHz, $CDCl_3$) $\delta_H$ 3.52 (q, J=6.8 Hz, 2H), 3.42 (q, J=9.2 Hz, 2H), 2.73 (br s, 1H), 2.68-2.57 (m, 1H), 1.99-1.75 (m, 5H), 1.74 (br s, 2H), 1.60 (br dd, J=13.2, 17.2 Hz, 5H), 1.51-1.31 (m, 8H), 1.28-0.99 (m, 12H), 0.98-0.87 (m, 3H), 0.70-0.62 (m, 3H).

Synthesis of 493

To a solution of 5-bromopyridine-2-carbonitrile (139 mg, 0.762 mmol) in toluene (2 mL) were added 493.6 (96 mg, 0.254 mmol), $Cs_2CO_3$ (248 mg, 0.762 mmol) and BINAP (31.5 mg, 0.0508 mmol) under $N_2$. After stirring at 25° C. for 20 mins, Pd $(OAc)_2$ (11.4 mg, 0.0508 mmol) was added. After stirring at 110° C. for 16 h, the reaction was filtered and concentrated. The residue was purified by flash column (0~80% of EtOAc in PE) to give 493 (30 mg) as a solid, which was further purified by SFC (Column: DAICEL CHIRALCEL OD-H (250 mm*30 mm, 5 um); Condition: 0.1% $NH_3H_2O$ ETOH Begin B 35% End B 35%; FlowRate (ml/min): 60) to afford 493 (4.3 mg) as a solid.

$^1$H NMR (400 MHz, $CDCl_3$) $\delta_H$ 7.98 (d, J=2.8 Hz, 1H), 7.41 (d, J=8.8 Hz, 1H), 6.78 (dd, J=2.8, 8.5 Hz, 1H), 4.02 (br d, J=9.2 Hz, 1H), 3.53 (q, J=7.2 Hz, 2H), 3.42 (q, J=9.2 Hz, 3H), 2.72 (s, 1H), 1.93-1.73 (m, 6H), 1.71-1.60 (m, 3H), 1.52-1.29 (m, 10H), 1.28-1.11 (m, 8H), 1.07 (br s, 3H), 0.87 (t, J=7.3 Hz, 3H), 0.72 (s, 3H). LC-ELSD/MS purity 99%, MS ESI calcd for $C_{30}H_{44}N_3O$ [M−$H_2O$+H]$^+$ 462, found 471; $C_{30}H_{46}N_3O_2$ [M+H]$^+$ 480, found 480; $C_{30}H_{45}N_3O_2Na$ [M+Na]$^+$ 502, found 502.

563

Examples 494 & 495: Synthesis of 5-(((S)-1-((3R,5R,8R,9S,10S,13S,14S,17S)-3-(ethoxymethyl)-3-hydroxy-10,13-dimethylhexadecahydro-1H-cyclopenta[a]phenanthren-17-yl)propyl)amino)picolinonitrile (494) & 5-(((R)-1-((3R,5R,8R,9S,10S,13S,14S,17S)-3-(ethoxymethyl)-3-hydroxy-10,13-dimethylhexadecahydro-1H-cyclopenta[a]phenanthren-17-yl)propyl)amino)picolinonitrile (495)

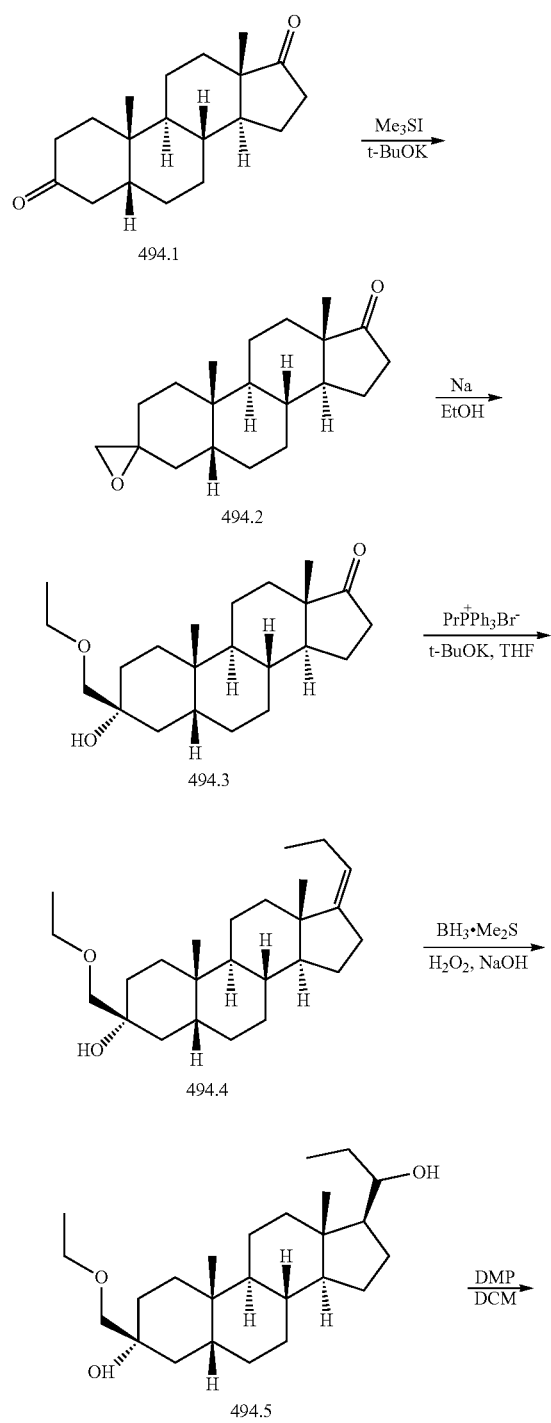

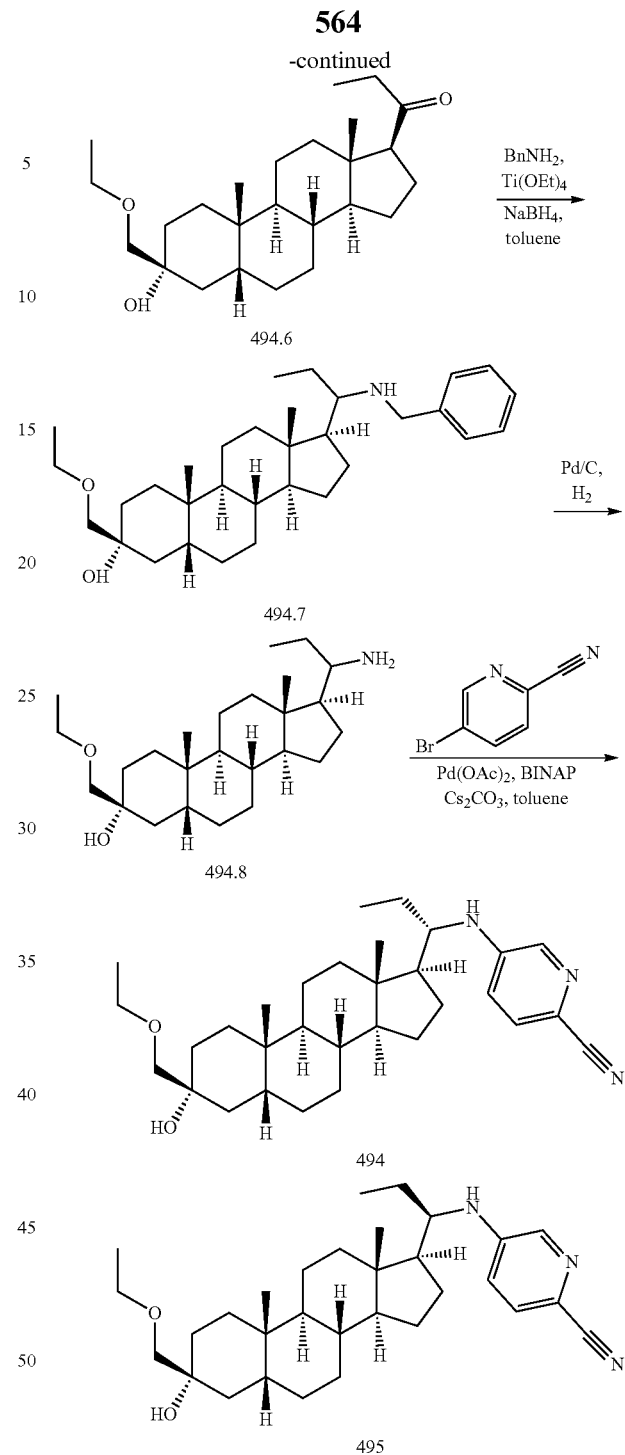

Synthesis of 492.2

To a solution of NaH (4.95 g, 60%, 124 mmol) in DMSO (100 mL) and THF (100 mL) was added iodotrimethylsulfane (25.3 g, 124 mmol) at 0° C. over 30 mins under $N_2$, then a solution of 494.1 (30 g, 104 mmol) in DMSO (100 mL) was added. After stirring at 25° C. for another 3 h, the resulting suspension was poured into ice-water (500 mL), stirred for 20 mins, and extracted with EtOAc (3×400 mL). The combined organic phase was washed with brine (2×300 mL), dried over anhydrous $Na_2SO_4$, filtered and concentrated to give 494.2 (28 g) as an oil.

Synthesis of 494.3

Add Na (23.6 g, 594 mmol) to EtOH (500 mL) in batches at 25° C. under N₂. After stirred at 25° C. for 30 mins, 494.2 (30 g, 99.1 mmol) was added at 25° C. After stirring at 65° C. 16 h, the resulting solution was poured into water (500 mL) and extracted with EtOAc (3×400 mL). The combined organic phase was washed with brine (2×200 mL), dried over anhydrous Na₂SO₄, filtered and concentrated. The residue was purified by flash column (0~15% of EtOAc in PE) to give 494.3 (8.7 g, 25.2%) as an oil.

¹H NMR (400 MHz, CDCl₃) δ$_H$ 3.53 (q, J=6.9 Hz, 2H), 3.48-3.35 (m, 2H), 2.70 (s, 1H), 2.43 (br dd, J=8.8, 19.1 Hz, 1H), 2.09 (br d, J=9.3 Hz, 1H), 1.97-1.59 (m, 6H), 1.57-1.14 (m, 16H), 1.10-0.93 (m, 4H), 0.84 (s, 3H).

Synthesis of 494.4

To a suspension of [triphenyl(propyl)-k-phosphanyl]-λ-bromanide (16.5 g, 42.9 mmol) in THF (70 mL) was added t-BuOK (4.80 g, 42.9 mmol) at 25° C. under N₂. After stirring at 60° C. for 1 h, 494.3 (5 g, 14.3 mmol) in THF (20 mL) was added. After stirring at 60° C. for 16 h, the resulting solution was quenched with NH₄Cl (100 mL) and extracted by EtOAc (3×40 mL). The combined organic phase was washed with brine (2×100 mL), dried over anhydrous Na₂SO₄, filtered and concentrated. The residue was purified by flash column (5% of EtOAc in PE) to give 494.4 (2.3 g) as a solid.

¹H NMR (400 MHz, CDCl₃) δ 5.00 (br t, J=7.4 Hz, 1H), 3.53 (q, J=6.9 Hz, 2H), 3.48-3.35 (m, 2H), 2.67 (s, 1H), 2.36 (br dd, J=8.8, 16.6 Hz, 1H), 2.24-2.01 (m, 4H), 1.98-1.60 (m, 5H), 1.53-1.27 (m, 9H), 1.25-1.10 (m, 7H), 0.96-0.89 (m, 7H), 0.84 (s, 3H).

Synthesis of 494.5

To a solution of 494.4 (2.2 g, 5.87 mmol) in THF (30 mL) was added BH₃/Me₂S (2.92 mL, 10 M, 29.3 mmol) dropwise at 25° C. under N₂. After stirring at 25° C. for 2 h, the mixture was cooled, quenched by EtOH (3.41 mL, 58.7 mmol, 0.79 g/mL) at 0° C. and dropwise with NaOH (11.7 mL, 5M, 58.7 mmol). After addition, H₂O₂ (11.7 mL, 10 M, 117 mmol) was added slowly until the inner temperature no longer rises and the inner temperature was maintained below 0° C. The mixture was poured into aqueous Na₂S₂O₃ (30 mL, sat.), stirred for 30 min and extracted with EtOAc (2×30 mL). The combined organic solution was washed with water (2×30 mL), dried over anhydrous Na₂SO₄, filtered and concentrated to give 494.5 (2.2 g) as oil.

Synthesis of 494.6

To a solution of 494.5 (2.20 g, 5.60 mmol) in DCM (50 mL) was added DMP (4.74 g, 11.2 mmol) at 25° C. After stirring at 25° C. for 1 h, the mixture was quenched with NaHCO₃ (50 mL) and Na₂S₂O₃ (50 mL, sat.) and extracted with DCM (2×50 mL). The combined organic phase was washed with NaHCO₃ (100 mL), Na₂S₂O₃ (100 mL, sat.) and brine (100 mL), dried over anhydrous Na₂SO₄, filtered and concentrated. The residue was purified by flash column (0~15% of EtOAc in PE) to give 494.6 (1.30 g, 60%) as an oil.

¹H NMR (400 MHz, CDCl₃) δ$_H$ 3.53 (q, J=6.5 Hz, 2H), 3.47-3.36 (m, 2H), 2.72 (s, 1H), 2.55-2.49 (m, 1H), 2.37 (q, J=7.1 Hz, 2H), 2.24-2.09 (m, 1H), 2.02-1.77 (m, 4H), 1.75-1.58 (m, 4H), 1.49-1.16 (m, 15H), 1.07-0.96 (m, 4H), 0.93 (s, 3H), 0.57 (s, 3H). LC-ELSD/MS purity 99%, MS ESI calcd. for C₂₅H₄₁O₂ [M−H₂O+H]⁺ 373.3 found 373.3.

Synthesis of 494.7

To a solution of 494.6 (800 mg, 2.04 mmol) in toluene (15 mL) were added TsOH (17.5 mg, 0.102 mmol), 1-phenylmethanamine (1.09 g, 10.2 mmol), and Ti(OCH₂CH₃)₄ (2.32 g, 10.2 mmol). After stirring at 110° C. for 16 h, MeOH (10 mL) and borane sodium hydride (627 mg, 16.6 mmol) were added in one portion at 25° C. After stirring at 25° C. for 16 h, the resulting solution was poured into water (50 mL) and filtered. The aqueous phase was extracted with EtOAc (3×40 mL). The combined organic phase was washed with brine (2×40 mL), dried over anhydrous Na₂SO₄, filtered and concentrated. The residue was purified by flash column (0~15% of EtOAc in PE) to give 494.7 (800 mg) as an oil.

Synthesis of 494.8

To a solution of 494.7 (800 mg, 1.66 mmol) in EtOH (50 mL) was added Pd/C (dry, 400 mg) under N₂. The suspension was degassed under vacuum and purged with H₂ for three times. After stirring under H₂ (50 psi) at 25° C. for 16 h, the resulting suspension was filtered through a pad of Celite and washed with THF (3×10 mL). The filtrate was concentrated to give 494.8 (480 mg) as an oil.

¹H NMR (400 MHz, CDCl₃) δ$_H$ 3.53 (q, J=6.9 Hz, 2H), 3.47-3.35 (m, 2H), 2.62 (br s, 1H), 2.12-1.64 (m, 8H), 1.64-1.31 (m, 13H), 1.30-1.16 (m, 9H), 1.15-0.84 (m, 7H), 0.72 (s, 3H).

Synthesis of 494 & 495

To a solution of 5-bromopyridine-2-carbonitrile (65.1 mg, 0.356 mmol) in toluene (2 mL) were added 494.8 (200 mg, 0.510 mmol), Cs₂CO₃ (498 mg, 1.52 mmol) and BINAP (62.7 mg, 0.101 mmol) under N₂. After stirring at 25° C. for 20 mins, Pd(OAc)₂ (22.6 mg, 0.101 mmol) was added. After stirring at 110° C. for 16 h, the reaction was filtered and concentrated. The residue was purified by flash column (0~30% of EtOAc in PE) to give 494 (30 mg) and 495 (50 mg, 19.9%) both as solids. 494 (30 mg, 0.0607 mmol) was further purified by SFC (Column DAICEL CHIRALCEL OJ-H (250 mm*30 mm, 5 um); Condition 0.1% NH₃H₂O ETOH Begin B 25%; End B 25% Gradient Time (min); 100% B Hold Time (min) FlowRate (ml/min) 60) to give 494 (5.4 mg, 2%) as a solid.

494: ¹H NMR (400 MHz, CDCl₃) δ$_H$ 7.95 (d, J=2.8 Hz, 1H), 7.47 (d, J=8.5 Hz, 1H), 6.76 (dd, J=2.8, 8.8 Hz, 1H), 3.99 (br d, J=8.5 Hz, 1H), 3.52 (q, J=7.0 Hz, 2H), 3.46-3.34 (m, 2H), 3.30 (br d, J=8.3 Hz, 1H), 2.76 (s, 1H), 1.98-1.60 (m, 7H), 1.52-1.30 (m, 10H), 1.29-1.03 (m, 10H), 1.02-0.93 (m, 1H), 0.91 (s, 3H), 0.86 (t, J=7.4 Hz, 3H), 0.82 (s, 3H). LC-ELSD/MS purity 99%, MS ESI calcd. for C₃₁H₄₆N₃O [M−H₂O+H]⁺ 476.3 found 476.3.

495: ¹H NMR (400 MHz, CDCl₃) δ$_H$ 7.95 (d, J=2.8 Hz, 1H), 7.42 (d, J=8.8 Hz, 1H), 6.76 (dd, J=2.9, 8.7 Hz, 1H), 3.98 (br d, J=9.3 Hz, 1H), 3.53 (q, J=7.0 Hz, 2H), 3.47-3.30 (m, 3H), 2.73 (s, 1H), 1.98-1.56 (m, 9H), 1.50-1.05 (m, 19H), 1.01-0.79 (m, 6H), 0.58 (s, 3H). LC-ELSD/MS purity 99%, MS ESI calcd. for C₃₁H₄₆N₃O [M−H2O+H]⁺ 476.3 found 476.3.

Example 496: Synthesis of 3-(((S)-1-((3R,5R,8R, 9R,10S,13S,14S,17S)-3-hydroxy-3-(methoxymethyl)-13-methylhexadecahydro-1H-cyclopenta[a]phenanthren-17-yl)propyl)amino)benzonitrile (496)

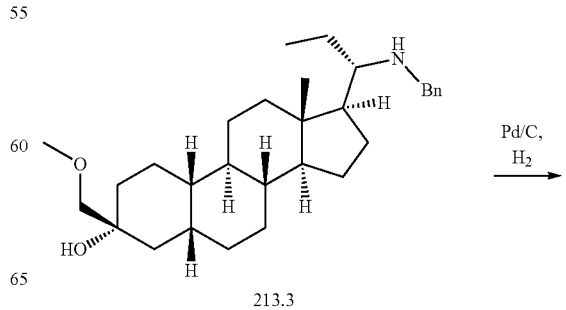

213.3

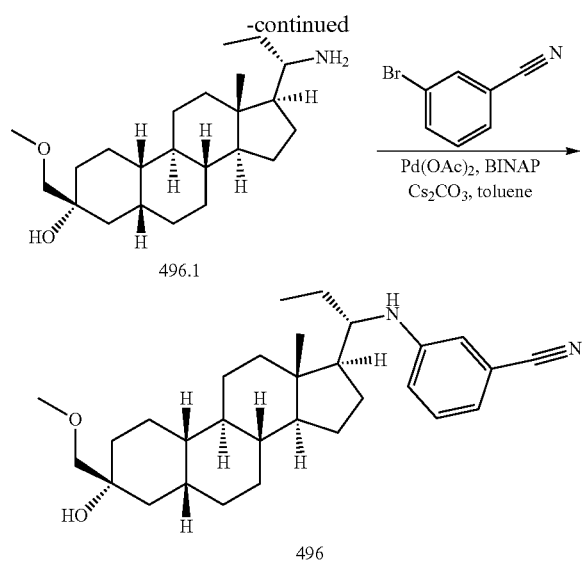

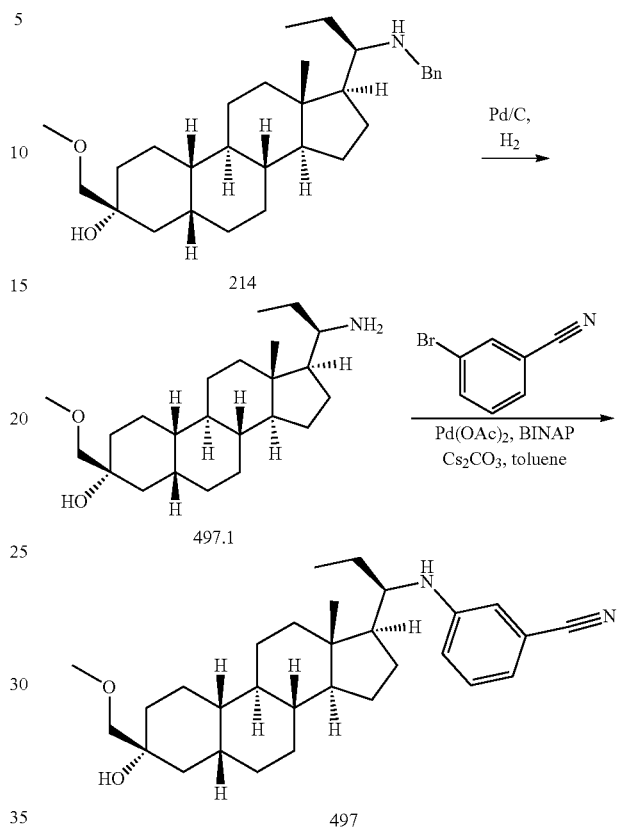

Example 497: Synthesis of 3-(((R)-1-((3R,5R,8R,9R,10S,13S,14S,17S)-3-hydroxy-3-(methoxymethyl)-13-methylhexadecahydro-1H-cyclopenta[a]phenanthren-17-yl)propyl)amino)benzonitrile (497)

To a solution of 213 (370 mg, 0.815 mmol) in EtOH (20 mL) was added Pd—C (dry, 200 mg) and one drop $NH_3H_2O$. After stirring under $H_2$ (50 psi) at 50° C. for 48 h, the resulting suspension was filtered through a pad of Celite and washed with EtOH (3×20 mL). The filtrate was concentrated to give 496.1 (300 mg) as an oil.

$^1$H NMR (400 MHz, $CDCl_3$) $\delta_H$ 3.42-3.36 (m, 5H), 2.35 (s, 1H), 2.10-1.51 (m, 12H), 1.50-1.20 (m, 11H), 1.20-0.93 (m, 8H), 0.87-0.64 (m, 4H).

Synthesis of 496

To a solution of 496.1 (200 mg, 0.55 mmol), 3-bromobenzonitrile (198 mg, 1.09 mmol), BINAP (34.2 mg, 0.055 mmol) and $Cs_2CO_3$ (355 mg, 1.09 mmol) in toluene (5 mL) was added $Pd(OAc)_2$ (12.3 mg, 0.055 mmol) under $N_2$. After stirring at 120° C. for 18 h, water (10 mL) was added to the resulting solution and extracted with EtOAc (3×20 mL). The combined organic phase was washed with water (3×20 mL), brine (50 mL), dried over anhydrous $Na_2SO_4$, filtered and concentrated. The residue was purified by column (10%~30% of EtOAc in PE) to give 496 (73 mg) as an oil, which was further purified by SFC (Column: DAICEL CHIRALCEL OD-H (250 mm*30 mm, 5 um), Condition: 0.1% $NH_3H_2O$ ETOH, Begin B: 30%, End B: 30%) to give 496 (33.8 mg) as a solid.

$^1$H NMR (400 MHz, $CDCl_3$) $\delta_H$ 7.26 (t, J=8 Hz, 1H), 6.88-6.86 (m, 1H), 6.70-6.67 (m, 2H), 3.59-3.57 (m, 1H), 3.41-3.34 (m, 5H), 3.28-3.22 (m, 1H), 2.58 (s, 1H), 1.93-1.50 (m, 12H), 1.50-1.10 (m, 12H), 1.10-0.96 (m, 2H), 0.86-0.82 (m, 6H). LC-ELSD/MS purity 99%, MS ESI calcd. for $C_{30}H_{45}N_2O_2$ [M+H]$^+$ 465 found 465.

To a solution of 214 (625 mg, 1.37 mmol) in EtOH (20 mL) was added Pd/C (dry, 200 mg) and one drop $NH_3H_2O$. After stirring under $H_2$ (50 psi) at 50° C. for 48 h, the resulting suspension was filtered through a pad of Celite and washed with EtOH (3×10 mL). The filtrate was concentrated to give 497.1 (520 mg) as oil.

$^1$H NMR (400 MHz, $CDCl_3$) $\delta_H$ 3.42-3.34 (m, 5H), 3.00-2.70 (m, 2H), 2.34 (s, 1H), 1.98-1.51 (m, 10H), 1.50-1.17 (m, 11H), 1.16-0.88 (m, 8H), 0.77-0.54 (m, 4H).

Synthesis of 497

To a solution of 497.1 (200 mg, 0.55 mmol), 3-bromobenzonitrile (198 mg, 1.09 mmol), BINAP (34.2 mg, 0.055 mmol) and $Cs_2CO_3$ (355 mg, 1.09 mmol) in toluene (5 mL) was added $Pd(OAc)_2$ (12.3 mg, 0.055 mmol) at 25° C. under $N_2$. After stirring at 120° C. for 18 h, the resulting solution was treated with water (10 mL) and extracted with EtOAc (3×10 mL). The combined organic phase was washed with water (3×20 mL), brine (50 mL), dried over anhydrous $Na_2SO_4$, filtered and concentrated. The residue was purified by flash column (10%~30% of EtOAc in PE) to 497 (100 mg) as an oil, which was further purified by SFC (Column: DAICEL CHIRALCEL OD-H (250 mm*30 mm, 5 um), Condition: 0.1% $NH_3H_2O$ ETOH, Begin B: 35%, End B: 35%) and then HPLC separation (column: Xtimate $C_{18}$ 150*40 mm*10 um, condition: water (0.225% FA)-ACN, Begin B: 93, End B: 97) to give 497 (26.2 mg, 48%) as a solid.

$^1$H NMR (400 MHz, $CDCl_3$) $\delta_H$ 7.16 (t, J=8 Hz, 1H), 6.85-6.83 (m, 1H), 6.72-6.67 (m, 2H), 3.62-3.59 (m, 1H), 3.41-3.31 (m, 6H), 2.61 (s, 1H), 1.89-1.51 (m, 10H), 1.50-1.25 (m, 9H), 1.21-0.81 (m, 10H), 0.60 (s, 3H). LC-ELSD/MS purity 99%, MS ESI calcd. for $C_{30}H_{45}N_2O_2$ [M+H]$^+$ 465 found 465.

Examples 498-501: Synthesis of 1-((R)-2-((3R,5R,8R,9R,10S,13S,14S,17R)-3-(ethoxymethyl)-3-hydroxy-13-methylhexadecahydro-1H-cyclopenta[a]phenanthren-17-yl)butyl)-1H-pyrazole-3-carbonitrile (498) & 1-((S)-2-((3R,5R,8R,9R,10S,13S,14S,17R)-3-(ethoxymethyl)-3-hydroxy-13-methylhexadecahydro-1H-cyclopenta[a]phenanthren-17-yl)butyl)-1H-pyrazole-3-carbonitrile (499) & 1-((R)-2-((3R,5R,8R,9R,10S,13S,14S,17R)-3-(ethoxymethyl)-3-hydroxy-13-methylhexadecahydro-1H-cyclopenta[a]phenanthren-17-yl)butyl)-1H-pyrazole-5-carbonitrile (500) & 1-((S)-2-((3R,5R,8R,9R,10S,13S,14S,17R)-3-(ethoxymethyl)-3-hydroxy-13-methylhexadecahydro-1H-cyclopenta[a]phenanthren-17-yl)butyl)-1H-pyrazole-5-carbonitrile (501)

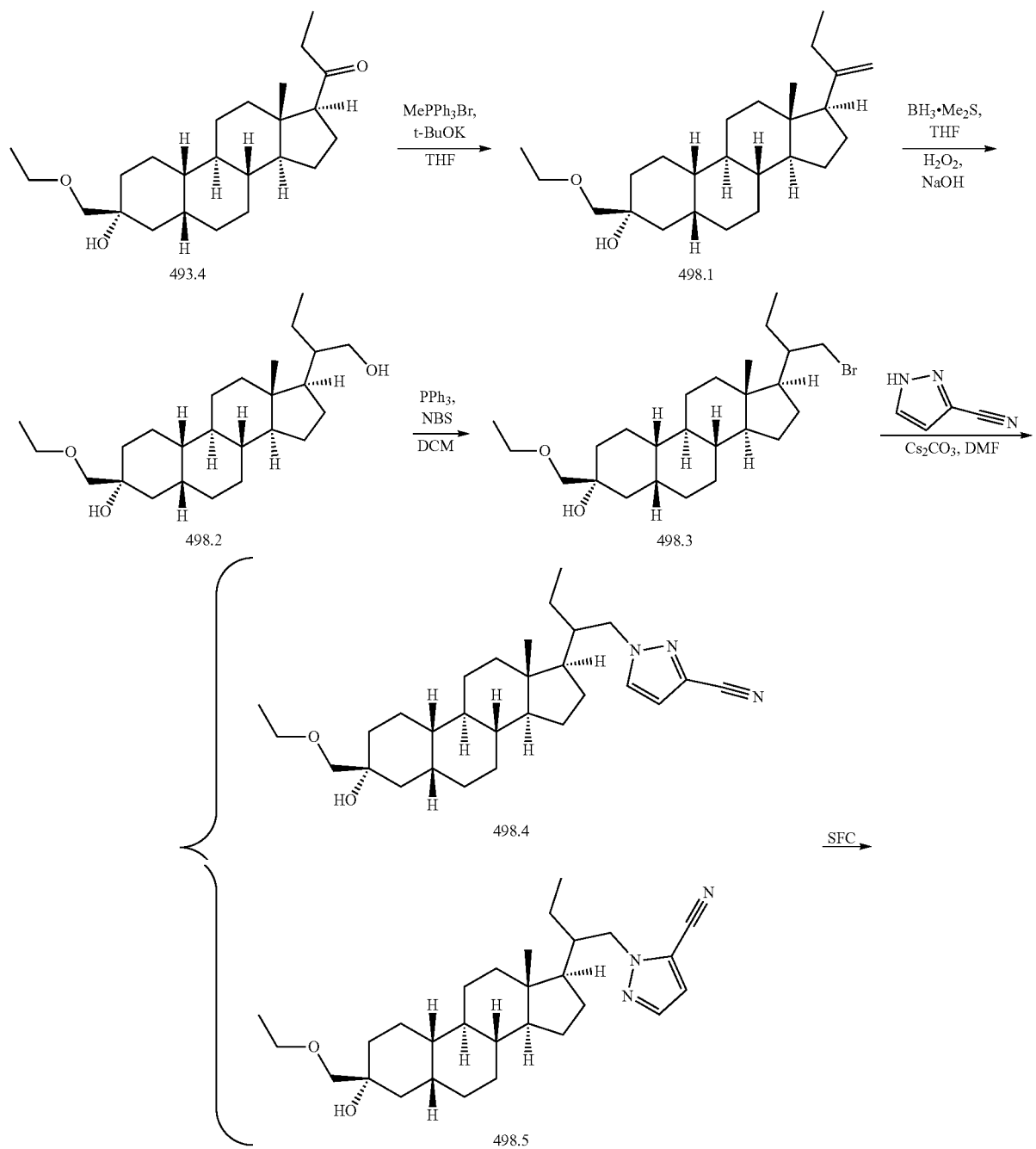

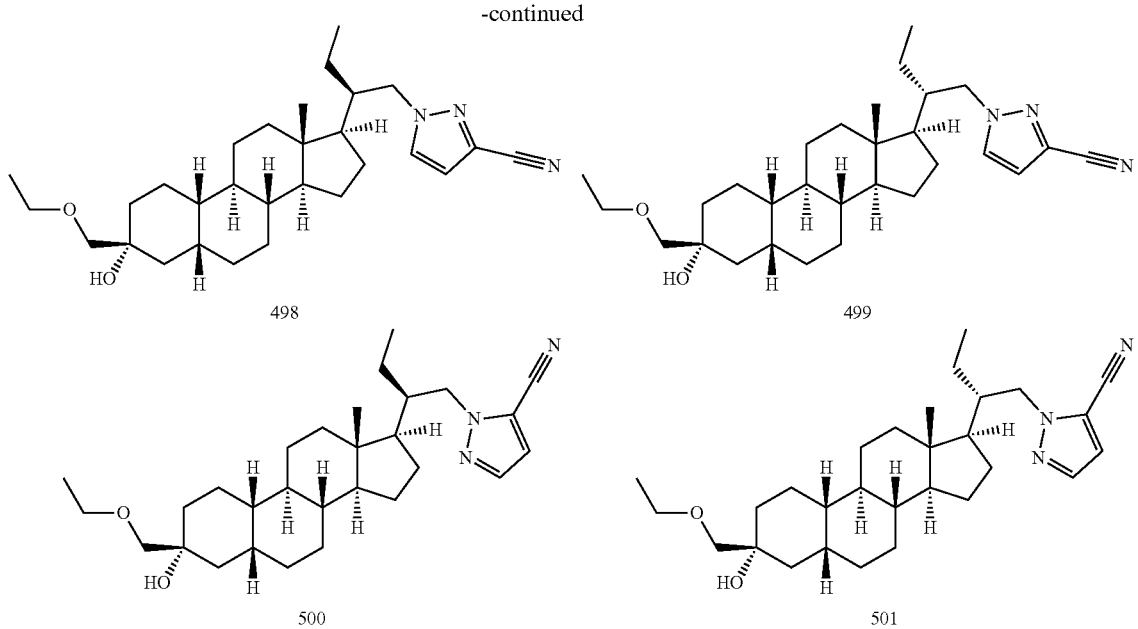

498 499 500 501

Synthesis of 498.1

To a mixture of MePPh₃Br (20 g, 56.2 mmol) in THF (80 mL) was added t-BuOK (6.30 g, 56.2 mmol) at 25° C. under N₂. After stirring at 50° C. for 30 min, 493.4 (8.5 g, 22.5 mmol) in THF (15 mL) was added in portions at 50° C. After stirring at 50° C. for 3 h, the reaction mixture was quenched with 10% NH₄Cl aqueous (200 mL) at 15° C. and extracted with EtOAc (2×200 mL). The combined organic phase was concentrated under vacuum. The residue was purified by flash column (0~10% of EtOAc in PE) twice to give 498.1 (8 g, 94.1%, with 6.6% of epimer at C3 by HNMR) as a solid.

$^1$H NMR (400 MHz, CDCl₃) δ$_H$ 4.87-4.82 (m, 1H), 4.75 (s, 1H), 4.11 (d, J=7.3 Hz, 1H), 3.55-3.37 (m, 4H), 2.11-1.97 (m, 4H), 1.84-1.55 (m, 8H), 1.49-1.32 (m, 6H), 1.27-1.09 (m, 9H), 1.07-0.97 (m, 5H), 0.55 (s, 3H).

Synthesis of 498.2

To a solution of 498.1 (8 g, 21.3 mmol) in THF (80 mL) was added BH₃Me₂S (6.39 mL, 10 M, 63.9 mmol) at 0° C. After stirring at 20° C. for 3 h, the reaction was sequentially treated with EtOH (15 mL) at 25° C., NaOH (42.6 mL, 5 M, 213 mmol) at 0° C. and H₂O₂ (27.6 mL, 276 mmol, 10 M) slowly. After stirring at 70° C. for 1 h, the reaction mixture was extracted with EtOAc (3×80 mL). The combined organic layer was washed with Na₂S₂O₃ (100 mL, sat.), brine (80 mL), dried over anhydrous Na₂SO₄, filtered and concentrated. The residue was purified by flash column (0~20% of EtOAc in PE) to give 498.2 (7.5 g) as a solid.

$^1$H NMR (400 MHz, CDCl₃) δ$_H$ 3.73-3.51 (m, 2H), 3.63-3.38 (m, 5H), 2.04 (s, 2H), 1.95-1.70 (m, 4H), 1.69-1.48 (m, 6H), 1.45-1.22 (m, 9H), 1.26-1.21 (m, 1H), 1.20 (t, J=7.0 Hz, 4H), 1.14-0.98 (m, 5H), 0.94-0.81 (m, 3H), 0.70-0.65 (m, 3H).

Synthesis of 498.3

To a solution of 498.2 (2 g, 5.09 mmol) in DCM (20 mL) were added PPh₃ (1.71 g, 6.51 mmol) and NBS (1.16 g, 6.51 mmol) at 0° C. After stirring at 25° C. for 2 h, the reaction was added to water (20 mL) and extracted with DCM (2×20 mL). The combined organic phase was washed with brine (20 mL), dried over anhydrous Na₂SO₄, filtered and concentrated. The residue was purified by flash column (0~10% of EtOAc in PE) to give 498.3 (1.5 g, 64.9%, with 7% of epimer at C₃ by HNMR) as oil.

$^1$H NMR (400 MHz, CDCl₃) δ$_H$ 3.53 (d, J=7.0 Hz, 3H), 3.42 (d, J=12.0 Hz, 2H), 1.84-1.70 (m, 5H), 1.67-1.46 (m, 9H), 1.45-1.31 (m, 7H), 1.30-1.08 (m, 7H), 0.98-0.78 (m, 7H), 0.70-0.65 (m, 3H).

Synthesis of 498.4 & 498.5

To a solution of 498.3 (1.3 g, 2.85 mmol) and Cs₂CO₃ (1.85 g, 5.70 mmol) in DMF (8 mL) was added 1H-pyrazole-3-carbonitrile (530 mg, 5.70 mmol) at 25° C. under N₂. After stirring at 80° C. for 16 h, the reaction was poured into water (10 mL) and extracted with EtOAc (3×10 mL). The combined organic phase was washed with brine (2×10 mL), dried over anhydrous Na₂SO₄, filtered and concentrated. The residue was purified by flash column (0~20% of EtOAc in PE) to give 498.4 (1 g, with 8% of epimer at C₃ by HNMR) and 498.5 (500 mg) both as a solid.

498.4: $^1$H NMR (400 MHz, CDCl₃) δ$_H$ 7.56 (s, 1H), 6.79-6.75 (m, 1H), 3.56-3.38 (m, 4H), 2.69 (s, 1H), 1.94-1.68 (m, 9H), 1.67-1.55 (m, 2H), 1.50-1.35 (m, 6H), 1.31-1.18 (m, 7H), 1.16-0.95 (m, 8H), 0.91-0.81 (m, 1H). LC-ELSD/MS purity 66.5%; MS ESI calcd. for C₂₉H₄₄N₃O [M+H−H₂O]⁺ 450, found 450.

498.5: $^1$H NMR (400 MHz, CDCl₃) δ$_H$ 7.69 (d, J=2.5 Hz, 2H), 7.43-7.40 (m, 1H), 6.75 (d, J=2.5 Hz, 2H), 6.66-6.63 (m, 1H), 4.38 (dd, J=4.8, 13.6 Hz, 1H), 4.20-4.08 (m, 1H), 4.11 (d, J=7.0 Hz, 2H), 3.96 (dd, J=10.4, 13.4 Hz, 1H), 3.57-3.40 (m, 4H), 1.91-1.70 (m, 5H), 1.67-1.54 (m, 3H), 1.48-1.32 (m, 8H), 1.15-1.00 (m, 7H), 0.85-0.73 (m, 6H), 0.70 (s, 1H). LC-ELSD/MS purity 33.5%; MS ESI calcd. for C₂₉H₄₄N₃O [M+H−H₂O]⁺ 450, found 450.

Separation of 498 & 499 & 500 & 501

498.4 (1 g, 2.13 mmol) was separated by SFC (Column: DAICEL CHIRALPAK AD (250 mm*30 mm, 10 um), Condition: 0.1% NH₃H₂O ETOH, Begin B: 40%, End B: 40%, FlowRate (ml/min): 70) to afford 498 (Rt=3.387 min, 580 mg, 38.9%) & 499 (Rt=2.535 min, 340 mg, 22.8%).

498.5 (500 mg, 1.07 mmol) was separated by SFC (Column: DAICEL CHIRALPAK AD (250 mm*30 mm, 10 um), Condition: 0.1% NH₃H₂O ETOH, Begin B: 40%, End B: 40%, FlowRate (ml/min): 70) to afford 500 (Rt=1.511 min, 150 mg, 10%) and 501 (Rt=2.635 min, 100 mg, 6.71%).

500 (150 mg, 0.320 mmol) was further purified by SFC (Column: DAICEL CHIRALPAK AS-H (250 mm*30 mm, 5 um), Condition: 0.1% NH₃H₂O ETOH, Begin B: 20%, End B: 20%, FlowRate (ml/min): 60) to afford 500 (97 mg, 65.1%) as a solid.

501 (100 mg, 0.213 mmol) was further purified by SFC (Column: DAICEL CHIRALPAK AD-H (250 mm*30 mm, 5 um), Condition: 0.1% NH₃H₂O ETOH, Begin B: 40%, End B: 40%, FlowRate (ml/min): 50) to afford 501 (38 mg, 38.0%) as a solid.

498: $^1$H NMR (400 MHz, CDCl₃) $\delta_H$ 7.42-7.38 (m, 1H), 7.26 (s, 1H), 6.66-6.63 (m, 1H), 4.38 (dd, J=4.8, 13.6 Hz, 1H), 3.95 (dd, J=10.7, 13.4 Hz, 1H), 3.56-3.38 (m, 4H), 2.71 (s, 1H), 2.13-2.04 (m, 1H), 1.87-1.70 (m, 5H), 1.68-1.55 (m, 2H), 1.49 (br s, 1H), 1.45-1.18 (m, 13H), 1.16-1.00 (m, 7H), 0.83-0.73 (m, 6H). LC-ELSD/MS purity 99%; MS ESI calcd. for $C_{27}H_{38}N_3$ [M+H−H₂O−EtOH]⁺ 404, found 404; $C_{29}H_{44}N_3O$ [M+H−H₂O]⁺ 450, found 450; $C_{29}H_{45}N_3O_2Na$ [M+Na]⁺ 490, found 490. analytic SFC 100% de 499: $^1$H NMR (400 MHz, CDCl₃) $\delta_H$ 7.40 (s, 1H), 7.26 (s, 1H), 6.65 (s, 1H), 4.22 (dd, J=4.1, 13.7 Hz, 1H), 3.98 (dd, J=9.8, 13.6 Hz, 1H), 3.56-3.38 (m, 3H), 3.46-3.36 (m, 1H), 2.69 (s, 1H), 2.01 (br s, 1H), 1.93-1.86 (m, 2H), 1.86-1.71 (m, 3H), 1.67-1.55 (m, 3H), 1.50-1.32 (m, 9H), 1.27-1.16 (m, 5H), 1.15-0.99 (m, 6H), 0.84 (t, J=7.4 Hz, 3H), 0.71 (s, 3H). LC-ELSD/MS purity 99%; MS ESI calcd. for $C_{29}H_{44}N_3O$ [M+H−H₂O]⁺ 450, found 450; $C_{29}H_{45}N_3O_2Na$ [M+Na]⁺ 490, found 490. analytic SFC 98% de 500: $^1$H NMR (400 MHz, CDCl₃) $\delta_H$ 7.56 (s, 1H), 6.78 (s, 1H), 4.46 (dd, J=5.2, 13.7 Hz, 1H), 4.15 (dd, J=10.9, 13.6 Hz, 1H), 3.53 (d, J=7.0 Hz, 2H), 3.42 (d, J=9.1 Hz, 2H), 2.70 (s, 1H), 2.18 (br s, 1H), 1.84 (br s, 3H), 1.75 (s, 2H), 1.68-1.59 (m, 5H), 1.48-1.30 (m, 7H), 1.21 (t, J=7.0 Hz, 5H), 1.16-0.96 (m, 7H), 0.86-0.78 (m, 6H). LC-ELSD/MS purity 99%; MS ESI calcd. for $C_{29}H_{44}N_3O$ [M+H−H₂O]⁺ 450, found 450; $C_{29}H_{45}N_3O_2Na$ [M+Na]⁺ 490, found 490. analytic SFC 100% de 501: $^1$H NMR (400 MHz, CDCl₃) $\delta_H$ 7.56 (s, 1H), 6.77 (s, 1H), 4.26 (d, J=4.1 Hz, 1H), 4.18 (d, J=10.6 Hz, 1H), 3.56-3.38 (m, 4H), 2.69 (s, 1H), 1.95-1.71 (m, 5H), 1.70-1.59 (m, 7H), 1.59-1.34 (m, 8H), 1.31-1.16 (m, 3H), 1.15-0.99 (m, 7H), 0.85 (t, J=7.4 Hz, 3H), 0.73 (s, 3H). LC-ELSD/MS purity 99%; MS ESI calcd. for $C_{29}H_{44}N_3O$ [M+H−H₂O]⁺ 450, found 450; $C_{29}H_{45}N_3O_2Na$ [M+Na]⁺ 490, found 490. analytic SFC 100% de The following examples were synthesized similar to Example 33 with the listed aryl halide and appropriate SM. In the case of diasteriomeric products, typically the diastereomeric isomers were separated by SFC (e.g. Column: DAICEL CHIRALPAK AS-H (250 mm*30 mm, 5 um), Condition: 0.1% NH₃H₂O EtOH, Begin B: 30%, End B 30%) or prep-HPLC (column: DuraShell 150*25 mm*5 um; Condition: water (10 mM NH₄HCO₃)-ACN; 75%-95% in 7 min. FlowRate: 25 mL/min) yielding both diastereomers after separation. The diastereomers were assigned based on 1H NMR of C21-Me.

| Example | SM | Aryl halide | STRUCTURE | Analytical |
|---|---|---|---|---|
| 502 | 77.2 | 1-(6-fluoropyridin-3-yl)-1H-pyrazole-3-carbonitrile | 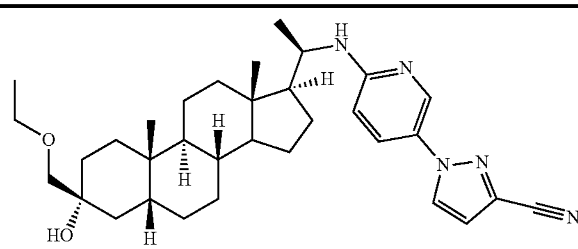 | $^1$H NMR (400 MHz, CDCl₃) $\delta_H$ 8.31 (d, J = 2.8 Hz, 1H), 7.78 (d, J = 2.5 Hz, 1H), 7.70 (dd, J = 2.8, 9.0 Hz, 1H), 6.83 (d, J = 2.5 Hz, 1H), 6.39 (d, J = 9.0 Hz, 1H), 4.51 (br d, J = 9.3 Hz, 1H), 3.81 (br s, 1H), 3.53 (q, J = 7.0 Hz, 2H), 3.46-3.35 (m, 2H), 2.74 (s, 1H), 2.01-1.77 (m, 4H), 1.65 (br s, 3H), 1.54-1.27 (m, 9H), 1.25-1.05 (m, 12H), 1.02-0.93 (m, 1H), 0.90 (s, 3H), 0.63 (s, 3H). LC-ELSD/MS purity 99%, MS ESI calcd. for $C_{33}H_{48}N_5O_2$ [M + H]⁺ 546.4 found 546.4. |
| 503 | 492.4 | 5-bromopyridine-2-carbonitrile | 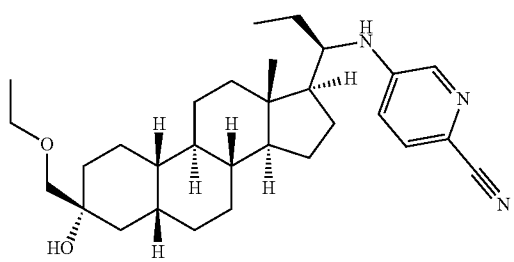 | $^1$H NMR (400 MHz, CDCl₃) $\delta_H$ 7.96 (d, J = 2.4 Hz, 1H), 7.42 (d, J = 8.4 Hz, 1H), 6.77 (dd, J = 2.8, 8.7 Hz, 1H), 3.99 (br d, J = 9.2 Hz, 1H), 3.52 (q, J = 6.8 Hz, 2H), 3.41 (q, J = 9.2 Hz, 3H), 1.88-1.72 (m, 6H), 1.69-1.60 (m, 3H), 1.50-1.29 (m, 10H), 1.27-1.10 (m, 8H), 1.09-0.91 (m, 3H), 0.86 (t, J = 7.2 Hz, 2H), 0.82-0.79 (m, 1H), 0.59 (s, 3H). LC-ELSD/MS purity 99%, MS ESI calcd for $C_{30}H_{44}N_3O$ [M − H₂O + H]⁺ 462, found 462; $C_{30}H_{46}N_3O_2$ [M + H]⁺ 480, found 480; |

-continued

| Example | SM | Aryl halide | STRUCTURE | Analytical |
|---|---|---|---|---|
| | | | | $C_{30}H_{45}N_3O_2Na[M + Na]^+$ 502, found 502. |
| 504 | 77.2 | 1-(6-bromopyridin-3-yl)-1H-pyrazole-4-carbonitrile | 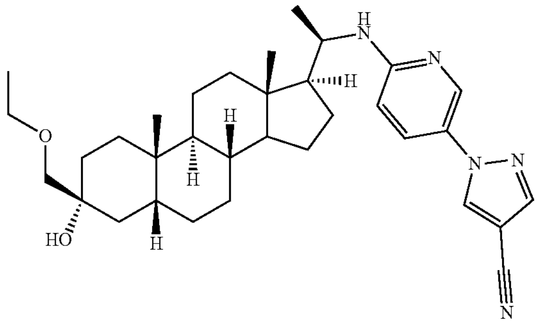 | $^1$H NMR (400 MHz, CDCl$_3$) δ$_H$ 8.29-8.28 (d, J = 4 Hz, 1H), 8.10 (s, 1H), 7.95 (s, 1H), 7.67-7.64 (m, 1H), 3.81 (s, 1H), 3.55-3.37 (m, 2H), 2.73 (s, 1H), 1.96-1.55 (m, 11H), 1.49-1.30 (m, 9H), 1.25-1.06 (m, 13H). 0.9 (s, 3H), 0.63 (s, 3H). LC-ELSD/MS purity 99%, MS ESI calcd. for $C_{33}H_{48}N_5O_2$ [M + H]$^+$ 546, found 546. |
| 505 | 489.4 | bromobenzene | 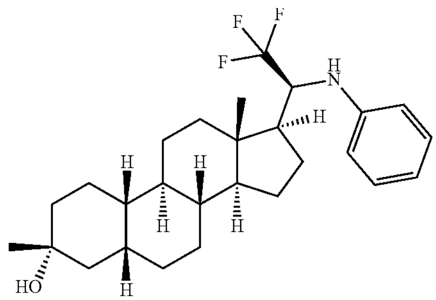 | $^1$H NMR (400 MHz, CDCl$_3$) δ$_H$ 7.19 (t, J = 4 Hz, 2H), 6.73 (t, J = 8 Hz, 1H), 6.60-5.58 (d, J = 8 Hz, 2H), 3.86-3.77 (m, 1H), 3.52 (d, J = 12 Hz, 1H), 1.99-1.94 (m, 1H), 1.84-1.56 (m, 9H), 1.48-1.25 (m, 13H), 1.19-0.92 (m, 5H), 0.62 (s, 3H). $^{19}$F NMR (400 MHz, CDCl$_3$) δ$_F$ −72.953. LC-ELSD/MS purity 99%, MS ESI calcd. for $C_{27}H_{39}F_3NO$ [M + H]$^+$ 450, found 450. |
| 506 | | | 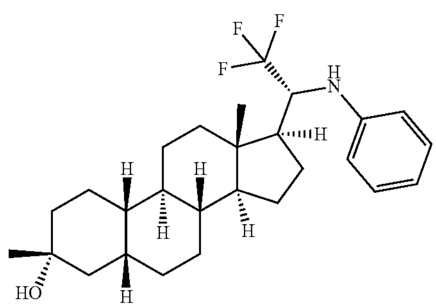 | $^1$H NMR (400 MHz, CDCl$_3$) δ$_H$ 7.19 (t, J = 8 Hz, 2H), 6.75 (t, J = 8 Hz, 1H), 6.64 (d, J = 8 Hz, 2H), 3.99-3.90 (m, 1H), 1.87-1.55 (m, 11H), 1.48-1.26 (m, 12H), 1.22-0.96 (m, 6H), 0.58 (s, 3H). $^{19}$F NMR (400 MHz, CDCl$_3$) δ$_F$ −74.740. LC-ELSD/MS purity 99%, MS ESI calcd. for $C_{27}H_{38}F_3NO$ [M + H]$^+$ 450, found 450. |

Example 507: Steroid Inhibition of TBPS Binding

[$^{35}$S]-t-Butylbicyclophosphorothionate (TBPS) binding assays using rat brain cortical membranes in the presence of 5 mM GABA has been described (Gee et al, *J. Pharmacol. Exp. Ther.* 1987, 241, 346-353; Hawkinson et al, *Mol. Pharmacol.* 1994, 46, 977-985; Lewin, A. H et al., *Mol. Pharmacol.* 1989, 35, 189-194).

Briefly, cortices are rapidly removed following decapitation of carbon dioxide-anesthetized Sprague-Dawley rats (200-250 g). The cortices are homogenized in 10 volumes of ice-cold 0.32 M sucrose using a glass/teflon homogenizer and centrifuged at 1500×g for 10 min at 4° C. The resultant supernatants are centrifuged at 10,000×g for 20 min at 4° C. to obtain the P2 pellets. The P2 pellets are resuspended in 200 mM NaCl/50 mM Na—K phosphate pH 7.4 buffer and centrifuged at 10,000×g for 10 min at 4° C. This washing procedure is repeated twice and the pellets are resuspended in 10 volumes of buffer. Aliquots (100 mL) of the membrane suspensions are incubated with 3 nM [$^3$S]-TBPS and 5 mL aliquots of test drug dissolved in dimethyl sulfoxide (DMSO) (final 0.5%) in the presence of 5 mM GABA. The incubation is brought to a final volume of 1.0 mL with buffer. Nonspecific binding is determined in the presence of 2 mM unlabeled TBPS and ranged from 15 to 25%. Following a 90 min incubation at room temp, the assays are terminated by filtration through glass fiber filters (Schleicher and Schuell No. 32) using a cell harvester (Brandel) and rinsed three times with ice-cold buffer. Filter bound radioactivity is measured by liquid scintillation spectrometry. Non-linear curve fitting of the overall data for each drug averaged for each concentration is done using Prism (GraphPad). The data are fit to a partial instead of a full inhibition model if the sum of squares is significantly lower by F-test. Similarly, the data are fit to a two component instead of a one component inhibition model if the sum of squares is significantly lower by F-test. The concentration of test compound producing 50% inhibition (IC$_{50}$) of specific binding and the maximal extent of inhibition (I$_{max}$) are determined for the individual experiments with the same model used for the overall data and then the means±SEM.s of the individual experiments are calculated. Picrotoxin serves as the positive control for these studies as it has been demonstrated to robustly inhibit TBPS binding.

Various compounds are or can be screened to determine their potential as modulators of [$^3$S]-TBPS binding in vitro. These assays are or can be performed in accordance with the above In Table 2 below, A indicates a TBPS $IC_{50}$ (μM)<0.1 μM, B indicates a TBPS $IC_{50}$ (μM) of 0.1 μM to <1 μM, C indicates a TBPS $IC_{50}$ (μM) of 1 μM to <10 μM, D indicates a TBPS $IC_{50}$ (μM) of ≥10 μM.

TABLE 2

| Example | $IC_{50}$ |
|---|---|
| 1 | C |
| 2 | B |
| 3 | A |
| 4 | B |
| 5 | A |
| 6 | C |
| 7 | C |
| 8 | A |
| 9 | B |
| 10 | B |
| 11 | B |
| 12 | A |
| 13 | A |
| 14 | B |
| 15 | A |
| 16 | A |
| 17 | C |
| 18 | A |
| 19 | C |
| 20 | B |
| 21 | C |
| 22 | A |
| 23 | C |
| 24 | A |
| 25 | A |
| 26 | C |
| 29 | B |
| 30 | C |
| 31 | B |
| 32 | C |
| 33 | A |
| 34 | A |
| 35 | A |
| 36 | A |
| 37 | A |
| 38 | B |
| 39 | C |
| 40 | A |
| 41 | B |
| 42 | B |
| 43 | B |
| 44 | A |
| 45 | A |
| 46 | A |
| 47 | A |
| 48 | A |
| 49 | A |
| 50 | A |
| 51 | A |
| 52 | A |
| 53 | B |
| 54 | B |
| 55 | A |
| 56 | B |
| 57 | B |
| 58 | C |
| 59 | B |
| 60 | B |
| 61 | A |
| 62 | A |
| 63 | A |
| 64 | A |
| 65 | A |
| 66 | A |
| 67 | A |
| 68 | A |
| 69 | A |

TABLE 2-continued

| Example | $IC_{50}$ |
|---|---|
| 70 | A |
| 71 | B |
| 72 | A |
| 73 | A |
| 74 | A |
| 75 | A |
| 76 | B |
| 77 | A |
| 78 | A |
| 87 | A |
| 88 | A |
| 90 | B |
| 91 | B |
| 92 | A |
| 100 | B |
| 101 | C |
| 102 | C |
| 103 | A |
| 103 | A |
| 104 | A |
| 105 | C |
| 106 | B |
| 107 | C |
| 108 | B |
| 109 | A |
| 110 | C |
| 111 | A |
| 112 | B |
| 113 | B |
| 114 | C |
| 115 | C |
| 116 | A |
| 117 | C |
| 118 | B |
| 119 | C |
| 120 | A |
| 121 | C |
| 122 | B |
| 123 | D |
| 124 | B |
| 125 | B |
| 126 | C |
| 127 | B |
| 128 | B |
| 129 | B |
| 130 | A |
| 131 | A |
| 132 | A |
| 133 | A |
| 134 | A |
| 135 | C |
| 150 | A |
| 151 | C |
| 152 | C |
| 153 | C |
| 154 | C |
| 155 | C |
| 156 | A |
| 157 | C |
| 158 | B |
| 159 | D |
| 160 | C |
| 161 | C |
| 162 | B |
| 163 | C |
| 164 | C |
| 201 | B |
| 202 | A |
| 203 | A |
| 204 | B |
| 205 | C |
| 206 | B |
| 207 | C |
| 208 | B |
| 209 | B |
| 210 | C |
| 211 | B |
| 212 | C |

TABLE 2-continued

| Example | IC$_{50}$ |
|---|---|
| 213 | C |
| 214 | C |
| 250 | A |
| 251 | B |
| 252 | A |
| 253 | C |
| 254 | A |
| 255 | C |
| 256 | A |
| 257 | B |
| 258 | B |
| 259 | A |
| 260 | A |
| 261 | B |
| 262 | A |
| 263 | A |
| 264 | B |
| 265 | B |
| 266 | B |
| 267 | A |
| 268 | A |
| 269 | A |
| 270 | A |
| 271 | A |
| 272 | A |
| 273 | A |
| 274 | B |
| 275 | A |
| 276 | A |
| 278 | A |
| 279 | A |
| 280 | A |
| 282 | B |
| 283 | B |
| 285 | A |
| 286 | A |
| 287 | A |
| 288 | A |
| 289 | A |
| 290 | A |
| 293 | A |
| 294 | A |
| 295 | A |
| 296 | A |
| 297 | A |
| 298 | A |
| 299 | A |
| 300 | A |
| 301 | A |
| 302 | A |
| 303 | A |
| 304 | A |
| 305 | A |
| 306 | A |
| 307 | A |
| 308 | A |
| 309 | A |
| 310 | B |
| 311 | A |
| 312 | A |
| 313 | A |
| 314 | B |
| 315 | A |
| 316 | A |
| 317 | A |
| 318 | A |
| 319 | A |
| 320 | A |
| 321 | A |
| 322 | A |
| 323 | A |
| 324 | A |
| 325 | A |
| 326 | A |
| 327 | B |
| 328 | B |
| 329 | D |
| 330 | D |

TABLE 2-continued

| Example | IC$_{50}$ |
|---|---|
| 331 | D |
| 332 | B |
| 333 | B |
| 334 | D |
| 335 | B |
| 336 | D |
| 337 | B |
| 338 | B |
| 339 | A |
| 340 | A |
| 341 | A |
| 342 | B |
| 343 | B |
| 344 | D |
| 345 | C |
| 346 | C |
| 347 | C |
| 348 | C |
| 349 | D |
| 350 | D |
| 351 | C |
| 352 | C |
| 353 | C |
| 354 | C |
| 355 | A |
| 356 | A |
| 357 | B |
| 358 | B |
| 359 | D |
| 360 | C |
| 362 | C |
| 363 | C |
| 364 | B |
| 365 | A |
| 400 | A |
| 401 | A |
| 402 | A |
| 403 | B |
| 404 | A |
| 405 | A |
| 406 | A |
| 407 | A |
| 410 | B |
| 411 | A |
| 412 | B |
| 413 | A |
| 414 | A |
| 415 | A |
| 416 | B |
| 417 | A |
| 418 | C |
| 420 | A |
| 421 | B |
| 422 | A |
| 423 | B |
| 424 | A |
| 425 | C |
| 426 | B |
| 427 | A |
| 428 | A |
| 429 | A |
| 430 | B |
| 431 | B |
| 432 | A |
| 433 | A |
| 434 | B |
| 435 | A |
| 436 | B |
| 437 | A |
| 438 | B |
| 439 | A |
| 440 | A |
| 441 | A |
| 442 | B |
| 443 | A |
| 444 | B |
| 445 | A |
| 446 | A |

TABLE 2-continued

| Example | IC$_{50}$ |
|---|---|
| 449 | A |
| 450 | B |
| 451 | B |
| 453 | A |
| 454 | B |
| 455 | A |
| 456 | B |
| 487 | B |
| 488 | C |
| 489 | C |
| 490 | B |
| 491 | B |
| 492 | C |
| 493 | C |
| 494 | B |
| 495 | B |
| 496 | B |
| 497 | B |
| 498 | B |
| 499 | A |
| 500 | C |
| 501 | B |
| 502 | B |
| 503 | B |
| 504 | B |
| 505 | B |

Example 508: α1β2γ2 and α4β3δ SyncroPatch Assay

The SyncroPatch 384PE (Nanion, Germany) automated patch clamp platform was used to obtain recordings from human embryonic kidney cells stably expressing human GABA$_A$ receptors composed of the α1β2γ2 and α4β3δ subunits. Cells were bathed in an extracellular solution containing: 140 mM NaCl, 4 mM KCl, 2 mM CaCl$_2$), 1 mM MgCl$_2$, 10 mM HEPES, 5 mM glucose and 0.1% DMSO. Solution was maintained at pH 7.4 with NaOH and 300 mOsm/L. Chips with multi-hole (4×) medium resistance (2-3 MΩ) are used for the recombinant cell line experiments. Once harvested, cells are stored in extracellular solution set to 10° C. in the cell hotel with a minimum shaking speed of 200 rpm before addition to the chip at the beginning of each experiment. Whole cell patch clamp recordings were made using an intracellular solution containing: 90 mM KCl, 50 mM KF, 1.5 mM MgCl$_2$, 11.1 mM EGTA and 10 mM HEPES, 2 mM NaATP, maintained at pH 7.2 with KOH. Currents are leak corrected (using P/2 leak correction protocol) and sampled at 5 kHz. Cells were clamped at −120 mV. After establishing a stable baseline, a submaximal concentration of GABA (3-5 µM for cells expressing α1β2γ2 and 10 µM for cells expressing α1β2γ2) was applied at a rate of 10 µl/second, immediately followed by application of GABA+ compound (10 µl/second) at a single concentration of compound per cell. Compounds were tested at six concentrations (0.029, 0.12, 0.47, 1.88, 7.5, and 30 µM) in n=8-12 cells per concentration. Compound effect was determined by dividing peak current amplitude after GABA+compound by peak current amplitude after GABA alone. EC$_{50}$ and E$_{max}$ values were determined from average values for each concentration.

In Table 3 below, for α1β2γ2 EC$_{50}$ and α4β3δ EC$_{50}$, A indicates an EC$_{50}$ (µM)<0.2 µM, B indicates an EC$_{50}$ (µM) of 0.2 µM to <1 µM, C indicates an EC$_{50}$ (µM) of ≥1 µM.

For α1β2γ2 E$_{max}$, A indicates an E$_{max}$ response <8, B indicates an E$_{max}$ response 8 to <10, C indicates an E$_{max}$ response ≥10. For α4β3δ E$_{max}$, A indicates an E$_{max}$ response <30, B indicates an E$_{max}$ response 30 to <45, C indicates an E$_{max}$ response ≥45.

TABLE 3

| Example | α1β2γ2 EC$_{50}$ | α1β2γ2 E$_{MAX}$ | α4β3δ EC$_{50}$ | α4β3δ E$_{MAX}$ |
|---|---|---|---|---|
| 41 | C | A | C | B |
| 53 | C | A | C | A |
| 61 | A | C | A | A |
| 65 | C | A | A | B |
| 72 | B | C | B | C |
| 132 | C | C | C | B |
| 263 | B | A | B | A |
| 270 | B | C | B | C |
| 272 | A | C | A | A |
| 276 | B | B | A | A |
| 278 | A | A | A | A |
| 280 | A | C | A | B |
| 286 | A | B | B | A |
| 287 | B | B | B | A |
| 293 | C | A | B | A |
| 294 | B | C | B | B |
| 299 | C |   | A | B |
| 303 | A | C | A | B |
| 311 | A | C | B | B |
| 320 | B | B | B | C |
| 323 | A | C | B | B |
| 332 | A | A | B | A |
| 339 | C | C | A | C |
| 341 | A | A | A | A |
| 357 | B | B | B | B |
| 358 | C | A | C | B |
| 365 | C | B | B | B |
| 401 | C | C | C | A |
| 405 | C | C | A | B |
| 406 | A | A | A | B |
| 407 | A | C | C | C |
| 413 | A | C | A | B |
| 420 | A | B | A | B |
| 430 | B | B | A | A |
| 436 | B | A | C | B |
| 438 | B | A | C | B |
| 439 | A | C | A | C |
| 443 | A | C | A | B |
| 453 | B | A | A | A |
| 499 | A | A | A | A |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed:

1. A compound of Formula (I-l):

or a pharmaceutically acceptable salt thereof, wherein
each of $R^{1a}$, $R^{1b}$, $R^{2a}$, $R^{2b}$, $R^{4a}$, $R^{4b}$, $R^{6a}$, $R^{6b}$, $R^{7a}$, $R^{7b}$, $R^{11a}$, $R^{11b}$, $R^{12a}$, and $R^{12b}$ is hydrogen;
$R^{3a}$ is ethyl, n-propyl, iso-propyl, n-butyl, iso-butyl, cyclopropyl, or cyclopropylmethyl;
$R^{18}$ is methyl;
$R^{19}$ is hydrogen, methyl, or ethyl;
$R^Y$ is methyl;
each $R^D$ is hydrogen;
q is 0, 1, 2, 3, 4, or 5; and
$R^{55a}$ and $R^{55b}$ join together with their intervening atoms to form wherein
p is 1, and
$R^a$ is —CN.

2. The compound or pharmaceutically acceptable salt of claim 1, wherein $R^{19}$ is methyl or hydrogen.

3. The compound or pharmaceutically acceptable salt of claim 2, wherein $R^{3a}$ is ethyl, n-propyl, iso-propyl, n-butyl, or iso-butyl.

4. The compound or pharmaceutically acceptable salt of claim 3, wherein $R^{3a}$ is ethyl, n-propyl, or n-butyl.

5. The compound or pharmaceutically acceptable salt of claim 4, wherein $R^{55a}$ and $R^{55b}$ join together with their intervening atoms to form 6. The compound or pharmaceutically acceptable salt of claim 1, wherein the compound of Formula (I-l) is a compound of Formula (I-m) or a compound of Formula (I-n):

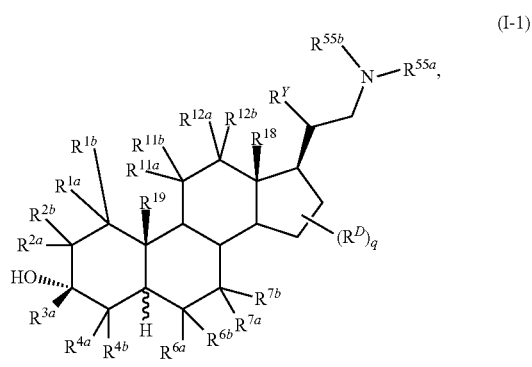

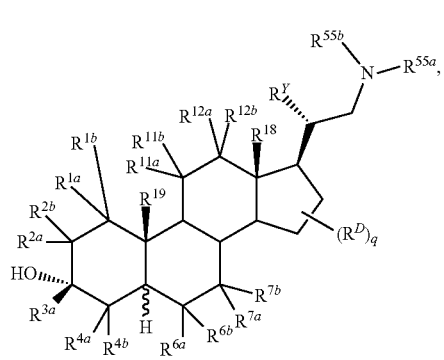

(I-n)

or a pharmaceutically acceptable salt thereof.

7. The compound or pharmaceutically acceptable salt of claim 6, wherein the compound of Formula (I-l) is a compound of Formula (I-m)

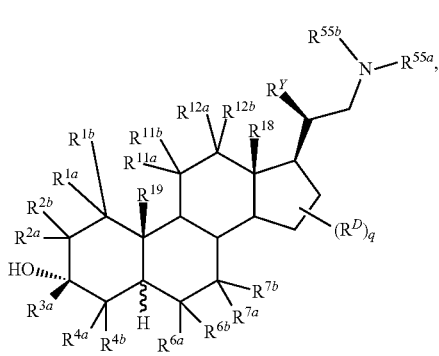

(I-m)

or a pharmaceutically acceptable salt thereof.

8. The compound or pharmaceutically acceptable salt of claim 7, wherein $R^{19}$ is methyl or hydrogen.

9. The compound or pharmaceutically acceptable salt of claim 7, wherein $R^{3a}$ is ethyl, n-propyl, iso-propyl, n-butyl, or iso-butyl.

10. The compound or pharmaceutically acceptable salt of claim 9, wherein $R^{3a}$ is ethyl, n-propyl, or n-butyl.

11. The compound or pharmaceutically acceptable salt of claim 7, wherein $R^{55a}$ and $R^{55b}$ join together with their intervening atoms to form

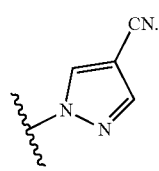 [SMILES: *n1cc(C#N)cn1]

12. The compound or pharmaceutically acceptable salt of claim 1, wherein the compound of Formula (I-l) is a compound of Formula (I-II):

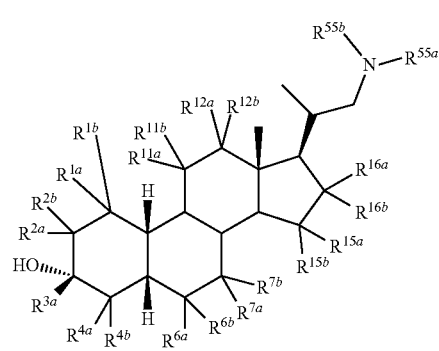

(I-II)

or a pharmaceutically acceptable salt thereof, wherein each of $R^{15a}$, $R^{15b}$, $R^{16a}$, and $R^{16b}$ is hydrogen.

13. The compound or pharmaceutically acceptable salt of claim 12, wherein $R^{3a}$ is ethyl, n-propyl, or n-butyl.

14. The compound or pharmaceutically acceptable salt of claim 13, wherein $R^{55a}$ and $R^{55b}$ join together with their intervening atoms to form

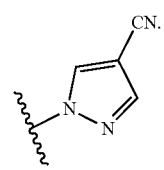

15. The compound or pharmaceutically acceptable salt of claim 12, wherein the compound of Formula (I-II) is a compound of Formula (I-Im) or a compound of Formula (I-In)

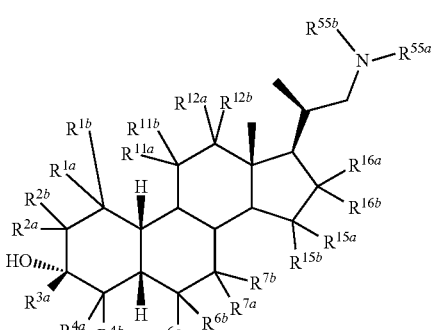

(I-Im)

or

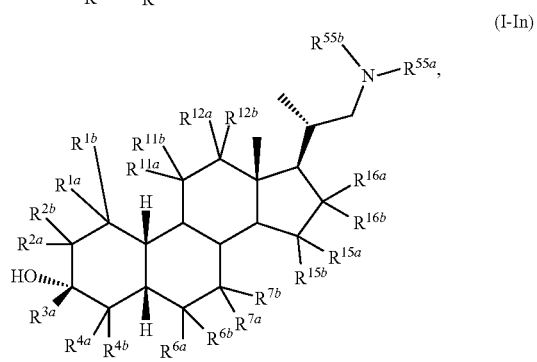

(I-In)

or a pharmaceutically acceptable salt thereof.

16. The compound or pharmaceutically acceptable salt of claim 15, wherein the compound of Formula (I-Il) is a compound of Formula (I-Im)

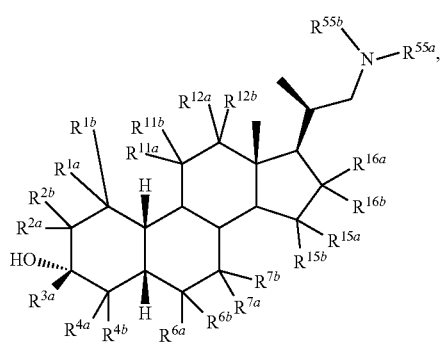

(I-Im)

or a pharmaceutically acceptable salt thereof.

17. The compound or pharmaceutically acceptable salt of claim 16, wherein $R^{3a}$ is ethyl, n-propyl, or n-butyl.

18. The compound or pharmaceutically acceptable salt of claim 17, wherein $R^{55a}$ and $R^{55b}$ join together with their intervening atoms to form

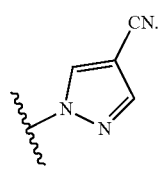

19. A compound selected from

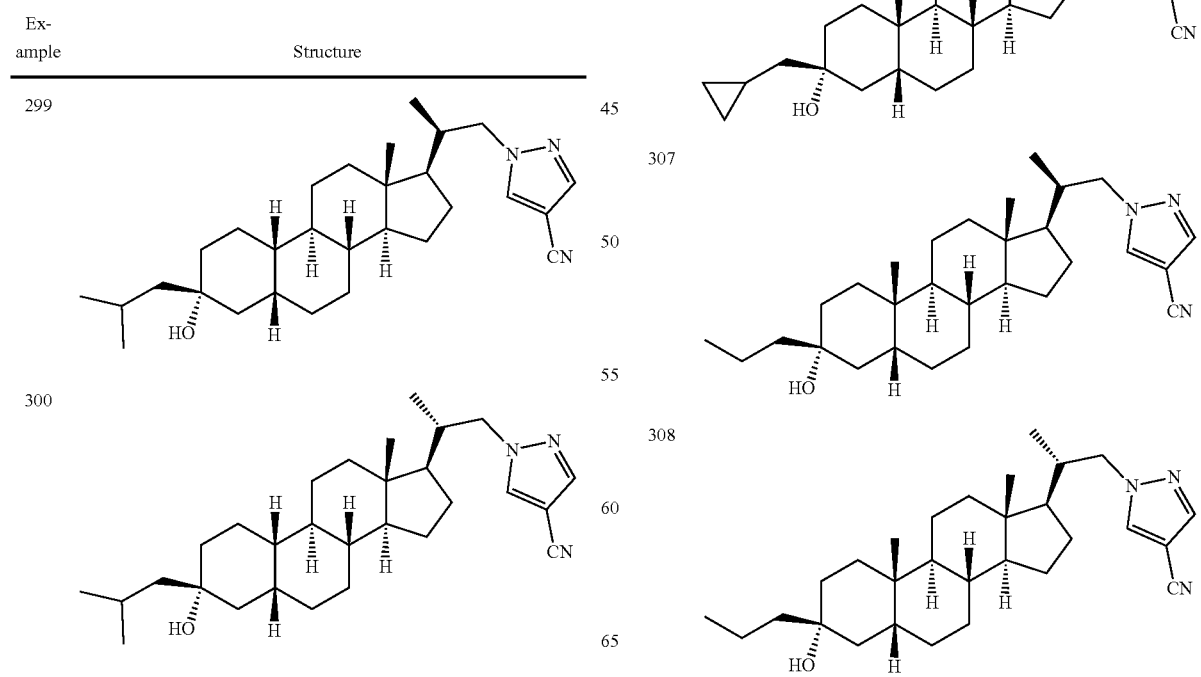

| Example | Structure |
|---|---|
| 311 | 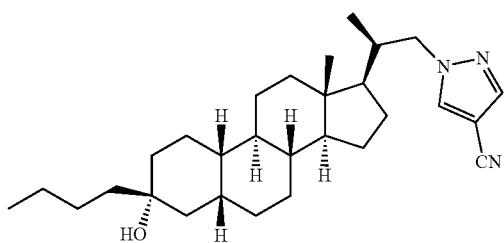 |
| 312 | 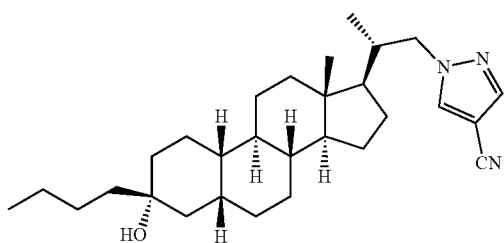 |
| 65 | 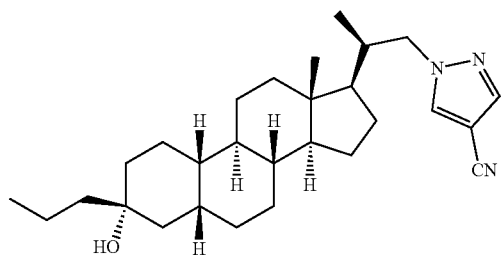 |
| 66 | 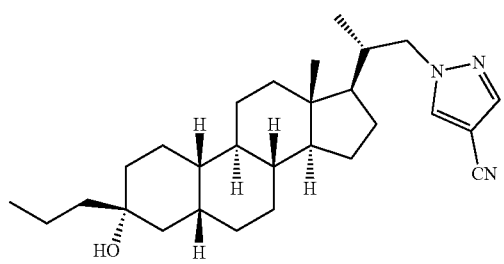 |
| 341 | 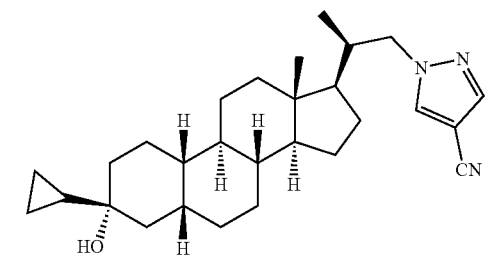 |
| Example | Structure |
|---|---|
| 342 | 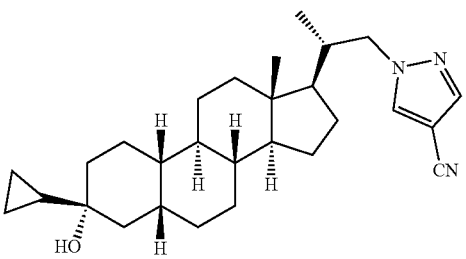 |
| 343 | 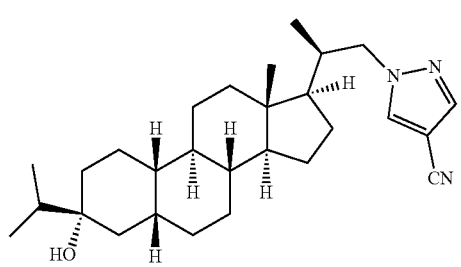 |
| 344 | 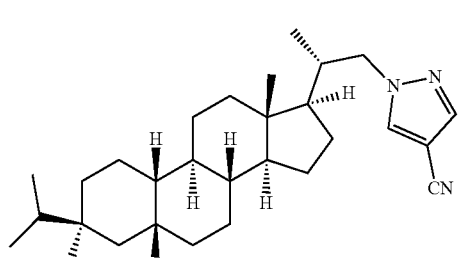 |
| 349 | 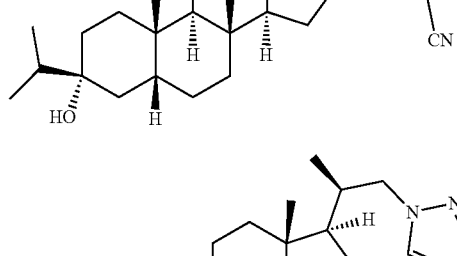 |
| 350 | 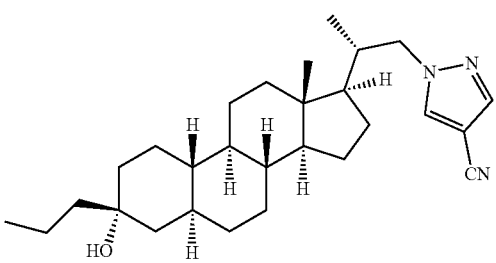 |
or a pharmaceutically acceptable salt thereof.
20. A pharmaceutical composition comprising a compound or pharmaceutically acceptable salt according to claim 1 and a pharmaceutically acceptable excipient.
* * * * *